United States Patent
Schulze et al.

(10) Patent No.: US 10,894,784 B2
(45) Date of Patent: Jan. 19, 2021

(54) HETEROARYLBENZIMIDAZOLE COMPOUNDS

(71) Applicant: BAYER PHARMA AKTIENGESELLSCHAFT, Berlin (DE)

(72) Inventors: Volker Schulze, OT Bergf (DE); Tobias Heinrich, Berlin (DE); Florian Prinz, Berlin (DE); Julien Lefranc, Berlin (DE); Jens Schröder, Berlin (DE); Anne Mengel, Berlin (DE); Wilhelm Bone, Berlin (DE); Joszef Bálint, Berlin (DE); Antje Margret Wengner, Berlin (DE); Knut Eis, Berlin (DE); Horst Irlbacher, Berlin (DE); Marcus Koppitz, Berlin (DE); Ulf Bömer, Glienicke (DE); Benjamin Bader, Berlin (DE); Hans Briem, Berlin (DE); Philip Lienau, Berlin (DE); Clara Christ, Berlin (DE); Detlef Stöckigt, Potsdam (DE); Roman Hillig, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/063,370

(22) PCT Filed: Dec. 15, 2016

(86) PCT No.: PCT/EP2016/002126
§ 371 (c)(1),
(2) Date: Jun. 18, 2018

(87) PCT Pub. No.: WO2017/102091
PCT Pub. Date: Jun. 22, 2017

(65) Prior Publication Data
US 2019/0047980 A1 Feb. 14, 2019

(30) Foreign Application Priority Data

Dec. 18, 2015 (EP) ..................... 15201230
Mar. 17, 2016 (EP) ..................... 16160885
Oct. 12, 2016 (EP) ..................... 16193418

(51) Int. Cl.
*C07D 401/12* (2006.01)
*C07D 401/14* (2006.01)
*C07D 405/14* (2006.01)
*C07D 409/14* (2006.01)
*C07D 451/14* (2006.01)
*C07D 471/08* (2006.01)
(Continued)

(52) U.S. Cl.
CPC ............ *C07D 401/12* (2013.01); *A61P 35/00* (2018.01); *C07D 401/14* (2013.01); *C07D 405/14* (2013.01); *C07D 409/14* (2013.01); *C07D 451/14* (2013.01); *C07D 471/08* (2013.01); *C07D 487/08* (2013.01)

(58) Field of Classification Search
CPC ..... A61P 35/00; C07D 401/12; C07D 401/14; C07D 405/14; C07D 409/14; C07D 451/14; C07D 471/08; C07D 487/08
See application file for complete search history.

(56) References Cited

U.S. PATENT DOCUMENTS

2005/0038023 A1 2/2005 Bebbington et al.
2015/0344473 A1 12/2015 Du et al.
(Continued)

FOREIGN PATENT DOCUMENTS

CN 103251600 A 8/2013
WO 1998056376 A1 12/1998
(Continued)

OTHER PUBLICATIONS

Mciver, Edward G. et al., "Synthesis and structure-activity relationships of a novel series of pyrimidines as potent inhibitors of TBK1/IKKε kinases", Biooraanic & Medicinal Chemistry Letters, 2012, pp. 7169-7173, vol. 22.
(Continued)

*Primary Examiner* — Kara R McMillian

(57) ABSTRACT

The present invention covers heteroarylbenzimidazole compounds of general formula (I) in which $R^1$, $R^2$, $R^3$, $R^4$ and $R^5$ are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of hyperproliferative and/or inflammatory disorders, as a sole agent or in combination with other active ingredients.

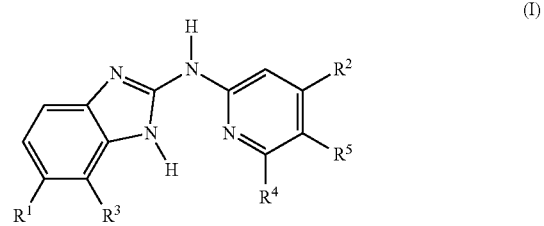

(I)

15 Claims, No Drawings
Specification includes a Sequence Listing.

(51) Int. Cl.
C07D 487/08 (2006.01)
A61P 35/00 (2006.01)

(56) References Cited

U.S. PATENT DOCUMENTS

2016/0289196 A1 10/2016 Choi et al.
2016/0297815 A1 10/2016 Choi et al.

FOREIGN PATENT DOCUMENTS

| WO | 2002076438 A2 | 10/2002 |
|---|---|---|
| WO | 2004058762 A1 | 7/2004 |
| WO | 2004085425 A1 | 10/2004 |
| WO | 2005020921 A2 | 3/2005 |
| WO | 2006099379 A2 | 9/2006 |
| WO | 2007084390 A2 | 7/2007 |
| WO | 2007089512 A1 | 8/2007 |
| WO | 2007100646 A1 | 9/2007 |
| WO | 2008057280 A1 | 5/2008 |
| WO | 2010034797 A1 | 4/2010 |
| WO | 2010115736 A2 | 10/2010 |
| WO | 2010122754 A1 | 11/2010 |
| WO | 2011046970 A1 | 4/2011 |
| WO | 2011161159 A1 | 12/2011 |
| WO | 2012010826 A1 | 1/2012 |
| WO | 2012/068546 | 5/2012 |
| WO | 2012068546 A1 | 5/2012 |
| WO | 2012104007 A2 | 8/2012 |
| WO | 2012161877 A1 | 11/2012 |
| WO | 2012161879 A1 | 11/2012 |
| WO | 2013/024282 | 2/2013 |
| WO | 2013024282 A2 | 2/2013 |
| WO | 2013034238 A1 | 3/2013 |
| WO | 2013075785 A1 | 5/2013 |
| WO | 2013117285 A1 | 8/2013 |
| WO | 2014004863 A2 | 1/2014 |
| WO | 2015031564 A2 | 3/2015 |

OTHER PUBLICATIONS

Wang, Tao et al., "Discovery of azabenzimidazole derivatives as potent, selective inhibitors of TBK1/IKKε kinases", Bioorganic & Medicinal Chemistry Letters, 2012, pp. 2063-2069, vol. 22.
Johannes, Jeffrey W. et al., "Discovery of 6-aryl-azabenzimidaoles that inhibit the TBK1/IKK-ε kinases", Bioorganic & Medicinal Chemistry Letters, 2014, pp. 1138-1143, vol. 24.
Yu, Tao et al., "TBK1 inhibitors: a review of patent literature (2011-2014)", Expert Opinion on Therapeutic Patents, 2015, vol. 25, No. 12.
Boehm, Jesse S. et al., "Integrative Genomic Approaches Identify IKBKE as a Breast Cancer Oncogene", Cell, Jun. 15, 2007, pp. 1065-1079, vol. 129.
Barbie, Thanh U. et al., "Targeting an IKBKE cytokine network impairs triple-negative breast cancer growth", The Journal of Clinical Investigation, Dec. 2014, vol. 124, No. 12, 5411-5423.
Jiang, Zhe et al., "Targeting HER2+ breast cancer: the TBK1/IKKε axis", Oncoscience, 2014, pp. 180-182, vol. 1, No. 2.
Guan, Hongyu et al., "IKBKE is over-expressed in glioma and contributes to resistance of glioma cells to apoptosis via activating NF-κB", Journal of Pathology, 2011, pp. 436-445, vol. 223.
Korherr, Christian et al., "Identification of proangiogenic genes and pathways by high-throughput functional genomics: TBK1 and the IRF3 pathway", PNAS, Mar. 14, 2006, pp. 4240-4245, vol. 103, No. 11.
Chien, Yuchen et al., "RalB GTPase-Mediated Activation of the IκB Family Kinase TBK1 Couples Innate Immune Signaling to Tumor Cell Survival", Cell, Oct. 6, 2006, pp. 157-170, vol. 127.
Barbie, David A. et al., "Systematic RNA interference reveals that oncogenic KRAS-driven cancers require TBK1", Nature, Nov. 5, 2009, pp. 108-112, vol. 462.
Zhu, Zehua et al., "Inhibition of KRAS-driven tumorigenicity by interruption of an autocrine cytokine circuit", Cancer Discovery, Apr. 2014, pp. 452-465, vol. 4, No. 4.
Aiello, Lloyd P. et al., "Vascular Endothelial Growth Factor in Ocular Fluid of Patients With Diabetic Retinopathy and Other Retinal Disorders", The New England Journal of Medicine, Dec. 1, 1994, pp. 1480-1487, vol. 331, No. 22.
Pe'er Jacob et al., "Hypoxia-Induced Expression of Vascular Endothelial Growth Factor by Retinal Cells is a Common Factor in Neovascularizing Ocular Diseases", Laboratory Investigation, 1995, pp. 638-645, vol. 72, No. 6.
Lopez, Pedro F. et al., "Transdifferentiated Retinal Pigment Epithelial Cells Are Immunoreactive for Vascular Endothelial Growth Factor in Surgically Excised Age-Related Macular Degeneration-Related Choroidal Neovascular Membranes", Investigative Ophthalmology & Visual Science, Apr. 1996, pp. 855-868, vol. 37, No. 5.
Carbone, Carmine et al., "NF-κB as a target for pancreatic cancer therapy", Expert Opinion, 2012, vol. 16, S1-S10.
Clement, Jean-Francois et al., "The IKK-related kinases: from innate immunity to oncogenesis", Cell Research, Sep. 2008, pp. 889-899, vol. 18, No. 9.
Godl, Klaus et al., "Proteomic Characterization of the Angiogenesis Inhibitor SU6668 Reveals Multiple Impacts on Cellular Kinase Signaling", Cancer Research, Aug. 1, 2005, pp. 6919-6926, vol. 65, No. 15.
Guo, Jian-Ping et al., "IKKε Phosphorylation of Estrogen Receptor α Ser-167 and Contribution to Tamoxifen Resistance in Breast Cancer", The Journal of Biological Chemistry, Feb. 5, 2010, pp. 3676-3684, vol. 285, No. 6.
Guo, Jian-Ping et al., "IKBKE Protein Activates Akt Independent of Phosphatidylinositol 3-Kinase/PDK1/mTORC2 and the Pleckstrin Homology Domain to Sustain Malignant Transformation", The Journal of Biological Chemistry, Oct. 28, 2011, pp. 37389-37398, vol. 286, No. 43.
Richards, Burt et al., "Cellular and In Vivo Properties of MPI-0485520, a Novel and Potent Small Molecule Inhibitor of IKKε", Experimental Biology 2010, Apr. 24-28, 2010, Abstract No. 3439.
Lee, Dung-Fang et al., "Advances in Targeting IKK and IKK-Related Kinases for Cancer Therapy", Clinical Cancer Research, Sep. 15, 2008, pp. 5656-5662, vol. 14, No. 18.
Ou, Yi-Hung et al., "TBK1 Directly Engages Akt/PKB Survival Signaling to Support Oncogenic Transformation", Molecular Cell, Feb. 18, 2011, pp. 458-470, vol. 41.
Peant, Benjamin et al., "IκB-Kinase-ε (IKKε/IKKi/IκBKε) Expression and Localization in Prostate Cancer Tissues", The Prostate, 2011, pp. 1131-1138, vol. 71.
Richards, Burt et al., "Inhibition of Cytosolic Nucleic Acid Receptor Pathways Using the Small Molecule IKKε/TBK1 Kinase Inhibitor MPI-0485520", American College of Rheumatology, Nov. 7-11, 2010, Abstract No. 493.
Li, Jijia et al., "Selective TBK1/IKKi dual inhibitors with anticancer potency", International Journal of Cancer, 2014, pp. 1972-1980, vol. 134.
International Search Report for PCT/EP2016/002126, dated Mar. 16, 2017, 3 pages.
Written Opinion of the ISA for PCT/EP2016/002126, dated Mar. 16, 2017, 6 pages.
Lefranc, et al., "Discovery of BAY-985, a Highly Selective TBK1/IKKe Inhibitor", Journal of Medicinal Chemistry, 2020, vol. 63, 601-612.
Lefranc, et al., "Discovery of BAY-985 a highly selective TBK1/IKKe Inhibitor—Supporting Information", S1-S90, 2020.

SEQUENCE LISTING

<160> NUMBER OF SEQ ID NOS: 3

<210> SEQ ID NO 1
<211> LENGTH: 1920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aatagtagac ataatagcaa cagacataca aactaaagaa ttacaaaaac aaattacaaa      60
aattcaaaat tttatcgata ctagttctta cgcgtggtac cgagctctta cgcgtgctag     120
cgaaactgaa actgaaactg aaactgaaac tgaaactgaa actgaaactg aaactgaaac     180
tagatctggg tatataatgg aagcttggca ttccggtact gttggtaaag ccaccatgga     240

```
agatgccaaa acattaaga agggcccagc gccattctac ccactcgaag acgggaccgc      300
cggcgagcag ctgcacaaag ccatgaagcg ctacgccctg gtgcccggca ccatcgcctt     360
taccgacgca catatcgagg tggacattac ctacgccgag tacttcgaga tgagcgttcg     420
gctggcagaa gctatgaagc gctatgggct gaatacaaac catcggatcg tggtgtgcag     480
cgagaatagc ttgcagttct tcatgcccgt gttgggtgcc ctgttcatcg gtgtggctgt     540
ggccccagct aacgacatct acaacgagcg cgagctgctg aacagcatgg gcatcagcca     600
gcccaccgtc gtattcgtga gcaagaaagg gctgcaaaag atcctcaacg tgcaaaagaa     660
gctaccgatc atacaaaaga tcatcatcat ggatagcaag accgactacc agggcttcca     720
aagcatgtac accttcgtga cttcccattt gccacccggc ttcaacgagt acgacttcgt     780 gccccgagagc ttcgaccggg acaaaaccat cgccctgatc atgaacagta gtggcagtac     840
cggattgccc aagggcgtag ccctaccgca ccgcaccgct tgtgtccgat tcagtcatgc     900
ccgcgacccc atcttcggca accagatcat ccccgacacc gctatcctca gcgtggtgcc     960
atttcaccac ggcttcggca tgttcaccac gctgggctac ttgatctgcg gctttcgggt    1020
cgtgctcatg taccgcttcg aggaggagct attcttgcgc agcttgcaag actataagat    1080
tcaatctgcc ctgctggtgc ccacactatt tagcttcttc gctaagagca ctctcatcga    1140
caagtacgac ctaagcaact tgcacgagat cgccagcggc ggggcgccgc tcagcaagga    1200
ggtaggtgag gccgtggcca aacgcttcca cctaccaggc atccgccagg gctacggcct    1260
gacagaaaca accagcgcca ttctgatcac ccccgaaggg gacgacaagc ctggcgcagt    1320
aggcaaggtg gtgcccttct tcgaggctaa ggtggtggac ttggacaccg gtaagacact    1380
gggtgtgaac cagcgcggcg agctgtgcgt ccgtggcccc atgatcatga gcggctacgt    1440
taacaacccc gaggctacaa acgctctcat cgacaaggac ggctggctgc acagcggcga    1500
catcgcctac tgggacgagg acgagcactt cttcatcgtg gaccggctga agagcctgat    1560
caaatacaag ggctaccagg tagccccagc cgaactggag agcatcctgc tgcaacaccc    1620
caacatcttc gacgccgggg tcgccggcct gcccgacgac gatgccggcg agctgccccg    1680
cgcagtcgtc gtgctggaac acggtaaaac catgaccgag aaggagatcg tggactatgt    1740
ggccagccag gttacaaccg ccaagaagct gcgcggtggt gttgtgttcg tggacgaggt    1800
gcctaaagga ctgaccggca gttggacgcc ccgcaagatc cgcgagattc tcattaaggc    1860
caagaagggc ggcaagatcg ccgtgtaata attctagaac gaagcggccg cagggtttaa    1920
```

<210> SEQ ID NO 2
<211> LENGTH: 2760
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ctcgagatcc ggccattagc catattattc attggttata tagcataaat caatattggc       60
tattggccat tgcatacgtt gtatccatat cataatatgt acatttatat ggctcatgt      120 ccaacattac cgccatgttg acattgatta ttgactagtt attaatagta atcaattacg     180
gggtcattag ttcatagccc atatatggag ttccgcgtta caacttacg gtaaatggc      240 ccgcctggct gaccgcccaa cgaccccgc ccattgacgt caataatgac gtatgttccc     300
atagtaacgc caatagggac tttccattga cgtcaatggg tggagtattt acggtaaact    360
```

-continued

```
gcccacttgg cagtacatca agtgtatcat atgccaagta cgccccctat tgacgtcaat    420
gacggtaaat ggcccgcctg gcattatgcc cagtacatga ccttatggga ctttcctact    480
tggcagtaca tctacgtatt agtcatcgct attaccatgg tgatgcggtt ttggcagtac    540
atcaatgggc gtggatagcg gtttgactca cggggatttc caagtctcca ccccattgac    600
gtcaatggga gtttgttttg gcaccaaaat caacgggact ttccaaaatg tcgtaacaac    660
tccgccccat tgacgcaaat gggcggtagg catgtacggt gggaggtcta tataagcaga    720
gctcgtttag tgaaccgtca gatcgcctgg agacgccatc cacgctgttt tgacctccat    780
agaagacacc gggaccgatc cagcctccgc ggccccaagc ttggcaatcc ggtactgttg    840
gtaaagccac catggaagat gccaaaaaca ttaagaaggg cccagcgcca ttctacccac    900
tcgaagacgg gaccgccggc gagcagctgc acaaagccat gaagcgctac gccctggtgc    960
ccggcaccat cgcctttacc gacgcacata tcgaggtgga cattacctac gccgagtact   1020
tcgagatgag cgttcggctg gcagaagcta tgaagcgcta tgggctgaat acaaaccatc   1080
ggatcgtggt gtgcagcgag aatagcttgc agttcttcat gccgtgttg ggtgccctgt   1140 tcatcggtgt ggctgtggcc ccagctaacg acatctacaa cgagcgcgag ctgctgaaca   1200
gcatgggcat cagccagccc accgtcgtat tcgtgagcaa gaaagggctg caaaagatcc   1260
tcaacgtgca aaagaagcta ccgatcatac aaaagatcat catcatggat agcaagaccg   1320
actaccaggg cttccaaagc atgtacacct tcgtgacttc ccatttgcca cccggcttca   1380
acgagtacga cttcgtgccc gagagcttcg accgggacaa aaccatcgcc ctgatcatga   1440
acagtagtgg cagtaccgga ttgcccaagg gcgtagccct accgcaccgc accgcttgtg   1500
tccgattcag tcatgcccgc gaccccatct cggcaacca gatcatcccc gacaccgcta   1560
tcctcagcgt ggtgccattt caccacggct tcggcatgtt caccacgctg gctacttga   1620 tctgcggctt tcgggtcgtg ctcatgtacc gcttcgagga ggagctattc ttgcgcagct   1680
tgcaagacta taagattcaa tctgccctgc tggtgcccac actatttagc ttcttcgcta   1740
agagcactct catcgacaag tacgacctaa gcaacttgca cgagatcgcc agcggcgggg   1800
cgccgctcag caaggaggta ggtgaggccg tggccaaacg cttccaccta ccaggcatcc   1860
gccagggcta cggcctgaca gaaacaacca gcgccattct gatcaccccc gaaggggacg   1920
acaagcctgg cgcagtaggc aaggtggtgc ccttcttcga ggctaaggtg gtggacttgg   1980
acaccggtaa gactctgggt gtgaaccagc gcggcgagct gtgcgtccgt ggccccatga   2040
tcatgagcgg ctacgttaac aaccccgagg ctacaaacgc tctcatcgac aaggacggct   2100
ggctgcacag cggcgacatc gcctactggg acgaggacga gcacttcttc atcgtggacc   2160
ggctgaagag cctgatcaaa tacaagggct accaggtagc cccagccgaa ctggagagca   2220
tcctgctgca acaccccaac atcttcgacg ccggggtcgc cggcctgccc gacgacgatg   2280
ccggcgagct gccgcgcgca gtcgtcgtgc tggaacacgg taaaaccatg accgagaagg   2340
agatcgtgga ctatgtggcc agccaggtta caaccgccaa gaagctgcgc ggtggtgttg   2400
tgttcgtgga cgaggtgcct aaaggactga ccggcaagtt ggacgcccgc aagatccgcg   2460
agattctcat taaggccaag aagggcggca agatcgccgt gtaataattc tagaacgaag   2520
cggccgcagg gtttaaacac ggtcgacggt accgcgggcc caacatcgat aaaataaaag   2580
attttattta gtctccagaa aaggggggga atgaaagacc ccacctgtag gtttggcaag   2640
ctagcttaag taacgccatt ttgcaaggca tggaaaaata cataactgag aatagagaag   2700
```

```
ttcagatcaa ggtcaggaac agatggaaca gctgaatatg ggccaaacag gatatctgtg    2760
```

<210> SEQ ID NO 3
<211> LENGTH: 1736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
actagtatta tgcccagtac atgaccttat gggactttcc tacttggcag tacatctacg      60
tattagtcat cgctattacc atggtgatgc ggttttggca gtacatcaat gggcgtggat     120
agcggtttga ctcacgggga tttccaagtc tccacccat tgacgtcaat gggagtttgt      180
tttggcacca aaatcaacgg gactttccaa aatgtcgtaa caactccgcc ccattgacgc     240
aaatgggcgg taggcgtgta cggtgggagg tctatataag cagagctcgt ttagtgaacc     300
gtcagatcgc ctggagacgc catccacgct gttttgacct ccatagaaga ttctagagct     360
agcgctcaac tttgtataga aaagttgact agtccagtgt ggtggaattc tgcagatatc     420
aacaagtttg tacaaaaaag caggctgcca ccatgggaac cccaaagcca cggatcctgc     480
cctggctggt gtcgcagctg gacctgggc aactggaggg cgtggcctgg gtgaacaaga      540
gccgcacgcg cttccgcatc ccttggaagc acggcctacg gcaggatgca cagcaggagg     600
atttcggaat cttccaggcc tgggccgagg ccactggtgc atatgttccc ggagggata     660 agccagacct gccaacctgg aagaggaatt tccgctctgc cctcaaccgc aaagaagggt     720
tgcgtttagc agaggaccgg agcaaggacc ctcacgaccc acataaaatc tacgagtttg     780
tgaactcagg agttggggac ttttcccagc cagacacctc tccggacacc aatggtggag     840
gcagtacttc tgatacccag gaagacattc tggatgagtt actgggtaac atggtgttgg     900
ccccactccc agatccggga ccccaagcc tggctgtagc ccctgagccc tgccctcagc      960
ccctgcggag ccccagcttg gacaatccca ctcccttccc aaacctgggg ccctctgaga    1020
acccactgaa gcggctgttg gtgccggggg aagagtggga gttcgaggtg acagccttct    1080
accgggggcg ccaagtcttc cagcagacca tctcctgccc ggagggcctg cggctggtgg    1140
ggtccgaagt gggagacagg acgctgcctg gatggccagt cacactgcca gaccctggca    1200
tgtccctgac agacagggga gtgatgagct acgtgaggca tgtgctgagc tgcctgggtg    1260
ggggactggc tctctggcgg gccgggcagt ggctctgggc ccagcggctg ggcactgcc     1320 acacatactg ggcagtgagc gaggagctgc tccccaacag cgggcatggg cctgatggcg    1380
aggtccccaa ggacaaggaa ggaggcgtgt tgacctggg gccttcatt gtagatctga      1440 ttaccttcac ggaaggaagc ggacgctcac cacgctatgc cctctggttc tgtgtggggg    1500
agtcatggcc ccaggaccag ccgtggacca agaggctcgt gatggtcaag gttgtgccca    1560
cgtgcctcag ggccttggta gaaatggccc gggtagggg tgcctcctcc ctggagaata    1620
ctgtggacct gcacatttcc aacagccacc cactctccct cacctccgac cagtacaagg    1680
cctacctgca ggacttggtg gagggcatgg atttccaggg ccctggggag agctga        1736
```

HETEROARYLBENZIMIDAZOLE COMPOUNDS

This application is the U.S. national phase of International Application No. PCT/EP2016/002126 filed Dec. 15, 2016, which designated the U.S. and claims priority to EP Patent Application No. 15201230.8, filed Dec. 18, 2015, EP Patent Application No. 16160885.6, filed Mar. 17, 2016, EP Patent Application No. 16193418.7, filed Oct. 12, 2016, the entire contents of each of which are hereby incorporated by reference.

SEQUENCE LISTING

The instant application contains a Sequence Listing which has been filed electronically in ASCII format and is hereby incorporated by reference in its entirety. Said ASCII copy, created on Oct. 10, 2018, is named 6487-0210_SL.txt and is 9,221 bytes in size.

The present invention covers heteroarylbenzimidazole compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative and/or inflammatory disorders, as a sole agent or in combination with other active ingredients.

BACKGROUND

The present invention covers heteroarylbenzimidazole compounds of general formula (I) which inhibit Tank-binding kinase 1 (TBK1) and/or IκB kinase epsilon (IKKε).

Tank-binding kinase 1 (TBK1) and IκB kinase epsilon (IKKε) are two non-canonical IκB kinases (IKKs). They play crucial roles in interferon regulatory factor (IRF) and nuclear factor kappaB (NF-κB) signaling cascades. TBK1 and IKKε share 49% identity and 65% similarity with each other and the kinase domains are 27% identical to IKKα and IKKβ (Shen R R & Hahn W C (2011) Emerging roles for the non-canonical IKKs in cancer. Oncogene 30(6):631-641). Both IKKε and TBK1 are comprised of an N-terminal kinase domain, an ubiquitin-like domain, a C-terminal LZ and a HLH motif (Larabi A, et al. (2013) Crystal structure and mechanism of activation of TANK-binding kinase 1. Cell reports 3(3):734-746). Despite their similarity in structure, TBK1 and IKKε exhibit differential expression patterns. TBK1, like IKKα and IKKβ, is ubiquitously expressed. In contrast, IKKε expression is restricted to particular tissue compartments, with highest levels detected in lymphoid tissues, peripheral blood lymphocytes and the pancreas. Various epithelial-derived cell lines also exhibit IKKε expression (reviewed in Shen R R & Hahn W C (2011) Emerging roles for the non-canonical IKKs in cancer. Oncogene 30(6):631-641).

TBK1 was originally identified as an IKK-related Serine/Threonine kinase which, in complex with IKKε, induces the transcription of IFN-I genes as part of the anti-viral innate immune response. Within this pathway, TBK1 resides downstream of Toll-like receptors and has as natural substrates the transcription factors IRF3 and IRF7 which, upon phosphorylation by TBK1, translocate to the nucleus and trigger IFN-I gene transcription (Han K J, et al. (2004) Mechanisms of the TRIF-induced interferon-stimulated response element and NF-kappaB activation and apoptosis pathways. *The Journal of biological chemistry* 279(15): 15652-15661).

Although TBK1 and IKKε are not a part of the classical IKKα/β/γ signaling complex, these kinases were originally characterized as activators of NF-κB and target multiple NF-κB members and effectors. Both IKK-related kinases phosphorylate IκBα at one of the two-serine residues typically targeted on IκBα (Shen R R & Hahn W C (2011) Emerging roles for the non-canonical IKKs in cancer. *Oncogene* 30(6):631-641).

TBK1 and IKKε have been linked to the pathophysiology of several diseases and represent promising potential targets for drug development as is demonstrated by several drug finding projects, both from academia and from the pharmaceutical industry as reviewed recently by Yu and colleagues (Yu T, et al. (2015) TBK1 inhibitors: a review of patent literature (2011-2014). *Expert opinion on therapeutic patents:* 1-12).

Recent literature data have provided clear and robust evidence for a role of TBK1 and IKKε in cancer biology.

IKKε was found to be amplified in breast cancer lines and breast carcinomas. Subsequent experiments identified IKKε as a breast cancer oncogene (Boehm J S, et al. (2007) Integrative genomic approaches identify IKBKE as a breast cancer oncogene. *Cell* 129(6):1065-1079). Work by other groups further confirmed the role of IKKε (and TBK1) in breast cancer (e.g. Barbie T U, et al. (2014) Targeting an IKBKE cytokine network impairs triple-negative breast cancer growth. *The Journal of clinical investigation* 124(12): 5411-5423, Jiang Z, Liu J C, Chung P E, Egan S E, & Zacksenhaus E (2014) Targeting HER2(+) breast cancer: the TBK1/IKKepsilon axis. *Oncoscience* 1(2):180-182) and demonstrated a role in glioma (Guan H, et al. (2011) IKBKE is over-expressed in glioma and contributes to resistance of glioma cells to apoptosis via activating NF-kappaB. *The Journal of pathology* 223(3):436-445).

TBK1 is up-regulated under hypoxic conditions and was shown to behave as a pro-angiogenic factor (Korherr C, et al. (2006) Identification of proangiogenic genes and pathways by high-throughput functional genomics: TBK1 and the IRF3 pathway. *Proceedings of the National Academy of Sciences of the United States of America* 103(11):4240-4245). Moreover, TBK1 over-expression in HUVEC cells induces the secretion of pro-angiogenic factors via the activation of IRF3 (Korherr C, et al. (2006) Identification of proangiogenic genes and pathways by high-throughput functional genomics: TBK1 and the IRF3 pathway. *Proceedings of the National Academy of Sciences of the United States of America* 103(11):4240-4245). In addition, TBK1 has been identified as a key factor linking innate immune signaling to tumor cell survival via the small GTPase and Ras effector RalB (Chien Y, et al. (2006) RalB GTPase-mediated activation of the IkappaB family kinase TBK1 couples innate immune signaling to tumor cell survival. *Cell* 127(1):157-170).

Apparently, Ras-transformed cancer cells are addicted to TBK1-induced survival signals, and TBK1 kinase inhibition may therefore constitute a tumor cell-specific approach to cancer treatment. In line with this, TBK1 was shown to be essential for cell lines with activated KRas. This links RalB mediated activation of TBK1 to the generation of specific NF-κB-regulated survival signals downstream of oncogenic KRas (Barbie D A, et al. (2009) Systematic RNA interference reveals that oncogenic KRAS-driven cancers require TBK1. *Nature* 462(7269):108-112). Moreover, it was shown that an autocrine circuit between KRAs via TBK1/IKKε to CCL5 and IL-6 secretion could be responsible for an autostimulatory growth stimulus of tumor cells. This was shown for lung adenocarcinomas, especially for non-small cell lung cancers (NSCLC) (Zhu Z, et al. (2014) Inhibition of KRAS-driven tumorigenicity by interruption of an autocrine cytokine circuit. *Cancer discovery* 4(4):452-465).

Besides its role in cancer, TBK1 has been proposed as a target for the treatment of autoimmune diseases, inflammation and other diseases. TBK1 is involved in regulating rheumatoid synovitis and also acts as a key regulator in neuroinflammation, microvascular inflammation and gastritis. Additional potential indications include obesity and type 2 diabetes. TBK1 signaling has also been shown to be involved in mediating normal tension glaucoma, familial amyotrophic lateral sclerosis (ALS) and frontotemporal dementia diseases. In the field of cancer, there are an increasing number of reports demonstrating that TBK1 mediates cell apoptosis and proliferation in cancer cell lines, especially those that depend on oncogenic KRAS expression. Additionally, it was shown that TBK1 plays a key role in maintaining drug resistance in prostate cancer (PCa) cells by interaction with mammalian target of rapamycin and inhibiting its function, which can induce cell-cycle arrest in PCa cells. Also, several reports have suggested that TBK1 is involved in breast cancer regulation, especially in human HER2-positive breast cancer cells. TBK1 silencing decreased the expression of epithelial markers and increased the expression of mesenchymal markers in ERα (estrogen receptor)-positive breast cancer cells. Furthermore, TBK1 plays a significant role in radiation-induced epithelial-mesenchymal transition. Additionally, TBK1-dependent mechanism for NF-κB signaling pathway contributes to autophagy addiction in K-Ras-driven non-small-cell lung cancer cells (reviewed in Yu T, et al. (2015) TBK1 inhibitors: a review of patent literature (2011-2014). *Expert opinion on therapeutic patents:* 1-12).

PRIOR ART

Various inhibitors of TBK1 and/or IKKε derived from chemotypes different from the compounds of the present invention have been described in patent applications and scientific publications as listed below:

WO 2010127754 discloses 3-([1,2,3]-triazol-4-yl-pyrrolo[2.3-b]pyridine derivatives as inhibitors of PDK1, IKKs and TBK 1.

WO 2011046970 discloses amino-pyrimidine compounds as inhibitors of TBK1 and/or IKKε.

WO 2012010826 discloses pyrimidine compounds as inhibitors of TBK1 and/or IKKε.

WO 2012104007 discloses 7-azaindole derivatives as inhibitors or PDK1, IKKε, TBK 1 and TGF-beta.

WO 2012161877 discloses pyridine and pyrazine derivatives as inhibitors of TBK1 and IKKε.

WO 2012161879 discloses thiazole derivatives as inhibitors of TBK1 and IKKε.

E. G. McIver et al., *Bioorg. Med. Chem. Lett.* 2012, 22, 7169-7173, disclose pyrimidine derivatives as inhibitors of TBK1 and IKKε.

T. Wang et al., *Bioorg. Med. Chem. Lett.* 2012, 22, 2063-2069, disclose azabenzimidazole derivatives as inhibitors of TBK1 and IKKε.

CN 103251600 discloses a 2-amino-4-(3'-cyano-4'-pyrrolidyl)phenyl pyrimidine compound inter alia as inhibitor of TBK-1.

WO 2013024282 discloses an inhibitor of one or both of TBK1 and IKKε, or a down-regulator of the expression of one or both TBK1 and IKKε, for use in a method of treating a cancer that is dependent on the PI3kinase pathway, and cites multiple further patent applications and scientific publications disclosing further inhibitors of TBK1 and IKKε.

WO 2013034238 discloses benzonitrile derivatives as inhibitors of TBK1 and IKKε.

WO 2013075785 discloses 3-cyanaryl-1H-pyrazolo[2.3-b]pyridine derivatives as inhibitors of TBK1 and IKKε.

WO 2013117285 discloses furo-[3,2b] and thieno-[3.2-b]pyridine derivatives as inhibitors of TBK1 and IKKε.

WO 2014004863 discloses heteroaromatic compounds as inhibitors of TBK1 and/or IKKε.

J. W. Johannes et al., *Bioorg. Med. Chem. Lett.* 2014, 24, 1138-1143, disclose 6-aryl-azabenzimidazole derivatives as inhibitors of TBK1 and IKKε.

US 20150344473 discloses fused heteroaromatic compounds as inhibitors of TBK1 and IKKε.

US 20160289196 discloses pyrazole derivatives as inhibitors of TNIK, TBK1 and/or IKKε.

US 20160297815 discloses 7-azaindole and 4,7-diazaindole derivatives as inhibitors of TBK1 and/or IKKε.

The subject is also addressed by a recent review article, see T. Yu, Y. Yang, D. Q. Yin, S. Hong, Y.-J. Son, J.-H. Kim and J. Y, Cho, TBK1 inhibitors: a review of patent literature (2011-2014), *Expert Opin. Ther. Patents* 2015, 25(11), 1385-1396.

A number of published patent applications disclose chemical structures showing a certain structural similarity to the compounds of the present invention which however address different mechanisms of biological activity and/or different technical fields:

WO 1998056376 discloses heteroaryl compounds for the modulation of protein tyrosine kinase related signal transduction.

WO 2002076438 discloses ligands of the Flt-1 receptor.

WO 2004058762 discloses inhibitors of Mitogen Activated Protein Kinase-activated Protein Kinase-2 (MK-2).

WO 2004085425 discloses fused azole derivatives as Kinase inhibitors.

WO 2005020921 discloses c-Kit modulators and method of use.

US 2005038023 discloses pyrazole compounds as Protein Kinase inhibitors.

WO 2006099379 discloses benzazole derivatives as beta-Secretase inhibitors.

WO 2007084390 discloses organic compounds as HDAC inhibitors.

WO 2007089512 discloses heterocyclic compounds as activators of Glucokinase.

WO 2007100646 discloses multicyclic compounds as modulators of various protein kinase receptor enzymes, such as Tie-2 and Aurora kinase.

WO 2008057280 discloses multicyclic compounds as modulators of various protein kinase receptors, such as Tie-2 and Aurora kinase.

WO 2010034797 discloses 1H-benzimidazole-5-carboxamides as anti-inflammatory agents.

WO 2010115736 discloses heterocyclic compounds as inhibitors of dihydroorotate dehydrogenase.

WO 2011161159 discloses heterocyclic compounds as Kinase inhibitors.

WO 2012068546 discloses heterocycle amines as inhibitors of IRAK-1 and IRAK-4.

WO 2015031564 discloses substituted 1H-benzo[d]imidazole series compounds as lysine specific demethylase (LSD-1) inhibitors.

However, the state of the art does not describe the heteroarylbenzimidazole compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively inhibit TBK1 and/or IKKε and may therefore be used for the treatment or prophylaxis of hyperproliferative and/or inflammatory disorders, such as cancer, for example.

DESCRIPTION OF THE INVENTION

In accordance with a first aspect, the present invention covers compounds of general formula (I):

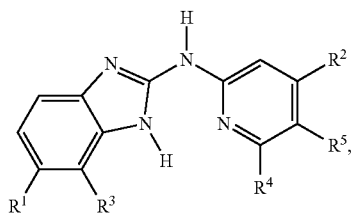

in which
$R^1$ represents a group selected from
  pyrazolyl, imidazolyl, oxadiazolyl, triazolyl, isoxazolyl, thienyl, pyridin-2-yl, pyridin-4-yl, pyrimidinyl, triazinyl and pyrazinyl, said group being optionally substituted with one $R^6$ group, and said group being, additionally, optionally substituted one or two times, differently or identically, with a $R^7$ group, or
$R^1$ represents a group selected from

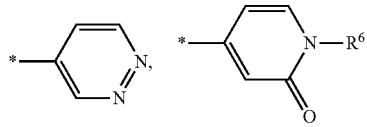

the ring of said group being, besides $R^6$, optionally substituted further one or two times, differently or identically, with a $R^7$ group,
  in which "*" represents the point of attachment to the rest of the molecule, or
$R^1$ represents a group selected from pyridine-3-yl or pyridazin-3-yl, optionally substituted with one $R^8$ group;
$R^2$ represents a group selected from

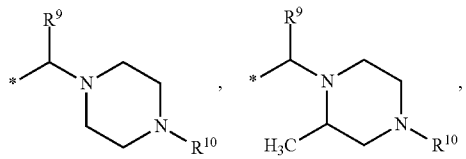

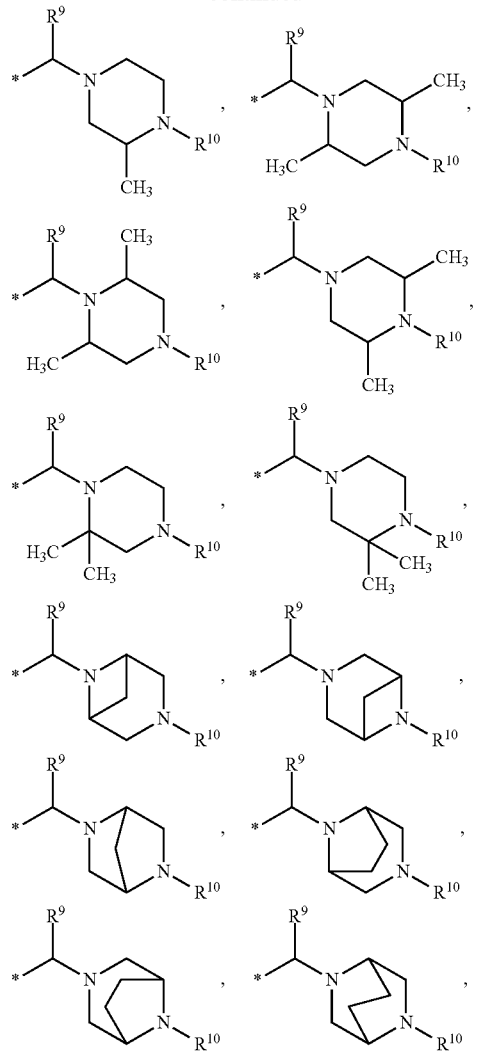

in which "*" represents the point of attachment to the rest of the molecule;
$R^3$ represents a hydrogen atom or a halogen atom or a group selected from $C_1$-$C_4$-alkyl and $C_1$-$C_6$-alkoxy;
$R^4$ represents a hydrogen atom or a halogen atom or a group selected from $C_1$-$C_4$-alkyl, $C_1$-$C_4$-haloalkyl, $C_1$-$C_4$-alkoxy and $C_1$-$C_4$-haloalkoxy;
$R^5$ represents a hydrogen atom or a halogen atom or a group selected from $C_1$-$C_4$-alkyl, $C_1$-$C_4$-haloalkyl and $C_3$-$C_6$-cycloalkyl;
$R^6$ represents a hydrogen atom or a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, $C_3$-$C_6$-cycloalkyl and ($C_3$-$C_6$-cycloalkyl)-($C_1$-$C_3$-alkyl)-,
  said $C_3$-$C_6$-cycloalkyl and said ($C_3$-$C_6$-cycloalkyl)-($C_1$-$C_3$-alkyl)- group being optionally substituted one, two or three times, identically or differently, with a fluorine atom, a chlorine atom or with a group selected from $C_1$-$C_3$-alkyl and $C_1$-$C_3$-haloalkyl;
$R^7$ represents a halogen atom or a group selected from hydroxy, $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, ($C_1$-$C_3$-haloalkoxy)-($C_1$-$C_3$-alkyl)-, $C_2$-$C_6$-alkenyl, $C_2$-$C_6$-alkynyl, $C_3$-$C_8$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, heterospirocycloalkyl, phenyl, heteroaryl, —CN, —($CH_2$)—N($R^{11}$)$R^{11a}$, —C(=O)$R^{13}$, —C(=O)—$OR^{13}$, —C(=O)—N($R^{11}$)$R^{11a}$, —N($R^{11}$)$R^{11a}$, —N($R^{16}$)—C(=O)—$R^{13}$, —N($R^{16}$)—S(=O)$_2$—$R^{13}$, —N($R^{16}$)—C(=O)—N($R^{11}$)$R^{11a}$, —N($R^{16}$)—C(=O)—$OR^{13}$, $C_1$-$C_6$-alkoxy, $C_1$-$C_6$-haloalkoxy, $C_3$-$C_8$-cycloalkoxy-, ($C_3$-$C_8$-cycloalkyl)-($C_1$-$C_3$-alkoxy)-, phenyloxy-, heteroaryloxy-, —O—($CH_2$)$_x$-phenyl, —O—($CH_2$)$_x$-heteroaryl, —O—C(=O)—$R^{13}$, —O—C(=O)—N($R^{11}$)$R^{11a}$, $C_1$-$C_6$-alkylsulfanyl, $C_1$-$C_6$-haloalkylsulfanyl, —S(=O)—$R^{13}$, —S(=O)$_2$—$R^{13}$, —S(=O)$_2$—N($R^{11}$)$R^{11a}$ and —S(=O)(=N$R^{17}$)$R^{13}$,
said $C_3$-$C_6$-cycloalkyl, said ($C_3$-$C_8$-cycloalkyl)-($C_1$-$C_3$-alkyl)- and said ($C_3$-$C_8$-cycloalkyl)-($C_1$-$C_3$-alkoxy)- group being optionally substituted one, two or three times, identically or differently, with a fluorine atom, a chlorine atom or with a group selected from $C_1$-$C_3$-alkyl and $C_1$-$C_3$-haloalkyl, said 4- to 7-membered heterocycloalkyl, said 5- to 7-membered heterocycloalkenyl and said heterospirocycloalkyl group being optionally substituted one, two or three times, identically or differently, with a fluorine atom, a chlorine atom or with a group selected from oxo, $C_1$-$C_3$-alkyl and $C_1$-$C_3$-haloalkyl, and said heteroaryl group and said phenyl group being optionally substituted one, two or three times, identically or differently, with a halogen atom or a group selected from —CN, $C_1$-$C_3$-alkyl, trifluoromethyl, $C_1$-$C_3$-alkoxy and trifluoromethoxy; or $R^6$ and $R^7$, or two $R^7$ groups, when being attached to adjacent ring atoms of the group $R^1$, together form a group selected from:
—(O—$CH_2$—O)—, —(O—($CH_2$)$_2$—O)—, —(O—($CH_2$)$_2$)—, —($CH_2$—O—$CH_2$)—, —(N$R^{16}$—($CH_2$)$_2$—O)—, —(N$R^{16}$—($CH_2$)$_3$—O)—, —(S—($CH_2$)$_2$)—, —(O—($CH_2$)$_3$)—, —(($CH_2$)$_3$)—, —(($CH_2$)$_4$)—, —(O—CH=CH)—, —(S—CH=CH)—;

$R^8$ represents a hydrogen atom or a group selected from methyl, ethyl, methoxy, ethoxy and dimethylamino;

$R^9$ represents a hydrogen atom or a —CN or $C_1$-$C_3$-alkyl group;

$R^{10}$ represents a group selected from —C(=O)$R^{12}$, —C(=O)$OR^{13}$, —C(=O)N($R^{14}$)$R^{14a}$, —S(=O)$_2$$R^{15}$, —S(=O)$_2$N($R^{14}$)$R^{14a}$, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy;

$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl, $C_1$-$C_6$-hydroxyalkyl, ($C_1$-$C_3$-alkoxy)-($C_1$-$C_3$-alkyl)-, ($C_3$-$C_6$-cycloalkyl)-($C_1$-$C_3$-alkyl)- and benzyl, or $R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, $C_1$-$C_3$-haloalkyl, $C_1$-$C_3$-alkoxy, —C(=O)$R^{18}$, —C(=O)$OR^{18}$ and —S(=O)$_2$$R^{18}$;

$R^{12}$ represents a hydrogen atom or a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, $C_3$-$C_6$-cycloalkyl, ($C_3$-$C_6$-cycloalkyl)-($C_1$-$C_3$-alkyl)-, $C_2$-$C_6$-alkenyl, $C_2$-$C_6$-alkynyl, 4- to 7-membered heterocycloalkyl, 5- to 7-membered heterocycloalkenyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy,
said $C_3$-$C_6$-cycloalkyl group being optionally substituted one, two or three times, identically or differently, with a halogen atom or a group selected from —CN, $C_1$-$C_3$-alkyl and $C_1$-$C_3$-haloalkyl;

$R^{13}$ represents a group selected from $C_1$-$C_4$-alkyl and benzyl;

$R^{14}$ and $R^{14a}$, independently from each other, represent a hydrogen atom or a group selected from $C_1$-$C_4$-alkyl, $C_1$-$C_4$-haloalkyl, $C_3$-$C_6$-cycloalkyl and benzyl, or $R^{14}$ and $R^{14a}$, together with the nitrogen atom they are attached to, represent a 4- to 7-membered heterocycloalkyl group, said group being optionally substituted one or two times, identically or differently, with a halogen atom or a group selected from hydroxyl, —CN, $C_1$-$C_3$-alkyl, $C_1$-$C_3$-haloalkyl, $C_1$-$C_3$-alkoxy, $C_1$-$C_3$-haloalkoxy and ($C_1$-$C_3$-alkoxy)-($C_1$-$C_3$-alkyl)-;

$R^{15}$ represents a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_6$-alkyl)-, ($C_1$-$C_3$-alkoxy)-($C_2$-$C_3$-alkoxy)-($C_1$-$C_6$-alkyl)-, $C_3$-$C_6$-cycloalkyl, ($C_3$-$C_6$-cycloalkyl)-($C_1$-$C_3$-alkyl)-, 4- to 7-membered heterocycloalkyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy;

$R^{16}$ represents a hydrogen atom or a group selected from $C_1$-$C_4$-alkyl and benzyl;

$R^{17}$ represents a hydrogen atom or a group selected from —CN, —C(=O)$OR^{13}$, $C_1$-$C_4$-alkyl and benzyl;

$R^{18}$ represents a $C_1$-$C_3$-alkyl group;

x represents an integer selected from 1, 2, 3 and 4, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen or sulfur atom. Commonly, and if not stated otherwise, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "supra" within the description it is referred to any of the respective disclosures made within the specification in any of the preceding pages, or above on the same page.

If within the present text any item is referred to as "infra" within the description it is referred to any of the respective disclosures made within the specification in any of the subsequent pages, or below on the same page.

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

As used herein, an oxo substituent represents an oxygen atom, which is bound to a carbon atom or to a sulfur atom via a double bond.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_2$-$C_6$-alkylene" means a linear or branched, saturated, divalent hydrocarbon chain (or "tether") having 2, 3, 4, 5 or 6 carbon atoms, e.g. —$CH_2$—$CH_2$— ("ethylene" or "$C_2$-alkylene"), —$CH_2$—$CH_2$—$CH_2$—, —C(H)($CH_3$)—$CH_2$— or —C($CH_3$)$_2$—) ("propylene" or "$C_3$-alkylene"), or, for example —$CH_2$—C(H)($CH_3$)—$CH_2$—, —$CH_2$—C($CH_3$)$_2$—), —$CH_2$—$CH_2$—$CH_2$—$CH_2$— ("butylene" or "$C_4$-alkylene"), "$C_5$-alkylene", e.g. —$CH_2$—$CH_2$—$CH_2$—$CH_2$—$CH_2$— ("n-pentylene"), or "—$C_6$-alkylene-", e.g. —$CH_2$—$CH_2$—$CH_2$—$CH_2$—$CH_2$—$CH_2$— ("n-hexylene") or —C($CH_3$)$_2$—C($CH_3$)$_2$— group. Particularly, said alkylene is a —C($CH_3$)$_2$—C($CH_3$)$_2$— group.

The term "$C_1$-$C_6$-hydroxyalkyl" means a linear or branched, saturated, monovalent hydrocarbon group in which the term "$C_1$-$C_6$-alkyl" is defined supra, and in which 1, 2 or 3 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_6$-alkylsulfanyl" means a linear or branched, saturated, monovalent group of formula ($C_1$-$C_6$-alkyl)-S—, in which the term "$C_1$-$C_6$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom, to give rise to a "$C_1$-$C_6$-fluoroalkyl" group, particularly a "$C_1$-$C_4$-fluoroalkyl" group, more particularly, a "$C_1$-$C_3$-fluoroalkyl" group. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom to give rise to a "$C_1$-$C_6$-fluoroalkoxy" group, particularly a "$C_1$-$C_4$-fluoroalkoxy" group, more particularly, a "$C_1$-$C_3$-fluoroalkoxy" group. Said $C_1$-$C_6$-haloalkoxy group is, for example, fluoromethoxy, difluoromethoxy, trifluoromethoxy, 2,2,2-trifluoroethoxy, pentafluoroethoxy or pentafluoropropoxy.

The term "$C_1$-$C_6$-haloalkylsulfanyl" means a linear or branched, saturated, monovalent $C_1$-$C_6$-alkylsulfanyl group, as defined supra, in which one or more of the hydrogen atoms is replaced, identically or differently, with a halogen atom. Particularly, said halogen atom is a fluorine atom to give rise to a "$C_1$-$C_6$-fluoroalkylsulfanyl" group, particularly a "$C_1$-$C_4$-fluoroalkylsulfanyl" group, more particularly, a "$C_1$-$C_3$-fluoroalkylsulfanyl" group. Said $C_1$-$C_6$-haloalkylsulfanyl group is, for example, fluoromethylsulfanyl, difluoromethylsulfanyl, trifluoromethylsulfanyl, 2,2,2-trifluoroethylsulfanyl or pentafluoroethylsulfanyl.

The term "$C_2$-$C_6$-alkenyl" means a linear or branched, monovalent hydrocarbon group, which contains one double bond, and which has 2, 3, 4, 5 or 6 carbon atoms, particularly 2 or 3 carbon atoms ("$C_2$-$C_3$-alkenyl"). Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl group. Particularly, said group is vinyl or allyl.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. Particularly, said alkynyl group is ethynyl, prop-1-ynyl or prop-2-ynyl.

The term "$C_3$-$C_8$-cycloalkyl" means a saturated, monovalent, mono- or bicyclic hydrocarbon ring which contains 3, 4, 5, 6, 7 or 8 carbon atoms ("$C_3$-$C_6$-cycloalkyl"). Particularly, said group is monocyclic and has 3, 4, 5 or 6 carbon atoms ("$C_3$-$C_6$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g. a cyclobutenyl, cyclopentenyl, cyclohexenyl, cycloheptenyl or cyclooctenyl group, or a bicyclic hydrocarbon ring, e.g. a bicyclo[2.2.1]hept-2-enyl or bicyclo[2.2.2]oct-2-enyl.

The term "$C_3$-$C_8$-cycloalkoxy" means a saturated, monovalent, mono- or bicyclic group of formula ($C_3$-$C_8$-cycloalkyl)-O—, which contains 3, 4, 5, 6, 7 or 8 carbon atoms ("$C_3$-$C_8$-cycloalkyloxy"), in which the term "$C_3$-$C_8$-cycloalkyl" is defined supra, e.g. a cyclopropyloxy, cyclobutyloxy, cyclopentyloxy, cyclohexyloxy, cycloheptyloxy or cyclooctyloxy group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The terms "4- to 7-membered heterocycloalkyl" and "4- to 6-membered heterocycloalkyl" mean a monocyclic, saturated heterocycle with 4, 5, 6 or 7 or, respectively, 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

Particularly, "4- to 6-membered heterocycloalkyl" means a 4- to 6-membered heterocycloalkyl as defined supra containing one ring nitrogen atom and optionally one further ring heteroatom from the series: N, O, S. More particularly, "5- or 6-membered heterocycloalkyl" means a monocyclic, saturated heterocycle with 5 or 6 ring atoms in total, containing at least one heteroatom from the series: N, O.

The term "5- to 7-membered heterocycloalkenyl" means a monocyclic, unsaturated, non-aromatic heterocycle with 5, 6 or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "fused heterocycloalkyl" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]-nonyl or azabicyclo[4.4.0]decyl.

The term "bridged heterocycloalkyl" means a bicyclic, saturated heterocycle with 7, 8, 9 or 10 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms, except the spiro carbon atom, or, if present, a nitrogen atom.

Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]-nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl or azabicyclo[4.2.2]decyl.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a 5- or 6-membered heteroaryl group.

The term "heteroaryloxy" means a monovalent, monocyclic, bicyclic or tricyclic aromatic group of the formula (heteroaryl)-O—, in which the term "heteroaryl" is as defined supra, e.g. thienyloxy, thiazolyloxy, pyridinyloxy, pyrimidinyloxy, benzofuranyloxy, for example.

The term "phenyloxy" means a group of the formula (phenyl)-O.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_8$, and $C_5$-$C_6$;

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$;

"$C_1$-$C_3$" encompasses $C_1$, $C_2$, $C_3$, $C_1$-$C_3$, $C_1$-$C_2$ and $C_2$-$C_3$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_8$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_8$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_8$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_8$, and $C_5$-$C_6$;

"$C_{4-8}$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_{4-7}$" encompasses $C_4$, $C_5$, $C_6$, $C_7$, $C_4$-$C_7$, $C_4$-$C_6$, $C_4$-$C_8$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_8$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

As used herein, the term "protective group" is a protective group attached to an oxygen or nitrogen atom in intermediates used for the preparation of compounds of the general formula (I). Such groups are introduced e.g. by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis*, 4$^{th}$ edition, Wiley 2006; more specifically, protective groups for amino groups can be selected from substituted sulfonyl groups, such as mesyl-, tosyl- or phenylsulfonyl-, acyl groups such as benzoyl, acetyl or tetrahydropyranoyl, or carbamate based groups, such as tert.-butoxycarbonyl (Boc). Protective groups for hydroxy groups can be selected from acyl groups such as benzoyl, acetyl, pivaloyl or tetrahydropyranoyl, or can include silicon, as in e.g. tert-butyldimethylsilyl, tert-butyldiphenylsilyl, triethylsilyl or triisopropylsilyl.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention can exist, as shown below, as a tautomer 1, or tautomer 2 or tautomer 3, or even a mixture in any amount of the three tautomers, namely:

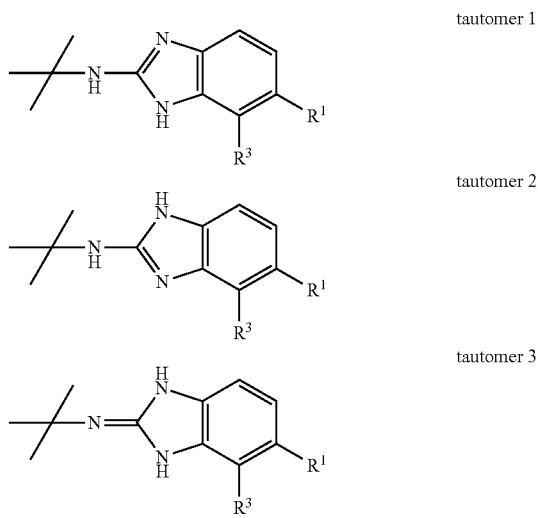

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of compounds and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "×HCl", "×CF$_3$COOH", "×Na$^+$", for example, mean a salt form, the stoichiometry of which salt form not being specified.

This applies analogously to cases in which compounds or examples or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

In accordance with a second embodiment of the first aspect, the present invention covers compounds of general formula (I):

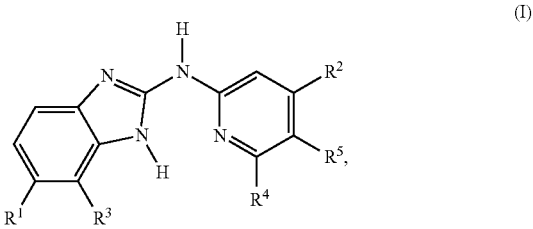

in which:

$R^1$ represents a group selected from
  pyrazolyl, imidazolyl, oxadiazolyl, triazolyl, isoxazolyl, thienyl, pyridin-2-yl, pyridin-4-yl, pyrimidinyl, triazinyl and pyrazinyl, said group being optionally substituted with one $R^6$ group, and said group being, additionally, optionally substituted one or two times, differently or identically, with a $R^7$ group, or $R^1$ represents a group selected from

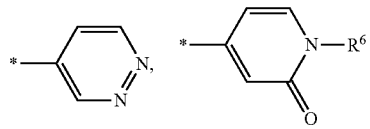

the ring of said group being, besides $R^6$, optionally substituted further one or two times, differently or identically, with a $R^7$ group,
  in which "*" represents the point of attachment to the rest of the molecule, or $R^1$ represents a group selected from pyridine-3-yl or pyridazin-3-yl, optionally substituted with one $R^8$ group;

$R^2$ represents a group selected from

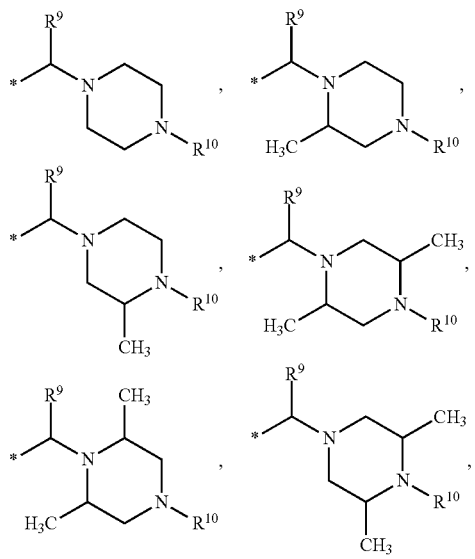

-continued

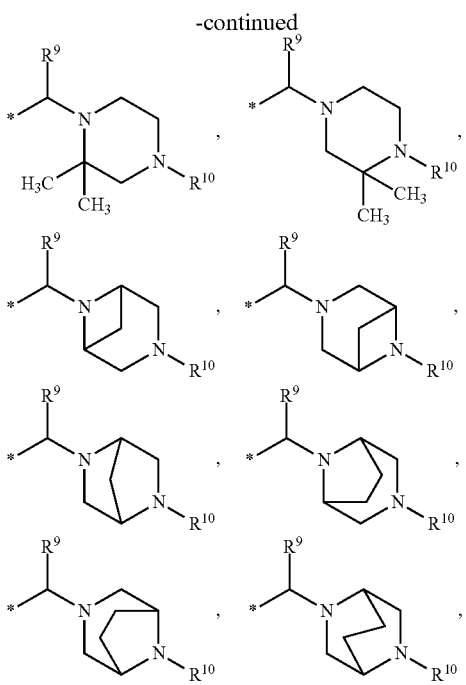

in which "h" represents the point of attachment to the rest of the molecule;

$R^3$ represents a hydrogen atom or a halogen atom or a group selected from $C_1$-$C_4$-alkyl and $C_1$-$C_6$-alkoxy;

$R^4$ represents a hydrogen atom or a halogen atom or a group selected from $C_1$-$C_4$-alkyl, $C_1$-$C_4$-haloalkyl, $C_1$-$C_4$-alkoxy and $C_1$-$C_4$-haloalkoxy;

$R^5$ represents a hydrogen atom or a halogen atom or a group selected from $C_1$-$C_4$-alkyl, $C_1$-$C_4$-haloalkyl and $C_3$-$C_6$-cycloalkyl;

$R^6$ represents a hydrogen atom or a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, $C_3$-$C_6$-cycloalkyl and ($C_3$-$C_6$-cycloalkyl)-($C_1$-$C_3$-alkyl)-, said $C_3$-$C_6$-cycloalkyl and said ($C_3$-$C_6$-cycloalkyl)-($C_1$-$C_3$-alkyl)- group being optionally substituted one, two or three times, identically or differently, with a fluorine atom, a chlorine atom or with a group selected from $C_1$-$C_3$-alkyl and $C_1$-$C_3$-haloalkyl;

$R^7$ represents a halogen atom or a group selected from hydroxy, $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, ($C_1$-$C_3$-haloalkoxy)-($C_1$-$C_3$-alkyl)-, $C_2$-$C_6$-alkenyl, $C_2$-$C_6$-alkynyl, $C_3$-$C_8$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, heterospirocycloalkyl, phenyl, heteroaryl, —CN, —(CH$_2$)$_x$—N(R$^{11}$)R$^{11a}$, —C(=O)R$^{13}$, —C(=O)—OR$^{13}$, —C(=O)—N(R$^{11}$)R$^{11a}$, —N(R$^{11}$)R$^{11a}$, —N(R$^{16}$)—C(=O)—R$^{13}$, —N(R$^{16}$)—S(=O)$_2$—R$^{13}$, —N(R$^{16}$)—C(=O)—N(R$^{11}$)R$^{11a}$, —N(R$^{16}$)—C(=O)—OR$^{13}$, $C_1$-$C_6$-alkoxy, $C_1$-$C_6$-haloalkoxy, $C_3$-$C_8$-cycloalkoxy-, ($C_3$-$C_8$-cycloalkyl)-($C_1$-$C_3$-alkoxy)-, phenyloxy-, heteroaryloxy-, —O—(CH$_2$)$_x$-phenyl, —O—(CH$_2$)$_x$-heteroaryl, —O—C(=O)—R$^{13}$, —O—C(=O)—N(R$^{11}$)R$^{11a}$, $C_1$-$C_6$-alkylsulfanyl, $C_1$-$C_6$-haloalkylsulfanyl, —S(=O)—R$^{13}$, —S(=O)$_2$—R$^{13}$, —S(=O)$_2$—N(R$^{11}$)R$^{11a}$ and —S(=O)(=NR$^{17}$)R$^{13}$, said $C_3$-$C_8$-cycloalkyl, said ($C_3$-$C_8$-cycloalkyl)-($C_1$-$C_3$-alkyl)- and said ($C_3$-$C_8$-cycloalkyl)-($C_1$-$C_3$-alkoxy)-group being optionally substituted one, two or three times, identically or differently, with a fluorine atom, a chlorine atom or with a group selected from $C_1$-$C_3$-alkyl and $C_1$-$C_3$-haloalkyl, said 4- to 7-membered heterocycloalkyl, said 5- to 7-membered heterocycloalkenyl and said heterospirocycloalkyl group being optionally substituted one, two or three times, identically or differently, with a fluorine atom, a chlorine atom or with a group selected from oxo, $C_1$-$C_3$-alkyl and $C_1$-$C_3$-haloalkyl, and said heteroaryl group and said phenyl group being optionally substituted one, two or three times, identically or differently, with a halogen atom or a group selected from —CN, $C_1$-$C_3$-alkyl, trifluoromethyl, $C_1$-$C_3$-alkoxy and trifluoromethoxy; or $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —(CH$_2$—O—CH$_2$)—, —(NR$^{16}$—(CH$_2$)$_2$—O)—, —(NR$^{16}$—(CH$_2$)$_3$—O)—, —(S—(CH$_2$)$_2$)—, —(O—(CH$_2$)$_3$)—, —((CH$_2$)$_3$)—, —((CH$_2$)$_4$)—, —(O—CH=CH)—, —(S—CH=CH)—;

$R^8$ represents a hydrogen atom or a group selected from methyl, ethyl, methoxy, ethoxy and dimethylamino;

$R^9$ represents a hydrogen atom or a —CN or $C_1$-$C_3$-alkyl group;

$R^{10}$ represents a group selected from —C(=O)R$^{12}$, —C(=O)OR$^{13}$, —C(=O)N(R$^{14}$)R$^{14a}$, —S(=O)$_2$R$^{15}$, —S(=O)$_2$N(R$^{14}$)R$^{14a}$, 5- to 6-membered heteroaryl and phenyl, said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy;

$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl, $C_1$-$C_6$-hydroxyalkyl, ($C_1$-$C_3$-alkoxy)-($C_1$-$C_3$-alkyl)-, ($C_3$-$C_6$-cycloalkyl)-($C_1$-$C_3$-alkyl)- and benzyl, or $R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, $C_1$-$C_3$-haloalkyl, $C_1$-$C_3$-alkoxy, —C(=O)R$^{18}$, —C(=O)OR$^{18}$ and —S(=O)$_2$R$^{18}$;

$R^{12}$ represents a hydrogen atom or a group selected from $C_1$-$C_6$-alkyl, $C_1$-$C_6$-haloalkyl, $C_1$-$C_6$-hydroxyalkyl, $C_3$-$C_6$-cycloalkyl, ($C_3$-$C_6$-cycloalkyl)-($C_1$-$C_3$-alkyl)-, $C_2$-$C_6$-alkenyl, $C_2$-$C_6$-alkynyl, 4- to 7-membered heterocycloalkyl, 5- to 7-membered heterocycloalkenyl, 5- to 6-membered heteroaryl and phenyl, said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy, said $C_3$-$C_6$-cycloalkyl group being optionally substituted one, two or three times, identically or differently, with a halogen atom or a group selected from —CN, $C_1$-$C_3$-alkyl and $C_1$-$C_3$-haloalkyl;

$R^{13}$ represents a group selected from $C_1$-$C_4$-alkyl and benzyl; $R^{14}$ and $R^{14a}$, independently from each other, represent a hydrogen atom or a group selected from $C_1$-$C_4$-alkyl, $C_1$-$C_4$-haloalkyl, $C_3$-$C_6$-cycloalkyl and benzyl, or $R^{14}$ and $R^{14a}$, together with the nitrogen atom they are attached to, represent a 4- to 7-membered heterocycloalkyl group, said group being optionally substituted one or two times, identically or differently, with a halogen atom or a group selected from hydroxyl, —CN, $C_1$-$C_3$-alkyl, $C_1$-$C_3$-haloalkyl, $C_1$-$C_3$-alkoxy, $C_1$-$C_3$-haloalkoxy and ($C_1$-$C_3$-alkoxy)-($C_1$-$C_3$-alkyl)-;

$R^{15}$ represents a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_6$-alkyl)-, ($C_1$-$C_3$-alkoxy)-($C_2$-$C_3$-alkoxy)-($C_1$-$C_6$-alkyl)-, $C_3$-$C_6$-cycloalkyl, ($C_3$-$C_6$-cycloalkyl)-($C_1$-$C_3$-alkyl)-, 4- to 7-membered heterocycloalkyl, 5- to 6-membered heteroaryl and phenyl, said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy;

$R^{16}$ represents a hydrogen atom or a group selected from $C_1$-$C_4$-alkyl and benzyl;

$R^{17}$ represents a hydrogen atom or a group selected from —CN, —C(=O)O$R^{13}$, $C_1$-$C_4$-alkyl and benzyl;

$R^{18}$ represents a $C_1$-$C_3$-alkyl group;

x represents an integer selected from 1, 2, 3 and 4, and stereoisomers, tautomers, N-oxides, hydrates, solvates, and salts thereof, and mixtures of same.

In accordance with a third embodiment of the first aspect, the present invention covers compounds of general formula (I):

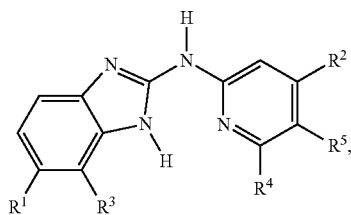

in which:

$R^1$ represents a group selected from pyrazolyl, imidazolyl, oxadiazolyl, triazolyl, pyridin-2-yl, pyridin-4-yl, pyrimidinyl and pyrazinyl, said group being optionally substituted with one $R^6$ group, and said group being, additionally, optionally substituted one or two times, differently or identically, with a $R^7$ group, or $R^1$ represents a group selected from

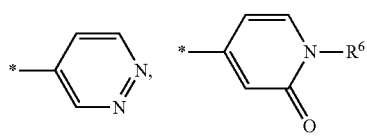

the ring of said group being, besides $R^6$, optionally substituted further one or two times, differently or identically, with a $R^7$ group, in which "*" represents the point of attachment to the rest of the molecule, or $R^1$ represents a group selected from pyridine-3-yl or pyridazin-3-yl, optionally substituted with one $R^8$ group;

$R^2$ represents a group selected from

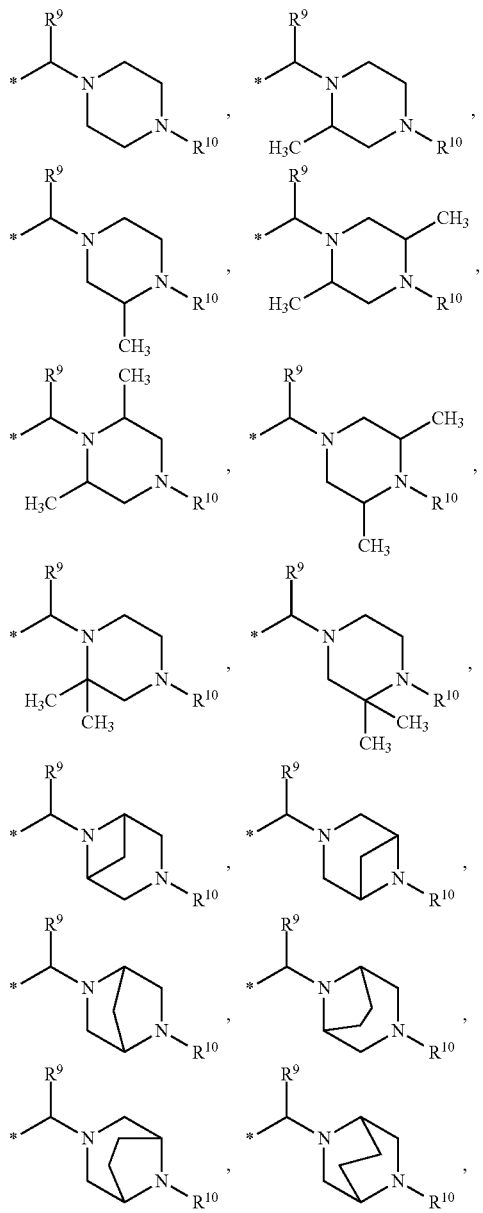

in which "*" represents the point of attachment to the rest of the molecule;

$R^3$ represents a hydrogen atom or a halogen atom or a group selected from $C_1$-$C_4$-alkyl and $C_1$-$C_6$-alkoxy;

$R^4$ represents a hydrogen atom or a halogen atom or a group selected from $C_1$-$C_4$-alkyl, $C_1$-$C_4$-haloalkyl, $C_1$-$C_4$-alkoxy and $C_1$-$C_4$-haloalkoxy;

$R^5$ represents a hydrogen atom or a halogen atom or a group selected from $C_1$-$C_4$-alkyl, $C_1$-$C_4$-haloalkyl and $C_3$-$C_6$-cycloalkyl;

$R^6$ represents a hydrogen atom or a group selected from $C_1$-$C_6$-alkyl, $C_1$-$C_6$-haloalkyl, $C_3$-$C_6$-cycloalkyl and ($C_3$-$C_6$-cycloalkyl)-($C_1$-$C_3$-alkyl)-, said $C_3$-$C_6$-cycloalkyl and said ($C_3$-$C_6$-cycloalkyl)-($C_1$-$C_3$-alkyl)- group being optionally substituted one, two or three times, identically or differently, with a fluorine atom, a chlorine atom or with a $C_1$-$C_3$-alkyl group;

R⁷ represents a halogen atom or a group selected from C₁-C₆-alkyl, C₁-C₆-haloalkyl, C₁-C₆-hydroxyalkyl, C₂-C₆-alkenyl, C₂-C₆-alkynyl, C₃-C₈-cycloalkyl, C₄-C₈-cycloalkenyl, (C₃-C₈-cycloalkyl)-(C₁-C₃-alkyl)-, (phenyl)-C₁-C₃-alkyl-, 4- to 7-membered heterocycloalkyl, 5- to 7-membered heterocycloalkenyl, phenyl, heteroaryl, —CN, —C(=O)R¹³, —C(=O)—OR¹³, —C(=O)—N(R¹¹)R¹¹ᵃ, —N(R¹¹)R¹¹ᵃ, —N(R¹⁶)—C(=O)—R¹³, —N(R¹⁶)—S(=O)₂—R¹³, —N(R¹⁶)—C(=O)—N(R¹¹)R¹¹ᵃ, —N(R¹⁶)—C(=O)—OR¹³, C₁-C₆-alkoxy, C₁-C₆-haloalkoxy, C₃-C₈-cycloalkoxy-, (C₃-C₈-cycloalkyl)-(C₁-C₃-alkoxy)-, phenyloxy-, heteroaryloxy-, —O—(CH₂)ₓ-phenyl, —O—(CH₂)ₓ-heteroaryl, —O—C(=O)—R¹³—O—C(=O)—N(R¹¹)R¹¹ᵃ, C₁-C₆-alkylsulfanyl, C₁-C₆-haloalkylsulfanyl, —S(=O)₂—R¹³, —S(=O)₂—N(R¹¹)R¹¹ᵃ and —S(=O)(=NR¹⁷)R¹³; or R⁶ and R⁷, or two R⁷ groups, when being attached to adjacent ring atoms of the group R¹, together form a group selected from:
—(O—CH₂—O)—, —(O—(CH₂)₂—O)—, —(O—(CH₂)₂)—, —(S—(CH₂)₂)—, —(O—(CH₂)₃)—, —((CH₂)₃)—, —((CH₂)₄)—, —(O—CH=CH)—, —(S—CH=CH);

R⁸ represents a hydrogen atom or a group selected from methyl, ethyl, methoxy and ethoxy;

R⁹ represents a hydrogen atom or a C₁-C₃-alkyl group;

R¹⁰ represents a group selected from —C(=O)R¹², —C(=O)OR¹³, —C(=O)N(R¹⁴)R¹⁴ᵃ, —S(=O)₂R¹⁵, —S(=O)₂N(R¹⁴)R¹⁴ᵃ, 5- to 6-membered heteroaryl and phenyl,
said 5- to 6-membered heteroaryl group and said phenyl group being optionally substituted one, two or three times, identically or differently, with a halogen atom or a group selected from —CN, C₁-C₃-alkyl, C₁-C₃-haloalkyl, C₁-C₃-alkoxy and C₁-C₃-haloalkoxy;

R¹¹ and R¹¹ᵃ, independently from each other, represent a hydrogen atom or a group selected from C₁-C₄-alkyl, C₁-C₄-haloalkyl, C₃-C₆-cycloalkyl and benzyl, or R¹¹ and R¹¹ᵃ, together with the nitrogen atom they are attached to, represent a 4- to 7-membered heterocycloalkyl group, said group being optionally substituted one or two times, identically or differently, with a halogen atom, or a group selected from hydroxy, oxo, —CN, C₁-C₃-alkyl, —C(=O)R¹⁸, C(=O)OR¹⁸ and S(=O)₂R¹⁸;

R¹² represents a group selected from C₁-C₆-alkyl, C₁-C₆-haloalkyl, C₁-C₆-hydroxyalkyl, C₃-C₆-cycloalkyl, (C₃-C₆-cycloalkyl)-(C₁-C₃-alkyl)-, C₂-C₆-alkenyl, C₂-C₆-alkynyl, 4- to 7-membered heterocycloalkyl, 5- to 7-membered heterocycloalkenyl, 5- to 6-membered heteroaryl and phenyl,
said 5- to 6-membered heteroaryl group and said phenyl group being optionally substituted one, two or three times, identically or differently, with a halogen atom or a group selected from —CN, C₁-C₃-alkyl, C₁-C₃-haloalkyl, C₁-C₃-alkoxy and C₁-C₃-haloalkoxy;

R¹³ represents a group selected from C₁-C₄-alkyl and benzyl;

R¹⁴ and R¹⁴ᵃ, independently from each other, represent a hydrogen atom or a group selected from C₁-C₄-alkyl, C₁-C₄-haloalkyl, C₃-C₆-cycloalkyl and benzyl, or R¹⁴ and R¹⁴ᵃ, together with the nitrogen atom they are attached to, represent a 4- to 7-membered heterocycloalkyl group, said group being optionally substituted one or two times, identically or differently, with a halogen atom or a group selected from hydroxyl, —CN, C₁-C₃-alkyl, C₁-C₃-haloalkyl, C₁-C₃-alkoxy, C₁-C₃-haloalkoxy and (C₁-C₃-alkoxy)-(C₁-C₃-alkyl)-;

R¹⁵ represents a group selected from C₁-C₆-alkyl, C₁-C₆-haloalkyl, C₁-C₆-hydroxyalkyl, (C₁-C₃-alkoxy)-(C₁-C₆-alkyl)-, (C₁-C₃-alkoxy)-(C₂-C₃-alkoxy)-(C₁-C₆-alkyl)-, C₃-C₆-cycloalkyl, (C₃-C₆-cycloalkyl)-(C₁-C₃-alkyl)-, 4- to 7-membered heterocycloalkyl, 5- to 6-membered heteroaryl and phenyl,
said 5- to 6-membered heteroaryl group and said phenyl group being optionally substituted one, two or three times, identically or differently, with a halogen atom or a group selected from —CN, C₁-C₃-alkyl, C₁-C₃-haloalkyl, C₁-C₃-alkoxy and C₁-C₃-haloalkoxy;

R¹⁶ represents a hydrogen atom or a group selected from C₁-C₄-alkyl and benzyl;

R¹⁷ represents a hydrogen atom or a group selected from —CN, —C(=O)OR¹³, C₁-C₄-alkyl and benzyl;

R¹⁸ represents a C₁-C₃-alkyl group;

x represents an integer selected from 1, 2, 3 and 4, and stereoisomers, tautomers, N-oxides, hydrates, solvates, and salts thereof, and mixtures of same.

In accordance with a fourth embodiment of the first aspect, the present invention covers compounds of general formula (I), supra, in which:

R¹ represents a group selected from

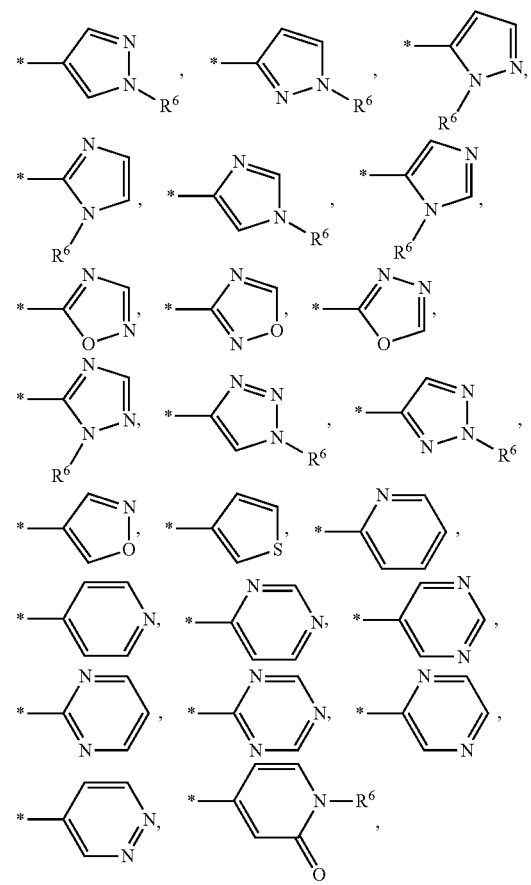

in which "*" represents the point of attachment to the rest of the molecule;

the ring of said group being, besides R⁶, optionally substituted further one or two times, differently or identically, with a R⁷ group, or $R^1$ represents a group selected from

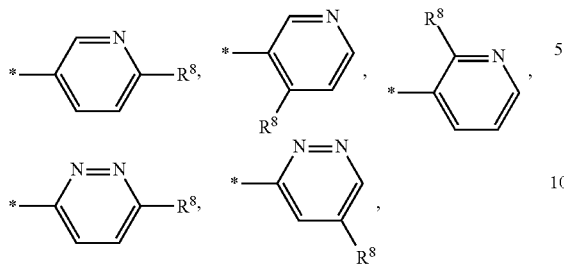

in which "*" represents the point of attachment to the rest of the molecule;

$R^2$ represents a group selected from

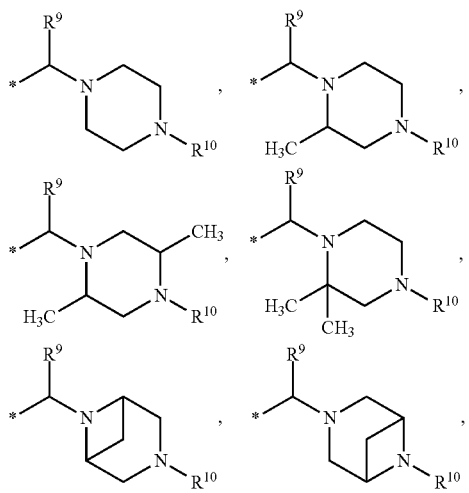

in which "*" represents the point of attachment to the rest of the molecule;

$R^3$ represents a hydrogen atom or a halogen atom or a group selected from $C_1$-$C_4$-alkyl and $C_1$-$C_4$-alkoxy;

$R^4$ represents a hydrogen atom or a group selected from $C_1$-$C_3$-alkyl and $C_1$-$C_3$-fluoroalkyl;

$R^5$ represents a hydrogen atom or a bromine atom;

$R^6$ represents a hydrogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_5$-cycloalkyl and ($C_3$-$C_5$-cycloalkyl)-(methyl)-,
said $C_3$-$C_5$-cycloalkyl and said ($C_3$-$C_5$-cycloalkyl)-(methyl)- group being optionally substituted one, two or three times, identically or differently, with a fluorine atom, a chlorine atom or with a group selected from methyl and trifluoromethyl;

$R^7$ represents a halogen atom or a group selected from hydroxy, $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, ($C_1$-$C_2$-fluoroalkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, 5- to 6-membered heteroaryl, —CN, —$(CH_2)_x$—$N(R^{11})R^{11a}$, —C(=O)$R^{13}$, —C(=O)—$N(R^{11})R^{11a}$, —$N(R^{11})R^{11a}$, $C_1$-$C_6$-alkoxy, $C_1$-$C_4$-fluoroalkoxy, ($C_3$-$C_4$-cycloalkyl)-(methoxy)-, $C_1$-$C_4$-alkylsulfanyl, S(=O)—$R^{13}$ and —S(=O)$_2$—$R^{13}$ said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl,
said 4- to 7-membered heterocycloalkyl and said heterospirocycloalkyl group being optionally substituted one, two or three times, identically or differently, with a fluorine atom or with a group selected from oxo, methyl and trifluoromethyl, and
said 5- to 6-membered heteroaryl group being optionally substituted one, two or three times, identically or differently, with a halogen atom or a group selected from methyl, trifluoromethyl and methoxy; or $R^6$ and $R^7$, or two $R^7$ groups, when being attached to adjacent ring atoms of the group $R^1$, together form a group selected from:
—(O—$CH_2$—O)—, —(O—$(CH_2)_2$—O)—, —(O—$(CH_2)_2$)—, —($CH_2$—O—$CH_2$)—, —($NR^{16}$—$(CH_2)_2$—O)—, —($(CH_2)_3$)—, —($(CH_2)_4$)—, —(O—CH=CH)—, —(S—CH=CH)—;

$R^8$ represents a hydrogen atom or a group selected from methoxy and ethoxy;

$R^9$ represents a hydrogen atom or a methyl or ethyl group;

$R^{10}$ represents a group selected from —C(=O)$R^{12}$, —C(=O)O$R^{13}$, —C(=O)$N(R^{14})R^{14a}$, —S(=O)$_2R^{15}$, —S(=O)$_2$$N(R^{14})R^{14a}$, 5- to 6-membered heteroaryl and phenyl,
said 5- to 6-membered heteroaryl group and said phenyl group being optionally substituted one or two times, identically or differently, with a fluorine atom, chlorine atom or bromine atom, or a group selected from —CN, methyl, trifluoromethyl and methoxy;

$R^{11}$ and $R^{11a}$, independently from each other, represent a hydrogen atom or a group selected from $C_1$-$C_4$-alkyl, $C_1$-$C_4$-fluoroalkyl, $C_3$-$C_4$-cycloalkyl, $C_1$-$C_4$-hydroxyalkyl, ($C_1$-$C_2$-alkoxy)-($C_1$-$C_3$-alkyl)-, ($C_3$-$C_4$-cycloalkyl)-(methyl)- and benzyl, or $R^{11}$ and $R^{11a}$, together with the nitrogen atom they are attached to, represent a 4- to 6-membered heterocycloalkyl group, said group being optionally substituted one or two times, identically or differently, with a fluorine atom, or a group selected from hydroxy, oxo, —CN, methyl, trifluoromethyl and methoxy;

$R^{12}$ represents a hydrogen atom or a group selected from $C_1$-$C_4$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_6$-cycloalkyl, ($C_3$-$C_6$-cycloalkyl)-($C_1$-$C_2$-alkyl)-, $C_2$-$C_4$-alkenyl, 5- to 6-membered heteroaryl and phenyl,
said 5- to 6-membered heteroaryl group and said phenyl group being optionally substituted one, two or three times, identically or differently, with a fluorine atom, a chlorine atom or a group selected from methyl, trifluoromethyl and methoxy,
said $C_3$-$C_6$-cycloalkyl group being optionally substituted one, two or three times, identically or differently, with a fluorine atom, a chlorine atom or a group selected from —CN, methyl and trifluoromethyl;

$R^{13}$ represents a group selected from $C_1$-$C_4$-alkyl and benzyl;

$R^{14}$ and $R^{14a}$, independently from each other, represent a hydrogen atom or a group selected from $C_1$-$C_3$-alkyl, trifluoromethyl and cyclopropyl, or $R^{14}$ and $R^{14a}$, together with the nitrogen atom they are attached to, represent a 4- to 7-membered heterocycloalkyl group, said group being optionally substituted one or two times, identically or differently, with a group selected from $C_1$-$C_3$-alkyl, $C_1$-$C_3$-fluoroalkyl, $C_1$-$C_3$-alkoxy, trifluoromethoxy and ($C_1$-$C_2$-alkoxy)-($C_1$-$C_2$-alkyl)-;

$R^{15}$ represents a group selected from $C_1$-$C_4$-alkyl, $C_1$-$C_4$-fluoroalkyl, ($C_1$-$C_2$-alkoxy)-($C_1$-$C_3$-alkyl)-, ($C_1$-$C_2$-alkoxy)-(ethoxy)-($C_1$-$C_3$-alkyl)-, $C_3$-$C_6$-cycloalkyl, ($C_3$-$C_6$-cycloalkyl)-($C_1$-$C_2$-alkyl)- and 4- to 7-membered heterocycloalkyl;

$R^{16}$ represents a hydrogen atom or a $C_1$-$C_3$-alkyl group;

x represents an integer selected from 1 and 2, and stereoisomers, tautomers, N-oxides, hydrates, solvates, and salts thereof, and mixtures of same.

In accordance with a fifth embodiment of the first aspect, the present invention covers compounds of general formula (I), supra, in which:

$R^1$ represents a group selected from

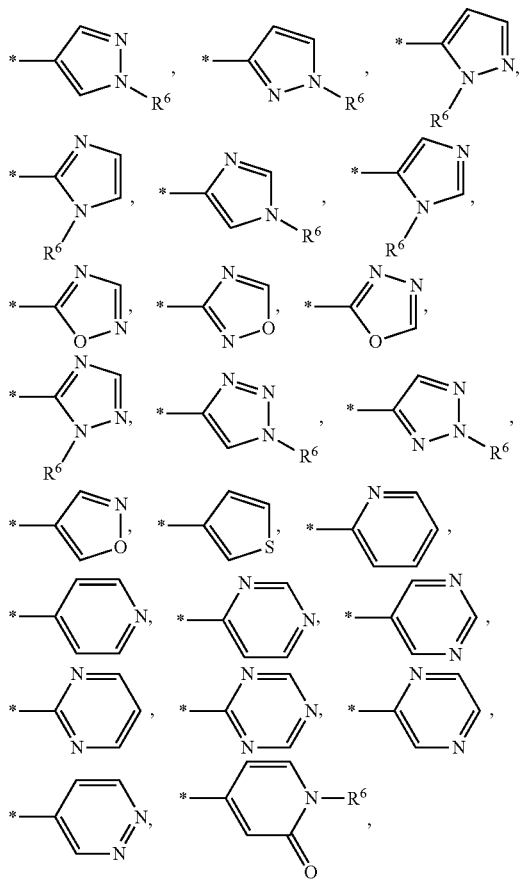

in which "*" represents the point of attachment to the rest of the molecule;

the ring of said group being, besides $R^6$, optionally substituted further one or two times, differently or identically, with a $R^7$ group, or $R^1$ represents a group selected from

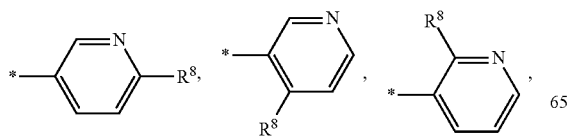

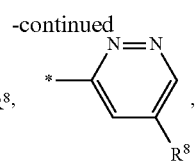

in which "*" represents the point of attachment to the rest of the molecule;

$R^2$ represents a group selected from

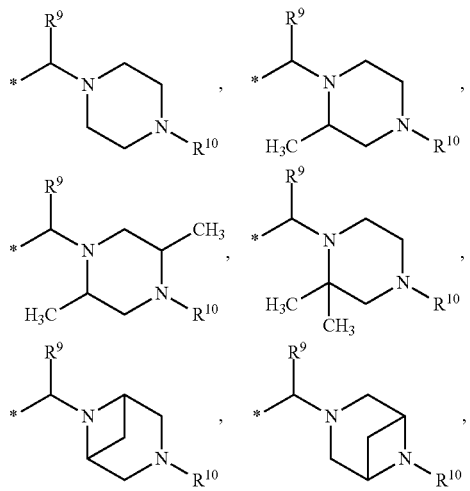

in which "*" represents the point of attachment to the rest of the molecule;

$R^3$ represents a hydrogen atom or a halogen atom or a group selected from $C_1$-$C_4$-alkyl and $C_1$-$C_4$-alkoxy;

$R^4$ represents a hydrogen atom or a group selected from $C_1$-$C_3$-alkyl and $C_1$-$C_3$-fluoroalkyl;

$R^5$ represents a hydrogen atom or a bromine atom;

$R^6$ represents a hydrogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_5$-cycloalkyl and ($C_3$-$C_5$-cycloalkyl)-(methyl)-, said $C_3$-$C_5$-cycloalkyl and said ($C_3$-$C_5$-cycloalkyl)-(methyl)- group being optionally substituted one, two or three times, identically or differently, with a fluorine atom, a chlorine atom or with a group selected from methyl and trifluoromethyl;

$R^7$ represents a halogen atom or a group selected from hydroxy, $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, ($C_1$-$C_2$-fluoroalkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, 5- to 6-membered heteroaryl, —CN, —$(CH_2)_x$—N($R^{11}$)$R^{11a}$, —C(=O)$R^{13}$, —C(=O)—N($R^{11}$)$R^{11a}$, —N($R^{11}$)$R^{11a}$, $C_1$-$C_6$-alkoxy, $C_1$-$C_4$-fluoroalkoxy, ($C_3$-$C_4$-cycloalkyl)-(methoxy)-, $C_1$-$C_4$-alkylsulfanyl, S(=O)—$R^{13}$ and —S(=O)$_2$—$R^{13}$ said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, said 4- to 7-membered heterocycloalkyl and said heterospirocycloalkyl group being optionally one, two or three times, identically or differently, with a fluorine atom or with a group selected from oxo, methyl and trifluoromethyl, and said 5- to 6-membered heteroaryl group being optionally substituted one, two or three times, identically or differently, with a halogen atom or a group selected from methyl, trifluoromethyl and methoxy; or $R^6$ and $R^7$, or two $R^7$ groups, when being attached to adjacent ring atoms of the group $R^1$, together form a group selected from:

—(O—CH$_2$—O)—, —(O—(CH$_2$)$_2$—O)—, —(O—(CH$_2$)$_2$)—, —(CH$_2$—O—CH$_2$)—, —(NR$^{16}$—(CH$_2$)$_2$—O)—, —((CH$_2$)$_3$)—, —((CH$_2$)$_4$)—, —(O—CH=CH)—, —(S—CH=CH)—;

$R^8$ represents a hydrogen atom or a group selected from methoxy and ethoxy;

$R^9$ represents a hydrogen atom or a methyl or ethyl group;

$R^{10}$ represents a group selected from —C(=O)R$^{12}$, —C(=O)OR$^{13}$, —C(=O)N(R$^{14}$)R$^{14a}$, —S(=O)$_2$R$^{15}$, —S(=O)$_2$N(R$^{14}$)R$^{14a}$, 5- to 6-membered heteroaryl and phenyl, said 5- to 6-membered heteroaryl group and said phenyl group being optionally substituted one or two times, identically or differently, with a fluorine atom, chlorine atom or bromine atom, or a group selected from —CN, methyl, trifluoromethyl and methoxy;

$R^{11}$ and $R^{11a}$, independently from each other, represent a hydrogen atom or a group selected from C$_1$-C$_4$-alkyl, C$_1$-C$_4$-fluoroalkyl, C$_3$-C$_4$-cycloalkyl, C$_1$-C$_4$-hydroxyalkyl, (C$_1$-C$_2$-alkoxy)-(C$_1$-C$_3$-alkyl)-, (C$_3$-C$_4$-cycloalkyl)-(methyl)- and benzyl, or $R^{11}$ and $R^{11a}$, together with the nitrogen atom they are attached to, represent a 4- to 6-membered heterocycloalkyl group, said group being optionally substituted one or two times, identically or differently, with a fluorine atom, or a group selected from hydroxy, oxo, —CN, methyl, trifluoromethyl and methoxy;

$R^{12}$ represents a hydrogen atom or a group selected from C$_1$-C$_4$-alkyl, C$_1$-C$_4$-fluoroalkyl, C$_3$-C$_6$-cycloalkyl, (C$_3$-C$_6$-cycloalkyl)-(C$_1$-C$_2$-alkyl)-, C$_2$-C$_4$-alkenyl, 5- to 6-membered heteroaryl and phenyl, said 5- to 6-membered heteroaryl group and said phenyl group being optionally substituted one, two or three times, identically or differently, with a fluorine atom, a chlorine atom or a group selected from methyl, trifluoromethyl and methoxy, said C$_3$-C$_6$-cycloalkyl group being optionally substituted one, two or three times, identically or differently, with a fluorine atom, a chlorine atom or a group selected from —CN, methyl and trifluoromethyl;

$R^{13}$ represents a group selected from C$_1$-C$_4$-alkyl and benzyl;

$R^{14}$ and $R^{14a}$, independently from each other, represent a hydrogen atom or a group selected from C$_1$-C$_3$-alkyl, trifluoromethyl and cyclopropyl, or $R^{14}$ and $R^{14a}$, together with the nitrogen atom they are attached to, represent a 4- to 7-membered heterocycloalkyl group, said group being optionally substituted one or two times, identically or differently, with a group selected from C$_1$-C$_3$-alkyl, C$_1$-C$_3$-fluoroalkyl, C$_1$-C$_3$-alkoxy, trifluoromethoxy and (C$_1$-C$_2$-alkoxy)-(C$_1$-C$_2$-alkyl)-;

$R^{15}$ represents a group selected from C$_1$-C$_4$-alkyl, C$_1$-C$_4$-fluoroalkyl, (C$_1$-C$_2$-alkoxy)-(C$_1$-C$_3$-alkyl)-, (C$_1$-C$_2$-alkoxy)-(ethoxy)-(C$_1$-C$_3$-alkyl)-, C$_3$-C$_6$-cycloalkyl, (C$_3$-C$_6$-cycloalkyl)-(C$_1$-C$_2$-alkyl)- and 4- to 7-membered heterocycloalkyl;

$R^{16}$ represents a hydrogen atom or a C$_1$-C$_3$-alkyl group;

x represents an integer selected from 1 and 2, and stereoisomers, tautomers, N-oxides, hydrates, solvates, and salts thereof, and mixtures of same.

In accordance with a sixth embodiment of the first aspect, the present invention covers compounds of general formula (I), supra, in which:

$R^1$ represents a group selected from

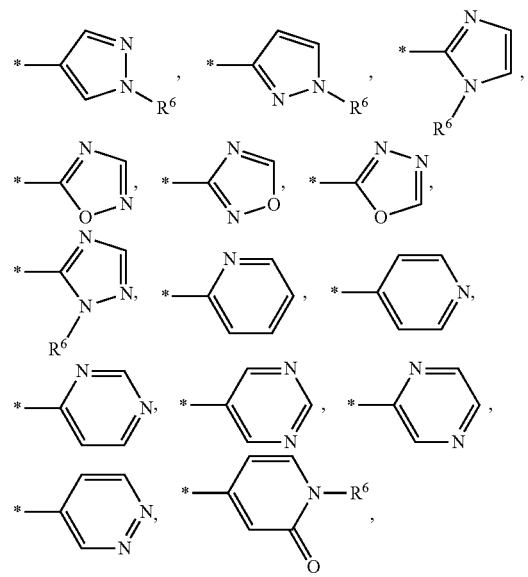

in which "*" represents the point of attachment to the rest of the molecule, the ring of said group being, besides $R^6$, optionally substituted further one or two times, differently or identically, with a $R^7$ group, or $R^1$ represents a group selected from

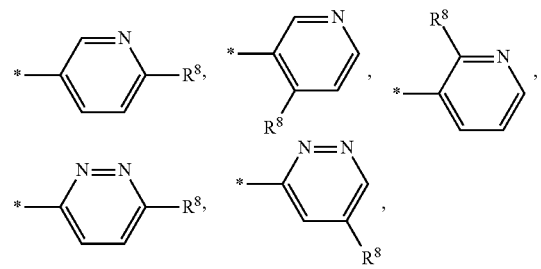

in which "*" represents the point of attachment to the rest of the molecule;

$R^2$ represents a group selected from

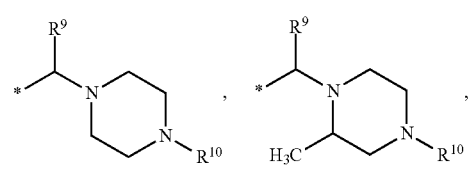

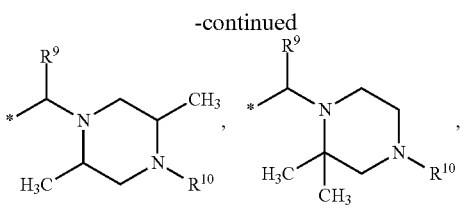

in which "*" represents the point of attachment to the rest of the molecule;

R³ represents a hydrogen atom or a group selected from $C_1$-$C_4$-alkyl and $C_1$-$C_4$-alkoxy;

R⁴ represents a hydrogen atom or a group selected from $C_1$-$C_3$-alkyl and $C_1$-$C_3$-fluoroalkyl;

R⁵ represents a hydrogen atom;

R⁶ represents a hydrogen atom or a group selected from $C_1$-$C_6$-alkyl, $C_1$-$C_4$-fluoroalkyl, $C_3$-$C_4$-cycloalkyl and ($C_3$-$C_4$-cycloalkyl)-(methyl)-,
said $C_3$-$C_4$-cycloalkyl and said ($C_3$-$C_4$-cycloalkyl)-(methyl)- group being optionally substituted one, two or three times, identically or differently, with a fluorine atom, a chlorine atom or with a methyl group;

R⁷ represents a halogen atom or a group selected from $C_1$-$C_6$-alkyl, $C_1$-$C_4$-fluoroalkyl, $C_3$-$C_4$-cycloalkyl, ($C_3$-$C_4$-cycloalkyl)-(methyl)-, (phenyl)-($C_1$-$C_3$-alkyl)-, —C(=O)—N(R¹¹)R¹¹ᵃ, $C_1$-$C_6$-alkoxy, $C_1$-$C_4$-fluoroalkoxy, ($C_3$-$C_4$-cycloalkyl)-(methoxy)- and $C_1$-$C_4$-alkylsulfanyl; or R⁶ and R⁷, or two R⁷ groups, when being attached to adjacent ring atoms of the group R¹, together form a group selected from:
—(O—CH₂—O)—, —(O—(CH₂)₂—O)—, —(O—(CH₂)₂)—, —((CH₂)₃)—, —((CH₂)₄)—;

R⁸ represents a hydrogen atom or a group selected from methoxy and ethoxy;

R⁹ represents a hydrogen atom or a methyl or ethyl group;

R¹⁰ represents a group selected from —C(=O)R¹², —C(=O)OR¹³, —C(=O)N(R¹⁴)R¹⁴ᵃ, —S(=O)₂R¹⁵, —S(=O)₂N(R¹⁴)R¹⁴ᵃ and phenyl,
said phenyl group being optionally substituted one or two times, identically or differently, with a fluorine atom, chlorine atom or bromine atom, or a group selected from —CN, methyl, trifluoromethyl and methoxy;

R¹¹ and R¹¹ᵃ, independently from each other, represent a hydrogen atom or a group selected from $C_1$-$C_4$-alkyl and benzyl, or R¹¹ and R¹¹ᵃ, together with the nitrogen atom they are attached to, represent a 5- to 6-membered heterocycloalkyl group, said group being optionally substituted once with a methyl group;

R¹² represents a group selected from $C_1$-$C_4$-alkyl, $C_1$-$C_4$-fluoroalkyl, $C_3$-$C_6$-cycloalkyl, ($C_3$-$C_6$-cycloalkyl)-($C_1$-$C_2$-alkyl)- and $C_2$-$C_4$-alkenyl;

R¹³ represents a group selected from $C_1$-$C_4$-alkyl and benzyl;

R¹⁴ and R¹⁴ᵃ, independently from each other, represent a hydrogen atom or a group selected from $C_1$-$C_3$-alkyl, trifluoromethyl and cyclopropyl, or R¹⁴ and R¹⁴ᵃ, together with the nitrogen atom they are attached to, represent a 4- to 7-membered heterocycloalkyl group, said group being optionally substituted one or two times, identically or differently, with a group selected from $C_1$-$C_3$-alkyl, $C_1$-$C_3$-fluoroalkyl, $C_1$-$C_3$-alkoxy, trifluoromethoxy and ($C_1$-$C_2$-alkoxy)-($C_1$-$C_2$-alkyl)-;

R¹⁵ represents a group selected from $C_1$-$C_4$-alkyl, $C_1$-$C_4$-fluoroalkyl, ($C_1$-$C_2$-alkoxy)-($C_1$-$C_3$-alkyl)-, ($C_1$-$C_2$-alkoxy)-(ethoxy)-($C_1$-$C_3$-alkyl)-, $C_3$-$C_6$-cycloalkyl, ($C_3$-$C_6$-cycloalkyl)-($C_1$-$C_2$-alkyl)- and 4- to 7-membered heterocycloalkyl, and stereoisomers, tautomers, N-oxides, hydrates, solvates, and salts thereof, and mixtures of same.

In accordance with a seventh embodiment of the first aspect, the present invention covers compounds of general formula (I), supra, in which:

R¹ represents a group selected from

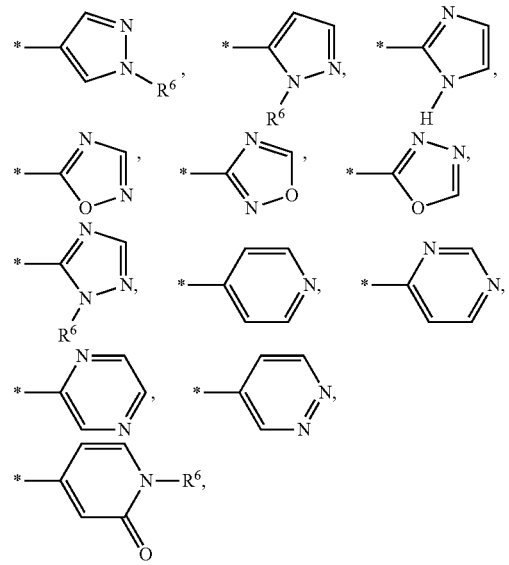

in which "*" represents the point of attachment to the rest of the molecule,
the ring of said group being, besides R⁶, optionally substituted further one or two times, differently or identically, with a R⁷ group, or R¹ represents a group selected from

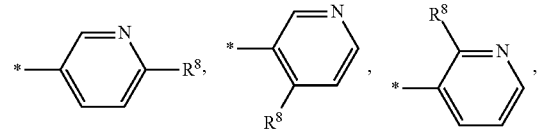

in which "*" represents the point of attachment to the rest of the molecule;

R² represents a group selected from

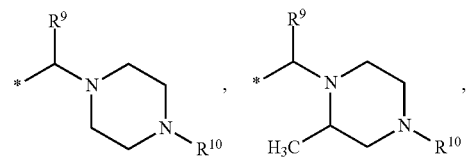

in which "*" represents the point of attachment to the rest of the molecule;

R³ represents a hydrogen atom, a fluorine atom, a chlorine atom, a bromine atom or a group selected from methyl, ethoxy and iso-butoxy;

R⁴ represents a hydrogen atom or a group selected from methyl and trifluoromethyl;

R⁵ represents a hydrogen atom;

R⁶ represents a hydrogen atom or a group selected from $C_1$-$C_6$-alkyl, $C_1$-$C_4$-fluoroalkyl, $C_1$-$C_4$-hydroxyalkyl, (methoxy)-($C_1$-$C_3$-alkyl)-, $C_3$-$C_5$-cycloalkyl and ($C_3$-$C_5$-cycloalkyl)-(methyl)-, said $C_3$-$C_5$-cycloalkyl and said ($C_3$-$C_5$-cycloalkyl)-(methyl)- group being optionally substituted one, two or three times, identically or differently, with a fluorine atom, a chlorine atom or with a methyl group;

R⁷ represents a halogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, —CN, —$(CH_2)_x$—$N(R^{11})R^{11a}$, —$C(=O)R^{13}$, —$C(=O)$—$N(R^{11})R^{11a}$, —$N(R^{11})R^{11a}$, $C_1$-$C_6$-alkoxy, $C_1$-$C_4$-fluoroalkoxy and ($C_3$-$C_4$-cycloalkyl)-(methoxy)-, said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, and said 4- to 7-membered heterocycloalkyl and said heterospirocycloalkyl group being optionally substituted one, two or three times, identically or differently, with a fluorine atom or with a group selected from methyl and trifluoromethyl, or R⁶ and R⁷, or two R⁷ groups, when being attached to adjacent ring atoms of the group R¹, together form a group selected from —(O—CH=CH)— and —($NR^{16}$—$(CH_2)_2$—O)—;

R⁸ represents a hydrogen atom or a methoxy group;

R⁹ represents a hydrogen atom or a methyl group;

R¹¹ represents a group selected from —$C(=O)R^{12}$, —$C(=O)N(R^{14})R^{14a}$, —$S(=O)_2R^{15}$ and —$S(=O)_2N(R^{14})R^{14a}$;

R¹¹ and R¹¹ᵃ, independently from each other, represent a hydrogen atom or a group selected from $C_1$-$C_3$-alkyl, $C_1$-$C_3$-fluoroalkyl, $C_3$-$C_4$-cycloalkyl, $C_1$-$C_3$-hydroxyalkyl, ($C_1$-$C_2$-alkoxy)-($C_1$-$C_3$-alkyl)-, ($C_3$-$C_4$-cycloalkyl)-(methyl)- and benzyl, or R¹¹ and R¹¹ᵃ, together with the nitrogen atom they are attached to, represent a 4- to 6-membered heterocycloalkyl group, said group being optionally substituted one or two times, identically or differently, with a fluorine atom or a group selected from methyl and trifluoromethyl;

R¹² represents a group selected from $C_1$-$C_4$-alkyl, $C_1$-$C_3$-fluoroalkyl, $C_1$-$C_3$-hydroxyalkyl, (methoxy)-($C_1$-$C_3$-alkyl)-, $C_3$-$C_4$-cycloalkyl, (cyclopropyl)-(methyl)- and allyl, said $C_3$-$C_4$-cycloalkyl group being optionally substituted one, two or three times, identically or differently, with a fluorine atom or a group selected from methyl and trifluoromethyl;

R¹³ represents a $C_1$-$C_3$-alkyl group;

R¹⁴ and R¹⁴ᵃ, independently from each other, represent a hydrogen atom or a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

R¹⁶ represents a hydrogen atom or a $C_1$-$C_2$-alkyl group;

x represents an integer 1, and stereoisomers, tautomers, N-oxides, hydrates, solvates, and salts thereof, and mixtures of same.

In accordance with a eighth embodiment of the first aspect, the present invention covers compounds of general formula (I), supra, in which:

R¹ represents a group selected from

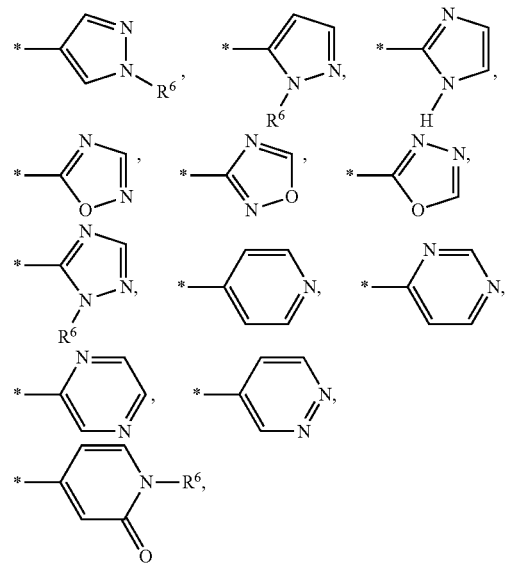

in which "*" represents the point of attachment to the rest of the molecule, the ring of said group being, besides R⁶, optionally substituted further one or two times, differently or identically, with a R⁷ group, or R¹ represents a group selected from

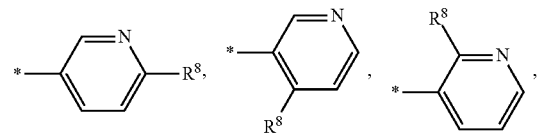

in which "*" represents the point of attachment to the rest of the molecule;

R² represents a group selected from

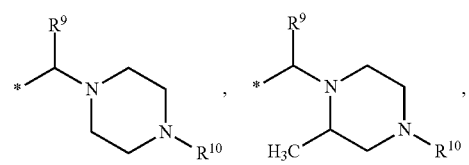

in which "*" represents the point of attachment to the rest of the molecule;

R³ represents a hydrogen atom, a fluorine atom, a chlorine atom, a bromine atom or a group selected from methyl, ethoxy and iso-butoxy;

R⁴ represents a hydrogen atom, or a group selected from methyl and trifluoromethyl;

R⁵ represents a hydrogen atom;

R⁶ represents a hydrogen atom or a group selected from C₁-C₆-alkyl, C₁-C₄-fluoroalkyl, C₁-C₄-hydroxyalkyl, (methoxy)-(C₁-C₃-alkyl)-, C₃-C₅-cycloalkyl and (C₃—C-cycloalkyl)-(methyl)-,
said C₃-C₅-cycloalkyl and said (C₃-C₅-cycloalkyl)-(methyl)- group being optionally substituted one, two or three times, identically or differently, with a fluorine atom, a chlorine atom or with a methyl group;

R⁷ represents a halogen atom or a group selected from C₁-C₆-alkyl, C₁-C₄-fluoroalkyl, C₁-C₄-hydroxyalkyl, (C₁-C₂-alkoxy)-(C₁-C₃-alkyl)-, C₃-C₄-cycloalkyl, (C₃-C₄-cycloalkyl)-(methyl)-, (phenyl)-(C₁-C₃-alkyl)-, 4- to 7-membered heterocycloalkyl, heterospirocycloalkyl, —CN, —(CH₂)ₓ—N(R¹¹)R¹¹ᵃ, —C(=O)R¹³, —C(=O)—N(R¹¹)R¹¹ᵃ, —N(R¹¹)R¹¹ᵃ, C₁-C₆-alkoxy, C₁-C₄-fluoroalkoxy and (C₃-C₄-cycloalkyl)-(methoxy)-,
said C₃-C₄-cycloalkyl, said (C₃-C₄-cycloalkyl)-(methyl)- and said (C₃-C₄-cycloalkyl)-(methoxy)- group being optionally substituted one, two or three times, identically or differently, with a fluorine atom or with a group selected from methyl and trifluoromethyl, and
said 4- to 7-membered heterocycloalkyl and said heterospirocycloalkyl group being optionally substituted one, two or three times, identically or differently, with a fluorine atom or with a group selected from methyl and trifluoromethyl, or R⁶ and R⁷, or two R⁷ groups, when being attached to adjacent ring atoms of the group R¹, together form a group selected from —(O—CH=CH)— and —(NR¹⁶—(CH₂)₂—O)—;

R⁸ represents a hydrogen atom or a methoxy group;

R⁹ represents a hydrogen atom or a methyl group;

R¹⁰ represents a group selected from —C(=O)R¹², —C(=O)N(R¹⁴)R¹⁴ᵃ, —S(=O)₂R¹⁵ and —S(=O)₂N(R¹⁴)R¹⁴ᵃ;

R¹¹ and R¹¹ᵃ, independently from each other, represent a hydrogen atom or a group selected from C₁-C₃-alkyl, C₁-C₃-fluoroalkyl, C₃-C₄-cycloalkyl, C₁-C₃-hydroxyalkyl, (C₁-C₂-alkoxy)-(C₁-C₃-alkyl)-, (C₃-C₄-cycloalkyl)-(methyl)- and benzyl, or R¹¹ and R¹¹ᵃ, together with the nitrogen atom they are attached to, represent a 4- to 6-membered heterocycloalkyl group, said group being optionally substituted one or two times, identically or differently, with a fluorine atom or a group selected from methyl and trifluoromethyl;

R¹² represents a group selected from C₁-C₄-alkyl, C₁-C₃-fluoroalkyl, C₃-C₄-cycloalkyl, (cyclopropyl)-(methyl)- and allyl,
said C₃-C₄-cycloalkyl group being optionally substituted one, two or three times, identically or differently, with a fluorine atom or a group selected from methyl and trifluoromethyl;

R¹³ represents a C₁-C₃-alkyl group;

R¹⁴ and R¹⁴ᵃ, independently from each other, represent a hydrogen atom or a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

R¹⁶ represents a hydrogen atom or a C₁-C₂-alkyl group;

x represents an integer 1, and stereoisomers, tautomers, N-oxides, hydrates, solvates, and salts thereof, and mixtures of same.

In accordance with a ninth embodiment of the first aspect, the present invention covers compounds of general formula (I), supra, in which:

R¹ represents a group selected from

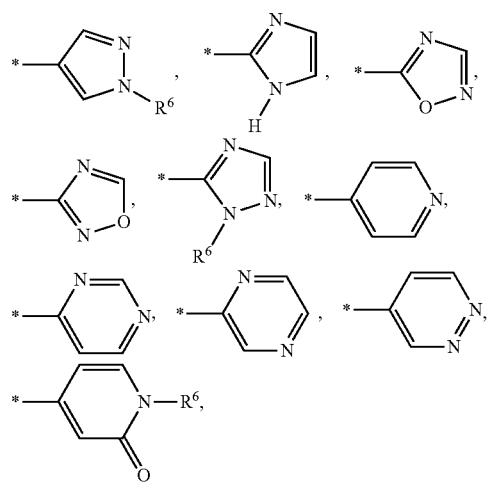

in which "*" represents the point of attachment to the rest of the molecule,
the ring of said group being, besides R⁶, optionally substituted further one or two times, differently or identically, with a R⁷ group, or R¹ represents a group selected from

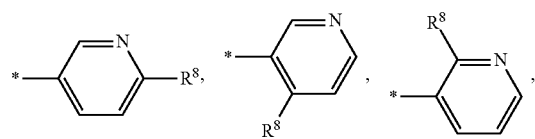

in which "*" represents the point of attachment to the rest of the molecule;

R² represents a group selected from

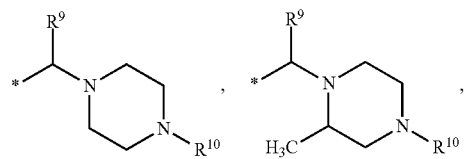

in which "*" represents the point of attachment to the rest of the molecule;

R³ represents a hydrogen atom or a group selected from methyl, ethoxy and iso-butoxy;

R⁴ represents a hydrogen atom, or a group selected from methyl and trifluoromethyl;

R⁵ represents a hydrogen atom;

R⁶ represents a group selected from C₁-C₄-alkyl, C₁-C₄-fluoroalkyl, cyclopropyl and (cyclopropyl)-(methyl)-, said cyclopropyl and (cyclopropyl)-(methyl)- group being optionally substituted one or two times with a fluorine atom;

R⁷ represents a fluorine atom or a group selected from C₁-C₅-alkyl, C₁-C₂-fluoroalkyl, cyclopropyl, benzyl, —C(=O)—N(R¹¹)R¹¹ᵃ, C₁-C₃-alkoxy, C₁-C₂-fluoroalkoxy and (cyclopropyl)-(methoxy)-;

R⁸ represents a hydrogen atom or a methoxy group;

R⁹ represents a hydrogen atom or a methyl group;

R¹⁰ represents a group selected from —C(=O)R¹², —C(=O)N(R¹⁴)R¹⁴ᵃ, —S(=O)₂R¹⁵, —S(=O)₂N(R¹⁴)R¹⁴ᵃ and 2-chlorophenyl;

R¹¹ and R¹¹ᵃ, independently from each other, represent a hydrogen atom or a group selected from methyl and ethyl;

R¹² represents a group selected from C₁-C₄-alkyl, C₁-C₃-fluoroalkyl, C₃-C₄-cycloalkyl, (cyclopropyl)-(methyl)- and allyl;

R¹⁴ and R¹⁴ᵃ, independently from each other, represent a hydrogen atom or a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted once with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl, and stereoisomers, tautomers, N-oxides, hydrates, solvates, and salts thereof, and mixtures of same.

In accordance with a tenth embodiment of the first aspect, the present invention covers compounds of general formula (I), supra, in which:

R¹ represents a group selected from

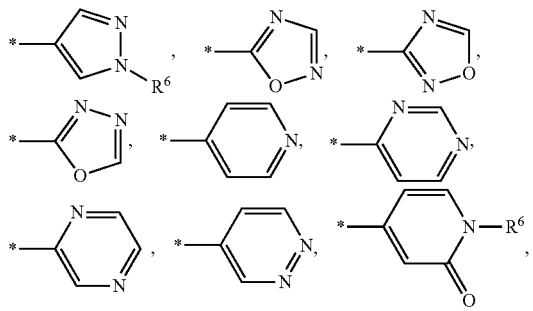

in which "*" represents the point of attachment to the rest of the molecule,
the ring of said group being, besides R⁶, optionally substituted further one or two times, differently or identically, with a R⁷ group;

R² represents a group

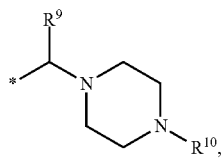

in which "*" represents the point of attachment to the rest of the molecule;

R³ represents a hydrogen atom, a fluorine atom or a chlorine atom;

R⁴ represents a hydrogen atom or a methyl group;

R⁵ represents a hydrogen atom;

R⁶ represents a group selected from methyl, ethyl, 2,2-difluoroethyl, 2,2,2-trifluoroethyl and (C₃-C₅-cycloalkyl)-(methyl)-, said (C₃-C₅-cycloalkyl)-(methyl)- group being optionally substituted one or two times, identically or differently, with a fluorine atom, a chlorine atom or with a methyl group;

R⁷ represents a group selected from C₁-C₃-alkyl, difluoromethyl, trifluoromethyl, (methoxy)-(methyl)-, cyclopropyl, —NR¹¹R¹¹ᵃ, C₁-C₃-alkoxy, C₁-C₃-fluoroalkoxy, (C₃-C₄-cycloalkyl)-(methoxy)- and [1-(trifluoromethyl)cyclopropyl]-(methoxy)-;

R⁶ and R⁷, or two R⁷ groups, when being attached to adjacent ring atoms of the group R¹, together form a group selected from —(O—CH=CH)— and —(NR¹⁶—(CH₂)₂—O)—;

R⁹ represents a hydrogen atom or a methyl group;

R¹⁰ represents a group selected from —C(=O)R¹², —C(=O)N(R¹⁴)R¹⁴ᵃ, —S(=O)₂R¹⁵ and —S(=O)₂N(R¹⁴)R¹⁴ᵃ;

R¹¹ and R¹¹ᵃ, independently from each other, represent a hydrogen atom or a group selected from C₁-C₃-alkyl, 2,2,2-trifluoroethyl, C₃-C₄-cycloalkyl, (C₁-C₂-alkoxy)-(C₁-C₃-alkyl)- and (C₃-C₄-cycloalkyl)-(methyl)-, or R¹¹ and R¹¹ᵃ, together with the nitrogen atom they are attached to, represent a 4- to 6-membered heterocycloalkyl group, said group being optionally substituted one or two times with a fluorine atom or a trifluoromethyl group;

R¹² represents a group selected from C₁-C₂-fluoroalkyl, C₃-C₄-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-;

R¹⁴ and R¹⁴ᵃ, independently from each other, represent a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

R¹⁶ represents a hydrogen atom or a methyl group, and stereoisomers, tautomers, N-oxides, hydrates, solvates, and salts thereof, and mixtures of same.

In accordance with a eleventh embodiment of the first aspect, the present invention covers compounds of general formula (I), supra, in which:

R¹ represents a group selected from

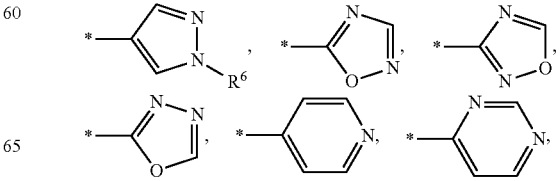

-continued

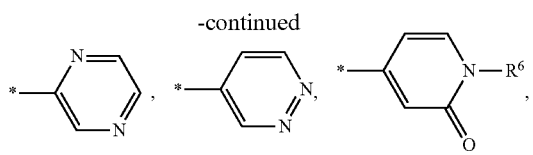

in which "*" represents the point of attachment to the rest of the molecule,
the ring of said group being, besides R⁶, optionally substituted further one or two times, differently or identically, with a R⁷ group;

R² represents a group

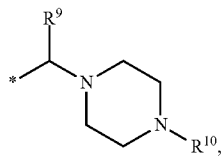

in which "*" represents the point of attachment to the rest of the molecule;

R³ represents a hydrogen atom, a fluorine atom or a chlorine atom;

R⁴ represents a hydrogen atom or a methyl group;

R⁵ represents a hydrogen atom;

R⁶ represents a group selected from methyl, ethyl, 2,2-difluoroethyl, 2,2,2-trifluoroethyl and (C₃-C₅-cycloalkyl)-(methyl)-,
said (C₃-C₅-cycloalkyl)-(methyl)- group being optionally substituted one or two times, identically or differently, with a fluorine atom, a chlorine atom or with a methyl group;

R⁷ represents a group selected from C₁-C₃-alkyl, difluoromethyl, trifluoromethyl, (methoxy)-(methyl)-, cyclopropyl, —NR¹¹R¹¹ᵃ, C₁-C₃-alkoxy, C₁-C₃-fluoroalkoxy, (C₃-C₄-cycloalkyl)-(methoxy)- and [1-(trifluoromethyl)cyclopropyl]-(methoxy)-;

R⁶ and R⁷, or two R⁷ groups, when being attached to adjacent ring atoms of the group R¹, together form a group selected from —(O—CH═CH)— and —(NR¹⁶—(CH₂)₂—O)—;

R⁹ represents a methyl group;

R¹⁰ represents a group selected from —C(═O)R¹², —C(═O)N(R¹⁴)R¹⁴ᵃ, —S(═O)₂R¹⁵ and —S(═O)₂N(R¹⁴)R¹⁴ᵃ;

R¹¹ and R¹¹ᵃ, independently from each other, represent a hydrogen atom or a group selected from C₁-C₃-alkyl, 2,2,2-trifluoroethyl, C₃-C₄-cycloalkyl, (C₁-C₂-alkoxy)-(C₁-C₃-alkyl)- and (C₃-C₄-cycloalkyl)-(methyl)-, or R¹¹ and R¹¹ᵃ, together with the nitrogen atom they are attached to, represent a 4- to 6-membered heterocycloalkyl group, said group being optionally substituted one or two times with a fluorine atom or a trifluoromethyl group;

R¹² represents a group selected from C₁-C₂-fluoroalkyl, C₃-C₄-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-;

R¹⁴ and R¹⁴ᵃ, independently from each other, represent a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

R¹⁶ represents a hydrogen atom or a methyl group, and stereoisomers, tautomers, N-oxides, hydrates, solvates, and salts thereof, and mixtures of same.

In accordance with a twelfth embodiment of the first aspect, the present invention covers compounds of general formula (I), supra, in which:

R¹ represents a group selected from

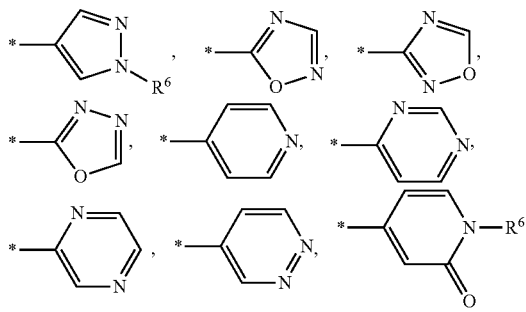

in which "*" represents the point of attachment to the rest of the molecule,
the ring of said group being, besides R⁶, optionally substituted further one or two times, differently or identically, with a R⁷ group;

R² represents a group

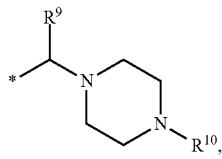

in which "*" represents the point of attachment to the rest of the molecule;

R³ represents a hydrogen atom, a fluorine atom or a chlorine atom;

R⁴ represents a hydrogen atom or a methyl group;

R⁵ represents a hydrogen atom;

R⁶ represents a group selected from methyl, ethyl, 2,2-difluoroethyl, 2,2,2-trifluoroethyl and (C₃-C₅-cycloalkyl)-(methyl)-,
said (C₃-C₅-cycloalkyl)-(methyl)- group being optionally substituted one or two times, identically or differently, with a fluorine atom, a chlorine atom or with a methyl group;

R⁷ represents a group selected from C₁-C₃-alkyl, difluoromethyl, trifluoromethyl, (methoxy)-(methyl)-, cyclopropyl, —NR¹¹R¹¹ᵃ, C₁-C₃-alkoxy, C₁-C₃-fluoroalkoxy, (C₃-C₄-cycloalkyl)-(methoxy)- and [1-(trifluoromethyl)cyclopropyl]-(methoxy)-; or R⁶ and R⁷, or two R⁷ groups, when being attached to adjacent ring atoms of the group R¹, together form a group selected from —(O—CH═CH)— and —(NR¹⁶—(CH₂)₂—O)—;

R⁹ represents a hydrogen atom or a methyl group;
R¹⁰ represents a group selected from —C(=O)R¹² and —C(=O)N(R¹⁴)R¹⁴ᵃ;
R¹¹ and R¹¹ᵃ, independently from each other, represent a hydrogen atom or a group selected from C₁-C₃-alkyl, 2,2,2-trifluoroethyl, C₃-C₄-cycloalkyl, (C₁-C₂-alkoxy)-(C₁-C₃-alkyl)- and (C₃-C₄-cycloalkyl)-(methyl)-, or
R¹¹ and R¹¹ᵃ, together with the nitrogen atom they are attached to, represent a 4- to 6-membered heterocycloalkyl group, said group being optionally substituted one or two times with a fluorine atom or a trifluoromethyl group;
R¹² represents a group selected from C₁-C₂-fluoroalkyl, C₃-C₄-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-;
R¹⁴ and R¹⁴ᵃ, independently from each other, represent a group selected from methyl and ethyl, or
R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;
R¹⁶ represents a hydrogen atom or a methyl group,
and stereoisomers, tautomers, N-oxides, hydrates, solvates, and salts thereof, and mixtures of same.

In accordance with a thirteenth embodiment of the first aspect, the present invention covers compounds of general formula (I), supra, in which:
R¹ represents a group selected from

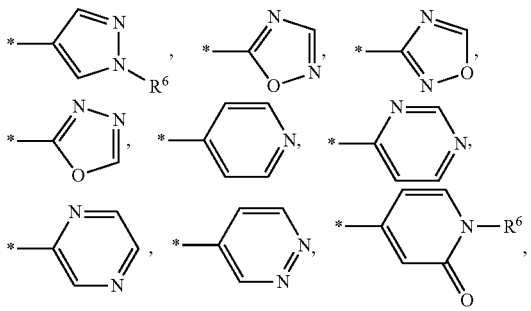

in which "*" represents the point of attachment to the rest of the molecule,
the ring of said group being, besides R⁶, optionally substituted further one or two times, differently or identically, with a R⁷ group;
R² represents a group

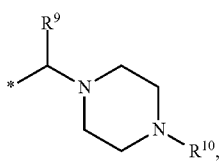

in which "*" represents the point of attachment to the rest of the molecule;
R³ represents a hydrogen atom, a fluorine atom or a chlorine atom;
R⁴ represents a hydrogen atom or a methyl group;
R⁵ represents a hydrogen atom;
R⁶ represents a group selected from methyl, ethyl, 2,2-difluoroethyl, 2,2,2-trifluoroethyl and (C₃-C₅-cycloalkyl)-(methyl)-,
said (C₃-C₅-cycloalkyl)-(methyl)- group being optionally substituted one or two times, identically or differently, with a fluorine atom, a chlorine atom or with a methyl group;
R⁷ represents a group selected from C₁-C₃-alkyl, difluoromethyl, trifluoromethyl, (methoxy)-(methyl)-, cyclopropyl, —NR¹¹R¹¹ᵃ, C₁-C₃-alkoxy, C₁-C₃-fluoroalkoxy, (C₃-C₄-cycloalkyl)-(methoxy)- and [1-(trifluoromethyl)cyclopropyl]-(methoxy)-; or
R⁶ and R⁷, or two R⁷ groups, when being attached to adjacent ring atoms of the group R¹, together form a group selected from —(O—CH=CH)— and —(NR¹⁶—(CH₂)₂—O)—;
R⁹ represents a methyl group;
R¹⁰ represents a group selected from —C(=O)R¹² and —C(=O)N(R¹⁴)R¹⁴ᵃ;
R¹¹ and R¹¹ᵃ, independently from each other, represent a hydrogen atom or a group selected from C₁-C₃-alkyl, 2,2,2-trifluoroethyl, C₃-C₄-cycloalkyl, (C₁-C₂-alkoxy)-(C₁-C₃-alkyl)- and (C₃-C₄-cycloalkyl)-(methyl)-, or
R¹¹ and R¹¹ᵃ, together with the nitrogen atom they are attached to, represent a 4- to 6-membered heterocycloalkyl group, said group being optionally substituted one or two times with a fluorine atom or a trifluoromethyl group;
R¹² represents a group selected from C₁-C₂-fluoroalkyl, C₃-C₄-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-;
R¹⁴ and R¹⁴ᵃ, independently from each other, represent a group selected from methyl and ethyl, or
R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;
R¹⁶ represents a hydrogen atom or a methyl group,
and stereoisomers, tautomers, N-oxides, hydrates, solvates, and salts thereof, and mixtures of same.

In accordance with a fourteenth embodiment of the first aspect, the present invention covers compounds of general formula (I), supra, in which:
R¹ represents a group selected from

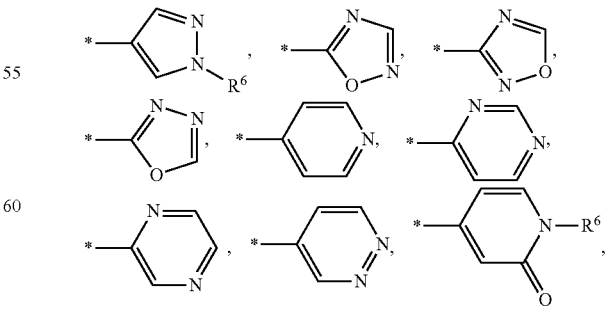

in which "*" represents the point of attachment to the rest of the molecule, the ring of said group being, besides R⁶, optionally substituted further one or two times, differently or identically, with a R⁷ group;

R² represents a group

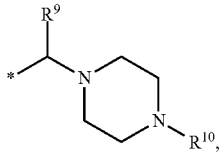

in which "*" represents the point of attachment to the rest of the molecule;

R³ represents a hydrogen atom, a fluorine atom or a chlorine atom;

R⁴ represents a hydrogen atom or a methyl group;

R⁵ represents a hydrogen atom;

R⁶ represents a group selected from methyl, ethyl, 2,2-difluoroethyl, 2,2,2-trifluoroethyl and ($C_3$-$C_5$-cycloalkyl)-(methyl)-, said ($C_3$-$C_5$-cycloalkyl)-(methyl)- group being optionally substituted one or two times, identically or differently, with a fluorine atom, a chlorine atom or with a methyl group;

R⁷ represents a group selected from $C_1$-$C_3$-alkyl, difluoromethyl, trifluoromethyl, (methoxy)-(methyl)-, cyclopropyl, 2-oxa-6-azaspiro[3.3]heptyl-, —NR¹¹R¹¹ᵃ, $C_1$-$C_3$-alkoxy, trifluoromethoxy, 2,2,2-trifluoroethoxy, ($C_3$-$C_4$-cycloalkyl)-(methoxy)- and [1-(trifluoromethyl)cyclopropyl]-(methoxy)-;

R⁶ and R⁷, or two R⁷ groups, when being attached to adjacent ring atoms of the group R¹, together form a group selected from —(O—CH=CH)— and —(NR¹⁶—(CH₂)₂—O)—;

R⁹ represents a hydrogen atom or a methyl group;

R¹⁰ represents a group selected from —C(=O)R¹², —C(=O)N(R¹⁴)R¹⁴ᵃ, —S(=O)₂R¹⁵ and —S(=O)₂N(R¹⁴)R¹⁴ᵃ;

R¹¹ and R¹¹ᵃ, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or R¹¹ and R¹¹ᵃ, together with the nitrogen atom they are attached to, represent a 4- to 6-membered heterocycloalkyl group, said group being optionally substituted one or two times with a fluorine atom or a trifluoromethyl group;

R¹² represents a group selected from $C_1$-$C_2$-fluoroalkyl, $C_3$-$C_4$-cycloalkyl, (1-trifluoromethyl)-(cyclopropyl)- and (cyclopropyl)-(methyl)-;

R¹⁴ and R¹⁴ᵃ, independently from each other, represent a group selected from methyl and ethyl, or R¹⁴ and R¹⁴ᵃ, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

R¹⁵ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

R¹⁶ represents a hydrogen atom or a methyl group, and stereoisomers, tautomers, N-oxides, hydrates, solvates, and salts thereof, and mixtures of same.

In accordance with a fifteenth embodiment of the first aspect, the present invention covers compounds of general formula (I), supra, in which:

R¹ represents a group selected from

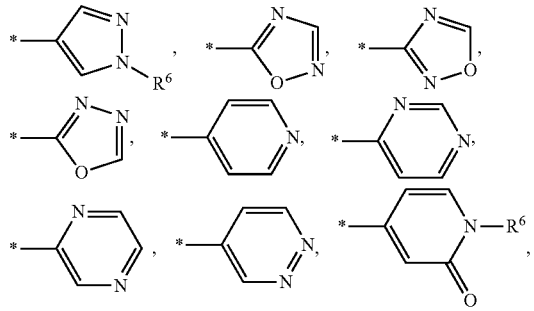

in which "*" represents the point of attachment to the rest of the molecule, the ring of said group being, besides R⁶, optionally substituted further one or two times, differently or identically, with a R⁷ group;

R² represents a group

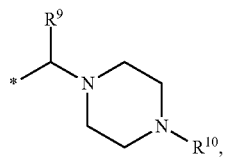

in which "*" represents the point of attachment to the rest of the molecule;

R³ represents a hydrogen atom, a fluorine atom or a chlorine atom;

R⁴ represents a hydrogen atom or a methyl group;

R⁵ represents a hydrogen atom;

R⁶ represents a group selected from methyl, ethyl, 2,2-difluoroethyl, 2,2,2-trifluoroethyl and ($C_3$-$C_5$-cycloalkyl)-(methyl)-, said ($C_3$-$C_5$-cycloalkyl)-(methyl)- group being optionally substituted one or two times, identically or differently, with a fluorine atom, a chlorine atom or with a methyl group;

R⁷ represents a group selected from $C_1$-$C_3$-alkyl, difluoromethyl, trifluoromethyl, (methoxy)-(methyl)-, cyclopropyl, 2-oxa-6-azaspiro[3.3]heptyl-, —NR¹¹R¹¹ᵃ, $C_1$-$C_3$-alkoxy, trifluoromethoxy, 2,2,2-trifluoroethoxy, ($C_3$-$C_4$-cycloalkyl)-(methoxy)- and [1-(trifluoromethyl)cyclopropyl]-(methoxy)-;

R⁶ and R⁷, or two R⁷ groups, when being attached to adjacent ring atoms of the group R¹, together form a group selected from —(O—CH=CH)— and —(NR¹⁶—(CH₂)₂—O)—;

R⁹ represents a methyl group;

R¹⁰ represents a group selected from —C(=O)R¹², —C(=O)N(R¹⁴)R¹⁴ᵃ, —S(=O)₂R¹⁵ and —S(=O)₂N(R¹⁴)R¹⁴ᵃ;

R¹¹ and R¹¹ᵃ, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom or a trifluoromethyl group;

$R^{12}$ represents a group selected from $C_1$-$C_2$-fluoroalkyl, $C_3$-$C_4$-cycloalkyl, (1-trifluoromethyl)-(cyclopropyl)- and (cyclopropyl)-(methyl)-;

$R^{14}$ and $R^{14a}$, independently from each other, represent a group selected from methyl and ethyl, or $R^{14}$ and $R^{14a}$, together with the nitrogen atom they are attached to, represent a 5- to 6-membered heterocycloalkyl group selected from pyrrolidinyl, piperidinyl and morpholinyl, said group being optionally substituted one or two times, identically or differently, with a group selected from methyl, methoxy and (methoxy)-(methyl)-;

$R^{15}$ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl;

$R^{16}$ represents a hydrogen atom or a methyl group, and stereoisomers, tautomers, N-oxides, hydrates, solvates, and salts thereof, and mixtures of same.

In accordance with a sixteenth embodiment of the first aspect, the present invention covers compounds of general formula (I), supra, in which:

$R^1$ represents a group selected from

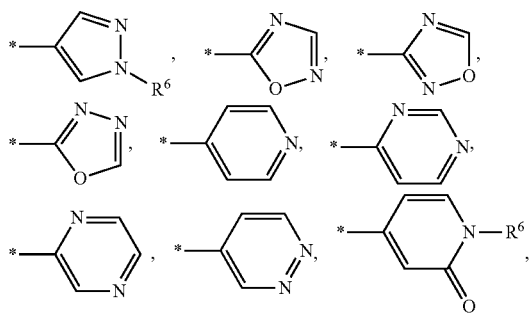

in which "*" represents the point of attachment to the rest of the molecule,
the ring of said group being, besides $R^6$, optionally substituted further one or two times, differently or identically, with a $R^7$ group;

$R^2$ represents a group

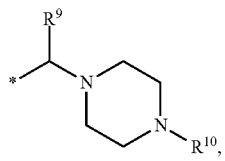

in which "*" represents the point of attachment to the rest of the molecule;

$R^3$ represents a hydrogen atom, a fluorine atom or a chlorine atom;

$R^4$ represents a hydrogen atom or a methyl group;

$R^5$ represents a hydrogen atom;

$R^6$ represents a group selected from methyl, ethyl, 2,2-difluoroethyl, 2,2,2-trifluoroethyl and ($C_3$-$C_5$-cycloalkyl)-(methyl)-,
said ($C_3$-$C_5$-cycloalkyl)-(methyl)- group being optionally substituted one or two times, identically or differently, with a fluorine atom, a chlorine atom or with a methyl group;

$R^7$ represents a group selected from $C_1$-$C_3$-alkyl, difluoromethyl, trifluoromethyl, (methoxy)-(methyl)-, cyclopropyl, 2-oxa-6-azaspiro[3.3]heptyl-, —$NR^{11}R^{11a}$, $C_1$-$C_3$-alkoxy, trifluoromethoxy, 2,2,2-trifluoroethoxy, ($C_3$-$C_4$-cycloalkyl)-(methoxy)- and [1-(trifluoromethyl)cyclopropyl]-(methoxy)-;

$R^6$ and $R^7$, or two $R^7$ groups, when being attached to adjacent ring atoms of the group $R^1$, together form a group selected from —(O—CH=CH)— and —(NR$^{16}$—(CH$_2$)$_2$—O)—;

$R^9$ represents a hydrogen atom or a methyl group;

$R^{10}$ represents a group selected from —C(=O)R$^{12}$ and —C(=O)N(R$^{14}$)R$^{14a}$;

$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom or a trifluoromethyl group;

$R^{12}$ represents a group selected from $C_1$-$C_2$-fluoroalkyl, $C_3$-$C_4$-cycloalkyl, (1-trifluoromethyl)-(cyclopropyl)- and (cyclopropyl)-(methyl)-;

$R^{14}$ and $R^{14a}$, independently from each other, represent a group selected from methyl and ethyl, or $R^{14}$ and $R^{14a}$, together with the nitrogen atom they are attached to, represent a 5- to 6-membered heterocycloalkyl group selected from pyrrolidinyl, piperidinyl and morpholinyl;

$R^{16}$ represents a hydrogen atom or a methyl group, and stereoisomers, tautomers, N-oxides, hydrates, solvates, and salts thereof, and mixtures of same.

In accordance with a seventeenth embodiment of the first aspect, the present invention covers compounds of general formula (I), supra, in which:

$R^1$ represents a group selected from

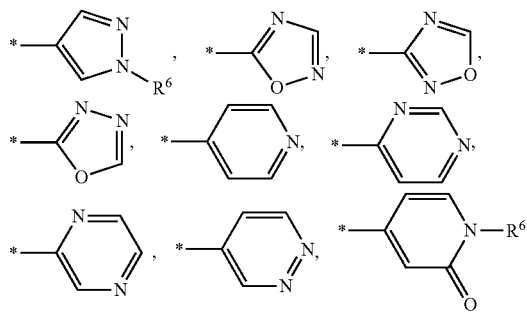

in which "*" represents the point of attachment to the rest of the molecule,
the ring of said group being, besides $R^6$, optionally substituted further one or two times, differently or identically, with a $R^7$ group;

$R^2$ represents a group

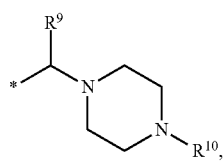

in which "*" represents the point of attachment to the rest of the molecule;

R$^3$ represents a hydrogen atom, a fluorine atom or a chlorine atom;

R$^4$ represents a hydrogen atom or a methyl group;

R$^5$ represents a hydrogen atom;

R$^6$ represents a group selected from methyl, ethyl, 2,2-difluoroethyl, 2,2,2-trifluoroethyl and (C$_3$-C$_5$-cycloalkyl)-(methyl)-,
said (C$_3$-C$_5$-cycloalkyl)-(methyl)- group being optionally substituted one or two times, identically or differently, with a fluorine atom, a chlorine atom or with a methyl group;

R$^7$ represents a group selected from C$_1$-C$_3$-alkyl, difluoromethyl, trifluoromethyl, (methoxy)-(methyl)-, cyclopropyl, 2-oxa-6-azaspiro[3.3]heptyl-, —NR$^{11}$R$^{11a}$, C$_1$-C$_3$-alkoxy, trifluoromethoxy, 2,2,2-trifluoroethoxy, (C$_3$-C$_4$-cycloalkyl)-(methoxy)- and [1-(trifluoromethyl)cyclopropyl]-(methoxy)-;

R$^6$ and R$^7$, or two R$^7$ groups, when being attached to adjacent ring atoms of the group R$^1$, together form a group selected from —(O—CH=CH)— and —(NR$^{16}$—(CH$_2$)$_2$—O)—;

R$^9$ represents a methyl group;

R$^{10}$ represents a group selected from —C(=O)R$^{12}$ and —C(=O)N(R$^{14}$)R$^{14a}$;

R$^{11}$ and R$^{11a}$, independently from each other, represent a hydrogen atom or a group selected from C$_1$-C$_3$-alkyl, 2,2,2-trifluoroethyl, C$_3$-C$_4$-cycloalkyl, (C$_1$-C$_2$-alkoxy)-(C$_1$-C$_3$-alkyl)- and (C$_3$-C$_4$-cycloalkyl)-(methyl)-, or R$^{11}$ and R$^{11a}$, together with the nitrogen atom they are attached to, represent a 4- to 6-membered heterocycloalkyl group, said group being optionally substituted one or two times with a fluorine atom or a trifluoromethyl group;

R$^{12}$ represents a group selected from C$_1$-C$_2$-fluoroalkyl, C$_3$-C$_4$-cycloalkyl, (1-trifluoromethyl)-(cyclopropyl)- and (cyclopropyl)-(methyl)-;

R$^{14}$ and R$^{14a}$, independently from each other, represent a group selected from methyl and ethyl, or R$^{14}$ and R$^{14a}$, together with the nitrogen atom they are attached to, represent a 5- to 6-membered heterocycloalkyl group selected from pyrrolidinyl, piperidinyl and morpholinyl;

R$^{16}$ represents a hydrogen atom or a methyl group, and stereoisomers, tautomers, N-oxides, hydrates, solvates, and salts thereof, and mixtures of same.

In accordance with a eighteenth embodiment of the first aspect, the present invention covers compounds of general formula (I), supra, in which:

R$^1$ represents a group selected from

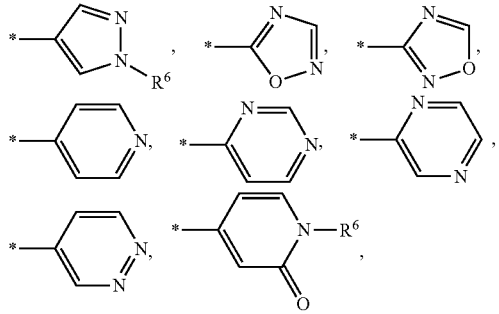

in which "*" represents the point of attachment to the rest of the molecule,
the ring of said group being, besides R$^6$, optionally substituted with one further R$^7$ group;

R$^2$ represents a group

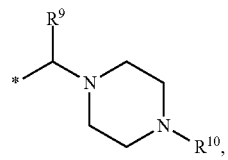

in which "*" represents the point of attachment to the rest of the molecule;

R$^3$ represents a hydrogen atom;

R$^4$ represents a hydrogen atom or a methyl group;

R$^5$ represents a hydrogen atom;

R$^6$ represents a group selected from methyl, ethyl, 2,2,2-trifluoroethyl and (cyclopropyl)-(methyl)-,
said (cyclopropyl)-(methyl)- group being optionally substituted one or two times with a fluorine atom;

R$^7$ represents a group selected from C$_1$-C$_3$-alkyl, trifluoromethyl, cyclopropyl, C$_1$-C$_3$-alkoxy, trifluoromethoxy, 2,2,2-trifluoroethoxy and (cyclopropyl)-(methoxy)-;

R$^9$ represents a hydrogen atom or a methyl group;

R$^{10}$ represents a group selected from —C(=O)R$^{12}$, —C(=O)N(R$^{14}$)R$^{14a}$, —S(=O)$_2$R$^{15}$ and —S(=O)$_2$N(R$^{14}$)R$^{14a}$, R$^{12}$ represents a group selected from C$_1$-C$_2$-fluoroalkyl, C$_3$-C$_4$-cycloalkyl and (cyclopropyl)-(methyl)-;

R$^{14}$ and R$^{14a}$, independently from each other, represent a group selected from methyl and ethyl, or R$^{14}$ and R$^{14a}$, together with the nitrogen atom they are attached to, represent a 5- to 6-membered heterocycloalkyl group selected from pyrrolidinyl, piperidinyl and morpholinyl, said group being optionally substituted once with a group selected from methyl, methoxy and (methoxy)-(methyl)-;

R$^{15}$ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl,
and stereoisomers, tautomers, N-oxides, hydrates, solvates, and salts thereof, and mixtures of same.

In accordance with a nineteenth embodiment of the first aspect, the present invention covers compounds of general formula (I), supra, in which:

R$^1$ represents a group selected from

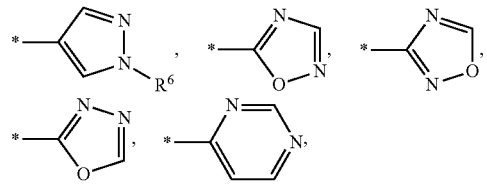

in which "*" represents the point of attachment to the rest of the molecule,
the ring of said group being, besides R$^6$, optionally substituted further one or two times, differently or identically, with a R$^7$ group;

R² represents a group

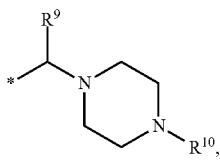

in which "*" represents the point of attachment to the rest of the molecule;

R³ represents a hydrogen atom, a fluorine atom or a chlorine atom;

R⁴ represents a hydrogen atom;

R⁵ represents a hydrogen atom;

R⁶ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

R⁷ represents a group selected from $C_1$-$C_3$-alkyl, trifluoromethyl, (methoxy)-(methyl)-, cyclopropyl, —$NR^{11}R^{11a}$, $C_1$-$C_3$-alkoxy, $C_1$-$C_3$-fluoroalkoxy and ($C_3$-$C_4$-cycloalkyl)-(methoxy)-;

R⁹ represents a hydrogen atom or a methyl group;

R¹⁰ represents a —C(=O)R¹² group;

R¹¹ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or R¹¹ and $R^{11a}$, together with the nitrogen atom they are attached to, represent a 4- to 6-membered heterocycloalkyl group, said group being optionally substituted one or two times with a fluorine atom or a trifluoromethyl group;

R¹² represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-, and stereoisomers, tautomers, N-oxides, hydrates, solvates, and salts thereof, and mixtures of same.

In accordance with a twentieth embodiment of the first aspect, the present invention covers compounds of general formula (I), supra, in which:

R¹ represents a group selected from

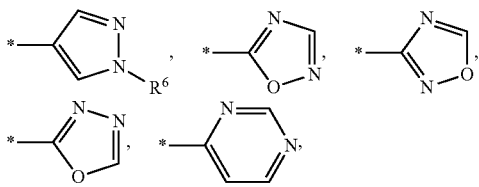

in which "*" represents the point of attachment to the rest of the molecule,
the ring of said group being, besides R⁶, optionally substituted further one or two times, differently or identically, with a R⁷ group;

R² represents a group

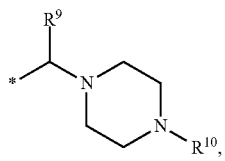

in which "*" represents the point of attachment to the rest of the molecule;

R³ represents a hydrogen atom, a fluorine atom or a chlorine atom;

R⁴ represents a hydrogen atom;

R⁵ represents a hydrogen atom;

R⁶ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

R⁷ represents a group selected from $C_1$-$C_3$-alkyl, trifluoromethyl, (methoxy)-(methyl)-, cyclopropyl, —$NR^{11}R^{11a}$, $C_1$-$C_3$-alkoxy, $C_1$-$C_3$-fluoroalkoxy and ($C_3$-$C_4$-cycloalkyl)-(methoxy)-;

R⁹ represents a methyl group;

R¹⁰ represents a —C(=O)R¹² group;

R¹¹ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or R¹¹ and $R^{11a}$, together with the nitrogen atom they are attached to, represent a 4- to 6-membered heterocycloalkyl group, said group being optionally substituted one or two times with a fluorine atom or a trifluoromethyl group;

R¹² represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-, and stereoisomers, tautomers, N-oxides, hydrates, solvates, and salts thereof, and mixtures of same.

In accordance with a twenty-first embodiment of the first aspect, the present invention covers compounds of general formula (I), supra, in which:

R¹ represents a group selected from

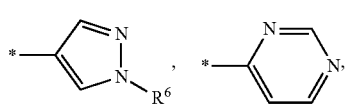

in which "*" represents the point of attachment to the rest of the molecule,
the ring of said group being, besides R⁶, optionally substituted further one or two times, differently or identically, with a R⁷ group;

$R^2$ represents a group

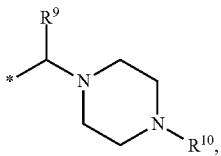

in which "*" represents the point of attachment to the rest of the molecule;

$R^3$ represents a hydrogen atom, a fluorine atom or a chlorine atom;

$R^4$ represents a hydrogen atom;

$R^5$ represents a hydrogen atom;

$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

$R^7$ represents a group selected from $C_1$-$C_3$-alkyl, trifluoromethyl, (methoxy)-(methyl)-, cyclopropyl, —$NR^{11}R^{11a}$, $C_1$-$C_3$-alkoxy, $C_1$-$C_3$-fluoroalkoxy and ($C_3$-$C_4$-cycloalkyl)-(methoxy)-;

$R^9$ represents a hydrogen atom or a methyl group;

$R^{11}$ represents a —C(=O)$R^{12}$ group;

$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom or a trifluoromethyl group;

$R^{12}$ represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-, and stereoisomers, tautomers, N-oxides, hydrates, solvates, and salts thereof, and mixtures of same.

In accordance with a twenty-second embodiment of the first aspect, the present invention covers compounds of general formula (I), supra, in which:

$R^1$ represents a group selected from

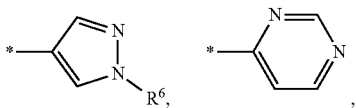

in which "*" represents the point of attachment to the rest of the molecule, the ring of said group being, besides $R^6$, optionally substituted further one or two times, differently or identically, with a $R^7$ group;

$R^2$ represents a group

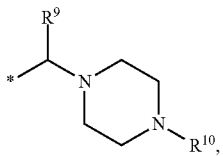

in which "*" represents the point of attachment to the rest of the molecule;

$R^3$ represents a hydrogen atom, a fluorine atom or a chlorine atom;

$R^4$ represents a hydrogen atom;

$R^5$ represents a hydrogen atom;

$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

$R^7$ represents a group selected from $C_1$-$C_3$-alkyl, trifluoromethyl, (methoxy)-(methyl)-, cyclopropyl,
—$NR^{11}R^{11a}$, $C_1$-$C_3$-alkoxy, $C_1$-$C_3$-fluoroalkoxy and ($C_3$-$C_4$-cycloalkyl)-(methoxy)-;

$R^9$ represents a methyl group;

$R^{10}$ represents a —C(=O)$R^{12}$ group;

$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom or a trifluoromethyl group;

$R^{12}$ represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-, and stereoisomers, tautomers, N-oxides, hydrates, solvates, and salts thereof, and mixtures of same.

In accordance with a twenty-third embodiment of the first aspect, the present invention covers compounds of general formula (I), supra, in which:

$R^1$ represents a group selected from

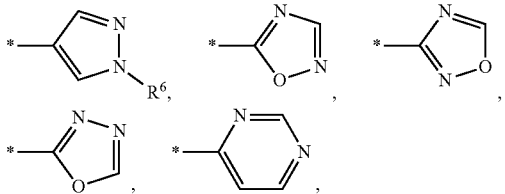

in which "*" represents the point of attachment to the rest of the molecule, the ring of said group being, besides $R^6$, optionally substituted further one or two times, differently or identically, with a $R^7$ group;

R² represents a group

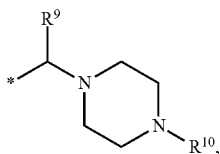

in which "*" represents the point of attachment to the rest of the molecule;

R³ represents a hydrogen atom, a fluorine atom or a chlorine atom;

R⁴ represents a hydrogen atom;

R⁵ represents a hydrogen atom;

R⁶ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

R⁷ represents a group selected from $C_1$-$C_3$-alkyl, (methoxy)-(methyl)-, cyclopropyl, —NR¹¹R¹¹ᵃ, $C_1$-$C_3$-alkoxy and ($C_3$-$C_4$-cycloalkyl)-(methoxy)-;

R⁹ represents a hydrogen atom or a methyl group;

R¹⁰ represents a —C(=O)R¹² group;

R¹¹ and R¹¹ᵃ, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or R¹¹ and R¹¹ᵃ, together with the nitrogen atom they are attached to, represent a 4- to 6-membered heterocycloalkyl group, said group being optionally substituted one or two times with a fluorine atom;

R¹² represents a group selected from $C_1$-$C_2$-fluoroalkyl, $C_3$-$C_4$-cycloalkyl, (1-trifluoromethyl)-(cyclopropyl)- and (cyclopropyl)-(methyl)-, and stereoisomers, tautomers, N-oxides, hydrates, solvates, and salts thereof, and mixtures of same.

In accordance with a twenty-fourth embodiment of the first aspect, the present invention covers compounds of general formula (I), supra, in which:

R¹ represents a group selected from

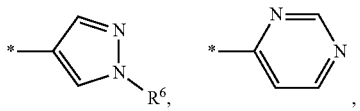

in which "*" represents the point of attachment to the rest of the molecule, the ring of said group being, besides R⁶, optionally substituted further one or two times, differently or identically, with a R⁷ group;

R² represents a group

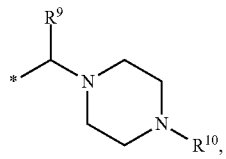

in which "*" represents the point of attachment to the rest of the molecule;

R³ represents a hydrogen atom, a fluorine atom or a chlorine atom;

R⁴ represents a hydrogen atom;

R⁵ represents a hydrogen atom;

R⁶ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

R⁷ represents a group selected from $C_1$-$C_3$-alkyl, (methoxy)-(methyl)-, cyclopropyl, —NR¹¹R¹¹ᵃ, $C_1$-$C_3$-alkoxy and ($C_3$-$C_4$-cycloalkyl)-(methoxy)-;

R⁹ represents a hydrogen atom or a methyl group;

R¹⁰ represents a —C(=O)R¹² group;

R¹¹ and R¹¹ᵃ, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or R¹¹ and R¹¹ᵃ, together with the nitrogen atom they are attached to, represent a 4- to 6-membered heterocycloalkyl group, said group being optionally substituted one or two times with a fluorine atom;

R¹² represents a group selected from $C_1$-$C_2$-fluoroalkyl, $C_3$-$C_4$-cycloalkyl, (1-trifluoromethyl)-(cyclopropyl)- and (cyclopropyl)-(methyl)-, and stereoisomers, tautomers, N-oxides, hydrates, solvates, and salts thereof, and mixtures of same.

In accordance with a twenty-fifth embodiment of the first aspect, the present invention covers compounds of general formula (I), supra, in which:

R¹ represents a group selected from

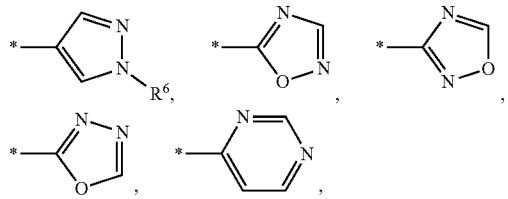

in which "*" represents the point of attachment to the rest of the molecule, the ring of said group being, besides R⁶, optionally substituted further one or two times, differently or identically, with a R⁷ group;

$R^2$ represents a group

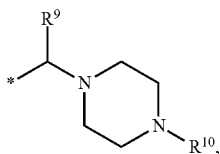

in which "*" represents the point of attachment to the rest of the molecule;

$R^3$ represents a hydrogen atom, a fluorine atom or a chlorine atom;

$R^4$ represents a hydrogen atom;

$R^5$ represents a hydrogen atom;

$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

$R^7$ represents a group selected from $C_1$-$C_3$-alkyl, (methoxy)-(methyl)-, cyclopropyl, —$NR^{11}R^{11a}$, $C_1$-$C_3$-alkoxy and ($C_3$-$C_4$-cycloalkyl)-(methoxy)-;

$R^9$ represents a methyl group;

$R^{10}$ represents a —C(=O)$R^{12}$ group;

$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom;

$R^{12}$ represents a group selected from $C_1$-$C_2$-fluoroalkyl, $C_3$-$C_4$-cycloalkyl, (1-trifluoromethyl)-(cyclopropyl)- and (cyclopropyl)-(methyl)-, and stereoisomers, tautomers, N-oxides, hydrates, solvates, and salts thereof, and mixtures of same.

In accordance with a twenty-sixth embodiment of the first aspect, the present invention covers compounds of general formula (I), supra, in which:

$R^1$ represents a group selected from

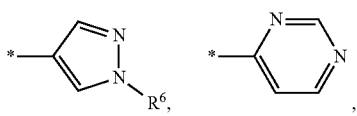

in which "*" represents the point of attachment to the rest of the molecule, the ring of said group being, besides $R^6$, optionally substituted further one or two times, differently or identically, with a $R^7$ group;

$R^2$ represents a group

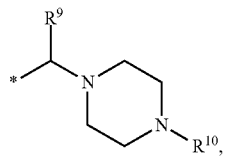

in which "*" represents the point of attachment to the rest of the molecule;

$R^3$ represents a hydrogen atom, a fluorine atom or a chlorine atom;

$R^4$ represents a hydrogen atom;

$R^5$ represents a hydrogen atom;

$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;

$R^7$ represents a group selected from $C_1$-$C_3$-alkyl, (methoxy)-(methyl)-, cyclopropyl, —$NR^{11}R^{11a}$, $C_1$-$C_3$-alkoxy and ($C_3$-$C_4$-cycloalkyl)-(methoxy)-;

$R^9$ represents a methyl group;

$R^{11}$ represents a —C(=O)$R^{12}$ group;

$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or $R^{11}$ and $R^{11a}$, together with the nitrogen atom they are attached to, represent a 4- to 6-membered heterocycloalkyl group, said group being optionally substituted one or two times with a fluorine atom;

$R^{12}$ represents a group selected from $C_1$-$C_2$-fluoroalkyl, $C_3$-$C_4$-cycloalkyl, (1-trifluoromethyl)-(cyclopropyl)- and (cyclopropyl)-(methyl)-, and stereoisomers, tautomers, N-oxides, hydrates, solvates, and salts thereof, and mixtures of same.

In accordance with a twenty-seventh embodiment of the first aspect, the present invention covers compounds of general formula (I), supra, in which:

$R^1$ represents a group selected from

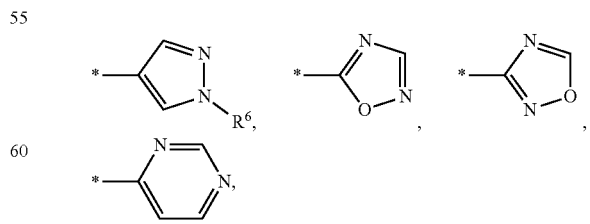

in which "*" represents the point of attachment to the rest of the molecule, the ring of said group being, besides $R^6$, optionally substituted with one further $R^7$ group;

$R^2$ represents a group

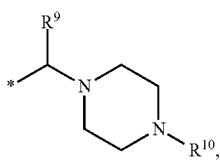

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2,2-trifluoroethyl, (cyclopropyl)-(methyl)- and (2,2-difluorocyclopropyl)-(methyl)-;
$R^7$ represents a group selected from methyl, trifluoromethyl, cyclopropyl, methoxy, ethoxy, iso-propoxy, 2,2,2-trifluoroethoxy and (cyclopropyl)-(methoxy)-;
$R^9$ represents a hydrogen atom or a methyl group;
$R^{10}$ represents a —C(=O)$R^{12}$ group;
$R^{12}$ represents a group selected from $C_1$-$C_2$-fluoroalkyl, $C_3$-$C_4$-cycloalkyl and (cyclopropyl)-(methyl)-; and stereoisomers, tautomers, N-oxides, hydrates, solvates, and salts thereof, and mixtures of same.

In accordance with a twenty-eight embodiment of the first aspect, the present invention covers compounds of general formula (I), supra, in which:
$R^1$ represents a group selected from

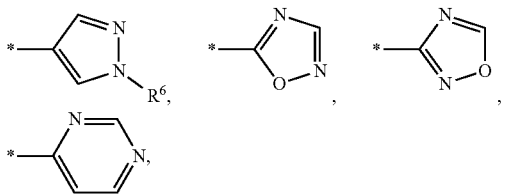

in which "*" represents the point of attachment to the rest of the molecule,
the ring of said group being, besides $R^6$, optionally substituted with one further $R^7$ group;
$R^2$ represents a group

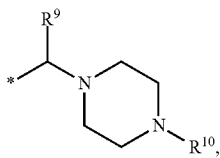

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2,2-trifluoroethyl, (cyclopropyl)-(methyl)- and (2,2-difluorocyclopropyl)-(methyl)-;
$R^7$ represents a group selected from methyl, trifluoromethyl, cyclopropyl, methoxy, ethoxy, iso-propoxy, 2,2,2-trifluoroethoxy and (cyclopropyl)-(methoxy)-;
$R^9$ represents a methyl group;
$R^{10}$ represents a —C(=O)$R^{12}$ group;
$R^{12}$ represents a group selected from $C_1$-$C_2$-fluoroalkyl, $C_3$-$C_4$-cycloalkyl and (cyclopropyl)-(methyl)-;
and stereoisomers, tautomers, N-oxides, hydrates, solvates, and salts thereof, and mixtures of same.

In accordance with a twenty-ninth embodiment of the first aspect, the present invention covers compounds of general formula (I), supra, in which:
$R^1$ represents a group selected from

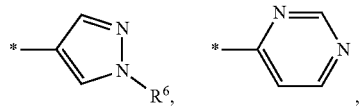

in which "*" represents the point of attachment to the rest of the molecule,
the ring of said group being, besides $R^6$, optionally substituted further one or two times, differently or identically, with a $R^7$ group;
$R^2$ represents a group

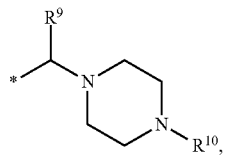

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-(methyl)-;
$R^7$ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-;
$R^9$ represents a hydrogen atom or a methyl group;
$R^{10}$ represents a —C(=O)$R^{12}$ group;
$R^{12}$ represents a group selected from 2,2,2-trifluoroethyl, cyclopropyl, (1-trifluoromethyl)-(cyclopropyl)-, 2,2-difluorocyclopropyl and 2,2-difluoro-1-methylcyclopropyl,
and stereoisomers, tautomers, N-oxides, hydrates, solvates, and salts thereof, and mixtures of same.

In accordance with a thirtieth embodiment of the first aspect, the present invention covers compounds of general formula (I), supra, in which:

$R^1$ represents a group selected from

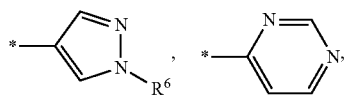

in which "*" represents the point of attachment to the rest of the molecule,
the ring of said group being, besides $R^6$, optionally substituted further one or two times, differently or identically, with a $R^7$ group;
$R^2$ represents a group

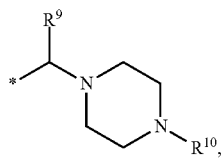

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;
$R^7$ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-;
$R^9$ represents a methyl group;
$R^{10}$ represents a —C(=O)R$^{12}$ group;
$R^{12}$ represents a group selected from 2,2,2-trifluoroethyl, cyclopropyl, (1-trifluoromethyl)-(cyclopropyl)-, 2,2-difluorocyclopropyl and 2,2-difluoro-1-methylcyclopropyl,
and stereoisomers, tautomers, N-oxides, hydrates, solvates, and salts thereof, and mixtures of same.

In accordance with a thirty-first embodiment of the first aspect, the present invention covers compounds of general formula (I), supra, in which:
$R^1$ represents a group selected from

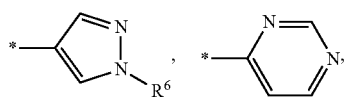

in which "*" represents the point of attachment to the rest of the molecule,
the ring of said group being, besides $R^6$, optionally substituted further one or two times, differently or identically, with a $R^7$ group;
$R^2$ represents a group

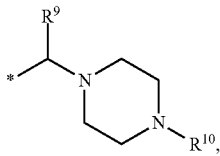

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;
$R^7$ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl, morpholinyl, methoxy, ethoxy, iso-propoxy and (cyclopropyl)-(methoxy)-;
$R^9$ represents a hydrogen atom or a methyl group;
$R^{11}$ represents a —C(=O)R$^{12}$ group;
$R^{12}$ represents a group selected from 2,2,2-trifluoroethyl, cyclopropyl, (1-trifluoromethyl)-(cyclopropyl)-,
and stereoisomers, tautomers, N-oxides, hydrates, solvates, and salts thereof, and mixtures of same.

In accordance with a thirty-second embodiment of the first aspect, the present invention covers compounds of general formula (I), supra, in which:
$R^1$ represents a group selected from

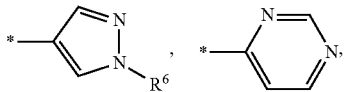

in which "*" represents the point of attachment to the rest of the molecule,
the ring of said group being, besides $R^6$, optionally substituted further one or two times, differently or identically, with a $R^7$ group;
$R^2$ represents a group

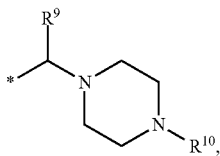

in which "*" represents the point of attachment to the rest of the molecule;
R³ represents a hydrogen atom;
R⁴ represents a hydrogen atom;
R⁵ represents a hydrogen atom;
R⁶ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;
R⁷ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl, morpholinyl, methoxy, ethoxy, iso-propoxy and (cyclopropyl)-(methoxy)-;
R⁹ represents a methyl group;
R¹⁰ represents a —C(=O)R¹² group;
R¹² represents a group selected from 2,2,2-trifluoroethyl, cyclopropyl, (1-trifluoromethyl)-(cyclopropyl)-,
and stereoisomers, tautomers, N-oxides, hydrates, solvates, and salts thereof, and mixtures of same.

In accordance with a thirty-third embodiment of the first aspect, the present invention covers compounds of general formula (I), supra, in which:
R¹ represents a group selected from

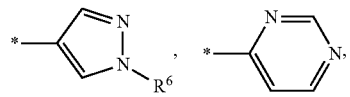

in which "*" represents the point of attachment to the rest of the molecule,
the ring of said group being, besides R⁶, optionally substituted with one further R⁷ group;
R² represents a group

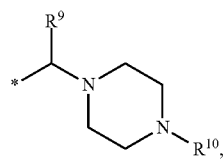

in which "*" represents the point of attachment to the rest of the molecule;
R³ represents a hydrogen atom;
R⁴ represents a hydrogen atom;
R⁵ represents a hydrogen atom;
R⁶ represents a group selected from methyl, ethyl, 2,2,2-trifluoroethyl, (cyclopropyl)-(methyl)- and (2,2-difluorocyclopropyl)-(methyl)-;
R⁷ represents a group selected from methyl, trifluoromethyl, methoxy, ethoxy, iso-propoxy and (cyclopropyl)-(methoxy)-;
R⁹ represents a hydrogen atom or a methyl group;
R¹⁰ represents a —C(=O)R¹² group;
R¹² represents a group selected from 2,2,2-trifluoroethyl, cyclopropyl, cyclobutyl and (cyclopropyl)-(methyl)-;
and stereoisomers, tautomers, N-oxides, hydrates, solvates, and salts thereof, and mixtures of same.

In accordance with an thirty-fourth embodiment of the first aspect, the present invention covers compounds of general formula (I), supra, in which:
R¹ represents a group selected from

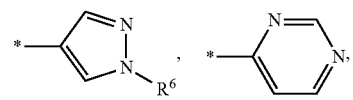

in which "*" represents the point of attachment to the rest of the molecule,
the ring of said group being, besides R⁶, optionally substituted with one further R⁷ group;
R² represents a group

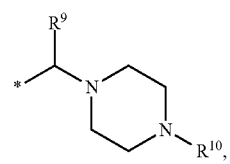

in which "*" represents the point of attachment to the rest of the molecule;
R³ represents a hydrogen atom;
R⁴ represents a hydrogen atom;
R⁵ represents a hydrogen atom;
R⁶ represents a group selected from methyl, ethyl, 2,2,2-trifluoroethyl, (cyclopropyl)-(methyl)- and (2,2-difluorocyclopropyl)-(methyl)-;
R⁷ represents a group selected from methyl, trifluoromethyl, methoxy, ethoxy, iso-propoxy and (cyclopropyl)-(methoxy)-;
R⁹ represents a methyl group;
R¹⁰ represents a —C(=O)R¹² group;
R¹² represents a group selected from 2,2,2-trifluoroethyl, cyclopropyl, cyclobutyl and (cyclopropyl)-(methyl)-;
and stereoisomers, tautomers, N-oxides, hydrates, solvates, and salts thereof, and mixtures of same.

In accordance with a thirty-fifth embodiment of the first aspect, the present invention covers compounds of general formula (I), supra, in which:
R¹ represents a group

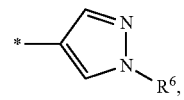

in which "*" represents the point of attachment to the rest of the molecule;

$R^2$ represents a group

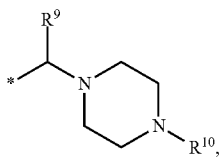

in which "*" represents the point of attachment to the rest of the molecule;
$R^3$ represents a hydrogen atom, a fluorine atom or a chlorine atom;
$R^4$ represents a hydrogen atom;
$R^5$ represents a hydrogen atom;
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;
$R^9$ represents a methyl group;
$R^{10}$ represents a $-C(=O)R^{12}$ group;
$R^{12}$ represents a group selected from 2,2,2-trifluoroethyl, cyclopropyl, (1-trifluoromethyl)-(cyclopropyl)-, cyclobutyl and (cyclopropyl)-(methyl)-,
and stereoisomers, tautomers, N-oxides, hydrates, solvates, and salts thereof, and mixtures of same.

In accordance with a thirty-sixth embodiment of the first aspect, the present invention covers compounds of general formula (I), supra, in which:
$R^1$ represents a group

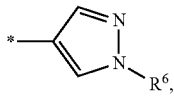

in which "*" represents the point of attachment to the rest of the molecule;
$R^2$ represents a group

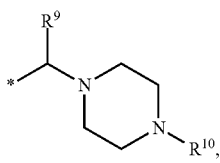

in which "*" represents the point of attachment to the rest of the molecule;
$R^3$ represents a hydrogen atom, a fluorine atom or a chlorine atom;
$R^4$ represents a hydrogen atom;
$R^5$ represents a hydrogen atom;
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-;
$R^9$ represents a methyl group;
$R^{10}$ represents a $-C(=O)R^{12}$ group;
$R^{12}$ represents a group selected from 2,2,2-trifluoroethyl, cyclopropyl, (1-trifluoromethyl)-(cyclopropyl)-, cyclobutyl and (cyclopropyl)-(methyl)-,
and stereoisomers, tautomers, N-oxides, hydrates, solvates, and salts thereof, and mixtures of same.

In accordance with a thirty-seventh embodiment of the first aspect, the present invention covers compounds of general formula (I), supra, in which:
$R^1$ represents a group

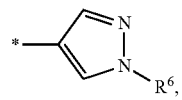

in which "*" represents the point of attachment to the rest of the molecule;
$R^2$ represents a group

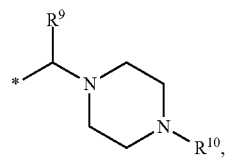

in which "*" represents the point of attachment to the rest of the molecule;
$R^3$ represents a hydrogen atom;
$R^4$ represents a hydrogen atom;
$R^5$ represents a hydrogen atom;
$R^6$ represents a group selected from methyl, ethyl, 2,2,2-trifluoroethyl, (cyclopropyl)-(methyl)- and (2,2-difluorocyclopropyl)-(methyl)-;
$R^9$ represents a methyl group;
$R^{10}$ represents a $-C(=O)R^{12}$ group;
$R^{12}$ represents a group selected from 2,2,2-trifluoroethyl, cyclopropyl, cyclobutyl and (cyclopropyl)-(methyl)-;
and stereoisomers, tautomers, N-oxides, hydrates, solvates, and salts thereof, and mixtures of same.

In accordance with a thirty-eighth embodiment of the first aspect, the present invention covers compounds of general formula (I), supra, in which:
$R^1$ represents a group selected from

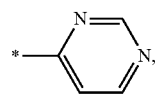

in which "*" represents the point of attachment to the rest of the molecule,
said group being optionally substituted one or two times, differently or identically, with a $R^7$ group;

R² represents a group

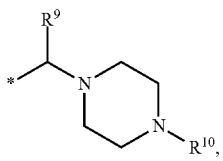

in which "*" represents the point of attachment to the rest of the molecule;
R³ represents a hydrogen atom;
R⁴ represents a hydrogen atom;
R⁵ represents a hydrogen atom;
R⁷ represents a group selected from methyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-;
R⁹ represents a methyl group;
R¹⁰ represents a —C(=O)R¹² group;
R¹² represents a group selected from 2,2,2-trifluoroethyl, cyclopropyl, (1-trifluoromethyl)-(cyclopropyl)-, 2,2-difluorocyclopropyl and 2,2-difluoro-1-methylcyclopropyl,
and stereoisomers, tautomers, N-oxides, hydrates, solvates, and salts thereof, and mixtures of same.

In accordance with a thirty-ninth embodiment of the first aspect, the present invention covers compounds of general formula (I), supra, in which:
R¹ represents a group selected from

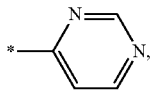

in which "*" represents the point of attachment to the rest of the molecule,
said group being optionally substituted one or two times, differently or identically, with a R⁷ group;
R² represents a group

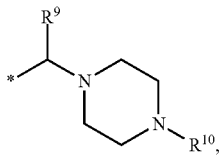

in which "*" represents the point of attachment to the rest of the molecule;
R³ represents a hydrogen atom;
R⁴ represents a hydrogen atom;
R⁵ represents a hydrogen atom;
R⁷ represents a group selected from methyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl, morpholinyl, methoxy, ethoxy, iso-propoxy and (cyclopropyl)-(methoxy)-;
R⁹ represents a methyl group;
R¹⁰ represents a —C(=O)R¹² group;
R¹² represents a group selected from 2,2,2-trifluoroethyl, cyclopropyl, (1-trifluoromethyl)-(cyclopropyl)-, cyclobutyl and (cyclopropyl)-(methyl)-,
and stereoisomers, tautomers, N-oxides, hydrates, solvates, and salts thereof, and mixtures of same.

In accordance with a fortieth embodiment of the first aspect, the present invention covers compounds of general formula (I), supra, in which:
R¹ represents a group selected from

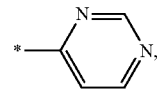

in which "*" represents the point of attachment to the rest of the molecule;
said group being optionally substituted with one R⁷ group,
R² represents a group

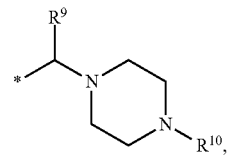

in which "*" represents the point of attachment to the rest of the molecule;
R³ represents a hydrogen atom;
R⁴ represents a hydrogen atom;
R⁵ represents a hydrogen atom;
R⁷ represents a group selected from methyl, trifluoromethyl, methoxy, ethoxy, iso-propoxy and (cyclopropyl)-(methoxy)-;
R⁹ represents a methyl group;
R¹⁰ represents a —C(=O)R¹² group;
R¹² represents a group selected from 2,2,2-trifluoroethyl, cyclopropyl, cyclobutyl and (cyclopropyl)-(methyl)-;
and stereoisomers, tautomers, N-oxides, hydrates, solvates, and salts thereof, and mixtures of same.

In accordance with an forty-first embodiment of the first aspect, the present invention covers compounds of general formula (I), supra, in which:
R¹ represents a group selected from

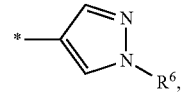

in which "*" represents the point of attachment to the rest of the molecule,
R² represents a group

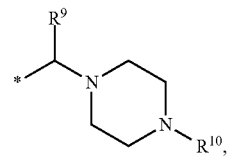

in which "*" represents the point of attachment to the rest of the molecule;

R³ represents a hydrogen atom;
R⁴ represents a hydrogen atom;
R⁵ represents a hydrogen atom;
R⁶ represents a hydrogen atom or a group selected from (C₃-C₄-cycloalkyl)-(methyl)- and C₂-C₄-fluoroalkyl,
  said (C₃-C₄-cycloalkyl)-(methyl)- group being optionally substituted one or two times with a fluorine atom or a methyl group;
R⁹ represents a hydrogen atom or a methyl group;
R¹⁰ represents a —C(=O)R¹² group;
R¹² represents a group selected from C₁-C₂-fluoroalkyl, C₃-C₄-cycloalkyl and (cyclopropyl)-(methyl)-;
and stereoisomers, tautomers, N-oxides, hydrates, solvates, and salts thereof, and mixtures of same.

In accordance with a forty-second embodiment of the first aspect, the present invention covers compounds of general formula (I), supra, in which:
R¹ represents a group selected from

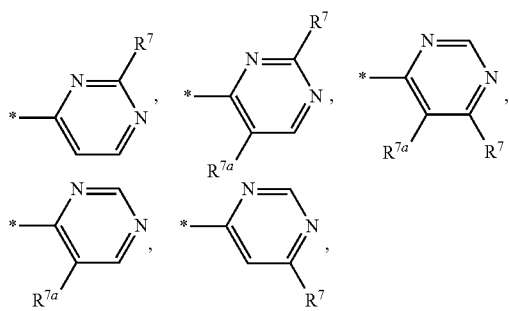

in which "*" represents the point of attachment to the rest of the molecule;
R² represents a group

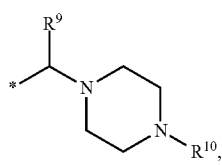

in which "*" represents the point of attachment to the rest of the molecule;
R³ represents a hydrogen atom;
R⁴ represents a hydrogen atom;
R⁵ represents a hydrogen atom;
R⁷ represents a chlorine atom or a group selected from C₁-C₃-alkyl, cyclopropyl, dimethylamino, cyclopropylamino, C₁-C₃-alkoxy and (cyclopropyl)-(methoxy)-;
R⁷ᵃ represents an additional R⁷ group, selected from a chlorine atom and a group selected from C₁-C₃-alkoxy and (cyclopropyl)-(methoxy)-;
R⁹ represents a hydrogen atom or a methyl group;
R¹⁰ represents a —C(=O)R¹² group;
R¹² represents a group selected from C₁-C₂-fluoroalkyl, C₃-C₄-cycloalkyl and (cyclopropyl)-(methyl)-;
and stereoisomers, tautomers, N-oxides, hydrates, solvates, and salts thereof, and mixtures of same.

Further Embodiments of the First Aspect of the Present Invention

In a further embodiment of the first aspect, the present invention covers compounds of formula (I), supra, in which:
R¹ represents a group selected from
  pyrazolyl, imidazolyl, oxadiazolyl, triazolyl, isoxazolyl, thienyl, pyridin-2-yl, pyridin-4-yl, pyrimidinyl, triazinyl and pyrazinyl, said group being optionally substituted with one R⁶ group, and said group being, additionally, optionally substituted one or two times, differently or identically, with a R⁷ group, or
R¹ represents a group selected from

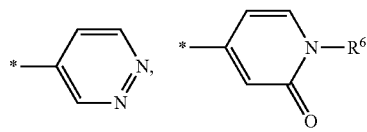

the ring of said group being, besides R⁶, optionally substituted further one or two times, differently or identically, with a R⁷ group,
in which "*" represents the point of attachment to the rest of the molecule, or
R¹ represents a group selected from pyridine-3-yl or pyridazin-3-yl, optionally substituted with one R⁸ group,
and stereoisomers, tautomers, N-oxides, hydrates, solvates, and salts thereof, and mixtures of same.

In a further embodiment of the first aspect, the present invention covers compounds of formula (I), supra, in which:
R¹ represents a group selected from
  pyrazolyl, imidazolyl, oxadiazolyl, triazolyl, isoxazolyl, thienyl, pyridin-2-yl, pyridin-4-yl, pyrimidinyl, triazinyl and pyrazinyl, said group being optionally substituted with one R⁶ group, and said group being, additionally, optionally substituted one or two times, differently or identically, with a R⁷ group,
and stereoisomers, tautomers, N-oxides, hydrates, solvates, and salts thereof, and mixtures of same.

In a further embodiment of the first aspect, the present invention covers compounds of formula (I), supra, in which:
R¹ represents a group selected from pyrazolyl, imidazolyl, oxadiazolyl, triazolyl, pyridin-2-yl, pyridin-4-yl, pyrimidinyl and pyrazinyl, said group being optionally substituted with one R⁶ group, and said group being, additionally, optionally substituted one or two times, differently or identically, with a R⁷ group, or
R¹ represents a group selected from

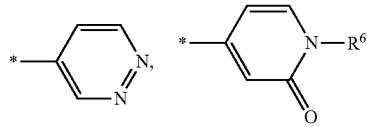

the ring of said group being, besides R⁶, optionally substituted further one or two times, differently or identically, with a R⁷ group,
in which "*" represents the point of attachment to the rest of the molecule, or $R^1$ represents a group selected from pyridine-3-yl or pyridazin-3-yl, optionally substituted with one $R^8$ group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from
  pyrazolyl, imidazolyl, oxadiazolyl, triazolyl, pyridin-2-yl, pyridin-4-yl, pyrimidinyl and pyrazinyl, said group being optionally substituted with one $R^6$ group, and said group being, additionally, optionally substituted one or two times, differently or identically, with a $R^7$ group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

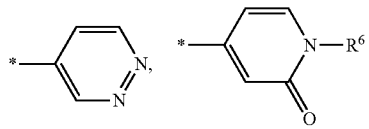

the ring of said group being, besides $R^6$, optionally substituted further one or two times, differently or identically, with a $R^7$ group,
in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from pyridine-3-yl or pyridazin-3-yl, optionally substituted with one $R^8$ group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

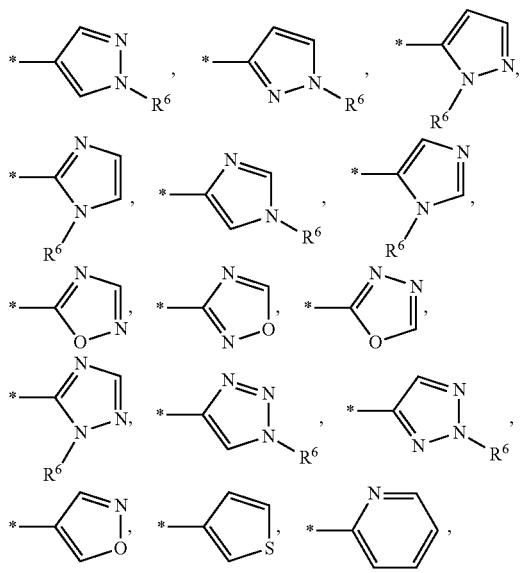

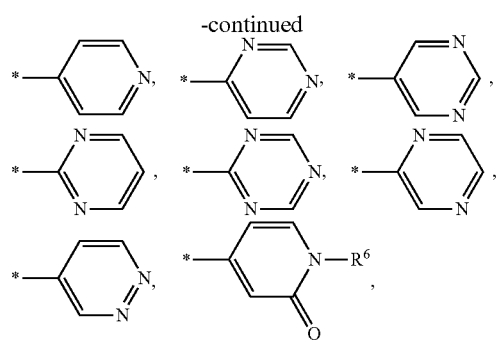

in which "*" represents the point of attachment to the rest of the molecule,
the ring of said group being, besides $R^6$, optionally substituted further one or two times, differently or identically, with a $R^7$ group, or
$R^1$ represents a group selected from

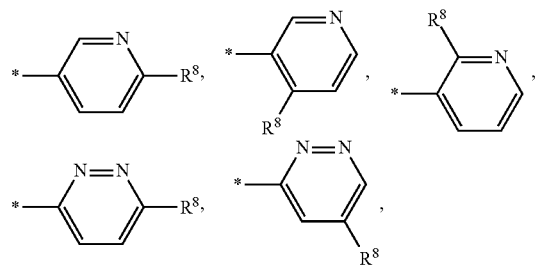

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

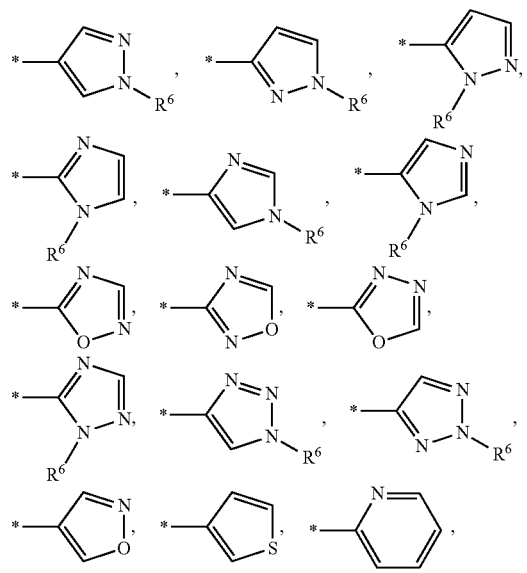

-continued

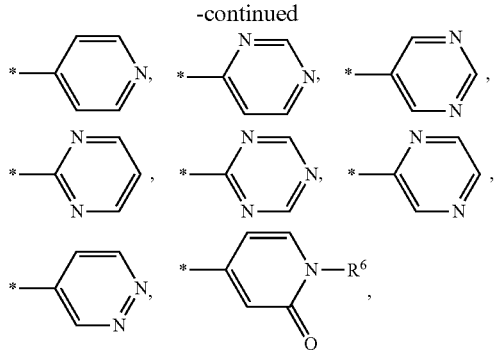

in which "*" represents the point of attachment to the rest of the molecule, the ring of said group being, besides $R^6$, optionally substituted further one or two times, differently or identically, with a $R^7$ group, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from

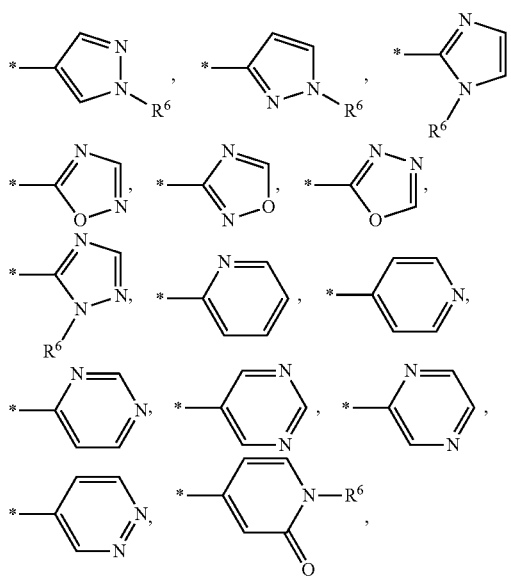

in which "*" represents the point of attachment to the rest of the molecule, the ring of said group being, besides $R^6$, optionally substituted further one or two times, differently or identically, with a $R^7$ group, or $R^1$ represents a group selected from

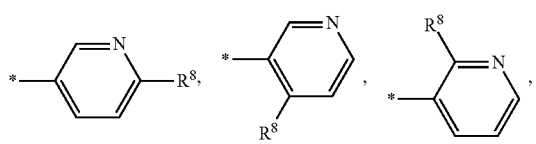

-continued

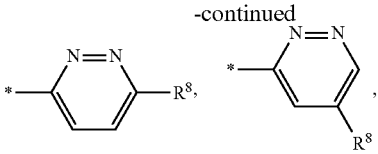

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from

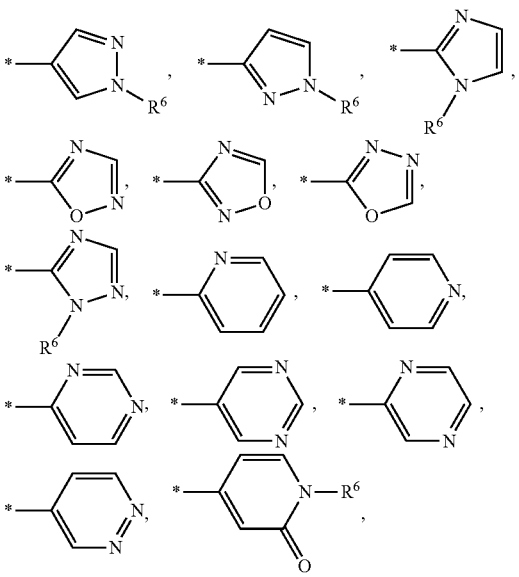

in which "*" represents the point of attachment to the rest of the molecule, the ring of said group being, besides $R^6$, optionally substituted further one or two times, differently or identically, with a $R^7$ group, and stereoisomers, tautomers, N-oxides, hydrates, solvates, and salts thereof, and mixtures of same.

In a further embodiment of the first aspect, the present invention covers compounds of formula (I), supra, in which:

$R^1$ represents a group selected from

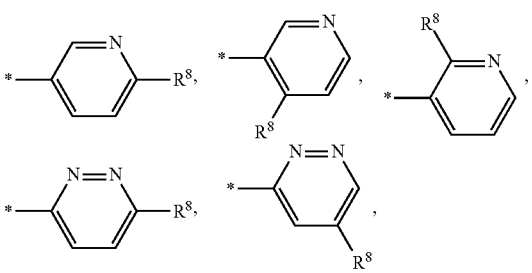

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

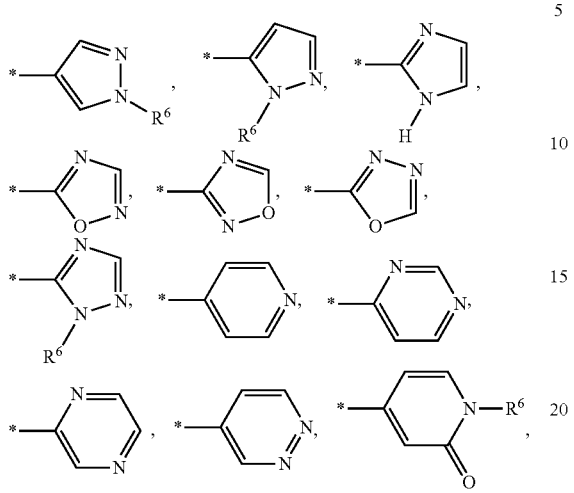

in which "*" represents the point of attachment to the rest of the molecule,
the ring of said group being, besides $R^6$, optionally substituted further one or two times, differently or identically, with a $R^7$ group, or
$R^1$ represents a group selected from

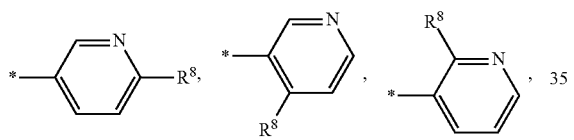

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

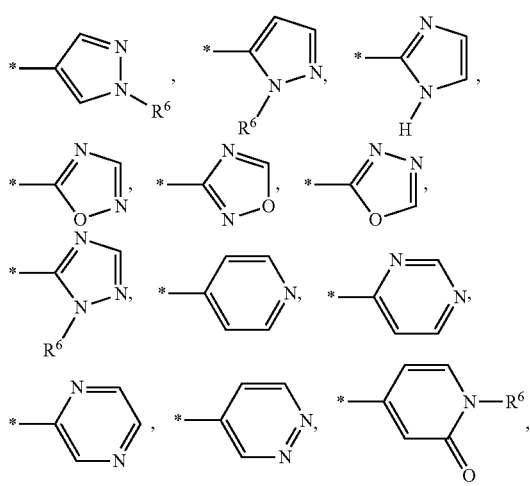

in which "*" represents the point of attachment to the rest of the molecule,
the ring of said group being, besides $R^6$, optionally substituted further one or two times, differently or identically, with a $R^7$ group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

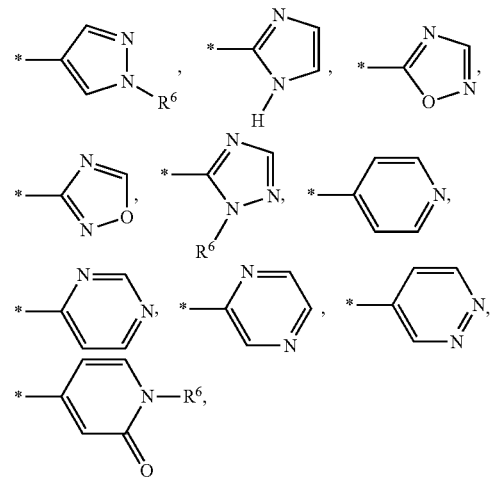

in which "*" represents the point of attachment to the rest of the molecule,
the ring of said group being, besides $R^6$, optionally substituted further one or two times, differently or identically, with a $R^7$ group, or
$R^1$ represents a group selected from

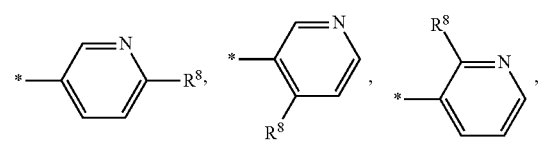

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

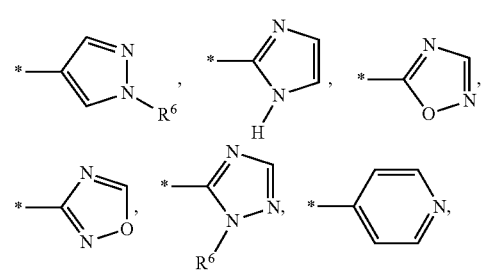

-continued

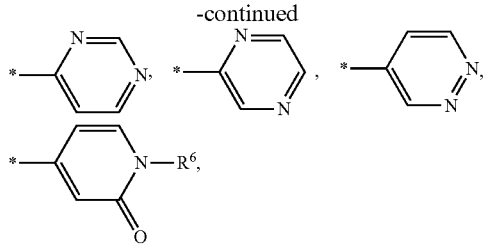

in which "*" represents the point of attachment to the rest of the molecule,
the ring of said group being, besides $R^6$, optionally substituted further one or two times, differently or identically, with a $R^7$ group, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

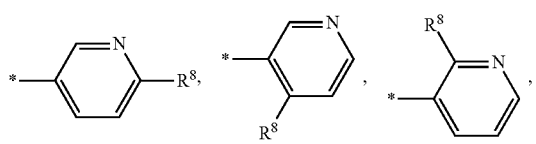

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

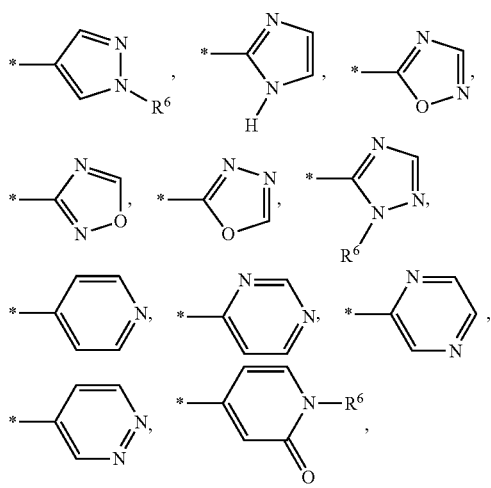

in which "*" represents the point of attachment to the rest of the molecule,
the ring of said group being, besides $R^6$, optionally substituted further one or two times, differently or identically, with a $R^7$ group, or $R^1$ represents a group selected from

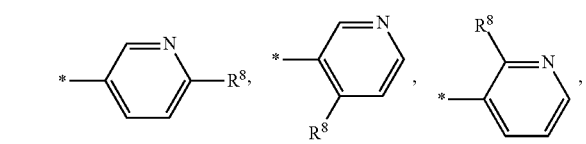

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

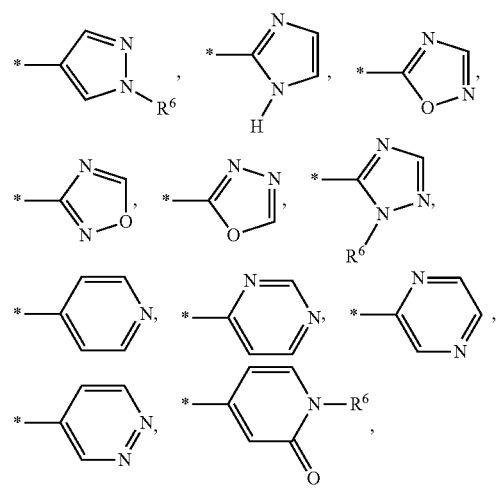

in which "*" represents the point of attachment to the rest of the molecule,
the ring of said group being, besides $R^6$, optionally substituted further one or two times, differently or identically, with a $R^7$ group, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

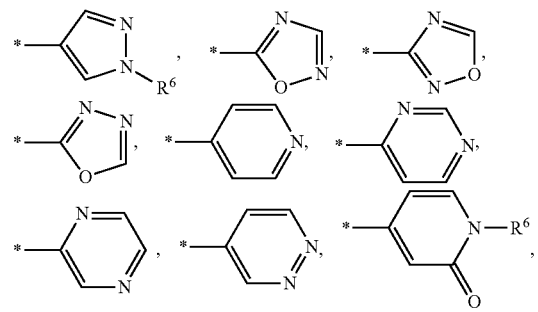

in which "*" represents the point of attachment to the rest of the molecule,
the ring of said group being, besides $R^6$, optionally substituted further one or two times, differently or identically, with a $R^7$ group, and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

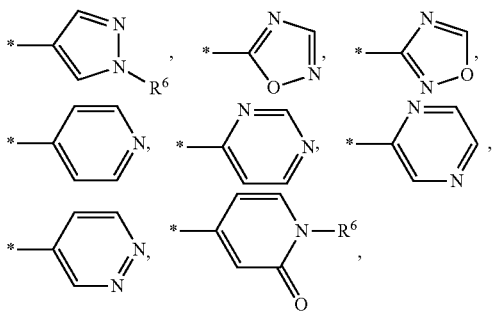

in which "*" represents the point of attachment to the rest of the molecule,
the ring of said group being, besides $R^6$, optionally substituted with one further $R^7$ group,
and stereoisomers, tautomers, N-oxides, hydrates, solvates, and salts thereof, and mixtures of same.

In a further embodiment of the first aspect, the present invention covers compounds of formula (I), supra, in which:
$R^1$ represents a group selected from

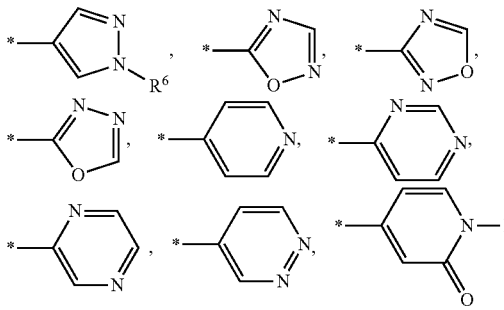

in which "*" represents the point of attachment to the rest of the molecule,
the ring of said group being, besides $R^6$, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

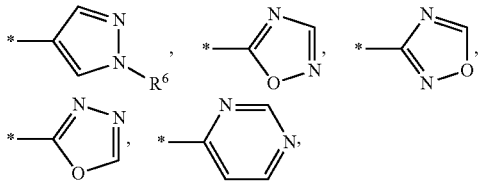

in which "*" represents the point of attachment to the rest of the molecule,
the ring of said group being, besides $R^6$, optionally substituted further one or two times, differently or identically, with a $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

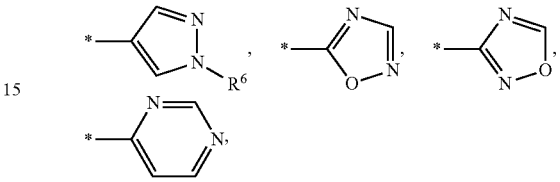

in which "*" represents the point of attachment to the rest of the molecule,
the ring of said group being, besides $R^6$, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

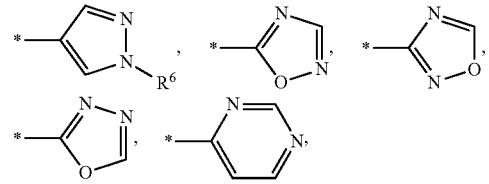

in which "*" represents the point of attachment to the rest of the molecule,
the ring of said group being, besides $R^6$, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

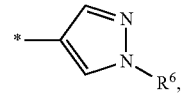

in which "*" represents the point of attachment to the rest of the molecule,
the ring of said group being, besides $R^6$, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

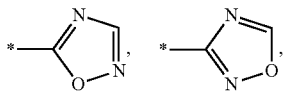

in which "*" represents the point of attachment to the rest of the molecule,
the ring of said group being, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

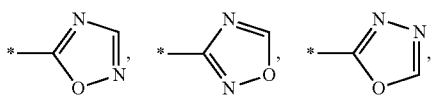

in which "*" represents the point of attachment to the rest of the molecule,
the ring of said group being, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

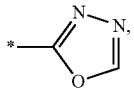

the ring of said group being, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

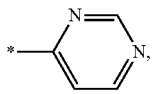

in which "*" represents the point of attachment to the rest of the molecule,
the ring of said group being, optionally substituted with one further $R^7$ group,
and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group

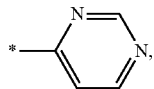

in which "*" represents the point of attachment to the rest of the molecule; the ring of said group being optionally substituted with one or two further $R^7$ groups,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

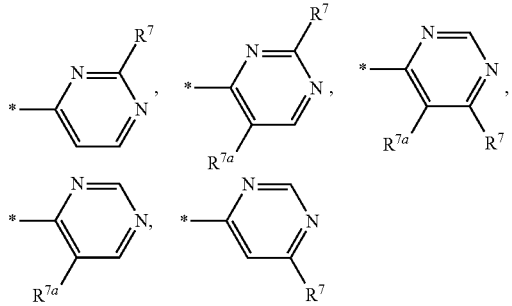

in which "*" represents the point of attachment to the rest of the molecule;
and in which $R^7$ represents a chlorine atom or a group selected from $C_1$-$C_3$-alkyl, cyclopropyl, dimethylamino, cyclopropylamino, $C_1$-$C_3$-alkoxy and (cyclopropyl)-(methoxy)-,
and $R^{7a}$ represents an additional $R^7$ group, selected from a chlorine atom and a group selected from $C_1$-$C_6$-alkoxy and (cyclopropyl)-(methoxy)-;
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

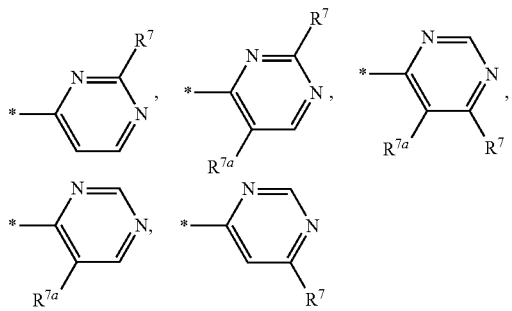

in which "*" represents the point of attachment to the rest of the molecule;
and in which $R^7$ represents a chlorine atom or a group selected from $C_1$-$C_3$-alkyl, $C_1$-$C_3$-alkoxy, and (cyclopropyl)-(methoxy)-,
and $R^{7a}$ represents an additional $R^7$ group, representing a $C_1$-$C_3$-alkoxy group;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

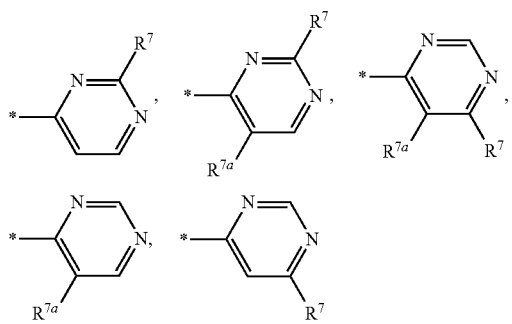

in which "*" represents the point of attachment to the rest of the molecule;

and in which $R^7$ represents a group selected from $C_1$-$C_3$-alkyl, $C_1$-$C_3$-alkoxy, and (cyclopropyl)-(methoxy)-, and $R^{7a}$ represents an additional $R^7$ group, representing a $C_1$-$C_3$-alkoxy group;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

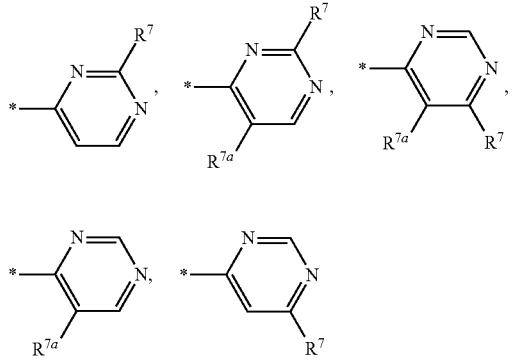

in which "*" represents the point of attachment to the rest of the molecule;

and in which $R^7$ represents a group selected from $C_1$-$C_3$-alkyl, $C_1$-$C_3$-alkoxy and (cyclopropyl)-(methoxy)-, and $R^{7a}$ represents an additional $R^7$ group, representing a methoxy group;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

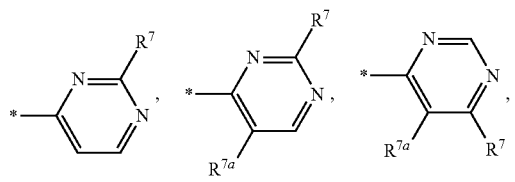

in which "*" represents the point of attachment to the rest of the molecule;

and in which $R^7$ represents a chlorine atom or a group selected from $C_1$-$C_3$-alkyl, $C_1$-$C_3$-alkoxy and (cyclopropyl)-(methoxy)-, and $R^{7a}$ represents an additional $R^7$ group selected from a chlorine atom and a group selected from $C_1$-$C_3$-alkoxy and (cyclopropyl)-(methoxy)-;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

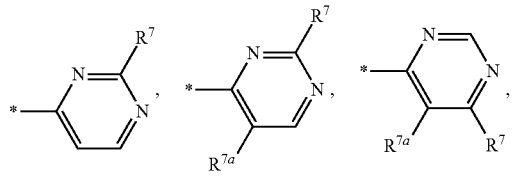

in which "*" represents the point of attachment to the rest of the molecule;

and in which $R^7$ represents a group selected from methyl, methoxy and (cyclopropyl)-(methoxy)-, and $R^{7a}$ represents an additional $R^7$ group selected from methoxy and (cyclopropyl)-(methoxy)-;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

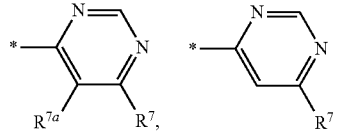

in which "*" represents the point of attachment to the rest of the molecule;

and in which $R^7$ represents a group selected from $C_1$-$C_3$-alkyl, $C_1$-$C_3$-alkoxy, and (cyclopropyl)-(methoxy)-, and $R^{7a}$ represents an additional $R^7$ group, representing a $C_1$-$C_3$-alkoxy group;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

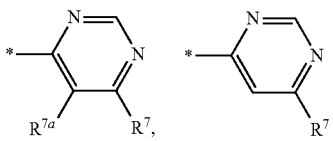

in which "*" represents the point of attachment to the rest of the molecule;
and in which $R^7$ represents a group selected from $C_1$-$C_3$-alkyl, $C_1$-$C_3$-alkoxy and (cyclopropyl)-(methoxy)-,
and $R^{7a}$ represents an additional $R^7$ group, representing a methoxy group;
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

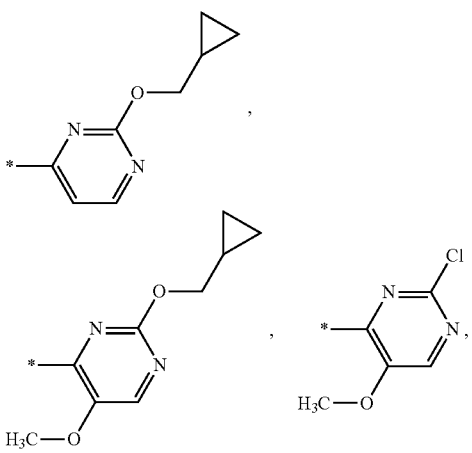

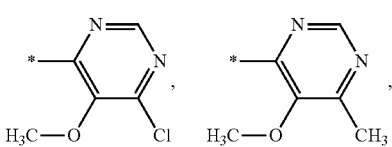

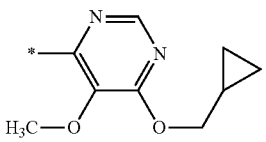

in which "*" represents the point of attachment to the rest of the molecule;
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

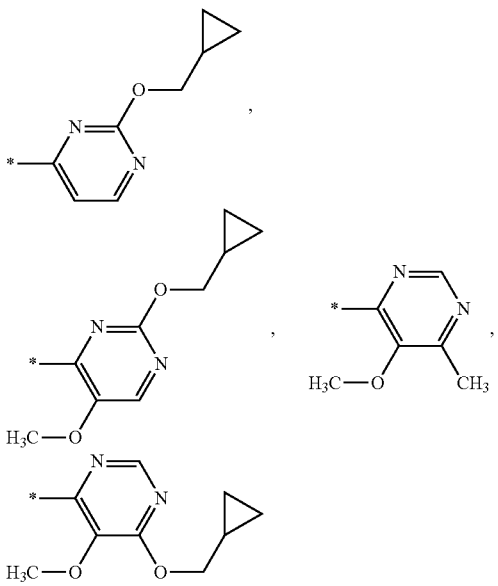

in which "*" represents the point of attachment to the rest of the molecule;
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

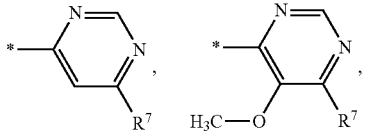

in which "*" represents the point of attachment to the rest of the molecule, and in which $R^7$ represents a group selected from methyl, trifluoromethyl, cyclopropyl, methoxy, ethoxy, iso-propoxy, 2,2,2-trifluoroethoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group selected from

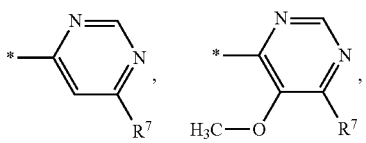

in which "*" represents the point of attachment to the rest of the molecule, and in which $R^7$ represents a group selected from methyl, trifluoromethyl, cyclopropyl, methoxy, ethoxy, iso-propoxy and (cyclopropyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

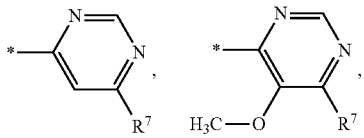

in which "*" represents the point of attachment to the rest of the molecule, and in which R⁷ represents an iso-propoxy group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

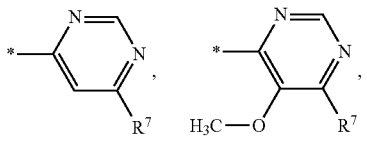

in which "*" represents the point of attachment to the rest of the molecule, and in which R⁷ represents a 2,2,2-trifluoroethoxy group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

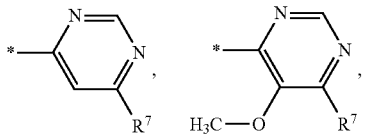

in which "*" represents the point of attachment to the rest of the molecule, and in which R⁷ represents a group selected from methyl, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl and morpholinyl, and stereoisomers, tautomers, N-oxides, hydrates, solvates, and salts thereof, and mixtures of same.

In a particular further embodiment of the first aspect, present invention covers compounds of formula (I), supra, in which:

R¹ represents a group

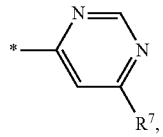

in which "*" represents the point of attachment to the rest of the molecule, and in which R⁷ represents a group selected from ethylamino, isopropylamino, cyclopropylamino, cyclobutylamino, dimethylamino, azetidin-1-yl and 3,3-difluoroazetidin-1-yl, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

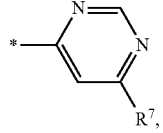

in which "*" represents the point of attachment to the rest of the molecule, and in which R⁷ represents a group selected from isopropylamino, cyclopropylamino, cyclobutylamino, dimethylamino, azetidin-1-yl and 3,3-difluoroazetidin-1-yl, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

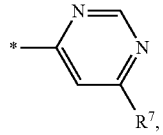

in which "*" represents the point of attachment to the rest of the molecule, and in which R⁷ represents a group selected from (methoxy)-(methyl)- and (cyclopropyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

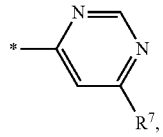

in which "*" represents the point of attachment to the rest of the molecule,
and in which $R^7$ represents a ethylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

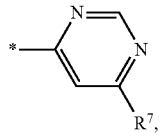

in which "*" represents the point of attachment to the rest of the molecule,
and in which $R^7$ represents a isopropylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

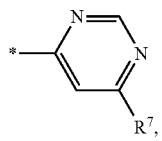

in which "*" represents the point of attachment to the rest of the molecule,
and in which $R^7$ represents a cyclopropylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

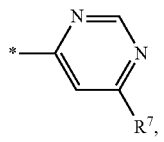

in which "*" represents the point of attachment to the rest of the molecule,
and in which $R^7$ represents a cyclobutylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

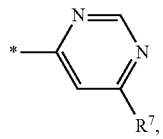

in which "*" represents the point of attachment to the rest of the molecule,
and in which $R^7$ represents a dimethylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

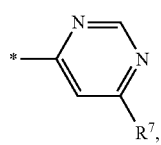

in which "*" represents the point of attachment to the rest of the molecule,
and in which $R^7$ represents a azetidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

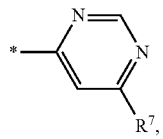

in which "*" represents the point of attachment to the rest of the molecule,
and in which $R^7$ represents a 3,3-difluoroazetidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

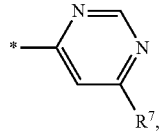

in which "*" represents the point of attachment to the rest of the molecule,
and in which $R^7$ represents a (methoxy)-(methyl)- group,
and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

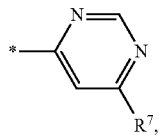

in which "*" represents the point of attachment to the rest of the molecule, and in which R⁷ represents a (cyclopropyl)-(methoxy)- group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

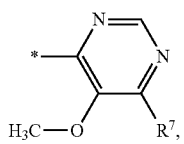

in which "*" represents the point of attachment to the rest of the molecule, and in which R⁷ represents a group selected from methyl, (cyclopropyl)-(methyl)-amino-, azetidin-1-yl, 3,3-difluoroazetidin-1-yl and pyrrolidin-1-yl, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

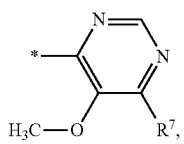

in which "*" represents the point of attachment to the rest of the molecule, and in which R⁷ represents a group selected from azetidin-1-yl, 3,3-difluoroazetidin-1-yl and pyrrolidin-1-yl, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

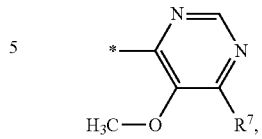

in which "*" represents the point of attachment to the rest of the molecule, and in which R⁷ represents a methyl group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

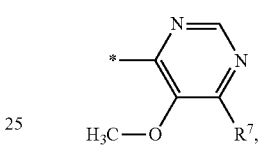

in which "*" represents the point of attachment to the rest of the molecule, and in which R⁷ represents a (cyclopropyl)-(methyl)-amino- group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

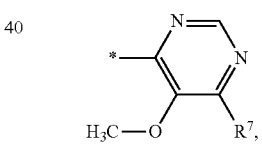

in which "*" represents the point of attachment to the rest of the molecule, and in which R⁷ represents a azetidin-1-yl group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

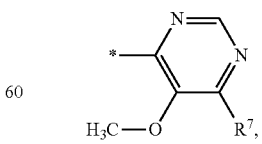

in which "*" represents the point of attachment to the rest of the molecule, and in which R⁷ represents a 3,3-difluoroazetidin-1-yl group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

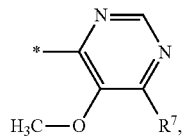

in which "*" represents the point of attachment to the rest of the molecule, and in which R⁷ represents a pyrrolidin-1-yl group, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

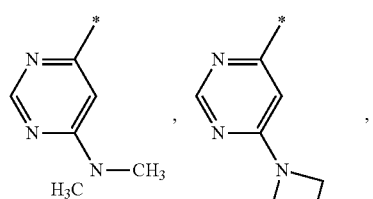

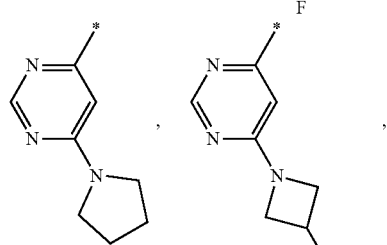

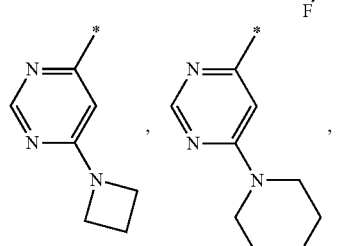

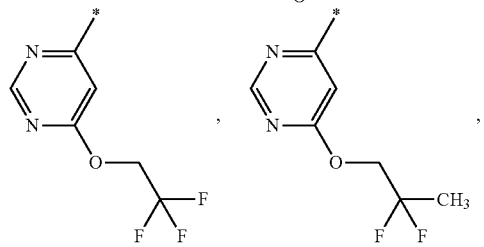

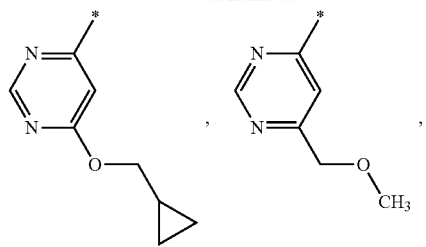

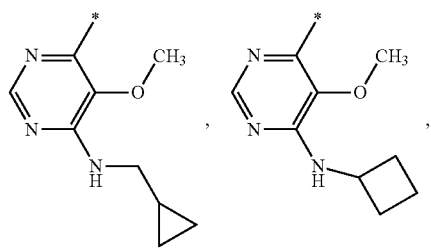

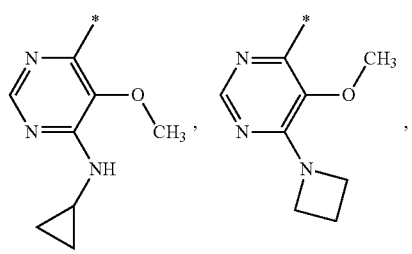

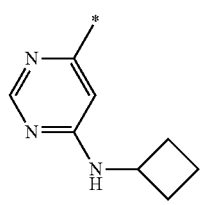

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

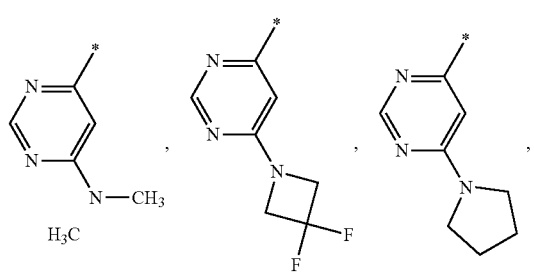

-continued

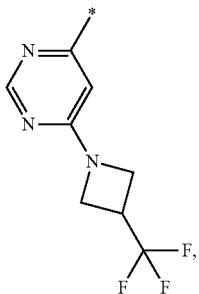

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

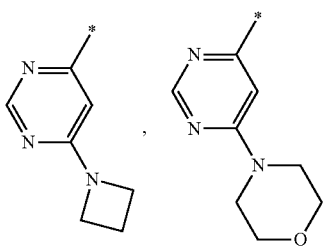

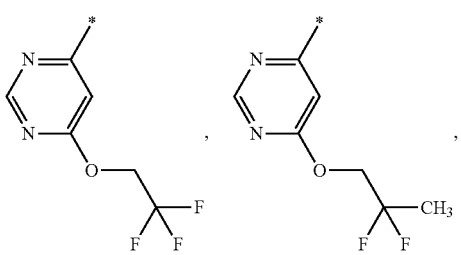

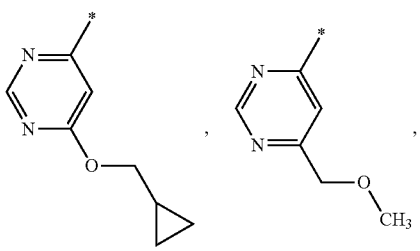

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group selected from

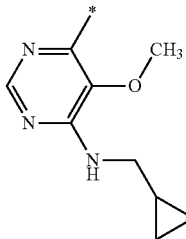 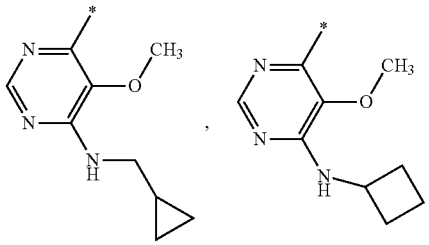

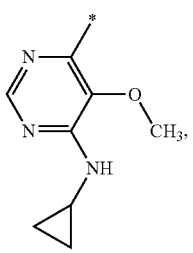 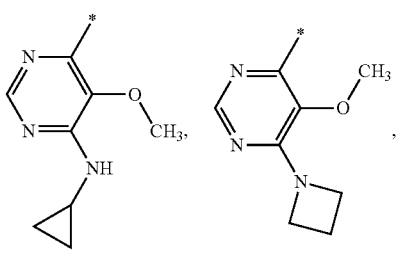

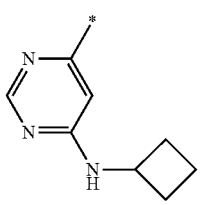

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

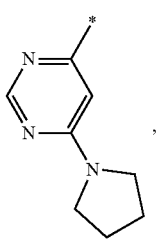 [SMILES: *c1cc(N2CCCC2)ncn1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

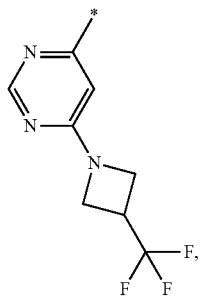 [SMILES: *c1cc(N2CC(C(F)(F)F)C2)ncn1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

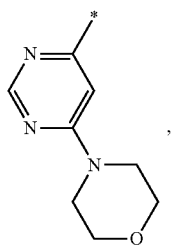 [SMILES: *c1cc(N2CCOCC2)ncn1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

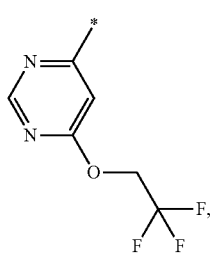 [SMILES: *c1cc(OCC(F)(F)F)ncn1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

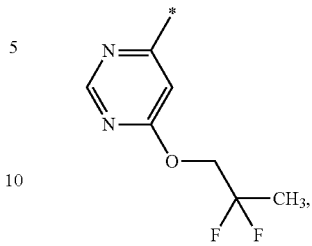

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

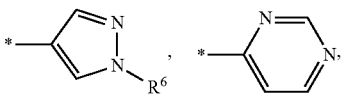

in which "*" represents the point of attachment to the rest of the molecule;
the ring of said group being, besides R⁶, optionally substituted further one or two times, differently or identically, with a R⁷ group;

and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

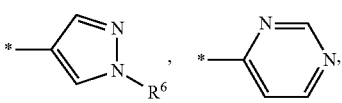

in which "*" represents the point of attachment to the rest of the molecule;
the ring of said group being, besides R⁶, optionally substituted with one or two further R⁷ groups, and stereoisomers, tautomers, N-oxides, hydrates, solvates, and salts thereof, and mixtures of same.

In a particular further embodiment of the first aspect, the present invention covers compounds of formula (I), supra, in which:

R¹ represents a group

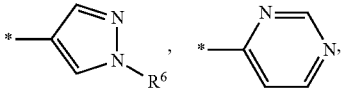

in which "*" represents the point of attachment to the rest of the molecule;
the ring of said group being, besides R⁶, optionally substituted with one further R⁷ group, and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

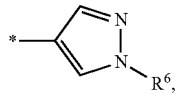

in which "*" represents the point of attachment to the rest of the molecule;
the ring of said group being, besides R⁶, optionally substituted with one or two further R⁷ groups,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

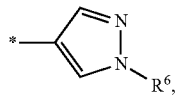

in which "*" represents the point of attachment to the rest of the molecule;
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

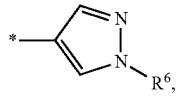

in which "*" represents the point of attachment to the rest of the molecule; and
R⁶ represents a (cycloalkyl)-(methyl)-group,
said (cycloalkyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

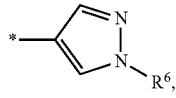

in which "*" represents the point of attachment to the rest of the molecule; and
R⁶ represents a hydrogen atom or a group selected from ($C_3$-$C_4$-cycloalkyl)-(methyl)- and $C_2$-$C_4$-fluoroalkyl,
said ($C_3$-$C_4$-cycloalkyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

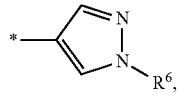

in which "*" represents the point of attachment to the rest of the molecule; and
R⁶ represents a group selected from (cyclopropyl)-(methyl)-, (cyclobutyl)-(methyl)- and 2,2,2-trifluoroethyl,
said (cyclopropyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

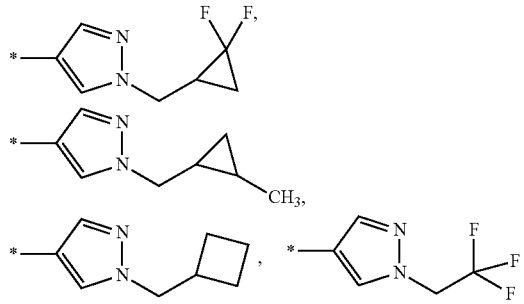

in which "*" represents the point of attachment to the rest of the molecule;
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

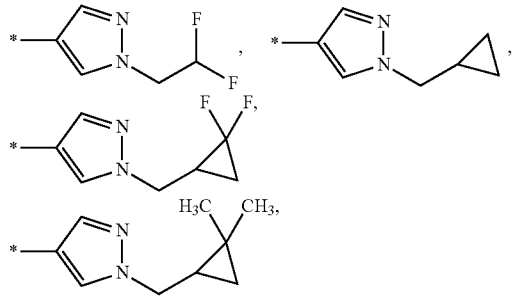

-continued

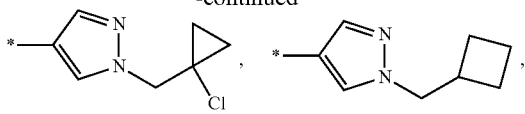

in which "*" represents the point of attachment to the rest of the molecule;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group selected from

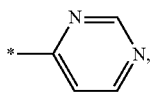

in which "*" represents the point of attachment to the rest of the molecule, said group being optionally substituted one or two times, differently or identically, with a $R^7$ group;

and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group

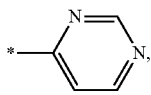

in which "*" represents the point of attachment to the rest of the molecule; said group being optionally substituted with one $R^7$ group, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from

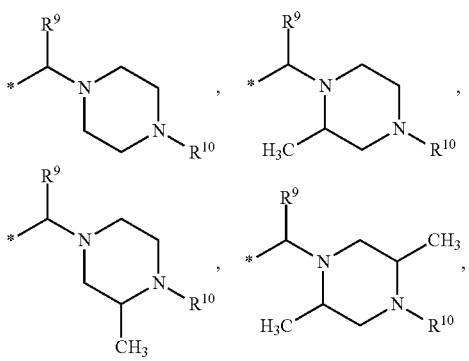

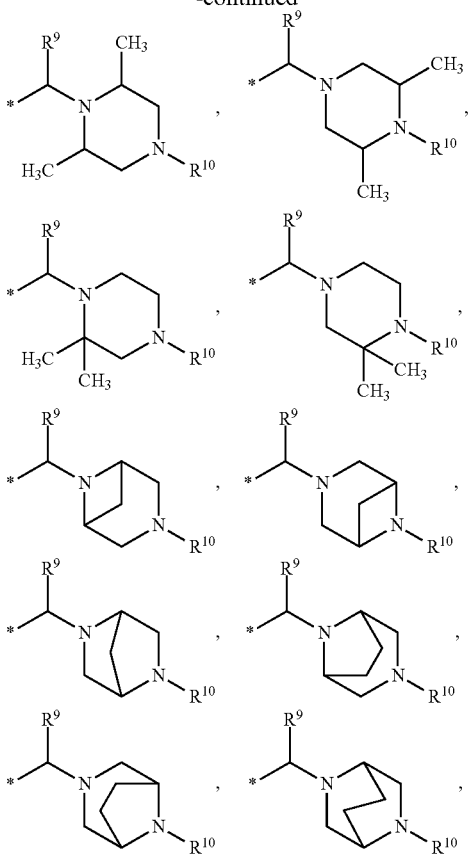

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group selected from

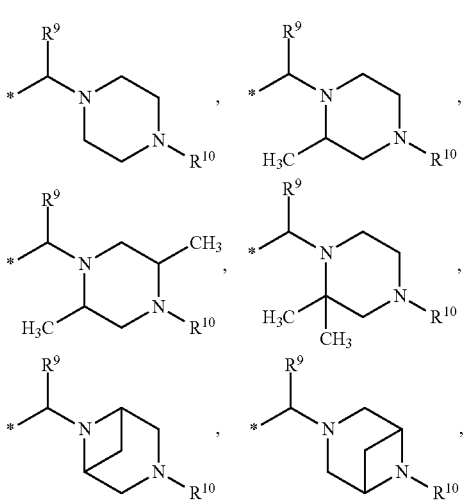

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:
R² represents a group selected from

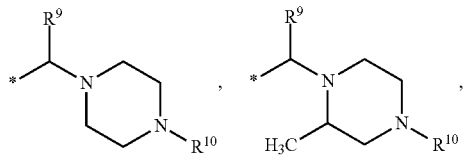

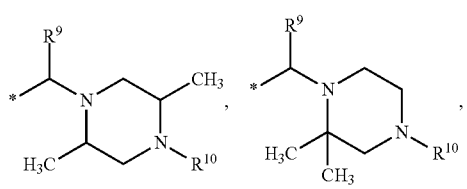

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
R² represents a group selected from

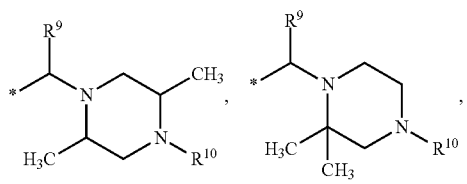

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
R² represents a group

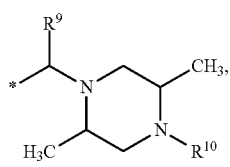

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
R² represents a group

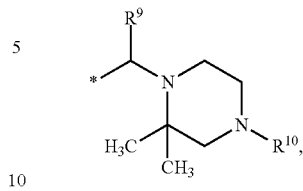

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
R² represents a group selected from

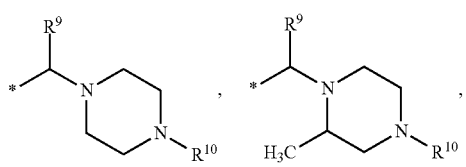

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:
R² represents a group

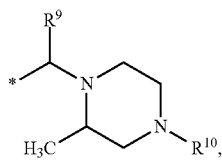

and stereoisomers, tautomers, N-oxides, hydrates, solvates, and salts thereof, and mixtures of same.

In a particular further embodiment of the first aspect, the present invention covers compounds of formula (I), supra, in which:
R² represents a group

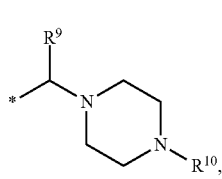

in which "*" represents the point of attachment to the rest of the molecule,
and stereoisomers, tautomers, N-oxides, hydrates, solvates, and salts thereof, and mixtures of same.

In a further embodiment of the first aspect, the present invention covers compounds of formula (I), supra, in which:

$R^2$ represents a group

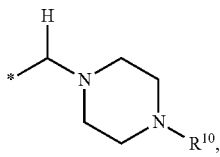

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

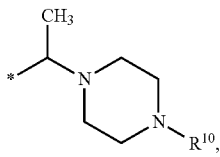

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

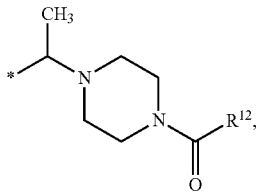

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

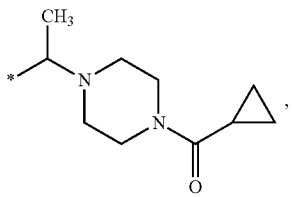 [SMILES: *C(C)N1CCN(C(=O)C2CC2)CC1]

-continued

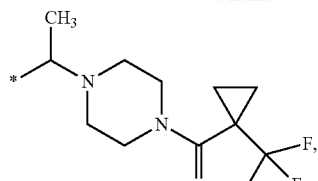

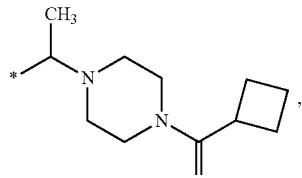

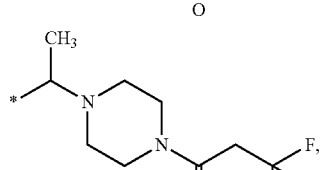

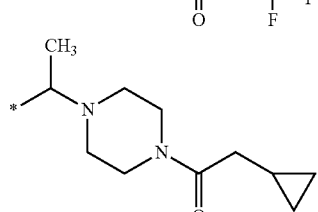

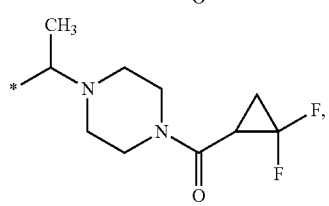

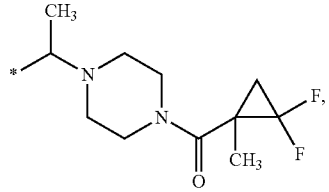

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

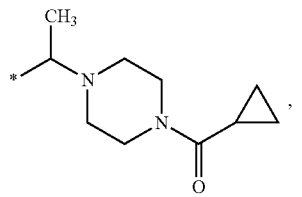

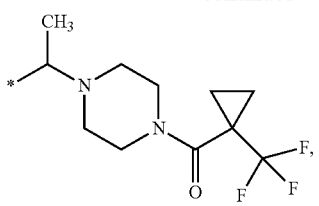 [SMILES: *C(C)N1CCN(C(=O)C2(C(F)(F)F)CC2)CC1]

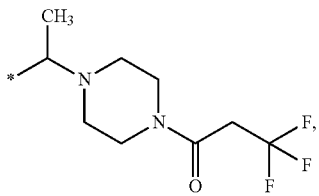

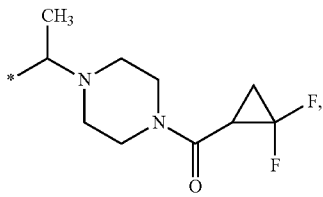

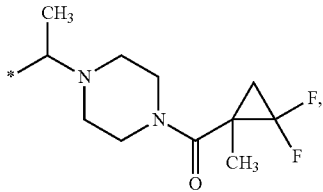

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

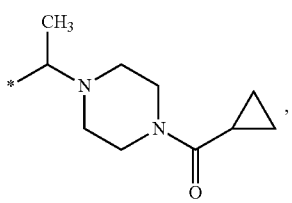

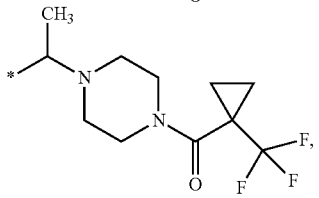

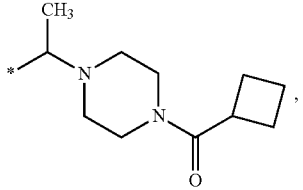

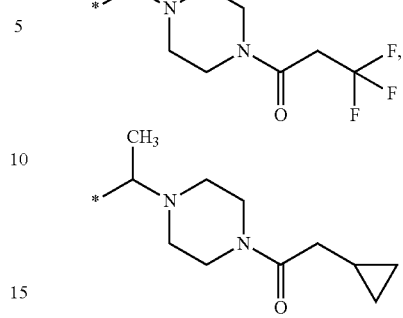

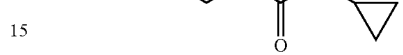

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

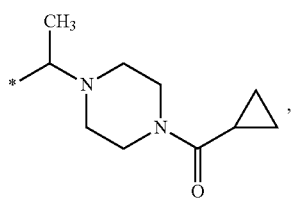

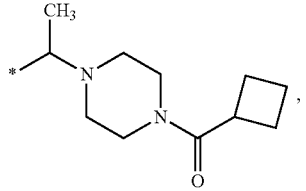 [SMILES: *C(C)N1CCN(C(=O)C2CCC2)CC1]

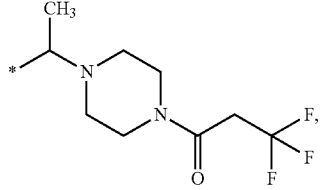 [SMILES: *C(C)N1CCN(C(=O)CC(F)(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

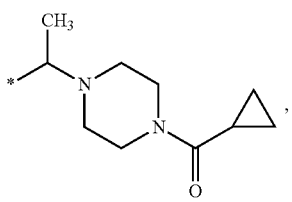

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

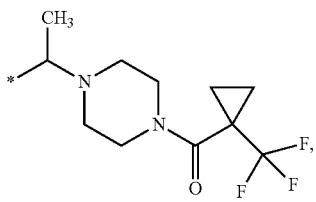

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

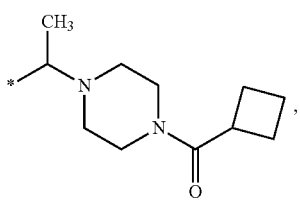

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

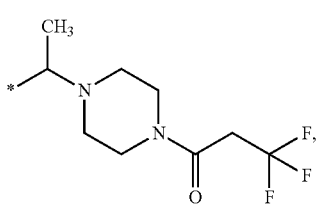

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

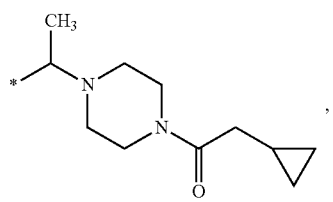 [SMILES: *C(C)N1CCN(C(=O)CC2CC2)CC1]

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

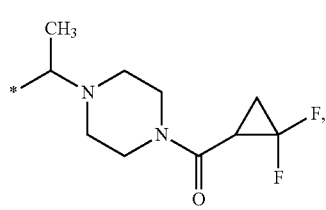 [SMILES: *C(C)N1CCN(C(=O)C2CC2(F)F)CC1]

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

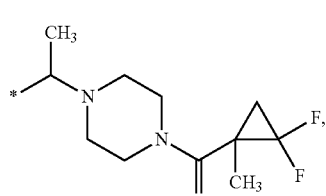

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

R² represents a group

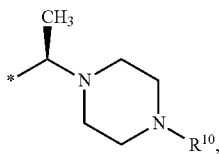

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

R² represents a group

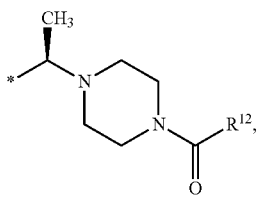

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

R² represents a group selected from

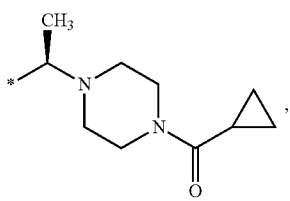 [SMILES: *[C@@H](C)N1CCN(C(=O)C2CC2)CC1]

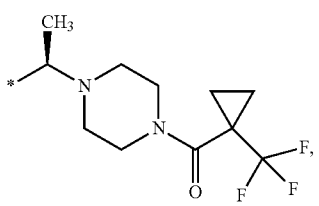 [SMILES: *[C@@H](C)N1CCN(C(=O)C2(C(F)(F)F)CC2)CC1]

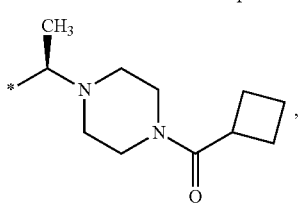

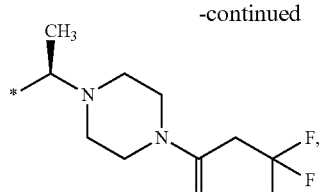

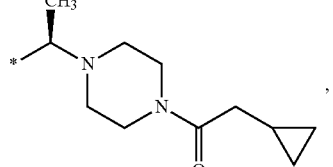

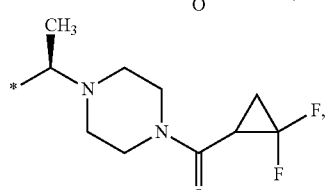

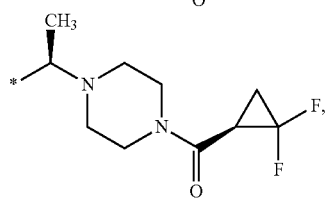

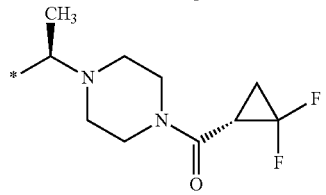

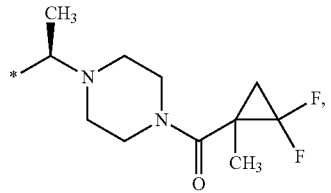

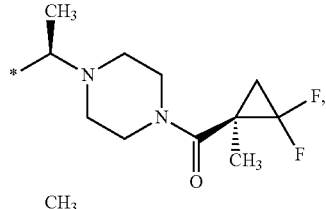

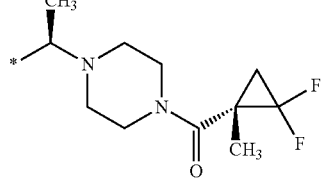

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

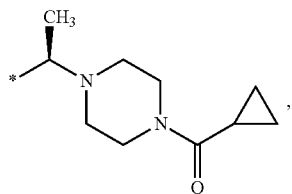

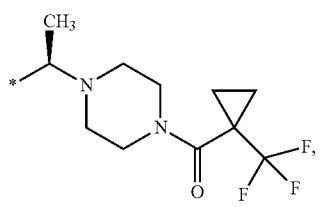

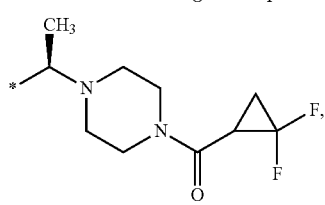

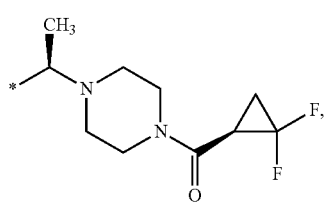

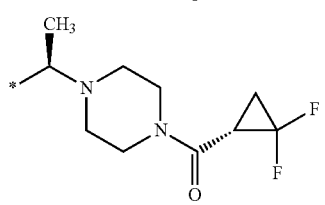

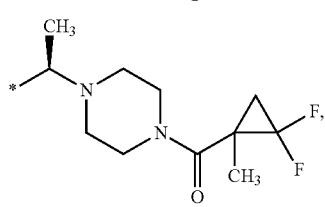

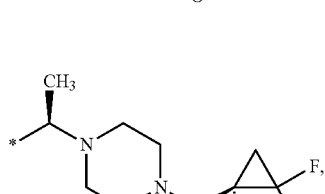

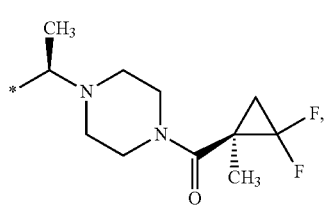

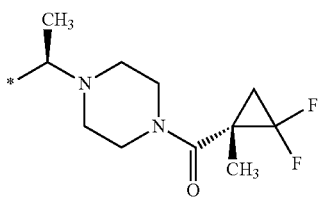

and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

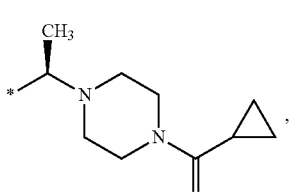

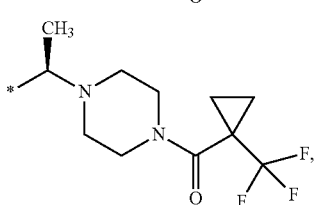

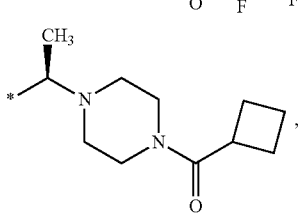

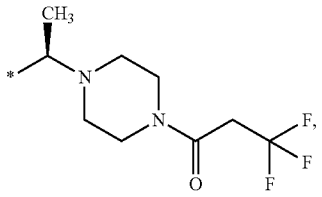 [SMILES: *[C@@H](C)N1CCN(C(=O)CC(F)(F)F)CC1]

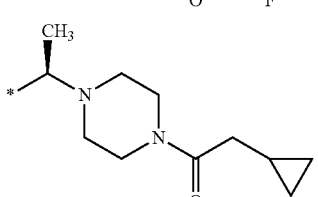

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

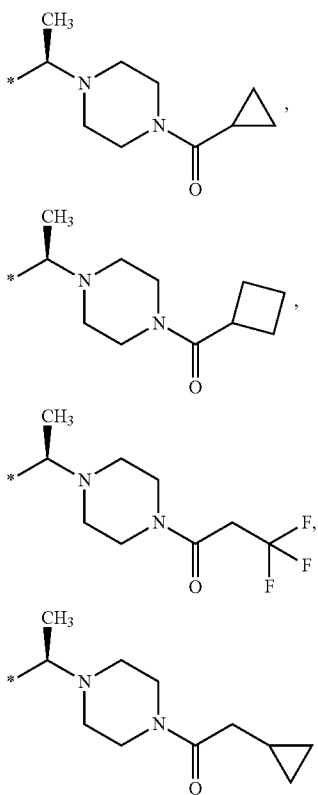

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

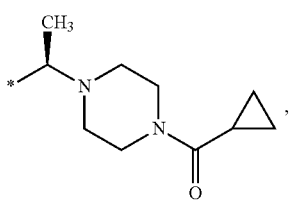

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

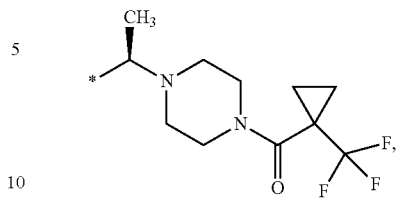

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

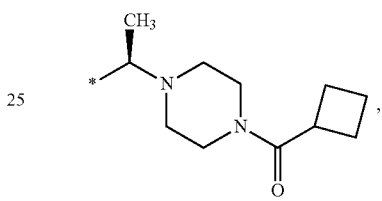

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

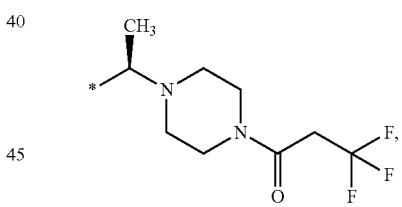

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

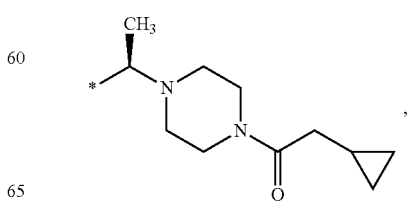

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

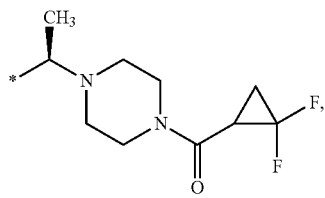 [SMILES: *[C@@H](C)N1CCN(C(=O)C2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

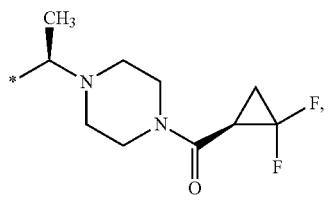 [SMILES: *[C@@H](C)N1CCN(C(=O)[C@H]2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

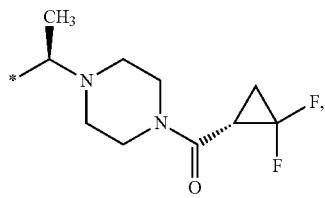 [SMILES: *[C@@H](C)N1CCN(C(=O)[C@@H]2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

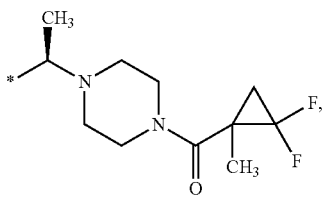 [SMILES: *[C@@H](C)N1CCN(C(=O)C2(C)CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

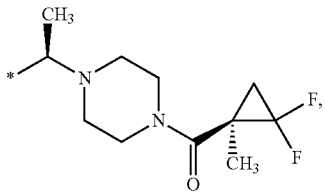 [SMILES: *[C@@H](C)N1CCN(C(=O)[C@@]2(C)CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

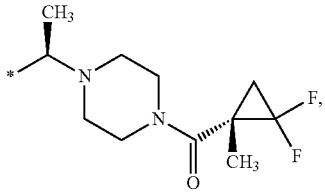 [SMILES: *[C@@H](C)N1CCN(C(=O)[C@]2(C)CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R² represents a group

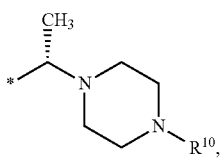

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

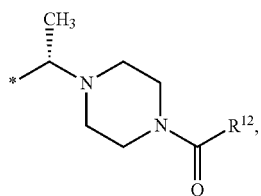

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

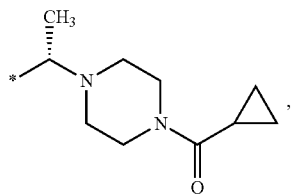

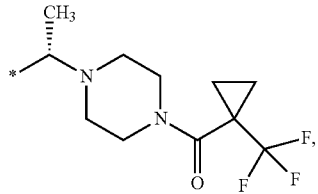

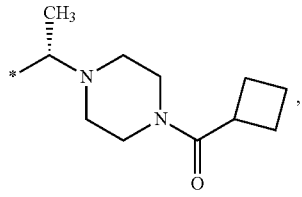

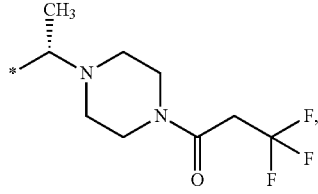

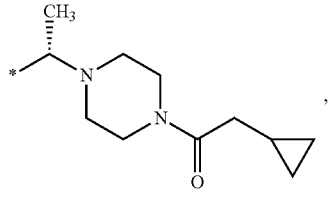

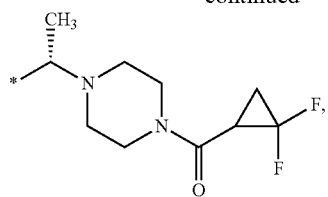

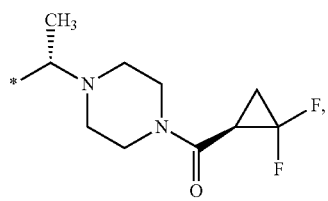

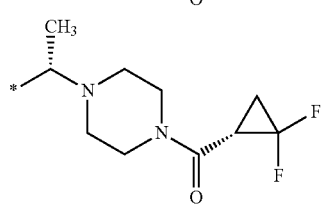

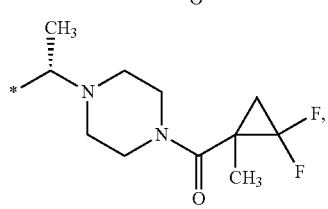

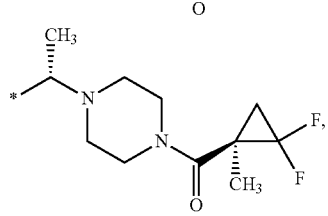

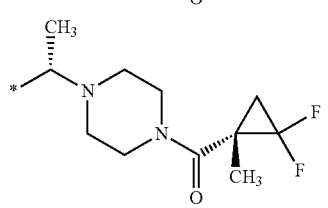

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

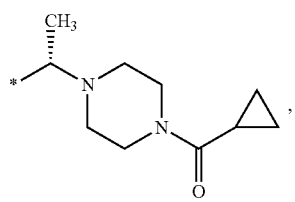 [SMILES: *[C@H](C)N1CCN(C(=O)C2CC2)CC1]

121

-continued

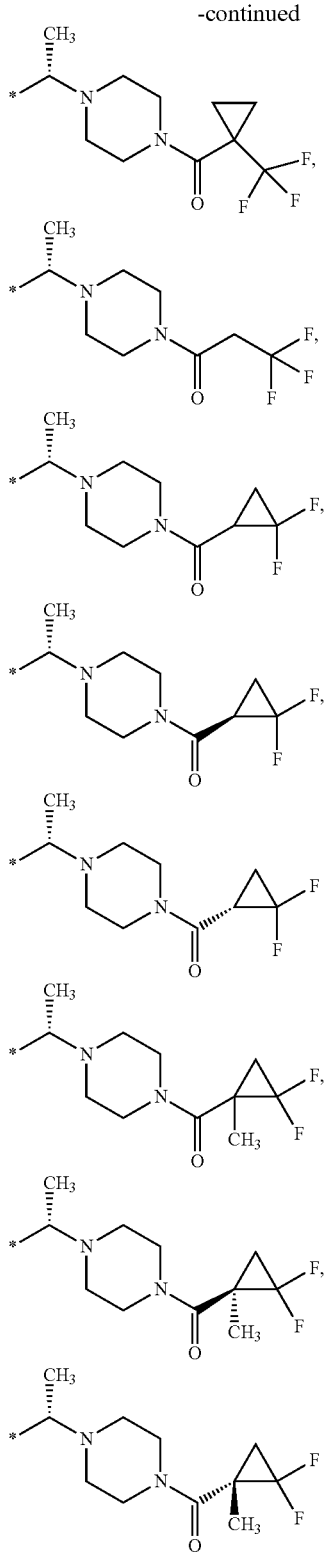

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

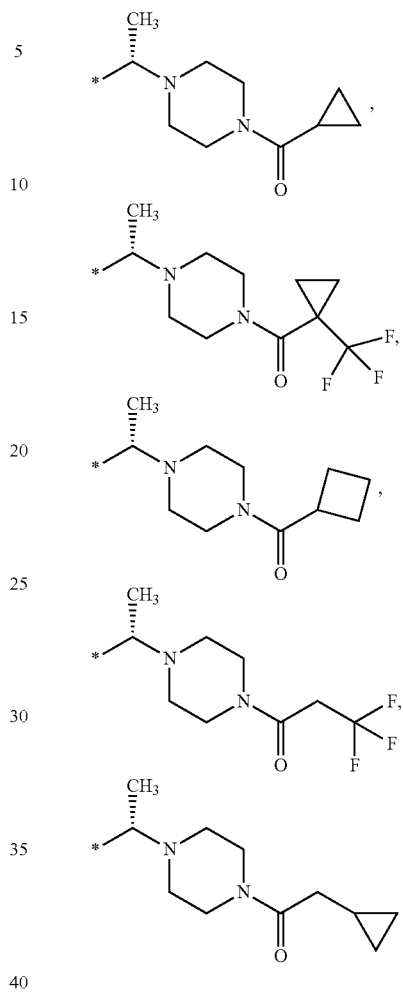

in which "*" represents the point of attachment to the rest of the molecule,
and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group selected from

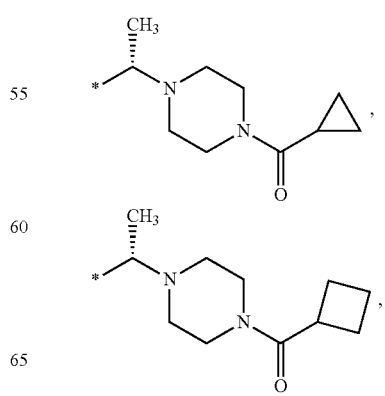

-continued

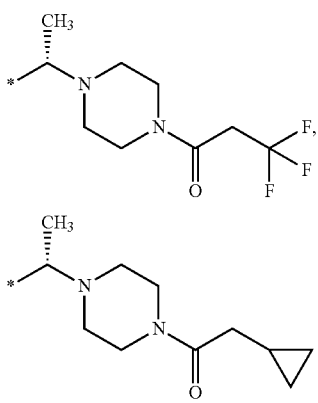

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

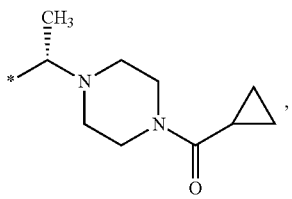

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

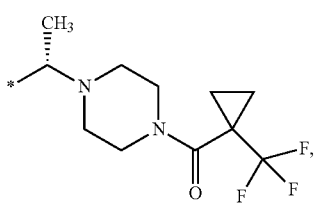 [SMILES: *[C@H](C)N1CCN(C(=O)C2(C(F)(F)F)CC2)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

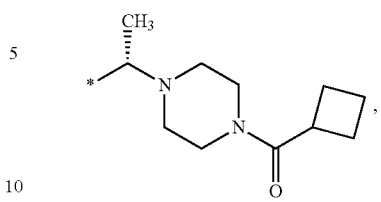

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

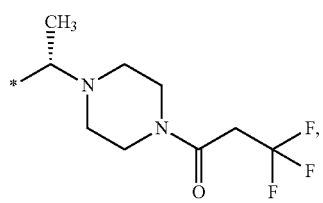 [SMILES: *[C@H](C)N1CCN(C(=O)CC(F)(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

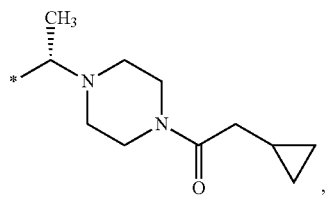 [SMILES: *[C@H](C)N1CCN(C(=O)CC2CC2)CC1 ; ","]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

R$^2$ represents a group

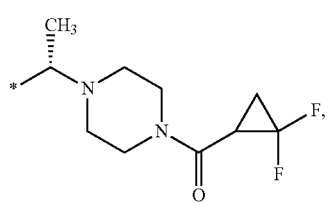 [SMILES: *[C@H](C)N1CCN(C(=O)C2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

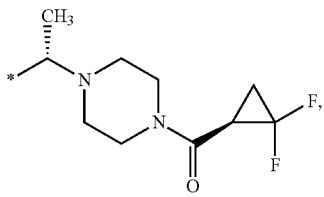 [SMILES: *[C@H](C)N1CCN(C(=O)[C@H]2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

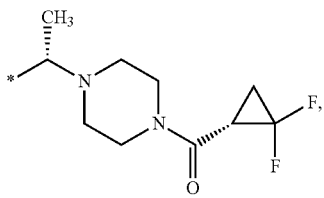 [SMILES: *[C@H](C)N1CCN(C(=O)[C@@H]2CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

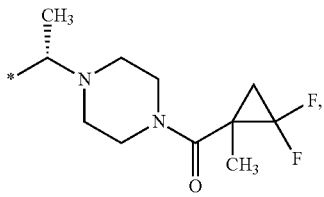 [SMILES: *[C@H](C)N1CCN(C(=O)C2(C)CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

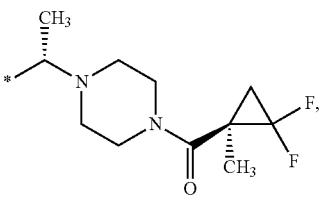 [SMILES: *[C@H](C)N1CCN(C(=O)[C@@]2(C)CC2(F)F)CC1]

in which "*" represents the point of attachment to the rest of the molecule, and stereoisomers, tautomers, N-oxides, hydrates, solvates, and salts thereof, and mixtures of same.

In a particular further embodiment of the first aspect, the present invention covers compounds of formula (I), supra, in which:

$R^2$ represents a group

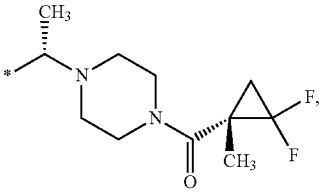 [SMILES: *[C@H](C)N1CCN(C(=O)[C@]2(C)CC2(F)F)CC1]

in which "*" represents the point of attachment to the rest of the molecule, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_4$-alkyl and $C_1$-$C_6$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a halogen atom or a group selected from $C_1$-$C_4$-alkyl and $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a group selected from $C_1$-$C_4$-alkyl and $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom, a fluorine atom, a chlorine atom, a bromine atom or a group selected from methyl, ethoxy and iso-butoxy, and stereoisomers, tautomers, N-oxides, hydrates, solvates, and salts thereof, and mixtures of same.

In a further embodiment of the first aspect, the present invention covers compounds of formula (I), supra, in which:

$R^3$ represents a hydrogen atom or a group selected from methyl, ethoxy and iso-butoxy, and stereoisomers, tautomers, N-oxides, hydrates, solvates, and salts thereof, and mixtures of same.

In a particular further embodiment of the first aspect, the present invention covers compounds of formula (I), supra, in which:

$R^3$ represents a hydrogen atom, a fluorine atom or a chlorine atom, and stereoisomers, tautomers, N-oxides, hydrates, solvates, and salts thereof, and mixtures of same.

In a particular further embodiment of the first aspect, the present invention covers compounds of formula (I), supra, in which:

$R^3$ represents a hydrogen atom, and stereoisomers, tautomers, N-oxides, hydrates, solvates, and salts thereof, and mixtures of same.

In a particular further embodiment of the first aspect, the present invention covers compounds of formula (I), supra, in which:

$R^3$ represents a fluorine atom, and stereoisomers, tautomers, N-oxides, hydrates, solvates, and salts thereof, and mixtures of same.

In a particular further embodiment of the first aspect, the present invention covers compounds of formula (I), supra, in which:

$R^3$ represents a chlorine atom, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a halogen atom or a group selected from $C_1$-$C_4$-alkyl, $C_1$-$C_4$-haloalkyl, $C_1$-$C_4$-alkoxy and $C_1$-$C_4$-haloalkoxy, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a group selected from $C_1$-$C_3$-alkyl and $C_1$-$C_3$-fluoroalkyl, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom, or a group selected from methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a hydrogen atom or a methyl group, and stereoisomers, tautomers, N-oxides, hydrates, solvates, and salts thereof, and mixtures of same.

In a further embodiment of the first aspect, the present invention covers compounds of formula (I), supra, in which:

$R^4$ represents a methyl group, and stereoisomers, tautomers, N-oxides, hydrates, solvates, and salts thereof, and mixtures of same.

In a particular further embodiment of the first aspect, the present invention covers compounds of formula (I), supra, in which:

$R^4$ represents a hydrogen atom, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a halogen atom or a group selected from $C_1$-$C_4$-alkyl, $C_1$-$C_4$-haloalkyl and $C_3$-$C_6$-cycloalkyl, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a fluorine atom or a chlorine atom or a bromine atom or or a group selected from methyl, trifluoromethyl and cyclopropyl, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a fluorine atom or a chlorine atom or a group selected from methyl, trifluoromethyl and cyclopropyl, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a fluorine atom or a chlorine atom a group selected from methyl, trifluoromethyl and cyclopropyl, and stereoisomers, tautomers, N-oxides, hydrates, solvates, and salts thereof, and mixtures of same.

In a further embodiment of the first aspect, the present invention covers compounds of formula (I), supra, in which:

$R^5$ represents a hydrogen atom or a bromine atom, and stereoisomers, tautomers, N-oxides, hydrates, solvates, and salts thereof, and mixtures of same.

In a particular further embodiment of the first aspect, the present invention covers compounds of formula (I), supra, in which:

$R^5$ represents a hydrogen atom;

and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom or a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, $C_3$-$C_6$-cycloalkyl and ($C_3$-$C_6$-cycloalkyl)-($C_1$-$C_3$-alkyl)-, said $C_3$-$C_6$-cycloalkyl and said ($C_3$-$C_6$-cycloalkyl)-($C_1$-$C_3$-alkyl)- group being optionally substituted one, two or three times, identically or differently, with a fluorine atom, a chlorine atom or with a group selected from $C_1$-$C_3$-alkyl and $C_1$-$C_3$-haloalkyl, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom or a group selected from $C_1$-$C_6$-alkyl, $C_1$-$C_6$-haloalkyl, $C_3$-$C_6$-cycloalkyl and ($C_3$-$C_6$-cycloalkyl)-($C_1$-$C_3$-alkyl)-, said $C_3$-$C_6$-cycloalkyl and said ($C_3$-$C_6$-cycloalkyl)-($C_1$-$C_3$-alkyl)- group being optionally substituted one, two or three times, identically or differently, with a fluorine atom, a chlorine atom or with a $C_1$-$C_3$-alkyl group, and stereoisomers, tautomers, N-oxides, hydrates, solvates, and salts thereof, and mixtures of same.

In a further embodiment of the first aspect, the present invention covers compounds of formula (I), supra, in which:

$R^6$ represents a hydrogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_5$-cycloalkyl and ($C_3$-$C_5$-cycloalkyl)-(methyl)-, said $C_3$-$C_5$-cycloalkyl and said ($C_3$-$C_5$-cycloalkyl)-(methyl)- group being optionally substituted one, two or three times, identically or differently, with a fluorine atom, a chlorine atom or with a group selected from methyl and trifluoromethyl;

and stereoisomers, tautomers, N-oxides, hydrates, solvates, and salts thereof, and mixtures of same.

In a further embodiment of the first aspect, the present invention covers compounds of formula (I), supra, in which:
$R^6$ represents a hydrogen atom or a group selected from $C_1$-$C_6$-alkyl, $C_1$-$C_4$-fluoroalkyl, $C_3$-$C_4$-cycloalkyl and ($C_3$-$C_4$-cycloalkyl)-(methyl)-,
said $C_3$-$C_4$-cycloalkyl and said ($C_3$-$C_4$-cycloalkyl)-(methyl)- group being optionally substituted one, two or three times, identically or differently, with a fluorine atom, a chlorine atom or with a methyl group;
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a hydrogen atom or a group selected from $C_1$-$C_6$-alkyl, $C_1$-$C_4$-fluoroalkyl, $C_1$-$C_4$-hydroxyalkyl, (methoxy)-($C_1$-$C_3$-alkyl)-, $C_3$-$C_5$-cycloalkyl and ($C_3$-$C_5$-cycloalkyl)-(methyl)-,
said $C_3$-$C_5$-cycloalkyl and said ($C_3$-$C_5$-cycloalkyl)-(methyl)- group being optionally substituted one, two or three times, identically or differently, with a fluorine atom, a chlorine atom or with a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_1$-$C_4$-alkyl, $C_1$-$C_4$-fluoroalkyl, cyclopropyl and (cyclopropyl)-(methyl)-,
said cyclopropyl and (cyclopropyl)-(methyl)- group being optionally substituted one or two times with a fluorine atom,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from methyl, ethyl 2,2-difluoroethyl, 2,2,2-trifluoroethyl and ($C_3$-$C_5$-cycloalkyl)-(methyl)-,
said ($C_3$-$C_5$-cycloalkyl)-(methyl)- group being optionally substituted one or two times, identically or differently, with a fluorine atom, a chlorine atom or with a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-alkyl, $C_2$-$C_4$-fluoroalkyl and ($C_3$-$C_4$-cycloalkyl)-(methyl)-,
said ($C_3$-$C_4$-cycloalkyl)-(methyl)- group being optionally substituted one or two times, identically or differently, with a fluorine atom or a chlorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-alkyl, $C_2$-$C_4$-fluoroalkyl and (cyclopropyl)-(methyl)-,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-fluoroalkyl and ($C_3$-$C_4$-cycloalkyl)-(methyl)-,
said ($C_3$-$C_4$-cycloalkyl)-(methyl)- group being optionally substituted one or two times, identically or differently, with a fluorine atom or a chlorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-fluoroalkyl and (cyclopropyl)-(methyl)-,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_3$-fluoroalkyl and ($C_3$-$C_4$-cycloalkyl)-(methyl)-,
said ($C_3$-$C_4$-cycloalkyl)-(methyl)- group being optionally substituted one or two times, identically or differently, with a fluorine atom or a chlorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_3$-fluoroalkyl and (cyclopropyl)-(methyl)-,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-fluoroalkyl and ($C_3$-$C_4$-cycloalkyl)-(methyl)-,
said ($C_3$-$C_4$-cycloalkyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from $C_2$-$C_4$-fluoroalkyl and (cyclopropyl)-(methyl)-,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a $(C_3$-$C_4$-cycloalkyl)-(methyl)- group,
said $(C_3$-$C_4$-cycloalkyl)-(methyl)- group being optionally substituted one or two times, identically or differently, with a fluorine atom or a chlorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a (cyclopropyl)-(methyl)- group,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a $(C_3$-$C_4$-cycloalkyl)-(methyl)- group,
said $(C_3$-$C_4$-cycloalkyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a (cyclopropyl)-(methyl)- group,
said (cyclopropyl)-(methyl)- group being optionally substituted one or two times, identically or differently, with a fluorine atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^6$ represents a group selected from methyl, ethyl 2,2,2-trifluoroethyl and (cyclopropyl)-(methyl)-,
said (cyclopropyl)-(methyl)- group being optionally substituted one or two times with a fluorine atom,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from methyl, ethyl, 2,2,2-trifluoroethyl, (cyclopropyl)-(methyl)- and (2,2-difluorocyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from ethyl, 2,2,2-trifluoroethyl, (cyclopropyl)-(methyl)- and (2,2-difluorocyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents an ethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a 2,2,2-trifluoroethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from 2,2,2-trifluoroethyl, (cyclopropyl)-(methyl)- and (2,2-difluorocyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (cyclopropyl)-(methyl)- and (2,2-difluorocyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (cyclopropyl)-(methyl)- group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (2,2-difluorocyclopropyl)-(methyl)- group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a hydrogen atom or a group selected from $(C_3$-$C_4$-cycloalkyl)-(methyl)- and $C_2$-$C_4$-fluoroalkyl,
said $(C_3$-$C_4$-cycloalkyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a hydrogen atom or a group selected from (cyclopropyl)-(methyl)-, (cyclobutyl)-(methyl)- and 2,2,2-trifluoroethyl,
said (cyclopropyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (cyclopropyl)-(methyl)-, (cyclobutyl)-(methyl)- and 2,2,2-trifluoroethyl,
said (cyclopropyl)-(methyl)- group being optionally substituted one or two times with a fluorine atom or a methyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (2-methylcyclopropyl)-(methyl)-, (2,2-difluorocyclopropyl)-(methyl)-, (cyclobutyl)-(methyl)- and 2,2,2-trifluoroethyl, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (2-methylcyclopropyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (cyclobutyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from methyl, ethyl, 2,2-difluoroethyl, 2,2,2-trifluoroethyl, (cyclopropyl)-(methyl)-, (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from methyl, ethyl, 2,2-difluoroethyl and 2,2,2-trifluoroethyl,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from methyl, ethyl, 2,2-difluoroethyl, 2,2,2-trifluoroethyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (2,2-difluorocyclopropyl)-(methyl)-, (2,2-dichlorocyclopropyl)-(methyl)-, (2,2-dimethylcyclopropyl)-(methyl)-, (2-methylcyclopropyl)-(methyl)-, (1-methylcyclopropyl)-(methyl)-, (1-chlorocyclopropyl)-(methyl)-, (cyclobutyl)-(methyl)-, 3,3-difluorocyclobutyl-(methyl)- and (cyclopentyl)-methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (2,2-difluorocyclopropyl)-(methyl)-, (2,2-dichlorocyclopropyl)-(methyl)- and (2,2-dimethylcyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (2-methylcyclopropyl)-(methyl)-, (1-methylcyclopropyl)-(methyl)- and (1-chlorocyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^8$ represents a group selected from (cyclopropyl)-(methyl)-, (cyclobutyl)-(methyl)-, 3,3-difluorocyclobutyl-(methyl)- and (cyclopentyl)-methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (cyclobutyl)-(methyl)-, 3,3-difluorocyclobutyl-(methyl)- and (cyclopentyl)-methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from 2,2-difluoroethyl, (cyclopropyl)-(methyl)-, (2,2-difluorocyclopropyl)-(methyl)-, (2,2-dimethylcyclopropyl)-(methyl)-, (1-chlorocyclopropyl)-(methyl)- and (cyclobutyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a 2,2-difluoroethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (2,2-difluorocyclopropyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (2,2-dimethylcyclopropyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (1-chlorocyclopropyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a (cyclobutyl)-(methyl)- group, and stereoisomers, tautomers, N-oxides, hydrates, solvates, and salts thereof, and mixtures of same.

In a particular further embodiment of the first aspect, the present invention covers compounds of formula (I), supra, in which:
$R^6$ represents a group selected from (2,2-difluorocyclopropyl)-(methyl)-, (2,2-dimethylcyclopropyl)-(methyl)- and (1-chlorocyclopropyl)-(methyl)-, and stereoisomers, tautomers, N-oxides, hydrates, solvates, and salts thereof, and mixtures of same.

In a particular further embodiment of the first aspect, the present invention covers compounds of formula (I), supra, in which:

$R^6$ represents a group selected from (2,2-difluorocyclopropyl)-(methyl)- and (2,2-dimethylcyclopropyl)-(methyl)-, and stereoisomers, tautomers, N-oxides, hydrates, solvates, and salts thereof, and mixtures of same.

In a particular further embodiment of the first aspect, the present invention covers compounds of formula (I), supra, in which:

$R^6$ represents a group selected from 2,2-difluoroethyl, (2,2-difluorocyclopropyl)-(methyl)-, (2,2-dimethylcyclopropyl)-(methyl),-(1-chlorocyclopropyl)-(methyl)- and (cyclobutyl)-(methyl)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a halogen atom or a group selected from hydroxy, $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, ($C_1$-$C_3$-haloalkoxy)-($C_1$-$C_3$-alkyl)-, $C_2$-$C_6$-alkenyl, $C_2$-$C_6$-alkynyl, $C_3$-$C_8$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, heterospirocycloalkyl, phenyl, heteroaryl, —CN, —(CH$_2$)—N(R$^{11}$)R$^{11a}$, —C(=O)R$^{13}$, —C(=O)—OR$^{13}$, —C(=O)—N(R$^{11}$)R$^{11a}$, —N(R$^{11}$)R$^{11a}$, —N(R$^{16}$)—C(=O)—R$^{13}$, —N(R$^{16}$)—S(=O)$_2$—R$^{13}$, —N(R$^{16}$)—C(=O)—N(R$^{11}$)R$^{11a}$, —N(R$^{16}$)—C(=O)—OR$^{13}$, $C_1$-$C_6$-alkoxy, $C_1$-$C_6$-haloalkoxy, $C_3$-$C_8$-cycloalkoxy-, ($C_3$-$C_8$-cycloalkyl)-($C_1$-$C_3$-alkoxy)-, phenyloxy-, heteroaryloxy-, —O—(CH$_2$)$_x$-phenyl, —O—(CH$_2$)$_x$-heteroaryl, —O—C(=O)—R$^{13}$, —O—C(=O)—N(R$^{11}$)R$^{11a}$, $C_1$-$C_6$-alkylsulfanyl, $C_1$-$C_6$-haloalkylsulfanyl, —S(=O)—R$^{13}$, —S(=O)$_2$—R$^{13}$, —S(=O)$_2$—N(R$^1$)R$^{11a}$ and —S(=O)(=NR$^{17}$)R$^{13}$, said $C_3$-$C_8$-cycloalkyl, said ($C_3$-$C_8$-cycloalkyl)-($C_1$-$C_3$-alkyl)- and said ($C_3$-$C_8$-cycloalkyl)-($C_1$-$C_3$-alkoxy)-group being optionally substituted one, two or three times, identically or differently, with a fluorine atom, a chlorine atom or with a group selected from $C_1$-$C_3$-alkyl and $C_1$-$C_3$-haloalkyl, said 4- to 7-membered heterocycloalkyl, said 5- to 7-membered heterocycloalkenyl and said heterospirocycloalkyl group being optionally substituted one, two or three times, identically or differently, with a fluorine atom, a chlorine atom or with a group selected from oxo, $C_1$-$C_3$-alkyl and $C_1$-$C_3$-haloalkyl, and said heteroaryl group and said phenyl group being optionally substituted one, two or three times, identically or differently, with a halogen atom or a group selected from —CN, $C_1$-$C_3$-alkyl, trifluoromethyl, $C_1$-$C_3$-alkoxy and trifluoromethoxy, or $R^6$ and $R^7$, or two $R^7$ groups, when being attached to adjacent ring atoms of the group $R^1$, together form a group selected from:

—(O—CH$_2$—O)—, —(O—(CH$_2$)$_2$—O)—, —(O—(CH$_2$)$_2$)—, —(CH$_2$—O—CH$_2$)—, —(NR$^{16}$—(CH$_2$)$_2$—O)—, —(NR$^{16}$—(CH$_2$)$_3$—O)—, —(S—(CH$_2$)$_2$)—, —(O—(CH$_2$)$_3$)—, —((CH$_2$)$_3$)—, —((CH$_2$)$_4$)—, —(O—CH=CH)—, —(S—CH=CH)—, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a halogen atom or a group selected from hydroxy, $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, ($C_1$-$C_3$-haloalkoxy)-($C_1$-$C_3$-alkyl)-, $C_2$-$C_6$-alkenyl, $C_2$-$C_6$-alkynyl, $C_3$-$C_8$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, heterospirocycloalkyl, phenyl, heteroaryl, —CN, —(CH$_2$)$_x$—N(R$^{11}$)R$^{11a}$, —C(=O)R$^{13}$, —C(=O)—OR$^{13}$, —C(=O)—N(R$^{11}$)R$^{11a}$, N(R$^{11}$)R$^{11a}$, —N(R$^{16}$)—C(=O)—R$^{13}$, —N(R$^{16}$)—S(=O)$_2$—R$^{13}$, —N(R$^{16}$)—C(=O)—N(R$^{11}$)R$^{11a}$, —N(R$^{16}$)—C(=O)—OR$^{13}$, $C_1$-$C_6$-alkoxy, $C_1$-$C_6$-haloalkoxy, $C_3$-$C_8$-cycloalkoxy-, ($C_3$-$C_8$-cycloalkyl)-($C_1$-$C_3$-alkoxy)-, phenyloxy-, heteroaryloxy-, —O—(CH$_2$)$_x$-phenyl, —O—(CH$_2$)$_x$-heteroaryl, —O—C(=O)—R$^{13}$, —O—C(=O)—N(R$^{11}$)R$^{11a}$, $C_1$-$C_6$-alkylsulfanyl, $C_1$-$C_6$-haloalkylsulfanyl, —S(=O)—R$^{13}$, —S(=O)$_2$—R$^{13}$, —S(=O)$_2$—N(R$^{11}$)R$^{11a}$ and —S(=O)(=NR$^7$)R$^{13}$, said $C_3$-$C_8$-cycloalkyl, said ($C_3$-$C_8$-cycloalkyl)-($C_1$-$C_3$-alkyl)- and said ($C_3$-$C_8$-cycloalkyl)-($C_1$-$C_3$-alkoxy)-group being optionally substituted one, two or three times, identically or differently, with a fluorine atom, a chlorine atom or with a group selected from $C_1$-$C_3$-alkyl and $C_1$-$C_3$-haloalkyl, said 4- to 7-membered heterocycloalkyl, said 5- to 7-membered heterocycloalkenyl and said heterospirocycloalkyl group being optionally substituted one, two or three times, identically or differently, with a fluorine atom, a chlorine atom or with a group selected from oxo, $C_1$-$C_3$-alkyl and $C_1$-$C_3$-haloalkyl, and said heteroaryl group and said phenyl group being optionally substituted one, two or three times, identically or differently, with a halogen atom or a group selected from —CN, $C_1$-$C_3$-alkyl, trifluoromethyl, $C_1$-$C_3$-alkoxy and trifluoromethoxy, and stereoisomers, tautomers, N-oxides, hydrates, solvates, and salts thereof, and mixtures of same.

In a further embodiment of the first aspect, the present invention covers compounds of formula (I), supra, in which:

$R^6$ and $R^7$, or two $R^7$ groups, when being attached to adjacent ring atoms of the group $R^1$, together form a group selected from:

—(O—CH$_2$—O)—, —(O—(CH$_2$)$_2$—O)—, —(O—(CH$_2$)$_2$)—, —(CH$_2$—O—CH$_2$)—, —(NR$^{16}$—(CH$_2$)$_2$—O)—, —(NR$^{18}$—(CH$_2$)$_3$—O)—, —(S—(CH$_2$)$_2$)—, —(O—(CH$_2$)$_3$)—, —((CH$_2$)$_3$)—, —((CH$_2$)$_4$)—, —(O—CH=CH)—, —(S—CH=CH)—, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a halogen atom or a group selected from $C_1$-$C_6$-alkyl, $C_1$-$C_6$-haloalkyl, $C_1$-$C_6$-hydroxyalkyl, $C_2$-$C_6$-alkenyl, $C_2$-$C_6$-alkynyl, $C_3$-$C_6$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, phenyl, heteroaryl, —CN, —C(=O)R$^{13}$, —C(=O)—OR$^{13}$, —C(=O)—N(R$^{11}$)R$^{11a}$, —N(R$^{11}$)R$^{11a}$, —N(R$^{16}$)—C(=O)—R$^{13}$, —N(R$^{16}$)—S(=O)$_2$—R$^{13}$, —N(R$^{16}$)—C(=O)—N(R$^{11}$)R$^{11a}$, —N(R$^{16}$)—C(=O)—OR$^{13}$, $C_1$-$C_6$-alkoxy, $C_1$-$C_6$-haloalkoxy, $C_3$-$C_8$-cycloalkoxy-, ($C_3$-$C_6$-cycloalkyl)-($C_1$-$C_3$-alkoxy)-, phenyloxy-, heteroaryloxy-, —O—(CH$_2$)$_x$-phenyl, —O—(CH$_2$)$_x$-heteroaryl, —O—C(=O)—R$^{13}$—

O—C(=O)—N($R^{11}$)$R^{11a}$, $C_1$-$C_6$-alkylsulfanyl, $C_1$-$C_6$-haloalkylsulfanyl, —S(=O)$_2$—$R^{13}$, —S(=O)$_2$—N($R^{11}$)$R^{11a}$ and —S(=O)(=N$R^{17}$)$R^{13}$; or $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —(S—(CH$_2$)$_2$)—, —(O—(CH$_2$)$_3$)—, —((CH$_2$)$_3$)—, —((CH$_2$)$_4$)—, —(O—CH=CH)—, —(S—CH=CH), and stereoisomers, tautomers, N-oxides, hydrates, solvates, and salts thereof, and mixtures of same.

In a further embodiment of the first aspect, the present invention covers compounds of formula (I), supra, in which: $R^7$ represents a halogen atom or a group selected from $C_1$-$C_6$-alkyl, $C_1$-$C_6$-haloalkyl, $C_1$-$C_6$-hydroxyalkyl, $C_2$-$C_6$-alkenyl, $C_2$-$C_6$-alkynyl, $C_3$-$C_8$-cycloalkyl, $C_4$-$C_8$-cycloalkenyl, ($C_3$-$C_8$-cycloalkyl)-($C_1$-$C_3$-alkyl)-, (phenyl)-$C_1$-$C_3$-alkyl-, 4- to 7-membered heterocycloalkyl, 5- to 7-membered heterocycloalkenyl, phenyl, heteroaryl, —CN, —C(=O)$R^{13}$, —C(=O)—O$R^{13}$, —C(=O)—N($R^{11}$)$R^{11a}$, —N($R^{11}$)$R^{11a}$, —N($R^{16}$)—C(=O)—$R^{13}$, —N($R^{16}$)—S(=O)$_2$—$R^{13}$, —N($R^{16}$)—C(=O)—N($R^{11}$)$R^{11a}$, —N($R^{16}$)—C(=O)—O$R^{13}$, $C_1$-$C_6$-alkoxy, $C_1$-$C_6$-haloalkoxy, $C_3$-$C_8$-cycloalkoxy-, ($C_3$-$C_8$-cycloalkyl)-($C_1$-$C_3$-alkoxy)-, phenyloxy-, heteroaryloxy-, —O—(CH$_2$)$_x$-phenyl, —O—(CH$_2$)$_x$-heteroaryl, —O—C(=O)—$R^{13}$—O—C(=O)—N($R^{11}$)$R^{11a}$, $C_1$-$C_6$-alkylsulfanyl, $C_1$-$C_6$-haloalkylsulfanyl, —S(=O)$_2$—$R^{13}$, —S(=O)$_2$—N($R^{11}$)$R^{11a}$ and —S(=O)(=N$R^{17}$)$R^{13}$;

and stereoisomers, tautomers, N-oxides, hydrates, solvates, and salts thereof, and mixtures of same.

In a further embodiment of the first aspect, the present invention covers compounds of formula (I), supra, in which: $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —(S—(CH$_2$)$_2$)—, —(O—(CH$_2$)$_3$)—, —((CH$_2$)$_3$)—, —((CH$_2$)$_4$)—, —(O—CH=CH)—, —(S—CH=CH);

and stereoisomers, tautomers, N-oxides, hydrates, solvates, and salts thereof, and mixtures of same.

In a further embodiment of the first aspect, the present invention covers compounds of formula (I), supra, in which: $R^7$ represents a halogen atom or a group selected from hydroxy, $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, ($C_1$-$C_2$-fluoroalkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, 5- to 6-membered heteroaryl, —CN, —(CH$_2$)$_x$—N($R^{11}$)$R^{11a}$, —C(=O)$R^{13}$, —C(=O)—N($R^{11}$)$R^{11a}$, —N($R^{11}$)$R^{11a}$, $C_1$-$C_6$-alkoxy, $C_1$-$C_4$-fluoroalkoxy, ($C_3$-$C_4$-cycloalkyl)-(methoxy)-, $C_1$-$C_4$-alkylsulfanyl, S(=O)—$R^{13}$ and —S(=O)$_2$—$R^{13}$, said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, said 4- to 7-membered heterocycloalkyl and said heterospirocycloalkyl group being optionally substituted one, two or three times, identically or differently, with a fluorine atom or with a group selected from oxo, methyl and trifluoromethyl, and said 5- to 6-membered heteroaryl group being optionally substituted one, two or three times, identically or differently, with a halogen atom or a group selected from methyl, trifluoromethyl and methoxy, or $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —(CH$_2$—O—CH$_2$)—, —(N$R^{16}$—(CH$_2$)$_2$—O)—, —((CH$_2$)$_3$)—, —((CH$_2$)$_4$)—, —(O—CH=CH)—, —(S—CH=CH)—, and stereoisomers, tautomers, N-oxides, hydrates, solvates, and salts thereof, and mixtures of same.

In a further embodiment of the first aspect, the present invention covers compounds of formula (I), supra, in which: $R^7$ represents a halogen atom or a group selected from hydroxy, $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, ($C_1$-$C_2$-fluoroalkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, 5- to 6-membered heteroaryl, —CN, —(CH$_2$)$_x$—N($R^{11}$)$R^{11a}$, —C(=O)$R^{13}$, —C(=O)—N($R^{11}$)$R^{11a}$, —N($R^{11}$)$R^{11a}$, —$C_1$-$C_6$-alkoxy, $C_1$-$C_4$-fluoroalkoxy, ($C_3$-$C_4$-cycloalkyl)-(methoxy)-, $C_1$-$C_4$-alkylsulfanyl, S(=O)—$R^{13}$ and —S(=O)$_2$—$R^{13}$ said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, said 4- to 7-membered heterocycloalkyl and said heterospirocycloalkyl group being optionally substituted one, two or three times, identically or differently, with a fluorine atom or with a group selected from oxo, methyl and trifluoromethyl, and said 5- to 6-membered heteroaryl group being optionally substituted one, two or three times, identically or differently, with a halogen atom or a group selected from methyl, trifluoromethyl and methoxy, and stereoisomers, tautomers, N-oxides, hydrates, solvates, and salts thereof, and mixtures of same.

In a further embodiment of the first aspect, the present invention covers compounds of formula (I), supra, in which: $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —(CH$_2$—O—CH$_2$)—, —(N$R^{16}$—(CH$_2$)$_2$—O)—, —((CH$_2$)$_3$)—, —((CH$_2$)$_4$)—, —(O—CH=CH)—, —(S—CH=CH)—, and stereoisomers, tautomers, N-oxides, hydrates, solvates, and salts thereof, and mixtures of same.

In a further embodiment of the first aspect, the present invention covers compounds of formula (I), supra, in which: $R^7$ represents a halogen atom or a group selected from $C_1$-$C_6$-alkyl, $C_1$-$C_4$-fluoroalkyl, $C_3$-$C_4$-cycloalkyl, ($C_3$-$C_4$-cycloalkyl)-(methyl)-, (phenyl)-($C_1$-$C_3$-alkyl)-, —C(=O)—N($R^{1'}$)$R^{11a}$, $C_1$-$C_6$-alkoxy, $C_1$-$C_4$-fluoroalkoxy, ($C_3$-$C_4$-cycloalkyl)-(methoxy)- and $C_1$-$C_4$-alkylsulfanyl; or $R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —((CH$_2$)$_3$)—, —((CH$_2$)$_4$)—, and stereoisomers, tautomers, N-oxides, hydrates, solvates, and salts thereof, and mixtures of same.

In a further embodiment of the first aspect, the present invention covers compounds of formula (I), supra, in which:
$R^7$ represents a halogen atom or a group selected from $C_1$-$C_6$-alkyl, $C_1$-$C_4$-fluoroalkyl, $C_3$-$C_4$-cycloalkyl, ($C_3$-$C_4$-cycloalkyl)-(methyl)-, (phenyl)-($C_1$-$C_3$-alkyl)-, —C(=O)—N($R^{11}$)$R^{11a}$, $C_1$-$C_6$-alkoxy, $C_1$-$C_4$-fluoroalkoxy, ($C_3$-$C_4$-cycloalkyl)-(methoxy)- and $C_1$-$C_4$-alkylsulfanyl,
and stereoisomers, tautomers, N-oxides, hydrates, solvates, and salts thereof, and mixtures of same.

In a further embodiment of the first aspect, the present invention covers compounds of formula (I), supra, in which:
$R^6$ and $R^7$, or two $R^7$ groups, when being attached to adjacent ring atoms of the group $R^1$, together form a group selected from:
—(O—CH$_2$—O)—, —(O—(CH$_2$)$_2$—O)—, —(O—(CH$_2$)$_2$)—, —((CH$_2$)$_3$)—, —((CH$_2$)$_4$)—,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a halogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_3$-alkyl)-, 4- to 7-membered heterocycloalkyl, heterospirocycloalkyl, —CN, —(CH$_2$)$_x$—N($R^{11}$)$R^{11a}$, —C(=O)$R^{13}$, —C(=O)—N($R^{11}$)$R^{11a}$, N($R^{11}$)$R^{11a}$, $C_1$-$C_6$-alkoxy, $C_1$-$C_4$-fluoroalkoxy and ($C_3$-$C_4$-cycloalkyl)-(methoxy)-,
said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, and
said 4- to 7-membered heterocycloalkyl and said heterospirocycloalkyl group being optionally substituted one, two or three times, identically or differently, with a fluorine atom or with a group selected from methyl and trifluoromethyl, or
$R^6$ and $R^7$, or two $R^7$ groups, when being attached to adjacent ring atoms of the group $R^1$, together form a group selected from:
—(O—CH=CH)— and —(NR$^{16}$—(CH$_2$)$_2$—O)—,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a halogen atom or a group selected from $C_1$-$C_6$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_4$-cycloalkyl, ($C_3$-$C_4$-cycloalkyl)-(methyl)-, (phenyl)-($C_1$-$C_6$-alkyl)-, 4- to 7-membered heterocycloalkyl, heterospirocycloalkyl, —CN, —(CH$_2$)$_x$—N($R^{11}$)$R^{11a}$, —C(=O)$R^{13}$, —C(=O)—N($R^{11}$)$R^{11a}$, —N($R^{11}$)$R^{11a}$, $C_1$-$C_6$-alkoxy, $C_1$-$C_4$-fluoroalkoxy and ($C_3$-$C_4$-cycloalkyl)-(methoxy)-,
said $C_3$-$C_4$-cycloalkyl, said ($C_3$-$C_4$-cycloalkyl)-(methyl)- and said ($C_3$-$C_4$-cycloalkyl)-(methoxy)- group being optionally substituted one, two or three times, identically or differently, with a fluorine atom or with a group selected from methyl and trifluoromethyl, and
said 4- to 7-membered heterocycloalkyl and said heterospirocycloalkyl group being optionally substituted one, two or three times, identically or differently, with a fluorine atom or with a group selected from methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:
$R^6$ and $R^7$, or two $R^7$ groups, when being attached to adjacent ring atoms of the group $R^1$, together form a group selected from:
—(O—CH=CH)— and —(NR$^{16}$—(CH$_2$)$_2$—O)—,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a halogen atom or a group selected from $C_1$-$C_6$-alkyl, $C_1$-$C_4$-fluoroalkyl, ($C_3$-$C_4$-cycloalkyl)-(methyl)-, $C_1$-$C_6$-alkoxy, $C_1$-$C_4$-fluoroalkoxy, ($C_3$-$C_4$-cycloalkyl)-(methoxy)- and $C_1$-$C_4$-alkylsulfanyl,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a group selected from $C_1$-$C_3$-alkyl, difluoromethyl, trifluoromethyl, (methoxy)-(methyl)-, cyclopropyl, —NR$^{11}$R$^{11a}$, $C_1$-$C_3$-alkoxy, $C_1$-$C_3$-fluoroalkoxy, ($C_3$-$C_4$-cycloalkyl)-(methoxy)- and [1-(trifluoromethyl)cyclopropyl]-(methoxy)-, or
$R^6$ and $R^7$, or two $R^7$ groups, when being attached to adjacent ring atoms of the group $R^1$, together form a group selected from:
—(O—CH=CH)— and —(NR$^{16}$—(CH$_2$)$_2$—O)—,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a group selected from $C_1$-$C_3$-alkyl, difluoromethyl, trifluoromethyl, (methoxy)-(methyl)-, cyclopropyl, —NR$^{11}$R$^{11a}$, $C_1$-$C_3$-alkoxy, $C_1$-$C_3$-fluoroalkoxy, ($C_3$-$C_4$-cycloalkyl)-(methoxy)- and [1-(trifluoromethyl)cyclopropyl]-(methoxy)-,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a group selected from $C_1$-$C_3$-alkyl, difluoromethyl, trifluoromethyl, (methoxy)-(methyl)-, cyclopropyl, 2-oxa-6-azaspiro[3.3]heptyl-, —NR$^{11}$R$^{11a}$, $C_1$-$C_3$-alkoxy, trifluoromethoxy, 2,2,2-trifluoroethoxy, ($C_3$-$C_4$-cycloalkyl)-(methoxy)- and [1-(trifluoromethyl)cyclopropyl]-(methoxy)-, or
$R^6$ and $R^7$, or two $R^7$ groups, when being attached to adjacent ring atoms of the group $R^1$, together form a group selected from:
—(O—CH=CH)— and —(NR$^{16}$—(CH$_2$)$_2$—O)—,
and stereoisomers, tautomers, N-oxides, hydrates, solvates, and salts thereof, and mixtures of same.

In a further embodiment of the first aspect, the present invention covers compounds of formula (I), supra, in which:
$R^7$ represents a group selected from $C_1$-$C_3$-alkyl, difluoromethyl, trifluoromethyl, (methoxy)-(methyl)-, cyclopropyl, 2-oxa-6-azaspiro[3.3]heptyl-, —NR$^{11}$R$^{11a}$, $C_1$-$C_3$-alkoxy, trifluoromethoxy, 2,2,2-trifluoroethoxy, ($C_3$-$C_4$-cycloalkyl)-(methoxy)- and [1-(trifluoromethyl)cyclopropyl]-(methoxy)-,
and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from $C_1$-$C_6$-alkyl, $C_1$-$C_4$-fluoroalkyl, ($C_3$-$C_4$-cycloalkyl)-(methyl)-, $C_1$-$C_6$-alkoxy, $C_1$-$C_4$-fluroalkoxy, ($C_3$-$C_4$-cycloalkyl)-(methoxy)- and $C_1$-$C_4$-alkylsulfanyl, and stereoisomers, tautomers, N-oxides, hydrates, solvates, and salts thereof, and mixtures of same.

In a particular further embodiment of the first aspect, the present invention covers compounds of formula (I), supra, in which:

$R^7$ represents a group selected from $C_1$-$C_3$-alkyl, trifluoromethyl, (methoxy)-(methyl)-, cyclopropyl, —$NR^{11}R^{11a}$, $C_1$-$C_3$-alkoxy, $C_1$-$C_3$-fluoroalkoxy and ($C_3$-$C_4$-cycloalkyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

$R^7$ represents a group selected from $C_1$-$C_3$-alkyl, (methoxy)-(methyl)-, cyclopropyl, —$NR^{11}R^{11a}$, $C_1$-$C_3$-alkoxy and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a halogen atom or a group selected from $C_1$-$C_6$-alkyl, $C_1$-$C_4$-fluoroalkyl, ($C_3$-$C_4$-cycloalkyl)-(methyl)-, $C_1$-$C_6$-alkoxy, $C_1$-$C_4$-fluoroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from
$C_1$-$C_6$-alkyl, $C_1$-$C_4$-fluoroalkyl, ($C_3$-$C_4$-cycloalkyl)-(methyl)-, $C_1$-$C_6$-alkoxy, $C_1$-$C_4$-fluoroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a halogen atom or a group selected from
$C_1$-$C_6$-alkyl, $C_1$-$C_4$-fluoroalkyl, ($C_3$-$C_4$-cycloalkyl)-(methyl)-, $C_1$-$C_4$-alkoxy, $C_1$-$C_4$-fluoroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from
$C_1$-$C_6$-alkyl, $C_1$-$C_4$-fluoroalkyl, ($C_3$-$C_4$-cycloalkyl)-(methyl)-, $C_1$-$C_4$-alkoxy, $C_1$-$C_4$-fluroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from $C_1$-$C_6$-alkyl, $C_1$-$C_4$-fluoroalkyl, ($C_3$-$C_4$-cycloalkyl)-(methyl)-, $C_1$-$C_4$-alkoxy, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from
$C_1$-$C_4$-alkoxy, $C_1$-$C_4$-fluroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from
$C_1$-$C_6$-alkyl, $C_1$-$C_4$-fluoroalkyl, ($C_3$-$C_4$-cycloalkyl)-(methyl)-, methoxy, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from
methoxy, $C_1$-$C_4$-fluroalkoxy, and ($C_3$-$C_4$-cycloalkyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a —$NR^{11}R^{11a}$ group, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a $C_1$-$C_4$-fluroalkoxy group, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a $C_1$-$C_3$-fluroalkoxy group, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a fluorine atom or a group selected from $C_1$-$C_5$-alkyl, $C_1$-$C_2$-fluoroalkyl, cyclopropyl, benzyl, —C(=O)—N($R^{11}$)$R^{11a}$, $C_1$-$C_3$-alkoxy, $C_1$-$C_2$-fluoroalkoxy and (cyclopropyl)-(methoxy)-, and stereoisomers, tautomers, N-oxides, hydrates, solvates, and salts thereof, and mixtures of same.

In a further embodiment of the first aspect, the present invention covers compounds of formula (I), supra, in which:

$R^7$ represents a group selected from $C_1$-$C_3$-alkyl, trifluoromethyl, cyclopropyl, $C_1$-$C_3$-alkoxy, trifluoromethoxy, 2,2,2-trifluoroethoxy and (cyclopropyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

$R^7$ represents a group selected from methyl, trifluoromethyl, cyclopropyl, methoxy, ethoxy, iso-propoxy, 2,2,2-trifluoroethoxy and (cyclopropyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

$R^7$ represents a group selected from methyl, trifluoromethyl, methoxy, ethoxy, iso-propoxy and (cyclopropyl)-(methoxy)-, and stereoisomers, tautomers, N-oxides, hydrates, solvates, and salts thereof, and mixtures of same.

In a particular further embodiment of the first aspect, the present invention covers compounds of formula (I), supra, in which:

$R^7$ represents a group selected from methyl and trifluoromethyl, and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy, 2,2,2-trifluoroethoxy, 2,2-difluoropropoxy, iso-propoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy, 2,2,2-trifluoroethoxy, iso-propoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy, 2,2,2-trifluoroethoxy, 2,2-difluoropropoxy and iso-propoxy,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy, 2,2,2-trifluoroethoxy and iso-propoxy,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy, iso-propoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, ethoxy and iso-propoxy,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a methoxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from 2,2,2-trifluoroethoxy and 2,2-difluoropropoxy,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a 2,2-difluoroprooxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a 2,2,2-trifluoroethoxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents an ethoxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents an iso-propoxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a (cyclopropyl)-(methoxy)-group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a chlorine atom or a group selected from $C_1$-$C_3$-alkyl, cyclopropyl, dimethylamino, cyclopropylamino, $C_1$-$C_3$-alkoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a chlorine atom or a group selected from $C_1$-$C_3$-alkyl, $C_1$-$C_3$-alkoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from $C_1$-$C_3$-alkyl, $C_1$-$C_3$-alkoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a chlorine atom or a group selected from $C_1$-$C_3$-alkoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from $C_1$-$C_3$-alkoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a chlorine atom or a group selected from methyl, methoxy and (cyclopropyl)-(methoxy)-, In a particular further embodiment of the first aspect, the present invention covers compounds of formula (I), supra, in which:
$R^7$ represents a group selected from methyl, methoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a chlorine atom or a group selected from methoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methoxy, 2,2,2-trifluoroethoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl, trifluoromethyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl, morpholinyl, methoxy, ethoxy, iso-propoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl, morpholinyl, methoxy, ethoxy, iso-propoxy and (cyclopropyl)-(methoxy)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl, trifluoromethyl and (methoxy)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from methyl and (methoxy)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a methyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a (methoxy)-(methyl)- group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from ethylamino, isopropylamino, (cyclopropyl)-(methyl)-amino-, cyclopropylamino, cyclobutylamino, dimethylamino, azetidin-1-yl, 3,3-difluoroazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from ethylamino, isopropylamino, (cyclopropyl)-(methyl)-amino-, cyclopropylamino, cyclobutylamino,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a ethylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a isopropylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a (cyclopropyl)-(methyl)-amino- group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a cyclopropylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a cyclobutylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from dimethylamino, azetidin-1-yl, 3,3-difluoroazetidin-1-yl, 3-trifluoromethylazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from dimethylamino, azetidin-1-yl, 3,3-difluoroazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a dimethylamino group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from azetidin-1-yl, 3,3-difluoroazetidin-1-yl, 3-trifluoromethylazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a group selected from azetidin-1-yl, 3,3-difluoroazetidin-1-yl, pyrrolidin-1-yl, piperidin-1-yl and morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a azetidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a 3,3-difluoroazetidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a 3-trifluoromethylazetidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a piperidin-1-yl group,
and stereoisomers, tautomers, N-oxides, hydrates, solvates, and salts thereof, and mixtures of same.

In a particular further embodiment of the first aspect, the present invention covers compounds of formula (I), supra, in which:
$R^7$ represents a morpholinyl group,
and stereoisomers, tautomers, N-oxides, hydrates, solvates, and salts thereof, and mixtures of same.

In a further embodiment of the first aspect, the present invention covers compounds of formula (I), supra, in which:
$R^8$ represents a hydrogen atom or a group selected from methyl, ethyl, methoxy, ethoxy and dimethylamino,
and stereoisomers, tautomers, N-oxides, hydrates, solvates, and salts thereof, and mixtures of same.

In a further embodiment of the first aspect, the present invention covers compounds of formula (I), supra, in which:
$R^8$ represents a hydrogen atom or a group selected from methyl, ethyl, methoxy and ethoxy,
and stereoisomers, tautomers, N-oxides, hydrates, solvates, and salts thereof, and mixtures of same.

In a further embodiment of the first aspect, the present invention covers compounds of formula (I), supra, in which:
$R^8$ represents a hydrogen atom or a group selected from methoxy and ethoxy,
and stereoisomers, tautomers, N-oxides, hydrates, solvates, and salts thereof, and mixtures of same.

In a further embodiment of the first aspect, the present invention covers compounds of formula (I), supra, in which:
$R^8$ represents a hydrogen atom or a methoxy group,
and stereoisomers, tautomers, N-oxides, hydrates, solvates, and salts thereof, and mixtures of same.

In a particular further embodiment of the first aspect, the present invention covers compounds of formula (I), supra, in which:
$R^8$ represents a methoxy group,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a —CN or $C_1$-$C_3$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a $C_1$-$C_3$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a methyl or an ethyl group,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^9$ represents a hydrogen atom,
and stereoisomers, tautomers, N-oxides, hydrates, solvates, and salts thereof, and mixtures of same.

In a particular further embodiment of the first aspect, the present invention covers compounds of formula (I), supra, in which:
$R^9$ represents a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ represents a group selected from —C(=O)$R^{12}$, —C(=O)O$R^{13}$, —C(=O)N($R^{14}$)$R^{14a}$, —S(=O)$_2R^{15}$, —S(=O)$_2$N($R^{14}$)$R^{14a}$, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ represents a group selected from —C(=O)$R^{12}$, —C(=O)O$R^{13}$, —C(=O)N($R^{14}$)$R^{14a}$, —S(=O)$_2R^{15}$, —S(=O)$_2$N($R^{14}$)$R^{14a}$, 5- to 6-membered heteroaryl and phenyl,
said 5- to 6-membered heteroaryl group and said phenyl group being optionally substituted one or two times, identically or differently, with a fluorine atom, chlorine atom or bromine atom, or a group selected from —CN, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ represents a group selected from —C(=O)$R^{12}$, —C(=O)O$R^{13}$, —C(=O)N($R^{14}$)$R^{14a}$, —S(=O)$_2R^{15}$, —S(=O)$_2$N($R^{14}$)$R^{14a}$ and phenyl,
said phenyl group being optionally substituted one or two times, identically or differently, with a fluorine atom, chlorine atom or bromine atom, or a group selected from —CN, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{10}$ represents a group selected from —C(=O)$R^{12}$, —C(=O)N($R^{14}$)$R^{14a}$, —S(=O)$_2R^{15}$, —S(=O)$_2$N($R^{14}$)$R^{14a}$ and 2-chlorophenyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a group selected from —C(=O)$R^{12}$, —C(=O)N($R^{14}$)$R^{14a}$, —S(=O)$_2R^{15}$ and —S(=O)$_2$N($R^{14}$)$R^{14a}$,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a group selected from —C(=O)$R^{12}$ and —C(=O)N($R^{14}$)$R^{14a}$,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a, —C(=O)N($R^{14}$)$R^{14a}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —S(=O)$_2R^{15}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —S(=O)$_2$N($R^{14}$)$R^{14a}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a group selected from 2,2,2-trifluoroethyl, cyclopropyl, cyclobutyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a group selected from 2,2,2-trifluoroethyl, cyclopropyl, (1-trifluoromethyl)-(cyclopropyl)-, cyclobutyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a group selected from 2,2,2-trifluoroethyl, cyclopropyl and (1-trifluoromethyl)-(cyclopropyl)-, In a particular further embodiment of the first aspect, the present invention covers compounds of formula (I), supra, in which:
$R^{10}$ represents a —C(=O)$R^{12}$ group, and in which $R^{12}$ represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a group selected from 2-hydroxyprop-2-yl, (2-methoxy)-(prop-2-yl)-, 2,2,2-trifluoroethyl, cyclopropyl, (1-trifluoromethyl)-(cyclopropyl)-, 2,2-difluorocyclopropyl and 2,2-difluoro-1-methylcyclopropyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a group selected from 2,2,2-trifluoroethyl, cyclopropyl, (1-trifluoromethyl)-(cyclopropyl)-, 2,2-difluorocyclopropyl and 2,2-difluoro-1-methylcyclopropyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a 2,2,2-trifluoroethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a cyclopropyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{10}$ represents a —C(=O)$R^{12}$ group, and in which $R^{12}$ represents a (1-trifluoromethyl)-(cyclopropyl)- group,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl, $C_1$-$C_6$-hydroxyalkyl, ($C_1$-$C_3$-alkoxy)-($C_1$-$C_3$-alkyl)-, ($C_3$-$C_6$-cycloalkyl)-($C_1$-$C_3$-alkyl)- and benzyl, or
$R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, $C_1$-$C_3$-haloalkyl, $C_1$-$C_3$-alkoxy, —C(=O)$R^{18}$, —C(=O)O$R^{18}$ and —S(=O)$_2R^{18}$,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl, $C_1$-$C_6$-hydroxyalkyl, ($C_1$-$C_3$-alkoxy)-($C_1$-$C_3$-alkyl)-, ($C_3$-$C_6$-cycloalkyl)-($C_1$-$C_3$-alkyl)- and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, $C_1$-$C_3$-haloalkyl, $C_1$-$C_3$-alkoxy, —C(=O)$R^{18}$, —C(=O)O$R^{18}$ and —S(=O)$_2R^{18}$,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl and benzyl, or
$R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, —C(=O)$R^{18}$, C(=O)O$R^{18}$ and S(=O)$_2R^{18}$,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-haloalkyl, $C_3$-$C_6$-cycloalkyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 4- to 7-membered heterocycloalkyl group, said group being optionally substituted one or two times, identically or differently, with a halogen atom, or a group selected from hydroxy, oxo, —CN, $C_1$-$C_3$-alkyl, —C(=O)$R^{18}$, C(=O)O$R^{18}$ and S(=O)$_2R^{18}$,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-fluoroalkyl, $C_3$-$C_4$-cycloalkyl, $C_1$-$C_4$-hydroxyalkyl, ($C_1$-$C_2$-alkoxy)-($C_1$-$C_3$-alkyl)-, ($C_3$-$C_4$-cycloalkyl)-(methyl)- and benzyl,
$R^{11}$ and $R^{11a}$, together with the nitrogen atom they are attached to, represent a 4- to 6-membered heterocycloalkyl group, said group being optionally substituted one or two times, identically or differently, with a fluorine atom, or a group selected from hydroxy, oxo, —CN, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl, $C_1$-$C_4$-fluoroalkyl, $C_3$-$C_4$-cycloalkyl, $C_1$-$C_4$-hydroxyalkyl, ($C_1$-$C_2$-alkoxy)-($C_1$-$C_3$-alkyl)-, ($C_3$-$C_4$-cycloalkyl)-(methyl)- and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 4- to 6-membered heterocycloalkyl group, said group being optionally substituted one or two times, identically or differently, with a fluorine atom, or a group selected from hydroxy, oxo, —CN, methyl, trifluoromethyl and methoxy,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl and benzyl, or
$R^{11}$ and $R^{11a}$, together with the nitrogen atom they are attached to, represent a 5- to 6-membered heterocycloalkyl group, said group being optionally substituted once with a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_4$-alkyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 5- to 6-membered heterocycloalkyl group, said group being optionally substituted once with a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, $C_1$-$C_3$-fluoroalkyl, $C_3$-$C_4$-cycloalkyl, $C_1$-$C_3$-hydroxyalkyl, ($C_1$-$C_2$-alkoxy)-($C_1$-$C_3$-alkyl)-, ($C_3$-$C_4$-cycloalkyl)-(methyl)- and benzyl, or
$R^{11}$ and $R^{11a}$, together with the nitrogen atom they are attached to, represent a 4- to 6-membered heterocycloalkyl group, said group being optionally substituted one or two times, identically or differently, with a fluorine atom or with a group selected from methyl and trifluoromethyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, $C_1$-$C_3$-fluoroalkyl, $C_3$-$C_4$-cycloalkyl, $C_1$-$C_3$-hydroxyalkyl, ($C_1$-$C_2$-alkoxy)-($C_1$-$C_3$-alkyl)-, ($C_3$-$C_4$-cycloalkyl)-(methyl)- and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 4- to 6-membered heterocycloalkyl group, said group being optionally substituted one or two times, identically or differently, with a fluorine atom or with a group selected from methyl and trifluoromethyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from methyl and ethyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or
$R^{11}$ and $R^{11a}$, together with the nitrogen atom they are attached to, represent a 4- to 6-membered heterocycloalkyl group, said group being optionally substituted one or two times with a fluorine atom or a trifluoromethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-,
and stereoisomers, tautomers, N-oxides, hydrates, solvates, and salts thereof, and mixtures of same.

In a further embodiment of the first aspect, the present invention covers compounds of formula (I), supra, in which:
$R^{11}$ and $R^{11a}$, together with the nitrogen atom they are attached to, represent a 4- to 6-membered heterocycloalkyl group, said group being optionally substituted one or two times with a fluorine atom or a trifluoromethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-, or
$R^{11}$ and $R^{11a}$, together with the nitrogen atom they are attached to, represent a 4- to 6-membered heterocycloalkyl group, said group being optionally substituted one or two times with a fluorine atom,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from $C_1$-$C_3$-alkyl, 2,2,2-trifluoroethyl, $C_3$-$C_4$-cycloalkyl, ($C_1$-$C_2$-alkoxy)-($C_1$-$C_3$-alkyl)- and ($C_3$-$C_4$-cycloalkyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, together with the nitrogen atom they are attached to, represent a 4- to 6-membered heterocycloalkyl group, said group being optionally substituted one or two times with a fluorine atom,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from methyl, ethyl, 2,2,2-trifluoroethyl, cyclopropyl, cyclobutyl and (cyclopropyl)-(methyl)-, or
$R^{11}$ and $R^{11a}$, together with the nitrogen atom they are attached to, represent a group selected from azetidin-1-yl, 3-fluoroazetidin-1-yl, 3,3-difluoroazetidin-1-yl, 3-trifluoromethylazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from methyl, ethyl, 2,2,2-trifluoroethyl, cyclopropyl, cyclobutyl and (cyclopropyl)-(methyl)-,
$R^{11}$ and $R^{11a}$, together with the nitrogen atom they are attached to, represent a group selected from azetidin-1-yl, 3-fluoroazetidin-1-yl, 3,3-difluoroazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from a hydrogen atom or a group selected from methyl, ethyl, 2,2,2-trifluoroethyl, cyclopropyl, cyclobutyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, together with the nitrogen atom they are attached to, represent a group selected from azetidin-1-yl, 3-fluoroazetidin-1-yl, 3,3-difluoroazetidin-1-yl, 3-trifluoromethylazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, together with the nitrogen atom they are attached to, represent a group selected from azetidin-1-yl, 3,3-difluoroazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, independently from each other, represent a hydrogen atom or a group selected from methyl, ethyl, 2,2,2-trifluoroethyl, cyclopropyl, cyclobutyl and (cyclopropyl)-(methyl)-, or
$R^{11}$ and $R^{11a}$, together with the nitrogen atom they are attached to, represent a group selected from azetidin-1-yl, 3,3-difluoroazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, together with the nitrogen atom they are attached to, represent a group selected from azetidin-1-yl, 3,3-difluoroazetidin-1-yl, 3-trifluoromethylazetidin-1-yl, pyrrolidin-1-yl, piperidin-1-yl, morpholinyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{11}$ and $R^{11a}$, together with the nitrogen atom they are attached to, represent a group selected from azetidin-1-yl, 3,3-difluoroazetidin-1-yl, pyrrolidin-1-yl, piperidin-1-yl, morpholinyl,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a hydrogen atom or a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_3$-alkyl)-, $C_3$-$C_6$-cycloalkyl, ($C_3$-$C_6$-cycloalkyl)-($C_1$-$C_3$-alkyl)-, $C_2$-$C_6$-alkenyl, $C_2$-$C_6$-alkynyl, 4- to 7-membered heterocycloalkyl, 5- to 7-membered heterocycloalkenyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy,
said $C_3$-$C_6$-cycloalkyl group being optionally substituted one, two or three times, identically or differently, with a halogen atom or a group selected from —CN, $C_1$-$C_3$-alkyl and $C_1$-$C_3$-haloalkyl,
and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a hydrogen atom or a group selected from $C_1$-$C_6$-alkyl, $C_1$-$C_6$-haloalkyl, $C_1$-$C_6$-hydroxyalkyl, $C_3$-$C_6$-cycloalkyl, ($C_3$-$C_6$-cycloalkyl)-($C_1$-$C_3$-alkyl)-, $C_2$-$C_6$-alkenyl, $C_2$-$C_6$-alkynyl, 4- to 7-membered heterocycloalkyl, 5- to 7-membered heterocycloalkenyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy, said $C_3$-$C_6$-cycloalkyl group being optionally substituted one, two or three times, identically or differently, with a halogen atom or a group selected from —CN, $C_1$-$C_3$-alkyl and $C_1$-$C_3$-haloalkyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a group selected from $C_1$-$C_6$-alkyl, $C_1$-$C_6$-haloalkyl, $C_1$-$C_6$-hydroxyalkyl, $C_3$-$C_6$-cycloalkyl, ($C_3$-$C_6$-cycloalkyl)-($C_1$-$C_3$-alkyl)-, $C_2$-$C_6$-alkenyl, $C_2$-$C_6$-alkynyl, 4- to 7-membered heterocycloalkyl, 5- to 7-membered heterocycloalkenyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a hydrogen atom or a group selected from $C_1$-$C_4$-alkyl, $C_1$-$C_4$-fluoroalkyl, $C_1$-$C_4$-hydroxyalkyl, ($C_1$-$C_2$-alkoxy)-($C_1$-$C_3$-alkyl)-, $C_3$-$C_6$-cycloalkyl, ($C_3$-$C_6$-cycloalkyl)-($C_1$-$C_2$-alkyl)-, $C_2$-$C_4$-alkenyl, 5- to 6-membered heteroaryl and phenyl,
said 5- to 6-membered heteroaryl group and said phenyl group being optionally substituted one, two or three times, identically or differently, with a fluorine atom, a chlorine atom or a group selected from methyl, trifluormethyl and methoxy,
said $C_3$-$C_6$-cycloalkyl group being optionally substituted one, two or three times, identically or differently, with a fluorine atom, a chlorine atom or a group selected from —CN, methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a hydrogen atom or a group selected from $C_1$-$C_4$-alkyl, $C_1$-$C_4$-fluoroalkyl, $C_3$-$C_6$-cycloalkyl, ($C_3$-$C_6$-cycloalkyl)-($C_1$-$C_2$-alkyl)-, $C_2$-$C_4$-alkenyl, 5- to 6-membered heteroaryl and phenyl,
said 5- to 6-membered heteroaryl group and said phenyl group being optionally substituted one, two or three times, identically or differently, with a fluorine atom, a chlorine atom or a group selected from methyl, trifluormethyl and methoxy,
said $C_3$-$C_6$-cycloalkyl group being optionally substituted one, two or three times, identically or differently, with a fluorine atom, a chlorine atom or a group selected from —CN, methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a group selected from $C_1$-$C_4$-alkyl, $C_1$-$C_4$-fluoroalkyl, $C_3$-$C_6$-cycloalkyl, ($C_3$-$C_6$-cycloalkyl)-($C_1$-$C_2$-alkyl)- and $C_2$-$C_4$-alkenyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a group selected from $C_1$-$C_4$-alkyl, $C_1$-$C_3$-fluoroalkyl, $C_1$-$C_3$-hydroxyalkyl, (methoxy)-($C_1$-$C_3$-alkyl)-, $C_3$-$C_4$-cycloalkyl, (cyclopropyl)-(methyl)- and allyl,
said $C_3$-$C_4$-cycloalkyl group being optionally substituted one, two or three times, identically or differently, with a fluorine atom or a group selected from methyl and trifluoromethyl, and stereoisomers, tautomers, N-oxides, hydrates, solvates, and salts thereof, and mixtures of same.

In a further particular embodiment of the first aspect, the present invention covers compounds of formula (I), supra, in which:
$R^{12}$ represents a $C_3$-$C_4$-cycloalkyl group,
said $C_3$-$C_4$-cycloalkyl group being optionally substituted one, two or three times, identically or differently, with a fluorine atom or a group selected from methyl and trifluoromethyl, and stereoisomers, tautomers, N-oxides, hydrates, solvates, and salts thereof, and mixtures of same.

In a further particular embodiment of the first aspect, the present invention covers compounds of formula (I), supra, in which:
$R^{12}$ represents a cyclopropyl group,
said cyclopropyl group being optionally substituted one, two or three times, identically or differently, with a fluorine atom or a group selected from methyl and trifluoromethyl, and stereoisomers, tautomers, N-oxides, hydrates, solvates, and salts thereof, and mixtures of same.

In a further particular embodiment of the first aspect, the present invention covers compounds of formula (I), supra, in which:
$R^{12}$ represents a group selected from (1-trifluoromethyl)-(cyclopropyl)-, 2,2-difluorocyclopropyl and 2,2-difluoro-1-methylcyclopropyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a group selected from $C_1$-$C_4$-alkyl, $C_1$-$C_3$-fluoroalkyl, $C_3$-$C_4$-cycloalkyl, (cyclopropyl)-(methyl)- and allyl,
said $C_3$-$C_4$-cycloalkyl group being optionally substituted one, two or three times, identically or differently, with a fluorine atom or a group selected from methyl and trifluoromethyl, and stereoisomers, tautomers, N-oxides, hydrates, solvates, and salts thereof, and mixtures of same.

In a further embodiment of the first aspect, the present invention covers compounds of formula (I), supra, in which:
$R^{12}$ represents a group selected from $C_1$-$C_4$-alkyl, $C_1$-$C_3$-fluoroalkyl, $C_3$-$C_4$-cycloalkyl, (cyclopropyl)-(methyl)- and allyl, and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from $C_1$-$C_2$-fluoroalkyl, $C_3$-$C_4$-cycloalkyl, 2-hydroxyprop-2-yl, (2-methoxy)-(prop-2-yl)-, (1-trifluoromethyl)-(cyclopropyl)-, 2,2-difluorocyclopropyl, 2,2-difluoro-1-methylcyclopropyl and (cyclopropyl)-(methyl)-, and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from $C_1$-$C_2$-fluoroalkyl, $C_3$-$C_4$-cycloalkyl, (1-trifluoromethyl)-(cyclopropyl)- and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from $C_1$-$C_2$-fluoroalkyl, $C_3$-$C_4$-cycloalkyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a $C_1$-$C_2$-fluoroalkyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a $C_3$-$C_4$-cycloalkyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a (cyclopropyl)-(methyl)- group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from 2,2,2-trifluoroethyl, cyclopropyl, cyclobutyl, 2-hydroxyprop-2-yl, (2-methoxy)-(prop-2-yl)-, (1-trifluoromethyl)-(cyclopropyl)-2,2-difluorocyclopropyl, 2,2-difluoro-1-methylcyclopropyl and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from 2,2,2-trifluoroethyl, cyclopropyl, cyclobutyl, (1-trifluoromethyl)-(cyclopropyl)- and (cyclopropyl)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from 2,2,2-trifluoroethyl, cyclopropyl, cyclobutyl and (cyclopropyl)-(methyl)-;
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a group selected from 2,2,2-trifluoroethyl, cyclopropyl and (1-trifluoromethyl)-(cyclopropyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a 2,2,2-trifluoroethyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a cyclopropyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a cyclobutyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a (1-trifluoromethyl)-(cyclopropyl)- group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a 2,2-difluorocyclopropyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a 2,2-difluoro-1-methylcyclopropyl group,
and stereoisomers, tautomers, N-oxides, hydrates, solvates, and salts thereof, and mixtures of same.

In a particular further embodiment of the first aspect, the present invention covers compounds of formula (I), supra, in which:
$R^{12}$ represents a (cyclopropyl)-(methyl)- group,
and stereoisomers, tautomers, N-oxides, hydrates, solvates, and salts thereof, and mixtures of same.

In a further embodiment of the first aspect, the present invention covers compounds of formula (I), supra, in which:
$R^{13}$ represents a group selected from $C_1$-$C_4$-alkyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{13}$ represents a group selected from methyl, ethyl, tert-butyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{13}$ represents a benzyl group,
and stereoisomers, tautomers, N-oxides, hydrates, solvates, and salts thereof, and mixtures of same.

In a further embodiment of the first aspect, the present invention covers compounds of formula (I), supra, in which:
$R^{13}$ represents a $C_1$-$C_4$-alkyl group,
and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents a group selected from methyl, ethyl and tert-butyl, and stereoisomers, tautomers, N-oxides, hydrates, solvates, and salts thereof, and mixtures of same.

In a further embodiment of the first aspect, the present invention covers compounds of formula (I), supra, in which:
$R^{13}$ represents a tert-butyl group,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, independently from each other, represent a hydrogen atom or a group selected from $C_1$-$C_4$-alkyl, $C_1$-$C_4$-haloalkyl, $C_3$-$C_6$-cycloalkyl and benzyl, or
$R^{14}$ and $R^{14a}$, together with the nitrogen atom they are attached to, represent a 4- to 7-membered heterocycloalkyl group, said group being optionally substituted one or two times, identically or differently, with a halogen atom or a group selected from hydroxyl, —CN, $C_1$-$C_3$-alkyl, $C_1$-$C_3$-haloalkyl, $C_1$-$C_3$-alkoxy, $C_1$-$C_3$-haloalkoxy and ($C_1$-$C_3$-alkoxy)-($C_1$-$C_3$-alkyl)-,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, independently from each other, represent a hydrogen atom or a group selected from $C_1$-$C_4$-alkyl, $C_1$-$C_4$-haloalkyl, $C_3$-$C_6$-cycloalkyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, together with the nitrogen atom they are attached to, represent a 4- to 7-membered heterocycloalkyl group, said group being optionally substituted one or two times, identically or differently, with a halogen atom or a group selected from hydroxyl, —CN, $C_1$-$C_3$-alkyl, $C_1$-$C_3$-haloalkyl, $C_1$-$C_3$-alkoxy, $C_1$-$C_3$-haloalkoxy and ($C_1$-$C_3$-alkoxy)-($C_1$-$C_3$-alkyl)-,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, independently from each other, represent a hydrogen atom or a group selected from $C_1$-$C_3$-alkyl, trifluoromethyl and cyclopropyl, or
$R^{14}$ and $R^{14a}$, together with the nitrogen atom they are attached to, represent a 4- to 7-membered heterocycloalkyl group, said group being optionally substituted one or two times, identically or differently, with a group selected from $C_1$-$C_3$-alkyl, $C_1$-$C_3$-fluoroalkyl, $C_1$-$C_3$-alkoxy, trifluoromethoxy and ($C_1$-$C_2$-alkoxy)-($C_1$-$C_2$-alkyl)-,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, independently from each other, represent a hydrogen atom or a group selected from $C_1$-$C_3$-alkyl, trifluoromethyl and cyclopropyl,
and stereoisomers, tautomers, N-oxides, hydrates, solvates, and salts thereof, and mixtures of same.

In a further embodiment of the first aspect, the present invention covers compounds of formula (I), supra, in which:
$R^{14}$ and $R^{14a}$, together with the nitrogen atom they are attached to, represent a 4- to 7-membered heterocycloalkyl group, said group being optionally substituted one or two times, identically or differently, with a group selected from $C_1$-$C_3$-alkyl, $C_1$-$C_3$-fluoroalkyl, $C_1$-$C_3$-alkoxy, trifluoromethoxy and ($C_1$-$C_2$-alkoxy)-($C_1$-$C_2$-alkyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{14}$ and $R^{14a}$, independently from each other, represent a hydrogen atom or a group selected from methyl and ethyl, or
$R^{14}$ and $R^{14a}$, together with the nitrogen atom they are attached to, represent a 5- to 6-membered heterocycloalkyl group selected from pyrrolidinyl, piperidinyl and morpholinyl, said group being optionally substituted once with a group selected from methyl, methoxy and (methoxy)-(methyl)-,
and stereoisomers, tautomers, N-oxides, hydrates, solvates, and salts thereof, and mixtures of same.

In a particular further embodiment of the first aspect, the present invention covers compounds of formula (I), supra, in which:
$R^{14}$ and $R^{14a}$, independently from each other, represent a hydrogen atom or a group selected from methyl and ethyl,
and stereoisomers, tautomers, N-oxides, hydrates, solvates, and salts thereof, and mixtures of same.

In a particular further embodiment of the first aspect, the present invention covers compounds of formula (I), supra, in which:
$R^{14}$ and $R^{14a}$, together with the nitrogen atom they are attached to, represent a 5- to 6-membered heterocycloalkyl group selected from pyrrolidinyl, piperidinyl and morpholinyl, said group being optionally substituted once with a group selected from methyl, methoxy and (methoxy)-(methyl)-,
and stereoisomers, tautomers, N-oxides, hydrates, solvates, and salts thereof, and mixtures of same.

In a further embodiment of the first aspect, the present invention covers compounds of formula (I), supra, in which:
$R^{15}$ represents a group selected from $C_1$-$C_6$-alkyl, $C_1$-$C_6$-haloalkyl, $C_1$-$C_6$-hydroxyalkyl, ($C_1$-$C_3$-alkoxy)-($C_1$-$C_6$-alkyl)-, ($C_1$-$C_3$-alkoxy)-($C_2$-$C_3$-alkoxy)-($C_1$-$C_6$-alkyl)-, $C_3$-$C_6$-cycloalkyl, ($C_3$-$C_6$-cycloalkyl)-($C_1$-$C_3$-alkyl)-, 4- to 7-membered heterocycloalkyl, 5- to 6-membered heteroaryl and phenyl,
said 5- to 6-membered heteroaryl group and said phenyl group being optionally substituted one, two or three times, identically or differently, with a halogen atom or a group selected from —CN, $C_1$-$C_3$-alkyl, $C_1$-$C_3$-haloalkyl, $C_1$-$C_3$-alkoxy and $C_1$-$C_3$-haloalkoxy,
and stereoisomers, tautomers, N-oxides, hydrates, solvates, and salts thereof, and mixtures of same.

In a further embodiment of the first aspect, the present invention covers compounds of formula (I), supra, in which:
$R^{15}$ represents a group selected from $C_1$-$C_4$-alkyl, $C_1$-$C_4$-fluoroalkyl, ($C_1$-$C_2$-alkoxy)-($C_1$-$C_3$-alkyl)-, ($C_1$-$C_2$-alkoxy)-(ethoxy)-($C_1$-$C_3$-alkyl)-, $C_3$-$C_6$-cycloalkyl, ($C_3$-$C_6$-cycloalkyl)-($C_1$-$C_2$-alkyl)- and 4- to 7-membered heterocycloalkyl,
and stereoisomers, tautomers, N-oxides, hydrates, solvates, and salts thereof, and mixtures of same.

In a further embodiment of the first aspect, the present invention covers compounds of formula (I), supra, in which:
$R^{15}$ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl,
and stereoisomers, tautomers, N-oxides, hydrates, solvates, and salts thereof, and mixtures of same.

In a further embodiment of the first aspect, the present invention covers compounds of formula (I), supra, in which:
$R^{15}$ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl, and stereoisomers, tautomers, N-oxides, hydrates, solvates, and salts thereof, and mixtures of same.

In a further embodiment of the first aspect, the present invention covers compounds of formula (I), supra, in which:
$R^{15}$ represents a group selected from ethyl, 3,3,3-trifluoropropyl, (3-methoxy)-(propyl)-, (2'-methoxy)-(2-ethoxy)-(ethyl)-, cyclopropyl, cyclohexyl and tetrahydropyranyl, and stereoisomers, tautomers, N-oxides, hydrates, solvates, and salts thereof, and mixtures of same.

In a further embodiment of the first aspect, the present invention covers compounds of formula (I), supra, in which:
$R^{16}$ represents a hydrogen atom or a group selected from $C_1$-$C_4$-alkyl and benzyl,
and stereoisomers, tautomers, N-oxides, hydrates, solvates, and salts thereof, and mixtures of same.

In a further embodiment of the first aspect, the present invention covers compounds of formula (I), supra, in which:
$R^{16}$ represents a hydrogen atom or a $C_1$-$C_3$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{16}$ represents a hydrogen atom or a $C_1$-$C_2$-alkyl group,
and stereoisomers, tautomers, N-oxides, hydrates, solvates, and salts thereof, and mixtures of same.

In a further embodiment of the first aspect, the present invention covers compounds of formula (I), supra, in which:
$R^{16}$ represents a hydrogen atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
$R^{16}$ represents a hydrogen atom or a methyl group,
and stereoisomers, tautomers, N-oxides, hydrates, solvates, and salts thereof, and mixtures of same.

In a further embodiment of the first aspect, the present invention covers compounds of formula (I), supra, in which:
x represents an integer selected from 1, 2, 3 and 4,
and stereoisomers, tautomers, N-oxides, hydrates, solvates, and salts thereof, and mixtures of same.

In a further embodiment of the first aspect, the present invention covers compounds of formula (I), supra, in which:
x represents an integer selected from 1 and 2,
and stereoisomers, tautomers, N-oxides, hydrates, solvates, and salts thereof, and mixtures of same.

In a further embodiment of the first aspect, the present invention covers compounds of formula (I), supra, in which:
x represents an integer 1,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

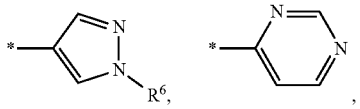

in which "*" represents the point of attachment to the rest of the molecule;
the ring of said group being, besides $R^6$, optionally substituted further one or two times, differently or identically, with a $R^7$ group;
$R^2$ represents a group

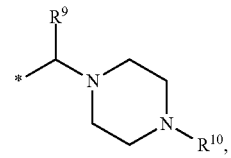

in which "*" represents the point of attachment to the rest of the molecule, and
$R^{10}$ represents a —C(=O)$R^{12}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

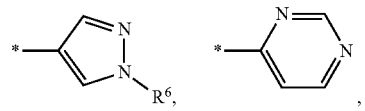

in which "*" represents the point of attachment to the rest of the molecule;
the ring of said group being, besides $R^6$, optionally substituted further one or two times, differently or identically, with a $R^7$ group;
$R^2$ represents a group

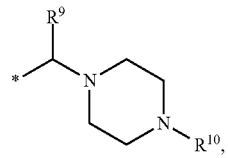

in which "*" represents the point of attachment to the rest of the molecule,
$R^9$ represents a methyl group, and
$R^{10}$ represents a —C(=O)$R^{12}$ group,
and stereoisomers, tautomers, N-oxides, hydrates, solvates, and salts thereof, and mixtures of same.

In a particular further embodiment of the first aspect, the present invention covers compounds of formula (I), supra, in which:
$R^1$ represents a group

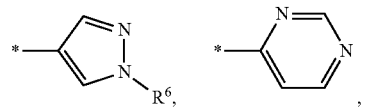

in which "*" represents the point of attachment to the rest of the molecule;

the ring of said group being, besides R⁶, optionally substituted with one further R⁷ group;
R² represents a group

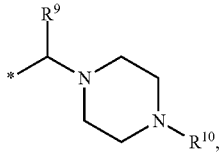

in which "*" represents the point of attachment to the rest of the molecule, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

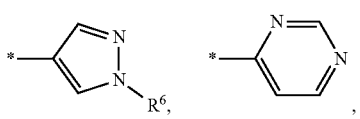

in which "*" represents the point of attachment to the rest of the molecule;
the ring of said group being, besides R⁶, optionally substituted further one or two times, differently or identically, with a R⁷ group;
R² represents a group

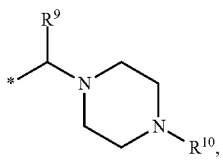

in which "*" represents the point of attachment to the rest of the molecule,
R³ represents a hydrogen atom,
R⁹ represents a methyl group, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

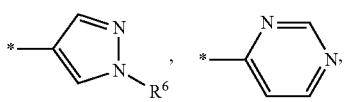

in which "*" represents the point of attachment to the rest of the molecule;
the ring of said group being, besides R⁶, optionally substituted with one further R⁷ group;

R² represents a group

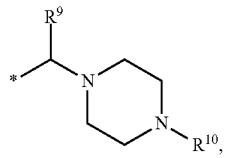

in which "*" represents the point of attachment to the rest of the molecule,
R³ represents a hydrogen atom, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

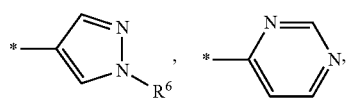

in which "*" represents the point of attachment to the rest of the molecule;
the ring of said group being, besides R⁶, optionally substituted further one or two times, differently or identically, with a R⁷ group;
R² represents a group

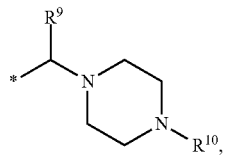

in which "*" represents the point of attachment to the rest of the molecule,
R³ represents a hydrogen atom,
R⁴ represents a hydrogen atom,
R⁵ represents a hydrogen atom, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

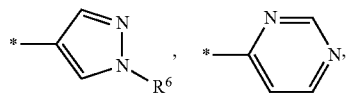

in which "*" represents the point of attachment to the rest of the molecule;
the ring of said group being, besides R⁶, optionally substituted further one or two times, differently or identically, with a R⁷ group;

R² represents a group

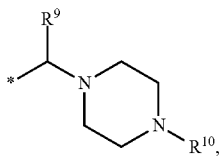

in which "*" represents the point of attachment to the rest of the molecule,
R³ represents a hydrogen atom,
R⁴ represents a hydrogen atom,
R⁵ represents a hydrogen atom,
R⁹ represents a methyl group, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

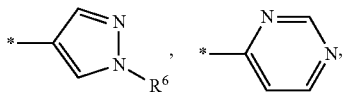

in which "*" represents the point of attachment to the rest of the molecule;
the ring of said group being, besides R⁶, optionally substituted with one further R⁷ group;
R² represents a group

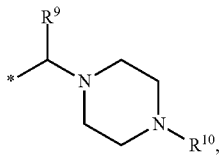

in which "*" represents the point of attachment to the rest of the molecule,
R³ represents a hydrogen atom,
R⁴ represents a hydrogen atom,
R⁵ represents a hydrogen atom, and
R¹⁰ represents a —C(=O)R¹² group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

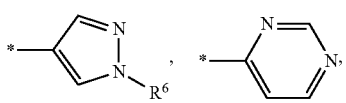

in which "*" represents the point of attachment to the rest of the molecule;
the ring of said group being, besides R⁶, optionally substituted further one or two times, differently or identically, with a R⁷ group;
R³ represents a hydrogen atom,
R⁴ represents a hydrogen atom,
R⁵ represents a hydrogen atom,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

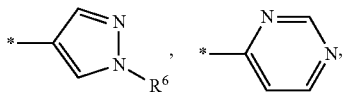

in which "*" represents the point of attachment to the rest of the molecule;
the ring of said group being, besides R⁶, optionally substituted further one or two times, differently or identically, with a R⁷ group;
R³ represents a hydrogen atom,
R⁴ represents a hydrogen atom,
R⁵ represents a hydrogen atom, and
R⁹ represents a methyl group,
and stereoisomers, tautomers, N-oxides, hydrates, solvates, and salts thereof, and mixtures of same.

In a particular further embodiment of the first aspect, the present invention covers compounds of formula (I), supra, in which:
R¹ represents a group

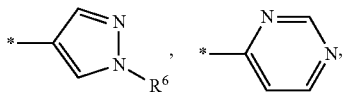

in which "*" represents the point of attachment to the rest of the molecule;
the ring of said group being, besides R⁶, optionally substituted with one further R⁷ group;
R³ represents a hydrogen atom,
R⁴ represents a hydrogen atom,
R⁵ represents a hydrogen atom, and
and stereoisomers, tautomers, N-oxides, hydrates, solvates, and salts thereof, and mixtures of same.

In a particular further embodiment of the first aspect, the present invention covers compounds of formula (I), supra, in which:
R² represents a group

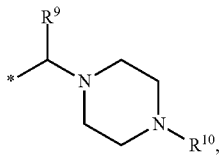

in which "*" represents the point of attachment to the rest of the molecule,
R³ represents a hydrogen atom,
R⁴ represents a hydrogen atom,
R⁵ represents a hydrogen atom, and
R¹⁰ represents a —C(=O)R¹² group, and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group

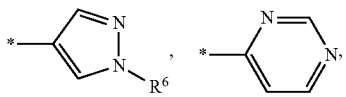

in which "*" represents the point of attachment to the rest of the molecule;

the ring of said group being, besides $R^6$, optionally substituted further one or two times, differently or identically, with a $R^7$ group;

$R^2$ represents a group

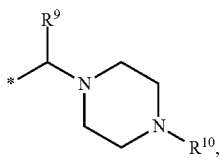

in which "*" represents the point of attachment to the rest of the molecule, $R^3$ represents a hydrogen atom, $R^4$ represents a hydrogen atom, $R^5$ represents a hydrogen atom, and $R^{10}$ represents a —C(=O)$R^{12}$ group, in which $R^{12}$ represents a group selected from 2,2,2-trifluoroethyl, cyclopropyl, cyclobutyl and (cyclopropyl)-(methyl)-, and stereoisomers, tautomers, N-oxides, hydrates, solvates, and salts thereof, and mixtures of same.

In a particular further embodiment of the first aspect, the present invention covers compounds of formula (I), supra, in which:

$R^1$ represents a group

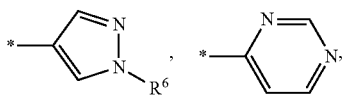

in which "*" represents the point of attachment to the rest of the molecule;

the ring of said group being, besides $R^6$, optionally substituted with one further $R^7$ group;

$R^2$ represents a group

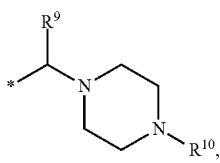

in which "*" represents the point of attachment to the rest of the molecule, $R^3$ represents a hydrogen atom, $R^4$ represents a hydrogen atom, $R^5$ represents a hydrogen atom, and $R^{10}$ represents a —C(=O)$R^{12}$ group, in which $R^{12}$ represents a group selected from 2,2,2-trifluoroethyl, cyclopropyl, cyclobutyl and (cyclopropyl)-(methyl)-, and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (XL).

The present invention covers the compounds of general formula (I) which are disclosed in the Example Section of this text, infra.

General Syntheses of Compounds of Formula (I)

The following paragraphs outline a variety of synthetic approaches suitable to prepare compounds of the general formula (I), and intermediates useful for their synthesis.

In addition to the routes described below, also other routes may be used to synthesise the compounds of the general formula (I), in accordance with common general knowledge of a person skilled in the art of organic synthesis. The order of transformations exemplified in the following schemes is therefore not intended to be limiting, and suitable synthesis steps from various schemes can be combined to form additional synthesis sequences. In addition, modification of any of the substituents, such as $R^1$, $R^2$, $R^3$, $R^4$ or $R^5$, or of substituents contained therein, such as $R^{10}$ in $R^2$, can be achieved before and/or after the exemplified transformations. These modifications can be such as the introduction of protective groups, cleavage of protective groups, reduction or oxidation of functional groups, halogenation, alkylation, acylation, sulfonylation, metallation, metal catalysed coupling reactions, exemplified by but not limited to Suzuki, Sonogashira, Negishi and Ullmann couplings, ester saponifications, amide coupling reactions, formation and cleavage of ethers, reductive aminations, hydrogenolyses e.g. of halogen atoms bonded to aromatic rings, Mitsunobu type reactions of an alcohol with a nucleophile in the presence of an dialkyl azodicarboxylate, such as DIAD (diisopropyl azodicarboxylate) and a tertiary phosphine, such as triphenylphosphine, and/or substitution or other reactions known to a person skilled in the art. These transformations include those which introduce a functionality allowing for further modification of substituents. Appropriate protective groups and their introduction and cleavage are well-known to a person skilled in the art (see for example T. W. Greene and P. G. M. Wuts in Protective Groups in Organic Synthesis, $4^{th}$ edition, Wiley 2006).

Compounds of formula (I), and the intermediates used in their synthesis, may be chiral, e.g. in case of $R^9$ being different from hydrogen, and may then be formed as mixtures of stereoisomers. Said mixtures of stereoisomers can be separated by methods well known the person skilled in the art, such as preparative chromatography, such as high pressure liquid chromatography (HPLC) or superfluid chromatography (SFC) using chiral stationary phases, which are commercially available in considerable variety. If compounds of formula (I), or intermediates used in their synthesis, are sufficiently basic or acidic, stereoisomeric mixtures, in particular mixtures of enantiomers, can be resolved using chiral, enantiomerically pure acids, such as tartaric acid and 2,3-bis(benzoyloxy)succinic acid, or chiral, enantiomerically pure amines, such as 1-phenylethylamine or strychnine, respectively, via the formation of diastereomeric salts which can be separated.

The general synthesis strategy to compounds of the general formula (I) is outlined in Scheme 1. As starting materials, diaminobenzene derivatives of formula (II), in which $R^3$ is as defined for the compounds of general formula (I) and X represents a group selected from a boronic acid, a boronic acid ester, a —CN group, a —C(=O)—O—$R^E$ group, in which $R^E$ represents a $C_1$-$C_3$-alkyl group, and a $R^1$ group which is as defined for the compounds of general formula (I), and aminopyridine derivatives of formula (III), in which $R^4$ and $R^5$ are as defined for the compounds of general formula (I), and in which Y represents a group selected from —CH$_2$—O-PG$^1$, in which PG$^1$ represents a protective group suitable for hydroxy groups, as present e.g. in alcohols, as defined supra, such as tert-butyl dimethylsilyl, a $R^2$ group, which is as defined for the compounds of general formula (I), and a $G^1$ group, in which $R^9$ is as defined for the compounds of general formula (I), and in which "#" indicates that the piperazine ring may be either unsubstituted or bridged, or substituted with one or two methyl groups, according to the definition of $R^2$ in general formula (I), can be employed.

In a first key step, said aminopyridines of formula (III) can be reacted with di-1H-imidazol-1-ylmethanethione or thiophosgene, in the presence of a catalytic amount of 1H-imidazole, in a solvent such as dichloromethane, tetrahydrofuran, N,N-dimethylformamide or dioxane, followed by the addition of diaminobenzene derivatives of formula (II), to give thioureas of formulae (IV) and (IVa) as regioisomeric mixtures. Said thioureas of formulae (IV) and (IVa) can be, in a second key step, further converted into benzimidazole derivatives of formula (V) by reaction with a carbodiimide, such as N,N'-dipropan-2-ylcarbodiimide or 1-ethyl-3-(3-dimethylaminopropyl)carbodiimide, or a salt thereof, in an aliphatic chlorinated hydrocarbon, such as dichloromethane and chloroform, as a solvent. Noteworthily, regioisomeric mixtures of thioureas of formulae (IV) and (IVa) give rise to a homogeneous benzimidazole isomer as a result of imidazole tautomery.

Scheme 1 General synthesis strategy for the preparation of the compounds of the present invention.

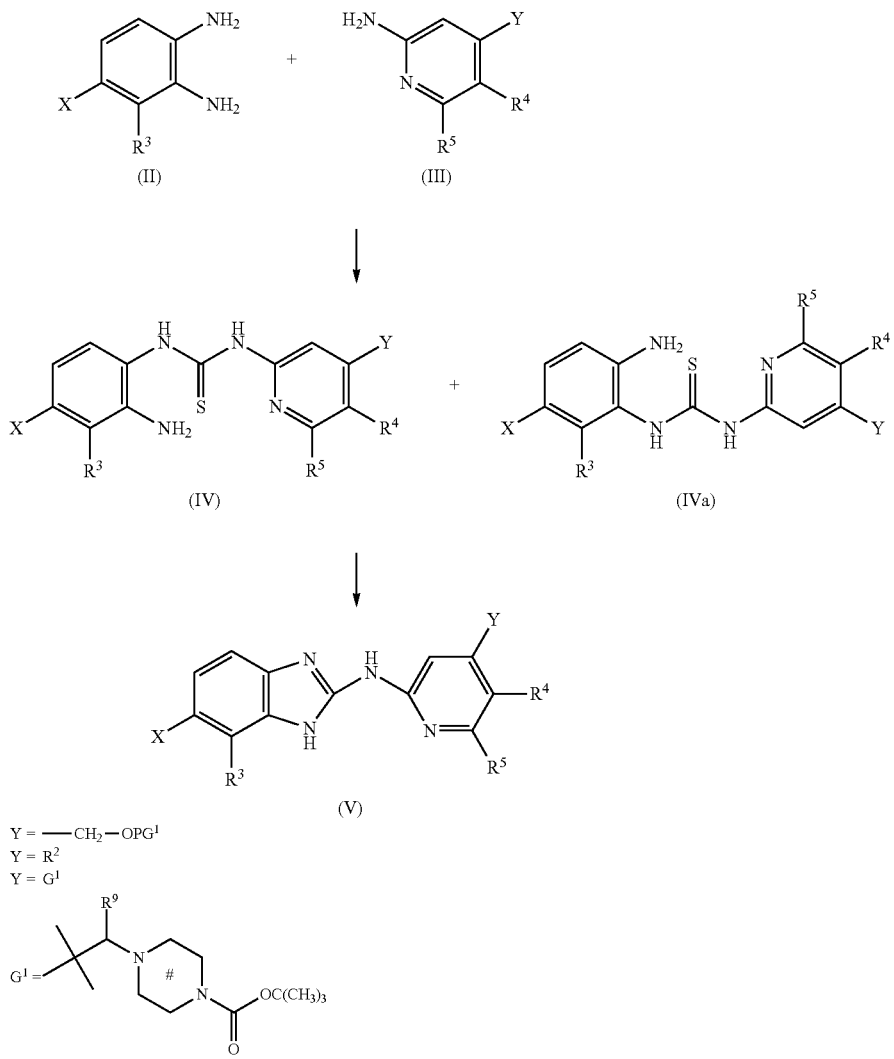

Dependent of the nature of the X and Y groups, compounds of formula (V) can either already constitute compounds of the general formula (I), or various synthetic intermediates thereof. More detailed synthesis routes to compounds of general formula (I) are given below, as outlined in the Schemes 2a, 2b, 2c, 2d, 2e, 2f, 3a, 3b, 3c, 4 and 5.

Schemes 2a and 2d outline an approach to compounds of general formula (I), in which $R^1$ can be introduced in a late step by means of the well-known Suzuki coupling, from nitroaniline derivatives of formula (VI), diaminobenzene derivatives of formula (VII), aminopyridine derivatives of formula (VIII), and piperazine derivatives of formula (IX).

KGaA, Weinheim, ISBN 3-527-30991-8 and references cited therein. Subsequently, boronic acid derivatives of formula (X) can be reduced to the corresponding diamines of formula (XI) by methods well known to the person skilled in the art, e.g. by palladium catalysed hydrogenolysis.

In an analogous fashion as described supra for the conversion of compounds of formula (VI) into boronic acid derivatives of formula (X), diaminobenzene derivatives of formula (VII), in which $R^3$ is as defined for the compounds of general formula (I), and in which $LG^1$ represents a leaving group, preferably chloride, bromide or iodide, can be converted into compounds of formula (XI) in one step. Prefer- Scheme 2a Synthesis of intermediates of formulae (XI) and (XII) from starting materials of formulae (VI), (VII), (VIII) and (IX).

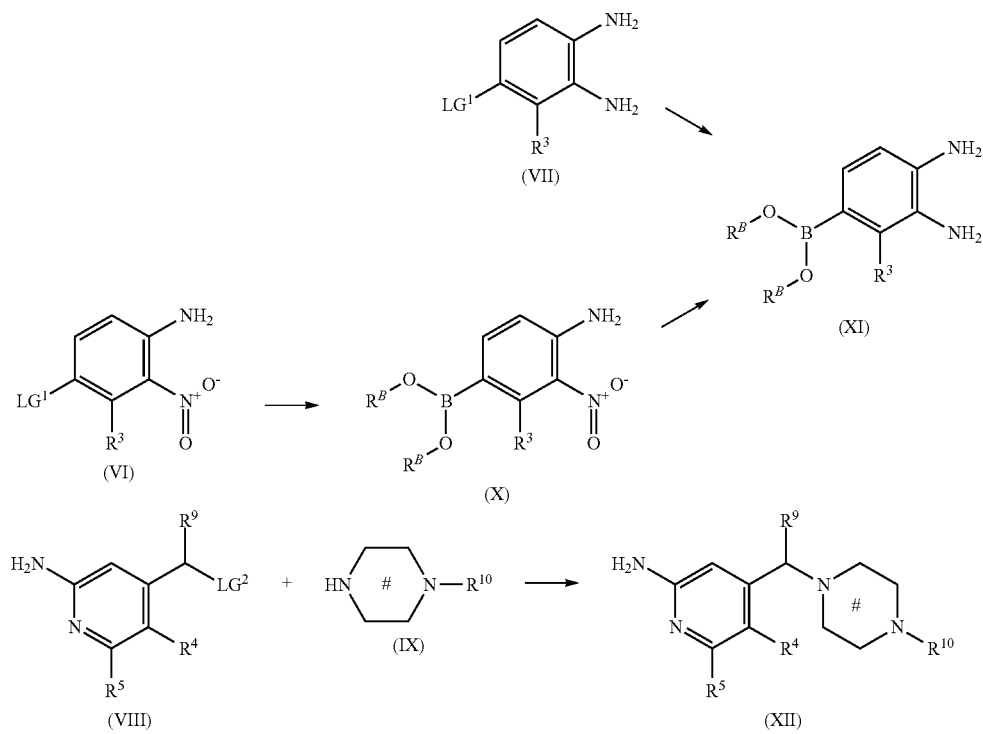

Nitroanilines of formula (VI), in which $R^3$ is as defined for compounds of general formula (I), and in which $LG^1$ represents a leaving group, preferably chloride, bromide or iodide, can be converted, using methods well known to the person skilled in the art, e.g. by reacting with a suitable boron reagent, such as 4,4,4',4',5,5,5',5'-octamethyl-2,2'-bi-1,3,2-dioxaborolane, in the presence of a palladium catalyst, such as bis(diphenylphosphino)ferrocene-palladium(II)dichloride dichloromethane adduct, to give boronic acid derivatives of formula (X).

Said boronic acid derivatives of formula (X) may be a boronic acid ($R^B$=—H) or an ester of the boronic acid, e.g. its isopropyl ester ($R^B$=$C_1$-$C_4$-alkyl, e.g. —CH(CH$_3$)$_2$), or an ester derived from a diol such as pinacol in which the boronic acid intermediate forms a cyclic boronic ester, such as a 4,4,5,5-tetramethyl-1,3,2-dioxaborolane ($R^B$—$R^B$=$C_2$-$C_6$-alkylene, e.g. —C(CH$_3$)$_2$—C(CH$_3$)$_2$—). Many boronic acids and their esters are commercially available and well-known to the person skilled in the art; see e.g. D. G. Hall, Boronic Acids, 2005 WILEY-VCH Verlag GmbH & Co.

ably, dichloropalladium-tricyclohexylphosphane (1:2) is used as a catalyst in this Suzuki coupling reaction.

Further, aminopyridines of formula (VIII), in which $R^4$, $R^5$ and $R^9$ are as defined for compounds of general formula (I), and in which $LG^2$ represents a leaving group, preferably chloride or bromide, can be reacted with piperazine derivatives of formula (IX), in which $R^{10}$ is as defined for compounds of general formula (I), and in which "#" indicates that the piperazine ring may be either unsubstituted or bridged, or substituted with one or two methyl groups, according to the definition of $R^2$ in general formula (I), to give intermediates of formula (XII). The aminopyridines of formula (VIII) may be employed as free bases or as salts; furthermore, their amino group can optionally be protected by a protective group which is removed on later stage. Suitable groups for protection of amines, e.g. the phthalimido group, and methods for their introduction and removal, are well known to the person skilled in the art, see e.g. T. W. Greene and P. G. M. Wuts in *Protective Groups in Organic Synthesis*, 4th edition, Wiley 2006.

The reader is further referred to the fact that the definition of $R^{10}$ for compounds of general formula (I) includes some protective groups, such as tert-butoxycarbonyl, which may be cleaved off and replaced by another $R^{10}$ group at a later stage.

Starting materials of formulae (VI), (VII) (VIII) and (IX) are well known to the person skilled in the art and are commercially available in considerable variety, or can be prepared by well-known synthesis methods. Special reference is being made to protected aminopyridine derivatives of formula (XV), which are useful in particular for the preparation of compounds of general formula (I) and advanced intermediates thereof, in which $R^9$ is different from a hydrogen atom. They can be prepared according to Scheme 2b from aminopyridines of formula (XIII), in which $R^4$, $R^5$ and $R^9$ are as described for the compounds of general formula (I) with the proviso that $R^9$ is different from a hydrogen atom, by reaction with benzene-1,2-dicarbonyl dichloride (also known as phthaloyl chloride) in the presence of a base, e.g. an aliphatic tertiary amine such as triethylamine, in an aliphatic halogenated hydrocarbon, such as dichloromethane, as a solvent, to give phthalimide derivatives of formula (XIV). Said phthalimide derivatives can subsequently be reacted with reagents suitable for the introduction of $LG^2$, such as N-halo succinimides, e.g. N-bromo succinimide, and a radical starter, such as 2,2'-(E)-diazene-1,2-diylbis(2-methylpropanenitrile) (also known as AIBN), to give compounds of formula (XV), in which $R^4$, $R^5$ and $R^9$ are as described for the compounds of general formula (I) with the proviso that $R^9$ is different from hydrogen, and in which $LG^2$ represents a leaving group, preferably chloride or bromide.

Diamines of formula (XIa), in which $R^3$ represents a $C_1$-$C_4$-alkoxy group, thus constituting a sub-compartment of formula (XI), can be advantageously approached using the modified approach shown below in Scheme 2c. Commercially available 2-bromo-5-nitrophenol (XVI) can be reacted with 1,1,1-tri-($C_1$-$C_3$-alkyl)methylhydrazinium salts such as 1,1,1-trimethylhydrazinium iodide in the presence of a suitable base, such as an alkali alkoxide, such as sodium 2-methylbutan-2-olate, to give 2-amino-6-bromo-3-nitrophenol (XVII), which in turn can be reacted with a compound of formula $R^4$-$LG^3$, in which $R^4$ represents a $C_1$-$C_4$-alkyl group, and $LG^3$ represents a leaving group, preferably bromide or iodide, in the presence of a base such as sodium carbonate in a solvent such as acetonitrile or N,N-dimethylformamide, to yield a phenyl ether compound of formula (XVIII). Said aryl ether compounds of formula (XVIII) can be converted into the corresponding boronic acid derivatives of formula (XIX), which may be a boronic acid ($R^B$=—H) or an ester of the boronic acid, e.g. its isopropyl ester ($R^B$=$C_1$-$C_4$-alkyl, e.g. —CH(CH$_3$)$_2$), or an ester derived from a diol such as pinacol in which the boronic acid intermediate forms a cyclic boronic ester, such as a 4,4,5,5-tetramethyl-1,3,2-dioxaborolane ($R^B$—$R^B$=$C_2$-$C_6$-alkylene, e.g. —C(CH$_3$)$_2$—C(CH$_3$)$_2$—), in an analogous fashion as described supra for the conversion of compounds of formula (VI) into boronic acid derivatives of formula (X).

Subsequently, boronic acid derivatives of formula (XIX) can be reduced to the corresponding diamines of formula (XIa), in which $R^3$ represents —$OR^4$, i.e. $C_1$-$C_4$-alkoxy, by methods well known to the person skilled in the art, e.g. by palladium catalysed hydrogenolysis.

Scheme 2b Synthesis of protected aminopyridine intermediates of formula (XV).

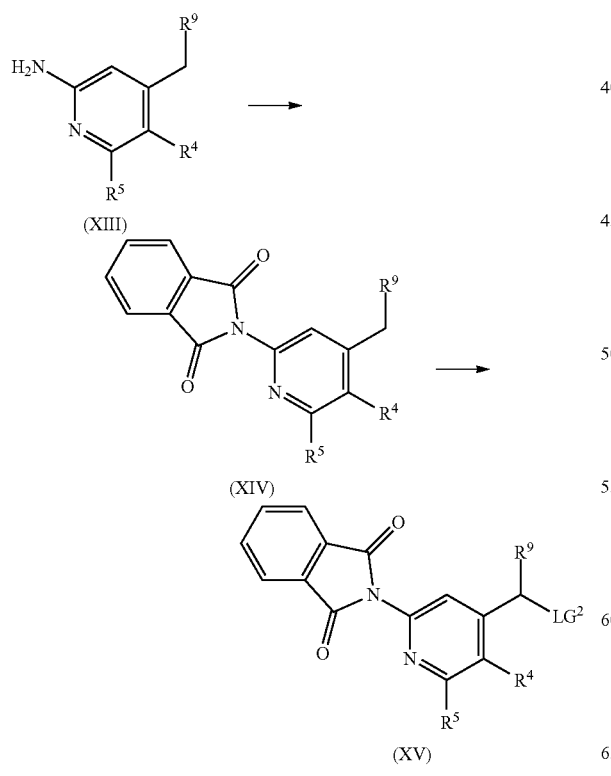

Scheme 2c Synthesis of intermediates of formula (XIa) from 2-bromo-5-nitrophenol (XVI).

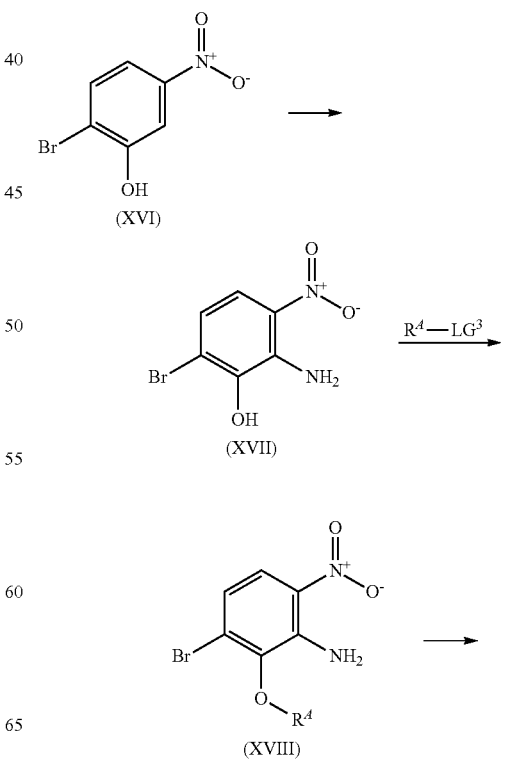

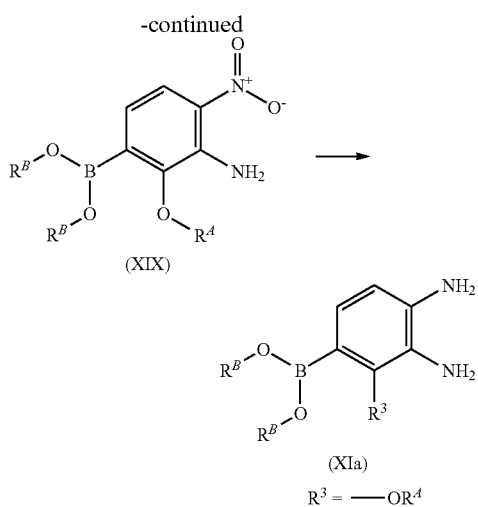

As outlined in Scheme 2d, infra, compounds of formula (XIIa), formula (XIIa) being equivalent to formula (XII) in Scheme 2a, can be reacted with di-1H-imidazol-1-ylmethanethione or thiophosgene, in the presence of a catalytic amount of 1H-imidazole, in a solvent such as dichloromethane, tetrahydrofuran, N,N-dimethylformamide or dioxane, preferably dichloromethane, followed by the addition of diaminobenzene derivatives of formula (XI), to give thioureas of formulae (XX) and (XXa) as regioisomeric mixtures. Said thiourea derivatives can be further converted into benzimidazole derivatives of formula (XXI) by reaction with a carbodiimide of formula $R^{D1}$—N=C=N—$R^{D2}$ (or a salt thereof), in which $R^{D1}$ and $R^{D2}$ represent, independently from each other, a $C_1$-$C_4$-alkyl group optionally substituted with one N,N-dimethylamino group, preferably $R^{D1}$ being ethyl and $R^{D2}$ being 3-N,N-dimethylaminopropyl, or both $R^{D1}$ and $R^{D2}$ being isopropyl, in a halogenated aliphatic hydrocarbon comprising 1, 2 or 3 carbon atoms and 1, 2, 3, 4, 5 or 6 halogen atoms, preferably chlorine atoms, as a solvent, particularly preferred solvents being dichloromethane and chloroform. As mentioned supra, regioisomeric mixtures of thioureas of formulae (XX) and (XXa) give rise to a homogeneous benzimidazole isomer as a result of imidazole tautomery. In a final step, the resulting benzimidazole derivatives of formula (XXI) can be reacted with compounds of formula (XXII), in which $R^1$ is as defined for compounds of general formula (I), and in which $LG^4$ represents a leaving group, preferably chloride, bromide or iodide, in a Suzuki coupling to give compounds of general formula (I). Specific examples are described in the Experimental Section.

Scheme 2d Conversion of intermediates of formulae (XI) and (XIIa) into compounds of general formula (I).

-continued

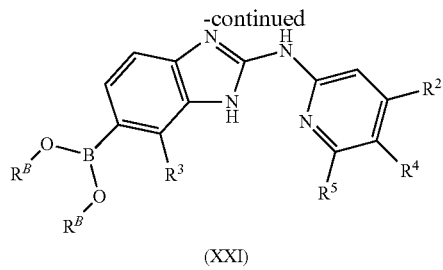

(XXI)

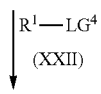

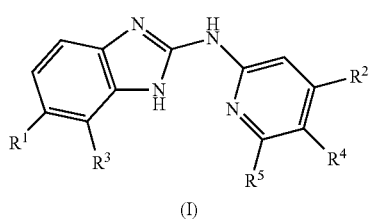

(I)

Said Suzuki coupling reaction is catalysed by palladium catalysts, e.g. by Pd(O) catalysts such as tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts such as dichlorobis(triphenylphosphine)-palladium(II) [Pd(PPh$_3$)$_2$Cl$_2$], dichloropalladium—tricyclohexylphosphane (1:2) and palladium(II) acetate in combination with triphenylphosphine or by [1,1'-bis(diphenylphosphino)ferrocene]palladium dichloride, in free form [Pd(dppf)Cl$_2$] or as dichloromethane adduct [Pd(dppf)C$_2$×CH$_2$Cl$_2$]. Preferred is the use of dichlorobis(triphenylphosphine)-palladium(II) [Pd(PPh$_3$)$_2$Cl$_2$] in combination with triphenylphosphine or the use of [1,1'-bis(diphenylphosphino)ferrocene]palladium dichloride dichloromethane adduct [Pd(dppf)Cl$_2$×CH$_2$Cl$_2$] as a catalyst.

The reaction is preferably carried out in a mixture of a solvent such as 1,2-dimethoxyethane, dioxane, DMF, THF, or n-propanol with water and in the presence of a base such as aqueous potassium carbonate, aqueous sodium bicarbonate or potassium phosphate.

The reaction is performed at temperatures ranging from room temperature (i.e. 20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Compounds of formula (XXII) are well known to the person skilled in the art and are commercially available in considerable variety, or can be prepared by well-known synthesis methods. For the preparation of less common compounds of formula (XXII), the reader is also referred to the methods described in the Experimental section, see e.g. the protocols describing the syntheses of Compounds 07.04. and 08.06.

In a somewhat related approach, certain $R^1$ groups such as 1,2,4-oxadiazol-5-yl and 1,2,4-triazol-5-yl can be formed from acyclic precursor groups.

As shown in Scheme 2e, aminopyridine derivatives of formula (XXIV), in which $R^4$, $R^5$ and $R^9$ are as defined for compounds of general formula (I), and in which $PG^1$ represents a protective group suitable for hydroxy groups, as present e.g. in alcohols, as defined supra, such as tert-butyl dimethylsilyl, are reacted with di-1H-imidazol-1-ylmethanethione or thiophosgene, in the presence of a catalytic amount of 1H-imidazole, in dichloromethane as a solvent, followed by the addition of esters of 3,4-diaminobenzoic acid of formula (XXIII), in which $R^3$ is as defined for compounds of general formula (I), and in which $R^E$ represents a $C_1$-$C_3$-alkyl group, to give thiourea derivatives of formulae (XXV) and (XXVa) as regioisomeric mixtures. Said thiourea derivatives can be further converted into benzimidazole derivatives of formula (XXVI) by reaction with a carbodiimide, such as N,N'-dipropan-2-ylcarbodiimide or 1-ethyl-3-(3-dimethylaminopropyl)carbodiimide, or a salt thereof, in an aliphatic chlorinated hydrocarbon such as dichloromethane or chloroform as a solvent. As mentioned supra, regioisomeric mixtures of thioureas of formulae (XXV) and (XXVa) give rise to a homogeneous benzimidazole isomer as a result of imidazole tautomery.

Scheme 2e Synthesis of intermediates of formulae (XXVIII) from starting materials of formulae (XXIII) and (XXIV).

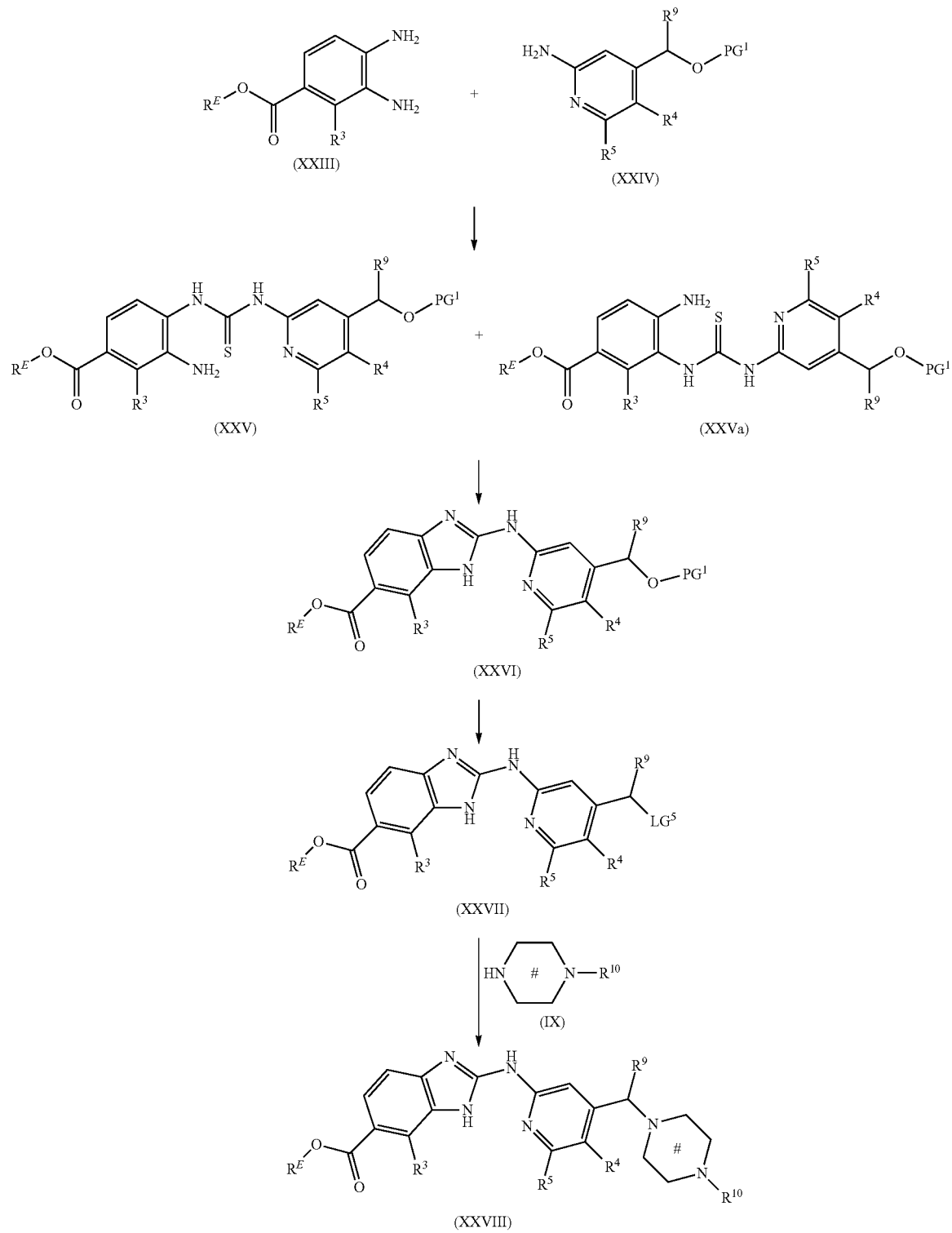

The moiety —OPG$^1$ present in formula (XXVI) is then converted into a group LG$^5$, which is a leaving group as defined supra, preferably chloride, giving rise to compounds of formula (XXVII), by first cleaving off said protective group PG$^1$ by a method known to the person skilled in the art, e.g. by treatment with tetra-n-butylammonium fluoride in case said PG$^1$ is tert-butyl dimethylsilyl, followed by treatment e.g. with a halogenating agent such as thionyl chloride (SOCl$_2$), phosphoroxychloride (POCl$_3$), or phosphorus trichloride (PCl$_3$), or with a sulfonyl chloride such as methylsulfonyl chloride. In a similar fashion as discussed in context of Scheme 2a, supra, said compounds of formula (XXVII) can be reacted with piperazine derivatives of formula (IX), in which $R^{10}$ is as defined for compounds of general formula (I), and in which "#" indicates that the piperazine ring may be either unsubstituted or bridged, or substituted with one or two methyl groups, according to the definition of $R^2$ in general formula (I), to give intermediates of formula (XXVIII).

Starting materials of formulae (XXIII) and (XXIV) are well known to the person skilled in the art and can be purchased commercially in many cases, or can be prepared by known methods.

As shown in Scheme 2f, the further elaboration of compounds of formula (XXVIIIa), which is equivalent to formula (XXVIII) in Scheme 2e, commences with the hydrolytic cleavage of the carboxylic ester moiety present in formulae (XXVIII) and (XXVIIa), using methodology well known to the person skilled in the art, such as by treatment with an aqueous alkali hydroxide, such as lithium hydroxide, sodium hydroxide or potassium hydroxide, in a solvent such as methanol, ethanol or tetrahydrofuran, or a mixture thereof, at elevated temperature, preferably between 40° C. and 80 t, to give carboxylic acids of formula (XXIX). Said carboxylic acids of formula (XXIX) can be subsequently reacted with compounds of formula (XXX), in which $R^7$ is as defined for compounds of general formula (I), and in which Q represents —O— or —N($R^6$)—, in which, in turn, $R^6$ is as defined for compounds of general formula (I), in the presence of a suitable coupling agent, such as benzotriazol-1-yl-oxytripyrrolidinophosphonium hexafluorophosphate (PyBOP), and a base, such as N,N'-diisopropyethylamine, to give intermediates of formula (XXXI). Cyclisation to compounds of formula (Ia), constituting a sub-compartment of general formula (I), can be accomplished by heating said compounds of formula (XXXI) in a mixture of an aliphatic alcohol of the formula $C_1$-$C_4$-alkyl-OH, such as n-propanol, and water, in the presence of an alkali acetate, such as sodium acetate or potassium acetate. Optionally, a carboxamide based solvent such as N,N-dimethylformamide, N,N-dimethylacetamide or N-methylpyrrolidin-2-one can be added as a co-solvent to enhance solubility of the reactants. Specific examples are described in the Experimental Section.

Compounds of formula (XXX) are well known to the person skilled in the art, and can be prepared using known methods, the reader is further referred to the protocols e.g. for the preparation of Compounds 18.01, 19.01, 20.01, and 42.02 in the Experimental Section.

In a similar fashion, $R^1$=1,2,4-oxadiazol-3-yl can be elaborated from a cyano group, see Examples 22.01 and 22.02 and the corresponding precursors, e.g. Compounds 22.06 and 22.07, in the Experimental Section.

In a similar fashion, $R^1$=1,3,4-oxadiazol-2-yl can be elaborated from a carboxy group, see e.g.

Compounds 126.01, 126.02 and 126.03, in the Experimental Section.

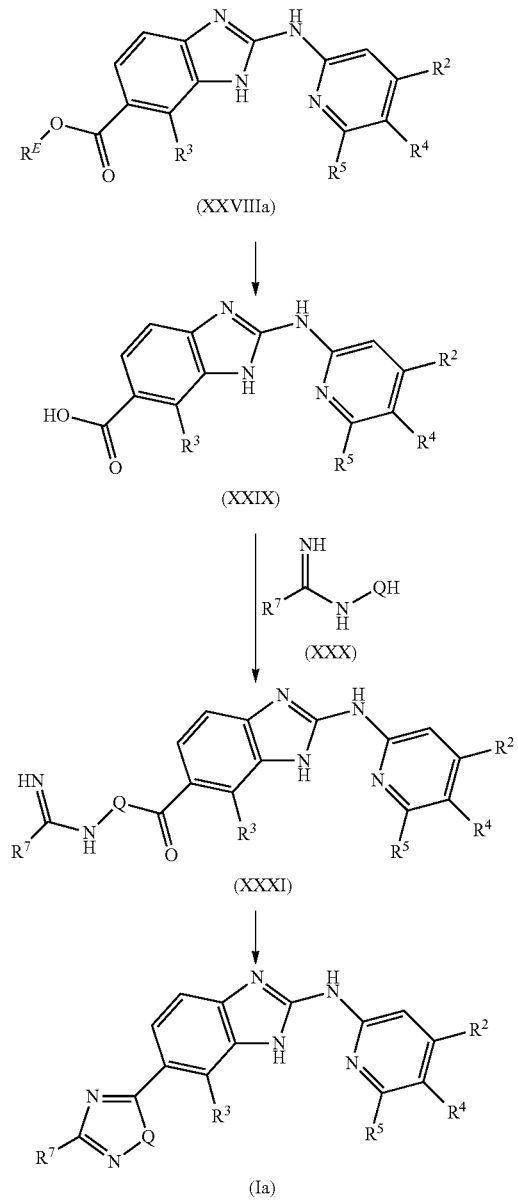

Scheme 2f Conversion of intermediates of formula (XVIa) into compounds of formula (Ia).

In an alternative approach, the benzimidazole core in formula (I) is constructed on late stage. This synthesis route proceeds via diamines of formula (XXXIV), the synthesis of which is outlined in Scheme 3a, and which can be prepared from nitroaniline derivatives of formula (XXXIII) by methods well known to the person skilled in the art, such as catalytic hydrogenolysis, e.g. by reacting an ethanolic solution of compounds of formula (XXXIII) with an atmosphere of hydrogen in the presence of palladium on carbon. Alternatively, diamines of formula (XXXIV) can be prepared by a Suzuki coupling, as discussed supra, from compounds of formula (VII) in which $R^3$ is as defined for the compounds of general formula (I), and in which $LG^1$ represents a leaving group, preferably chloride, bromide or iodide (see Scheme 2a). Said nitroaniline derivatives of formula (XXXIII) can also be prepared by a Suzuki coupling as discussed supra, either employing boronic acid derivatives of formula (XXXII) and nitroaniline derivatives of formula (VI), cf. protocols of Compounds 39.01, 39.02 and 39.03. in the Experimental section, or employing boronic acid derivatives of formula (X) and compounds of formula (XXII). In said compounds of formulae (VI), (X), (XXII) and (XXXII), $R^1$ and $R^3$ are as defined for compounds of general formula (I), (XXX) (see also Scheme 2f) in a solvent such as dioxane in the presence of a base such as cesium carbonate. Diaminobenzoate derivatives of formula (XXIII) are known to the person skilled in the art, and can be prepared by known methods and can be purchased commercially in certain cases.

Scheme 3a Synthesis of intermediates of formulae (XXXIV) and (XXXIVa).

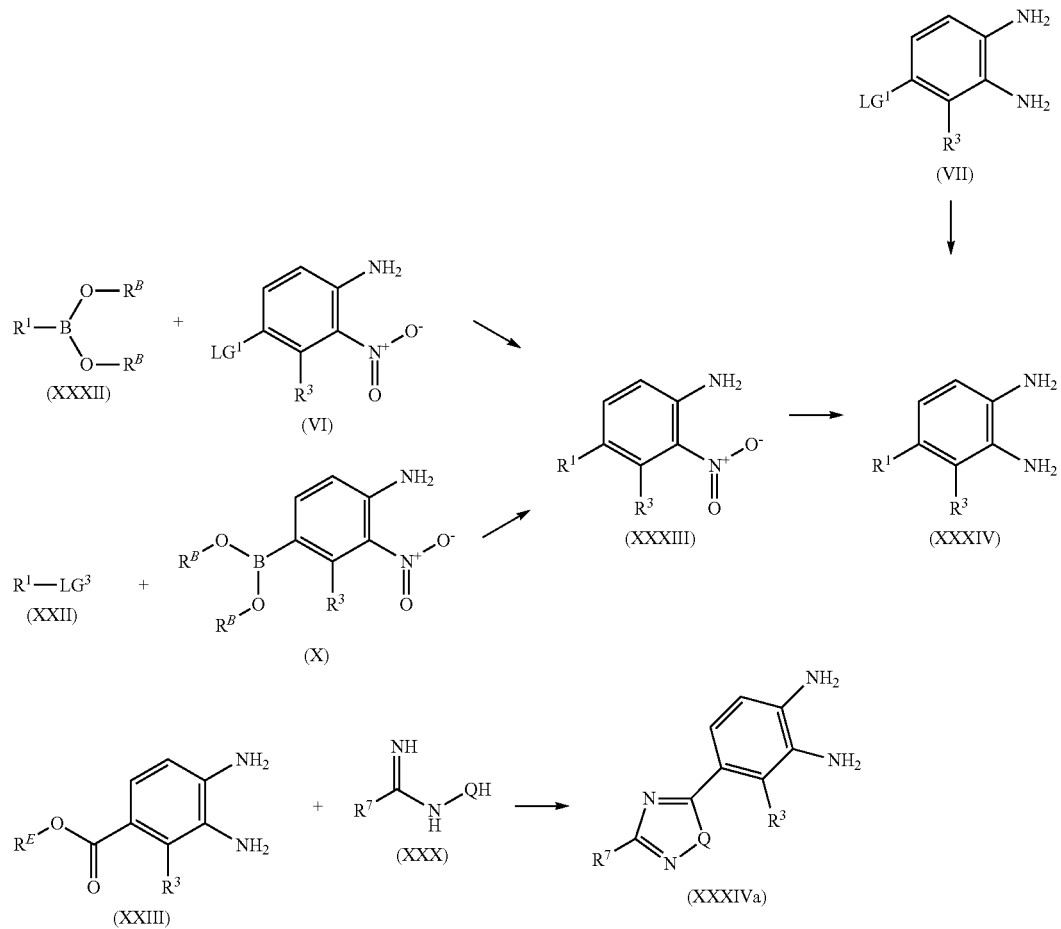

$LG^1$ and $LG^4$ represent, independently from each other, a leaving group, preferably chloride, bromide or iodide, and $R^B$ represents hydrogen, a $C_1$-$C_4$-alkyl group such as isopropyl, or $R^B$—$R^B$ together form a $C_2$-$C_6$-alkylene group, such as a —$C(CH_3)_2$—$C(CH_3)_2$— group, giving rise e.g. to a 4,4,5,5-tetramethyl-1,3,2-dioxaborolane. The availability of compounds of formulae (VI), (VII), (X) and (XXII) is described supra; boronic acid derivatives of formula (XXXII) are well known to the person skilled in the art and are commercially available in considerable variety.

Diaminobenzene derivatives of formula (XXXIVa), constituting a sub-compartment of formula (XXXIV), can be prepared in one step from diaminobenzoate derivatives of formula (XXIII), in which $R^3$ is as defined for the compounds of general formula (I), and in which $R^E$ represents $C_1$-$C_3$-alkyl, by reaction with a compound of formula Within said synthesis routes to diamines of formula (XXXIV), R groups such as $R^6$ or $R^7$ groups, which constitute substituents of heteroaromatic $R^1$ groups, can be modified as outlined in the initial paragraphs of this chapter. Instructive examples of such modifications can be readily found in the Experimental section, see e.g. the protocols of Compounds 36.01., 36.02., 36.03. and 36.04., for diamines of formula (XXXIV) in which $R^1$ is a substituted pyrimidine, and e.g. the protocols of Compounds 39.01., 67.01., 68.01., 69.02., and 78.01., for diamines of formula (XXXIV) in which $R^1$ is a pyrazole.

As shown below in Scheme 3b, diamines of formula (XXXIVb), in which $R^1$ is as defined for the compounds of general formula (I), and in which $R^3$ represents a $C_1$-$C_4$-alkoxy group, said diamines constituting a further sub-compartment of formula (XXXIV), can be prepared advantageously in certain cases from aryl ether derivatives of formula (XVIII), in which $R^4$ represents a $C_1$-$C_4$-alkyl group (see Scheme 2c), by means of Suzuki coupling as discussed supra, by reacting with boronic acid derivatives of formula (XXXII) resulting in intermediates of formula (XXXV) followed by reduction of the nitro group, e.g. by palladium catalysed hydrogenolysis, to give diamines of formula (XXXIVb).

Scheme 3b Synthesis of intermediates of formula (XXIIb).

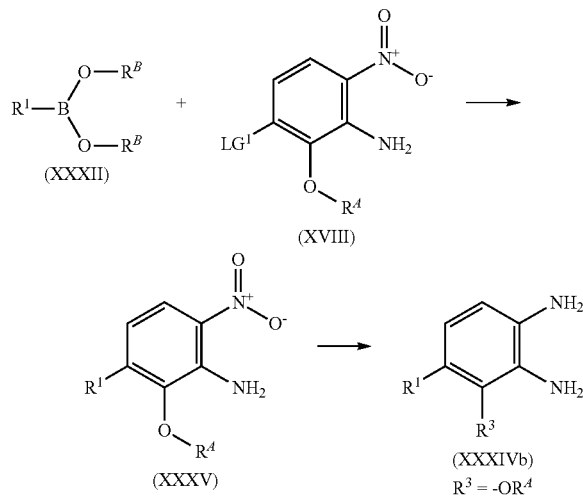

The further transformation of said diamine intermediates of formula (XXXIV) can be, as outlined in Scheme 3c, accomplished by reacting aminopyridines of formula (XIIa) (see Scheme 2d), in which $R^2$, $R^4$ and $R^5$ are as defined for compounds of general formula (I), with di-1H-imidazol-1-ylmethanethione or thiophosgene, in the presence of a catalytic amount of 1H-imidazole, in a solvent such as dichloromethane, tetrahydrofuran, N,N-dimethylformamide or dioxane, followed by the addition of diaminobenzene derivatives of formula (XXXIV), to give thioureas of formulae (XXXVI) and (XXXVIa) as regioisomeric mixture. Said thiourea derivatives can be further converted into compounds of general formula (I) by reaction with a carbodiimide of formula $R^{D1}$-N=C=N—$R^{D2}$ (or a salt thereof), in which $R^{D1}$ and $R^{D2}$ represent, independently from each other, a $C_1$-$C_4$-alkyl group optionally substituted with one N,N-dimethylamino group, preferably $R^{D1}$ being ethyl and $R^{D2}$ being 3-N,N-dimethylaminopropyl, or both $R^{D1}$ and $R^{D2}$ being isopropyl, in a halogenated aliphatic hydrocarbon comprising 1, 2 or 3 carbon atoms and 1, 2, 3, 4, 5 or 6 halogen atoms, preferably chlorine atoms, as a solvent, particularly preferred solvents being dichloromethane and chloroform. As mentioned supra, regioisomeric mixtures of thioureas of formulae (XXXVI) and (XXXVIa) give rise to a homogeneous benzimidazole isomer as a result of imidazole tautomery. Specific examples are described in the Experimental Section.

Scheme 3c Synthesis of compounds of general formula (I) from diamine intermediates of formula (XXXIV).

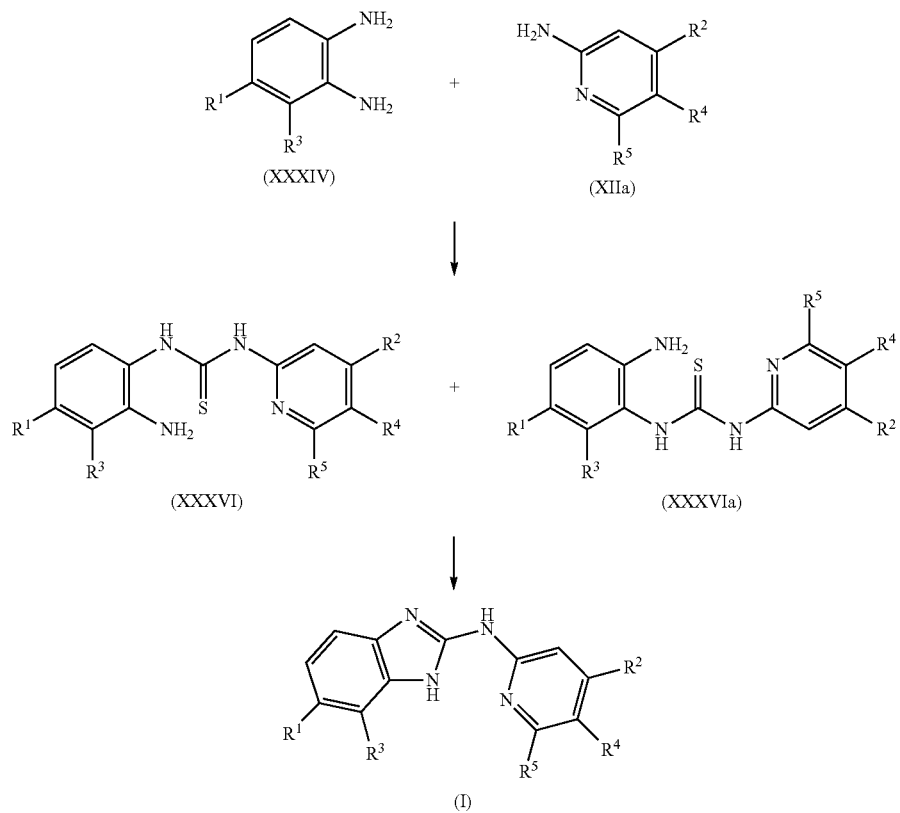

A third approach proceeds via late-stage elaboration of the R² moiety by attaching its piperazine pharmacophore, using nucleophilic substitution. As shown in Scheme 4, aminopyridine derivatives of formula (XXIV) (see also Scheme 2e), in which $R^4$, $R^5$ and $R^9$ are as defined for compounds of general formula (I), and in which $PG^1$ represents a protective group suitable for hydroxy groups, as present e.g. in alcohols, as defined supra, such as tert-butyl dimethylsilyl, can be reacted with di-1H-imidazol-1-ylmethanethione or thiophosgene, in the presence of a catalytic amount of 1H-imidazole, a solvent such as dichloromethane, tetrahydrofuran, N,N-dimethylformamide or dioxane, followed by the addition of diamine intermediates of formula (XXXIV) (see also Scheme 3a), in which $R^1$ and $R^3$ are as defined for compounds of general formula (I), to give thiourea derivatives of formulae (XXXVII) and (XXXVIIIa) as regioisomeric mixtures. Said thiourea derivatives can be further converted into benzimidazole derivatives of formula (XXXVIII) by reaction with a carbodiimide, such as N,N'-dipropan-2-ylcarbodiimide or 1-ethyl-3-(3-dimethylaminopropyl)carbodiimide, or a salt thereof, in an aliphatic chlorinated hydrocarbon such as dichloromethane or chloroform as a solvent. As mentioned supra, regioisomeric mixtures of thioureas of formulae (XXXVII) and (XXXVIIa) give rise to a homogeneous benzimidazole isomer as a result of imidazole tautomery. The moiety —$OPG^1$ present in formula (XXXVIII) is then converted into a group $LG^6$, which is a leaving group as defined supra, preferably chloride or (methylsulfonyl)oxy, giving rise to compounds of formula (XXXIX), by first cleaving off said protective group $PG^1$ by a method known to the person skilled in the art, e.g. by treatment with tetra-n-butylammonium fluoride in case said $PG^1$ is tert-butyl dimethylsilyl, followed by treatment e.g. with a halogenating agent such as thionyl chloride ($SOCl_2$), phosphoroxychloride ($POCl_3$), or phosphorus trichloride ($PCl_3$), or with a sulfonyl chloride such as methylsulfonyl chloride. In a similar fashion as discussed in context of Schemes 2a and 2e, supra, said compounds of formula (XXXIX) can be reacted with piperazine derivatives of formula (IX), in which $R^{10}$ is as defined for compounds of general formula (I), and in which "#" indicates that the piperazine ring may be either unsubstituted or bridged, or substituted with one or two methyl groups, according to the definition of $R^2$ in general formula (I), to give compounds of formula (Ib), which is equivalent to general formula (I). Specific examples are described in the Experimental Section.

Scheme 4 Synthesis of compounds of general formula (I) from diamine intermediates of formula (XXXIV) and aminopyridine derivatives of formula (XXIV).

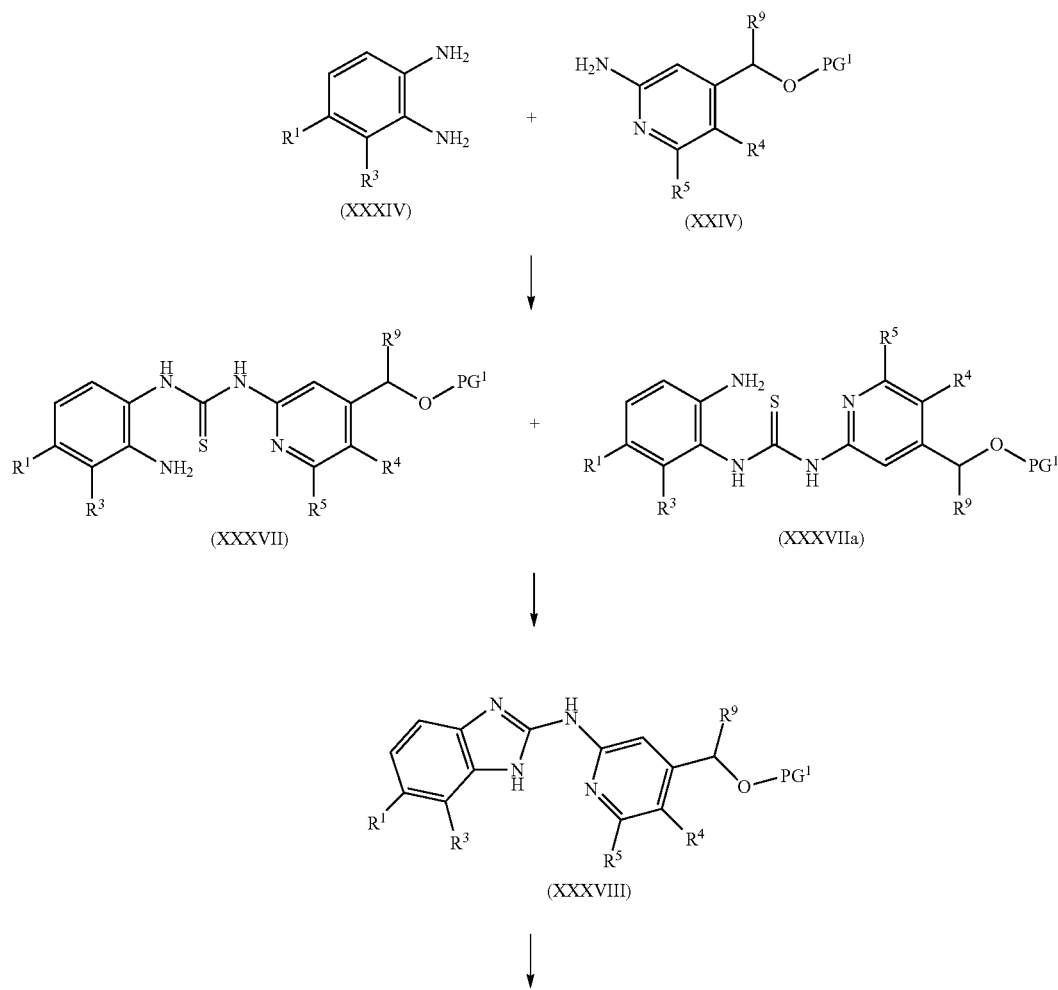

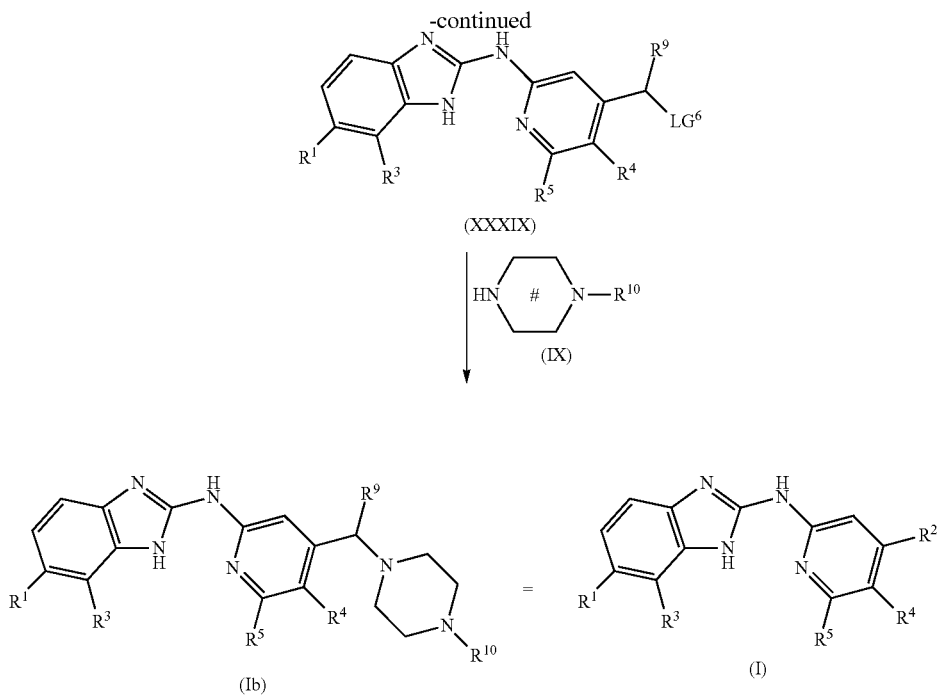

The reader is referred to the fact that the definition of $R^{10}$ for compounds of general formula (I) includes some protective groups, such as tert-butoxycarbonyl, which may be cleaved off and replaced by another $R^{10}$ group at a later stage, thus particularly qualifying this synthesis route for late-stage diversification of $R^{10}$, by e.g. acidic cleavage of said tert-butoxycarbonyl group, followed by reaction of the resulting free NH group with reagents (RG) suitable for the introduction of $R^{10}$ groups, such as $R^{12}$—C(=O)OH, $R^{12}$—C(=O)-$LG^7$, $R^{13}$O—C(=O)-$LG^7$, $R^{14a}(R^{14})$N—C(=O)-$LG^7$, $R^{14a}(R^{14})$N—S(=O)$_2$-$LG^7$ and $R^{15}$—S(=O)$_2$-$LG^7$, in which $R^{12}$, $R^{13}$, $R^{14}$, $R^{14a}$ and $R^{15}$ are as defined for the compounds of general formula (I), and in which $LG^7$ represents a leaving group as defined supra, preferably chloride, using methods well known to the person skilled in the art and as broadly exemplified in the Experimental Section.

This sequence is also outlined in Scheme 5, according to which tert-butoxycarbonyl derivatives of formula (Ic), in which $R^1$, $R^3$, $R^4$, $R^5$ and $R^9$ are as defined for the compounds of general formula (I), and in which "#" indicates that the piperazine ring may be either unsubstituted or bridged, or substituted with one or two methyl groups, according to the definition of $R^2$ in general formula (I), rendering formula (Ic) yet another sub-set of general formula (I), can be converted into the corresponding monosubstituted piperazines of formula (XL), by treatment with a strong acid, preferably hydrochloric acid or trifluoroacetic acid. Said monosubstituted piperazines of formula (XL) can be formed as free bases or as salts, and can be reacted with one reagent selected from the group (RG) consisting of $R^{12}$—C(=O)OH, $R^{12}$—C(=O)-$LG^7$, $R^{13}$O—C(=O)-$LG^7$, $R^{14a}(R^{14})$N—C(=O)-$LG^7$, $R^{14a}(R^{14})$N—S(=O)$_2$-$LG^7$ and $R^{15}$—S(=O)$_2$-$LG^7$, in which $R^{12}$, $R^{13}$, $R^{14}$, $R^{14a}$ and $R^{15}$ are as defined for the compounds of general formula (I), and in which $LG^7$ represents a leaving group as defined supra, preferably chloride, as described in the preceding paragraph. Said reagents are all well known to the person skilled in the art and are commercially available in considerable variety.

Scheme 5 Synthesis of compounds of general formula (I) from compounds of formula (Ic) via monosubstituted piperazine derivatives of formula (XL).

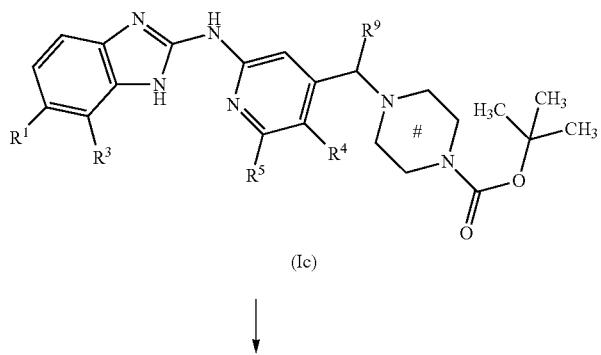

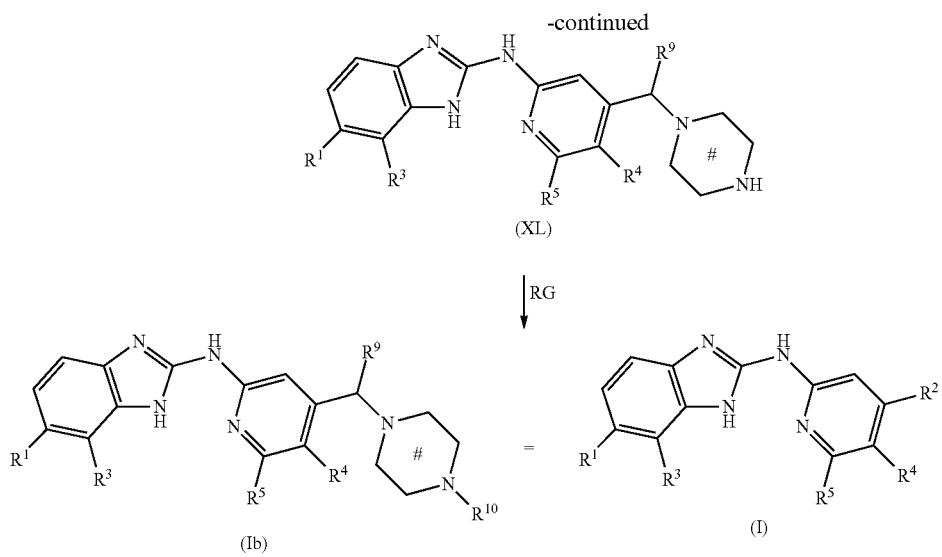

(XL)

↓ RG

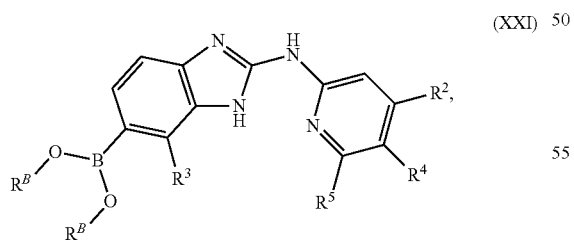

(Ib) = (I)

Particularly, said free NH group can be subjected to a peptide coupling by reaction with a carboxylic acid of formula $R^{12}$—C(=O)OH, in which $R^{12}$ is as defined for compounds of general formula (I), in the presence of a peptide coupling reagent, selected from HATU (0-(7-azabenzotriazol-1-yl)-N,N,N',N'-tetramethyluronium hexafluorophosphate), TBTU (O-(benzotriazol-1-yl)-N,N,N',N'-tetramethyluronium tetrafluoroborate), PyBOP (benzotriazol-1-yl-oxytripyrrolidinophosphonium hexafluorophosphate), or T3P (2,4,6-tripropyl-1,3,5,2,4,6-trioxatriphosphinane 2,4,6-trioxide), all of them being well known to the person skilled in the art and all of them being commercially available, in the presence of a base such as a tertiary aliphatic amine of the formula $N(C_1$-$C_4$-alkyl$)_3$, or sodium bicarbonate, in an appropriate solvent such as N,N-dimethylformamide, N,N-dimethylacetamide, dimethylsulfoxide or N-methyl pyrrolidin-2-one. Specific examples are described in the Experimental Section.

In accordance with a second aspect, the present invention covers methods of preparing compounds of general formula (I) as defined supra.

In one embodiment of the invention, said methods comprise the step of allowing an intermediate compound of general formula (XXI):

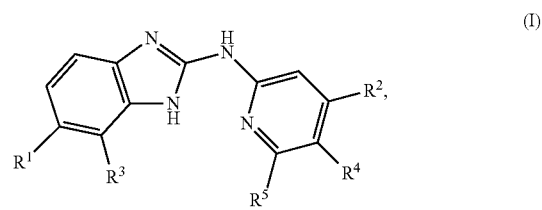

(XXI)

in which $R^2$, $R^3$, $R^4$ and $R^5$ are as defined for the compound of general formula (I) as defined supra, and in which $R^B$, which can be different or identical, represent a hydrogen atom or a $C_1$-$C_4$-alkyl group, or both $R^B$ groups together form a $C_2$-$C_6$-alkylene group, to react with a compound of general formula (XXII):

$R^1LG^4$ (XXII), in which $R^1$ is as defined for the compound of general formula (I) as defined supra, and in which $LG^4$ represents a leaving group, in the presence of a palladium catalyst, thereby giving a compound of general formula (I):

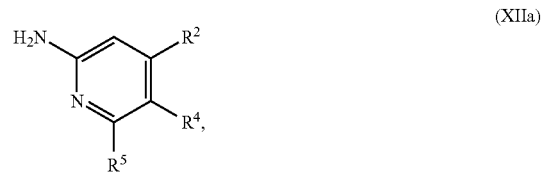

(I)

in which $R^1$, $R^2$, $R^3$, $R^4$ and $R^5$ are as defined for the compound of general formula (I) as defined supra.

In another embodiment of the invention, said methods comprise the steps of i. allowing an intermediate compound of general formula (XIIa):

(XIIa)

in which $R^2$, $R^4$ and $R^5$ are as defined for the compound of general formula (I) as defined supra, to react with a reagent selected from thiophosgene and di-1H-imidazol-1-ylmethanethione, in the presence of a catalytic amount of 1H-imidazole, followed by the addition of an intermediate compound of general formula (XXXIV):

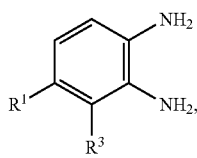

(XXXIV)

in which R¹ and R³ are as defined for the compound of general formula (I) as defined supra, thereby giving a regioisomeric mixture of intermediates of formulae (XXXVI) and (XXXVIa):

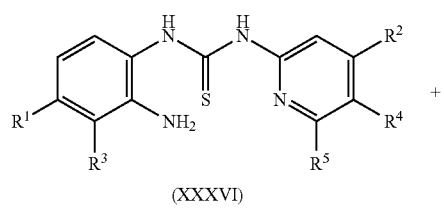

(XXXVI)

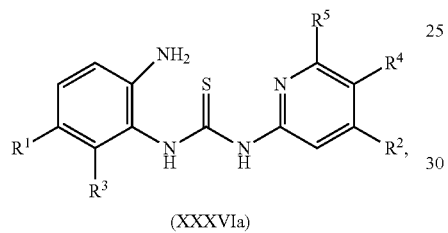

(XXXVIa)

in which R¹, R², R³, R⁴ and R⁵ are as defined for the compound of general formula (I) as defined supra, followed by ii. allowing said regioisomeric mixture of intermediates of formulae (XXXVI) and (XXXVIa):

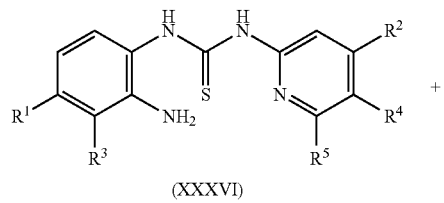

(XXXVI)

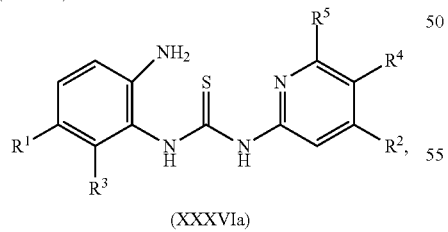

(XXXVIa)

in which R¹, R², R³, R⁴ and R⁵ are as defined for the compound of general formula (I) as defined supra, to react with a carbodiimide of formula $R^{D1}$—N=C=N—$R^{D2}$, in which $R^{D1}$ and $R^{D2}$ represent, independently from each other, a $C_1$-$C_4$-alkyl group optionally substituted with one N,N-dimethylamino group, thereby giving a compound of general formula (I):

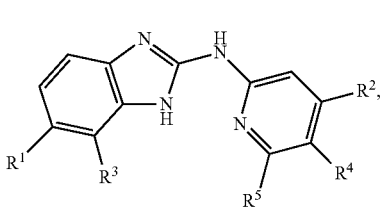

(I)

in which R¹, R², R³, R⁴ and R⁵ are as defined for the compound of general formula (I) as defined supra.

In another embodiment of the invention, said methods comprise the steps of i. allowing an intermediate compound of general formula (XIIa):

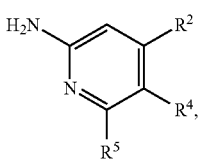

(XIIa)

in which R², R⁴ and R⁵ are as defined for the compound of general formula (I) as defined supra, to react with a reagent selected from thiophosgene and di-1H-imidazol-1-ylmethanethione, in the presence of a catalytic amount of 1H-imidazole, followed by the addition of an intermediate compound of general formula (XXXIV):

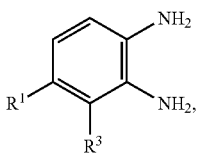

(XXXIV)

in which R¹ and R³ are as defined for the compound of general formula (I) as defined supra, thereby giving a regioisomeric mixture of intermediates of formulae (XXXVI) and (XXXVIa):

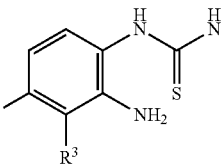

(XXXVI)

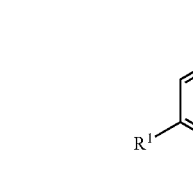

(XXXVIa)

in which R$^1$, R$^2$, R$^3$, R$^4$ and R$^5$ are as defined for the compound of general formula (I) as defined supra, followed by ii. allowing said regioisomeric mixture of intermediates of formulae (XXXVI) and (XXXVIa):

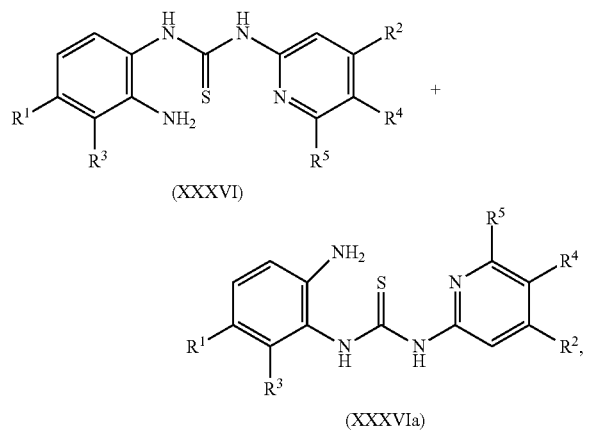

(XXXVI)

(XXXVIa)

in which R$^1$, R$^2$, R$^3$, R$^4$ and R$^5$ are as defined for the compound of general formula (I) as defined supra, to react with a carbodiimide of formula R$^{D1}$—N=C=N—R$^{D2}$ or a salt thereof, in which R$^{D1}$ and R$^{D2}$ represent, independently from each other, a C$_1$-C$_4$-alkyl group optionally substituted with one N,N-dimethylamino group, thereby giving a compound of general formula (I):

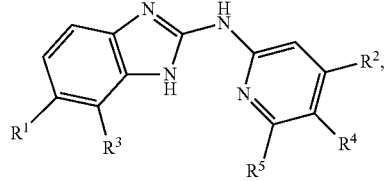

(I)

in which R$^1$, R$^2$, R$^3$, R$^4$ and R$^5$ are as defined for the compound of general formula (I) as defined supra.

In another embodiment of the invention, said methods comprise the step of allowing an intermediate compound of general formula (XL) or a salt thereof:

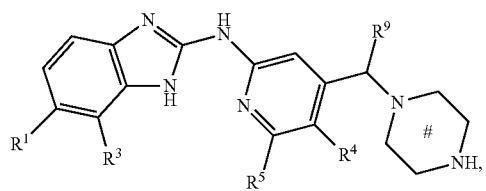

(XL)

in which R$^1$, R$^3$, R$^4$, R$^5$ and R$^9$ are as defined for the compound of general formula (I) as defined supra, and in which "#" indicates that the piperazine ring can be either unsubstituted or bridged, or substituted with one or two methyl groups, according to the definition of R$^2$ in general formula (I) as defined supra, to react with one reagent selected from the group (RG) consisting of R$^{12}$—C(=O)OH, R$^{12}$—C(=O)-LG$^7$, R$^{13}$O—C(=O)-LG$^7$, R$^{14a}$(R$^{14}$)N—C(=O)-LG$^7$, R$^{14a}$(R$^{14}$)N—S(=O)$_2$-LG$^7$ and R$^{15}$—S(=O)$_2$-LG$^7$, in which R$^{12}$, R$^{13}$, R$^{14}$, R$^{14a}$ and R$^{15}$ are as defined for the compounds of general formula (I) as defined supra, and in which LG$^7$ represents a leaving group, thereby giving a compound of general formula (I):

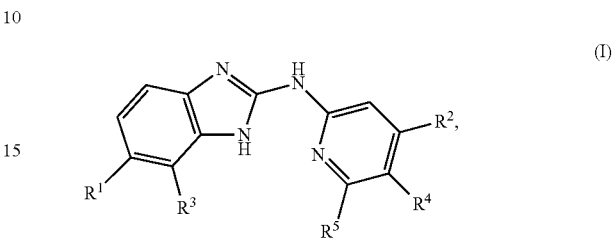

(I)

in which R$^1$, R$^2$, R$^3$, R$^4$ and R$^5$ are as defined for the compound of general formula (I) as defined supra.

In accordance with a third aspect, the present invention covers further methods of preparing compounds of general formula (I) as defined supra.

In one embodiment of the invention, said methods comprise the step of allowing an intermediate compound of general formula (XXI):

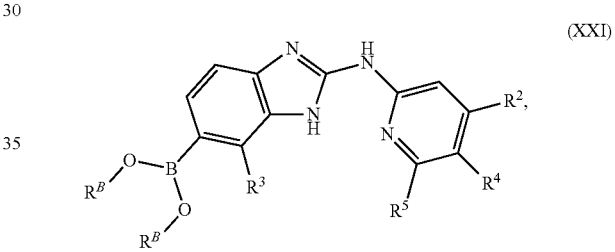

(XXI)

in which R$^2$, R$^3$, R$^4$ and R$^5$ are as defined for the compound of general formula (I) as defined supra, and in which R$^B$, which can be different or identical, represent a hydrogen atom or a C$_1$-C$_4$-alkyl group, or both R$^B$ groups together form a C$_2$-C$_6$-alkylene group, to react with a compound of general formula (XXII):

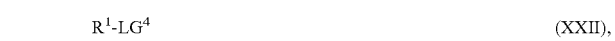

R$^1$-LG$^4$ (XXII), in which R$^1$ is as defined for the compound of general formula (I) as defined supra, and in which LG$^4$ represents a leaving group, in the presence of a palladium catalyst, thereby giving a compound of general formula (I):

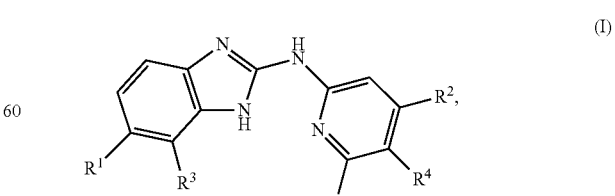

(I)

in which R$^1$, R$^2$, R$^3$, R$^4$ and R$^5$ are as defined for the compound of general formula (I) as defined supra, then optionally converting said compound into solvates, salts and/or solvates of such salts using the corresponding (i) solvents and/or (ii) bases or acids.

In another embodiment of the invention, said methods comprise the steps of i. allowing an intermediate compound of general formula (XIIa):

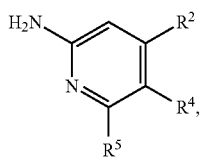

(XIIa)

in which $R^2$, $R^4$ and $R^5$ are as defined for the compound of general formula (I) as defined supra, to react with a reagent selected from thiophosgene and di-1H-imidazol-1-ylmethanethione, in the presence of a catalytic amount of 1H-imidazole, followed by the addition of an intermediate compound of general formula (XXXIV):

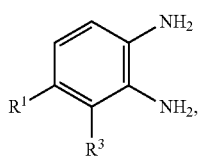

(XXXIV)

in which $R^1$ and $R^3$ are as defined for the compound of general formula (I) as defined supra, thereby giving a regioisomeric mixture of intermediates of formulae (XXXVI) and (XXXVIa):

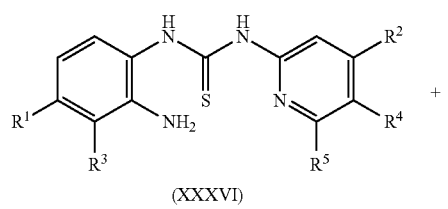

(XXXVI)

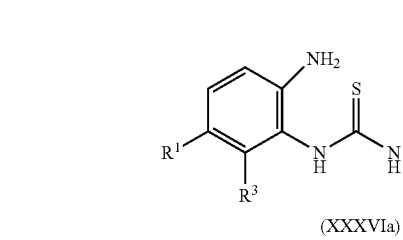

(XXXVIa)

in which $R^1$, $R^2$, $R^3$, $R^4$ and $R^5$ are as defined for the compound of general formula (I) as defined supra, followed by ii. allowing said regioisomeric mixture of intermediates of formulae (XXXVI) and (XXXVIa):

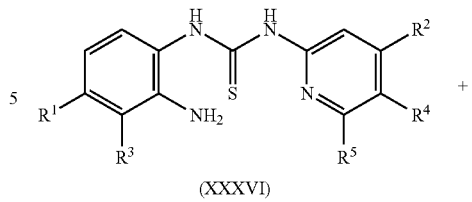

(XXXVI)

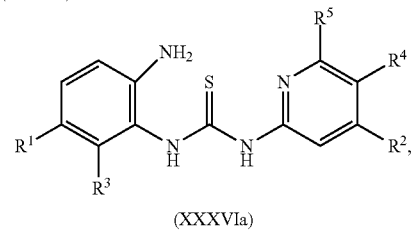

(XXXVIa)

in which $R^1$, $R^2$, $R^3$, $R^4$ and $R^5$ are as defined for the compound of general formula (I) as defined supra, to react with a carbodiimide of formula $R^{D1}$—N=C=N—$R^{D2}$, in which $R^{D1}$ and $R^{D2}$ represent, independently from each other, a $C_1$-$C_4$-alkyl group optionally substituted with one N,N-dimethylamino group, thereby giving a compound of general formula (I):

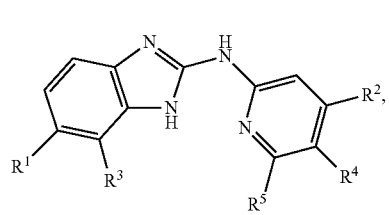

(I)

in which $R^1$, $R^2$, $R^3$, $R^4$ and $R^5$ are as defined for the compound of general formula (I) as defined supra, then optionally converting said compound into solvates, salts and/or solvates of such salts using the corresponding (i) solvents and/or (ii) bases or acids.

In another embodiment of the invention, said methods comprise the steps of i. allowing an intermediate compound of general formula (XIIa):

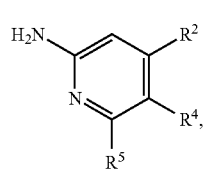

(XIIa)

in which $R^2$, $R^4$ and $R^5$ are as defined for the compound of general formula (I) as defined supra, to react with a reagent selected from thiophosgene and di-1H-imidazol-1-ylmethanethione, in the presence of a catalytic amount of 1H-imidazole, followed by the addition of an intermediate compound of general formula (XXXIV):

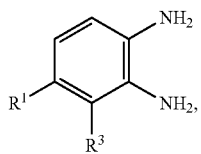

(XXXIV)

in which $R^1$ and $R^3$ are as defined for the compound of general formula (I) as defined supra, thereby giving a regioisomeric mixture of intermediates of formulae (XXXVI) and (XXXVIa):

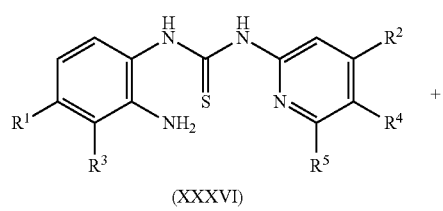

(XXXVI)

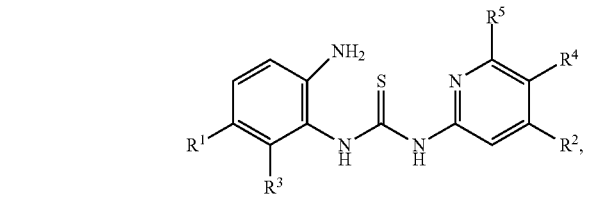

(XXXVIa)

in which $R^1$, $R^2$, $R^3$, $R^4$ and $R^5$ are as defined for the compound of general formula (I) as defined supra, followed by ii. allowing said regioisomeric mixture of intermediates of formulae (XXXVI) and (XXXVIa):

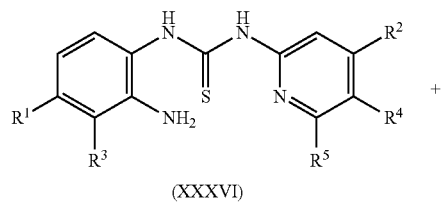

(XXXVI)

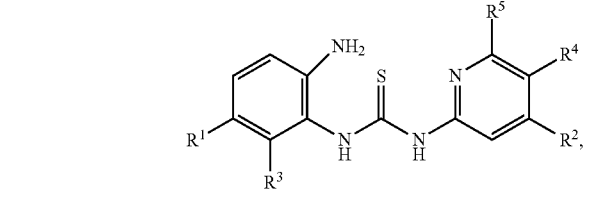

(XXXVIa)

in which $R^1$, $R^2$, $R^3$, $R^4$ and $R^5$ are as defined for the compound of general formula (I) as defined supra, to react with a carbodiimide of formula $R^{D1}$—N=C=N—$R^{D2}$ or a salt thereof, in which $R^{D1}$ and $R^{D2}$ represent, independently from each other, a $C_1$-$C_4$-alkyl group optionally substituted with one N,N-dimethylamino group, thereby giving a compound of general formula (I):

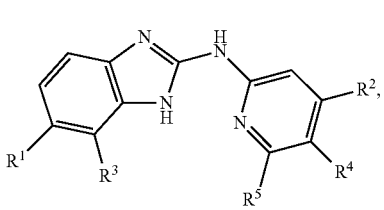

(I)

in which $R^1$, $R^2$, $R^3$, $R^4$ and $R^5$ are as defined for the compound of general formula (I) as defined supra, then optionally converting said compound into solvates, salts and/or solvates of such salts using the corresponding (i) solvents and/or (ii) bases or acids.

In another embodiment of the invention, said methods comprise the step of allowing an intermediate compound of general formula (XL) or a salt thereof:

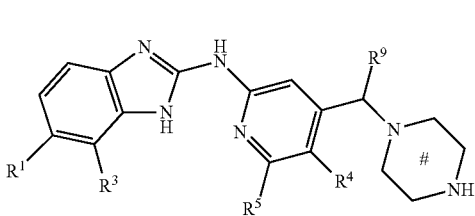

(XL)

in which $R^1$, $R^3$, $R^4$, $R^5$ and $R^9$ are as defined for the compound of general formula (I) as defined supra, and in which "#" indicates that the piperazine ring can be either unsubstituted or bridged, or substituted with one or two methyl groups, according to the definition of $R^2$ in general formula (I) as defined supra, to react with one reagent selected from the group (RG) consisting of $R^{12}$—C(=O)OH, $R^{12}$—C(=O)-$LG^7$, $R^{13}$O—C(=O)-$LG^7$, $R^{14a}(R^{14})$N—C(=O)-$LG^7$, $R^{14a}(R^{14})$N—S(=O)$_2$-$LG^7$ and $R^{15}$—S(=O)$_2$-$LG^7$, in which $R^{12}$, $R^{13}$, $R^{14}$, $R^{14a}$ and $R^{15}$ are as defined for the compounds of general formula (I) as defined supra, and in which $LG^7$ represents a leaving group, thereby giving a compound of general formula (I):

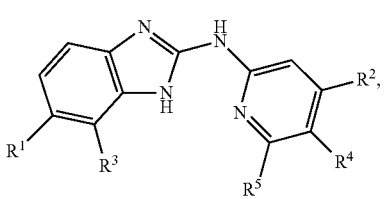

(I)

in which $R^1$, $R^2$, $R^3$, $R^4$ and $R^5$ are as defined for the compound of general formula (I) as defined supra, then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

In accordance with a fourth aspect, the present invention covers intermediate compounds which are useful for the preparation of the compounds of general formula (I), supra.

In one embodiment, the invention covers the intermediate compounds of general formula (XXI):

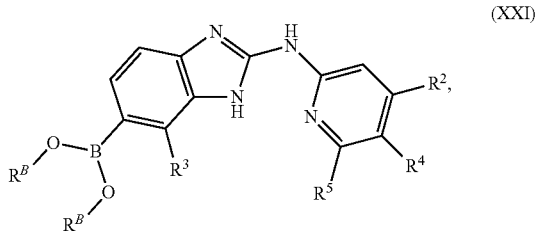

(XXI)

in which $R^2$, $R^3$, $R^4$ and $R^5$ are as defined for the compound of general formula (I) as defined supra, and in which $R^B$, which can be different or identical, represent a hydrogen atom or a $C_1$-$C_4$-alkyl group, or both $R^B$ groups together form a $C_2$-$C_6$-alkylene group.

In another embodiment, the invention covers the intermediate compounds of general formula (XIIa):

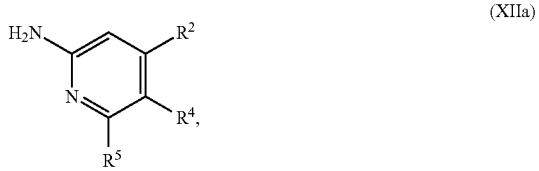

(XIIa)

in which $R^2$, $R^4$ and $R^5$ are as defined for the compound of general formula (I) as defined supra.

In another embodiment, the invention covers the intermediate compounds of general formula (XXXIV):

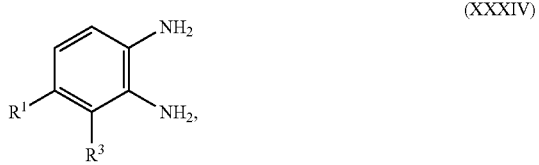

(XXXIV)

in which $R^1$ and $R^3$ are as defined for the compound of general formula (I) as defined supra.

In another embodiment, the invention covers the intermediate compounds of general formula (XL):

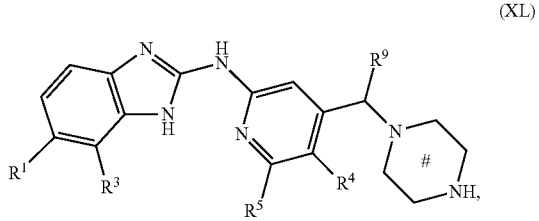

(XL)

in which $R^1$, $R^3$, $R^4$, $R^5$ and $R^9$ are as defined for the compound of general formula (I) as defined supra, and in which "#" indicates that the piperazine ring can be either unsubstituted or bridged, or substituted with one or two methyl groups, according to the definition of $R^2$ in general formula (I) as defined supra.

In accordance with a fifth aspect, the present invention covers the use of said intermediate compounds for the preparation of a compound of general formula (I) as defined supra.

In one embodiment, the invention covers the use of intermediate compounds of general formula (XXI):

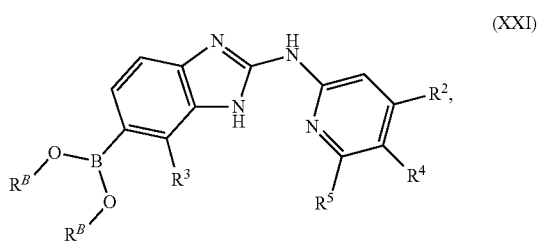

(XXI)

in which $R^2$, $R^3$, $R^4$ and $R^5$ are as defined for the compound of general formula (I) as defined supra, and in which $R^B$, which can be different or identical, represent a hydrogen atom or a $C_1$-$C_4$-alkyl group, or both $R^B$ groups together form a $C_2$-$C_6$-alkylene group, for the preparation of a compound of general formula (I) as defined supra.

In another embodiment, the invention covers the use of intermediate compounds of general formula (XIIa):

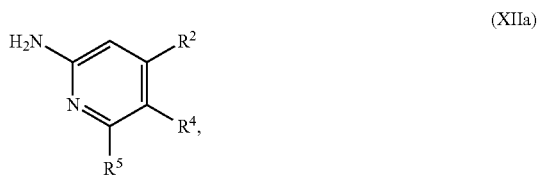

(XIIa)

in which $R^2$, $R^4$ and $R^5$ are as defined for the compound of general formula (I) as defined supra, for the preparation of a compound of general formula (I) as defined supra.

In another embodiment, the invention covers the use of intermediate compounds of general formula (XXXIV):

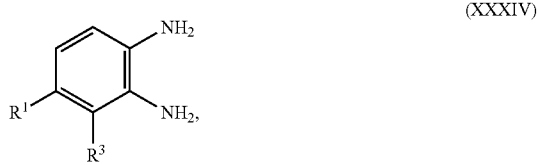

(XXXIV)

in which $R^1$ and $R^3$ are as defined for the compound of general formula (I) as defined supra, for the preparation of a compound of general formula (I) as defined supra.

In another embodiment, the invention covers the use of intermediate compounds of general formula (XL):

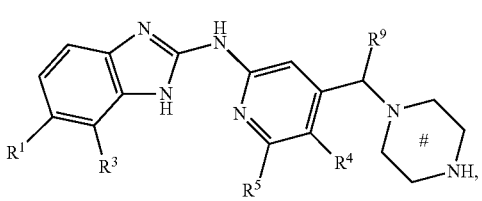

in which $R^1$, $R^3$, $R^4$, $R^5$ and $R^9$ are as defined for the compound of general formula (I) as defined supra, and in which "#" indicates that the piperazine ring can be either unsubstituted or bridged, or substituted with one or two methyl groups, according to the definition of $R^2$ in general formula (I) as defined supra, for the preparation of a compound of general formula (I) as defined supra.

The present invention covers the intermediate compounds which are disclosed in the Example Section of this text, infra.

The present invention covers any sub-combination within any embodiment or aspect of the present invention of intermediate compounds of general formula (XL), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action which could not have been predicted. Compounds of the present invention have surprisingly been found to effectively inhibit TBK1 kinase and/or IKKε kinase and it is possible therefore that said compounds be used for the treatment or prophylaxis of diseases, preferably hyperproliferative and/or inflammatory disorders in humans and animals.

Compounds of the present invention can be utilized to inhibit the activity of TBK1 and/or IKKε kinases. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat hyperproliferative and/or inflammatory disorders.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthhalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc.

endothelial cell proliferation, or other types involved in angiogenesis, as well as causing cell death or apoptosis of such cell types.

In yet another aspect, the present invention provides methods of treating or preventing a disease or condition associated with inflammation, a metabolic disorder, infection or an immune disease or condition by administering to a subject having such a condition or disease, a therapeutically effective amount of a compound or composition of the invention. In one group of embodiments, diseases or conditions, including chronic diseases, of humans or other species can be treated or prevented by inhibition of IRF-3 phosphorylation through inhibition of TBK1 kinase and/or IKKε kinase. These diseases or conditions include (1) inflammatory or allergic diseases such as systemic anaphylaxis and hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis and urticaria, (5) vasculitis, (6) spondyloarthropathies, (7) scleroderma, (8) asthma and respiratory allergic diseases such as allergic asthma, allergic rhinitis, allergic conjunctivitis, hypersensitivity lung diseases and the like, and (9) autoimmune diseases, such as arthritis (including rheumatoid and psoriatic), systemic lupus erythematosus, type I diabetes, glomerulonephritis and the like, (10) graft rejection (including allograft rejection and graft-v-host disease), (11) other diseases in which undesired inflammatory responses are to be inhibited, e.g., atherosclerosis, myositis, neurological disorders such as stroke, ischemic reperfusion injury, traumatic brain injury and closed-head injuries, neurodegenerative diseases (e.g., Parkinson's disease), multiple sclerosis, Alzheimer's disease, encephalitis, meningitis, osteoporosis, gout, hepatitis, nephritis, gall bladder disease, sepsis, sarcoidosis, conjunctivitis, otitis, chronic obstructive pulmonary disease, sinusitis and Behcet's syndrome; (12) metabolic disorders that are sensitive to inhibition of TNF or IL-1 signaling, such as obesity, type II diabetes, Syndrome X, insulin resistance, hyperglycemia, hyperuricemia, hyperinsulinemia, cachexia, hypercholesterolemia, hyperhpidemia, dyslipidemia, mixed dyslipidemia and hypertriglyceridemia, eating disorders, such as anorexia nervosa and bulimia, (13) infectious diseases, e.g., bacteremia and septic shock; (14) cardiovascular disorders, such as acute heart failure, hypotension, hypertension, angina pectoris, myocardial infarction, cardiomyopathy, congestive heart failure, atherosclerosis, coronary artery disease, restenosis and vascular stenosis; and (15) immune diseases or conditions.

These disorders have been well characterized in humans, but also exist with a similar etiology in other mammals, and can be treated by administering pharmaceutical compositions of the present invention.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

yield better efficacy in reducing the growth of a tumour or even eliminate the tumour as compared to administration of either agent alone, provide for the administration of lesser amounts of the administered chemotherapeutic agents, provide for a chemotherapeutic treatment that is well tolerated in the patient with fewer deleterious pharmacological complications than observed with single agent chemotherapies and certain other combined therapies, provide for treating a broader spectrum of different cancer types in mammals, especially humans, provide for a higher response rate among treated patients, provide for a longer survival time among treated patients compared to standard chemotherapy treatments, provide a longer time for tumour progression, and/or yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of hyperproliferative and/or inflammatory disorders.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative and/or inflammatory disorders.

The pharmaceutical activity of the compounds according to the invention can be explained by their activity as inhibitors of TBK1 and/or IKKε kinase.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular hyperproliferative and/or inflammatory disorders, particularly cancer.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular hyperproliferative and/or inflammatory disorders, particularly cancer.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative and/or inflammatory disorders, particularly cancer.

In accordance with a further aspect, the present invention covers a method of treatment or prophylaxis of diseases, in particular hyperproliferative and/or inflammatory disorders, particularly cancer, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers a compound inhibiting TBK1 kinase and/or IKKε kinase, for the treatment of a hyperproliferative and/or inflammatory disease, such as cancer.

In accordance with a further aspect, the present invention covers a method for controlling the activity of TBK1 kinase and/or IKKε kinase in humans and animals by administering an effective amount of at least one compound of the general formula (I), as defined supra, or of a medicament comprising the same.

In accordance with a further aspect, the present invention covers a method for controlling the activity of IRF-3 phosphorylation in humans and animals by administering an effective amount of at least one compound of the general formula (I), as defined supra, or of a medicament comprising the same.

In accordance with a further aspect, the present invention covers a method for controlling a hyperproliferative and/or inflammatory disease, such as cancer, in humans and animals by administering an effective amount of at least one compound of the general formula (I), as defined supra, or of a medicament comprising the same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal).

Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropyl-cellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention covers a pharmaceutical combination, which comprises:

one or more first active ingredients, in particular compounds of general formula (I) as defined supra, and one or more further active ingredients, in particular for the treatment and/or prophylaxis of a hyperproliferative disorder, more particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known agents for the treatment and/or prophylaxis of cancer.

Examples of agents for the treatment and/or prophylaxis of cancer include: 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative and/or inflammatory disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Section—General Part

The following Table 1 lists the abbreviations used herein, in particular in the Compounds part and the Examples part of the Experimental Section:

TABLE 1

| Abbreviation | Meaning |
| --- | --- |
| Ac | Acetyl |
| AIBN | 2,2'-(E)-diazene-1,2-diylbis(2-methylpropanenitrile) |
| BINAP | 2,2'-bis(diphenylphosphino)-1,1'-binaphthyl |
| Boc | tert-butyloxycarbonyl |
| br | Broad |
| Brett-Phos | 2-(dicyclohexylphosphino)-3,6-dimethoxy-2'-4'-6'-tri-i-propyl-1,1'-biphenyl |
| c- | cyclo- |
| 1-Chloroethyl chloroformate | 1-chloroethyl carbonochloridate |
| Chloromethyl chloroformate | chloromethyl carbonochloridate |
| d | doublet |
| dd | doublet of doublets |
| DCM | dichloromethane |
| DME | 1,2-dimethoxyethane |
| DIPE | diisopropylether |
| DIPEA | N,N-diisopropylethylamine |
| DMA | N,N-dimethylacetamide |
| DMF | N,N-dimethylformamide |
| DIC | Diisopropyl carbodiimide |
| DMSO | dimethyl sulfoxide |
| Dppf | 1,1'-bis(diphenylphosphino)ferrocene |
| EDC, EDCI | N-[3-(dimethylamino)propyl]-N'-ethylcarbodiimide hydrochloride |
| Eq | equivalent |
| ESI | electrospray ionisation |
| HATU | N-[(dimethylamino)(3H-[1,2,3]triazolo[4,5-b]pyridin-3-yloxy)-methylene]-N-methylmethanaminium hexafluorophosphate |
| Hünig Base | N,N-diisopropylethylamine |
| m | multiplet |
| m.p. | melting point in ° C. |
| MS | mass spectrometry |
| MW | molecular weight |
| NaOtBu | sodium tert-butoxide; sodium 2-methylpropan-2-olate |
| NBS | 2-bromo-1H-isoindole-1,3(2H)-dione |
| NMM | N-Methyl morpholine |
| NMP | N-methylpyrrolidinone |
| NMR | nuclear magnetic resonance spectroscopy: chemical shifts ($\delta$) are given in ppm. |
| PdCl$_2$(PPh$_3$)$_2$ | dichlorobis(triphenylphosphine)palladium(II) |
| Pd(dba)$_2$ | bis-(dibenzylideneacetone)palladium(0) complex |
| Pd$_2$(dba)$_3$ | tris-(dibenzylideneacetone)dipalladium(0) chloroform complex |
| Pd(dppf)Cl$_2$ | dichloro[1,1'-bis(diphenylphosphino)ferrocene]palladium(II) |
| Pd(dppf)Cl$_2$•CH$_2$Cl$_2$ | dichloro[1,1'-bis(diphenylphosphino)ferrocene]palladium(II) dichloromethane adduct |
| Pd-Brett-Phos-pre-cat | chloro[2-(dicyclohexylphosphino)-3,6-dimethoxy-2'-4'-6'-tri-iso-propyl-1,1'-biphenyl][2-(2-aminoethyl)phenyl]palladium(II) |
| Pd-tBu-X-Phos-pre-cat | chloro(2-di-tert-butylphosphino-2',4',6'-tri-isopropyl-1,1'-biphenyl)[2-(2-aminoethyl)phenyl] palladium(II) |
| Pd-X-Phos-pre-cat | chloro(2-dicyclohexylphosphino-2',4',6'-tri-isopropyl-1,1'-biphenyl)[2-(2-aminoethyl)phenyl] palladium(II) methyl-tert-butylether adduct |

TABLE 1-continued

| Abbreviation | Meaning |
|---|---|
| PPh$_3$ | triphenylphosphine |
| P(oTol)$_3$ | tri-o-tolylphosphine |
| PyBOP | benzotriazol-1-yl-oxytripyrrolidinophosphonium hexafluorophosphate |
| q | quartet |
| quin | quintett |
| Rac | racemic |
| r.t. | room temperature |
| R$_t$ | retention time in minutes |
| s | singlet |
| S-Phos | dicyclohexyl(2',6'-dimethoxybiphenyl-2-yl)phosphine |
| t | triplet |
| T3P | 2,4,6-tripropyl-1,3,5,2,4,6-trioxatriphosphinane 2,4,6-trioxide |
| TBAF | tetrabutylammoniumfluoride |
| tBu-X-Phos | 2-di-tert-butylphosphino-2',4',6'-tri-isopropyl-1,1'-biphenyl |
| TBDPS | tert-butyldiphenylsilyl |
| TBTU | N-[(1H-benzotriazol-1-yloxy)(dimethylamino)methylene]-N-methylmethanaminium tetrafluoroborate |
| TEA | triethylamine |
| TCDI | di-1H-imidazol-1-ylmethanethione (Thiocarbonyldiimidazole) |
| TFA | trifluoroacetic acid |
| THF | tetrahydrofuran |
| TMS | trimethylsilyl |
| Ts | para toluenesulfonyl; (tosyl) |
| UPLC | ultra performance liquid chromatography |
| X-Phos | 2-dicyclohexylphosphino-2',4',6'-triisopropylbiphenyl |
| Xantphos | 4,5-Bis(diphenylphosphino)-9,9-dimethylxanthene; CAS RN: 161265-03-8 |

All reagents, for which the synthesis is not described in the experimental part, are either commercially available, or are known compounds or may be formed from known compounds by known methods by a person skilled in the art.

Wherever specified, NMR peak multiplicities and peak forms are stated as they appear in the spectra. Possible higher order effects have not been considered.

The $^1$H-NMR data of selected compounds and examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: δ$_1$ (intensity$_1$), δ$_2$ (intensity$_2$), ... δ$_i$ (intensity$_i$), ..., δ$_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures).

In the peak picking routine, as described in the Research. Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

The examples and compounds produced according to the methods of the invention may require purification. Purification of organic compounds is well known to the person skilled in the art and there may be several ways of purifying the same compound. In some cases, no purification may be necessary. In some cases, the examples and compounds may be purified by crystallisation. In some cases, impurities may be removed by trituration using a suitable solvent or solvent mixture. In some cases, the examples and compounds may be purified by chromatography, particularly flash chromatography, using for example pre-packed silica gel cartridges, e.g. Isolute® Flash silica gel (Separtis) or SNAP cartridges KP-Sil® (Biotage) for purifications referred to herein as "silicagel chromatography"; or using e.g. Isolute® Flash NH$_2$ silica gel (Separtis) or SNAP cartridges KP-NH® (Biotage), for purifications referred to herein as "aminophase silicagel chromatography", said cartridges being used in combination with a suitable chromatographic system such as a Flashmaster II (Separtis) or an Isolera® system (Biotage) and eluents such as, for example, gradients of hexane/ethyl acetate or DCM/methanol. In some cases, the examples and compounds may be purified by preparative HPLC using standard commercial HPLC equipment, such as a Waters autopurifier equipped with a diode array detector and/or on-line electrospray ionisation mass spectrometer in combination with a suitable pre-packed reverse phase column, and eluants such as, for example, gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Chemical names were generated using the ACD/Name software from ACD/Labs. In some cases generally accepted names of commercially available reagents were used in place of ACD/Name generated names.

Optical rotations were measured using a JASCO P2000 Polarimeter. Typical, a solution of the compound with a concentration of 1 mg/mL to 15 mg/mL was used for the measurement. The specific rotation $[\alpha]_D$ was calculated according to the following formula:

$$[\alpha]D = \frac{\alpha}{\beta \times d}$$

In this equation, a is the measured rotation in degrees; d is the path length in decimetres and 3 is the concentration in g/mL.

UPLC-MS Standard Procedures

Analytical UPLC-MS was performed as described below.
Method 1:
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.
Method 2:
Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.
Method 3:
Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.
Method 4:
Instrument: Waters Acquity UPLCMS SingleQuad; Column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.
Method 5:
column: Ascentis Express C18, 2.7 µm, 3 cm×2.1 mm
column temp.: 30° C.
injection volume: 1 µl
detection: MM-ES+APCI+DAD (254 nm)
fragment.potential: 50 V
mass range: 80-800 m/z
mobile phase A: water/0.1% formic acid
mobile phase B: methanol/0.1% formic acid
system time delay: 0.2 min
Gradient:

| time in min | % A | % B | flow rate in mL/min |
| --- | --- | --- | --- |
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

Method 6:
Instrument: Waters Acquity UPLCMS SingleQuad; Column: Chiralpak IF 3µ 100×4.6; solvent: 20-50% EtOH/Hexan; buffer: +0.1% DEA; gradient: S6_20_ethanol hexane DEA; solution: 1 mg/mL, flow 1.4 mL/min; DAD scan: 254 nm; run time: 10 min.; injection volume: 5.0 µL.
Method 7:
Instrument MS: Waters ZQ; Instrument HPLC: Waters UPLC Acquity; Column: Acquity BEH C18 (Waters), 50 mm×2.1 mm, 1.7 µm; eluent A: water+0.1 vol % formic acid, eluent B: acetonitrile (Lichrosolv Merck); gradient: 0.0 min 99% A—1.6 min 1% A—1.8 min 1% A—1.81 min 99% A—2.0 min 99% A; temperature: 60° C.; flow: 0.8 mL/min; UV-Detection PDA 210-400 nm.

Experimental Section—Description of Compounds

Compound 01.01

4-(bromomethyl)pyridin-2-amine hydrobromide

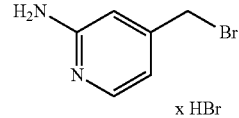

A mixture of (2-aminopyridin-4-yl)methanol (5.00 g, 40.3 mmol) and aqueous hydrobromic acid (50 mL, c=. 48%, 440 mmol) was heated at 100° C. for 24 hours. The mixture was cooled to room temperature and concentrated under reduced pressure. Ethyl acetate was added to the crude product and the resulting solid was filtered, washed with ethyl acetate and dried under reduced pressure to give 7.70 g (71%) of the title compound as a crude product that was used without further purification.

LC-MS (Method 2): $R_t$=0.68 min; MS (ESIpos): m/z=186; 188 [M+H]$^+$.

¹H-NMR (400 MHz, d₆-DMSO): δ [ppm]=8.10 (brs, 2H), 7.90 (d, J=6.9 Hz, 1H), 6.98 (s, 1H), 6.84 (dd, J=1.8 and 6.9 Hz, 1H), 4.65 (s, 2H).

Compound 01.02 tert-butyl 4-[(2-aminopyridin-4-yl)methyl]piperazine-1-carboxylate

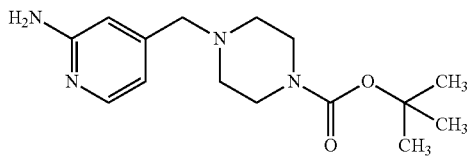 [SMILES: CC(C)(C)OC(=O)N1CCN(Cc2ccnc(N)c2)CC1]

To a stirred suspension of 4-(bromomethyl)pyridin-2-amine hydrobromide (9.90 g, 36.9 mmol) in acetonitrile (75 mL) was added potassium carbonate (15.6 g, 113 mmol) and tert-butyl piperazine-1-carboxylate (7.50 g, 40.3 mmol). The mixture was stirred at 75° C. for 2 h. Direct silicagel chromatography of the reaction mixture gave 10.3 g (95% yield) of the title compound.

LC-MS (Method 2): $R_t$=1.00 min; MS (ESIpos): m/z=293 [M+H]⁺.

¹H-NMR (400 MHz, DMSO-d6) δ[ppm]: 1.386 (16.00), 1.392 (3.05), 2.278 (0.86), 2.291 (1.25), 2.303 (0.96), 5.815 (1.05), 6.383 (0.87), 6.385 (0.70), 6.407 (0.54), 6.419 (0.52), 7.802 (0.68), 7.815 (0.66), 7.817 (0.66).

Compound 01.03

4-(4,4,5,5-tetramethyl-1,3,2-dioxaborolan-2-yl)benzene-1,2-diamine

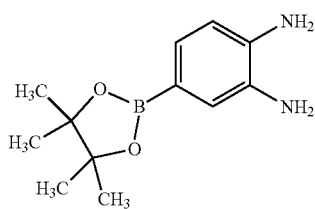 [SMILES: CC1(C)OB(c2ccc(N)c(N)c2)OC1(C)C]

To a solution of 4-bromobenzene-1,2-diamine (25.3 g, 135 mmol) and 4,4,4',4',5,5,5',5'-octamethyl-2,2'-bi-1,3,2-dioxaborolane (42.9 g, 169 mmol) in dioxane (120 mL) was added potassium acetate (19.9 g, 203 mmol), the mixture was purged with Argon, dichloropalladium-tricyclohexylphosphane (1:2) (5.00 g, 6.77 mmol) was added and the mixture was stirred at 100° C. for 5 h. Diethyl ether was added and the mixture was filtered through celite and the solvent was removed in vacuum. Silicagel chromatography gave 21.7 g (65% yield) of the title compound.

LC-MS (METHOD 5): $R_t$=2.49 min; MS (ESIpos): m/z=235 [M+H]⁺.

¹H-NMR (400 MHz, DMSO-d6) δ[ppm]: 1.077 (8.15), 1.161 (4.45), 1.176 (0.50), 1.231 (16.00), 1.988 (0.71), 6.457 (1.17), 6.476 (1.28), 6.765 (0.68), 6.768 (0.71), 6.784 (0.57), 6.787 (0.63), 6.889 (1.18), 6.892 (1.12).

Compound 01.04 tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate

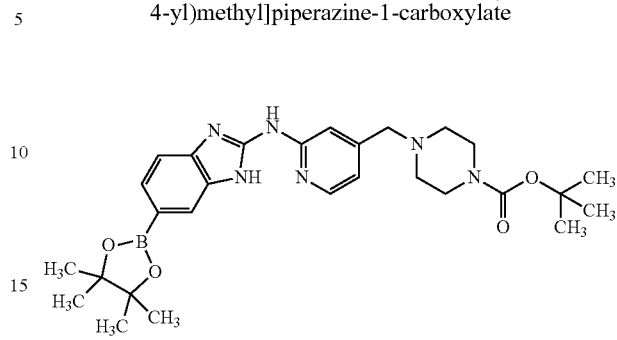

To a stirred solution of di-1H-imidazol-1-ylmethanethione (2.14 g, 12.0 mmol) and imidazole (159 mg, 2.34 mmol) in dichloromethane (30 mL) was added tert-butyl 4-[(2-aminopyridin-4-yl)methyl]piperazine-1-carboxylate (3.18 g, 10.9 mmol), dissolved in dichloromethane (30 mL), at 0° C. The mixture was stirred at 0° C. for 4 h. 4-(4,4,5,5-tetramethyl-1,3,2-dioxaborolan-2-yl)benzene-1,2-diamine (2.55 g, 10.9 mmol), dissolved in dichloromethane (20 mL), was added and the mixture was stirred at r.t. for 18 h. Water was added and the mixture was extracted with dichloromethane.

The organic phase was dried (magnesium sulfate) and filtered. N,N'-dipropan-2-ylcarbodiimide (2.6 mL, 17 mmol) was added and the mixture was stirred at 40° C. for 24 h. Saturated ammonium chloride solution was added, the mixture was stirred for 30 minutes and the mixture was extracted with dichloromethane. The organic phase was dried (magnesium sulfate) and the solvent was removed in vacuum. Silicagel chromatography gave a solid that was triturated with diethyl ether to give 2.22 g (38% yield) of the title compound.

LC-MS (Method 5): $R_t$=3.30 min; MS (ESIpos): m/z=535 [M+H]⁺.

¹H-NMR (400 MHz, DMSO-d6) δ [ppm]: 1.086 (0.41), 1.171 (0.44), 1.299 (16.00), 1.392 (15.47), 1.984 (0.91), 2.336 (1.27), 2.348 (1.85), 2.360 (1.33), 2.495 (0.68), 2.499 (0.91), 2.504 (0.68), 3.320 (3.52), 3.342 (1.92), 3.368 (0.48), 3.481 (2.17), 6.901 (0.63), 6.914 (0.66), 8.235 (0.89), 8.248 (0.89).

Compound 01.05

6-(2-methylpyridin-4-yl)-N-[4-(piperazin-1-ylmethyl)pyridin-2-yl]-1H-benzimidazol-2-amine hydrochloride

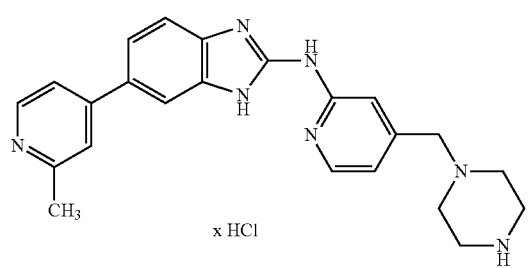 [SMILES: Cc1cc(-c2ccc3nc(Nc4cc(CN5CCNCC5)ccn4)[nH]c3c2)ccn1]

To a stirred solution of tert-butyl 4-[(2-{[6-(2-methyl pyridin-4-yl)-1H-benzimidazol-2-yl]amino}pyridin-4-yl)methyl]piperazine-1-carboxylate (388 mg, 777 μmol) in dichloromethane (10 mL) and methanol (1.6 mL) was added HCl in dioxane (2.9 mL, 4.0 M, 12 mmol). The mixture was stirred at room temperature for 16 h. The solvent was removed in vacuum to give 326 mg of the title compound as crude product that was used for the next step without purification.

LC-MS (Method 2): $R_t$=0.92 min; MS (ESIneg): m/z=398 [M−H]+.

Compound 02.01

4-(2-methoxypyridin-4-yl)-2-nitroaniline

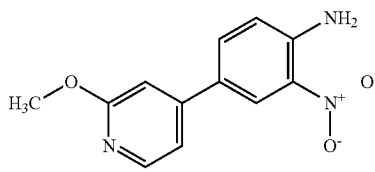

To a stirred solution of 4-bromo-2-nitroaniline (3.00 g, 13.8 mmol) in 1-propanol (130 mL) was added potassium carbonate solution (21 mL, 2.0 M, 41 mmol), (2-methoxypyridin-4-yl)boronic acid (4.23 g, 27.6 mmol), triphenylphosphine (181 mg, 691 μmol) and PdCl$_2$(PPh$_3$)$_2$ (485 mg, 691 μmol). The mixture was heated to reflux for 2 h, the solvent was removed in vacuum, water was added and the mixture was extracted with ethyl acetate. The organic phase was dried (sodium sulfate), filtered and the solvent was removed in vacuum. Silicagel chromatography gave a solid that was triturated with warm ethanol to give 2.20 g (65% yield) of the title compound.

LC-MS (Method 2): $R_t$=1.05 min; MS (ESIpos): m/z=246 [M+H]+.

$^1$H-NMR (400 MHz, DMSO-d6) δ[ppm]: 3.309 (16.00), 3.903 (0.89), 5.752 (0.76), 7.058 (6.56), 7.062 (7.47), 7.119 (7.28), 7.141 (7.58), 7.271 (4.73), 7.275 (4.50), 7.285 (4.72), 7.289 (4.72), 7.666 (8.49), 7.862 (3.74), 7.867 (3.82), 7.884 (3.49), 7.889 (3.62), 8.169 (6.51), 8.183 (6.28), 8.339 (7.41), 8.345 (7.24).

Compound 02.02

4-(2-methoxypyridin-4-yl)benzene-1,2-diamine

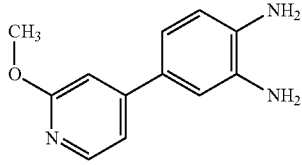 [SMILES: COc1cc(-c2ccc(N)c(N)c2)ccn1]

To a stirred solution of 4-(2-methoxypyridin-4-yl)-2-nitroaniline (2.20 g, 8.97 mmol) in ethanol (30 mL) was added Raney Nickel (53 mg) and the mixture was stirred at r.t. in a hydrogen atmosphere for 144 h. The mixture was filtered, and the solution was concentrated in vacuum to give 1.90 g (98% yield) mg of the title compound as crude product, that was used for the next step without purification.

LC-MS (Method 2): $R_t$=0.83 min; MS (ESIpos): m/z=216 [M+H]+.

$^1$H-NMR (400 MHz, DMSO-d6) δ[ppm]: 3.334 (5.14), 4.828 (8.22), 5.752 (5.73), 6.587 (8.30), 6.844 (16.00), 6.947 (10.92), 7.103 (11.29), 7.683 (0.89), 8.070 (9.76).

Compound 02.03

6-(2-methoxypyridin-4-yl)-N-[4-(piperazin-1-ylmethyl)pyridin-2-yl]-1H-benzimidazol-2-amine hydrochloride

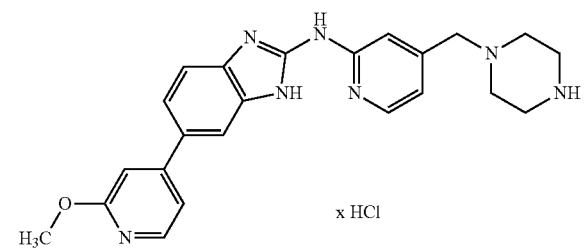 [SMILES: COc1cc(-c2ccc3nc(Nc4cc(CN5CCNCC5)ccn4)[nH]c3c2)ccn1]

Starting with tert-butyl 4-[(2-{[6-(2-methoxypyridin-4-yl)-1H-benzimidazol-2-yl]amino}pyridin-4-yl)methyl]piperazine-1-carboxylate (575 mg, 1.12 mmol) Compound 02.03 was prepared analogously to the procedure for the preparation of Compound 01.05.

Yield: 540 mg of the title compound as crude product that was used for the next step without purification.

LC-MS (Method 2): $R_t$=1.07 min; MS (ESIneg): m/z=414 [M−H]+.

$^1$H-NMR (400 MHz, DMSO-d6) δ[ppm]: 3.162 (8.02), 3.442 (1.95), 3.561 (16.00), 3.934 (15.50), 4.507 (2.69), 5.751 (2.51), 7.135 (2.88), 7.139 (2.96), 7.333 (1.77), 7.336 (1.71), 7.346 (1.74), 7.350 (1.75), 7.591 (2.75), 7.648 (1.24), 7.661 (1.38), 7.786 (6.74), 7.788 (6.71), 8.021 (2.19), 8.024 (3.45), 8.027 (2.12), 8.272 (2.66), 8.286 (2.55), 8.560 (2.19), 8.574 (2.06), 9.976 (0.86).

Compound 03.01

4-(5-fluoro-2-methoxypyridin-4-yl)-2-nitroaniline

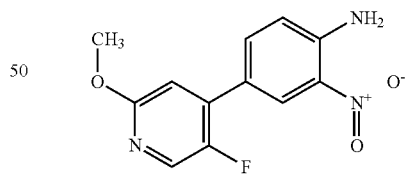

Starting with 4-bromo-2-nitroaniline (3.00 g, 13.5 mmol) and (5-fluoro-2-methoxypyridin-4-yl)boronic acid (2.55 g, 14.9 mmol), Compound 03.01 was prepared analogously to the procedure for the preparation of Compound 02.01.

Yield: 1.70 g (48%) of the title compound.

LC-MS (Method 2): $R_t$=1.16 min; MS (ESIpos): m/z=264 [M+H]+.

$^1$H-NMR (400 MHz, DMSO-d6) δ [ppm]: 3.319 (16.00), 7.024 (1.93), 7.038 (1.89), 7.126 (1.91), 7.148 (1.99), 7.724 (0.87), 7.730 (1.58), 7.734 (2.38), 7.747 (0.85), 7.752 (0.85), 8.201 (1.92), 8.209 (1.93), 8.300 (1.24), 8.302 (1.31), 8.306 (1.29), 8.308 (1.14).

Compound 03.02

4-(5-fluoro-2-methoxypyridin-4-yl)benzene-1,2-diamine

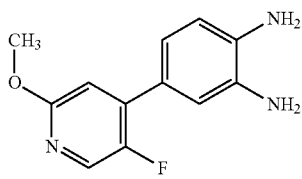 [SMILES: COc1cc(-c2ccc(N)c(N)c2)c(F)cn1]

To a stirred solution of 4-(5-fluoro-2-methoxypyridin-4-yl)-2-nitroaniline (1.70 g, 6.46 mmol) in ethanol (200 mL) and dichloromethane (70 mL) was added palladium on carbon (10% w/w palladium) (344 mg, 323 µmol) and the mixture was stirred at r.t. in a hydrogen atmosphere for 14 h. The mixture was filtered through aminophase silicagel, and the solution was concentrated in vacuum to give 1.50 g (100% yield) of the title compound as crude product, that was used for the next step without purification.

LC-MS (Method 2): $R_t$=0.87 min; MS (ESIpos): m/z=234 [M+H]$^+$.

$^1$H-NMR (400 MHz, DMSO-d6) δ [ppm]: 1.037 (0.99), 1.054 (2.00), 1.071 (1.74), 1.089 (2.01), 1.106 (0.86), 3.321 (16.00), 3.371 (0.86), 3.389 (0.95), 3.424 (0.47), 3.436 (0.48), 3.454 (0.42), 4.344 (0.63), 4.628 (2.93), 4.920 (3.66), 6.573 (2.89), 6.593 (3.49), 6.744 (0.88), 6.749 (1.52), 6.754 (0.97), 6.764 (0.78), 6.769 (1.65), 6.772 (3.61), 6.786 (3.01), 6.859 (1.59), 6.863 (2.64), 6.868 (1.43), 7.546 (0.79), 7.549 (0.71), 7.554 (0.65), 7.557 (0.65), 7.564 (0.94), 7.566 (0.71), 7.572 (0.68), 7.597 (1.01), 7.614 (0.92), 7.622 (0.90), 7.626 (1.33), 7.631 (0.64), 7.643 (0.64), 8.079 (3.09), 8.087 (3.02).

Compound 03.03 tert-butyl 4-[(2-{[6-(5-fluoro-2-methoxypyridin-4-yl)-1H-benzimidazol-2-yl]amino}pyridin-4-yl)methyl]piperazine-1-carboxylate

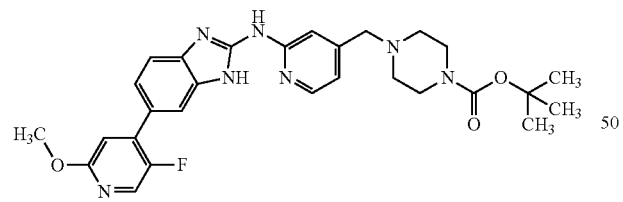

To a stirred solution of 1H-imidazole (61.3 mg, 900 µmol) and di-1H-imidazol-1-ylmethanethione (844 mg, 95% purity, 4.50 mmol) in dichloromethane (30 mL) was added tert-butyl 4-[(2-aminopyridin-4-yl)methyl]piperazine-1-carboxylate (1.32 g, 4.50 mmol) dissolved in dichloromethane (50 mL), at 0° C. The mixture was stirred at r.t. for 14 h. 4-(5-fluoro-2-methoxypyridin-4-yl)benzene-1,2-diamine (1.50 g, 70% purity, 4.50 mmol), dissolved in dichloromethane (10 mL), was added and the mixture was stirred at r.t. for 65 h. Water was added and the mixture was extracted with dichloromethane.

The organic phase was dried (sodium sulfate) and filtered. N,N'-dipropan-2-ylcarbodiimide (2.8 mL, 18 mmol) was added and the mixture was stirred at r.t. for 1 h. Further N,N'-dipropan-2-ylcarbodiimide (2.8 mL, 18 mmol) was added and the mixture was stirred at r.t. for 2 h. Again, further N,N'-dipropan-2-ylcarbodiimide (2.8 mL, 18 mmol) was added and the mixture was stirred at r.t. for 14 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography gave a solid that was triturated with ethanol. The solid was removed by filtration and was discarded. The solution was concentrated in vacuum. Aminophase-silicagel chromatography followed by silicagel chromatography gave 1.20 g of the title compound as a crude product, that was used without further purification.

LC-MS (Method 2): $R_t$=1.38 min; MS (ESIpos): m/z=534 [M+H]$^+$.

$^1$H-NMR (400 MHz, DMSO-d6) δ [ppm]: 0.993 (4.37), 1.009 (4.35), 1.038 (0.52), 1.056 (0.95), 1.073 (0.53), 1.387 (2.07), 1.396 (16.00), 1.987 (0.43), 2.350 (0.95), 2.362 (1.36), 2.374 (1.00), 3.351 (1.15), 3.503 (1.68), 3.845 (0.47), 3.879 (5.30), 6.930 (0.56), 7.187 (0.65), 8.201 (0.63), 8.208 (0.62), 8.261 (0.77), 8.274 (0.76).

Compound 03.04

6-(5-fluoro-2-methoxypyridin-4-yl)-N-[4-(piperazin-1-ylmethyl)pyridin-2-yl]-1H-benzimidazol-2-amine hydrochloride

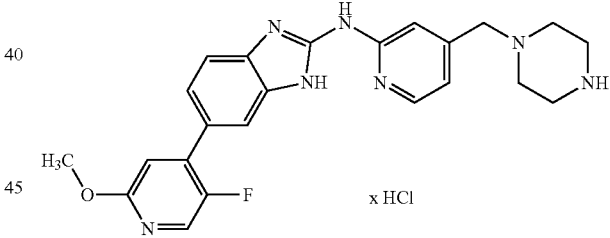

Starting with tert-butyl 4-[(2-{[6-(5-fluoro-2-methoxy-pyridin-4-yl)-1H-benzimidazol-2-yl]amino}pyridin-4-yl)methyl]piperazine-1-carboxylate (1.20 g, 1.80 mmol), Compound 03.04 was prepared analogously to the procedure for the preparation of Compound 01.05.

Yield: 0.58 g of the title compound as crude product that was used for the next step without purification.

LC-MS (Method 2): $R_t$=1.13 min; MS (ESIpos): m/z=434 [M+H]$^+$.

$^1$H-NMR (400 MHz, DMSO-d6) δ[ppm]: 0.968 (1.58), 0.985 (1.59), 2.296 (2.44), 2.300 (2.59), 2.304 (2.49), 2.309 (2.10), 2.684 (3.09), 2.696 (4.52), 2.708 (2.73), 3.410 (5.47), 3.856 (16.00), 5.733 (0.91), 6.893 (1.33), 6.896 (1.35), 6.906 (1.39), 6.909 (1.37), 7.148 (2.37), 8.182 (2.25), 8.188 (2.15), 8.226 (2.29), 8.239 (2.17).

Compound 04.01

4-(3-methoxypyridin-4-yl)-2-nitroaniline

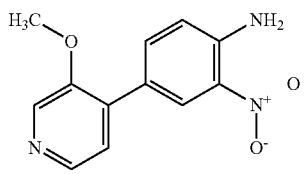

Starting with 4-bromo-2-nitroaniline (2.40 g, 11.1 mmol) and (3-methoxypyridin-4-yl)boronic acid (3.38 g, 22.1 mmol), Compound 04.01 was prepared analogously to the procedure for the preparation of Compound 02.01.

Yield: 2.20 g (73%) of the title compound.

LC-MS (Method 1): $R_t$=0.64 min; MS (ESIpos): m/z=246 [M+H]$^+$.

$^1$H-NMR (400 MHz, DMSO-d6) δ[ppm]: 3.917 (16.00), 7.082 (2.37), 7.105 (2.52), 7.382 (2.44), 7.394 (2.50), 7.613 (2.41), 7.677 (1.37), 7.683 (1.37), 7.699 (1.24), 7.705 (1.27), 8.240 (3.19), 8.252 (2.99), 8.271 (2.48), 8.277 (2.46), 8.437 (4.31).

Compound 04.02

4-(3-methoxypyridin-4-yl)benzene-1,2-diamine

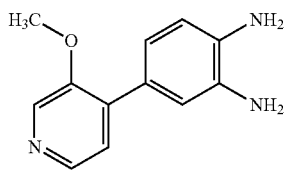 [SMILES: COc1cnccc1-c1ccc(N)c(N)c1]

To a stirred solution of 4-(3-methoxypyridin-4-yl)-2-nitroaniline (2.10 g, 8.56 mmol) in ethanol (30 mL) was added Raney Nickel (50 mg) and the mixture was stirred at r.t. in a hydrogen atmosphere for 16 h. The mixture was filtered, and the solution was concentrated in vacuum to give 1.80 g (88% yield) of the title compound as crude product, that was used for the next step without purification.

LC-MS (Method 2): $R_t$=0.69 min; MS (ESIpos): m/z=216 [M+H]$^+$.

$^1$H-NMR (400 MHz, DMSO-d6) δ[ppm]: 3.315 (4.62), 4.614 (1.94), 5.752 (0.66), 6.541 (8.22), 6.562 (10.75), 6.689 (5.56), 6.694 (5.89), 6.709 (4.10), 6.714 (4.55), 6.828 (10.07), 6.833 (9.39), 7.192 (8.70), 7.204 (9.09), 8.150 (10.53), 8.162 (10.08), 8.322 (16.00).

Compound 04.03

4-({[tert-butyl(dimethyl)silyl]oxy}methyl)pyridin-2-amine

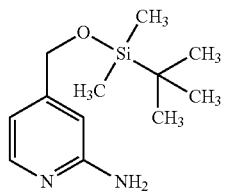

To a stirred solution of (2-aminopyridin-4-yl)methanol (10.0 g, 97% purity, 78.1 mmol) and 1H-imidazole (5.32 g, 78.1 mmol) in DMF (70 mL), was added tert-butyl(chloro)dimethylsilane (12.1 g, 97% purity, 78.1 mmol) at 0° C. and the mixture was stirred at r.t. for 14 h. The solvent was removed in vacuum. Water was added and the mixture was extracted with ethyl acetate.

The organic phase was dried (sodium sulfate), filtered and the solvent was removed in vacuum. Silicagel chromatography gave 16.0 g (86% yield) of the title compound.

LC-MS (Method 2): $R_t$=1.29 min; MS (ESIpos): m/z=239 [M+H]$^+$.

$^1$H-NMR (400 MHz, DMSO-d6) δ[ppm]: −0.061 (0.42), 0.059 (11.41), 0.822 (0.66), 0.881 (0.84), 0.889 (16.00), 0.896 (0.76), 4.539 (1.92), 5.830 (0.78), 6.370 (0.66), 6.372 (0.76), 7.780 (0.59), 7.782 (0.52), 7.793 (0.56), 7.795 (0.54).

Compound 04.04

N-[4-({[tert-butyl(dimethyl)silyl]oxy}methyl)pyridin-2-yl]-6-(3-methoxypyridin-4-yl)-1H-benzimidazol-2-amine

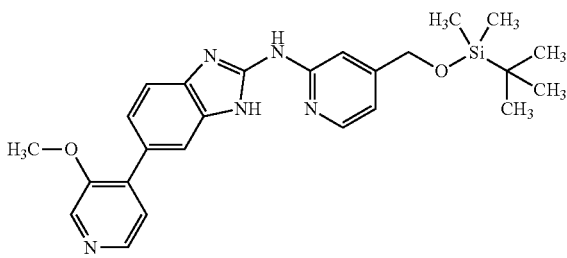 [SMILES: COc1cnccc1-c1ccc2nc(Nc3cc(CO[Si](C)(C)C(C)(C)C)ccn3)[nH]c2c1]

To a stirred solution of 1H-imidazole (92.0 mg, 1.35 mmol) and di-1H-imidazol-1-ylmethanethione (1.52 g, 95% purity, 8.11 mmol) in dichloromethane (200 mL) was added 4-({[tert-butyl(dimethyl)silyl]oxy}methyl)pyridin-2-amine (1.61 g, 6.76 mmol), dissolved in dichloromethane (200 mL) at 0° C. The mixture was stirred at r.t. for 14 h. 4-(3-methoxypyridin-4-yl)benzene-1,2-diamine (1.80 g, 97% purity, 8.11 mmol), dissolved in dichloromethane was added and the mixture was stirred at r.t. for 4 h. Water was added and the mixture was extracted with dichloromethane/methanol (10:1).

The organic phase was dried (sodium sulfate) and filtered. N,N'-dipropan-2-ylcarbodiimide (3.1 mL, 20 mmol) was added and the mixture was stirred at r.t. for 14 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography gave a solid that was triturated with ethyl acetate. The solid was removed by filtration and was discarded. The solution was concentrated in vacuum. Aminophase-silicagel chromatography gave 1.10 g of the title compound as a crude product, that was used without further purification.

LC-MS (Method 2): $R_t$=1.51 min; MS (ESIpos): m/z=462 [M+H]$^+$.

$^1$H-NMR (400 MHz, DMSO-d6) δ [ppm]: 0.150 (12.43), 0.970 (1.01), 0.978 (16.00), 0.985 (0.93), 1.015 (0.74), 1.031 (0.76), 1.196 (0.72), 2.010 (1.31), 3.930 (3.13), 4.766 (1.90), 7.394 (0.57), 8.266 (0.79), 8.272 (0.94), 8.280 (0.86), 8.284 (0.91), 8.458 (1.50).

Compound 04.05

(2-{[6-(3-methoxypyridin-4-yl)-1H-benzimidazol-2-yl]amino}pyridin-4-yl)methanol

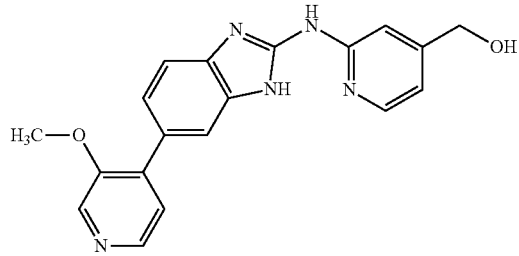 [SMILES: COc1cnccc1-c1ccc2nc(Nc3cc(CO)ccn3)[nH]c2c1]

To a stirred solution of crude N-[4-({[tert-butyl(dimethyl)silyl]oxy}methyl)pyridin-2-yl]-6-(3-methoxypyridin-4-yl)-1H-benzimidazol-2-amine (1.10 g, approx. 2.38 mmol) in THF (27 mL), was added tetra-n-butylammoniumfluoride (4.8 mL, 1.0 M, 4.8 mmol), and the mixture was stirred at r.t. for 1 h. Water was added, the mixture was stirred for 30 minutes and the mixture was extracted with ethyl acetate and then with dichloromethane/methanol (100:1). The combined organic phases were dried (sodium sulfate), filtered and the solvent was removed in vacuum. The solid was triturated with ethanol to give 700 mg (76% yield) of the title compound.

LC-MS (Method 2): $R_t$=0.87 min; MS (ESIpos): m/z=348 [M+H]$^+$.

$^1$H-NMR (400 MHz, DMSO-d6) δ [ppm]: 1.172 (0.73), 1.986 (1.45), 3.906 (16.00), 4.517 (4.11), 4.531 (4.20), 5.430 (1.79), 5.444 (3.84), 5.458 (1.68), 5.755 (0.46), 6.880 (1.85), 6.884 (1.82), 6.894 (1.88), 6.897 (1.84), 7.202 (2.63), 7.268 (0.62), 7.360 (2.65), 7.372 (2.73), 8.236 (2.92), 8.248 (6.20), 8.260 (3.55), 8.434 (6.22), 10.666 (1.23), 12.194 (0.86).

Compound 04.06

N-[4-(chloromethyl)pyridin-2-yl]-6-(3-methoxypyridin-4-yl)-1H-benzimidazol-2-amine

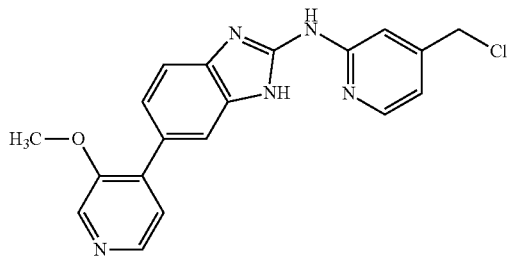 [SMILES: COc1cnccc1-c1ccc2nc(Nc3cc(CCl)ccn3)[nH]c2c1]

To a suspension of (2-{[6-(3-methoxypyridin-4-yl)-1H-benzimidazol-2-yl]amino}pyridin-4-yl)methanol (700 mg, 2.02 mmol) in dioxane (50 mL, 580 mmol) was added thionyl dichloride (590 μl, 8.1 mmol) and the mixture was stirred for 86 h. A solution of sodium bicarbonate was added and the mixture was extracted with ethyl acetate. The organic phase was dried (sodium sulfate), filtered and the solvent was removed in vacuum to give 870 mg of the title compound as a crude product.

LC-MS (Method 2): $R_t$=1.08 min; MS (ESIpos): m/z=366 [M+H]$^+$.

$^1$H-NMR (500 MHz, DMSO-d6) δ[ppm]: 1.355 (0.44), 3.311 (16.00), 3.908 (8.77), 4.779 (6.30), 7.007 (1.14), 7.010 (1.09), 7.017 (1.09), 7.020 (1.15), 7.301 (1.13), 7.363 (1.37), 7.372 (1.37), 8.251 (2.25), 8.261 (2.07), 8.321 (1.72), 8.332 (1.63), 8.437 (3.54).

Compound 04.07

6-(3-methoxypyridin-4-yl)-N-[4-(piperazin-1-ylmethyl)pyridin-2-yl]-1H-benzimidazol-2-amine hydrochloride

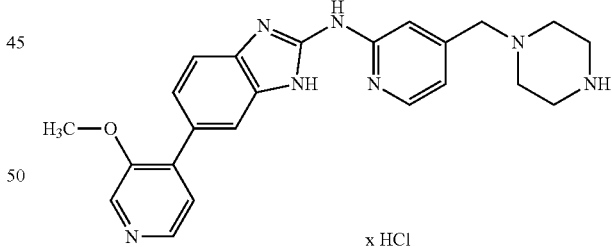

Starting with tert-butyl 4-[(2-{[6-(3-methoxypyridin-4-yl)-1H-benzimidazol-2-yl]amino}pyridin-4-yl)methyl]piperazine-1-carboxylate (800 mg, 1.55 mmol), Compound 04.07 was prepared analogously to the procedure for the preparation of Compound 01.05.

Yield: 0.80 g of the title compound as crude product that was used for the next step without purification.

LC-MS (Method 2): $R_t$=0.90 min; MS (ESIpos): m/z=460 [M+H]$^+$.

$^1$H-NMR (400 MHz, DMSO-d6) δ[ppm]: 2.523 (1.48), 2.526 (1.48), 2.728 (1.49), 2.889 (1.73), 3.258 (0.93), 3.401 (2.10), 4.048 (16.00), 4.322 (0.66), 7.555 (2.55), 7.650 (1.48), 7.654 (1.39), 7.671 (1.78), 7.675 (1.84), 7.795 (2.28), 7.815 (1.71), 7.942 (1.81), 7.956 (1.94), 8.036 (2.43), 8.040 (2.42), 8.529 (1.27), 8.543 (1.19), 8.589 (2.47), 8.603 (2.36), 8.744 (4.60).

Compound 05.01

4-bromo-3-(2,2,2-trifluoroethoxy)pyridine

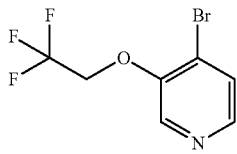 [SMILES: FC(F)(F)COc1cnccc1Br]

To a stirred solution of 4-bromopyridin-3-ol (1.00 g, 95% purity, 5.46 mmol) in DMA (15 mL) was added potassium carbonate (981 mg, 7.10 mmol) and 2,2,2-trifluoroethyl trifluoromethanesulfonate (1.2 mL, 97% purity, 8.2 mmol). The mixture was stirred at r.t. for 48 h. Water was added (250 mL) and ammonium chloride was added until pH7 was reached. The mixture was extracted with ethyl acetate. The organic phase was washed with half-saturated sodium chloride solution, dried (sodium sulfate) and the solvent was removed in vacuum to give 1.43 g of the title compound as crude product, that was used without further purification.

LC-MS (Method 2): $R_t$=1.06 min; MS (ESIpos): m/z=256 [M+H]$^+$.

$^1$H-NMR (500 MHz, DMSO-d6) δ[ppm]: 4.663 (0.53), 4.682 (1.51), 4.700 (1.45), 4.718 (0.46), 4.910 (0.99), 4.928 (0.93), 4.997 (4.67), 5.015 (13.93), 5.033 (13.29), 5.050 (4.20), 6.310 (1.35), 6.325 (1.31), 7.739 (10.77), 7.749 (11.23), 7.845 (0.86), 7.850 (0.75), 8.156 (10.52), 8.166 (10.05), 8.511 (16.00).

Compound 05.02

2-nitro-4-[3-(2,2,2-trifluoroethoxy)pyridin-4-yl]aniline

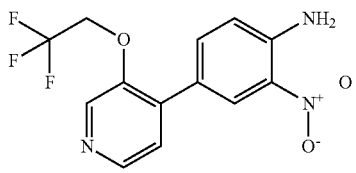

Starting with crude 4-bromo-3-(2,2,2-trifluoroethoxy) pyridine (1.43 g, approx. 5.03 mmol) and 2-nitro-4-(4,4,5,5-tetramethyl-1,3,2-dioxaborolan-2-yl)aniline (1.37 g, 97% purity, 5.03 mmol), Compound 05.02 was prepared analogously to the procedure for the preparation of Compound 02.01.

Yield: 1.25 g of the title compound.

LC-MS (Method 2): $R_t$=1.01 min; MS (ESIpos): m/z=314 [M+H]$^+$.

$^1$H-NMR (400 MHz, DMSO-d6) δ[ppm]: 1.069 (4.06), 2.327 (0.66), 2.523 (1.31), 2.669 (0.61), 3.162 (0.58), 3.175 (0.61), 3.912 (0.67), 4.909 (3.12), 4.931 (9.05), 4.953 (8.56), 4.975 (2.54), 5.752 (1.17), 7.091 (7.76), 7.113 (8.10), 7.470 (7.97), 7.482 (8.31), 7.525 (0.91), 7.528 (1.46), 7.533 (1.18), 7.536 (1.28), 7.540 (1.01), 7.544 (2.45), 7.547 (3.52), 7.549 (3.47), 7.555 (2.81), 7.558 (2.69), 7.564 (4.23), 7.572 (3.19), 7.592 (2.66), 7.597 (5.22), 7.605 (2.18), 7.610 (2.99), 7.614 (4.87), 7.618 (2.57), 7.623 (5.80), 7.626 (8.20), 7.631 (7.26), 7.637 (9.43), 7.644 (6.29), 7.647 (3.90), 7.651 (1.34), 7.673 (4.28), 7.679 (4.38), 7.696 (3.89), 7.701 (3.93), 8.327 (9.81), 8.340 (16.00), 8.346 (8.10), 8.511 (14.24).

Compound 05.03

4-[3-(2,2,2-trifluoroethoxy)pyridin-4-yl]benzene-1,2-diamine

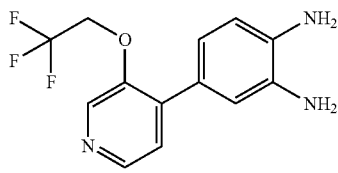 [SMILES: Nc1ccc(-c2ccncc2OCC(F)(F)F)cc1N]

To a stirred solution of 2-nitro-4-[3-(2,2,2-trifluoroethoxy)pyridin-4-yl]aniline (1.25 g, 3.99 mmol) in ethanol (20 mL) and dichloromethane (40 mL) was added palladium on carbon (10% w/w palladium) (425 mg) and the mixture was stirred at r.t. in a hydrogen atmosphere for 3 h. The mixture was filtered, and the solution was concentrated in vacuum. Aminophase-silicagel chromatography gave 0.74 g (65% yield) of the title compound.

LC-MS (Method 2): $R_t$=0.82 min; MS (ESIpos): m/z=284 [M+H]$^+$.

$^1$H-NMR (400 MHz, DMSO-d6) δ[ppm]: 4.514 (8.54), 4.758 (3.76), 4.780 (14.97), 4.785 (11.17), 4.802 (10.43), 4.824 (3.10), 5.752 (16.00), 6.545 (7.92), 6.565 (9.38), 6.753 (4.60), 6.758 (5.54), 6.773 (3.47), 6.778 (4.69), 6.802 (9.61), 6.807 (7.41), 7.262 (8.62), 7.274 (8.94), 7.525 (0.59), 7.528 (1.02), 7.533 (0.81), 7.536 (0.90), 7.544 (1.71), 7.547 (2.38), 7.549 (2.42), 7.555 (2.01), 7.558 (1.77), 7.564 (2.85), 7.566 (2.29), 7.572 (2.19), 7.574 (2.08), 7.594 (1.83), 7.598 (3.47), 7.604 (1.71), 7.607 (1.27), 7.611 (1.89), 7.615 (2.51), 7.619 (1.68), 7.624 (3.79), 7.626 (4.54), 7.631 (2.38), 7.640 (1.20), 7.644 (2.45), 7.647 (1.89), 8.240 (11.48), 8.252 (10.23), 8.392 (15.29).

233

Compound 05.04 tert-butyl 4-{[2-({6-[3-(2,2,2-trifluoroethoxy)pyridin-4-yl]-1H-benzimidazol-2-yl}amino)pyridin-4-yl]methyl}piperazine-1-carboxylate

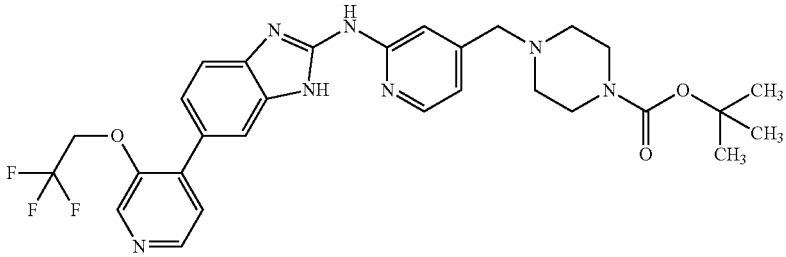 [SMILES: CC(C)(C)OC(=O)N1CCN(Cc2ccnc(Nc3nc4ccc(-c5ccncc5OCC(F)(F)F)cc4[nH]3)c2)CC1]

To a stirred solution of 1H-imidazole (43.3 mg, 635 μmol) and di-1H-imidazol-1-ylmethanethione (596 mg, 95% purity, 3.18 mmol) in dichloromethane (35 mL) was added tert-butyl 4-[(2-aminopyridin-4-yl)methyl]piperazine-1-carboxylate (929 mg, 3.18 mmol), dissolved in dichloromethane (18 mL), at 0° C. The mixture was stirred at r.t. for 14 h. 4-[3-(2,2,2-trifluoroethoxy)pyridin-4-yl]benzene-1,2-diamine (900 mg, 3.18 mmol), dissolved in dichloromethane (18 mL), was added and the mixture was stirred at r.t. for 3 h. Water was added and the mixture was extracted with dichloromethane.

The organic phase was dried (sodium sulfate) and filtered. N,N'-dipropan-2-ylcarbodiimide (1.4 mL, 9.2 mmol) was added and the mixture was stirred at r.t. for 56 h. Saturated ammonium chloride solution was added, the mixture was stirred for 30 minutes and the mixture was extracted with dichloromethane. The organic phase was dried (sodium sulfate) and the solvent was removed in vacuum. Aminophase-silicagel chromatography gave 130 mg of the title compound as a crude product, that was used without further purification.

LC-MS (Method 2): $R_t$=1.29 min; MS (ESIpos): m/z=584 [M+H]$^+$.

$^1$H-NMR (400 MHz, DMSO-d6) δ[ppm]: 1.385 (1.81), 1.389 (11.21), 1.394 (16.00), 2.322 (0.78), 2.327 (0.86), 2.332 (0.98), 2.336 (0.95), 2.346 (1.29), 2.359 (1.27), 2.371 (0.95), 2.518 (3.42), 2.523 (2.13), 3.499 (1.96), 5.760 (1.92), 8.210 (0.46), 8.212 (0.47), 8.224 (0.47), 8.258 (0.70), 8.272 (0.70), 8.513 (1.10).

Compound 05.05

N-[4-(piperazin-1-ylmethyl)pyridin-2-yl]-6-[3-(2,2,2-trifluoroethoxy)pyridin-4-yl]-1H-benzimidazol-2-amine hydrochloride

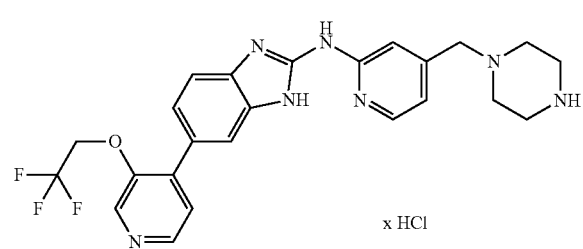 [SMILES: FC(F)(F)COc1cnccc1-c1ccc2nc(Nc3cc(CN4CCNCC4)ccn3)[nH]c2c1]
x HCl

234

Starting with tert-butyl 4-{[2-({6-[3-(2,2,2-trifluoroethoxy)pyridin-4-yl]-1H-benzimidazol-2-yl}amino)pyridin-4-yl]methyl}piperazine-1-carboxylate (130 mg, 223 μmol), Compound 05.05 was prepared analogously to the procedure for the preparation of Compound 01.05.

Yield: 159 mg of the title compound as crude product that was used for the next step without purification.

LC-MS (Method 2): $R_t$=1.02 min; MS (ESIpos): m/z=484 [M+H]$^+$.

$^1$H-NMR (400 MHz, DMSO-d6) δ[ppm]: 1.003 (0.46), 2.083 (0.49), 2.323 (1.09), 2.327 (1.51), 2.332 (1.14), 2.523 (10.22), 2.665 (1.46), 2.669 (1.82), 2.673 (1.41), 3.162 (1.94), 3.296 (1.97), 3.485 (1.19), 3.561 (2.67), 3.563 (16.00), 4.366 (1.24), 5.023 (1.82), 5.045 (4.52), 5.067 (4.35), 5.088 (1.72), 5.760 (4.81), 7.558 (3.59), 7.616 (2.50), 7.620 (2.43), 7.637 (2.79), 7.641 (3.03), 7.778 (3.71), 7.787 (2.38), 7.799 (4.71), 7.913 (4.37), 8.376 (1.36), 8.390 (1.41), 8.547 (1.77), 8.560 (1.89), 8.583 (3.71), 8.596 (3.54), 8.782 (5.97), 9.690 (1.09).

Compound 06.01

4-bromo-3-(propan-2-yloxy)pyridine

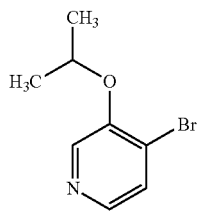

To a stirred solution of 4-bromopyridin-3-ol (5.00 g, 28.7 mmol) in DMA (150 mL) was added potassium carbonate (11.9 g, 86.2 mmol) and 2-iodopropane (4.3 mL, 43 mmol) and the mixture was stirred at 70° C. for 3 h. Water was added and the mixture was extracted with ethyl acetate. The organic phase was washed with half-saturated sodium chloride solution, dried (sodium sulfate) and the solvent was removed in vacuum. Aminophase-silicagel chromatography gave 4.41 g (71% yield) of the title compound.

LC-MS (Method 2): $R_t$=1.07 min; MS (ESIpos): m/z=216 [M+H]$^+$.

$^1$H-NMR (400 MHz, DMSO-d6) δ[ppm]: 1.307 (15.82), 1.311 (2.09), 1.322 (16.00), 1.326 (1.88), 4.803 (0.88), 4.818 (1.18), 4.833 (0.88), 7.662 (2.23), 7.674 (2.33), 8.030 (2.72), 8.042 (2.52), 8.413 (3.82).

Compound 06.02

2-nitro-4-[3-(propan-2-yloxy)pyridin-4-yl]aniline

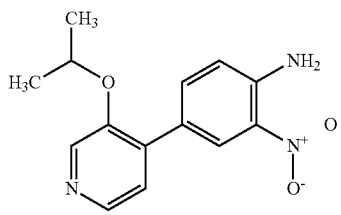

Starting with 4-bromo-3-(propan-2-yloxy)pyridine (1.78 g, 8.07 mmol) and (4-amino-3-nitrophenyl)boronic acid (2.64 g, 14.5 mmol), Compound 06.02 was prepared analogously to the procedure for the preparation of Compound 02.01.

Yield: 1.10 g (45%) of the title compound.

LC-MS (Method 2): $R_t$=1.04 min; MS (ESIpos): m/z=274 [M+H]$^+$.

$^1$H-NMR (400 MHz, DMSO-d6) δ[ppm]: 1.263 (15.64), 1.279 (16.00), 4.716 (0.97), 4.731 (1.31), 4.747 (0.97), 7.077 (2.39), 7.099 (2.51), 7.404 (2.46), 7.417 (2.51), 7.546 (0.77), 7.549 (0.76), 7.554 (0.62), 7.564 (0.86), 7.566 (0.70), 7.571 (0.69), 7.596 (1.10), 7.609 (0.93), 7.613 (1.53), 7.622 (3.99), 7.625 (4.03), 7.630 (1.72), 7.638 (0.70), 7.643 (0.88), 7.712 (1.42), 7.718 (1.37), 7.735 (1.30), 7.740 (1.27), 8.206 (3.03), 8.218 (2.82), 8.412 (3.15), 8.417 (6.33).

Compound 06.03

4-[3-(propan-2-yloxy)pyridin-4-yl]benzene-1,2-diamine

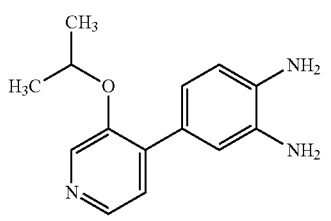 [SMILES: CC(C)Oc1cnccc1-c1ccc(N)c(N)c1]

To a stirred solution of 2-nitro-4-[3-(propan-2-yloxy)pyridin-4-yl]aniline (1.10 g, 4.02 mmol) in ethanol (16 mL) was added palladium on carbon (10% w/w palladium) (428 mg, 402 µmol) and the mixture was stirred at r.t. in a hydrogen atmosphere for 48 h. The mixture was filtered, and the solution was concentrated in vacuum. Silicagel chromatography gave 840 mg (77% yield) of the title compound.

LC-MS (Method 2): $R_t$=0.80 min; MS (ESIpos): m/z=244 [M+H]$^+$.

$^1$H-NMR (400 MHz, DMSO-d6) δ[ppm]: 1.207 (15.79), 1.222 (16.00), 2.083 (0.57), 4.492 (1.02), 4.507 (1.80), 4.516 (2.48), 4.522 (1.99), 4.713 (2.77), 5.751 (0.60), 6.542 (2.17), 6.562 (2.55), 6.744 (1.35), 6.749 (1.48), 6.764 (1.10), 6.769 (1.18), 6.872 (2.44), 6.877 (2.25), 7.198 (2.30), 7.210 (2.34), 7.545 (0.63), 7.548 (0.73), 7.553 (0.64), 7.562 (0.72), 7.565 (0.70), 7.570 (0.61), 7.572 (0.57), 7.598 (1.01), 7.603 (0.58), 7.615 (0.62), 7.625 (1.28), 7.630 (0.72), 7.646 (0.70), 8.127 (3.11), 8.139 (3.13), 8.270 (4.43).

Compound 06.04 tert-butyl 4-{[2-({6-[3-(propan-2-yloxy)pyridin-4-yl]-1H-benzimidazol-2-yl}amino)pyridin-4-yl]methyl}piperazine-1-carboxylate

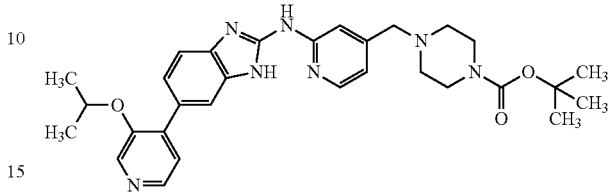

To a stirred solution of 1H-imidazole (39.6 mg, 582 µmol) and di-1H-imidazol-1-ylmethanethione (692 mg, 90% purity, 3.49 mmol) in dichloromethane (20 mL) was added tert-butyl 4-[(2-aminopyridin-4-yl)methyl]piperazine-1-carboxylate (851 mg, 2.91 mmol), dissolved in dichloromethane (20 mL), at 0° C. The mixture was stirred at r.t. for 14 h. 4-[3-(propan-2-yloxy)pyridin-4-yl]benzene-1,2-diamine (840 mg, 97% purity, 3.35 mmol), dissolved in dichloromethane (15 mL), was added and the mixture was stirred at r.t. for 2 h. Water was added and the mixture was extracted with dichloromethane The organic phase was dried (sodium sulfate) and filtered. N,N'-dipropan-2-ylcarbodiimide (620 µl, 4.0 mmol) was added. The mixture was stirred at r.t. for 14 h. Further N,N'-dipropan-2-ylcarbodiimide (230 µl, 1.5 mmol) was added and the mixture was stirred at r.t. for 14 h. Saturated ammonium chloride solution was added, the mixture was stirred for 30 minutes and was extracted with dichloromethane. Aminophase-silicagel chromatography gave 240 mg of the title compound as a crude product, that was used without further purification.

LC-MS (Method 2): $R_t$=1.32 min; MS (ESIpos): m/z=544 [M+H]$^+$.

$^1$H-NMR (400 MHz, DMSO-d6) δ [ppm]: 1.054 (1.16), 1.227 (2.03), 1.241 (2.01), 1.391 (7.80), 1.396 (16.00), 2.349 (1.18), 2.362 (1.33), 2.374 (0.96), 3.349 (1.19), 3.501 (1.96), 8.222 (1.22), 8.234 (0.98), 8.396 (1.66).

Compound 06.05

N-[4-(piperazin-1-ylmethyl)pyridin-2-yl]-6-[3-(propan-2-yloxy)pyridin-4-yl]-1H-benzimidazol-2-amine hydrochloride

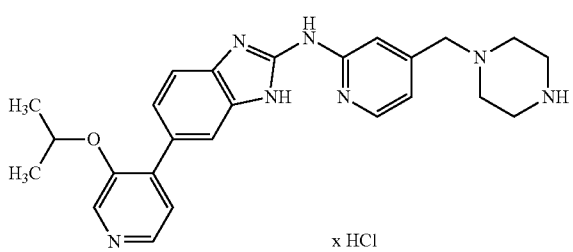 [SMILES: CC(C)Oc1cnccc1-c1ccc2nc(Nc3cc(CN4CCNCC4)ccn3)[nH]c2c1]

Starting with tert-butyl 4-{[2-({6-[3-(propan-2-yloxy)pyridin-4-yl]-1H-benzimidazol-2-yl}amino)pyridin-4-yl]methyl}piperazine-1-carboxylate (240 mg, 441 µmol), Compound 06.05 was prepared analogously to the procedure for the preparation of Compound 01.05.

Yield: 340 mg of the title compound as crude product that was used for the next step without purification.

LC-MS (Method 2): $R_t$=1.03 min; MS (ESIpos): m/z=444 [M+H]$^+$.

Compound 07.01

2-methyl-5-{[2-(trimethylsilyl)ethoxy]methoxy}pyridine

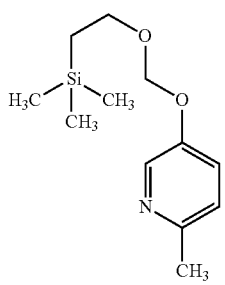 [SMILES: Cc1ccc(OCOCC[Si](C)(C)C)cn1]

To a stirred suspension of 6-methylpyridin-3-ol (15.7 g, 144 mmol) in dichloromethane (130 mL), was added N,N-diisopropylethylamine (30 mL, 170 mmol), and [2-(chloromethoxy)ethyl](trimethyl)silane (26 mL, 150 mmol) and the mixture was stirred at r.t. for 19 h. The mixture was washed with water and the organic phase was dried (magnesium sulfate), filtered and the solvent was removed in vacuum. Silicagel chromatography gave 32.8 g (95% yield) of the title compound.

LC-MS (Method 5): $R_t$=3.26 min; MS (ESIpos): m/z=240 [M+H]$^+$.

$^1$H-NMR (400 MHz, DMSO-d6) δ[ppm]: −0.042 (2.31), −0.025 (2.20), 0.000 (1.67), 0.858 (2.60), 0.879 (2.81), 0.881 (2.00), 0.899 (2.80), 2.390 (16.00), 2.498 (0.68), 2.502 (0.97), 2.506 (0.66), 3.315 (6.15), 3.681 (2.75), 3.699 (2.28), 3.701 (3.30), 3.703 (2.44), 3.721 (2.80), 5.237 (13.03), 7.155 (1.62), 7.176 (2.32), 7.322 (1.60), 7.329 (1.74), 7.344 (1.25), 7.350 (1.42), 8.184 (1.85), 8.191 (2.16).

Compound 07.02

4-iodo-2-methyl-5-{[2-(trimethylsiyl)ethoxy]methoxy}pyridine

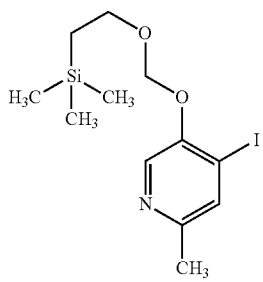 [SMILES: Cc1cc(I)c(OCOCC[Si](C)(C)C)cn1]

To a stirred solution of 2-methyl-5-{[2-(trimethylsilyl)ethoxy]methoxy}pyridine (22.5 g, 94.0 mmol) in diethyl ether (360 mL) was added a solution of tert-butyllithium in pentane (55 mL, 1.9 M, 100 mmol) at −70° C. The solution was stirred at −78° C. for 5 minutes. Iodine (24.3 g, 95.7 mmol), dissolved in THF (50 mL) was added at −70° C., and the mixture was stirred at −78° C. for 0.5 h and then allowed to warm up to room temperature. An aqueous solution of disodium sulfurothioate (c=1M; 300 mL) was added and the reaction mixture was stirred for 5 minutes. The phases were separated and the aqueous phase was extracted with diethyl ether. The combined organic phases were dried (magnesium sulfate), filtered and the solvent was removed in vacuum. The residue was crystallized from pentane to give 24.8 g (72% yield) of the title compound.

Compound 07.03

4-iodo-6-methylpyridin-3-ol

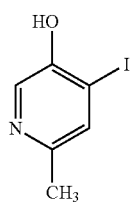

To a stirred solution of 4-iodo-2-methyl-5-{[2-(trimethylsilyl)ethoxy]methoxy}pyridine (24.8 g, 67.9 mmol) in dioxane (120 mL) was added aqueous hydrochloric acid (15 mL, 37%, 180 mmol). The mixture was stirred at 60° C. for 0.5 h. Sodium bicarbonate (45 g) was added and the mixture was stirred for 30 minutes. THF (300 mL) was added, the mixture was filtered through sodium sulfate and the solvent was removed in vacuum. Diethyl ether was added to the residue, solids were removed by filtration and the solvent was removed in vacuum to give 15.1 g (95% yield) of the title compound.

LC-MS (Method 5): $R_t$=0.38 min; MS (ESIpos): m/z=236 [M+H]$^+$.

Compound 07.04

4-iodo-5-methoxy-2-methylpyridine

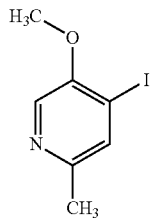

To a stirred solution of 4-iodo-6-methylpyridin-3-ol (4.80 g, 20.4 mmol) in dichloromethane (60 mL) and methanol (30 mL) was added (diazomethyl)(trimethyl)silane (12 mL, 2.0 M solution in hexane, 24 mmol). The mixture was stirred at r.t. for 1 h. The solvent was removed in vacuum. Silicagel chromatography gave 3.5 g (69% yield) of the title compound.

LC-MS (Method 5): $R_t$=0.90 min; MS (ESIpos): m/z=250 M+H]$^+$.

¹H-NMR (400 MHz, DMSO-d6) δ[ppm]: 2.357 (14.33), 2.493 (0.60), 2.499 (0.80), 2.503 (0.59), 3.310 (3.81), 3.891 (16.00), 7.697 (3.86), 8.070 (4.16).

Compound 07.05 tert-butyl 4-[(2-{[6-(5-methoxy-2-methylpyridin-4-yl)-1H-benzimidazol-2-yl]amino}pyridin-4-yl)methyl]piperazine-1-carboxylate

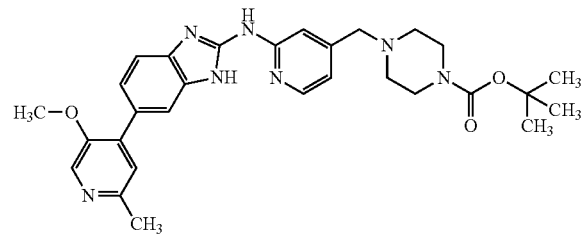 [SMILES: COc1cnc(C)cc1-c1ccc2nc(Nc3cc(CN4CCN(C(=O)OC(C)(C)C)CC4)ccn3)[nH]c2c1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (1.10 g, 2.06 mmol) and 4-iodo-5-methoxy-2-methylpyridine (600 mg, 2.41 mmol) in dioxane (10 mL) and water (2.0 mL) was added sodium carbonate (660 mg, 6.23 mmol) and Pd(dppf)C₂·CH₂Cl₂ (250 mg, 306 μmol). The mixture was heated to reflux for 24 h. Chloroform was added, the mixture was dried (magnesium sulfate), filtered and the solvent was removed in vacuum. Silicagel chromatography gave 915 mg (84% yield) of the title compound.

LC-MS (Method 5): $R_t$=2.56 min; MS (ESIpos): m/z=530 [M+H]⁺.

¹H-NMR (400 MHz, DMSO-d6) δ [ppm]: 1.142 (1.07), 1.394 (16.00), 1.909 (0.53), 2.081 (2.48), 2.115 (0.47), 2.354 (0.96), 2.367 (1.45), 2.379 (1.07), 2.451 (4.85), 2.495 (0.89), 2.500 (1.23), 2.505 (0.94), 3.340 (1.11), 3.351 (1.50), 3.364 (1.12), 3.503 (1.71), 3.853 (5.50), 6.915 (0.54), 6.918 (0.56), 6.928 (0.56), 6.931 (0.57), 7.196 (0.97), 7.233 (1.62), 7.242 (0.59), 7.246 (0.56), 7.263 (0.59), 7.267 (0.62), 7.444 (0.62), 7.465 (0.53), 7.661 (0.65), 8.254 (0.85), 8.270 (2.02).

Compound 07.06

6-(5-methoxy-2-methylpyridin-4-yl)-N-[4-(piperazin-1-ylmethyl)pyridin-2-yl]-1H-benzimidazol-2-amine

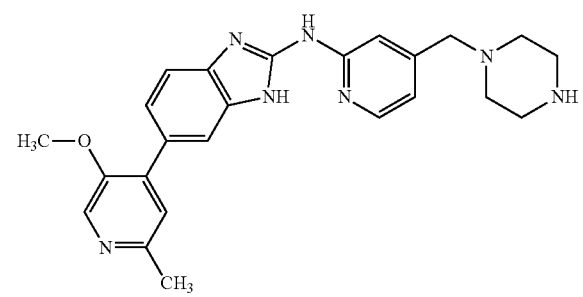 [SMILES: COc1cnc(C)cc1-c1ccc2nc(Nc3cc(CN4CCNCC4)ccn3)[nH]c2c1]

To a stirred solution tert-butyl 4-[(2-{[6-(5-methoxy-2-methylpyridin-4-yl)-1H-benzimidazol-2-yl]amino}pyridin-4-yl)methyl]piperazine-1-carboxylate (900 mg, 1.70 mmol) in dioxane (8 mL) was added aqueous hydrochloric acid (1.4 mL, 6.0 M, 8.4 mmol). The mixture was stirred at room temperature for 2 h. Sodium bicarbonate (5.0 g) was added and the mixture was stirred for 30 minutes. THF (50 mL) was added, the mixture was filtered through magnesium sulfate and the solvent was removed in vacuum. Diethyl ether was added to the residue, solids were removed by filtration and the solvent was removed in vacuum to give 695 mg (95% yield) of the title compound.

LC-MS (Method 5): $R_t$=3.30 min; MS (ESIpos): m/z=535 [M+H]⁺.

¹H-NMR (400 MHz, DMSO-d6) δ [ppm]: 1.062 (4.84), 1.079 (9.70), 1.097 (4.89), 1.215 (1.04), 1.730 (2.43), 1.737 (3.18), 1.746 (6.66), 1.754 (3.18), 1.763 (2.43), 2.442 (15.71), 2.495 (5.78), 2.499 (7.44), 2.503 (6.92), 2.508 (5.84), 2.517 (5.16), 2.938 (4.94), 3.163 (1.92), 3.344 (2.08), 3.362 (5.49), 3.379 (5.47), 3.397 (2.11), 3.505 (5.84), 3.573 (3.33), 3.589 (6.93), 3.596 (3.22), 3.606 (2.92), 3.845 (16.00), 6.890 (0.40), 6.905 (2.05), 6.919 (2.00), 7.219 (5.34), 7.249 (4.53), 7.439 (0.74), 7.648 (0.44), 8.243 (2.62), 8.259 (6.56).

Compound 08.01

{4-[(2-aminopyridin-4-yl)methyl]piperazin-1-yl}(cyclopropyl)methanone

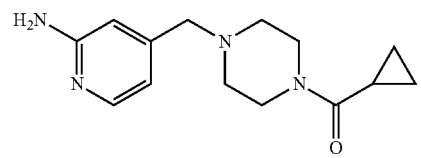 [SMILES: Nc1cc(CN2CCN(C(=O)C3CC3)CC2)ccn1]

To a stirred suspension of 4-(bromomethyl)pyridin-2-amine hydrobromide (10.0 g, 37.3 mmol) in acetonitrile (75 mL) was added potassium carbonate (16.0 g, 116 mmol) and cyclopropyl(piperazin-1-yl)methanone (6.10 g, 39.6 mmol) (CAS-RN 59878-57-8) The mixture was stirred at 75° C. for 2 h. Direct silicagel chromatography of the reaction mixture gave a solid which was triturated with ether to give 7.20 g (74% yield) of the title compound.

LC-MS (Method 5): $R_t$=0.14 min; MS (ESIpos): m/z=261 [M+H]⁺.

¹H-NMR (400 MHz, DMSO-d6) δ [ppm]: 0.655 (0.49), 0.667 (1.47), 0.674 (3.50), 0.680 (2.08), 0.687 (1.70), 0.694 (4.26), 0.699 (3.30), 0.705 (3.66), 0.712 (3.58), 0.717 (4.34), 0.724 (1.98), 0.737 (0.54), 1.905 (0.42), 1.917 (0.87), 1.924 (0.93), 1.928 (0.69), 1.936 (1.55), 1.942 (0.73), 1.948 (0.90), 1.956 (0.83), 2.304 (1.43), 2.376 (1.45), 2.490 (0.57), 2.495 (1.18), 2.500 (1.61), 2.504 (1.18), 2.509 (0.57), 3.332 (16.00), 3.355 (0.68), 3.462 (1.29), 3.599 (0.53), 3.615 (0.43), 3.661 (1.28), 5.805 (4.16), 6.408 (3.74), 6.428 (2.21), 6.431 (1.88), 6.441 (2.19), 6.444 (1.89), 7.815 (2.34), 7.828 (2.29).

Compound 08.02 cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone

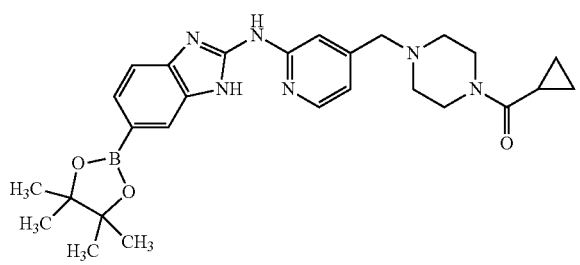 [SMILES: CC1(C)OB(c2ccc3nc(Nc4cc(CN5CCN(C(=O)C6CC6)CC5)ccn4)[nH]c3c2)OC1(C)C]

To a stirred solution of di-1H-imidazol-1-ylmethanethione (5.20 g, 29.2 mmol) and imidazole (400 mg, 5.88 mmol) in dichloromethane (50 mL) was added {4-[(2-aminopyridin-4-yl)methyl]piperazin-1-yl}(cyclopropyl)methanone (7.20 g, 27.7 mmol), dissolved in dichloromethane (50 mL) at 0° C. The mixture was stirred at 0° C. for 4 h. 4-(4,4,5,5-tetramethyl-1,3,2-dioxaborolan-2-yl)benzene-1,2-diamine (6.50 g, 27.8 mmol) dissolved in dichloromethane (50 mL) was added and the mixture was stirred at r.t. for 18 h. Water was added and the mixture was extracted with chloroform.

The organic phase was dried (magnesium sulfate) and filtered. N,N'-dipropan-2-ylcarbodiimide (6.0 mL, 39 mmol) was added and the mixture was stirred at 40° C. for 8 h. Direct silicagel chromatography of the crude mixture gave 5.25 g (38% yield) of the title compound.

LC-MS (Method 5): $R_t$=2.94 min; MS (ESIpos): m/z=503 [M+H]$^+$.

$^1$H-NMR (400 MHz, DMSO-d6) δ[ppm]: 0.666 (0.49), 0.673 (0.85), 0.678 (0.68), 0.686 (0.56), 0.694 (0.98), 0.706 (0.71), 0.711 (0.96), 0.718 (1.06), 0.722 (1.13), 0.730 (0.61), 1.298 (16.00), 1.931 (0.44), 2.360 (0.56), 2.421 (0.56), 2.495 (0.71), 2.499 (0.84), 2.503 (0.58), 3.334 (8.11), 3.501 (2.68), 6.916 (0.70), 6.929 (0.67), 7.185 (0.49), 7.379 (0.50), 8.244 (0.93), 8.257 (0.88).

Compound 08.03

2-(hydroxymethyl)-5-methoxy-4H-pyran-4-one

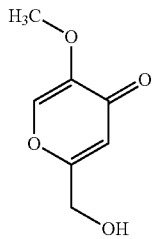

To a solution of potassium hydroxide (4.50 g, 80.2 mmol) in 40 mL water was added 5-hydroxy-2-(hydroxymethyl)-4H-pyran-4-one (10.0 g, 70.4 mmol, CAS-RN 6269-25-6) and the mixture was stirred at r.t. until a solution had formed.

Dimethyl sulfate (6.7 mL, 71 mmol) was added slowly, and the mixture was stirred at 23° C. for 1 h and then at 0° C. for 1 h. A solid precipitated and was collected by filtration, washed with water, and dried to give 7.35 g (67% yield) of the title compound.

LC-MS (Method 5): $R_t$=0.25 min; MS (ESIpos): m/z=157 [M+H]$^+$.

$^1$H-NMR (400 MHz, DMSO-d6) δ[ppm]: 2.499 (0.58), 2.503 (0.45), 3.313 (2.22), 3.644 (16.00), 4.285 (2.03), 4.298 (2.05), 5.657 (0.84), 6.285 (1.58), 6.287 (3.03), 6.289 (1.50), 8.070 (5.73).

Compound 08.04

2-(hydroxymethyl)-5-methoxypyridin-4-ol

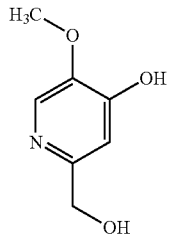

To a stirred mixture of 2-(hydroxymethyl)-5-methoxy-4H-pyran-4-one (6.68 g, 42.8 mmol) in methanol (10 mL) was added aqueous ammonium hydroxide solution (20 mL, c=25%, 130 mmol). The mixture was heated to 100° C. in a sealed tube for 6 h. The solvent was removed in vacuum. Silicagel chromatography gave 4.97 g (75% yield) of the title compound.

LC-MS (Method 5): $R_t$=0.14 min; MS (ESIpos): m/z=156 [M+H]$^+$.

$^1$H-NMR (400 MHz, DMSO-d6) δ[ppm]: 2.490 (0.83), 2.495 (1.96), 2.499 (2.75), 2.503 (1.80), 2.509 (0.83), 3.320 (16.00), 3.643 (1.52), 4.330 (2.40), 4.343 (2.35).

Compound 08.05

4-hydroxy-5-methoxypyridine-2-carboxylic acid

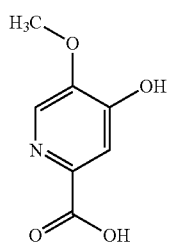

Concentrated nitric acid (25 mL, c=65%) and fuming nitric acid (5.0 mL, c=90%) were added to 2-(hydroxymethyl)-5-methoxypyridin-4-ol (4.97 g, 32.0 mmol). The mixture was stirred at r.t. for 1 day, then poured into icewater. The precipitate was collected by filtration and the dissolved in diluted sodium hydroxide solution. Hydrochloric acid (c=2N) was added until pH4 was reached. A solid precipitated and was collected by filtration to give 2.90 g of the title compound.

LC-MS (Method 5): $R_t$=0.17 min; MS (ESIpos): m/z=170 [M+H]$^+$.

Compound 08.06

4-bromo-5-methoxy-N,N-dimethylpyridine-2-carboxamide

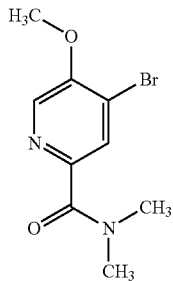

To a solution of 4-hydroxy-5-methoxypyridine-2-carboxylic acid (1.00 g, 5.91 mmol) in DMF (20 mL, 260 mmol), was slowly added phosphorus tribromide (2.0 mL, 21 mmol) with water bath cooling. The mixture was stirred at 23° C. for 1 h, and then slowly added to an aqueous solution of N-methylmethanamine-(20 mL, c=40%, 160 mmol) with water bath cooling. The mixture was stirred at 23° C. for 1 h. A saturated sodium chloride solution was added and the mixture was extracted with ethyl acetate, dried (magnesium sulfate) and the solvent was removed in vacuum. The residue was crystallized from cyclohexane to give 535 mg (35% yield) of the title compound.

LC-MS (Method 5): $R_t$=2.70 min; MS (ESIpos): m/z=259 [M+H]$^+$.

$^1$H-NMR (400 MHz, DMSO-d6) δ [ppm]: 2.495 (0.70), 2.500 (0.96), 2.505 (0.71), 2.989 (11.95), 2.996 (12.87), 3.314 (9.25), 4.023 (16.00), 4.028 (1.69), 7.831 (5.65), 8.371 (4.82).

Compound 09.01

5-ethoxy-4-iodo-2-methylpyridine

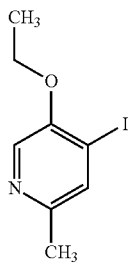

To a stirred solution of 4-iodo-6-methylpyridin-3-ol (4.00 g, 17.0 mmol) in DMF (10 mL) was added potassium carbonate (5.00 g, 36.2 mmol) and iodoethane (2.0 mL, 25 mmol). The mixture was stirred at r.t. for 3 h. Water was added and the mixture was extracted with ethyl acetate. The organic phase was washed with half-saturated sodium chloride solution, dried (magnesium sulfate) and the solvent was removed in vacuum. Silicagel chromatography gave 2.54 g (57% yield) of the title compound.

LC-MS (Method 5): $R_t$=2.38 min; MS (ESIpos): m/z=264 [M+H]$^+$.

$^1$H-NMR (400 MHz, DMSO-d6) δ [ppm]: 1.337 (4.18), 1.355 (9.04), 1.373 (4.31), 2.352 (16.00), 2.495 (0.65), 2.499 (0.91), 2.503 (0.65), 3.310 (5.16), 4.126 (1.41), 4.144 (4.20), 4.162 (3.90), 4.178 (1.24), 7.694 (4.21), 8.050 (4.86).

Compound 09.02 tert-butyl 4-[(2-{[6-(5-ethoxy-2-methylpyridin-4-yl)-1H-benzimidazol-2-yl]amino}pyridin-4-yl)methyl]piperazine-1-carboxylate

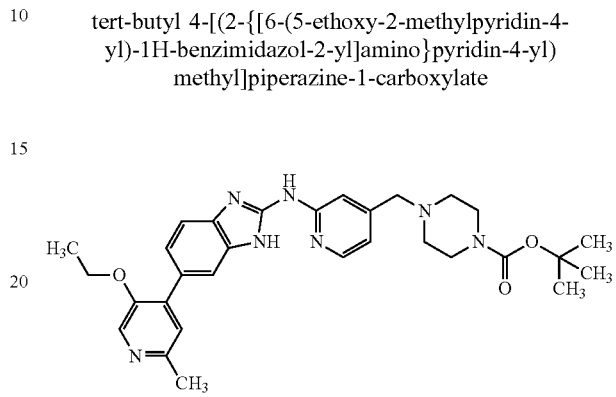

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (1.10 g, 2.06 mmol) and 5-ethoxy-4-iodo-2-methylpyridine (700 mg, 2.66 mmol) in dioxane (10 mL) and water (2.0 mL) was added sodium carbonate (660 mg, 6.23 mmol) and Pd(dppf)Cl$_2$.CH$_2$Cl$_2$ (250 mg, 306 μmol). The mixture was heated to reflux for 24 h. Chloroform was added, the mixture was dried (magnesium sulfate), filtered and the solvent was removed in vacuum. Silicagel chromatography gave 790 mg (70% yield) of the title compound.

LC-MS (Method 5): $R_t$=2.68 min; MS (ESIpos): m/z=544 [M+H]$^+$.

$^1$H-NMR (400 MHz, DMSO-d6) δ [ppm]: 1.072 (0.43), 1.141 (2.99), 1.155 (0.73), 1.264 (1.16), 1.281 (2.53), 1.299 (1.27), 1.391 (16.00), 2.079 (1.77), 2.113 (1.18), 2.342 (1.05), 2.354 (1.52), 2.366 (1.07), 2.441 (4.84), 2.480 (0.75), 2.495 (0.66), 2.499 (0.90), 2.503 (0.63), 3.334 (2.49), 3.344 (2.36), 3.488 (1.91), 4.069 (0.45), 4.087 (1.36), 4.103 (1.35), 6.904 (0.58), 6.917 (0.58), 7.194 (0.99), 7.229 (1.49), 8.241 (1.75), 8.250 (0.94), 8.264 (0.85).

Compound 09.03

6-(5-ethoxy-2-methylpyridin-4-yl)-N-[4-(piperazin-1-ylmethyl)pyridin-2-yl]-1H-benzimidazol-2-amine

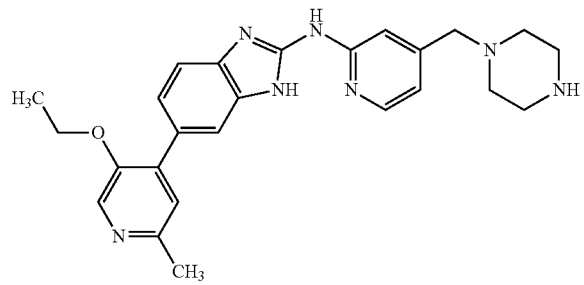 [SMILES: CCOc1cnc(C)cc1-c1ccc2nc(Nc3cc(CN4CCNCC4)ccn3)[nH]c2c1]

Starting with tert-butyl 4-[(2-{[6-(5-ethoxy-2-methylpyridin-4-yl)-1H-benzimidazol-2-yl]amino}pyridin-4-yl)methyl]piperazine-1-carboxylate (780 mg, 1.43 mmol), Compound 09.03 was prepared analogously to the procedure for the preparation of Example 07.06 Yield: 500 mg (79% of the title compound.

LC-MS (Method 5): R$_t$=1.99 min; MS (ESIpos): m/z=444 [M+H]$^+$.

$^1$H-NMR (400 MHz, DMSO-d6) δ[ppm]: 1.066 (0.71), 1.083 (1.41), 1.101 (0.74), 1.265 (3.53), 1.283 (7.33), 1.300 (3.82), 2.343 (4.05), 2.442 (16.00), 2.491 (1.40), 2.495 (2.68), 2.500 (3.55), 2.504 (2.68), 2.509 (1.41), 2.754 (4.84), 3.348 (3.72), 3.366 (3.58), 3.383 (2.82), 3.401 (1.80), 3.434 (7.34), 4.070 (1.38), 4.087 (4.27), 4.105 (4.28), 4.122 (1.41), 6.897 (1.89), 6.910 (1.95), 7.184 (3.19), 7.229 (4.01), 7.281 (1.14), 7.301 (1.42), 7.445 (0.55), 8.242 (7.80), 8.256 (2.66).

Compound 09.04

Cyclopropylacetyl Chloride

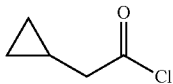

To a stirred solution of cyclopropylacetic acid (930 µl, 10 mmol) in dichloromethane (4 mL) was added ethanedioyl dichloride (500 µl, 5.7 mmol) and the mixture was stirred at r.t. for 4 h. The mixture was carefully concentrated in vacuum to give 1.00 g of the title compound as crude product that was used without purification.

Compound 10.01

4-iodo-2-methoxy-3-methylpyridine

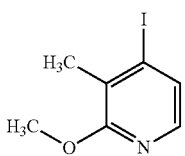

To a stirred solution of 2-fluoro-4-iodo-3-methylpyridine (250 mg, 1.05 mmol) in methanol (100 mL) was added lithium methoxide (1.00 g, 26.3 mmol), and the mixture was heated to reflux for 30 minutes. The reaction mixture was cooled down and water was added. A solid precipitated and was collected by filtration, washed with water, and dried to give 260 mg (99% yield) of the title compound.

LC-MS (Method 5): R$_t$=3.78 min; MS (ESIpos): m/z=250 [M+H]$^+$.

$^1$H-NMR (400 MHz, DMSO-d6) δ[ppm]: 2.253 (11.45), 2.493 (0.56), 2.499 (0.76), 2.503 (0.56), 3.319 (15.44), 3.851 (16.00), 7.391 (1.89), 7.404 (2.16), 7.645 (1.63), 7.658 (1.48).

Compound 11.01

4-iodo-3-methyl-2-(propan-2-yloxy)pyridine

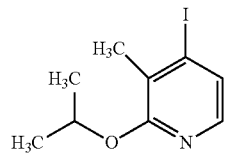

Sodium hydride (500 mg, 60% in oil, 12.5 mmol) was carefully added to propan-2-ol (10 mL, 130 mmol). After stirring for 15 minutes, 2-fluoro-4-iodo-3-methylpyridine (250 mg, 1.05 mmol) was added, and the mixture was stirred at reflux for 30 minutes. The reaction mixture was cooled down and water (50 mL) was added. The mixture was extracted with diethyl ether, the organic phase was dried (sodium sulfate), filtered and the solvent was removed in vacuum to give 210 mg of the title compound as a crude product that was used without purification.

LC-MS (Method 5): R$_t$=0.32 min; MS (ESIpos): m/z=186 [M+H]$^+$.

$^1$H-NMR (400 MHz, DMSO-d6) δ[ppm]: 1.089 (0.80), 1.273 (0.76), 1.278 (7.25), 1.295 (7.12), 1.354 (0.43), 2.235 (5.53), 2.490 (0.85), 2.495 (1.64), 2.499 (2.12), 2.504 (1.45), 2.509 (0.68), 3.285 (1.16), 3.309 (16.00), 5.200 (0.48), 5.215 (0.64), 5.231 (0.47), 7.356 (1.00), 7.369 (1.11), 7.624 (0.72), 7.639 (0.71).

Compound 12.01

6-(6-methylpyridin-2-yl)-N-[4-(piperazin-1-ylmethyl)pyridin-2-yl]-1H-benzimidazol-2-amine hydrochloride

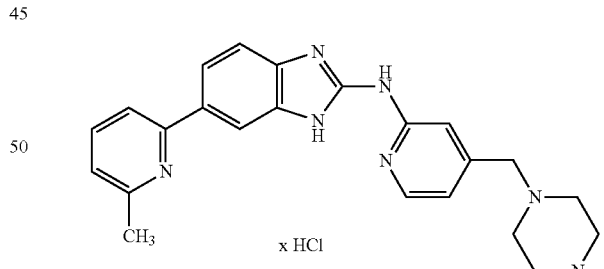

Starting with tert-butyl 4-[(2-{[6-(6-methylpyridin-2-yl)-1H-benzimidazol-2-yl]amino}pyridin-4-yl)methyl]piperazine-1-carboxylate (380 mg, 761 µmol), Compound 12.01 was prepared analogously to the procedure for the preparation of Compound 01.05.

Yield: 350 mg of the title compound as crude product that was used for the next step without purification.

LC-MS (Method 2): R$_t$=1.03 min; MS (ESIpos): m/z=400 [M+H]$^+$.

Compound 13.01

4-(6-methoxypyridin-3-yl)benzene-1,2-diamine

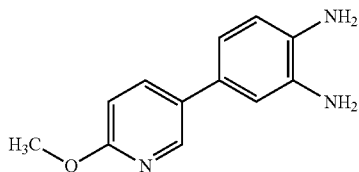 [SMILES: COc1ccc(-c2ccc(N)c(N)c2)cn1]

To a stirred solution of 5-bromo-2-methoxypyridine (350 µl, 95% purity, 2.5 mmol) in 1-propanol (12 mL) was added a potassium carbonate solution (3.8 mL, 2.0 M, 7.6 mmol), 4-(4,4,5,5-tetramethyl-1,3,2-dioxaborolan-2-yl)benzene-1,2-diamine (660 mg, 90% purity, 2.54 mmol) triphenylphosphine (66.6 mg, 254 µmol) and PdCl$_2$(PPh$_3$)$_2$ (178 mg, 254 µmol) The mixture was heated to 120° C. in a sealed tube for 14 h. The mixture was filtered and the solvent was removed in vacuum. Aminophase-silicagel chromatography gave 500 mg (82% yield) of the title compound.

LC-MS (Method 1): R$_t$=0.61 min; MS (ESIpos): m/z=216 [M+H]$^+$.

$^1$H-NMR (400 MHz, DMSO-d6) δ[ppm]: 1.067 (4.34), 1.154 (0.74), 1.172 (1.54), 1.189 (0.76), 1.988 (2.57), 3.337 (16.00), 3.908 (2.00), 3.943 (0.72), 4.017 (0.59), 4.035 (0.59), 4.567 (1.80), 4.602 (2.04), 5.760 (2.04), 6.555 (3.35), 6.575 (4.68), 6.656 (2.41), 6.661 (2.63), 6.675 (1.69), 6.680 (1.82), 6.775 (4.27), 6.780 (3.75), 6.797 (3.17), 6.799 (2.96), 6.818 (3.24), 6.820 (2.94), 7.528 (0.77), 7.536 (0.79), 7.544 (1.44), 7.547 (2.01), 7.549 (1.90), 7.552 (1.40), 7.555 (1.73), 7.558 (1.65), 7.564 (2.49), 7.566 (1.92), 7.572 (1.83), 7.574 (1.71), 7.592 (1.50), 7.596 (2.56), 7.605 (1.07), 7.610 (1.42), 7.614 (2.27), 7.617 (1.25), 7.622 (2.84), 7.626 (3.62), 7.631 (1.69), 7.639 (1.24), 7.643 (1.96), 7.646 (1.49), 7.762 (2.51), 7.769 (2.45), 7.784 (2.32), 7.790 (2.37), 8.249 (2.86), 8.251 (3.09), 8.256 (3.04).

Compound 13.02

6-(6-methoxypyridin-3-yl)-N-[4-(piperazin-1-ylmethyl)pyridin-2-yl]-1H-benzimidazol-2-amine hydrochloride

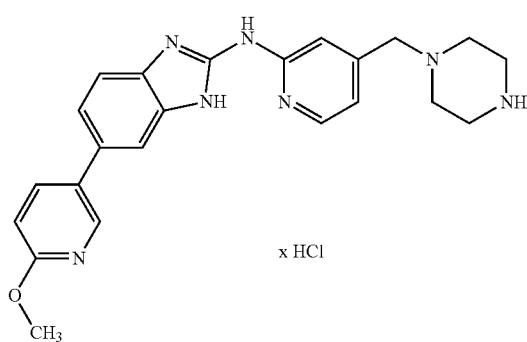 [SMILES: COc1ccc(-c2ccc3nc(Nc4cc(CN5CCNCC5)ccn4)[nH]c3c2)cn1]

Starting with tert-butyl 4-[(2-{[6-(6-methoxypyridin-3-yl)-1H-benzimidazol-2-yl]amino}pyridin-4-yl)methyl]piperazine-1-carboxylate (110 mg, 213 µmol), Compound 13.02 was prepared analogously to the procedure for the preparation of Compound 01.05.

Yield: 110 mg of the title compound as crude product that was used for the next step without purification.

LC-MS (Method 2): R$_t$=1.05 min; MS (ESIpos): m/z=416 [M+H]$^+$.

$^1$H-NMR (400 MHz, DMSO-d6) δ[ppm]: 3.022 (5.63), 3.358 (1.08), 3.500 (0.69), 3.527 (16.00), 3.878 (9.50), 4.438 (0.98), 6.495 (1.32), 6.520 (1.35), 6.922 (0.98), 6.924 (1.01), 6.944 (1.04), 7.508 (0.90), 7.512 (1.01), 7.523 (1.65), 7.530 (2.24), 7.534 (1.97), 7.599 (1.14), 7.603 (0.93), 7.619 (0.87), 7.624 (0.91), 7.649 (1.47), 7.670 (1.07), 7.709 (1.98), 7.713 (1.43), 7.730 (2.31), 7.735 (1.66), 7.814 (0.90), 7.821 (0.81), 7.838 (1.86), 7.845 (0.92), 7.978 (0.78), 7.984 (0.77), 7.999 (0.69), 8.006 (0.73), 8.450 (1.07), 8.452 (1.04), 8.456 (1.02), 8.458 (1.04), 8.511 (1.03), 8.523 (1.45), 8.535 (0.77).

Compound 14.01 tert-butyl 4-[(2-{[6-(4-methoxypyridin-3-yl)-1H-benzimidazol-2-yl]amino}pyridin-4-yl)methyl]piperazine-1-carboxylate

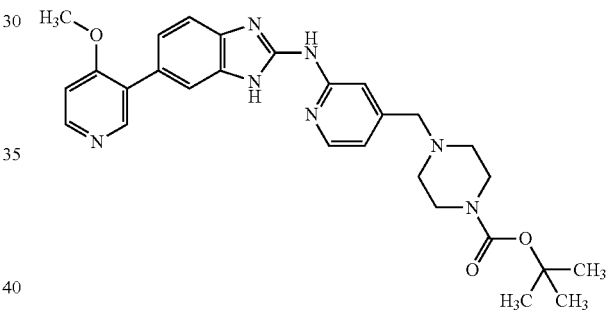

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (400 mg, 748 µmol) and 3-bromo-4-methoxypyridine (169 mg, 898 µmol) in dioxane (4 mL) and water (0.7 mL) was added sodium carbonate (238 mg, 2.25 mmol) and Pd(dppf)Cl$_2$·CH$_2$Cl$_2$ (91.7 mg, 112 µmol). The mixture was heated to reflux for 24 h. Further 3-bromo-4-methoxypyridine (70 mg) was added and the mixture was heated to reflux for 24 h. Dichloromethane was added, the mixture was dried (magnesium sulfate), filtered and the solvent was removed in vacuum. Silicagel chromatography gave 16.0 mg (4% yield) of the title compound as a crude product that was used without further purification.

LC-MS (Method 2): R$_t$=1.20 min; MS (ESIpos): m/z=516 [M+H]$^+$.

$^1$H-NMR (400 MHz, CHLOROFORM-d) δ [ppm]: 1.261 (0.74), 1.468 (16.00), 2.330 (1.89), 3.394 (1.99), 3.444 (1.92), 3.927 (1.16), 6.927 (0.58), 6.941 (0.64), 6.953 (0.79), 6.965 (0.70), 7.081 (1.09), 8.283 (0.78), 8.296 (0.74), 8.483 (0.57), 8.497 (0.56), 8.540 (1.04).

Compound 14.02

6-(4-methoxypyridin-3-yl)-N-[4-(piperazin-1-ylmethyl)pyridin-2-yl]-1H-benzimidazol-2-amine hydrochloride

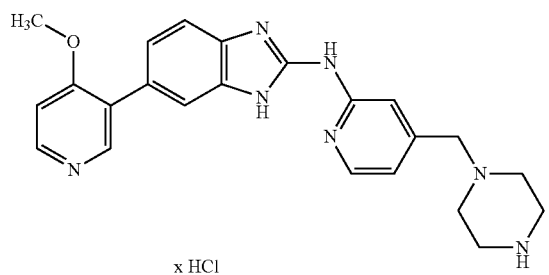 [SMILES: COc1ccncc1-c1ccc2nc(Nc3cc(CN4CCNCC4)ccn3)[nH]c2c1]

x HCl

Starting with tert-butyl 4-[(2-{[6-(4-methoxypyridin-3-yl)-1H-benzimidazol-2-yl]amino}pyridin-4-yl)methyl]piperazine-1-carboxylate (173 mg, 336 µmol), Compound 14.02 was prepared analogously to the procedure for the preparation of Compound 01.05.

Yield: 203 mg of the title compound as crude product that was used for the next step without purification.

LC-MS (Method 2): $R_t$=0.87 min; MS (ESIpos): m/z=416 [M+H]$^+$.

Compound 15.01 tert-butyl 4-[(2-{[6-(2-methoxypyridin-3-yl)-1H-benzimidazol-2-yl]amino}pyridin-4-yl)methyl]piperazine-1-carboxylate

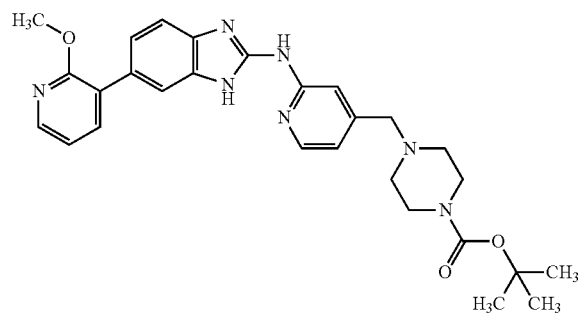 [SMILES: COc1ncccc1-c1ccc2nc(Nc3cc(CN4CCN(C(=O)OC(C)(C)C)CC4)ccn3)[nH]c2c1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 µmol) and 3-iodo-2-methoxypyridine (158 mg, 674 µmol) in dioxane (3 mL) and water (0.55 mL) was added sodium carbonate (178 mg, 1.68 mmol) and Pd(dppf)Cl$_2$·CH$_2$Cl$_2$ (68.8 mg, 84.2 µmol). The mixture was heated to reflux for 24 h. Dichloromethane was added, the mixture was dried (magnesium sulfate), filtered and the solvent was removed in vacuum. Silicagel chromatography gave 125 mg (43% yield) of the title compound.

LC-MS (Method 2): $R_t$=1.03 min; MS (ESIpos): m/z=400 [M+H]$^+$.

Compound 15.02

6-(2-methoxypyridin-3-yl)-N-[4-(piperazin-1-ylmethyl)pyridin-2-yl]-1H-benzimidazol-2-amine hydrochloride

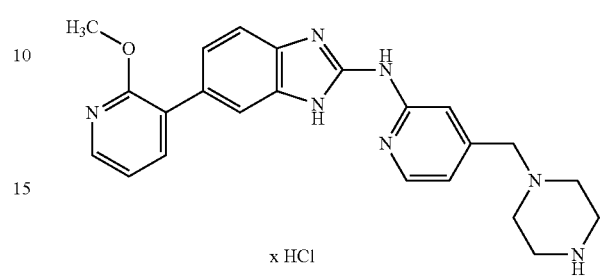

x HCl

Starting with tert-butyl 4-[(2-{[6-(2-methoxypyridin-3-yl)-1H-benzimidazol-2-yl]amino}pyridin-4-yl)methyl]piperazine-1-carboxylate (124 mg, 240 µmol), Compound 15.02 was prepared analogously to the procedure for the preparation of Compound 01.05.

Yield: 133 mg of the title compound as crude product that was used for the next step without purification.

LC-MS (Method 2): $R_t$=1.03 min; MS (ESIpos): m/z=416 [M+H]$^+$

Compound 16.01 methyl 2-{[4-({[tert-butyl(dimethyl)silyl]oxy}methyl)pyridin-2-yl]amino}-1H-benzimidazole-5-carboxylate

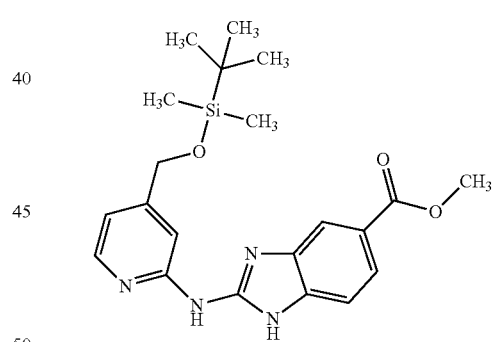

To a stirred solution of 1H-imidazole (474 mg, 6.96 mmol) and di-1H-imidazol-1-ylmethanethione (9.65 g, 90% purity, 48.7 mmol) in dichloromethane (200 mL) was added 4-({[tert-butyl(dimethyl)silyl]oxy}methyl)pyridin-2-amine (8.30 g, 34.8 mmol), dissolved in dichloromethane (100 mL) at 0° C. The mixture was stirred at r.t. for 18 h. Methyl 3,4-diaminobenzoate (8.95 g, 97% purity, 52.2 mmol), dissolved in dichloromethane (10 mL), was added and the mixture was stirred at r.t. for 16 h. Water was added and the mixture was extracted with dichloromethane.

The organic phase was dried (sodium sulfate) and filtered. N,N'-dipropan-2-ylcarbodiimide (6.5 mL, 42 mmol) was added and the mixture was stirred at r.t. for 48 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography gave 18.3 g of the title compound as a crude product, that was used without further purification.

LC-MS (Method 2): $R_t$=1.49 min; MS (ESIpos): m/z=413 [M+H]$^+$.

$^1$H-NMR (300 MHz, DMSO-d6) δ [ppm]: 0.000 (0.95), 0.055 (1.12), 0.822 (0.79), 0.829 (1.03), 0.873 (16.00), 0.883 (2.39), 0.911 (4.69), 0.932 (4.64), 0.994 (2.85), 1.016 (2.90), 3.762 (4.24), 4.667 (2.03), 5.680 (0.82), 8.175 (0.58), 8.192 (0.54).

Compound 16.02 methyl 2-{[4-(hydroxymethyl)pyridin-2-yl]amino}-1H-benzimidazole-6-carboxylate

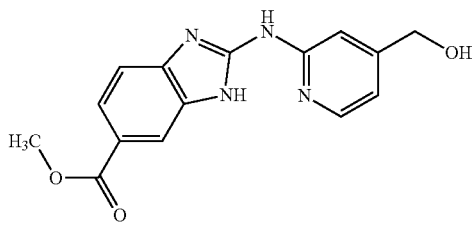 [SMILES: COC(=O)c1ccc2nc(Nc3cc(CO)ccn3)[nH]c2c1]

To a stirred solution of methyl 2-{[4-({[tert-butyl(dimethyl)silyl]oxy}methyl)pyridin-2-yl]amino}-1H-benzimidazole-6-carboxylate (18.3 g, approx. 31.9 mmol) in THF (780 mL), was added tetra-n-butylammoniumfluoride (48 mL, 1.0 M, 48 mmol), and the mixture was stirred at r.t. for 1 h. A sodium bicarbonate solution was added, the mixture was stirred for 30 minutes and the mixture was extracted with ethyl acetate. The organic phase was dried (sodium sulfate), filtered and the solvent was removed in vacuum. The solid was triturated with ethanol to give 4.30 g of the title compound.

LC-MS (Method 1): $R_t$=0.66 min; MS (ESIpos): m/z=299 [M+H]$^+$.

$^1$H-NMR (400 MHz, DMSO-d6) δ[ppm]: 2.523 (0.90), 3.311 (16.00), 4.519 (5.40), 4.532 (5.60), 5.421 (1.89), 5.435 (4.13), 5.450 (1.83), 6.907 (2.02), 6.921 (2.10), 7.179 (4.42), 7.704 (1.10), 8.247 (3.52), 8.260 (3.44), 10.840 (0.74), 12.396 (1.46).

Compound 16.03 methyl 2-{[4-(chloromethyl)pyridin-2-yl]amino}-1H-benzimidazole-6-carboxylate

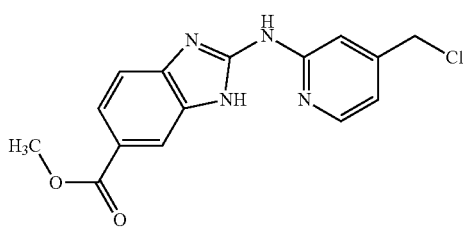 [SMILES: COC(=O)c1ccc2nc(Nc3cc(CCl)ccn3)[nH]c2c1]

To a suspension of methyl 2-{[4-(hydroxymethyl)pyridin-2-yl]amino}-1H-benzimidazole-6-carboxylate (4.79 g, 16.1 mmol) in dichloromethane (70 mL) and DMF (100 mL) was added thionyl dichloride (2.3 mL, 32 mmol) and the mixture was stirred for 72 h. A solution of sodium bicarbonate was added and the mixture was extracted with ethyl acetate. The organic phase was washed with water, dried (sodium sulfate), filtered and the solvent was removed in vacuum to give 4.46 g of the title compound as a crude product.

LC-MS (Method 1): $R_t$=0.90 min; MS (ESIpos): m/z=317 [M+H]$^+$.

$^1$H-NMR (400 MHz, DMSO-d6) δ [ppm]: 2.523 (1.18), 3.842 (16.00), 4.784 (7.77), 7.031 (1.30), 7.034 (1.26), 7.044 (1.25), 7.048 (1.17), 7.271 (2.54), 7.709 (0.95), 7.730 (0.79), 8.330 (2.10), 8.344 (1.97).

Compound 16.04 methyl 2-[(4-{[4-(tert-butoxycarbonyl)piperazin-1-yl]methyl}pyridin-2-yl)amino]-1H-benzimidazole-6-carboxylate

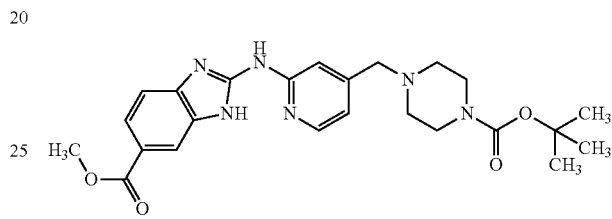

To a stirred solution of methyl 2-{[4-(chloromethyl)pyridin-2-yl]amino}-1H-benzimidazole-6-carboxylate (2.00 g, 6.31 mmol) in DMF (120 mL) was added potassium carbonate (4.36 g, 31.6 mmol) and tert-butyl piperazine-1-carboxylate (2.35 g, 12.6 mmol). The mixture was stirred at r.t. for 14 h. Further tert-butyl piperazine-1-carboxylate (290 mg) was added and the mixture was stirred at r.t. for 14 h. Water was added and the mixture was extracted with ethyl acetate. The organic phase was washed with half-saturated sodium chloride solution, dried (sodium sulfate) and the solvent was removed in vacuum. Silicagel chromatography gave a solid that was triturated with dichloromethane/hexane to LC-MS (Method 2): $R_t$=1.27 min; MS (ESIpos): m/z=467 [M+H]$^+$.

$^1$H-NMR (300 MHz, DMSO-d6) δ[ppm]: 1.393 (16.00), 1.417 (1.02), 2.354 (1.79), 2.369 (1.32), 3.500 (2.12), 3.838 (5.36), 6.941 (0.53), 7.158 (1.22), 8.264 (0.74), 8.281 (0.75), 12.382 (0.53).

Compound 16.05

2-[(4-{[4-(tert-butoxycarbonyl)piperazin-1-yl]methyl}pyridin-2-yl)amino]-1H-benzimidazole-6-carboxylic acid

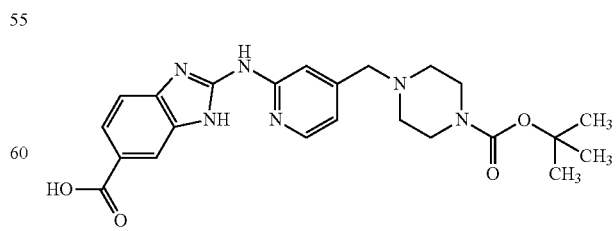

To a stirred solution of methyl 2-[(4-{[4-(tert-butoxycarbonyl)piperazin-1-yl]methyl}pyridin-2-yl)amino]-1H-benzimidazole-6-carboxylate (12.0 g, 25.7 mmol) in methanol (380 mL, 9.5 mol) and THF (130 mL, 1.6 mol) was added an aqueous solution of sodium hydroxide (130 mL, 2.0 M, 260 mmol). The mixture was stirred at 70° C. for 14 h. The solution was cooled to room temperature, hydrochloric acid was added until pH 7 was reached and the solvent was removed in vacuum. Toluene and dichloromethane were added, the mixture was stirred for 10 minutes and the solvent was removed in vacuum. The solid was dried in a vacuum oven at 60° C. overnight, to give 26.4 g (purity approx. 47%) of the title compound as a crude product that was used for the next step without purification.

LC-MS (Method 2): $R_t$=0.66 min; MS (ESIpos): m/z=453 [M+H]$^+$.

$^1$H-NMR (400 MHz, DMSO-d6) δ[ppm]: 1.396 (16.00), 3.361 (0.71), 3.409 (0.69), 7.252 (0.73), 7.696 (0.71), 7.700 (0.70), 7.717 (0.58), 7.721 (0.61), 8.293 (0.59), 8.306 (0.56).

Compound 16.06 tert-butyl 4-({2-[(6-{[(ethanimidoylamino)oxy]carbonyl}-1H-benzimidazol-2-yl)amino]pyridin-4-yl}methyl)piperazine-1-carboxylate

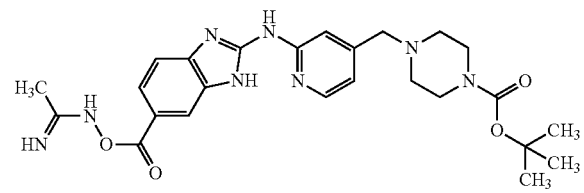 [SMILES: CC(=N)NOC(=O)c1ccc2nc(Nc3cc(CN4CCN(C(=O)OC(C)(C)C)CC4)ccn3)[nH]c2c1]

To a stirred solution of 2-[(4-{[4-(tert-butoxycarbonyl)piperazin-1-yl]methyl}pyridin-2-yl)amino]-1H-benzimidazole-6-carboxylic acid (26.4 g, approx. 25.7 mmol) in DMA (250 mL) was added DIPEA (18 mL, 100 mmol), (1Z)—N'-hydroxyethanimidamide (2.85 g, 38.5 mmol) and PyBOP (20.0 g, 38.5 mmol). The mixture was stirred at r.t. for 1 h. An aqueous sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum to give a solid. The solid was triturated with dichloromethane to give 12.1 g of the title compound.

LC-MS (Method 2): $R_t$=1.05 min; MS (ESIpos): m/z=509 [M+H]$^+$.

$^1$H-NMR (400 MHz, DMSO-d6) δ[ppm]: 1.172 (0.56), 1.394 (16.00), 1.822 (4.66), 1.986 (0.98), 2.344 (0.81), 2.357 (1.19), 2.369 (0.85), 3.324 (4.96), 3.336 (0.82), 3.348 (0.97), 3.362 (0.65), 5.755 (3.12), 7.193 (0.72), 8.258 (0.74), 8.272 (0.71).

Compound 16.07

6-(3-methyl-1,2,4-oxadiazol-5-yl)-N-[4-(piperazin-1-ylmethyl)pyridin-2-yl]-1H-benzimidazol-2-amine hydrochloride

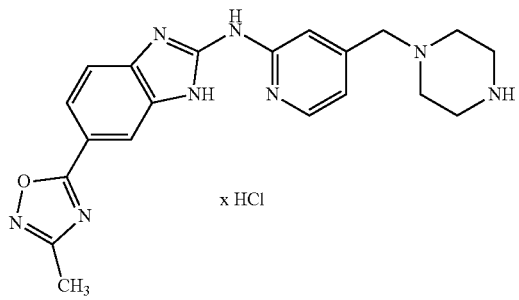 [SMILES: Cc1noc(-c2ccc3nc(Nc4cc(CN5CCNCC5)ccn4)[nH]c3c2)n1]

Starting with tert-butyl 4-[(2-{[6-(3-methyl-1,2,4-oxadiazol-5-yl)-1H-benzimidazol-2-yl]amino}pyridin-4-yl)methyl]piperazine-1-carboxylate (8.30 g, 16.9 mmol), Compound 16.07 was prepared analogously to the procedure for the preparation of Compound 01.05.

Yield: 8.50 g of the title compound as crude product that was used for the next step without purification.

LC-MS (Method 2): $R_t$=0.92 min; MS (ESIpos): m/z=391 [M+H]$^+$.

$^1$H-NMR (400 MHz, DMSO-d6) δ [ppm]: 1.952 (0.54), 2.428 (15.44), 2.938 (0.58), 3.160 (16.00), 3.331 (1.01), 3.352 (1.18), 3.444 (2.47), 3.455 (1.91), 3.466 (1.15), 3.560 (3.34), 7.585 (2.37), 7.823 (1.72), 7.844 (2.03), 8.037 (1.93), 8.041 (1.88), 8.058 (1.49), 8.063 (1.63), 8.341 (2.28), 8.344 (2.31), 8.536 (1.41), 8.550 (1.38).

Compound 16.08 tert-butyl (2R,5S)-4-[(2-aminopyridin-4-yl)methyl]-2,5-dimethylpiperazine-1-carboxylate

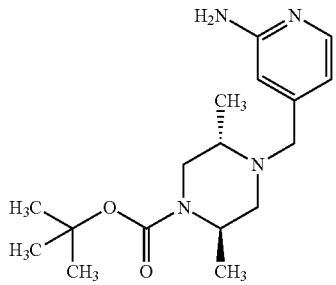 [SMILES: C[C@@H]1CN(Cc2ccnc(N)c2)[C@@H](C)CN1C(=O)OC(C)(C)C]

To a stirred suspension of 4-(bromomethyl)pyridin-2-amine hydrobromide (2.00 g, 7.46 mmol) in acetonitrile (16 mL) was added potassium carbonate and tert-butyl (2R,5S)-2,5-dimethylpiperazine-1-carboxylate (1.76 g, 8.21 mmol). The mixture was stirred at r.t. for 14 h. Water was added and the mixture was extracted with ethyl acetate. The organic phase was washed with half-saturated sodium chloride solution, dried (sodium sulfate) and the solvent was removed in vacuum. Silicagel chromatography gave 1.72 g (65% yield) of the title compound.

LC-MS (Method 2): $R_t$=1.18 min; MS (ESIpos): m/z=321 [M+H]$^+$.

¹H-NMR (400 MHz, DMSO-d6) δ[ppm]: 0.874 (1.89), 0.890 (1.97), 1.160 (2.09), 1.177 (2.13), 1.381 (1.15), 1.389 (16.00), 5.805 (1.23), 7.796 (0.77), 7.809 (0.78).

Compound 16.09 methyl 2-[(4-{[(2S,5R)-4-(tert-butoxycarbonyl)-2,5-dimethylpiperazin-1-yl]methyl}pyridin-2-yl)amino]-1H-benzimidazole-6-carboxylate

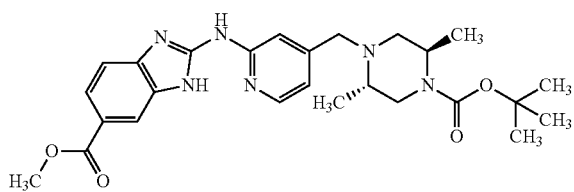 [SMILES: COC(=O)c1ccc2nc(Nc3cc(CN4C[C@@H](C)N(C(=O)OC(C)(C)C)C[C@@H]4C)ccn3)[nH]c2c1]

To a stirred solution of 1H-imidazole (72.2 mg, 1.06 mmol) and di-1H-imidazol-1-ylmethanethione (1.26 g, 90% purity, 6.37 mmol) in dichloromethane (45 mL) was added tert-butyl (2R,5S)-4-[(2-aminopyridin-4-yl)methyl]-2,5-dimethylpiperazine-1-carboxylate (1.70 g, 5.31 mmol), dissolved in dichloromethane (25 mL) at 0° C. The mixture was stirred at r.t. for 14 h. Methyl 3,4-diaminobenzoate (1.36 g, 97% purity, 7.96 mmol), dissolved in dichloromethane (30 mL) was added and the mixture was stirred at r.t. for 2 h. Water was added and the mixture was extracted with dichloromethane.

The organic phase was dried (sodium sulfate) and filtered. N,N'-dipropan-2-ylcarbodiimide (1.18 mL, 7.4 mmol) was added. The mixture was stirred at r.t. for 14 h. Further N,N'-dipropan-2-ylcarbodiimide (0.42 mL, 2.6 mmol) was added and the mixture was stirred at r.t. for 14 h. Saturated ammonium chloride solution was added, the mixture was stirred for 30 minutes and was extracted with dichloromethane. Aminophase-silicagel chromatography followed by silicagel chromatography gave 564 mg (21% yield) of the title compound.

LC-MS (Method 2): $R_t$=1.41 min; MS (ESIpos): m/z=495 [M+H]⁺ ¹H-NMR (600 MHz, DMSO-d6) δ [ppm]: 0.921 (2.33), 0.932 (2.35), 1.227 (2.34), 1.238 (2.33), 1.398 (16.00), 3.448 (0.76), 3.835 (5.47), 7.262 (0.83), 8.250 (0.76), 8.259 (0.74).

Compound 16.10

2-[(4-{[(2S,5R)-4-(tert-butoxycarbonyl)-2,5-dimethylpiperazin-1-yl]methyl}pyridin-2-yl)amino]-1H-benzimidazole-6-carboxylic acid

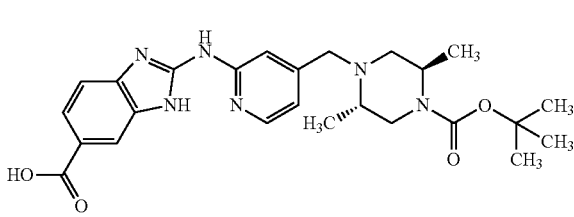 [SMILES: C[C@@H]1CN(Cc2ccnc(Nc3nc4ccc(C(=O)O)cc4[nH]3)c2)[C@@H](C)CN1C(=O)OC(C)(C)C]

To a stirred solution of methyl 2-[(4-{[(2S,5R)-4-(tert-butoxycarbonyl)-2,5-dimethylpiperazin-1-yl]methyl}pyridin-2-yl)amino]-1H-benzimidazole-6-carboxylate (560 mg, 1.13 mmol) in methanol (17 mL) and THF (5.6 mL) was added an aqueous solution of sodium hydroxide (5.7 mL, 2.0 M, 11 mmol). The mixture was stirred at 70° C. for 14 h. The solution was cooled to room temperature, hydrochloric acid was added until pH 7 was reached and the solvent was removed in vacuum. Toluene and dichloromethane were added, the mixture was stirred for 10 minutes and the solvent was removed in vacuum. The solid was dried in a vacuum oven at 60° C. overnight, to give 1.15 g (purity approx. 47%) of the title compound as a crude product that was used for the next step without purification.

LC-MS (Method 2): $R_t$=0.74 min; MS (ESIpos): m/z=481 [M+H]⁺.

¹H-NMR (400 MHz, DMSO-d6) δ [ppm]: 0.916 (1.78), 0.933 (1.81), 0.980 (0.75), 0.997 (0.79), 1.227 (1.90), 1.244 (1.92), 1.394 (16.00), 8.205 (0.83), 8.218 (0.78).

Compound 16.11 tert-butyl (2R,5S)-4-({2-[(6-{[(ethanimidoylamino)oxy]carbonyl}-1H-benzimidazol-2-yl)amino]pyridin-4-yl}methyl)-2,5-dimethylpiperazine-1-carboxylate

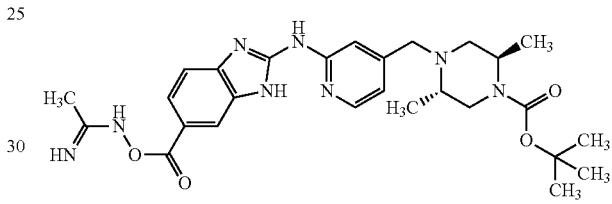

Starting with 2-[(4-{[(2S,5R)-4-(tert-butoxycarbonyl)-2,5-dimethylpiperazin-1-yl]methyl}pyridin-2-yl)amino]-1H-benzimidazole-6-carboxylic acid (1.15 g, approx. 1.12 mmol) and (1Z)—N'-hydroxyethanimidamide (124 mg, 1.68 mmol), Compound 16.11. was prepared analogously to the procedure for the preparation of Compound 16.06.

Yield: 508 mg of the title compound.

LC-MS (Method 2): $R_t$=1.21 min; MS (ESIpos): m/z=537 [M+H]⁺.

¹H-NMR (400 MHz, DMSO-d6) δ[ppm]: 0.921 (1.98), 0.937 (2.00), 1.225 (2.06), 1.242 (2.11), 1.400 (16.00), 1.819 (4.52), 5.758 (2.55), 8.248 (0.85), 8.261 (0.82).

Compound 16.12

N-(4-{[(2S,5R)-2,5-dimethylpiperazin-1-yl]methyl}pyridin-2-yl)-6-(3-methyl-1,2,4-oxadiazol-5-yl)-1H-benzimidazol-2-amine hydrochloride

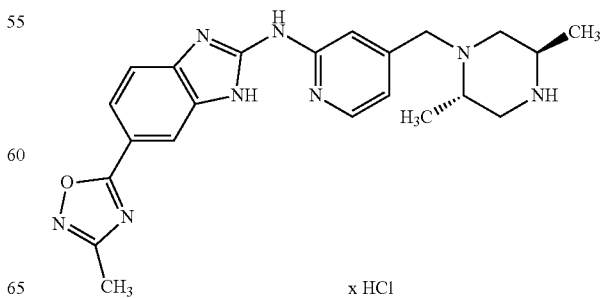

Starting with tert-butyl (2R,5S)-2,5-dimethyl-4-[(2-{[6-(3-methyl-1,2,4-oxadiazol-5-yl)-1H-benzimidazol-2-yl]amino}pyridin-4-yl)methyl]piperazine-1-carboxylate (360 mg, 694 µmol), Compound 16.12 was prepared analogously to the procedure for the preparation of Compound 01.05.

Yield: 392 mg of the title compound as crude product that was used for the next step without purification.

LC-MS (Method 2): $R_t$=1.01 min; MS (ESIpos): m/z=419 [M+H]$^+$.

$^1$H-NMR (400 MHz, DMSO-d6) δ[ppm]: 1.218 (4.02), 1.234 (4.10), 2.433 (16.00), 3.161 (0.73), 5.759 (10.36), 7.540 (1.48), 7.811 (1.53), 7.832 (1.73), 8.044 (1.83), 8.048 (1.82), 8.065 (1.47), 8.069 (1.54), 8.332 (2.19).

Compound 16.13 tert-butyl (3R)-4-[(2-aminopyridin-4-yl)methyl]-3-methylpiperazine-1-carboxylate

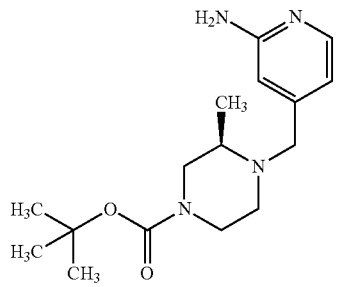 [SMILES: C[C@@H]1CN(C(=O)OC(C)(C)C)CCN1Cc1ccnc(N)c1]

To a stirred suspension of 4-(bromomethyl)pyridin-2-amine hydrobromide (2.00 g, 7.46 mmol) in acetonitrile (16 mL) was added potassium carbonate and tert-butyl (3R)-3-methylpiperazine-1-carboxylate (1.64 g, 8.21 mmol). The mixture was stirred at r.t. for 14 h. Water was added and the mixture was extracted with ethyl acetate. The organic phase was washed with half-saturated sodium chloride solution, dried (sodium sulfate) and the solvent was removed in vacuum. Aminophase silicagel chromatography gave 1.41 g (55% yield) of the title compound.

LC-MS (Method 2): $R_t$=1.07 min; MS (ESIpos): m/z=307 [M+H]$^+$.

$^1$H-NMR (400 MHz, DMSO-d6) δ[ppm]: 0.913 (0.82), 0.929 (0.82), 0.995 (1.59), 1.011 (1.61), 1.386 (16.00), 3.307 (1.84), 5.751 (1.86), 5.784 (0.94), 6.401 (0.75), 7.793 (0.57), 7.807 (0.57).

Compound 16.14 methyl 2-[(4-{[(2R)-4-(tert-butoxycarbonyl)-2-methylpiperazin-1-yl]methyl}pyridin-2-yl)amino]-1H-benzimidazole-6-carboxylate

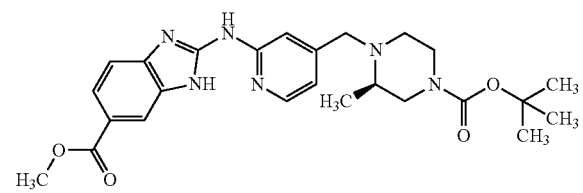 [SMILES: COC(=O)c1ccc2nc(Nc3cc(CN4CCN(C(=O)OC(C)(C)C)C[C@H]4C)ccn3)[nH]c2c1]

To a stirred solution of 1H-imidazole (62.2 mg, 914 µmol) and di-1H-imidazol-1-ylmethanethione (1.18 g, 90% purity, 5.94 mmol) in dichloromethane (35 mL) was added tert-butyl (3R)-4-[(2-aminopyridin-4-yl)methyl]-3-methylpiperazine-1-carboxylate (1.40 g, 4.57 mmol), dissolved in dichloromethane (35 mL) at 0° C. The mixture was stirred at r.t. for 14 h. Further di-1H-imidazol-1-ylmethanethione (1.18 g, 90% purity, 5.94 mmol) was added and the mixture was stirred at r.t. for 14 h. Methyl 3,4-diaminobenzoate (2.04 g, 97% purity, 11.9 mmol), dissolved in dichloromethane (30 mL) was added and the mixture was stirred at r.t. for 2 h. Water was added and the mixture was extracted with dichloromethane.

The organic phase was dried (sodium sulfate) and filtered. N,N'-dipropan-2-ylcarbodiimide (1.03 mL, 6.4 mmol) was added. The mixture was stirred at r.t. for 72 h. Further N,N'-dipropan-2-ylcarbodiimide (0.37 mL, 2.3 mmol) was added and the mixture was stirred at r.t. for 14 h. Saturated ammonium chloride solution was added, the mixture was stirred for 30 minutes and was extracted with dichloromethane. Aminophase-silicagel chromatography gave 583 mg of the title compound as a crude product, that was used without further purification.

LC-MS (Method 2): $R_t$=1.31 min; MS (ESIpos): m/z=481 [M+H]$^+$.

$^1$H-NMR (500 MHz, DMSO-d6) δ[ppm]: 1.026 (2.36), 1.039 (2.36), 1.394 (16.00), 3.839 (6.00), 5.752 (3.00), 7.190 (0.86), 8.253 (0.81), 8.264 (0.76).

Compound 16.15

2-[(4-{[(2R)-4-(tert-butoxycarbonyl)-2-methylpiperazin-1-yl]methyl}pyridin-2-yl)amino]-1H-benzimidazole-6-carboxylic acid

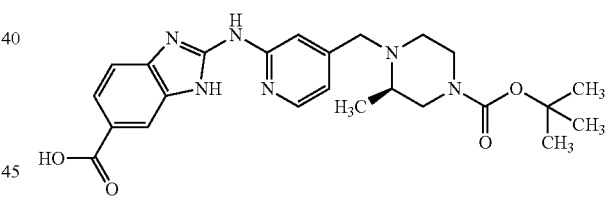

To a stirred solution of methyl 2-[(4-{[(2R)-4-(tert-butoxycarbonyl)-2-methylpiperazin-1-yl]methyl}pyridin-2-yl)amino]-1H-benzimidazole-6-carboxylate (580 mg, 1.21 mmol) in methanol (18 mL, 440 mmol) and THF (6.0 mL, 74 mmol) was added an aqueous solution of sodium hydroxide (6.0 mL, 2.0 M, 12 mmol). The mixture was stirred at 70° C. for 14 h. The solution was cooled to room temperature, hydrochloric acid was added until pH 7 was reached and the solvent was removed in vacuum. Toluene and dichloromethane were added, the mixture was stirred for 10 minutes and the solvent was removed in vacuum. The solid was dried in a vacuum oven at 60° C. overnight to give 1.4 g (purity: approx. 40%) of the title compound as a crude product that was used for the next step without purification.

LC-MS (Method 2): $R_t$=0.79 min; MS (ESIpos): m/z=467 [M+H]$^+$.

$^1$H-NMR (400 MHz, DMSO-d6) δ [ppm]: 1.396 (16.00), 5.758 (3.59), 7.707 (0.70), 7.711 (0.70), 7.728 (0.58), 7.732 (0.61).

Compound 16.16 tert-butyl (3R)-4-({2-[(6-{[(ethanimidoylamino)oxy]carbonyl}-1H-benzimidazol-2-yl)amino]pyridin-4-yl}methyl)-3-methylpiperazine-1-carboxylate

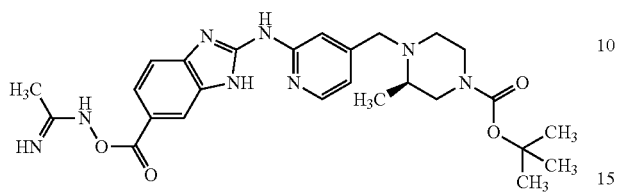

To a stirred solution of 2-[(4-{[(2R)-4-(tert-butoxycarbonyl)-2-methylpiperazin-1-yl]methyl}pyridin-2-yl)amino]-1H-benzimidazole-6-carboxylic acid (1.40 g, approx. 1.20 mmol) in DMA (12 mL) was added DIPEA (840 μl, 4.8 mmol), (1Z)—N'-hydroxyethanimidamide (133 mg, 1.80 mmol) and PyBOP (937 mg, 1.80 mmol). The mixture was stirred at room temperature for 1 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-Silicagel chromatography gave 514 mg of the title compound.

LC-MS (Method 2): R$_t$=1.12 min; MS (ESIpos): m/z=523 [M+H]$^+$.

$^1$H-NMR (400 MHz, DMSO-d6) δ[ppm]: 1.026 (2.27), 1.036 (1.39), 1.042 (2.35), 1.054 (1.99), 1.071 (0.87), 1.393 (16.00), 1.821 (5.17), 5.755 (2.41), 7.199 (1.00), 8.249 (0.93), 8.262 (0.88).

Compound 16.17 tert-butyl (3R)-3-methyl-4-[(2-{[6-(3-methyl-1,2,4-oxadiazol-5-yl)-1H-benzimidazol-2-yl]amino}pyridin-4-yl)methyl]piperazine-1-carboxylate

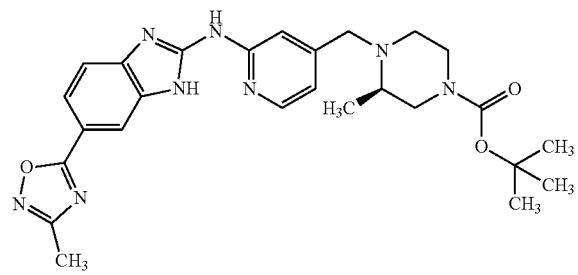 [SMILES: Cc1noc(-c2ccc3nc(Nc4cc(CN5CCN(C(=O)OC(C)(C)C)C[C@H]5C)ccn4)[nH]c3c2)n1]

A mixture of tert-butyl (3R)-4-({2-[(6-{[(ethanimidoylamino)oxy]carbonyl}-1H-benzimidazol-2-yl)amino]pyridin-4-yl}methyl)-3-methylpiperazine-1-carboxylate (510 mg, 976 μmol) and sodium acetate (88.1 mg, 1.07 mmol) in 1-propanol (20 mL) and water (10 mL) was heated to 100° C. for 40 h. The solvent was removed in vacuum. Aminophase-silicagel chromatography gave 310 mg (57% yield) of the title compound.

LC-MS (Method 2): R$_t$=1.33 min; MS (ESIpos): m/z=505 [M+H]$^+$.

$^1$H-NMR (400 MHz, DMSO-d6) δ[ppm]: 1.029 (2.19), 1.045 (2.23), 1.396 (16.00), 2.085 (3.57), 2.398 (5.85), 7.206 (0.89), 8.273 (0.76), 8.286 (0.73).

Compound 16.18

6-(3-methyl-1,2,4-oxadiazol-5-yl)-N-(4-{[(2R)-2-methylpiperazin-1-yl]methyl}pyridin-2-yl)-1H-benzimidazol-2-amine hydrochloride

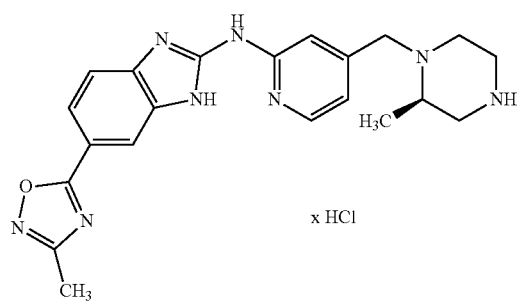 [SMILES: Cc1noc(-c2ccc3nc(Nc4cc(CN5CCNC[C@H]5C)ccn4)[nH]c3c2)n1]

Starting with tert-butyl (3R)-3-methyl-4-[(2-{[6-(3-methyl-1,2,4-oxadiazol-5-yl)-1H-benzimidazol-2-yl]amino}pyridin-4-yl)methyl]piperazine-1-carboxylate (300 mg, 595 μmol), Compound 16.18 was prepared analogously to the procedure for the preparation of Compound 01.05.

Yield: 310 mg of the title compound as crude product that was used for the next step without purification.

LC-MS (Method 2): R$_t$=0.99 min; MS (ESIpos): m/z=405 [M+H]$^+$.

$^1$H-NMR (400 MHz, DMSO-d6) δ[ppm]: 1.473 (1.02), 2.432 (16.00), 3.332 (0.67), 3.371 (0.83), 3.486 (0.73), 3.488 (0.73), 3.498 (0.72), 5.755 (1.37), 7.575 (1.61), 7.815 (1.54), 7.836 (1.75), 8.042 (1.77), 8.046 (1.80), 8.063 (1.40), 8.067 (1.49), 8.335 (2.06), 8.339 (2.02), 8.527 (0.95), 8.540 (0.87).

Compound 16.19 tert-butyl 4-[(2-aminopyridin-4-yl)methyl]-3,3-dimethylpiperazine-1-carboxylate

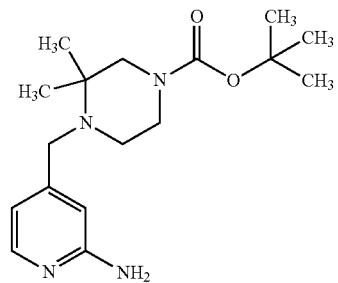 [SMILES: CC(C)(C)OC(=O)N1CCN(Cc2ccnc(N)c2)C(C)(C)C1]

To a stirred solution of 4-(bromomethyl)pyridin-2-amine hydrobromide (2.50 g, 9.33 mmol) in DMF (30 mL) was added potassium carbonate (5.16 g, 37.3 mmol) and tert-butyl 3,3-dimethylpiperazine-1-carboxylate (2.40 g, 11.2 mmol). The mixture was stirred at r.t. for 14 h. Water was added and the mixture was extracted with ethyl acetate. The organic phase was washed with half-saturated sodium chloride solution, dried (sodium sulfate) and the solvent was removed in vacuum. Aminophase-silicagel chromatography followed by silicagel chromatography gave 2.20 g (74% yield) of the title compound.

LC-MS (Method 2): $R_t$=1.16 min; MS (ESIpos): m/z=321 [M+H]$^+$.

$^1$H-NMR (400 MHz, DMSO-d6) δ[ppm]: 1.004 (9.22), 1.027 (0.55), 1.042 (0.53), 1.390 (16.00), 2.276 (0.67), 3.126 (0.69), 3.335 (3.19), 5.788 (1.25), 6.414 (0.98), 6.423 (0.68), 6.435 (0.58), 7.775 (0.78), 7.777 (0.73), 7.788 (0.73), 7.790 (0.73).

Compound 16.20

4-(3-methyl-1,2,4-oxadiazol-5-yl)benzene-1,2-diamine

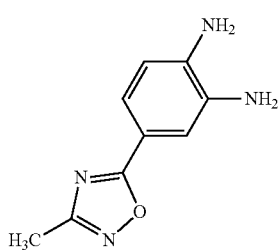

To a stirred suspension of methyl 3,4-diaminobenzoate (10.0 g, 60.2 mmol) and N-hydroxyethanimidamide (10.6 g, 95% purity, 135 mmol) in dioxane (20 mL) was added caesium carbonate (19.6 g, 60.2 mmol) and the mixture was stirred at 110° C. for 2 h. Water was added and the mixture was extracted with ethyl acetate. The organic phase was dried (sodium sulfate), filtered and the solvent was removed in vacuum to give a solid that was triturated with methanol to give 8.00 g (70% yield) of the title compound.

LC-MS (Method 2): $R_t$=0.67 min; MS (ESIpos): m/z=191 [M+H]$^+$.

$^1$H-NMR (400 MHz, DMSO-d6) δ[ppm]: 2.308 (16.00), 4.831 (2.74), 5.429 (3.11), 6.583 (2.69), 6.603 (2.81), 7.148 (1.50), 7.153 (1.72), 7.169 (1.30), 7.174 (1.62), 7.212 (3.04), 7.217 (2.53).

Compound 16.21

N-{4-[(2,2-dimethylpiperazin-1-yl)methyl]pyridin-2-yl}-6-(3-methyl-1,2,4-oxadiazol-5-yl)-1H-benzimidazol-2-amine hydrochloride

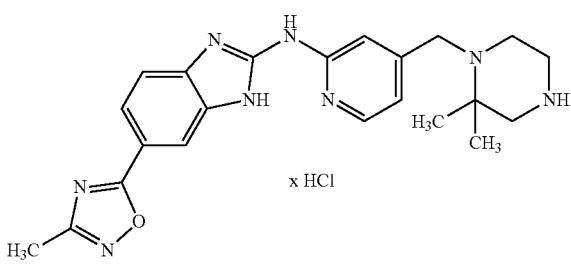 [SMILES: Cc1noc(-c2ccc3nc(Nc4cc(CN5CCNCC5(C)C)ccn4)[nH]c3c2)n1]

Starting with tert-butyl 3,3-dimethyl-4-[(2-{[6-(3-methyl-1,2,4-oxadiazol-5-yl)-1H-benzimidazol-2-yl]amino}pyridin-4-yl)methyl]piperazine-1-carboxylate (980 mg, 1.89 mmol), Compound 16.21 was prepared analogously to the procedure for the preparation of Compound 01.05.

Yield: 1.06 g of the title compound as crude product that was used for the next step without purification.

LC-MS (Method 2): $R_t$=1.07 min; MS (ESIpos): m/z=419 [M+H]$^+$.

$^1$H-NMR (400 MHz, DMSO-d6) δ[ppm]: 2.431 (16.00), 2.523 (0.93), 7.616 (1.03), 7.824 (1.32), 7.845 (1.53), 8.047 (1.81), 8.051 (1.86), 8.068 (1.46), 8.072 (1.56), 8.342 (1.90).

Compound 16.22

2-(4-ethylpyridin-2-yl)-1H-isoindole-1,3(2H)-dione

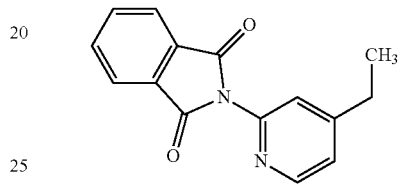

To a stirred solution of 4-ethylpyridin-2-amine (20.0 g, 164 mmol) in dichloromethane (600 mL) was added benzene-1,2-dicarbonyl dichloride (26 mL, 180 mmol), followed by triethylamine (60 mL, 430 mmol) with water bath cooling. The mixture was stirred at r.t. for 1 h. The mixture was washed with water, the organic phase was separated, dried (magnesium sulfate), filtered and the solvent was removed in vacuum. Silicagel chromatography gave 37.0 g (90% yield) of the title compound.

LC-MS (Method 5): $R_t$=3.21 min; MS (ESIpos): m/z=253 [M+H]$^+$.

Compound 16.23

(rac)-2-{4-[1-bromoethyl]pyridin-2-yl}-1H-isoindole-1,3(2H)-dione

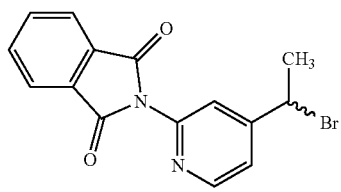 [SMILES: CC(Br)c1ccnc(N2C(=O)c3ccccc3C2=O)c1]

To a stirred suspension of 2-(4-ethylpyridin-2-yl)-1H-isoindole-1,3(2H)-dione (24.7 g, 97.9 mmol) and NBS (19.0 g, 107 mmol) in dichloroethane (300 mL) was added AIBN (800 mg, 4.87 mmol), and the mixture was stirred at reflux for 1 h. The mixture was washed with water, the organic phase was separated, dried (magnesium sulfate), filtered and the solvent was removed in vacuum. Diethyl ether was added and the mixture was stirred at r.t. for 19 h. A precipitated solid was collected by filtration to give 27.8 g (86% yield) of the title compound.

LC-MS (Method 5): $R_t$=3.34 min; MS (ESIpos): m/z=331 [M+H]$^+$.

Compound 16.24

(rac)-tert-butyl 4-[1-{2-[(2-{[4-(tert-butoxycarbonyl)piperazin-1-yl]carbonyl}benzoyl)amino]pyridin-4-yl}ethyl]piperazine-1-carboxylate

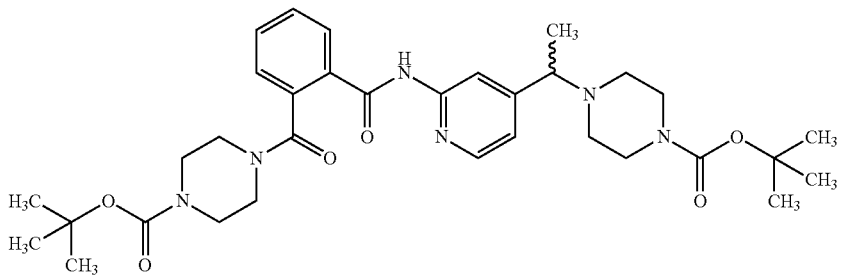 [SMILES: CC(c1ccnc(NC(=O)c2ccccc2C(=O)N2CCN(C(=O)OC(C)(C)C)CC2)c1)N1CCN(C(=O)OC(C)(C)C)CC1]

To a stirred suspension of (rac)-2-{4-[1-bromoethyl]pyridin-2-yl}-1H-isoindole-1,3(2H)-dione (41.7 g, 126 mmol) in acetonitrile (200 mL) was added potassium carbonate (22.0 g, 159 mmol) and tert-butyl piperazine-1-carboxylate (53.0 g, 285 mmol). The mixture was stirred at 75° C. for 1 h. The solvent was removed in vacuum. Water was added and the mixture was extracted with diethyl ether. The organic phase was washed with half saturated sodium chloride solution, dried (magnesium sulfate) and the solvent was removed in vacuum to give 91.6 g of the title compound as a crude product, that was used for the next step without further purification.

LC-MS (Method 5): $R_t$=3.36 min; MS (ESIpos): m/z=623 [M+H]$^+$.

Compound 16.25

(rac)-tert-butyl 4-[1-(2-aminopyridin-4-yl)ethyl]piperazine-1-carboxylate

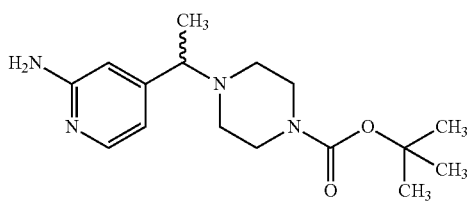 [SMILES: CC(c1ccnc(N)c1)N1CCN(C(=O)OC(C)(C)C)CC1]

To a stirred solution of (rac)-tert-butyl 4-[1-{2-[(2-{[4-(tert-butoxycarbonyl)piperazin-1-yl]carbonyl}benzoyl)amino]pyridin-4-yl}ethyl]piperazine-1-carboxylate (91.6 g, approx. 113 mmol) in dioxane (350 mL) was added hydrazine hydrate (50 mL, 1.0 mol), and the mixture was stirred at reflux for 3 h. The mixture was cooled to r.t., and a precipitate was removed by filtration. Diethyl ether was added and the mixture was washed with water. The organic phase was separated, dried (magnesium sulfate), filtered and the solvent was removed in vacuum. Silicagel chromatography gave 32.35 g of the title compound.

LC-MS (Method 5): $R_t$=0.71 min; MS (ESIpos): m/z=307 [M+H]$^+$.

Compound 16.26

(rac)-6-(3-methyl-1,2,4-oxadiazol-5-yl)-N-{4-[1-(piperazin-1-yl)ethyl]pyridin-2-yl}-1H-benzimidazol-2-amine hydrochloride

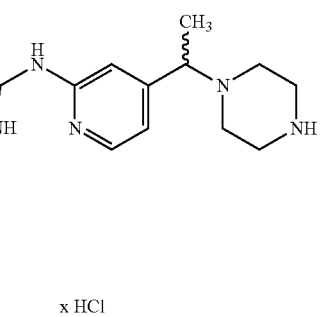

x HCl

Starting with tert-butyl (rac)-4-[1-(2-{[6-(3-methyl-1,2,4-oxadiazol-5-yl)-1H-benzimidazol-2-yl]amino}pyridin-4-yl)ethyl]piperazine-1-carboxylate (20.1 g, 39.8 mmol), Compound 16.26 was prepared analogously to the procedure for the preparation of Compound 01.05.

Yield: 23.3 g of the title compound as crude product that was used for the next step without purification.

LC-MS (Method 2): $R_t$=1.01 min; MS (ESIpos): m/z=405 [M+H]$^+$.

$^1$H-NMR (400 MHz, DMSO-d6) δ [ppm]: 2.432 (16.00), 7.568 (1.28), 7.818 (1.34), 7.839 (1.61), 8.045 (1.77), 8.048 (1.67), 8.066 (1.34), 8.070 (1.39), 8.338 (1.75), 8.342 (1.72).

Compound 16.27

6-(3-methyl-1,2,4-oxadiazol-5-yl)-N-{4-[(1R or 1S)-1-(piperazin-1-yl)ethyl]pyridin-2-yl}-1H-benzimidazol-2-amine hydrochloride

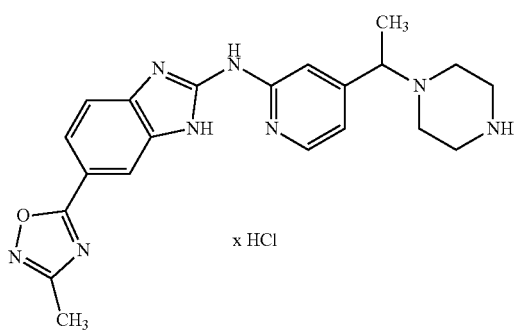 [SMILES: Cc1noc(-c2ccc3nc(Nc4cc(C(C)N5CCNCC5)ccn4)[nH]c3c2)n1]

Starting with tert-butyl 4-[(1R or 1S)-1-(2-{[6-(3-methyl-1,2,4-oxadiazol-5-yl)-1H-benzimidazol-2-yl]amino}pyridin-4-yl)ethyl]piperazine-1-carboxylate (100 mg, 198 µmol), Compound 16.27 was prepared analogously to the procedure for the preparation of Compound 01.05.

Yield: 100 mg of the title compound as crude product that was used for the next step without purification.

LC-MS (Method 2): $R_t$=1.02 min; MS (ESIpos): m/z=405 [M+H]$^+$.

$^1$H-NMR (400 MHz, DMSO-d6) δ [ppm]: 1.085 (0.81), 1.104 (0.65), 1.678 (1.45), 2.434 (16.00), 3.367 (0.61), 3.385 (0.67), 3.452 (0.88), 5.760 (0.52), 7.583 (1.64), 7.830 (1.64), 7.851 (1.88), 8.057 (2.08), 8.060 (1.97), 8.078 (1.56), 8.082 (1.62), 8.347 (2.10), 8.350 (2.06), 8.573 (1.12), 8.586 (1.05).

Compound 16.28

N-[4-({[tert-butyl(dimethyl)silyl]oxy}methyl)pyridin-2-yl]-6-(3-methyl-1,2,4-oxadiazol-5-yl)-1H-benzimidazol-2-amine

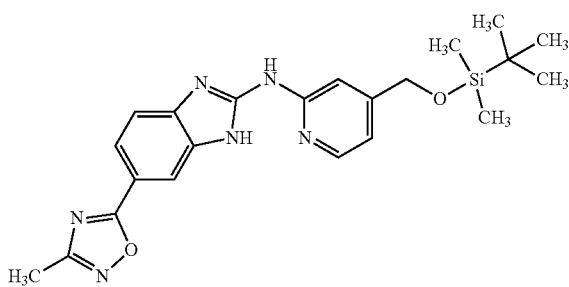 [SMILES: Cc1noc(-c2ccc3nc(Nc4cc(CO[Si](C)(C)C(C)(C)C)ccn4)[nH]c3c2)n1]

To a stirred solution of 1H-imidazole (143 mg) and di-1H-imidazol-1-ylmethanethione (2.18 g, 90% purity) in dichloromethane (10 mL) was added 4-({[tert-butyl(dimethyl)silyl]oxy}methyl)pyridin-2-amine (2.50 g, see Compound 04.03), dissolved in dichloromethane (20 mL) at 0° C. The mixture was stirred at r.t. for 18 h. 4-(3-methyl-1,2,4-oxadiazol-5-yl)benzene-1,2-diamine (2.06 g, 97. % purity; see Compound 16.20), dissolved in dichloromethane (20 mL), was added and the mixture was stirred at r.t. for 16 h. Water was added and the mixture was extracted with dichloromethane. The organic phase was separated and filtered through a silicagel to give 4.7 g of a solid that was dissolved in dichloromethane (50 mL). N,N'-dipropan-2-ylcarbodiimide (3.0 ml) was added and the mixture was stirred at r.t. for 16 h. Further N,N'-dipropan-2-ylcarbodiimide (3.0 ml) was added and the mixture was stirred for 3 h. The solvent was removed in vacuum. Water was added and the mixture was extracted with ethyl acetate. The organic phase was dried (sodium sulfate), filtered and the solvent was removed in vacuum. Silicagel chromatography gave a solid that was triturated with ethanol to give 1.7 g of the title compound as a crude product, that was used without further purification.

LC-MS (Method 2): $R_t$=1.52 min; MS (ESIpos): m/z=436 [M+H]$^+$.

$^1$H-NMR (400 MHz, DMSO-d6) δ[ppm]: 0.150 (13.83), 0.970 (1.53), 0.978 (16.00), 2.424 (3.52), 4.777 (1.65).

Compound 16.29

(2-{[6-(3-methyl-1,2,4-oxadiazol-5-yl)-1H-benzimidazol-2-yl]amino}pyridin-4-yl)methanol

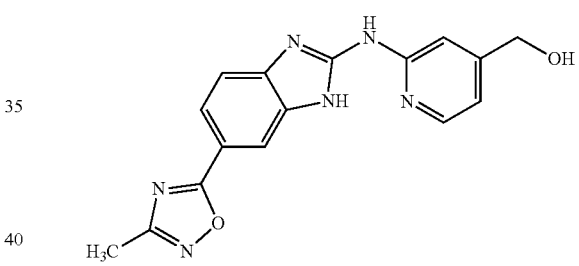

To a stirred solution of crude N-[4-({[tert-butyl(dimethyl)silyl]oxy}methyl)pyridin-2-yl]-6-(3-methyl-1,2,4-oxadiazol-5-yl)-1H-benzimidazol-2-amine (1.70 g) in THF (51 mL) and ethanol (17 mL), was added aqueous hydrochloric acid (5.8 ml, 2.0 M) and the solution was stirred for 1 h. Water was added and the mixture was extracted with ethyl acetate and hexane (1:1 mixture). The organic phase was removed. An aqueous 2 M solution of sodium hydroxide was added to the aqueous phase until pH 6.5 was reached, and the solution was extracted with ethyl acetate. The organic phase was dried (sodium sulfate), filtered and the solvent was removed in vacuum. The gummy material was suspended in chloroform and concentrated in vacuum for two times to give 2.2 g of the crude product, that was used for the next step without further purification.

LC-MS (Method 2): $R_t$=0.86 min; MS (ESIpos): m/z=322 [M+H]$^+$.

$^1$H-NMR (400 MHz, DMSO-d6) δ[ppm]: 1.688 (16.00), 2.390 (12.03), 4.529 (4.87), 6.898 (1.15), 6.901 (1.15), 6.912 (1.17), 6.915 (1.15), 7.498 (1.28), 7.519 (1.51), 7.552 (0.99), 7.744 (1.31), 7.749 (1.31), 7.765 (1.08), 7.769 (1.09), 8.084 (1.35), 8.225 (1.78), 8.237 (1.77).

Compound 16.30

N-[4-(chloromethyl)pyridin-2-yl]-6-(3-methyl-1,2,4-oxadiazol-5-yl)-1H-benzimidazol-2-amine

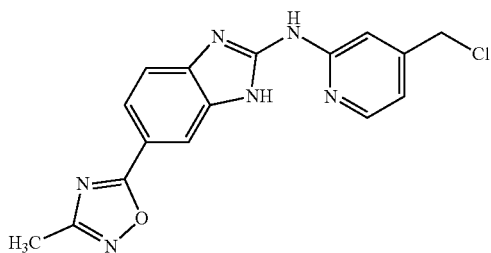 [SMILES: Cc1noc(-c2ccc3nc(Nc4cc(CCl)ccn4)[nH]c3c2)n1]

To a suspension of crude (2-{[6-(3-methyl-1,2,4-oxadiazol-5-yl)-1H-benzimidazol-2-yl]amino}pyridin-4-yl)methanol (2.20 g) in dichloromethane (100 mL) was added thionyl dichloride (570 µl) and the mixture was stirred for 19 h. An aqueous solution of sodium bicarbonate was added and the mixture was extracted with a mixture of dichloromethane and methanol (10:1) and afterwards with a mixture of chloroform and methanol (5:1). The organic phases were combined, dried (sodium sulfate), filtered and the solvent was removed in vacuum. The residue was triturated with ethanol to give 900 mg of the title compound.

LC-MS (Method 1): $R_t$=0.89 min; MS (ESIpos): m/z=340 [M+H]$^+$.

$^1$H-NMR (400 MHz, DMSO-d6) δ[ppm]: 2.155 (5.25), 2.399 (16.00), 4.793 (6.94), 5.134 (1.31), 7.049 (0.91), 7.062 (0.91), 7.272 (2.11), 8.352 (1.10), 8.365 (1.03).

Compound 17.01 tert-butyl 4-[(2-{[6-({[(cyclopropylcarbonoimidoyl)amino]oxy}carbonyl)-1H-benzimidazol-2-yl]amino}pyridin-4-yl)methyl]piperazine-1-carboxylate

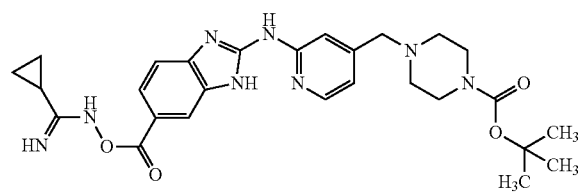 [SMILES: CC(C)(C)OC(=O)N1CCN(Cc2ccnc(Nc3nc4ccc(C(=O)ONC(=N)C5CC5)cc4[nH]3)c2)CC1]

To a stirred solution of 2-[(4-{[4-(tert-butoxycarbonyl)piperazin-1-yl]methyl}pyridin-2-yl)amino]-1H-benzimidazole-6-carboxylic acid (18.6 g, approx. 19.3 mmol) in DMA (440 mL) was added DIPEA (67 mL, 390 mmol), N'-hydroxycyclopropanecarboximidamide (5.80 g, 57.9 mmol) and PyBOP (15.1 g, 29.0 mmol). The mixture was stirred at r.t. for 14 h. Further PyBOP (15.1 g, 29.0 mmol) was added and the mixture was stirred at r.t. for 1 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 7.50 g of the title compound.

LC-MS (Method 2): $R_t$=1.12 min; MS (ESIpos): m/z=535 [M+H]$^+$.

$^1$H-NMR (400 MHz, DMSO-d6) δ[ppm]: 0.743 (0.52), 0.749 (0.69), 0.764 (0.53), 0.770 (0.72), 0.830 (0.73), 0.835 (0.76), 0.842 (0.81), 0.849 (0.68), 1.394 (16.00), 1.513 (0.46), 2.083 (4.98), 2.343 (0.85), 2.356 (1.30), 2.369 (0.95), 3.323 (3.31), 3.502 (1.61), 5.755 (1.09), 7.182 (0.88), 8.259 (0.78), 8.272 (0.74).

Compound 17.02

6-(3-cyclopropyl-1,2,4-oxadiazol-5-yl)-N-[4-(piperazin-1-ylmethyl)pyridin-2-yl]-1H-benzimidazol-2-amine hydrochloride

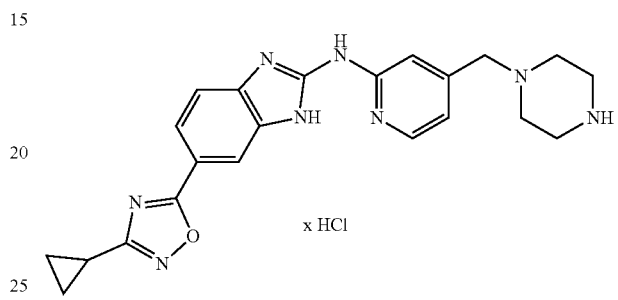

Starting with tert-butyl 4-[(2-{[6-(3-cyclopropyl-1,2,4-oxadiazol-5-yl)-1H-benzimidazol-2-yl]amino}pyridin-4-yl)methyl]piperazine-1-carboxylate (6.40 g, 12.4 mmol), Compound 17.02 was prepared analogously to the procedure for the preparation of Compound 01.05.

Yield: 6.11 g of the title compound as crude product that was used for the next step without purification.

LC-MS (Method 2): $R_t$=1.05 min; MS (ESIpos): m/z=417 [M+H]$^+$.

$^1$H-NMR (400 MHz, DMSO-d6) δ [ppm]: 0.985 (0.72), 0.995 (2.52), 1.002 (2.55), 1.007 (2.47), 1.014 (2.28), 1.023 (0.89), 1.107 (0.89), 1.116 (2.27), 1.122 (1.78), 1.127 (1.43), 1.137 (2.33), 1.143 (1.84), 2.180 (0.86), 2.188 (0.94), 2.201 (1.58), 2.213 (0.81), 2.221 (0.74), 3.159 (1.66), 3.165 (16.00), 3.218 (1.33), 3.381 (2.84), 3.565 (2.36), 7.533 (2.14), 7.785 (1.79), 7.806 (2.06), 7.994 (2.23), 7.999 (1.96), 8.016 (1.68), 8.019 (1.65), 8.305 (2.44), 8.505 (1.49), 8.517 (1.38).

Compound 17.03 methyl 2-[(4-{[(methylsulfonyl)oxy]methyl}pyridin-2-yl)amino]-1H-benzimidazole-6-carboxylate

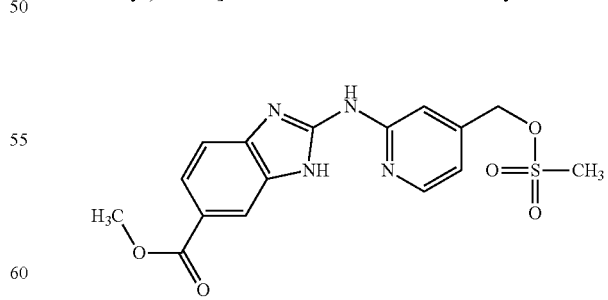

To a stirred solution of methyl 2-{[4-(hydroxymethyl)pyridin-2-yl]amino}-1H-benzimidazole-6-carboxylate (4.30 g, 14.4 mmol) and DIPEA (25 mL, 140 mmol) in dichloromethane (71 mL), methanesulfonyl chloride (1.7 mL, 22 mmol) was added at 0° C. The mixture was stirred at r.t. for

Compound 17.04 methyl 2-[(4-{[4-(2-chlorophenyl)piperazin-1-yl]methyl}pyridin-2-yl)amino]-1H-benzimidazole-6-carboxylate

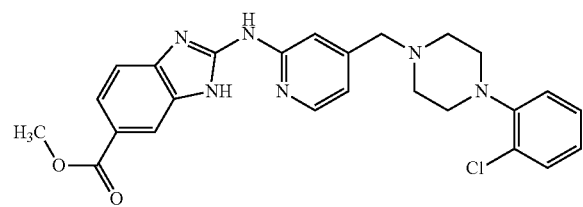 [SMILES: COC(=O)c1ccc2nc(Nc3cc(CN4CCN(c5ccccc5Cl)CC4)ccn3)[nH]c2c1]

To a stirred solution of methyl 2-[(4-{[(methylsulfonyl)oxy]methyl}pyridin-2-yl)amino]-1H-benzimidazole-6-carboxylate (7.50 g, approx. 15.9 mmol) in DMF (120 mL) was added potassium carbonate (11.0 g, 79.7 mmol) and 1-(2-chlorophenyl)piperazine (6.27 g, 31.9 mmol). The mixture was stirred at r.t. for 48 h. Water was added and the mixture was extracted with ethyl acetate. The organic phase was washed with half-saturated sodium chloride solution, dried (sodium sulfate) and the solvent was removed in vacuum. Silicagel chromatography gave 1.65 g of the title compound.

LC-MS (Method 2): R$_t$=1.41 min; MS (ESIpos): m/z=477 [M+H]$^+$.

$^1$H-NMR (400 MHz, DMSO-d6) δ[ppm]: 1.156 (0.92), 1.174 (2.03), 1.192 (1.05), 1.987 (3.67), 2.523 (1.28), 2.598 (2.17), 2.609 (1.96), 2.730 (7.89), 2.732 (7.36), 2.890 (9.81), 3.023 (2.71), 3.571 (4.51), 3.842 (16.00), 3.845 (5.51), 4.020 (0.79), 4.038 (0.80), 6.982 (0.90), 6.993 (0.85), 7.017 (0.89), 7.021 (0.95), 7.036 (1.45), 7.040 (1.55), 7.055 (1.06), 7.059 (1.11), 7.159 (1.28), 7.163 (1.32), 7.180 (1.94), 7.183 (1.64), 7.207 (2.42), 7.279 (1.26), 7.283 (1.30), 7.298 (1.23), 7.302 (1.51), 7.303 (1.31), 7.318 (0.81), 7.322 (0.93), 7.389 (2.38), 7.393 (2.27), 7.409 (2.01), 7.413 (1.82), 7.716 (0.67), 7.952 (1.30), 8.157 (0.67), 8.284 (1.38), 8.297 (1.33), 12.381 (1.03).

Compound 17.05

2-[(4-{[4-(2-chlorophenyl)piperazin-1-yl]methyl}pyridin-2-yl)amino]-1H-benzimidazole-6-carboxylic acid

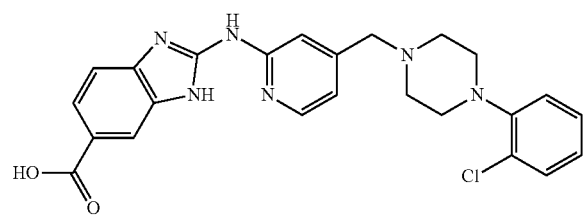 [SMILES: O=C(O)c1ccc2nc(Nc3cc(CN4CCN(c5ccccc5Cl)CC4)ccn3)[nH]c2c1]

To a stirred solution of methyl 2-[(4-{[4-(2-chlorophenyl)piperazin-1-yl]methyl}pyridin-2-yl)amino]-1H-benzimidazole-6-carboxylate (3.00 g, 6.29 mmol) in methanol (130 mL) and THF (42 mL) was added an aqueous solution of sodium hydroxide (42 mL, 2.0 M, 85 mmol). The mixture was stirred at 70° C. for 14 h. Water was added and the mixture was stirred for 10 minutes and extracted with ethyl acetate. The organic phase was concentrated in vacuum to give 3.1 g of the title compound as a crude product that was used for the next step without purification.

LC-MS (Method 2): R$_t$=0.80 min; MS (ESIpos): m/z=463 [M+H]$^+$.

$^1$H-NMR (400 MHz, DMSO-d6) δ[ppm]: 1.715 (1.69), 2.296 (1.01), 2.327 (0.61), 2.518 (4.70), 2.523 (3.85), 2.601 (8.03), 2.665 (0.92), 2.669 (1.02), 2.673 (0.79), 3.022 (10.32), 3.167 (16.00), 3.567 (15.58), 3.625 (0.72), 3.844 (0.68), 5.756 (9.34), 6.919 (5.22), 6.922 (5.09), 6.932 (5.24), 6.935 (5.17), 7.009 (3.42), 7.013 (3.64), 7.027 (5.24), 7.032 (5.50), 7.047 (4.23), 7.051 (4.39), 7.156 (5.01), 7.160 (5.24), 7.176 (7.20), 7.180 (6.40), 7.260 (1.62), 7.264 (1.80), 7.274 (5.92), 7.278 (6.21), 7.293 (5.97), 7.296 (6.19), 7.298 (5.25), 7.302 (1.47), 7.313 (3.23), 7.317 (3.23), 7.383 (8.45), 7.387 (8.10), 7.403 (8.10), 7.407 (7.33), 7.498 (3.31), 7.719 (3.82), 7.723 (3.74), 7.743 (3.49), 8.029 (2.18), 8.246 (8.37), 8.260 (7.70).

Compound 17.06

N-[({2-[(4-{[4-(2-chlorophenyl)piperazin-1-yl]methyl}pyridin-2-yl)amino]-1H-benzimidazol-6-yl}carbonyl)oxy]cyclopropanecarboximidamide

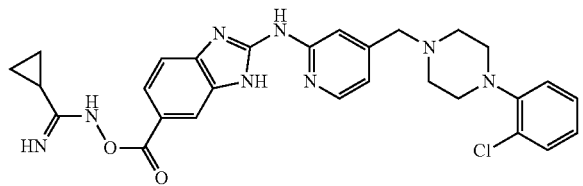 [SMILES: N=C(NOC(=O)c1ccc2nc(Nc3cc(CN4CCN(c5ccccc5Cl)CC4)ccn3)[nH]c2c1)C1CC1]

To a stirred solution of 2-[(4-{[4-(2-chlorophenyl)piperazin-1-yl]methyl}pyridin-2-yl)amino]-1H-benzimidazole-6-carboxylic acid (200 mg, approx. 432 µmol) in DMA (5 mL) was added DIPEA (450 µl, 2.6 mmol), N'-hydroxycyclopropanecarboximidamide (38 µl, 97% purity, 650 µmol) and PyBOP (337 mg, 648 µmol). The mixture was stirred at r.t. for 14 h. Further PyBOP (337 mg, 648 µmol) and DIPEA (450 µl, 2.6 mmol) was added and the mixture was stirred at r.t. for 14 h. Water was added and a solid precipitated and was collected by filtration. A potassium carbonate solution was added to the solid and the mixture was extracted with dichloromethane/methanol (20:1). The organic phase was washed with saturated sodium chloride solution, dried (sodium sulfate), filtered and the solvent was removed in vacuum to give a solid. The solid was triturated with warm ethanol to give 160 mg of the title compound as a crude product that was used for the next step without purification.

LC-MS (Method 2): R$_t$=1.25 min; MS (ESIneg): m/z=543 [M−H]$^+$.

$^1$H-NMR (400 MHz, DMSO-d6) δ[ppm]: 0.732 (1.54), 0.744 (4.70), 0.751 (6.32), 0.759 (4.26), 0.766 (4.71), 0.771 (6.47), 0.780 (3.04), 0.787 (0.83), 0.795 (0.71), 0.800 (0.86), 0.816 (0.90), 0.823 (2.80), 0.831 (6.59), 0.837 (7.03), 0.844 (7.27), 0.850 (6.17), 0.855 (1.98), 0.863 (1.71), 1.090 (0.84), 1.107 (0.42), 1.481 (1.17), 1.494 (2.25), 1.503 (2.23), 1.507 (1.42), 1.515 (4.12), 1.523 (1.25), 1.528 (2.06), 1.536 (1.99), 1.549 (0.86), 2.322 (0.73), 2.327 (1.03), 2.331 (0.73), 2.523 (2.38), 2.664 (0.88), 2.669 (1.12), 2.674 (0.84), 3.024 (10.36), 3.391 (0.41), 3.481 (1.00), 3.573 (16.00), 6.242 (4.83), 6.959 (0.56), 6.976 (4.07), 6.989 (4.02), 7.017 (2.92), 7.021 (3.04), 7.036 (5.10), 7.039 (5.42), 7.055 (3.62), 7.058 (3.80), 7.159 (4.43), 7.163 (4.71), 7.180 (6.40), 7.183 (5.91), 7.236 (6.35), 7.279 (3.73), 7.283 (4.05), 7.298 (4.56), 7.302 (5.12), 7.318 (2.55), 7.322 (2.67), 7.389 (7.59), 7.393 (7.42), 7.408 (6.71), 7.412 (6.50), 7.810 (1.76), 8.174 (0.81), 8.277 (7.27), 8.290 (6.89), 10.774 (0.64), 12.323 (1.01).

Compound 18.01

N-hydroxy-3-methylbutanimidamide

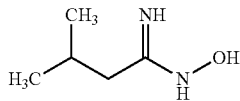

To a stirred mixture of 3-methylbutanenitrile (1.00 g, 98% purity, 11.8 mmol) and hydroxylamine hydrochloride (1.84 g, 98% purity, 25.9 mmol) in ethanol (12 mL) was added triethyl amine (3.8 mL, 27 mmol), and the mixture was heated to 75° C. for 14 h. The mixture was cooled to r.t. and a solid was removed by filtration. The solution was concentrated in vacuum. Ethyl acetate was added to the residue, the mixture was stirred and again, a solid was removed by filtration. The solution was concentrated in vacuum to give 0.60 g (44% yield) of the title compound as a crude product that was used without further purification.

LC-MS (Method 2): $R_t$=0.53 min; MS (ESIpos): m/z=117 [M+H]$^+$.

$^1$H-NMR (400 MHz, DMSO-d6) δ[ppm]: 0.842 (15.79), 0.858 (16.00), 0.874 (0.68), 1.793 (2.16), 1.795 (2.19), 1.812 (4.22), 1.891 (0.72), 1.907 (1.14), 1.911 (0.68), 1.988 (0.44), 5.354 (1.03), 8.709 (0.81).

Compound 18.02 tert-butyl 4-[(2-{[6-({[(3-methylbutanimidoyl) amino]oxy}carbonyl)-1H-benzimidazol-2-yl] amino}pyridin-4-yl)methyl]piperazine-1-carboxylate

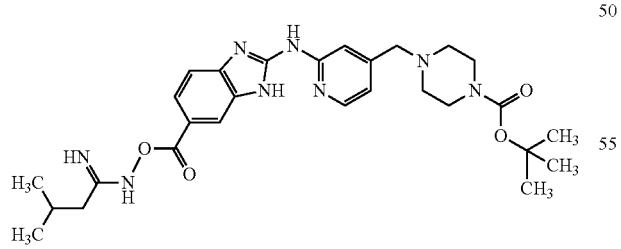

To a stirred solution of 2-[(4-{[4-(tert-butoxycarbonyl) piperazin-1-yl]methyl}pyridin-2-yl)amino]-1H-benzimidazole-6-carboxylic acid (400 mg, approx. 407 µmol) in NMP (10 mL) was added DIPEA (1.4 mL, 8.1 mmol), crude N-hydroxy-3-methylbutanimidamide (142 mg) and PyBOP (635 mg, 1.22 mmol). The mixture was stirred at room temperature for 1 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 190 mg of the title compound.

LC-MS (Method 2): $R_t$=1.23 min; MS (ESIpos): m/z=551 [M+H]$^+$.

$^1$H-NMR (400 MHz, DMSO-d6) δ[ppm]: 0.929 (3.45), 0.944 (3.59), 1.396 (16.00), 1.713 (2.29), 1.721 (2.32), 1.729 (6.21), 1.738 (2.36), 1.746 (2.41), 1.989 (1.27), 2.348 (0.91), 2.360 (1.35), 2.372 (0.97), 2.992 (1.59), 2.998 (1.06), 3.001 (2.44), 3.008 (4.48), 3.012 (2.08), 3.015 (2.15), 3.018 (4.50), 3.021 (1.61), 3.025 (2.43), 3.028 (1.02), 3.034 (1.54), 3.351 (1.14), 3.505 (1.50), 7.187 (0.82), 8.259 (0.67), 8.273 (0.66).

Compound 18.03 tert-butyl 4-{[2-({6-[3-(2-methylpropyl)-1,2,4-oxadiazol-5-yl]-1H-benzimidazol-2-yl}amino)pyridin-4-yl]methyl}piperazine-1-carboxylate

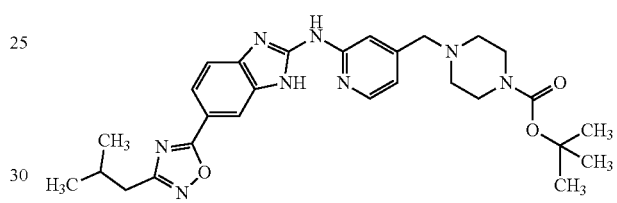

A mixture of tert-butyl 4-[(2-{[6-({[(3-methylbutanimidoyl)amino]oxy}carbonyl)-1H-benzimidazol-2-yl] amino}pyridin-4-yl)methyl]piperazine-1-carboxylate (190 mg, 345 µmol) and sodium acetate (31.1 mg, 380 µmol) in 1-propanol (9 mL) and water (4.5 mL) was heated to 100° C. for 14 h. The solvent was removed in vacuum. Silicagel chromatography gave 133 mg (72% yield) of the title compound.

LC-MS (Method 2): $R_t$=1.51 min; MS (ESIpos): m/z=533 [M+H]$^+$.

$^1$H-NMR (400 MHz, DMSO-d6) δ[ppm]: 0.974 (5.62), 0.991 (5.63), 1.396 (16.00), 1.712 (2.85), 1.721 (3.16), 1.729 (7.23), 1.737 (3.05), 1.746 (2.79), 2.327 (0.58), 2.349 (1.21), 2.362 (1.74), 2.374 (1.25), 2.523 (1.53), 2.624 (1.61), 2.641 (1.47), 2.990 (1.91), 3.000 (3.08), 3.006 (5.08), 3.010 (3.00), 3.017 (5.10), 3.023 (2.87), 3.033 (1.74), 3.351 (1.62), 3.511 (2.00), 7.193 (0.59), 8.279 (0.76), 8.292 (0.71).

Compound 18.04

6-[3-(2-methylpropyl)-1,2,4-oxadiazol-5-yl]-N-[4-(piperazin-1-ylmethyl)pyridin-2-yl]-1H-benzimidazol-2-amine hydrochloride

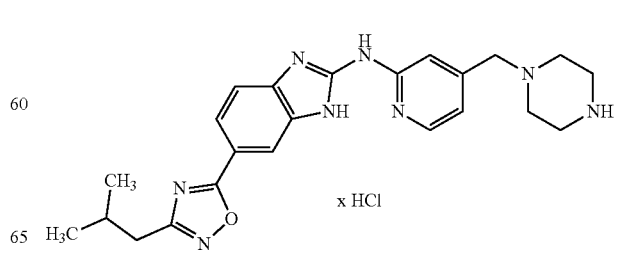

Starting with tert-butyl 4-{[2-({6-[3-(2-methylpropyl)-1,2,4-oxadiazol-5-yl]-1H-benzimidazol-2-yl}amino)pyridin-4-yl]methyl}piperazine-1-carboxylate (133 mg, 250 μmol), Compound 18.04 was prepared analogously to the procedure for the preparation of Compound 01.05.

Yield: 139 mg of the title compound as crude product that was used for the next step without purification.

LC-MS (Method 2): R$_t$=1.20 min; MS (ESIpos): m/z=433 [M+H]$^+$.

$^1$H-NMR (400 MHz, DMSO-d6) δ [ppm]: 0.979 (15.36), 0.995 (16.00), 1.720 (5.48), 1.729 (5.52), 1.737 (14.93), 1.745 (5.57), 1.754 (5.66), 2.117 (0.80), 2.134 (1.03), 2.151 (0.79), 2.327 (0.57), 2.523 (1.24), 2.661 (4.05), 2.669 (1.10), 2.678 (3.82), 3.001 (4.02), 3.004 (1.82), 3.007 (2.55), 3.010 (5.85), 3.017 (11.15), 3.021 (4.90), 3.024 (4.97), 3.027 (11.03), 3.031 (3.65), 3.034 (5.78), 3.038 (2.36), 3.040 (1.75), 3.044 (3.67), 3.386 (1.76), 3.565 (1.12), 3.910 (0.94), 7.533 (1.44), 7.805 (1.18), 7.826 (1.36), 8.047 (1.40), 8.052 (1.43), 8.069 (1.17), 8.073 (1.22), 8.346 (1.72), 8.519 (0.95), 8.532 (0.93).

Compound 18.05 methyl 2-{[4-(piperazin-1-ylmethyl)pyridin-2-yl]amino}-1H-benzimidazole-6-carboxylate hydrochloride

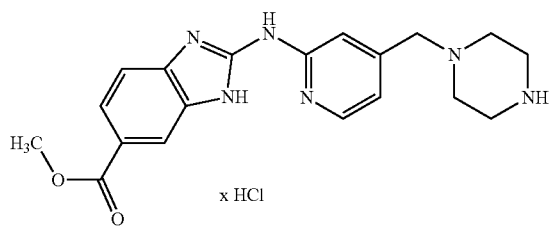 [SMILES: COC(=O)c1ccc2nc(Nc3cc(CN4CCNCC4)ccn3)[nH]c2c1]

Starting with methyl 2-[(4-{[4-(tert-butoxycarbonyl)piperazin-1-yl]methyl}pyridin-2-yl)amino]-1H-benzimidazole-6-carboxylate (5.00 g, 10.7 mmol), Compound 18.05 was prepared analogously to the procedure for the preparation of Compound 01.05.

Yield: 5.20 g of the title compound as crude product that was used for the next step without purification.

LC-MS (Method 2): R$_t$=0.92 min; MS (ESIpos): m/z=367 [M+H]$^+$.

$^1$H-NMR (400 MHz, DMSO-d6) δ[ppm]: 2.518 (1.07), 2.523 (0.74), 3.892 (16.00), 7.543 (1.71), 7.726 (1.47), 7.747 (1.72), 7.949 (1.93), 7.952 (1.99), 7.969 (1.57), 7.973 (1.65), 8.258 (1.94), 8.261 (1.92), 8.514 (0.98), 8.527 (0.95).

Compound 18.06 methyl 2-[(4-{[4-(cyclopropylcarbonyl)piperazin-1-yl]methyl}pyridin-2-yl)amino]-1H-benzimidazole-6-carboxylate

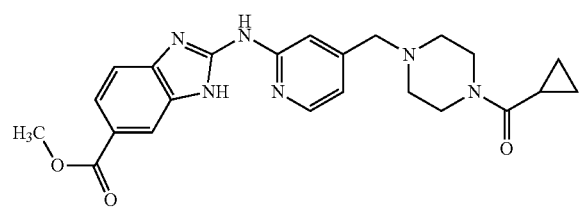 [SMILES: COC(=O)c1ccc2nc(Nc3cc(CN4CCN(C(=O)C5CC5)CC4)ccn3)[nH]c2c1]

To a stirred solution of methyl 2-{[4-(piperazin-1-ylmethyl)pyridin-2-yl]amino}-1H-benzimidazole-6-carboxylate hydrochloride (2.10 g, approx. 5.21 mmol) in DMA (85 mL) was added DIPEA (3.6 mL, 21 mmol), cyclopropanecarboxylic acid (650 μl, 95% purity, 7.8 mmol) and PyBOP (4.07 g, 7.82 mmol). The mixture was stirred at room temperature for 14 h. A sodium bicarbonate solution was added, the mixture was stirred for 15 minutes and the mixture was extracted with dichloromethane/methanol (20:1). The organic phase was dried (sodium sulfate), filtered and the solvent was removed in vacuum. Silicagel chromatography followed by trituration with ethanol/water (1:1) gave 1.45 g of the title compound.

LC-MS (Method 2): R$_t$=1.00 min; MS (ESIpos): m/z=435 [M+H]$^+$.

$^1$H-NMR (400 MHz, DMSO-d6) δ [ppm]: 0.677 (0.96), 0.684 (2.29), 0.690 (1.36), 0.697 (1.07), 0.704 (2.77), 0.710 (2.23), 0.715 (2.35), 0.722 (2.34), 0.727 (2.83), 0.734 (1.28), 1.940 (0.57), 1.947 (0.59), 1.959 (1.02), 1.971 (0.57), 1.979 (0.53), 2.327 (0.53), 2.367 (0.92), 2.442 (0.93), 2.523 (1.60), 3.527 (5.36), 3.703 (0.84), 3.841 (16.00), 6.959 (1.16), 6.971 (1.18), 7.192 (2.36), 7.700 (0.70), 8.273 (1.99), 8.287 (1.92).

Compound 18.07

2-[(4-{[4-(cyclopropylcarbonyl)piperazin-1-yl]methyl}pyridin-2-yl)amino]-1H-benzimidazole-6-carboxylic acid

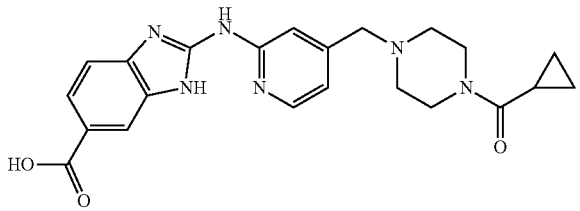 [SMILES: O=C(O)c1ccc2nc(Nc3cc(CN4CCN(C(=O)C5CC5)CC4)ccn3)[nH]c2c1]

To a stirred solution of methyl 2-[(4-{[4-(cyclopropylcarbonyl)piperazin-1-yl]methyl}pyridin-2-yl)amino]-1H-benzimidazole-6-carboxylate (1.42 g, 3.27 mmol) in methanol (10 mL) and THF (26 mL) was added an aqueous solution of sodium hydroxide (15 mL, 2.0 M, 31 mmol). The mixture was stirred at 70° C. for 56 h. Hydrochloric acid was added until pH 7 was reached. The organic solvent was removed in vacuum and the aqueous mixture was lyophilized. The residue was dissolved in DMA (50 mL) and potassium carbonate (2.47 g, 17.9 mmol), cyclopropanecarboxylic acid (420 μl, 5.4 mmol) and HATU (1.77 g, 4.65 mmol) was added. The mixture was stirred at r.t. for 14 h. Water was added, the mixture was stirred for 30 minutes and the mixture was extracted with hexane. The aqueous phase was lyophilized to give 8.5 g (purity approx. 17%) of the title compound as a crude product, that was used without purification.

LC-MS (Method 2): R$_t$=0.59 min; MS (ESIpos): m/z=421 [M+H]$^+$.

Compound 18.08

N-[({2-[(4-{[4-(cyclopropylcarbonyl)piperazin-1-yl]methyl}pyridin-2-yl)amino]-1H-benzimidazol-6-yl}carbonyl)oxy]-3-methylbutanimidamide

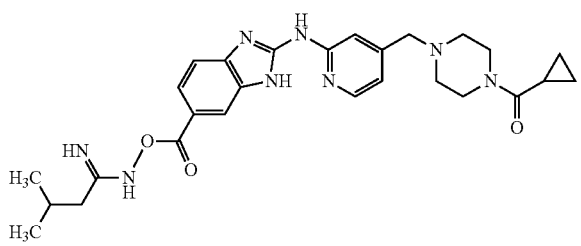 [SMILES: CC(C)CC(=N)NOC(=O)c1ccc2nc(Nc3cc(CN4CCN(C(=O)C5CC5)CC4)ccn3)[nH]c2c1]

To a stirred solution of 2-[(4-{[4-(cyclopropylcarbonyl)piperazin-1-yl]methyl}pyridin-2-yl)amino]-1H-benzimidazole-6-carboxylic acid (1.20 g, approx 485 μmol) in DMA (15 mL) was added DIPEA (1.7 mL, 9.7 mmol), crude N-hydroxy-3-methylbutanimidamide (169 mg, approx. 1.46 mmol) and PyBOP (757 mg, 1.46 mmol). The mixture was stirred at room temperature for 1 h. Further crude N-hydroxy-3-methylbutanimidamide (60 mg) and PyBOP (251 mg) was added and the mixture was stirred at r.t. for 56 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 134 mg of the title compound.

LC-MS (Method 2): $R_t$=1.01 min; MS (ESIpos): m/z=519 [M+H]$^+$.

$^1$H-NMR (400 MHz, DMSO-d6) δ[ppm]: 0.666 (0.50), 0.678 (1.55), 0.685 (3.64), 0.690 (2.19), 0.697 (1.70), 0.704 (4.39), 0.709 (3.70), 0.714 (3.96), 0.721 (3.64), 0.726 (4.32), 0.733 (1.95), 0.745 (0.44), 0.928 (15.47), 0.943 (16.00), 1.254 (0.54), 1.931 (0.44), 1.944 (0.93), 1.951 (1.02), 1.956 (0.94), 1.964 (2.24), 1.969 (2.08), 1.975 (2.46), 1.988 (5.61), 2.007 (1.11), 2.021 (1.01), 2.038 (0.62), 2.043 (0.48), 2.323 (0.75), 2.327 (1.05), 2.331 (0.87), 2.337 (0.65), 2.365 (1.56), 2.444 (1.59), 2.518 (3.06), 2.523 (2.10), 2.665 (0.64), 2.669 (0.89), 2.673 (0.64), 3.498 (1.54), 3.528 (6.67), 3.704 (1.47), 6.347 (0.62), 6.389 (1.08), 6.965 (1.37), 7.200 (3.74), 7.351 (0.68), 7.372 (0.75), 7.842 (0.72), 7.863 (0.62), 8.098 (0.72), 8.222 (1.15), 8.270 (2.80), 8.283 (2.66), 10.830 (0.76), 12.307 (1.30), 12.330 (0.82).

Compound 19.01

N-hydroxycyclopentanecarboximidamide

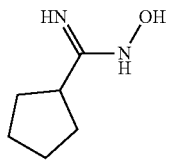

To a stirred mixture of cyclopentanecarbonitrile (1.00 g, 98% purity, 10.3 mmol) and hydroxylamine hydrochloride (876 mg, 98% purity, 12.4 mmol) in ethanol (10 mL) was added triethylamine (2.2 mL, 15 mmol), and the mixture was heated to 75° C. for 14 h. The mixture was cooled to r.t., diethyl ether was added and a solid was removed by filtration. The solution was concentrated in vacuum. Diethyl ether was added to the residue, the mixture was stirred and again, a solid was removed by filtration. The solution was concentrated in vacuum to give 0.65 g of the title compound as a crude product that was used without further purification.

LC-MS (Method 2): $R_t$=0.57 min; MS (ESIpos): m/z=129 [M+H]$^+$.

$^1$H-NMR (400 MHz, DMSO-d6) δ [ppm]: 1.405 (0.46), 1.410 (0.50), 1.414 (0.67), 1.417 (0.65), 1.421 (0.89), 1.425 (1.10), 1.432 (1.65), 1.441 (2.49), 1.445 (4.74), 1.448 (4.53), 1.455 (6.07), 1.458 (6.87), 1.462 (4.86), 1.465 (4.66), 1.472 (3.11), 1.475 (2.97), 1.481 (2.83), 1.483 (2.79), 1.488 (2.65), 1.495 (1.88), 1.500 (1.64), 1.505 (1.30), 1.512 (1.03), 1.517 (1.26), 1.520 (1.29), 1.526 (2.12), 1.533 (2.56), 1.535 (3.01), 1.538 (3.27), 1.541 (3.73), 1.546 (4.38), 1.549 (4.07), 1.552 (4.53), 1.554 (5.91), 1.557 (6.02), 1.559 (5.09), 1.562 (5.68), 1.566 (7.60), 1.571 (8.03), 1.576 (9.74), 1.583 (16.00), 1.587 (13.59), 1.591 (13.44), 1.597 (8.52), 1.605 (6.46), 1.609 (5.18), 1.611 (4.77), 1.618 (3.33), 1.622 (2.81), 1.628 (3.65), 1.635 (2.16), 1.638 (2.30), 1.642 (2.10), 1.646 (2.59), 1.648 (2.16), 1.653 (2.33), 1.658 (4.23), 1.663 (7.67), 1.669 (6.27), 1.677 (4.23), 1.679 (3.96), 1.688 (8.76), 1.693 (6.26), 1.703 (7.30), 1.705 (6.79), 1.707 (6.87), 1.715 (2.99), 1.718 (3.28), 1.721 (3.66), 1.726 (2.39), 1.728 (2.29), 1.732 (1.80), 1.736 (1.73), 1.739 (1.19), 1.743 (0.82), 1.885 (1.39), 1.900 (0.48), 1.905 (0.70), 1.908 (1.01), 1.914 (1.52), 1.918 (1.25), 1.920 (1.09), 1.923 (1.34), 1.925 (1.60), 1.928 (2.55), 1.933 (1.93), 1.938 (0.90), 1.941 (1.05), 1.943 (1.11), 1.947 (2.19), 1.957 (1.48), 1.961 (0.96), 1.964 (0.61), 1.969 (0.77), 1.973 (0.47), 1.976 (0.62), 1.978 (0.66), 1.980 (0.65), 2.349 (1.24), 2.351 (0.64), 2.355 (0.59), 2.358 (0.57), 2.368 (3.27), 2.376 (1.38), 2.380 (1.50), 2.382 (1.58), 2.388 (4.88), 2.396 (2.01), 2.403 (1.49), 2.409 (2.89), 2.414 (1.03), 2.423 (0.50), 2.430 (1.11), 2.496 (1.18), 2.500 (0.79), 2.517 (4.88), 2.872 (0.84), 2.889 (1.64), 2.893 (1.35), 2.895 (0.57), 2.906 (1.23), 2.910 (2.12), 2.913 (0.98), 2.926 (1.33), 2.930 (0.88), 2.946 (0.54), 5.241 (9.25), 8.733 (6.43).

Compound 19.02

N-[({2-[(4-{[4-(cyclopropylcarbonyl)piperazin-1-yl]methyl}pyridin-2-yl)amino]-1H-benzimidazol-6-yl}carbonyl)oxy]cyclopentanecarboximidamide

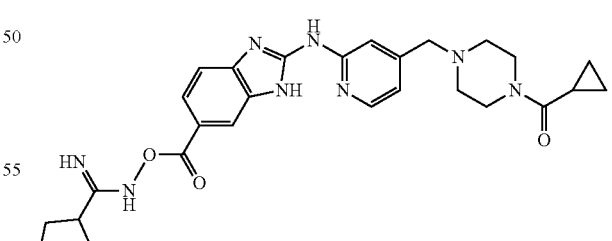

To a stirred solution of crude 2-[(4-{[4-(cyclopropylcarbonyl)piperazin-1-yl]methyl}pyridin-2-yl)amino]-1H-benzimidazole-6-carboxylic acid (1.20 g, approx. 485 μmol) in DMA (15 mL) was added DIPEA (1.7 mL, 9.7 mmol), crude N-hydroxycyclopentanecarboximidamide (187 mg, approx. 1.46 mmol) and PyBOP (252 mg, 485 μmol). The mixture was stirred at room temperature for 14 h. Further crude N-hydroxycyclopentanecarboximidamide (62 mg) and PyBOP (252 mg, 485 µmol) was added and the mixture was stirred at r.t. for 5 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 140 mg of the title compound.

LC-MS (Method 2): $R_t$=1.00 min; MS (ESIpos): m/z=531 [M+H]$^+$.

$^1$H-NMR (400 MHz, DMSO-d6) δ[ppm]: 0.667 (1.11), 0.679 (3.59), 0.686 (8.58), 0.691 (5.07), 0.699 (4.01), 0.706 (10.11), 0.710 (8.37), 0.716 (9.05), 0.723 (8.30), 0.728 (10.16), 0.735 (4.55), 0.747 (1.01), 1.236 (0.65), 1.540 (3.44), 1.552 (4.58), 1.557 (4.14), 1.639 (1.40), 1.708 (7.39), 1.718 (9.20), 1.757 (3.00), 1.824 (2.35), 1.843 (4.14), 1.863 (3.46), 1.908 (0.59), 1.929 (0.96), 1.942 (2.09), 1.949 (2.27), 1.961 (3.77), 1.973 (2.12), 1.980 (1.94), 1.992 (0.90), 2.322 (1.34), 2.327 (1.91), 2.331 (1.55), 2.373 (3.46), 2.449 (3.59), 2.523 (3.72), 2.559 (1.99), 2.580 (2.69), 2.600 (1.76), 2.664 (1.03), 2.669 (1.60), 2.674 (1.14), 3.532 (16.00), 3.703 (3.13), 5.752 (12.23), 6.268 (2.87), 6.961 (3.75), 6.973 (3.80), 7.206 (9.18), 7.369 (0.83), 7.830 (1.50), 8.212 (1.01), 8.271 (7.78), 8.285 (7.42), 10.799 (0.85), 12.308 (1.58).

Compound 20.01

N-hydroxy-2-methylbutanimidamide

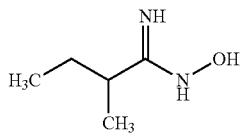

To a stirred mixture of 2-methylbutanenitrile (1.00 g, 98% purity, 11.8 mmol) and hydroxylamine hydrochloride (1.00 g, 98% purity, 14.1 mmol) in ethanol (12 mL) was added triethyl amine (2.5 mL, 18 mmol), and the mixture was heated to 75° C. for 14 h. The mixture was cooled to r.t., diethyl ether was added and a solid was removed by filtration. The solution was concentrated in vacuum. Diethyl ether was added to the residue, the mixture was stirred and again, a solid was removed by filtration. The solution was concentrated in vacuum to give 0.54 g (39% yield) of the title compound as a crude product that was used without further purification.

LC-MS (Method 2): $R_t$=0.52 min; MS (ESIpos): m/z=117 [M+H]$^+$.

$^1$H-NMR (400 MHz, DMSO-d6) δ [ppm]: 0.783 (6.25), 0.789 (1.05), 0.802 (15.54), 0.808 (2.07), 0.821 (7.30), 0.826 (1.00), 0.955 (1.44), 0.972 (1.42), 1.014 (14.96), 1.032 (16.00), 1.301 (0.82), 1.317 (1.17), 1.319 (0.98), 1.335 (1.66), 1.351 (1.34), 1.353 (1.43), 1.369 (1.08), 1.489 (1.17), 1.509 (1.59), 1.522 (0.95), 1.527 (1.34), 1.543 (1.18), 1.561 (0.89), 1.903 (0.42), 1.970 (0.97), 1.987 (1.52), 2.007 (1.44), 2.024 (0.81), 5.204 (2.90), 8.644 (6.67).

Compound 20.02

N-[({2-[(4-{[4-(cyclopropylcarbonyl)piperazin-1-yl]methyl}pyridin-2-yl)amino]-1H-benzimidazol-6-yl}carbonyl)oxy]-2-methylbutanimidamide

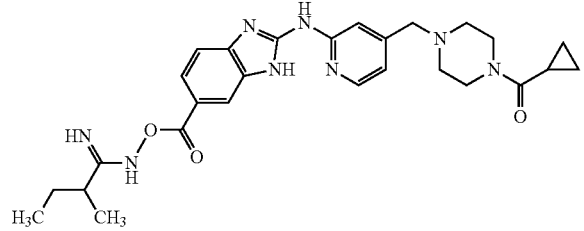 [SMILES: CCC(C)C(=N)NOC(=O)c1ccc2nc(Nc3cc(CN4CCN(C(=O)C5CC5)CC4)ccn3)[nH]c2c1]

To a stirred solution of 2-[(4-{[4-(cyclopropylcarbonyl)piperazin-1-yl]methyl}pyridin-2-yl)amino]-1H-benzimidazole-6-carboxylic acid (1.20 g, approx. 485 µmol) in DMA (15 mL) was added DIPEA (1.7 mL, 9.7 mmol), crude N-hydroxy-2-methylbutanimidamide (169 mg, approx. 1.46 mmol) and PyBOP (757 mg, 1.46 mmol). The mixture was stirred at room temperature for 14 h. Further crude N-hydroxy-2-methylbutanimidamide (56 mg) and PyBOP (251 mgl) was added and the mixture was stirred at r.t. for 5 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 194 mg of the title compound.

LC-MS (Method 2): $R_t$=0.97 min; MS (ESIpos): m/z=519 [M+H]$^+$.

$^1$H-NMR (400 MHz, DMSO-d6) δ[ppm]: 0.682 (2.06), 0.690 (4.66), 0.702 (2.35), 0.710 (5.65), 0.713 (5.14), 0.718 (5.39), 0.725 (4.78), 0.730 (5.60), 0.737 (2.45), 0.750 (0.59), 0.871 (6.74), 0.889 (16.00), 0.908 (7.36), 1.144 (13.99), 1.162 (14.42), 1.234 (0.62), 1.431 (0.85), 1.448 (1.37), 1.466 (1.96), 1.483 (1.72), 1.500 (1.05), 1.599 (1.12), 1.620 (1.55), 1.638 (1.37), 1.654 (1.12), 1.672 (0.78), 1.932 (0.57), 1.944 (1.16), 1.951 (1.28), 1.964 (2.08), 1.976 (1.21), 1.983 (1.10), 2.160 (1.08), 2.178 (1.76), 2.199 (1.64), 2.215 (0.98), 2.322 (1.12), 2.327 (1.46), 2.332 (1.17), 2.400 (1.32), 2.523 (2.65), 2.664 (0.76), 2.669 (1.07), 2.674 (0.76), 3.169 (1.42), 3.545 (2.01), 3.711 (1.32), 5.752 (4.20), 6.278 (2.99), 6.971 (2.08), 6.985 (2.13), 7.214 (3.82), 7.832 (1.62), 7.853 (1.46), 8.180 (0.80), 8.281 (2.52), 8.294 (2.51), 10.821 (0.59).

Compound 21.01

N-hydroxy-2-phenylethanimidamide

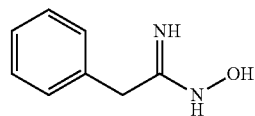 [SMILES: N=C(Cc1ccccc1)NO]

To a stirred mixture of phenylacetonitrile (1.00 g, 98% purity, 8.37 mmol) and hydroxylamine hydrochloride (712 mg, 98% purity, 10.0 mmol) in ethanol (9 mL) was added triethyl amine (1.7 mL, 13 mmol), and the mixture was heated to 75° C. for 14 h. The mixture was cooled to r.t., diethyl ether was added and a solid was removed by filtration. The solution was concentrated in vacuum. Diethyl ether was added to the residue, the mixture was stirred and again, a solid was removed by filtration. The solution was concentrated in vacuum to give 0.98 g (78% yield) of the title compound as a crude product that was used without further purification.

LC-MS (Method 2): $R_t$=0.63 min; MS (ESIpos): m/z=151 [M+H]$^+$.

$^1$H-NMR (400 MHz, DMSO-d6) δ [ppm]: 3.327 (2.14), 4.035 (7.91), 5.366 (2.52), 7.184 (0.84), 7.188 (0.59), 7.195 (1.50), 7.206 (1.41), 7.208 (1.14), 7.217 (1.07), 7.260 (0.81), 7.271 (16.00), 7.275 (2.33), 7.282 (9.43), 7.327 (1.32), 7.334 (0.89), 7.336 (1.18), 7.340 (1.88), 7.342 (1.67), 7.344 (1.43), 7.346 (1.39), 7.348 (1.45), 7.357 (3.49), 7.360 (2.33), 7.362 (1.84), 7.379 (0.97), 7.381 (2.35), 7.383 (3.05), 7.389 (1.05), 7.398 (1.78), 7.401 (2.45), 7.404 (1.62), 7.419 (0.99), 7.422 (0.63), 8.869 (6.19).

Compound 21.02

N-[({2-[(4-{[4-(cyclopropylcarbonyl)piperazin-1-yl]methyl}pyridin-2-yl)amino]-1H-benzimidazol-6-yl}carbonyl)oxy]-2-phenylethanimidamide LC-MS (Method 2): $R_t$=1.00 min; MS (ESIpos): m/z=553 [M+H]$^+$.

$^1$H-NMR (400 MHz, DMSO-d6) δ [ppm]: 0.665 (1.11), 0.677 (3.37), 0.685 (8.15), 0.690 (4.78), 0.697 (3.75), 0.705 (9.57), 0.709 (8.11), 0.714 (8.57), 0.722 (8.08), 0.727 (9.45), 0.734 (4.29), 0.746 (1.03), 1.242 (0.96), 1.258 (0.84), 1.714 (0.77), 1.730 (2.22), 1.747 (0.80), 1.908 (0.61), 1.927 (0.96), 1.940 (1.88), 1.948 (2.03), 1.960 (3.56), 1.972 (1.99), 1.979 (1.80), 1.991 (0.92), 2.322 (1.57), 2.327 (2.18), 2.332 (1.80), 2.366 (3.37), 2.444 (3.25), 2.523 (4.48), 2.665 (1.26), 2.669 (1.68), 2.674 (1.26), 3.009 (1.42), 3.019 (1.45), 3.162 (0.57), 3.175 (0.65), 3.443 (16.00), 3.528 (15.08), 3.703 (3.06), 5.752 (3.22), 6.518 (2.26), 6.962 (2.95), 7.204 (8.54), 7.236 (1.80), 7.248 (1.26), 7.254 (5.47), 7.259 (1.80), 7.272 (4.29), 7.319 (6.28), 7.334 (5.40), 7.338 (12.71), 7.351 (3.25), 7.356 (7.66), 7.396 (12.56), 7.414 (7.31), 7.418 (5.36), 7.537 (0.80), 7.850 (1.34), 8.110 (1.19), 8.225 (1.88), 8.268 (7.08), 8.282 (6.66), 10.818 (1.26), 12.299 (2.07).

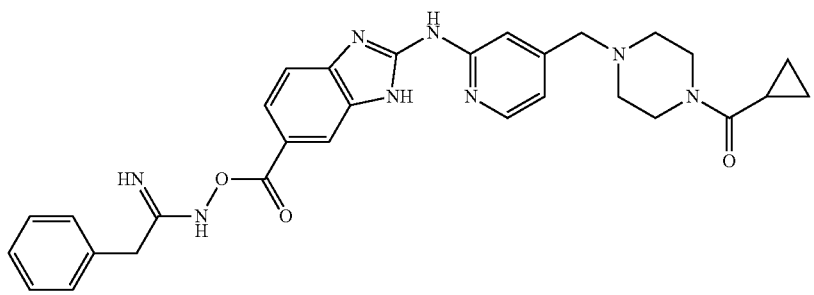 [SMILES: N=C(Cc1ccccc1)NOC(=O)c1ccc2nc(Nc3cc(CN4CCN(C(=O)C5CC5)CC4)ccn3)[nH]c2c1]

To a stirred solution of crude 2-[(4-{[4-(cyclopropylcarbonyl)piperazin-1-yl]methyl}pyridin-2-yl)amino]-1H-benzimidazole-6-carboxylic acid (1.20 g, approx. 485 µmol) in DMA (15 mL) was added DIPEA (1.7 mL, 9.7 mmol), crude N-hydroxy-2-phenylethanimidamide (219 mg, approx. 1.46 mmol) and PyBOP (757 mg, 1.46 mmol). The mixture was stirred at room temperature for 14 h. Further crude N-hydroxy-2-phenylethanimidamide (73 mg) and PyBOP (251 mg) was added and the mixture was stirred at r.t. for 5 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Silicagel chromatography gave 239 mg of the title compound.

Compound 22.01

2-{[4-({[tert-butyl(dimethyl)silyl]oxy}methyl)pyridin-2-yl]amino}-1H-benzimidazole-5-carbonitrile

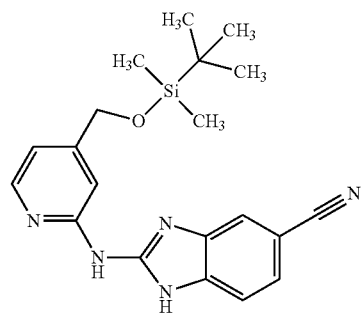 [SMILES: CC(C)(C)[Si](C)(C)OCc1ccnc(Nc2nc3cc(C#N)ccc3[nH]2)c1]

To a stirred solution of 1H-imidazole (383 mg, 5.62 mmol) and di-1H-imidazol-1-ylmethanethione (6.68 g, 90% purity, 33.7 mmol) in dichloromethane (100 mL) was added 4-({[tert-butyl(dimethyl)silyl]oxy}methyl)pyridin-2-amine (6.70 g, 28.1 mmol), dissolved in dichloromethane (100 mL) at 0° C. The mixture was stirred at r.t. for 3 h. 3,4-diaminobenzonitrile (4.63 g, 97% purity, 33.7 mmol) was added and the mixture was stirred at r.t. for 1 h. Water was added and the mixture was extracted with dichloromethane. The organic phase was dried (sodium sulfate) and filtered. N,N'-dipropan-2-ylcarbodiimide (4.9 mL, 32 mmol) was added and the mixture was stirred at r.t. for 14 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography gave a solid that was triturated with warm methanol to give 3.6 g of the title compound.

LC-MS (Method 2): $R_t$=1.51 min; MS (ESIpos): m/z=380 [M+H]$^+$.

$^1$H-NMR (400 MHz, DMSO-d6) δ[ppm]: 0.150 (12.85), 0.970 (0.98), 0.977 (16.00), 0.985 (0.93), 3.353 (2.20), 4.777 (1.37).

Compound 22.02

2-{[4-(hydroxymethyl)pyridin-2-yl]amino}-1H-benzimidazole-6-carbonitrile

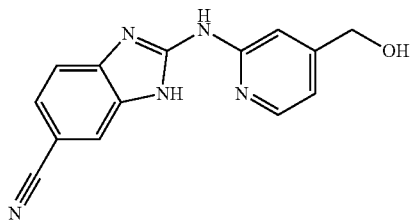 [SMILES: N#Cc1ccc2nc(Nc3cc(CO)ccn3)[nH]c2c1]

To a stirred solution 2-{[4-({[tert-butyl(dimethyl)silyl]oxy}methyl)pyridin-2-yl]amino}-1H-benzimidazole-6-carbonitrile (9.00 g, 23.7 mmol) in dioxane (230 mL) was added HCl in dioxane (36 mL, 4.0 M, 140 mmol). The mixture was stirred at 50° C. for 14 h. Further HCl (10 mL, 4.0 M, 40 mmol) in dioxane was added and the mixture was stirred at 50° C. for 14 h. Sodium bicarbonate (5.0 g) was added and the mixture was stirred for 30 minutes. THF (50 mL) was added, the mixture was filtered through magnesium sulfate and the solvent was removed in vacuum. Diethyl ether was added and a solid precipitated and was collected by filtration to give 8.20 g of the title compound as a salt that was used for the next step without purification.

LC-MS (Method 1): $R_t$=0.67 min; MS (ESIpos): m/z=266 [M+H]$^+$.

$^1$H-NMR (300 MHz, DMSO-d6) δ[ppm]: 0.000 (0.83), 0.178 (1.17), 0.884 (1.14), 0.993 (1.55), 3.627 (1.26), 4.650 (16.00), 7.184 (3.79), 7.205 (3.96), 7.428 (6.96), 7.728 (1.15), 7.756 (7.13), 7.761 (8.49), 7.768 (8.76), 7.796 (1.58), 8.031 (7.18), 8.420 (4.31), 8.438 (4.37).

Compound 22.03

2-{[4-(chloromethyl)pyridin-2-yl]amino}-1H-benzimidazole-6-carbonitrile

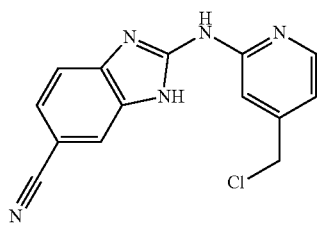 [SMILES: N#Cc1ccc2nc(Nc3cc(CCl)ccn3)[nH]c2c1]

To a suspension of 2-{[4-(hydroxymethyl)pyridin-2-yl]amino}-1H-benzimidazole-6-carbonitrile hydrochloride (6.00 g, 19.9 mmol) in dichloromethane (400 mL) and DMF (15 mL, 190 mmol) was added thionyl dichloride (2.9 mL, 40 mmol) and the mixture was stirred at r.t. for 14 h. A solution of potassium carbonate was added and the mixture was extracted with dichloromethane/methanol (20:1). A solid precipitated and was collected. The organic phase was separated, dried (sodium sulfate), filtered and the solvent was removed in vacuum to give a second solid batch. Both solids were combined and triturated with ethanol to give 4.50 g (80% yield) of the title compound.

LC-MS (Method 2): $R_t$=1.06 min; MS (ESIpos): m/z=284 [M+H]$^+$.

$^1$H-NMR (300 MHz, DMSO-d6) δ[ppm]: 2.525 (1.09), 4.790 (16.00), 5.756 (2.25), 7.052 (2.82), 7.057 (2.80), 7.069 (2.89), 7.074 (2.90), 7.276 (5.26), 7.425 (2.15), 7.430 (2.17), 7.452 (3.55), 7.457 (3.57), 7.533 (1.13), 7.825 (3.89), 8.346 (4.38), 8.364 (4.23), 11.063 (1.26).

Compound 22.04

2-[(4-{[4-(2-chlorophenyl)piperazin-1-yl]methyl}pyridin-2-yl)amino]-1H-benzimidazole-6-carbonitrile

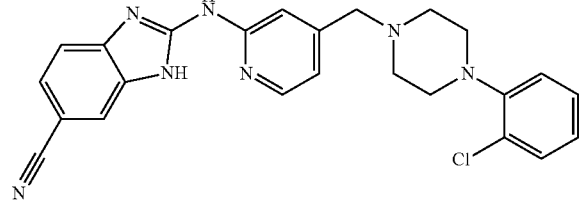

To a stirred solution of 2-{[4-(chloromethyl)pyridin-2-yl]amino}-1H-benzimidazole-6-carbonitrile (1.00 g, 3.52 mmol) in DMF (30 mL) was added potassium carbonate (2.44 g, 17.6 mmol) and 1-(2-chlorophenyl)piperazine (1.73 g, 8.81 mmol). The mixture was stirred at 60° C. for 2 h. Water was added and the mixture was extracted with ethyl acetate. The organic phase was washed with half-saturated sodium chloride solution, dried (sodium sulfate) and the solvent was removed in vacuum. Silicagel chromatography gave a solid that was triturated with ethanol to give 1.30 g (83% yield) of the title compound.

LC-MS (Method 2): R$_t$=1.40 min; MS (ESIpos): m/z=444 [M+H]$^+$.

$^1$H-NMR (400 MHz, DMSO-d6) δ[ppm]: 1.038 (0.69), 1.055 (1.42), 1.073 (0.75), 2.322 (0.42), 2.327 (0.59), 2.331 (0.43), 2.523 (2.21), 2.596 (8.11), 2.665 (0.63), 2.669 (0.80), 2.674 (0.58), 2.731 (0.45), 2.889 (0.56), 3.021 (9.78), 3.575 (16.00), 4.331 (0.42), 7.000 (3.25), 7.015 (5.11), 7.019 (4.03), 7.034 (4.70), 7.038 (4.89), 7.053 (3.29), 7.057 (3.44), 7.156 (3.89), 7.160 (4.13), 7.176 (5.48), 7.180 (5.06), 7.218 (8.23), 7.278 (3.35), 7.281 (3.67), 7.296 (4.01), 7.300 (4.57), 7.316 (2.30), 7.320 (2.26), 7.387 (6.39), 7.391 (6.28), 7.407 (6.65), 7.411 (6.45), 7.441 (2.92), 7.630 (0.62), 7.775 (0.77), 7.856 (1.10), 8.300 (3.08), 8.312 (3.02), 10.932 (0.69), 12.485 (0.98).

Compound 22.05

2-[(4-{[4-(2-chlorophenyl)piperazin-1-yl]methyl}pyridin-2-yl)amino]-N'-hydroxy-1H-benzimidazole-6-carboximidamide

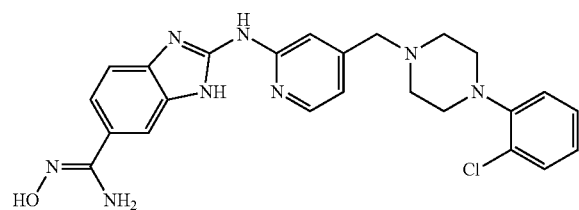 [SMILES: N/C(=N\O)c1ccc2nc(Nc3cc(CN4CCN(c5ccccc5Cl)CC4)ccn3)[nH]c2c1]

To a stirred suspension of 2-[(4-{[4-(2-chlorophenyl)piperazin-1-yl]methyl}pyridin-2-yl)amino]-1H-benzimidazole-6-carbonitrile (500 mg, 1.13 mmol) and triethylamine (360 µl, 2.6 mmol) in DMSO (15 mL, 210 mmol) was added hydroxylamine hydrochloride (176 mg, 98% purity, 2.48 mmol). The mixture was stirred at 75° C. for 14 h. Water was added, a solid precipitated and was collected by filtration and washed with water. The solid was dissolved in ethyl acetate/ethanol (1:1), filtered and the solvent was removed in vacuum to give 670 mg of the title compound as a crude product that was used without purification.

LC-MS (Method 2): R$_t$=1.17 min; MS (ESIpos): m/z=477 [M+H]$^+$.

$^1$H-NMR (400 MHz, DMSO-d6) δ[ppm]: 2.539 (16.00), 3.560 (0.97), 7.387 (0.73), 7.391 (0.68), 7.407 (0.52).

Compound 22.06

2-[(4-{[4-(2-chlorophenyl)piperazin-1-yl]methyl}pyridin-2-yl)amino]-N'-[(cyclopropylcarbonyl)oxy]-1H-benzimidazole-6-carboximidamide

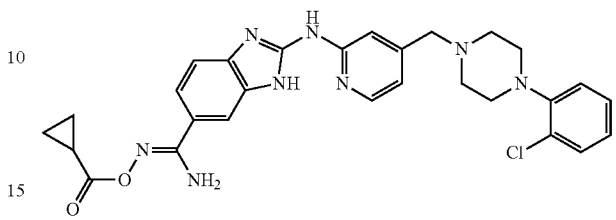

To a stirred solution of crude 2-[(4-{[4-(2-chlorophenyl)piperazin-1-yl]methyl}pyridin-2-yl)amino]-N'-hydroxy-1H-benzimidazole-6-carboximidamide (330 mg, approx. 553 µmol) in DMA (5 mL) was added DIPEA (390 µl, 2.2 mmol), cyclopropanecarboxylic acid (69 µl, 95% purity, 830 µmol) and PyBOP (432 mg, 830 µmol). The mixture was stirred at room temperature for 3 h. Water was added and a solid precipitated and was collected by filtration. The solid was triturated with ethanol. Aminophase-Silicagel chromatography gave 160 mg of the title compound.

LC-MS (Method 2): R$_t$=1.30 min; MS (ESIpos): m/z=545 [M+H]$^+$.

$^1$H-NMR (400 MHz, DMSO-d6) δ[ppm]: 0.067 (0.54), 0.799 (0.60), 0.816 (0.63), 0.822 (0.70), 0.852 (0.92), 0.860 (1.14), 0.874 (3.79), 0.882 (7.87), 0.885 (7.27), 0.894 (8.70), 0.900 (9.26), 0.907 (3.86), 0.915 (3.95), 0.920 (7.18), 0.928 (3.13), 0.941 (0.92), 1.037 (0.57), 1.054 (1.17), 1.071 (0.70), 1.232 (2.59), 1.257 (1.11), 1.296 (0.57), 1.712 (1.20), 1.720 (1.33), 1.728 (3.26), 1.737 (1.26), 1.745 (1.20), 1.888 (0.85), 1.901 (1.71), 1.908 (1.87), 1.920 (2.94), 1.932 (1.74), 1.939 (1.55), 1.955 (1.93), 1.986 (0.44), 2.084 (0.73), 2.322 (1.42), 2.326 (1.96), 2.331 (1.36), 2.523 (4.46), 2.539 (1.52), 2.596 (8.66), 2.664 (1.77), 2.668 (2.21), 2.673 (1.71), 2.782 (1.64), 2.942 (2.15), 2.990 (2.34), 3.006 (8.70), 3.016 (11.95), 3.022 (12.02), 3.565 (16.00), 5.169 (0.54), 5.755 (0.76), 6.701 (2.88), 6.958 (4.52), 6.971 (4.52), 7.017 (3.04), 7.021 (3.13), 7.036 (5.50), 7.040 (5.38), 7.055 (3.76), 7.059 (3.73), 7.098 (0.66), 7.161 (4.71), 7.165 (4.84), 7.181 (6.61), 7.185 (5.94), 7.215 (3.42), 7.280 (3.79), 7.284 (3.98), 7.303 (5.38), 7.318 (2.94), 7.322 (2.75), 7.357 (1.23), 7.390 (8.09), 7.394 (7.65), 7.410 (8.92), 7.414 (7.84), 7.484 (1.39), 7.612 (0.63), 7.713 (1.52), 7.864 (1.64), 8.264 (4.90), 8.277 (5.03), 10.701 (2.37), 12.231 (2.75).

Compound 22.07

2-[(4-{[4-(2-chlorophenyl)piperazin-1-yl]methyl}pyridin-2-yl)amino]-N'-[(3,3-dimethylbutanoyl)oxy]-1H-benzimidazole-6-carboximidamide

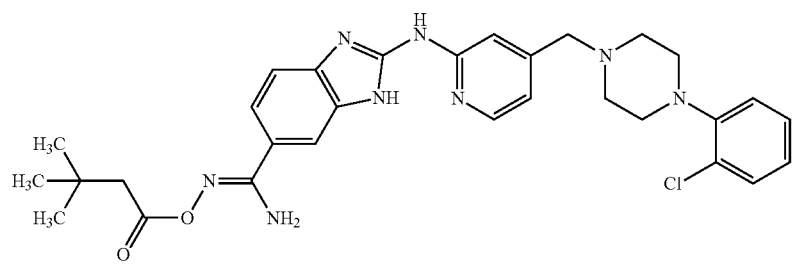 [SMILES: CC(C)(C)CC(=O)O/N=C(\N)c1ccc2nc(Nc3cc(CN4CCN(c5ccccc5Cl)CC4)ccn3)[nH]c2c1]

To a stirred solution of 2-[(4-{[4-(2-chlorophenyl)piperazin-1-yl]methyl}pyridin-2-yl)amino]-N'-hydroxy-1H-benzimidazole-6-carboximidamide (330 mg, approx. 553 µmol) in DMA (5 mL) was added DIPEA (390 µl, 2.2 mmol), 3,3-dimethylbutanoic acid (110 µl, 98% purity, 830 µmol) and PyBOP (432 mg, 830 µmol). The mixture was stirred at room temperature for 3 h. A sodium bicarbonate solution was added, the mixture was stirred for 15 minutes and the mixture was extracted with dichloromethane/methanol (20:1). The organic phase was dried (sodium sulfate), filtered and the solvent was removed in vacuum. Aminophase-silicagel chromatography gave 130 mg of the title compound.

LC-MS (Method 2): $R_t$=1.43 min; MS (ESIpos): m/z=575 [M+H]$^+$.

$^1$H-NMR (400 MHz, DMSO-d6) δ[ppm]: 1.040 (16.00), 2.346 (3.10), 2.598 (0.83), 3.018 (0.98), 3.025 (1.07), 3.567 (1.59), 7.036 (0.53), 7.040 (0.50), 7.058 (0.41), 7.161 (0.46), 7.165 (0.47), 7.182 (0.68), 7.185 (0.59), 7.280 (0.41), 7.284 (0.42), 7.389 (0.80), 7.393 (0.76), 7.409 (0.96), 7.413 (0.91), 8.265 (0.63), 8.279 (0.59).

Compound 23.01 tert-butyl 4-[(2-{[6-(pyrimidin-4-yl)-1H-benzimidazol-2-yl]amino}pyridin-4-yl)methyl]piperazine-1-carboxylate

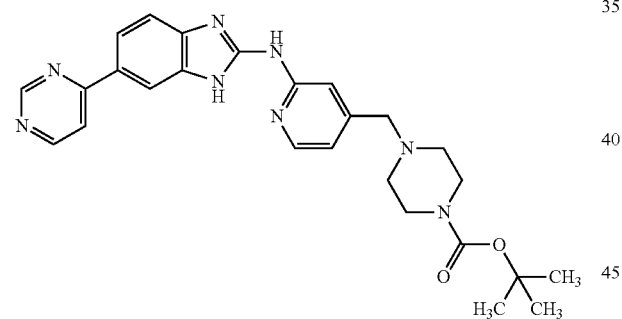

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-bromopyrimidine (208 mg, 1.31 mmol) in dioxane (5 mL) and water (0.9 mL) was added sodium carbonate (297 mg, 2.81 mmol) and Pd(dppf)Cl$_2$ (115 mg, 140 µmol) CH$_2$Cl$_2$. The mixture was heated to reflux for 19 h. Another 0.5 equivalents of 4-bromopyrimidine (74 mg, 0.47 mmol) were added and the reaction mixture was stirred for 24 h at 105° C. After cooling to r.t., dichloromethane was added, the mixture was dried (magnesium sulfate), filtered and the solvent was removed in vacuum. Silicagel chromatography gave 290 mg (64% yield) of the title compound.

LC-MS (Method 2): $R_t$=1.17 min; MS (ESIpos): m/z=487 [M+H]$^+$.

Compound 23.02

N-[4-(piperazin-1-ylmethyl)pyridin-2-yl]-6-(pyrimidin-4-yl)-1H-benzimidazol-2-amine hydrochloride

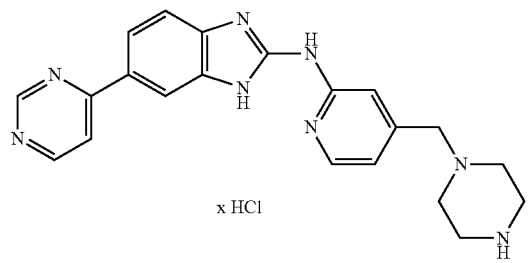 [SMILES: c1cc(-c2ccc3nc(Nc4cc(CN5CCNCC5)ccn4)[nH]c3c2)ncn1]

x HCl

Starting with tert-butyl 4-[(2-{[6-(pyrimidin-4-yl)-1H-benzimidazol-2-yl]amino}pyridin-4-yl)methyl]piperazine-1-carboxylate (290 mg, 596 µmol), Compound 23.02 was prepared analogously to the procedure for the preparation of Compound 01.05.

Yield: 288 mg of the title compound as crude product that was used for the next step without purification.

LC-MS (Method 2): $R_t$=0.81 min; MS (ESIpos): m/z=387 [M+H]$^+$.

Compound 23.03

(2-chloro-6-methylpyridin-4-yl)methanol

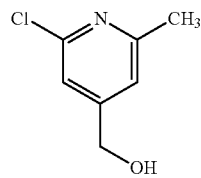

Methyl 2-chloro-6-methylpyridine-4-carboxylate (6.50 g, 35.0 mmol) was dissolved in dry THF (110 mL). Lithium aluminium hydride (1.65 g, 43.4 mmol) was added portionwise within 60 min. The reaction mixture was stirred at room temperature for the next 1.5 hours. Afterwards 50 mL water and 100 mL of an aqueous sodium hydroxide solution (15%) were added. This mixture was stirred for another hour and extracted three times with dichloromethane. The organic phase was washed with saturated sodium carbonate solution, dried (Whatman filter) and the solvent was removed in vacuum to give 4.4 g (80% yield) of the title compound which was used without further purification.

LC-MS (Method 2): $R_t$=0.67 min; MS (ESIpos): m/z=158 [M+H]$^+$.

$^1$H-NMR (400 MHz, DMSO-d6) δ[ppm]: 1.352 (0.50), 1.854 (0.64), 1.859 (0.61), 2.427 (16.00), 2.437 (1.41), 2.523 (0.74), 3.158 (1.14), 3.172 (1.31), 3.386 (1.09), 4.499 (3.82), 4.513 (3.88), 5.491 (1.29), 5.506 (2.86), 5.520 (1.25), 7.185 (3.22), 7.200 (3.13).

Compound 23.04

{2-[(2,4-dimethoxybenzyl)amino]-6-methylpyridin-4-yl}methanol

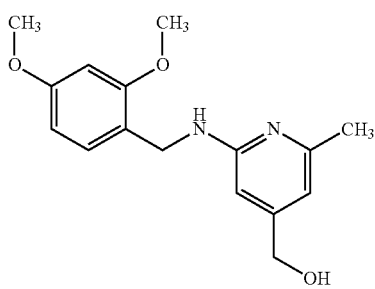 [SMILES: COc1ccc(CNc2cc(CO)cc(C)n2)c(OC)c1]

To a stirred solution of 2-chloro-6-methylpyridin-4-yl) methanol (2.10 g, 13.3 mmol) and 1-(2,4-dimethoxyphenyl) methanamine (8.0 mL, 53 mmol) in dioxane (57 mL) was added tris-(dibenzylidenaceton)-dipalladium(0) (1.22 g, 1.33 mmol), Xantphos (1.54 g, 2.66 mmol) and cesium carbonate (6.51 g, 20.0 mmol). The mixture was heated for 4 h at 100° C. under an argon atmosphere. The reaction mixture was allowed to cool down to room temperature and stirred for another 10 hours at room temperature. Ethyl acetate was added and the precipitate was filtered off. Amino phase silicagel chromatography gave 2.1 g (55% yield) of the title compound.

LC-MS (Method 2): $R_t$=0.98 min; MS (ESIpos): m/z=289 [M+H]$^+$.

$^1$H-NMR (400 MHz, DMSO-d6) δ[ppm]: 1.154 (1.09), 1.172 (2.08), 1.190 (1.07), 1.612 (1.86), 1.987 (4.10), 2.202 (7.99), 2.222 (2.21), 2.332 (1.98), 2.341 (0.64), 2.437 (0.65), 2.518 (1.15), 3.568 (1.26), 3.718 (2.13), 3.721 (16.00), 3.728 (3.92), 3.757 (3.16), 3.783 (0.91), 3.789 (2.88), 3.796 (10.81), 4.017 (0.95), 4.035 (0.94), 4.291 (2.41), 4.297 (2.61), 4.305 (2.61), 4.312 (2.25), 5.123 (0.61), 5.137 (1.33), 5.147 (1.21), 5.151 (1.05), 6.253 (3.87), 6.425 (1.12), 6.431 (1.02), 6.446 (1.29), 6.452 (1.11), 6.497 (0.71), 6.502 (0.75), 6.515 (1.01), 6.527 (0.97), 6.530 (2.54), 6.536 (1.79), 7.105 (1.64), 7.125 (1.51), 7.306 (0.68), 7.311 (0.85), 7.320 (0.79), 7.325 (0.77), 7.327 (0.69).

Compound 23.05

4-(bromomethyl)-6-methylpyridin-2-amine hydrobromide

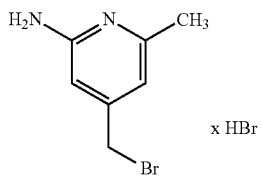

{2-[(2,4-dimethoxybenzyl)amino]-6-methylpyridin-4-yl}methanol (1.96 g, 6.80 mmol) was dissolved in aqueous hydrobromic acid (48%; 7.7 mL) and stirred for 3 h at 120° C. The reaction mixture was cooled down with ice water and the precipitate was filtered off. The precipitate was washed with acetone. Ethanol was added. The further precipitated solid was filtered off and combined with the first precipitate and discarded. The pH of the aqueous filtrate was brought to a basic range with saturated soda solution, extracted with ethyl acetate and dichloro methane. The combined organic phases were dried (Whatman filter) and the solvent was removed in vacuum to give 500 mg (26% yield) of the title compound.

LC-MS (Method 2): $R_t$=1.03 min; MS (ESIpos): m/z=307 [M+H]$^+$.

$^1$H-NMR (400 MHz, DMSO-d6) δ[ppm]: 1.173 (0.74), 1.368 (0.64), 1.385 (16.00), 1.988 (1.43), 2.189 (3.79), 2.266 (0.77), 2.279 (1.12), 2.292 (0.82), 3.305 (0.85), 3.323 (5.02), 5.736 (1.04), 6.187 (0.80), 6.277 (0.85).

Compound 23.06 tert-butyl 4-[(2-amino-6-methylpyridin-4-yl)methyl]piperazine-1-carboxylate

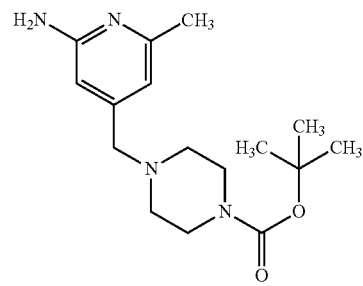 [SMILES: Cc1cc(CN2CCN(C(=O)OC(C)(C)C)CC2)cc(N)n1]

To a stirred suspension of 4-(bromomethyl)-6-methylpyridin-2-amine hydrobromide (920 mg, 3.26 mmol) in acetonitrile (6.9 mL) was added potassium carbonate (1.35 g, 9.79 mmol) and tert-butyl piperazine-1-carboxylate (668 mg, 3.59 mmol). The mixture was stirred at r.t. for 14 h. Water was added and the mixture was extracted with ethyl acetate. The organic phase was washed with half-saturated sodium chloride solution, dried (sodium sulfate) and the solvent was removed in vacuum. Aminophase-silicagel chromatography gave 1.00 g (100% yield) of the title compound.

LC-MS (Method 2): $R_t$=1.03 min; MS (ESIpos): m/z=307 [M+H]$^+$.

$^1$H-NMR (400 MHz, DMSO-d6) δ[ppm]: 1.173 (0.74), 1.368 (0.64), 1.385 (16.00), 1.988 (1.43), 2.189 (3.79), 2.266 (0.77), 2.279 (1.12), 2.292 (0.82), 3.305 (0.85), 3.323 (5.02), 5.736 (1.04), 6.187 (0.80), 6.277 (0.85).

Compound 23.07 tert-butyl 4-[(2-methyl-6-{[6-(4,4,5,5-tetramethyl-1,3,2-dioxaborolan-2-yl)-1H-benzimidazol-2-yl]amino}pyridin-4-yl)methyl]piperazine-1-carboxylate

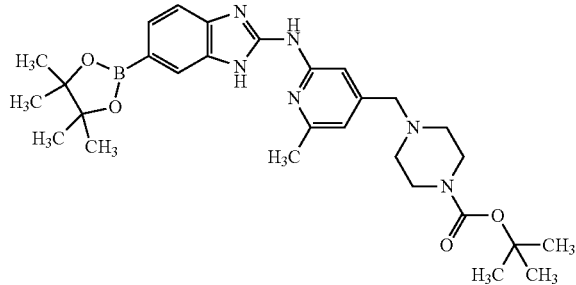 [SMILES: Cc1cc(CN2CCN(C(=O)OC(C)(C)C)CC2)cc(Nc2nc3ccc(B4OC(C)(C)C(C)(C)O4)cc3[nH]2)n1]

To a stirred solution of 1H-imidazole (63.5 mg, 933 µmol) and di-1H-imidazol-1-ylmethanethione (907 mg, 5.09 mmol) in dichloromethane (30 mL) was added tert-butyl 4-[(2-amino-6-methylpyridin-4-yl)methyl]piperazine-1-carboxylate (1.30 g, 4.24 mmol), dissolved in dichloromethane (30 mL) at 0° C. The mixture was stirred at r.t. for 14 h. 4-(4,4,5,5-tetramethyl-1,3,2-dioxaborolan-2-yl)benzene-1,2-diamine (1.19 g, 5.09 mmol) dissolved in dichloromethane (30 mL), was added and the mixture was stirred at r.t. for 5 h. Water was added and the mixture was extracted with dichloromethane. The organic phase was dried (sodium sulfate), and filtered. N,N'-dipropan-2-ylcarbodiimide (920 µl, 5.9 mmol) was added. The mixture was stirred at r.t. for 24 h. Further N,N'-dipropan-2-ylcarbodiimide (460 µl, 2.95 mmol) was added and the mixture was stirred at r.t. for 56 h. Saturated ammonium chloride solution was added, the mixture was stirred for 30 minutes and was extracted with dichloromethane. Silicagel chromatography gave 1.40 g (60% yield) of the title compound as a crude product, that was used without further purification.

LC-MS (Method 2): $R_t$=1.51 min; MS (ESIpos): m/z=549 [M+H]$^+$.

$^1$H-NMR (400 MHz, DMSO-d6) δ[ppm]: 1.035 (1.25), 1.052 (2.99), 1.070 (1.37), 1.241 (0.80), 1.289 (1.14), 1.301 (10.12), 1.385 (16.00), 1.389 (6.94), 1.392 (13.65), 2.193 (3.72), 2.267 (0.78), 2.280 (1.14), 2.292 (0.84), 2.323 (1.05), 2.327 (1.18), 2.331 (1.11), 2.337 (1.25), 2.349 (0.79), 2.399 (0.61), 2.518 (2.12), 2.523 (1.51), 2.530 (2.10), 2.728 (0.85), 2.888 (1.05), 3.267 (1.73), 3.307 (1.04), 3.422 (0.66), 3.435 (1.71), 3.439 (1.67), 3.452 (0.61), 4.358 (0.69), 6.199 (0.74), 6.284 (0.80), 6.761 (0.62), 6.984 (0.59).

Compound 23.08 tert-butyl 4-[(2-methyl-6-{[6-(pyrimidin-4-yl)-1H-benzimidazol-2-yl]amino}pyridin-4-yl)methyl]piperazine-1-carboxylate

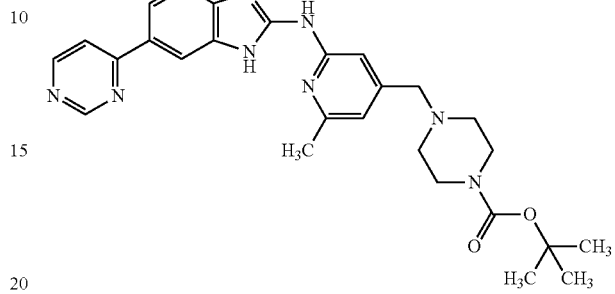

To a stirred solution of tert-butyl 4-[(2-methyl-6-{[6-(4,4,5,5-tetramethyl-1,3,2-dioxaborolan-2-yl)-1H-benzimidazol-2-yl]amino}pyridin-4-yl)methyl]piperazine-1-carboxylate (700 mg, 1.28 mmol) and 4-bromopyrimidine (365 mg, 2.30 mmol) in dioxane (6 mL) and water (1.2 mL) was added sodium carbonate (406 mg, 3.83 mmol) and Pd(dppf)Cl$_2$ (156 mg, 191 µmol). The mixture was heated to reflux for 24 h. Further 4-bromopyrimidine (101 mg, 0.64 mmol) was added and the mixture was heated to reflux for 4 h. Dichloromethane was added, the mixture was dried (magnesium sulfate), filtered and the solvent was removed in vacuum. Silicagel chromatography followed by aminophase-silicagel chromatography gave 130 mg (20% yield) of the title compound.

LC-MS (Method 2): $R_t$=1.27 min; MS (ESIpos): m/z=501 [M+H]$^+$.

Compound 23.09

N-[6-methyl-4-(piperazin-1-ylmethyl)pyridin-2-yl]-6-(pyrimidin-4-yl)-1H-benzimidazol-2-amine hydrochloride

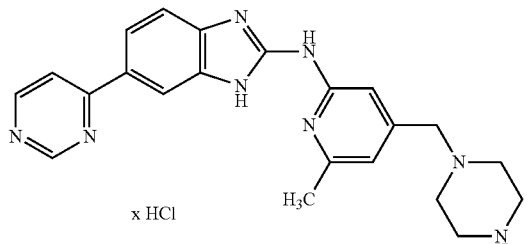

Starting with tert-butyl 4-[(2-methyl-6-{[6-(pyrimidin-4-yl)-1H-benzimidazol-2-yl]amino}pyridin-4-yl)methyl]piperazine-1-carboxylate (130 mg, 260 µmol), Compound 23.09 was prepared analogously to the procedure for the preparation of Compound 01.05.

Yield: 137 mg of the title compound as crude product that was used for the next step without purification.

LC-MS (Method 2): $R_t$=0.89 min; MS (ESIpos): m/z=401 [M+H]$^+$.

Compound 23.10

{2-[(diphenylmethylidene)amino]-6-(trifluoromethyl)pyridin-4-yl}methanol

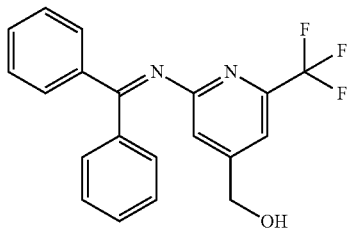 [SMILES: OCc1cc(N=C(c2ccccc2)c2ccccc2)nc(C(F)(F)F)c1]

To a stirred solution of (2-chloro-6-trifluoromethyl-pyridin-4-yl)-methanol: (10.0 g, 47.3 mmol) and -1,1-diphenylmethanimine (16 mL, 95 mmol) in dioxane (340 mL) was added tris-(dibenzylidenaceton)-dipalladium(0) (5.89 g, 9.45 mmol), (R)-(+)-2,2'-bis(diphenylphosphino)-1,1'-binaphthyl (5.89 g, 9.45 mmol) and cesium carbonate (38.5 g, 118 mmol). The mixture was heated overnight at 80° C. under an argon atmosphere. The reaction mixture was allowed to cool down to room temperature. The solvent was removed in vacuo and Amino phase silicagel chromatography gave 14.6 g (87% yield) of the title compound.

LC-MS (Method 2): $R_t$=1.29 min; MS (ESIpos): m/z=357 [M+H]$^+$.

Compound 23.11

[2-amino-6-(trifluoromethyl)pyridin-4-yl]methanol

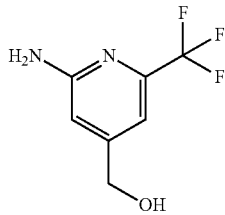 [SMILES: Nc1cc(CO)cc(C(F)(F)F)n1]

{2-[(diphenylmethylidene)amino]-6-(trifluoromethyl)pyridin-4-yl}methanol (14.6 g, 41.0 mmol) was dissolved in THF and 112 mL aqueous HCl (1M) were added. The reaction mixture was stirred at room temperature for 30 min. THF was removed in vacuo. The crude residue was dissolved in 1N NaOH and extracted with saturated sodium chloride solution, dried (Whatman filter) and the solvent was removed in vacuo. Amino phase silicagel chromatography gave 1.4 g (18% yield) of the title compound.

LC-MS (Method 2): $R_t$=0.67 min; MS (ESIpos): m/z=193 [M+H]$^+$.

Compound 23.12

4-(bromomethyl)-6-(trifluoromethyl)pyridin-2-amine hydrobromide

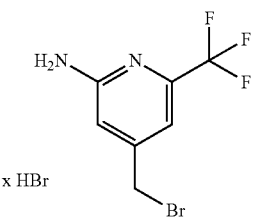 [SMILES: Nc1cc(CBr)cc(C(F)(F)F)n1]

x HBr

[2-amino-6-(trifluoromethyl)pyridin-4-yl]methanol (1.40 g, 7.29 mmol) was dissolved in aqueous hydrobromic acid (48%; 16.5 mL) and stirred for 4 h at 120° C. The reaction mixture was allowed to cool down to room temperature. The pH of the reaction mixture was brought to a basic range with saturated sodium carbonate solution. The mixture was extracted with ethyl acetate and dichloromethane. The combined organic phases were dried (Whatman filter) and the solvent was removed in vacuum to give 1.7 g (69% yield) of the title compound.

LC-MS (Method 2): $R_t$=1.04 min; MS (ESIpos): m/z=255 [M+H]$^+$.

Compound 23.13

(4-{[2-amino-6-(trifluoromethyl)pyridin-4-yl]methyl}piperazin-1-yl)(cyclopropyl)methanone

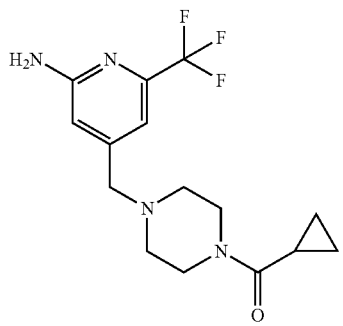 [SMILES: Nc1cc(CN2CCN(C(=O)C3CC3)CC2)cc(C(F)(F)F)n1]

To a stirred suspension of 4-(bromomethyl)-6-(trifluoromethyl)pyridin-2-amine hydrobromide (2.10 g, 6.25 mmol) in acetonitrile (13 mL) was added potassium carbonate and cyclopropyl(piperazin-1-yl)methanone (1.06 g, 6.88 mmol). The mixture was stirred at r.t. for 14 h. Water was added and the mixture was extracted with ethyl acetate. The organic phase was washed with half-saturated sodium chloride solution, dried (sodium sulfate) and the solvent was removed in vacuum. Silicagel chromatography gave 2.00 g (98% yield) of the title compound.

LC-MS (Method 2): $R_t$=0.94 min; MS (ESIpos): m/z=329 [M+H]$^+$.

Compound 23.14 cyclopropyl(4-{[2-{[6-(4,4,5,5-tetramethyl-1,3,2-dioxaborolan-2-yl)-1H-benzimidazol-2-yl]amino}-6-(trifluoromethyl)pyridin-4-yl]methyl}piperazin-1-yl)methanone

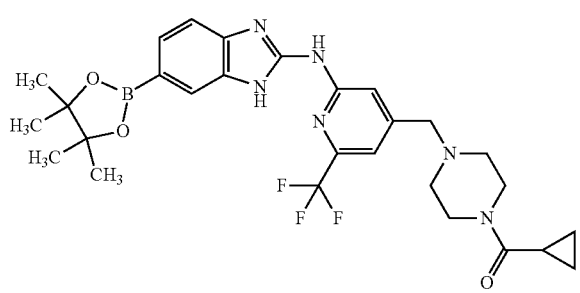 [SMILES: CC1(C)OB(c2ccc3nc(Nc4cc(CN5CCN(C(=O)C6CC6)CC5)cc(C(F)(F)F)n4)[nH]c3c2)OC1(C)C]

To a stirred solution of 1H-imidazole (91.2 mg, 1.34 mmol) and di-1H-imidazol-1-ylmethanethione (1.30 g, 7.31 mmol) in dichloromethane (50 mL) was added (4-{[2-amino-6-(trifluoromethyl)pyridin-4-yl]methyl}piperazin-1-yl)(cyclopropyl)methanone (2.00 g, 6.09 mmol), dissolved in dichloromethane (50 mL) at 0° C. The mixture was stirred at r.t. for 14 h. Further di-1H-imidazol-1-ylmethanethione (6.09 mmol) dissolved in dichloromethane was added and the mixture was stirred at r.t. for 14 h. 4-(4,4,5,5-tetramethyl-1,3,2-dioxaborolan-2-yl)benzene-1,2-diamine (1.71 g, 7.31 mmol) dissolved in dichloromethane (50 mL) was added and the mixture was stirred at r.t. for 56 h. Water was added and the mixture was extracted with dichloromethane. The organic phase was dried (sodium sulfate) and filtered. N,N'-dipropan-2-ylcarbodiimide (2.8 mL, 18 mmol) was added. The mixture was stirred at r.t. for 14 h. Further N,N'-dipropan-2-ylcarbodiimide (1.4 mL, 9.0 mmol) was added and the mixture was stirred at r.t. for 5 h. Saturated ammonium chloride solution was added, the mixture was stirred for 30 minutes and was extracted with dichloromethane. Silicagel chromatography gave 2.10 g of the title compound as a crude product, that was used without further purification.

LC-MS (Method 2): $R_t$=1.41 min; MS (ESIpos): m/z=571 [M+H]$^+$.

$^1$H-NMR (400 MHz, DMSO-d6) δ [ppm]: 0.686 (0.81), 0.705 (1.06), 0.710 (0.83), 0.716 (0.94), 0.724 (0.85), 0.728 (0.99), 1.035 (0.79), 1.052 (1.78), 1.065 (16.00), 1.070 (1.68), 1.272 (5.52), 1.289 (1.55), 1.301 (13.37), 3.439 (0.42), 3.452 (0.42), 3.654 (1.77), 3.942 (2.75), 4.360 (0.53), 7.370 (0.86).

Compound 23.15

(rac)-tert-butyl 4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate

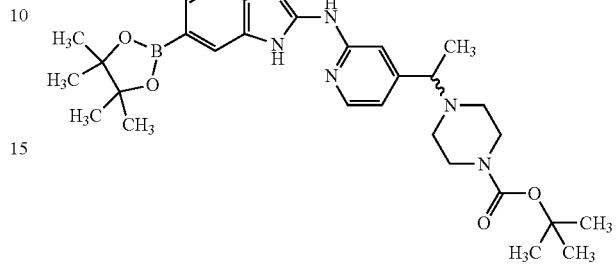

To a stirred solution of 1H-imidazole (502 mg, 7.37 mmol) and di-1H-imidazol-1-ylmethanethione (6.56 g, 36.8 mmol) in dichloromethane (90 mL) was added (rac)-tert-butyl 4-[1-(2-aminopyridin-4-yl)ethyl]piperazine-1-carboxylate (10.3 g, 33.5 mmol), dissolved in dichloromethane (90 mL) at 0° C. The mixture was stirred at r.t. for 4 h. 4-(4,4,5,5-tetramethyl-1,3,2-dioxaborolan-2-yl)benzene-1,2-diamine (7.84 g, 33.5 mmol), dissolved in dichloromethane (60 mL) was added and the mixture was stirred at r.t. for 14 h. Water was added and the mixture was extracted with dichloromethane. The organic phase was dried (sodium sulfate) and filtered. N,N'-dipropan-2-ylcarbodiimide (7.3 mL, 47 mmol) was added. The mixture was stirred at r.t. for 14 h. Saturated ammonium chloride solution was added, the mixture was stirred for 30 minutes and was extracted with dichloromethane. Silicagel chromatography followed by trituration with methanol/water gave 10.8 g (59% yield) of the title compound as a crude product, that was used without further purification.

LC-MS (Method 2): $R_t$=1.49 min; MS (ESIpos): m/z=549 [M+H]$^+$.

Compound 23.15.01 tert-butyl 4-[(1R or 1S)-1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate

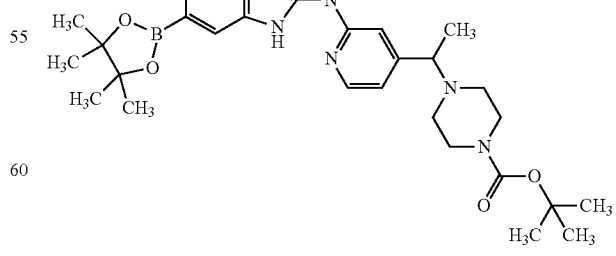

Starting with 4-(4,4,5,5-tetramethyl-1,3,2-dioxaborolan-2-yl)benzene-1,2-diamine (7.69 g, see Compound 01.03) and tert-butyl 4-[(1R or 1S)-1-(2-aminopyridin-4-yl)ethyl]

piperazine-1-carboxylate, see Compound 36.05.), Compound 23.15.01 was prepared analogously to the procedure for the preparation of Compound 23.15.

Yield: 6.9 g of the 85% pure title compound.
LC-MS (Method 2): $R_t$=1.48 min; MS (ESIpos): m/z=549 [M+H]$^+$.

Compound 23.16

(rac)-tert-butyl 4-[1-(2-{[6-(pyrimidin-4-yl)-1H-benzimidazol-2-yl]amino}pyridin-4-yl)ethyl]piperazine-1-carboxylate

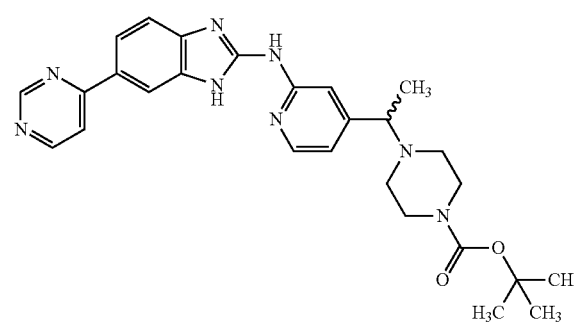

To a stirred solution of (rac)-tert-butyl 4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.00 g, 1.82 mmol) and 4-bromopyrimidine hydrochloride (570 mg, 2.92 mmol) in dioxane (9 mL) and water (1.8 mL) was added sodium carbonate (773 mg, 7.29 mmol) and Pd(dppf)C$_2$.CH$_2$Cl$_2$ (223 mg, 273 μmol). The mixture was heated to reflux for 24 h. Further 4-bromopyrimidine (180 mg) was added and the mixture was heated to reflux for 24 h. Dichloromethane was added, the mixture was dried (magnesium sulfate), filtered and the solvent was removed in vacuum. Silicagel chromatography gave 0.40 g (44% yield) of the title compound.

LC-MS (Method 2): $R_t$=1.21 min; MS (ESIpos): m/z=501 [M+H]$^+$.

Compound 23.17

(rac)-N-{4-[1-(piperazin-1-yl)ethyl]pyridin-2-yl}-6-(pyrimidin-4-yl)-1H-benzimidazol-2-amine hydrochloride

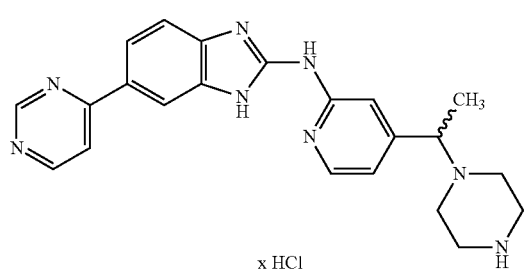 [SMILES: CC(c1ccnc(Nc2nc3ccc(-c4ccncn4)cc3[nH]2)c1)N1CCNCC1]

Starting with (rac)-tert-butyl 4-[1-(2-{[6-(pyrimidin-4-yl)-1H-benzimidazol-2-yl]amino}pyridin-4-yl)ethyl]piperazine-1-carboxylate (400 mg, 799 μmol), Compound 23.17 was prepared analogously to the procedure for the preparation of Compound 01.05.

Yield: 420 mg of the title compound as crude product that was used for the next step without purification.
LC-MS (Method 2): $R_t$=0.85 min; MS (ESIpos): m/z=401 [M+H]$^+$.

Compound 24.01

4-(2-methylpyrimidin-4-yl)-2-nitroaniline

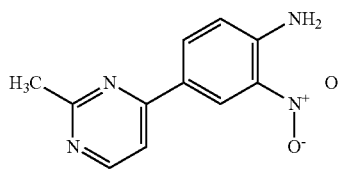

Starting with 4-chloro-2-methylpyrimidine (1.35 g, 10.5 mmol) and 2-nitro-4-(4,4,5,5-tetramethyl-1,3,2-dioxaborolan-2-yl)aniline (3.04 g, 11.5 mmol), Compound 24.01 was prepared analogously to the procedure for the preparation of Compound 02.01.

Yield: 1.85 g (78%) of the title compound.
LC-MS (Method 2): $R_t$=0.87 min; MS (ESIpos): m/z=231 [M+H]$^+$.

$^1$H-NMR (400 MHz, DMSO-d6) δ[ppm]: 2.363 (0.42), 2.647 (16.00), 7.114 (0.45), 7.127 (3.05), 7.150 (3.09), 7.506 (0.58), 7.774 (2.31), 7.788 (2.41), 7.818 (3.12), 8.139 (0.43), 8.145 (0.42), 8.183 (1.53), 8.188 (1.51), 8.205 (1.44), 8.211 (1.44), 8.653 (3.24), 8.667 (3.22), 8.866 (3.08), 8.871 (2.96).

Compound 24.02

4-(2-methylpyrimidin-4-yl)benzene-1,2-diamine

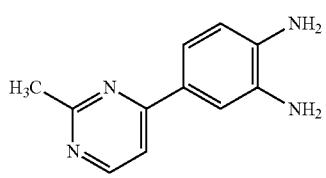

To a stirred solution of 4-(2-methylpyrimidin-4-yl)-2-nitroaniline (1.16 g, 5.03 mmol) in methanol (100 mL) was added palladium on carbon (10% w/w palladium) (161 mg, 151 μmol) and the mixture was stirred at r.t. in a hydrogen atmosphere for 3 h. The mixture was filtered and the solution was concentrated in vacuum. Silicagel chromatography gave 0.61 g (100% yield) of the title compound.

LC-MS (Method 2): $R_t$=0.65 min; MS (ESIpos): m/z=201 [M+H]$^+$.

Compound 24.03 tert-butyl 4-[(2-{[6-(2-methylpyrimidin-4-yl)-1H-benzimidazol-2-yl]amino}pyridin-4-yl)methyl]piperazine-1-carboxylate

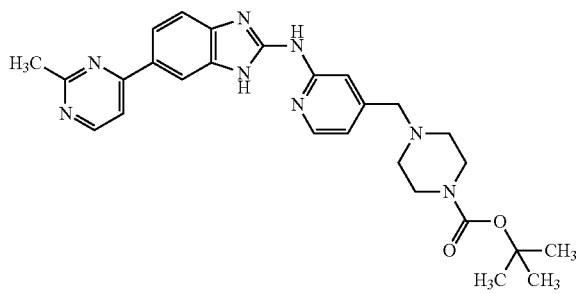 [SMILES: Cc1nccc(-c2ccc3nc(Nc4cc(CN5CCN(C(=O)OC(C)(C)C)CC5)ccn4)[nH]c3c2)n1]

To a stirred solution of 1H-imidazole (61.9 mg, 909 µmol) and di-1H-imidazol-1-ylmethanethione (810 mg, 4.54 mmol) in dichloromethane (50 mL) was added tert-butyl 4-[(2-aminopyridin-4-yl)methyl]piperazine-1-carboxylate (1.33 g, 4.54 mmol), dissolved in dichloromethane (25 mL), at 0° C. The mixture was stirred at r.t. for 14 h. 4-(2-methylpyrimidin-4-yl)benzene-1,2-diamine (910 mg, 4.54 mmol), dissolved in dichloromethane (25 mL), was added and the mixture was stirred at r.t. for 2 h. Water was added, and the mixture was extracted with dichloromethane. The organic phase was dried (sodium sulfate) and filtered. N,N'-dipropan-2-ylcarbodiimide (330 µl, 2.1 mmol) was added. The mixture was stirred at r.t. for 14 h. Further N,N'-dipropan-2-ylcarbodiimide (330 µl, 2.1 mmol) was added and the mixture was stirred at r.t. for 14 h. Saturated ammonium chloride solution was added, the mixture was stirred for 30 minutes and was extracted with dichloromethane. Silicagel chromatography gave 509 mg (67% yield) of the title compound as a crude product, that was used without further purification.

LC-MS (Method 2): $R_t$=1.22 min; MS (ESIpos): m/z=501 [M+H]$^+$.

$^1$H-NMR (400 MHz, DMSO-d6) δ[ppm]: 1.394 (16.00), 2.344 (1.50), 2.356 (2.01), 2.368 (1.46), 2.523 (1.06), 2.558 (0.70), 2.663 (4.99), 3.308 (0.91), 3.385 (1.13), 3.395 (0.98), 3.410 (1.12), 3.500 (2.18), 6.934 (0.54), 6.946 (0.54), 7.171 (0.84), 7.922 (0.52), 8.260 (1.01), 8.272 (0.94), 8.638 (1.13), 8.652 (1.02).

Compound 24.04

6-(2-methylpyrimidin-4-yl)-N-[4-(piperazin-1-ylmethyl)pyridin-2-yl]-1H-benzimidazol-2-amine hydrochloride

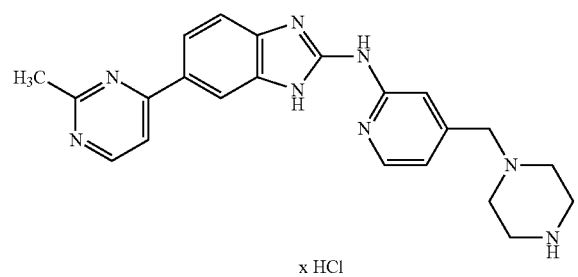 [SMILES: Cc1nccc(-c2ccc3nc(Nc4cc(CN5CCNCC5)ccn4)[nH]c3c2)n1]

Starting with tert-butyl 4-[(2-{[6-(2-methylpyrimidin-4-yl)-1H-benzimidazol-2-yl]amino}pyridin-4-yl)methyl]piperazine-1-carboxylate (504 mg, 1.01 mmol), Compound 24.04 was prepared analogously to the procedure for the preparation of Compound 01.05.

Yield: 560 mg of the title compound as crude product that was used for the next step without purification.

LC-MS (Method 2): $R_t$=0.87 min; MS (ESIpos): m/z=401 [M+H]$^+$.

Compound 24.05 tert-butyl 4-[(2-methyl-6-{[6-(2-methylpyrimidin-4-yl)-1H-benzimidazol-2-yl]amino}pyridin-4-yl)methyl]piperazine-1-carboxylate

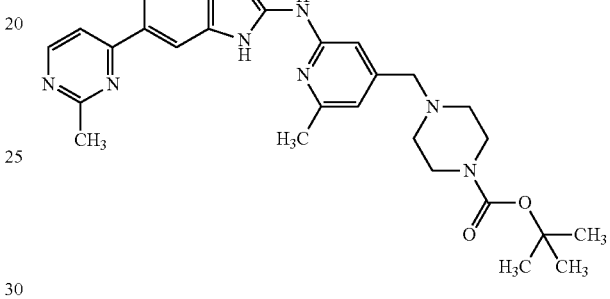

To a stirred solution of tert-butyl 4-[(2-methyl-6-{[6-(4,4,5,5-tetramethyl-1,3,2-dioxaborolan-2-yl)-1H-benzimidazol-2-yl]amino}pyridin-4-yl)methyl]piperazine-1-carboxylate (600 mg, 1.09 mmol) and 4-chloro-2-methylpyrimidine (253 mg, 1.97 mmol) in dioxane (5 mL) and water (1.1 mL) was added sodium carbonate (348 mg, 3.28 mmol) and Pd(dppf)C$_2$. CH$_2$Cl$_2$ (134 mg, 164 µmol). The mixture was heated to reflux for 24 h. Dichloromethane was added, the mixture was dried (magnesium sulfate), filtered and the solvent was removed in vacuum. Aminophase-silicagel chromatography followed by preparative reverse phase HPLC (gradient of water and acetonitrile containing trifluoroacetic acid as additive) gave 132 mg (24% yield) of the title compound.

LC-MS (Method 2): $R_t$=1.28 min; MS (ESIpos): m/z=515 [M+H]$^+$.

Compound 24.06

N-[6-methyl-4-(piperazin-1-ylmethyl)pyridin-2-yl]-6-(2-methylpyrimidin-4-yl)-1H-benzimidazol-2-amine hydrochloride

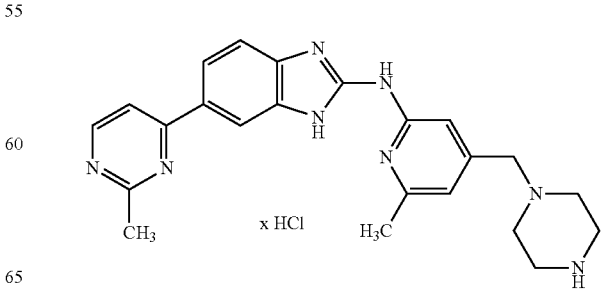

Starting with tert-butyl 4-[(2-methyl-6-{[6-(2-methylpyrimidin-4-yl)-1H-benzimidazol-2-yl]amino}pyridin-4-yl)methyl]piperazine-1-carboxylate (132 mg, 256 μmol), Compound 24.06 was prepared analogously to the procedure for the preparation of Compound 01.05.

Yield: 150 mg of the title compound as crude product that was used for the next step without purification.

LC-MS (Method 2): $R_t$=0.94 min; MS (ESIpos): m/z=415 [M+H]$^+$.

Compound 24.07

(rac)-tert-butyl 4-[1-(2-{[6-(2-methylpyrimidin-4-yl)-1H-benzimidazol-2-yl]amino}pyridin-4-yl)ethyl]piperazine-1-carboxylate

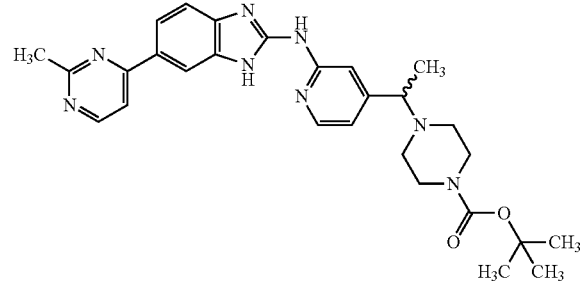 [SMILES: Cc1nccc(-c2ccc3nc(Nc4cc(C(C)N5CCN(C(=O)OC(C)(C)C)CC5)ccn4)[nH]c3c2)n1]

To a stirred solution of (rac)-tert-butyl 4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.00 g, 1.82 mmol) and 4-bromo-2-methylpyrimidine (505 mg, 2.92 mmol) in dioxane (9 mL) and water (1.8 mL) was added sodium carbonate (773 mg, 7.29 mmol) and Pd(dppf)Cl$_2$·CH$_2$Cl$_2$ (223 mg, 273 μmol). The mixture was heated to reflux for 24 h. Dichloromethane was added, the mixture was dried (magnesium sulfate), filtered and the solvent was removed in vacuum. Silicagel chromatography gave 0.70 g (75% yield) of the title compound.

LC-MS (Method 2): $R_t$=1.25 min; MS (ESIpos): m/z=515 [M+H]$^+$.

Compound 24.08

(rac)-6-(2-methylpyrimidin-4-yl)-N-{4-[1-(piperazin-1-yl)ethyl]pyridin-2-yl}-1H-benzimidazol-2-amine hydrochloride

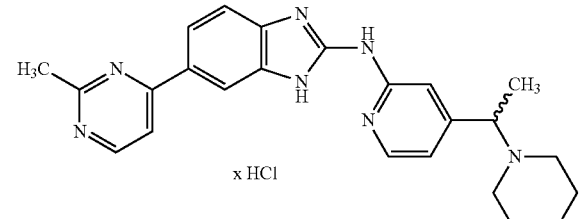

Starting with (rac)-tert-butyl 4-[1-(2-{[6-(2-methylpyrimidin-4-yl)-1H-benzimidazol-2-yl]amino}pyridin-4-yl)ethyl]piperazine-1-carboxylate (700 mg, 1.36 mmol), Compound 24.08 was prepared analogously to the procedure for the preparation of Compound 01.05.

Yield: 830 mg of the title compound as crude product that was used for the next step without purification.

LC-MS (Method 2): $R_t$=0.89 min; MS (ESIpos): m/z=415 [M+H]$^+$.

Compound 25.01

6-(2-methoxypyrimidin-4-yl)-N-[4-(piperazin-1-ylmethyl)pyridin-2-yl]-1H-benzimidazol-2-amine hydrochloride

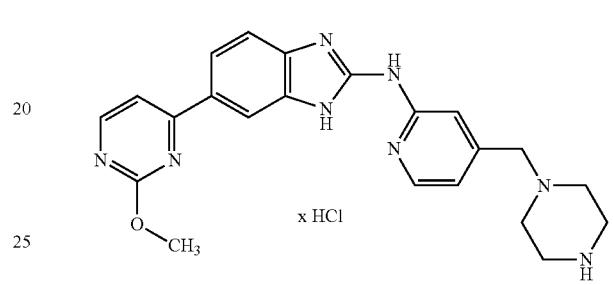

Starting with tert-butyl 4-[(2-{[6-(2-methoxypyrimidin-4-yl)-1H-benzimidazol-2-yl]amino}pyridin-4-yl)methyl]piperazine-1-carboxylate (480 mg, 929 μmol), Compound 25.01 was prepared analogously to the procedure for the preparation of Compound 01.05.

Yield: 460 mg of the title compound as crude product that was used for the next step without purification.

LC-MS (Method 2): $R_t$=0.92 min; MS (ESIpos): m/z=417 [M+H]$^+$.

Compound 26.01

6-(2-ethoxypyrimidin-4-yl)-N-[4-(piperazin-1-ylmethyl)pyridin-2-yl]-1H-benzimidazol-2-amine hydrochloride

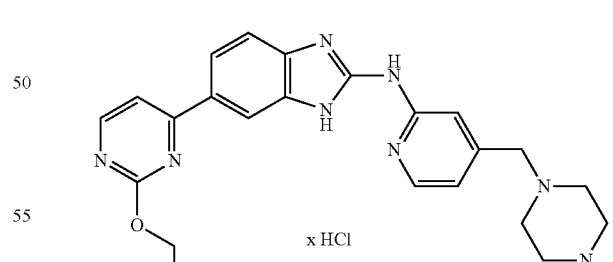

Starting with tert-butyl 4-[(2-{[6-(2-ethoxypyrimidin-4-yl)-1H-benzimidazol-2-yl]amino}pyridin-4-yl)methyl]piperazine-1-carboxylate (460 mg, 867 μmol), Compound 26.01 was prepared analogously to the procedure for the preparation of Compound 01.05.

Yield: 480 mg of the title compound as crude product that was used for the next step without purification.

LC-MS (Method 2): $R_t$=1.03 min; MS (ESIpos): m/z=431 [M+H]$^+$.

Compound 26.02

(rac)-tert-butyl 4-[-1-(2-{[6-(2-ethoxypyrimidin-4-yl)-1H-benzimidazol-2-yl]amino}pyridin-4-yl)ethyl]piperazine-1-carboxylate

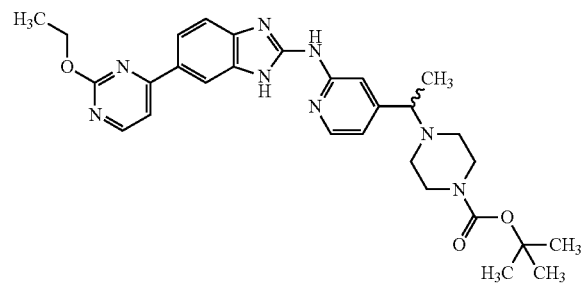 [SMILES: CCOc1nccc(-c2ccc3nc(Nc4cc(C(C)N5CCN(C(=O)OC(C)(C)C)CC5)ccn4)[nH]c3c2)n1]

To a stirred solution of tert-butyl (rac)-4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (435 mg, 793 µmol) and 4-chloro-2-ethoxypyrimidine (176 mg, 1.11 mmol) in dioxane (5 mL) and water (0.8 mL) was added sodium carbonate (252 mg, 2.38 mmol) and Pd(dppf)Cl$_2$. CH$_2$Cl$_2$ (97.1 mg, 119 µmol). The mixture was heated to reflux for 24 h. Dichloromethane was added, the mixture was dried (magnesium sulfate), filtered and the solvent was removed in vacuum. Silicagel chromatography gave 215 mg (50% yield) of the title compound.

LC-MS (Method 2): $R_t$=1.36 min; MS (ESIpos): m/z=545 [M+H]$^+$.

Compound 26.03

(rac)-6-(2-ethoxypyrimidin-4-yl)-N-{4-[1-(piperazin-1-yl)ethyl]pyridin-2-yl}-1H-benzimidazol-2-amine hydrochloride

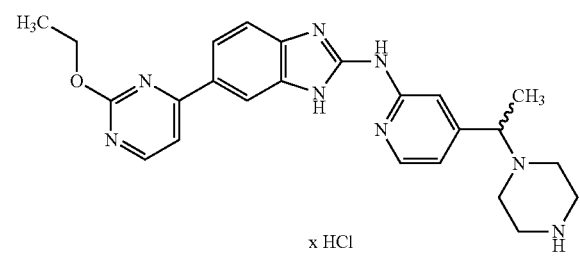 [SMILES: CCOc1nccc(-c2ccc3nc(Nc4cc(C(C)N5CCNCC5)ccn4)[nH]c3c2)n1]

Starting with (rac)-tert-butyl 4-[1-(2-{[6-(2-ethoxypyrimidin-4-yl)-1H-benzimidazol-2-yl]amino}pyridin-4-yl)ethyl]piperazine-1-carboxylate (215 mg, 395 µmol), Compound 26.03 was prepared analogously to the procedure for the preparation of Compound 01.05.

Yield: 370 mg of the title compound as crude product that was used for the next step without purification.

LC-MS (Method 2): $R_t$=1.04 min; MS (ESIpos): m/z=445 [M+H]$^+$.

Compound 27.01 tert-butyl 4-{[2-({6-[2-(trifluoromethyl)pyrimidin-4-yl]-1H-benzimidazol-2-yl}amino)pyridin-4-yl]methyl}piperazine-1-carboxylate

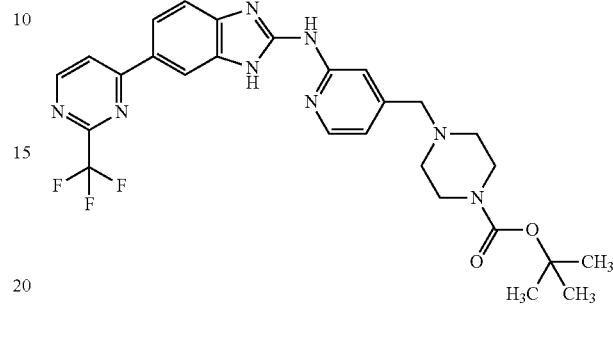

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-2-(trifluoromethyl)pyrimidine (307 mg, 1.68 mmol) in dioxane (5 mL) and water (0.9 mL) was added sodium carbonate (297 mg, 2.81 mmol) and Pd(dppf)Cl$_2$. CH$_2$Cl$_2$ (115 mg, 140 µmol). The mixture was heated to reflux for 24 h. Dichloromethane was added, the mixture was dried (magnesium sulfate), filtered and the solvent was removed in vacuum. Silicagel chromatography gave 540 mg (83% yield) of the title compound.

LC-MS (Method 2): $R_t$=1.40 min; MS (ESIpos): m/z=555 [M+H]$^+$.

Compound 27.02

N-[4-(piperazin-1-ylmethyl)pyridin-2-yl]-6-[2-(trifluoromethyl)pyrimidin-4-yl]-1H-benzimidazol-2-amine hydrochloride

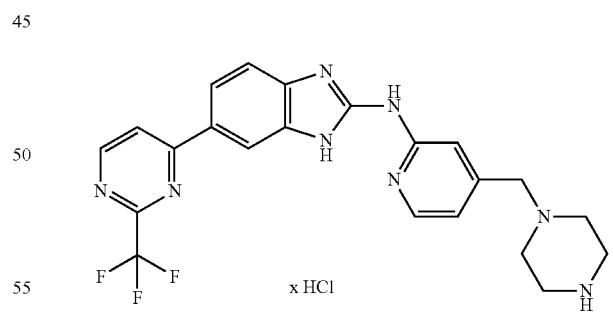

Starting with tert-butyl 4-{[2-({6-[2-(trifluoromethyl)pyrimidin-4-yl]-1H-benzimidazol-2-yl}amino)pyridin-4-yl]methyl}piperazine-1-carboxylate (540 mg, 974 µmol), Compound 27.02 was prepared analogously to the procedure for the preparation of Compound 01.05.

Yield: 560 mg of the title compound as crude product that was used for the next step without purification.

LC-MS (Method 2): $R_t$=1.08 min; MS (ESIpos): m/z=455 [M+H]$^+$.

Compound 29.01

(rac)-tert-butyl 4-{1-[2-({6-[6-(trifluoromethyl)py-rimidin-4-yl]-1H-benzimidazol-2-yl}amino)pyridin-4-yl]ethyl}piperazine-1-carboxylate

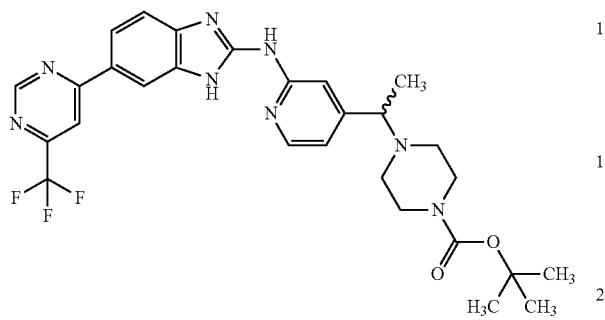

To a stirred solution of tert-butyl (rac)-4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.00 g, 1.82 mmol) and 4-bromo-6-(trifluoromethyl)pyrimidine (786 mg, 3.46 mmol) in dioxane (9 mL) and water (1.8 mL) was added sodium carbonate (773 mg, 7.29 mmol) and Pd(dppf)Cl$_2$·CH$_2$Cl$_2$ (223 mg, 273 µmol). The mixture was heated to reflux for 24 h. Dichloromethane was added, the mixture was dried (magnesium sulfate), filtered and the solvent was removed in vacuum. Silicagel chromatography gave 330 mg (32% yield) of the title compound.

LC-MS (Method 2): R$_t$=1.42 min; MS (ESIpos): m/z=569 [M+H]$^+$.

Compound 29.02

(rac)-N-{4-[1-(piperazin-1-yl)ethyl]pyridin-2-yl}-6-[6-(trifluoromethyl)pyrimidin-4-yl]-1H-benzimidazol-2-amine

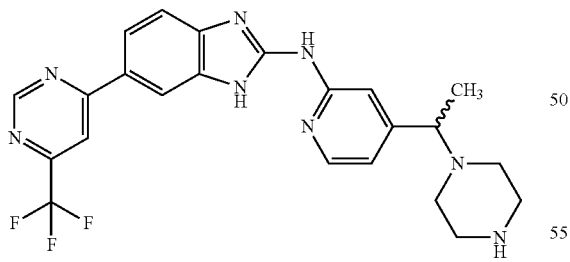

Starting with (rac)-tert-butyl 4-{1-[2-({6-[6-(trifluoromethyl)pyrimidin-4-yl]-1H-benzimidazol-2-yl}amino)pyridin-4-yl]ethyl}piperazine-1-carboxylate (330 mg, 580 µmol), Compound 29.02 was prepared analogously to the procedure for the preparation of Compound 01.05.

Yield: 370 mg of the title compound as crude product that was used for the next step without purification.

LC-MS (Method 2): R$_t$=1.12 min; MS (ESIpos): m/z=469 [M+H]$^+$.

Compound 30.01 tert-butyl 4-[(2-{[6-(6-methyl pyrimidin-4-yl)-1H-benzimidazol-2-yl]amino}pyridin-4-yl)methyl]piperazine-1-carboxylate

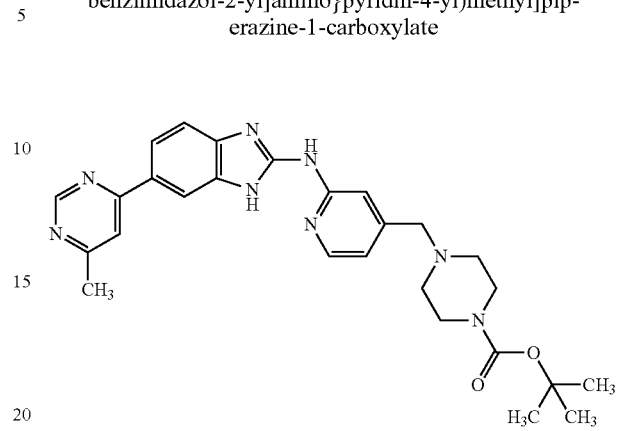

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-bromo-6-methylpyrimidine (291 mg, 1.68 mmol) in dioxane (5 mL) and water (0.9 mL) was added sodium carbonate (297 mg, 2.81 mmol) and Pd(dppf)Cl$_2$·CH$_2$Cl$_2$ (153 mg, 187 µmol). The mixture was heated to reflux for 24 h. Dichloromethane was added, the mixture was dried (magnesium sulfate), filtered and the solvent was removed in vacuum. Aminophase-silicagel chromatography gave 480 mg (100% yield) of the title compound as a crude product that was used without further purification.

LC-MS (Method 2): R$_t$=1.20 min; MS (ESIpos): m/z=501 [M+H]$^+$.

Compound 30.02

6-(6-methylpyrimidin-4-yl)-N-[4-(piperazin-1-ylmethyl)pyridin-2-yl]-1H-benzimidazol-2-amine hydrochloride

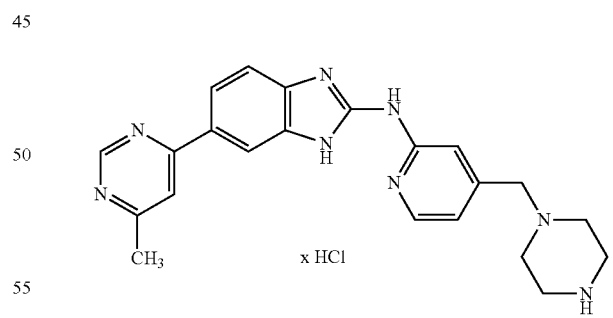

Starting with tert-butyl 4-[(2-{[6-(6-methylpyrimidin-4-yl)-1H-benzimidazol-2-yl]amino}pyridin-4-yl)methyl]piperazine-1-carboxylate (480 mg, 959 µmol), Compound 30.02 was prepared analogously to the procedure for the preparation of Compound 01.05.

Yield: 600 mg of the title compound as crude product that was used for the next step without purification.

LC-MS (Method 2): R$_t$=0.86 min; MS (ESIpos): m/z=401 [M+H]$^+$.

Compound 30.03

(rac)-tert-butyl 4-[1-(2-{[6-(6-methylpyrimidin-4-yl)-1H-benzimidazol-2-yl]amino}pyridin-4-yl)ethyl]piperazine-1-carboxylate

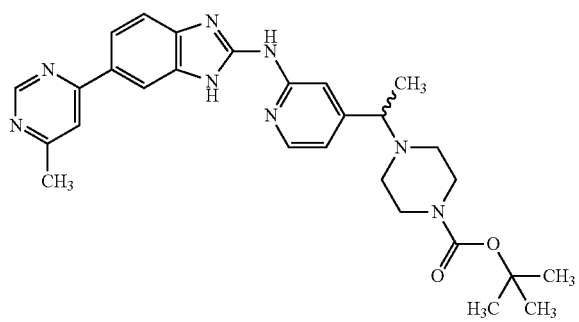

To a stirred solution of (rac)-tert-butyl 4-[(1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.00 g, 1.82 mmol) and 4-bromo-6-methylpyrimidine (631 mg, 3.65 mmol) in dioxane (9 mL) and water (1.8 mL) was added sodium carbonate (773 mg, 7.29 mmol) and Pd(dppf)Cl$_2$·CH$_2$Cl$_2$ (223 mg, 273 µmol). The mixture was heated to reflux for 24 h. Dichloromethane was added, the mixture was dried (magnesium sulfate), filtered and the solvent was removed in vacuum. Aminophase-silicagel chromatography gave 0.70 g (75% yield) of the title compound.

LC-MS (Method 2): R$_t$=1.24 min; MS (ESIpos): m/z=515 [M+H]$^+$.

Compound 30.04

(rac) 6-(6-methylpyrimidin-4-yl)-N-{4-[1-(piperazin-1-yl)ethyl]pyridin-2-yl}-1H-benzimidazol-2-amine hydrochloride

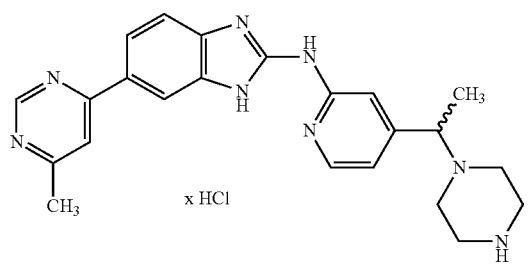 [SMILES: Cc1cc(-c2ccc3nc(Nc4cc(C(C)N5CCNCC5)ccn4)[nH]c3c2)ncn1]

Starting with (rac)-tert-butyl 4-[1-(2-{[6-(6-methylpyrimidin-4-yl)-1H-benzimidazol-2-yl]amino}pyridin-4-yl)ethyl]piperazine-1-carboxylate (700 mg, 1.36 mmol), Compound 30.04 was prepared analogously to the procedure for the preparation of Compound 01.05.

Yield: 600 mg of the title compound as crude product that was used for the next step without purification.

LC-MS (Method 2): R$_t$=0.89 min; MS (ESIpos): m/z=415 [M+H]$^+$.

Compound 31.01 tert-butyl 4-[(2-{[6-(2,6-dimethylpyrimidin-4-yl)-1H-benzimidazol-2-yl]amino}pyridin-4-yl)methyl]piperazine-1-carboxylate

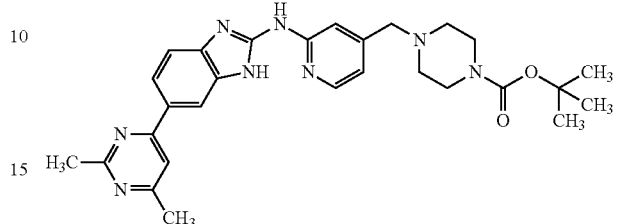

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-2,6-dimethylpyrimidine (267 mg, 1.87 mmol), Compound 31.01 was prepared analogously to the procedure for the preparation of Compound 02.01.

Yield: 180 mg (37% yield) of the title compound.

LC-MS (Method 2): R$_t$=1.23 min; MS (ESIpos): m/z=515 [M+H]$^+$.

$^1$H-NMR (400 MHz, DMSO-d6) δ [ppm]: 1.395 (16.00), 2.344 (0.90), 2.357 (1.30), 2.369 (0.91), 2.461 (4.52), 2.615 (4.62), 3.348 (1.11), 3.500 (1.59), 5.759 (1.20), 7.900 (0.62), 7.904 (0.60), 8.256 (0.82), 8.270 (0.78).

Compound 31.02

6-(2,6-dimethylpyrimidin-4-yl)-N-[4-(piperazin-1-ylmethyl)pyridin-2-yl]-1H-benzimidazol-2-amine hydrochloride

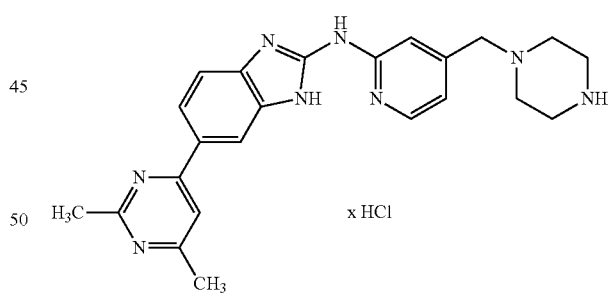

Starting with tert-butyl 4-[(2-{[6-(2,6-dimethylpyrimidin-4-yl)-1H-benzimidazol-2-yl]amino}pyridin-4-yl)methyl]piperazine-1-carboxylate (180 mg, 350 µmol), Compound 31.02 was prepared analogously to the procedure for the preparation of Compound 01.05.

Yield: 300 mg of the title compound as crude product that was used for the next step without purification.

LC-MS (Method 2): R$_t$=0.88 min; MS (ESIpos): m/z=415 [M+H]$^+$.

$^1$H-NMR (400 MHz, DMSO-d6) δ[ppm]: 1.050 (1.02), 1.063 (2.72), 1.067 (0.66), 2.618 (14.37), 2.754 (16.00), 3.162 (6.96), 3.341 (1.31), 3.383 (1.12), 3.393 (1.07), 3.408 (1.39), 3.425 (2.78), 3.443 (3.83), 3.455 (2.82), 3.460 (2.44), 3.484 (0.79), 3.551 (1.21), 4.424 (1.10), 7.566 (2.80), 7.588 (1.03), 7.783 (2.68), 7.805 (2.74), 8.062 (2.21), 8.220 (2.22), 8.224 (2.16), 8.241 (1.97), 8.246 (1.88), 8.536 (2.01), 8.549 (1.84), 8.586 (3.18), 8.589 (3.09).

Compound 32.01 tert-butyl 4-[(2-{[6-(5,6-dimethylpyrimidin-4-yl)-1H-benzimidazol-2-yl]amino}pyridin-4-yl)methyl]piperazine-1-carboxylate

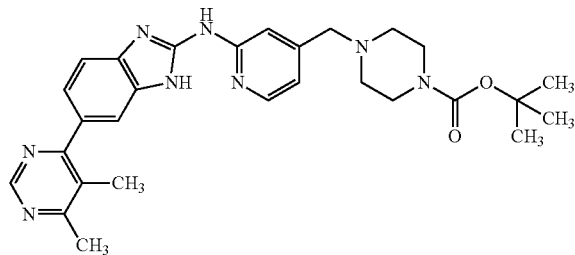 [SMILES: Cc1ncnc(-c2ccc3nc(Nc4cc(CN5CCN(C(=O)OC(C)(C)C)CC5)ccn4)[nH]c3c2)c1C]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-5,6-dimethylpyrimidine (267 mg, 1.87 mmol), Compound 32.01 was prepared analogously to the procedure for the preparation of Compound 02.01.

Yield: 210 mg (44%) of the title compound.

LC-MS (Method 2): $R_t$=1.19 min; MS (ESIpos): m/z=515 [M+H]$^+$.

$^1$H-NMR (400 MHz, DMSO-d6) δ[ppm]: 1.066 (16.00), 1.395 (9.02), 2.519 (2.20), 3.159 (1.79), 3.172 (1.91), 3.939 (2.61).

Compound 32.02

6-(5,6-dimethylpyrimidin-4-yl)-N-[4-(piperazin-1-ylmethyl)pyridin-2-yl]-1H-benzimidazol-2-amine hydrochloride

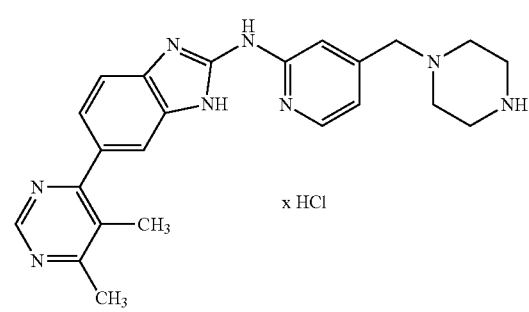 [SMILES: Cc1ncnc(-c2ccc3nc(Nc4cc(CN5CCNCC5)ccn4)[nH]c3c2)c1C]

Starting with tert-butyl 4-[(2-{[6-(5,6-dimethylpyrimidin-4-yl)-1H-benzimidazol-2-yl]amino}pyridin-4-yl)methyl]piperazine-1-carboxylate (280 mg, 544 µmol), Compound 32.02 was prepared analogously to the procedure for the preparation of Compound 01.05.

Yield: 300 mg of the title compound as crude product that was used for the next step without purification.

LC-MS (Method 2): $R_t$=0.87 min; MS (ESIpos): m/z=416 [M+H]$^+$.

$^1$H-NMR (400 MHz, DMSO-d6) δ[ppm]: 1.062 (16.00), 2.318 (0.97), 2.321 (1.01), 2.335 (5.05), 2.582 (5.48), 3.161 (8.07), 3.456 (1.17), 7.592 (0.96), 7.596 (0.87), 7.613 (1.21), 7.617 (1.23), 7.780 (1.05), 7.801 (0.83), 7.914 (1.09), 7.918 (1.14), 8.988 (1.86).

Compound 33.01

6-(2,5-dimethylpyrimidin-4-yl)-N-[4-(piperazin-1-ylmethyl)pyridin-2-yl]-1H-benzimidazol-2-amine hydrochloride

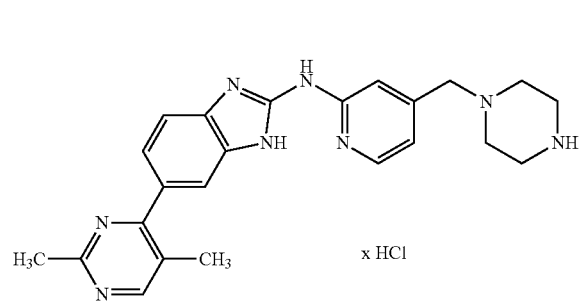 [SMILES: Cc1ncc(C)c(-c2ccc3nc(Nc4cc(CN5CCNCC5)ccn4)[nH]c3c2)n1]

Starting with tert-butyl 4-[(2-{[6-(2,5-dimethylpyrimidin-4-yl)-1H-benzimidazol-2-yl]amino}pyridin-4-yl)methyl]piperazine-1-carboxylate (390 mg, 758 µmol), Compound 33.01 was prepared analogously to the procedure for the preparation of Compound 01.05.

Yield: 400 mg of the title compound as crude product that was used for the next step without purification.

LC-MS (Method 2): $R_t$=0.86 min; MS (ESIpos): m/z=415 [M+H]$^+$.

$^1$H-NMR (400 MHz, DMSO-d6) δ[ppm]: 2.409 (11.56), 2.695 (13.19), 3.057 (1.28), 3.160 (16.00), 3.468 (2.69), 5.760 (7.21), 7.582 (2.42), 7.726 (1.42), 7.730 (1.37), 7.747 (2.31), 7.750 (2.42), 7.789 (3.08), 7.811 (1.58), 8.049 (2.58), 8.053 (2.81), 8.559 (1.87), 8.572 (1.71), 8.760 (4.15).

Compound 34.01

(rac)-tert-butyl 4-[1-(2-{[6-(6-methoxypyrimidin-4-yl)-1H-benzimidazol-2-yl]amino}pyridin-4-yl)ethyl]piperazine-1-carboxylate

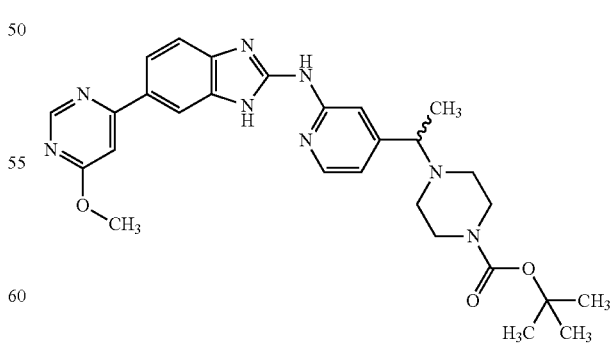

To a stirred solution of (rac)-tert-butyl 4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.00 g, 1.82 mmol) and 4-chloro-6-methoxypyrimidine (422 mg, 2.92 mmol) in dioxane (9 mL) and water (1.8 mL) was added sodium carbonate (773 mg, 7.29 mmol) and Pd(dppf)Cl$_2$. CH$_2$Cl$_2$ (223 mg, 273 µmol). The mixture was heated to reflux for 24 h. Further 4-chloro-6-methoxypyrimidine (130 mg) was added and the mixture was heated to reflux for 24 h. Dichloromethane was added, the mixture was dried (magnesium sulfate), filtered and the solvent was removed in vacuum.

Silicagel chromatography gave 0.43 g (45% yield) of the title compound.

LC-MS (Method 2): R$_t$=1.34 min; MS (ESIpos): m/z=531 [M+H]$^+$.

Compound 34.02

(rac)-6-(6-methoxypyrimidin-4-yl)-N-{4-[1-(piperazin-1-yl)ethyl]pyridin-2-yl}-1H-benzimidazol-2-amine hydrochloride

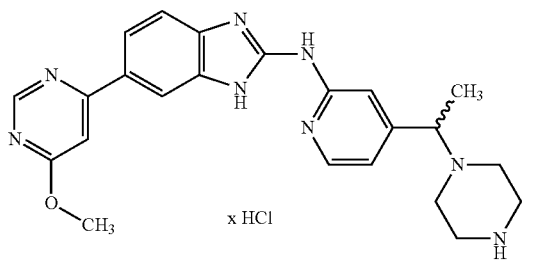 [SMILES: COc1cc(-c2ccc3nc(Nc4cc(C(C)N5CCNCC5)ccn4)[nH]c3c2)ncn1]

Starting with (rac)-tert-butyl 4-[1-(2-{[6-(6-methoxypyrimidin-4-yl)-1H-benzimidazol-2-yl]amino}pyridin-4-yl)ethyl]piperazine-1-carboxylate (430 mg, 810 µmol), Compound 34.02 was prepared analogously to the procedure for the preparation of Compound 01.05.

Yield: 530 mg of the title compound as crude product that was used for the next step without purification.

LC-MS (Method 2): R$_t$=0.97 min; MS (ESIpos): m/z=431 [M+H]$^+$.

Compound 35.01 tert-butyl 4-[(2-{[6-(5-methoxypyrimidin-4-yl)-1H-benzimidazol-2-yl]amino}pyridin-4-yl)methyl]piperazine-1-carboxylate

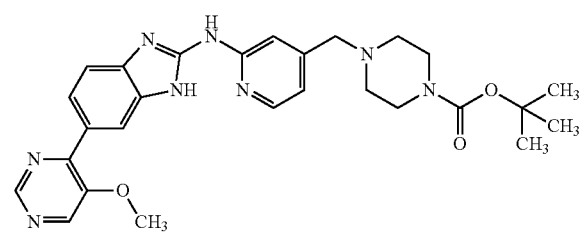 [SMILES: COc1cncnc1-c1ccc2nc(Nc3cc(CN4CCN(C(=O)OC(C)(C)C)CC4)ccn3)[nH]c2c1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (800 mg, 1.50 mmol) in dioxane (20 mL, 230 mmol) was added aqueous sodium carbonate solution (2.2 mL, 2.0 M, 4.5 mmol), 4-chloro-5-methoxypyrimidine (335 mg, 97% purity, 2.25 mmol) and Pd(dppf)Cl$_2$. CH$_2$Cl$_2$ (183 mg, 225 µmol). The mixture was heated to 120° C. in a sealed tube over night under argon atmosphere. Further 4-chloro-5-methoxypyrimidine (165 mg, 97% purity, 1.12 mmol) and Pd(dppf)Cl$_2$. CH$_2$Cl$_2$ (122 mg, 150 µmol) were added and the mixture was stirred at 120° C. Dichloromethane/methanol (100:1) was added and the mixture was extracted with half-saturated potassium carbonate solution. The solvent of the organic phase was removed in vacuum and silicagel chromatography gave 900 mg of the title compound as a crude product that was used for the next step without further purification.

LC-MS (Method 2): R$_t$=1.17 min; MS (ESIpos): m/z=517 [M+H]$^+$.

Compound 35.02

6-(5-methoxypyrimidin-4-yl)-N-[4-(piperazin-1-ylmethyl)pyridin-2-yl]-1H-benzimidazol-2-amine

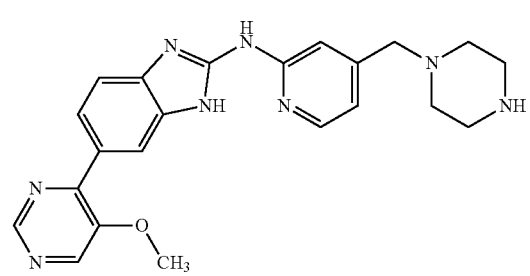 [SMILES: COc1cncnc1-c1ccc2nc(Nc3cc(CN4CCNCC4)ccn3)[nH]c2c1]

To a stirred solution of crude tert-butyl 4-[(2-{[6-(5-methoxypyrimidin-4-yl)-1H-benzimidazol-2-yl]amino}pyridin-4-yl)methyl]piperazine-1-carboxylate (900 mg, approx. 1.05 mmol) in dichloromethane (10 mL) and methanol (1 mL) was added TFA (20 mL). The mixture was stirred at r.t. for 0.5 h. The solvent was removed in vacuum. A half-saturated solution of potassium carbonate was added and the mixture was extracted with a mixture of chloroform and methanol (5:1). The organic phase was dried (sodium sulfate), filtered and the solvent was removed in vacuum. Aminophase-silicagel chromatography gave 180 mg of the title compound.

LC-MS (Method 2): R$_t$=0.89 min; MS (ESIpos): m/z=417 [M+H]$^+$.

$^1$H-NMR (400 MHz, DMSO-d6) δ[ppm]: 0.828 (0.67), 0.846 (0.50), 0.855 (0.59), 0.934 (0.96), 0.950 (1.04), 1.066 (11.80), 1.234 (0.54), 1.299 (8.49), 1.392 (4.25), 1.955 (1.55), 2.083 (0.70), 2.327 (1.20), 2.357 (4.27), 2.523 (1.17), 2.669 (0.42), 2.758 (4.61), 2.770 (6.71), 2.781 (5.30), 2.940 (1.91), 3.355 (1.29), 3.438 (2.63), 3.451 (7.61), 3.474 (1.16), 4.021 (16.00), 5.758 (11.44), 6.899 (0.57), 6.916 (1.96), 6.930 (1.89), 7.172 (2.98), 8.228 (0.79), 8.241 (0.83), 8.253 (3.16), 8.266 (3.03), 8.631 (6.84), 8.828 (6.58).

Compound 35.03

(rac)-tert-butyl 4-[1-(2-{[6-(5-methoxypyrimidin-4-yl)-1H-benzimidazol-2-yl]amino}pyridin-4-yl)ethyl]piperazine-1-carboxylate

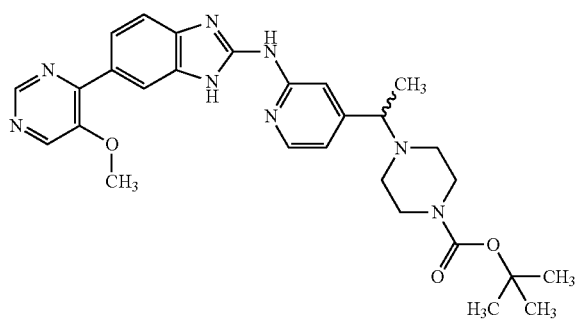 [SMILES: COc1cncnc1-c1ccc2nc(Nc3cc(C(C)N4CCN(C(=O)OC(C)(C)C)CC4)ccn3)[nH]c2c1]

To a stirred solution of (rac)-tert-butyl 4-[1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.60 g, 2.92 mmol) and 4-chloro-5-methoxypyrimidine (759 mg, 5.25 mmol) in dioxane (14 mL) and water (2.8 mL) was added sodium carbonate (1.24 g, 11.7 mmol) and Pd(dppf)Cl$_2$·CH$_2$Cl$_2$ (357 mg, 438 µmol). The mixture was heated to reflux for 24 h. Dichloromethane was added, the mixture was dried (magnesium sulfate), filtered and the solvent was removed in vacuum. Silicagel chromatography gave 880 mg (57% yield) of the title compound.

LC-MS (Method 2): R$_t$=1.27 min; MS (ESIpos): m/z=531 [M+H]$^+$.

Compound 35.04

(rac)-6-(5-methoxypyrimidin-4-yl)-N-{4-[1-(piperazin-1-yl)ethyl]pyridin-2-yl}-1H-benzimidazol-2-amine hydrochloride

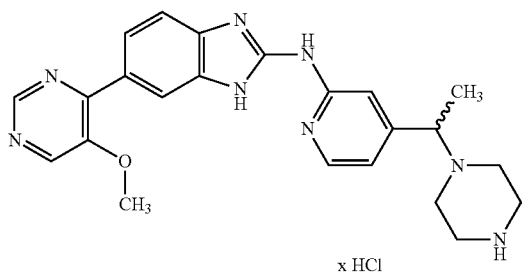 [SMILES: COc1cncnc1-c1ccc2nc(Nc3cc(C(C)N4CCNCC4)ccn3)[nH]c2c1]

Starting with (rac)-tert-butyl 4-[(1R)-1-(2-{[6-(5-methoxypyrimidin-4-yl)-1H-benzimidazol-2-yl]amino}pyridin-4-yl)ethyl]piperazine-1-carboxylate (880 mg, 1.66 mmol), Compound 35.04 was prepared analogously to the procedure for the preparation of Compound 01.05.

Yield: 900 mg of the title compound as crude product that was used for the next step without purification.

LC-MS (Method 2): R$_t$=0.87 min; MS (ESIpos): m/z=431 [M+H]$^+$.

Compound 36.01

4-(5-methoxypyrimidin-4-yl)-2-nitroaniline

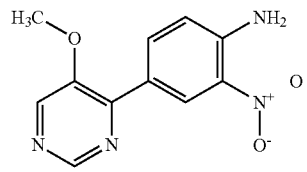

Starting with 4-chloro-5-methoxypyrimidine (1.10 g, 98% purity, 7.46 mmol) and (4-amino-3-nitrophenyl)boronic acid (2.44 g, 13.4 mmol), Compound 36.01 was prepared analogously to the procedure for the preparation of Compound 02.01.

Yield: 1.59 g (86% yield) of the title compound.

LC-MS (Method 2): R$_t$=0.85 min; MS (ESIpos): m/z=247 [M+H]$^+$.

$^1$H-NMR (400 MHz, DMSO-d6) δ[ppm]: 4.023 (16.00), 7.094 (2.83), 7.117 (2.85), 7.527 (0.70), 7.531 (0.82), 7.535 (0.62), 7.543 (0.71), 7.545 (0.96), 7.548 (0.93), 7.554 (0.78), 7.556 (0.72), 7.563 (1.11), 7.565 (0.83), 7.571 (0.89), 7.591 (0.72), 7.595 (1.34), 7.612 (1.18), 7.621 (1.23), 7.624 (1.71), 7.629 (0.83), 7.642 (0.84), 7.645 (0.62), 7.821 (2.69), 8.234 (1.52), 8.239 (1.49), 8.256 (1.34), 8.262 (1.44), 8.646 (5.99), 8.808 (6.57), 8.961 (2.72), 8.966 (2.76).

Compound 36.02

4-(4-amino-3-nitrophenyl)pyrimidin-5-ol

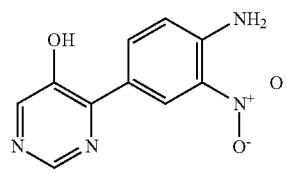

To a stirred solution of 4-(5-methoxypyrimidin-4-yl)-2-nitroaniline (1.40 g, 5.69 mmol) in DMF (21 mL) was added sodium methanethiolate (1.99 g, 28.4 mmol) and the mixture was stirred at 60° C. for 3 h. A half-saturated sodium chloride solution was added and the mixture was extracted with chloroform/methanol (9:1). The aqueous phase was concentrated in vacuum to give 15.7 g of the title compound as a crude product that was used without purification.

LC-MS (Method 1): R$_t$=0.70 min; MS (ESIpos): m/z=233 [M+H]$^+$.

Compound 36.03

2-nitro-4-[5-(propan-2-yloxy)pyrimidin-4-yl]aniline

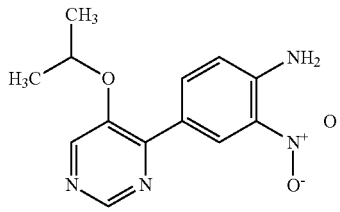

To a stirred solution of 4-(4-amino-3-nitrophenyl)pyrimidin-5-ol (15.7 g, approx. 5.69 mmol) in DMA (30 mL) was added potassium carbonate (2.36 g, 17.1 mmol) and 2-iodopropane (850 µl, 8.5 mmol) and the mixture was stirred at 70° C. for 1 h. Water was added and the mixture was extracted with ethyl acetate. The organic phase was washed with half-saturated sodium chloride solution, dried (sodium sulfate), filtered and the solvent was removed in vacuum. Silicagel chromatography gave 822 mg of the title compound.

LC-MS (Method 1): $R_t$=1.00 min; MS (ESIpos): m/z=275 [M+H]$^+$.

$^1$H-NMR (400 MHz, DMSO-d6) δ [ppm]: 1.364 (14.90), 1.379 (16.00), 4.909 (0.81), 4.924 (1.10), 4.939 (0.81), 7.090 (2.41), 7.112 (2.38), 7.820 (2.06), 8.267 (1.30), 8.272 (1.33), 8.290 (1.19), 8.295 (1.25), 8.656 (4.48), 8.782 (6.98), 9.120 (2.42), 9.126 (2.45).

Compound 36.04

4-[5-(propan-2-yloxy)pyrimidin-4-yl]benzene-1,2-diamine

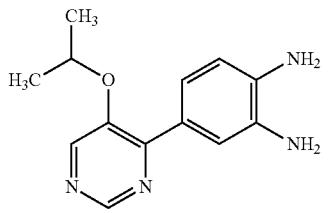 [SMILES: CC(C)Oc1cncnc1-c1ccc(N)c(N)c1]

To a stirred solution of 2-nitro-4-[5-(propan-2-yloxy)pyrimidin-4-yl]aniline (865 mg, 3.15 mmol) in ethanol (34 mL) and dichloromethane (34 mL) was added palladium on carbon (10% w/w palladium) (336 mg) and the mixture was stirred at r.t. in a hydrogen atmosphere for 2 h. The mixture was filtered, and the solution was concentrated in vacuum to give 750 mg (88% yield) of the title compound as crude product, that was used for the next step without purification.

LC-MS (Method 1): $R_t$=0.63 min; MS (ESIpos): m/z=245 [M+H]$^+$.

$^1$H-NMR (400 MHz, DMSO-d6) δ[ppm]: 1.229 (1.13), 1.246 (1.11), 1.308 (16.00), 1.323 (15.97), 2.903 (0.65), 4.733 (0.90), 4.748 (1.21), 4.763 (0.92), 5.758 (1.01), 6.530 (2.76), 6.550 (2.66), 7.440 (1.46), 7.445 (1.65), 7.460 (1.23), 7.466 (1.45), 7.511 (3.05), 7.516 (2.62), 8.454 (4.48), 8.662 (7.08).

Compound 36.05

(+)-tert-butyl 4-[(1R or 1S)-1-(2-aminopyridin-4-yl)ethyl]piperazine-1-carboxylate (Single Stereoisomer A)

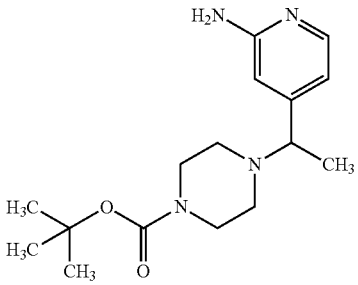 [SMILES: CC(c1ccnc(N)c1)N1CCN(C(=O)OC(C)(C)C)CC1]

To a stirred solution of (2R,3R)-2,3-bis(benzoyloxy)butanedioic acid (5.85 g, 16.3 mmol) in 2-propanol (200 mL) was added (rac)-tert-butyl-4-[1-(2-aminopyridin-4-yl)ethyl]piperazine-1-carboxylate (10.0 g, 32.6 mmol), dissolved in warm 2-propanol (420 mL). A clear solution formed, and after 30 minutes a precipitate started to form. The mixture was stirred at r.t. for 16 h. The precipitate was collected by filtration and was dissolved in dichloromethane/methanol (100:1) and half-saturated potassium carbonate solution. The phases were separated, the organic phase was dried (sodium sulfate), filtered and the solvent was removed in vacuum to give 3.42 g of enantiomerically enriched tert-butyl 4-[(1R or 1S)-1-(2-aminopyridin-4-yl)ethyl]piperazine-1-carboxylate (Optical rotation: [α]$_D$=+17.5° from DMSO solution, c=4.4 mg/mL; enantiomeric purity: 92.5%)

The enantiomerically enriched tert-butyl 4-[(1R or 1S)-1-(2-aminopyridin-4-yl)ethyl]piperazine-1-carboxylate (3.40 g, 11.1 mmol) was dissolved in warm 2-propanol (130 mL) and added to a stirred solution of (2R,3R)-2,3-bis(benzoyloxy)butanedioic acid (3.38 g, 9.43 mmol) in 2-propanol (50 mL). A clear solution formed, and after 30 minutes a precipitate started to form. The mixture was stirred at r.t. for 72 h. The precipitate was collected by filtration and was dissolved in dichloromethane/methanol (100:1) and half-saturated potassium carbonate solution. The phases were separated, the organic phase was dried (sodium sulfate), filtered and the solvent was removed in vacuum to give 3.04 g of the title compound.

Optical rotation: [α]$_D$=+20.1° from DMSO solution, c=3.5 mg/mL;

Chiral HPLC (Instrument: Agilent HPLC 1260; Column: Chiralpak IA 3µ 100×4.6 mm; Eluent A: acetonitrile+0.1 Vol-% diethylamine (99%); isocratic: 100% A; Flow 1.0 mL/min; Temperature: 25° C.; DAD 280 nm): $R_t$=5.34 min (99.15%); (Minor Isomer: $R_t$=3.24 min (0.85%)).

LC-MS (Method 2): $R_t$=1.01 min; MS (ESIpos): m/z=307 [M+H]$^+$.

$^1$H-NMR (400 MHz, DMSO-d6) δ [ppm]: 1.027 (0.93), 1.042 (0.92), 1.053 (0.51), 1.200 (1.79), 1.216 (1.84), 1.370 (16.00), 3.332 (3.69), 5.757 (5.64), 5.808 (1.32), 6.355 (0.91), 6.409 (0.54), 6.413 (0.51), 6.422 (0.56), 6.426 (0.52), 7.803 (0.75), 7.804 (0.73), 7.816 (0.73).

Compound 36.06

N-{4-[(1R or 1S)-1-(piperazin-1-yl)ethyl]pyridin-2-yl}-6-[5-(propan-2-yloxy)pyrimidin-4-yl]-1H-benzimidazol-2-amine hydrochloride

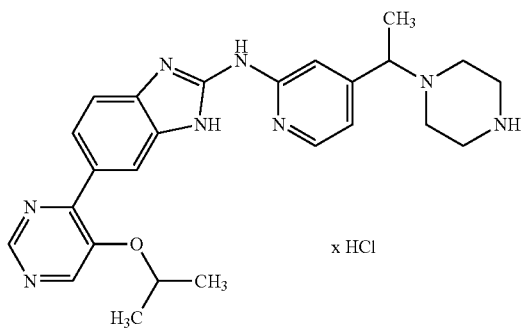 [SMILES: CC(C)Oc1cncnc1-c1ccc2nc(Nc3cc(C(C)N4CCNCC4)ccn3)[nH]c2c1]

x HCl

Starting with tert-butyl 4-{(1R or 1S)-1-[2-({6-[5-(propan-2-yloxy)pyrimidin-4-yl]-1H-benzimidazol-2-yl}amino)pyridin-4-yl]ethyl}piperazine-1-carboxylate (450 mg, 805 μmol), Compound 36.06 was prepared analogously to the procedure for the preparation of Compound 01.05.

Yield: 645 mg of the title compound as crude product that was used for the next step without purification.

LC-MS (Method 2): $R_t$=0.98 min; MS (ESIpos): m/z=459 [M+H]+.

$^1$H-NMR (400 MHz, DMSO-d6) δ[ppm]: 1.357 (1.50), 1.372 (16.00), 1.386 (15.28), 1.710 (2.53), 1.727 (2.57), 3.466 (0.99), 3.483 (1.08), 3.495 (1.03), 4.924 (0.98), 4.939 (1.33), 4.954 (0.99), 5.758 (4.99), 7.605 (2.21), 7.766 (2.03), 7.787 (2.15), 8.151 (1.73), 8.154 (1.68), 8.172 (1.42), 8.176 (1.51), 8.496 (2.63), 8.500 (2.50), 8.593 (1.65), 8.607 (1.53), 8.764 (4.88), 8.887 (6.75).

Compound 37.01

4-(1-methyl-1H-pyrazol-4-yl)-2-nitroaniline

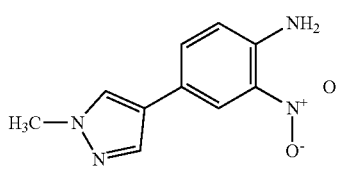

Starting with (4-amino-3-nitrophenyl)boronic acid (2.00 g, 11.0 mmol) and 4-bromo-1-methyl-1H-pyrazole (1.1 mL, 11 mmol), Compound 37.01 was prepared analogously to the procedure for the preparation of Compound 02.01.

Yield: 1.78 g (74% yield) of the title compound.

LC-MS (Method 2): $R_t$=0.82 min; MS (ESIpos): m/z=219 [M+H]+.

$^1$H-NMR (400 MHz, DMSO-d6) δ[ppm]: 1.171 (0.58), 1.986 (1.13), 3.325 (16.00), 7.027 (6.54), 7.048 (6.92), 7.093 (2.33), 7.115 (2.43), 7.415 (7.31), 7.522 (3.25), 7.528 (1.47), 7.543 (0.68), 7.546 (0.90), 7.549 (0.86), 7.554 (0.69), 7.564 (1.07), 7.566 (0.82), 7.571 (0.75), 7.573 (0.71), 7.596 (1.16), 7.613 (1.10), 7.622 (1.77), 7.625 (5.38), 7.631 (4.47), 7.643 (1.13), 7.647 (3.78), 7.652 (3.56), 7.742 (1.29), 7.748 (1.30), 7.764 (1.16), 7.770 (1.23), 7.797 (9.14), 7.799 (9.90), 8.071 (6.92), 8.077 (6.71), 8.091 (9.29), 8.144 (2.50), 8.150 (2.42).

Compound 37.02

4-(1-methyl-1H-pyrazol-4-yl)benzene-1,2-diamine

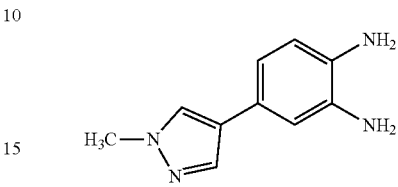

To a stirred solution of 4-(1-methyl-H-pyrazol-4-yl)-2-nitroaniline (3.28 g, 15.0 mmol) in ethanol (15 mL) and dichloromethane (35 mL) was added palladium on carbon (10% w/w palladium) (800 mg) and the mixture was stirred at r.t. in a hydrogen atmosphere for 48 h. The mixture was filtered, and the solution was concentrated in vacuum. Aminophase silicagel chromatography gave 2.17 g (77% yield) of the title compound.

LC-MS (Method 2): $R_t$=0.56 min; MS (ESIpos): m/z=189 [M+H]+.

$^1$H-NMR (400 MHz, DMSO-d6) δ[ppm]: 3.163 (0.68), 3.177 (0.71), 3.311 (16.00), 4.390 (5.12), 4.420 (5.20), 6.467 (4.63), 6.487 (6.97), 6.560 (3.87), 6.565 (4.03), 6.579 (2.52), 6.584 (2.80), 6.673 (6.39), 6.678 (5.99), 7.528 (8.51), 7.530 (8.53), 7.547 (0.68), 7.550 (0.67), 7.565 (0.81), 7.572 (0.61), 7.574 (0.57), 7.598 (0.96), 7.615 (0.81), 7.624 (0.98), 7.627 (1.29), 7.632 (0.66), 7.644 (0.69), 7.647 (0.52), 7.745 (7.87), 7.747 (7.47).

Compound 37.03 tert-butyl 4-[(2-{[6-(1-methyl-1H-pyrazol-4-yl)-1H-benzimidazol-2-yl]amino}pyridin-4-yl)methyl]piperazine-1-carboxylate

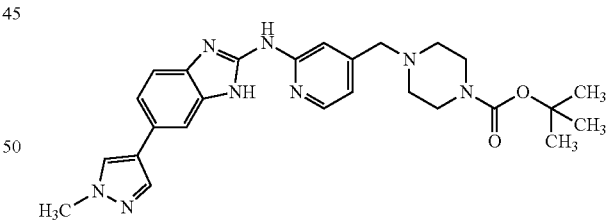

To a stirred solution of 1H-imidazole (157 mg, 2.31 mmol) and di-1H-imidazol-1-ylmethanethione (2.16 g, 95% purity, 11.5 mmol) in dichloromethane (150 mL) was added tert-butyl 4-[(2-aminopyridin-4-yl)methyl]piperazine-1-carboxylate (3.37 g, 11.5 mmol), dissolved in dichloromethane (50 mL), at 0° C. The mixture was stirred at r.t. for 14 h. 4-(1-methyl-1H-pyrazol-4-yl)benzene-1,2-diamine (2.17 g, 11.5 mmol), suspended in dichloromethane (50 mL), was added and the mixture was stirred at r.t. for 2 h. Water was added and the mixture was extracted with dichloromethane. The organic phase was dried (sodium sulfate) and filtered. N,N'-dipropan-2-ylcarbodiimide (5.3 mL, 34 mmol) was added and the mixture was stirred at r.t. for 14 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography followed by aminophase-silicagel chromatography gave 900 mg of the title compound as a crude product, that was used without further purification.

LC-MS (Method 2): $R_t$=1.17 min; MS (ESIpos): m/z=489 [M+H]$^+$.

$^1$H-NMR (400 MHz, DMSO-d6) δ[ppm]: 0.989 (4.82), 1.005 (5.00), 1.072 (0.41), 1.088 (0.42), 1.385 (5.47), 1.390 (4.18), 1.394 (16.00), 1.988 (0.57), 2.341 (1.05), 2.354 (1.52), 2.366 (1.16), 2.523 (1.79), 2.539 (0.79), 3.308 (1.10), 3.489 (1.86), 3.860 (2.88), 5.760 (0.69), 6.895 (0.54), 6.898 (0.53), 6.908 (0.59), 6.911 (0.58), 7.176 (0.70), 8.234 (0.85), 8.248 (0.81).

Compound 37.04

6-(1-methyl-1H-pyrazol-4-yl)-N-[4-(piperazin-1-ylmethyl)pyridin-2-yl]-1H-benzimidazol-2-amine hydrochloride

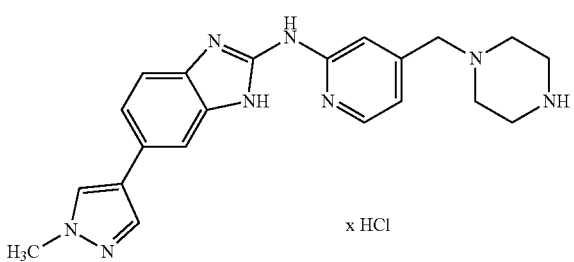 [SMILES: Cn1cc(-c2ccc3nc(Nc4cc(CN5CCNCC5)ccn4)[nH]c3c2)cn1]

Starting with tert-butyl 4-[(2-{[6-(1-methyl-1H-pyrazol-4-yl)-1H-benzimidazol-2-yl]amino}pyridin-4-yl)methyl]piperazine-1-carboxylate (900 mg, 1.84 mmol), Compound 37.04 was prepared analogously to the procedure for the preparation of Compound 01.05.

Yield: 930 mg of the title compound as crude product that was used for the next step without purification.

LC-MS (Method 2): $R_t$=0.86 min; MS (ESIpos): m/z=389 [M+H]$^+$.

$^1$H-NMR (400 MHz, DMSO-d6) δ[ppm]: 0.987 (14.24), 1.004 (14.09), 2.323 (0.52), 2.327 (0.73), 2.331 (0.52), 2.523 (2.28), 2.665 (0.56), 2.669 (0.78), 2.673 (0.55), 3.162 (0.63), 3.326 (1.27), 3.564 (4.94), 3.610 (0.88), 3.627 (1.12), 3.643 (0.83), 3.892 (16.00), 4.880 (0.70), 5.760 (1.11), 7.524 (2.18), 7.555 (1.90), 7.559 (2.01), 7.576 (2.81), 7.580 (2.89), 7.631 (3.04), 7.653 (1.71), 7.753 (2.90), 7.756 (2.90), 7.861 (5.11), 7.863 (5.41), 8.157 (4.62), 8.536 (1.47), 8.549 (1.42).

Compound 38.01

4-(1-ethyl-1H-pyrazol-4-yl)-2-nitroaniline

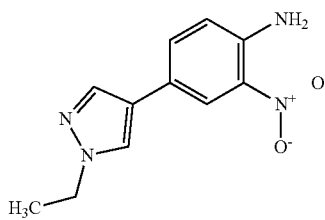

Starting with 4-bromo-2-nitroaniline (2.00 g, 9.22 mmol) and (1-ethyl-1H-pyrazol-4-yl)boronic acid (2.17 g, 95% purity, 14.7 mmol), Compound 38.01 was prepared analogously to the procedure for the preparation of Compound 02.01.

Yield: 1.31 g (55%) of the title compound.

LC-MS (Method 2): $R_t$=0.90 min; MS (ESIpos): m/z=233 [M+H]$^+$.

$^1$H-NMR (400 MHz, DMSO-d$_6$) δ [ppm]: 1.369 (6.76), 1.388 (16.00), 1.406 (6.71), 4.093 (1.84), 4.111 (5.81), 4.130 (5.62), 4.147 (1.80), 7.024 (3.78), 7.046 (4.02), 7.424 (4.59), 7.640 (2.21), 7.645 (2.35), 7.661 (2.09), 7.667 (2.13), 7.808 (6.27), 7.810 (6.28), 8.086 (4.16), 8.091 (4.12), 8.159 (5.65), 8.161 (5.49).

Compound 38.02

4-(1-ethyl-1H-pyrazol-4-yl)benzene-1,2-diamine

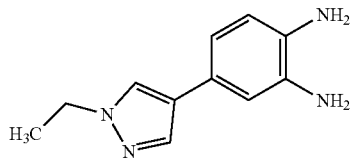

To a stirred solution of 4-(1-ethyl-1H-pyrazol-4-yl)-2-nitroaniline (1.30 g, 5.60 mmol) in ethanol (60 mL) and dichloromethane (60 mL) was added palladium on carbon (10% w/w palladium) (596 mg) and the mixture was stirred at r.t. in a hydrogen atmosphere for 2 h. The mixture was filtered and the solution was concentrated in vacuum. Aminophase-silicagel chromatography gave 1.00 g (79% yield) of the title compound.

LC-MS (Method 2): $R_t$=0.64 min; MS (ESIpos): m/z=203 [M+H]$^+$.

$^1$H-NMR (400 MHz, DMSO-d$_6$) δ [ppm]: 1.347 (7.43), 1.366 (16.00), 1.369 (2.33), 1.383 (8.05), 1.404 (1.10), 2.522 (1.43), 4.062 (2.22), 4.081 (6.84), 4.099 (6.77), 4.117 (2.44), 4.406 (5.69), 4.433 (5.86), 5.759 (0.93), 6.464 (3.89), 6.484 (5.52), 6.570 (3.00), 6.575 (3.27), 6.589 (2.16), 6.594 (2.44), 6.681 (4.96), 6.686 (5.02), 7.542 (7.65), 7.803 (7.45).

Compound 38.03

6-(1-ethyl-1H-pyrazol-4-yl)-N-[4-(piperazin-1-ylmethyl)pyridin-2-yl]-1H-benzimidazol-2-amine hydrochloride

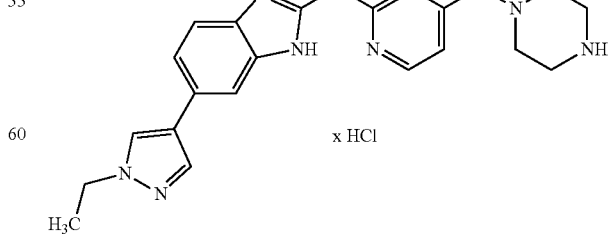

Starting with tert-butyl 4-[(2-{[6-(1-ethyl-1H-pyrazol-4-yl)-1H-benzimidazol-2-yl]amino}pyridin-4-yl)methyl]piperazine-1-carboxylate (300 mg, 597 µmol), Compound 38.03 was prepared analogously to the procedure for the preparation of Compound 01.05.

Yield: 125 mg of the title compound as crude product that was used for the next step without purification.

LC-MS (Method 2): $R_t$=0.91 min; MS (ESIpos): m/z=403 [M+H]$^+$.

$^1$H-NMR (400 MHz, DMSO-d6) δ[ppm]: 1.402 (6.92), 1.420 (16.00), 1.439 (6.91), 2.327 (0.52), 2.523 (2.74), 2.669 (0.52), 3.338 (1.36), 3.486 (0.74), 3.564 (2.89), 4.153 (1.66), 4.171 (5.01), 4.189 (5.08), 4.207 (1.73), 4.417 (1.08), 4.585 (0.85), 7.533 (2.86), 7.564 (2.37), 7.568 (2.59), 7.585 (3.60), 7.589 (3.77), 7.633 (4.03), 7.654 (2.17), 7.766 (3.34), 7.770 (3.75), 7.865 (6.59), 7.867 (6.85), 8.205 (5.94), 8.534 (2.00), 8.548 (1.93).

Compound 39.01

1-(cyclopropylmethyl)-4-(4,4,5,5-tetramethyl-1,3,2-dioxaborolan-2-yl)-1H-pyrazole

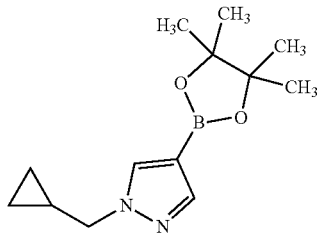 [SMILES: CC1(C)OB(c2cnn(CC3CC3)c2)OC1(C)C]

To a stirred solution of 4-(4,4,5,5-tetramethyl-1,3,2-dioxaborolan-2-yl)-1H-pyrazole (8.00 g, 41.2 mmol) in DMF (130 mL) was added potassium carbonate (17.1 g, 124 mmol) and (bromomethyl)cyclopropane (6.0 mL, 62 mmol). The mixture was stirred at 60° C. for 14 h. Water was added and the mixture was extracted with ethyl acetate. The organic phase was washed with half-saturated sodium chloride solution, dried (sodium sulfate) and the solvent was removed in vacuum. Silicagel chromatography gave 4.95 g (48% yield) of the title compound.

LC-MS (Method 2): $R_t$=1.12 min; MS (ESIpos): m/z=249 [M+H]$^+$.

$^1$H-NMR (400 MHz, DMSO-d6) δ [ppm]: 0.314 (0.66), 0.318 (0.59), 0.325 (0.56), 0.330 (0.65), 0.471 (0.53), 0.476 (0.61), 0.492 (0.62), 0.496 (0.57), 1.045 (0.78), 1.219 (1.70), 1.224 (16.00), 3.295 (1.54), 3.927 (1.24), 3.946 (1.22), 7.542 (1.07), 7.544 (1.08), 7.932 (1.09).

Compound 39.02

4-[1-(cyclopropylmethyl)-1H-pyrazol-4-yl]-2-nitroaniline

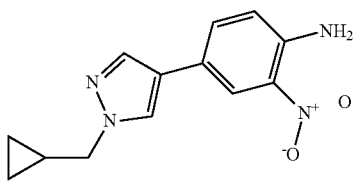

To a stirred solution of 4-bromo-2-nitroaniline (2.62 g, 12.1 mmol) in 1-propanol (110 mL) was added potassium carbonate solution (18 mL, 2.0 M, 36 mmol), 1-(cyclopropylmethyl)-4-(4,4,5,5-tetramethyl-1,3,2-dioxaborolan-2-yl)-1H-pyrazole (4.10 g, 95% purity, 15.7 mmol), triphenylphosphine (158 mg, 604 µmol) and PdCl$_2$(PPh$_3$)$_2$ (424 mg, 604 µmol). The mixture was heated to reflux for 2 h, the solvent was removed in vacuum. Aminophase silicagel chromatography gave a solid that was triturated with dichloromethane to give 2.61 g (84% yield) of the title compound.

LC-MS (Method 2): $R_t$=1.02 min; MS (ESIpos): m/z=259 [M+H]$^+$.

$^1$H-NMR (400 MHz, DMSO-d$_6$) δ [ppm]: 0.359 (2.19), 0.370 (8.88), 0.374 (7.54), 0.382 (8.21), 0.386 (8.43), 0.396 (3.08), 0.510 (3.12), 0.520 (7.14), 0.525 (7.44), 0.530 (3.96), 0.536 (4.01), 0.541 (7.72), 0.545 (7.00), 0.556 (2.35), 0.864 (2.72), 1.066 (0.76), 1.210 (0.68), 1.216 (1.04), 1.228 (2.00), 1.235 (1.86), 1.240 (1.45), 1.247 (3.09), 1.256 (1.46), 1.259 (1.73), 1.267 (1.82), 1.279 (0.90), 1.285 (0.61), 3.166 (1.17), 3.336 (1.85), 3.941 (16.00), 3.959 (15.90), 5.758 (2.12), 7.032 (9.58), 7.054 (9.93), 7.431 (7.13), 7.650 (6.13), 7.655 (6.01), 7.672 (5.41), 7.677 (5.69), 7.811 (15.49), 7.813 (15.69), 8.093 (11.18), 8.098 (10.99), 8.177 (15.24).

Compound 39.03

4-[1-(cyclopropylmethyl)-1H-pyrazol-4-yl]benzene-1,2-diamine

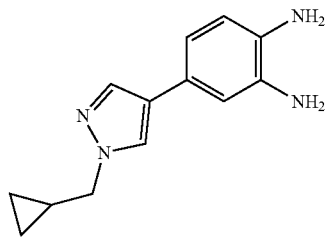 [SMILES: Nc1ccc(-c2cnn(CC3CC3)c2)cc1N]

To a stirred solution of 4-[1-(cyclopropylmethyl)-1H-pyrazol-4-yl]-2-nitroaniline (2.60 g, 10.1 mmol) in ethanol (110 mL) and dichloromethane (110 mL) was added palladium on carbon (10% w/w palladium, 1.07 g) and the mixture was stirred at r.t. in a hydrogen atmosphere for 6 h. The mixture was filtered and the solution was concentrated in vacuum. Aminophase-silicagel chromatography gave 2.25 g (98% yield) of the title compound.

LC-MS (Method 1): $R_t$=0.61 min; MS (ESIpos): m/z=229 [M+H]$^+$.

$^1$H-NMR (400 MHz, DMSO-d$_6$) δ [ppm]: 1.067 (16.00), 3.917 (1.17), 3.935 (1.27), 3.941 (0.96), 5.759 (1.12), 6.502 (0.71), 6.521 (1.00), 6.714 (0.90), 6.719 (0.83), 7.554 (1.25), 7.556 (1.23), 7.841 (1.11), 7.843 (1.10).

Compound 39.04

6-[1-(cyclopropylmethyl)-1H-pyrazol-4-yl]-N-[4-(piperazin-1-ylmethyl)pyridin-2-yl]-1H-benzimidazol-2-amine hydrochloride

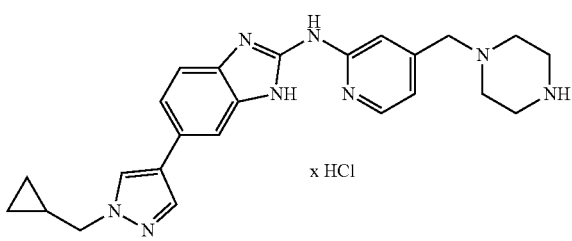 [SMILES: c1cc(CN2CCNCC2)cc(Nc2nc3ccc(-c4cnn(CC5CC5)c4)cc3[nH]2)n1]

x HCl

Starting with tert-butyl 4-{[2-({6-[1-(cyclopropylmethyl)-1H-pyrazol-4-yl]-1H-benzimidazol-2-yl}amino)pyridin-4-yl]methyl}piperazine-1-carboxylate (355 mg, 672 µmol), Compound 39.04 was prepared analogously to the procedure for the preparation of Compound 01.05.

Yield: 320 mg of the title compound as crude product that was used for the next step without purification.

LC-MS (Method 2): $R_t$=1.01 min; MS (ESIpos): m/z=429 [M+H]$^+$.

$^1$H-NMR (400 MHz, DMSO-d6) δ[ppm]: 0.400 (2.31), 0.403 (2.02), 0.412 (2.28), 0.415 (2.18), 0.540 (1.93), 0.544 (1.84), 0.550 (1.07), 0.560 (2.08), 0.565 (1.65), 1.282 (0.86), 3.160 (7.56), 3.443 (1.44), 3.454 (1.79), 3.467 (2.51), 3.477 (2.63), 3.483 (2.57), 3.561 (16.00), 4.001 (3.49), 4.019 (3.50), 4.503 (1.89), 7.554 (2.34), 7.574 (1.20), 7.578 (1.18), 7.595 (1.86), 7.599 (1.99), 7.641 (3.58), 7.662 (1.51), 7.784 (2.36), 7.788 (2.55), 7.871 (4.39), 7.873 (4.38), 8.228 (3.94), 8.230 (3.80), 8.546 (1.82), 8.558 (1.70).

Compound 39.05

6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride

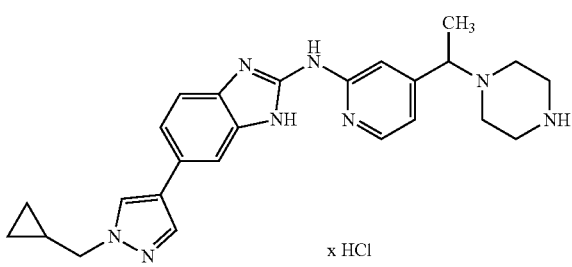 [SMILES: CC(c1ccnc(Nc2nc3ccc(-c4cnn(CC5CC5)c4)cc3[nH]2)c1)N1CCNCC1]

x HCl

Starting with tert-butyl 4-{(1R or 1S)-1-[2-({6-[1-(cyclopropylmethyl)-1H-pyrazol-4-yl]-1H-benzimidazol-2-yl}amino)pyridin-4-yl]ethyl}piperazine-1-carboxylate (385 mg, 709 µmol), Compound 39.05 was prepared analogously to the procedure for the preparation of Compound 01.05.

Yield: 360 mg of the title compound as crude product that was used for the next step without purification.

LC-MS (Method 2): $R_t$=1.00 min; MS (ESIpos): m/z=443 [M+H]$^+$.

$^1$H-NMR (400 MHz, DMSO-d6) δ[ppm]: 0.390 (1.60), 0.401 (6.25), 0.405 (5.43), 0.413 (5.95), 0.417 (6.00), 0.427 (2.20), 0.532 (2.25), 0.542 (5.29), 0.546 (5.04), 0.552 (2.83), 0.558 (2.91), 0.562 (5.67), 0.567 (4.38), 0.578 (1.63), 1.264 (1.48), 1.272 (1.41), 1.284 (2.41), 1.295 (1.27), 1.304 (1.41), 1.702 (3.96), 2.082 (1.05), 2.669 (0.84), 3.162 (8.65), 3.271 (1.50), 3.384 (1.08), 3.440 (2.01), 3.444 (2.16), 3.450 (2.28), 3.456 (2.74), 3.457 (2.52), 3.466 (2.73), 3.468 (2.79), 3.484 (2.52), 3.487 (2.40), 3.495 (1.99), 3.497 (2.14), 3.502 (1.68), 3.508 (1.38), 3.513 (1.29), 3.675 (0.87), 3.697 (0.90), 4.002 (9.79), 4.020 (9.75), 4.780 (1.89), 5.759 (16.00), 7.538 (5.02), 7.577 (3.15), 7.580 (3.01), 7.597 (5.22), 7.601 (5.52), 7.638 (8.05), 7.660 (4.93), 7.777 (6.13), 7.781 (6.70), 7.871 (11.32), 7.874 (11.83), 8.226 (10.39), 8.228 (10.77), 8.561 (3.52), 8.575 (3.30).

Compound 40.01

4-(1-methyl-1H-pyrazol-3-yl)-2-nitroaniline

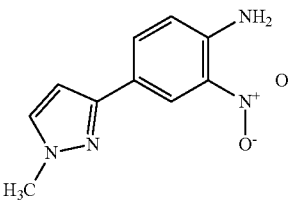

Starting with 3-bromo-1-methyl-1H-pyrazole (2.00 g, 12.4 mmol) and 2-nitro-4-(4,4,5,5-tetramethyl-1,3,2-dioxaborolan-2-yl)aniline (3.44 g, 13.0 mmol), Compound 40.01 was prepared analogously to the procedure for the preparation of Compound 02.01.

Yield: 2.18 g (80% yield) of the title compound.

LC-MS (Method 2): $R_t$=0.87 min; MS (ESIpos): m/z=219 [M+H]$^+$.

Compound 40.02

4-(1-methyl-1H-pyrazol-3-yl)benzene-1,2-diamine

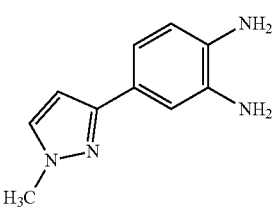

To a stirred solution of 4-(1-methyl-1H-pyrazol-3-yl)-2-nitroaniline (2.54 g, 11.6 mmol) in methanol (140 mL) and THF (70 mL) was added palladium on carbon (10% w/w palladium) (1.24 g, 1.16 mmol) and the mixture was stirred at r.t. in a hydrogen atmosphere for 3.25 h. The mixture was filtered and the solution was concentrated in vacuum. Aminophase-silicagel chromatography gave 1.74 g (80% yield) of the title compound.

LC-MS (Method 2): $R_t$=0.61 min; MS (ESIpos): m/z=189 [M+H]$^+$.

$^1$H-NMR (400 MHz, DMSO-d6) δ[ppm]: 1.066 (3.45), 3.797 (16.00), 3.948 (0.57), 4.465 (1.75), 4.500 (1.99), 6.337 (3.38), 6.343 (3.31), 6.471 (2.67), 6.490 (3.03), 6.780

(1.59), 6.785 (1.71), 6.800 (1.41), 6.804 (1.49), 6.988 (3.07), 6.993 (2.98), 7.574 (2.98), 7.580 (2.83).

Compound 40.03 tert-butyl 4-[(2-{[6-(1-methyl-1H-pyrazol-3-yl)-1H-benzimidazol-2-yl]amino}pyridin-4-yl)methyl]piperazine-1-carboxylate

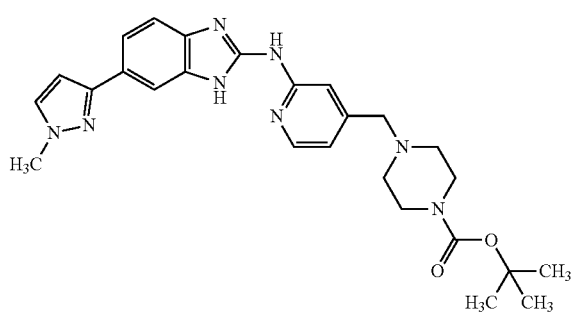 [SMILES: Cn1ccc(-c2ccc3nc(Nc4cc(CN5CCN(C(=O)OC(C)(C)C)CC5)ccn4)[nH]c3c2)n1]

To a stirred solution of 1H-imidazole (126 mg, 1.85 mmol) and di-1H-imidazol-1-ylmethanethione (1.65 g, 9.24 mmol) in dichloromethane (110 mL) was added tert-butyl 4-[(2-aminopyridin-4-yl)methyl]piperazine-1-carboxylate (2.70 g, 9.24 mmol)=TH-004=ASCB369=, dissolved in dichloromethane (55 mL), at 0° C. The mixture was stirred at r.t. for 14 h. 4-(1-methyl-1H-pyrazol-3-yl)benzene-1,2-diamine (1.74 g, 9.24 mmol), dissolved in dichloromethane (55 mL), was added and the mixture was stirred at r.t. for 3 h. Water was added and the mixture was extracted with dichloromethane. The organic phase was dried (sodium sulfate) and filtered. N,N'-dipropan-2-ylcarbodiimide (2.0 mL, 13 mmol) was added. The mixture was stirred at r.t. for 14 h. Further N,N'-dipropan-2-ylcarbodiimide (2.0 mL, 13 mmol) was added and the mixture was stirred at r.t. for 4 h. Further N,N'-dipropan-2-ylcarbodiimide (4.0 mL, 26 mmol) was added and the mixture was stirred at r.t. for 56 h. Saturated ammonium chloride solution was added, the mixture was stirred for 30 minutes and was extracted with dichloromethane. Aminophase silicagel chromatography gave 1.72 g of the title compound as a crude product, that was used without further purification.

LC-MS (Method 2): $R_t$=1.21 min; MS (ESIpos): m/z=489 [M+H]$^+$.

$^1$H-NMR (400 MHz, DMSO-d6) δ [ppm]: 1.035 (0.59), 1.052 (1.11), 1.066 (0.47), 1.070 (0.65), 1.385 (11.31), 1.389 (7.08), 1.394 (16.00), 2.275 (0.62), 2.288 (0.89), 2.301 (0.65), 2.342 (1.10), 2.354 (1.36), 2.367 (0.97), 3.308 (2.05), 3.319 (0.93), 3.491 (1.89), 3.870 (4.92), 5.758 (0.42), 5.826 (0.77), 6.380 (0.60), 6.900 (0.51), 6.912 (0.50), 6.915 (0.52), 7.682 (0.80), 7.687 (0.79), 7.802 (0.49), 7.814 (0.46), 8.239 (0.77), 8.253 (0.73).

Compound 40.04

6-(1-methyl-1H-pyrazol-3-yl)-N-[4-(piperazin-1-ylmethyl)pyridin-2-yl]-1H-benzimidazol-2-amine hydrochloride

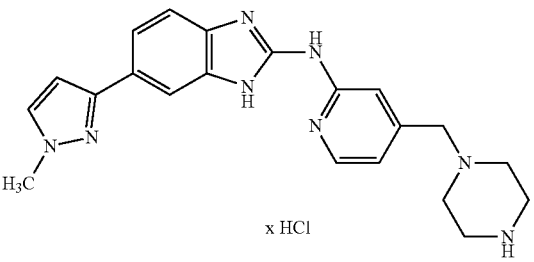 [SMILES: Cn1ccc(-c2ccc3nc(Nc4cc(CN5CCNCC5)ccn4)[nH]c3c2)n1]

Starting with tert-butyl 4-[(2-{[6-(1-methyl-1H-pyrazol-3-yl)-1H-benzimidazol-2-yl]amino}pyridin-4-yl)methyl]piperazine-1-carboxylate (1.70 g, 3.48 mmol), Compound 40.04 was prepared analogously to the procedure for the preparation of Compound 01.05.

Yield: 1.85 g of the title compound as crude product that was used for the next step without purification.

LC-MS (Method 2): $R_t$=0.85 min; MS (ESIpos): m/z=389 [M+H]$^+$.

Compound 41.01

6-(1-methyl-1H-1,2,4-triazol-5-yl)-N-[4-(piperazin-1-ylmethyl)pyridin-2-yl]-1H-benzimidazol-2-amine hydrochloride

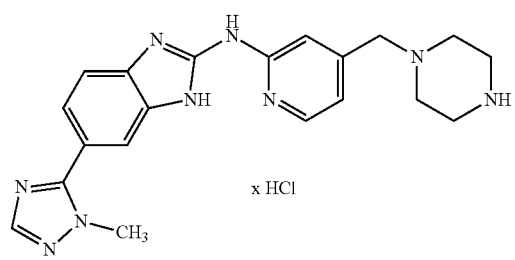 [SMILES: Cn1ncnc1-c1ccc2nc(Nc3cc(CN4CCNCC4)ccn3)[nH]c2c1]

Starting with tert-butyl 4-[(2-{[6-(1-methyl-1H-1,2,4-triazol-5-yl)-1H-benzimidazol-2-yl]amino}pyridin-4-yl)methyl]piperazine-1-carboxylate (99.0 mg, 202 μmol), Compound 41.01 was prepared analogously to the procedure for the preparation of Compound 01.05.

Yield: 111 mg of the title compound as crude product that was used for the next step without purification.

LC-MS (Method 2): $R_t$=0.75 min; MS (ESIpos): m/z=391 [M+H]$^+$.

Compound 42.01 ethyl 3-methylbutanimidate hydrochloride

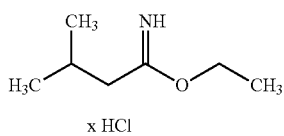

To 3-methylbutanenitrile (3.8 mL, 98% purity, 35 mmol) was added hydrochloric acid in dioxane (44 mL, c=4.0 M, 180 mmol) and ethanol (21 mL, 350 mmol). The mixture was stirred at room temperature overnight. The solvent was removed in vacuum, toluene was added, and the mixture was concentrated and dried under high vacuum to give 2.64 g of the title compound as a crude product that was used without purification.

$^1$H-NMR (400 MHz, DMSO-d6) δ[ppm]: 0.919 (14.99), 0.936 (16.00), 0.955 (0.83), 0.972 (0.67), 1.332 (3.80), 1.349 (8.21), 1.366 (4.01), 2.016 (0.71), 2.033 (0.90), 2.050 (0.73), 2.472 (4.76), 2.523 (0.81), 3.563 (0.79), 4.394 (1.14), 4.412 (3.80), 4.429 (3.85), 4.447 (1.18).

Compound 42.02

N',3-dimethylbutanimidohydrazide hydrochloride

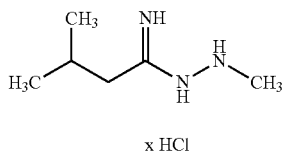

To a stirred solution of crude ethyl 3-methylbutanimidate hydrochloride (2.60 g, approx. 15.7 mmol) in pyridine (25 mL, 310 mmol) was added methylhydrazine (840 μl, 98% purity, 16 mmol). The mixture was stirred at room temperature overnight. The solvent was removed in vacuum, the residue was triturated with dichloromethane/hexane to give 2.32 g of the title compound as a crude product that was used without purification.

$^1$H-NMR (400 MHz, DMSO-d6) δ[ppm]: 0.855 (0.55), 0.872 (0.59), 0.891 (13.71), 0.894 (3.91), 0.907 (16.00), 0.911 (4.29), 0.916 (1.17), 0.920 (1.35), 0.924 (2.25), 0.932 (1.74), 0.949 (1.59), 2.025 (0.60), 2.042 (0.76), 2.059 (0.64), 2.239 (3.53), 2.258 (2.92), 2.609 (1.04), 3.280 (0.45), 5.755 (5.30).

Compound 42.03 tert-butyl 4-({2-[(6-{[1-methyl-2-(3-methylbutanimidoyl)hydrazinyl]carbonyl}-1H-benzimidazol-2-yl)amino]pyridin-4-yl}methyl)piperazine-1-carboxylate

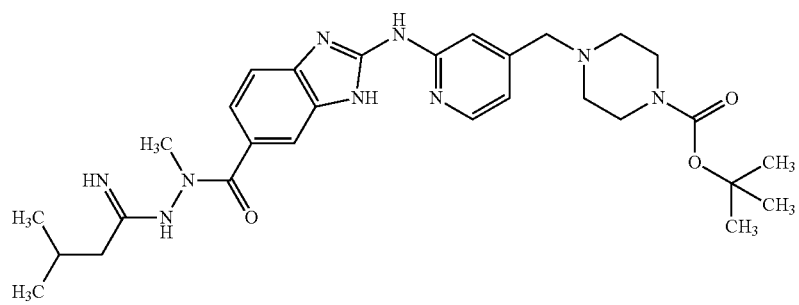 [SMILES: CC(C)CC(=N)NN(C)C(=O)c1ccc2nc(Nc3cc(CN4CCN(C(=O)OC(C)(C)C)CC4)ccn3)[nH]c2c1]

To a stirred solution of crude 2-[(4-{[4-(tert-butoxycarbonyl)piperazin-1-yl]methyl}pyridin-2-yl)amino]-1H-benzimidazole-6-carboxylic acid (450 mg, approx. 428 μmol) in DMA (6 mL) was added DIPEA (1.5 mL, 8.6 mmol), crude N',3-dimethylbutanimidohydrazide hydrochloride (259 mg, approx. 1.28 mmol) and PyBOP (668 mg, 1.28 mmol). The mixture was stirred at room temperature for 3 h. A sodium bicarbonate solution was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-Silicagel chromatography gave 125 mg of the title compound.

LC-MS (Method 2): R$_t$=1.09 min; MS (ESIpos): m/z=564 [M+H]$^+$.

$^1$H-NMR (400 MHz, DMSO-d6) δ[ppm]: 0.750 (0.81), 0.765 (0.85), 1.064 (0.84), 1.081 (0.89), 1.395 (16.00), 1.828 (0.78), 2.343 (0.78), 2.356 (1.28), 2.367 (1.03), 2.518 (1.23), 2.523 (0.94), 2.996 (2.11), 3.145 (0.41), 3.320 (6.69), 3.492 (1.02), 3.497 (1.01), 3.932 (0.76), 5.755 (4.26).

Compound 42.04

6-[1-methyl-3-(2-methylpropyl)-1H-1,2,4-triazol-5-yl]-N-[4-(piperazin-1-ylmethyl)pyridin-2-yl]-1H-benzimidazol-2-amine hydrochloride

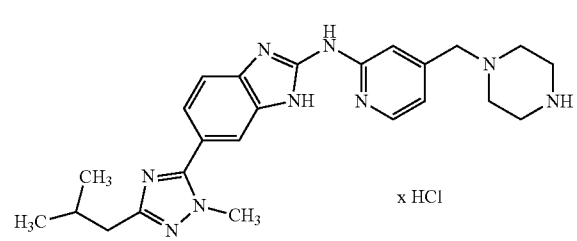 [SMILES: CC(C)Cc1nc(-c2ccc3nc(Nc4cc(CN5CCNCC5)ccn4)[nH]c3c2)n(C)n1]

Starting with tert-butyl 4-{[2-({6-[1-methyl-3-(2-methyl-propyl)-1H-1,2,4-triazol-5-yl]-1H-benzimidazol-2-yl}amino)pyridin-4-yl]methyl}piperazine-1-carboxylate (26.0 mg, 47.6 μmol), Compound 42.04 was prepared analogously to the procedure for the preparation of Compound 01.05.

Yield: 26.0 mg of the title compound as crude product that was used for the next step without purification.

LC-MS (Method 2): $R_t$=0.97 min; MS (ESIpos): m/z=446 [M+H]$^+$.

$^1$H-NMR (400 MHz, DMSO-d6) δ[ppm]: 0.957 (15.16), 0.974 (16.00), 1.986 (0.54), 2.062 (0.74), 2.080 (0.94), 2.096 (0.75), 2.327 (0.47), 2.518 (3.54), 2.523 (2.79), 2.541 (4.32), 2.559 (3.66), 2.669 (0.50), 3.300 (0.70), 3.564 (2.68), 3.968 (15.34), 5.756 (3.02), 7.553 (1.89), 7.755 (0.76), 7.759 (0.75), 7.776 (1.72), 7.781 (1.91), 7.800 (2.31), 7.821 (0.84), 8.070 (1.97), 8.539 (0.97), 8.553 (0.96).

Compound 44.01

4-bromo-1-(cyclopropylmethyl)pyridin-2(1H)-one

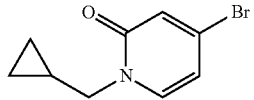

To a stirred solution of 4-bromopyridin-2(1H)-one (3.00 g, 97% purity, 16.7 mmol) in DMA (50 mL) was added potassium carbonate (6.93 g, 50.2 mmol) and (bromomethyl)cyclopropane (2.5 mL, 96% purity, 25 mmol). The mixture was stirred at r.t. for 48 h. Water was added and the mixture was extracted with dichloromethane/methanol. The organic phase was washed with half-saturated sodium chloride solution, dried (sodium sulfate), filtered and the solvent was removed in vacuum. Silicagel chromatography gave 3.10 g (81% yield) of the title compound.

LC-MS (Method 2): $R_t$=0.88 min; MS (ESIpos): m/z=228 [M+H]$^+$.

$^1$H-NMR (400 MHz, DMSO-d6) δ[ppm]: 0.336 (1.69), 0.348 (6.66), 0.352 (6.12), 0.361 (7.13), 0.364 (6.84), 0.374 (3.08), 0.398 (0.51), 0.404 (0.58), 0.411 (0.45), 0.423 (0.51), 0.440 (3.15), 0.449 (5.97), 0.454 (5.46), 0.460 (3.57), 0.465 (3.15), 0.470 (6.93), 0.475 (5.12), 0.485 (2.07), 1.139 (0.68), 1.145 (0.87), 1.158 (1.83), 1.165 (1.61), 1.170 (1.15), 1.177 (2.89), 1.184 (1.04), 1.186 (1.18), 1.190 (1.53), 1.196 (1.61), 1.198 (1.61), 1.208 (0.80), 1.210 (0.80), 1.216 (0.60), 2.523 (0.70), 3.695 (15.77), 3.714 (16.00), 6.450 (6.11), 6.456 (6.44), 6.468 (6.73), 6.474 (7.06), 6.704 (9.38), 6.710 (8.95), 7.716 (9.54), 7.733 (9.21).

Compound 44.02

1-(cyclopropylmethyl)-4-(3,4-diaminophenyl)pyridin-2(1H)-one

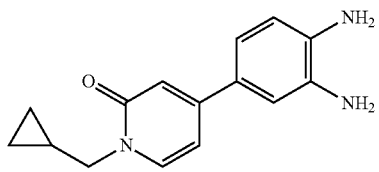 [SMILES: Nc1ccc(-c2ccn(CC3CC3)c(=O)c2)cc1N]

To a stirred solution of 4-bromo-1-(cyclopropylmethyl)pyridin-2(1H)-one (1.70 g, 7.45 mmol) in 1-propanol (85 mL) was added potassium carbonate solution (11 mL, 2.0 M, 22 mmol), 4-(4,4,5,5-tetramethyl-1,3,2-dioxaborolan-2-yl)benzene-1,2-diamine (2.42 g, 90% purity, 9.32 mmol), triphenylphosphine (82.1 mg, 745 μmol) and PdCl$_2$(PPh$_3$)$_2$ (523 mg, 745 μmol). The mixture was heated to reflux for 14 h, the solvent was removed in vacuum, water was added and the mixture was extracted with ethyl acetate. The organic phase was dried (sodium sulfate), filtered and the solvent was removed in vacuum. Aminophase-silicagel chromatography gave 1.89 g (99% yield) of the title compound.

LC-MS (Method 2): $R_t$=0.73 min; MS (ESIpos): m/z=256 [M+H]$^+$.

$^1$H-NMR (400 MHz, DMSO-d6) δ [ppm]: 0.346 (1.48), 0.358 (5.63), 0.361 (5.39), 0.370 (6.52), 0.373 (5.91), 0.383 (2.77), 0.406 (0.89), 0.442 (2.50), 0.451 (5.08), 0.456 (4.60), 0.462 (3.27), 0.467 (2.72), 0.471 (5.88), 0.475 (4.43), 0.487 (1.83), 1.067 (3.34), 1.168 (0.74), 1.181 (1.42), 1.183 (1.26), 1.188 (1.36), 1.193 (1.00), 1.201 (2.40), 1.206 (0.95), 1.208 (1.06), 1.213 (1.34), 1.220 (1.41), 1.233 (0.71), 2.518 (1.35), 2.523 (1.00), 3.160 (0.45), 3.173 (0.56), 3.342 (16.00), 3.687 (11.37), 3.705 (11.31), 3.944 (0.61), 4.611 (7.29), 4.920 (9.49), 5.759 (3.84), 6.399 (2.52), 6.401 (4.91), 6.406 (15.98), 6.411 (2.36), 6.423 (6.02), 6.428 (4.08), 6.540 (8.92), 6.561 (10.16), 6.801 (4.61), 6.807 (5.16), 6.821 (3.86), 6.827 (4.56), 6.889 (8.61), 6.894 (7.93), 7.632 (5.72), 7.634 (5.60), 7.649 (5.19), 7.651 (5.79).

Compound 44.03 tert-butyl 4-{[2-({6-[1-(cyclopropylmethyl)-2-oxo-1,2-dihydropyridin-4-yl]-1H-benzimidazol-2-yl}amino)pyridin-4-yl]methyl}piperazine-1-carboxylate

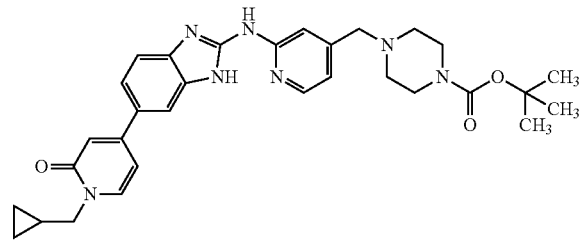 [SMILES: CC(C)(C)OC(=O)N1CCN(Cc2ccnc(Nc3nc4ccc(-c5ccn(CC6CC6)c(=O)c5)cc4[nH]3)c2)CC1]

To a stirred solution of 1H-imidazole (84.0 mg, 1.23 mmol) and di-1H-imidazol-1-ylmethanethione (1.39 g, 95% purity, 7.40 mmol) in dichloromethane (60 mL) was added tert-butyl 4-[(2-aminopyridin-4-yl)methyl]piperazine-1-carboxylate (1.80 g, 6.17 mmol), dissolved in dichloromethane (30 mL), at 0° C. The mixture was stirred at r.t. for 14 h. 1-(cyclopropylmethyl)-4-(3,4-diaminophenyl)pyridin-2(1H)-one (1.89 g, 7.40 mmol), dissolved in dichloromethane (30 mL), was added and the mixture was stirred at r.t. for 2 h. Further 1-(cyclopropylmethyl)-4-(3,4-diaminophenyl)pyridin-2(1H)-one (88 mg) was added and the mixture was stirred at r.t. for 56 h. Water was added and the mixture was extracted with dichloromethane.

The organic phase was dried (sodium sulfate) and filtered. N,N'-dipropan-2-ylcarbodiimide (2.8 mL, 18 mmol) was added and the mixture was stirred at r.t. for 14 h. Sodium bicarbonate solution was added, the mixture was stirred for 30 minutes and the mixture was extracted with dichloromethane. The organic phase was dried (sodium sulfate) and the solvent was removed in vacuum. Aminophase-silicagel chromatography gave 2.36 g of the title compound as a crude product, that was used without further purification.

LC-MS (Method 2): R$_t$=1.22 min; MS (ESIpos): m/z=556 [M+H]$^+$.

$^1$H-NMR (400 MHz, DMSO-d6) δ [ppm]: 0.397 (1.13), 0.409 (1.29), 0.483 (0.93), 0.498 (1.01), 1.384 (4.19), 1.394 (16.00), 2.358 (2.24), 3.308 (0.94), 3.500 (2.17), 3.745 (1.35), 3.763 (1.42), 6.928 (0.63), 6.941 (0.69), 7.183 (1.16), 7.761 (0.54), 7.776 (0.56), 8.263 (0.75), 8.275 (0.78), 12.225 (0.62).

Compound 44.04

1-(cyclopropylmethyl)-4-(2-{[4-(piperazin-1-ylmethyl)pyridin-2-yl]amino}-1H-benzimidazol-6-yl)pyridin-2(1H)-one hydrochloride

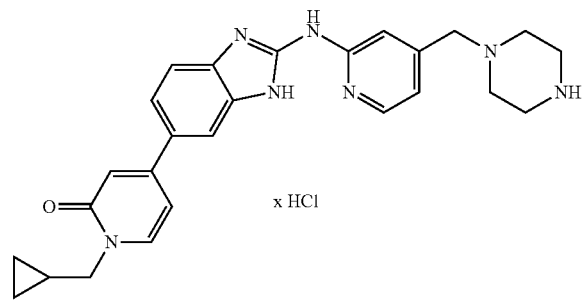 [SMILES: O=c1cc(-c2ccc3nc(Nc4cc(CN5CCNCC5)ccn4)[nH]c3c2)ccn1CC1CC1]

Starting with tert-butyl 4-{[2-({6-[1-(cyclopropylmethyl)-2-oxo-1,2-dihydropyridin-4-yl]-1H-benzimidazol-2-yl}amino)pyridin-4-yl]methyl}piperazine-1-carboxylate (2.36 g, 4.25 mmol), Compound 44.04 was prepared analogously to the procedure for the preparation of Compound 01.05.

Yield: 2.65 g of the title compound as crude product that was used for the next step without purification.

LC-MS (Method 2): R$_t$=0.93 min; MS (ESIpos): m/z=456 [M+H]$^+$.

$^1$H-NMR (400 MHz, DMSO-d6) δ[ppm]: 0.391 (2.81), 0.403 (10.02), 0.407 (9.74), 0.415 (11.78), 0.419 (9.87), 0.428 (4.35), 0.438 (1.51), 0.451 (1.48), 0.457 (1.43), 0.465 (1.61), 0.473 (4.45), 0.481 (9.10), 0.486 (7.57), 0.492 (5.98), 0.502 (9.64), 0.505 (7.64), 0.518 (2.56), 1.058 (0.49), 1.210 (1.12), 1.216 (1.79), 1.228 (3.12), 1.236 (2.81), 1.242 (2.33), 1.248 (4.19), 1.255 (2.20), 1.260 (2.53), 1.267 (2.63), 1.279 (1.48), 1.286 (0.97), 1.423 (1.35), 1.442 (3.22), 1.461 (1.46), 2.323 (1.05), 2.327 (1.51), 2.331 (1.10), 2.523 (9.18), 2.665 (1.10), 2.669 (1.56), 2.674 (1.07), 2.722 (1.92), 2.884 (2.35), 3.149 (0.59), 3.168 (1.41), 3.187 (1.41), 3.207 (0.79), 3.422 (10.22), 3.451 (10.63), 3.464 (13.32), 3.480 (14.65), 3.482 (14.21), 3.559 (16.00), 3.569 (1.35), 3.645 (0.69), 3.653 (0.79), 3.656 (0.97), 3.661 (0.79), 3.668 (0.92), 3.671 (0.97), 3.697 (0.95), 3.699 (0.89), 3.707 (0.74), 3.712 (0.84), 3.773 (14.19), 3.791 (14.24), 4.328 (1.81), 4.519 (7.44), 4.757 (3.14), 6.587 (6.29), 6.593 (7.11), 6.606 (6.26), 6.611 (7.26), 6.655 (0.66), 6.661 (0.84), 6.675 (13.55), 6.680 (12.19), 6.763 (0.84), 6.768 (0.77), 7.166 (4.65), 7.207 (1.33), 7.580 (10.68), 7.649 (4.50), 7.663 (4.60), 7.696 (2.58), 7.699 (2.58), 7.709 (4.04), 7.713 (3.96), 7.730 (9.71), 7.735 (10.12), 7.750 (14.36), 7.771 (4.88), 7.857 (2.61), 7.860 (2.50), 7.870 (10.91), 7.887 (10.30), 7.953 (11.02), 7.957 (11.63), 8.028 (3.42), 8.044 (4.19), 8.142 (0.51), 8.394 (1.43), 8.406 (1.38), 8.567 (8.20), 8.580 (7.62), 9.135 (0.92), 9.941 (4.12).

Compound 45.01 tert-butyl 4-[(2-{[6-(pyrimidin-5-yl)-1H-benzimidazol-2-yl]amino}pyridin-4-yl)methyl]piperazine-1-carboxylate

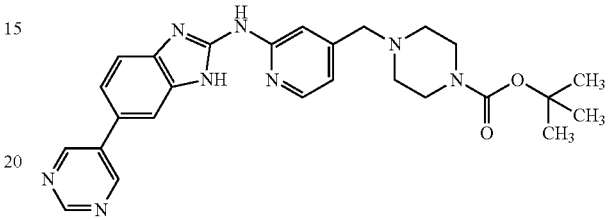

Tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 μmol), 5-bromopyrimidine (116 mg, 730 μmol) and an aqueous sodium carbonate solution (700 μl, 2.0 M, 1.4 mmol) were stirred in DME (15 mL), sparged with argon for 2 min, Pd(dppf)Cl$_2$·CH$_2$Cl$_2$ (45.8 mg, 56.1 μmol) was added and the mixture was stirred at 150° C. in a sealed tube for 2.5 h. The mixture was filtered through a silicone filter and concentrated under reduced pressure to give 597 mg of the title compound as a crude product that was used without further purification.

LC-MS (Method 2): R$_t$=1.14 min; MS (ESIpos): m/z=487 [M+H]$^+$.

Compound 45.02

N-[4-(piperazin-1-ylmethyl)pyridin-2-yl]-6-(pyrimidin-5-yl)-1H-benzimidazol-2-amine hydrochloride

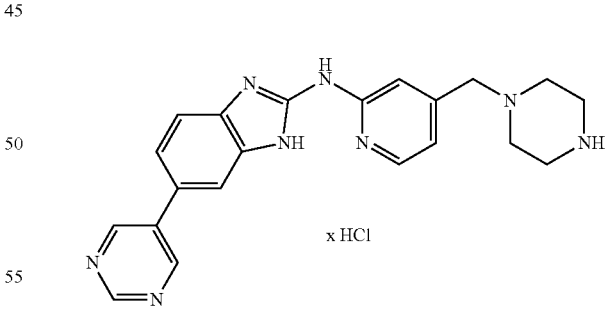

Starting with tert-butyl 4-[(2-{[6-(pyrimidin-5-yl)-1H-benzimidazol-2-yl]amino}pyridin-4-yl)methyl]piperazine-1-carboxylate (597 mg, 1.23 mmol), Compound 45.02 was prepared analogously to the procedure for the preparation of Compound 01.05.

Yield: 672 mg of the title compound as crude product were used for the next step without purification.

LC-MS (Method 2): R$_t$=0.80 min; MS (ESIpos): m/z=387 [M+H]$^+$.

Compound 45.03 tert-butyl 4-[(2-{[6-(2-chloropyrimidin-5-yl)-1H-benzimidazol-2-yl]amino}pyridin-4-yl)methyl]piperazine-1-carboxylate

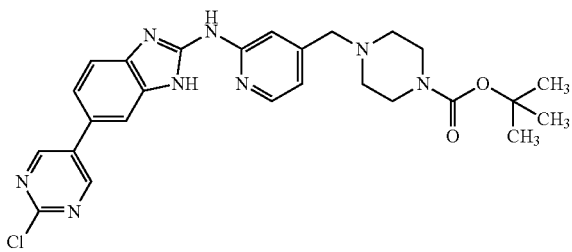 [SMILES: CC(C)(C)OC(=O)N1CCN(Cc2ccnc(Nc3nc4ccc(-c5cnc(Cl)nc5)cc4[nH]3)c2)CC1]

tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 µmol), 5-bromo-2-chloropyrimidine (141 mg, 730 µmol) and an aqueous sodium carbonate solution (700 µl, 2.0 M, 1.4 mmol) were stirred in DME (15 mL), sparged with argon for 2 min, Pd(dppf)Cl$_2$.CH$_2$Cl$_2$ (45.8 mg, 56.1 µmol) was added and the mixture was stirred at 150° C. in a sealed tube for 5 h. The mixture was filtered through a silicone filter and concentrated under reduced pressure to give 456 mg of the title compound as a crude product that was used without further purification.

LC-MS (Method 2): R$_t$=1.29 min; MS (ESIpos): m/z=521 [M+H]$^+$.

Compound 45.04

6-(2-chloropyrimidin-5-yl)-N-[4-(piperazin-1-ylmethyl)pyridin-2-yl]-1H-benzimidazol-2-amine hydrochloride salt

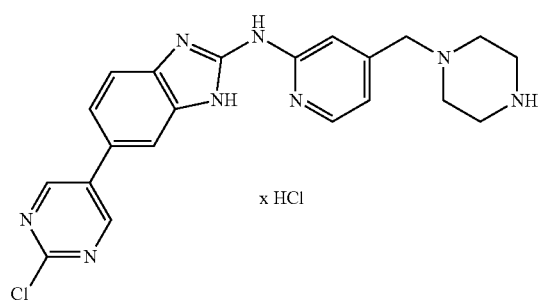 [SMILES: Clc1ncc(-c2ccc3nc(Nc4cc(CN5CCNCC5)ccn4)[nH]c3c2)cn1]

Starting with tert-butyl 4-[(2-{[6-(2-chloropyrimidin-5-yl)-1H-benzimidazol-2-yl]amino}pyridin-4-yl)methyl]piperazine-1-carboxylate (456 mg, 876 µmol), Compound 45.04 was prepared analogously to the procedure for the preparation of Compound 01.05.

Yield: 611 mg of the title compound as crude product were used for the next step without purification.

LC-MS (Method 2): R$_t$=0.94 min; MS (ESIpos): m/z=421 [M+H]$^+$.

Compound 45.05 tert-butyl 4-[(2-{[6-(2-methylpyrimidin-5-yl)-1H-benzimidazol-2-yl]amino}pyridin-4-yl)methyl]piperazine-1-carboxylate

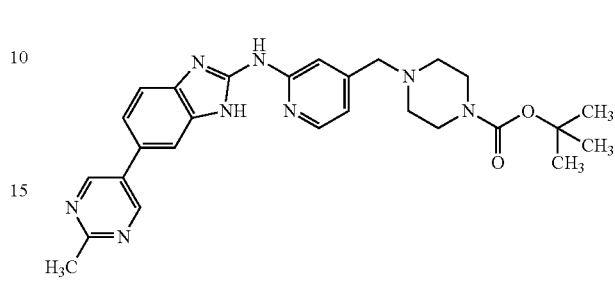

tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 µmol), 5-bromo-2-methylpyrimidine (126 mg, 730 µmol) and an aqueous sodium carbonate solution (700 µl, 2.0 M, 1.4 mmol) were stirred in DME (15 mL), sparged with Ar for 2 min, Pd(dppf)Cl$_2$.CH$_2$Cl$_2$ (45.8 mg, 56.1 µmol) was added and the mixture was stirred at 150° C. in a sealed tube for 5 h. The mixture was filtered through a silicone filter and concentrated under reduced pressure to give 366 mg of the title compound as a crude product that was used without further purification.

LC-MS (Method 2): R$_t$=1.17 min; MS (ESIpos): m/z=501 [M+H]$^+$.

Compound 45.06

6-(2-methylpyrimidin-5-yl)-N-[4-(piperazin-1-ylmethyl)pyridin-2-yl]-1H-benzimidazol-2-amine hydrochloride salt

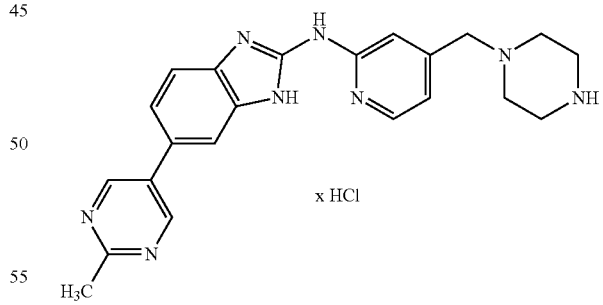

Starting with tert-butyl 4-[(2-{[6-(2-methylpyrimidin-5-yl)-1H-benzimidazol-2-yl]amino}pyridin-4-yl)methyl]piperazine-1-carboxylate (366 mg, 731 µmol), Compound 45.06 was prepared analogously to the procedure for the preparation of Compound 01.05.

Yield: 409 mg of the title compound as crude product were used for the next step without purification.

LC-MS (Method 2): R$_t$=0.82 min; MS (ESIpos): m/z=401 [M+H]$^+$.

Compound 45.07 tert-butyl 4-[(2-{[6-(2-cyclopropylpyrimidin-5-yl)-1H-benzimidazol-2-yl]amino}pyridin-4-yl)methyl]piperazine-1-carboxylate

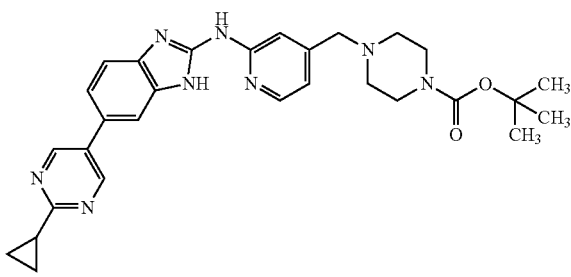 [SMILES: CC(C)(C)OC(=O)N1CCN(Cc2ccnc(Nc3nc4ccc(-c5cnc(C6CC6)nc5)cc4[nH]3)c2)CC1]

tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 µmol), 5-bromo-2-cyclopropylpyrimidine (145 mg, 730 µmol) and an aqueous sodium carbonate solution (700 µl, 2.0 M, 1.4 mmol) were stirred in DME (15 mL), sparged with argon for 2 min, Pd(dppf)C$_2$·CH$_2$Cl$_2$ (45.8 mg, 56.1 µmol) was added and the mixture was stirred at 150° C. in a sealed tube for 5 h. The mixture was filtered through a silicone filter and concentrated under reduced pressure to give 455 mg of the title compound as a crude product that was used without further purification.

LC-MS (Method 2): R$_t$=1.31 min; MS (ESIpos): m/z=527 [M+H]$^+$.

Compound 45.08

6-(2-cyclopropylpyrimidin-5-yl)-N-[4-(piperazin-1-ylmethyl)pyridin-2-yl]-1H-benzimidazol-2-amine hydrochloride

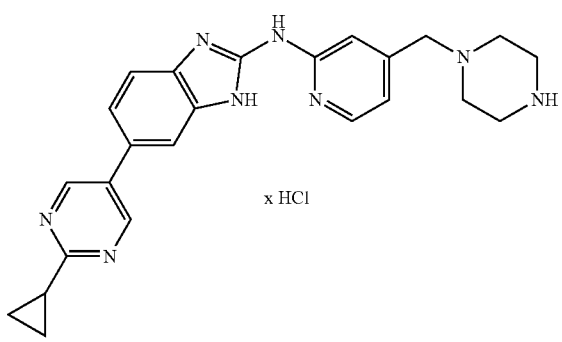 [SMILES: c1cc(CN2CCNCC2)cc(Nc2nc3ccc(-c4cnc(C5CC5)nc4)cc3[nH]2)n1]

x HCl

Starting with tert-butyl 4-[(2-{[6-(2-cyclopropylpyrimidin-5-yl)-1H-benzimidazol-2-yl]amino}pyridin-4-yl)methyl]piperazine-1-carboxylate (455 mg, 863 µmol), Compound 45.08 was prepared analogously to the procedure for the preparation of Compound 01.05.

Yield: 733 mg of the title compound as crude product that was were used for the next step without purification.

LC-MS (Method 2): R$_t$=0.98 min; MS (ESIpos): m/z=428 [M+H]$^+$.

Compound 45.09 tert-butyl 4-{[2-({6-[2-(methylsulfanyl)pyrimidin-5-yl]-1H-benzimidazol-2-yl}amino)pyridin-4-yl]methyl}piperazine-1-carboxylate

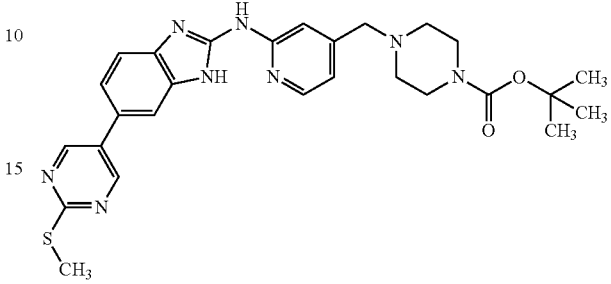

tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (300 mg, 561 µmol), 5-bromo-2-(methylsulfanyl)pyrimidine (150 mg, 730 µmol) and an aqueous sodium carbonate solution (700 µl, 2.0 M, 1.4 mmol) were stirred in DME (15 mL), sparged with argon for 2 min, Pd(dppf)Cl$_2$·CH$_2$Cl$_2$ (45.8 mg, 56.1 µmol) was added and the mixture was stirred at 150° C. in a sealed tube for 2.5 h. The mixture was filtered through a silicone filter and concentrated under reduced pressure to give 564 mg of the title compound as a crude product that was used without further purification.

LC-MS (Method 2): R$_t$=1.33 min; MS (ESIpos): m/z=533 [M+H]$^+$.

Compound 45.10

6-[2-(methylsulfanyl)pyrimidin-5-yl]-N-[4-(piperazin-1-ylmethyl)pyridin-2-yl]-1H-benzimidazol-2-amine hydrochloride

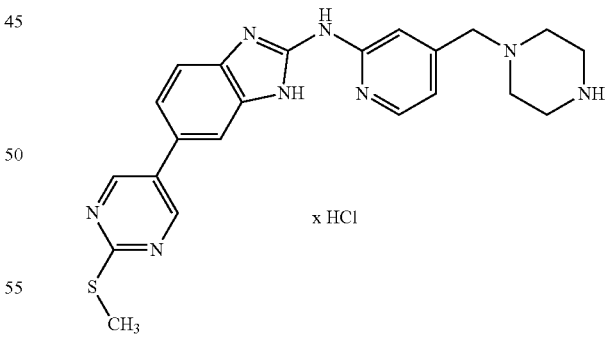

x HCl

Starting with tert-butyl 4-{[2-({6-[2-(methylsulfanyl)pyrimidin-5-yl]-1H-benzimidazol-2-yl}amino)pyridin-4-yl]methyl}piperazine-1-carboxylate (564 mg, 1.06 mmol), Compound 45.10 was prepared analogously to the procedure for the preparation of Compound 01.05.

Yield: 590 mg of the title compound as crude product that was used for the next step without purification.

LC-MS (Method 2): R$_t$=1.03 min; MS (ESIpos): m/z=433 [M+H]$^+$.

Compound 46.01

6-chloro-4-iodo-3-methoxypyridazine

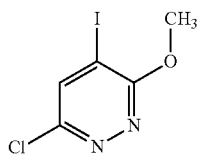

To a stirred solution of 2,2,6,6-tetramethylpiperidine (6.9 mL, 41 mmol) in tetrahydrofuran (200 mL, 2.5 mol), was added n-butyllithium (16 mL, c=2.5 M in hexanes, 40 mmol) at −70° C. 3-chloro-6-methoxypyridazine (2.90 g, 20.1 mmol) dissolved in tetrahydrofuran (150 mL) was added dropwise and the reaction mixture was stirred at −78° C. for 30 minutes. Iodine (5.30 g, 20.9 mmol) dissolved in tetrahydrofuran (50 mL) was added and the mixture was stirred at −78° C. for 2 hours. An aqueous solution of disodium sulfurothioate (c=1M; 150 mL) was added and the mixture was extracted with diethyl ether. The organic phase was dried (magnesium sulfate), filtered and the solvent was removed in vacuum. Silicagel chromatography gave 925 mg of the title compound.

LC-MS (Method 5): $R_t$=2.94 min; MS (ESIpos): m/z=271 [M+H]$^+$.

$^1$H-NMR (400 MHz, DMSO-d6) δ [ppm]: 2.495 (0.64), 2.500 (0.88), 2.505 (0.64), 3.316 (11.53), 3.992 (0.76), 4.049 (16.00), 8.416 (5.48).

Compound 47.01

4-bromo-5-methoxypyridazin-3(2H)-one

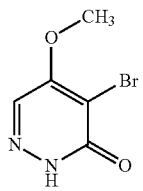

To a stirred suspension of 4,5-dibromopyridazin-3(2H)-one (4.00 g, 15.8 mmol) in methanol (40 mL, 990 mmol), was added potassium carbonate (4.00 g, 28.9 mmol) and the mixture was stirred at 80° C. for 67 hours. The solvent was removed in vacuum. Water was added to the residue and acetic acid was added until acidic pH was reached. A solid precipitated and was collected by filtration, washed with water, and dried to give 2.23 g (69% yield) of the title compound as a crude product.

LC-MS (Method 5): $R_t$=0.57 min; MS (ESIpos): m/z=205 [M+H]$^+$.

Compound 47.02

5-methoxypyridazin-3(2H)-one

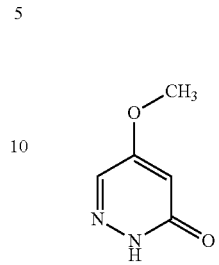

To a stirred solution of 4-bromo-5-methoxypyridazin-3 (2H)-one (900 mg, 4.39 mmol) in water (20 mL) was added sodium hydroxide (180 mg, 4.50 mmol) and palladium on carbon (10% w/w palladium) (300 mg) and the mixture was stirred at r.t. under a pressure of 2 bar of hydrogen for 2 h. The warm mixture was filtered through celite and the catalyst was washed with water. The filtrate was cooled to 0° C. and stir red at 0° C. for 2 hours. A solid precipitated and was collected by filtration to give 260 mg (47% yield) of the title compound.

LC-MS (Method 5): $R_t$=0.31 min; MS (ESIpos): m/z=127 [M+H]$^+$.

$^1$H-NMR (400 MHz, DMSO-d6) δ[ppm]: 2.500 (1.36), 3.328 (11.32), 3.779 (16.00), 6.167 (3.61), 6.173 (3.48), 7.657 (3.28), 7.663 (3.14), 12.613 (0.81).

Compound 47.03

3-chloro-5-methoxypyridazine

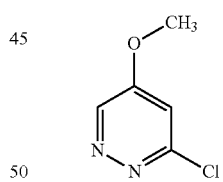

A suspension of 5-methoxypyridazin-3(2H)-one (250 mg, 1.98 mmol) in phosphorus oxychloride (1.5 mL, 16 mmol) was stirred at 100° C. for 10 minutes. The reaction mixture was poured into ice water and sodium carbonate was added until a basic pH—was reached. The mixture was extracted with diethyl ether, the organic phase was dried (magnesium sulfate), filtered and the solvent was removed in vacuum. The residue was crystallized from 1,2-dichloroethane to give 130 mg (45% yield) of the title compound.

LC-MS (Method 5): $R_t$=0.85 min; MS (ESIpos): m/z=145 [M+H]$^+$.

$^1$H-NMR (400 MHz, DMSO-d6) δ [ppm]: 2.495 (0.78), 2.499 (1.07), 2.503 (0.84), 3.317 (11.94), 3.944 (16.00), 7.528 (2.28), 7.534 (2.29), 8.988 (2.34), 8.994 (2.34).

Compound 49.01

2-amino-6-bromo-3-nitrophenol

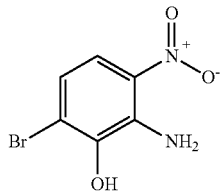

To a stirred solution of 2-bromo-5-nitrophenol (10.0 g, 45.9 mmol) in DMSO (150 mL) was added 1,1,1-trimethylhydrazinium iodide (10.5 g, 97% purity, 50.5 mmol). The mixture was stirred for 90 min, then sodium 2-methylbutan-2-olate (26.6 g, 95% purity, 229 mmol) was added. The reaction mixture was stirred at r.t. over night. Aqueous hydrochloric acid (70 mL, 4.0 M, 280 mmol) and water were added at 0° C. and the mixture was stirred for 3 h. The reaction mixture was extracted with ethyl acetate/hexane (4:1). The organic phase was washed with saturated sodium chloride solution, filtered and the solvent was removed in vacuum, to give 10.6 g (99% yield) of the title compound as a crude product.

$^1$H-NMR (400 MHz, DMSO-d6) δ [ppm]: 3.760 (0.77), 6.617 (0.73), 6.640 (0.74), 6.752 (15.43), 6.776 (15.64), 7.175 (2.66), 7.484 (16.00), 7.507 (13.75), 7.542 (0.71), 7.565 (0.68), 9.998 (1.15).

Compound 49.04

3-bromo-2-(2-methylpropoxy)-6-nitroaniline

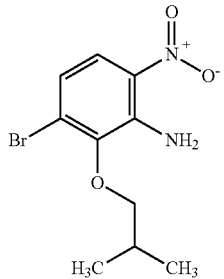

To a stirred solution of 2-amino-6-bromo-3-nitrophenol (10.6 g, 45.6 mmol) in acetonitrile (150 mL) was added potassium carbonate (12.6 g, 91.1 mmol) and 1-bromo-2-methylpropane (20 mL, 99% purity, 180 mmol). The mixture was stirred at 70° C. for 14 h. Water was added and the mixture was extracted with ethyl acetate/hexane (3:1). The organic phase was washed with half-saturated sodium chloride solution, dried (sodium sulfate) and the solvent was removed in vacuum. Silicagel chromatography gave 10.4 g (79% yield) of the title compound.

LC-MS (Method 2): $R_t$=1.45 min; MS (ESIpos): m/z=289 [M+H]$^+$.

$^1$H-NMR (400 MHz, DMSO-d6) δ [ppm]: 1.009 (1.50), 1.019 (16.00), 1.025 (2.30), 1.036 (15.86), 2.225 (0.92), 2.241 (1.11), 2.258 (0.88), 3.655 (5.08), 3.671 (5.15), 6.854 (4.03), 6.877 (4.24), 7.063 (1.60), 7.714 (3.64), 7.738 (3.66).

Compound 49.05

2-(2-methylpropoxy)-6-nitro-3-(4,4,5,5-tetramethyl-1,3,2-dioxaborolan-2-yl)aniline

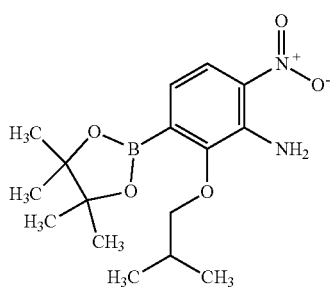

To a stirred solution of 3-bromo-2-(2-methylpropoxy)-6-nitroaniline (5.00 g, 17.3 mmol) in dioxane (500 mL, 5.8 mol) was added potassium acetate (5.09 g, 51.9 mmol), 1,1'-bis(diphenylphosphino)ferrocene-palladium(II)dichloride dichloromethane complex (706 mg, 865 µmol) and 4,4,4',4',5,5,5',5'-octamethyl-2,2'-bi-1,3,2-dioxaborolane (13.4 g, 98% purity, 51.9 mmol). The mixture was heated to 120° C. for 14 h. The reaction mixture was filtered through celite and the solvent was removed in vacuum. Aminophase silicagel chromatography gave 4.2 g (72% yield) of the title compound.

LC-MS (Method 1): $R_t$=1.56 min; MS (ESIpos): m/z=337 [M+H]$^+$.

$^1$H-NMR (400 MHz, DMSO-d6) δ[ppm]: 0.993 (4.30), 1.010 (4.68), 1.065 (0.99), 1.163 (1.66), 1.303 (16.00), 3.331 (2.01), 3.655 (1.27), 3.672 (1.22), 6.735 (1.00), 6.758 (0.99), 7.701 (0.92), 7.723 (0.88).

Compound 49.06

3-(2-methylpropoxy)-4-(4,4,5,5-tetramethyl-1,3,2-dioxaborolan-2-yl)benzene-1,2-diamine

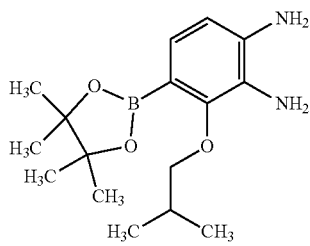 [SMILES: CC(C)COc1c(B2OC(C)(C)C(C)(C)O2)ccc(N)c1N]

To a stirred solution of 2-(2-methylpropoxy)-6-nitro-3-(4,4,5,5-tetramethyl-1,3,2-dioxaborolan-2-yl)aniline (4.20 g, 11.2 mmol) in ethanol (380 mL, 6.6 mol) was added palladium on carbon (10% w/w palladium, 1.2 g) and the mixture was hydrogenated for 6 h. The mixture was filtered through celite and the solution was concentrated in vacuum. Aminophase silicagel chromatography gave 4.20 g of the title compound as crude product that was used without purification.

LC-MS (Method 1): $R_t$=1.23 min; MS (ESIpos): m/z=307 [M+H]$^+$.

¹H-NMR (400 MHz, DMSO-d6) δ[ppm]: 0.986 (2.30), 1.003 (2.48), 1.066 (16.00), 1.154 (0.41), 1.172 (0.83), 1.190 (0.41), 1.230 (7.53), 1.987 (1.36), 3.335 (1.46), 3.495 (0.62), 3.511 (0.61), 3.941 (2.75), 6.268 (0.46), 6.288 (0.48), 6.721 (0.52), 6.741 (0.45).

Compound 49.07 cyclopropyl{4-[(2-{[7-(2-methylpropoxy)-6-(4,4,5,5-tetramethyl-1,3,2-dioxaborolan-2-yl)-1H-benzimidazol-2-yl]amino}pyridin-4-yl)methyl]piperazin-1-yl}methanone

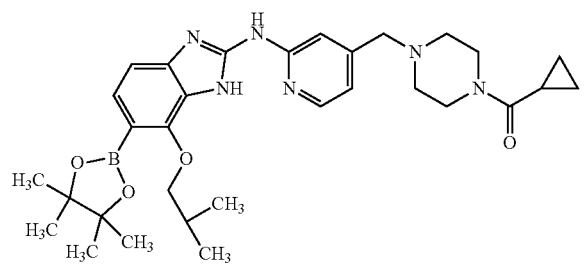 [SMILES: CC(C)COc1c(B2OC(C)(C)C(C)(C)O2)ccc2nc(Nc3cc(CN4CCN(C(=O)C5CC5)CC4)ccn3)[nH]c12]

To a stirred solution of 1H-imidazole (78.4 mg, 1.15 mmol) and di-1H-imidazol-1-ylmethanethione (1.30 g, 95% purity, 6.91 mmol) in dichloromethane (80 mL) was added {4-[(2-aminopyridin-4-yl)methyl]piperazin-1-yl}(cyclopropyl)methanone (1.50 g, 5.76 mmol), dissolved in dichloromethane (20 mL) at 0° C. The mixture was stirred at r.t. for 14 h. 3-(2-methylpropoxy)-4-(4,4,5,5-tetramethyl-1,3,2-dioxaborolan-2-yl)benzene-1,2-diamine (3.02 g, approx. 6.91 mmol), dissolved in dichloromethane (30 mL) was added and the mixture was stirred at r.t. for 14 h. Water was added and the mixture was extracted with dichloromethane. The organic phase was dried (sodium sulfate) and filtered. N,N'-dipropan-2-ylcarbodiimide (1.8 mL, 12 mmol) was added and the mixture was stirred at r.t. for 14 h. Saturated ammonium chloride solution was added, the mixture was stirred for 30 minutes and the mixture was extracted with dichloromethane. The organic phase was dried (sodium sulfate) and the solvent was removed in vacuum. Silicagel chromatography gave 1.90 g of the title compound as a crude product, that was used without further purification.

C-MS (Method 1): R$_t$=1.08 min; MS (ESIpos): m/z=575 [M+H]⁺.

¹H-NMR (400 MHz, DMSO-d6) δ[ppm]: 0.678 (0.71), 0.697 (0.88), 0.709 (0.80), 0.716 (0.77), 0.721 (0.83), 1.021 (1.48), 1.037 (1.57), 1.153 (4.30), 1.171 (8.54), 1.189 (4.15), 1.275 (5.80), 1.289 (1.45), 1.986 (16.00), 3.334 (3.12), 3.999 (1.11), 4.016 (3.39), 4.034 (3.43), 4.052 (1.16).

Compound 50.01

3-(3-methoxypyridin-4-yl)-2-(2-methyl propoxy)-6-nitroaniline

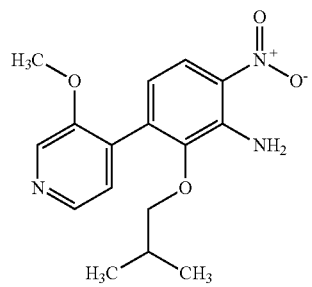

Starting with 3-bromo-2-(2-methylpropoxy)-6-nitroaniline (1.80 g, 6.23 mmol) and (3-methoxypyridin-4-yl)boronic acid (1.20 g, 95% purity, 7.47 mmol), Compound 50.01 was prepared analogously to the procedure for the preparation of Compound 02.01.

Yield: 1.30 g (66%) of the title compound.

LC-MS (Method 2): R$_t$=1.20 min; MS (ESIpos): m/z=318 [M+H]⁺.

¹H-NMR (400 MHz, DMSO-d6) δ[ppm]: 0.577 (15.14), 0.594 (16.00), 1.171 (0.47), 1.751 (0.86), 1.768 (1.09), 1.785 (0.86), 1.986 (0.85), 2.522 (1.18), 3.213 (4.36), 3.229 (4.46), 3.331 (1.89), 3.333 (8.36), 3.818 (1.87), 5.755 (0.88), 5.758 (6.05), 6.505 (4.02), 6.527 (3.78), 7.028 (2.65), 7.254 (2.68), 7.266 (2.80), 7.810 (3.47), 7.832 (3.26), 8.279 (3.46), 8.287 (0.91), 8.290 (3.62), 8.495 (4.82).

Compound 50.02

4-(3-methoxypyridin-4-yl)-3-(2-methylpropoxy)benzene-1,2-diamine

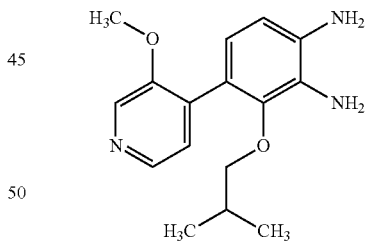

To a stirred solution of 3-(3-methoxypyridin-4-yl)-2-(2-methylpropoxy)-6-nitroaniline (1.30 g, 4.10 mmol) in ethanol (21 mL) and dichloromethane (41 mL) was added palladium on carbon (10% w/w palladium; 436 mg) and the mixture was stirred at r.t. in a hydrogen atmosphere for 3 h. The mixture was filtered, and the solution was concentrated in vacuum. Aminophase silicagel chromatography gave 1.00 g of the title compound as crude product that was used without further purification.

LC-MS (Method 2): R$_t$=0.90 min; MS (ESIpos): m/z=288 [M+H]⁺.

¹H-NMR (400 MHz, DMSO-d6) δ[ppm]: 0.628 (12.69), 0.644 (12.69), 1.663 (0.65), 1.681 (0.80), 1.697 (0.62), 3.102 (3.58), 3.117 (3.53), 3.332 (16.00), 4.179 (2.92), 4.738

(3.17), 5.760 (0.67), 6.288 (1.87), 6.308 (3.58), 6.348 (3.18), 6.368 (1.66), 7.138 (2.28), 7.150 (2.38), 8.145 (3.09), 8.156 (2.84), 8.332 (4.23).

Compound 50.03 tert-butyl 4-[(2-{[6-(3-methoxypyridin-4-yl)-7-(2-methylpropoxy)-1H-benzimidazol-2-yl]amino}pyridin-4-yl)methyl]piperazine-1-carboxylate

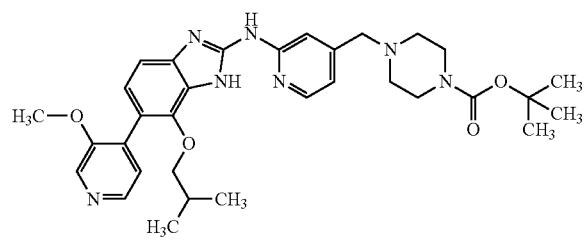 [SMILES: COc1cnccc1-c1ccc2nc(Nc3cc(CN4CCN(C(=O)OC(C)(C)C)CC4)ccn3)[nH]c2c1OCC(C)C]

To a stirred solution of 1H-imidazole (35.5 mg, 522 µmol) and di-1H-imidazol-1-ylmethanethione (490 mg, 95% purity, 2.61 mmol) in dichloromethane (25 mL) was added tert-butyl 4-[(2-aminopyridin-4-yl)methyl]piperazine-1-carboxylate (763 mg, 2.61 mmol), dissolved in dichloromethane (12 mL), at 0° C. The mixture was stirred at r.t. for 14 h. 4-(3-methoxypyridin-4-yl)-3-(2-methylpropoxy)benzene-1,2-diamine (1.00 g, approx. 2.61 mmol), dissolved in dichloromethane (15 mL), was added and the mixture was stirred at r.t. for 56 h.

Water was added and the mixture was extracted with dichloromethane.

The organic phase was dried (sodium sulfate) and filtered. N,N'-dipropan-2-ylcarbodiimide (1.2 mL, 7.7 mmol) was added and the mixture was stirred at r.t. for 14 h. Further N,N'-dipropan-2-ylcarbodiimide (0.8 mL, 5.1 mmol) was added and the mixture was stirred at r.t. for 14 h.

Sodium bicarbonate solution was added, the mixture was stirred for 30 minutes and the mixture was extracted with dichloromethane. The organic phase was dried (sodium sulfate) and the solvent was removed in vacuum. Aminophase-silicagel chromatography followed by silicagel chromatography gave 407 mg of the title compound.

LC-MS (Method 2): R$_t$=1.39 min; MS (ESIpos): m/z=588 [M+H]$^+$.

$^1$H-NMR (400 MHz, DMSO-d6) [ppm]: 0.736 (4.14), 0.752 (4.31), 1.393 (16.00), 2.338 (0.95), 2.350 (1.37), 2.363 (0.98), 3.344 (1.19), 3.486 (1.50), 3.802 (4.10), 4.233 (1.29), 4.249 (1.28), 5.760 (2.85), 6.784 (0.77), 6.804 (0.81), 7.184 (0.78), 7.196 (0.93), 7.203 (1.54), 7.223 (0.77), 8.199 (0.87), 8.211 (0.84), 8.248 (0.66), 8.262 (0.61), 8.373 (1.38), 10.682 (0.69).

Compound 50.04

6-(3-methoxypyridin-4-yl)-7-(2-methylpropoxy)-N-[4-(piperazin-1-ylmethyl)pyridin-2-yl]-1H-benzimidazol-2-amine hydrochloride

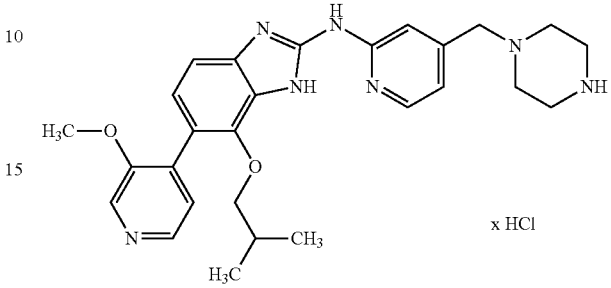

Starting with tert-butyl 4-[(2-{[6-(3-methoxypyridin-4-yl)-7-(2-methylpropoxy)-1H-benzimidazol-2-yl]amino}pyridin-4-yl)methyl]piperazine-1-carboxylate (407 mg, 692 µmol), Compound 50.04 was prepared analogously to the procedure for the preparation of Compound 01.05.

Yield: 474 mg of the title compound as crude product that was used for the next step without purification.

LC-MS (Method 2): R$_t$=1.10 min; MS (ESIpos): m/z=488 [M+H]$^+$.

$^1$H-NMR (400 MHz, DMSO-d6) δ[ppm]: 0.759 (15.96), 0.776 (16.00), 1.798 (0.51), 1.815 (0.99), 1.832 (1.21), 1.848 (0.94), 2.523 (1.01), 3.334 (0.82), 3.383 (0.72), 3.387 (0.68), 3.394 (0.74), 3.440 (2.22), 3.455 (1.76), 3.971 (15.15), 4.032 (1.31), 4.046 (1.27), 5.760 (3.82), 7.156 (1.26), 7.176 (1.38), 7.440 (2.45), 7.448 (1.55), 7.460 (2.02), 7.496 (0.65), 7.896 (2.14), 7.910 (2.13), 8.474 (1.14), 8.486 (1.09), 8.601 (2.44), 8.615 (2.26), 8.743 (4.26).

Compound 51.01

3-bromo-2-ethoxy-6-nitroaniline

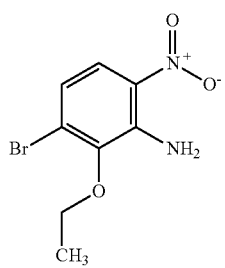

To a stirred solution of 2-amino-6-bromo-3-nitrophenol (4.41 g, 18.9 mmol) in acetonitrile (130 mL) was added potassium carbonate (5.23 g, 37.8 mmol) and iodoethane (2.8 mL, 98% purity, 34 mmol). The mixture was stirred at r.t. for 14 h. Further iodoethane (0.78 mL) was added and the mixture was stirred at r.t. for 14 h. Water was added and the mixture was extracted with ethyl acetate. The organic phase was washed with half-saturated sodium chloride solution, dried (sodium sulfate) and the solvent was removed in vacuum. Silicagel chromatography gave 3.6 g (73% yield) of the title compound.

LC-MS (Method 2): R$_t$=1.22 min; MS (ESIpos): m/z=261 [M+H]$^+$.

$^1$H-NMR (400 MHz, DMSO-d6) δ[ppm]: 1.392 (7.25), 1.409 (16.00), 1.427 (7.76), 3.957 (2.27), 3.975 (7.73), 3.992 (7.46), 4.010 (2.18), 6.841 (7.10), 6.864 (7.17), 7.235 (2.90), 7.707 (6.46), 7.731 (6.55).

Compound 51.02

2-ethoxy-3-(3-methoxypyridin-4-yl)-6-nitroaniline

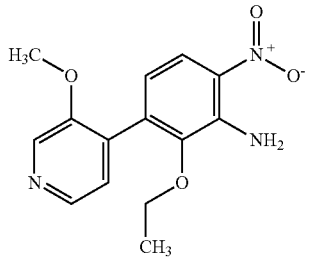

Starting with 3-bromo-2-ethoxy-6-nitroaniline (3.60 g, 13.5 mmol) and (3-methoxypyridin-4-yl)boronic acid (2.50 g, 15.5 mmol), Compound 51.02 was prepared analogously to the procedure for the preparation of Compound 02.01.

Yield: 2.80 g (72%) of the title compound.

LC-MS (Method 2): R$_t$=1.06 min; MS (ESIpos): m/z=290 [M+H]$^+$.

$^1$H-NMR (400 MHz, DMSO-d6) δ[ppm]: 0.953 (6.47), 0.971 (15.43), 0.988 (7.08), 1.174 (0.68), 1.987 (1.27), 3.309 (16.00), 3.507 (2.00), 3.524 (6.69), 3.542 (6.75), 3.559 (1.97), 6.512 (6.59), 6.535 (6.84), 7.135 (3.81), 7.277 (4.27), 7.289 (4.36), 7.543 (0.79), 7.546 (1.16), 7.548 (1.19), 7.554 (0.98), 7.557 (0.86), 7.563 (1.41), 7.565 (1.13), 7.571 (1.09), 7.573 (1.05), 7.593 (0.85), 7.597 (1.77), 7.604 (0.84), 7.610 (0.96), 7.613 (1.28), 7.618 (0.80), 7.623 (1.84), 7.625 (2.32), 7.630 (1.22), 7.644 (1.24), 7.647 (0.95), 7.796 (5.71), 7.819 (5.43), 8.292 (5.51), 8.303 (5.63), 8.519 (7.71).

Compound 51.03

3-ethoxy-4-(3-methoxypyridin-4-yl)benzene-1,2-diamine

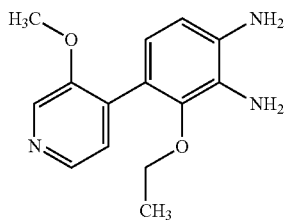 [SMILES: CCOc1c(-c2ccncc2OC)ccc(N)c1N]

To a stirred solution of 2-ethoxy-3-(3-methoxypyridin-4-yl)-6-nitroaniline (2.80 g, 90% purity, 8.71 mmol) in ethanol (100 mL) and dichloromethane (100 mL) was added palladium on carbon (10% w/w palladium; 463 mg) and the mixture was stirred at r.t. in a hydrogen atmosphere for 14 h. The mixture was filtered through celite and the solution was concentrated in vacuum. Aminophase-silicagel chromatography gave 2.80 g of the title compound as a crude product that was used without further purification.

LC-MS (Method 2): R$_t$=0.72 min; MS (ESIpos): m/z=260 [M+H]$^+$.

$^1$H-NMR (400 MHz, DMSO-d6) δ[ppm]: 0.937 (7.19), 0.954 (16.00), 0.972 (7.51), 3.312 (8.30), 3.393 (2.23), 3.410 (7.10), 3.427 (7.19), 3.445 (2.18), 4.232 (1.51), 4.723 (1.54), 5.751 (14.21), 6.315 (2.74), 6.335 (9.88), 6.349 (9.58), 6.369 (2.55), 7.172 (5.25), 7.184 (5.30), 7.527 (0.48), 7.543 (0.82), 7.545 (1.14), 7.548 (1.24), 7.554 (1.05), 7.556 (0.84), 7.563 (1.27), 7.565 (1.22), 7.570 (1.03), 7.572 (1.02), 7.594 (0.86), 7.598 (1.75), 7.604 (0.96), 7.613 (1.02), 7.615 (1.10), 7.618 (0.91), 7.625 (2.20), 7.630 (1.19), 7.644 (1.14), 8.156 (6.47), 8.168 (6.39), 8.356 (9.47).

Compound 51.04 tert-butyl 4-[(2-{[7-ethoxy-6-(3-methoxypyridin-4-yl)-1H-benzimidazol-2-yl]amino}pyridin-4-yl)methyl]piperazine-1-carboxylate

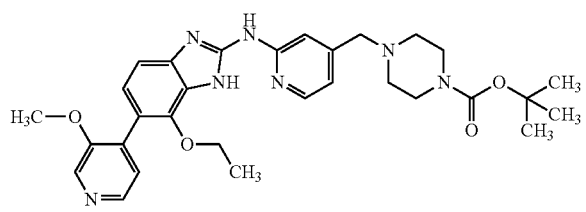 [SMILES: CCOc1c(-c2ccncc2OC)ccc2nc(Nc3cc(CN4CCN(C(=O)OC(C)(C)C)CC4)ccn3)[nH]c12]

To a stirred solution of 1H-imidazole (81.5 mg, 1.20 mmol) and di-1H-imidazol-1-ylmethanethione (1.12 g, 95% purity, 5.99 mmol) in dichloromethane (40 mL) was added tert-butyl 4-[(2-aminopyridin-4-yl)methyl]piperazine-1-carboxylate (1.75 g, 5.99 mmol), dissolved in dichloromethane (30 mL), at 0° C. The mixture was stirred at r.t. for 14 h. 3-ethoxy-4-(3-methoxypyridin-4-yl)benzene-1,2-diamine (2.22 g, 70% purity, 5.99 mmol), dissolved in dichloromethane (40 mL), was added and the mixture was stirred at r.t. for 56 h. Water was added and the mixture was extracted with dichloromethane.

The organic phase was dried (sodium sulfate) and filtered. N,N'-dipropan-2-ylcarbodiimide (3.7 mL, 24 mmol) was added. The mixture was stirred at r.t. for 1 h. Further N,N'-dipropan-2-ylcarbodiimide (3.7 mL, 24 mmol) was added and the mixture was stirred at r.t. for 2 h. Further N,N'-dipropan-2-ylcarbodiimide (1.8 mL, 12 mmol) was added and the mixture was stirred at r.t. for 14 h. Saturated ammonium chloride solution was added, the mixture was stirred for 30 minutes and was extracted with dichloromethane. Aminophase-silicagel chromatography gave 2.00 g of the title compound as a crude product, that was used without further purification.

LC-MS (Method 2): R$_t$=1.31 min; MS (ESIpos): m/z=560 [M+H]$^+$.

$^1$H-NMR (400 MHz, DMSO-d6) δ[ppm]: 1.130 (1.45), 1.147 (3.18), 1.155 (3.54), 1.165 (1.67), 1.173 (7.15), 1.191 (3.59), 1.394 (16.00), 1.987 (12.79), 2.343 (0.91), 2.356 (1.41), 2.367 (1.08), 3.346 (1.25), 3.488 (1.47), 3.796 (0.72), 3.820 (4.07), 4.001 (1.03), 4.018 (3.05), 4.036 (3.02), 4.054 (0.98), 4.549 (0.87), 4.567 (0.87), 5.755 (3.87), 6.791 (0.64), 6.811 (0.69), 7.179 (0.75), 7.191 (1.38), 7.211 (0.75), 7.231 (0.63), 8.206 (0.75), 8.218 (0.71), 8.248 (0.77), 8.262 (0.72), 8.384 (1.23), 10.678 (0.80), 12.123 (0.70).

Compound 51.05

7-ethoxy-6-(3-methoxypyridin-4-yl)-N-[4-(piperazin-1-ylmethyl)pyridin-2-yl]-1H-benzimidazol-2-amine hydrochloride

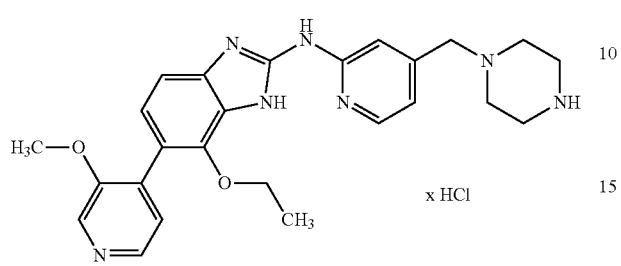

x HCl

Starting with tert-butyl 4-[(2-{[7-ethoxy-6-(3-methoxypyridin-4-yl)-1H-benzimidazol-2-yl]amino}pyridin-4-yl)methyl]piperazine-1-carboxylate (2.00 g, 3.22 mmol), Compound 51.05 was prepared analogously to the procedure for the preparation of Compound 01.05.

Yield: 2.30 g of the title compound as crude product that was used for the next step without purification.

LC-MS (Method 2): $R_t$=0.98 min; MS (ESIpos): m/z=460 [M+H]$^+$.

$^1$H-NMR (400 MHz, DMSO-d6) δ [ppm]: 1.078 (0.64), 1.176 (4.37), 1.193 (9.60), 1.211 (4.80), 2.522 (1.26), 3.049 (0.42), 3.197 (2.80), 3.223 (2.67), 3.370 (2.69), 3.384 (3.12), 3.396 (2.16), 3.692 (0.50), 3.958 (0.90), 3.967 (1.12), 3.975 (1.54), 3.980 (16.00), 4.178 (2.58), 4.275 (1.10), 4.292 (3.20), 4.310 (3.20), 4.327 (1.06), 7.171 (2.29), 7.192 (2.61), 7.417 (1.25), 7.434 (3.46), 7.454 (2.40), 7.546 (2.42), 7.786 (2.21), 7.800 (2.22), 8.442 (2.08), 8.456 (1.98), 8.509 (2.61), 8.523 (2.38), 8.667 (4.21).

Compound 52.01

3-(1-ethyl-1H-pyrazol-4-yl)-2-(2-methylpropoxy)-6-nitroaniline

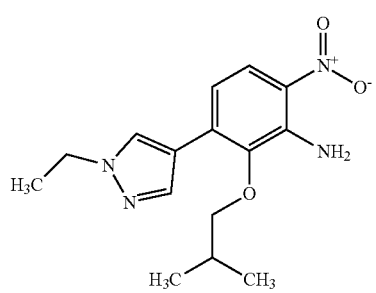 [SMILES: CCn1cc(-c2ccc([N+](=O)[O-])c(N)c2OCC(C)C)cn1]

Starting with 3-bromo-2-(2-methylpropoxy)-6-nitroaniline (1.80 g, 6.23 mmol) and (1-ethyl-1H-pyrazol-4-yl)boronic acid (1.05 g, 95% purity, 7.16 mmol), Compound 52.01 was prepared analogously to the procedure for the preparation of Compound 02.01.

Yield: 1.21 g (64%) of the title compound.

LC-MS (Method 2): $R_t$=1.27 min; MS (ESIpos): m/z=305 [M+H]$^+$.

$^1$H-NMR (400 MHz, DMSO-d6) δ [ppm]: 0.980 (15.04), 0.990 (1.38), 0.996 (16.00), 1.390 (4.64), 1.408 (11.63), 1.427 (5.07), 2.175 (0.78), 2.192 (1.01), 2.209 (0.79), 2.522 (1.49), 3.391 (4.03), 3.407 (4.01), 4.168 (1.24), 4.185 (3.93), 4.204 (4.04), 4.222 (1.30), 6.858 (1.31), 6.891 (4.38), 6.913 (4.15), 7.784 (3.92), 7.807 (3.39), 7.967 (4.54), 7.969 (4.52), 8.277 (4.11), 8.279 (4.14).

Compound 52.02

4-(1-ethyl-1H-pyrazol-4-yl)-3-(2-methylpropoxy)benzene-1,2-diamine

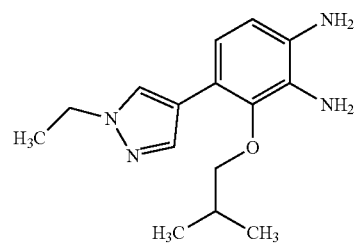 [SMILES: CCn1cc(-c2ccc(N)c(N)c2OCC(C)C)cn1]

To a stirred solution of 3-(1-ethyl-1H-pyrazol-4-yl)-2-(2-methylpropoxy)-6-nitroaniline (1.21 g, 3.98 mmol) in ethanol (20 mL) and dichloromethane (40 mL) was added palladium on carbon (10% w/w palladium; 423 mg) and the mixture was stirred at r.t. in a hydrogen atmosphere for 3 h. The mixture was filtered, and the solution was concentrated in vacuum. Aminophase silicagel chromatography gave 1.00 g (92% yield) of the title compound.

LC-MS (Method 2): $R_t$=0.95 min; MS (ESIpos): m/z=275 [M+H]$^+$.

$^1$H-NMR (400 MHz, DMSO-d6) δ[ppm]: 0.954 (14.62), 0.971 (16.00), 1.351 (4.90), 1.369 (12.10), 1.388 (4.87), 2.021 (0.78), 2.037 (0.95), 2.054 (0.74), 2.518 (2.78), 2.523 (1.83), 3.292 (3.77), 3.309 (3.89), 4.085 (1.42), 4.102 (7.13), 4.121 (4.47), 4.139 (1.38), 4.564 (3.70), 5.760 (7.51), 6.326 (2.95), 6.346 (3.44), 6.558 (3.73), 6.578 (3.17), 7.630 (4.62), 7.632 (4.66), 7.849 (4.24), 7.851 (4.01).

Compound 52.03 tert-butyl 4-[(2-{[6-(1-ethyl-1H-pyrazol-4-yl)-7-(2-methylpropoxy)-1H-benzimidazol-2-yl]amino}pyridin-4-yl)methyl]piperazine-1-carboxylate

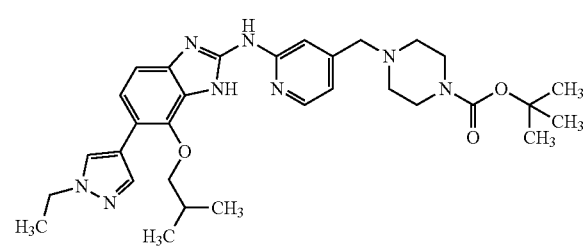 [SMILES: CCn1cc(-c2ccc3nc(Nc4cc(CN5CCN(C(=O)OC(C)(C)C)CC5)ccn4)[nH]c3c2OCC(C)C)cn1]

To a stirred solution of 1H-imidazole (49.6 mg, 729 μmol) and di-1H-imidazol-1-ylmethanethione (684 mg, 95% purity, 3.64 mmol) in dichloromethane (40 mL) was added tert-butyl 4-[(2-aminopyridin-4-yl)methyl]piperazine-1-carboxylate (1.07 g, 3.64 mmol), dissolved in dichloromethane (20 mL), at 0° C. The mixture was stirred at r.t. for 16 h. 4-(1-ethyl-1H-pyrazol-4-yl)-3-(2-methylpropoxy)benzene- 1,2-diamine (1.00 g, 3.64 mmol), dissolved in dichloromethane (20 mL), was added and the mixture was stirred at r.t. for 3 h. Water was added and the mixture was extracted with dichloromethane.

The organic phase was dried (sodium sulfate) and filtered. N,N'-dipropan-2-ylcarbodiimide (1.7 mL, 11 mmol) was added. The mixture was stirred at r.t. for 14 h. Further N,N'-dipropan-2-ylcarbodiimide (1.7 mL, 11 mmol) was added and the mixture was stirred at r.t. for 5 h. Further N,N'-dipropan-2-ylcarbodiimide (1.1 mL, 7.3 mmol) was added and the mixture was stirred at r.t. for 56 h. Sodium bicarbonate solution was added, the mixture was stirred for 30 minutes and was extracted with dichloromethane. Aminophase-silicagel chromatography gave 500 mg of the title compound as a crude product, that was used without further purification.

LC-MS (Method 2): $R_t$=1.46 min; MS (ESIpos): m/z=575 [M+H]$^+$.

$^1$H-NMR (400 MHz, DMSO-d6) δ[ppm]: 0.925 (2.06), 0.942 (2.14), 0.980 (4.06), 0.997 (4.21), 1.134 (0.74), 1.137 (0.73), 1.154 (0.65), 1.374 (1.14), 1.382 (2.45), 1.386 (4.43), 1.390 (7.33), 1.394 (16.00), 1.400 (4.28), 1.411 (1.46), 1.418 (1.33), 2.323 (0.59), 2.327 (0.77), 2.332 (0.99), 2.337 (1.20), 2.349 (1.43), 2.361 (1.03), 2.523 (1.99), 2.669 (0.42), 3.308 (0.76), 3.483 (1.33), 3.496 (0.57), 4.144 (1.02), 4.149 (0.84), 4.162 (1.08), 4.167 (0.87), 4.342 (1.26), 4.359 (1.26), 7.158 (1.13), 7.167 (1.20), 7.239 (0.74), 7.772 (0.77), 7.799 (1.23), 8.016 (1.13), 8.037 (0.50), 8.228 (0.61), 8.241 (0.56), 10.584 (0.64).

Compound 52.04

6-(1-ethyl-1H-pyrazol-4-yl)-7-(2-methylpropoxy)-N-[4-(piperazin-1-ylmethyl)pyridin-2-yl]-1H-benzimidazol-2-amine hydrochloride

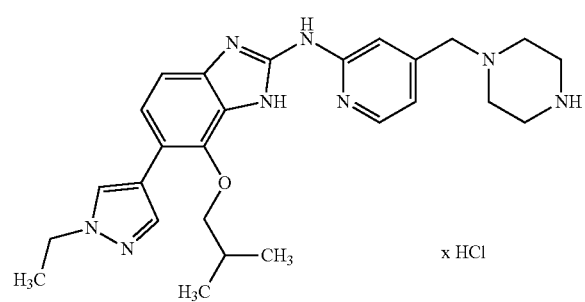 [SMILES: CCn1cc(-c2ccc3nc(Nc4cc(CN5CCNCC5)ccn4)[nH]c3c2OCC(C)C)cn1]

Starting with tert-butyl 4-[(2-{[6-(1-ethyl-1H-pyrazol-4-yl)-7-(2-methylpropoxy)-1H-benzimidazol-2-yl]amino}pyridin-4-yl)methyl]piperazine-1-carboxylate (500 mg, 870 µmol), Compound 52.04 was prepared analogously to the procedure for the preparation of Compound 01.05.

Yield: 497 mg of the title compound as crude product that was used for the next step without purification.

LC-MS (Method 2): $R_t$=1.17 min; MS (ESIpos): m/z=475 [M+H]$^+$.

$^1$H-NMR (400 MHz, DMSO-d6) δ[ppm]: 0.926 (6.49), 0.942 (6.56), 0.986 (0.94), 1.003 (1.47), 1.016 (15.77), 1.033 (16.00), 1.152 (2.83), 1.168 (2.89), 1.270 (3.81), 1.284 (5.50), 1.299 (3.69), 1.318 (3.06), 1.335 (3.06), 1.379 (2.98), 1.394 (5.87), 1.397 (6.71), 1.411 (10.37), 1.416 (3.81), 1.430 (4.73), 2.122 (0.55), 2.139 (1.06), 2.155 (1.33), 2.172 (1.15), 2.176 (0.87), 2.188 (0.67), 2.193 (0.62), 2.322 (0.60), 2.326 (0.77), 2.332 (0.58), 2.522 (4.95), 2.565 (2.99), 2.664 (0.55), 2.668 (0.71), 2.673 (0.51), 3.455 (3.51), 3.563 (9.69), 3.620 (0.70), 3.637 (0.90), 3.641 (1.07), 3.659 (0.98), 3.691 (0.96), 3.708 (1.13), 3.712 (0.87), 3.729 (0.60), 3.857 (2.91), 3.874 (2.85), 4.144 (0.98), 4.162 (3.23), 4.181 (5.12), 4.200 (4.10), 4.218 (1.35), 4.342 (0.68), 4.362 (0.75), 4.454 (1.03), 4.842 (0.91), 7.124 (1.57), 7.145 (1.47), 7.404 (1.80), 7.416 (2.26), 7.426 (2.34), 7.437 (1.84), 7.513 (2.04), 7.524 (2.83), 7.546 (1.85), 7.587 (0.85), 7.827 (2.76), 7.829 (2.38), 7.876 (4.70), 7.878 (4.52), 8.105 (2.57), 8.140 (4.45), 8.517 (1.25), 8.530 (1.20), 9.810 (0.76), 10.430 (0.71), 10.450 (0.71), 10.494 (0.63), 10.515 (0.64), 13.729 (1.38).

Compound 53.01

2-ethoxy-3-(1-ethyl-1H-pyrazol-4-yl)-6-nitroaniline

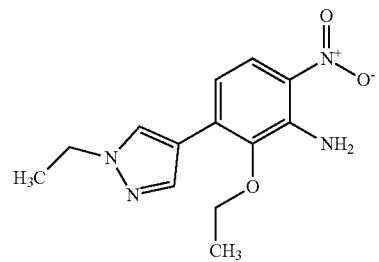 [SMILES: CCOc1c(-c2cnn(CC)c2)ccc([N+](=O)[O-])c1N]

Starting with 3-bromo-2-ethoxy-6-nitroaniline (950 mg, 3.64 mmol) and (1-ethyl-1H-pyrazol-4-yl)boronic acid (616 mg, 95% purity, 4.18 mmol), Compound 53.01 was prepared analogously to the procedure for the preparation of Compound 02.01.

Yield: 650 g (65% yield) of the title compound.

LC-MS (Method 2): $R_t$=1.10 min; MS (ESIpos): m/z=277 [M+H]$^+$.

$^1$H-NMR (400 MHz, DMSO-d6) δ[ppm]: 1.364 (5.55), 1.382 (12.43), 1.393 (7.41), 1.400 (5.47), 1.411 (16.00), 1.429 (6.72), 3.692 (1.41), 3.709 (4.85), 3.727 (4.82), 3.745 (1.37), 4.181 (1.86), 4.200 (5.87), 4.218 (5.73), 4.236 (1.73), 6.895 (5.71), 6.919 (5.64), 7.140 (2.81), 7.767 (5.29), 7.791 (4.74), 8.006 (6.65), 8.008 (6.76), 8.325 (6.24).

Compound 53.02

3-ethoxy-4-(1-ethyl-1H-pyrazol-4-yl)benzene-1,2-diamine

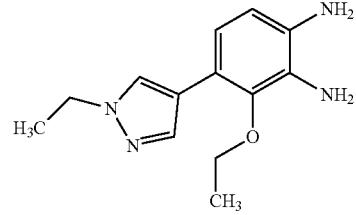 [SMILES: CCOc1c(-c2cnn(CC)c2)ccc(N)c1N]

To a stirred solution of 2-ethoxy-3-(1-ethyl-1H-pyrazol-4-yl)-6-nitroaniline (650 mg, 2.35 mmol) in ethanol (100 mL) and dichloromethane (100 mL) was added palladium on carbon (10% w/w palladium; 125 mg) and the mixture was stirred at r.t. in a hydrogen atmosphere for 3 h. The mixture was filtered, and the solution was concentrated in vacuum. Aminophase silicagel chromatography gave 0.45 g (78% yield) of the title compound.

LC-MS (Method 2): $R_t$=0.76 min; MS (ESIpos): m/z=247 [M+H]$^+$.

$^1$H-NMR (400 MHz, DMSO-d6) δ [ppm]: 1.155 (4.15), 1.172 (8.74), 1.190 (4.39), 1.275 (4.19), 1.292 (9.82), 1.310 (4.50), 1.357 (5.58), 1.375 (12.34), 1.393 (5.82), 1.987 (16.00), 3.337 (5.56), 3.586 (1.22), 3.604 (4.13), 3.621 (4.04), 3.638 (1.18), 4.000 (1.24), 4.018 (3.74), 4.035 (3.65), 4.053 (1.16), 4.096 (1.64), 4.114 (5.11), 4.133 (4.96), 4.150 (1.60), 4.207 (4.13), 4.544 (4.34), 5.758 (2.91), 6.318 (3.38), 6.338 (4.01), 6.570 (4.27), 6.591 (3.65), 7.670 (5.55), 7.671 (5.77), 7.885 (5.69).

Compound 53.03 tert-butyl 4-[(2-{[7-ethoxy-6-(1-ethyl-1H-pyrazol-4-yl)-1H-benzimidazol-2-yl]amino}pyridin-4-yl)methyl]piperazine-1-carboxylate

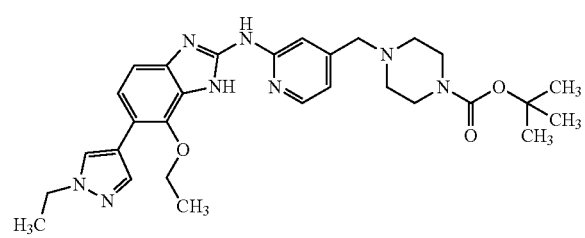 [SMILES: CCOc1c(-c2cnn(CC)c2)ccc2nc(Nc3cc(CN4CCN(C(=O)OC(C)(C)C)CC4)ccn3)[nH]c12]

To a stirred solution of 1H-imidazole (24.7 mg, 363 μmol) and di-1H-imidazol-1-ylmethanethione (340 mg, 95% purity, 1.81 mmol) in dichloromethane (20 mL) was added tert-butyl 4-[(2-aminopyridin-4-yl)methyl]piperazine-1-carboxylate (530 mg, 1.81 mmol), dissolved in dichloromethane (10 mL), at 0° C. The mixture was stirred at r.t. for 14 h. 3-Ethoxy-4-(1-ethyl-1H-pyrazol-4-yl)benzene-1,2-diamine (446 mg, 1.81 mmol), dissolved in dichloromethane (10 mL), was added and the mixture was stirred at r.t. for 2 h. Water was added and the mixture was extracted with dichloromethane/methanol (20:1).

The organic phase was dried (sodium sulfate) and filtered. N,N'-dipropan-2-ylcarbodiimide (700 μl, 4.5 mmol) was added and the mixture was stirred at r.t. for 14 h. Sodium bicarbonate solution was added, the mixture was stirred for 30 minutes and the mixture was extracted with dichloromethane. The organic phase was dried (sodium sulfate) and the solvent was removed in vacuum. The residue was triturated with ethanol, filtered and the solid was discarded. The solution was concentrated in vacuum. Silicagel chromatography followed by aminophase-silicagel chromatography gave 0.41 g of the title compound as a crude product, that was used without further purification.

LC-MS (Method 2): $R_t$=1.32 min; MS (ESIpos): m/z=547 [M+H]$^+$.

$^1$H-NMR (400 MHz, DMSO-d6) δ [ppm]: 1.364 (0.70), 1.386 (16.00), 1.390 (3.24), 1.395 (5.04), 1.408 (1.13), 1.427 (0.49), 2.277 (0.89), 2.290 (1.29), 2.302 (0.98), 3.309 (2.93), 3.322 (5.25), 5.756 (0.73), 5.815 (1.12), 6.382 (0.88), 6.406 (0.54), 6.419 (0.56), 7.802 (0.71), 7.804 (0.66), 7.815 (0.68), 7.816 (0.69).

Compound 53.04

7-ethoxy-6-(1-ethyl-1H-pyrazol-4-yl)-N-[4-(piperazin-1-ylmethyl)pyridin-2-yl]-1H-benzimidazol-2-amine hydrochloride

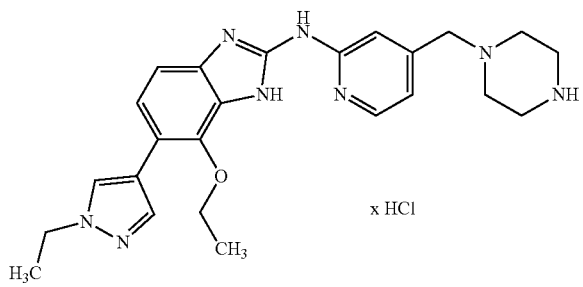 [SMILES: CCOc1c(-c2cnn(CC)c2)ccc2nc(Nc3cc(CN4CCNCC4)ccn3)[nH]c12]

Starting with tert-butyl 4-[(2-{[7-ethoxy-6-(1-ethyl-1H-pyrazol-4-yl)-1H-benzimidazol-2-yl]amino}pyridin-4-yl)methyl]piperazine-1-carboxylate (400 mg, 659 μmol), Compound 53.04 was prepared analogously to the procedure for the preparation of Compound 01.05.

Yield: 0.41 g of the title compound as crude product that was used for the next step without purification.

LC-MS (Method 2): $R_t$=0.97 min; MS (ESIpos): m/z=447 [M+H]$^+$.

$^1$H-NMR (400 MHz, DMSO-d6) δ [ppm]: 1.376 (6.03), 1.394 (13.61), 1.399 (7.64), 1.411 (7.18), 1.418 (16.00), 1.436 (6.58), 1.591 (0.50), 2.327 (1.51), 2.523 (6.71), 2.665 (1.18), 2.669 (1.51), 3.057 (1.68), 3.162 (5.88), 3.354 (8.97), 3.457 (4.19), 3.563 (3.29), 4.072 (1.41), 4.089 (4.07), 4.107 (4.12), 4.124 (1.86), 4.175 (2.96), 4.193 (6.53), 4.211 (6.33), 4.229 (2.56), 4.440 (1.18), 5.138 (0.78), 5.758 (3.01), 7.133 (9.07), 7.418 (2.21), 7.440 (2.84), 7.539 (2.61), 7.553 (4.30), 7.575 (3.67), 7.920 (7.08), 7.922 (6.63), 7.999 (5.53), 8.015 (5.30), 8.191 (6.41), 8.317 (1.86), 8.522 (1.56), 9.703 (1.51).

Compound 54.01

3-methyl-4-(3-methyl-1,2,4-oxadiazol-5-yl)benzene-1,2-diamine

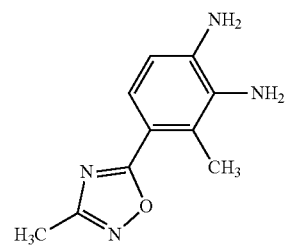

Methyl 3,4-diamino-2-methylbenzoate (PCT Int. Appl., 2009055077) (1.00 g, 5.55 mmol) N-hydroxyethanimidamide (974 mg, 95% purity, 12.5 mmol) and caesium carbonate (1.81 g, 5.55 mmol) were solubilized in dioxane (10 mL), and the reaction was stirred for 16 hours at 110° C. N-Hydroxyethanimidamide (974 mg, 95% purity, 12.5 mmol) and caesium carbonate (1.81 g, 5.55 mmol) were added again and the reaction was stirred for 24 h additional hours. The mixture was diluted with water and extracted with ethyl acetate. The organic phase was dried (silicone filter) and concentrated under reduced pressure. The residue was stirred with water at 60° C. The suspension was filtered and the solid was dried under reduced pressure to give 740 mg of the title compound (62% yield).

LC-MS (Method 2): R$_t$=0.74 min; MS (ESIpos): m/z=205 [M+H]$^+$.

1H-NMR (400 MHz, DMSO-d6) δ[ppm]: 2.340 (16.00), 2.405 (13.00), 4.517 (2.90), 5.375 (3.38), 6.513 (2.08), 6.534 (2.19), 7.136 (2.51), 7.157 (2.33).

Compound 54.02 tert-butyl 4-[(2-{[7-methyl-6-(3-methyl-1,2,4-oxadiazol-5-yl)-1H-benzimidazol-2-yl]amino}pyridin-4-yl)methyl]piperazine-1-carboxylate

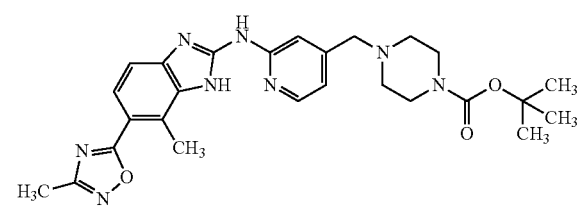 [SMILES: Cc1noc(-c2ccc3nc(Nc4cc(CN5CCN(C(=O)OC(C)(C)C)CC5)ccn4)[nH]c3c2C)n1]

To a stirred solution of di-1H-imidazol-1-ylmethanethione (314 mg, 1.76 mmol) and imidazole (20.0 mg, 294 µmol) in dichloromethane (10 mL) was added tert-butyl 4-[(2-aminopyridin-4-yl)methyl]piperazine-1-carboxylate (429 mg, 1.47 mmol), dissolved in dichloromethane (10 mL), at 0° C. The mixture was stirred at r.t. for 14 h. 3-methyl-4-(3-methyl-1,2,4-oxadiazol-5-yl)benzene-1,2-diamine (300 mg, 1.47 mmol) was added and the mixture was stirred at r.t. for 4 h. Water was added and the mixture was extracted with dichloromethane.

The organic phase was dried (sodium sulfate) and filtered. N,N'-dipropan-2-ylcarbodiimide (5.0 mL, 32 mmol) was added and the mixture was stirred at r.t. for 14 h. Sodium bicarbonate solution was added, the mixture was stirred for 30 minutes and the mixture was extracted with dichloromethane. The organic phase was dried and the solvent was removed in vacuum. Aminophase-silicagel chromatography gave 480 mg of the title compound LC-MS (Method 2): R$_t$=1.33 min; MS (ESIpos): m/z=505 [M+H]$^+$.

1H-NMR (400 MHz, DMSO-d6) δ[ppm]: 1.392 (4.86), 1.396 (16.00), 2.348 (0.93), 2.360 (1.42), 2.373 (1.08), 2.417 (6.35), 2.835 (4.62), 3.351 (1.21), 3.505 (1.44), 5.758 (4.48).

Compound 54.03

7-methyl-6-(3-methyl-1,2,4-oxadiazol-5-yl)-N-[4-(piperazin-1-ylmethyl)pyridin-2-yl]-1H-benzimidazol-2-amine hydrochloride salt

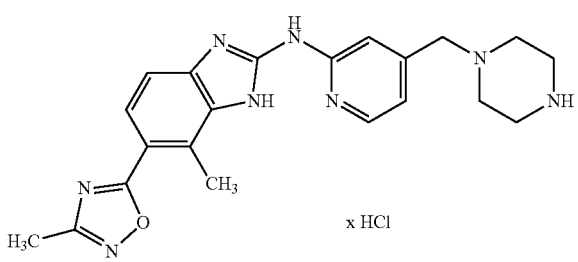 [SMILES: Cc1noc(-c2ccc3nc(Nc4cc(CN5CCNCC5)ccn4)[nH]c3c2C)n1]

Starting with tert-butyl 4-[(2-{[7-methyl-6-(3-methyl-1,2,4-oxadiazol-5-yl)-1H-benzimidazol-2-yl]amino}pyridin-4-yl)methyl]piperazine-1-carboxylate (480 mg, 951 µmol), Compound 54.03 was prepared analogously to the procedure for the preparation of Compound 01.05.

Yield: 470 mg of the title compound as crude product that was used for the next step without purification.

LC-MS (Method 2): R$_t$=1.00 min; MS (ESIpos): m/z=405 [M+H]$^+$.

$^1$H-NMR (400 MHz, DMSO-d6) δ[ppm]: 2.860 (16.00), 3.162 (9.15), 3.292 (1.38), 3.455 (1.63), 3.466 (1.46), 3.485 (1.25), 3.497 (1.06), 3.563 (3.11), 3.661 (0.97), 3.664 (0.82), 3.673 (1.04), 3.697 (1.09), 3.707 (0.87), 3.711 (0.99), 4.354 (0.95), 7.567 (1.46), 7.638 (1.43), 7.660 (1.53), 7.949 (3.09), 7.970 (2.66), 8.485 (1.07).

Compound 55.01

1-{[(1RS)-2,2-difluorocyclopropyl]methyl}-4-(4,4,5,5-tetramethyl-1,3,2-dioxaborolan-2-yl)-1H-pyrazole

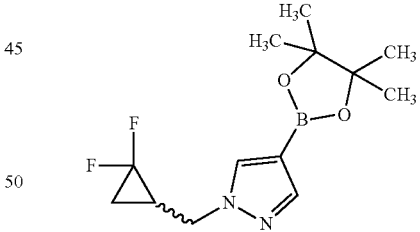

Starting with 4-(4,4,5,5-tetramethyl-1,3,2-dioxaborolan-2-yl)-1H-pyrazole (757 mg, 3.90 mmol) and 2,2-difluorocyclopropylmethyl bromide (CAS #77613-65-1), Compound 55.01 was prepared analogously to the procedure for the preparation of Compound 39.01. The mixture was stirred at 80° C. over night.

Yield: 1.02 g (85%) of the title compound as crude product with 92% purity that was used for the next step without purification.

LC-MS (Method 2): R$_t$=1.02 min; MS (ESIpos): m/z=285 [M+H]$^+$.

$^1$H-NMR (400 MHz, DMSO-d6) δ[ppm]: 1.22-1.32 (m, 12H), 1.42-1.57 (m, 1H), 1.60-1.72 (m, 1H), 2.15-2.30 (m, 1H), 4.13-4.35 (m, 2H), 7.61 (s, 1H), 7.98 (s, 1H).

Compound 55.02

4-(1-{[(1RS)-2,2-difluorocyclopropyl]methyl}-1H-pyrazol-4-yl)-2-nitroaniline

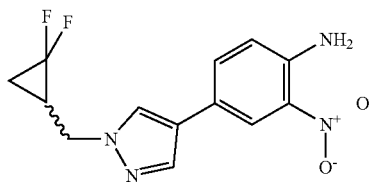

Starting with 1-{[(1RS)-2,2-difluorocyclopropyl]methyl}-4-(4,4,5,5-tetramethyl-1,3,2-dioxaborolan-2-yl)-1H-pyrazole (1.02 g, 3.59 mmol) compound 55.01, Compound 55.02 was prepared analogously to the procedure for the preparation of Compound 39.02.

Yield: 577 mg (49%) of the title compound with 90% purity.

LC-MS (Method 2): $R_t$=1.02 min; MS (ESIpos): m/z=295 [M+H]$^+$.

$^1$H-NMR (400 MHz, DMSO-d6) δ[ppm]: 1.45-1.58 (m, 1H), 1.61-1.76 (m, 1H), 2.17-2.31 (m, 1H), 4.13-4.34 (m, 2H), 7.05 (d, 1H), 7.44 (s, 2H), 7.66 (dd, 1H), 7.88 (d, 1H), 8.10 (d, 1H), 8.19 (s, 1H), Compound 55.02.01

4-(1-{[(1R or 1S)-2,2-difluorocyclopropyl]methyl}-1H-pyrazol-4-yl)-2-nitroaniline

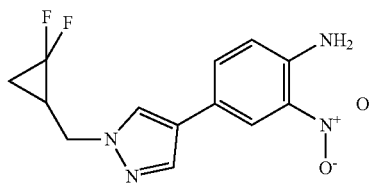

The racemic mixture of 4-(1-{[(1RS)-2,2-difluorocyclopropyl]methyl}-1H-pyrazol-4-yl)-2-nitroaniline compound 55.02 was separated by chiral HPLC.

Yield: 317 mg of the title compound with 97% purity.
Chiral HPLC (Method 6): $R_t$=4.75 min; >99.9% ee $^1$H-NMR (400 MHz, DMSO-d6) δ[ppm]: 1.45-1.58 (m, 1H), 1.61-1.76 (m, 1H), 2.17-2.31 (m, 1H), 4.13-4.34 (m, 2H), 7.05 (d, 1H), 7.44 (s, 2H), 7.66 (dd, 1H), 7.88 (d, 1H), 8.10 (d, 1H), 8.19 (s, 1H).

Compound 55.02.02

4-(1-{[(1R or 1S)-2,2-difluorocyclopropyl]methyl}-1H-pyrazol-4-yl)-2-nitroaniline

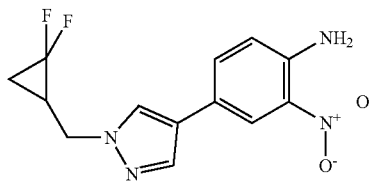

The racemic mixture of 4-(1-{[(1RS)-2,2-difluorocyclopropyl]methyl}-1H-pyrazol-4-yl)-2-nitroaniline compound 55.02 was separated by chiral HPLC.

Yield: 250 mg of the title compound with 96% purity.
Chiral HPLC (Method 6): $R_t$=5.34 min; 96.2% ee $^1$H-NMR (400 MHz, DMSO-d6) δ[ppm]=1.45-1.58 (m, 1H), 1.61-1.76 (m, 1H), 2.17-2.31 (m, 1H), 4.13-4.34 (m, 2H), 7.05 (d, 1H), 7.44 (s, 2H), 7.66 (dd, 1H), 7.88 (d, 1H), 8.10 (d, 1H), 8.19 (s, 1H).

Compound 55.03

4-(1-{[(1RS)-2,2-difluorocyclopropyl]methyl}-1H-pyrazol-4-yl)benzene-1,2-diamine

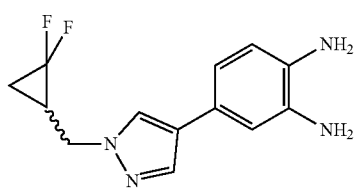 [SMILES: Nc1ccc(-c2cnn(CC3CC3(F)F)c2)cc1N]

Starting with 4-(1-{[(1RS)-2,2-difluorocyclopropyl]methyl}-1H-pyrazol-4-yl)-2-nitroaniline (570 mg, 1.94 mmol) Compound 55.02, Compound 55.03 was prepared analogously to the procedure for the preparation of Compound 39.03.

Yield: 365 mg (64%) of the title compound with 90% purity.

LC-MS (Method 2): $R_t$=0.78 min; MS (ESIpos): m/z=265 [M+H]$^+$.

$^1$H-NMR (400 MHz, DMSO-d6) δ[ppm]: 1.43-1.55 (m, 1H), 1.59-1.75 (m, 1H), 2.15-2.31 (m, 1H), 4.13-4.27 (m, 2H), 4.44 (br d, 4H), 6.48 (d, 1H), 6.59 (dd, 1H), 6.69 (d, 1H), 7.60 (d, 1H), 7.83 (s, 1H).

Compound 55.03.01

4-(1-{[(1R or 1S)-2,2-difluorocyclopropyl]methyl}-1H-pyrazol-4-yl)benzene-1,2-diamine

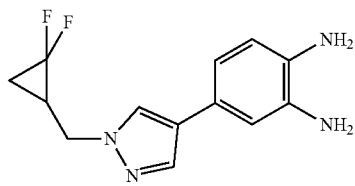 [SMILES: Nc1ccc(-c2cnn(CC3CC3(F)F)c2)cc1N]

Starting with 4-(1-{[(1R or 1S)-2,2-difluorocyclopropyl]methyl}-1H-pyrazol-4-yl)-2-nitroaniline (315 mg; see Compound 55.02.01), Compound 55.03.01 was prepared analogously to the procedure for the preparation of Compound 39.03.

Yield: 163 mg of the title compound with 80% purity.

LC-MS (Method 2): $R_t$=0.80 min; MS (ESIpos): m/z=265 [M+H]$^+$.

$^1$H-NMR (400 MHz, DMSO-d6) δ[ppm]=1.43-1.55 (m, 1H), 1.59-1.75 (m, 1H), 2.15-2.31 (m, 1H), 4.13-4.27 (m, 2H), 4.44 (br d, 4H), 6.48 (d, 1H), 6.59 (dd, 1H), 6.69 (d, 1H), 7.60 (d, 1H), 7.83 (s, 1H).

Compound 55.03.02

4-(1-{[(1R or 1S)-2,2-difluorocyclopropyl]methyl}-1H-pyrazol-4-yl)benzene-1,2-diamine

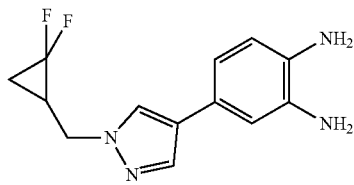 [SMILES: Nc1ccc(-c2cnn(CC3CC3(F)F)c2)cc1N]

Starting with 4-(1-{[(1R or 1S)-2,2-difluorocyclopropyl]methyl}-1H-pyrazol-4-yl)-2-nitroaniline (245 mg; see Compound 55.02.02), Compound 55.03.02 was prepared analogously to the procedure for the preparation of Compound 39.03.

Yield: 143 mg of the title compound with 76% purity.

LC-MS (Method 2): $R_t$=0.80 min; MS (ESIpos): m/z=265 [M+H]$^+$.

$^1$H-NMR (400 MHz, DMSO-d6) δ[ppm]=1.43-1.55 (m, 1H), 1.59-1.75 (m, 1H), 2.15-2.31 (m, 1H), 4.13-4.27 (m, 2H), 4.44 (br d, 4H), 6.48 (d, 1H), 6.59 (dd, 1H), 6.69 (d, 1H), 7.60 (d, 1H), 7.83 (s, 1H).

Compound 55.04

6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt

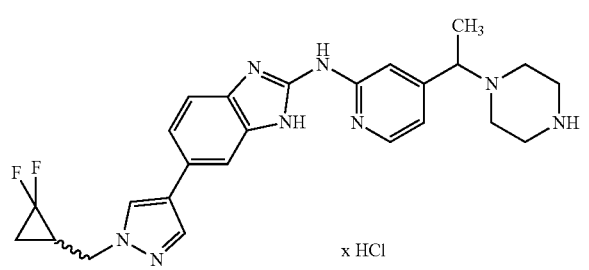 [SMILES: CC(c1ccnc(Nc2nc3ccc(-c4cnn(CC5CC5(F)F)c4)cc3[nH]2)c1)N1CCNCC1]

Starting with tert-butyl 4-[(1R or 1S)-1-(2-{[6-(1-{[(1RS)-2,2-difluorocyclopropyl]methyl}-1H-pyrazol-4-yl)-1H-benzimidazol-2-yl]amino}pyridin-4-yl)ethyl]piperazine-1-carboxylate (360 mg, 622 µmol; Example 55.01), Compound 55.04 was prepared analogously to the procedure for the preparation of Compound 39.05.

Yield: 427 mg of the title compound.

LC-MS (Method 2): $R_t$=1.01 min; MS (ESIpos): m/z=479 [M+H]$^+$.

$^1$H-NMR (400 MHz, DMSO-d6) δ[ppm:]=1.55 (ddt, 1H), 1.64-1.81 (m, 4H), 2.21-2.37 (m, 1H), 2.50-2.53 (m, 4H), 3.28 (br s, 2H), 3.39-3.53 (m, 3H), 4.23-4.36 (m, 2H), 7.55 (s, 1H), 7.56-7.61 (m, 1H), 7.66 (d, 2H), 7.79 (d, 1H), 7.93 (d, 1H), 8.23 (s, 1H), 8.57 (d, 1H), 9.80 (br s, 2H), 13.37 (br s, 2H). -2 HCl not detectable.

Compound 55.04.01

6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride

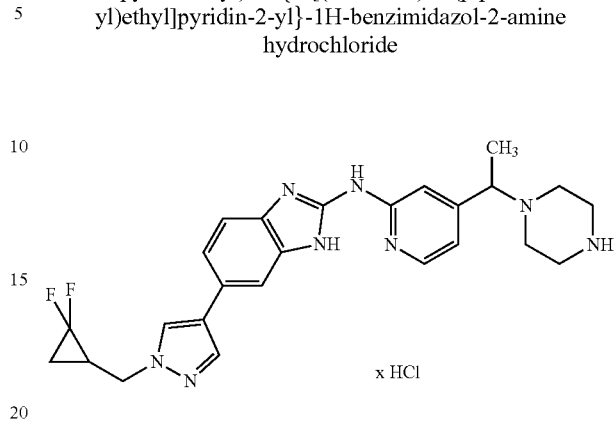

Starting with tert-butyl 4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazine-1-carboxylate (70.0 mg, see Example 55.01.01), Compound 55.04.01 was prepared analogously to the procedure for the preparation of Compound 39.05.

Yield: 96 mg of the 78% pure title compound.

LC-MS (Method 2): $R_t$=1.01 min; MS (ESIpos): m/z=479 [M+H]$^+$.

$^1$H-NMR (400 MHz, DMSO-d6) δ[ppm]=1.49-1.60 (m, 1H), 1.63-1.79 (m, 4H), 2.21-2.32 (m, 1H), 3.19-3.54 (m, 8H), 4.20-4.35 (m, 3H), 7.54 (s, 1H), 7.56-7.69 (m, 3H), 7.75-7.81 (m, 1H), 7.88-7.94 (m, 1H), 8.21-8.26 (m, 1H), 8.57 (d, 1H), 9.72 (br s, 2H), 12.83-13.53 (m, 3H).—2 HCl detectable.

Compound 55.04.02

6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride

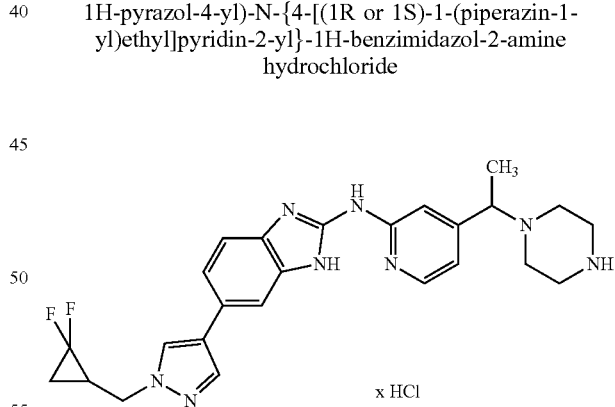

Starting with tert-butyl 4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazine-1-carboxylate (80.0 mg, see Example 55.01.02), Compound 55.04.02 was prepared analogously to the procedure for the preparation of Compound 39.05.

Yield: 79 mg of the 80% pure title compound.

LC-MS (Method 2): $R_t$=1.01 min; MS (ESIpos): m/z=479 [M+H]$^+$.

$^1$H-NMR (400 MHz, DMSO-d6) δ[ppm]=1.49-1.60 (m, 1H), 1.63-1.79 (m, 4H), 2.21-2.32 (m, 1H), 3.16 (s, 1H), 3.17-3.55 (m, 1H), 3.19-3.34 (m, 2H), 3.34-3.54 (m, 4H), 4.20-4.35 (m, 3H), 7.54 (s, 1H), 7.56-7.69 (m, 3H), 7.75-7.81 (m, 1H), 7.88-7.94 (m, 1H), 8.21-8.26 (m, 1H), 8.57 (d, 1H), 9.72 (br s, 2H), 12.83-13.53 (m, 3H). –2 HCl detectable.

Compound 56.01

1-{[(1RS,2RS)-2-methylcyclopropyl]methyl}-4-(4,4,5,5-tetramethyl-1,3,2-dioxaborolan-2-yl)-1H-pyrazole

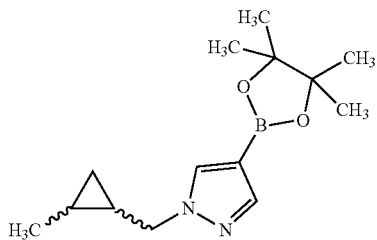

Starting with (1R,2S)-1-(bromomethyl)-2-methylcyclopropane (2.00 g, 13.4 mmol), Compound 56.01 was prepared analogously to the procedure for the preparation of Compound 39.01. The mixture was stirred at 80° C. overnight.

Yield: 890 mg (25%) of the title compound as crude product with 53% purity that was used for the next step without purification.

LC-MS (Method 2): $R_t$=1.19 min; MS (ESIpos): m/z=263.1 [M+H]$^+$.

Compound 56.02

4-(1-{[(1RS,2RS)-2-methylcyclopropyl]methyl}-1H-pyrazol-4-yl)-2-nitroaniline

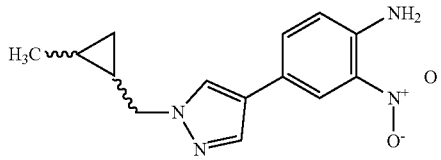

Starting with 1-{[(1RS,2RS)-2-methylcyclopropyl]methyl}-4-(4,4,5,5-tetramethyl-1,3,2-dioxaborolan-2-yl)-1H-pyrazole (890 mg, 3.39 mmol, compound 56.01), Compound 56.02 was prepared analogously to the procedure for the preparation of Compound 39.02.

Yield: 300 mg (30%) of the title compound with 92% purity.

LC-MS (Method 2): $R_t$=1.10 min; MS (ESIpos): m/z=273 [M+H]$^+$.

$^1$H-NMR (400 MHz, DMSO-d6) δ[ppm]: 0.06-0.32 (m, 1H), 0.44-0.57 (m, 1H), 0.68-0.86 (m, 1H), 0.91-0.98 (m, 1H), 0.98-1.14 (m, 3H), 3.84-4.14 (m, 2H), 7.01-7.09 (m, 1H), 7.42 (s, 2H), 7.62-7.70 (m, 1H), 7.78-7.86 (m, 1H), 8.07-8.12 (m, 1H), 8.13-8.20 (m, 1H).

Compound 56.03

4-(1-{[(1RS,2RS)-2-methylcyclopropyl]methyl}-1H-pyrazol-4-yl)benzene-1,2-diamine

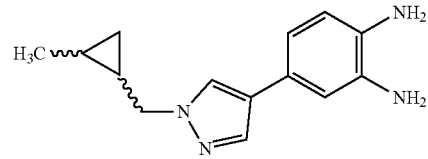 [SMILES: CC1CC1Cn1cc(-c2ccc(N)c(N)c2)cn1]

Starting with 4-(1-{[(1RS,2RS)-2-methylcyclopropyl]methyl}-1H-pyrazol-4-yl)-2-nitroaniline (300 mg, 1.10 mmol, Compound 56.02), Compound 56.03 was prepared analogously to the procedure for the preparation of Compound 39.03.

Yield: 356 mg (97%) of the title compound with 73% purity.

LC-MS (Method 2): $R_t$=0.87 min; MS (ESIpos): m/z=243 [M+H]$^+$.

$^1$H-NMR (400 MHz, DMSO-d6) δ[ppm]: 0.01-0.32 (m, 1H), 0.46-0.55 (m, 1H), 0.70-0.83 (m, 1H), 0.89-0.96 (m, 1H), 1.00 (d, 3H), 3.80-4.16 (m, 2H), 4.77 (br s, 4H), 6.48-6.54 (m, 1H), 6.59-6.66 (m, 1H), 6.68-6.75 (m, 1H), 7.52-7.58 (m, 1H), 7.77-7.86 (m, 1H)

Compound 56.04

6-(1-{[(1RS,2RS)-2-methylcyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt

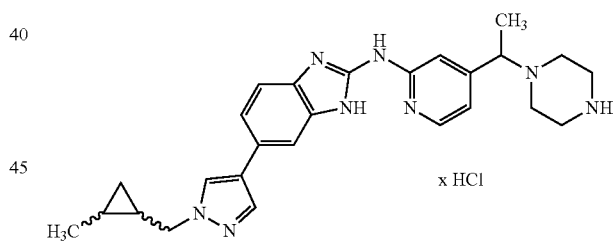

Starting with tert-butyl 4-[(1R or 1S)-1-(2-{[6-(1-{[(1RS,2RS)-2-methylcyclopropyl]methyl}-1H-pyrazol-4-yl)-1H-benzimidazol-2-yl]amino}pyridin-4-yl)ethyl]piperazine-1-carboxylate (235 mg, 422 μmol) Example 56.01, Compound 56.04 was prepared analogously to the procedure for the preparation of Compound 39.05.

Yield: 314 mg of the title compound.

LC-MS (Method 2): $R_t$=1.11 min; MS (ESIpos): m/z=457 [M+H]$^+$.

$^1$H-NMR (400 MHz, DMSO-d6) δ[ppm:]=0.132 (0.62), 0.145 (0.64), 0.288 (0.89), 0.300 (1.70), 0.312 (1.35), 0.320 (1.77), 0.332 (1.03), 0.539 (0.92), 0.550 (1.81), 0.561 (1.79), 0.571 (2.02), 0.582 (1.01), 0.734 (0.62), 0.745 (0.62), 0.755 (0.41), 0.807 (0.48), 0.821 (0.83), 0.832 (1.12), 0.845 (1.49), 0.849 (1.12), 0.863 (1.63), 0.881 (0.76), 0.967 (0.50), 0.979 (0.99), 0.986 (1.08), 0.991 (1.05), 0.996 (1.54), 1.013 (14.85), 1.028 (13.41), 1.044 (0.87), 1.130 (4.40), 1.146 (3.55), 1.231 (0.41), 1.277 (0.48), 1.281 (0.44), 1.295 (0.57), 1.696 (4.47), 1.712 (4.45), 2.327 (1.12), 2.331 (0.78), 2.518 (4.74), 2.523 (3.28), 2.669 (1.12), 2.674 (0.78), 2.727 (0.99), 2.887 (1.24), 3.162 (16.00), 3.202 (0.46), 3.219 (0.53), 3.288 (1.60), 3.360 (0.64), 3.371 (1.08), 3.382 (0.83), 3.387 (0.76), 3.393 (0.94), 3.456 (2.13), 3.466 (2.29), 3.468 (2.36), 3.485 (2.27), 3.487 (2.20), 3.497 (1.97), 3.595 (0.60), 3.602 (0.53), 3.613 (0.48), 3.661 (0.53), 3.665 (0.46), 3.673 (0.55), 3.675 (0.57), 3.697 (0.57), 3.699 (0.55), 3.711 (0.48), 3.728 (0.46), 3.948 (1.17), 3.967 (1.12), 3.983 (2.41), 4.001 (2.64), 4.022 (2.45), 4.040 (2.18), 4.058 (1.05), 4.075 (1.05), 4.118 (0.44), 4.134 (1.17), 4.154 (1.15), 4.163 (1.01), 4.181 (0.85), 4.702 (0.55), 5.300 (1.38), 7.544 (5.09), 7.577 (2.15), 7.581 (2.20), 7.587 (1.19), 7.598 (3.46), 7.602 (3.92), 7.608 (1.40), 7.640 (6.58), 7.661 (4.26), 7.771 (1.01), 7.779 (4.52), 7.783 (4.74), 7.870 (8.37), 7.871 (8.60), 7.881 (2.36), 7.883 (2.41), 8.194 (6.90), 8.206 (1.05), 8.217 (1.99), 8.566 (3.74), 8.579 (3.44), 9.794 (1.15), 13.357 (0.57).

Compound 57.01

2-nitro-4-(1-{[2-(trimethylsilyl)ethoxy]methyl}-1H-pyrazol-4-yl)aniline

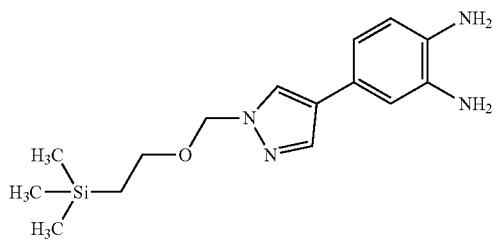

Starting with 4-(4,4,5,5-tetramethyl-1,3,2-dioxaborolan-2-yl)-1-{[2-(trimethylsilyl)ethoxy]methyl}-1H-pyrazole (CAS #894807-98-8; 3.51 g, 91% purity, 9.85 mmol), Compound 57.01 was prepared analogously to the procedure for the preparation of Compound 39.02.

Yield: 2.1 g (59%) of the title compound with 93% purity.

LC-MS (Method 2): $R_t$=1.30 min; MS (ESIpos): m/z=335 [M+H]$^+$.

$^1$H-NMR (400 MHz, DMSO-d6) δ[ppm]: 0.07--0.02 (m, 9H), 0.79-0.88 (m, 2H), 3.50-3.60 (m, 2H), 5.39 (s, 2H), 7.05 (d, 1H), 7.41-7.52 (m, 2H), 7.69 (dd, 1H), 7.90-7.99 (m, 1H), 8.13 (d, 1H), 8.29-8.36 (m, 1H)

Compound 57.02

4-(1-{[2-(trimethylsilyl)ethoxy]methyl}-1H-pyrazol-4-yl)benzene-1,2-diamine

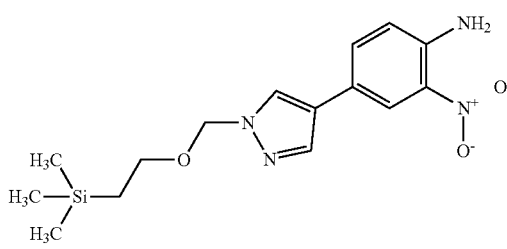

Starting with 2-nitro-4-(1-{[2-(trimethylsilyl)ethoxy]methyl}-1H-pyrazol-4-yl)aniline (2.10 g, 6.28 mmol) Compound 56.01, Compound 56.02 was prepared analogously to the procedure for the preparation of Compound 39.03.

Yield: 1.5 g (63%) of the title compound with 80% purity.

LC-MS (Method 2): $R_t$=1.10 min; MS (ESIpos): m/z=305 [M+H]$^+$.

$^1$H-NMR (400 MHz, DMSO-d6) δ[ppm]: 0.09-0.00 (m, 9H), 0.76-0.89 (m, 2H), 3.47-3.59 (m, 2H), 4.45 (br d, 4H), 5.32-5.40 (m, 2H), 6.49 (d, 1H), 6.62 (dd, 1H), 6.71 (d, 1H), 7.66 (s, 1H), 7.94 (d, 1H).—contains tBuOH.

Compound 57.03 tert-butyl 4-[(1R or 1S)-1-(2-{[6-(1-{[2-(trimethylsilyl)ethoxy]methyl}-1H-pyrazol-4-yl)-1H-benzimidazol-2-yl]amino}pyridin-4-yl)ethyl]piperazine-1-carboxylate

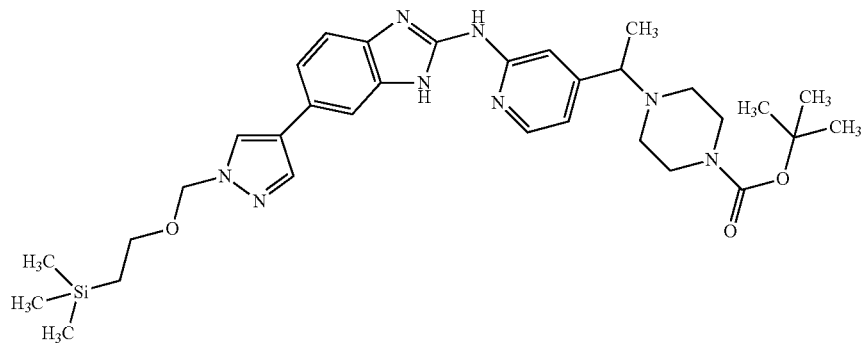 [SMILES: CC(c1ccnc(Nc2nc3ccc(-c4cnn(COCC[Si](C)(C)C)c4)cc3[nH]2)c1)N1CCN(C(=O)OC(C)(C)C)CC1]

1H-imidazole (67.1 mg, 985 μmol) and di-1H-imidazol-1-ylmethanethione (922 mg, 5.17 mmol) were dissolved in 15 mL dichloromethane. tert-butyl 4-[(1R or 1S)-1-(2-aminopyridin-4-yl)ethyl]piperazine-1-carboxylate (1.51 g, 4.93 mmol) dissolved in 15 mL dichloromethane was added. This mixture was stirred at rt for over night. 4-(1-{[2-(trimethylsilyl)ethoxy]methyl}-1H-pyrazol-4-yl)benzene-1,2-diamine (1.50 g, 4.93 mmol) compound 57.02 dissolved in 15 mL dichloromethane was added and it was stirred at rt for three hours. The reaction mixture was diluted with dichloromethane and water. The aqueous layer was extracted with dichloromethane twice. The organic layer was concentrated under reduced pressure and the residue was purified by flash chromatography to give 2.2 g of the intermediate thiourea in 76% purity. The intermediate tert-butyl 4-{(1R or 1S)-1-[2-({[2-amino-4-(1-{[2-(trimethylsilyl)ethoxy]methyl}-1H-pyrazol-4-yl)phenyl]carbamothioyl}amino)pyridin-4-yl]ethyl}piperazine-1-carboxylate (2.19 g, 76% purity, 2.55 mmol) was solved in 33 mL dichloromethane and N,N'-dipropan-2-ylcarbodiimide (1.2 ml, 7.6 mmol) was added. This mixture was stirred 72 h at rt. The reaction mixture was absorbed with isolute and purified by flash chromatography.

Yield: 1.39 g of the title compound with 85% purity.

LC-MS (Method 2): $R_t$=1.51 min; MS (ESIpos): m/z=619 [M+H]$^+$.

$^1$H-NMR (400 MHz, DMSO-d6) δ[ppm]: −0.020 (1.87), −0.017 (1.41), −0.014 (2.68), −0.008 (16.00), 0.000 (0.76), 0.863 (0.62), 0.883 (0.77), 0.904 (0.55), 1.166 (0.45), 1.301 (1.14), 1.318 (1.01), 1.404 (9.35), 1.409 (2.55), 2.111 (0.96), 3.348 (0.84), 3.361 (6.54), 3.586 (0.52), 3.606 (0.64), 3.626 (0.44), 5.442 (0.86), 7.189 (0.47), 8.270 (0.61), 8.283 (0.57).

Compound 58.01

4-(4,4,5,5-tetramethyl-1,3,2-dioxaborolan-2-yl)-1-(2,2,2-trifluoroethyl)-1H-pyrazole

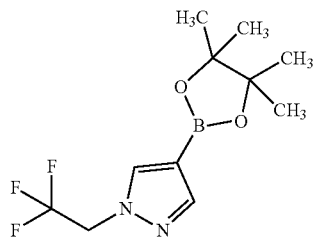

To a stirred solution of 4-(4,4,5,5-tetramethyl-1,3,2-dioxaborolan-2-yl)-1H-pyrazole (2.00 g, 10.3 mmol) in DMF (20 ml) was added potassium carbonate (4.27 g, 30.9 mmol) and 2,2,2-trifluoroethyl trifluoromethanesulfonate (2.2 ml, 15 mmol). The mixture was stirred at 80° C. for 14 h. Further 2,2,2-trifluoroethyl trifluoromethanesulfonate (420 μl, 2.9 mmol) was added and the mixture was stirred at 80° C. for 1 h. Water was added and the mixture was extracted with ethyl acetate. The organic phase was washed with half-saturated sodium chloride solution, dried (sodium sulfate), filtered and the solvent was removed in vacuum. Silicagel chromatography gave 1.76 g (62% yield) of the title compound.

$^1$H-NMR (400 MHz, DMSO-d6) δ[ppm]: 1.066 (1.33), 1.256 (16.00), 5.144 (0.85), 5.167 (0.81), 7.701 (1.31), 8.055 (1.26).

Compound 58.02

2-nitro-4-[1-(2,2,2-trifluoroethyl)-1H-pyrazol-4-yl]aniline

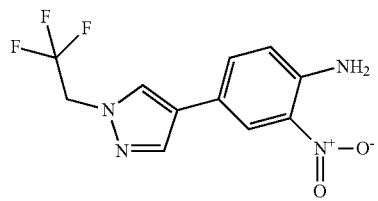 [SMILES: Nc1ccc(-c2cnn(CC(F)(F)F)c2)cc1[N+](=O)[O-]]

To a stirred solution of 4-(4,4,5,5-tetramethyl-1,3,2-dioxaborolan-2-yl)-1-(2,2,2-trifluoroethyl)-1H-pyrazole (1.76 g, 6.06 mmol) in 1-propanol (42 ml) was added potassium carbonate solution (7.0 ml, 2.0 M, 14 mmol), 4-bromo-2-nitroaniline (1.01 g, 4.66 mmol), triphenylphosphine (61.1 mg, 233 μmol) and PdCl$_2$(PPh$_3$)$_2$ (164 mg, 233 μmol). The mixture was heated to reflux for 2 h. Water was added and the mixture was extracted with ethyl acetate. The organic phase was dried (sodium sulfate), filtered and the solvent was removed in vacuum. Aminophase-silicagel chromatography gave 941 mg of the title compound.

LC-MS (Method 2): $R_t$=1.00 min; MS (ESIpos): m/z=287 [M+H]$^+$.

$^1$H-NMR (400 MHz, DMSO-d6) δ[ppm]: 1.066 (0.59), 1.172 (0.65), 1.987 (1.19), 2.518 (2.95), 2.523 (2.06), 5.090 (3.14), 5.113 (9.09), 5.136 (8.48), 5.159 (2.55), 7.045 (9.54), 7.067 (9.88), 7.471 (12.23), 7.671 (5.50), 7.676 (5.37), 7.693 (4.69), 7.698 (5.06), 8.004 (15.43), 8.006 (16.00), 8.132 (10.24), 8.137 (10.07), 8.253 (13.82).

Compound 58.03

4-[1-(2,2,2-trifluoroethyl)-1H-pyrazol-4-yl]benzene-1,2-diamine

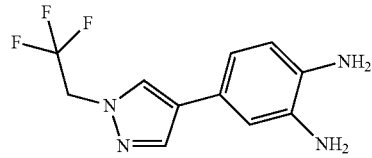

To a stirred solution of 2-nitro-4-[1-(2,2,2-trifluoroethyl)-1H-pyrazol-4-yl]aniline (921 mg, 3.22 mmol) in ethanol (34 ml) and dichloromethane (34 ml) was added palladium on carbon (10% w/w palladium; 342 mg, 322 μmol) and the mixture was stirred at r.t. in a hydrogen atmosphere for 2.5 h. The mixture was filtered and the solution was concentrated in vacuum to give 746 mg of the title compound as a crude product that was used without purification.

LC-MS (Method 2): $R_t$=0.76 min; MS (ESIpos): m/z=257 [M+H]$^+$.

$^1$H-NMR (400 MHz, DMSO-d6) δ[ppm]: 1.053 (0.76), 1.067 (0.70), 2.518 (2.53), 2.523 (1.87), 4.831 (2.46), 5.059 (3.14), 5.082 (8.79), 5.105 (8.37), 5.128 (2.66), 5.759 (1.38), 6.524 (8.66), 6.544 (12.21), 6.633 (6.20), 6.637 (6.58), 6.652 (4.35), 6.657 (4.87), 6.733 (11.20), 6.739 (9.83), 7.733 (15.43), 7.735 (16.00), 7.913 (12.86).

Compound 58.04 tert-butyl 4-{[2-({6-[1-(2,2,2-trifluoroethyl)-1H-pyrazol-4-yl]-1H-benzimidazol-2-yl}amino)pyridin-4-yl]methyl}piperazine-1-carboxylate

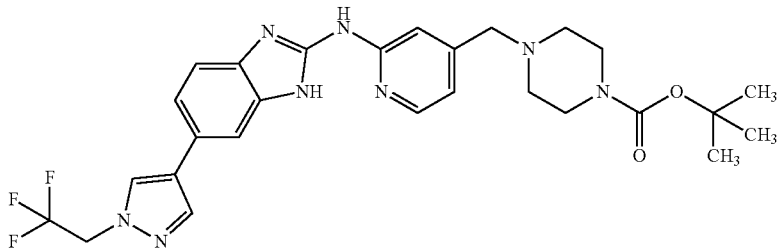 [SMILES: CC(C)(C)OC(=O)N1CCN(Cc2ccnc(Nc3nc4ccc(-c5cnn(CC(F)(F)F)c5)cc4[nH]3)c2)CC1]

To a stirred solution of 1H-imidazole (38.7 mg, 568 μmol) and di-1H-imidazol-1-ylmethanethione (590 mg, 90% purity, 2.98 mmol) in dichloromethane (5 mL) was added tert-butyl 4-[(2-aminopyridin-4-yl)methyl]piperazine-1-carboxylate (830 mg, 2.84 mmol), dissolved in dichloromethane (10 mL) at r.t. The mixture was stirred at r.t. for 14 h. 4-[1-(2,2,2-trifluoroethyl)-1H-pyrazol-4-yl]benzene-1,2-diamine (750 mg, 97% purity, 2.84 mmol), dissolved in dichloromethane (20 mL) was added and the mixture was stirred at r.t. for 14 h.

Water was added and the mixture was extracted with dichloromethane. The organic phase was dried (sodium sulfate), filtered and the solvent was removed in vacuum. Silicagel chromatography gave 1.90 g of a solid that was dissolved in dichloromethane (30 ml). N,N'-dipropan-2-ylcarbodiimide (1.2 ml, 7.9 mmol) was added and the mixture was stirred for 62 h.

Silicagel chromatography of the crude reaction mixture gave a solid that was triturated with ethanol to give 750 mg of the title compound as a crude product that was used for the next step without further purification.

LC-MS (Method 2): $R_t$=1.29 min; MS (ESIpos): m/z=557 [M+H]$^+$.

$^1$H-NMR (400 MHz, DMSO-d6) δ [ppm]: 0.990 (2.46), 1.006 (2.45), 1.053 (0.76), 1.386 (0.89), 1.395 (16.00), 2.342 (0.88), 2.355 (1.30), 2.368 (0.92), 3.348 (1.06), 3.492 (1.67), 5.759 (0.57), 6.902 (0.50), 6.919 (0.53), 7.174 (0.68), 8.240 (0.83), 8.254 (0.81).

Compound 58.05

N-[4-(piperazin-1-ylmethyl)pyridin-2-yl]-6-[1-(2,2,2-trifluoroethyl)-1H-pyrazol-4-yl]-1H-benzimidazol-2-amine hydrochloride

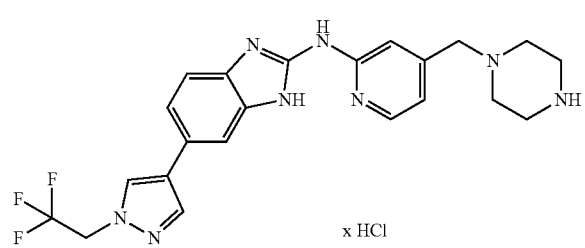 [SMILES: FC(F)(F)Cn1cc(-c2ccc3nc(Nc4cc(CN5CCNCC5)ccn4)[nH]c3c2)cn1]
x HCl

Starting with tert-butyl 4-{[2-({6-[1-(2,2,2-trifluoroethyl)-1H-pyrazol-4-yl]-1H-benzimidazol-2-yl}amino)pyridin-4-yl]methyl}piperazine-1-carboxylate (750 mg, 1.35 mmol), Compound 58.04 was prepared analogously to the procedure for the preparation of Compound 01.05.

Yield: 850 mg of the title compound as crude product that was used for the next step without purification.

LC-MS (Method 2): $R_t$=0.97 min; MS (ESIneg): m/z=457 [M−H]$^+$.

$^1$H-NMR (400 MHz, DMSO-d6) δ[ppm]: 0.985 (8.02), 1.001 (7.86), 2.518 (2.43), 2.523 (1.62), 3.160 (11.58), 3.388 (3.21), 3.404 (3.67), 3.420 (3.32), 3.455 (7.44), 3.457 (7.53), 3.465 (8.15), 3.467 (8.13), 3.483 (4.83), 3.493 (2.55), 3.495 (2.47), 3.507 (1.23), 3.609 (0.65), 3.620 (0.45), 3.625 (0.79), 3.637 (0.69), 3.642 (0.65), 3.647 (0.45), 3.654 (0.62), 3.658 (0.84), 3.662 (0.60), 3.671 (0.78), 3.673 (0.80), 3.695 (0.78), 3.697 (0.73), 3.706 (0.54), 3.709 (0.67), 4.473 (2.82), 5.171 (2.41), 5.194 (6.56), 5.217 (6.15), 5.240 (1.99), 7.555 (7.28), 7.599 (4.56), 7.603 (4.58), 7.619 (8.58), 7.624 (8.94), 7.666 (9.41), 7.687 (4.95), 7.815 (8.47), 7.818 (8.43), 8.046 (16.00), 8.317 (13.60), 8.543 (5.45), 8.556 (5.09), 9.940 (1.87), 13.332 (0.50).

Compound 59.01

1-(cyclobutylmethyl)-4-(4,4,5,5-tetramethyl-1,3,2-dioxaborolan-2-yl)-1H-pyrazole

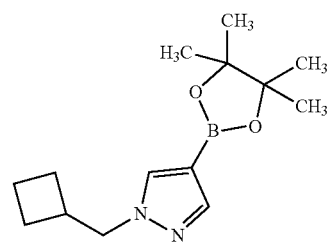 [SMILES: CC1(C)OB(c2cnn(CC3CCC3)c2)OC1(C)C]

To a stirred solution of 4-(4,4,5,5-tetramethyl-1,3,2-dioxaborolan-2-yl)-1H-pyrazole (2.00 g, 10.3 mmol) in N,N-dimethylacetamide (16 ml, 170 mmol) in a microwave tube was added potassium carbonate (2.85 g, 20.6 mmol) and (bromomethyl)cyclobutane (2.30 g, 15.5 mmol). The mixture was stirred at 80° C. for 14 h. Further potassium carbonate (2.85 g, 20.6 mmol) and (bromomethyl)cyclobutane (2.30 g, 15.5 mmol) was added and the mixture was stirred at 80° C. for 24 h. Water was added and the mixture was extracted with ethyl acetate. The organic phase was washed with half-saturated sodium chloride solution, dried (sodium sulfate), filtered and the solvent was removed in vacuum. Silicagel chromatography gave 1.90 g (70% yield) of the title compound.

¹H-NMR (400 MHz, DMSO-d6) δ[ppm]: 1.066 (1.56), 1.172 (0.85), 1.240 (16.00), 1.987 (1.36), 3.329 (2.68), 4.111 (1.24), 4.129 (1.23), 7.550 (1.22), 7.552 (1.23), 7.894 (1.22).

Compound 59.02

4-[1-(cyclobutylmethyl)-1H-pyrazol-4-yl]-2-nitroaniline

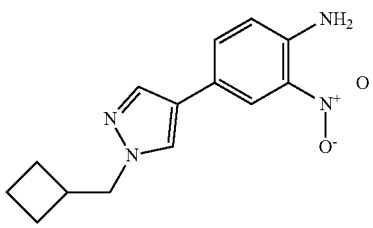

To a stirred solution of 4-bromo-2-nitroaniline (1.60 g, 7.37 mmol) in 1-propanol (110 ml) was added potassium carbonate solution (11 ml, 2.0 M, 22 mmol), 1-(cyclobutylmethyl)-4-(4,4,5,5-tetramethyl-1,3,2-dioxaborolan-2-yl)-1H-pyrazole (1.93 g, 7.37 mmol), triphenylphosphine (96.7 mg, 369 μmol) and PdCl₂(PPh₃)₂ (259 mg, 369 μmol). The mixture was heated to reflux for 2 h, the solvent was removed in vacuum. Aminophase silicagel chromatography gave a solid that was triturated with hexane to give 1.80 g of the title compound.

LC-MS (Method 2): $R_t$=1.13 min; MS (ESIpos): m/z=272 [M+H]⁺.

¹H-NMR (400 MHz, DMSO-d6) δ[ppm]: 1.743 (2.69), 1.749 (1.25), 1.762 (3.18), 1.764 (3.88), 1.771 (2.45), 1.774 (2.14), 1.779 (1.98), 1.783 (3.82), 1.788 (4.34), 1.793 (2.87), 1.798 (5.14), 1.805 (4.50), 1.810 (2.38), 1.814 (4.74), 1.820 (3.60), 1.823 (3.09), 1.830 (2.65), 1.833 (2.41), 1.842 (3.74), 1.845 (3.17), 1.859 (1.52), 1.863 (1.96), 1.866 (2.11), 1.881 (0.88), 1.942 (1.10), 1.946 (1.91), 1.949 (1.77), 1.957 (2.50), 1.963 (3.02), 1.968 (3.14), 1.969 (3.52), 1.977 (3.22), 1.982 (4.71), 1.991 (3.97), 1.995 (2.69), 1.998 (2.69), 2.006 (1.54), 2.010 (1.51), 2.518 (2.40), 2.523 (1.62), 2.717 (0.95), 2.735 (2.26), 2.755 (3.13), 2.773 (2.56), 2.792 (1.03), 4.096 (16.00), 4.115 (15.56), 5.758 (1.29), 7.022 (10.13), 7.044 (10.59), 7.422 (12.78), 7.636 (6.10), 7.642 (5.93), 7.659 (5.31), 7.664 (5.49), 7.800 (15.99), 7.803 (16.00), 8.081 (10.75), 8.087 (10.86), 8.123 (15.12), 8.125 (15.10).

Compound 59.03

4-[1-(cyclobutylmethyl)-1H-pyrazol-4-yl]benzene-1,2-diamine

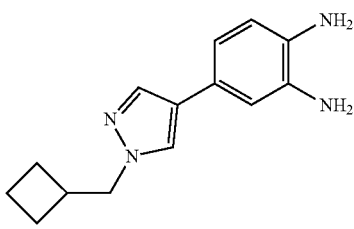 [SMILES: Nc1ccc(-c2cnn(CC3CCC3)c2)cc1N]

To a stirred solution of 4-[1-(cyclobutylmethyl)-1H-pyrazol-4-yl]-2-nitroaniline (1.80 g, 6.61 mmol) in ethanol (200 ml) was added palladium on carbon (10% w/w palladium; 70.3 mg, 66.1 μmol) and the mixture was stirred at r.t. in a hydrogen atmosphere for 3 h. Further palladium on carbon (10% w/w palladium; 70.3 mg, 66.1 μmol) was added and the mixture was stirred at r.t. in a hydrogen atmosphere for 2 h. The mixture was filtered and the solution was concentrated in vacuum to give 1.55 g of the title compound as a crude product that was used without purification.

LC-MS (Method 2): $R_t$=0.87 min; MS (ESIpos): m/z=243 [M+H]⁺.

¹H-NMR (400 MHz, DMSO-d6) δ[ppm]: 1.037 (5.04), 1.055 (9.28), 1.069 (0.66), 1.072 (4.91), 1.715 (0.66), 1.727 (0.91), 1.733 (2.80), 1.739 (1.41), 1.745 (1.28), 1.750 (2.92), 1.752 (3.33), 1.755 (3.91), 1.761 (2.66), 1.765 (2.17), 1.770 (2.02), 1.775 (3.96), 1.779 (3.84), 1.782 (2.71), 1.791 (4.41), 1.797 (3.61), 1.802 (2.26), 1.807 (4.24), 1.814 (3.46), 1.816 (3.33), 1.823 (2.65), 1.834 (3.08), 1.836 (3.82), 1.839 (3.27), 1.841 (1.97), 1.853 (1.62), 1.857 (2.13), 1.859 (2.16), 1.875 (0.93), 1.880 (0.74), 1.931 (1.30), 1.934 (1.75), 1.937 (1.72), 1.945 (2.50), 1.951 (3.10), 1.956 (3.23), 1.957 (3.44), 1.965 (3.16), 1.969 (4.60), 1.980 (4.03), 1.983 (2.65), 1.987 (2.84), 1.998 (1.66), 2.004 (0.69), 2.518 (1.15), 2.522 (0.80), 2.694 (0.94), 2.713 (2.26), 2.732 (3.15), 2.750 (2.52), 2.769 (1.04), 3.162 (2.88), 3.174 (3.00), 3.339 (4.45), 3.407 (0.42), 3.420 (0.49), 3.425 (1.22), 3.437 (1.29), 3.442 (1.26), 3.455 (1.26), 4.066 (15.07), 4.085 (15.28), 4.101 (0.80), 4.114 (0.75), 4.348 (0.77), 4.361 (1.41), 4.374 (0.81), 4.457 (8.55), 6.467 (9.65), 6.487 (13.17), 6.568 (7.34), 6.573 (7.71), 6.587 (4.82), 6.592 (5.51), 6.679 (12.27), 6.684 (10.88), 7.535 (15.84), 7.537 (16.00), 7.762 (14.09), 7.764 (13.78).

Compound 59.04

6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride

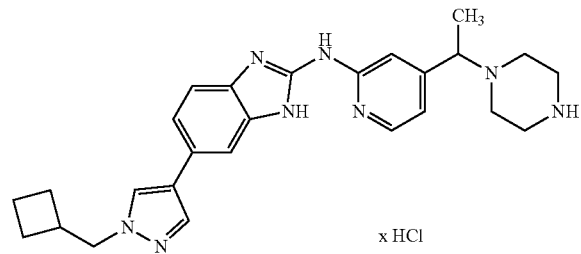 [SMILES: CC(c1ccnc(Nc2nc3ccc(-c4cnn(CC5CCC5)c4)cc3[nH]2)c1)N1CCNCC1]

To a stirred solution of tert-butyl 4-{(1R or 1S)-1-[2-({6-[1-(cyclobutylmethyl)-1H-pyrazol-4-yl]-1H-benzimidazol-2-yl}amino)pyridin-4-yl]ethyl}piperazine-1-carboxylate (600 mg, 1.08 mmol, Example 59.01.01) in dichloromethane (10 mL) and methanol (1.0 mL) was added HCl in dioxane (5.4 ml, 4.0 M, 22 mmol). The mixture was stirred at room temperature for 16 h. The solvent was removed in vacuum to give 1.0 g of the title compound as crude product that was used for the next step without purification.

LC-MS (Method 2): $R_t$=1.12 min; MS (ESIpos): m/z=457 [M+H]⁺.

¹H-NMR (400 MHz, DMSO-d6) δ[ppm]: 0.987 (16.00), 1.004 (15.59), 1.713 (1.73), 1.730 (1.85), 1.772 (0.41), 1.793 (0.63), 1.812 (0.96), 1.823 (1.03), 1.828 (1.00), 1.833 (1.13), 1.840 (0.68), 1.850 (0.45), 1.859 (0.55), 1.980 (0.50), 1.988 (0.68), 1.997 (0.62), 2.009 (0.63), 2.523 (0.59), 2.784 (0.42), 3.159 (10.62), 3.330 (0.62), 3.443 (0.40), 3.454 (0.58), 3.466 (0.67), 3.483 (0.71), 3.495 (0.68), 3.499 (0.60), 3.506 (0.57), 3.519 (0.51), 3.532 (0.53), 3.596 (0.62), 3.613 (1.17), 3.629 (1.49), 3.645 (1.13), 3.661 (0.54), 4.157 (1.76), 4.175 (1.72), 5.758 (5.01), 7.558 (1.39), 7.566 (0.77), 7.583 (0.96), 7.587 (1.03), 7.636 (1.48), 7.657 (0.84), 7.702 (0.66), 7.712 (0.60), 7.770 (1.43), 7.772 (1.43), 7.861 (2.31), 8.177 (2.11), 8.568 (1.05), 8.581 (0.96), 9.937 (0.48).

Compound 59.05 tert-butyl 4-{[2-({6-[1-(cyclobutylmethyl)-1H-pyrazol-4-yl]-1H-benzimidazol-2-yl}amino)pyridin-4-yl]methyl}piperazine-1-carboxylate

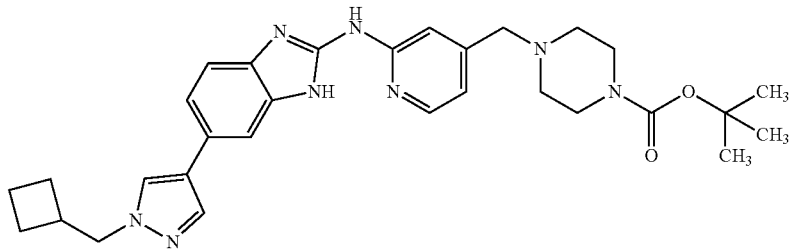 [SMILES: CC(C)(C)OC(=O)N1CCN(Cc2ccnc(Nc3nc4ccc(-c5cnn(CC6CCC6)c5)cc4[nH]3)c2)CC1]

To a stirred solution of 1H-imidazole (23.3 mg, 342 μmol) and di-1H-imidazol-1-ylmethanethione (356 mg, 90% purity, 1.80 mmol) in dichloromethane (5 mL) was added tert-butyl 4-[(2-aminopyridin-4-yl)methyl]piperazine-1-carboxylate (500 mg, 1.71 mmol), dissolved in dichloromethane (10 mL) at r.t. The mixture was stirred at r.t. for 14 h. 4-[1-(cyclobutylmethyl)-1H-pyrazol-4-yl]benzene-1,2-diamine (427 mg, 1.71 mmol), dissolved in dichloromethane (10 mL) was added and the mixture was stirred at r.t. for 62 h. Silicagel chromatography of the crude reaction mixture gave 1.10 g of a solid that was dissolved in dichloromethane (20 ml). N,N'-dipropan-2-ylcarbodiimide (800 μl, 5.1 mmol) was added and the mixture was stirred for 14 h. Further N,N'-dipropan-2-ylcarbodiimide (300 μl) was added and the mixture was stirred for 24 h. Silicagel chromatography of the crude reaction mixture followed by aminophase-silicagel chromatography gave 380 mg of the title compound as a crude product that was used for the next step without further purification.

LC-MS (Method 2): $R_t$=1.37 min; MS (ESIpos): m/z=543 [M+H]$^+$.

Compound 59.06

6-[1-(cyclobutylmethyl)-1H-pyrazol-4-yl]-N-[4-(piperazin-1-ylmethyl)pyridin-2-yl]-1H-benzimidazol-2-amineydrochloride

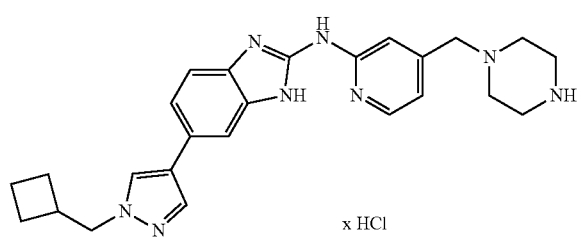 [SMILES: c1cc(CN2CCNCC2)cc(Nc2nc3ccc(-c4cnn(CC5CCC5)c4)cc3[nH]2)n1]

x HCl

To a stirred solution of tert-butyl 4-{[2-({6-[1-(cyclobutylmethyl)-1H-pyrazol-4-yl]-1H-benzimidazol-2-yl}amino)pyridin-4-yl]methyl}piperazine-1-carboxylate (380 mg, 700 μmol) in dichloromethane (10 mL) and methanol (1.0 mL) was added HCl in dioxane (3.5 ml, 4.0 M, 14 mmol). The mixture was stirred at room temperature for 16 h. Further HCl in dioxane (3.5 ml, 4.0 M, 14 mmol) was added and the mixture was stirred at room temperature for 24 h. The solvent was removed in vacuum to give 500 mg of the title compound as crude product that was used for the next step without purification.

LC-MS (Method 2): $R_t$=1.06 min; MS (ESIpos): m/z=443 [M+H]$^+$.

$^1$H-NMR (400 MHz, DMSO-d6) δ[ppm]: 1.148 (2.30), 1.166 (5.00), 1.184 (3.02), 1.222 (1.14), 1.771 (2.88), 1.792 (4.75), 1.810 (7.18), 1.822 (7.70), 1.826 (7.55), 1.831 (8.29), 1.857 (4.09), 1.873 (1.86), 1.880 (2.43), 1.904 (1.78), 1.921 (0.40), 1.964 (2.65), 1.982 (12.44), 1.996 (4.93), 2.007 (4.61), 2.327 (0.87), 2.669 (0.86), 2.726 (0.45), 2.745 (1.26), 2.763 (2.47), 2.782 (3.04), 2.800 (2.42), 2.819 (1.04), 3.159 (13.82), 3.466 (14.04), 3.482 (15.56), 3.559 (1.44), 3.646 (0.60), 3.657 (1.27), 3.662 (1.01), 3.671 (1.43), 3.696 (1.34), 3.704 (0.91), 3.709 (1.14), 3.719 (0.45), 3.993 (0.74), 4.011 (2.06), 4.028 (2.03), 4.046 (0.67), 4.113 (1.31), 4.131 (1.53), 4.155 (11.97), 4.173 (11.69), 4.521 (7.06), 4.626 (1.31), 6.282 (0.47), 7.016 (0.52), 7.070 (0.81), 7.090 (0.54), 7.120 (0.81), 7.558 (13.27), 7.580 (6.49), 7.583 (6.79), 7.636 (12.33), 7.656 (8.40), 7.697 (1.51), 7.773 (10.16), 7.858 (16.00), 7.885 (1.09), 8.004 (1.29), 8.141 (1.73), 8.175 (14.34), 8.545 (6.79), 8.557 (6.31), 9.040 (1.26), 9.055 (1.17), 10.014 (3.54), 13.324 (0.70).

Compound 60.01 tert-butyl 4-[(2-{[6-(6-chloro-5-methoxypyrimidin-4-yl)-1H-benzimidazol-2-yl]amino}pyridin-4-yl)methyl]piperazine-1-carboxylate

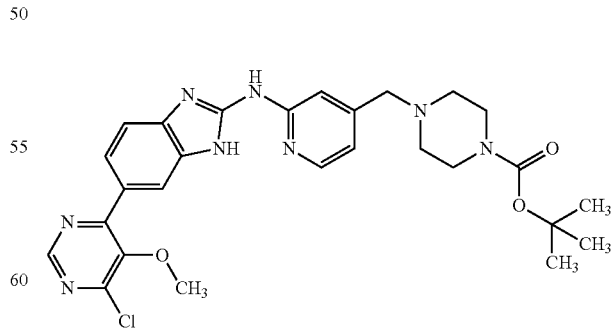

To a stirred suspension of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (7.50 g, 14.0 mmol, Compound 01.04) in 1-propanol (100 ml) was added 4,6-dichloro-5-methoxypyrimidine (7.69 g, 98% purity, 42.1 mmol), triphenylphosphine (368 mg, 1.40 mmol), PdCl$_2$(PPh$_3$)$_2$ (2.29 g, 2.81 mmol) and sodium carbonate solution (21 ml, 2.0 M, 42 mmol). The mixture was heated to reflux for 20 h. Water and a solution of potassium carbonate was added and the mixture was extracted with ethyl acetate. The organic phase was dried (sodium sulfate), filtered and the solvent was removed in vacuum. Silicagel chromatography gave a solid that was triturated with warm ethanol to give 3.0 g of the title compound.

LC-MS (Method 2): R$_t$=1.34 min; MS (ESIpos): m/z=551 [M+H]$^+$.

$^1$H-NMR (400 MHz, DMSO-d6) δ[ppm]: 1.395 (16.00), 2.084 (1.04), 2.349 (0.93), 2.361 (1.30), 2.373 (0.88), 2.518 (0.68), 2.523 (0.48), 3.351 (1.04), 3.506 (1.64), 3.734 (0.76), 5.758 (0.58), 7.174 (0.40), 8.274 (0.58), 8.287 (0.55), 8.797 (0.49).

Compound 60.02

6-(6-chloro-5-methoxypyrimidin-4-yl)-N-[4-(piperazin-1-ylmethyl)pyridin-2-yl]-1H-benzimidazol-2-amine hydrochloride

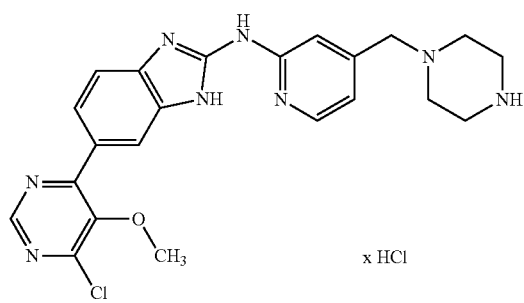 [SMILES: COc1c(Cl)ncnc1-c1ccc2nc(Nc3cc(CN4CCNCC4)ccn3)[nH]c2c1]

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (300 mg, 544 μmol) in dichloromethane (10 mL) and methanol (1.0 mL) was added HCl in dioxane (1.4 ml, 4.0 M, 5.4 mmol). The mixture was stirred at room temperature for 16 h. Further HCl in dioxane (0.5 ml, 4.0 M) was added and the mixture was stirred at room temperature for 24 h. The solvent was removed in vacuum to give 315 mg of the title compound as crude product that was used for the next step without purification.

Compound 61.01 tert-butyl 4-[(2-{[6-(5-methoxy-6-methylpyrimidin-4-yl)-1H-benzimidazol-2-yl]amino}pyridin-4-yl)methyl]piperazine-1-carboxylate

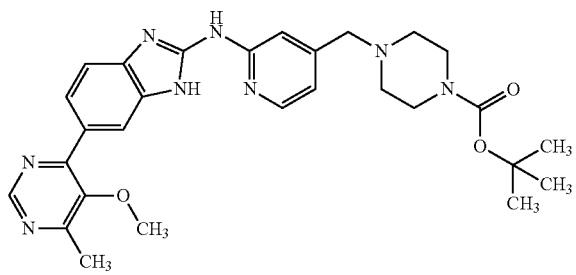 [SMILES: COc1c(C)ncnc1-c1ccc2nc(Nc3cc(CN4CCN(C(=O)OC(C)(C)C)CC4)ccn3)[nH]c2c1]

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (425 mg, 771 μmol) in tetrahydrofurane (50 mL) was added trimethylaluminum (770 μl, 2.0 M, 1.5 mmol), triphenylphosphine (20.2 mg, 77.1 μmol) and PdCl$_2$(PPh$_3$)$_2$ (54.1 mg, 77.1 μmol). The mixture was heated to reflux for 2 h. Further trimethylaluminum (200 μL, 2.0 M, 0.4 mmol) was added and the mixture was heated to reflux for 0.5 h. Water and a solution of sodium bicarbonate was added and the mixture was extracted with ethyl acetate. The organic phase was dried (sodium sulfate), filtered and the solvent was removed in vacuum. Aminophase-silicagel chromatography gave 186 mg of the title compound.

LC-MS (Method 2): R$_t$=1.23 min; MS (ESIpos): m/z=531.6 [M+H]$^+$.

$^1$H-NMR (400 MHz, DMSO-d6) δ[ppm]: 1.066 (12.65), 1.137 (1.07), 1.396 (16.00), 2.349 (1.05), 2.361 (1.38), 2.373 (0.91), 3.353 (1.16), 3.504 (1.66), 3.939 (2.14), 5.759 (0.87), 8.266 (0.79), 8.279 (0.74), 8.799 (0.85).

Compound 61.02

6-(5-methoxy-6-methylpyrimidin-4-yl)-N-[4-(piperazin-1-ylmethyl)pyridin-2-yl]-1H-benzimidazol-2-amine hydrochloride

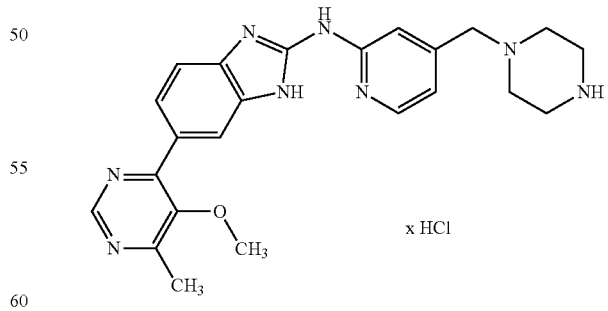

To a stirred solution of tert-butyl 4-[(2-{[6-(5-methoxy-6-methylpyrimidin-4-yl)-1H-benzimidazol-2-yl]amino}pyridin-4-yl)methyl]piperazine-1-carboxylate (180 mg, 339 μmol) in dichloromethane (10 mL) and methanol (1.0 mL) was added HCl in dioxane (3.4 ml, 4.0 M, 14 mmol). The mixture was stirred at room temperature for 64 h. The solvent was removed in vacuum to give 180 mg of the title compound as crude product that was used for the next step without purification.

LC-MS (Method 2): $R_t$=0.90 min; MS (ESIpos): m/z=431 [M+H]$^+$.

$^1$H-NMR (400 MHz, DMSO-d6) δ[ppm]: 1.062 (13.13), 1.233 (0.90), 1.320 (0.47), 1.542 (0.74), 2.467 (0.71), 2.518 (1.56), 2.523 (1.09), 2.555 (11.73), 3.161 (5.30), 3.408 (1.02), 3.431 (1.02), 3.440 (1.16), 3.444 (1.34), 3.455 (2.27), 3.457 (2.24), 3.466 (2.81), 3.468 (2.89), 3.484 (2.40), 3.486 (2.18), 3.494 (1.38), 3.497 (1.39), 3.502 (0.86), 3.507 (0.61), 3.513 (0.47), 3.562 (16.00), 3.660 (0.54), 3.664 (0.44), 3.672 (0.56), 3.674 (0.64), 3.697 (0.61), 3.699 (0.52), 3.707 (0.41), 3.711 (0.49), 3.962 (0.90), 4.487 (0.90), 5.759 (3.75), 7.381 (0.42), 7.548 (0.46), 7.587 (1.83), 7.613 (0.44), 7.630 (0.83), 7.642 (0.77), 7.673 (0.49), 7.791 (1.63), 7.813 (1.76), 8.112 (1.67), 8.116 (1.64), 8.133 (1.29), 8.137 (1.45), 8.459 (1.98), 8.462 (2.00), 8.560 (1.47), 8.574 (1.22), 8.893 (5.19), 9.879 (0.61).

Compound 62.01 tert-butyl 4-[(2-{[6-(2-chloropyrimidin-4-yl)-1H-benzimidazol-2-yl]amino}pyridin-4-yl)methyl]piperazine-1-carboxylate

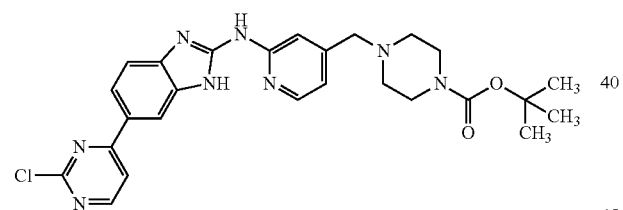

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (2.00 g, 50% purity, 1.87 mmol, Compound 01.04) in 1,4-dioxane (15 ml) was added 2,4-dichloropyrimidine (836 mg, 5.61 mmol), Pd(dppf)Cl$_2$×CH$_2$Cl$_2$ (153 mg, 187 µmol) and sodium carbonate solution (2.8 ml, 2.0 M, 5.6 mmol). The mixture was heated to reflux for 14 h. Water was added and the mixture was extracted with ethyl acetate. The organic phase was dried (sodium sulfate), filtered and the solvent was removed in vacuum. Aminophase-silicagel chromatography gave 400 mg of the title compound as a crude product that was used without further purification.

LC-MS (Method 2): $R_t$=1.30 min; MS (ESIpos): m/z=521 [M+H]$^+$.

Compound 62.02

6-[2-(cyclopropylmethoxy)pyrimidin-4-yl]-N-[4-(piperazin-1-ylmethyl)pyridin-2-yl]-1H-benzimidazol-2-amine hydrochloride

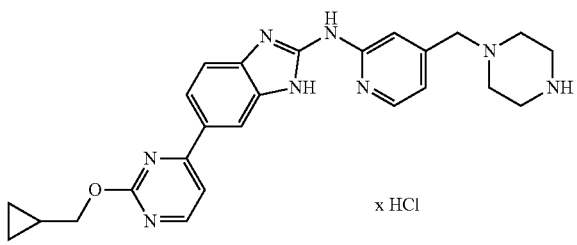 [SMILES: c1cc(CN2CCNCC2)cc(Nc2nc3ccc(-c4ccnc(OCC5CC5)n4)cc3[nH]2)n1]

To a stirred solution of tert-butyl 4-{[2-({6-[2-(cyclopropylmethoxy)pyrimidin-4-yl]-1H-benzimidazol-2-yl}amino)pyridin-4-yl]methyl}piperazine-1-carboxylate (440 mg, 790 µmol) in dichloromethane (10 mL) and methanol (1.0 mL) was added HCl in dioxane (2.0 ml, 4.0 M, 7.9 mmol). The mixture was stirred at room temperature for 3 h. Further HCl in dioxane (2.0 ml, 4.0 M, 7.9 mmol) was added and the mixture was stirred at room temperature for 16 h. The solvent was removed in vacuum to give 590 mg of the title compound as crude product that was used for the next step without purification.

LC-MS (Method 2): $R_t$=1.05 min; MS (ESIpos): m/z=457 [M+H]$^+$.

Compound 64.01

6-[2-(cyclopropylmethoxy)-5-methoxypyrimidin-4-yl]-N-[4-(piperazin-1-ylmethyl)pyridin-2-yl]-1H-benzimidazol-2-amine hydrochloride

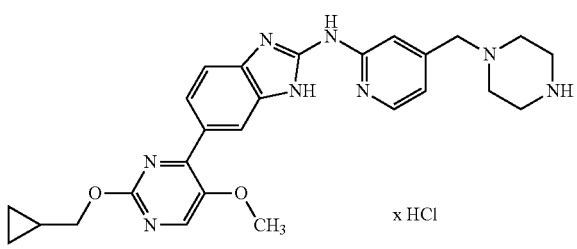 [SMILES: COc1cnc(OCC2CC2)nc1-c1ccc2nc(Nc3cc(CN4CCNCC4)ccn3)[nH]c2c1]

To a stirred solution of tert-butyl 4-{[2-({6-[2-(cyclopropylmethoxy)-5-methoxypyrimidin-4-yl]-1H-benzimidazol-2-yl}amino)pyridin-4-yl]methyl}piperazine-1-carboxylate (230 mg, 392 µmol) in dichloromethane (5.0 mL) and methanol (0.5 mL) was added HCl in dioxane (2.0 ml, 4.0 M, 7.8 mmol). The mixture was stirred at room temperature for 16 h. The solvent was removed in vacuum to give 230 mg of the title compound as crude product that was used for the next step without purification.

LC-MS (Method 2): $R_t$=1.18 min; MS (ESIpos): m/z=487 [M+H]$^+$.

$^1$H-NMR (400 MHz, DMSO-d6) δ [ppm]: 0.345 (0.57), 0.356 (2.25), 0.360 (1.92), 0.368 (2.14), 0.372 (2.05), 0.382 (0.71), 0.555 (0.69), 0.565 (1.86), 0.570 (1.81), 0.575 (0.90), 0.581 (0.89), 0.585 (1.94), 0.590 (1.73), 0.601 (0.58), 1.000 (0.46), 1.278 (0.50), 1.286 (0.48), 1.298 (0.84), 1.310 (0.44), 1.318 (0.46), 2.518 (1.05), 2.523 (0.75), 3.327 (0.69), 3.431 (1.86), 3.455 (1.16), 3.466 (0.79), 3.468 (0.77), 3.484 (0.54), 3.486 (0.50), 3.497 (0.43), 3.561 (2.91), 3.830 (1.68), 3.962 (16.00), 4.161 (4.26), 4.178 (4.27), 4.282 (0.44), 4.393 (0.51), 7.561 (1.97), 7.749 (1.78), 7.771 (1.85), 8.143 (1.97), 8.148 (2.01), 8.165 (1.48), 8.169 (1.57), 8.487 (2.20), 8.490 (2.19), 8.542 (7.61), 8.557 (1.14).

Compound 65.01

6-[6-(cyclopropylmethoxy)-5-methoxypyrimidin-4-yl]-N-[4-(piperazin-1-ylmethyl)pyridin-2-yl]-1H-benzimidazol-2-amine hydrochloride

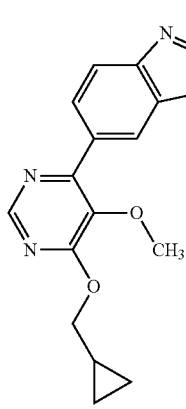

x HCl

To a stirred solution of tert-butyl 4-{[2-({6-[6-(cyclopropylmethoxy)-5-methoxypyrimidin-4-yl]-1H-benzimidazol-2-yl}amino)pyridin-4-yl]methyl}piperazine-1-carboxylate (200 mg, 341 µmol) in dichloromethane (7.5 mL) and methanol (0.75 mL) was added HCl in 2-propanol (1.7 ml, 6.0 M, 10 mmol). The mixture was stirred at room temperature for 16 h. The solvent was removed in vacuum to give 210 mg of the title compound as crude product that was used for the next step without purification.

LC-MS (Method 2): $R_t$=1.15 min; MS (ESIpos): m/z=487 [M+H]$^+$.

Compound 66.01

6-(5-methyl-1,3,4-oxadiazol-2-yl)-N-[4-(piperazin-1-ylmethyl)pyridin-2-yl]-1H-benzimidazol-2-amine hydrochloride

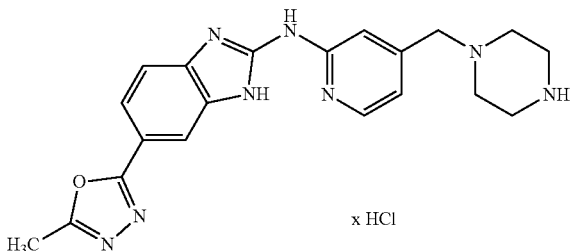

x HCl

To a stirred solution of tert-butyl 4-[(2-{[6-(5-methyl-1,3,4-oxadiazol-2-yl)-1H-benzimidazol-2-yl]amino}pyridin-4-yl)methyl]piperazine-1-carboxylate (44.7 mg, 91.1 µmol) in dichloromethane (1.0 mL) and methanol (0.1 mL) was added HCl in dioxane (1.5 ml, 6.0 mmol). The mixture was stirred at room temperature for 16 h. The solvent was removed in vacuum to give 26.0 mg of the title compound as crude product that was used for the next step without purification.

LC-MS (Method 2): $R_t$=0.78 min; MS (ESIpos): m/z=391 [M+H]$^+$.

Compound 67.01

1-{[(1RS)-2,2-dimethylcyclopropyl]methyl}-4-(4,4,5,5-tetramethyl-1,3,2-dioxaborolan-2-yl)-1H-pyrazole

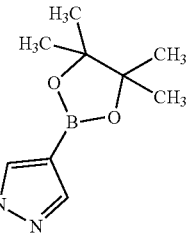

4-(4,4,5,5-tetramethyl-1,3,2-dioxaborolan-2-yl)-1H-pyrazole (587 mg), [(1RS)-2,2-dimethylcyclopropyl]methanol (1.00 g) and polymer bound triphenylphosphine (5.67 g) were dissolved in 29 mL THF and heated to 60° C. At this temperature diisopropylazodicarboxylate (1.8 ml), dissolved in 4.8 mL toluene, was added dropwise. The mixture was stirred 1 hour at 60° C. The polymer was filtered off. The filter cake was washed with ethyl acetate. The filtrate was concentrated under reduced pressure. The crude product was purified by flash chromatography to provide the title compound as mixture with {1-[(RS-2,2-dimethylcyclopropyl)methyl]-1H-pyrazol-4-yl}boronic acid which was used without any further purification: 683 mg, 82% pure.

LC-MS (Method 2): $R_t$=1.28 min; MS (ESIpos): m/z=277 [M+H]$^+$.

Compound 67.02

4-(1-{[(1RS)-2,2-dimethylcyclopropyl]methyl}-1H-pyrazol-4-yl)benzene-1,2-diamine

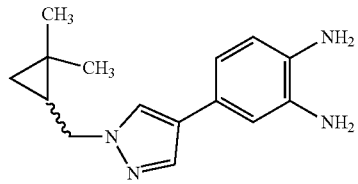 [SMILES: CC1(C)CC1Cn1cc(-c2ccc(N)c(N)c2)cn1]

Starting with 1-{[(1RS)-2,2-dimethylcyclopropyl]methyl}-4-(4,4,5,5-tetramethyl-1,3,2-dioxaborolan-2-yl)-1H-pyrazole (683 mg, 82% purity; see Compound 67.01), Compound 67.02 was prepared analogously to the procedure for the preparation of Compound 44.02.

Yield: 153 mg of the title compound with 85% purity.

LC-MS (Method 2): $R_t$=0.98 min; MS (ESIpos): m/z=257 [M+H]$^+$.

¹H-NMR (400 MHz, DMSO-d6) δ [ppm]: 0.29 (t, 1H), 0.50 (dd, 1H), 1.05 (s, 3H), 1.06-1.11 (m, 1H), 1.13 (s, 3H), 4.04-4.10 (m, 2H), 4.42 (br d, 4H), 6.48 (d, 1H), 6.59 (dd, 1H), 6.69 (d, 1H), 7.55 (d, 1H), 7.77 (d, 1H).

Compound 67.03

6-(1-{[(1RS)-2,2-dimethylcyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride

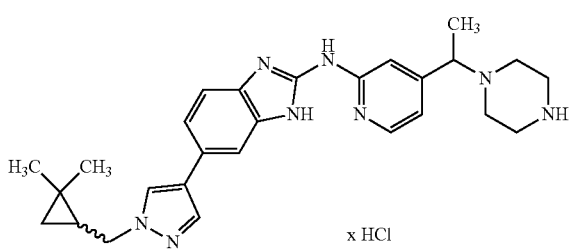 [SMILES: CC(c1ccnc(Nc2nc3ccc(-c4cnn(CC5CC5(C)C)c4)cc3[nH]2)c1)N1CCNCC1]

x HCl

Starting with tert-butyl 4-[(1R or 1S)-1-(2-{[6-(1-{[(1RS)-2,2-dimethylcyclopropyl]methyl}-1H-pyrazol-4-yl)-1H-benzimidazol-2-yl]amino}pyridin-4-yl)ethyl]piperazine-1-carboxylate (140 mg, see Example 67.01), Compound 67.03 was prepared analogously to the procedure for the preparation of Compound 39.05.

Yield: 130 mg of 90% pure target compound.

LC-MS (Method 2): $R_t$=1.16 min; MS (ESIpos): m/z=471 [M+H]⁺.

¹H-NMR (400 MHz, DMSO-d6) δ[ppm]: 0.327 (0.60), 0.339 (1.02), 0.351 (0.65), 0.521 (0.65), 0.531 (0.67), 0.542 (0.75), 0.552 (0.63), 0.987 (0.70), 1.004 (0.75), 1.063 (16.00), 1.084 (0.45), 1.109 (0.51), 1.122 (0.54), 1.130 (0.56), 1.143 (0.57), 1.161 (9.81), 1.548 (0.51), 1.683 (1.04), 2.518 (1.69), 2.522 (1.16), 2.527 (0.84), 2.685 (1.77), 2.726 (5.79), 2.887 (6.98), 3.162 (6.06), 3.456 (0.69), 3.468 (0.67), 3.485 (0.57), 4.149 (2.83), 4.167 (3.07), 4.238 (2.60), 4.385 (0.40), 5.758 (2.35), 7.530 (1.24), 7.581 (0.75), 7.585 (0.67), 7.602 (1.30), 7.605 (1.33), 7.636 (2.18), 7.657 (1.03), 7.778 (1.62), 7.882 (2.81), 7.949 (0.88), 8.165 (2.58), 8.560 (0.89), 8.573 (0.81).

Compound 68.01

1-[(1-methylcyclopropyl)methyl]-4-(4,4,5,5-tetramethyl-1,3,2-dioxaborolan-2-yl)-1H-pyrazole

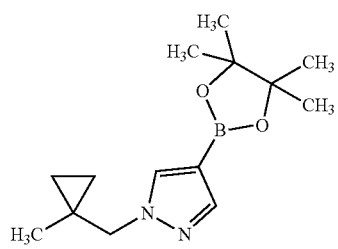

Starting with (1-methylcyclopropyl)methanol (1.00 g), Compound 68.01 was prepared analogously to the procedure for the preparation of Compound 67.01.

Yield: 1.24 g of the title compound in mixture with {1-[(1-methylcyclopropyl)methyl]-1H-pyrazole-4-yl}boronic acid with 60% purity.

LC-MS (Method 2): $R_t$=1.20 min; MS (ESIpos): m/z=263 [M+H]⁺.

Compound 68.02

4-{1-[(1-methylcyclopropyl)methyl]-1H-pyrazol-4-yl}benzene-1,2-diamine

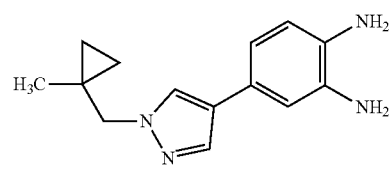 [SMILES: CC1(Cn2cc(-c3ccc(N)c(N)c3)cn2)CC1]

Starting with 1-[(1-methylcyclopropyl)methyl]-4-(4,4,5,5-tetramethyl-1,3,2-dioxaborolan-2-yl)-1H-pyrazole (700 mg, see Compound 68.01), Compound 68.02 was prepared analogously to the procedure for the preparation of Compound 44.02.

Yield: 94 mg of the title compound with 85% purity.

LC-MS (Method 2): $R_t$=0.85 min; MS (ESIpos): m/z=243 [M+H]⁺.

¹H-NMR (400 MHz, DMSO-d6) δ[ppm]=0.30-0.38 (m, 2H), 0.58-0.64 (m, 2H), 0.96 (s, 3H), 3.91 (s, 2H), 4.44 (br s, 4H), 6.48 (d, 1H), 6.60 (dd, 1H), 6.70 (d, 1H), 7.55 (d, 1H), 7.80 (d, 1H).

Compound 68.03

6-{1-[(1-methylcyclopropyl)methyl]-1H-pyrazol-4-yl}-N-{4-[(1R or S)-1-(piperazin-1-yl)ethyl]pyridin-2-yl}-1H-benzimidazol-2-amine hydrochloride

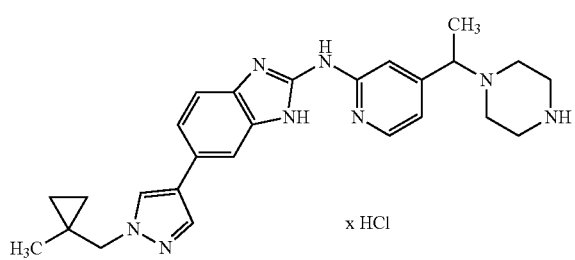 [SMILES: CC(c1ccnc(Nc2nc3ccc(-c4cnn(CC5(C)CC5)c4)cc3[nH]2)c1)N1CCNCC1]

x HCl

Starting with tert-butyl 4-[(1R or 1S)-1-{2-[(6-{1-[(1-methylcyclopropyl)methyl]-1H-pyrazol-4-yl}-1H-benzimidazol-2-yl)amino]pyridin-4-yl}ethyl]piperazine-1-carboxylate (85.0 mg, see Example 68.01), Compound 68.03 was prepared analogously to the procedure for the preparation of Compound 39.05.

Yield: 86 mg of 86% pure target compound.

LC-MS (Method 2): $R_t$=1.13 min; MS (ESIpos): m/z=457 [M+H]⁺.

¹H-NMR (400 MHz, DMSO-d6) δ[ppm]=0.34-0.43 (m, 2H), 0.63-0.72 (m, 2H), 1.00 (s, 3H), 1.68 (br s, 3H), 3.14-3.54 (m, 9H), 4.00 (s, 2H), 7.53 (s, 1H), 7.58-7.69 (m, 3H), 7.79 (s, 1H), 7.88 (s, 1H), 8.21 (s, 1H), 8.57 (d, 1H), 9.71 (br s, 2H), 12.76-13.52 (m, 3H).—2 HCl.

Compound 69.01

(1-chlorocyclopropyl)methanol

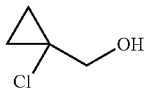

Lithiumaluminium hydride (1.02 g) was suspended in 14 mL THF. Ethyl 1-chlorocyclopropanecarboxylate (1.00 g; CAS-No. 1631082-82-0; corresponding carboxylic acid readily commercially available from multiple vendors), dissolved in 7 mL THF, was added dropwise to the reaction mixture under cooling with an ice bath. The mixture was stirred for 1 hour at rt. The reaction mixture was diluted with ethyl acetate and 5 mL water was added carefully. The grey slurry in the mixture was filtered off under vacuo. The clear filtrate was diluted with more water. The layers were separated and the organic layer was extracted with ethyl acetate twice. The combined organic layers were dried using a water resistant filter and the filtrate was concentrated under reduced pressure (200 mbar) at 50° C. to provide the 90% pure title compound: 704 mg $^1$H-NMR (400 MHz, DMSO-d6) δ[ppm]=0.88-0.97 (m, 4H), 3.52 (d, 2H), 5.13 (t, 1H).

Compound 69.02

1-[(1-chlorocyclopropyl)methyl]-4-(4,4,5,5-tetramethyl-1,3,2-dioxaborolan-2-yl)-1H-pyrazole

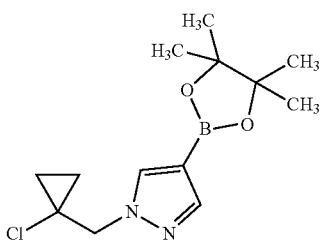 [SMILES: CC1(C)OB(c2cnn(CC3(Cl)CC3)c2)OC1(C)C]

Starting with (1-chlorocyclopropyl)methanol (695 mg, see Compound 69.01; CAS No. 154985-94-1), Compound 69.02 was prepared analogously to the procedure for the preparation of Compound 67.01.

Yield: 346 mg of the title compound with 92% purity.
LC-MS (Method 2): $R_t$=1.15 min; MS (ESIpos): m/z=283 [M+H]$^+$.

Compound 69.03

4-{1-[(1-chlorocyclopropyl)methyl]-1H-pyrazol-4-yl}benzene-1,2-diamine

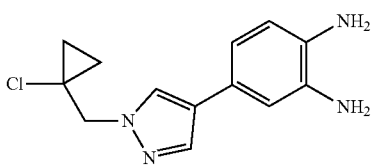 [SMILES: Nc1ccc(-c2cnn(CC3(Cl)CC3)c2)cc1N]

Starting with 1-[(1-chlorocyclopropyl)methyl]-4-(4,4,5,5-tetramethyl-1,3,2-dioxaborolan-2-yl)-1H-pyrazole (342 mg, see Compound 69.02), Compound 69.03 was prepared analogously to the procedure for the preparation of Compound 44.02.

Yield: 71 mg of the title compound with 85% purity.
LC-MS (Method 2): $R_t$=0.83 min; MS (ESIpos): m/z=263 [M+H]$^+$.
$^1$H-NMR (400 MHz, DMSO-d6) δ[ppm]=1.08-1.15 (m, 2H), 1.19-1.26 (m, 2H), 4.35 (s, 2H), 4.37-4.70 (m, 4H), 6.49 (d, 1H), 6.61 (dd, 1H), 6.71 (d, 1H), 7.61 (s, 1H), 7.87 (s, 1H).

Compound 69.04

6-{1-[(1-chlorocyclopropyl)methyl]-1H-pyrazol-4-yl}-N-{4-[(1R or 1S)-1-(piperazin-1-yl)ethyl]pyridin-2-yl}-1H-benzimidazol-2-amine hydrochloride

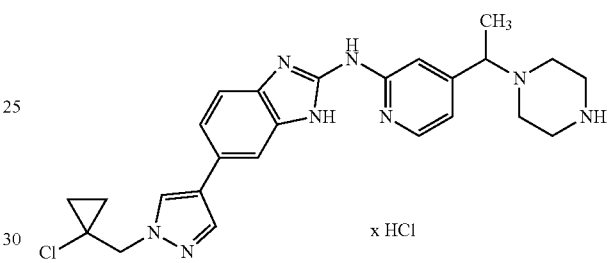

Starting with tert-butyl 4-[(1R or 1S)-1-{2-[(6-{1-[(1-chlorocyclopropyl)methyl]-1H-pyrazol-4-yl}-1H-benzimidazol-2-yl)amino]pyridin-4-yl}ethyl]piperazine-1-carboxylate (45.0 mg, see Example 69.01), Compound 69.04 was prepared analogously to the procedure for the preparation of Compound 39.05.

Yield: 48 mg of 90% pure target compound.
LC-MS (Method 2): $R_t$=1.04 min; MS (ESIpos): m/z=477 [M+H]$^+$.
$^1$H-NMR (400 MHz, DMSO-d6) δ[ppm]=1.09-1.18 (m, 2H), 1.24-1.32 (m, 2H), 1.66 (br s, 3H), 2.39-2.48 (m, 4H), 3.18-3.52 (m, 5H), 4.44 (s, 2H), 7.52 (br s, 1H), 7.56-7.69 (m, 3H), 7.80 (s, 1H), 7.94 (s, 1H), 8.27 (s, 1H), 8.56 (br d, 1H), 9.62 (br s, 2H), 12.96 (br s, 1H), 13.35 (br s, 1H).—1 HCl Compound 70.01

3-chloro-4-(1-{[(1RS)-2,2-difluorocyclopropyl]methyl}-1H-pyrazol-4-yl)benzene-1,2-diamine

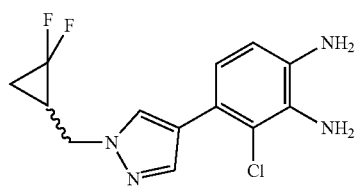 [SMILES: Nc1ccc(-c2cnn(CC3CC3(F)F)c2)c(Cl)c1N]

Starting with 1-{[(1RS)-2,2-difluorocyclopropyl]methyl}-4-(4,4,5,5-tetramethyl-1,3,2-dioxaborolan-2-yl)-1H-pyrazole (2.72 g, see Compound 55.01), Compound 70.01 was prepared analogously to the procedure for the preparation of Compound 44.02.

Yield: 1.22 g of the title compound with 85% purity.

LC-MS (Method 2): $R_t$=0.91 min; MS (ESIpos): m/z=299 [M+H]$^+$.

$^1$H-NMR (400 MHz, DMSO-d6) δ[ppm]=1.40-1.56 (m, 1H), 1.59-1.76 (m, 1H), 2.17-2.31 (m, 1H), 4.15-4.36 (m, 2H), 4.72 (s, 2H), 4.83 (s, 2H), 6.47-6.53 (m, 1H), 6.55-6.62 (m, 1H), 7.61-7.70 (m, 1H), 7.95 (s, 1H).

Compound 70.02 tert-butyl 4-[(1R or 1S)-1-(2-{[7-chloro-6-(1-{[(1RS)-2,2-difluorocyclopropyl]methyl}-1H-pyrazol-4-yl)-1H-benzimidazol-2-yl]amino}pyridin-4-yl)ethyl]piperazine-1-carboxylate

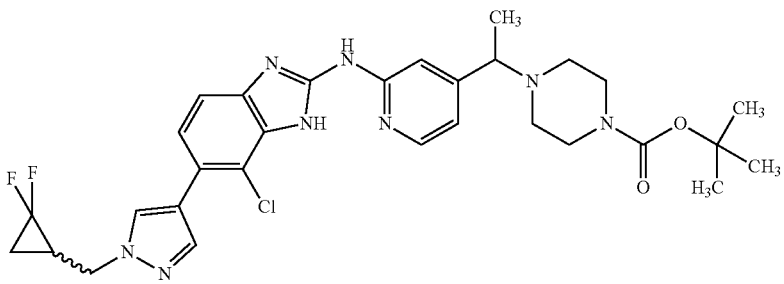 [SMILES: CC(c1ccnc(Nc2nc3ccc(-c4cnn(CC5CC5(F)F)c4)c(Cl)c3[nH]2)c1)N1CCN(C(=O)OC(C)(C)C)CC1]

Starting with 3-chloro-4-(1-{[(1RS)-2,2-difluorocyclopropyl]methyl}-1H-pyrazol-4-yl)benzene-1,2-diamine (1.22 g, 85% purity, see Compound 70.01), Compound 70.02 was prepared analogously to the procedure for the preparation of Example 39.02.01. The intermediate thiourea was purified by flash chromatography.

Yield: 854 mg of the 90% pure title compound.

LC-MS (Method 2): $R_t$=1.41 min; MS (ESIpos): m/z=613 [M+H]$^+$.

$^1$H-NMR (400 MHz, DMSO-d6): δ [ppm]=1.28 (d, 3H), 1.38 (s, 9H), 1.46-1.60 (m, 1H), 1.64-1.80 (m, 1H), 2.22-2.44 (m, 5H), 3.25-3.33 (m, 4H), 3.40-3.50 (m, 1H), 4.19-4.39 (m, 2H), 6.95 (d, 1H), 7.08 (s, 1H), 7.19 (d, 1H), 7.45 (d, 1H), 7.83 (s, 1H), 8.15 (s, 1H), 8.27 (d, 1H), 10.96 (s, 1H), 12.31 (s, 1H).

Compound 70.03

7-chloro-6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride

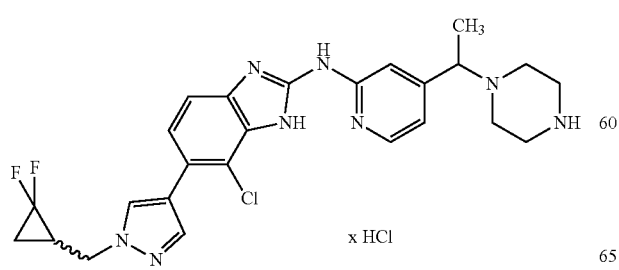

x HCl

Starting with tert-butyl 4-[(1R or 1S)-1-(2-{[7-chloro-6-(1-{[(1RS)-2,2-difluorocyclopropyl]methyl}-1H-pyrazol-4-yl)-1H-benzimidazol-2-yl]amino}pyridin-4-yl)ethyl]piperazine-1-carboxylate (850 mg, see Compound 70.02), Compound 70.03 was prepared analogously to the procedure for the preparation of Compound 39.05.

Yield: 795 mg of 90% pure target compound.

LC-MS (Method 2): $R_t$=1.13 min; MS (ESIpos): m/z=513 [M+H]$^+$.

Compound 71.01

1-(cyclopentylmethyl)-4-(4,4,5,5-tetramethyl-1,3,2-dioxaborolan-2-yl)-1H-pyrazole

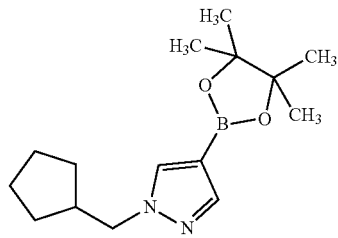 [SMILES: CC1(C)OB(c2cnn(CC3CCCC3)c2)OC1(C)C]

Starting with (bromomethyl)cyclopentane (420 mg), Compound 71.01 was prepared analogously to the procedure for the preparation of Compound 39.01.

Yield: 293 mg of the title compound with 80% purity.

LC-MS (Method 2): $R_t$=1.33 min; MS (ESIpos): m/z=277 [M+H]$^+$.

Compound 71.02

4-[1-(cyclopentylmethyl)-1H-pyrazol-4-yl]-2-nitroaniline

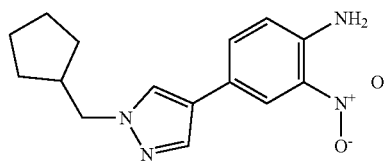

Starting with 1-(cyclopentylmethyl)-4-(4,4,5,5-tetramethyl-1,3,2-dioxaborolan-2-yl)-1H-pyrazole (290 mg, see Compound 71.01), Compound 71.02 was prepared analogously to the procedure for the preparation of Compound 39.02.

Yield: 135 mg of the title compound with 91% purity.

LC-MS (Method 2): $R_t$=1.21 min; MS (ESIpos): m/z=287 [M+H]$^+$.

$^1$H-NMR (400 MHz, DMSO-d6) δ[ppm]=1.20-1.33 (m, 2H), 1.43-1.67 (m, 6H), 2.31-2.42 (m, 1H), 4.00 (d, 2H), 7.03 (d, 1H), 7.42 (s, 2H), 7.65 (dd, 1H), 7.81 (d, 1H), 8.09 (d, 1H), 8.16 (s, 1H)

Compound 71.03

4-[1-(cyclopentylmethyl)-1H-pyrazol-4-yl]benzene-1,2-diamine

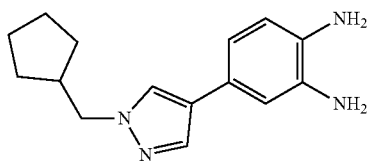 [SMILES: Nc1ccc(-c2cnn(CC3CCCC3)c2)cc1N]

Starting with 4-[1-(cyclopentylmethyl)-1H-pyrazol-4-yl]-2-nitroaniline (180 mg, see Compound 71.02), Compound 71.03 was prepared analogously to the procedure for the preparation of Compound 39.03.

Yield: 63 mg of the title compound with 62% purity.

LC-MS (Method 2): $R_t$=0.96 min; MS (ESIpos): m/z=257 [M+H]$^+$.

Compound 71.04

6-[1-(cyclopentylmethyl)-1H-pyrazol-4-yl]-N-{4-[(1R or 1S)-1-(piperazin-1-yl)ethyl]pyridin-2-yl}-1H-benzimidazol-2-amine hydrochloride

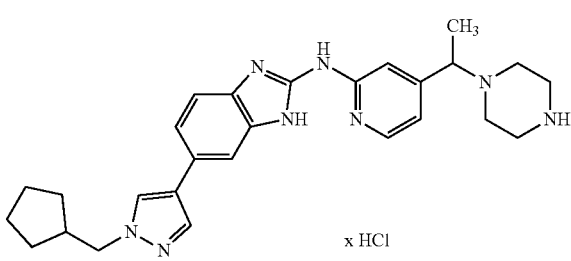 [SMILES: CC(c1ccnc(Nc2nc3ccc(-c4cnn(CC5CCCC5)c4)cc3[nH]2)c1)N1CCNCC1]

Starting with tert-butyl 4-{(1R or 1S)-1-[2-({6-[1-(cyclopentylmethyl)-1H-pyrazol-4-yl]-1H-benzimidazol-2-yl}amino)pyridin-4-yl]ethyl}piperazine-1-carboxylate (37.7 mg, see Example 71.01), Compound 71.04 was prepared analogously to the procedure for the preparation of Compound 39.05.

Yield: 42 mg of 90% pure target compound.

LC-MS (Method 2): $R_t$=1.18 min; MS (ESIpos): m/z=471 [M+H]$^+$.

Compound 72.01

4-[1-(propan-2-yl)-1H-pyrazol-5-yl]benzene-1,2-diamine

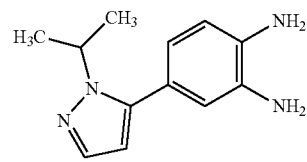 [SMILES: CC(C)n1nccc1-c1ccc(N)c(N)c1]

Starting with 1-(propan-2-yl)-1H-pyrazol-5-yl]boronic acid (570 mg), Compound 72.01 was prepared analogously to the procedure for the preparation of Compound 44.02.

Yield: 550 mg of the title compound with 90% purity.

LC-MS (Method 2): $R_t$=0.75 min; MS (ESIpos): m/z=217 [M+H]$^+$ $^1$H-NMR (400 MHz, DMSO-d6) δ [ppm]=1.33 (d, 6H), 4.50-4.60 (m, 1H), 4.62 (s, 2H), 4.70 (s, 2H), 6.04 (d, 1H), 6.40 (dd, 1H), 6.53 (d, 1H), 6.57 (d, 1H), 7.40 (d, 1H).

Compound 72.02

N-{4-[(1R or 1S)-1-(piperazin-1-yl)ethyl]pyridin-2-yl}-6-[1-(propan-2-yl)-1H-pyrazol-5-yl]-1H-benzimidazol-2-amine hydrochloride

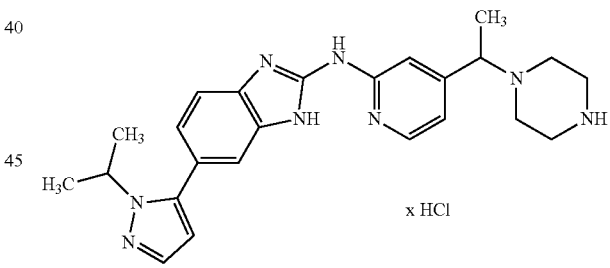

Starting with tert-butyl 4-{(1R or 1S)-1-[2-({6-[1-(propan-2-yl)-1H-pyrazol-5-yl]-1H-benzimidazol-2-yl}amino)pyridin-4-yl]ethyl}piperazine-1-carboxylate (288 mg, see Example 72.01), Compound 72.02 was prepared analogously to the procedure for the preparation of Compound 39.05.

Yield: 377 mg of 92% pure target compound.

LC-MS (Method 2): $R_t$=1.01 min; MS (ESIpos): m/z=431 [M+H]$^+$.

$^1$H-NMR (400 MHz, DMSO-d6) δ[ppm]=1.40 (d, 6H), 1.57-1.74 (m, 3H), 3.32-3.54 (m, 4H), 3.63-3.75 (m, 1H), 4.50-4.61 (m, 1H), 6.34 (d, 1H), 7.41 (dd, 1H), 7.49-7.65 (m, 3H), 7.69 (s, 1H), 7.78 (d, 1H), 8.37-8.62 (m, 1H), 9.29-9.77 (m, 2H), 13.02-13.28 (m, 1H).—4 piperazine-H not detectable.

Compound 73.01

4-(1,4-dimethyl-1H-pyrazol-5-yl)benzene-1,2-diamine

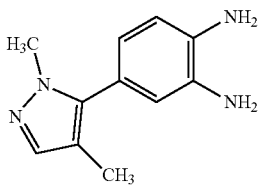

Starting with (1,4-dimethyl-1H-pyrazol-5-yl)boronic acid (434 mg), Compound 73.01 was prepared analogously to the procedure for the preparation of Compound 44.02.

Yield: 54 mg of the title compound with 90% purity.

LC-MS (Method 2): $R_t$=0.68 min; MS (ESIpos): m/z=203 [M+H]$^+$.

$^1$H-NMR (400 MHz, DMSO-d6) δ[ppm]=1.91 (s, 3H), 3.63 (s, 3H), 4.59 (br s, 2H), 4.69 (br s, 2H), 6.37 (dd, 1H), 6.49 (d, 1H), 6.58 (d, 1H), 7.22 (s, 1H).

Compound 73.02 tert-butyl 4-[(1R or 1S)-1-(2-{[6-(1,4-dimethyl-1H-pyrazol-5-yl)-1H-benzimidazol-2-yl]amino}pyridin-4-yl)ethyl]piperazine-1-carboxylate

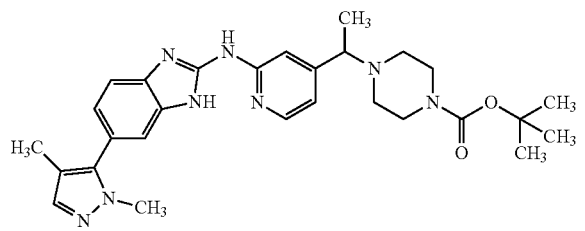 [SMILES: Cc1cnn(C)c1-c1ccc2nc(Nc3cc(C(C)N4CCN(C(=O)OC(C)(C)C)CC4)ccn3)[nH]c2c1]

Starting with 4-(1,4-dimethyl-1H-pyrazol-5-yl)benzene-1,2-diamine (54.4 mg, see Compound 73.01), Compound 73.02 was prepared analogously to the procedure for the preparation of Example 39.02.01. The intermediate thiourea was purified by flash chromatography.

Yield: 29 mg of the 90% pure title compound.

LC-MS (Method 2): $R_t$=1.27 min; MS (ESIpos): m/z=517 [M+H]$^+$.

$^1$H-NMR (400 MHz, DMSO-d6): δ [ppm]=1.26-1.31 (m, 3H), 1.38 (s, 9H), 1.99 (s, 3H), 2.23-2.44 (m, 4H), 3.25-3.32 (m, 4H), 3.45 (q, 1H), 3.71 (br d, 3H), 6.88-7.63 (m, 6H), 8.27 (d, 1H), 10.57-10.73 (m, 1H), 12.21 (br d, 1H).

Compound 73.03

6-(1,4-dimethyl-1H-pyrazol-5-yl)-N-{4-[(1R or 1S)-1-(piperazin-1-yl)ethyl]pyridin-2-yl}-1H-benzimidazol-2-amine hydrochloride

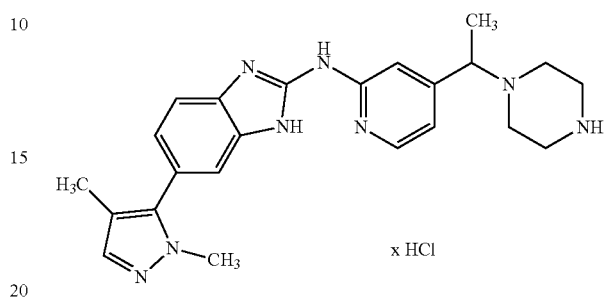

Starting with tert-butyl 4-[(1R or 1S)-1-(2-{[6-(1,4-dimethyl-1H-pyrazol-5-yl)-1H-benzimidazol-2-yl]amino}pyridin-4-yl)ethyl]piperazine-1-carboxylate (29.3 mg, see Compound 73.02), Compound 73.03 was prepared analogously to the procedure for the preparation of Compound 39.05.

Yield: 33 mg of 85% pure target compound.

LC-MS (Method 2): $R_t$=0.95 min; MS (ESIpos): m/z=418 [M+H]$^+$.

Compound 74.01

1-[(1RS)-1-cyclopropylethyl]-4-(4,4,5,5-tetramethyl-1,3,2-dioxaborolan-2-yl)-1H-pyrazole

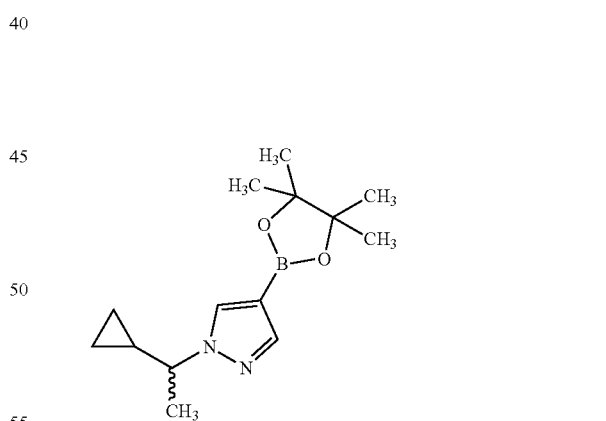

Starting with (1RS)-1-cyclopropylethanol (820 µl), Compound 74.01 was prepared analogously to the procedure for the preparation of Compound 67.01.

Yield: 470 mg of the title compound with 85% purity.

LC-MS (Method 2): $R_t$=1.18 min; MS (ESIpos): m/z=263 [M+H]$^+$.

Compound 74.02

4-{1-[(1RS)-1-cyclopropylethyl]-1H-pyrazol-4-yl}benzene-1,2-diamine

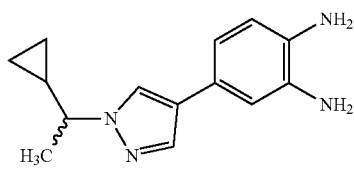

Starting from 1-[(1RS)-1-cyclopropylethyl]-4-(4,4,5,5-tetramethyl-1,3,2-dioxaborolan-2-yl)-1H-pyrazole (393 mg, see Compound 74.01), Compound 74.02 was prepared analogously to the procedure for the preparation of Compound 44.02.

Yield: 59 mg of the title compound with 80% purity.

LC-MS (Method 2): $R_t$=0.86 min; MS (ESIpos): m/z=243 [M+H]$^+$.

$^1$H-NMR (400 MHz, DMSO-d6) δ[ppm]=0.25-0.37 (m, 2H), 0.38-0.48 (m, 1H), 0.52-0.62 (m, 1H), 1.15-1.29 (m, 1H), 1.49 (d, 3H), 3.59 (dq, 1H), 4.42 (br d, 4H), 6.48 (d, 1H), 6.59 (dd, 1H), 6.70 (d, 1H), 7.55 (d, 1H), 7.86 (d, 1H).

Compound 74.03

6-{1-[(1RS)-1-cyclopropylethyl]-1H-pyrazol-4-yl}-N-{4-[(1R or 1S)-1-(piperazin-1-yl)ethyl]pyridin-2-yl}-1H-benzimidazol-2-amine hydrochloride

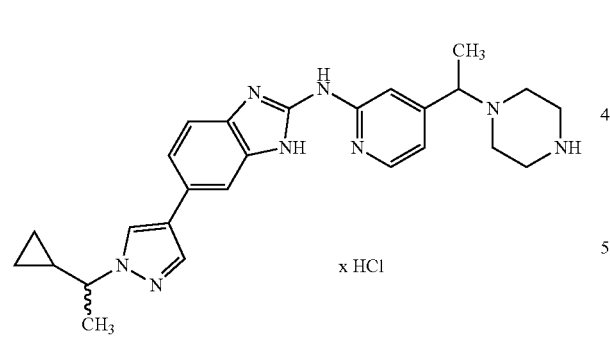

Starting with tert-butyl 4-[(1R or 1S)-1-{2-[(6-{1-[(1RS)-1-cyclopropylethyl]-1H-pyrazol-4-yl}-1H-benzimidazol-2-yl)amino]pyridin-4-yl}ethyl]piperazine-1-carboxylate (80.0 mg, see Example 74.01), Compound 74.03 was prepared analogously to the procedure for the preparation of Compound 39.05.

Yield: 88 mg of 95% pure target compound.

LC-MS (Method 2): $R_t$=1.10 min; MS (ESIpos): m/z=457 [M+H]$^+$.

Compound 75.01

1-(cyclobutylmethyl)-4-(4,4,5,5-tetramethyl-1,3,2-dioxaborolan-2-yl)-1H-pyrazole

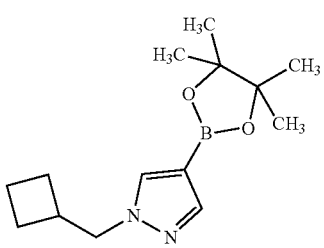 [SMILES: CC1(C)OB(c2cnn(CC3CCC3)c2)OC1(C)C]

Starting with (bromomethyl)cyclobutane (870 μl), Compound 75.01 was prepared analogously to the procedure for the preparation of Compound 39.01.

Yield: 1.0 g of the title compound with 84% purity.

LC-MS (Method 2): $R_t$=1.24 min; MS (ESIpos): m/z=263 [M+H]$^+$.

Compound 75.02

3-chloro-4-[1-(cyclobutylmethyl)-1H-pyrazol-4-yl]benzene-1,2-diamine

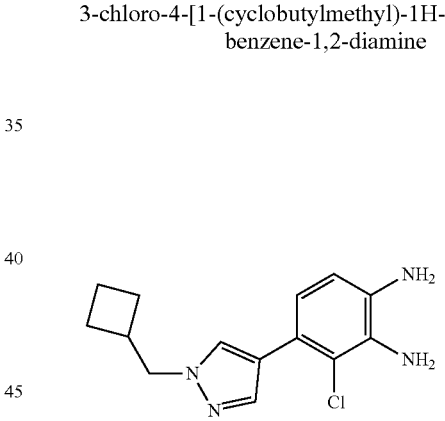

Starting with 1-(cyclobutylmethyl)-4-(4,4,5,5-tetramethyl-1,3,2-dioxaborolan-2-yl)-1H-pyrazole (1.00 g, see Compound 75.01), Compound 75.02 was prepared analogously to the procedure for the preparation of Compound 44.02.

Yield: 171 mg of the title compound with 86% purity.

LC-MS (Method 2): $R_t$=1.02 min; MS (ESIpos): m/z=277 [M+H]$^+$.

$^1$H-NMR (400 MHz, DMSO-d6) δ[ppm]=1.68-1.90 (m, 4H), 1.92-2.04 (m, 2H), 2.69-2.80 (m, 1H), 4.12 (d, 2H), 4.70 (s, 2H), 4.81 (s, 2H), 6.46-6.52 (m, 1H), 6.54-6.60 (m, 1H), 7.58 (s, 1H), 7.87 (s, 1H).

Compound 75.03

7-chloro-6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride

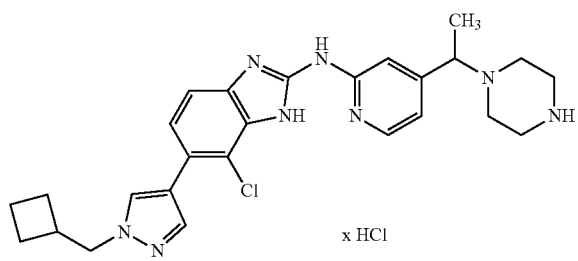 [SMILES: CC(c1ccnc(Nc2nc3ccc(-c4cnn(CC5CCC5)c4)c(Cl)c3[nH]2)c1)N1CCNCC1]

x HCl

Starting with tert-butyl 4-{(1R or 1S)-1-[2-({7-chloro-6-[1-(cyclobutylmethyl)-1H-pyrazol-4-yl]-1H-benzimidazol-2-yl}amino)pyridin-4-yl]ethyl}piperazine-1-carboxylate (110 mg, see Example 75.01), Compound 75.03 was prepared analogously to the procedure for the preparation of Compound 39.05.

Yield: 122 mg of 93% pure target compound.

LC-MS (Method 2): $R_t$=1.23 min; MS (ESIpos): m/z=491 [M+H]$^+$.

Compound 76.01 tert-butyl 4-[(2-{[6-(6-cyclopropylpyrimidin-4-yl)-1H-benzimidazol-2-yl]amino}pyridin-4-yl)methyl]piperazine-1-carboxylate

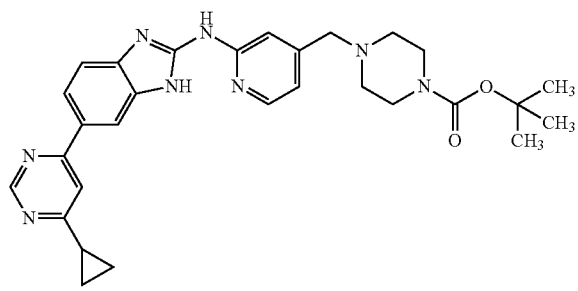 [SMILES: CC(C)(C)OC(=O)N1CCN(Cc2ccnc(Nc3nc4ccc(-c5cc(C6CC6)ncn5)cc4[nH]3)c2)CC1]

tert-Butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (1.00 g, see Compound 01.04), 4-chloro-6-cyclopropylpyrimidine (868 mg), [1,1'-bis(diphenylphosphino)ferrocene]palladium(II) dichloride dichloromethane adduct (153 mg) and aqueous sodium carbonate solution (2.8 ml, 2.0 M) were dissolved in 15 mL dioxane and the reaction mixture was stirred at 120° C. overnight. The reaction mixture was treated with water and dichloromethane. The aqueous layer was extracted with dichloromethane three times, the collected organic layers were washed with water and brine, filtered through a silicone coated filter and concentrated under reduced pressure. The crude product was purified by flash chromatography.

Yield: 1.3 g of 70% pure target compound.

LC-MS (Method 2): $R_t$=1.30 min; MS (ESIpos): m/z=527 [M+H]$^+$.

Compound 76.02

6-(6-cyclopropylpyrimidin-4-yl)-N-[4-(piperazin-1-ylmethyl)pyridin-2-yl]-1H-benzimidazol-2-amine hydrochloride

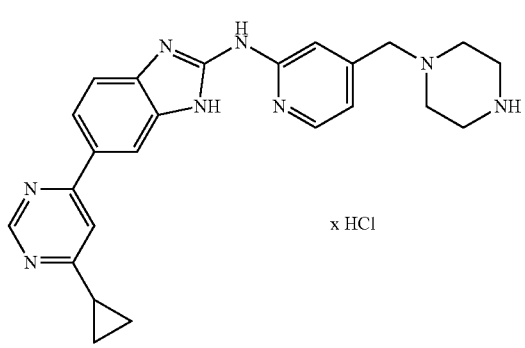 [SMILES: c1cc(CN2CCNCC2)cc(Nc2nc3ccc(-c4cc(C5CC5)ncn4)cc3[nH]2)n1]

x HCl

Starting with tert-butyl 4-[(2-{[6-(6-cyclopropylpyrimidin-4-yl)-1H-benzimidazol-2-yl]amino}pyridin-4-yl)methyl]piperazine-1-carboxylate (1.26 g, see Compound 76.01), Compound 76.02 was prepared analogously to the procedure for the preparation of Compound 39.05.

Yield: 1.3 g of 81% pure target compound.

LC-MS (Method 2): $R_t$=1.30 min; MS (ESIpos): m/z=428 [M+H]$^+$.

Compound 77.01 tert-butyl 4-[(2-{[6-(6-cyanopyrimidin-4-yl)-1H-benzimidazol-2-yl]amino}pyridin-4-yl)methyl]piperazine-1-carboxylate

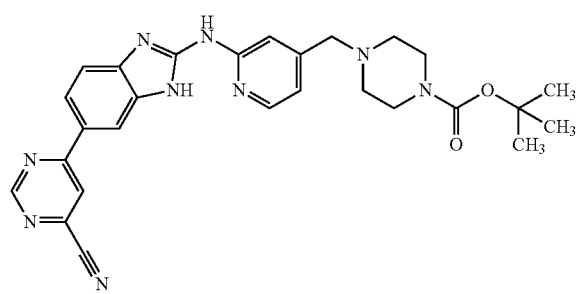 [SMILES: CC(C)(C)OC(=O)N1CCN(Cc2ccnc(Nc3nc4ccc(-c5cc(C#N)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (425 mg, see Compound 01.04), Compound 77.01 was prepared analogously to the procedure for the preparation of Compound 76.01.

Yield: 113 mg of the title compound with 36% purity.

LC-MS (Method 2): $R_t$=1.27 min; MS (ESIpos): m/z=512 [M+H]$^+$.

Compound 77.02

6-(2-{[4-(piperazin-1-ylmethyl)pyridin-2-yl]amino}-1H-benzimidazol-6-yl)pyrimidine-4-carbonitrile hydrochloride

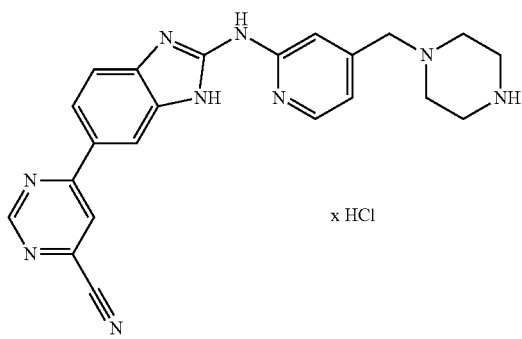 [SMILES: N#Cc1cc(-c2ccc3nc(Nc4cc(CN5CCNCC5)ccn4)[nH]c3c2)ncn1]

x HCl

Starting with tert-butyl 4-[(2-{[6-(6-cyanopyrimidin-4-yl)-1H-benzimidazol-2-yl]amino}pyridin-4-yl)methyl]piperazine-1-carboxylate (113 mg, see Compound 77.01), Compound 77.02 was prepared analogously to the procedure for the preparation of Compound 39.05.

Yield: 120 mg of 38% pure target compound.

LC-MS (Method 2): $R_t$=0.94 min; MS (ESIpos): m/z=412 [M+H]$^+$.

Compound 78.02

N-[4-(piperazin-1-ylmethyl)pyridin-2-yl]-6-[6-(propan-2-yl)pyrimidin-4-yl]-1H-benzimidazol-2-amine hydrochloride

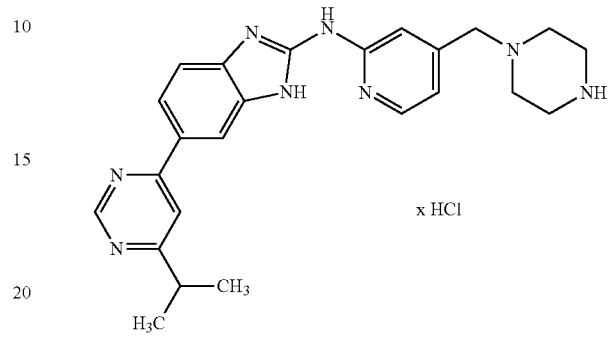

x HCl

Starting with tert-butyl 4-{[2-({6-[6-(propan-2-yl)pyrimidin-4-yl]-1H-benzimidazol-2-yl}amino)pyridin-4-yl]methyl}piperazine-1-carboxylate (240 mg, see Compound 78.01), Compound 78.02 was prepared analogously to the procedure for the preparation of Compound 39.05.

Yield: 350 mg of 70% pure target compound.

LC-MS (Method 2): $R_t$=1.03 min; MS (ESIpos): m/z=429 [M+H]$^+$.

Compound 78.01 tert-butyl 4-{[2-({6-[6-(propan-2-yl)pyrimidin-4-yl]-1H-benzimidazol-2-yl}amino)pyridin-4-yl]methyl}piperazine-1-carboxylate

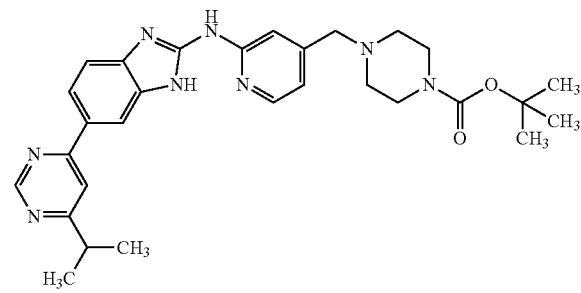 [SMILES: CC(C)c1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (1000 mg, see Compound 01.04), Compound 78.01 was prepared analogously to the procedure for the preparation of Compound 76.01.

Yield: 240 mg of the title compound with 63% purity.

LC-MS (Method 2): $R_t$=1.34 min; MS (ESIpos): m/z=529 [M+H]$^+$.

Compound 79.01 tert-butyl 4-{[2-({6-[6-(methoxymethyl)pyrimidin-4-yl]-1H-benzimidazol-2-yl}amino)pyridin-4-yl]methyl}piperazine-1-carboxylate

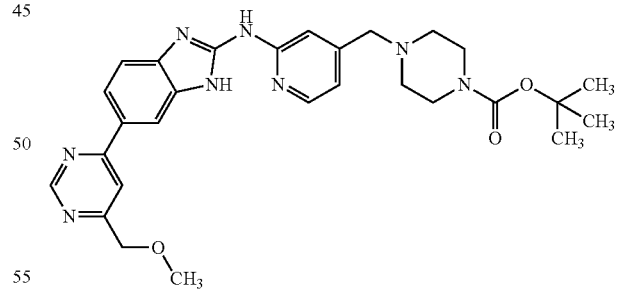

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (1000 mg, see Compound 01.04), Compound 79.01 was prepared analogously to the procedure for the preparation of Compound 76.01.

Yield: 891 mg of the title compound with 76% purity.

LC-MS (Method 2): $R_t$=1.22 min; MS (ESIpos): m/z=531 [M+H]$^+$.

Compound 79.02

6-[6-(methoxymethyl)pyrimidin-4-yl]-N-[4-(piperazin-1-ylmethyl)pyridin-2-yl]-1H-benzimidazol-2-amine hydrochloride

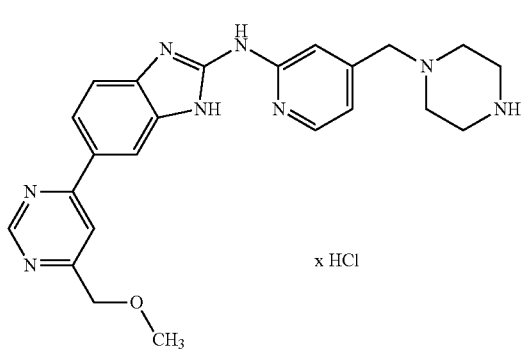 [SMILES: COCc1cc(-c2ccc3nc(Nc4cc(CN5CCNCC5)ccn4)[nH]c3c2)ncn1]

x HCl

Starting with tert-butyl 4-{[2-({6-[6-(methoxymethyl)pyrimidin-4-yl]-1H-benzimidazol-2-yl}amino)pyridin-4-yl]methyl}piperazine-1-carboxylate (72.0 mg, see Compound 79.01), Compound 79.02 was prepared analogously to the procedure for the preparation of Compound 39.05.

Yield: 465 mg of 61% pure target compound.

LC-MS (Method 2): $R_t$=0.89 min; MS (ESIpos): m/z=431 [M+H]$^+$.

Compound 80.01 tert-butyl 4-[(2-{[6-(6-chloropyrimidin-4-yl)-1H-benzimidazol-2-yl]amino}pyridin-4-yl)methyl]piperazine-1-carboxylate

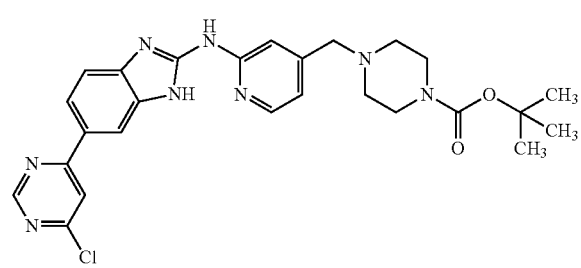 [SMILES: CC(C)(C)OC(=O)N1CCN(Cc2ccnc(Nc3nc4ccc(-c5cc(Cl)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (3.0 g 756 mg, 22% purity, see Compound 01.04), Compound 80.01 was prepared analogously to the procedure for the preparation of Compound 76.01.

Yield: 542 mg of the title compound as a crude product, that was used in the next step without further purification.

LC-MS (Method 2): $R_t$=1.33 min; MS (ESIpos): m/z=521 [M+H]$^+$.

Compound 80.02

6-[6-(cyclopropylmethoxy)pyrimidin-4-yl]-N-[4-(piperazin-1-ylmethyl)pyridin-2-yl]-1H-benzimidazol-2-amine hydrochloride

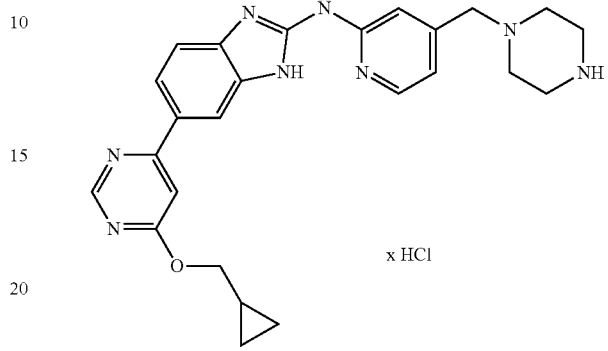

x HCl

Starting with tert-butyl 4-{[2-({6-[6-(cyclopropylmethoxy)pyrimidin-4-yl]-1H-benzimidazol-2-yl}amino)pyridin-4-yl]methyl}piperazine-1-carboxylate (310 mg, see Example 80.01), Compound 80.02 was prepared analogously to the procedure for the preparation of Compound 39.05.

Yield: 311 mg of 79% pure target compound.

LC-MS (Method 2): $R_t$=1.13 min; MS (ESIpos): m/z=457 [M+H]$^+$.

Compound 83.01

4-(6-chloro-5-methoxypyrimidin-4-yl)-2-nitroaniline

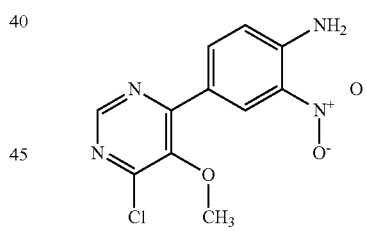

2-Nitro-4-(4,4,5,5-tetramethyl-1,3,2-dioxaborolan-2-yl)aniline (5.18 g), 4,6-dichloro-5-methoxypyrimidine (3.86 g), tetrakis(triphenylphosphane)palladium(0) (1.13 g) and aqueous sodium carbonate solution (29 ml, 2.0 M) were dissolved in 160 mL dioxane. The reaction mixture was stirred at 80° C. for 3 h. Undissolved compounds were filtered off and washed with dichloromethane. The filtrate was concentrated under reduced pressure, treated with ethyl acetate and the undissolved precipitate was filtered off. The filtrate was concentrated under reduced pressure and purified by flash chromatography. The precipitate and the purified compound were combined.

Yield: 1.92 g of 100% pure title compound.

LC-MS (Method 2): $R_t$=1.08 min; MS (ESIpos): m/z=281 [M+H]$^+$.

$^1$H-NMR (400 MHz, DMSO-d6) δ[ppm]=3.70-3.83 (m, 3H), 7.15 (d, 1H), 7.94 (s, 2H), 8.20 (dd, 1H), 8.79 (s, 1H), 8.95 (d, 1H).

Compound 83.02

4-(6-chloro-5-methoxypyrimidin-4-yl)benzene-1,2-diamine

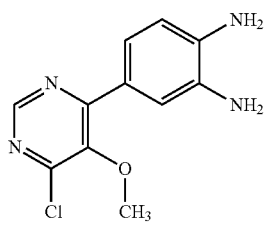 [SMILES: COc1c(Cl)ncnc1-c1ccc(N)c(N)c1]

5-(6-chloro-5-methoxypyrimidin-4-yl)-2-nitroaniline (2.03 g, see Compound 83.01) was dissolved in 160 mL dichloromethane and platinum on activated charcoal (1.41 g, 10% purity) was added. The reaction vessel was evacuated and flushed with hydrogen. The mixture was stirred at room temperature for 5 h. Platinum on activated charcoal (0.70 g, 10% purity) was added. The reaction vessel was evacuated and flushed with hydrogen. The mixture was stirred at room temperature overnight. The catalyst was carefully filtered off, washed with dichloromethane and ethanol and the combined filtrates were concentrated under reduced pressure.

Yield: 1.01 g of 87% pure title compound.

LC-MS (Method 2): $R_t$=0.82 min; MS (ESIpos): m/z=251 [M+H]$^+$.

$^1$H-NMR (400 MHz, DMSO-d6) δ[ppm]=3.68 (s, 3H), 4.69 (s, 2H), 5.27 (s, 2H), 6.58 (d, 1H), 7.43 (dd, 1H), 7.50 (d, 1H), 8.52-8.70 (m, 1H)

Compound 83.03

6-(5-methoxy-6-methylpyrimidin-4-yl)-N-{4-[(1R or 1S)-1-(piperazin-1-yl)ethyl]pyridin-2-yl}-1H-benzimidazol-2-amine hydrochloride

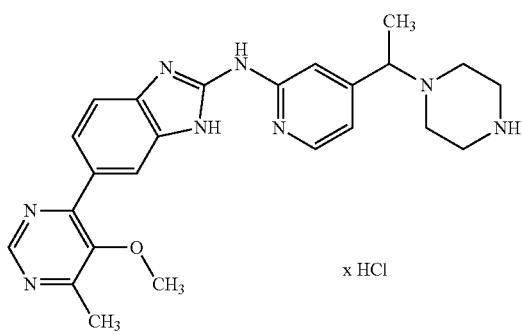 [SMILES: COc1c(C)ncnc1-c1ccc2nc(Nc3cc(C(C)N4CCNCC4)ccn3)[nH]c2c1]

Starting with tert-butyl 4-[(1R or 1S)-1-(2-{[6-(5-methoxy-6-methylpyrimidin-4-yl)-1H-benzimidazol-2-yl]amino}pyridin-4-yl)ethyl]piperazine-1-carboxylate (630 mg, see Example 83.02), Compound 83.03 was prepared analogously to the procedure for the preparation of Compound 39.05.

Yield: 805 mg of 96% pure target compound.

LC-MS (Method 2): $R_t$=0.94 min; MS (ESIpos): m/z=446 [M+H]$^+$.

$^1$H-NMR (400 MHz, DMSO-d6): δ [ppm]=1.69 (d, 3H), 2.55 (s, 3H), 3.19-3.52 (m, 9H), 3.59-3.65 (m, 3H), 7.57 (s, 1H), 7.67 (br s, 1H), 7.80 (d, 1H), 8.07-8.18 (m, 1H), 8.46 (d, 1H), 8.58 (d, 1H), 8.89 (s, 1H), 9.72 (br s, 2H), 13.25 (br s, 2H).—1 HCl

Compound 84.01

6-[6-(methoxymethyl)pyrimidin-4-yl]-N-{4-[(1R or 1S)-1-(piperazin-1-yl)ethyl]pyridin-2-yl}-1H-benzimidazol-2-amine hydrochloride

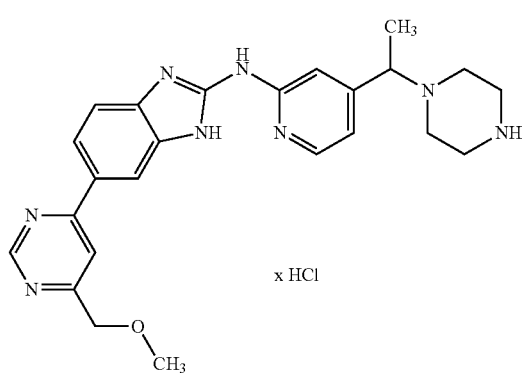 [SMILES: COCc1cc(-c2ccc3nc(Nc4cc(C(C)N5CCNCC5)ccn4)[nH]c3c2)ncn1]

Starting with tert-butyl 4-{(1R or 1S)-1-[2-({6-[6-(methoxymethyl)pyrimidin-4-yl]-1H-benzimidazol-2-yl}amino)pyridin-4-yl]ethyl}piperazine-1-carboxylate (325 mg, see Example 84.01), Compound 84.01 was prepared analogously to the procedure for the preparation of Compound 39.05.

Yield: 378 mg of the title 85% pure target compound.

LC-MS (Method 2): $R_t$=0.95 min; MS (ESIpos): m/z=445 [M+H]$^+$.

$^1$H-NMR (400 MHz, DMSO-d6): δ [ppm]=1.70 (br d, 3H), 3.21-3.53 (m, 12H), 4.60 (s, 2H), 7.57-7.60 (m, 1H), 7.66-7.73 (m, 1H), 7.80 (d, 1H), 8.00 (d, 1H), 8.24 (dd, 1H), 8.55 (d, 1H), 8.58 (d, 1H), 9.20 (d, 1H), 9.79 (br s, 2H), 13.31 (br s, 3H).—2 HCl

Compound 85.01

4-(6-chloropyrimidin-4-yl)-2-nitroaniline

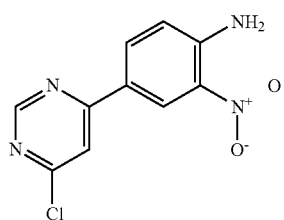

To a stirred solution of 2-nitro-4-(4,4,5,5-tetramethyl-1,3,2-dioxaborolan-2-yl)aniline (5.20 g, 97% purity) in 1-propanol (110 ml) was added potassium carbonate solution (19 ml, 2.0 M), 4,6-dichloropyrimidine (3.23 g, 97% purity), triphenylphosphine (250 mg) and PdCl$_2$(PPh$_3$)$_2$ (672 mg). The mixture was heated to 90° C. for 3 h. Water was added and a solid was collected by filtration. The solid was dissolved in acetone, filtered and the solution was concentrated in vacuum to give a solid that was triturated with ethanol to give 3.10 g of the title compound.

LC-MS (Method 2): $R_t$=1.03 min; MS (ESIpos): m/z=251 [M+H]$^+$.

$^1$H-NMR (400 MHz, DMSO-d6) δ[ppm]: 2.084 (1.18), 2.518 (2.66), 2.523 (1.73), 7.111 (0.53), 7.119 (8.72), 7.141 (8.76), 7.155 (0.53), 7.178 (0.46), 7.529 (0.43), 7.852 (0.55), 7.936 (7.61), 8.238 (14.54), 8.241 (16.00), 8.259 (4.08), 8.264 (4.34), 8.944 (8.80), 8.950 (9.06), 8.995 (12.27), 8.998 (11.92), 9.026 (0.53), 9.031 (0.55).

Compound 85.02

4-(6-chloropyrimidin-4-yl)benzene-1,2-diamine

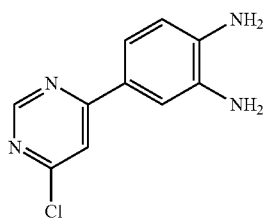 [SMILES: Nc1ccc(-c2cc(Cl)ncn2)cc1N]

To a stirred solution of 4-(6-chloropyrimidin-4-yl)-2-nitroaniline (1.00 g) in ethyl acetate (150 ml) was added platinum on carbon (389 mg, 10% w/w platinum) and the mixture was stirred at r.t. in a hydrogen atmosphere for 2 h. The mixture was filtered and the solution was concentrated in vacuum to give 480 mg of the title compound that was used without further purification.

LC-MS (Method 2): $R_t$=0.76 min; MS (ESIpos): m/z=221 [M+H]$^+$.

$^1$H-NMR (400 MHz, DMSO-d6) δ[ppm]: 1.053 (0.50), 1.153 (0.73), 1.171 (1.38), 1.189 (0.68), 1.987 (2.54), 2.518 (1.36), 2.523 (0.93), 4.016 (0.57), 4.034 (0.56), 4.689 (2.71), 5.332 (5.05), 6.495 (0.83), 6.515 (0.46), 6.520 (0.46), 6.564 (12.78), 6.572 (0.65), 6.585 (13.12), 6.592 (0.58), 6.674 (0.59), 6.679 (0.57), 7.363 (6.29), 7.368 (6.51), 7.384 (5.58), 7.389 (6.48), 7.475 (13.57), 7.480 (11.64), 7.849 (16.00), 7.852 (15.42), 8.828 (15.58), 8.831 (14.87).

Compound 85.03

6-[6-(cyclopropylmethoxy)pyrimidin-4-yl]-N-{4-[(1R or 1S)-1-(piperazin-1-yl)ethyl]pyridin-2-yl}-1H-benzimidazol-2-amine hydrochloride

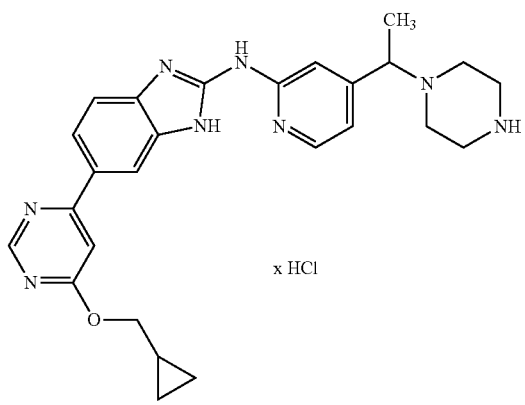 [SMILES: CC(c1ccnc(Nc2nc3ccc(-c4cc(OCC5CC5)ncn4)cc3[nH]2)c1)N1CCNCC1]

tert-Butyl 4-{(1R or 1S)-1-[2-({6-[6-(cyclopropylmethoxy)pyrimidin-4-yl]-1H-benzimidazol-2-yl}amino)pyridin-4-yl]ethyl}piperazine-1-carboxylate (62.0 mg, see Example 85.02) was dissolved in 1.4 mL dichloromethane and 130 μL methanol and cooled to 0° C. At this temperature hydrochloric acid (270 μl, 4.0 M in dioxane) was added and this mixture was stirred under cooling for 2 hours. The reaction mixture was stirred under cooling for additional 2 hours and stored in the refrigerator overnight, during which it solidified to assume a jelly-like texture. The jelly-like reaction mixture was diluted with dichloromethane/isopropanol (7:3) and saturated sodium bicarbonate solution. After several minutes of shaking, the jelly got solved. The layers were separated and the aqueous layer was extracted with dichloromethane/isopropanol (7:3) twice. The combined organic layers were concentrated under reduced pressure. The crude product was used without further purification.

Yield: 46 mg of 81% pure target compound.

LC-MS (Method 2): $R_t$=1.25 min; MS (ESIpos): m/z=471 [M+H]$^+$.

Compound 86.01

4-(1-{[(1RS)-2,2-difluorocyclopropyl]methyl}-1H-pyrazol-4-yl)-3-fluorobenzene-1,2-diamine

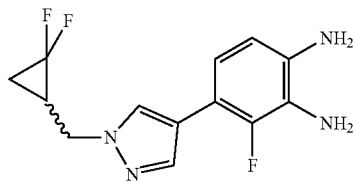 [SMILES: Nc1ccc(-c2cnn(CC3CC3(F)F)c2)c(F)c1N]

Starting with 1-{[(1RS)-2,2-difluorocyclopropyl]methyl}-4-(4,4,5,5-tetramethyl-1,3,2-dioxaborolan-2-yl)-1H-pyrazole (2.72 g, see Compound 55.01), Compound 86.01 was prepared analogously to the procedure for the preparation of Compound 44.02.

Yield: 1.67 g of the title compound with 75% purity.

LC-MS (Method 2): $R_t$=0.87 min; MS (ESIpos): m/z=283 [M+H]$^+$.

$^1$H-NMR (400 MHz, DMSO-d6) δ[ppm]=1.41-1.56 (m, 1H), 1.59-1.76 (m, 1H), 2.16-2.31 (m, 1H), 4.17-4.31 (m, 2H), 4.43 (s, 2H), 4.79 (s, 2H), 6.29-6.42 (m, 1H), 6.66 (t, 1H), 7.72 (s, 1H), 7.92 (d, 1H)

Compound 86.02

6-(1-{[(1RS)-2,2-difluorocyclopropyl]methyl}-1H-pyrazol-4-yl)-7-fluoro-N-{4-[(1R or 1S)-1-(piperazin-1-yl)ethyl]pyridin-2-yl}-1H-benzimidazol-2-amine hydrochloride

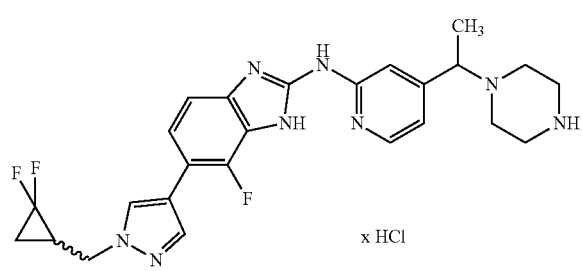 [SMILES: CC(c1ccnc(Nc2nc3ccc(-c4cnn(CC5CC5(F)F)c4)c(F)c3[nH]2)c1)N1CCNCC1]

Starting with tert-butyl 4-[(1R or 1S)-1-(2-{[6-(1-{[(1RS)-2,2-difluorocyclopropyl]methyl}-1H-pyrazol-4-yl)-7-fluoro-1H-benzimidazol-2-yl]amino}pyridin-4-yl)ethyl]piperazine-1-carboxylate (1.50 g, see Example 86.01), Compound 86.02 was prepared analogously to the procedure for the preparation of Compound 39.05.

Yield: 1.7 g of 90% pure target compound.

LC-MS (Method 2): $R_t$=1.11 min; MS (ESIpos): m/z=497 [M+H]$^+$.

Compound 87.01

1-(2,2-difluoroethyl)-4-(4,4,5,5-tetramethyl-1,3,2-dioxaborolan-2-yl)-1H-pyrazole

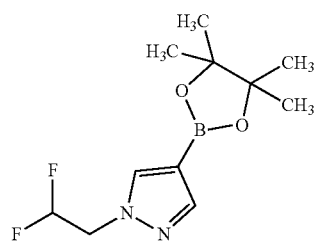 [SMILES: CC1(C)OB(c2cnn(CC(F)F)c2)OC1(C)C]

4-(4,4,5,5-tetramethyl-1,3,2-dioxaborolan-2-yl)-1H-pyrazole (1.00 g) was dissolved in 9.9 mL DMF and potassium carbonate (2.14 g) and 2,2-difluoroethyl trifluoromethanesulfonate (970 μl) were added. This mixture was stirred at 80° C. overnight. The reaction mixture was diluted with ethyl acetate and water. The layers were separated and the aqueous layer was extracted with ethyl acetate. The combined organic layers were dried using a water resistant filter. The filtrate was concentrated under reduced pressure. The crude product was used without further purification.

Yield: 1.8 g of 69% pure target compound.

LC-MS (Method 2): $R_t$=0.82 min; MS (ESIpos): m/z=259 [M+H]$^+$.

$^1$H-NMR (400 MHz, DMSO-d6) δ[ppm]=1.25 (s, 12H), 4.64 (td, 2H), 6.17-6.53 (m, 1H), 7.65 (s, 1H), 7.99 (s, 1H)

Compound 87.02

4-[1-(2,2-difluoroethyl)-1H-pyrazol-4-yl]benzene-1,2-diamine

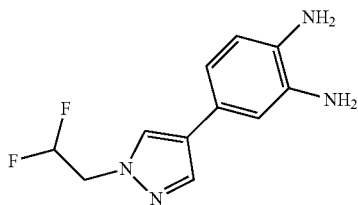 [SMILES: Nc1ccc(-c2cnn(CC(F)F)c2)cc1N]

Starting with 1-(2,2-difluoroethyl)-4-(4,4,5,5-tetramethyl-1,3,2-dioxaborolan-2-yl)-1H-pyrazole (1.60 g, see Compound 87.01), Compound 87.02 was prepared analogously to the procedure for the preparation of Compound 44.02.

Yield: 421 mg of the title compound with 68% purity.

LC-MS (Method 2): $R_t$=0.68 min; MS (ESIpos): m/z=239 [M+H]$^+$.

$^1$H-NMR (400 MHz, DMSO-d6) δ [ppm]=4.45 (s, 2H), 4.47 (s, 2H), 4.58 (td, 2H), 6.18-6.52 (m, 2H), 6.56-6.63 (m, 1H), 6.69 (d, 1H), 7.66 (s, 1H), 7.85 (s, 1H).

Compound 87.03 tert-butyl 4-{(1R or 1S)-1-[2-({6-[1-(2,2-difluoroethyl)-1H-pyrazol-4-yl]-1H-benzimidazol-2-yl}amino)pyridin-4-yl]ethyl}piperazine-1-carboxylate

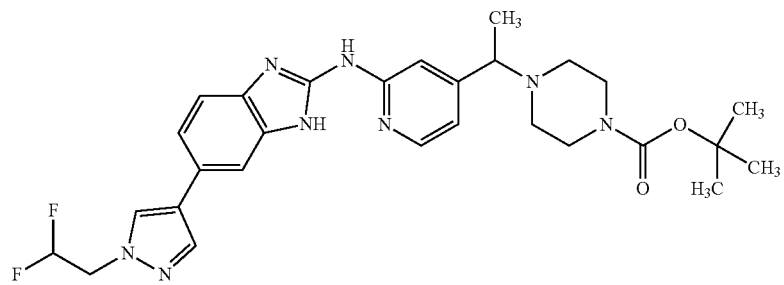 [SMILES: CC(c1ccnc(Nc2nc3ccc(-c4cnn(CC(F)F)c4)cc3[nH]2)c1)N1CCN(C(=O)OC(C)(C)C)CC1]

Starting with 4-[1-(2,2-difluoroethyl)-1H-pyrazol-4-yl]benzene-1,2-diamine (415 mg, 85% purity; see Compound 87.02), Compound 87.03 was prepared analogously to the procedure for the preparation of Example 39.02.01. The intermediate thiourea was purified by flash chromatography.

Yield: 549 mg of the 96% pure title compound.

LC-MS (Method 2): $R_t$=1.28 min; MS (ESIpos): m/z=553 [M+H]$^+$.

Compound 87.04

6-[1-(2,2-difluoroethyl)-1H-pyrazol-4-yl]-N-{4-[(1R or 1S)-1-(piperazin-1-yl)ethyl]pyridin-2-yl}-1H-benzimidazol-2-amine hydrochloride

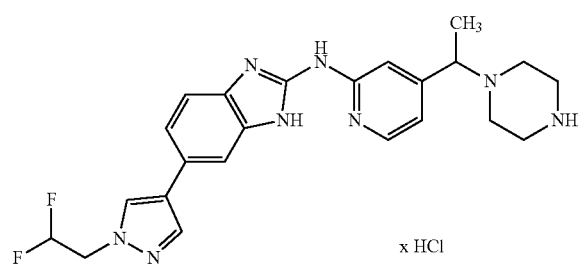 [SMILES: CC(c1ccnc(Nc2nc3ccc(-c4cnn(CC(F)F)c4)cc3[nH]2)c1)N1CCNCC1]

x HCl

Starting with tert-butyl 4-{(1R or 1S)-1-[2-({6-[1-(2,2-difluoroethyl)-1H-pyrazol-4-yl]-1H-benzimidazol-2-yl}amino)pyridin-4-yl]ethyl}piperazine-1-carboxylate (549 mg, see Compound 87.03), Compound 87.04 was prepared analogously to the procedure for the preparation of Compound 39.05.

Yield: 706 mg of the 85% pure target compound.

LC-MS (Method 2): $R_t$=0.98 min; MS (ESIpos): m/z=453 [M+H]$^+$.

$^1$H-NMR (400 MHz, DMSO-d6) δ[ppm]=1.70 (br d, 3H), 3.20-3.53 (m, 9H), 4.68 (td, 2H), 6.23-6.58 (m, 1H), 7.55 (s, 2H), 7.60 (dd, 1H), 7.64-7.71 (m, 2H), 7.79 (d, 1H), 7.96-8.01 (m, 1H), 8.22-8.27 (m, 1H), 8.57 (d, 1H), 9.79 (br s, 3H).—1 HCl Compound 88.01

4-[1-methyl-3-(trifluoromethyl)-1H-pyrazol-5-yl]benzene-1,2-diamine

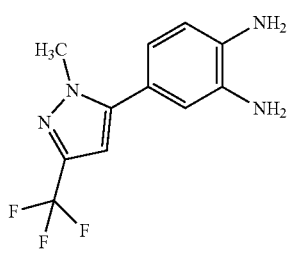 [SMILES: Cn1nc(C(F)(F)F)cc1-c1ccc(N)c(N)c1]

Starting with 1-methyl-5-(4,4,5,5-tetramethyl-1,3,2-dioxaborolan-2-yl)-3-(trifluoromethyl)-1H-pyrazole (903 mg), Compound 88.01 was prepared analogously to the procedure for the preparation of Compound 44.02.

Yield: 590 mg of the title compound with 91% purity.

LC-MS (Method 2): $R_t$=0.92 min; MS (ESIpos): m/z=257 [M+H]$^+$.

$^1$H-NMR (400 MHz, DMSO-d6) δ[ppm]=3.86 (s, 3H), 4.66 (s, 2H), 4.85 (s, 2H), 6.53-6.62 (m, 3H), 6.67 (d, 1H).

Compound 88.02

6-[1-methyl-3-(trifluoromethyl)-1H-pyrazol-5-yl]-N-{4-[(1R or 1S)-1-(piperazin-1-yl)ethyl]pyridin-2-yl}-1H-benzimidazol-2-amine hydrochloride

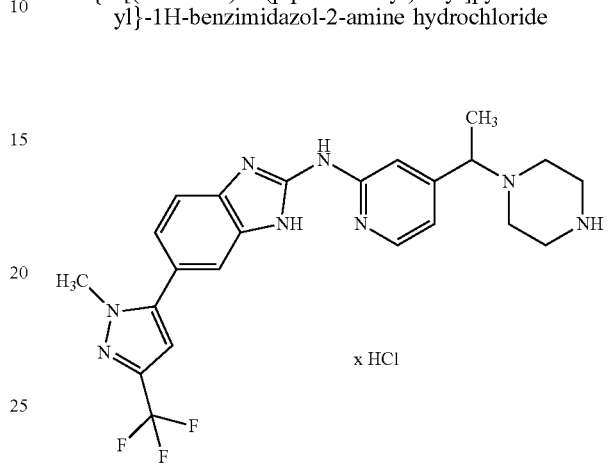

x HCl

Starting with tert-butyl 4-{(1R or 1S)-1-[2-({6-[1-methyl-3-(trifluoromethyl)-1H-pyrazol-5-yl]-1H-benzimidazol-2-yl}amino)pyridin-4-yl]ethyl}piperazine-1-carboxylate (250 mg, see Example 88.01), Compound 88.02 was prepared analogously to the procedure for the preparation of Compound 39.05.

Yield: 201 mg of the 95% pure target compound.

LC-MS (Method 2): $R_t$=1.21 min; MS (ESIpos): m/z=471 [M+H]$^+$.

$^1$H-NMR (400 MHz, DMSO-d6) δ[ppm]=1.55 (br s, 3H), 3.10-3.48 (m, 5H), 3.53-3.60 (m, 4H), 3.96 (s, 3H), 6.95 (s, 1H), 7.40-7.66 (m, 3H), 7.74-7.87 (m, 2H), 8.53 (br s, 1H), 8.87-9.76 (m, 2H), 12.51-13.74 (m, 2H).—1 HCl Compound 89.01

4-(1,3-dimethyl-1H-pyrazol-5-yl)benzene-1,2-diamine

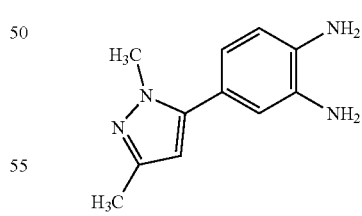

Starting with (1,3-dimethyl-1H-pyrazol-5-yl)boronic acid (600 mg), Compound 89.01 was prepared analogously to the procedure for the preparation of Compound 44.02.

Yield: 350 mg of the title compound with 96% purity.

LC-MS (Method 2): $R_t$=0.67 min; MS (ESIpos): m/z=203 [M+H]$^+$.

$^1$H-NMR (400 MHz, DMSO-d6) δ[ppm]=2.11 (s, 3H), 3.68 (s, 3H), 4.59 (s, 2H), 4.70 (s, 2H), 5.90 (s, 1H), 6.42-6.50 (m, 1H), 6.51-6.56 (m, 1H), 6.59 (d, 1H).

Compound 89.02

6-(1,3-dimethyl-1H-pyrazol-5-yl)-N-{4-[(1R or 1S)-1-(piperazin-1-yl)ethyl]pyridin-2-yl}-1H-benzimidazol-2-amine hydrochloride

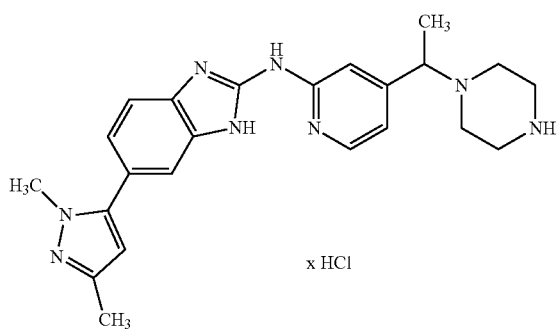 [SMILES: Cc1cc(-c2ccc3nc(Nc4cc(C(C)N5CCNCC5)ccn4)[nH]c3c2)n(C)n1]

x HCl

Starting with tert-butyl 4-[(1R or 1S)-1-(2-{[6-(1,3-dimethyl-1H-pyrazol-5-yl)-1H-benzimidazol-2-yl]amino}pyridin-4-yl)ethyl]piperazine-1-carboxylate (190 mg, see Example 89.01), Compound 89.02 was prepared analogously to the procedure for the preparation of Compound 39.05.

Yield: 164 mg of the 95% pure target compound.

LC-MS (Method 2): $R_t$=1.01 min; MS (ESIpos): m/z=417 [M+H]$^+$.

$^1$H-NMR (400 MHz, DMSO-d6) δ [ppm]=1.52-1.76 (m, 3H), 2.19 (s, 3H), 2.97-3.51 (m, 5H), 3.56 (s, 3H), 3.79 (s, 4H), 6.22 (s, 1H), 7.42-7.80 (m, 5H), 8.57 (br d, 1H), 9.54 (br s, 2H), 13.12 (br s, 2H).—1 HCl

Compound 90.01

6-{6-[(3-methoxypropyl)amino]pyrimidin-4-yl}-N-[4-(piperazin-1-ylmethyl)pyridin-2-yl]-1H-benzimidazol-2-amine hydrochloride

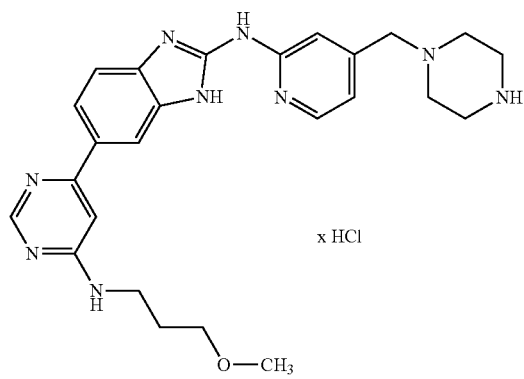 [SMILES: COCCCNc1cc(-c2ccc3nc(Nc4cc(CN5CCNCC5)ccn4)[nH]c3c2)ncn1]

x HCl

Starting with tert-butyl 4-({2-[(6-{6-[(3-methoxypropyl)amino]pyrimidin-4-yl}-1H-benzimidazol-2-yl)amino]pyridin-4-yl}methyl)piperazine-1-carboxylate (90.0 mg, see Example 90.01), Compound 90.01 was prepared analogously to the procedure for the preparation of Compound 39.05.

Yield: 86 mg of the 96% pure target compound.

LC-MS (Method 2): $R_t$=0.86 min; MS (ESIpos): m/z=475 [M+H]$^+$.

$^1$H-NMR (400 MHz, DMSO-d6) δ[ppm]: 1.229 (0.85), 1.365 (1.03), 1.382 (1.10), 1.828 (2.30), 1.845 (3.42), 1.861 (2.51), 2.326 (1.03), 2.669 (1.03), 3.207 (1.69), 3.228 (5.14), 3.257 (16.00), 3.343 (1.73), 3.359 (2.53), 3.414 (6.28), 3.429 (7.19), 3.444 (3.65), 3.467 (1.10), 3.485 (1.14), 3.502 (1.37), 3.563 (4.65), 3.578 (2.51), 3.661 (0.59), 3.674 (0.64), 3.697 (0.64), 3.712 (0.57), 3.925 (0.69), 4.315 (1.01), 5.759 (1.25), 7.159 (6.30), 7.549 (3.31), 7.685 (0.61), 7.823 (3.72), 8.096 (2.19), 8.215 (0.50), 8.521 (1.82), 8.719 (0.53), 8.808 (3.11), 8.961 (0.41), 9.718 (0.73), 9.877 (0.66).

Compound 91.01

6-(6-ethylpyrimidin-4-yl)-N-[4-(piperazin-1-ylmethyl)pyridin-2-yl]-1H-benzimidazol-2-amine hydrochloride

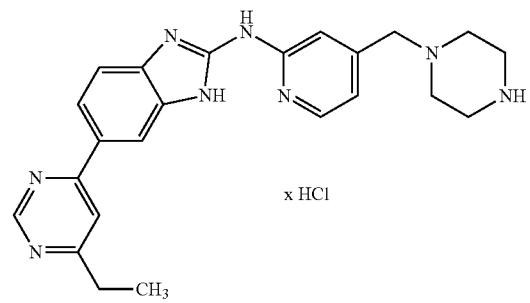 [SMILES: CCc1cc(-c2ccc3nc(Nc4cc(CN5CCNCC5)ccn4)[nH]c3c2)ncn1]

x HCl

Starting with tert-butyl 4-[(2-{[6-(6-ethylpyrimidin-4-yl)-1H-benzimidazol-2-yl]amino}pyridin-4-yl)methyl]piperazine-1-carboxylate (160 mg, see Example 91.01), Compound 91.01 was prepared analogously to the procedure for the preparation of Compound 39.05.

Yield: 169 mg of the 90% pure target compound.

LC-MS (Method 2): $R_t$=0.93 min; MS (ESIpos): m/z=416 [M+H]$^+$.

$^1$H-NMR (400 MHz, DMSO-d6) δ[ppm]=1.31 (t, 3H), 2.85 (q, 2H), 3.19-3.53 (m, 8H), 4.42 (br s, 2H), 7.57 (s, 2H), 7.79 (d, 1H), 8.03 (s, 1H), 8.23 (dd, 1H), 8.51-8.60 (m, 2H), 9.17 (d, 1H), 9.75 (br s, 2H), 13.18 (br s, 2H).—1 HCl.

Compound 92.01

6-[6-(3,5-dimethyl-1,2-oxazol-4-yl)pyrimidin-4-yl]-N-[4-(piperazin-1-ylmethyl)pyridin-2-yl]-1H-benzimidazol-2-amine hydrochloride

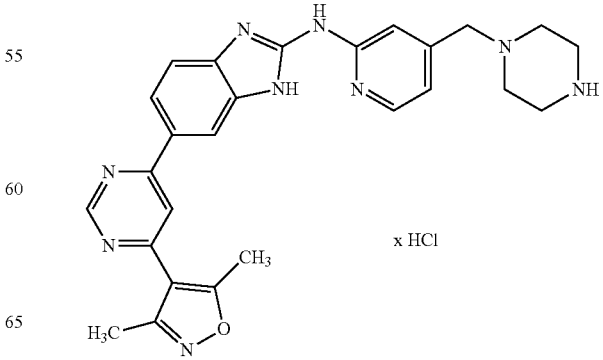

x HCl

Starting with tert-butyl 4-{[2-({6-[6-(3,5-dimethyl-1,2-oxazol-4-yl)pyrimidin-4-yl]-1H-benzimidazol-2-yl}amino)pyridin-4-yl]methyl}piperazine-1-carboxylate (100 mg, see Example 92.01), Compound 92.01 was prepared analogously to the procedure for the preparation of Compound 39.05.

Yield: 110 mg of the 92% pure target compound.

LC-MS (Method 2): R$_t$=1.01 min; MS (ESIpos): m/z=482 [M+H]$^+$.

$^1$H-NMR (400 MHz, DMSO-d6) δ[ppm]=2.53 (s, 3H), 2.74 (s, 3H), 3.16-3.52 (m, 8H), 4.28-4.51 (m, 2H), 7.54-7.64 (m, 2H), 7.82 (d, 1H), 8.13 (d, 1H), 8.28 (dd, 1H), 8.50-8.61 (m, 2H), 9.31 (d, 1H), 9.74 (br s, 2H), 12.88-13.64 (m, 2H).—1 HCl Compound 93.01 tert-butyl 4-{[2-({6-[6-(pyrrolidin-1-yl)pyrimidin-4-yl]-1H-benzimidazol-2-yl}amino)pyridin-4-yl]methyl}piperazine-1-carboxylate

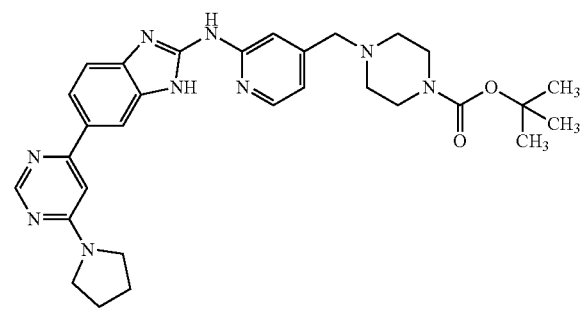 [SMILES: CC(C)(C)OC(=O)N1CCN(Cc2ccnc(Nc3nc4ccc(-c5cc(N6CCCC6)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (485 mg, see Compound 01.04), Compound 93.01 was prepared analogously to the procedure for the preparation of Compound 76.01.

Yield: 106 mg of the title compound with 73% purity.

LC-MS (Method 2): R$_t$=1.27 min; MS (ESIpos): m/z=557 [M+H]$^+$.

$^1$H-NMR (400 MHz, DMSO-d6): δ [ppm]: 0.797 (0.47), 0.814 (0.49), 0.821 (0.49), 0.904 (0.48), 1.299 (0.97), 1.386 (1.52), 1.395 (14.74), 1.881 (0.85), 1.907 (0.45), 1.974 (0.78), 1.987 (0.74), 2.326 (0.51), 2.331 (0.45), 2.346 (1.03), 2.357 (1.53), 2.369 (1.09), 3.499 (2.35), 5.284 (0.47), 5.758 (16.00), 6.924 (0.57), 6.936 (0.54), 7.181 (0.90), 7.888 (0.59), 8.252 (0.92), 8.264 (0.82), 8.498 (1.40).

Compound 93.02

N-[4-(piperazin-1-ylmethyl)pyridin-2-yl]-6-[6-(pyrrolidin-1-yl)pyrimidin-4-yl]-1H-benzimidazol-2-amine hydrochloride

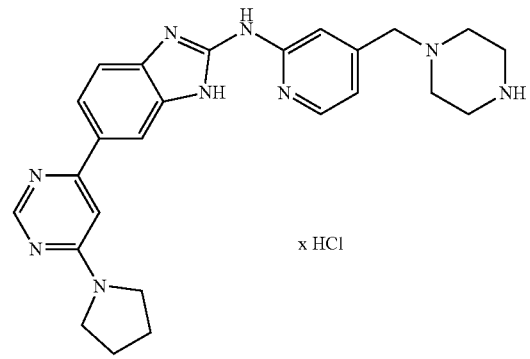 [SMILES: c1cc(CN2CCNCC2)cc(Nc2nc3ccc(-c4cc(N5CCCC5)ncn4)cc3[nH]2)n1]

Starting with tert-butyl 4-{[2-({6-[6-(pyrrolidin-1-yl)pyrimidin-4-yl]-1H-benzimidazol-2-yl}amino)pyridin-4-yl]methyl}piperazine-1-carboxylate (106 mg, see Compound 93.01), Compound 93.02 was prepared analogously to the procedure for the preparation of Compound 39.05.

Yield: 104 mg of the 73% pure target compound.

LC-MS (Method 2): R$_t$=0.96 min; MS (ESIpos): m/z=457 [M+H]$^+$.

$^1$H-NMR (400 MHz, DMSO-d6) δ[ppm]: 1.064 (1.53), 1.144 (0.48), 1.322 (3.45), 1.907 (0.62), 1.984 (2.30), 1.991 (2.35), 2.000 (2.59), 2.016 (1.96), 2.059 (1.68), 2.073 (1.68), 2.518 (16.00), 2.523 (10.49), 3.164 (1.20), 3.345 (1.92), 3.384 (1.20), 3.457 (0.62), 3.469 (0.62), 3.487 (0.62), 3.499 (0.62), 3.606 (0.77), 3.621 (0.86), 3.636 (0.91), 3.677 (1.87), 3.695 (2.44), 3.713 (2.59), 3.731 (2.49), 4.147 (1.68), 5.480 (1.34), 6.963 (0.43), 7.124 (3.93), 7.487 (1.63), 7.553 (0.48), 7.581 (0.86), 7.606 (0.57), 7.657 (0.62), 7.788 (1.15), 7.809 (1.49), 7.920 (1.20), 7.942 (0.91), 8.191 (1.82), 8.284 (1.05), 8.493 (0.96), 8.506 (0.86), 8.720 (0.62), 8.805 (3.69).

Compound 94.01 tert-butyl 4-{[2-({6-[6-(morpholin-4-yl)pyrimidin-4-yl]-1H-benzimidazol-2-yl}amino)pyridin-4-yl]methyl}piperazine-1-carboxylate

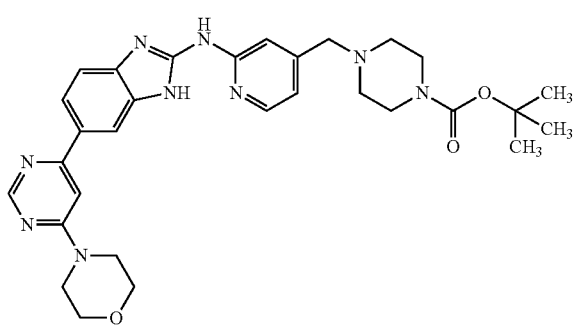 [SMILES: CC(C)(C)OC(=O)N1CCN(Cc2ccnc(Nc3nc4ccc(-c5cc(N6CCOCC6)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (446 mg, see Compound 01.04), Compound 94.01 was prepared analogously to the procedure for the preparation of Compound 76.01.

Yield: 119 mg of the title compound with 77% purity.

LC-MS (Method 4): $R_t$=1.20 min; MS (ESIpos): m/z=573 [M+H]$^+$.

$^1$H-NMR (400 MHz, DMSO-d6): δ [ppm]: 1.172 (0.52), 1.300 (1.65), 1.386 (2.45), 1.395 (16.00), 1.987 (0.92), 2.327 (0.51), 2.331 (0.60), 2.345 (1.31), 2.357 (1.66), 2.369 (1.03), 2.518 (1.90), 2.523 (1.30), 3.308 (0.42), 3.353 (1.68), 3.364 (1.19), 3.378 (0.61), 3.471 (0.51), 3.499 (1.61), 3.621 (0.71), 3.634 (0.89), 3.645 (0.83), 3.666 (0.44), 3.703 (5.60), 5.759 (2.28), 6.925 (0.40), 6.938 (0.40), 7.184 (0.83), 8.251 (0.89), 8.264 (0.72), 8.568 (1.19), 8.570 (1.22).

Compound 94.02

6-[6-(morpholin-4-yl)pyrimidin-4-yl]-N-[4-(piperazin-1-ylmethyl)pyridin-2-yl]-1H-benzimidazol-2-amine hydrochloride

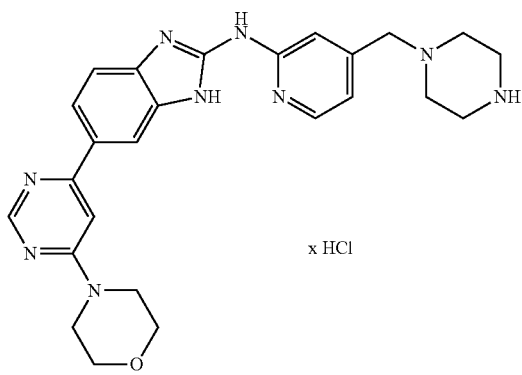 [SMILES: c1cc(CN2CCNCC2)cc(Nc2nc3ccc(-c4cc(N5CCOCC5)ncn4)cc3[nH]2)n1]

Starting with tert-butyl 4-{[2-({6-[6-(morpholin-4-yl)pyrimidin-4-yl]-1H-benzimidazol-2-yl}amino)pyridin-4-yl]methyl}piperazine-1-carboxylate (115 mg, see Compound 94.01), Compound 94.02 was prepared analogously to the procedure for the preparation of Compound 39.05.

Yield: 142 mg of the 78% pure target compound.

LC-MS (Method 2): $R_t$=0.87 min; MS (ESIpos): m/z=470 [M+H]$^+$.

$^1$H-NMR (400 MHz, DMSO-d6) δ [ppm]: 1.064 (2.31), 1.322 (4.84), 2.327 (1.84), 2.669 (1.81), 3.163 (1.03), 3.384 (2.69), 3.564 (16.00), 3.615 (1.16), 3.754 (5.34), 3.765 (4.28), 3.936 (3.72), 4.312 (1.09), 5.760 (6.41), 5.800 (1.22), 6.797 (0.41), 6.820 (0.41), 7.088 (0.78), 7.353 (0.56), 7.438 (1.28), 7.460 (1.34), 7.474 (3.84), 7.517 (2.06), 7.660 (0.91), 7.783 (1.47), 7.806 (1.59), 7.981 (1.31), 8.000 (0.94), 8.253 (1.69), 8.338 (1.25), 8.499 (1.22), 8.525 (0.84), 8.810 (3.03), 9.607 (0.47).

Compound 95.01 tert-butyl 4-{[2-({6-[6-(methylsulfanyl)pyrimidin-4-yl]-1H-benzimidazol-2-yl}amino)pyridin-4-yl]methyl}piperazine-1-carboxylate

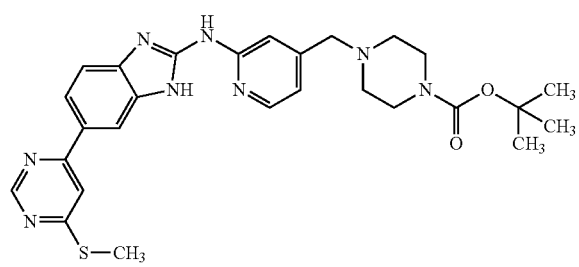 [SMILES: CSc1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (200 mg, see Compound 01.04), Compound 95.01 was prepared analogously to the procedure for the preparation of Compound 60.01.

Yield: 178 mg of the title compound with 48% purity.

LC-MS (Method 4): $R_t$=1.32 min; MS (ESIpos): m/z=534 [M+H]$^+$.

Compound 95.02

6-[6-(methylsulfanyl)pyrimidin-4-yl]-N-[4-(piperazin-1-ylmethyl)pyridin-2-yl]-1H-benzimidazol-2-amine hydrochloride

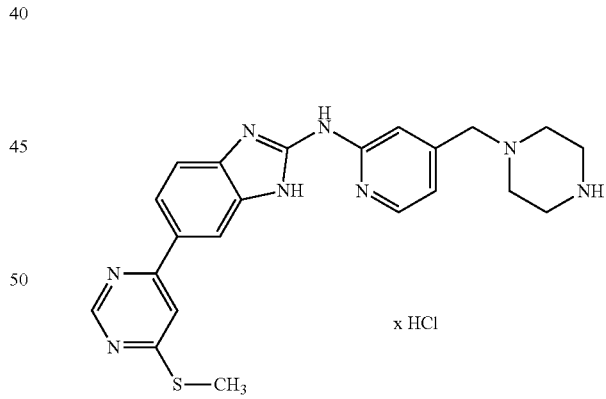

Starting with tert-butyl 4-{[2-({6-[6-(methylsulfanyl)pyrimidin-4-yl]-1H-benzimidazol-2-yl}amino)pyridin-4-yl]methyl}piperazine-1-carboxylate (170 mg, see Compound 95.01), Compound 95.02 was prepared analogously to the procedure for the preparation of Compound 39.05.

Yield: 331 mg of the 33% pure target compound.

LC-MS (Method 2): $R_t$=1.07 min; MS (ESIpos): m/z=433 [M+H]$^+$.

Compound 96.01

2-(6-chloropyrimidin-4-yl)propan-2-ol

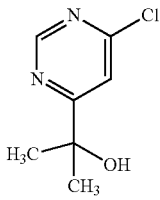

Methyl magnesiumbromide (12 ml, 1.4 M in THF/toluene 1:3) was treated with 5.5 mL THF and cooled down to −78° C. (ethanol/dry ice). methyl 6-chloropyrimidine-4-carboxylate (1.00 g), suspended in 8.5 mL THF, was added. The reaction mixture was stirred at this temperature for 2 hours. The reaction mixture was allowed to reach room temperature over night. The reaction mixture was poured into HCl (1 mol/L) and stirred for 15 minutes. Then the pH was adjusted to 7 by addition of saturated aqueous sodium bicarbonate solution. The aqueous layer was extracted three times with ethyl acetate, the combined organic layers were washed with water and brine, filtered through a silicone coated filter and concentrated under reduced pressure. The crude product was purified by flash chromatography.

Yield: 180 mg of the 90% pure target compound.

$^1$H-NMR (400 MHz, DMSO-d6) δ[ppm]=1.42 (s, 6H), 5.61 (s, 1H), 7.77 (d, 1H), 8.98 (d, 1H).

Compound 96.02

2-[6-(2-{[4-(piperazin-1-ylmethyl)pyridin-2-yl]amino}-1H-benzimidazol-6-yl)pyrimidin-4-yl]propan-2-ol hydrochloride

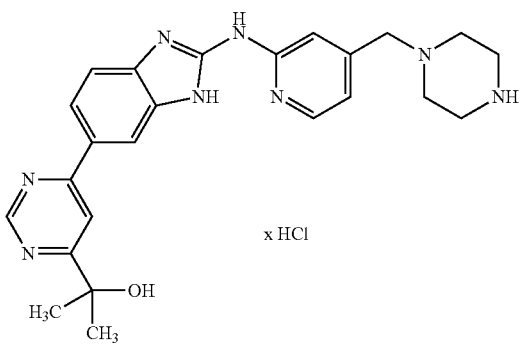 [SMILES: CC(C)(O)c1cc(-c2ccc3nc(Nc4cc(CN5CCNCC5)ccn4)[nH]c3c2)ncn1]

Starting with tert-butyl 4-{[2-({6-[6-(2-hydroxypropan-2-yl)pyrimidin-4-yl]-1H-benzimidazol-2-yl}amino)pyridin-4-yl]methyl}piperazine-1-carboxylate (100 mg, see Example 96.01), Compound 96.02 was prepared analogously to the procedure for the preparation of Compound 39.05.

Yield: 122 mg of the 94% pure target compound.

LC-MS (Method 2): $R_t$=0.90 min; MS (ESIpos): m/z=445 [M+H]$^+$.

$^1$H-NMR (400 MHz, DMSO-d6) δ[ppm]=1.50 (s, 6H), 3.24-3.52 (m, 8H), 4.45 (br s, 2H), 7.53-7.66 (m, 2H), 7.81 (d, 1H), 8.22 (dd, 1H), 8.26 (d, 1H), 8.49-8.60 (m, 2H), 9.18 (d, 1H), 9.80 (br s, 2H), 13.24 (br s, 1H). —OH not detectable

Compound 97.01

(rac)-1-(6-chloropyrimidin-4-yl)ethanol

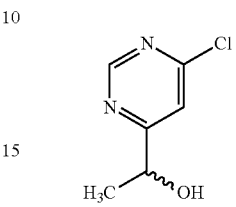

1-(6-chloropyrimidin-4-yl)ethanone (1.00 g) was suspended in 5 mL methanol and cooled to 0° C. with an ice bath. Then sodium borohydride (266 m g) was added portionwise, and the resulting mixture was then stirred at room temperature for 1.5 hours. Methanol was removed under reduced pressure, the residue was treated with water and the pH was adjusted to 3 by addition of aqueous HCl (1 mol/L). The aqueous layer was extracted with ethyl acetate three times, washed with water and brine, filtered through a silicone coated filter and dried under reduced pressure. The crude product was used without further purification.

Yield: 614 mg of the 99% pure target compound.

LC-MS (Method 2): $R_t$=0.61 min; MS (ESIpos): m/z=161 [M+H]$^+$.

$^1$H-NMR (400 MHz, DMSO-d6) δ[ppm]=1.38 (d, 3H), 4.62-4.78 (m, 1H), 5.75 (d, 1H), 7.68 (s, 1H), 8.96 (d, 1H).

Compound 97.02

(rac)-1-[6-(2-{[4-(piperazin-1-ylmethyl)pyridin-2-yl]amino}-1H-benzimidazol-6-yl)pyrimidin-4-yl]ethanol hydrochloride

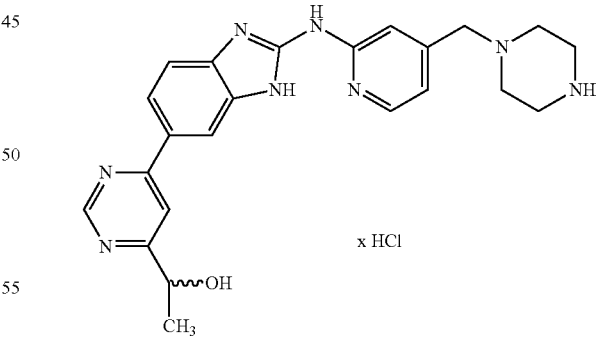

Starting with (rac)-tert-butyl 4-({2-[(6-{6-[1-hydroxyethyl]pyrimidin-4-yl}-1H-benzimidazol-2-yl)amino]pyridin-4-yl}methyl)piperazine-1-carboxylate (132 mg, see Example 97.01), Compound 97.02 was prepared analogously to the procedure for the preparation of Compound 39.05.

Yield: 164 mg of the 32% pure target compound.

LC-MS (Method 2): $R_t$=0.84 min; MS (ESIpos): m/z=432 [M+H]$^+$.

Compound 98.01

3-chloro-4-(4,4,5,5-tetramethyl-1,3,2-dioxaborolan-2-yl)benzene-1,2-diamine

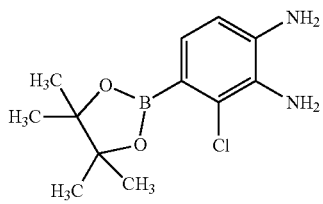 [SMILES: CC1(C)OB(c2ccc(N)c(N)c2Cl)OC1(C)C]

Starting with 4-bromo-3-chlorobenzene-1,2-diamine (1.50 g) and 4,4,4',4',5,5,5',5'-octamethyl-2,2'-bi-1,3,2-dioxaborolane, Compound 98.01 was prepared analogously to the procedure for the preparation of Compound 01.04.

Yield: 650 mg of the 96% pure target compound.

LC-MS (Method 2): $R_t$=1.05 min; MS (ESIpos): m/z=269 [M+H]$^+$.

Compound 98.02

3-chloro-4-(6-methylpyrimidin-4-yl)benzene-1,2-diamine

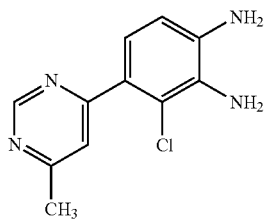 [SMILES: Cc1cc(-c2ccc(N)c(N)c2Cl)ncn1]

Starting with 3-chloro-4-(4,4,5,5-tetramethyl-1,3,2-dioxaborolan-2-yl)benzene-1,2-diamine (540 mg) and 4-chloro-6-methylpyrimidine (775 mg), Compound 98.02 was prepared analogously to the procedure for the preparation of Compound 76.01.

Yield: 390 mg of the 86% pure target compound.

LC-MS (Method 2): $R_t$=0.71 min; MS (ESIpos): m/z=235 [M+H]$^+$.

$^1$H-NMR (400 MHz, DMSO-d6) δ[ppm]=2.47 (s, 3H), 4.88 (s, 2H), 5.27 (s, 2H), 6.57 (d, 1H), 6.77 (d, 1H), 7.54 (d, 1H), 8.99 (d, 1H).

Compound 98.03

7-chloro-6-(6-methylpyrimidin-4-yl)-N-{4-[(1R or 1S)-1-(piperazin-1-yl)ethyl]pyridin-2-yl}-1H-benzimidazol-2-amine hydrochloride

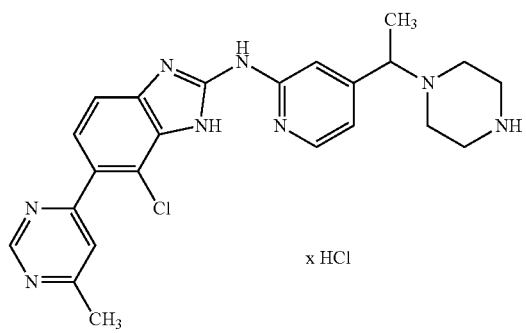 [SMILES: Cc1cc(-c2ccc3nc(Nc4cc(C(C)N5CCNCC5)ccn4)[nH]c3c2Cl)ncn1]

Starting with tert-butyl 4-[(1R or 1S)-1-(2-{[7-chloro-6-(6-methylpyrimidin-4-yl)-1H-benzimidazol-2-yl]amino}pyridin-4-yl)ethyl]piperazine-1-carboxylate (245 mg, see Example 98.01), Compound 98.03 was prepared analogously to the procedure for the preparation of Compound 39.05.

Yield: 278 mg of the 90% pure target compound.

LC-MS (Method 2): $R_t$=0.95 min; MS (ESIpos): m/z=450 [M+H]$^+$.

$^1$H-NMR (400 MHz, DMSO-d6): δ [ppm]=1.68 (br d, 3H), 2.56 (s, 3H), 3.14-3.53 (m, 5H), 4.61 (br s, 4H), 7.39 (br s, 1H), 7.46 (d, 1H), 7.55 (br s, 1H), 7.61-7.70 (m, 1H), 7.78 (s, 1H), 8.49 (br d, 1H), 9.07-9.20 (m, 1H), 9.59 (br s, 2H), 11.25-13.05 (m, 1H).

Compound 99.01 tert-butyl 4-[(1R or 1S)-1-(2-{[7-chloro-6-(4,4,5,5-tetramethyl-1,3,2-dioxaborolan-2-yl)-1H-benzimidazol-2-yl]amino}pyridin-4-yl)ethyl]piperazine-1-carboxylate

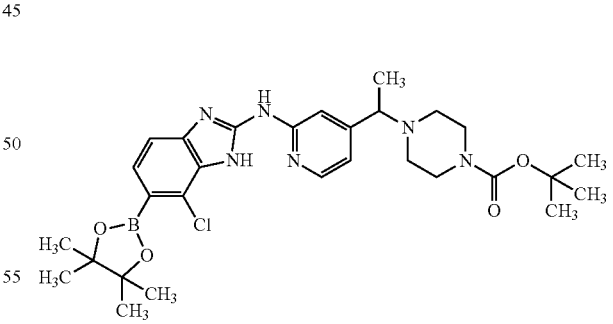

Starting with 3-chloro-4-(4,4,5,5-tetramethyl-1,3,2-dioxaborolan-2-yl)benzene-1,2-diamine (870 mg, see Compound 98.01), Compound 99.01 was prepared analogously to the procedure for the preparation of Example 39.02.01. The intermediate thiourea was purified by flash chromatography.

Yield: 940 mg of the 44% pure title compound.

LC-MS (Method 2): $R_t$=1.56 min; MS (ESIpos): m/z=583 [M+H]$^+$.

411

Compound 99.02 tert-butyl 4-{(1R or 1S)-1-[2-({7-chloro-6-[6-(methoxymethyl)pyrimidin-4-yl]-1H-benzimidazol-2-yl}amino)pyridin-4-yl]ethyl}piperazine-1-carboxylate

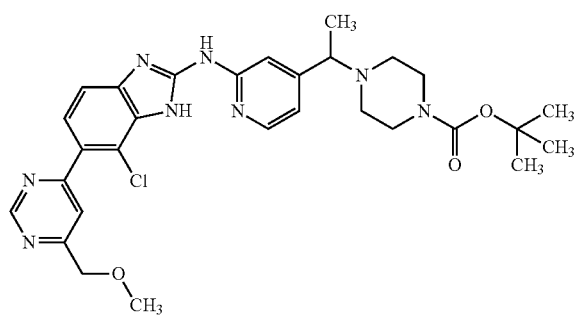 [SMILES: COCc1cc(-c2ccc3nc(Nc4cc(C(C)N5CCN(C(=O)OC(C)(C)C)CC5)ccn4)[nH]c3c2Cl)ncn1]

Starting with tert-butyl 4-[(1R or 1S)-1-(2-{[7-chloro-6-(4,4,5,5-tetramethyl-1,3,2-dioxaborolan-2-yl)-1H-benzimidazol-2-yl]amino}pyridin-4-yl)ethyl]piperazine-1-carboxylate (200 mg, see Compound 99.01), Compound 99.02 was prepared analogously to the procedure for the preparation of Compound 60.01.

Yield: 111 mg of the 41% pure target compound.

LC-MS (Method 2): $R_t$=1.31 min; MS (ESIpos): m/z=580 [M+H]$^+$.

Compound 99.03

7-chloro-6-[6-(methoxymethyl)pyrimidin-4-yl]-N-{4-[(1R or 1S)-1-(piperazin-1-yl)ethyl]pyridin-2-yl}-1H-benzimidazol-2-amine hydrochloride

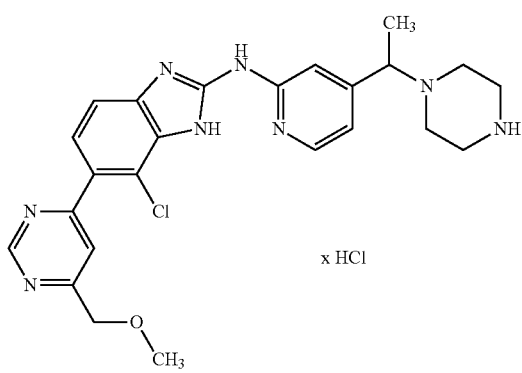 [SMILES: COCc1cc(-c2ccc3nc(Nc4cc(C(C)N5CCNCC5)ccn4)[nH]c3c2Cl)ncn1]

x HCl

Starting with tert-butyl 4-{(1R or 1S)-1-[2-({7-chloro-6-[6-(methoxymethyl)pyrimidin-4-yl]-1H-benzimidazol-2-yl}amino)pyridin-4-yl]ethyl}piperazine-1-carboxylate (105 mg, see Compound 99.02), Compound 99.03 was prepared analogously to the procedure for the preparation of Compound 39.05.

Yield: 151 mg of the 47% pure target compound.

LC-MS (Method 2): $R_t$=0.94 min; MS (ESIpos): m/z=481 [M+H]$^+$.

412

Compound 100.01 tert-butyl 4-{(1R or 1S)-1-[2-({6-[6-(dimethylamino)pyrimidin-4-yl]-1H-benzimidazol-2-yl}amino)pyridin-4-yl]ethyl}piperazine-1-carboxylate

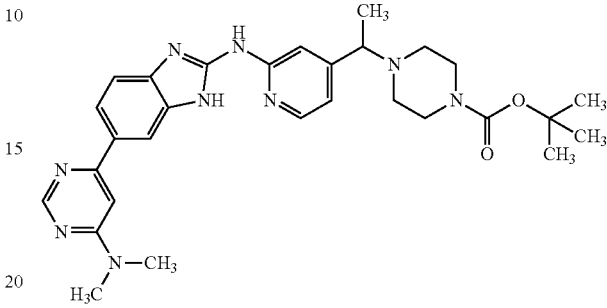

tert-Butyl 4-[(1R or 1S)-1-(2-{[6-(6-chloropyrimidin-4-yl)-1H-benzimidazol-2-yl]amino}pyridin-4-yl)ethyl]piperazine-1-carboxylate (85.0 mg, see Example 85.01) was dissolved in 2 mL dioxane and N-methylmethanamine (120 µl, 2.0 M in THF) was added. This mixture was stirred 3 hour at 110° C. N-methylmethanamine (240 µl, 2.0 M in TH F) were added and the mixture was stirred additional 2 hours at 110° C. The reaction mixture was concentrated under reduced pressure to provide the crude title compound which was used without further purification.

Yield: 119 mg of the 87% pure target compound.

LC-MS (Method 2): $R_t$=1.27 min; MS (ESIpos): m/z=544 [M+H]$^+$.

$^1$H-NMR (400 MHz, DMSO-d6): δ [ppm]=1.29 (br d, 3H), 1.34-1.42 (m, 9H), 2.23-2.45 (m, 4H), 3.15 (s, 6H), 3.27-3.33 (m, 4H), 3.44 (br s, 1H), 6.95 (br d, 1H), 7.08 (s, 1H), 7.17 (s, 1H), 7.46 (br s, 1H), 7.89 (br d, 1H), 8.27 (br d, 2H), 8.53 (d, 1H), 10.72 (br s, 1H), 12.27 (br s, 1H).

Compound 100.02

6-[6-(dimethylamino)pyrimidin-4-yl]-N-{4-[(1R or 1S)-1-(piperazin-1-yl)ethyl]pyridin-2-yl}-1H-benzimidazol-2-amine hydrochloride

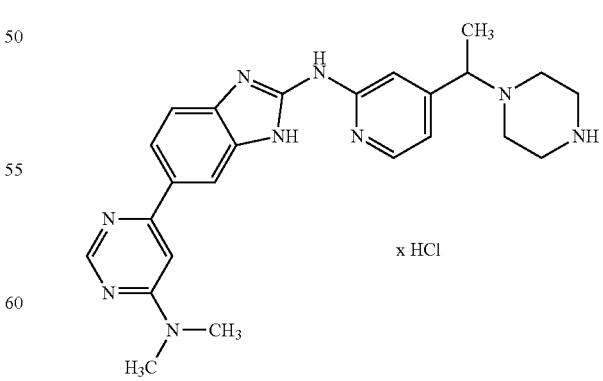

x HCl

Starting with tert-butyl 4-{(1R or 1S)-1-[2-({6-[6-(dimethylamino)pyrimidin-4-yl]-1H-benzimidazol-2-yl}amino)pyridin-4-yl]ethyl}piperazine-1-carboxylate (115 mg, see Compound 100.01), Compound 100.02 was prepared analogously to the procedure for the preparation of Compound 39.05.

Yield: 108 mg of the 90% pure target compound.

LC-MS (Method 2): $R_t$=0.99 min; MS (ESIpos): m/z=444 [M+H]$^+$.

$^1$H-NMR (400 MHz, DMSO-d6): δ [ppm]: 1.225 (0.48), 1.652 (1.18), 2.518 (13.32), 3.378 (1.16), 3.416 (1.02), 3.452 (0.99), 3.464 (0.93), 3.480 (0.83), 3.492 (0.68), 3.559 (16.00), 3.656 (0.42), 3.671 (0.48), 3.695 (0.48), 3.707 (0.42), 3.991 (0.63), 4.177 (0.47), 4.198 (0.45), 7.280 (3.81), 7.554 (1.56), 7.810 (1.28), 7.832 (1.57), 7.961 (1.28), 7.982 (0.99), 8.219 (2.07), 8.535 (0.90), 8.547 (0.90), 8.691 (0.45), 8.805 (4.00).

Compound 107.01.01

6-[6-(dimethylamino)-5-methoxypyrimidin-4-yl]-N-[4-(piperazin-1-ylmethyl)pyridin-2-yl]-1H-benzimidazol-2-amine hydrochloride

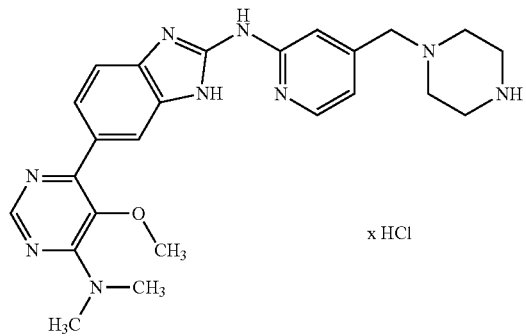 [SMILES: COc1c(-c2ccc3nc(Nc4cc(CN5CCNCC5)ccn4)[nH]c3c2)ncnc1N(C)C]

To a stirred solution of tert-butyl 4-{[2-({6-[6-(dimethylamino)-5-methoxypyrimidin-4-yl]-1H-benzimidazol-2-yl}amino)pyridin-4-yl]methyl}piperazine-1-carboxylate (200 mg, see Example 107.01.01) in dichloromethane (8.2 mL) and methanol (820 μL) was added HCl in dioxane (3.6 ml, 4.0 M). The mixture was stirred at room temperature for 16 h. The solvent was removed in vacuum to give 220 mg of the title compound as crude product that was used for the next step without purification.

LC-MS (Method 2): $R_t$=0.94 min; MS (ESIneg): m/z=458 [M−H]$^-$ $^1$H-NMR (400 MHz, DMSO-d6) δ[ppm]: 1.023 (9.11), 1.039 (9.21), 2.518 (1.16), 2.523 (0.80), 3.160 (0.86), 3.384 (16.00), 3.751 (0.63), 3.766 (0.83), 3.782 (0.64), 4.410 (0.47), 5.760 (2.59), 7.577 (1.91), 7.749 (0.89), 7.753 (0.88), 7.771 (1.38), 7.774 (1.42), 7.829 (2.01), 7.851 (1.16), 8.134 (1.97), 8.533 (1.16), 8.546 (1.08), 8.659 (3.77).

The compounds in the table 2 below were prepared analogously to the procedure for the preparation of Compound 107.01.01.

TABLE 2

| Compound | Structure<br>IUPAC-Name<br>LC-MS (method): Retention time; Mass found<br>$^1$H-NMR<br>Starting material |
|---|---|
| Compound 107.02.01 | ![structure] <br>6[6-(dimethylamino)-5-methoxypyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 1.03 min; MS (ESIneg): m/z = 472 [M − H]$^-$<br>$^1$H-NMR (400 MHz, DMSO-d6) δ [ppm]: 2.331 (1.30), 2.336 (0.59), 2.518 (6.93), 2.522 (4.80), 2.673 (1.36), 2.677 (0.65), 2.751 (0.68), 3.164 (1.95), 3.334 (0.87), 3.386 (16.00), 3.457 (0.59), 3.469 (0.62), |

TABLE 2-continued

| | Structure<br>IUPAC-Name<br>LC-MS (method): Retention time; Mass found<br>¹H-NMR |
|---|---|
| Compound | Starting material |

3.486 (0.59), 3.499 (0.53), 3.676 (0.43), 3.699 (0.46), 4.051 (0.46), 4.356 (0.68), 5.759 (0.71), 7.480 (0.56), 7.781 (1.42), 8.120 (0.65), 8.620 (0.90).

Example 107.02.01

Compound 108.01 x HCl

6-[6-(cyclopropylamino)-5-methoxypyrimidin-4-yl]-N-[4-(piperazin-1-ylmethyl)pyridin-2-yl]-1H-benzimidazol-2-amine hydrochloride LC-MS (Method 2): $R_t$ = 0.88 min; MS (ESIpos): m/z = 472.3 [M + H]⁺

¹H-NMR (400 MHz, DMSO-d6) δ [ppm]: 0.810 (0.46), 0.815 (0.52), 0.824 (0.82), 0.862 (0.55), 0.867 (0.53), 0.884 (0.54), 2.518 (0.67), 2.523 (0.49), 3.161 (1.84), 3.563 (16.00), 5.759 (4.97), 7.580 (0.64), 7.846 (0.63), 8.138 (0.55), 8.727 (0.90).

Example 108.01

Compound 109.01.01 x HCl

6-{6-[(cyclopropylmethyl)amino]-5-methoxypyrimidin-4-yl}-N-[4-(piperazin-1-ylmethyl)pyridin-2-yl]-1H-benzimidazol-2-amine hydrochloride LC-MS (Method 2): $R_t$ = 1 min; MS (ESIneg): m/z = 484 [M − H]⁻

¹H-NMR (400 MHz, DMSO-d6) δ [ppm]: 0.335 (1.61), 0.348 (1.70), 0.360 (0.55), 0.473 (0.48), 0.482 (1.34), 0.486 (1.27), 0.492 (0.74), 0.502 (1.43), 0.506 (1.30), 0.517 (0.41), 1.063 (0.52), 1.181 (0.54), 2.518 (2.63), 2.523 (1.75), 3.162 (16.00), 3.333 (0.42), 3.390 (1.01), 3.425 (1.36), 3.442 (1.83), 3.457 (1.17), 3.564 (2.07), 5.760 (0.95), 7.545 (1.04), 7.750 (0.52), 7.771 (0.79), 7.830 (1.13), 7.851 (0.68), 8.125 (1.12), 8.522 (0.60), 8.533 (0.58), 8.663 (1.59).

Example 109.01.01

TABLE 2-continued

| Compound | Structure<br>IUPAC-Name<br>LC-MS (method): Retention time; Mass found<br>¹H-NMR<br>Starting material |
|---|---|
| Compound 109.02.01 | 6-{6-[(cyclopropylmethyl)amino]-5-methoxypyrimidin-4-yl}-N-{4-[(1R or 1S)-1-(piperazin-1-yl)ethyl]pyridin-2-yl}-1H-benzimidazol-2-amine hydrochloride<br>LC-MS (Method 2): $R_t$ = 1.04 min; MS (ESIneg): m/z = 498 [M − H]⁻<br>¹H-NMR (400 MHz, DMSO-d6) δ [ppm]: 0.328 (0.57), 0.339 (2.29), 0.342 (2.02), 0.351 (2.35), 0.364 (0.76), 0.473 (0.70), 0.483 (1.89), 0.487 (1.79), 0.493 (1.03), 0.503 (2.00), 0.507 (1.83), 0.519 (0.57), 1.163 (0.47), 1.171 (0.47), 1.183 (0.77), 1.195 (0.44), 1.201 (0.46), 1.685 (1.53), 2.518 (1.34), 2.523 (0.91), 3.160 (1.83), 3.275 (0.59), 3.371 (0.45), 3.381 (0.48), 3.393 (0.54), 3.433 (2.11), 3.450 (3.23), 3.466 (2.58), 3.493 (16.00), 3.660 (0.44), 3.674 (0.54), 3.696 (0.47), 3.699 (0.46), 3.711 (0.42), 5.759 (4.42), 7.596 (1.69), 7.690 (0.46), 7.755 (0.99), 7.759 (0.99), 7.776 (1.34), 7.780 (1.42), 7.857 (2.01), 7.878 (1.32), 8.138 (2.08), 8.572 (1.08), 8.585 (1.03), 8.683 (3.69), 9.378 (0.41).<br>Example 109.02.01 |
| Compound 110.01 | 6-{6-[(cyclopropylmethyl)(methyl)amino]-5-methoxypyrimidin-4-yl}-N-[4-(piperazin-1-ylmethyl)pyridin-2-yl]-1H-benzimidazol-2-amine hydrochloride<br>LC-MS (Method 2): $R_t$ = 1.13 min; MS (ESIpos): m/z = 500 [M + H]⁺<br>¹H-NMR (400 MHz, DMSO-d6) δ [ppm]: 0.366 (0.55), 0.377 (2.08), 0.390 (2.18), 0.403 (0.64), 0.523 (0.68), 0.533 (1.82), 0.537 (1.69), 0.543 (1.00), 0.553 (1.87), 0.557 (1.66), 0.568 (0.51), 1.061 (1.17), 1.188 (0.45), 1.195 (0.45), 1.207 (0.70), 1.220 (0.46), 1.225 (0.55), 2.518 (0.84), 2.523 (0.57), 3.371 (16.00), 3.391 (1.21), 3.454 (2.62), 3.476 (5.88), 3.738 (1.99), 3.755 (1.89), 4.453 (0.61), 7.592 (1.84), 7.626 (0.65), 7.757 (0.97), 7.761 (0.92), 7.778 (1.40), 7.781 (1.41), 7.842 (2.03), 7.863 (1.21), 8.144 (2.00), 8.541 (1.30), 8.555 (1.18), 8.666 (3.68), 9.989 (0.51).<br>Example 110.01 |

TABLE 2-continued

Structure
IUPAC-Name
LC-MS (method): Retention time; Mass found
¹H-NMR

| Compound | Starting material |
|---|---|

Compound 111.01

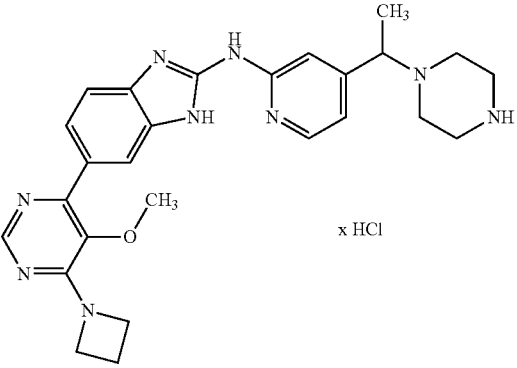 [SMILES: COc1c(-c2ccc3nc(Nc4cc(C(C)N5CCNCC5)ccn4)[nH]c3c2)ncnc1N1CCC1]

x HCl

6-[6-(azetidin-1-yl)-5-methoxypyrimidin-4-yl]-N-{4-[(1R or 1S)-1-
(piperazin-1-yl)ethyl]pyridin-2-yl}-1H-benzimidazol-2-amine
hydrochloride LC-MS (Method 2): $R_t$ = 1.02 min; MS (ESIneg): m/z = 484 [M − H]⁻
¹H-NMR (400 MHz, DMSO-d6) δ [ppm]: 1.656 (1.06), 2.438 (0.75),
2.458 (1.17), 2.518 (3.50), 2.522 (2.23), 3.161 (1.87), 3.221 (0.47),
3.372 (0.63), 3.382 (0.77), 3.406 (16.00), 3.425 (1.16), 3.443 (0.98),
3.456 (0.92), 3.468 (0.83), 3.487 (3.34), 3.497 (0.69), 3.508 (0.44),
3.661 (0.42), 3.673 (0.51), 3.675 (0.50), 3.687 (0.47), 3.699 (0.61),
3.707 (0.49), 3.712 (0.49), 3.728 (0.70), 3.745 (1.06), 3.762 (0.58),
4.069 (0.46), 4.478 (0.94), 5.759 (3.23), 7.559 (1.28), 7.755 (0.72),
7.776 (1.25), 7.822 (1.69), 7.843 (1.02), 8.138 (1.68), 8.546 (0.74),
8.557 (0.83), 8.595 (3.18).

Example 111.01

Compound 112.01

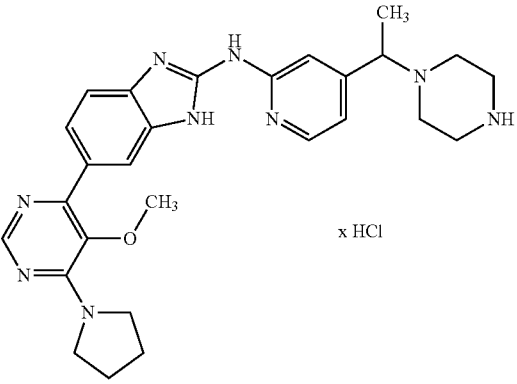 [SMILES: COc1c(-c2ccc3nc(Nc4cc(C(C)N5CCNCC5)ccn4)[nH]c3c2)ncnc1N1CCCC1]

x HCl

6-[5-methoxy-6-(pyrrolidin-1-yl)pyrimidin-4-yl]-N-{4-[(1R or 1S)-1-
(piperazin-1-yl)ethyl]pyridin-2-yl}-1H-benzimidazol-2-amine
hydrochloride LC-MS (Method 2): $R_t$ = 1.11 min; MS (ESIneg): m/z = 498 [M − H]⁻
¹H-NMR (400 MHz, DMSO-d6) δ [ppm]: 1.655 (0.82), 1.985 (2.43),
2.083 (0.55), 2.518 (2.47), 2.522 (1.57), 3.162 (2.12), 3.368 (16.00),
3.383 (0.81), 3.387 (0.68), 3.394 (0.79), 3.426 (0.73), 3.456 (0.68),
3.466 (0.62), 3.468 (0.62), 3.485 (0.55), 3.487 (0.51), 3.497 (0.44),
3.549 (0.60), 3.577 (0.73), 3.728 (0.40), 3.869 (1.35), 4.032 (0.53),
7.563 (1.12), 7.734 (0.73), 7.738 (0.75), 7.759 (1.10), 7.836 (1.50),
7.856 (1.01), 8.116 (1.48), 8.547 (0.66), 8.561 (0.66), 8.669 (3.04).

Example 112.01

TABLE 2-continued

Structure
IUPAC-Name
LC-MS (method): Retention time; Mass found
¹H-NMR
Compound | Starting material Compound 113.01

6-[6-(3,3-difluoroazetidin-1-yl)-5-methoxypyrimidin-4-yl]-N-{4-[(1R or 1S)-1-(piperazin-1-yl)ethyl]pyridin-2-yl}-1H-benzimidazol-2-amine hydrochloride
LC-MS (Method 2): $R_t$ = 1.11 min; MS (ESIpos): m/z = 522 [M + H]⁺
¹H-NMR (400 MHz, DMSO-d6) δ [ppm]: 1.683 (1.29), 2.518 (2.27), 2.523 (1.60), 3.162 (5.87), 3.281 (0.49), 3.383 (0.52), 3.394 (0.54), 3.466 (16.00), 3.485 (1.09), 3.497 (0.88), 3.507 (0.62), 3.661 (0.41), 3.676 (0.45), 3.697 (0.44), 3.712 (0.41), 4.727 (1.80), 4.758 (3.32), 4.789 (1.71), 5.759 (1.51), 7.568 (1.56), 7.660 (0.40), 7.792 (1.56), 7.813 (1.89), 7.951 (1.15), 7.973 (0.86), 8.313 (1.81), 8.563 (1.15), 8.578 (4.16).
Example 113.01

Compound 114.01

6-[6-(cyclobutylamino)-5-methoxypyrimidin-4-yl]-N-{4-[(1R or 1S)-1-(piperazin-1-yl)ethyl]pyridin-2-yl}-1H-benzimidazol-2-amine hydrochloride
LC-MS (Method 2): $R_t$ = 1.27 min; MS (ESIpos): m/z = 499.6 [M + H]⁺
¹H-NMR (400 MHz, DMSO-d6) δ [ppm]: 0.986 (0.99), 1.003 (1.08), 1.665 (1.31), 1.709 (0.55), 1.730 (0.82), 1.742 (0.78), 1.754 (1.34), 1.771 (1.05), 1.792 (0.52), 2.263 (0.67), 2.284 (2.22), 2.301 (2.80), 2.322 (1.76), 2.327 (0.90), 2.332 (0.58), 2.518 (1.93), 2.523 (1.39), 2.665 (0.44), 2.669 (0.59), 3.245 (0.54), 3.383 (0.82), 3.394 (0.86), 3.425 (1.12), 3.443 (1.07), 3.456 (1.14), 3.476 (16.00), 3.497 (0.81), 3.549 (0.55), 4.691 (0.63), 4.712 (0.96), 4.732 (0.92), 4.752 (0.55), 5.760 (3.97), 7.576 (1.31), 7.736 (0.77), 7.759 (1.05), 7.841 (1.66), 7.862 (1.13), 8.112 (1.60), 8.561 (0.79), 8.573 (0.73), 8.666 (2.39).
Example 114.01

TABLE 2-continued

| Compound | Structure<br>IUPAC-Name<br>LC-MS (method): Retention time; Mass found<br>¹H-NMR<br>Starting material |
|---|---|
| Compound 115.01 | 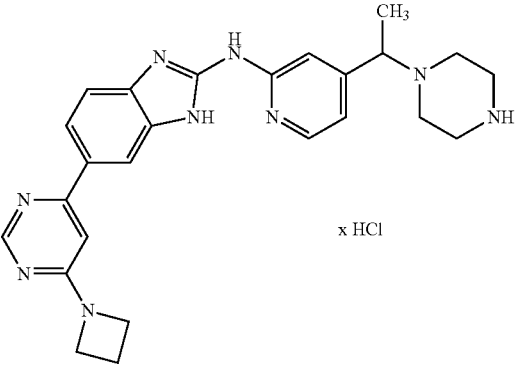 [SMILES: CC(c1ccnc(Nc2nc3ccc(-c4cc(N5CCC5)ncn4)cc3[nH]2)c1)N1CCNCC1]<br>6-[6-(azetidin-1-yl)pyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 0.97 min; MS (ESIpos): m/z = 456 [M + H]⁺<br>¹H-NMR (400 MHz, DMSO-d6) δ [ppm]: 1.144 (0.69), 1.231 (0.55), 1.617 (2.27), 2.432 (1.51), 2.451 (3.64), 2.472 (6.94), 2.518 (16.00), 2.523 (10.92), 3.163 (2.68), 3.384 (2.68), 3.457 (1.79), 3.469 (1.65), 3.486 (1.58), 3.499 (1.30), 3.662 (0.96), 3.676 (1.03), 3.699 (1.03), 3.713 (1.03), 4.348 (7.90), 5.760 (0.55), 6.997 (13.80), 7.514 (4.12), 7.782 (3.91), 7.803 (5.08), 7.919 (3.78), 7.942 (2.88), 8.194 (5.70), 8.522 (2.40), 8.740 (13.80), 9.538 (0.62), 12.763 (0.41).<br>Example 115.01 |
| Compound 116.01 | 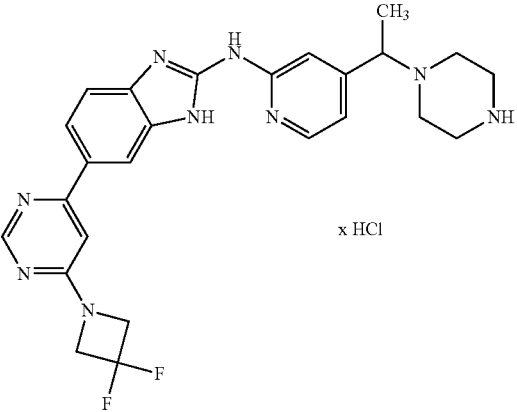 [SMILES: CC(c1ccnc(Nc2nc3ccc(-c4cc(N5CC(F)(F)C5)ncn4)cc3[nH]2)c1)N1CCNCC1]<br>6-[6-(3,3-difluoroazetidin-1-yl)pyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 0.99 min; MS (ESIpos): m/z = 491.6 [M + H]⁺<br>¹H-NMR (400 MHz, DMSO-d6) δ [ppm]: 0.819 (0.45), 0.986 (15.51), 1.002 (16.00), 1.009 (2.16), 1.011 (1.38), 1.021 (0.82), 1.025 (1.91), 1.037 (0.70), 1.087 (1.56), 1.104 (1.58), 1.128 (1.44), 1.145 (1.56), 1.172 (0.47), 1.194 (2.37), 1.210 (2.43), 1.227 (0.86), 1.257 (5.86), 1.273 (5.96), 1.279 (3.80), 1.293 (5.88), 1.310 (5.39), 1.693 (5.26), 1.707 (5.27), 1.740 (3.91), 1.749 (2.02), 1.777 (3.41), 1.976 (1.71), 2.131 (0.86), 2.518 (3.85), 2.523 (2.39), 2.669 (1.03), 2.673 (0.70), 3.096 (0.84), 3.107 (0.86), 3.114 (0.88), 3.125 (0.88), 3.133 (0.43), 3.143 (0.43), 3.160 (0.90), 3.218 (0.88), 3.276 (2.02), 3.288 (2.10), 3.371 (1.27), 3.403 (1.46), 3.449 (2.90), 3.455 (3.46), 3.465 (3.60), 3.467 (3.64), 3.483 (3.62), 3.485 (3.54), 3.495 (2.96), 3.507 (1.97), 3.578 (1.05), 3.585 (1.17), 3.594 (1.25), 3.601 (0.97), 3.609 (1.48), 3.625 (1.64), 3.641 (1.30), 3.649 (0.66), 3.660 (1.13), 3.664 (0.88), 3.672 (1.15), 3.674 (1.23), 3.696 (1.13), 3.698 (1.05), 3.706 (0.78), 3.710 (0.95), 3.715 (0.53), 3.722 (0.51), 3.726 (0.53), 4.105 (0.62), 4.247 (0.72), 4.283 (0.41), 4.466 (0.78), 4.496 (1.44), 4.525 (0.78), 4.738 (5.45), 4.768 (10.18), 4.798 (5.08), 7.211 (10.02), 7.591 (5.45), 7.691 (1.77), 7.813 (4.98), 7.834 (5.53), 8.059 (3.87), 8.064 (3.91), 8.081 (3.17), 8.085 (3.27), 8.343 (5.88), 8.565 (3.74), 8.578 (3.52), 8.822 (9.89), 9.879 (1.38).<br>Example 116.01 |

TABLE 2-continued

| Compound | Structure<br>IUPAC-Name<br>LC-MS (method): Retention time; Mass found<br>¹H-NMR<br>Starting material |
|---|---|

Compound 117.01

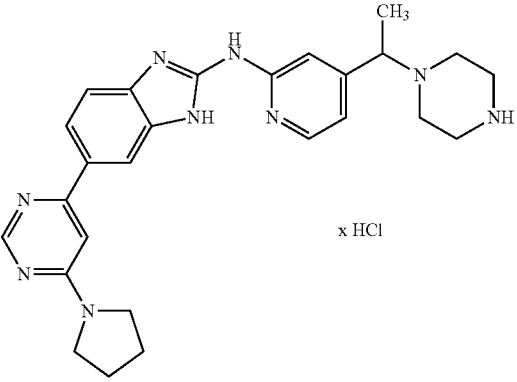 [SMILES: CC(c1ccnc(Nc2nc3ccc(-c4cc(N5CCCC5)ncn4)cc3[nH]2)c1)N1CCNCC1]

x HCl

N-{4-[(1R or 1S)-1-(piperazin-1-yl)ethyl]pyridin-2-yl}-6-[6-(pyrrolidin-1-yl)pyrimidin-4-yl]-1H-benzimidazol-2-amine hydrochloride
LC-MS (Method 2): $R_t$ = 1 min; MS (ESIpos): m/z = 469.6 [M + H]⁺
¹H-NMR (400 MHz, DMSO-d6) δ [ppm]: 0.987 (1.48), 1.003 (1.56), 1.179 (0.44), 1.229 (1.56), 1.258 (4.41), 1.274 (4.44), 1.665 (4.15), 1.985 (3.00), 2.002 (5.41), 2.017 (4.96), 2.033 (2.67), 2.043 (2.56), 2.057 (4.56), 2.074 (5.00), 2.090 (2.81), 2.518 (7.93), 2.523 (5.52), 3.235 (1.59), 3.440 (3.11), 3.456 (3.48), 3.469 (3.26), 3.485 (2.81), 3.497 (2.44), 3.597 (0.78), 3.650 (0.85), 3.661 (1.41), 3.666 (1.22), 3.676 (2.22), 3.687 (4.07), 3.704 (7.67), 3.719 (8.19), 3.735 (7.89), 3.752 (4.04), 4.636 (0.56), 5.760 (0.59), 7.134 (13.59), 7.334 (0.70), 7.568 (5.44), 7.636 (1.15), 7.694 (0.74), 7.733 (0.93), 7.824 (4.96), 7.845 (6.15), 7.963 (4.89), 7.967 (4.89), 7.985 (3.59), 7.988 (3.67), 8.222 (7.59), 8.415 (0.48), 8.546 (3.30), 8.558 (3.07), 8.810 (16.00), 9.754 (0.93).
Example 117.01

Compound 118.01

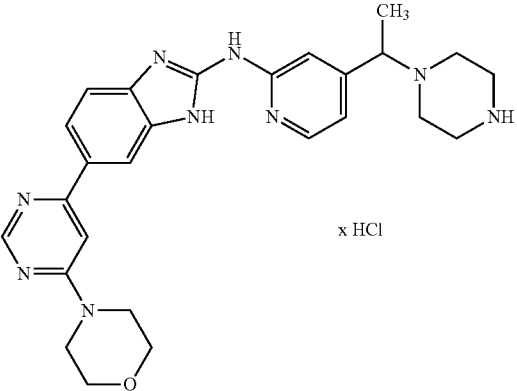 [SMILES: CC(c1ccnc(Nc2nc3ccc(-c4cc(N5CCOCC5)ncn4)cc3[nH]2)c1)N1CCNCC1]

x HCl

6-[6-(morpholin-4-yl)pyrimidin-4-yl]-N-{4-[(1R or 1S)-1-(piperazin--yl)ethyl]pyridin-2-yl}-1H-benzimidazol-2-amine hydrochloride
LC-MS (Method 2): $R_t$ = 0.92 min; MS (ESIpos): m/z = 485.6 [M + H]⁺
¹H-NMR (400 MHz, DMSO-d6) δ [ppm]: 0.829 (0.64), 0.850 (0.64), 0.856 (0.85), 0.987 (4.69), 1.004 (4.65), 1.064 (0.81), 1.179 (0.43), 1.230 (2.01), 1.655 (3.58), 2.518 (8.53), 2.523 (6.06), 3.046 (1.24), 3.058 (2.13), 3.069 (2.86), 3.081 (2.22), 3.093 (1.37), 3.221 (1.54), 3.418 (2.94), 3.441 (2.90), 3.457 (3.33), 3.469 (3.37), 3.485 (2.94), 3.498 (2.52), 3.509 (1.62), 3.627 (0.94), 3.650 (1.07), 3.661 (1.62), 3.666 (1.37), 3.676 (1.83), 3.698 (1.92), 3.708 (1.54), 3.712 (1.83), 3.744 (10.28), 3.755 (16.00), 3.764 (14.38), 3.789 (3.71), 3.946 (11.78), 4.182 (0.47), 4.203 (0.55), 4.628 (0.60), 7.483 (11.48), 7.552 (5.03), 7.575 (1.28), 7.749 (0.55), 7.798 (5.12), 7.819 (5.76), 7.990 (4.22), 8.009 (3.46), 8.258 (6.66), 8.536 (2.94), 8.817 (13.01), 9.257 (0.60), 9.709 (0.85), 12.904 (0.47).
Example 118.01

TABLE 2-continued

Structure
IUPAC-Name
LC-MS (method): Retention time; Mass found
¹H-NMR

| Compound | Starting material |
|---|---|

Compound 119.01

N-{4-[(1R or 1S)-1-(piperazin-1-yl)ethyl]pyridin-2-yl}-6-[6-(2,2,2-trifluoroethoxy)pyrimidin-4-yl]-1H-benzimidazol-2-amine hydrochloride
LC-MS (Method 2): $R_t$ = 1.15 min; MS (ESIpos): m/z = 498.5 [M + H]⁺
¹H-NMR (400 MHz, DMSO-d6) δ [ppm]: 0.986 (3.23), 1.002 (3.40), 1.061 (0.96), 1.223 (0.69), 1.704 (10.04), 1.720 (10.30), 2.081 (3.64), 2.518 (5.49), 2.523 (3.78), 3.160 (1.08), 3.301 (3.57), 3.383 (2.25), 3.391 (1.72), 3.443 (3.69), 3.455 (4.96), 3.467 (5.58), 3.483 (5.60), 3.495 (4.93), 3.507 (3.57), 3.594 (1.15), 3.601 (1.01), 3.611 (0.96), 3.625 (0.84), 3.643 (0.91), 3.648 (0.91), 3.655 (0.91), 3.659 (1.58), 3.663 (1.25), 3.671 (1.60), 3.673 (1.68), 3.695 (1.58), 3.698 (1.56), 3.706 (1.10), 3.710 (1.44), 3.714 (0.81), 3.721 (0.69), 3.725 (0.79), 3.737 (0.53), 3.830 (0.55), 3.838 (0.48), 3.854 (1.17), 3.879 (1.15), 3.903 (0.55), 3.911 (0.46), 3.931 (0.74), 3.949 (0.89), 3.969 (0.60), 3.994 (11.71), 4.169 (0.43), 4.181 (0.50), 4.728 (1.15), 5.137 (3.54), 5.159 (10.35), 5.182 (9.70), 5.204 (3.14), 5.759 (0.81), 6.193 (0.46), 6.199 (0.46), 6.209 (0.48), 6.215 (0.46), 6.351 (0.57), 6.889 (0.77), 7.493 (2.83), 7.496 (2.78), 7.597 (7.78), 7.700 (2.99), 7.710 (2.99), 7.731 (13.05), 7.733 (13.25), 7.745 (1.41), 7.750 (0.91), 7.768 (7.28), 7.788 (7.50), 7.836 (0.55), 7.840 (0.81), 7.845 (0.48), 7.912 (0.57), 8.063 (0.41), 8.115 (0.72), 8.170 (1.20), 8.174 (1.20), 8.192 (1.03), 8.196 (1.08), 8.222 (5.46), 8.226 (5.39), 8.243 (4.84), 8.248 (4.89), 8.332 (0.86), 8.379 (0.55), 8.498 (1.87), 8.501 (1.84), 8.548 (8.62), 8.552 (8.55), 8.579 (6.11), 8.593 (5.56), 8.890 (3.26), 8.893 (3.23), 8.954 (15.95), 8.957 (16.00), 9.059 (0.86), 9.074 (0.81), 9.274 (0.74), 9.877 (2.63).
Example 119.01

Compound 120.01

4-[1-(cyclopropylmethyl)-3,5-dimethyl-1H-pyrazol-4-yl]benzene-1,2-diamine

4-Bromobenzene-1,2-diamine (388 mg), 1-(cyclopropylmethyl)-3,5-dimethyl-4-(4,4,5,5-tetramethyl-1,3,2-dioxaborolan-2-yl)-1H-pyrazole (1.05 g, 60% purity) and tetrakis(triphenylphosphine)palladium(0) (120 mg) were added to $K_2CO_3$ (3.1 ml, 2.0 M) and 1-propanol (39 ml). The mixture was stirred under inert atmosphere for 2 h at 120° C. The mixture was then filtered (silicone filter) and concentrated under reduced pressure. The crude mixture was purified by flash chromatography on silica gel to give 110 mg of the title compound.

¹H-NMR (400 MHz, DMSO-d6): δ [ppm]=0.29-0.35 (m, 2H), 0.45-0.51 (m, 2H), 1.17 (br t, 1H), 2.06 (s, 3H), 2.16 (s, 3H), 3.83 (d, 2H), 4.41 (br d, 4H), 6.25 (dd, 1H), 6.41 (d, 1H), 6.52 (d, 1H).

Compound 120.02 tert-butyl 4-[(1R or 1S)-1-{2-[({2-amino-4-[1-(cyclopropylmethyl)-3,5-dimethyl-1H-pyrazol-4-yl]phenyl}carbamothioyl)amino]pyridin-4-yl}ethyl]piperazine-1-carboxylate

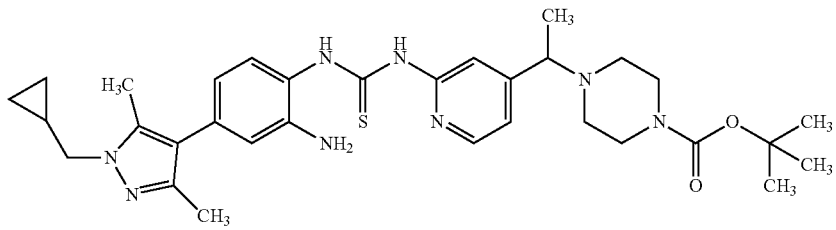 [SMILES: Cc1nn(CC2CC2)c(C)c1-c1ccc(NC(=S)Nc2cc(C(C)N3CCN(C(=O)OC(C)(C)C)CC3)ccn2)c(N)c1]

Imidazole (5.84 mg, 85.8 μmol) and TCDI (91.8 mg) were solubilised in dichloromethane (5.6 ml) under argon. The solution was cooled to 0° C. and tert-butyl 4-[(1R or 1S)-1-(2-aminopyridin-4-yl)ethyl]piperazine-1-carboxylate (131 mg) was added. The mixture was allowed to warm up to rt overnight. 4-[1-(cyclopropylmethyl)-3,5-dimethyl-1H-pyrazol-4-yl]benzene-1,2-diamine (110 mg) was added and the mixture was stirred for 4 h at rt. The reaction mixture was diluted with water and extracted three times with DCM. The combined organic phases were dried (silicone filter) and concentrated under reduced pressure. The crude material was used without further purification.

Compound 120.03

6-[1-(cyclopropylmethyl)-3,5-dimethyl-1H-pyrazol-4-yl]-N-{4-[(1R or 1S)-1-(piperazin-1-yl)ethyl]pyridin-2-yl}-1H-benzimidazol-2-amine hydrochloride

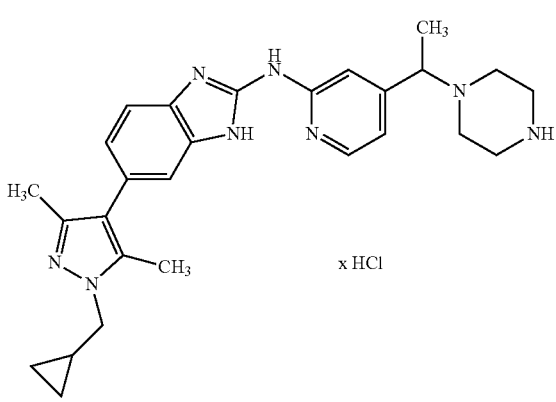 [SMILES: Cc1nn(CC2CC2)c(C)c1-c1ccc2nc(Nc3cc(C(C)N4CCNCC4)ccn3)[nH]c2c1]

tert-butyl 4-{(1R or 1S)-1-[2-({6-[1-(cyclopropylmethyl)-3,5-dimethyl-1H-pyrazol-4-yl]-1H-benzimidazol-2-yl}amino)pyridin-4-yl]ethyl}piperazine-1-carboxylate (55.0 mg; see Example 120.01) was dissolved in a mixture of dichloromethane (950 μl) and methanol (480 μl), HCl in dioxane (240 μl, 4.0 M) was added and the mixture stirred for overnight at rt. The mixture was concentrated under reduced pressure and the crude residue (56 mg) was used without further purification.

LC-MS (Method 2): $R_t$=1.05 min; MS (ESIpos): m/z=471 [M+H]$^+$.

Compound 121.01

4-[1-(cyclopropylmethyl)-1H-pyrazol-4-yl]-3-fluorobenzene-1,2-diamine

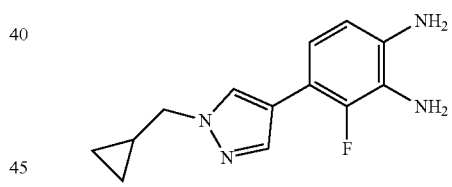

4-Bromo-3-fluorobenzene-1,2-diamine (500 mg), 1-(cyclopropylmethyl)-4-(4,4,5,5-tetramethyl-1,3,2-dioxaborolan-2-yl)-1H-pyrazole (666 mg), triphenyl phosphine (32.0 mg) and bis(triphenylphosphine)palladium(II) dichloride (85.6 mg) were added to aqueous $K_2CO_3$ (3.7 ml, 2.0 M) and 1-propanol (10 ml). The mixture was stirred under argon for 2 h at 120° C. The reaction mixture was diluted with DCM and water. The aqueous phase was extracted three times with DCM. The organic phase was washed sequentially with water and brine. The organic phase was then dried (silicone filter) and concentrated under reduced pressure. The crude mixture was purified by flash chromatography on silica gel to give 445 mg of the title compound.

LC-MS (Method 2): $R_t$=0.84 min; MS (ESIpos): m/z=247 [M+H]$^+$.

$^1$H-NMR (400 MHz, DMSO-d6): δ [ppm]=0.33-0.40 (m, 2H), 0.46-0.55 (m, 2H), 1.17-1.29 (m, 1H), 3.96 (d, 2H), 4.42 (s, 2H), 4.76 (s, 2H), 6.35 (dd, 1H), 6.65 (t, 1H), 7.65 (s, 1H), 7.91 (d, 1H).

Compound 121.02 tert-butyl 4-[(1R or 1S)-1-{2-[({2-amino-4-[1-(cyclopropylmethyl)-1H-pyrazol-4-yl]-3-fluorophenyl}carbamothioyl)amino]pyridin-4-yl}ethyl]piperazine-1-carboxylate

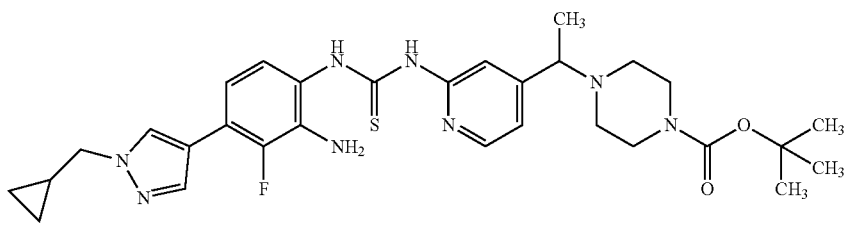 [SMILES: CC(c1ccnc(NC(=S)Nc2ccc(-c3cnn(CC4CC4)c3)c(F)c2N)c1)N1CCN(C(=O)OC(C)(C)C)CC1]

Imidazole (24.6 mg) and TCDI (386 mg) were solubilised in dichloromethane (15 ml) under argon. The solution was cooled to 0° C. and tert-butyl 4-[(1R or 1S)-1-(2-aminopyridin-4-yl)ethyl]piperazine-1-carboxylate (554 mg; see Compound 36.05) was added. The mixture was allowed to warm up to rt overnight. 4-[1-(cyclopropylmethyl)-1H-pyrazol-4-yl]-3-fluorobenzene-1,2-diamine (445 mg) was added and the mixture was stirred for 4 h at rt. The mixture was diluted with water and extracted three times with DCM. The combined organic phases were dried (silicone filter) and concentrated under reduced pressure. The crude title compound (1.3 g) was used without further purification.

LC-MS (Method 2): $R_t$=1.39 min; MS (ESIpos): m/z=595 [M+H]$^+$.

Compound 121.03

6-[1-(cyclopropylmethyl)-1H-pyrazol-4-yl]-7-fluoro-N-{4-[(1R or 1S)-1-(piperazin-1-yl)ethyl]pyridin-2-yl}-1H-benzimidazol-2-amine hydrochloride

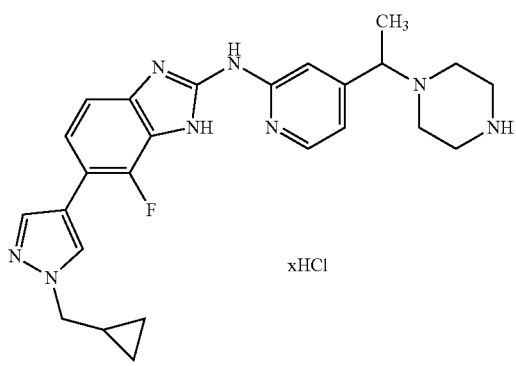 [SMILES: CC(c1ccnc(Nc2nc3ccc(-c4cnn(CC5CC5)c4)c(F)c3[nH]2)c1)N1CCNCC1]

tert-Butyl 4-{(1R or 1S)-1-[2-({6-[1-(cyclopropylmethyl)-1H-pyrazol-4-yl]-7-fluoro-1H-benzimidazol-2-yl}amino)pyridin-4-yl]ethyl}piperazine-1-carboxylate (708 mg; see Example 121.02) was solubilised in dichloromethane (7.2 ml) and HCl in dioxane (1.8 ml, 4.0 M) was added. The mixture was stirred overnight at rt. The mixture was concentrated under reduced pressure and the crude residue (730 mg) was used without further purification.

LC-MS (method 2): $R_t$=1.05 min; MS (ESIpos): m/z=461 [M+H]$^+$.

$^1$H-NMR (400 MHz, DMSO-d6) δ[ppm]: 0.388 (0.72), 0.399 (2.74), 0.403 (2.39), 0.411 (2.69), 0.414 (2.57), 0.424 (0.94), 0.526 (0.98), 0.536 (2.32), 0.541 (2.17), 0.546 (1.29), 0.556 (2.44), 0.560 (2.00), 0.572 (0.69), 1.269 (0.64), 1.277 (0.61), 1.289 (1.00), 1.296 (0.46), 1.301 (0.56), 1.308 (0.57), 1.686 (2.56), 1.701 (2.34), 2.518 (1.28), 2.522 (0.81), 3.160 (16.00), 3.331 (0.55), 3.467 (1.48), 4.031 (4.29), 4.049 (4.19), 4.655 (0.48), 7.476 (1.62), 7.498 (2.05), 7.565 (2.05), 7.592 (1.38), 7.608 (1.61), 7.612 (1.43), 7.629 (1.59), 7.922 (3.44), 8.238 (2.69), 8.241 (2.54), 8.524 (1.15), 8.536 (1.07), 9.831 (0.68).

Compound 122.01

3-chloro-4-[1-(cyclopropylmethyl)-1H-pyrazol-4-yl]benzene-1,2-diamine

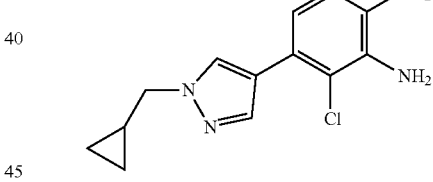

4-Bromo-3-chlorobenzene-1,2-diamine (500 mg), 1-(cyclopropylmethyl)-4-(4,4,5,5-tetramethyl-1,3,2-dioxaborolan-2-yl)-1H-pyrazole (616 mg), triphenylphosphine (29.6 mg) and bis(triphenylphosphine)palladium(II) dichloride (79.2 mg) were added to aqueous K$_2$CO$_3$ (3.4 ml, 2.0 M) and 1-propanol (10 ml). The mixture was stirred under argon for 2 h at 1209'. The reaction mixture was then diluted with DCM and water and the aqueous phase was extracted three times with DCM. The organic phase was sequentially washed with water and brine, dried (silicone filter) and concentrated under reduced pressure. The crude mixture was purified by flash chromatography on silica gel to give 441 mg of the title compound.

LC-MS (Method 2): $R_t$=0.90 min; MS (ESIpos): m/z=263 [M+H]$^+$.

$^1$H-NMR (400 MHz, DMSO-d6): δ [ppm]=0.35-0.39 (m, 2H), 0.50-0.55 (m, 1H), 1.20-1.29 (m, 1H), 3.96 (d, 2H), 4.71 (s, 2H), 4.81 (s, 2H), 6.48-6.52 (m, 1H), 6.58 (d, 1H), 7.59 (d, 1H), 7.92 (d, 1H).

Compound 122.02 tert-butyl 4-[(1R or 1S)-1-{2-[({2-amino-3-chloro-4-[1-(cyclopropylmethyl)-1H-pyrazol-4-yl]phenyl}carbamothioyl)amino]pyridin-4-yl}ethyl]piperazine-1-carboxylate

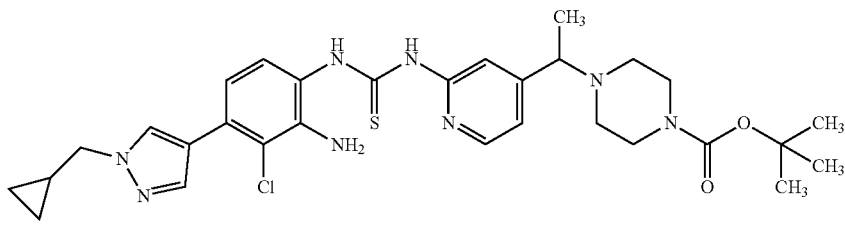 [SMILES: CC(c1ccnc(NC(=S)Nc2ccc(-c3cnn(CC4CC4)c3)c(Cl)c2N)c1)N1CCN(C(=O)OC(C)(C)C)CC1]

Imidazole (22.9 mg) and TCDI (359 mg) were solubilised in dichloromethane (15 ml) under argon. The solution was cooled to 0° C. and tert-butyl 4-[(1R or 1S)-1-(2-aminopyridin-4-yl)ethyl]piperazine-1-carboxylate (514 mg) was added. The mixture was allowed to warm up to rt overnight. 3-chloro-4-[1-(cyclopropylmethyl)-1H-pyrazol-4-yl]benzene-1,2-diamine (441 mg) was added and the mixture was stirred for 4 h at rt. The mixture was diluted with water and extracted three times with DCM. The combined organic phases were dried (silicone filter) and concentrated under reduced pressure. The crude mixture (1 g) was used without further purification.

Compound 122.03

7-chloro-6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride

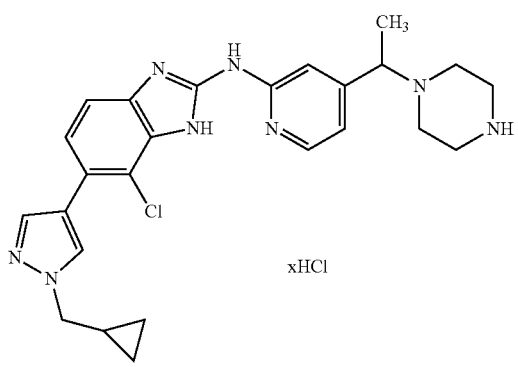 [SMILES: CC(c1ccnc(Nc2nc3ccc(-c4cnn(CC5CC5)c4)c(Cl)c3[nH]2)c1)N1CCNCC1]

tert-butyl 4-{(1R or 1S)-1-[2-({7-chloro-6-[1-(cyclopropylmethyl)-1H-pyrazol-4-yl]-1H-benzimidazol-2-yl}amino)pyridin-4-yl]ethyl}piperazine-1-carboxylate (534 mg; see Example 122.01) was solubilised in dichloromethane (5.3 ml) and HCl in dioxane (1.3 ml, 4.0 M) was added. The mixture was stirred overnight at rt and then concentrated under reduced pressure.

The crude mixture was used without further purification.

LC-MS (method 2): $R_t$=1.08 min; MS (ESIpos): m/z=477 [M+H]$^+$.

Compound 123.01

4-(1-methyl-1H-pyrazol-5-yl)benzene-1,2-diamine

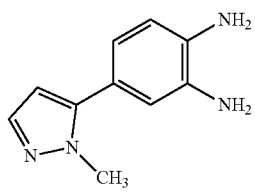

4-Bromobenzene-1,2-diamine (300 mg), 1-methyl-5-(4,4,5,5-tetramethyl-1,3,2-dioxaborolan-2-yl)-1H-pyrazole (667 mg) and the bis(triphenylphosphine)palladium(II) dichloride (113 mg) were solubilised in 1,2-dimethoxyethane (10 ml) and aqueous K$_2$CO$_3$ (1.8 ml, 2.0 M) was added. The reaction was stirred for 10 min under microwave radiation at 130° C. The reaction mixture was filtered (silicone filter) and concentrated under reduced pressure. The crude mixture was purified by flash chromatography on silica gel to give 125 mg (99% purity) of the title compound.

LC-MS (Method 2): $R_t$=0.60 min; MS (ESIpos): m/z=189 [M+H]$^+$.

$^1$H-NMR (500 MHz, DMSO-d6): δ [ppm]=3.77 (s, 3H), 4.60 (s, 2H), 4.72 (s, 2H), 6.13 (d, 1H), 6.50-6.53 (m, 1H), 6.57 (d, 1H), 6.63 (d, 1H), 7.35 (d, 1H).

Compound 123.02 tert-butyl 4-{(1R or 1S)-1-[2-({[2-amino-4-(1-methyl-1H-pyrazol-5-yl)phenyl]carbamothioyl}amino)pyridin-4-yl]ethyl}piperazine-1-carboxylate

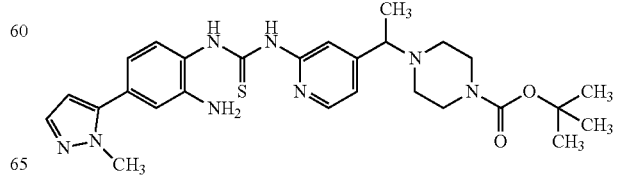

Imidazole (9.04 mg) and TCDI (142 mg) were solubilised in dichloromethane (2.0 ml) under argon. The solution was cooled to 0° C. and tert-butyl 4-[(1R or 1S)-1-(2-aminopyridin-4-yl)ethyl]piperazine-1-carboxylate (203 mg; see Compound 36.05) was added. The mixture was allowed to warm up to rt overnight. 4-(1-methyl-1H-pyrazol-5-yl)benzene-1,2-diamine (125 mg) was added and the mixture was stirred for 4 h at rt. The mixture was diluted with water and extracted three with DCM. The combined organic phases were dried (silicone filter) and concentrated under reduced pressure. The crude title compound was used without further purification.

LC-MS (Method 2): $R_t$=1.24 min; MS (ESIpos): m/z=537 [M+H]$^+$.

Compound 123.03

6-(1-methyl-1H-pyrazol-5-yl)-N-{4-[(1R or 1S)-1-(piperazin-1-yl)ethyl]pyridin-2-yl}-1H-benzimidazol-2-amine hydrochloride

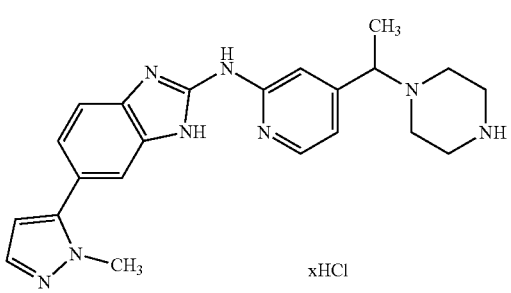 [SMILES: CC(c1ccnc(Nc2nc3ccc(-c4ccnn4C)cc3[nH]2)c1)N1CCNCC1]

tert-butyl 4-[(1R or 1S)-1-(2-{[6-(1-methyl-1H-pyrazol-5-yl)-1H-benzimidazol-2-yl]amino}pyridin-4-yl)ethyl]piperazine-1-carboxylate (191 mg; see Example 123.01) was solubilised in dichloromethane (2.2 ml) and HCl in dioxane (550 µl, 4.0 M) was added. The mixture was stirred overnight at rt. The mixture was concentrated under reduced pressure and used without further purification.

LC-MS (method 2): $R_t$=0.90 min; MS (ESIpos): m/z=403 [M+H]$^+$.

Compound 124.01

(rac)-4-{1-[tetrahydro-2H-pyran-2-yl]-1H-pyrazol-5-yl}benzene-1,2-diamine

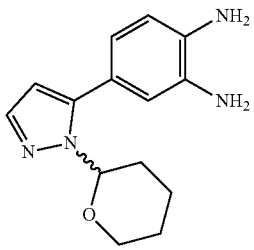 [SMILES: Nc1ccc(-c2ccnn2C2CCCCO2)cc1N]

4-Bromobenzene-1,2-diamine (300 mg), (rac)-1-[tetrahydro-2H-pyran-2-yl]-5-(4,4,5,5-tetramethyl-1,3,2-dioxaborolan-2-yl)-1H-pyrazole (892 mg) and the bis(triphenylphosphine)palladium(II) dichloride (113 mg) were solubilised in 1,2-dimethoxyethane (3.0 ml) and aqueous K$_2$CO$_3$ (1.8 ml, 2.0 M) was added. The reaction was stirred for 10 min under microwave radiation at 130° C. The reaction mixture was filtered (silicone filter) and concentrated under reduced pressure. The crude mixture was purified by flash chromatography on silica gel to give 139 mg (90% purity) of the title compound.

$^1$H-NMR (400 MHz, DMSO-d6): δ [ppm]=1.46-1.62 (m, 3H), 1.66-1.75 (m, 1H), 1.89-1.97 (m, 1H), 2.30-2.42 (m, 1H), 3.47-3.57 (m, 1H), 3.93-4.06 (m, 1H), 4.62 (s, 2H), 4.75 (s, 2H), 5.18 (dd, 1H), 6.16 (d, 1H), 6.50-6.60 (m, 2H), 6.64 (d, 1H), 7.44 (d, 1H).

Compound 124.02

(rac)-tert-butyl 4-[(2-{[(2-amino-5-{1-[tetrahydro-2H-pyran-2-yl]-1H-pyrazol-5-yl}phenyl)carbamothioyl]amino}pyridin-4-yl)methyl]piperazine-1-carboxylate

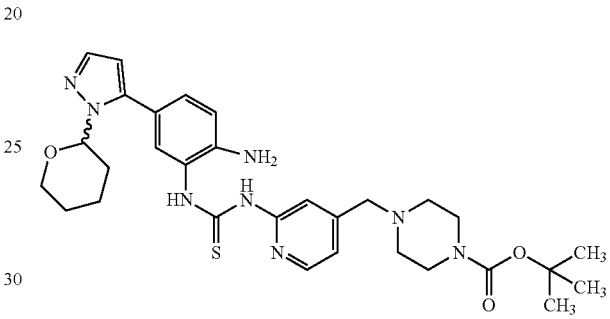

Imidazole (6.85 mg) was added to TCDI (108 mg) and solubilized in dichloromethane (4.0 ml) at 0° C. under argon. tert-Butyl 4-[(2-aminopyridin-4-yl)methyl]piperazine-1-carboxylate (147 mg; see Compound 01.02) (solubilized in 4 ml DCM) was added and the reaction was stirred at rt overnight. (rac)-4-{1-[tetrahydro-2H-pyran-2-yl]-1H-pyrazol-5-yl}benzene-1,2-diamine (130 mg, 503 µmol) (in 2 ml DCM) was then added to the mixture and the reaction was stirred for 4 h at rt. The reaction mixture was diluted with water and extracted three times with DCM. The organic layer was filtered (silicone filter) and concentrated under reduced pressure. The crude material was used without further purification.

LC-MS (Method 2): $R_t$=1.30 min; MS (ESIneg): m/z=591 [M−H]$^-$

Compound 124.03

(rac)-tert-butyl 4-({2-[(6-{1-[tetrahydro-2H-pyran-2-yl]-1H-pyrazol-5-yl}-1H-benzimidazol-2-yl)amino]pyridin-4-yl}methyl)piperazine-1-carboxylate

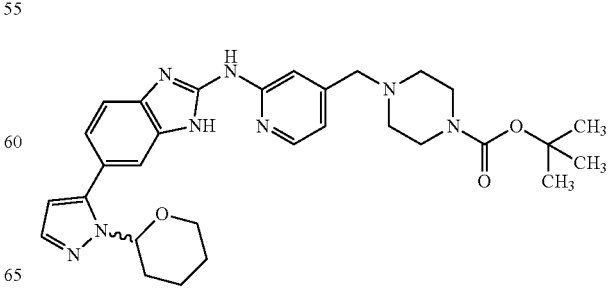

N,N'-dipropan-2-ylcarbodiimide (1.0 ml) was added to (rac)-tert-butyl 4-[(2-{[(2-amino-5-{1-[tetrahydro-2H-pyran-2-yl]-1H-pyrazol-5-yl}phenyl)carbamothioyl]amino}pyridin-4-yl)methyl]piperazine-1-carboxylate (100 mg) in dichloromethane (4 ml) under argon and the reaction was stirred overnight at rt. The mixture was diluted with sat. NaHCO₃ and extracted three times with DCM. The organic phase was dried (MgSO₄), filtered and concentrated under reduced pressure. The crude mixture was purified by flash chromatography on silica gel to give 34.7 mg (84% purity) of the title compound.

LC-MS (Method 2): $R_t$=1.30 min; MS (ESIneg): m/z=557 [M−H]⁻

¹H-NMR (400 MHz, DMSO-d6) δ[ppm]: 0.989 (0.59), 1.005 (0.60), 1.389 (11.36), 1.395 (16.00), 1.412 (0.85), 2.322 (1.17), 2.326 (1.29), 2.331 (1.28), 2.336 (1.14), 2.347 (1.47), 2.359 (1.41), 2.372 (0.99), 2.518 (2.33), 2.522 (1.54), 2.668 (0.71), 3.501 (2.08), 7.541 (0.79), 8.263 (0.83), 8.276 (0.79).

Compound 124.04

N-[4-(piperazin-1-ylmethyl)pyridin-2-yl]-6-(1H-pyrazol-5-yl)-1H-benzimidazol-2-amine hydrochloride

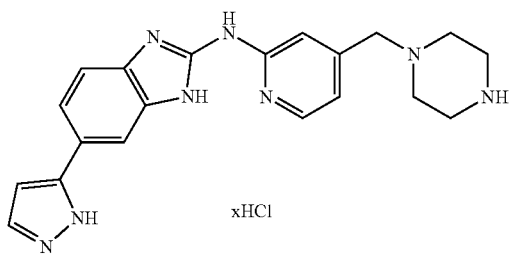 [SMILES: c1cc(-c2ccc3nc(Nc4cc(CN5CCNCC5)ccn4)[nH]c3c2)[nH]n1]

(rac)-tert-Butyl 4-({2-[(6-{1-[tetrahydro-2H-pyran-2-yl]-1H-pyrazol-5-yl}-1H-benzimidazol-2-yl)amino]pyridin-4-yl}methyl)piperazine-1-carboxylate (33.0 mg; see Compound 124.03) was solubilised in a mixture of dichloromethane (950 µl)/methanol (950 µl) and HCl in dioxane (1.4 ml, 4.0 M) was added. The mixture was stirred for 3 h at rt and concentrated under reduced pressure. The crude material was used without further purification.

LC-MS (Method 2): $R_t$=0.81 min; MS (ESIneg): m/z=373 [M−H]⁻

Compound 125.01

(2-amino-5-bromopyridin-4-yl)methanol

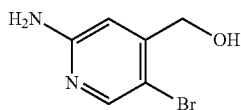

Methyl 2-amino-5-bromopyridine-4-carboxylate (500 mg) was solubilised in THF (10 ml, 120 mmol) and the mixture was cooled to 0° C. DIBAL in hexane (9.7 ml, 1.0 M) was added dropwise. The mixture stirred overnight at rt. The reaction mixture was diluted carefully with 2-propanol and water. The mixture stirred 24 h at rt, the precipitate was filtered, stirred twice in EtOAc and filtered each time. The filtrate was concentrated under reduced pressure and dried under reduced pressure. The crude product was used without further purification.

LC-MS (Method 2): $R_t$=0.57 min; MS (ESIpos): m/z=203 [M+H]⁺.

Compound 125.02

5-bromo-4-(bromomethyl)pyridin-2-amine hydrobromide (1:1)

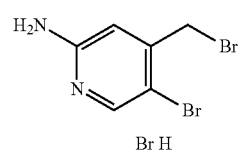

(2-Amino-5-bromopyridin-4-yl)methanol (436 mg) was stirred in aqueous HBr (5.0 ml, 48% purity) 72 h at 120° C. The reaction mixture was then concentrated under reduced pressure and used without further purification.

Compound 125.03 tert-butyl 4-[(2-amino-5-bromopyridin-4-yl)methyl]piperazine-1-carboxylate

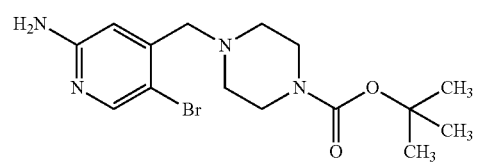 [SMILES: CC(C)(C)OC(=O)N1CCN(Cc2cc(N)ncc2Br)CC1]

5-Bromo-4-(bromomethyl)pyridin-2-amine hydrobromide (1:1) (630 mg, 80% purity), tert-butyl piperazine-1-carboxylate (460 mg) and K₂CO₃ (1.00 g) were solubilised in DMF (10 ml). The mixture was stirred overnight at 50° C. The reaction mixture was diluted with EtOAc and washed with half conc. NaCl solution. The organic layer was dried (MgSO₄) filtered and concentrated under reduced pressure. The crude mixture was purified by flash chromatography on silica gel to give 80.0 mg of the title compound.

LC-MS (Method 2): $R_t$=1.18 min; MS (ESIpos): m/z=371 [M+H]⁺.

¹H-NMR (400 MHz, DMSO-d6): δ [ppm]=1.40 (s, 9H), 2.38 (t, 4H), 3.31-3.36 (m, 4H), 3.38 (s, 2H), 6.10 (s, 2H), 6.62 (s, 1H), 7.93 (s, 1H).

Compound 125.04 tert-butyl 4-{[2-({[2-amino-4-(3-methyl-1,2,4-oxadiazol-5-yl)phenyl]carbamothioyl}amino)-5-bromopyridin-4-yl]methyl}piperazine-1-carboxylate

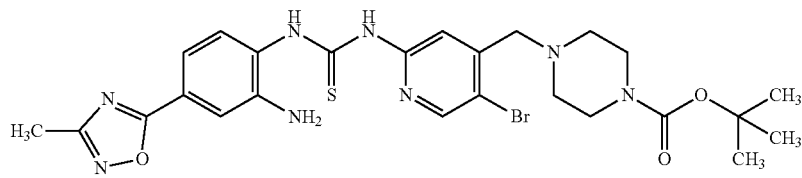 [SMILES: Cc1noc(-c2ccc(NC(=S)Nc3cc(CN4CCN(C(=O)OC(C)(C)C)CC4)c(Br)cn3)c(N)c2)n1]

Imidazole (5.13 mg) and TCDI (80.6 mg) were solubilised in dry dichloromethane (2.5 ml) under argon. The solution was cooled to 0° C. and tert-butyl 4-[(2-amino-5-bromopyridin-4-yl)methyl]piperazine-1-carboxylate (140 mg), solubilised in dry dichloromethane (2.5 ml), was added. The mixture was stirred at rt overnight. 4-(3-methyl-1,2,4-oxadiazol-5-yl)benzene-1,2-diamine (71.7 mg; see Compound 16.20) was then added to the mixture and it was stirred overnight at rt. The reaction mixture was diluted with water and extracted three times with DCM. The organic phase was dried (silicone filter) and concentrated under reduced pressure.

The crude was used without further purification

LC-MS (Method 2): $R_t$=1.18 min; MS (ESIpos): m/z=603 [M+H]$^+$

Compound 125.05

N-[5-bromo-4-(piperazin-1-ylmethyl)pyridin-2-yl]-6-(3-methyl-1,2,4-oxadiazol-5-yl)-1H-benzimidazol-2-amine hydrochloride

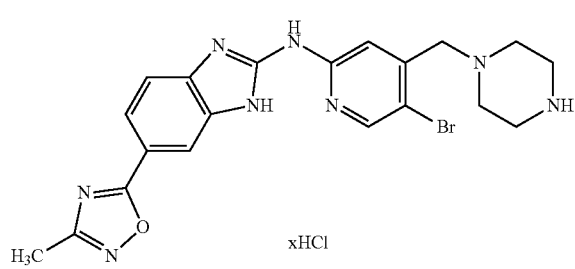 [SMILES: Cc1noc(-c2ccc3nc(Nc4cc(CN5CCNCC5)c(Br)cn4)[nH]c3c2)n1]

Tert-Butyl 4-[(5-bromo-2-{[6-(3-methyl-1,2,4-oxadiazol-5-yl)-1H-benzimidazol-2-yl]amino}pyridin-4-yl)methyl]piperazine-1-carboxylate (90.0 mg; see Example 125.01) was solubilised in dichloromethane (1.6 ml) and HCl in dioxane (160 μl, 4.0 M) was added. The mixture was stirred at rt overnight. The reaction was concentrated under reduced pressure and the crude residue (90 mg) was used without further purification.

LC-MS (Method 2): $R_t$=1.05 min; MS (ESIpos): m/z=469 [M+H]$^+$.

Compound 126.01 tert-butyl 4-[(2-{[6-(hydrazinylcarbonyl)-1H-benzimidazol-2-yl]amino}pyridin-4-yl)methyl]piperazine-1-carboxylate

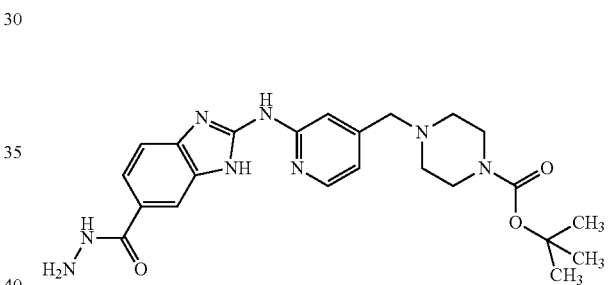

2-[(4-{[4-(tert-Butoxycarbonyl)piperazin-1-yl]methyl}pyridin-2-yl)amino]-1H-benzimidazole-6-carboxylic acid (500 mg, 50% purity; see compound 16.05), hydrazine in THF (2.2 ml, 1.0 M), K$_2$CO$_3$ (382 mg) and HATU (630 mg) were dissolved in DMF. The mixture stirred overnight at rt. Hydrazine in THF (2.2 ml, 1.0 M) and HATU (630 mg) were added again and the mixture stirred overnight at rt. The reaction mixture was diluted with water and stirred 24 h at rt. The precipitate was filtered, washed with water and dried overnight at 60° C. The product was used without further purification.

LC-MS (Method 2): $R_t$=0.97 min; MS (ESIpos): m/z=467 [M+H]$^+$.

$^1$H-NMR (400 MHz, DMSO-d6): δ [ppm]=1.39 (s, 9H), 2.36 (br d, 4H), 3.35 (br s, 4H), 3.50 (s, 2H), 4.42 (br s, 2H), 6.93 (br d, 1H), 7.17 (br s, 1H), 7.28-7.51 (m, 1H), 7.52-7.59 (m, 1H), 7.82-8.02 (m, 1H), 8.26 (d, 1H), 9.52-9.63 (m, 1H), 10.67-10.79 (m, 1H), 12.19-12.35 (m, 1H).

Compound 126.02 tert-butyl 4-({2-[(6-{[2-(cyclobutylacetyl)hydrazinyl]carbonyl}-1H-benzimidazol-2-yl)amino]pyridin-4-yl}methyl)piperazine-1-carboxylate

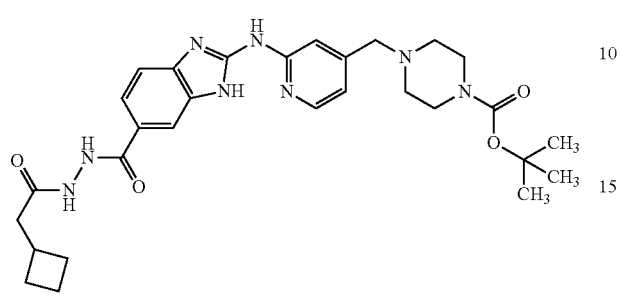

tert-Butyl 4-[(2-{[6-(hydrazinylcarbonyl)-1H-benzimidazol-2-yl]amino}pyridin-4-yl)methyl]piperazine-1-carboxylate (75.0 mg), cyclobutylacetic acid (55.0 mg), K$_2$CO$_3$ (133 mg) and HATU (183 mg) were dissolved in DMF (3.8 ml). The mixture stirred overnight at rt. Water was added and the mixture stirred for 1 h at rt and then filtered. The crude mixture was purified without work up by preparative HPLC to give 7 mg of the title compound.

LC-MS (Method 2): R$_t$=1.07 min; MS (ESIpos): m/z=563 [M+H]$^+$.

$^1$H-NMR (400 MHz, DMSO-d6): δ [ppm]=1.40 (s, 9H), 1.69-1.87 (m, 4H), 2.01-2.11 (m, 2H), 2.30 (d, 2H), 2.36 (br t, 4H), 2.59-2.66 (m, 1H), 3.35 (br s, 4H), 3.50 (s, 2H), 6.94 (br s, 1H), 7.17 (br d, 1H), 7.31-7.55 (m, 1H), 7.61 (br dd, 1H), 7.89-8.03 (m, 1H), 8.27 (d, 1H), 9.72 (s, 1H), 10.08 (br d, 1H), 10.74 (br s, 1H), 12.29 (br s, 1H).

Compound 126.03

6-[5-(cyclobutylmethyl)-1,3,4-oxadiazol-2-yl]-N-[4-(piperazin-1-ylmethyl)pyridin-2-yl]-1H-benzimidazol-2-amine

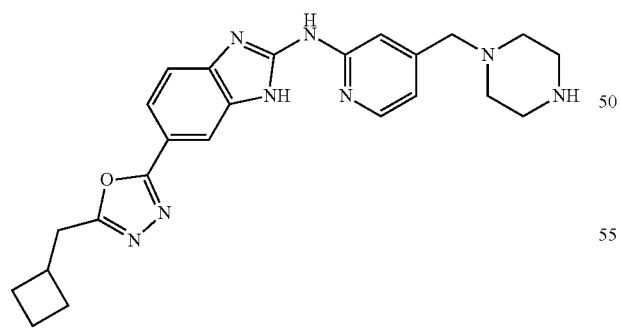

tert-Butyl 4-({2-[(6-{[2-(cyclobutylacetyl)hydrazinyl]carbonyl}-1H-benzimidazol-2-yl)amino]pyridin-4-yl}methyl)piperazine-1-carboxylate (7.00 mg, 80% purity) was dissolved in SOCl$_2$ (110 µl) and the mixture stirred overnight at 50° C. The reaction mixture was concentrated under reduced pressure and the crude title compound (6 mg) was used without further purification.

Compound 127.01

6-chloro-N-(cyclopropylmethyl)-N-methylpyrimidin-4-amine

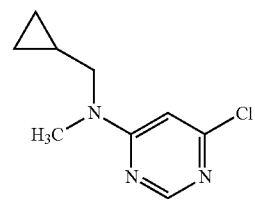

4,6-Dichloropyrimidine (300 mg), 1-cyclopropyl-N-methylmethanamine hydrochloride (1:1) (257 mg) and K$_2$CO$_3$ (306 mg) were stirred in dioxane 1,4-dioxane (4.0 ml) overnight at 110° C. The mixture diluted in water and EtOAc. The aqueous phase was extracted two times with EtOAc. The organic phase was then dried (silicone filter) and concentrated under reduced pressure. The crude mixture was purified by flash chromatography on silica gel to give 158 mg (95% purity) of the title compound.

LC-MS (method 2): R$_t$=1.08 min; MS (ESIpos): m/z=199 [M+H]$^+$. $^1$H NMR (400 MHz, DMSO-d6) b ppm 0.23-0.33 (m, 2H) 0.39-0.49 (m, 2H) 0.98-1.08 (m, 1H) 3.07 (br s, 3H) 3.35-3.59 (m, 2H) 6.76 (br s, 1H) 8.30 (s, 1H)

$^1$H-NMR (400 MHz, DMSO-d6) δ [ppm]: 0.259 (2.95), 0.270 (11.68), 0.273 (10.68), 0.282 (12.22), 0.285 (11.46), 0.295 (4.07), 0.320 (0.41), 0.427 (2.85), 0.438 (7.41), 0.441 (7.66), 0.447 (4.61), 0.457 (8.07), 0.472 (2.34), 0.978 (0.51), 0.991 (1.05), 0.995 (1.34), 1.002 (0.83), 1.007 (2.68), 1.010 (2.49), 1.015 (2.49), 1.019 (1.88), 1.027 (4.44), 1.035 (1.85), 1.040 (2.34), 1.045 (2.44), 1.047 (2.34), 1.052 (0.78), 1.057 (1.15), 1.059 (1.15), 1.064 (0.95), 1.077 (0.41), 2.518 (5.37), 2.523 (3.80), 3.069 (10.66), 3.469 (2.27), 6.761 (1.29), 8.300 (16.00).

Compound 128.01

6-bromo-N-(cyclopropylmethyl)pyrimidin-4-amine

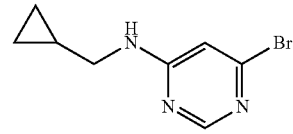 [SMILES: Brc1cc(NCC2CC2)ncn1]

4,6-dibromopyrimidine (300 mg) and 1-cyclopropylmethanamine (130 µl) were stirred in dioxane 1,4-dioxane (6.0 ml) for 2 h at 110° C. The mixture was then concentrated under reduced pressure. The crude was solubilised in DCM and water was added. The aqueous phase was extracted two times with EtOAc. The organic phase was dried (silicone filter) and concentrated under reduced pressure. The crude was used without further purification.

LC-MS (Method 2): R$_t$=0.99 min; MS (ESIpos): m/z=228 [M+H]$^+$.

Compound 129.01

6-bromo-N,N-dimethylpyrimidin-4-amine

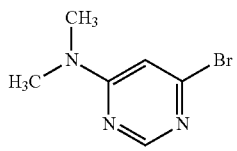

4,6-Dibromopyrimidine (300 mg) and N-methylmethanamine in THF (760 µl, 2.0 M) were stirred in dioxane 1,4-dioxane (6.0 ml) overnight at 110° C. The mixture was then concentrated under reduced pressure and the crude mixture was purified by flash chromatography on silica gel to give 116 mg of the title compound.

$^1$H-NMR (400 MHz, DMSO-d6): δ [ppm]=3.00-3.14 (m, 6H), 6.86-6.93 (m, 1H), 8.21-8.28 (m, 1H).

The following compounds shown in table 3, below, were prepared according to the general procedure:

The corresponding Boc protected amine (see Examples 130.01. to 162.01., tables 14 and 15, or as specified below for the respective Compound) (1 eq.) was solubilized in a mixture of DCM and MeOH (generally 2:1) and 4N HCl in dioxane (5 eq.) was added slowly. The reaction was stirred between 2 and 48 hours at rt and then concentrated. The crude mixture was used without further purification.

TABLE 3

| Compound | Structure<br>IUPAC-Name<br>LC-MS (method): Retention time; Mass found<br>$^1$H-NMR |
|---|---|
| Compound 130.01 | 6-(3-chloro-2-methylpyridin-4-yl)-N-[4-(piperazin-1-ylmethyl)pyridin-2-yl]-1H-benzimidazol-2-amine hydrochloride<br>LC-MS (Method 2): R$_t$ = 1.02 min; MS (ESIpos): m/z = 434 [M + H]$^+$ |
| Compound 131.01 | 6-(5-fluoro-2-methylpyridin-4-yl)-N-[4-(piperazin-1-ylmethyl)pyridin-2-yl]-1H-benzimidazol-2-amine hydrochloride<br>LC-MS (Method 2): R$_t$ = 0.97 min; MS (ESIpos): m/z = 418 [M + H]$^+$ |
| Compound 132.01 | 6-(3-chloro-5-fluoropyridin-4-yl)-N-[4-(piperazin-1-ylmethyl)pyridin-2-yl]-1H-benzimidazol-2-amine hydrochloride<br>LC-MS (Method 2): R$_t$ = 1.02 min; MS (ESIpos): m/z = 438 [M + H]$^+$ |

TABLE 3-continued

Structure
IUPAC-Name
LC-MS (method): Retention time; Mass found

| Compound | $^1$H-NMR |
|---|---|

Compound 133.01

4-(2-{[4-(piperazin-1-ylmethyl)pyridin-2-yl]amino}-1H-benzimidazol-6-yl)pyridine-3-carbonitrile hydrochloride
LC-MS (Method 2): R$_t$ = 0.88 min; MS (ESIpos): m/z = 411 [M + H]$^+$ Compound 134.01

6-[2-(morpholin-4-yl)pyridin-4-yl]-N-[4-(piperazin-1-ylmethyl)pyridin-2-yl]-1H-benzimidazol-2-amine hydrochloride
LC-MS (Method 2): R$_t$ = 0.98 min; MS (ESIpos): m/z = 471 [M + H]$^+$ Compound 135.01

6-[2-(dimethylamino)pyridin-4-yl]-N-[4-(piperazin-1-ylmethyl)pyridin-2-yl]-1H-benzimidazol-2-amine hydrochloride
LC-MS (Method 2): R$_t$ = 1.01 min; MS (ESIneg): m/z = 427 [M − H]$^-$ TABLE 3-continued

| | Structure<br>IUPAC-Name<br>LC-MS (method): Retention time; Mass found |
|---|---|
| Compound | $^1$H-NMR |

Compound 136.01

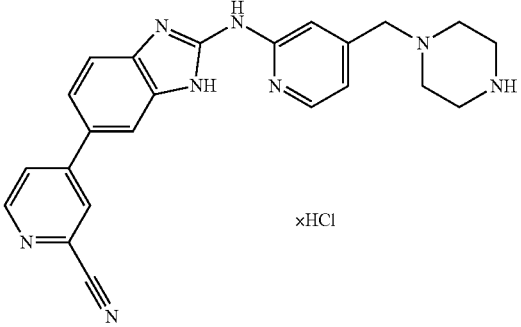 [SMILES: N#Cc1cc(-c2ccc3nc(Nc4cc(CN5CCNCC5)ccn4)[nH]c3c2)ccn1]

xHCl 6-methyl-4-(2-{[4-(piperazin-1-ylmethyl)pyridin-2-yl]amino}-1H-benzimidazol-6-yl)pyridine-2-carbonitrile hydrochloride
LC-MS (Method 2): $R_t$ = 1 min; MS (ESIpos): m/z = 425 [M + H]$^+$ Compound 137.01


xHCl 6-(2-fluoropyridin-4-yl)-N-[4-(piperazin-1-ylmethyl)pyridin-2-yl]-1H-benzimidazol-2-amine hydrochloride
LC-MS (Method 2): $R_t$ = 0.97 min; MS (ESIpos): m/z = 404 [M + H]$^+$ Compound 138.01

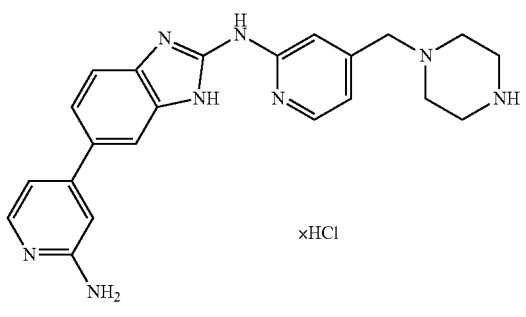 [SMILES: Nc1cc(-c2ccc3nc(Nc4cc(CN5CCNCC5)ccn4)[nH]c3c2)ccn1]

xHCl 6-(2-aminopyridin-4-yl)-N-[4-(piperazin-1-ylmethyl)pyridin-2-yl]-1H-benzimidazol-2-amine hydrochloride
LC-MS (Method 2): $R_t$ = 0.81 min; MS (ESIneg): m/z = 399 [M − H]$^−$ Compound 139.01

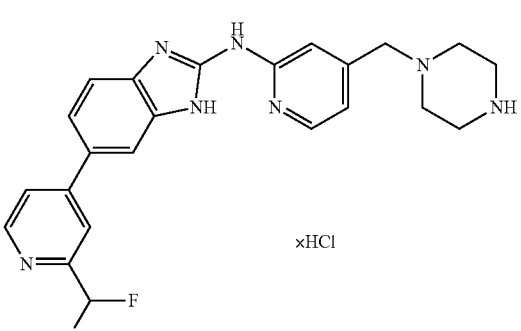

xHCl

TABLE 3-continued

| Compound | Structure<br>IUPAC-Name<br>LC-MS (method): Retention time; Mass found<br>¹H-NMR |
|---|---|
| Compound 140.01 | 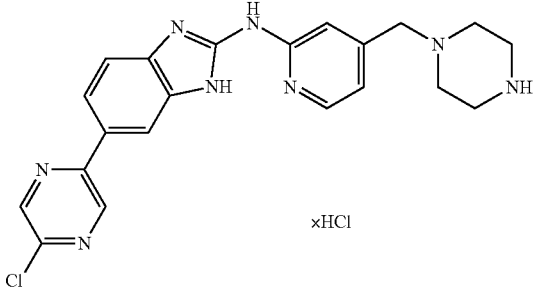 [SMILES: Clc1cnc(-c2ccc3nc(Nc4cc(CN5CCNCC5)ccn4)[nH]c3c2)cn1]<br>6-[2-(difluoromethyl)pyridin-4-yl]-N-[4-(piperazin-1-ylmethyl)pyridin-2-yl]-1H-benzimidazol-2-amine hydrochloride<br>LC-MS (Method 2): $R_t$ = 0.98 min; MS (ESIpos): m/z = 436 [M + H]⁺ |
| Compound 141.01 | 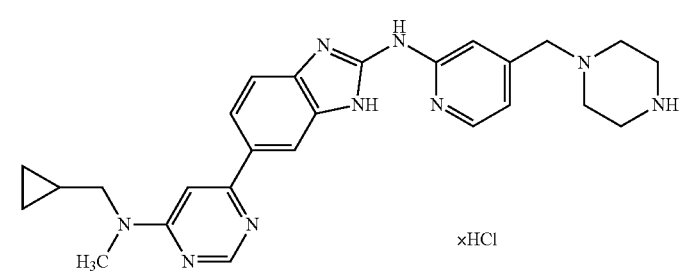<br>6-(5-chloropyrazin-2-yl)-N-[4-(piperazin-1-ylmethyl)pyridin-2-yl]-1H-benzimidazol-2-amine hydrochloride (starting from example 140.01)<br>LC-MS (Method 2): $R_t$ = 1.03 min; MS (ESIpos): m/z = 421 [M + H]⁺ |
| Compound 142.01 | 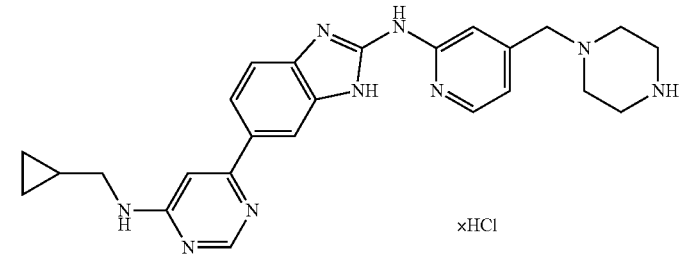 [SMILES: c1cc(CN2CCNCC2)cc(Nc2nc3ccc(-c4cc(NCC5CC5)ncn4)cc3[nH]2)n1]<br>6-{6-[(cyclopropylmethyl)(methyl)amino]pyrimidin-4-yl}-N-[4-(piperazin-1-ylmethyl)pyridin-2-yl]-1H-benzimidazol-2-amine hydrochloride<br>LC-MS (Method 2): $R_t$ = 1.02 min; MS (ESIpos): m/z = 468 [M − H]⁺ |
| Compound 143.01 | 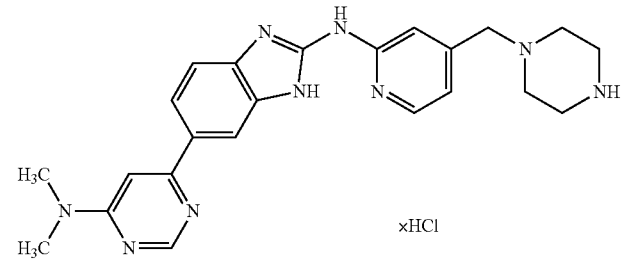<br>6-{6-[(cyclopropylmethyl)amino]pyrimidin-4-yl}-N-[4-(piperazin-1-ylmethyl)pyridin-2-yl]-1H-benzimidazol-2-amine hydrochloride<br>LC-MS (Method 2): $R_t$ = 0.95 min; MS (ESIpos): m/z = 454 [M − H]⁻ |
| | 6-[6-(dimethylamino)pyrimidin-4-yl]-N-[4-(piperazin-1-ylmethyl)pyridin-2-yl]-1H-benzimidazol-2-amine hydrochloride<br>LC-MS (Method 2): $R_t$ = 0.89 min; MS (ESIpos): m/z = 430 [M + H]⁺ |

TABLE 3-continued

Structure
IUPAC-Name
LC-MS (method): Retention time; Mass found
Compound ¹H-NMR

Compound 144.01

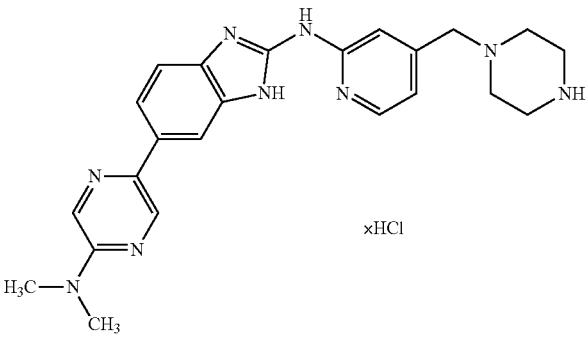 [SMILES: CN(C)c1cnc(-c2ccc3nc(Nc4cc(CN5CCNCC5)ccn4)[nH]c3c2)cn1]

6-[5-(dimethylamino)pyrazin-2-yl]-N-[4-(piperazin-1-ylmethyl)pyridin-2-yl]-1H-benzimidazol-2-amine hydrochloride
LC-MS (Method 2): $R_t$ = 0.93 min; MS (ESIpos): m/z = 430 [M + H]⁺

Compound 145.01

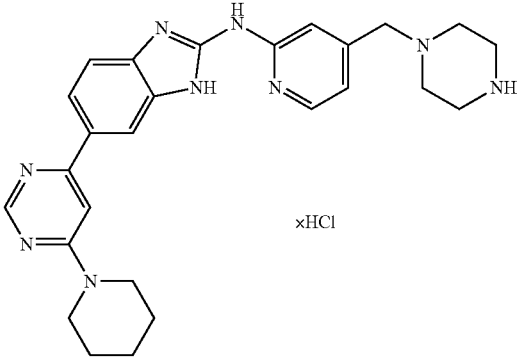 [SMILES: c1cc(CN2CCNCC2)cc(Nc2nc3ccc(-c4cc(N5CCCCC5)ncn4)cc3[nH]2)n1]

N-[4-(piperazin-1-ylmethyl)pyridin-2-yl]-6-[6-(piperidin-1-yl)pyrimidin-4-yl]-1H-benzimidazol-2-amine hydrochloride
LC-MS (Method 2): $R_t$ = 1.04 min; MS (ESIpos): m/z = 470 [M + H]⁺

Compound 146.01

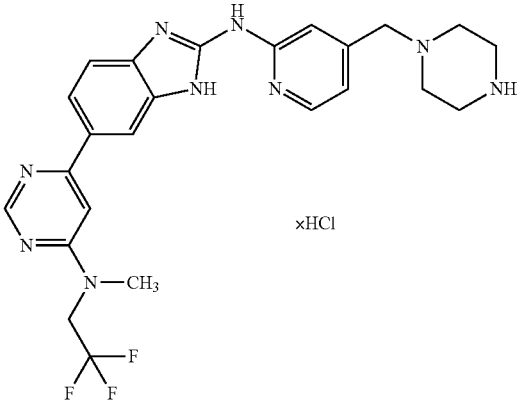 [SMILES: CN(CC(F)(F)F)c1cc(-c2ccc3nc(Nc4cc(CN5CCNCC5)ccn4)[nH]c3c2)ncn1]

6-{6-[methyl(2,2,2-trifluoroethyl)amino]pyrimidin-4-yl}-N-[4-(piperazin-1-ylmethyl)pyridin-2-yl]-1H-benzimidazol-2-amine hydrochloride
LC-MS (Method 2): $R_t$ = 1.06 min; MS (ESIpos): m/z = 498 [M + H]⁺

TABLE 3-continued

Structure
IUPAC-Name
LC-MS (method): Retention time; Mass found
Compound $^1$H-NMR Compound 147.01 xHCl

6-[6-(azetidin-1-yl)pyrimidin-4-yl]-N-[4-(piperazin-1-ylmethyl)pyridin-2-yl]-1H-benzimidazol-2-amine hydrochloride
LC-MS (Method 2): $R_t$ = 0.9 min; MS (ESIpos): m/z = 442 [M + H]$^+$ Compound 148.01 xHCl

6-{6-[ethyl(methyl)amino]pyrimidin-4-yl}-N-[4-(piperazin-1-ylmethyl)pyridin-2-yl]-1H-benzimidazol-2-amine hydrochloride
LC-MS (Method 2): $R_t$ = 0.98 min; MS (ESIpos): m/z = 444 [M + H]$^+$ Compound 149.01 xHCl

6-[6-(ethylamino)pyrimidin-4-yl]-N-[4-(piperazin-1-ylmethyl)pyridin-2-yl]-1H-benzimidazol-2-amine hydrochloride
LC-MS (Method 2): $R_t$ = 0.87 min; MS (ESIpos): m/z = 430 [M + H]$^+$ TABLE 3-continued Structure
IUPAC-Name
LC-MS (method): Retention time; Mass found

| Compound | $^1$H-NMR |
|---|---|

Compound 150.01

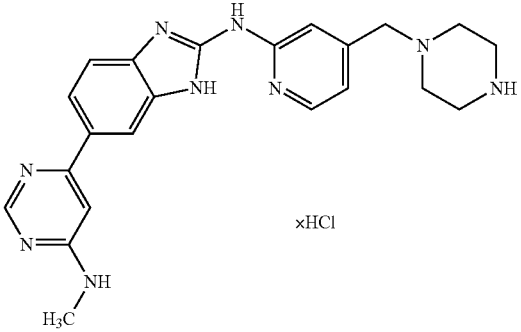 [SMILES: CNc1cc(-c2ccc3nc(Nc4cc(CN5CCNCC5)ccn4)[nH]c3c2)ncn1]

6-[6-(methylamino)pyrimidin-4-yl]-N-[4-(piperazin-1-ylmethyl)pyridin-2-yl]-1H-benzimidazol-2-amine hydrochloride
LC-MS (Method 2): R$_t$ = 0.81 min; MS (ESIpos): m/z = 414 [M + H]$^+$ Compound 151.01

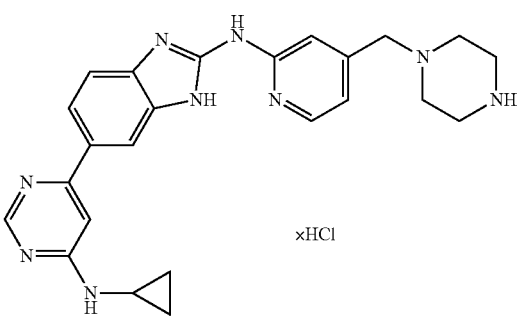 [SMILES: c1cc(CN2CCNCC2)cc(Nc2nc3ccc(-c4cc(NC5CC5)ncn4)cc3[nH]2)n1]

6-[6-(cyclopropylamino)pyrimidin-4-yl]-N-[4-(piperazin-1-ylmethyl)pyridin-2-yl]-1H-benzimidazol-2-amine hydrochloride
LC-MS (Method 2): R$_t$ = 0.89 min; MS (ESIneg): m/z = 440 [M − H]$^-$ Compound 152.01

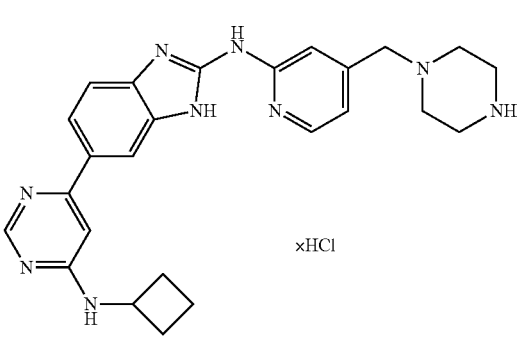 [SMILES: c1cc(CN2CCNCC2)cc(Nc2nc3ccc(-c4cc(NC5CCC5)ncn4)cc3[nH]2)n1]

6-[6-(cyclobutylamino)pyrimidin-4-yl]-N-[4-(piperazin-1-ylmethyl)pyridin-2-yl]-1H-benzimidazol-2-amine hydrochloride
LC-MS (Method 2): R$_t$ = 0.98 min; MS (ESIpos): m/z = 456 [M + H]$^+$ TABLE 3-continued Structure
IUPAC-Name
LC-MS (method): Retention time; Mass found
Compound  ¹H-NMR Compound 153.01

6-{6-[methyl(propan-2-yl)amino]pyrimidin-4-yl}-N-[4-(piperazin-1-ylmethyl)pyridin-2-yl]-1H-benzimidazol-2-amine hydrochloride
LC-MS (Method 2): $R_t$ = 1.04 min; MS (ESIneg): m/z = 456 [M − H]⁻

Compound 154.01

N-[4-(piperazin-1-ylmethyl)pyridin-2-yl]-6-[6-(propan-2-ylamino)pyrimidin-4-yl]-1H-benzimidazol-2-amine hydrochloride
LC-MS (Method 2): $R_t$ = 0.94 min; MS (ESIpos): m/z = 444 [M + H]⁺

Compound 155.01

6-[6-(diethylamino)pyrimidin-4-yl]-N-[4-(piperazin-1-ylmethyl)pyridin-2-yl]-1H-benzimidazol-2-amine hydrochloride
LC-MS (Method 2): $R_t$ = 1.05 min; MS (ESIpos): m/z = 458 [M + H]⁺

TABLE 3-continued

| Compound | Structure<br>IUPAC-Name<br>LC-MS (method): Retention time; Mass found<br>¹H-NMR |
|---|---|
| Compound 156.01 | 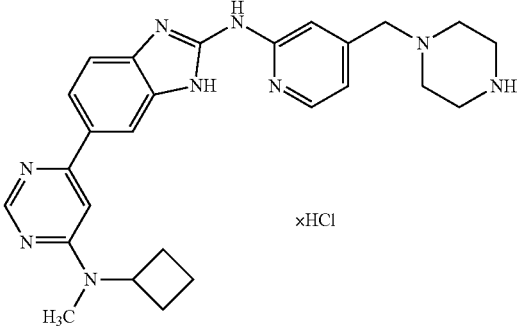 [SMILES: CN(c1cc(-c2ccc3nc(Nc4cc(CN5CCNCC5)ccn4)[nH]c3c2)ncn1)C1CCC1]<br>6-{6-[cyclobutyl(methyl)amino]pyrimidin-4-yl}-N-[4-(piperazin-1-ylmethyl)pyridin-2-yl]-1H-benzimidazol-2-amine hydrochloride<br>LC-MS (Method 2): $R_t$ = 1.11 min; MS (ESIpos): m/z = 470 [M + H]⁺ |
| Compound 157.01 | 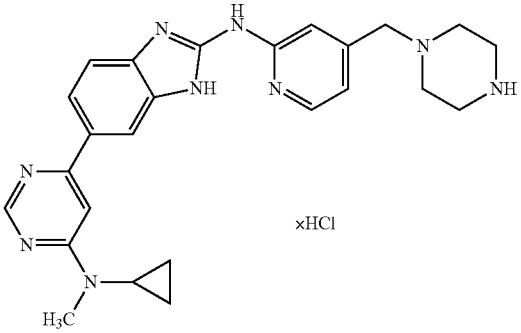 [SMILES: CN(c1cc(-c2ccc3nc(Nc4cc(CN5CCNCC5)ccn4)[nH]c3c2)ncn1)C1CC1]<br>6-{6-[cyclopropyl(methyl)amino]pyrimidin-4-yl}-N-[4-(piperazin-1-ylmethyl)pyridin-2-yl]-1H-benzimidazol-2-amine hydrochloride<br>LC-MS (Method 2): $R_t$ = 0.88 min; MS (ESIpos): m/z = 456 [M + H]⁺ |
| Compound 158.01 | 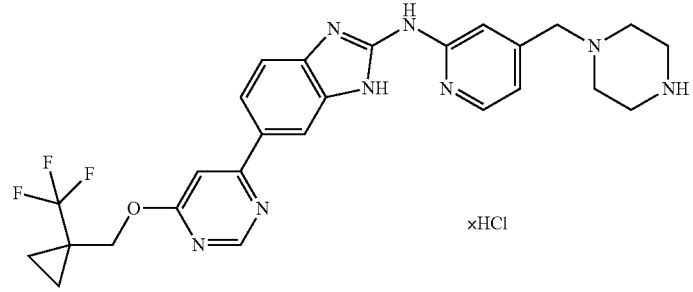 [SMILES: FC(F)(F)C1(COc2cc(-c3ccc4nc(Nc5cc(CN6CCNCC6)ccn5)[nH]c4c3)ncn2)CC1]<br>N-[4-(piperazin-1-ylmethyl)pyridin-2-yl]-6-(6-{[1-(trifluoromethyl)cyclopropyl]methoxy}pyrimidin-4-yl)-1H-benzimidazol-2-amine hydrochloride<br>LC-MS (Method 2): $R_t$ = 1.19 min; MS (ESIneg): m/z = 523 [M − H]⁻ |
| Compound 159.01 | 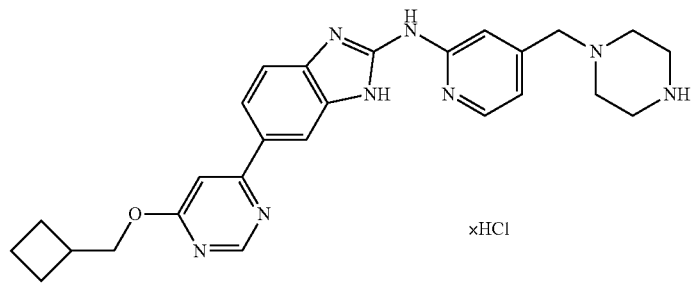 [SMILES: c1cc(CN2CCNCC2)cc(Nc2nc3ccc(-c4cc(OCC5CCC5)ncn4)cc3[nH]2)n1] |

TABLE 3-continued

Structure
IUPAC-Name
LC-MS (method): Retention time; Mass found
Compound                ¹H-NMR 6-[6-(cyclobutylmethoxy)pyrimidin-4-yl]-N-[4-(piperazin-1-
ylmethyl)pyridin-2-yl]-1H-benzimidazol-2-amine hydrochloride
LC-MS (Method 2): R$_t$ = 1.23 min; MS (ESIneg): m/z = 469 [M − H]⁻

Compound
160.01

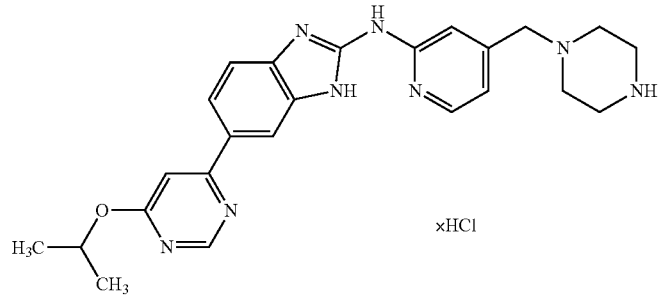 [SMILES: CC(C)Oc1cc(-c2ccc3nc(Nc4cc(CN5CCNCC5)ccn4)[nH]c3c2)ncn1]

xHCl

N-[4-(piperazin-1-ylmethyl)pyridin-2-yl]-6-[6-(propan-2-
yloxy)pyrimidin-4-yl]-1H-benzimidazol-2-amine hydrochloride
LC-MS (Method 2): R$_t$ = 1.1 min; MS (ESIneg): m/z = 443 [M − H]⁻

Compound
161.01

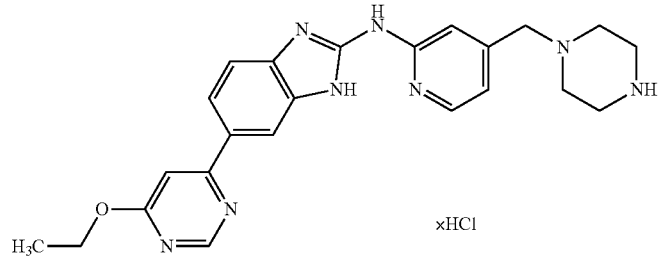 [SMILES: CCOc1cc(-c2ccc3nc(Nc4cc(CN5CCNCC5)ccn4)[nH]c3c2)ncn1]

xHCl 6-(6-ethoxypyrimidin-4-yl)-N-[4-(piperazin-1-ylmethyl)pyridin-2-yl]-
1H-benzimidazol-2-amine hydrochloride
LC-MS (Method 2): R$_t$ = 1.02 min; MS (ESIneg): m/z = 429 [M − H]⁻

Compound
162.01

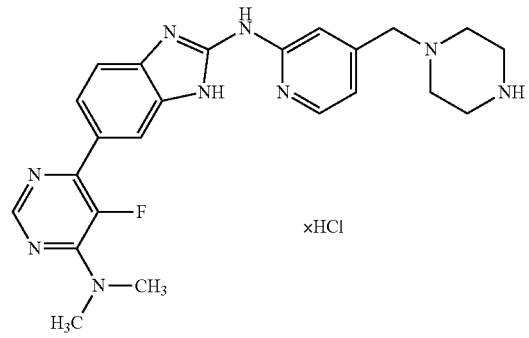 [SMILES: CN(C)c1ncnc(-c2ccc3nc(Nc4cc(CN5CCNCC5)ccn4)[nH]c3c2)c1F]

xHCl

6-[6-(dimethylamino)-5-fluoropyrimidin-4-yl]-N-[4-(piperazin-1-
ylmethyl)pyridin-2-yl]-1H-benzimidazol-2-amine hydrochloride
LC-MS (Method 2): R$_t$ = 1 min; MS (ESIpos): m/z = 448 [M + H]⁺

TABLE 3-continued

| Compound | Structure<br>IUPAC-Name<br>LC-MS (method): Retention time; Mass found<br>¹H-NMR |
|---|---|
| Compound 163.01 | 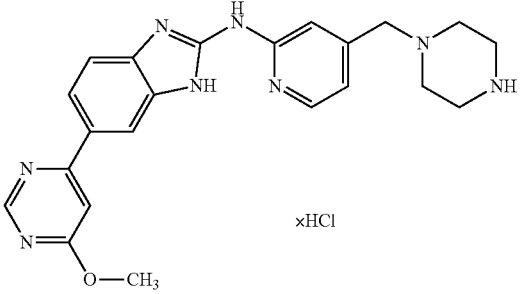 [SMILES: COc1cc(-c2ccc3nc(Nc4cc(CN5CCNCC5)ccn4)[nH]c3c2)ncn1]<br>6-(6-methoxypyrimidin-4-yl)-N-[4-(piperazin-1-ylmethyl)pyridin-2-yl]-1H-benzimidazol-2-amine hydrochloride (starting from example 145.01.01)<br>LC-MS (Method 2): $R_t$ = 0.93 min; MS (ESIpos): m/z = 417 [M + H]⁺ |

Compound 169.01

1,1-difluoro-3-(iodomethyl)cyclobutane

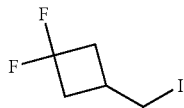

To a stirred solution of (3,3-difluorocyclobutyl)methanol (3.41 g) in THF (60 ml) was added triphenylphosphine (8.79 g) and imidazole (2.85 g). The mixture was cooled to 0° C. and iodine (8.50 g) was added. The mixture was stirred at r.t. for 16 h. An aqueous solution of disodium sulfurothioate (c=1M; 50 mL) was added and the reaction mixture was stirred for 5 minutes. The phases were separated and the aqueous phase was extracted with diethyl ether. The combined organic phases were washed with aqueous ammonium chloride solution, dried (sodium sulfate), filtered and the solvent was carefully removed in vacuum (750 mBar, 45° C.) to give 6.48 g of the title compound as a crude product that was used for the next step without purification.

The Compounds in the following table 4 were synthesised according to the preparations, and from starting materials (SM), as specified for the respective Compounds in their table entries below.

TABLE 4

| Compound | Structure<br>IUPAC-Name<br>LC-MS (method): Retention time; Mass found<br>¹H-NMR<br>Starting material (SM):<br>Synthesis procedure in analogy to the preparation of: |
|---|---|
| Compound 169.02 | 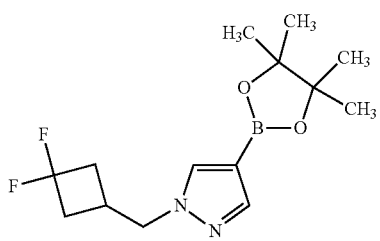 [SMILES: CC1(C)OB(c2cnn(CC3CC(F)(F)C3)c2)OC1(C)C]<br>1-[(3,3-difluorocyclobutyl)methyl]-4-(4,4,5,5-tetramethyl-1,3,2-dioxaborolan-2-yl)-1H-pyrazole<br>LC-MS (Method 1): $R_t$ = 1.18 min; MS (ESIpos): m/z = 299 [M + H]⁺<br>¹H-NMR (400 MHz, DMSO-d6) δ [ppm]: 1.066 (2.04), 1.172 (0.68), 1.244 (16.00), 1.987 (1.09), 4.235 (0.66), 4.250 (0.51), 7.589 (1.21), 7.591 (1.27), 7.981 (1.20).<br>SM: Compound 169.01 and 4-(4,4,5,5-tetramethyl-1,3,2-dioxaborolan-2-yl)-1H-pyrazole<br>Synthesis in analogy to the preparation of Compound 39.01 |

TABLE 4-continued

Structure
IUPAC-Name
LC-MS (method): Retention time; Mass found
¹H-NMR
Starting material (SM):
Compound     Synthesis procedure in analogy to the preparation of:

Compound 170.01

1-{[(1RS)-2,2-dichlorocyclopropyl]methyl}-4-(4,4,5,5-tetramethyl-1,3,2-dioxaborolan-2-yl)-1H-pyrazole
LC-MS (Method 2): R$_t$ = 1.23 min; MS (ESIpos): m/z = 316 [M − H]$^+$
¹H-NMR (400 MHz, DMSO-d6) δ [ppm]: 1.066 (4.21), 1.241 (0.58), 1.254 (16.00), 1.599 (0.75), 1.618 (0.48), 1.805 (0.53), 1.824 (0.50), 1.832 (0.59), 1.851 (0.52), 3.936 (0.65), 4.304 (0.66), 4.309 (0.70), 4.320 (0.65), 4.328 (0.58), 7.642 (1.29), 8.007 (1.26).
SM: (2RS)-2-(bromomethyl)-1,1-dichlorocyclopropane (CAS No. 3591-45-5) and 4-(4,4,5,5-tetramethyl-1,3,2-dioxaborolan-2-yl)-1H-pyrazole
Synthesis in analogy to the preparation of Compound 39.01

Compound 171.01

1-(cyclobutylmethyl)-4-(4,4,5,5-tetramethyl-1,3,2-dioxaborolan-2-yl)-1H-pyrazole
LC-MS (Method 2): R$_t$ = 1.24 min; MS (ESIpos): m/z = 263 [M + H]$^+$
¹H-NMR (400 MHz, DMSO-d6) δ [ppm]: 1.066 (1.56), 1.172 (0.85), 1.240 (16.00), 1.987 (1.36), 3.329 (2.68), 4.111 (1.24), 4.129 (1.23), 7.550 (1.22), 7.552 (1.23), 7.894 (1.22).
SM: (bromomethyl)cyclobutane and 4-(4,4,5,5-tetramethyl-1,3,2-dioxaborolan-2-yl)-1H-pyrazole
Synthesis in analogy to the preparation of Compound 39.01

Compound 172.01

3-fluoro-4-(4,4,5,5-tetramethyl-1,3,2-dioxaborolan-2-yl)benzene-1,2-diamine
LC-MS (Method 1): R$_t$ = 0.93 min; MS (ESIpos): m/z = 253 [M + H]$^+$
¹H-NMR (400 MHz, DMSO-d6) δ [ppm]: 1.066 (5.75), 1.156 (3.60), 1.173 (1.27), 1.191 (0.67), 1.234 (16.00), 1.988 (2.49), 3.938 (0.94), 4.018 (0.56), 4.035 (0.56), 4.235 (0.84), 5.206 (0.98), 6.294 (0.69), 6.314 (0.74), 6.659 (0.41), 6.675 (0.46), 6.678 (0.42).
SM: 4-bromo-3-fluorobenzene-1,2-diamine
Synthesis in analogy to the preparation of Compound 01.03

TABLE 4-continued

Structure
IUPAC-Name
LC-MS (method): Retention time; Mass found
¹H-NMR
Starting material (SM):
Compound    Synthesis procedure in analogy to the preparation of:

Compound 169.03

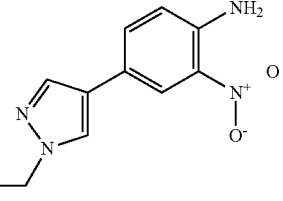

4-{1-[(3,3-difluorocyclobutyl)methyl]-1H-pyrazol-4-yl}-2-nitroaniline
LC-MS (Method 1): R$_t$ = 1.06 min; MS (ESIpos): m/z = 309 [M + H]$^+$
¹H-NMR (500 MHz, DMSO-d6) δ [ppm]: 2.358 (0.73), 2.361 (0.97), 2.365
(0.70), 2.412 (1.41), 2.421 (1.16), 2.428 (1.83), 2.438 (2.43), 2.443 (2.27),
2.453 (2.21), 2.458 (2.57), 2.470 (2.94), 2.515 (3.62), 2.518 (3.20), 2.522
(2.52), 2.618 (3.20), 2.632 (5.43), 2.635 (5.46), 2.639 (4.30), 2.642 (4.09),
2.653 (3.05), 2.657 (2.99), 2.679 (1.70), 2.687 (0.53), 2.696 (0.62), 3.161
(1.44), 3.171 (1.47), 4.220 (9.33), 4.232 (7.98), 5.758 (1.24), 7.030 (9.86),
7.047 (10.23), 7.429 (13.88), 7.644 (5.76), 7.649 (5.56), 7.662 (5.12), 7.666
(5.14), 7.849 (16.00), 7.851 (15.88), 8.098 (10.71), 8.101 (10.04), 8.203
(15.13), 8.204 (14.82).
SM: Compound 169.02 and 4-bromo-2-nitroaniline
Synthesis in analogy to the preparation of Compound 39.02

Compound 170.02

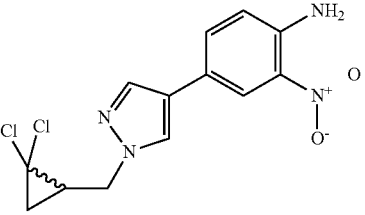

4-(1-{[(1RS)-2,2-dichlorocyclopropyl]methyl}-1H-pyrazol-4-yl)-2-
nitroaniline
LC-MS (Method 2): R$_t$ = 1.14 min; MS (ESIpos): m/z = 327 [M + H]$^+$
¹H-NMR (400 MHz, DMSO-d6) δ [ppm]: 1.203 (0.44), 1.219 (0.52), 1.228
(0.42), 1.604 (4.44), 1.623 (8.45), 1.643 (5.42), 1.825 (5.34), 1.844 (5.06),
1.852 (6.35), 1.871 (5.15), 2.261 (1.22), 2.278 (1.66), 2.281 (2.90), 2.288
(1.28), 2.297 (2.63), 2.300 (2.07), 2.305 (1.73), 2.307 (2.66), 2.317 (1.43),
2.325 (2.60), 2.327 (2.13), 2.344 (1.01), 2.518 (2.14), 2.523 (1.54), 2.532
(0.87), 2.665 (0.43), 2.669 (0.59), 3.963 (0.76), 4.238 (2.59), 4.254 (2.50),
4.274 (5.74), 4.290 (6.05), 4.299 (0.43), 4.319 (5.64), 4.338 (5.10), 4.355
(2.57), 4.374 (2.45), 5.758 (3.65), 7.041 (9.10), 7.063 (9.41), 7.445 (11.81),
7.525 (0.41), 7.528 (0.69), 7.533 (0.46), 7.536 (0.61), 7.540 (0.41), 7.544
(1.08), 7.547 (1.48), 7.549 (1.40), 7.555 (1.27), 7.558 (1.03), 7.565 (1.73),
7.566 (1.29), 7.572 (1.39), 7.592 (1.15), 7.596 (1.99), 7.601 (0.48), 7.606
(0.83), 7.609 (1.04), 7.613 (1.73), 7.615 (1.52), 7.622 (1.91), 7.625 (2.15),
7.630 (1.15), 7.638 (0.76), 7.642 (1.25), 7.645 (1.32), 7.649 (0.73), 7.655
(5.27), 7.661 (5.50), 7.677 (4.82), 7.683 (4.82), 7.689 (0.70), 7.827 (0.56),
7.829 (0.56), 7.903 (15.39), 7.905 (16.00), 7.968 (0.51), 7.970 (0.49), 7.986
(0.52), 7.988 (0.51), 8.109 (9.77), 8.114 (9.79), 8.155 (0.40), 8.182 (0.55),
8.227 (13.89), 8.229 (13.67), 8.316 (0.48).
Compound 170.01 and 4-bromo-2-nitroaniline
Synthesis in analogy to the preparation of Compound 39.02

Compound 171.02

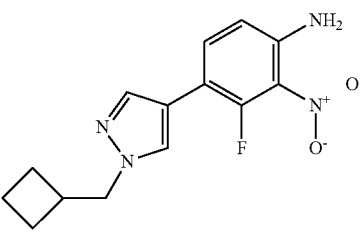

TABLE 4-continued

|  | Structure<br>IUPAC-Name<br>LC-MS (method): Retention time; Mass found<br>¹H-NMR<br>Starting material (SM): |
|---|---|
| Compound | Synthesis procedure in analogy to the preparation of: |

4-[1-(cyclobutylmethyl)-1H-pyrazol-4-yl]-3-fluoro-2-nitroaniline
LC-MS (Method 2): R$_t$ = min; MS (ESIpos): m/z = 291 [M + H]$^+$
¹H-NMR (400 MHz, DMSO-d6) δ [ppm]: 1.066 (16.00), 1.738 (1.01), 1.760 (1.38), 1.766 (0.92), 1.779 (1.47), 1.783 (1.44), 1.795 (1.64), 1.801 (1.52), 1.811 (1.66), 1.816 (1.25), 1.829 (0.92), 1.838 (1.32), 1.855 (0.57), 1.861 (0.82), 1.935 (0.66), 1.951 (1.10), 1.958 (1.27), 1.966 (1.22), 1.970 (1.72), 1.980 (1.37), 1.987 (1.20), 1.997 (0.57), 2.518 (0.93), 2.522 (0.63), 2.732 (0.81), 2.750 (1.13), 2.769 (0.89), 3.939 (2.78), 4.132 (5.27), 4.151 (5.14), 6.783 (1.80), 6.787 (1.72), 6.806 (1.85), 6.809 (1.79), 6.935 (4.65), 7.528 (0.60), 7.533 (0.49), 7.536 (0.59), 7.547 (1.45), 7.549 (1.37), 7.555 (1.21), 7.557 (1.06), 7.564 (1.65), 7.572 (1.41), 7.592 (1.23), 7.595 (2.13), 7.602 (0.60), 7.608 (2.52), 7.612 (1.98), 7.621 (2.18), 7.627 (3.03), 7.638 (0.84), 7.641 (1.36), 7.645 (1.32), 7.650 (1.56), 7.769 (3.55), 8.026 (2.74), 8.031 (2.59).
Compound 171.01 and 4-bromo-3-fluoro-2-nitroaniline
Synthesis in analogy to the preparation of Compound 39.02

Compound 169.04

4-{1-[(3,3-difluorocyclobutyl)methyl]-1H-pyrazol-4-yl}benzene-1,2-diamine
LC-MS (Method 1): R$_t$ = 0.66 min; MS (ESIpos): m/z = 279 [M + H]$^+$
¹H-NMR (400 MHz, DMSO-d6) δ [ppm]: 1.036 (8.07), 1.054 (16.00), 1.071 (8.12), 1.241 (1.00), 1.253 (0.86), 1.313 (1.99), 2.257 (0.63), 2.267 (0.52), 2.323 (0.50), 2.327 (0.63), 2.331 (0.47), 2.386 (1.40), 2.397 (1.24), 2.406 (1.83), 2.420 (2.38), 2.427 (2.36), 2.437 (2.25), 2.444 (2.49), 2.459 (3.03), 2.518 (2.43), 2.523 (1.71), 2.536 (0.53), 2.582 (1.75), 2.593 (3.29), 2.612 (5.12), 2.624 (3.88), 2.634 (3.05), 2.643 (3.15), 2.664 (1.78), 2.669 (2.21), 2.689 (0.57), 3.433 (1.74), 3.444 (1.66), 4.195 (8.65), 4.211 (7.42), 4.360 (1.07), 4.956 (4.34), 6.530 (7.04), 6.551 (10.53), 6.621 (5.72), 6.626 (5.99), 6.641 (3.58), 6.645 (4.07), 6.726 (9.90), 6.730 (8.83), 7.598 (14.58), 7.877 (13.84), 7.887 (0.66).
SM: Compound 169.03
Synthesis in analogy to the preparation of Compound 39.03

Compound 170.03

4-(1-{[(1RS)-2,2-dichlorocyclopropyl]methyl}-1H-pyrazol-4-yl)benzene-1,2-diamine
LC-MS (Method 1): R$_t$ = 0.75 min; MS (ESIpos): m/z = 297 [M + H]$^+$
¹H-NMR (400 MHz, DMSO-d6) δ [ppm]: 1.160 (0.42), 1.581 (4.22), 1.600 (8.40), 1.620 (5.17), 1.817 (5.08), 1.836 (4.93), 1.845 (6.17), 1.863 (5.11), 2.233 (1.20), 2.253 (2.92), 2.260 (1.31), 2.270 (2.70), 2.279 (2.75), 2.289 (1.41), 2.297 (2.34), 2.316 (1.08), 2.323 (0.44), 2.327 (0.47), 2.523 (1.14), 4.228 (0.66), 4.245 (0.85), 4.265 (9.57), 4.267 (9.89), 4.281 (8.52), 4.286 (7.98), 4.304 (0.75), 4.322 (0.71), 4.450 (11.78), 5.758 (7.53), 6.480 (8.42), 6.499 (11.39), 6.587 (6.25), 6.592 (6.52), 6.607 (4.24), 6.612 (4.68), 6.697 (10.79), 6.702 (10.22), 7.529 (0.62), 7.536 (0.60), 7.547 (1.56), 7.550 (1.55), 7.555 (1.31), 7.558 (1.23), 7.565 (1.83), 7.573 (1.47), 7.597 (2.23), 7.614 (2.04), 7.626 (3.39), 7.633 (16.00), 7.643 (1.81), 7.700 (0.46), 7.739 (0.47), 7.878 (14.74), 7.951 (0.44), 8.042 (0.44).
SM: Compound 170.02
Synthesis in analogy to the preparation of Compound 39.03

TABLE 4-continued

Structure
IUPAC-Name
LC-MS (method): Retention time; Mass found
¹H-NMR
Starting material (SM):
Compound          Synthesis procedure in analogy to the preparation of:

Compound 171.03

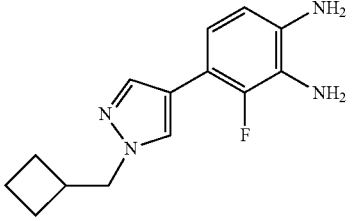 [SMILES: Nc1ccc(-c2cnn(CC3CCC3)c2)c(F)c1N]

4-[1-(cyclobutylmethyl)-1H-pyrazol-4-yl]-3-fluorobenzene-1,2-diamine
LC-MS (Method 2): $R_t$ = min; MS (ESIpos): m/z = 261 [M + H]⁺
¹H-NMR (400 MHz, DMSO-d6) δ [ppm]: 1.054 (0.73), 1.067 (16.00), 1.760 (0.41), 1.780 (0.45), 1.784 (0.46), 1.794 (0.52), 1.802 (0.47), 1.810 (0.49), 1.970 (0.48), 4.108 (1.48), 4.126 (1.41), 6.360 (0.55), 6.362 (0.52), 6.381 (0.62), 6.383 (0.57), 6.634 (0.48), 6.655 (0.84), 7.650 (0.99), 7.849 (0.79), 7.854 (0.75).
SM: Compound 171.02
Synthesis in analogy to the preparation of Compound 39.03

Compound 172.02

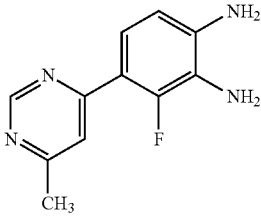 [SMILES: Cc1cc(-c2ccc(N)c(N)c2F)ncn1]

3-fluoro-4-(6-methylpyrimidin-4-yl)benzene-1,2-diamine
LC-MS (Method 1): $R_t$ = 0.62 min; MS (ESIpos): m/z = 219 [M + H]⁺
¹H-NMR (400 MHz, DMSO-d6) δ [ppm]: 2.454 (16.00), 4.562 (3.69), 5.437 (3.78), 6.441 (1.91), 6.463 (2.00), 7.238 (1.42), 7.259 (2.74), 7.280 (1.34), 7.570 (2.81), 8.939 (3.22), 8.942 (3.26).
SM: Compound 172.01 and 4-chloro-6-methylpyrimidine
Synthesis in analogy to the preparation of Compound 60.01

Compound 173.01

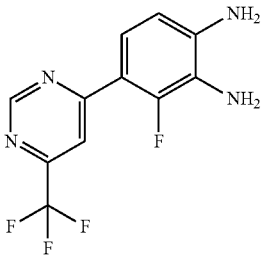 [SMILES: Nc1ccc(-c2cc(C(F)(F)F)ncn2)c(F)c1N]

3-fluoro-4-[6-(trifluoromethyl)pyrimidin-4-yl]benzene-1,2-diamine
LC-MS (Method 1): $R_t$ = 0.98 min; MS (ESIpos): m/z = 273 [M + H]⁺
¹H-NMR (400 MHz, DMSO-d6) δ [ppm]: 1.064 (11.03), 2.518 (3.10), 2.522 (2.08), 2.673 (0.64), 3.937 (1.87), 4.678 (15.60), 5.767 (16.00), 6.370 (0.55), 6.483 (8.83), 6.505 (9.10), 7.398 (6.44), 7.419 (11.68), 7.440 (5.88), 7.984 (0.65), 8.008 (15.70), 8.011 (15.29), 9.281 (13.20), 9.346 (1.02).
SM: Compound 172.01 and 4-bromo-6-(trifluoromethyl)pyrimidine
Synthesis in analogy to the preparation of Compound 60.01

The Compounds in the table 5 below were prepared analogously to the procedure for the preparation of Compound 107.01.01.

TABLE 5

| Compound | Structure<br>IUPAC-Name<br>LC-MS (method): Retention time; Mass found<br>¹H-NMR<br>Starting material (SM): |
|---|---|
| Compound 164.01 | 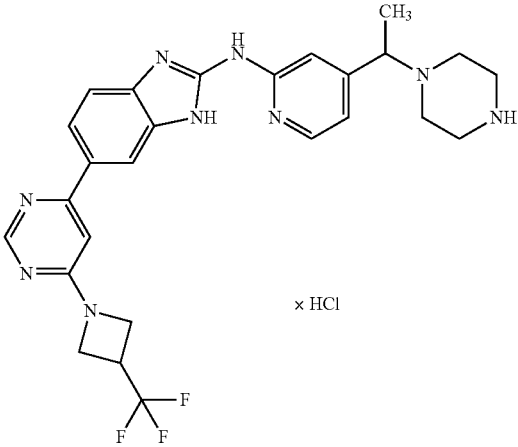 [SMILES: CC(c1ccnc(Nc2nc3ccc(-c4cc(N5CC(C(F)(F)F)C5)ncn4)cc3[nH]2)c1)N1CCNCC1]<br>N-{4-[(1R or 1S)-1-(piperazin-1-yl)ethyl]pyridin-2-yl}-6-{6-[3-(trifluoromethyl)azetidin-1-yl]pyrimidin-4-yl}-1H-benzimidazol-2-amine hydrochloride<br>LC-MS (Method 2): $R_t$ = 1.04 min; MS (ESIneg): m/z = 522 [M − H]⁻<br>¹H-NMR (400 MHz, DMSO-d6) δ [ppm]: 1.032 (6.77), 1.049 (16.00), 1.067 (7.12), 1.151 (0.57), 1.160 (5.76), 1.169 (1.28), 1.176 (5.98), 1.187 (0.49), 1.229 (0.68), 1.686 (2.47), 1.699 (2.49), 1.905 (1.15), 1.985 (1.07), 2.082 (0.68), 2.518 (2.53), 2.523 (1.79), 3.161 (0.64), 3.266 (0.98), 3.407 (3.03), 3.425 (8.59), 3.443 (7.67), 3.460 (3.88), 3.563 (0.46), 3.716 (0.47), 3.732 (0.50), 3.753 (0.55), 3.906 (0.90), 3.918 (0.87), 3.928 (0.90), 3.941 (0.75), 4.015 (0.56), 4.032 (0.57), 4.050 (0.42), 4.246 (0.75), 4.260 (0.75), 4.270 (0.84), 4.283 (0.83), 4.368 (1.51), 4 483 (0.78), 4.507 (1.06), 4.529 (0.72), 4.568 (1.49), 4.592 (2.14), 4.616 (1.28), 5.759 (9.20), 7.157 (5.03), 7.588 (2.42), 7.676 (0.79), 7.821 (2.21), 7.842 (2.51), 8.011 (1.78), 8.014 (1.78), 8.032 (1.41), 8.036 (1.49), 8.284 (2.74), 8.561 (1.64), 8.574 (1.55), 8.811 (4.92), 9.836 (0.64).<br>SM: Example 164.01 |
| Compound 165.01 | 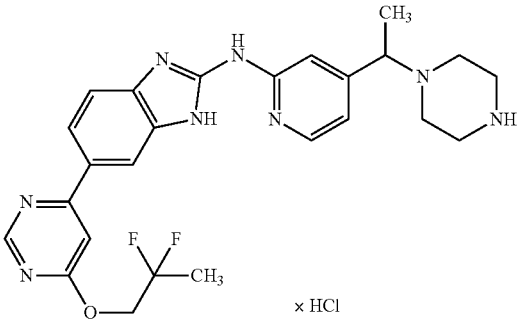 [SMILES: CC(c1ccnc(Nc2nc3ccc(-c4cc(OCC(C)(F)F)ncn4)cc3[nH]2)c1)N1CCNCC1]<br>6-[6-(2,2-difluoropropoxy)pyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 1.13 min; MS (ESIneg): m/z = 493 [M − H]⁻<br>¹H-NMR (400 MHz, DMSO-d6) δ [ppm]: 1.032 (0.74), 1.050 (1.46), 1.067 (0.74), 1.142 (0.42), 1.227 (0.84), 1.509 (0.62), 1.557 (1.49), 1.604 (0.68), 1.691 (5.80), 1.704 (5.80), 1.726 (8.91), 1.774 (16.00), 1.822 (6.96), 2.332 (1.30), 2.518 (6.90), 2.523 (4.79), 3.057 (0.42), 3.162 (7.61), 3.273 (2.17), 3.371 (1.30), 3.383 (1.75), 3.393 (1.59), 3.408 (1.85), 3.426 (2.75), 3.443 (3.56), 3.456 (4.15), 3.468 (4.47), 3.485 (4.18), 3.497 (3.43), 3.508 (2.20), 3.526 (1.98), 3.549 (2.01), 3.578 (1.00), 3.645 (0.71), 3.650 (0.78), 3.657 (0.81), 3.661 (1.33), 3.665 (1.17), 3.673 (1.39), 3.675 (1.55), 3.697 (1.46), 3.699 (1.43), 3.707 (0.97), 3.711 (1.26), 3.723 (0.65), 3.727 (0.81), 3.739 (0.52), 3.859 (0.45), 3.915 (0.42), 3.933 (0.74), 3.953 (0.78), 3.972 (0.45), 3.997 (11.17), 4.170 (0.55), 4.181 (0.81), 4.203 (0.52), 4.710 (5.44), 4.743 (9.91), 4.776 (4.89), 4.901 (1.59), 4.953 (1.72), 5.001 (1.68), 5.058 (1.55), 5.098 (1.33), 5.759 (0.45), 6.192 (0.42), 6.197 (0.45), 6.207 (0.45), 6.352 (0.42), 6.893 (0.52), 7.121 (0.45), 7.498 (2.69), 7.501 (2.72), 7.583 (5.93), 7.610 (0.84), 7.619 (0.62), 7.655 (10.43), 7.657 (10.75), 7.672 (2.01), 7.720 |

TABLE 5-continued

| Compound | Structure<br>IUPAC-Name<br>LC-MS (method): Retention time; Mass found<br>¹H-NMR<br>Starting material (SM): |
|---|---|
| | (0.45), 7.743 (0.94), 7.748 (1.20), 7.752 (1.10), 7.761 (6.80), 7.783 (6.90), 7.835 (0.65), 7.839 (1.00), 7.844 (0.62), 8.067 (0.45), 8.174 (1.17), 8.178 (1.20), 8.196 (1.20), 8.199 (1.20), 8.212 (4.24), 8.216 (4.40), 8.234 (3.63), 8.237 (3.89), 8.333 (0.65), 8.375 (0.45), 8.496 (1.78), 8.536 (6.54), 8.538 (6.41), 8.577 (4.34), 8.590 (3.95), 8.893 (3.14), 8.895 (3.24), 8.918 (12.28), 8.921 (12.44), 9.262 (1.00), 9.759 (1.59).<br>SM: Example 165.01 |
| Compound 166.01 | 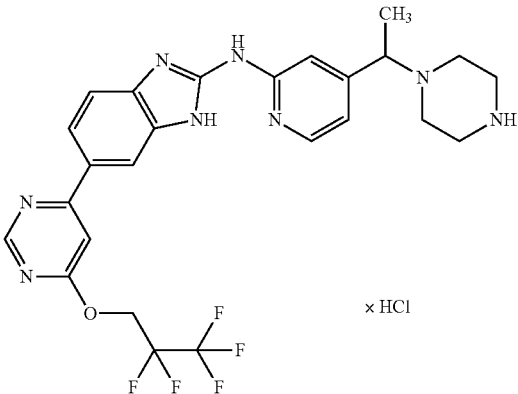 [SMILES: CC(c1ccnc(Nc2nc3ccc(-c4cc(OCC(F)(F)C(F)(F)F)ncn4)cc3[nH]2)c1)N1CCNCC1]<br>6-[6-(2,2,3,3,3-pentafluoropropoxy)pyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 1.27 min; MS (ESIneg): m/z = 547 [M − H]⁻<br>¹H-NMR (400 MHz, DMSO-d6) δ [ppm]: 1.031 (1.69), 1.049 (3.16), 1.066 (1.72), 1.168 (0.53), 1.227 (0.75), 1.376 (0.44), 1.698 (3.13), 1.713 (3.16), 1.905 (16.00), 1.984 (1.00), 2.518 (2.82), 2.522 (1.88), 3.282 (1.09), 3.407 (0.98), 3.425 (2.36), 3.442 (2.50), 3.459 (1.83), 3.472 (1.46), 3.996 (0.68), 4.712 (0.56), 5.061 (0.41), 5.183 (0.64), 5.217 (0.97), 5.240 (2.16), 5.274 (3.82), 5.309 (1.97), 6.934 (0.44), 6.956 (0.42), 7.444 (0.87), 7.446 (0.90), 7.590 (3.11), 7.694 (1.06), 7.715 (5.68), 7.718 (5.77), 7.764 (3.06), 7.785 (3.13), 8.126 (0.49), 8.131 (0.47), 8.233 (2.29), 8.238 (2.38), 8.255 (2.04), 8.259 (2.19), 8.552 (3.69), 8.555 (3.74), 8.579 (2.34), 8.592 (2.15), 8.830 (0.98), 8.833 (0.98), 8.968 (6.69), 8.971 (6.86), 9.794 (0.80).<br>SM: Example 166.01 |
| Compound 167.01 | 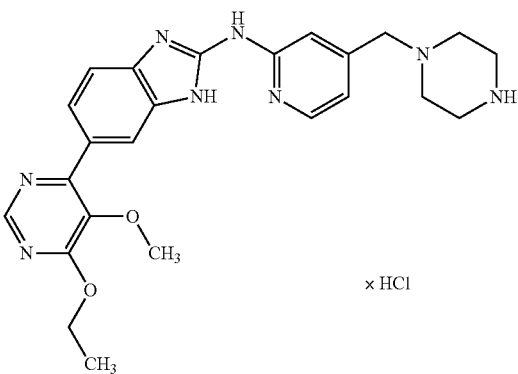 [SMILES: CCOc1ncnc(-c2ccc3nc(Nc4cc(CN5CCNCC5)ccn4)[nH]c3c2)c1OC]<br>6-(6-ethoxy-5-methoxypyrimidin-4-yl)-N-[4-(piperazin-1-ylmethyl)pyridin-2-yl]-1H-benzimidazol-2-amine hydrochloride<br>LC-MS (Method 2): $R_t$ = 1.03 min; MS (ESIpos): m/z = 461 [M + H]⁺<br>¹H-NMR (400 MHz, DMSO-d6) δ [ppm]: 1.400 (2.61), 1.417 (5.64), 1.435 (2.68), 2.518 (0.83), 2.522 (0.58), 3.160 (16.00), 3.476 (1.62), 3.811 (11.99), 4.488 (1.06), 4.505 (2.79), 4.522 (2.34), 4.540 (0.74), 7.585 (1.41), 7.638 (0.57), 7.650 (0.55), 7.765 (1.25), 7.786 (1.35), 8.067 (1.20), 8.071 (1.11), 8.089 (0.92), 8.092 (0.97), 8.411 (1.64), 8.414 (1.59), 8.564 (1.09), 8.577 (1.03), 8.592 (5.19), 9.902 (0.44).<br>SM: Example 167.01 |

TABLE 5-continued

Structure
IUPAC-Name
LC-MS (method): Retention time; Mass found
¹H-NMR

| Compound | Starting material (SM): |
|---|---|

Compound 168.01

6-(furo[3,2-d]pyrimidin-4-yl)-N-[4-(piperazin-1-ylmethyl)pyridin-2-yl]-1H-benzimidazol-2-amine hydrochloride
LC-MS (Method 2): $R_t$ = 0.87 min; MS (ESIpos): m/z = 427 [M + H]$^+$
¹H-NMR (400 MHz, DMSO-d6) δ [ppm]: 1.022 (16.00), 1.037 (15.72), 1.061 (4.53), 1.319 (0.99), 3.480 (0.65), 3.735 (0.46), 3.750 (1.12), 3.765 (1.47), 3.780 (1.07), 3.796 (0.41), 7.359 (0.90), 7.365 (0.89), 7.604 (0.50), 7.887 (0.45), 7.909 (0.46), 8.515 (0.40), 8.519 (0.40), 8.720 (0.83), 8.726 (0.82), 8.848 (0.53), 8.852 (0.53), 9.142 (1.60).
SM: Example 168.01

Compound 169.05

6-{1-[(3,3-difluorocyclobutyl)methyl]-1H-pyrazol-4-yl}-N-{4-[(1R or 1S)-1-(piperazin-1-yl)ethyl]pyridin-2-yl}-1H-benzimidazol-2-amine hydrochloride
LC-MS (Method 2): $R_t$ = 1.06 min; MS (ESIpos): m/z = 493 [M + H]$^+$
¹H-NMR (400 MHz, DMSO-d6) δ [ppm]: 1.023 (15.88), 1.039 (16.00), 1.667 (1.24), 1.684 (1.53), 1.709 (1.16), 2.518 (1.58), 2.522 (1.18), 2.654 (0.80), 2.664 (0.96), 2.669 (0.99), 3.276 (0.73), 3.463 (0.87), 3.736 (0.52), 3.751 (1.22), 3.766 (1.60), 3.782 (1.20), 3.797 (0.50), 4.282 (1.17), 4.296 (1.06), 5.758 (5.51), 7.544 (1.20), 7.570 (0.99), 7.574 (0.99), 7.591 (1.04), 7.595 (1.06), 7.640 (1.55), 7.661 (1.10), 7.770 (1.42), 7.906 (2.89), 8.256 (2.20), 8.415 (1.01), 8.429 (0.93), 8.564 (0.83), 8.577 (0.75), 9.736 (0.44).
SM: Example 169.01

Compound 170.04

6-(1-{[(1RS)-2,2-dichlorocyclopropyl]methyl}-1H-pyrazol-4-yl)-N-{4-[(1R or 1S)-1-(piperazin-1-yl)ethyl]pyridin-2-yl}-1H-benzimidazol-2-amine

TABLE 5-continued

| Compound | Structure<br>IUPAC-Name<br>LC-MS (method): Retention time; Mass found<br>¹H-NMR<br>Starting material (SM): |
|---|---|
| | hydrochloride<br>LC-MS (Method 2): R$_t$ = 1.11 min; MS (ESIpos): m/z = 511 [M + H]$^+$<br>¹H-NMR (400 MHz, DMSO-d6) δ [ppm]: 1.026 (16.00), 1.041 (15.69), 1.231 (0.84), 1.635 (2.11), 1.654 (3.68), 1.662 (0.84), 1.673 (2.19), 1.682 (0.50), 1.708 (0.46), 1.860 (1.88), 1.878 (2.11), 1.886 (2.57), 1.897 (0.42), 1.905 (1.84), 2.296 (0.50), 2.314 (1.23), 2.323 (2.07), 2.327 (2.53), 2.332 (2.49), 2.340 (1.27), 2.352 (0.58), 2.360 (1.15), 2.378 (0.54), 2.518 (8.29), 2.523 (5.68), 2.660 (0.77), 2.665 (1.61), 2.669 (2.23), 2.674 (1.57), 2.727 (8.79), 2.888 (10.94), 3.359 (0.84), 3.738 (0.73), 3.753 (1.38), 3.768 (1.73), 3.784 (1.38), 3.799 (0.84), 3.971 (7.02), 4.357 (4.53), 4.375 (4.87), 4.386 (0.81), 7.476 (1.04), 7.585 (1.34), 7.588 (1.34), 7.606 (2.30), 7.609 (2.53), 7.642 (2.95), 7.663 (1.46), 7.781 (2.99), 7.950 (1.46), 7.966 (6.06), 8.028 (0.61), 8.247 (0.42), 8.268 (5.49), 8.307 (0.50), 8.534 (0.84), 8.572 (0.65).<br>SM: Example 170.01 |
| Compound 171.04 | 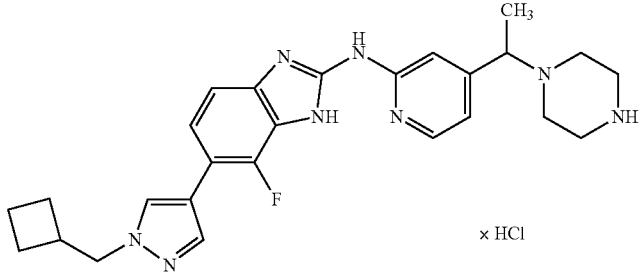 [SMILES: CC(c1ccnc(Nc2nc3ccc(-c4cnn(CC5CCC5)c4)c(F)c3[nH]2)c1)N1CCNCC1]<br>× HCl<br>6-[1-(cyclobutylmethyl)-1H-pyrazol-4-yl]-7-fluoro-N-{4-[(1R or 1S)-1-(piperazin-1-yl)ethyl]pyridin-2-yl}-1H-benzimidazol-2-amine hydrochloride<br>LC-MS (Method 2): R$_t$ = 1.14 min; MS (ESIpos): m/z = 475 [M + H]$^+$<br>¹H-NMR (400 MHz, DMSO-d6) δ [ppm]: 0.849 (0.82), 1.033 (0.88), 1.050 (1.52), 1.068 (1.23), 1.087 (0.88), 1.142 (1.58), 1.169 (1.35), 1.229 (3.75), 1.254 (2.52), 1.294 (1.64), 1.669 (10.55), 1.775 (3.46), 1.795 (5.04), 1.815 (7.38), 1.826 (8.67), 1.836 (10.26), 1.854 (4.28), 1.862 (4.69), 1.876 (2.34), 1.884 (3.16), 1.900 (1.35), 1.964 (2.70), 1.978 (4.10), 1.986 (5.45), 1.995 (5.10), 2.007 (5.33), 2.024 (2.58), 2.323 (2.40), 2.327 (3.28), 2.331 (2.46), 2.523 (13.19), 2.669 (3.40), 2.759 (1.64), 2.770 (2.87), 2.789 (3.75), 2.807 (3.22), 2.826 (1.64), 2.856 (1.11), 3.058 (1.47), 3.162 (3.69), 3.245 (3.87), 3.383 (5.22), 3.394 (5.57), 3.426 (6.80), 3.443 (7.38), 3.456 (7.44), 3.467 (6.86), 3.485 (5.80), 3.497 (4.69), 3.650 (1.41), 3.661 (2.11), 3.675 (2.29), 3.698 (2.34), 3.712 (2.05), 3.728 (1.88), 3.740 (1.47), 3.751 (1.41), 3.756 (1.47), 4.188 (16.00), 4.207 (15.71), 4.243 (1.76), 4.608 (2.64), 5.759 (0.47), 7.457 (5.16), 7.479 (7.09), 7.535 (7.74), 7.546 (5.51), 7.563 (7.79), 7.572 (5.92), 7.579 (6.86), 7.594 (7.91), 7.599 (5.98), 7.610 (5.33), 7.620 (5.63), 7.640 (3.46), 7.698 (0.82), 7.856 (1.17), 7.907 (13.48), 8.062 (1.64), 8.139 (0.70), 8.181 (9.96), 8.345 (0.76), 8.408 (1.35), 8.421 (1.35), 8.512 (3.63), 8.525 (3.52), 9.028 (2.40), 9.041 (2.34), 9.707 (2.64).<br>SM: Example 171.01 |
| Compound 172.03 | 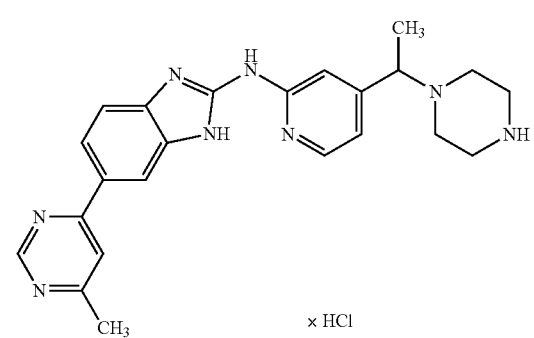<br>× HCl<br>7-fluoro-6-(6-methylpyrimidin-4-yl)-N-{4-[(1R or 1S)-1-(piperazin-1-yl)ethyl]pyridin-2-yl}-1H-benzimidazol-2-amine hydrochloride<br>LC-MS (Method 2): R$_t$ = 0.94 min; MS (ESIpos): m/z = 433 [M + H]$^+$<br>¹H-NMR (400 MHz, DMSO-d6) δ [ppm]: 1.023 (5.26), 1.039 (5.34), 1.696 (2.96), 1.713 (3.03), 2.518 (1.45), 2.523 (0.94), 2.588 (16.00), 3.481 (1.15), |

TABLE 5-continued

| Compound | Structure<br>IUPAC-Name<br>LC-MS (method): Retention time; Mass found<br>¹H-NMR<br>Starting material (SM): |
|---|---|
| | 3.751 (0.43), 3.766 (0.54), 3.781 (0.41), 4.667 (0.40), 7.517 (1.60), 7.569 (2.52), 7.590 (2.75), 7.607 (1.05), 7.619 (1.02), 7.898 (1.82), 7.906 (3.11), 7.915 (1.79), 7.918 (1.50), 7.935 (1.22), 8.505 (1.57), 8.519 (1.45), 9.193 (3.88), 9.195 (3.87), 9.820 (0.81).<br>SM: Example 172.01 |
| Compound 173.02 | 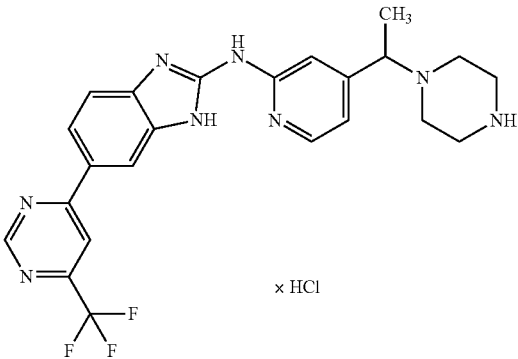<br>7-fluoro-N-{4-[(1R or 1S)-1-(piperazin-1-yl)ethyl]pyridin-2-yl}-6-[6-(trifluoromethyl)pyrimidin-4-yl]-1H-benzimidazol-2-amine hydrochloride<br>LC-MS (Method 2): R$_t$ = 1.14 min; MS (ESIpos): m/z = 487 [M + H]⁺<br>¹H-NMR (400 MHz, DMSO-d6) δ [ppm]: 1.023 (15.69), 1.039 (16.00), 1.681 (1.04), 1.697 (1.03), 2.518 (0.98), 2.522 (0.61), 3.161 (0.67), 3.466 (0.49), 3.735 (0.45), 3.751 (1.05), 3.766 (1.35), 3.782 (1.03), 3.797 (0.43), 5.758 (2.01), 7.429 (0.58), 7.563 (1.75), 7.584 (1.44), 7.930 (0.60), 7.947 (0.69), 7.951 (0.63), 7.968 (0.51), 8.334 (1.69), 8.479 (0.74), 8.493 (0.70), 9.522 (1.72).<br>SM: Example 173.01 |

Compound 174.01.01

4-[6-(difluoromethyl)pyrimidin-4-yl]benzene-1,2-diamine 4-(4,4,5,5-Tetramethyl-1,3,2-dioxaborolan-2-yl)benzene-1,2-diamine (500 mg, see Compound 01.03), 4-chloro-6-(difluoromethyl)pyrimidine (387 mg; for a preparation see e.g. WO2011/045353)). tetrakis(triphenylphosphine)palladium(0) (123 mg, 107 μmol) were solubilised in 1,4-dioxane (17 ml) and aqueous K$_2$CO$_3$ solution (3.2 ml, 2.0 M) was added. The reaction mixture was stirred at 80° C. for 3h. The reaction mixture was then filtered and concentrated under reduced pressure. The crude residue was purified by flash chromatography on silica gel to give 468 mg (73% purity) of the title compound.

LC-MS (Method 2): R$_t$=0.75 min; MS (ESIpos): m/z=237 [M+H]⁺

¹H-NMR (400 MHz, DMSO-d6) δ [ppm]: 1.066 (7.55), 1.156(0.56), 1.227 (16.00), 1.241 (3.30), 1.281 (1.02), 2.518 (1.67), 2.523 (1.16), 3.159 (11.42), 3.172 (11.15). 3.939 (1.16). 4.084 (0.85), 4.097 (2.57), 4.110 (2.57), 4.123 (0.82), 4.374 (0.49), 4.725 (3.86), 4.821 (1.04), 5.333 (4.96), 5.758 (0.50), 6.444 (0.98), 6.463 (1.06), 6.586 (4.11), 6.607 (4.04), 6.748 (0.59), 6.752 (0.63), 6.768 (0.52), 6.771 (0.55), 6.791 (1.97), 6.874 (1.05), 6.877 (1.01), 6.927 (4.03), 7.063 (1.67), 7.403 (2.01), 7.408 (2.16), 7.424 (1.83), 7.429 (2.08), 7.510 (4.12), 7.516 (3.83), 7.915 (3.85), 9.105 (3.82).

Compound 174.01.02 tert-butyl 4-[(1R or 1S)-1-{2-[({2-amino-4-[6-(difluoromethyl)pyrimidin-4-yl]phenyl}carbamothioyl)amino]pyridin-4-yl}ethyl]piperazine-1-carboxylate Imidazole (26.5 mg), TCDI (405 mg, 90% purity) and tert-butyl 4-[(1R or 1S)-1-(2-aminopyridin-4-yl)ethyl]piperazine-1-carboxylate (597 mg, see Compound 36.05) were combined in dichloromethane (9 ml) and the reaction mixture was stirred at 0° C. for 30 minutes.

Then the mixture was stored in a refrigerator overnight. The mixture was stirred at room temperature for 2 additional hours and additional portions of imidazole (26.5 mg) and TCDI (405 mg, 90% purity) were added. The reaction mixture was stirred at room temperature for 2 hours. 4-[6-(Difluoromethyl)pyrimidin-4-yl]benzene-1,2-diamine (460 mg), solubilised in dichloromethane (9 ml), was added and the mixture was stirred at room temperature overnight. The reaction mixture was diluted with water and extracted with DCM. The organic phase was washed with water and brine and then dried (silicone filter) and concentrated under reduced pressure. The crude residue was purified by flash chromatography on silica gel to give 601 mg of the title compound.

LC-MS (Method 2): $R_t$=1.33 min; MS (ESIpos): m/z=585 [M+H]$^+$.

Compound 175.01.01

4-(2-chlorothiophen-3-yl)benzene-1,2-diamine

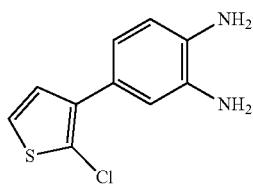 [SMILES: Nc1ccc(-c2ccsc2Cl)cc1N]

4-Bromobenzene-1,2-diamine (600 mg), (2-chlorothiophen-3-yl)boronic acid (1.04 g) and bis(triphenylphosphine)palladium(II) dichloride (113 mg) were solubilised in 1,2-dimethoxyethane (20 ml) and an aqueous solution of K$_2$CO$_3$ (4.8 ml, 2.0 M) was added. The reaction mixture was stirred for 10 min under microwave irradiation at 130° C. The mixture was filtered and concentrated under reduced pressure. The crude residue was purified by flash chromatography on silica gel to give 250 mg of the title compound.

LC-MS (Method 2): $R_t$=1.01 min; MS (ESIpos): m/z=225 [M+H]$^+$.

$^1$H-NMR (400 MHz, DMSO-d6): δ [ppm]=4.54-4.68 (m, 4H), 6.55 (d, 1H), 6.62-6.66 (m, 1H), 6.78 (d, 1H), 7.06 (d, 1H), 7.43 (d, 1H).

Compound 175.01.02 tert-butyl 4-{[2-({[4-amino-6-(2-chlorothiophen-3-yl)pyridin-3-yl]carbamothioyl}amino)pyridin-4-yl]methyl}piperazine-1-carboxylate

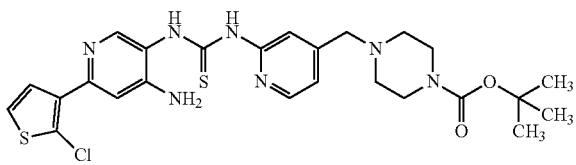 [SMILES: CC(C)(C)OC(=O)N1CCN(Cc2ccnc(NC(=S)Nc3cnc(-c4ccsc4Cl)cc3N)c2)CC1]

Imidazole (15.1 mg) and TCDI (238 mg) were solubilised in dichloromethane (9.1 ml) under inert atmosphere. The solution was cooled to 0° C. and a solution of tert-butyl 4-[(2-aminopyridin-4-yl)methyl]piperazine-1-carboxylate (325 mg, see Compound 01.02) in dichloromethane (9.1 ml) was added. The mixture was stored overnight in the refrigerator, after which 4-(2-chlorothiophen-3-yl)benzene-1,2-diamine (250 mg, 1.11 mmol) was added and the mixture was stirred for 5 h at rt. The mixture was diluted with water and extracted with DCM.

The combined organic phases were dried over a silicone filter and concentrated under reduced pressure. The crude title compound was used without further purification.

Compound 179.01.01

5,6-dichloro-N,N-dimethylpyrimidin-4-amine

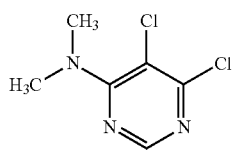

4,5,6-Trichloropyrimidine (500 mg), a solution of N-methylmethanamine in THF (1.5 ml, 2.0 M) and solid potassium carbonate (414 mg) were stirred in dioxane overnight at 110° C. The mixture was then diluted with water and extracted with DCM. The organic layer was dried over a silicone filter and concentrated under reduced pressure. The crude title compound (493 mg) was used without further purification LC-MS (Method 2): $R_t$=1.05 min; MS (ESIpos): m/z=192 [M+H]$^+$.

$^1$H-NMR (400 MHz, DMSO-d6) δ[ppm]: 2.518 (0.95), 2.523 (0.68), 3.017 (5.70), 3.191 (16.00), 8.303 (1.46).

The following Compounds shown in table 6, below, were prepared according to the following general procedure:

The corresponding Boc protected amine (see Examples 174.01 to 199.01, tables 20 and 21) (1 eq.) was solubilized in a mixture of DCM and MeOH (generally 2:1) and 4N HCl in dioxane (5 eq.) was added slowly. The reaction was stirred between 2 and 48 hours at rt and then concentrated. The crude mixture was used without further purification.

TABLE 6

| Compound | Structure<br>IUPAC-Name<br>LC-MS (method): Retention time; Mass found |
|---|---|
| Compound 174.01 | 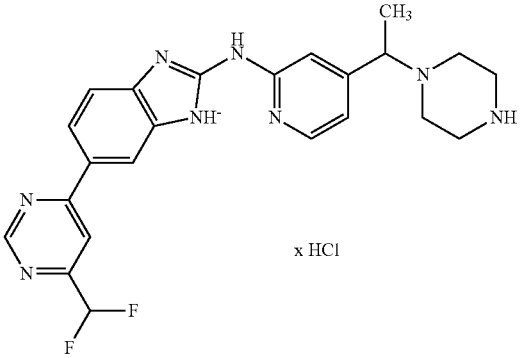 [SMILES: CC(c1ccnc(Nc2nc3ccc(-c4cc(C(F)F)ncn4)cc3[n-]2)c1)N1CCNCC1]<br>x HCl<br>6-[6-(difluoromethyl)pyrimidin-4-yl]-N-{4-[(1R or 1S)-1-(piperazin-1-yl)ethyl]pyridin-2-yl}-1H-benzimidazol-2-amine hydrochloride<br>LC-MS (Method 2): $R_t$ = 0.99 min; MS (ESIpos): m/z = 451.8 [M – H]$^+$ |
| Compound 175.01 | 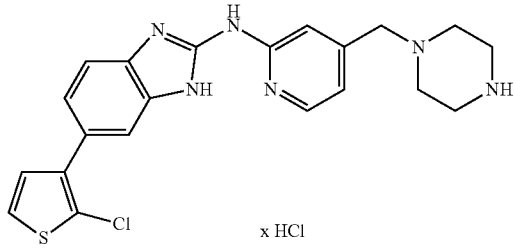 [SMILES: Clc1sccc1-c1ccc2nc(Nc3cc(CN4CCNCC4)ccn3)[nH]c2c1]<br>x HCl<br>6-(2-chlorothiophen-3-yl)-N-[4-(piperazin-1-ylmethyl)pyridin-2-yl]-1H-benzimidazol-2-amine hydrochloride<br>LC-MS (Method 2): $R_t$ = 1.18 min; MS (ESIpos): m/z = 425.5 [M – H]$^+$ |
| Compound 176.01 | 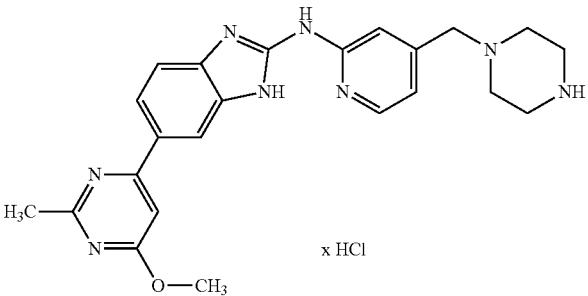 [SMILES: COc1cc(-c2ccc3nc(Nc4cc(CN5CCNCC5)ccn4)[nH]c3c2)nc(C)n1]<br>x HCl<br>From example 186.01<br>6-(6-methoxy-2-methylpyrimidin-4-yl)-N-[4-(piperazin-1-ylmethyl)pyridin-2-yl]-1H-benzimidazol-2-amine hydrochloride<br>LC-MS (Method 2): $R_t$ = 1.22 min; MS (ESIpos): m/z = 431.4 [M – H]$^+$ |
| Compound 177.01 | 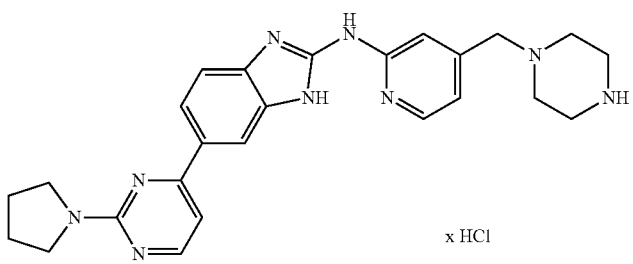 [SMILES: c1cc(CN2CCNCC2)cc(Nc2nc3ccc(-c4ccnc(N5CCCC5)n4)cc3[nH]2)n1]<br>x HCl<br>N-[4-(piperazin-1-ylmethyl)pyridin-2-yl]-6-[2-(pyrrolidin-1-yl)pyrimidin-4-yl]-1H-benzimidazol-2-amine hydrochloride<br>LC-MS (Method 2): $R_t$ = 1.07 min; MS (ESIpos): m/z = 456 [M – H]$^+$ |

TABLE 6-continued

Structure
IUPAC-Name
Compound    LC-MS (method): Retention time; Mass found

Compound 178.01

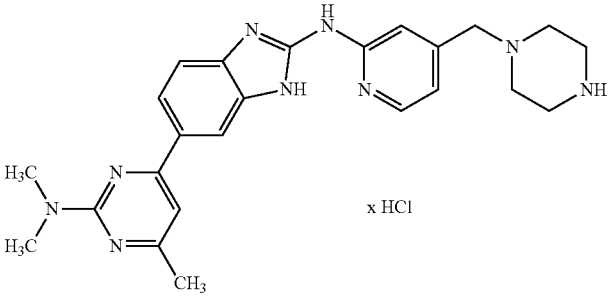 [SMILES: Cc1cc(-c2ccc3nc(Nc4cc(CN5CCNCC5)ccn4)[nH]c3c2)nc(N(C)C)n1]

6-[2-(dimethylamino)-6-methylpyrimidin-4-yl]-N-[4-(piperazin-1-ylmethyl)pyridin-2-yl]-1H-benzimidazol-2-amine hydrochloride
LC-MS (Method 2): $R_t$ = 1.14 min; MS (ESIpos): m/z = 444 [M − H]$^+$ Compound 179.01

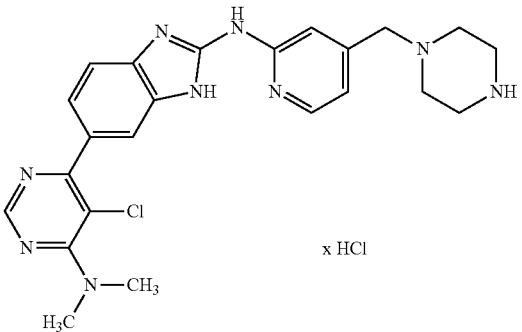 [SMILES: CN(C)c1ncnc(-c2ccc3nc(Nc4cc(CN5CCNCC5)ccn4)[nH]c3c2)c1Cl]

6-[5-chloro-6-(dimethylamino)pyrimidin-4-yl]-N-[4-(piperazin-1-ylmethyl)pyridin-2-yl]-1H-benzimidazol-2-amine hydrochloride
LC-MS (Method 2): $R_t$ = 1.01 min; MS (ESIpos): m/z = 464 [M + H]$^+$ Compound 180.01

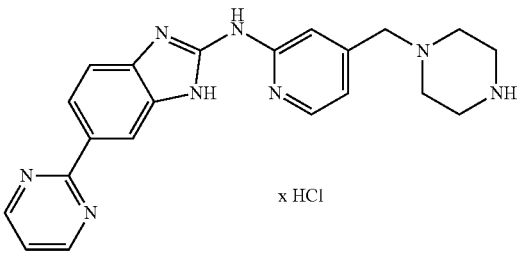 [SMILES: c1cnc(-c2ccc3nc(Nc4cc(CN5CCNCC5)ccn4)[nH]c3c2)nc1]

N-[4-(piperazin-1-ylmethyl)pyridin-2-yl]-6-(pyrimidin-2-yl)-1H-benzimidazol-2-amine hydrochloride
LC-MS (Method 2): $R_t$ = 1.01 min; MS (ESIpos): m/z = 387 [M + H]$^+$ TABLE 6-continued

| Compound | Structure<br>IUPAC-Name<br>LC-MS (method): Retention time; Mass found |
|---|---|
| Compound 181.01 | 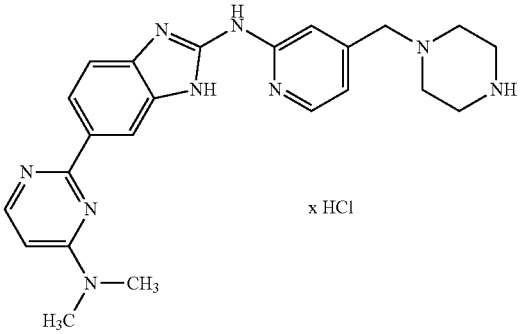 [SMILES: CN(C)c1ccnc(-c2ccc3nc(Nc4cc(CN5CCNCC5)ccn4)[nH]c3c2)n1]<br>6-[4-(dimethylamino)pyrimidin-2-yl]-N-[4-(piperazin-1-ylmethyl)pyridin-2-yl]-1H-benzimidazol-2-amine hydrochloride<br>LC-MS (Method 2): $R_t$ = 1.17 min; MS (ESIpos): m/z = 430 [M + H]$^+$ |
| Compound 182.01 | 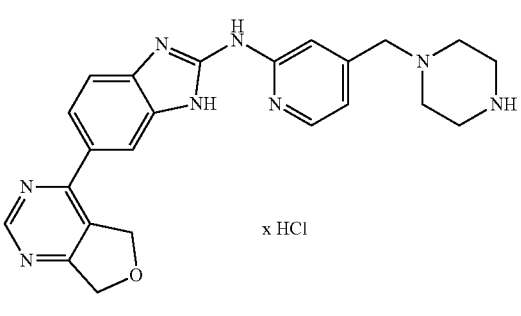 [SMILES: c1cc(CN2CCNCC2)cc(Nc2nc3ccc(-c4ncnc5c4COC5)cc3[nH]2)n1]<br>6-(5,7-dihydrofuro[3,4-d]pyrimidin-4-yl)-N-[4-(piperazin-1-ylmethyl)pyridin-2-yl]-1H-benzimidazol-2-amine hydrochloride<br>LC-MS (Method 2): $R_t$ = 0.83 min; MS (ESIpos): m/z = 429.7 [M + H]$^+$ |
| Compound 183.01 | 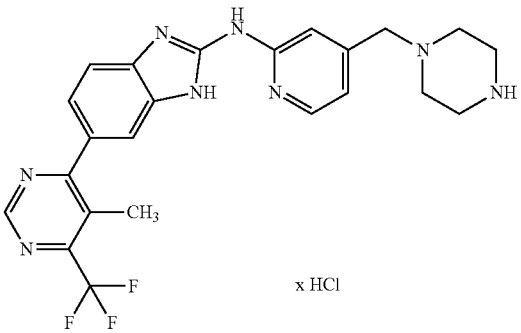 [SMILES: Cc1c(-c2ccc3nc(Nc4cc(CN5CCNCC5)ccn4)[nH]c3c2)ncnc1C(F)(F)F]<br>6-[5-methyl-6-(trifluoromethyl)pyrimidin-4-yl]-N-[4-(piperazin-1-ylmethyl)pyridin-2-yl]-1H-benzimidazol-2-amine hydrochloride<br>LC-MS (Method 2): $R_t$ = 1.08 min; MS (ESIpos): m/z = 469.8 [M + H]$^+$ |
| Compound 184.01 | 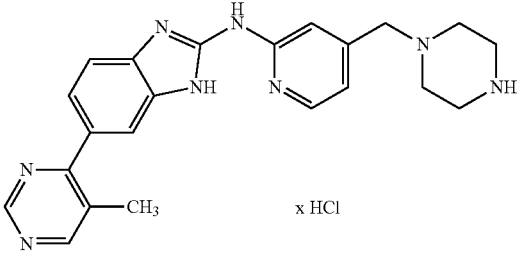 [SMILES: Cc1cncnc1-c1ccc2nc(Nc3cc(CN4CCNCC4)ccn3)[nH]c2c1]<br>6-(5-methylpyrimidin-4-yl)-N-[4-(piperazin-1-ylmethyl)pyridin-2-yl]-1H-benzimidazol-2-amine hydrochloride<br>LC-MS (Method 2): $R_t$ = 0.94 min; MS (ESIpos): m/z = 401 [M + H]$^+$ |

TABLE 6-continued

| | Structure<br>IUPAC-Name |
|---|---|
| Compound | LC-MS (method): Retention time; Mass found |

Compound 185.01

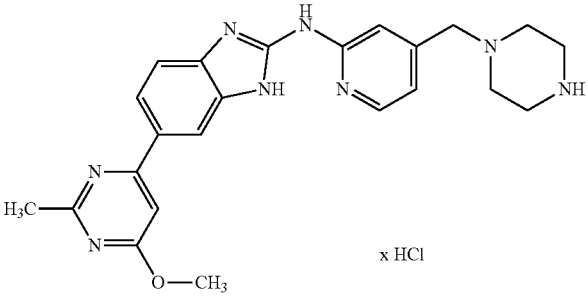 [SMILES: COc1cc(-c2ccc3nc(Nc4cc(CN5CCNCC5)ccn4)[nH]c3c2)nc(C)n1]

6-(6-methoxy-2-methylpyrimidin-4-yl)-N-[4-(piperazin-1-ylmethyl)pyridin-2-yl]-1H-benzimidazol-2-amine hydrochloride
LC-MS (Method 2): $R_t$ = 1.21 min; MS (ESIpos): m/z = 431 [M + H]$^+$ Compound 189.01

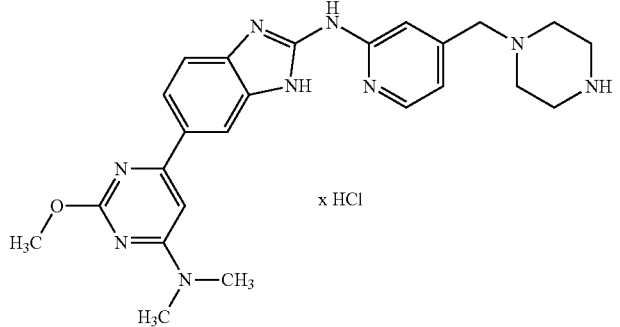 [SMILES: COc1nc(-c2ccc3nc(Nc4cc(CN5CCNCC5)ccn4)[nH]c3c2)cc(N(C)C)n1]

6-[6-(dimethylamino)-2-methoxypyrimidin-4-yl]-N-[4-(piperazin-1-ylmethyl)pyridin-2-yl]-1H-benzimidazol-2-amine hydrochloride
LC-MS (Method 2): $R_t$ = 1.23 min; MS (ESIpos): m/z = 460.5 [M + H]$^+$ Compound 190.01

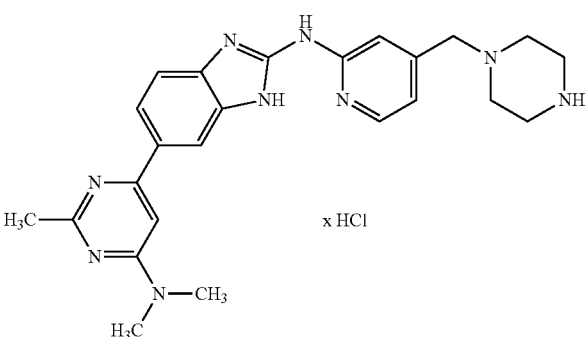 [SMILES: Cc1nc(-c2ccc3nc(Nc4cc(CN5CCNCC5)ccn4)[nH]c3c2)cc(N(C)C)n1]

6-[6-(dimethylamino)-2-methylpyrimidin-4-yl]-N-[4-(piperazin-1-ylmethyl)pyridin-2-yl]-1H-benzimidazol-2-amine hydrochloride
LC-MS (Method 2): $R_t$ = 1.18 min; MS (ESIpos): m/z = 444.5 [M + H]$^+$ TABLE 6-continued

| Compound | Structure<br>IUPAC-Name<br>LC-MS (method): Retention time; Mass found |
|---|---|
| Compound 191.01 | 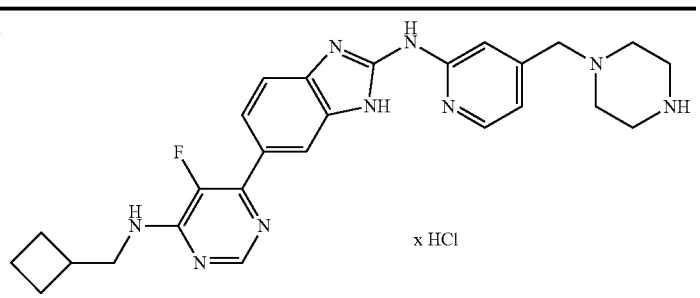<br>6-{6-[(cyclobutylmethyl)amino]-5-fluoropyrimidin-4-yl}-N-[4-(piperazin-1-ylmethyl)pyridin-2-yl]-1H-benzimidazol-2-amine hydrochloride<br>LC-MS (Method 2): $R_t$ = 1.12 min; MS (ESIpos): m/z = 488 [M + H]$^+$ |
| Compound 192.01 | 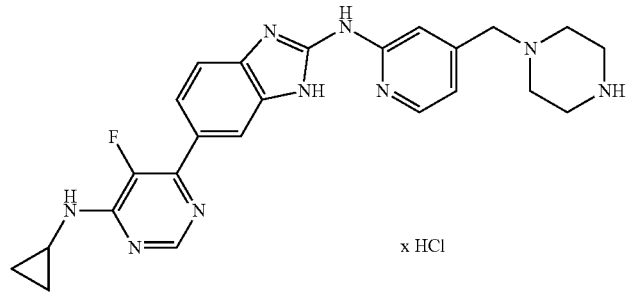 [SMILES: Fc1c(NC2CC2)ncnc1-c1ccc2nc(Nc3cc(CN4CCNCC4)ccn3)[nH]c2c1]<br>6-[6-(cyclopropylamino)-5-fluoropyrimidin-4-yl]-N-[4-(piperazin-1-ylmethyl)pyridin-2-yl]-1H-benzimidazol-2-amine hydrochloride<br>LC-MS (Method 2): $R_t$ = 0.93 min; MS (ESIpos): m/z = 460 [M + H]$^+$ |
| Compound 193.01 | 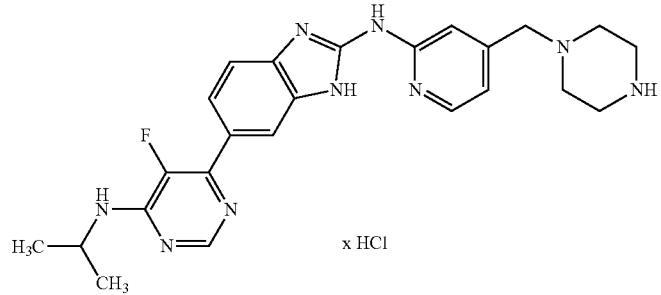 [SMILES: CC(C)Nc1ncnc(-c2ccc3nc(Nc4cc(CN5CCNCC5)ccn4)[nH]c3c2)c1F]<br>6-[5-fluoro-6-(propan-2-ylamino)pyrimidin-4-yl]-N-[4-(piperazin-1-ylmethyl)pyridin-2-yl]-1H-benzimidazol-2-amine hydrochloride<br>LC-MS (Method 2): $R_t$ = 1.02 min; MS (ESIpos): m/z = 462 [M + H]$^+$ |
| Compound 194.01 | 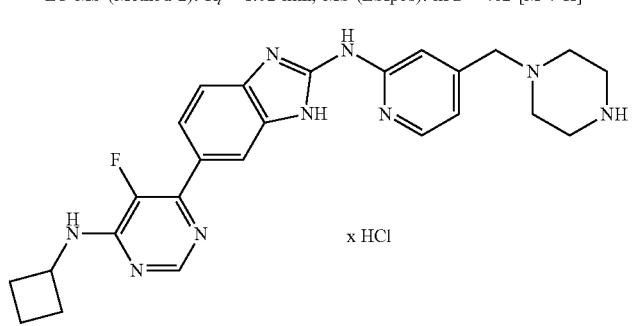<br>6-[6-(cyclobutylamino)-5-fluoropyrimidin-4-yl]-N-[4-(piperazin-1-ylmethyl)pyridin-2-yl]-1H-benzimidazol-2-amine hydrochloride<br>LC-MS (Method 2): $R_t$ = 1.02 min; MS (ESIpos): m/z = 462 [M + H]$^+$ |

TABLE 6-continued

| | Structure<br>IUPAC-Name |
|---|---|
| Compound | LC-MS (method): Retention time; Mass found |

Compound 195.01

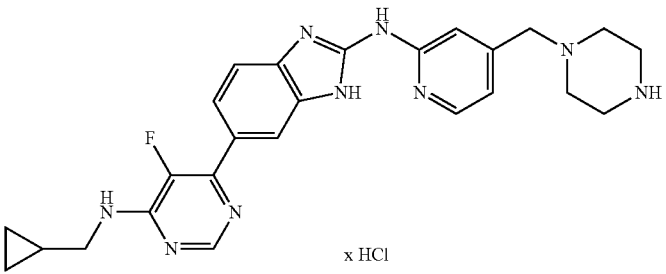 [SMILES: Fc1c(NCC2CC2)ncnc1-c1ccc2nc(Nc3cc(CN4CCNCC4)ccn3)[nH]c2c1]

x HCl

6-{6-[(cyclopropylmethyl)amino]-5-fluoropyrimidin-4-yl}-N-[4-
(piperazin-1-ylmethyl)pyridin-2-yl]-1H-benzimidazol-2-amine
hydrochloride
LC-MS (Method 2): $R_t$ = 1.01 min; MS (ESIpos): m/z = 474 [M + H]$^+$ Compound 196.01

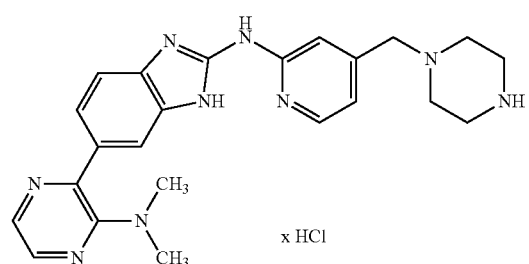

x HCl

6-[3-(dimethylamino)pyrazin-2-yl]-N-[4-(piperazin-1-
ylmethyl)pyridin-2-yl]-1H-benzimidazol-2-amine hydrochloride
LC-MS (Method 2): $R_t$ = 0.98 min; MS (ESIpos): m/z = 430 [M + H]$^+$ Compound 197.01

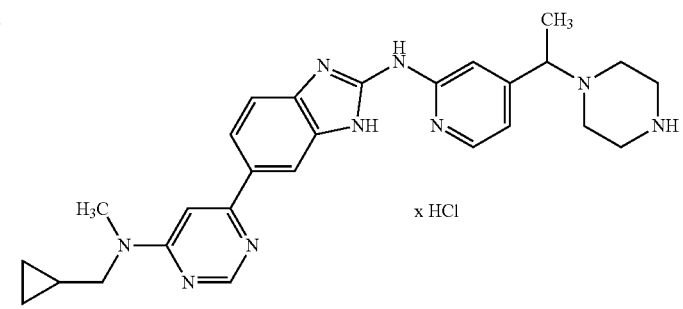 [SMILES: CC(c1ccnc(Nc2nc3ccc(-c4cc(N(C)CC5CC5)ncn4)cc3[nH]2)c1)N1CCNCC1]

x HCl

6-{6-[(cyclopropylmethyl)(methyl)amino]pyrimidin-4-yl}-N-{4-[(1R
or 1S)-1-(piperazin-1-yl)ethyl]pyridin-2-yl}-1H-benzimidazol-2-
amine hydrochloride
LC-MS (Method 2): $R_t$ = 1.07 min; MS (ESIpos): m/z = 484 [M + H]$^+$ Compound 199.01

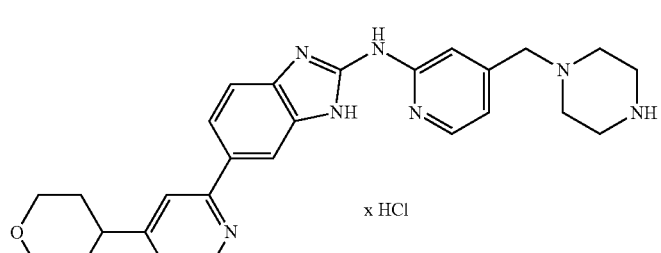

x HCl

N-[4-(piperazin-1-ylmethyl)pyridin-2-yl]-6-[6-(tetrahydro-2H-pyran-
4-yl)pyrimidin-4-yl]-1H-benzimidazol-2-amine hydrochloride
LC-MS (Method 2): $R_t$ = 0.88 min; MS (ESIpos): m/z = 471 [M + H]$^+$

Experimental Section—Description of Examples

Example 01.01 tert-butyl 4-[(2-{[6-(2-methylpyridin-4-yl)-1H-benzimidazol-2-yl]amino}pyridin-4-yl)methyl]piperazine-1-carboxylate

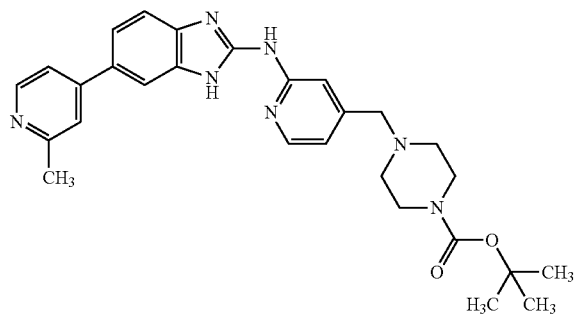 [SMILES: Cc1cc(-c2ccc3nc(Nc4cc(CN5CCN(C(=O)OC(C)(C)C)CC5)ccn4)[nH]c3c2)ccn1]

To a stirred solution of 4-bromo-2-methylpyridine (225 mg, 1.31 mmol) and tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 μmol) in dioxane (4.5 mL) and water (910 μl) was added sodium carbonate (297 mg, 2.81 mmol) and Pd(dppf) $C_2 \cdot CH_2Cl_2$ (115 mg, 140 μmol). The mixture was heated to reflux for 19 h. Dichloromethane was added, the mixture was filtered and the solvent was removed in vacuum. Aminophase-silicagel chromatography followed by preparative reverse phase HPLC (gradient of water and acetonitrile containing ammonia as additive) gave 21.0 mg (4% yield) of the title compound.

LC-MS (Method 2): $R_t$=1.24 min; MS (ESIpos): m/z=500 $[M+H]^+$.

$^1$H-NMR (400 MHz, DMSO-d6) δ [ppm]: 1.395 (16.00), 2.359 (2.40), 2.525 (9.91), 3.501 (2.39), 7.181 (1.30), 8.260 (0.95), 8.273 (0.95).

Example 01.02 cyclopropyl{4-[(2-{[6-(2-methylpyridin-4-yl)-1H-benzimidazol-2-yl]amino}pyridin-4-yl)methyl]piperazin-1-yl}methanone

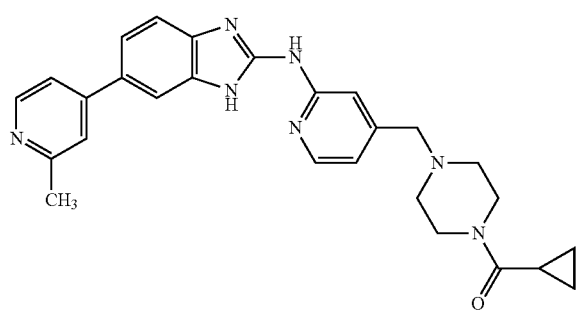 [SMILES: Cc1cc(-c2ccc3nc(Nc4cc(CN5CCN(C(=O)C6CC6)CC5)ccn4)[nH]c3c2)ccn1]

To a stirred solution of crude 6-(2-methylpyridin-4-yl)-N-[4-(piperazin-1-ylmethyl)pyridin-2-yl]-1H-benzimidazol-2-amine hydrochloride (81.0 mg, approx. 186 μmol) in DMF (4 mL) was added sodium bicarbonate (93.6 mg, 1.11 mmol), cyclopropanecarboxylic acid (24.0 mg, 279 μmol) and HATU (106 mg, 279 μmol). The mixture was stirred at room temperature for 16 h.

Water was added, the mixture was stirred for 15 minutes and the mixture was extracted with dichloromethane. The organic phase was washed with saturated sodium chloride solution, dried (sodium sulfate) and the solvent was removed in vacuum. Preparative reverse phase HPLC (gradient of water and acetonitrile containing ammonia as additive) gave 19 mg of the title compound.

LC-MS (Method 4): $R_t$=1.01 min; MS (ESIpos): m/z=468 $[M+H]^+$.

$^1$H-NMR (400 MHz, DMSO-d6) δ [ppm]: 0.678 (1.22), 0.685 (2.83), 0.691 (1.78), 0.698 (1.46), 0.705 (3.54), 0.709 (2.98), 0.713 (3.28), 0.721 (3.07), 0.726 (3.50), 0.733 (1.59), 1.949 (0.64), 1.956 (0.71), 1.969 (1.20), 1.981 (0.69), 2.323 (0.97), 2.327 (1.39), 2.332 (1.09), 2.366 (1.35), 2.446 (1.31), 2.518 (7.34), 2.526 (16.00), 2.539 (1.63), 2.665 (0.90), 2.669 (1.31), 2.673 (0.92), 3.525 (5.51), 3.710 (1.24), 6.946 (1.27), 6.959 (1.31), 7.202 (2.60), 7.457 (0.92), 8.271 (2.47), 8.284 (2.34), 8.439 (0.99).

Example 01.03

3,3,3-trifluoro-1-{4-[(2-{[6-(2-methylpyridin-4-yl)-1H-benzimidazol-2-yl]amino}pyridin-4-yl)methyl]piperazin-1-yl}propan-1-one

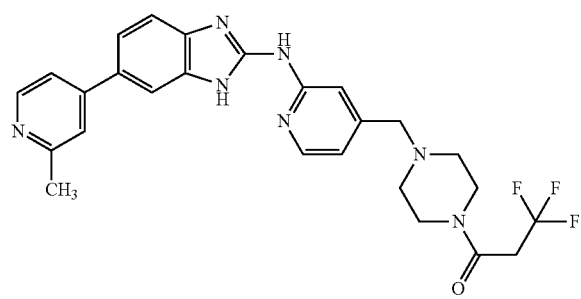 [SMILES: Cc1cc(-c2ccc3nc(Nc4cc(CN5CCN(C(=O)CC(F)(F)F)CC5)ccn4)[nH]c3c2)ccn1]

Starting with crude 6-(2-methylpyridin-4-yl)-N-[4-(piperazin-1-ylmethyl)pyridin-2-yl]-1H-benzimidazol-2-amine hydrochloride (81.0 mg, approx. 186 μmol) and 3,3,3-trifluoropropanoic acid (35.7 mg, 279 μmol), Example 01.03 was prepared analogously to the procedure for the preparation of Example 01.02.

Yield: 33.0 mg of the title compound.

LC-MS (Method 2): $R_t$=1.05 min; MS (ESIpos): m/z=510 $[M+H]^+$.

$^1$H-NMR (400 MHz, DMSO-d6) δ[ppm]: 2.322 (0.95), 2.327 (1.44), 2.332 (1.06), 2.370 (1.25), 2.383 (1.89), 2.395 (1.44), 2.411 (1.23), 2.425 (1.75), 2.437 (1.51), 2.518 (8.20), 2.525 (16.00), 2.539 (1.80), 2.665 (0.99), 2.669 (1.44), 2.673 (1.04), 3.472 (1.54), 3.484 (1.58), 3.510 (1.84), 3.526 (5.15), 3.613 (0.73), 3.640 (2.03), 3.667 (1.89), 4.050 (2.34), 6.936 (1.06), 6.949 (1.11), 7.197 (2.10), 7.457 (0.90), 8.267 (2.10), 8.281 (2.03), 8.439 (0.90).

Example 01.04

2-cyclopropyl-1-{4-[(2-{[6-(2-methylpyridin-4-yl)-1H-benzimidazol-2-yl]amino}pyridin-4-yl)methyl]piperazin-1-yl}ethanone

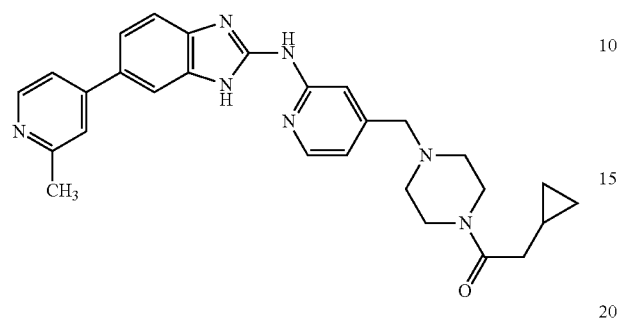

Starting with crude 6-(2-methylpyridin-4-yl)-N-[4-(piperazin-1-ylmethyl)pyridin-2-yl]-1H-benzimidazol-2-amine hydrochloride (81.0 mg, approx. 186 μmol) and cyclopropylacetic acid (27.9 mg, 279 μmol), Example 01.04 was prepared analogously to the procedure for the preparation of Example 01.02.

Yield: 10.0 mg of the title compound.

LC-MS (Method 4): $R_t$=1.05 min; MS (ESIpos): m/z=482 [M+H]$^+$.

$^1$H-NMR (400 MHz, DMSO-d6) δ[ppm]: 0.000 (0.93), 0.011 (3.08), 0.014 (2.78), 0.023 (3.17), 0.026 (2.88), 0.037 (1.07), 0.330 (1.15), 0.340 (2.73), 0.344 (2.82), 0.350 (1.53), 0.355 (1.38), 0.360 (2.93), 0.364 (2.77), 0.375 (1.11), 0.854 (1.02), 2.154 (4.93), 2.171 (4.75), 2.238 (0.86), 2.242 (1.22), 2.247 (0.93), 2.277 (2.02), 2.290 (1.82), 2.310 (2.02), 2.434 (5.35), 2.441 (16.00), 2.580 (0.80), 2.584 (1.13), 2.589 (0.80), 3.372 (1.98), 3.383 (1.80), 3.407 (1.97), 3.426 (5.59), 6.852 (1.26), 6.865 (1.31), 7.109 (2.69), 7.370 (0.96), 8.181 (2.51), 8.194 (2.44), 8.356 (0.98).

Example 01.05 cyclobutyl{4-[(2-{[6-(2-methyl pyridin-4-yl)-1H-benzimidazol-2-yl]amino}pyridin-4-yl)methyl]piperazin-1-yl}methanone

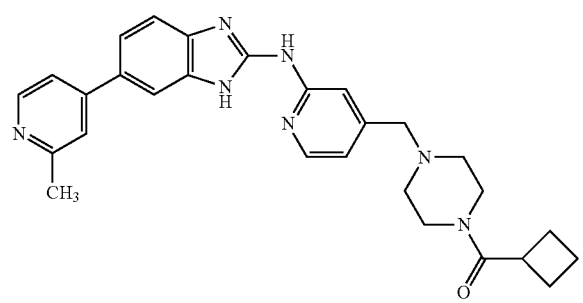 [SMILES: Cc1cc(-c2ccc3nc(Nc4cc(CN5CCN(C(=O)C6CCC6)CC5)ccn4)[nH]c3c2)ccn1]

Starting with crude 6-(2-methylpyridin-4-yl)-N-[4-(piperazin-1-ylmethyl)pyridin-2-yl]-1H-benzimidazol-2-amine hydrochloride (81.0 mg, approx. 186 μmol) and cyclobutanecarboxylic acid (27.9 mg, 279 μmol), Example 01.05 was prepared analogously to the procedure for the preparation of Example 01.02.

Yield: 31.0 mg of the title compound.

LC-MS (Method 4): $R_t$=1.08 min; MS (ESIpos): m/z=482 [M+H]$^+$.

$^1$H-NMR (400 MHz, DMSO-d6) δ [ppm]: 1.862 (1.09), 1.884 (0.84), 1.889 (0.82), 2.052 (1.21), 2.061 (0.94), 2.075 (1.43), 2.083 (1.14), 2.100 (0.93), 2.106 (0.84), 2.123 (1.62), 2.128 (1.12), 2.145 (1.75), 2.169 (0.84), 2.174 (0.91), 2.322 (0.91), 2.327 (1.41), 2.332 (1.50), 2.337 (1.96), 2.352 (3.28), 2.518 (6.90), 2.525 (16.00), 2.539 (1.87), 2.665 (0.73), 2.669 (1.05), 2.673 (0.75), 3.305 (1.05), 3.473 (1.75), 3.485 (1.66), 3.500 (4.99), 6.930 (1.27), 6.944 (1.28), 7.188 (2.49), 8.262 (2.23), 8.275 (2.24), 8.438 (1.18), 8.451 (1.18).

Example 02.01 tert-butyl 4-[(2-{[6-(2-methoxypyridin-4-yl)-1H-benzimidazol-2-yl]amino}pyridin-4-yl)methyl]piperazine-1-carboxylate

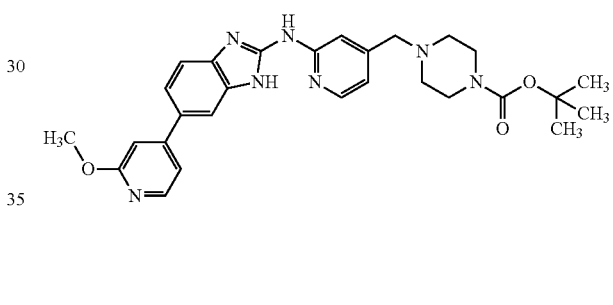

To a stirred solution of 1H-imidazole (83.8 mg, 1.23 mmol) and di-1H-imidazol-1-ylmethanethione (1.58 g, 90% purity, 8.00 mmol) in dichloromethane (50 mL) was added tert-butyl 4-[(2-aminopyridin-4-yl)methyl]piperazine-1-carboxylate (1.80 g, 6.16 mmol) dissolved in dichloromethane (50 mL) at 0° C. The mixture was stirred at r.t. for 14 h. 4-(2-methoxypyridin-4-yl)benzene-1,2-diamine (1.78 g, 97% purity, 8.00 mmol) dissolved in dichloromethane (27 mL) was added and the mixture was stirred at r.t. for 2 h. Water was added and the mixture was extracted with dichloromethane. The organic phase was dried (sodium sulfate) and filtered. N,N'-dipropan-2-ylcarbodiimide (1.33 mL, 8.8 mmol) was added. The mixture was stirred at r.t. for 14 h. Further N,N'-dipropan-2-ylcarbodiimide (0.47 mL, 3.1 mmol) was added and the mixture was stirred at r.t. for 14 h. Saturated ammonium chloride solution was added, the mixture was stirred for 30 minutes and was extracted with dichloromethane. Aminophase-silicagel chromatography gave 585 mg of the title compound.

LC-MS (Method 2): $R_t$=1.33 min; MS (ESIpos): m/z=516 [M+H]$^+$.

$^1$H-NMR (400 MHz, DMSO-d6) δ[ppm]: 1.390 (1.33), 1.396 (16.00), 2.347 (0.86), 2.360 (1.27), 2.372 (0.94), 3.321 (7.45), 3.501 (1.68), 3.894 (5.54), 5.756 (0.92), 7.194 (0.84), 8.177 (0.60), 8.190 (0.57), 8.261 (0.75), 8.273 (0.74).

Example 02.02 cyclopropyl{4-[(2-{[6-(2-methoxypyridin-4-yl)-1H-benzimidazol-2-yl]amino}pyridin-4-yl)methyl]piperazin-1-yl}methanone

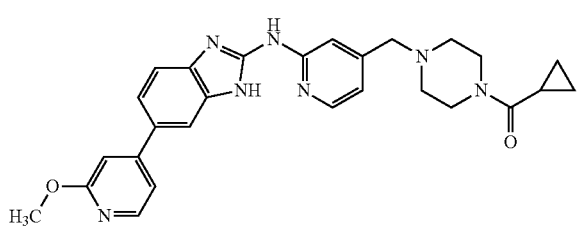 [SMILES: COc1cc(-c2ccc3nc(Nc4cc(CN5CCN(C(=O)C6CC6)CC5)ccn4)[nH]c3c2)ccn1]

To a stirred solution of 6-(2-methoxypyridin-4-yl)-N-[4-(piperazin-1-ylmethyl)pyridin-2-yl]-1H-benzimidazol-2-amine hydrochloride (100 mg, 221 µmol) in DMF (8 mL) was added potassium carbonate (153 mg, 1.11 mmol), cyclopropanecarboxylic acid (57.1 mg, 664 µmol) and HATU (252 mg, 664 µmol). The mixture was stirred at room temperature for 16 h. Water was added, the mixture was stirred for 15 minutes and the mixture was extracted with ethyl acetate. The organic phase was washed with saturated sodium chloride solution, dried (sodium sulfate) and the solvent was removed in vacuum. Aminophase-silicagel chromatography gave a solid that was triturated with dichloromethane to give 73.0 mg (61% yield) of the title compound.

LC-MS (Method 2): $R_t$=1.10 min; MS (ESIpos): m/z=484 [M+H]$^+$.

$^1$H-NMR (400 MHz, DMSO-d6) δ[ppm]: 0.677 (1.07), 0.685 (2.44), 0.691 (1.47), 0.698 (1.20), 0.705 (2.94), 0.710 (2.22), 0.716 (2.52), 0.723 (2.46), 0.728 (2.97), 0.735 (1.36), 1.940 (0.61), 1.948 (0.65), 1.960 (1.10), 1.972 (0.61), 1.979 (0.56), 2.370 (1.02), 2.444 (1.02), 2.523 (1.00), 3.525 (5.78), 3.712 (0.90), 3.896 (16.00), 6.942 (1.34), 6.945 (1.41), 6.958 (1.42), 7.065 (0.72), 7.218 (2.61), 8.177 (2.02), 8.191 (1.93), 8.270 (2.35), 8.283 (2.26).

Example 02.03

3,3,3-trifluoro-1-{4-[(2-{[6-(2-methoxypyridin-4-yl)-1H-benzimidazol-2-yl]amino}pyridin-4-yl)methyl]piperazin-1-yl}propan-1-one

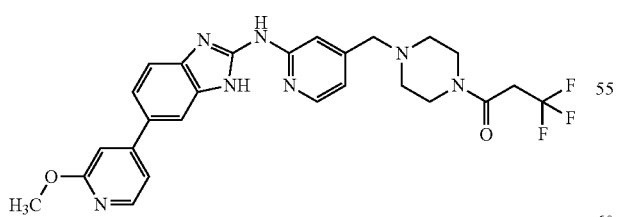

Starting with 6-(2-methoxypyridin-4-yl)-N-[4-(piperazin-1-ylmethyl)pyridin-2-yl]-1H-benzimidazol-2-amine hydrochloride (100.0 mg, 221 µmol) and 3,3,3-trifluoropropanoic acid (85.0 mg, 664 µmol) Example 02.03. was prepared analogously to the procedure for the preparation of Example 02.02.

Yield: 50.0 mg (39%) of the title compound.

LC-MS (Method 2): $R_t$=1.14 min; MS (ESIpos): m/z=526 [M+H]$^+$.

$^1$H-NMR (400 MHz, DMSO-d6) δ[ppm]: 2.375 (1.20), 2.388 (1.81), 2.400 (1.37), 2.415 (1.32), 2.523 (1.07), 3.463 (1.28), 3.477 (1.77), 3.487 (1.46), 3.499 (1.44), 3.513 (1.80), 3.528 (5.65), 3.601 (0.93), 3.628 (2.68), 3.656 (2.52), 3.683 (0.79), 3.896 (16.00), 6.935 (1.30), 6.948 (1.36), 6.951 (1.36), 7.213 (2.45), 8.178 (1.79), 8.191 (1.73), 8.268 (2.24), 8.282 (2.14).

Example 02.04 cyclobutyl{4-[(2-{[6-(2-methoxypyridin-4-yl)-1H-benzimidazol-2-yl]amino}pyridin-4-yl)methyl]piperazin-1-yl}methanone

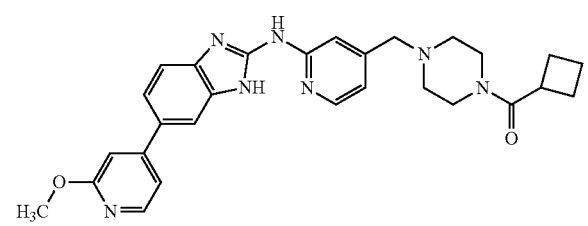 [SMILES: COc1cc(-c2ccc3nc(Nc4cc(CN5CCN(C(=O)C6CCC6)CC5)ccn4)[nH]c3c2)ccn1]

Starting with 6-(2-methoxypyridin-4-yl)-N-[4-(piperazin-1-ylmethyl)pyridin-2-yl]-1H-benzimidazol-2-amine hydrochloride (100 mg, 221 µmol) and cyclobutanecarboxylic acid (66.5 mg, 664 µmol) Example 02.04. was prepared analogously to the procedure for the preparation of Example 02.02.

Yield: 86.0 mg (70%) of the title compound.

LC-MS (Method 2): $R_t$=1.17 min; MS (ESIpos): m/z=498 [M+H]$^+$.

$^1$H-NMR (400 MHz, DMSO-d6) δ[ppm]: 1.737 (0.74), 1.841 (0.61), 1.862 (1.19), 1.885 (0.92), 1.889 (0.90), 1.912 (0.55), 2.045 (0.76), 2.054 (1.31), 2.063 (0.96), 2.069 (0.95), 2.076 (1.50), 2.085 (1.15), 2.100 (0.83), 2.104 (0.91), 2.126 (1.72), 2.131 (1.16), 2.147 (1.83), 2.152 (1.44), 2.171 (0.86), 2.177 (0.96), 2.354 (4.04), 2.366 (2.89), 2.523 (0.83), 3.301 (1.52), 3.308 (16.00), 3.322 (2.50), 3.341 (2.57), 3.474 (1.87), 3.487 (1.59), 3.499 (6.14), 6.925 (1.60), 6.928 (1.58), 6.938 (1.63), 6.941 (1.61), 7.062 (0.76), 7.204 (2.97), 7.309 (0.71), 7.465 (0.70), 8.177 (2.26), 8.190 (2.15), 8.261 (2.63), 8.274 (2.52).

Example 02.05

2-cyclopropyl-1-{4-[(2-{[6-(2-methoxypyridin-4-yl)-1H-benzimidazol-2-yl]amino}pyridin-4-yl)methyl]piperazin-1-yl}ethanone

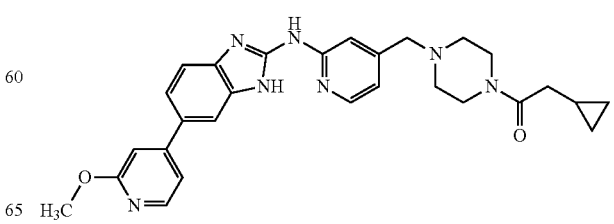

Starting with 6-(2-methoxypyridin-4-yl)-N-[4-(piperazin-1-ylmethyl)pyridin-2-yl]-1H-benzimidazol-2-amine hydrochloride (100 mg, 221 µmol) and cyclopropylacetic acid (66.5 mg, 664 µmol) Example 02.05. was prepared analogously to the procedure for the preparation of Example 02.02.

Yield: 69.0 mg (56%) of the title compound.

LC-MS (Method 2): $R_t$=1.14 min; MS (ESIpos): m/z=498 [M+H]⁺.

¹H-NMR (400 MHz, DMSO-d6) δ[ppm]: 0.000 (0.73), 0.011 (2.69), 0.014 (2.40), 0.023 (2.71), 0.026 (2.45), 0.037 (0.85), 0.329 (0.90), 0.339 (2.35), 0.343 (2.41), 0.349 (1.18), 0.354 (1.12), 0.359 (2.44), 0.364 (2.34), 0.374 (0.84), 0.855 (0.84), 2.151 (4.45), 2.168 (4.38), 2.279 (1.83), 2.291 (1.78), 2.309 (1.84), 2.436 (0.85), 3.370 (1.75), 3.404 (1.78), 3.425 (5.75), 3.809 (16.00), 6.846 (1.46), 6.859 (1.51), 6.976 (0.77), 7.123 (2.67), 7.222 (0.66), 7.379 (0.68), 8.090 (2.07), 8.104 (1.97), 8.177 (2.42), 8.191 (2.31).

Example 03.01 cyclopropyl{4-[(2-{[6-(5-fluoro-2-methoxypyridin-4-yl)-1H-benzimidazol-2-yl]amino}pyridin-4-yl)methyl]piperazin-1-yl}methanone

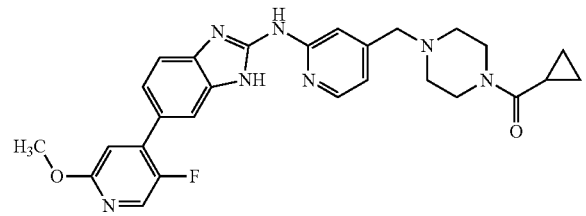 [SMILES: COc1cc(-c2ccc3nc(Nc4cc(CN5CCN(C(=O)C6CC6)CC5)ccn4)[nH]c3c2)c(F)cn1]

Starting with crude 6-(5-fluoro-2-methoxypyridin-4-yl)-N-[4-(piperazin-1-ylmethyl)pyridin-2-yl]-1H-benzimidazol-2-amine hydrochloride (150 mg, approx. 239 µmol) and cyclopropanecarboxylic acid (30 µl, 95% purity, 360 µmol) Example 03.01. was prepared analogously to the procedure for the preparation of Example 16.01.02.

Yield: 60.0 mg of the title compound.

LC-MS (Method 2): $R_t$=1.18 min; MS (ESIpos): m/z=502 [M+H]⁺.

¹H-NMR (400 MHz, DMSO-d6) δ[ppm]: 0.676 (1.05), 0.683 (2.38), 0.689 (1.42), 0.696 (1.18), 0.703 (2.86), 0.709 (2.14), 0.714 (2.45), 0.721 (2.40), 0.726 (2.85), 0.733 (1.30), 1.028 (0.98), 1.044 (1.01), 1.961 (1.06), 3.523 (5.42), 3.879 (16.00), 6.944 (1.46), 6.947 (1.39), 6.957 (1.54), 6.959 (1.56), 7.200 (2.45), 8.205 (2.04), 8.211 (1.91), 8.270 (2.36), 8.283 (2.22).

Example 03.02

3,3,3-trifluoro-1-{4-[(2-{[6-(5-fluoro-2-methoxy-pyridin-4-yl)-1H-benzimidazol-2-yl]amino}pyridin-4-yl)methyl]piperazin-1-yl}propan-1-one

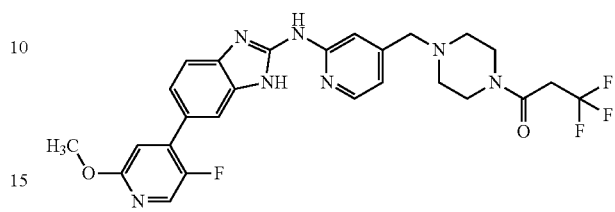

Starting with crude 6-(5-fluoro-2-methoxypyridin-4-yl)-N-[4-(piperazin-1-ylmethyl)pyridin-2-yl]-1H-benzimidazol-2-amine hydrochloride (150 mg, approx. 239 µmol) and 3,3,3-trifluoropropanoic acid (32 µl, 360 µmol) Example 03.02. was prepared analogously to the procedure for the preparation of Example 16.01.02.

Yield: 30.0 mg of the title compound.

LC-MS (Method 2): $R_t$=1.21 min; MS (ESIpos): m/z=544 [M+H]⁺.

¹H-NMR (400 MHz, DMSO-d6) δ[ppm]: 0.856 (0.76), 1.028 (1.39), 1.044 (1.44), 2.371 (1.33), 2.384 (2.03), 2.397 (1.53), 2.413 (1.49), 2.425 (1.97), 2.437 (1.43), 3.461 (1.47), 3.473 (1.98), 3.485 (1.64), 3.496 (1.61), 3.511 (2.06), 3.526 (5.91), 3.606 (0.95), 3.633 (2.72), 3.661 (2.55), 3.879 (16.00), 6.937 (1.47), 6.940 (1.53), 6.953 (1.58), 7.196 (2.70), 8.205 (1.96), 8.211 (1.84), 8.269 (2.46), 8.282 (2.33).

Example 03.03 cyclobutyl{4-[(2-{[6-(5-fluoro-2-methoxypyridin-4-yl)-1H-benzimidazol-2-yl]amino}pyridin-4-yl)methyl]piperazin-1-yl}methanone

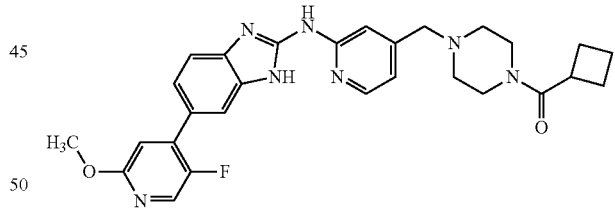

Starting with 6-(5-fluoro-2-methoxypyridin-4-yl)-N-[4-(piperazin-1-ylmethyl)pyridin-2-yl]-1H-benzimidazol-2-amine (100 mg, 231 µmol) and cyclobutanecarboxylic acid (34 µl, 98% purity, 350 µmol) Example 03.03. was prepared analogously to the procedure for the preparation of Example 16.01.02.

Yield: 60.0 mg of the title compound.

LC-MS (Method 2): $R_t$=1.25 min; MS (ESIpos): m/z=516 [M+H]⁺.

¹H-NMR (400 MHz, DMSO-d6) δ [ppm]: 0.831 (1.05), 0.858 (1.79), 0.936 (0.93), 0.953 (0.94), 1.239 (1.12), 1.396 (1.84), 1.728 (1.02), 1.863 (1.15), 2.054 (1.23), 2.076 (1.41), 2.085 (1.18), 2.126 (1.59), 2.147 (1.68), 2.177 (0.91), 2.355 (3.84), 2.539 (4.86), 2.730 (5.68), 2.889 (6.74), 3.323 (2.68), 3.342 (2.54), 3.474 (1.83), 3.501 (5.83), 3.879 (16.00), 5.752 (1.24), 6.928 (1.49), 6.944 (1.58), 7.192 (2.44), 7.952 (0.90), 8.201 (2.14), 8.208 (2.06), 8.261 (2.55), 8.275 (2.46).

Example 03.04

2-cyclopropyl-1-{4-[(2-{[6-(5-fluoro-2-methoxy-pyridin-4-yl)-1H-benzimidazol-2-yl]amino}pyridin-4-yl)methyl]piperazin-1-yl}ethanone

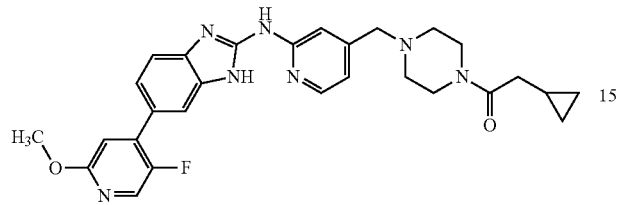

Starting with 6-(5-fluoro-2-methoxypyridin-4-yl)-N-[4-(piperazin-1-ylmethyl)pyridin-2-yl]-1H-benzimidazol-2-amine (100 mg, 231 µmol) and cyclopropylacetic acid (33 µl, 97% purity, 350 µmol) Example 03.04. was prepared analogously to the procedure for the preparation of Example 16.01.02.

Yield: 60.0 mg of the title compound.

LC-MS (Method 2): $R_t$=1.21 min; MS (ESIpos): m/z=516 [M+H]$^+$.

$^1$H-NMR (400 MHz, DMSO-d6) δ[ppm]: 0.011 (2.48), 0.014 (2.36), 0.023 (2.63), 0.027 (2.39), 0.037 (0.84), 0.330 (0.81), 0.339 (2.14), 0.343 (2.28), 0.350 (1.10), 0.354 (1.05), 0.360 (2.32), 0.364 (2.27), 0.374 (0.81), 0.744 (1.35), 0.766 (1.05), 0.771 (2.20), 0.850 (1.44), 0.855 (0.86), 0.866 (1.56), 1.152 (1.33), 1.310 (1.98), 2.152 (4.27), 2.168 (4.16), 2.279 (1.90), 2.309 (1.99), 3.425 (5.80), 3.793 (16.00), 5.665 (0.69), 6.848 (1.50), 6.864 (1.60), 7.111 (2.58), 8.115 (2.21), 8.121 (2.10), 8.179 (2.49), 8.192 (2.37).

Example 04.01 tert-butyl 4-[(2-{[6-(3-methoxypyridin-4-yl)-1H-benzimidazol-2-yl]amino}pyridin-4-yl)methyl]piperazine-1-carboxylate

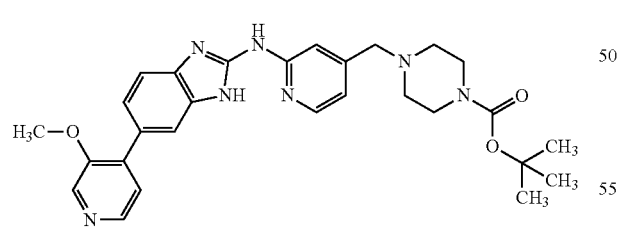

To a stirred solution of N-[4-(chloromethyl)pyridin-2-yl]-6-(3-methoxypyridin-4-yl)-1H-benzimidazol-2-amine (870 mg, 2.38 mmol) in DMF (20 mL) was added potassium carbonate (1.64 g, 11.9 mmol) and tert-butyl piperazine-1-carboxylate (685 mg, 97% purity, 3.57 mmol). The mixture was stirred at r.t. for 14 h. Water was added, and a solid precipitated and was collected by filtration. Ethyl acetate/methanol (1:1) was added to the solid and the mixture was stirred for 15 minutes. Solids were removed by filtration, and the solution was concentrated in vacuum. Silicagel chromatography gave 800 mg (59% yield) of the title compound.

LC-MS (Method 2): $R_t$=1.25 min; MS (ESIpos): m/z=516 [M+H]$^+$.

$^1$H-NMR (400 MHz, DMSO-d6) δ[ppm]: 1.039 (1.85), 1.056 (4.16), 1.074 (2.09), 1.396 (16.00), 2.349 (0.92), 2.361 (1.36), 2.374 (0.98), 2.730 (2.27), 2.889 (2.88), 3.312 (7.39), 3.427 (0.85), 3.439 (0.91), 3.444 (0.91), 3.457 (0.91), 3.499 (1.84), 3.905 (4.57), 4.320 (0.59), 4.332 (1.12), 4.346 (0.55), 6.913 (0.54), 6.916 (0.54), 6.926 (0.55), 6.930 (0.55), 7.189 (0.68), 7.357 (0.76), 7.369 (0.80), 8.248 (1.27), 8.254 (0.96), 8.260 (1.22), 8.268 (0.86), 8.434 (1.93).

Example 04.02

3,3,3-trifluoro-1-{4-[(2-{[6-(3-methoxypyridin-4-yl)-1H-benzimidazol-2-yl]amino}pyridin-4-yl)methyl]piperazin-1-yl}propan-1-one

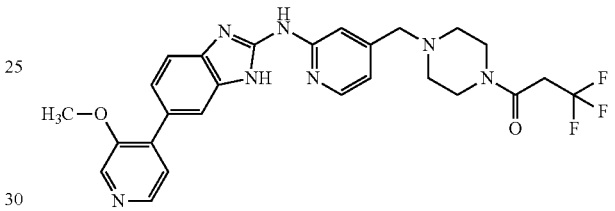

Starting with crude 6-(3-methoxypyridin-4-yl)-N-[4-(piperazin-1-ylmethyl)pyridin-2-yl]-1H-benzimidazol-2-amine hydrochloride (100 mg, approx. 191 µmol) and 3,3,3-trifluoropropanoic acid (26 µl, 98% purity, 290 µmol) Example 04.02. was prepared analogously to the procedure for the preparation of Example 16.01.02.

Yield: 50.0 mg of the title compound.

LC-MS (Method 2): $R_t$=1.07 min; MS (ESIpos): m/z=526 [M+H]$^+$.

$^1$H-NMR (400 MHz, DMSO-d$_6$): δ [ppm]=2.40 (dt, 4H), 3.43-3.55 (m, 6H), 3.63 (q, 2H), 3.90 (s, 3H), 6.92 (d, 1H), 7.15-7.85 (m, 5H), 8.19-8.30 (m, 2H), 8.42 (s, 1H), 10.63 (br s, 1H), 12.15 (br s, 1H).

Example 04.03 cyclopropyl{4-[(2-{[6-(3-methoxypyridin-4-yl)-1H-benzimidazol-2-yl]amino}pyridin-4-yl)methyl]piperazin-1-yl}methanone

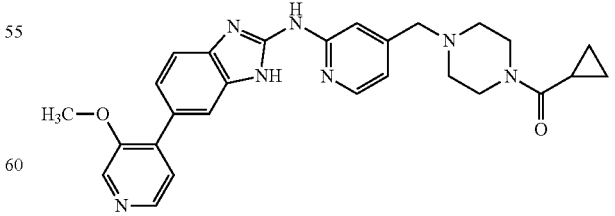

Starting with crude 6-(3-methoxypyridin-4-yl)-N-[4-(piperazin-1-ylmethyl)pyridin-2-yl]-1H-benzimidazol-2-amine hydrochloride (100 mg, approx. 191 µmol) and cyclopropanecarboxylic acid (24 µl, 95% purity, 290 µmol) Example 04.03. was prepared analogously to the procedure for the preparation of Example 16.01.02.

Yield: 60.0 mg of the title compound.

LC-MS (Method 2): $R_t$=1.03 min; MS (ESIneg): m/z=482 [M−H]⁺.

¹H-NMR (400 MHz, DMSO-d6) δ[ppm]: 0.685 (1.11), 0.690 (0.81), 0.698 (0.66), 0.705 (1.33), 0.710 (1.10), 0.717 (1.25), 0.723 (1.24), 0.729 (1.40), 0.735 (0.72), 1.396 (16.00), 3.523 (2.74), 3.907 (5.91), 5.752 (2.33), 6.935 (0.73), 6.949 (0.74), 7.207 (1.16), 7.358 (1.03), 7.370 (1.08), 8.249 (1.28), 8.261 (1.65), 8.278 (1.02), 8.435 (2.20).

Example 04.04 cyclobutyl{4-[(2-{[6-(3-methoxypyridin-4-yl)-1H-benzimidazol-2-yl]amino}pyridin-4-yl)methyl]piperazin-1-yl}methanone

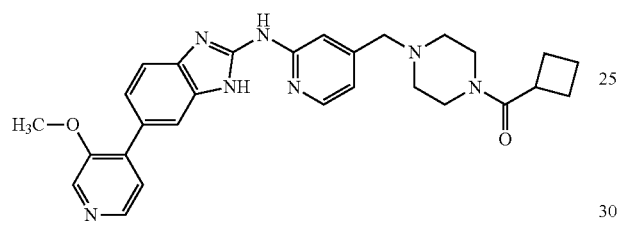

Starting with crude 6-(3-methoxypyridin-4-yl)-N-[4-(piperazin-1-ylmethyl)pyridin-2-yl]-1H-benzimidazol-2-amine hydrochloride (100 mg, approx. 191 μmol) and cyclobutanecarboxylic acid (28 μl, 97% purity, 290 μmol) Example 04.04. was prepared analogously to the procedure for the preparation of Example 16.01.02.

Yield: 40.0 mg of the title compound.

LC-MS (Method 2): $R_t$=1.09 min; MS (ESIpos): m/z=498 [M+H]⁺.

¹H-NMR (400 MHz, DMSO-d₆): δ [ppm]=1.66-1.78 (m, 1H), 1.80-1.95 (m, 1H), 1.99-2.21 (m, 4H), 2.29-2.41 (m, 4H), 3.32 (br d, 3H), 3.42-3.53 (m, 4H), 3.84-3.94 (m, 3H), 6.91 (d, 1H), 7.12-7.81 (m, 5H), 8.25 (dd, 2H), 8.42 (s, 1H), 10.62 (br s, 1H), 12.16 (br s, 1H).

Example 04.05

2-cyclopropyl-1-{4-[(2-{[6-(3-methoxypyridin-4-yl)-1H-benzimidazol-2-yl]amino}pyridin-4-yl)methyl]piperazin-1-yl}ethanone

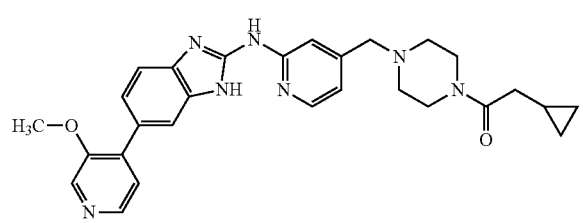 [SMILES: COc1cnccc1-c1ccc2nc(Nc3cc(CN4CCN(C(=O)CC5CC5)CC4)ccn3)[nH]c2c1]

Starting with crude 6-(3-methoxypyridin-4-yl)-N-[4-(piperazin-1-ylmethyl)pyridin-2-yl]-1H-benzimidazol-2-amine hydrochloride (100 mg, approx. 191 μmol) and cyclopropylacetic acid (26 μl, 98% purity, 290 μmol) Example 04.05. was prepared analogously to the procedure for the preparation of Example 16.01.02.

Yield: 40.0 mg of the title compound.

LC-MS (Method 2): $R_t$=1.07 min; MS (ESIpos): m/z=498 [M+H]⁺.

¹H-NMR (400 MHz, DMSO-d₆): δ [ppm]=0.09 (q, 2H), 0.37-0.47 (m, 2H), 0.90-0.96 (m, 1H), 2.24 (d, 2H), 2.32-2.43 (m, 4H), 3.39-3.62 (m, 6H), 3.90 (s, 3H), 6.92 (d, 1H), 7.15-7.30 (m, 2H), 7.32-7.84 (m, 3H), 8.18-8.32 (m, 2H), 8.42 (s, 1H), 10.63 (br s, 1H), 12.15 (br s, 1H).

Example 04.06

1-{4-[(2-{[6-(3-methoxypyridin-4-yl)-1H-benzimidazol-2-yl]amino}pyridin-4-yl)methyl]piperazin-1-yl}-2,2-dimethylpropan-1-one

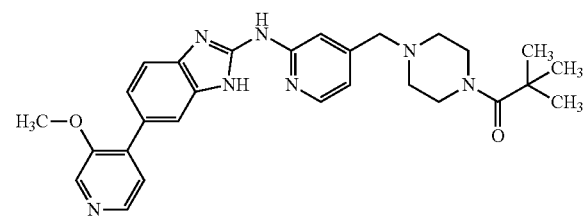 [SMILES: COc1cnccc1-c1ccc2nc(Nc3cc(CN4CCN(C(=O)C(C)(C)C)CC4)ccn3)[nH]c2c1]

Starting with crude 6-(3-methoxypyridin-4-yl)-N-[4-(piperazin-1-ylmethyl)pyridin-2-yl]-1H-benzimidazol-2-amine hydrochloride (80.0 mg, approx. 152 μmol) and 2,2-dimethylpropanoic acid (26 μl, 230 μmol) Example 04.06. was prepared analogously to the procedure for the preparation of Example 16.01.02.

Yield: 23.0 mg of the title compound.

LC-MS (Method 2): $R_t$=1.13 min; MS (ESIpos): m/z=500 [M+H]⁺.

¹H-NMR (400 MHz, DMSO-d6) δ[ppm]: 1.184 (16.00), 2.373 (0.92), 2.385 (1.40), 2.397 (0.98), 3.497 (2.02), 3.572 (1.14), 3.906 (3.59), 6.926 (0.61), 6.929 (0.59), 6.939 (0.59), 6.942 (0.58), 7.358 (0.63), 7.370 (0.67), 8.248 (1.17), 8.260 (1.99), 8.273 (0.88), 8.435 (1.89).

The Example compounds in the following table 7 were synthesized in analogy to the preparation of Example 117.02, followed by purification by preparative reverse phase HPLC or silicagel chromatography.

TABLE 7

| Example | Structure<br>IUPAC-Name<br>LC-MS (method): Retention time; Mass found<br>¹H-NMR<br>Starting materials (SM): |
|---|---|
| Example 04.07 | {4-[(2-{[6-(3-methoxypyridin-4-yl)-1H-benzimidazol-2-yl]amino}pyridin-4-yl)methyl]piperazin-1-yl}[1-(trifluoromethyl)cyclopropyl]methanone<br>LC-MS (Method 2): $R_t$ = 1.11 min; MS (ESIneg): m/z = 550 [M − H]⁻<br>¹H-NMR (400 MHz, DMSO-d6) δ [ppm]: 1.165 (0.71), 1.181 (3.07), 1.236 (0.50), 1.275 (1.89), 1.287 (3.70), 1.306 (1.28), 2.421 (3.75), 2.518 (1.58), 2.523 (1.15), 3.520 (6.95), 3.595 (2.05), 3.905 (16.00), 6.925 (2.15), 6.929 (2.18), 6.939 (2.17), 6.942 (2.23), 7.198 (2.33), 7.259 (0.60), 7.359 (2.74), 7.371 (2.85), 8.248 (5.17), 8.260 (6.22), 8.275 (3.31), 8.435 (7.74), 10.670 (0.75), 12.188 (0.65).<br>SM: Compound 04.07 and 1-(trifluoromethyl)cyclopropanecarboxylic acid |
| Example 04.08 | ((1RS)-2,2-difluorocyclopropyl){4-[(2-{[6-(3-methoxypyridin-4-yl)-1H-benzimidazol-2-yl]amino}pyridin-4-yl)methyl]piperazin-1-yl}methanone<br>LC-MS (Method 2): $R_t$ = 1.04 min; MS (ESIneg): m/z = 518 [M − H]⁻<br>¹H-NMR (400 MHz, DMSO-d6) δ [ppm]: 1.801 (0.43), 1.813 (0.58), 1.830 (0.66), 1.842 (0.69), 1.863 (0.52), 1.877 (0.47), 1.883 (0.68), 1.897 (0.86), 1.916 (0.80), 1.929 (0.52), 2.327 (0.55), 2.332 (0.48), 2.345 (0.78), 2.361 (0.82), 2.394 (1.30), 2.405 (1.54), 2.422 (1.03), 2.518 (1.51), 2.523 (1.37), 2.535 (0.49), 2.539 (0.56), 2.544 (0.49), 3.105 (0.55), 3.126 (0.60), 3.134 (0.69), 3.140 (0.69), 3.154 (0.61), 3.159 (0.73), 3.167 (0.62), 3.187 (0.52), 3.491 (0.40), 3.525 (7.20), 3.547 (1.50), 3.563 (1.24), 3.570 (0.82), 3.580 (0.96), 3.587 (0.97), 3.596 (0.96), 3.650 (0.76), 3.660 (0.68), 3.667 (0.68), 3.675 (0.46), 3.684 (0.40), 3.693 (0.41), 3.906 (16.00), 6.931 (2.09), 6.934 (2.07), 6.944 (2.06), 6.948 (2.07), 7.203 (2.56), 7.266 (0.60), 7.359 (2.69), 7.371 (2.76), 8.248 (4.80), 8.260 (4.55), 8.264 (3.54), 8.278 (3.08), 8.435 (7.33), 10.679 (0.66), 12.195 (0.59).<br>SM: Compound 04.07 and (1RS)-2,2-difluorocyclopropanecarboxylic acid |
| Example 04.09 | 2-hydroxy-1-{4-[(2-{[6-(3-methoxypyridin-4-yl)-1H-benzimidazol-2-yl]amino}pyridin-4-yl)methyl]piperazin-1-yl}-2-methylpropan-1-one<br>LC-MS (Method 2): $R_t$ = 0.95 min; MS (ESIneg): m/z = 500 [M − H]⁻<br>¹H-NMR (400 MHz, DMSO-d6) δ [ppm]: 1.303 (16.00), 1.323 (0.48), 2.399 (1.43), 3.495 (2.84), 3.905 (10.51), 6.921 (0.89), 6.924 (0.89), 6.934 (0.88), 6.937 (0.90), 7.243 (0.92), 7.247 (0.83), 7.264 (0.77), 7.268 (0.78), 7.359 |

TABLE 7-continued

| Example | Structure<br>IUPAC-Name<br>LC-MS (method): Retention time; Mass found<br>¹H-NMR<br>Starting materials (SM): |
|---|---|
| | (1.66), 7.371 (1.69), 8.246 (2.21), 8.255 (1.63), 8.258 (2.27), 8.267 (1.36), 8.433 (3.33).<br>SM: Compound 04.07 and 2-hydroxy-2-methylpropanoic acid |
| Example 04.10 | 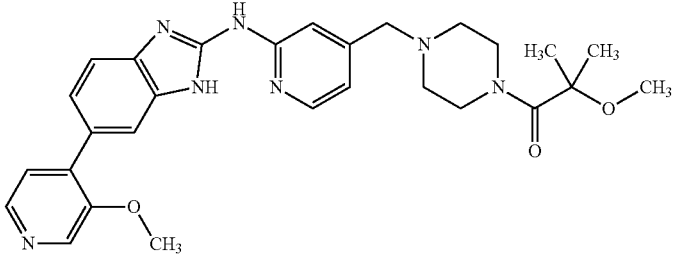 [SMILES: COc1cnccc1-c1ccc2nc(Nc3cc(CN4CCN(C(=O)C(C)(C)OC)CC4)ccn3)[nH]c2c1]<br>2-methoxy-1-{4-[(2-{[6-(3-methoxypyridin-4-yl)-1H-benzimidazol-2-yl]amino}pyridin-4-yl)methyl]piperazin-1-yl}-2-methylpropan-1-one<br>LC-MS (Method 2): $R_t$ = 1.06 min; MS (ESIneg): m/z = 514 [M − H]⁻<br>¹H-NMR (400 MHz, DMSO-d6) δ [ppm]: 1.315 (16.00), 2.419 (1.01), 2.518 (0.46), 3.130 (11.79), 3.501 (2.99), 3.905 (6.47), 6.927 (0.91), 6.930 (0.91), 6.941 (0.89), 6.943 (0.92), 7.197 (0.90), 7.358 (1.03), 7.370 (1.07), 8.247 (1.92), 8.260 (3.09), 8.274 (1.38), 8.435 (3.04).<br>SM: Compound 04.07 and 2-methoxy-2-methylpropanoic acid |

Example 05.01

3,3,3-trifluoro-1-(4-{[2-({6-[3-(2,2,2-trifluoroethoxy)pyridin-4-yl]-1H-benzimidazol-2-yl}amino)pyridin-4-yl]methyl}piperazin-1-yl)propan-1-one Example 06.01

3,3,3-trifluoro-1-(4-{[2-({6-[3-(propan-2-yloxy)pyridin-4-yl]-1H-benzimidazol-2-yl}amino)pyridin-4-yl]methyl}piperazin-1-yl)propan-1-one

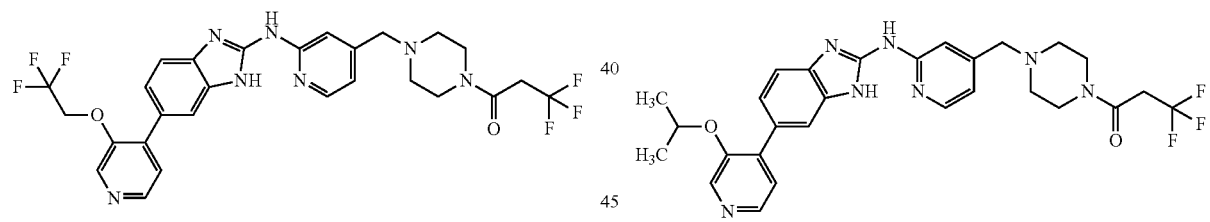

To a stirred solution of crude N-[4-(piperazin-1-ylmethyl)pyridin-2-yl]-6-[3-(2,2,2-trifluoroethoxy)pyridin-4-yl]-1H-benzimidazol-2-amine hydrochloride (159 mg, approx. 229 µmol) in DMF (5 mL) was added sodium bicarbonate (115 mg, 1.37 mmol), 3,3,3-trifluoropropanoic acid (31 µl, 98% purity, 340 µmol) and HATU (130 mg, 343 µmol). The mixture was stirred at room temperature for 16 h. Water was added, the mixture was stirred for 15 minutes and the mixture was extracted with ethyl acetate. The organic phase was washed with saturated sodium chloride solution, dried (sodium sulfate) and the solvent was removed in vacuum. Silicagel chromatography gave a solid that was triturated with a mixture of dichloromethane and hexane to give 43 mg of the title compound.

LC-MS (Method 2): $R_t$=1.13 min; MS (ESIpos): m/z=594 [M+H]⁺.

¹H-NMR (400 MHz, DMSO-d₆): δ [ppm]=2.41 (dt, 4H), 3.42-3.56 (m, 6H), 3.66 (q, 2H), 4.91 (q, 2H), 6.90-6.98 (m, 1H), 7.14-7.58 (m, 4H), 7.67 (br s, 1H), 8.28 (d, 1H), 8.35 (d, 1H), 8.52 (s, 1H), 12.20 (br s, 1H), 12.64-13.71 (m, 1H).

Starting with crude N-[4-(piperazin-1-ylmethyl)pyridin-2-yl]-6-[3-(propan-2-yloxy)pyridin-4-yl]-1H-benzimidazol-2-amine hydrochloride (110 mg, approx. 141 µmol) and 3,3,3-trifluoropropanoic acid (54.0 mg, 422 µmol) Example 06.01. was prepared analogously to the procedure for the preparation of Example 02.02.

Yield: 35.0 mg of the title compound.

LC-MS (Method 2): $R_t$=1.13 min; MS (ES+): m/z=554 [M+1]

¹H-NMR (400 MHz, DMSO-d6) δ[ppm]: 1.227 (16.00), 1.242 (15.73), 2.323 (0.69), 2.327 (0.94), 2.331 (0.71), 2.373 (3.11), 2.386 (4.75), 2.398 (3.61), 2.414 (3.40), 2.427 (4.67), 2.439 (3.31), 2.518 (3.60), 2.523 (2.54), 2.540 (1.57), 2.665 (0.67), 2.669 (0.92), 2.673 (0.67), 3.462 (3.42), 3.476 (4.71), 3.487 (3.91), 3.499 (3.82), 3.512 (5.03), 3.525 (15.50), 3.606 (2.34), 3.634 (6.70), 3.661 (6.28), 3.688 (2.02), 4.575 (1.11), 4.590 (2.83), 4.605 (3.87), 4.621 (2.86), 4.636 (1.12), 5.756 (9.43), 6.924 (3.82), 6.927 (3.70), 6.937 (3.75), 6.940 (3.88), 7.202 (6.21), 7.303 (1.19), 7.370 (2.14), 7.787 (0.87), 8.222 (8.15), 8.234 (7.52), 8.270 (5.42), 8.283 (5.13), 8.398 (12.48), 10.647 (1.53), 12.147 (3.07).

Example 06.02 cyclopropyl(4-{[2-({6-[3-(propan-2-yloxy)pyridin-4-yl]-1H-benzimidazol-2-yl}amino)pyridin-4-yl]methyl}piperazin-1-yl)methanone

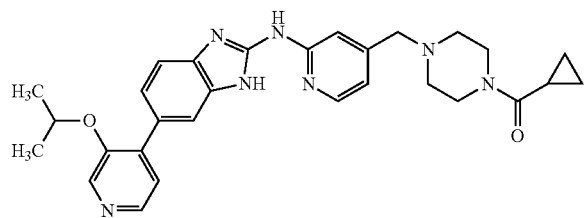 [SMILES: CC(C)Oc1cnccc1-c1ccc2nc(Nc3cc(CN4CCN(C(=O)C5CC5)CC4)ccn3)[nH]c2c1]

Starting with crude N-[4-(piperazin-1-ylmethyl)pyridin-2-yl]-6-[3-(propan-2-yloxy)pyridin-4-yl]-1H-benzimidazol-2-amine hydrochloride (110 mg, approx. 141 μmol) and cyclopropanecarboxylic acid (36.3 mg, 422 μmol) Example 06.02. was prepared analogously to the procedure for the preparation of Example 02.02.

Yield: 35.0 mg of the title compound.

LC-MS (Method 2): $R_t$=1.10 min; MS (ES+): m/z=512 [M+H]$^+$.

$^1$H-NMR (400 MHz, DMSO-d$_6$): δ [ppm]=0.63-0.77 (m, 4H), 1.24 (br d, 6H), 1.91-2.02 (m, 1H), 2.30-2.47 (m, 4H), 3.42-3.80 (m, 6H), 4.61 (dt, 1H), 6.95 (d, 1H), 7.22 (s, 1H), 7.25-7.85 (m, 4H), 8.24 (d, 1H), 8.29 (d, 1H), 8.40 (s, 1H), 10.66 (br s, 1H), 12.16 (br s, 1H).

Example 06.03

2-cyclopropyl-1-(4-{[2-({6-[3-(propan-2-yloxy)pyridin-4-yl]-1H-benzimidazol-2-yl}amino)pyridin-4-yl]methyl}piperazin-1-yl)ethanone

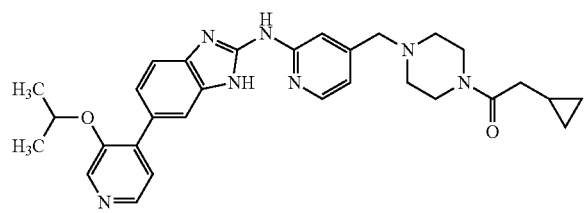 [SMILES: CC(C)Oc1cnccc1-c1ccc2nc(Nc3cc(CN4CCN(C(=O)CC5CC5)CC4)ccn3)[nH]c2c1]

Starting with crude N-[4-(piperazin-1-ylmethyl)pyridin-2-yl]-6-[3-(propan-2-yloxy)pyridin-4-yl]-1H-benzimidazol-2-amine hydrochloride (110 mg, approx. 141 μmol) and cyclopropylacetic acid (42.2 mg, 422 μmol) Example 06.03. was prepared analogously to the procedure for the preparation of Example 02.02.

Yield: 21.0 mg of the title compound.

LC-MS (Method 2): $R_t$=1.13 min; MS (ES+): m/z=526 [M+H]$^+$.

$^1$H-NMR (400 MHz, DMSO-d$_6$): δ [ppm]=0.06-0.15 (m, 2H), 0.39-0.49 (m, 2H), 0.88-1.01 (m, 1H), 1.24 (br d, 6H), 2.25 (d, 2H), 2.33-2.45 (m, 4H), 3.41-3.57 (m, 6H), 4.61 (dt, 1H), 6.94 (dd, 1H), 7.21 (s, 1H), 7.25-7.86 (m, 4H), 8.23 (d, 1H), 8.28 (d, 1H), 8.40 (s, 1H), 10.65 (br s, 1H), 12.15 (s, 1H).

Example 07.01 cyclopropyl{4-[(2-{[6-(5-methoxy-2-methylpyridin-4-yl)-1H-benzimidazol-2-yl]amino}pyridin-4-yl)methyl]piperazin-1-yl}methanone

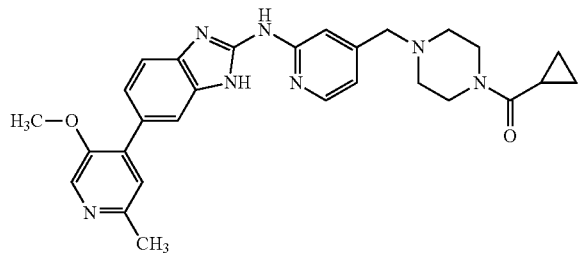

To a stirred solution of 6-(5-methoxy-2-methylpyridin-4-yl)-N-[4-(piperazin-1-ylmethyl)pyridin-2-yl]-1H-benzimidazol-2-amine (65.0 mg, 151 μmol) in dichloromethane (1.0 mL, 16 mmol) was added triethylamine (50 μl, 360 μmol) and cyclopropanecarbonyl chloride (17 μl, 190 μmol).

The mixture was stirred at r.t. for 1 h. A saturated sodium bicarbonate solution was added and the mixture was extracted with dichloromethane. The organic phase was dried (magnesium sulfate) and the solvent was removed in vacuum. Silicagel chromatography gave a solid that was triturated with diethylether to give 40 mg (53% yield) of the title compound.

LC-MS (Method 5): $R_t$=2.21 min; MS (ESIpos): m/z=498 [M+H]$^+$.

$^1$H-NMR (400 MHz, DMSO-d6): δ [ppm]=0.59-0.82 (m, 4H), 1.95 (m, 1H), 2.37 (m, 2H), 2.45 (m, 5H), 3.52 (m, 4H), 3.70 (m, 2H), 3.85 (s, 3H), 6.94 (m, 1H), 7.18-7.33 (m, 3H), 7.45 (m, 1H), 7.66 (s, 1H), 8.27 (m, 1H), 10.70 (s, 1H), 12.10 (s, 1H). $^{13}$C-NMR (101 MHz, DMSO-d6): δ [ppm]=6.9, 10.2, 23.1, 41.5, 44.8, 52.4, 53.0, 56.4, 60.6, 110.5, 116.5, 121.6, 123.7, 127.4, 133.9, 138.2, 146.9, 149.4, 150.2, 150.4, 150.5, 153.6, 170.9.

Example 07.02

3,3,3-trifluoro-1-{4-[(2-{[6-(5-methoxy-2-methylpyridin-4-yl)-1H-benzimidazol-2-yl]amino}pyridin-4-yl)methyl]piperazin-1-yl}propan-1-one

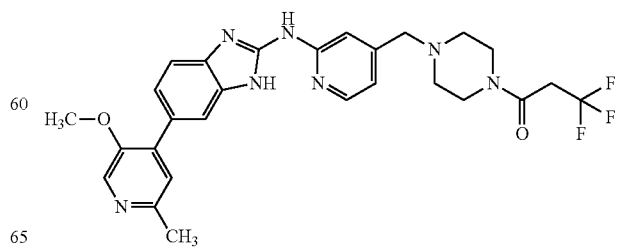

Starting with crude 6-(5-methoxy-2-methylpyridin-4-yl)-N-[4-(piperazin-1-ylmethyl)pyridin-2-yl]-1H-benzimidazol-2-amine hydrochloride (180 mg, approx. 309 µmol) and 3,3,3-trifluoropropanoic acid (35 µl, 400 µmol) Example 07.02. was prepared analogously to the procedure for the preparation of Example 16.01.02.

Yield: 100.0 mg of the title compound.

LC-MS (Method 2): $R_t$=1.07 min; MS (ESIpos): m/z=540 [M+H]$^+$.

$^1$H-NMR (400 MHz, DMSO-d$_6$): δ [ppm]=2.35-2.48 (m, 7H), 3.43-3.57 (m, 6H), 3.65 (q, 2H), 3.86 (s, 3H), 6.94 (d, 1H), 7.09-7.89 (m, 5H), 8.20-8.35 (m, 2H), 10.66 (br s, 1H), 12.17 (br s, 1H).

Example 07.03 cyclobutyl{4-[(2-{[6-(5-methoxy-2-methylpyridin-4-yl)-1H-benzimidazol-2-yl]amino}pyridin-4-yl)methyl]piperazin-1-yl}methanone

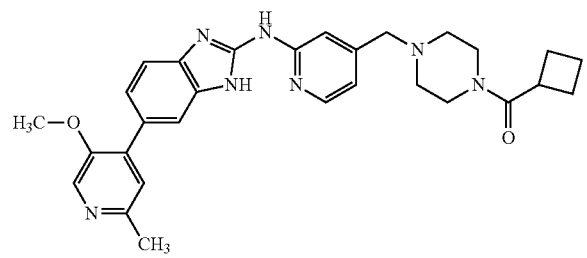 [SMILES: COc1cnc(C)cc1-c1ccc2nc(Nc3cc(CN4CCN(C(=O)C5CCC5)CC4)ccn3)[nH]c2c1]

To a stirred solution of 6-(5-methoxy-2-methylpyridin-4-yl)-N-[4-(piperazin-1-ylmethyl)pyridin-2-yl]-1H-benzimidazol-2-amine (100 mg, 233 µmol) in tetrahydrofurane (1.0 mL). was added triethylamine (100 µl, 720 µmol) and cyclobutanecarbonyl chloride (35 µl, 310 µmol). The mixture was stirred at r.t. for 1 h. A saturated sodium bicarbonate solution was added and the mixture was extracted with dichloromethane. The organic phase was dried (magnesium sulfate) and the solvent was removed in vacuum. Silicagel chromatography gave 62 mg (52% yield) of the title compound.

LC-MS (Method 5): $R_t$=2.33 min; MS (ESIpos): m/z=512 [M+H]$^+$.

$^1$H-NMR (400 MHz, DMSO-d6): δ [ppm]=1.72 (m, 1H), 1.87 (m, 1H), 1.98-2.22 (m, 4H), 2.34 (m, 4H), 2.45 (s, 3H), 3.48 (m, 4H), 3.85 (s, 3H), 7.12-7.33 (m, 3H), 7.33-7.90 (m, 2H), 8.22-8.34 (m, 2H), 10.66 (s, 1H), 12.17 (s, 1H).

$^{13}$C-NMR (101 MHz, DMSO-d6): δ [ppm]=17.3, 23.1, 24.5, 36.2, 41.1, 44.3, 52.4, 52.9, 56.4, 60.6, 110.4, 116.4, 123.6, 134.0, 138.1, 146.9, 149.4, 150.4, 153.6, 171.9.

Example 07.04

2-cyclopropyl-1-{4-[(2-{[6-(5-methoxy-2-methylpyridin-4-yl)-1H-benzimidazol-2-yl]amino}pyridin-4-yl)methyl]piperazin-1-yl}ethanone

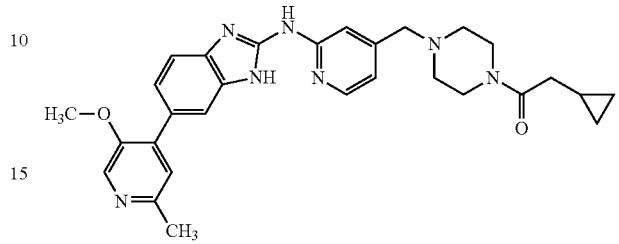

To a stirred solution of 6-(5-methoxy-2-methylpyridin-4-yl)-N-[4-(piperazin-1-ylmethyl)pyridin-2-yl]-1H-benzimidazol-2-amine (100 mg, 233 µmol) in tetrahydrofurane (1.0 mL). was added triethylamine (100 µl, 720 µmol) and cyclopropylacetyl chloride (45 µl, 440 µmol). The mixture was stirred at r.t. for 1 h. A saturated sodium bicarbonate solution was added and the mixture was extracted with dichloromethane. The organic phase was dried (magnesium sulfate) and the solvent was removed in vacuum. Silicagel chromatography gave a solid that was triturated with pentane to give 65 mg (55% yield) of the title compound LC-MS (Method 5): $R_t$=2.30 min; MS (ESIpos): m/z=512 [M+H]$^+$.

$^1$H-NMR (400 MHz, DMSO-d6): δ [ppm]=0.10 (m, 2H), 0.44 (m, 2H), 0.94 (m, 1H), 2.24 (d, 2H), 2.37 (m, 4H), 2.45 (s 3H), 3.45 (m, 2H), 3.50 (m, 4H), 3.85 (s, 3H), 6.92 (m, 1H), 7.09-7.32 (m, 3H), 7.32-7.88 (m, 2H), 8.17-8.31 (m, 2H), 10.66 (s, 1H), 12.16 (s, 1H).

$^{13}$C-NMR (101 MHz, DMSO-d6): δ [ppm]=4.2, 7.2, 23.1, 37.3, 40.9, 45.0, 52.3, 53.0, 56.4, 60.6, 110.4, 116.4, 123.6, 134.0, 138.1, 146.9, 149.4, 150.3, 150.41, 150.43, 153.6, 170.2.

Example 08.01

4-{2-[(4-{[4-(cyclopropylcarbonyl)piperazin-1-yl]methyl}pyridin-2-yl)amino]-1H-benzimidazol-6-yl}-5-methoxy-N,N-dimethylpyridine-2-carboxamide

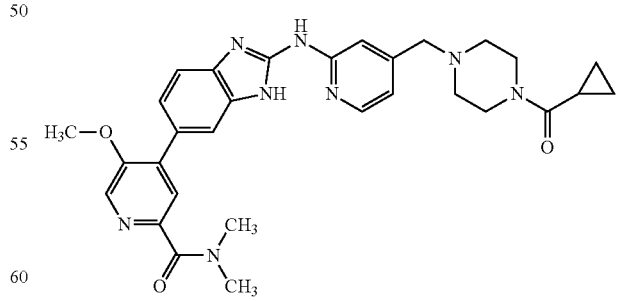

To a stirred solution of 4-bromo-5-methoxy-N,N-dimethylpyridine-2-carboxamide (206 mg, 796 µmol) and cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (200 mg, 398 µmol) in dioxane (2.5 mL) and water (500 µl) was added sodium carbonate (173 mg, 1.63 mmol) and Pd(dppf)Cl$_2$. CH$_2$Cl$_2$ (65.0 mg, 79.6 µmol). The mixture was heated to reflux for 16 h. Methanol was added, the mixture was filtered and the solvent was removed in vacuum. Silicagel chromatography gave 130 mg (57% yield) of the title compound.

LC-MS (Method 5): R$_t$=2.67 min; MS (ESIpos): m/z=555 [M+H]$^+$.

$^1$H-NMR (400 MHz, DMSO-d6) δ[ppm]: 0.675 (1.04), 0.682 (2.25), 0.688 (1.57), 0.695 (1.21), 0.702 (2.75), 0.708 (1.68), 0.710 (1.61), 0.716 (2.35), 0.723 (2.39), 0.728 (2.89), 0.735 (1.48), 1.089 (0.51), 1.934 (0.60), 1.941 (0.65), 1.945 (0.51), 1.953 (1.05), 1.959 (0.57), 1.965 (0.63), 1.972 (0.58), 2.373 (0.97), 2.443 (0.97), 2.490 (1.79), 2.495 (3.91), 2.500 (5.61), 2.505 (4.18), 2.509 (2.05), 3.019 (8.33), 3.078 (9.10), 3.309 (16.00), 3.521 (5.24), 3.701 (0.85), 3.970 (12.24), 6.933 (1.42), 6.936 (1.45), 6.946 (1.45), 6.950 (1.47), 7.208 (2.35), 7.278 (0.51), 7.297 (0.57), 7.562 (6.03), 7.567 (0.70), 8.262 (2.17), 8.277 (2.12), 8.416 (5.24), 10.663 (0.61).

Example 09.01

1-{4-[(2-{[6-(5-ethoxy-2-methylpyridin-4-yl)-1H-benzimidazol-2-yl]amino}pyridin-4-yl)methyl]piperazin-1-yl}-3,3,3-trifluoropropan-1-one

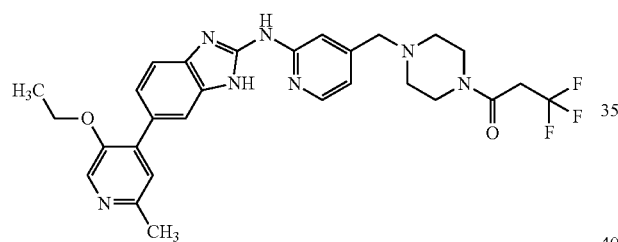

To a stirred solution of 6-(5-ethoxy-2-methylpyridin-4-yl)-N-[4-(piperazin-1-ylmethyl)pyridin-2-yl]-1H-benzimidazol-2-amine (80.0 mg, 180 µmol) in dichloromethane (1.0 mL) was added triethylamine (200 µl, 1.4 mmol) and 3,3,3-trifluoropropanoyl chloride (46 µl, 450 µmol). The mixture was stirred at r.t. for 0.5 h. A saturated sodium bicarbonate solution was added and the mixture was extracted with dichloromethane. The organic phase was dried (magnesium sulfate) and the solvent was removed in vacuum. Silicagel chromatography gave 23 mg (23% yield) of the title compound.

LC-MS (Method 5): R$_t$=2.50 min; MS (ESIpos): m/z=554 [M+H]$^+$.

$^1$H-NMR (400 MHz, DMSO-d6) δ[ppm]: 1.089 (0.47), 1.175 (0.68), 1.193 (0.46), 1.232 (0.95), 1.270 (3.65), 1.288 (7.67), 1.306 (4.05), 1.355 (0.43), 2.393 (2.80), 2.404 (2.38), 2.435 (3.69), 2.446 (16.00), 2.495 (9.42), 2.499 (11.12), 2.502 (8.84), 3.306 (14.41), 3.373 (1.00), 3.390 (1.51), 3.477 (3.06), 3.512 (3.28), 3.531 (7.20), 3.596 (1.20), 3.623 (3.28), 3.651 (3.20), 3.678 (1.08), 4.079 (1.38), 4.096 (4.11), 4.113 (4.09), 4.131 (1.32), 5.747 (1.42), 6.928 (2.04), 6.942 (2.08), 7.205 (3.50), 7.242 (4.75), 7.287 (1.55), 7.308 (1.94), 7.442 (1.38), 7.461 (1.10), 7.694 (1.44), 8.249 (5.15), 8.266 (2.72), 8.279 (2.50).

Example 09.02 cyclopropyl{4-[(2-{[6-(5-ethoxy-2-methylpyridin-4-yl)-1H-benzimidazol-2-yl]amino}pyridin-4-yl)methyl]piperazin-1-yl}methanone

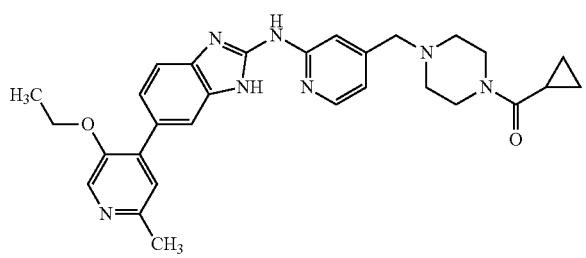 [SMILES: CCOc1cnc(C)cc1-c1ccc2nc(Nc3cc(CN4CCN(C(=O)C5CC5)CC4)ccn3)[nH]c2c1]

Starting with 6-(5-ethoxy-2-methylpyridin-4-yl)-N-[4-(piperazin-1-ylmethyl)pyridin-2-yl]-1H-benzimidazol-2-amine (80.0 mg, 180 µmol) and cyclopropanecarbonyl chloride (21 µl, 230 µmol), Example 09.02 was prepared analogously to the procedure for the preparation of Example 09.01.

Yield: 54.0 mg (56%) of the title compound.

LC-MS (Method 5): R$_t$=2.37 min; MS (ESIpos): m/z=512 [M+H]$^+$.

$^1$H-NMR (400 MHz, DMSO-d6) δ[ppm]: 2.444 (1.86), 2.490 (0.86), 2.495 (1.97), 2.500 (2.80), 2.505 (1.97), 2.509 (0.86), 3.302 (16.00), 8.245 (0.54).

Example 09.03

2-cyclopropyl-1-{4-[(2-{[6-(5-ethoxy-2-methyl pyridin-4-yl)-1H-benzimidazol-2-yl]amino}pyridin-4-yl)methyl]piperazin-1-yl}ethanone

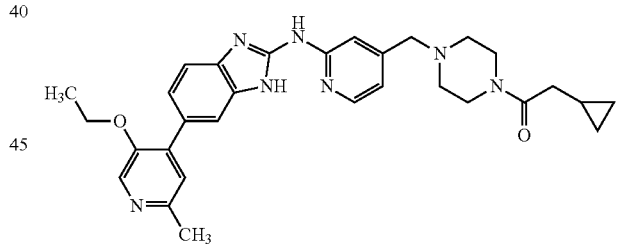

To a stirred solution of 6-(5-ethoxy-2-methylpyridin-4-yl)-N-[4-(piperazin-1-ylmethyl)pyridin-2-yl]-1H-benzimidazol-2-amine (80.0 mg, 180 µmol) in dichloromethane (1.0 mL) was added triethylamine (200 µl, 1.4 mmol) and cyclopropylacetyl chloride (27.8 mg, 234 µmol) The mixture was stirred at r.t. for 0.5 h. Further cyclopropylacetyl chloride (10 mg, 80 µmol) was added and the mixture was stirred at r.t. for 0.5 h. A saturated sodium bicarbonate solution was added and the mixture was extracted with dichloromethane. The organic phase was dried (sodium sulfate) and the solvent was removed in vacuum. Silicagel chromatography gave 65.0 mg (69% yield) of the title compound.

LC-MS (Method 5): R$_t$=2.50 min; MS (ESIpos): m/z=526 [M+H]$^+$.

$^1$H-NMR (400 MHz, DMSO-d6) δ[ppm]: 0.011 (1.54), 0.013 (1.62), 0.025 (1.73), 0.036 (0.52), 0.329 (0.44), 0.338 (1.28), 0.343 (1.40), 0.348 (0.77), 0.353 (0.73), 0.358 (1.41), 0.363 (1.49), 0.374 (0.48), 0.855 (0.51), 1.182 (1.46), 1.200 (2.82), 1.216 (1.51), 2.148 (2.73), 2.166 (2.68), 2.278 (1.61), 2.292 (1.77), 2.307 (1.64), 2.357 (8.76), 2.410 (1.78), 2.414 (2.31), 2.419 (1.76), 3.232 (16.00), 3.367 (1.54), 3.418 (4.57), 3.988 (0.78), 4.005 (2.30), 4.022 (2.23), 4.039 (0.70), 5.663 (0.89), 6.834 (1.15), 6.847 (1.16), 7.118 (2.10), 7.145 (1.58), 7.215 (0.52), 8.158 (3.14), 8.172 (1.66), 8.185 (1.51), 10.551 (0.47), 12.052 (0.50).

Example 09.04 cyclobutyl{4-[(2-{[6-(5-ethoxy-2-methylpyridin-4-yl)-1H-benzimidazol-2-yl]amino}pyridin-4-yl)methyl]piperazin-1-yl}methanone

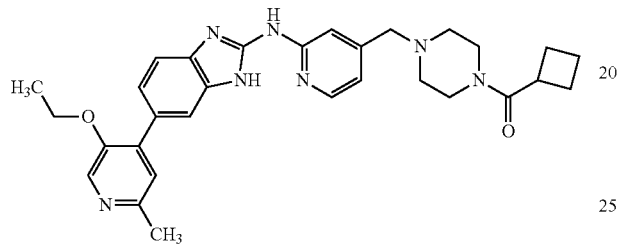

Starting with 6-(5-ethoxy-2-methylpyridin-4-yl)-N-[4-(piperazin-1-ylmethyl)pyridin-2-yl]-1H-benzimidazol-2-amine (80.0 mg, 180 μmol) and cyclobutanecarbonyl chloride (27 μl, 230 μmol), Example 09.04 was prepared analogously to the procedure for the preparation of Example 09.01

Yield: 71.0 mg (75%).

LC-MS (Method 5): $R_t$=2.53 min; MS (ESIpos): m/z=526 [M+H]$^+$.

$^1$H-NMR (400 MHz, DMSO-d6) δ[ppm]: 1.267 (1.48), 1.284 (2.78), 1.301 (1.63), 1.711 (0.45), 1.735 (0.56), 1.858 (0.66), 1.880 (0.67), 1.903 (0.41), 2.051 (1.03), 2.072 (1.23), 2.101 (0.84), 2.123 (1.25), 2.146 (1.40), 2.169 (0.82), 2.349 (3.71), 2.443 (6.82), 2.495 (2.34), 2.499 (2.58), 3.272 (0.47), 3.314 (16.00), 3.331 (3.28), 3.490 (4.38), 4.072 (0.74), 4.090 (1.93), 4.108 (1.86), 4.124 (0.67), 6.910 (1.20), 6.922 (1.16), 7.198 (2.03), 7.229 (1.66), 7.299 (0.65), 8.243 (2.55), 8.253 (1.57), 8.266 (1.31), 12.130 (0.48).

Example 10.01 cyclopropyl{4-[(2-{[6-(2-methoxy-3-methylpyridin-4-yl)-1H-benzimidazol-2-yl]amino}pyridin-4-yl)methyl]piperazin-1-yl}methanone

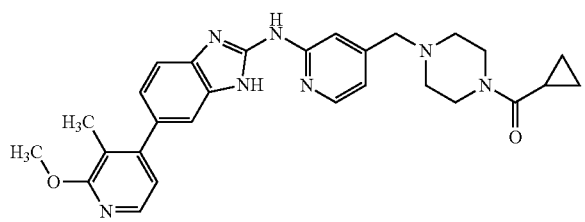 [SMILES: COc1nccc(-c2ccc3nc(Nc4cc(CN5CCN(C(=O)C6CC6)CC5)ccn4)[nH]c3c2)c1C]

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (200 mg, 398 μmol) and 4-iodo-2-methoxy-3-methylpyridine (130 mg, 522 μmol), Example 10.01 was prepared analogously to the procedure for the preparation of Example 08.01.

Yield: 125 mg (62%) of the title compound.

LC-MS (Method 5): $R_t$=2.96 min; MS (ESIpos): m/z=498 [M+H]$^+$.

$^1$H-NMR (400 MHz, DMSO-d6): δ [ppm]=0.70 (m, 4H), 1.94 (m, 1H), 2.13 (s, 3H), 2.40 (m, 4H), 3.51 (m, 4H), 3.69 (s, 2H), 3.92 (s, 3H), 6.83-6.97 (m, 2H), 6.94 (s, 1H), 7.21 (s, 1H), 7.26-7.68 (m, 2H), 8.01 (d, 1H), 8.27 (d, 1H), 10.66 (s, 1H), 12.17 (s, 1H). 13C-NMR (101 MHz, DMSO-d6): δ [ppm]=6.9, 10.2, 12.9, 41.6, 44.8, 52.4, 53.1, 53.3, 60.6, 110.4, 116.4, 118.7, 142.9, 146.9, 149.4, 150.3, 153.6, 162.2, 170.9.

Example 11.01 cyclopropyl(4-{[2-({6-[3-methyl-2-(propan-2-yloxy)pyridin-4-yl]-1H-benzimidazol-2-yl}amino)pyridin-4-yl]methyl}piperazin-1-yl)methanone

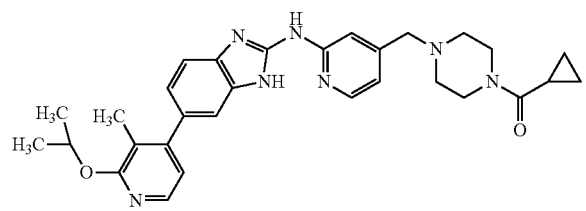 [SMILES: Cc1c(-c2ccc3nc(Nc4cc(CN5CCN(C(=O)C6CC6)CC5)ccn4)[nH]c3c2)ccnc1OC(C)C]

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (150 mg, 299 μmol) and 4-iodo-3-methyl-2-(propan-2-yloxy)pyridine (200 mg, 722 μmol) Example 11.01 was prepared analogously to the procedure for the preparation of Example 08.01.

Yield: 72 mg (46%) of the title compound.

LC-MS (Method 5): $R_t$=3.26 min; MS (ESIpos): m/z=526 [M+H]$^+$.

$^1$H-NMR (400 MHz, DMSO-d6): δ [ppm]=0.71 (m, 4H), 1.33 (d, 6H), 1.94 (m, 1H), 2.10 (s, 3H), 2.40 (m, 4H), 3.51 (s, 4H), 3.69 (s, 2H), 5.31 (quin, 1H), 6.84 (d, 1H), 6.93 (d, 1H), 7.01 (s, 1H), 7.22 (s, 1H), 7.26-7.72 (m, 2H), 7.98 (d, 1H), 8.27 (d, 1H), 10.66 (s, 1H), 12.17 (s, 1H).

$^{13}$C-NMR (101 MHz, DMSO-d6): δ [ppm]=6.9, 10.2, 13.0, 22.1, 41.6, 44.8, 52.4, 53.1, 60.6, 67.4, 110.4, 116.4, 117.2, 118.2, 143.0, 146.9, 149.4, 150.3, 151.8, 153.6, 161.5, 170.9.

Example 12.01 tert-butyl 4-[(2-{[6-(6-methylpyridin-2-yl)-1H-benz-imidazol-2-yl]amino}pyridin-4-yl)methyl]pipera-zine-1-carboxylate

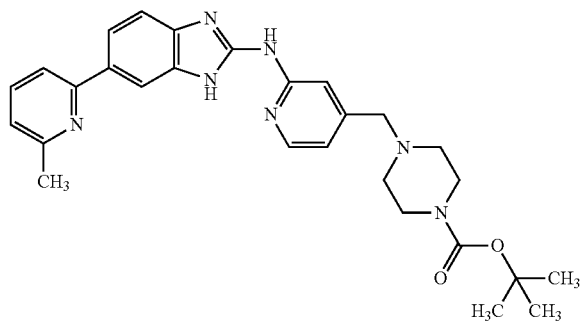 [SMILES: Cc1cccc(-c2ccc3nc(Nc4cc(CN5CCN(C(=O)OC(C)(C)C)CC5)ccn4)[nH]c3c2)n1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 2-bromo-6-methylpyridine (225 mg, 1.31 mmol), Example 12.01 was prepared analogously to the procedure for the preparation of Example 01.01.

Yield: 3.20 mg (1%) of the title compound.

LC-MS (Method 4): $R_t$=1.34 min; MS (ESIpos): m/z=500 [M+H]$^+$.

$^1$H-NMR (400 MHz, DMSO-d6) δ[ppm]: 1.395 (16.00), 2.358 (1.24), 2.537 (5.24), 3.335 (10.11), 8.250 (0.85), 8.264 (0.87).

Example 12.02 cyclopropyl{4-[(2-{[6-(6-methylpyridin-2-yl)-1H-benzimidazol-2-yl]amino}pyridin-4-yl)methyl]piper-azin-1-yl}methanone

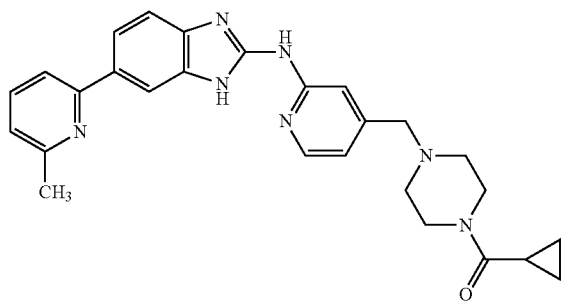 [SMILES: Cc1cccc(-c2ccc3nc(Nc4cc(CN5CCN(C(=O)C6CC6)CC5)ccn4)[nH]c3c2)n1]

Starting with crude 6-(6-methylpyridin-2-yl)-N-[4-(piper-azin-1-ylmethyl)pyridin-2-yl]-1H-benzimidazol-2-amine hydrochloride (190 mg, approx. 218 µmol) and cyclopro-panecarboxylic acid (28.1 mg, 327 µmol), Example 12.02 was prepared analogously to the procedure for the prepara-tion of Example 01.02.

Yield: 7.00 mg of the title compound.

LC-MS (Method 4): $R_t$=1.12 min; MS (ESIpos): m/z=468 [M+H]$^+$.

$^1$H-NMR (400 MHz, DMSO-d6) δ[ppm]: 0.679 (1.12), 0.686 (2.60), 0.691 (1.55), 0.698 (1.20), 0.705 (3.15), 0.710 (2.60), 0.715 (2.83), 0.722 (2.58), 0.727 (3.09), 0.734 (1.37), 1.968 (1.12), 2.322 (1.26), 2.327 (1.75), 2.332 (1.29), 2.365 (1.20), 2.518 (7.04), 2.523 (4.67), 2.538 (16.00), 2.665 (1.20), 2.669 (1.69), 2.674 (1.14), 3.523 (5.84), 3.708 (1.12), 6.935 (1.32), 6.951 (1.35), 7.115 (1.26), 7.136 (1.32), 7.193 (2.20), 7.721 (1.12), 8.260 (2.75), 8.273 (2.43), 10.680 (1.55).

Example 12.03

2-cyclopropyl-1-{4-[(2-{[6-(6-methylpyridin-2-yl)-1H-benzimidazol-2-yl]amino}pyridin-4-yl)methyl]piperazin-1-yl}ethanone

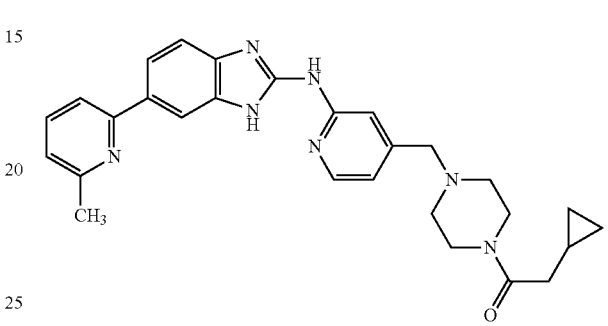

Starting with crude 6-(6-methylpyridin-2-yl)-N-[4-(piper-azin-1-ylmethyl)pyridin-2-yl]-1H-benzimidazol-2-amine hydrochloride (190 mg, approx. 218 µmol) and cyclopro-pylacetic acid (32.7 mg, 327 µmol), Example 12.03 was prepared analogously to the procedure for the preparation of Example 01.02.

Yield: 23.0 mg of the title compound.

LC-MS (Method 2): $R_t$=1.16 min; MS (ESIpos): m/z=500 [M+H]$^+$.

$^1$H-NMR (400 MHz, DMSO-d6) δ[ppm]: −0.011 (0.96), 0.000 (3.41), 0.012 (3.56), 0.026 (1.10), 0.319 (1.03), 0.329 (2.70), 0.333 (2.81), 0.339 (1.72), 0.349 (2.99), 0.353 (2.84), 0.364 (1.07), 0.843 (1.05), 0.871 (1.10), 0.893 (1.97), 0.909 (2.22), 1.011 (15.89), 2.004 (0.87), 2.143 (4.55), 2.159 (4.41), 2.231 (1.33), 2.297 (2.95), 2.427 (7.88), 2.441 (16.00), 2.573 (1.14), 3.360 (2.76), 3.412 (6.84), 4.098 (1.42), 6.832 (1.71), 6.845 (1.71), 7.019 (1.46), 7.040 (1.56), 7.089 (3.00), 7.622 (1.58), 7.690 (1.17), 8.159 (2.97), 8.172 (2.76).

Example 13.01 tert-butyl 4-[(2-{[6-(6-methoxypyridin-3-yl)-1H-benzimidazol-2-yl]amino}pyridin-4-yl)methyl]pip-erazine-1-carboxylate

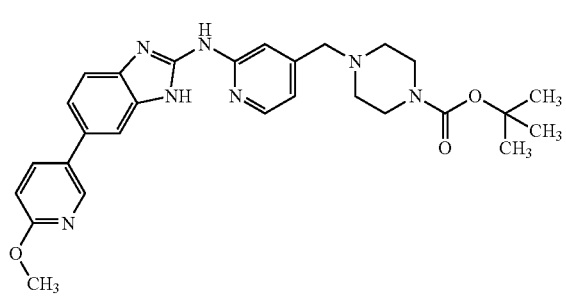 [SMILES: COc1ccc(-c2ccc3nc(Nc4cc(CN5CCN(C(=O)OC(C)(C)C)CC5)ccn4)[nH]c3c2)cn1]

523

To a stirred solution of 1H-imidazole (31.6 mg, 465 µmol) and di-1H-imidazol-1-ylmethanethione (436 mg, 95% purity, 2.32 mmol) in dichloromethane (20 mL) was added tert-butyl 4-[(2-aminopyridin-4-yl)methyl]piperazine-1-carboxylate (679 mg, 2.32 mmol) dissolved in dichloromethane (10 mL) at 0° C. The mixture was stirred at r.t. for 14 h. 4-(6-methoxypyridin-3-yl)benzene-1,2-diamine (500 mg, 2.32 mmol), dissolved in dichloromethane (10 mL) was added and the mixture was stirred at r.t. for 65 h. Water was added and the mixture was extracted with dichloromethane. The organic phase was dried (sodium sulfate) and filtered. N,N'-dipropan-2-ylcarbodiimide (720 µl, 4.7 mmol) was added. The mixture was stirred at r.t. for 14 h. Sodium bicarbonate solution was added and the mixture was extracted with dichloromethane. Silicagel chromatography followed by aminophase-silicagel chromatography gave 180 mg of the title compound.

LC-MS (Method 2): $R_t$=1.36 min; MS (ESIpos): m/z=516 [M+H]$^+$.

$^1$H-NMR (400 MHz, DMSO-d6) δ [ppm]: 1.394 (16.00), 2.356 (1.33), 3.495 (1.72), 3.892 (8.10), 7.184 (0.91), 8.253 (0.83), 8.267 (0.81).

Example 13.02 cyclopropyl{4-[(2-{[6-(6-methoxypyridin-3-yl)-1H-benzimidazol-2-yl]amino}pyridin-4-yl)methyl]piperazin-1-yl}methanone

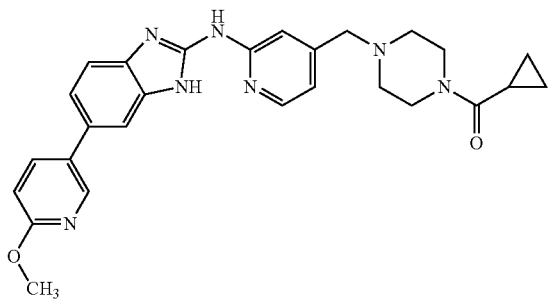 [SMILES: COc1ccc(-c2ccc3nc(Nc4cc(CN5CCN(C(=O)C6CC6)CC5)ccn4)[nH]c3c2)cn1]

Starting with 6-(6-methoxypyridin-3-yl)-N-[4-(piperazin-1-ylmethyl)pyridin-2-yl]-1H-benzimidazol-2-amine hydrochloride (45.0 mg, 90% purity, 89.6 µmol) and cyclopropanecarboxylic acid (11 µl, 130 µmol) Example 13.02. was prepared analogously to the procedure for the preparation of Example 16.01.02.

Yield: 20.0 mg (42%) of the title compound.

LC-MS (Method 2): $R_t$=1.12 min; MS (ESIpos): m/z=484 [M+H]$^+$.

$^1$H-NMR (400 MHz, DMSO-d6) δ[ppm]: 0.684 (2.14), 0.689 (1.34), 0.696 (1.07), 0.703 (2.58), 0.708 (2.25), 0.713 (2.36), 0.720 (2.21), 0.726 (2.54), 0.733 (1.19), 1.966 (0.92), 3.520 (4.95), 3.708 (1.11), 3.893 (16.00), 6.930 (1.35), 6.933 (1.38), 6.943 (1.35), 6.946 (1.37), 7.202 (2.29), 8.263 (2.10), 8.277 (2.00), 10.649 (1.63).

524

Example 13.03

3,3,3-trifluoro-1-{4-[(2-{[6-(6-methoxypyridin-3-yl)-1H-benzimidazol-2-yl]amino}pyridin-4-yl)methyl]piperazin-1-yl}propan-1-one

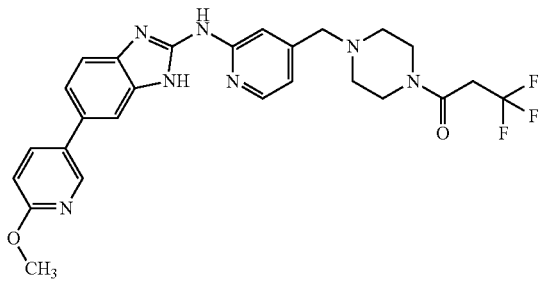 [SMILES: COc1ccc(-c2ccc3nc(Nc4cc(CN5CCN(C(=O)CC(F)(F)F)CC5)ccn4)[nH]c3c2)cn1]

Starting with 6-(6-methoxypyridin-3-yl)-N-[4-(piperazin-1-ylmethyl)pyridin-2-yl]-1H-benzimidazol-2-amine hydrochloride (110 mg, 90% purity, 219 µmol) and 3,3,3-trifluoropropanoic acid (29 µl, 330 µmol) Example 13.03. was prepared analogously to the procedure for the preparation of Example 16.01.02.

Yield: 27.0 mg (21%) of the title compound.

LC-MS (Method 1): $R_t$=0.84 min; MS (ESIpos): m/z=526 [M+H]$^+$.

$^1$H-NMR (400 MHz, DMSO-d6) δ[ppm]: 3.335 (16.00), 3.639 (1.58), 3.667 (1.48), 3.893 (12.15), 7.198 (1.44), 8.262 (1.48), 8.276 (1.40), 10.647 (1.11).

Example 14.01 cyclobutyl{4-[(2-{[6-(4-methoxypyridin-3-yl)-1H-benzimidazol-2-yl]amino}pyridin-4-yl)methyl]piperazin-1-yl}methanone

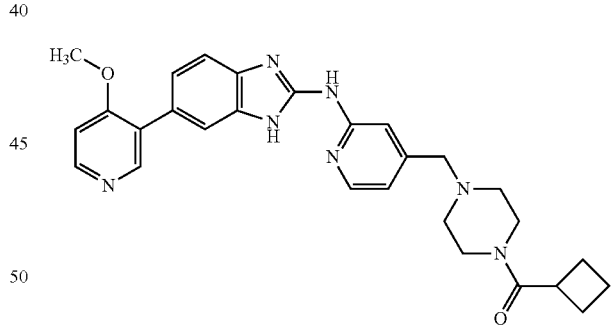

Starting with crude 6-(4-methoxypyridin-3-yl)-N-[4-(piperazin-1-ylmethyl)pyridin-2-yl]-1H-benzimidazol-2-amine hydrochloride (101 mg, approx. 167 µmol) cyclobutanecarboxylic acid (25.2 mg, 251 µmol), Example 14.01 was prepared analogously to the procedure for the preparation of Example 01.02.

Yield: 30 mg of the title compound.

LC-MS (Method 2): $R_t$=1.04 min; MS (ESIpos): m/z=498 [M+H]$^+$.

$^1$H-NMR (400 MHz, CHLOROFORM-d) δ [ppm]: 1.147 (0.84), 1.163 (0.83), 1.260 (1.55), 1.814 (0.98), 1.840 (2.06), 1.853 (1.91), 1.864 (2.70), 1.874 (1.82), 1.891 (1.91), 1.897 (1.16), 1.914 (2.38), 1.935 (4.04), 1.941 (1.71), 1.957 (2.98), 1.962 (2.68), 1.979 (1.50), 1.984 (1.80), 2.007 (0.95), 2.038

(0.48), 2.081 (1.45), 2.090 (1.66), 2.097 (1.55), 2.102 (2.64), 2.112 (4.35), 2.121 (3.05), 2.127 (2.98), 2.133 (4.55), 2.142 (3.27), 2.155 (1.89), 2.164 (1.47), 2.178 (0.46), 2.240 (0.49), 2.281 (5.27), 2.287 (6.09), 2.298 (11.36), 2.304 (13.23), 2.309 (13.78), 2.325 (9.16), 2.333 (5.73), 2.349 (3.31), 2.356 (3.86), 2.373 (1.02), 2.378 (1.40), 2.627 (4.15), 3.173 (0.82), 3.196 (2.93), 3.216 (4.35), 3.240 (5.88), 3.255 (6.54), 3.266 (4.60), 3.417 (16.00), 3.532 (5.49), 3.919 (10.64), 6.918 (5.81), 6.921 (6.38), 6.931 (7.87), 6.934 (7.59), 6.942 (3.75), 7.006 (0.75), 7.130 (7.90), 7.360 (2.14), 7.379 (2.45), 7.528 (1.23), 7.668 (1.26), 8.281 (7.19), 8.295 (6.97), 8.473 (1.74), 8.539 (8.43).

Example 14.02

2-cyclopropyl-1-{4-[(2-{[6-(4-methoxypyridin-3-yl)-1H-benzimidazol-2-yl]amino}pyridin-4-yl)methyl]piperazin-1-yl}ethanone

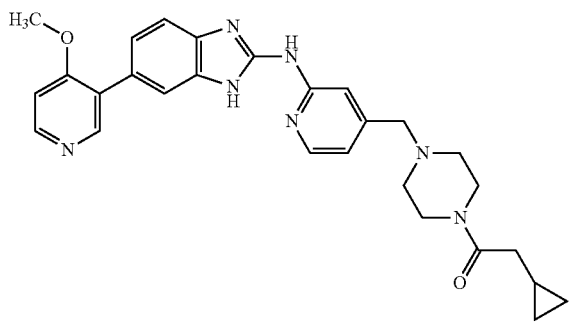 [SMILES: COc1ccncc1-c1ccc2nc(Nc3cc(CN4CCN(C(=O)CC5CC5)CC4)ccn3)[nH]c2c1]

Starting with crude 6-(4-methoxypyridin-3-yl)-N-[4-(piperazin-1-ylmethyl)pyridin-2-yl]-1H-benzimidazol-2-amine hydrochloride (40.0 mg) and cyclopropylacetic acid (7.75 mg, 77.4 μmol), Example 14.02 was prepared analogously to the procedure for the preparation of Example 01.02.

Yield: 3 mg of the title compound.

LC-MS (Method 2): $R_t$=1.01 min; MS (ESIpos): m/z=498 [M+H]$^+$.

$^1$H-NMR (400 MHz, CHLOROFORM-d) δ [ppm]: 0.078 (0.60), 0.103 (0.66), 0.155 (2.41), 0.167 (10.14), 0.181 (10.63), 0.193 (3.07), 0.545 (2.76), 0.556 (7.64), 0.559 (8.27), 0.565 (4.74), 0.572 (4:54), 0.577 (8.59), 0.580 (8.45), 0.592 (2.84), 0.888 (1.15), 1.004 (1.21), 1.016 (2.04), 1.024 (2.07), 1.036 (3.10), 1.049 (2.07), 1.053 (2.07), 1.261 (7.73), 1.293 (1.87), 1.612 (3.76), 1.896 (0.98), 2.178 (1.55), 2.252 (14.99), 2.269 (15.20), 2.286 (1.41), 2.360 (11.78), 2.371 (11.63), 3.397 (6.75), 3.454 (16.00), 3.526 (0.98), 3.589 (6.00), 3.930 (8.01), 6.944 (8.50), 6.955 (6.41), 7.006 (1.78), 7.093 (6.61), 7.286 (2.38), 7.364 (1.78), 7.529 (2.59), 7.641 (2.10), 7.749 (1.49), 8.290 (5.92), 8.303 (6.03), 8.485 (2.15), 8.536 (7.24), 12.328 (0.49).

Example 14.03 cyclopropyl{4-[(2-{[6-(4-methoxypyridin-3-yl)-1H-benzimidazol-2-yl]amino}pyridin-4-yl)methyl]piperazin-1-yl}methanone

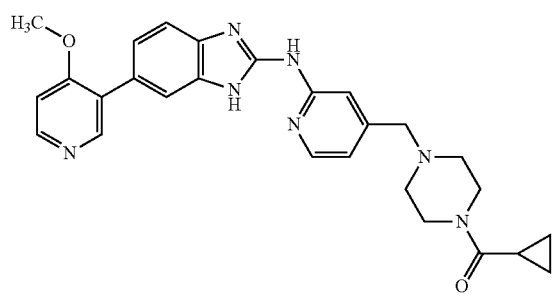 [SMILES: COc1ccncc1-c1ccc2nc(Nc3cc(CN4CCN(C(=O)C5CC5)CC4)ccn3)[nH]c2c1]

Starting with crude 6-(4-methoxypyridin-3-yl)-N-[4-(piperazin-1-ylmethyl)pyridin-2-yl]-1H-benzimidazol-2-amine hydrochloride (101 mg) and cyclopropanecarboxylic acid (21.6 mg, 251 μmol), Example 14.03 was prepared analogously to the procedure for the preparation of Example 01.02.

Yield: 21 mg of the title compound.

LC-MS (Method 2): $R_t$=0.98 min; MS (ESIpos): m/z=484 [M+H]$^+$.

$^1$H-NMR (400 MHz, CHLOROFORM-d) δ [ppm]: 0.746 (1.86), 0.756 (5.53), 0.763 (6.34), 0.773 (4.36), 0.776 (6.18), 0.784 (6.51), 0.792 (2.67), 0.974 (2.40), 0.982 (6.58), 0.989 (6.81), 0.994 (7.59), 1.001 (6.74), 1.011 (2.38), 1.261 (0.94), 1.678 (2.02), 1.690 (3.15), 1.698 (3.52), 1.709 (4.93), 1.721 (3.41), 1.729 (3.06), 1.741 (1.98), 2.179 (0.94), 2.315 (4.10), 2.375 (4.16), 3.425 (9.11), 3.430 (9.34), 3.577 (5.39), 3.848 (0.46), 3.893 (14.78), 3.938 (16.00), 6.914 (2.71), 6.931 (6.28), 6.939 (4.44), 6.944 (5.66), 6.946 (5.68), 6.953 (3.46), 7.006 (0.79), 7.131 (3.51), 7.153 (3.52), 7.282 (1.36), 7.289 (0.89), 7.334 (1.73), 7.338 (1.74), 7.354 (2.05), 7.358 (2.14), 7.386 (1.77), 7.390 (1.78), 7.406 (1.92), 7.410 (1.94), 7.518 (2.87), 7.528 (1.18), 7.538 (2.39), 7.646 (3.47), 7.649 (3.55), 7.709 (2.58), 7.730 (2.30), 7.774 (3.42), 8.286 (3.04), 8.294 (3.55), 8.298 (3.49), 8.306 (3.01), 8.458 (2.87), 8.472 (2.95), 8.490 (3.29), 8.505 (3.00), 8.549 (11.23), 12.369 (1.31).

Example 15.01

3,3,3-trifluoro-1-{4-[(2-{[6-(2-methoxypyridin-3-yl)-1H-benzimidazol-2-yl]amino}pyridin-4-yl)methyl]piperazin-1-yl}propan-1-one

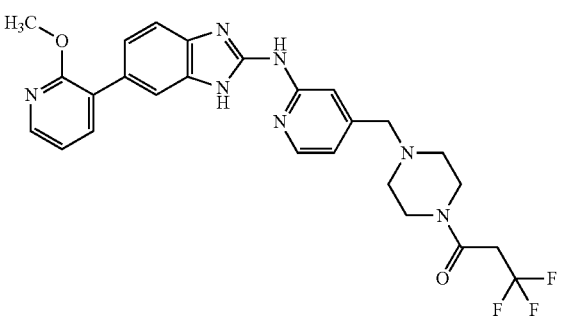 [SMILES: COc1ncccc1-c1ccc2nc(Nc3cc(CN4CCN(C(=O)CC(F)(F)F)CC4)ccn3)[nH]c2c1]

Starting with crude 6-(2-methoxypyridin-3-yl)-N-[4-(piperazin-1-ylmethyl)pyridin-2-yl]-1H-benzimidazol-2-amine hydrochloride (64.0 mg) and 3,3,3-trifluoropropanoic acid (21.4 mg, 167 µmol), Example 15.01 was prepared analogously to the procedure for the preparation of Example 01.02.

Yield: 7 mg of the title compound.

LC-MS (Method 2): R$_t$=1.16 min; MS (ESIpos): m/z=526 [M+H]$^+$.

$^1$H-NMR (400 MHz, CHLOROFORM-d) δ [ppm]: 0.078 (0.71), 0.103 (0.68), 0.136 (1.07), 0.865 (0.84), 0.889 (0.97), 1.148 (0.94), 1.164 (0.94), 1.263 (6.56), 1.385 (1.10), 1.610 (1.29), 2.236 (0.71), 2.254 (0.68), 2.380 (8.05), 2.627 (2.04), 2.638 (0.65), 2.653 (0.94), 3.179 (2.72), 3.205 (7.89), 3.230 (7.76), 3.255 (2.72), 3.369 (4.53), 3.452 (7.14), 3.592 (4.33), 3.988 (10.67), 4.034 (16.00), 6.909 (3.36), 6.923 (3.56), 6.981 (1.13), 6.993 (1.36), 6.999 (1.45), 7.006 (3.26), 7.020 (1.84), 7.026 (1.78), 7.039 (1.65), 7.083 (3.81), 7.286 (1.58), 7.386 (1.49), 7.402 (2.52), 7.421 (1.68), 7.494 (2.39), 7.514 (1.71), 7.529 (2.07), 7.661 (1.78), 7.682 (1.97), 7.687 (3.91), 7.692 (3.88), 7.706 (3.46), 7.710 (3.52), 7.722 (3.26), 7.792 (2.20), 8.141 (1.33), 8.145 (1.42), 8.153 (1.42), 8.158 (1.42), 8.172 (1.87), 8.176 (1.91), 8.184 (2.00), 8.189 (1.84), 8.290 (3.01), 8.295 (3.04), 8.303 (3.04), 8.309 (2.55), 12.295 (0.97).

Example 15.02

2-cyclopropyl-1-{4-[(2-{[6-(2-methoxypyridin-3-yl)-1H-benzimidazol-2-yl]amino}pyridin-4-yl)methyl]piperazin-1-yl}ethanone

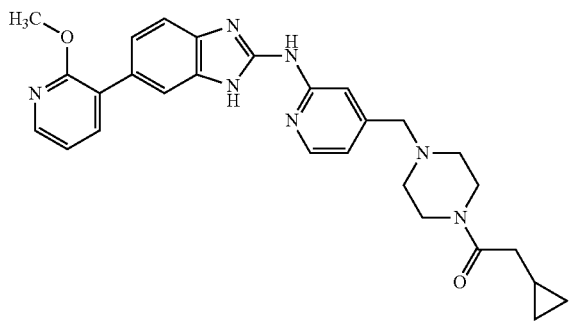 [SMILES: COc1ncccc1-c1ccc2nc(Nc3cc(CN4CCN(C(=O)CC5CC5)CC4)ccn3)[nH]c2c1]

Starting with crude 6-(2-methoxypyridin-3-yl)-N-[4-(piperazin-1-ylmethyl)pyridin-2-yl]-1H-benzimidazol-2-amine hydrochloride (69.0 mg) and cyclopropylacetic acid (18.1 mg, 180 µmol), Example 15.02 was prepared analogously to the procedure for the preparation of Example 01.02.

Yield: 8 mg of the title compound.

LC-MS (Method 2): R$_t$=1.15 min; MS (ESIpos): m/z=498 [M+H]$^+$.

$^1$H-NMR (400 MHz, CHLOROFORM-d) δ [ppm]: 0.102 (0.65), 0.148 (1.90), 0.161 (7.69), 0.175 (7.97), 0.187 (2.30), 0.539 (2.21), 0.549 (5.88), 0.553 (6.04), 0.559 (3.21), 0.565 (3.42), 0.570 (6.57), 0.573 (6.19), 0.585 (2.21), 0.888 (0.56), 0.996 (0.93), 1.009 (1.53), 1.029 (2.18), 1.045 (1.53), 1.055 (1.31), 1.074 (1.62), 1.092 (0.81), 1.252 (1.03), 1.261 (3.05), 1.385 (1.37), 1.692 (1.56), 2.038 (0.40), 2.180 (0.65), 2.240 (9.99), 2.257 (9.74), 2.366 (8.65), 2.627 (0.62), 2.653 (0.47), 3.380 (4.39), 3.445 (7.25), 3.592 (4.33), 3.988 (10.15), 4.033 (16.00), 6.923 (3.74), 6.937 (4.08), 6.977 (1.03), 6.994 (1.49), 7.006 (3.95), 7.017 (1.96), 7.022 (1.87), 7.035 (1.62), 7.088 (4.08), 7.283 (2.30), 7.384 (1.43), 7.400 (2.74), 7.416 (2.21), 7.487 (2.05), 7.507 (1.49), 7.528 (2.05), 7.669 (1.99), 7.689 (5.04), 7.707 (4.14), 7.712 (5.20), 7.785 (2.37), 8.147 (1.43), 8.160 (1.62), 8.168 (2.18), 8.172 (2.15), 8.180 (2.02), 8.184 (1.90), 8.285 (3.89), 8.298 (3.89), 12.308 (0.93).

Example 15.03 cyclopropyl{4-[(2-{[6-(2-methoxypyridin-3-yl)-1H-benzimidazol-2-yl]amino}pyridin-4-yl)methyl]piperazin-1-yl}methanone

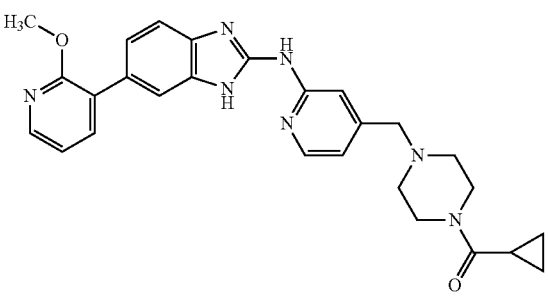 [SMILES: COc1ncccc1-c1ccc2nc(Nc3cc(CN4CCN(C(=O)C5CC5)CC4)ccn3)[nH]c2c1]

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (98.0 mg, 195 µmol) and 3-iodo-2-methoxypyridine (55.0 mg, 234 µmol), Example 15.03 was prepared analogously to the procedure for the preparation of Example 01.01.

Yield: 25 mg (27%) of the title compound.

LC-MS (Method 2): R$_t$=1.12 min; MS (ESIpos): m/z=484 [M+H]$^+$.

$^1$H-NMR (400 MHz, CHLOROFORM-d) δ [ppm]: 0.103 (0.41), 0.733 (2.96), 0.743 (8.63), 0.751 (9.56), 0.759 (6.48), 0.763 (8.81), 0.770 (9.50), 0.779 (3.48), 0.796 (0.49), 0.817 (0.55), 0.850 (0.77), 0.889 (0.63), 0.931 (0.43), 0.969 (3.87), 0.978 (10.63), 0.981 (7.92), 0.985 (10.21), 0.989 (11.20), 0.996 (9.58), 1.006 (3.20), 1.261 (3.48), 1.293 (0.83), 1.341 (0.51), 1.665 (1.82), 1.677 (3.26), 1.685 (3.77), 1.688 (2.90), 1.697 (5.73), 1.705 (2.73), 1.708 (3.32), 1.717 (2.90), 1.728 (1.52), 2.182 (0.53), 2.368 (7.13), 3.447 (16.00), 3.589 (11.71), 3.995 (5.02), 4.030 (7.62), 4.261 (0.61), 4.266 (0.63), 4.725 (0.57), 4.730 (0.59), 6.936 (6.44), 6.949 (6.18), 7.006 (3.56), 7.113 (0.75), 7.138 (10.67), 7.255 (1.26), 7.402 (3.69), 7.422 (4.31), 7.475 (0.63), 7.478 (0.75), 7.498 (1.36), 7.528 (1.72), 7.567 (0.61), 7.570 (0.65), 7.587 (0.61), 7.597 (0.65), 7.601 (0.71), 7.618 (0.57), 7.690 (6.83), 7.695 (6.93), 7.709 (6.99), 7.713 (6.97), 7.791 (1.48), 8.165 (3.65), 8.279 (0.93), 8.291 (9.15), 8.304 (8.36), 12.351 (0.75).

Example 16.01.01 tert-butyl 4-[(2-{[6-(3-methyl-1,2,4-oxadiazol-5-yl)-1H-benzimidazol-2-yl]amino}pyridin-4-yl)methyl]piperazine-1-carboxylate

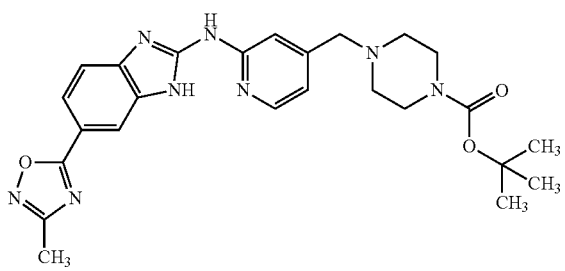 [SMILES: Cc1noc(-c2ccc3nc(Nc4cc(CN5CCN(C(=O)OC(C)(C)C)CC5)ccn4)[nH]c3c2)n1]

A mixture of tert-butyl 4-({2-[(6-{[(ethanimidoylamino)oxy]carbonyl}-1H-benzimidazol-2-yl)amino]pyridin-4-yl}methyl)piperazine-1-carboxylate (30.0 mg, 59.0 µmol) and sodium acetate (5.32 mg, 64.9 µmol) in 1-propanol (1.5 mL) and water (750 µl) was heated to 120° C. in a microwave oven for 2 h. The solvent was removed in vacuum. Silicagel chromatography gave 21.0 mg (65% yield) of the title compound.

LC-MS (Method 1): $R_t$=0.87 min; MS (ESIpos): m/z=491 [M+H]$^+$.

$^1$H-NMR (400 MHz, DMSO-d6) δ[ppm]: 1.396 (16.00), 2.349 (1.01), 2.361 (1.47), 2.373 (1.07), 2.398 (5.11), 3.319 (8.20), 3.510 (1.82), 5.755 (0.73), 7.181 (0.87), 8.284 (0.56), 8.297 (0.53).

Example 16.01.02

3,3,3-trifluoro-1-{4-[(2-{[6-(3-methyl-1,2,4-oxadiazol-5-yl)-1H-benzimidazol-2-yl]amino}pyridin-4-yl)methyl]piperazin-1-yl}propan-1-one

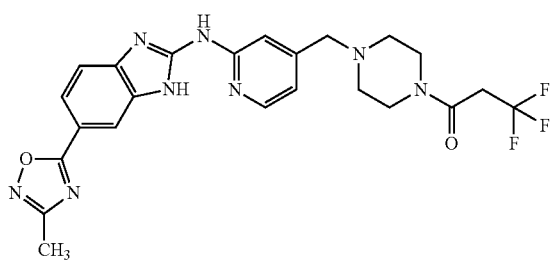 [SMILES: Cc1noc(-c2ccc3nc(Nc4cc(CN5CCN(C(=O)CC(F)(F)F)CC5)ccn4)[nH]c3c2)n1]

To a stirred solution of crude 6-(3-methyl-1,2,4-oxadiazol-5-yl)-N-[4-(piperazin-1-ylmethyl)pyridin-2-yl]-1H-benzimidazol-2-amine hydrochloride (3.55 g, approx. 7.65 mmol) in DMA (50 mL) was added DIPEA (8.0 mL, 46 mmol), 3,3,3-trifluoropropanoic acid (1.0 mL, 98% purity, 11 mmol) and PyBOP (5.97 g, 11.5 mmol). The mixture was stirred at room temperature for 1 h. Water was added, the mixture was stirred for 15 minutes and the mixture was extracted with dichloromethane and methanol (10:1 mixture). The organic phase was washed with saturated sodium chloride solution, dried (sodium sulfate) and the solvent was removed in vacuum. Aminophase-silicagel chromatography gave a solid that was triturated with dichloromethane/hexane (1:1) to give 2.98 g of the title compound.

LC-MS (Method 2): $R_t$=1.07 min; MS (ESIpos): m/z=501 [M+H]$^+$.

$^1$H-NMR (400 MHz, DMSO-d$_6$): δ [ppm]=2.34-2.46 (m, 7H), 3.55 (s, 1H), 3.61 (s, 1H), 3.63 (s, 1H), 3.63-3.70 (m, 2H), 6.97 (d, 1H), 7.20 (s, 1H), 7.38-7.87 (m, 2H), 7.89-8.38 (m, 2H), 10.89 (br s, 1H), 12.46 (br s, 1H).

Example 16.01.03

2-cyclopropyl-1-{4-[(2-{[6-(3-methyl-1,2,4-oxadiazol-5-yl)-1H-benzimidazol-2-yl]amino}pyridin-4-yl)methyl]piperazin-1-yl}ethanone

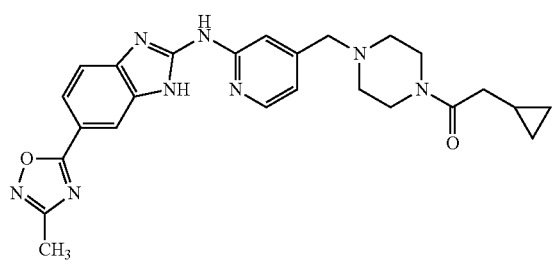 [SMILES: Cc1noc(-c2ccc3nc(Nc4cc(CN5CCN(C(=O)CC6CC6)CC5)ccn4)[nH]c3c2)n1]

To a stirred solution of crude 6-(3-methyl-1,2,4-oxadiazol-5-yl)-N-[4-(piperazin-1-ylmethyl)pyridin-2-yl]-1H-benzimidazol-2-amine hydrochloride (70.0 mg, approx. 164 µmol) in DMF (2 mL) was added DIPEA (140 µl, 820 µmol), T3P (170 µl, 50% in DMF, 300 µmol) and cyclopropylacetic acid (28.5 mg, 98% purity, 279 µmol). The mixture was stirred at r.t. for 14 h. Water was added, and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane/hexane to give 22 mg of the title compound.

LC-MS (Method 2): $R_t$=1.08 min; MS (ESIpos): m/z=473 [M+H]$^+$.

$^1$H-NMR (400 MHz, DMSO-d6) δ[ppm]: 0.000 (0.67), 0.011 (2.35), 0.014 (2.15), 0.023 (2.39), 0.026 (2.27), 0.037 (0.82), 0.330 (0.86), 0.340 (2.10), 0.343 (2.18), 0.350 (1.13), 0.354 (1.02), 0.360 (2.28), 0.364 (2.15), 0.374 (0.85), 0.855 (0.77), 2.152 (4.09), 2.169 (3.96), 2.279 (1.57), 2.292 (1.57), 2.302 (1.79), 2.311 (16.00), 2.436 (0.85), 3.371 (1.52), 3.382 (1.41), 3.393 (1.37), 3.406 (1.51), 3.433 (4.88), 6.877 (1.10), 6.893 (1.16), 7.109 (2.32), 7.701 (0.68), 8.201 (1.61), 8.215 (1.57).

Example 16.01.04 cyclopropyl{4-[(2-{[6-(3-methyl-1,2,4-oxadiazol-5-yl)-1H-benzimidazol-2-yl]amino}pyridin-4-yl)methyl]piperazin-1-yl}methanone

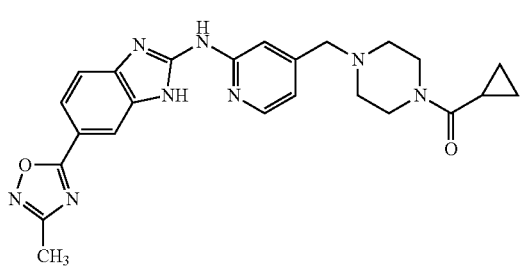 [SMILES: Cc1noc(-c2ccc3nc(Nc4cc(CN5CCN(C(=O)C6CC6)CC5)ccn4)[nH]c3c2)n1]

To a stirred solution of crude 6-(3-methyl-1,2,4-oxadiazol-5-yl)-N-[4-(piperazin-1-ylmethyl)pyridin-2-yl]-1H-benzimidazol-2-amine hydrochloride (70.0 mg, approx. 164 µmol) in DMF (2 mL) was added DIPEA (140 µl, 820 µmol), T3P (170 µl, 50% in DMF, 300 µmol) and cyclopropanecarboxylic acid (23 µl, 98% purity, 280 µmol). The mixture was stirred at r.t. for 14 h. Water was added, and the mixture was extracted with ethyl acetate. The organic phase was washed with saturated sodium chloride solution, dried (sodium sulfate), filtered and the solvent was removed in vacuum. Aminophase-silicagel chromatography gave 36.0 mg of the title compound.

LC-MS (Method 2): $R_t$=1.05 min; MS (ESIpos): m/z=459 [M+H]$^+$.

$^1$H-NMR (400 MHz, DMSO-d6) δ[ppm]: 0.678 (0.95), 0.685 (2.22), 0.691 (1.38), 0.698 (1.07), 0.705 (2.77), 0.710 (2.13), 0.717 (2.35), 0.723 (2.34), 0.728 (2.82), 0.735 (1.29), 1.941 (0.56), 1.948 (0.59), 1.960 (1.02), 1.972 (0.57), 1.980 (0.53), 2.370 (0.93), 2.389 (1.07), 2.399 (16.00), 2.447 (0.93), 2.523 (0.85), 3.503 (0.85), 3.534 (5.20), 3.704 (0.82), 6.973 (1.14), 6.986 (1.18), 7.204 (2.30), 7.790 (0.73), 8.294 (1.71), 8.307 (1.62).

Example 16.01.05 cyclobutyl{4-[(2-{[6-(3-methyl-1,2,4-oxadiazol-5-yl)-1H-benzimidazol-2-yl]amino}pyridin-4-yl)methyl]piperazin-1-yl}methanone

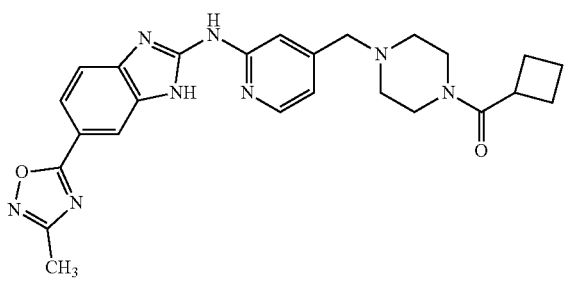 [SMILES: Cc1noc(-c2ccc3nc(Nc4cc(CN5CCN(C(=O)C6CCC6)CC5)ccn4)[nH]c3c2)n1]

To a stirred solution of crude 6-(3-methyl-1,2,4-oxadiazol-5-yl)-N-[4-(piperazin-1-ylmethyl)pyridin-2-yl]-1H-benzimidazol-2-amine hydrochloride (70.0 mg, approx. 164 µmol) in DMF (2 mL) was added DIPEA (140 µl, 820 µmol), T3P (170 µl, 50% in DMF, 300 µmol) and cyclobutanecarboxylic acid (28.5 mg, 98% purity, 279 µmol). The mixture was stirred at r.t. for 14 h. Water was added, and the mixture was extracted with ethyl acetate. The organic phase was washed with saturated sodium chloride solution, dried (sodium sulfate), filtered and the solvent was removed in vacuum. Aminophase-silicagel chromatography gave 33.0 mg of the title compound.

LC-MS (Method 2): $R_t$=1.11 min; MS (ESIpos): m/z=473 [M+H]$^+$.

$^1$H-NMR (400 MHz, DMSO-d6) δ[ppm]: 1.842 (0.50), 1.863 (0.98), 1.886 (0.73), 1.890 (0.74), 2.055 (1.04), 2.064 (0.77), 2.071 (0.74), 2.076 (1.19), 2.080 (0.92), 2.086 (0.94), 2.126 (1.39), 2.131 (0.92), 2.148 (1.54), 2.153 (1.16), 2.155 (1.02), 2.172 (0.71), 2.177 (0.78), 2.356 (3.13), 2.367 (2.36), 2.398 (16.00), 2.523 (0.90), 3.325 (2.38), 3.343 (2.20), 3.476 (1.49), 3.509 (5.00), 6.957 (1.14), 6.970 (1.21), 7.192 (2.34), 7.787 (0.80), 8.285 (1.78), 8.298 (1.72).

Example 16.01.06

2,2-dimethyl-1-{4-[(2-{[6-(3-methyl-1,2,4-oxadiazol-5-yl)-1H-benzimidazol-2-yl]amino}pyridin-4-yl)methyl]piperazin-1-yl}propan-1-one

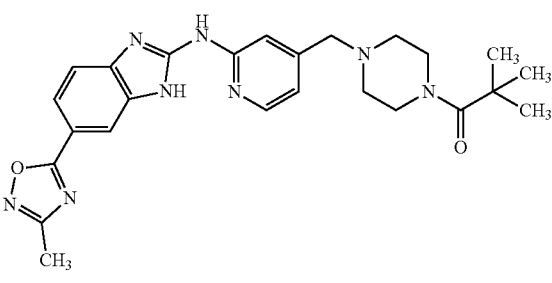 [SMILES: Cc1noc(-c2ccc3nc(Nc4cc(CN5CCN(C(=O)C(C)(C)C)CC5)ccn4)[nH]c3c2)n1]

Starting with crude 6-(3-methyl-1,2,4-oxadiazol-5-yl)-N-[4-(piperazin-1-ylmethyl)pyridin-2-yl]-1H-benzimidazol-2-amine hydrochloride (140 mg, approx. 328 µmol) and 2,2-dimethylpropanoic acid (57 µl, 490 µmol) Example 16.01.06 was prepared analogously to the procedure for the preparation of Example 16.01.02.

Yield: 160.0 mg of the title compound.

LC-MS (Method 2): $R_t$=1.16 min; MS (ESIpos): m/z=475 [M+H]$^+$.

$^1$H-NMR (400 MHz, DMSO-d6) δ[ppm]: 1.184 (16.00), 2.374 (0.94), 2.386 (1.48), 2.399 (7.16), 3.509 (1.97), 3.574 (1.10), 7.196 (0.87), 8.289 (0.73), 8.302 (0.70).

Example 16.02.01 tert-butyl (2R,5S)-2,5-dimethyl-4-[(2-{[6-(3-methyl-1,2,4-oxadiazol-5-yl)-1H-benzimidazol-2-yl]amino}pyridin-4-yl)methyl]piperazine-1-carboxylate

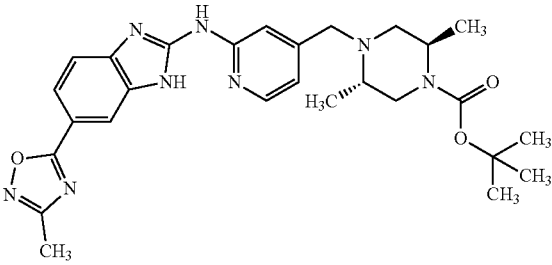 [SMILES: Cc1noc(-c2ccc3nc(Nc4cc(CN5C[C@@H](C)N(C(=O)OC(C)(C)C)C[C@@H]5C)ccn4)[nH]c3c2)n1]

A mixture of tert-butyl (2R,5S)-4-({2-[(6-{[(ethanimidoylamino)oxy]carbonyl}-1H-benzimidazol-2-yl)amino]pyridin-4-yl}methyl)-2,5-dimethylpiperazine-1-carboxylate (496 mg, 924 µmol) and sodium acetate (83.4 mg, 1.02 mmol) in 1-propanol (24 mL, 310 mmol) and water (12 mL) was heated to 100° C. in a microwave oven for 48 h. The solvent was removed in vacuum. Silicagel chromatography gave 374 mg (70% yield) of the title compound.

LC-MS (Method 2): $R_t$=1.40 min; MS (ESIpos): m/z=519 [M+H]$^+$.

$^1$H-NMR (400 MHz, DMSO-d6) δ[ppm]: 0.921 (1.85), 0.937 (1.91), 1.229 (1.95), 1.246 (1.99), 1.400 (16.00), 2.396 (5.59), 5.757 (3.66).

Example 16.02.02

1-{(2R,5S)-2,5-dimethyl-4-[(2-{[6-(3-methyl-1,2,4-oxadiazol-5-yl)-1H-benzimidazol-2-yl]amino}pyridin-4-yl)methyl]piperazin-1-yl}-3,3,3-trifluoropropan-1-one

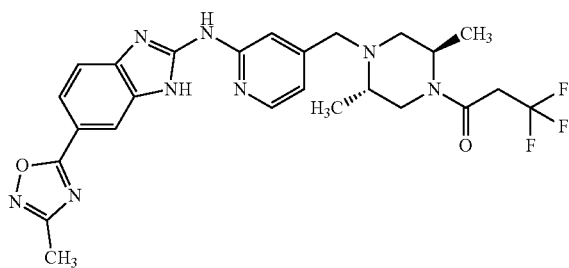 [SMILES: Cc1noc(-c2ccc3nc(Nc4cc(CN5C[C@@H](C)N(C(=O)CC(F)(F)F)C[C@@H]5C)ccn4)[nH]c3c2)n1]

Starting with crude N-(4-{[(2S,5R)-2,5-dimethylpiperazin-1-yl]methyl}pyridin-2-yl)-6-(3-methyl-1,2,4-oxadiazol-5-yl)-1H-benzimidazol-2-amine hydrochloride (100 mg, approx. 177 µmol) and 3,3,3-trifluoropropanoic acid (68.0 mg, 531 µmol) Example 16.02.02 was prepared analogously to the procedure for the preparation of Example 02.02.

Yield: 43.0 mg of the title compound.

LC-MS (Method 2): $R_t$=1.19 min; MS (ESIpos): m/z=529 [M+H]$^+$.

$^1$H-NMR (400 MHz, DMSO-d6) δ[ppm]: 0.868 (1.35), 0.884 (1.43), 0.964 (1.44), 0.980 (1.39), 1.230 (1.42), 1.248 (1.42), 1.352 (1.36), 1.369 (1.29), 2.398 (16.00), 3.441 (1.11), 3.478 (1.71), 3.530 (1.32), 3.664 (1.71), 3.703 (1.23), 6.991 (1.29), 7.290 (3.06), 7.488 (0.91), 8.233 (1.29), 8.283 (1.46), 8.297 (1.02), 12.440 (1.79).

Example 16.02.03

2-cyclopropyl-1-{(2R,5S)-2,5-dimethyl-4-[(2-{[6-(3-methyl-1,2,4-oxadiazol-5-yl)-1H-benzimidazol-2-yl]amino}pyridin-4-yl)methyl]piperazin-1-yl}ethanone

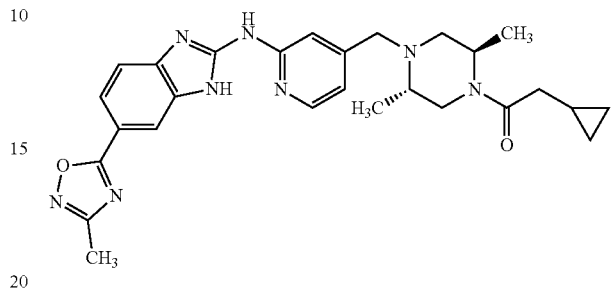

Starting with crude N-(4-{[(2S,5R)-2,5-dimethylpiperazin-1-yl]methyl}pyridin-2-yl)-6-(3-methyl-1,2,4-oxadiazol-5-yl)-1H-benzimidazol-2-amine hydrochloride (90.0 mg, approx. 159 µmol) and cyclopropylacetic acid (47.9 mg, 478 µmol) Example 16.02.03 was prepared analogously to the procedure for the preparation of Example 02.02.

Yield: 48.0 mg of the title compound.

LC-MS (Method 2): $R_t$=1.20 min; MS (ESIpos): m/z=501 [M+H]$^+$.

$^1$H-NMR (400 MHz, DMSO-d6) δ[ppm]: 0.113 (1.72), 0.433 (2.12), 0.437 (2.09), 0.453 (2.29), 0.457 (2.12), 0.934 (1.35), 0.950 (1.43), 2.123 (0.91), 2.140 (0.87), 2.161 (1.46), 2.178 (1.51), 2.207 (1.31), 2.233 (1.55), 2.397 (16.00), 3.427 (1.39), 3.466 (1.95), 3.656 (1.72), 3.695 (1.33), 6.988 (1.15), 7.286 (2.71), 8.231 (1.01), 8.281 (1.27), 12.444 (1.85).

Example 16.02.04 cyclopropyl{(2R,5S)-2,5-dimethyl-4-[(2-{[6-(3-methyl-1,2,4-oxadiazol-5-yl)-1H-benzimidazol-2-yl]amino}pyridin-4-yl)methyl]piperazin-1-yl}methanone

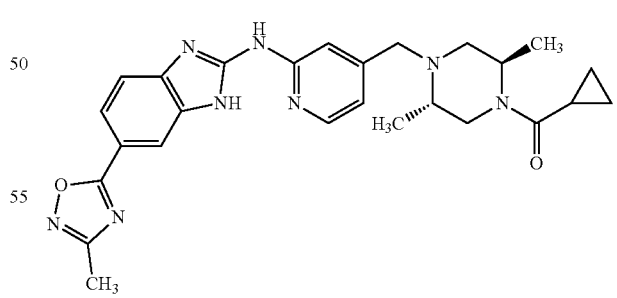

Starting with crude N-(4-{[(2S,5R)-2,5-dimethylpiperazin-1-yl]methyl}pyridin-2-yl)-6-(3-methyl-1,2,4-oxadiazol-5-yl)-1H-benzimidazol-2-amine hydrochloride (100 mg, approx. 177 µmol) and cyclopropanecarboxylic acid (45.7 mg, 531 µmol) Example 16.02.04 was prepared analogously to the procedure for the preparation of Example 02.02.

Yield: 56.0 mg of the title compound.

LC-MS (Method 2): $R_t$=1.16 min; MS (ESIpos): m/z=487 [M+H]$^+$.

$^1$H-NMR (400 MHz, DMSO-d6) δ[ppm]: 0.687 (1.49), 0.706 (1.59), 0.721 (2.06), 0.732 (2.15), 2.398 (16.00), 2.518 (1.85), 3.489 (1.22), 3.664 (1.54), 3.702 (1.14), 6.994 (1.07), 7.007 (1.10), 7.297 (2.29), 8.282 (1.44), 8.294 (1.38).

Example 16.02.05 cyclobutyl{(2R,5S)-2,5-dimethyl-4-[(2-{[6-(3-methyl-1,2,4-oxadiazol-5-yl)-1H-benzimidazol-2-yl]amino}pyridin-4-yl)methyl]piperazin-1-yl}methanone

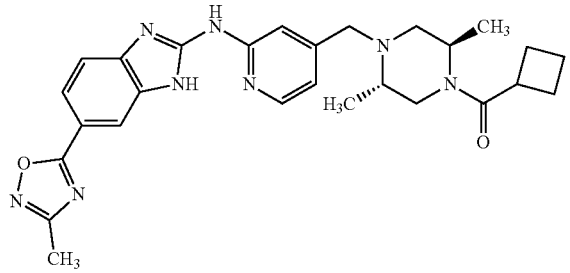 [SMILES: Cc1noc(-c2ccc3nc(Nc4cc(CN5C[C@@H](C)N(C(=O)C6CCC6)C[C@@H]5C)ccn4)[nH]c3c2)n1]

Starting with crude N-(4-{[(2S,5R)-2,5-dimethylpiperazin-1-yl]methyl}pyridin-2-yl)-6-(3-methyl-1,2,4-oxadiazol-5-yl)-1H-benzimidazol-2-amine hydrochloride (90.0 mg, approx. 159 μmol) and cyclobutanecarboxylic acid (47.9 mg, 478 μmol) Example 16.02.05 was prepared analogously to the procedure for the preparation of Example 02.02.

Yield: 34.0 mg of the title compound.

LC-MS (Method 2): $R_t$=1.23 min; MS (ESIpos): m/z=501 [M+H]$^+$.

$^1$H-NMR (400 MHz, DMSO-d6) δ [ppm]: 0.913 (1.23), 1.208 (1.18), 2.196 (1.27), 2.224 (1.33), 2.397 (16.00), 3.418 (1.16), 3.456 (1.51), 6.978 (1.17), 6.991 (1.18), 7.286 (1.93), 8.273 (1.69), 8.285 (1.60).

Example 16.03.01 tert-butyl (3R)-3-methyl-4-[(2-{[6-(3-methyl-1,2,4-oxadiazol-5-yl)-1H-benzimidazol-2-yl]amino}pyridin-4-yl)methyl]piperazine-1-carboxylate

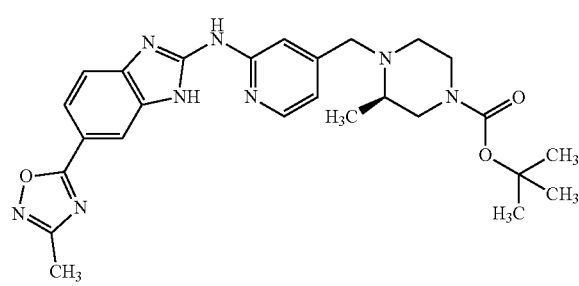 [SMILES: Cc1noc(-c2ccc3nc(Nc4cc(CN5CCN(C(=O)OC(C)(C)C)C[C@H]5C)ccn4)[nH]c3c2)n1]

A mixture of tert-butyl (3R)-4-({2-[(6-{[(ethanimidoylamino)oxy]carbonyl}-1H-benzimidazol-2-yl)amino]pyridin-4-yl}methyl)-3-methylpiperazine-1-carboxylate (510 mg, 976 μmol) and sodium acetate (88.1 mg, 1.07 mmol) in 1-propanol (20 mL, 270 mmol) and water (10 mL) was heated to 100° C. in a microwave oven for 40 h. The solvent was removed in vacuum. Aminophase-silicagel chromatography gave 310 mg (57% yield) of the title compound.

LC-MS (Method 2): $R_t$=1.33 min; MS (ESIpos): m/z=505 [M+H]$^+$.

$^1$H-NMR (400 MHz, DMSO-d$_6$): δ [ppm]=0.98-1.06 (m, 3H), 1.39 (s, 9H), 2.08-2.15 (m, 1H), 2.39 (s, 7H), 2.45 (br s, 1H), 2.56-2.64 (m, 1H), 3.06-3.16 (m, 1H), 3.45-3.64 (m, 2H), 3.88 (br d, 1H), 6.96 (d, 1H), 7.20 (s, 1H), 7.51 (br s, 1H), 7.79 (br d, 1H), 7.90-8.41 (m, 2H), 10.84 (br s, 1H), 12.45 (br s, 1H).

Example 16.03.02

3,3,3-trifluoro-1-{(3R)-3-methyl-4-[(2-{[6-(3-methyl-1,2,4-oxadiazol-5-yl)-1H-benzimidazol-2-yl]amino}pyridin-4-yl)methyl]piperazin-1-yl}propan-1-one

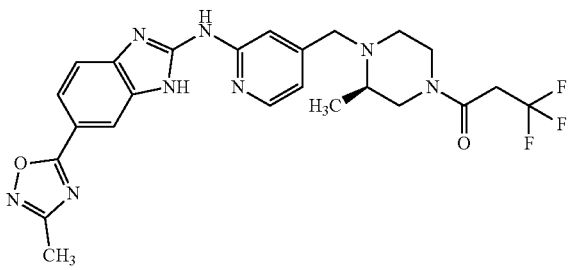 [SMILES: Cc1noc(-c2ccc3nc(Nc4cc(CN5CCN(C(=O)CC(F)(F)F)C[C@H]5C)ccn4)[nH]c3c2)n1]

To a stirred solution of crude 6-(3-methyl-1,2,4-oxadiazol-5-yl)-N-(4-{[(2R)-2-methylpiperazin-1-yl]methyl}pyridin-2-yl)-1H-benzimidazol-2-amine hydrochloride (75.0 mg, approx. 143 μmol) in DMF (5 mL) was added potassium carbonate (98.8 mg, 715 μmol), 3,3,3-trifluoropropanoic acid (54.9 mg, 429 μmol) and HATU (163 mg, 429 μmol). The mixture was stirred at r.t. for 2 h. A solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane/hexane to give 52.0 mg of the title compound.

LC-MS (Method 1): $R_t$=0.78 min; MS (ESIpos): m/z=515 [M+H]$^+$.

$^1$H-NMR (400 MHz, DMSO-d6) δ[ppm]: 1.042 (2.76), 1.058 (2.92), 1.070 (2.86), 1.086 (2.79), 2.398 (16.00), 3.621 (1.41), 3.649 (1.28), 6.976 (1.35), 6.989 (1.35), 7.213 (2.17), 8.281 (1.84), 8.294 (1.74).

Example 16.03.03

2-cyclopropyl-1-{(3R)-3-methyl-4-[(2-{[6-(3-methyl-1,2,4-oxadiazol-5-yl)-1H-benzimidazol-2-yl]amino}pyridin-4-yl)methyl]piperazin-1-yl}ethanone

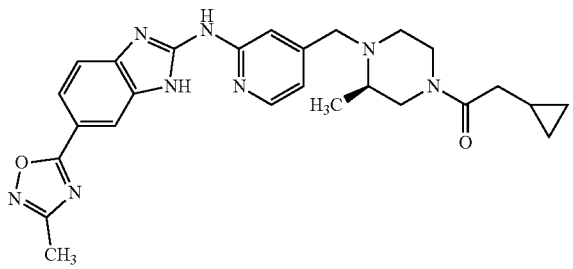 [SMILES: Cc1noc(-c2ccc3nc(Nc4cc(CN5CCN(C(=O)CC6CC6)C[C@H]5C)ccn4)[nH]c3c2)n1]

To a stirred solution of crude 6-(3-methyl-1,2,4-oxadiazol-5-yl)-N-(4-{[(2R)-2-methylpiperazin-1-yl]methyl}pyridin-2-yl)-1H-benzimidazol-2-amine hydrochloride (75.0 mg, approx. 143 μmol) in DMF (5 mL) was added potassium carbonate (98.8 mg, 715 μmol), cyclopropylacetic acid (42.9 mg, 429 μmol) and HATU (163 mg, 429 μmol). The mixture was stirred at r.t. for 2 h. A solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane/hexane to give 40.0 mg of the title compound.

LC-MS (Method 2): $R_t$=1.12 min; MS (ESIpos): m/z=487 [M+H]$^+$.

$^1$H-NMR (400 MHz, DMSO-d6) δ [ppm]: 0.090 (1.09), 0.094 (1.19), 0.103 (1.90), 0.111 (1.28), 0.423 (1.10), 0.427 (1.18), 0.438 (1.19), 0.442 (1.29), 1.038 (2.00), 1.055 (3.82), 1.071 (2.12), 2.228 (1.40), 2.245 (1.58), 2.256 (1.18), 2.397 (16.00), 2.518 (1.67), 2.523 (1.27), 3.254 (1.34), 3.291 (1.49), 6.974 (1.08), 6.989 (1.09), 7.201 (1.92), 8.279 (1.60), 8.292 (1.49).

Example 16.03.04 cyclopropyl{(3R)-3-methyl-4-[(2-{[6-(3-methyl-1,2,4-oxadiazol-5-yl)-1H-benzimidazol-2-yl]amino}pyridin-4-yl)methyl]piperazin-1-yl}methanone

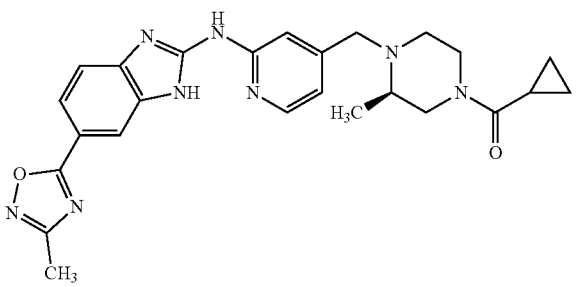 [SMILES: Cc1noc(-c2ccc3nc(Nc4cc(CN5CCN(C(=O)C6CC6)C[C@H]5C)ccn4)[nH]c3c2)n1]

To a stirred solution of crude 6-(3-methyl-1,2,4-oxadiazol-5-yl)-N-(4-{[(2R)-2-methylpiperazin-1-yl]methyl}pyridin-2-yl)-1H-benzimidazol-2-amine hydrochloride (75.0 mg, approx. 143 μmol) in DMF (5 mL) was added potassium carbonate (98.8 mg, 715 μmol), cyclopropanecarboxylic acid (36.9 mg, 429 μmol) and HATU (163 mg, 429 μmol). The mixture was stirred at r.t. for 14 h. A solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane/hexane to give 55.0 mg of the title compound.

LC-MS (Method 2): $R_t$=1.09 min; MS (ESIpos): m/z=473 [M+H]$^+$.

$^1$H-NMR (400 MHz, DMSO-d6) δ[ppm]: 0.683 (1.85), 0.703 (2.40), 0.722 (2.00), 1.078 (1.22), 2.399 (16.00), 6.984 (1.26), 6.999 (1.25), 7.218 (2.49), 8.283 (1.70), 8.296 (1.64).

Example 16.03.05 cyclobutyl{(3R)-3-methyl-4-[(2-{[6-(3-methyl-1,2,4-oxadiazol-5-yl)-1H-benzimidazol-2-yl]amino}pyridin-4-yl)methyl]piperazin-1-yl}methanone

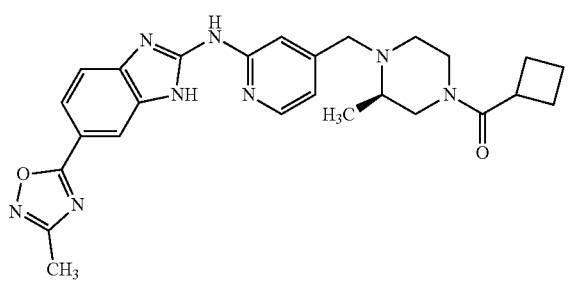 [SMILES: Cc1noc(-c2ccc3nc(Nc4cc(CN5CCN(C(=O)C6CCC6)C[C@H]5C)ccn4)[nH]c3c2)n1]

To a stirred solution of crude 6-(3-methyl-1,2,4-oxadiazol-5-yl)-N-(4-{[(2R)-2-methylpiperazin-1-yl]methyl}pyridin-2-yl)-1H-benzimidazol-2-amine hydrochloride (75.0 mg, approx. 143 μmol) in DMF (5 mL) was added potassium carbonate (98.8 mg, 715 μmol), cyclobutanecarboxylic acid (42.9 mg, 429 μmol) and HATU (163 mg, 429 μmol). The mixture was stirred at r.t. for 2 h. A solution of sodium bicarbonate was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with dichloromethane/hexane to give 51.0 mg of the title compound.

LC-MS (Method 2): $R_t$=1.15 min; MS (ESIpos): m/z=487 [M+H]$^+$.

$^1$H-NMR (400 MHz, DMSO-d6) δ [ppm]: 1.027 (2.71), 1.039 (3.40), 1.043 (3.55), 1.055 (2.68), 2.063 (1.27), 2.071 (1.35), 2.397 (16.00), 2.518 (1.61), 2.523 (1.18), 3.283 (1.13), 6.969 (1.08), 6.982 (1.10), 7.193 (2.18), 8.276 (1.41), 8.289 (1.34).

Example 16.04.01 tert-butyl 3,3-dimethyl-4-[(2-{[6-(3-methyl-1,2,4-oxadiazol-5-yl)-1H-benzimidazol-2-yl]amino}pyridin-4-yl)methyl]piperazine-1-carboxylate

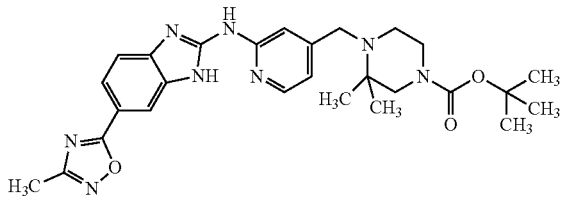 [SMILES: Cc1noc(-c2ccc3nc(Nc4cc(CN5CCN(C(=O)OC(C)(C)C)CC5(C)C)ccn4)[nH]c3c2)n1]

To a stirred solution of 1H-imidazole (65.9 mg, 967 µmol) and di-1H-imidazol-1-ylmethanethione (907 mg, 95% purity, 4.84 mmol) in dichloromethane (20 mL) was added tert-butyl 4-[(2-aminopyridin-4-yl)methyl]-3,3-dimethylpiperazine-1-carboxylate (1.55 g, 4.84 mmol), dissolved in dichloromethane (10 mL) at 0° C. The mixture was stirred at r.t. for 14 h. 4-(3-methyl-1,2,4-oxadiazol-5-yl)benzene-1,2-diamine (920 mg, 4.84 mmol), dissolved in dichloromethane (10 mL) was added and the mixture was stirred at r.t. for 14 h. Water was added and the mixture was extracted with dichloromethane/methanol (100:1). The organic phase was dried (sodium sulfate), filtered and the solvent was removed in vacuum. The residue was dissolved in dichloromethane (60 mL) and N,N'-dipropan-2-ylcarbodiimide (1.9 mL, 12 mmol) was added. The mixture was stirred at r.t. for 56 h. Sodium carbonate solution was added he mixture was extracted with dichloromethane/methanol (100:1) and the solvent was removed in vacuum. The residue was triturated with a mixture of ethanol and hexane to give 1.1 g of the title compound.

LC-MS (Method 2): R$_t$=1.41 min; MS (ESIpos): m/z=519 [M+H]$^+$.

$^1$H-NMR (400 MHz, DMSO-d6) δ [ppm]: 1.045 (8.53), 1.402 (16.00), 2.347 (0.68), 2.396 (5.52), 3.173 (0.79), 3.511 (1.27), 8.253 (0.76), 8.267 (0.73).

Example 16.04.02

1-{3,3-dimethyl-4-[(2-{[6-(3-methyl-1,2,4-oxadiazol-5-yl)-1H-benzimidazol-2-yl]amino}pyridin-4-yl)methyl]piperazin-1-yl}-3,3,3-trifluoropropan-1-one

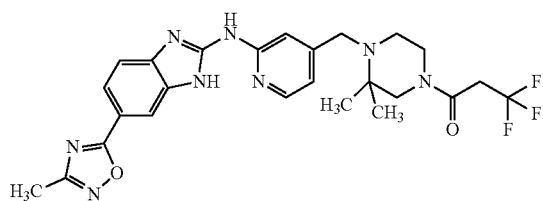 [SMILES: Cc1noc(-c2ccc3nc(Nc4cc(CN5CCN(C(=O)CC(F)(F)F)CC5(C)C)ccn4)[nH]c3c2)n1]

Starting with crude N-{4-[(2,2-dimethylpiperazin-1-yl)methyl]pyridin-2-yl}-6-(3-methyl-1,2,4-oxadiazol-5-yl)-1H-benzimidazol-2-amine hydrochloride (200 mg, approx. 330 µmol) and 3,3,3-trifluoropropanoic acid (44 µl, 490 µmol) Example 16.04.02 was prepared analogously to the procedure for the preparation of Example 16.01.02.

Yield: 130.0 mg of the title compound.

LC-MS (Method 2): R$_t$=1.19 min; MS (ESIpos): m/z=529 [M+H]$^+$.

$^1$H-NMR (400 MHz, DMSO-d6) δ[ppm]: 1.044 (13.97), 1.080 (12.82), 2.355 (0.83), 2.368 (1.33), 2.382 (1.15), 2.397 (16.00), 2.414 (1.48), 2.427 (0.96), 3.306 (2.51), 3.425 (0.90), 3.439 (1.29), 3.452 (1.23), 3.470 (0.97), 3.516 (2.63), 3.526 (2.79), 3.561 (0.56), 3.589 (1.42), 3.616 (1.35), 3.633 (0.71), 3.661 (1.75), 3.688 (1.64), 3.716 (0.51), 6.998 (1.29), 7.010 (1.18), 7.222 (1.51), 7.472 (0.56), 7.492 (0.64), 7.797 (0.83), 7.818 (0.59), 8.233 (0.98), 8.271 (1.37), 8.284 (1.16), 10.897 (0.60), 12.475 (1.40).

Example 16.04.03

2-cyclopropyl-1-{3,3-dimethyl-4-[(2-{[6-(3-methyl-1,2,4-oxadiazol-5-yl)-1H-benzimidazol-2-yl]amino}pyridin-4-yl)methyl]piperazin-1-yl}ethanone

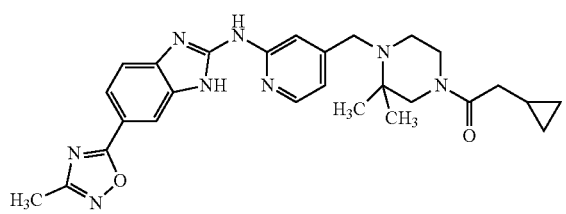 [SMILES: Cc1noc(-c2ccc3nc(Nc4cc(CN5CCN(C(=O)CC6CC6)CC5(C)C)ccn4)[nH]c3c2)n1]

Starting with crude N-{4-[(2,2-dimethylpiperazin-1-yl)methyl]pyridin-2-yl}-6-(3-methyl-1,2,4-oxadiazol-5-yl)-1H-benzimidazol-2-amine hydrochloride (120 mg, approx. 198 µmol) and cyclopropylacetic acid (29 µl, 95% purity, 300 µmol) Example 16.04.03 was prepared analogously to the procedure for the preparation of Example 16.01.02.

Yield: 90.0 mg of the title compound.

LC-MS (Method 2): R$_t$=1.19 min; MS (ESIpos): m/z=501 [M+H]$^+$.

$^1$H-NMR (400 MHz, DMSO-d6) δ[ppm]: 0.097 (1.64), 0.110 (2.84), 0.119 (1.86), 0.417 (0.96), 0.427 (2.63), 0.431 (2.70), 0.437 (1.44), 0.442 (1.39), 0.447 (2.81), 0.452 (2.70), 0.462 (0.91), 1.033 (10.16), 1.059 (10.62), 2.228 (1.97), 2.245 (2.30), 2.251 (2.39), 2.268 (1.89), 2.323 (0.98), 2.335 (1.28), 2.392 (16.00), 3.257 (2.18), 3.305 (1.48), 3.331 (10.35), 3.414 (1.18), 6.989 (1.35), 7.001 (1.31), 7.222 (1.73), 8.262 (1.48), 8.275 (1.37), 12.473 (1.50).

Example 16.04.04 cyclopropyl{3,3-dimethyl-4-[(2-{[6-(3-methyl-1,2,4-oxadiazol-5-yl)-1H-benzimidazol-2-yl]amino}pyridin-4-yl)methyl]piperazin-1-yl}methanone

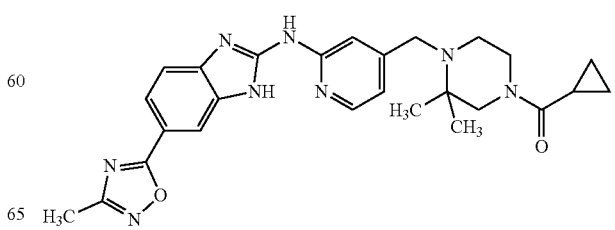

Starting with crude N-{4-[(2,2-dimethylpiperazin-1-yl)methyl]pyridin-2-yl}-6-(3-methyl-1,2,4-oxadiazol-5-yl)-1H-benzimidazol-2-amine hydrochloride (200 mg, approx. 330 μmol) and cyclopropanecarboxylic acid (41 μl, 95% purity, 490 μmol) Example 16.04.04 was prepared analogously to the procedure for the preparation of Example 16.01.02.

Yield: 120.0 mg of the title compound.

LC-MS (Method 2): $R_t$=1.17 min; MS (ESIpos): m/z=487 [M+H]$^+$.

$^1$H-NMR (400 MHz, DMSO-d6) δ [ppm]: 0.679 (1.19), 0.686 (2.31), 0.692 (1.75), 0.700 (1.32), 0.707 (2.72), 0.712 (1.56), 0.719 (1.67), 0.724 (1.97), 0.730 (2.27), 0.735 (2.39), 0.742 (1.28), 1.025 (2.67), 1.095 (5.12), 2.323 (0.84), 2.327 (1.01), 2.331 (0.96), 2.397 (14.05), 3.337 (16.00), 7.003 (1.10), 7.015 (1.04), 7.230 (1.76), 8.271 (1.12), 8.283 (1.01), 12.482 (1.19).

Example 16.04.05 cyclobutyl{3,3-dimethyl-4-[(2-{[6-(3-methyl-1,2,4-oxadiazol-5-yl)-1H-benzimidazol-2-yl]amino}pyridin-4-yl)methyl]piperazin-1-yl}methanone

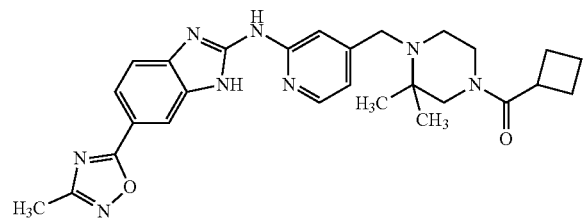 [SMILES: Cc1noc(-c2ccc3nc(Nc4cc(CN5CCN(C(=O)C6CCC6)CC5(C)C)ccn4)[nH]c3c2)n1]

Starting with crude N-{4-[(2,2-dimethylpiperazin-1-yl)methyl]pyridin-2-yl}-6-(3-methyl-1,2,4-oxadiazol-5-yl)-1H-benzimidazol-2-amine hydrochloride (120 mg, approx. 198 μmol) and cyclobutanecarboxylic acid (30 μl, 95% purity, 300 μmol) Example 16.04.05 was prepared analogously to the procedure for the preparation of Example 16.01.02.

Yield: 70.0 mg of the title compound.

LC-MS (Method 2): $R_t$=1.23 min; MS (ESIpos): m/z=501 [M+H]$^+$.

$^1$H-NMR (400 MHz, DMSO-d6) δ[ppm]: 1.025 (12.38), 1.048 (11.54), 2.055 (1.45), 2.064 (1.00), 2.074 (2.75), 2.078 (1.66), 2.085 (1.15), 2.140 (1.77), 2.145 (1.25), 2.161 (1.91), 2.168 (1.53), 2.185 (0.93), 2.190 (1.08), 2.327 (1.87), 2.341 (1.76), 2.397 (16.00), 3.152 (2.19), 3.285 (2.16), 3.504 (3.52), 6.989 (1.16), 7.221 (1.91), 8.230 (0.99), 8.266 (1.30), 8.278 (1.02), 12.475 (1.47).

Example 16.05.01

(rac)-tert-butyl 4-[1-(2-{[6-(3-methyl-1,2,4-oxadiazol-5-yl)-1H-benzimidazol-2-yl]amino}pyridin-4-yl)ethyl]piperazine-1-carboxylate

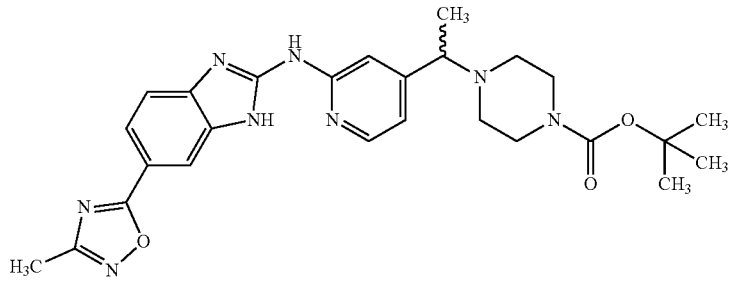 [SMILES: Cc1noc(-c2ccc3nc(Nc4cc(C(C)N5CCN(C(=O)OC(C)(C)C)CC5)ccn4)[nH]c3c2)n1]

To a stirred solution of 1H-imidazole (52.5 mg, 772 μmol) and di-1H-imidazol-1-ylmethanethione (917 mg, 90% purity, 4.63 mmol) in dichloromethane (30 mL) was added (rac)-tert-butyl 4-[1-(2-aminopyridin-4-yl)ethyl]piperazine-1-carboxylate (1.18 g, 3.86 mmol), dissolved in dichloromethane (30 mL) at 0° C. The mixture was stirred at r.t. for 14 h. 4-(3-methyl-1,2,4-oxadiazol-5-yl)benzene-1,2-diamine (908 mg, 97% purity, 4.63 mmol), dissolved in dichloromethane (15 mL) was added and the mixture was stirred at r.t. for 2 h. Water was added and the mixture was extracted with dichloromethane. The organic phase was dried (sodium sulfate) and filtered. N,N'-dipropan-2-ylcarbodiimide (0.87 mL, 5.4 mmol) was added. The mixture was stirred at r.t. for 4 h. Further N,N'-dipropan-2-ylcarbodiimide (0.43 mL, 2.7 mmol) was added and the mixture was stirred at r.t. for 56 h. Saturated sodium chloride solution was added, the mixture was stirred for 30 minutes and was extracted with dichloromethane, dried (sodium sulfate) and the solvent was removed in vacuum. Aminophase-silicagel chromatography followed by silicagel chromatography gave a solid that was triturated with ethanol to give 980 mg of the title compound.

LC-MS (Method 2): $R_t$=1.32 min; MS (ESIpos): m/z=505 [M+H]$^+$.

$^1$H-NMR (500 MHz, DMSO-d6) δ [ppm]: 1.156 (0.68), 1.170 (1.63), 1.185 (0.75), 1.278 (1.86), 1.292 (1.83), 1.369 (3.94), 1.375 (16.00), 1.986 (2.85), 2.397 (5.60), 3.333 (5.91), 4.032 (0.64), 5.758 (1.40), 7.164 (0.91).

Example 16.05.02

(rac)-3,3,3-trifluoro-1-{4-[1-(2-{[6-(3-methyl-1,2,4-oxadiazol-5-yl)-1H-benzimidazol-2-yl]amino}pyridin-4-yl)ethyl]piperazin-1-yl}propan-1-one

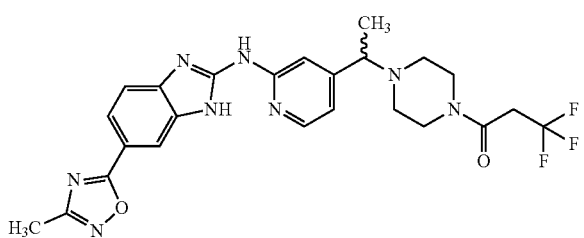 [SMILES: Cc1noc(-c2ccc3nc(Nc4cc(C(C)N5CCN(C(=O)CC(F)(F)F)CC5)ccn4)[nH]c3c2)n1]

To a stirred solution of crude (rac)-6-(3-methyl-1,2,4-oxadiazol-5-yl)-N-{4-[1-(piperazin-1-yl)ethyl]pyridin-2-yl}-1H-benzimidazol-2-amine hydrochloride (1.20 g, approx. 2.39 mmol) in DMF (30 mL) was added sodium bicarbonate (1.20 g, 14.3 mmol), 3,3,3-trifluoropropanoic acid (380 μl, 4.3 mmol) and HATU (2.00 g, 5.25 mmol). The mixture was stirred at room temperature for 3 h. Water was added, the mixture was stirred for 15 minutes and the mixture was extracted with ethyl acetate. The organic phase was washed with saturated sodium chloride solution, dried (sodium sulfate) and the solvent was removed in vacuum. Aminophase-silicagel chromatography followed by silicagel chromatography gave 760 mg of the title compound.

LC-MS (Method 2): $R_t$=1.10 min; MS (ESIpos): m/z=515 [M+H]$^+$.

$^1$H-NMR (400 MHz, DMSO-d$_6$): ([ppm]=1.31 (d, 3H), 2.29-2.48 (m, 7H), 3.40-3.54 (m, 5H), 3.63 (q, 2H), 7.00 (br d, 1H), 7.18 (s, 1H), 7.37-8.40 (m, 4H), 10.91 (br s, 1H), 12.49 (br s, 1H).

Example 16.05.03

(rac)-cyclopropyl{4-[1-(2-{[6-(3-methyl-1,2,4-oxadiazol-5-yl)-1H-benzimidazol-2-yl]amino}pyridin-4-yl)ethyl]piperazin-1-yl}methanone

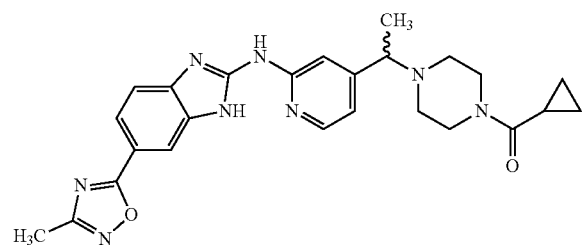 [SMILES: Cc1noc(-c2ccc3nc(Nc4cc(C(C)N5CCN(C(=O)C6CC6)CC5)ccn4)[nH]c3c2)n1]

Starting with crude (rac)-6-(3-methyl-1,2,4-oxadiazol-5-yl)-N-{4-[(1-(piperazin-1-yl)ethyl]pyridin-2-yl}-1H-benzimidazol-2-amine hydrochloride (255 mg, approx. 406 μmol) and cyclopropanecarboxylic acid (105 mg, 1.22 mmol) Example 16.05.03 was prepared analogously to the procedure for the preparation of Example 02.02.

Yield: 139.0 mg of the title compound.

LC-MS (Method 2): $R_t$=1.07 min; MS (ESIpos): m/z=473 [M+H]$^+$.

$^1$H-NMR (400 MHz, DMSO-d$_6$): δ [ppm]=0.60-0.75 (m, 4H), 1.31 (d, 3H), 1.85-2.00 (m, 1H), 2.41 (s, 7H), 3.48 (br d, 3H), 3.68 (br s, 2H), 6.94-7.07 (m, 1H), 7.19 (s, 1H), 7.38-8.38 (m, 4H), 10.91 (br s, 1H), 12.49 (br s, 1H).

Example 16.06.01.A tert-butyl 4-[(1R or 1S)-1-(2-{[6-(3-methyl-1,2,4-oxadiazol-5-yl)-1H-benzimidazol-2-yl]amino}pyridin-4-yl)ethyl]piperazine-1-carboxylate (single stereoisomer A)

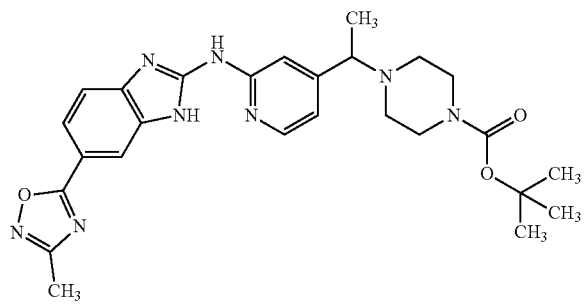 [SMILES: Cc1noc(-c2ccc3nc(Nc4cc(C(C)N5CCN(C(=O)OC(C)(C)C)CC5)ccn4)[nH]c3c2)n1]

To a stirred solution of 1H-imidazole (33.6 mg, 493 μmol) and di-1H-imidazol-1-ylmethanethione (523 mg, 2.94 mmol) in dichloromethane (30 mL) was added tert-butyl 4-[(1R or 1S)-1-(2-aminopyridin-4-yl)ethyl]piperazine-1-carboxylate (750 mg, 2.45 mmol), dissolved in dichloromethane (30 mL) at 0° C. The mixture was stirred at r.t. for 14 h. Further di-1H-imidazol-1-ylmethanethione (260 mg) dissolved in dichloromethane (15 mL) was added and the mixture was stirred for 4 h. 4-(3-methyl-1,2,4-oxadiazol-5-yl)benzene-1,2-diamine (605 mg, 3.18 mmol), dissolved in dichloromethane (15 mL) was added and the mixture was stirred at r.t. for 14 h. Dioxane (40 mL) and N,N'-dipropan-2-ylcarbodiimide (760 μl, 4.9 mmol) was added and the mixture was heated to reflux for 4 h. Water was added, the mixture was stirred for 30 minutes and the mixture was extracted with dichloromethane, dried (sodium sulfate) and the solvent was removed in vacuum. Silicagel chromatography followed by aminophase-silicagel chromatography gave 220 mg of the title compound.

Optical rotation [α]$_D$+28.8° (from solution in DMSO, c=6.0 mg/mL)

LC-MS (Method 2): $R_t$=1.29 min; MS (ESIpos): m/z=505 [M+H]$^+$.

$^1$H-NMR (400 MHz, DMSO-d6) δ[ppm]: 1.153 (1.19), 1.171 (2.41), 1.189 (1.18), 1.277 (1.68), 1.294 (1.69), 1.370 (1.72), 1.375 (16.00), 1.986 (4.01), 2.398 (4.43), 3.333 (8.90), 4.016 (0.90), 4.034 (0.89), 7.160 (0.95).

Example 16.06.02.A 3,3,3-trifluoro-1-{4-[(1R or 1S)-1-(2-{[6-(3-methyl-1,2,4-oxadiazol-5-yl)-1H-benzimidazol-2-yl]amino}pyridin-4-yl)ethyl]piperazin-1-yl}propan-1-one (single stereoisomer A)

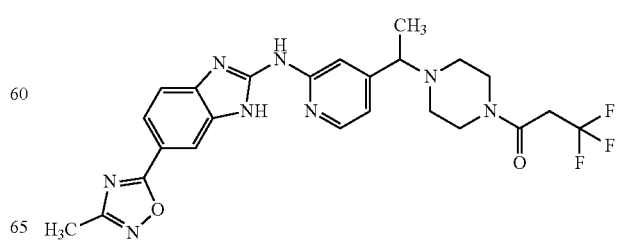

Example 16.06.02.B 3,3,3-trifluoro-1-{4-[(1S or 1R)-1-(2-{[6-(3-methyl-1,2,4-oxadiazol-5-yl)-1H-benzimidazol-2-yl]amino}pyridin-4-yl)ethyl]piperazin-1-yl}propan-1-one (single stereoisomer B)

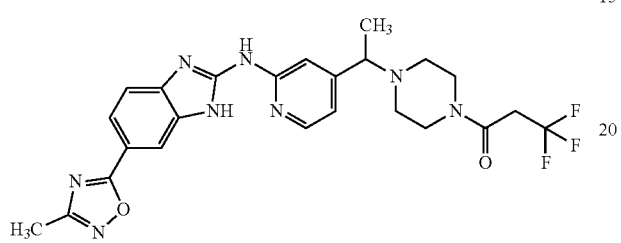

750 mg of (rac)-3,3,3-trifluoro-1-{4-[(1-(2-{[6-(3-methyl-1,2,4-oxadiazol-5-yl)-1H-benzimidazol-2-yl]amino}pyridin-4-yl)ethyl]piperazin-1-yl}propan-1-one was separated into the single stereoisomers (Example 16.6.2.A and Example 16.6.2.B) via preparative, chiral HPLC.

Instrument: Labomatic HD5000, Labocord-5000; Gilson GX-241, Labcol Vario 4000,
Column: Chiralpak IA 5µ 250×30 mm;
Eluent A: tert.-butyl methyl ether; Eluent B: ethanol; isocratic: 90% A+10% B;
Flow: 40.0 mL/min;
Solution: 750 mg/7.8 mL dichloromethane/methanol 1:1
Injection: 13×0.6 mL
Detection: UV 325 nm

|  | Retention time in min | purity in % | yield | Optical rotation $[\alpha]_D$ |
|---|---|---|---|---|
| Example 16.06.02.A Stereoisomer A | 10.6-13.9 | >99.9% | 270 mg | +36.9° (from solution in DMSO, c = 14.2 mg/mL) |
| Example 16.06.02.B Stereoisomer B | 15.4-18.6 | 98.3% | 275 mg | −35.0° (from solution in DMSO, c = 13.2 mg/mL) |

Example 16.06.02.A

LC-MS (Method 2): $R_t$=1.13 min; MS (ESIpos): m/z=515 [M+H]⁺.
¹H-NMR (400 MHz, DMSO-d₆): δ [ppm]=1.31 (d, 3H), 2.29-2.47 (m, 7H), 3.40-3.54 (m, 5H), 3.63 (q, 2H), 7.00 (br d, 1H), 7.18 (s, 1H), 7.44-7.87 (m, 2H), 7.97-8.27 (m, 1H), 8.31 (br d, 1H), 10.74-11.05 (m, 1H), 12.48 (br s, 1H).

Example 16.06.02.B

LC-MS (Method 2): $R_t$=1.13 min; MS (ESIpos): m/z=515 [M+H]⁺.

Example 16.06.03.A cyclopropyl{4-[(1R or 1S)-1-(2-{[6-(3-methyl-1,2,4-oxadiazol-5-yl)-1H-benzimidazol-2-yl]amino}pyridin-4-yl)ethyl]piperazin-1-yl}methanone (single stereoisomer A)

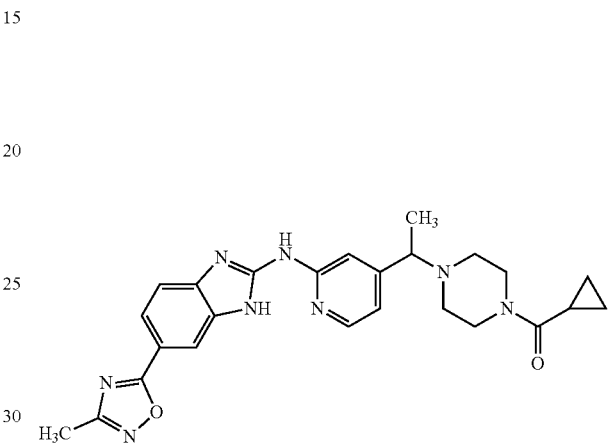

Starting with crude 6-(3-methyl-1,2,4-oxadiazol-5-yl)-N-{4-[(1R or 1S)-1-(piperazin-1-yl)ethyl]pyridin-2-yl}-1H-benzimidazol-2-amine hydrochloride (single stereoisomer A) (100 mg, approx. 198 µmol) and cyclopropanecarboxylic acid (23 µl, 300 µmol), Example 16.06.03.A was prepared analogously to the procedure for the preparation of Example 05.01.

Yield: 70.0 mg of the title compound.

Optical rotation $[\alpha]_D$+47.2° (DMSO) (from solution in DMSO, c=6.0 mg/mL)

LC-MS (Method 2): $R_t$=1.07 min; MS (ESIpos): m/z=473 [M+H]⁺.

¹H-NMR (400 MHz, DMSO-d6) δ[ppm]: 0.656 (1.40), 0.663 (3.18), 0.669 (2.03), 0.675 (1.67), 0.682 (3.92), 0.687 (3.54), 0.691 (3.80), 0.698 (3.30), 0.703 (3.74), 0.710 (1.79), 0.811 (1.03), 0.828 (1.72), 0.833 (0.78), 0.837 (0.95), 0.847 (1.05), 0.855 (1.93), 0.933 (0.92), 0.950 (0.96), 1.233 (1.40), 1.293 (6.16), 1.310 (6.16), 1.915 (0.75), 1.922 (0.85), 1.935 (1.35), 1.947 (0.80), 1.954 (0.73), 2.327 (0.87), 2.398 (16.00), 2.523 (1.30), 2.619 (0.67), 3.462 (2.74), 3.478 (2.68), 3.673 (1.63), 5.760 (0.78), 6.994 (1.39), 7.175 (3.19), 7.495 (0.84), 7.799 (0.96), 8.236 (1.28), 8.303 (1.51), 12.474 (1.58).

The Example compounds in the following table 8 were synthesized in analogy to the preparation of Example 117.02, followed by purification by preparative reverse phase HPLC or silicagel chromatography.

TABLE 8

| | Structure<br>IUPAC-Name<br>LC-MS (method): Retention time; Mass found<br>¹H-NMR |
|---|---|
| Example | Starting materials (SM): |

Example
16.06.04

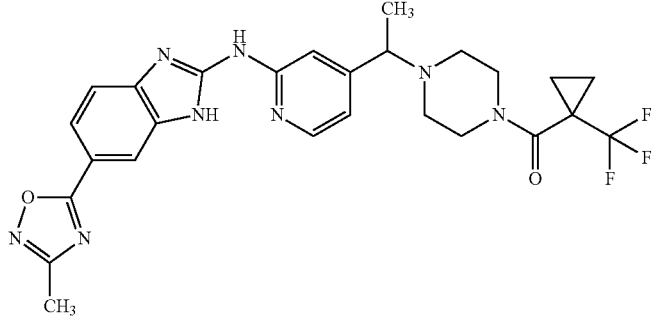 [SMILES: Cc1noc(-c2ccc3nc(Nc4cc(C(C)N5CCN(C(=O)C6(C(F)(F)F)CC6)CC5)ccn4)[nH]c3c2)n1]

{4-[(1R or 1S)-1-(2-{[6-(3-methyl-1,2,4-oxadiazol-5-yl)-1H-benzimidazol-2-yl]amino}pyridin-4-yl)ethyl]piperazin-1-yl}[1-(trifluoromethyl)cyclopropyl]methanone LC-MS (Method 2): $R_t$ = 1.18 min; MS (ESIneg): m/z = 539 [M − H]⁻
¹H-NMR (400 MHz, DMSO-d6) δ [ppm]: 1.157 (1.86), 1.251 (1.08), 1.263 (2.32), 1.286 (4.09), 1.302 (3.91), 2.327 (0.49), 2.338 (0.66), 2.353 (0.79), 2.367 (0.96), 2.394 (16.00), 2.450 (0.95), 2.463 (0.80), 2.479 (0.75), 2.518 (0.56), 2.523 (0.43), 3.339 (1.68), 3.456 (1.06), 3.473 (1.04), 6.967 (1.21), 6.970 (1.23), 6.980 (1.22), 6.983 (1.25), 7.271 (0.72), 7.533 (0.60), 7.554 (0.69), 7.768 (1.44), 7.772 (1.40), 7.789 (1.13), 7.793 (1.21), 8.140 (0.72), 8.282 (1.99), 8.295 (1.89).
SM: Compound 16.07 and 1-(trifluoromethyl)cyclopropanecarboxylic acid Example
16.06.05

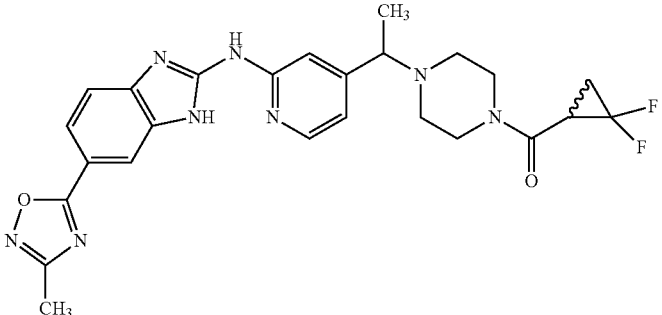 [SMILES: Cc1noc(-c2ccc3nc(Nc4cc(C(C)N5CCN(C(=O)C6CC6(F)F)CC5)ccn4)[nH]c3c2)n1]

((1RS)-2,2-difluorocyclopropyl){4-[(1R or 1S)-1-(2-{[6-(3-methyl-1,2,4-oxadiazol-5-yl)-1H-benzimidazol-2-yl]amino}pyridin-4-yl)ethyl]piperazin-1-yl}methanone LC-MS (Method 2): $R_t$ = 1.12 min; MS (ESIneg): m/z = 507 [M − H]⁻
¹H-NMR (400 MHz, DMSO-d6) δ [ppm]: 1.295 (5.02), 1.311 (5.05), 1.793 (0.46), 1.810 (0.52), 1.822 (0.53), 1.840 (0.52), 1.853 (0.49), 1.859 (0.56), 1.873 (0.67), 1.892 (0.62), 1.905 (0.40), 2.306 (0.47), 2.323 (0.70), 2.327 (0.76), 2.332 (0.80), 2.361 (0.87), 2.371 (0.73), 2.398 (16.00), 2.442 (1.05), 2.449 (1.00), 2.518 (1.27), 2.523 (0.92), 3.074 (0.43), 3.095 (0.48), 3.103 (0.55), 3.109 (0.56), 3.122 (0.49), 3.129 (0.59), 3.137 (0.49), 3.157 (0.41), 3.482 (1.06), 3.490 (1.32), 3.498 (1.35), 3.506 (1.49), 3.516 (1.23), 3.523 (1.22), 3.539 (0.78), 3.547 (0.69), 3.562 (0.82), 3.572 (0.64), 3.618 (0.61), 3.634 (0.54), 6.991 (0.98), 7.003 (0.91), 7.180 (2.15), 7.475 (0.43), 7.495 (0.49), 7.798 (0.67), 7.818 (0.46), 8.235 (0.75), 8.301 (1.09), 8.313 (0.98), 10.910 (0.47), 12.477 (0.98).
SM: Compound 16.07 and (1RS)-2,2-difluorocyclopropanecarboxylic acid

TABLE 8-continued

| Example | Structure<br>IUPAC-Name<br>LC-MS (method): Retention time; Mass found<br>$^1$H-NMR<br>Starting materials (SM): |
|---|---|
| Example 16.06.06 | 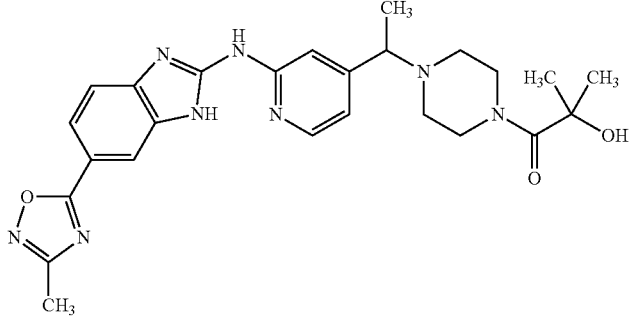 [SMILES: Cc1noc(-c2ccc3nc(Nc4cc(C(C)N5CCN(C(=O)C(C)(C)O)CC5)ccn4)[nH]c3c2)n1]<br>2-hydroxy-2-methyl-1-{4-[(1R or 1S)-1-(2-{[6-(3-methyl-1,2,4-oxadiazol-5-yl)-1H-benzimidazol-2-yl]amino}pyridin-4-yl)ethyl]piperazin-1-yl}propan-1-one<br>LC-MS (Method 2): $R_t$ = 1.02 min; MS (ESIneg): m/z = 489 [M − H]$^-$<br>$^1$H-NMR (400 MHz, DMSO-d6) δ [ppm]: 1.278 (16.00), 1.287 (3.46), 1.304 (2.87), 2.322 (0.53), 2.327 (0.46), 2.336 (0.67), 2.350 (0.75), 2.397 (10.66), 3.432 (0.81), 3.449 (0.82), 5.365 (2.64), 6.974 (0.81), 6.976 (0.82), 6.987 (0.82), 6.989 (0.82), 7.168 (1.53), 7.785 (0.60), 7.807 (0.51), 8.291 (1.29), 8.304 (1.21).<br>SM: Compound 16.07 and 2-hydroxy-2-methylpropanoic acid |

Example 17.01 tert-butyl 4-[(2-{[6-(3-cyclopropyl-1,2,4-oxadiazol-5-yl)-1H-benzimidazol-2-yl]amino}pyridin-4-yl)methyl]piperazine-1-carboxylate

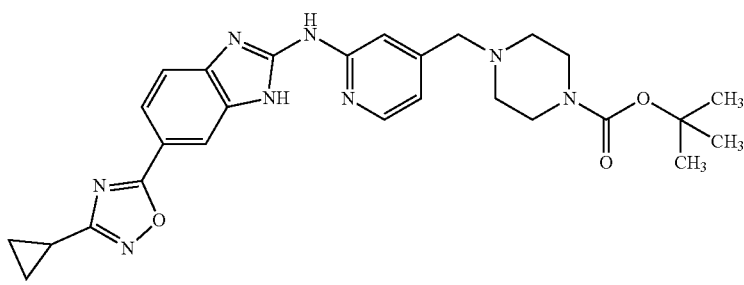 [SMILES: CC(C)(C)OC(=O)N1CCN(Cc2ccnc(Nc3nc4ccc(-c5nc(C6CC6)no5)cc4[nH]3)c2)CC1]

A mixture of tert-butyl 4-[(2-{[6-({[(cyclopropylcarbonoimidoyl)amino]oxy}carbonyl)-1H-benzimidazol-2-yl]amino}pyridin-4-yl)methyl]piperazine-1-carboxylate (7.50 g, 14.0 mmol) and sodium acetate (1.27 g, 15.4 mmol) in 1-propanol (330 mL) and water (170 mL) was heated to 100° C. for 72 h. The mixture was concentrated in vacuum, a half-saturated solution of sodium bicarbonate was added and the mixture was extracted with dichloromethane/methanol (9:1). The organic phase was washed with saturated sodium chloride solution, dried (sodium sulfate), filtered and the solvent was removed in vacuum. Aminophase-silicagel chromatography gave 6.40 g (88% yield) of the title compound.

LC-MS (Method 2): $R_t$=1.41 min; MS (ESIpos): m/z=517 [M+H]$^+$.

$^1$H-NMR (400 MHz, DMSO-d6) δ [ppm]: 0.986 (0.62), 0.992 (0.68), 0.997 (0.63), 1.004 (0.69), 1.054 (0.62), 1.085 (0.60), 1.106 (0.67), 1.395 (16.00), 2.162 (0.45), 2.346 (0.86), 2.359 (1.29), 2.371 (0.95), 2.518 (1.44), 2.523 (1.03), 3.347 (1.37), 3.360 (0.90), 3.507 (1.66), 5.755 (0.47), 8.271 (0.74), 8.284 (0.73).

Example 17.02

1-{4-[(2-{[6-(3-cyclopropyl-1,2,4-oxadiazol-5-yl)-1H-benzimidazol-2-yl]amino}pyridin-4-yl)methyl]piperazin-1-yl}-3,3,3-trifluoropropan-1-one

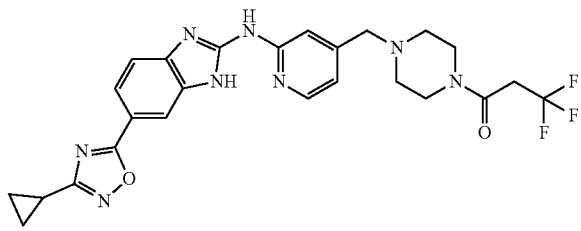 [SMILES: O=C(CC(F)(F)F)N1CCN(Cc2ccnc(Nc3nc4ccc(-c5nc(C6CC6)no5)cc4[nH]3)c2)CC1]

To a stirred solution of crude 6-(3-cyclopropyl-1,2,4-oxadiazol-5-yl)-N-[4-(piperazin-1-ylmethyl)pyridin-2-yl]-1H-benzimidazol-2-amine hydrochloride (100 mg, approx. 221 µmol) in DMF (2 mL) was added DIPEA (190 µl, 1.1 mmol), T3P (230 µl, 50% in DMF, 400 µmol) and 3,3,3-trifluoropropanoic acid (34 µl, 98% purity, 380 µmol). The mixture was stirred at r.t. for 14 h. Water was added, and the mixture was extracted with ethyl acetate. The organic phase was washed with saturated sodium chloride solution, dried (sodium sulfate), filtered and the solvent was removed in vacuum. Aminophase-silicagel chromatography gave 19.0 mg of the title compound.

LC-MS (Method 1): $R_t$=0.92 min; MS (ESIpos): m/z=527 [M+H]$^+$.

$^1$H-NMR (300 MHz, DMSO-d$_6$): δ [ppm]=0.94-1.14 (m, 4H), 2.09-2.21 (m, 1H), 2.32-2.45 (m, 4H), 3.40-3.56 (m, 6H), 3.64 (q, 2H), 6.96 (br d, 1H), 7.17 (s, 1H), 7.36-8.35 (m, 4H), 10.92 (br s, 1H), 12.47 (br s, 1H).

Example 17.03

2-cyclopropyl-1-{4-[(2-{[6-(3-cyclopropyl-1,2,4-oxadiazol-5-yl)-1H-benzimidazol-2-yl]amino}pyridin-4-yl)methyl]piperazin-1-yl}ethanone

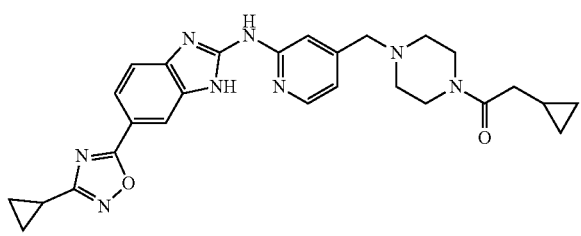 [SMILES: O=C(CC1CC1)N1CCN(Cc2ccnc(Nc3nc4ccc(-c5nc(C6CC6)no5)cc4[nH]3)c2)CC1]

Starting with crude 6-(3-cyclopropyl-1,2,4-oxadiazol-5-yl)-N-[4-(piperazin-1-ylmethyl)pyridin-2-yl]-1H-benzimidazol-2-amine hydrochloride (310 mg, approx. 548 µmol) and cyclopropylacetic acid (74 µl, 98% purity, 820 µmol) Example 17.03. was prepared analogously to the procedure for the preparation of Example 16.01.02.

Yield: 150.0 mg of the title compound.

LC-MS (Method 2): $R_t$=1.21 min; MS (ESIpos): m/z=499 [M+H]$^+$.

$^1$H-NMR (400 MHz, DMSO-d6) δ[ppm]: 0.000 (2.04), 0.011 (7.50), 0.014 (6.93), 0.023 (7.67), 0.026 (7.29), 0.037 (2.48), 0.330 (2.56), 0.340 (6.58), 0.344 (6.76), 0.350 (3.41), 0.354 (3.11), 0.360 (7.06), 0.364 (6.77), 0.374 (2.48), 0.818 (0.62), 0.822 (0.79), 0.835 (1.46), 0.838 (1.50), 0.842 (1.44), 0.847 (1.20), 0.854 (2.45), 0.859 (1.39), 0.862 (1.23), 0.867 (1.43), 0.871 (1.52), 0.874 (1.41), 0.890 (2.04), 0.902 (7.07), 0.908 (6.74), 0.914 (6.44), 0.920 (8.15), 0.928 (2.70), 0.939 (1.62), 0.954 (0.64), 0.975 (0.46), 0.991 (2.41), 0.999 (6.10), 1.006 (4.83), 1.011 (4.04), 1.020 (6.74), 1.027 (5.07), 1.039 (1.83), 2.044 (1.17), 2.056 (2.22), 2.064 (2.59), 2.077 (4.54), 2.089 (2.40), 2.097 (2.69), 2.109 (1.14), 2.151 (12.69), 2.168 (12.24), 2.237 (0.59), 2.241 (0.81), 2.247 (0.78), 2.278 (5.47), 2.296 (5.74), 2.309 (6.09), 2.437 (1.58), 2.579 (0.43), 2.584 (0.56), 2.589 (0.42), 3.370 (5.03), 3.380 (4.54), 3.405 (5.07), 3.430 (16.00), 6.363 (0.47), 6.608 (0.48), 6.878 (3.57), 6.890 (3.69), 7.100 (9.00), 7.393 (1.16), 7.571 (0.50), 7.668 (2.20), 7.888 (0.63), 8.130 (1.65), 8.192 (6.66), 8.205 (6.46), 10.811 (1.46), 12.377 (4.51).

Example 17.04

1-{4-[(2-{[6-(3-cyclopropyl-1,2,4-oxadiazol-5-yl)-1H-benzimidazol-2-yl]amino}pyridin-4-yl)methyl]piperazin-1-yl}but-3-en-1-one

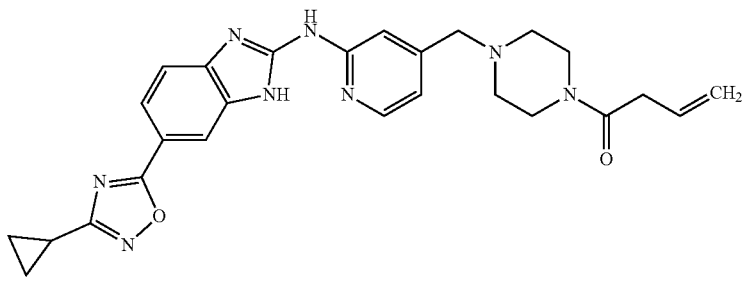 [SMILES: C=CCC(=O)N1CCN(Cc2ccnc(Nc3nc4ccc(-c5nc(C6CC6)no5)cc4[nH]3)c2)CC1]

Starting with crude 6-(3-cyclopropyl-1,2,4-oxadiazol-5-yl)-N-[4-(piperazin-1-ylmethyl)pyridin-2-yl]-1H-benzimidazol-2-amine hydrochloride (80.0 mg, approx. 141 µmol) and but-3-enoic acid (19 µl, 97% purity, 210 µmol) Example 17.04. was prepared analogously to the procedure for the preparation of Example 16.01.02.

Yield: 60.0 mg of the title compound.

LC-MS (Method 2): $R_t$=1.18 min; MS (ESIpos): m/z=485 [M+H]$^+$.

$^1$H-NMR (400 MHz, DMSO-d6) δ [ppm]: 0.975 (1.61), 0.987 (5.70), 0.993 (6.21), 0.998 (5.70), 1.000 (5.29), 1.004 (6.04), 1.013 (2.47), 1.042 (0.52), 1.077 (2.30), 1.086 (5.84), 1.092 (4.43), 1.097 (3.74), 1.107 (6.32), 1.113 (4.77), 1.125 (1.75), 1.818 (0.65), 1.822 (0.65), 1.835 (0.62), 1.839 (0.62), 1.955 (0.48), 2.131 (1.13), 2.143 (2.16), 2.151 (2.44), 2.155 (1.34), 2.163 (4.26), 2.172 (1.55), 2.175 (2.20), 2.184 (2.06), 2.196 (0.96), 2.318 (0.48), 2.323 (0.96), 2.327 (1.34), 2.332 (1.06), 2.337 (0.86), 2.349 (3.36), 2.361 (5.25), 2.375 (4.19), 2.392 (4.33), 2.404 (5.42), 2.416 (3.67), 2.518 (3.43), 2.523 (2.33), 2.665 (0.86), 2.669 (1.13), 2.674 (0.79), 2.782 (0.45), 2.942 (0.69), 3.133 (5.25), 3.137 (9.13), 3.141 (5.42), 3.150 (5.53), 3.153 (9.13), 3.157 (5.15), 3.472 (8.52), 3.482 (8.34), 3.519 (16.00), 5.069 (5.53), 5.073 (11.64), 5.076 (5.60), 5.093 (1.30), 5.097 (3.33), 5.101 (5.32), 5.105 (2.33), 5.109 (2.20), 5.113 (5.29), 5.118 (3.91), 5.122 (1.20), 5.826 (1.34), 5.843 (3.12), 5.850 (0.72), 5.854 (0.86), 5.859 (1.37), 5.867 (2.13), 5.871 (2.06), 5.883 (2.13), 5.888 (2.23), 5.895 (1.17), 5.899 (0.65), 5.904 (0.86), 5.911 (2.44), 5.928 (1.03), 6.965 (3.78), 6.978 (3.71), 7.187 (7.35), 7.483 (0.69), 7.750 (2.44), 7.769 (1.99), 8.210 (0.76), 8.278 (6.94), 8.292 (6.49), 10.894 (1.10), 12.473 (2.20).

Example 17.05 cyclopropyl{4-[(2-{[6-(3-cyclopropyl-1,2,4-oxadiazol-5-yl)-1H-benzimidazol-2-yl]amino}pyridin-4-yl)methyl]piperazin-1-yl}methanone

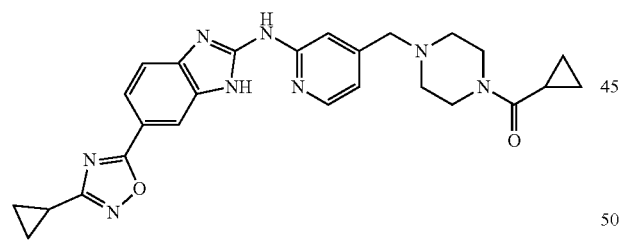

Starting with crude 6-(3-cyclopropyl-1,2,4-oxadiazol-5-yl)-N-[4-(piperazin-1-ylmethyl)pyridin-2-yl]-1H-benzimidazol-2-amine hydrochloride (6.10 g, approx. 13.5 mmol) and cyclopropanecarboxylic acid (2.7 mL, 98% purity, 34 mmol) Example 17.05. was prepared analogously to the procedure for the preparation of Example 02.02.

Yield: 5.12 g of the title compound.

LC-MS (Method 2): $R_t$=1.15 min; MS (ESIpos): m/z=485 [M+H]$^+$.

$^1$H-NMR (400 MHz, DMSO-d$_6$): δ [ppm]=0.63-0.79 (m, 4H), 0.97-1.03 (m, 2H), 1.07-1.14 (m, 2H), 1.89-2.03 (m, 1H), 2.11-2.22 (m, 1H), 2.32-2.48 (m, 4H), 3.43-3.59 (m, 4H), 3.71 (br s, 2H), 6.99 (d, 1H), 7.20 (s, 1H), 7.33-8.39 (m, 4H), 10.91 (br s, 1H), 12.49 (br s, 1H).

Example 17.06 cyclobutyl{4-[(2-{[6-(3-cyclopropyl-1,2,4-oxadiazol-5-yl)-1H-benzimidazol-2-yl]amino}pyridin-4-yl)methyl]piperazin-1-yl}methanone

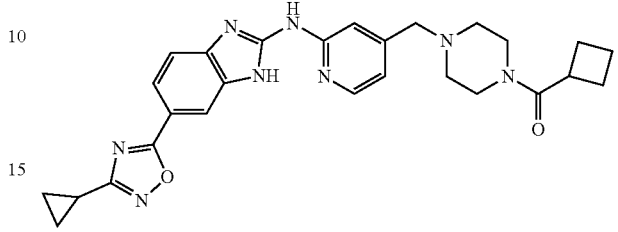

To a stirred solution of crude 6-(3-cyclopropyl-1,2,4-oxadiazol-5-yl)-N-[4-(piperazin-1-ylmethyl)pyridin-2-yl]-1H-benzimidazol-2-amine hydrochloride (100 mg, approx. 221 µmol) in DMF (2 mL) was added DIPEA (190 µl, 1.1 mmol), T3P (230 µl, 50% in DMF, 400 µmol) and cyclobutanecarboxylic acid (34 µl, 98% purity, 380 µmol). The mixture was stirred at r.t. for 2 h. Water was added, and the mixture was extracted with ethyl acetate. The organic phase was washed with saturated sodium chloride solution, dried (sodium sulfate), filtered and the solvent was removed in vacuum. Aminophase-silicagel chromatography gave 68.0 mg of the title compound.

LC-MS (Method 1): $R_t$=0.89 min; MS (ESIpos): m/z=499 [M+H]$^+$.

$^1$H-NMR (400 MHz, DMSO-d$_6$): δ [ppm]=0.94-1.02 (m, 2H), 1.05-1.14 (m, 2H), 1.65-1.78 (m, 1H), 1.80-1.93 (m, 1H), 2.00-2.20 (m, 5H), 2.34 (br s, 4H), 3.33 (br s, 3H), 3.41-3.53 (m, 4H), 6.95 (br d, 1H), 7.17 (s, 1H), 7.34-8.35 (m, 4H), 10.86 (br s, 1H), 12.45 (br s, 1H).

Example 17.07

N-(4-{[4-(2-chlorophenyl)piperazin-1-yl]methyl}pyridin-2-yl)-6-(3-cyclopropyl-1,2,4-oxadiazol-5-yl)-1H-benzimidazol-2-amine

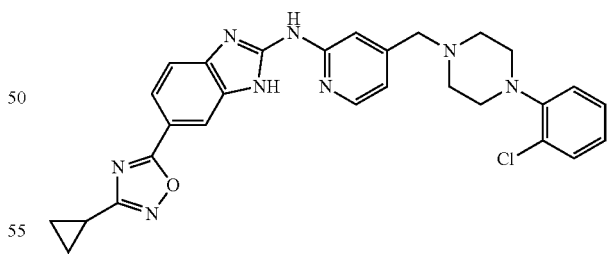

A mixture of N-[({2-[(4-{[4-(2-chlorophenyl)piperazin-1-yl]methyl}pyridin-2-yl)amino]-1H-benzimidazol-6-yl}carbonyl)oxy]cyclopropanecarboximidamide (160 mg, 294 µmol) and sodium acetate (26.5 mg, 323 µmol) in 1-propanol (7.0 mL), water (3.5 mL) and DMA (700 µl) was heated to 100° C. 30 h. The mixture was cooled to r.t. and a white solid precipitated. Filtration gave 110 mg (64% yield) of the title compound.

LC-MS (Method 2): $R_t$=1.49 min; MS (ESIpos): m/z=527.5 [M+H]$^+$.

¹H-NMR (400 MHz, DMSO-d6) δ [ppm]: 0.976 (1.51), 0.987 (5.57), 0.994 (6.21), 0.999 (5.89), 1.006 (5.87), 1.014 (2.39), 1.040 (0.65), 1.061 (0.43), 1.077 (2.29), 1.085 (5.83), 1.092 (4.50), 1.097 (3.78), 1.106 (6.35), 1.112 (4.78), 1.124 (1.74), 2.130 (1.06), 2.142 (2.03), 2.150 (2.32), 2.163 (3.94), 2.174 (2.13), 2.183 (1.91), 2.195 (0.89), 2.322 (0.49), 2.327 (0.66), 2.331 (0.50), 2.523 (1.85), 2.599 (7.95), 2.659 (0.49), 2.664 (0.69), 2.669 (0.84), 2.674 (0.61), 3.022 (9.56), 3.575 (16.00), 6.992 (3.44), 7.005 (3.51), 7.015 (3.07), 7.020 (2.89), 7.035 (4.83), 7.039 (4.86), 7.054 (3.32), 7.057 (3.38), 7.158 (4.02), 7.162 (4.09), 7.178 (5.89), 7.182 (5.18), 7.213 (7.67), 7.278 (3.26), 7.283 (3.50), 7.297 (4.15), 7.301 (4.58), 7.317 (2.23), 7.321 (2.25), 7.388 (6.45), 7.392 (6.11), 7.407 (5.86), 7.411 (5.42), 7.481 (1.05), 7.756 (2.05), 7.774 (1.54), 7.975 (0.54), 8.219 (1.45), 8.291 (6.52), 8.305 (6.21), 10.910 (1.28), 12.476 (3.81).

Example 18.01

3,3,3-trifluoro-1-(4-{[2-({6-[3-(2-methylpropyl)-1,2,4-oxadiazol-5-yl]-1H-benzimidazol-2-yl}amino)pyridin-4-yl]methyl}piperazin-1-yl)propan-1-one

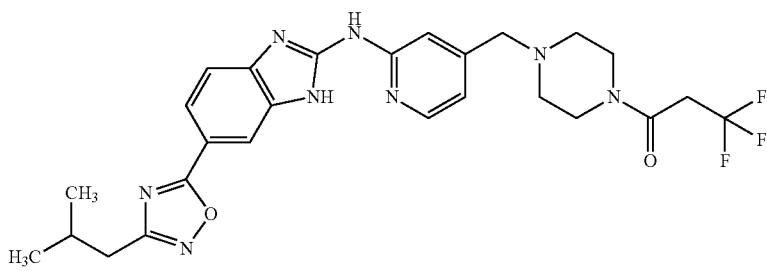 [SMILES: CC(C)Cc1noc(-c2ccc3nc(Nc4cc(CN5CCN(C(=O)CC(F)(F)F)CC5)ccn4)[nH]c3c2)n1]

Starting with crude 6-[3-(2-methylpropyl)-1,2,4-oxadiazol-5-yl]-N-[4-(piperazin-1-ylmethyl)pyridin-2-yl]-1H-benzimidazol-2-amine hydrochloride (139 mg, approx. 296 μmol) and 3,3,3-trifluoropropanoic acid (55 μl, 98% purity, 590 μmol) Example 18.01. was prepared analogously to the procedure for the preparation of Example 02.02.

Yield: 40.0 mg of the title compound.

LC-MS (Method 2): $R_t$=1.33 min; MS (ESIpos): m/z=543 [M+H]⁺.

¹H-NMR (400 MHz, DMSO-d6) δ [ppm]: 0.974 (15.10), 0.991 (16.00), 2.112 (0.86), 2.130 (1.07), 2.146 (0.84), 2.327 (0.47), 2.373 (1.22), 2.386 (1.82), 2.398 (1.37), 2.414 (1.34), 2.427 (1.80), 2.438 (1.32), 2.523 (0.96), 2.624 (4.30), 2.642 (3.99), 2.669 (0.50), 3.461 (1.30), 3.474 (1.81), 3.486 (1.46), 3.497 (1.43), 3.511 (1.76), 3.522 (1.48), 3.535 (4.95), 3.606 (0.90), 3.634 (2.58), 3.661 (2.42), 3.688 (0.76), 6.968 (1.14), 6.982 (1.16), 7.195 (2.16), 7.794 (0.65), 8.289 (1.85), 8.302 (1.72), 12.471 (0.78).

Example 18.02 cyclopropyl(4-{[2-({6-[3-(2-methylpropyl)-1,2,4-oxadiazol-5-yl]-1H-benzimidazol-2-yl}amino)pyridin-4-yl]methyl}piperazin-1-yl)methanone

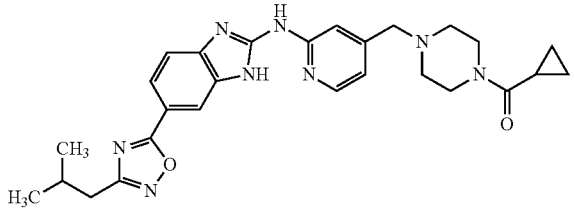 [SMILES: CC(C)Cc1noc(-c2ccc3nc(Nc4cc(CN5CCN(C(=O)C6CC6)CC5)ccn4)[nH]c3c2)n1]

A mixture of N-[({2-[(4-{[4-(cyclopropylcarbonyl)piperazin-1-yl]methyl}pyridin-2-yl)amino]-1H-benzimidazol-6-yl}carbonyl)oxy]-3-methylbutanimidamide (125 mg, 241 μmol) and sodium acetate (21.7 mg, 265 μmol) in 1-propanol (6 mL) and water (3 mL) was heated to 100° C. for 120 h. The solvent was removed in vacuum. Silicagel chromatography gave 95.0 mg (71% yield) of the title compound.

LC-MS (Method 2): $R_t$=1.29 min; MS (ESIpos): m/z=501 [M+H]⁺.

¹H-NMR (400 MHz, DMSO-d6) δ [ppm]: 0.679 (1.01), 0.686 (2.41), 0.692 (1.49), 0.699 (1.15), 0.706 (2.84), 0.711 (2.46), 0.717 (2.59), 0.723 (2.46), 0.729 (2.88), 0.735 (1.33), 0.976 (15.35), 0.993 (16.00), 1.943 (0.59), 1.949 (0.63), 1.962 (1.04), 1.974 (0.61), 1.981 (0.59), 2.114 (0.83), 2.131 (1.08), 2.148 (0.86), 2.327 (0.59), 2.375 (1.04), 2.447 (1.06), 2.523 (1.76), 2.625 (4.28), 2.642 (4.01), 2.669 (0.56), 3.501 (0.97), 3.535 (5.50), 3.705 (0.95), 6.976 (1.28), 6.989 (1.31), 7.209 (2.19), 7.793 (0.86), 7.813 (0.70), 8.290 (2.03), 8.303 (1.94).

Example 19.01

{4-[(2-{[6-(3-cyclopentyl-1,2,4-oxadiazol-5-yl)-1H-benzimidazol-2-yl]amino}pyridin-4-yl)methyl]piperazin-1-yl}(cyclopropyl)methanone

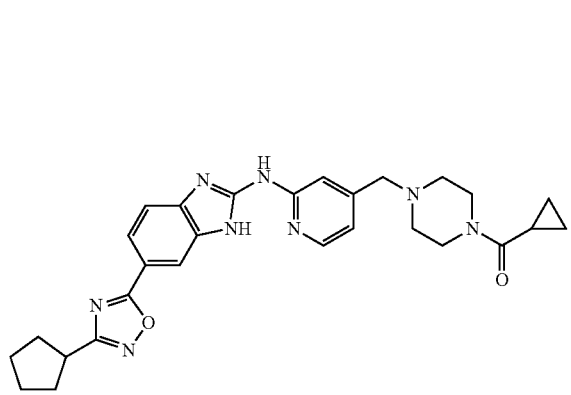 [SMILES: O=C(C1CC1)N1CCN(Cc2ccnc(Nc3nc4ccc(-c5nc(C6CCCC6)no5)cc4[nH]3)c2)CC1]

A mixture of N-[({2-[(4-{[4-(cyclopropylcarbonyl)piperazin-1-yl]methyl}pyridin-2-yl)amino]-1H-benzimidazol-6-yl}carbonyl)oxy]cyclopentanecarboximidamide (135 mg, 254 μmol) and sodium acetate (23.0 mg, 280 μmol) in 1-propanol (6.5 mL) and water (3.2 mL) was heated to 100° C. for 16 h. The solvent was removed in vacuum. Silicagel chromatography gave 90.0 mg (62% yield) of the title compound.

LC-MS (Method 2): $R_t$=1.33 min; MS (ESIpos): m/z=513 [M+H]$^+$.

$^1$H-NMR (400 MHz, DMSO-d6) δ[ppm]: 0.666 (0.99), 0.678 (3.12), 0.685 (7.47), 0.690 (4.50), 0.698 (3.50), 0.704 (8.91), 0.709 (7.62), 0.714 (8.08), 0.721 (7.47), 0.726 (8.76), 0.733 (3.81), 0.746 (0.91), 1.229 (0.76), 1.637 (0.46), 1.652 (0.99), 1.656 (1.52), 1.659 (2.13), 1.662 (1.98), 1.666 (2.21), 1.675 (2.97), 1.679 (3.43), 1.686 (2.97), 1.694 (3.28), 1.699 (2.90), 1.704 (1.52), 1.718 (1.30), 1.722 (1.52), 1.728 (1.60), 1.733 (1.52), 1.746 (1.83), 1.755 (2.74), 1.758 (2.44), 1.762 (1.98), 1.765 (2.51), 1.769 (2.97), 1.773 (3.35), 1.777 (2.51), 1.790 (4.50), 1.805 (3.20), 1.814 (2.51), 1.821 (2.82), 1.826 (2.51), 1.831 (2.06), 1.840 (3.50), 1.845 (2.59), 1.852 (1.52), 1.859 (2.59), 1.865 (1.07), 1.875 (0.84), 1.932 (0.84), 1.945 (1.83), 1.952 (1.98), 1.956 (1.45), 1.964 (3.28), 1.970 (1.60), 1.976 (1.83), 1.983 (1.75), 1.995 (0.91), 2.010 (0.91), 2.019 (1.68), 2.025 (2.21), 2.029 (2.13), 2.034 (2.44), 2.040 (3.96), 2.043 (3.05), 2.054 (1.90), 2.060 (3.43), 2.068 (2.36), 2.077 (0.91), 2.085 (0.84), 2.092 (0.91), 2.317 (0.76), 2.322 (1.60), 2.326 (2.21), 2.331 (1.83), 2.336 (1.22), 2.366 (3.20), 2.444 (3.35), 2.518 (5.87), 2.522 (3.96), 2.659 (0.69), 2.664 (1.45), 2.668 (1.98), 2.673 (1.37), 2.678 (0.61), 3.227 (1.14), 3.247 (3.35), 3.252 (0.76), 3.266 (4.50), 3.280 (1.14), 3.285 (3.05), 3.294 (1.60), 3.499 (3.12), 3.533 (16.00), 3.705 (3.05), 5.755 (1.30), 6.972 (3.66), 6.985 (3.73), 7.204 (5.33), 7.489 (0.61), 7.783 (2.59), 7.804 (2.21), 8.239 (0.61), 8.284 (6.78), 8.297 (6.32), 10.891 (0.91), 12.481 (1.45).

Example 20.01

(4-{[2-({6-[3-(butan-2-yl)-1,2,4-oxadiazol-5-yl]-1H-benzimidazol-2-yl}amino)pyridin-4-yl]methyl}piperazin-1-yl)(cyclopropyl)methanone

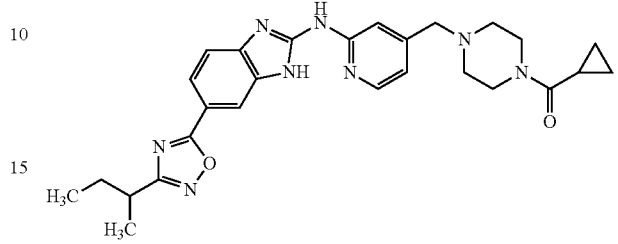

A mixture of N-[({2-[(4-{[4-(cyclopropylcarbonyl)piperazin-1-yl]methyl}pyridin-2-yl)amino]-1H-benzimidazol-6-yl}carbonyl)oxy]-2-methylbutanimidamide (190 mg, 366 μmol) and sodium acetate (33.1 mg, 403 μmol) in 1-propanol (10 mL) and water (5 mL) was heated to 100° C. for 16 h. The solvent was removed in vacuum. Silicagel chromatography gave 100 mg (49% yield) of the title compound.

LC-MS (Method 2): $R_t$=1.29 min; MS (ESIpos): m/z=501 [M+H]$^+$.

$^1$H-NMR (400 MHz, DMSO-d6) δ[ppm]: 0.664 (0.63), 0.676 (1.80), 0.683 (4.30), 0.689 (2.67), 0.696 (2.06), 0.703 (5.19), 0.709 (4.07), 0.714 (4.44), 0.721 (4.37), 0.726 (5.18), 0.733 (2.36), 0.745 (0.60), 0.866 (6.49), 0.885 (15.58), 0.904 (7.13), 1.295 (16.00), 1.312 (15.80), 1.631 (0.67), 1.647 (1.17), 1.650 (0.86), 1.665 (2.00), 1.681 (1.44), 1.683 (1.59), 1.699 (1.12), 1.741 (1.29), 1.759 (2.06), 1.774 (1.12), 1.778 (1.46), 1.793 (1.22), 1.812 (0.73), 1.942 (1.07), 1.949 (1.12), 1.953 (0.85), 1.961 (1.90), 1.967 (0.90), 1.973 (1.07), 1.980 (0.97), 2.366 (1.89), 2.446 (1.93), 2.899 (1.14), 2.917 (1.93), 2.933 (1.85), 2.951 (1.03), 3.501 (1.81), 3.531 (9.32), 3.704 (1.75), 6.974 (2.03), 6.987 (2.06), 7.194 (4.52), 7.797 (1.17), 7.818 (0.96), 8.287 (3.94), 8.299 (3.70), 12.480 (1.56).

Example 21.01

{4-[(2-{[6-(3-benzyl-1,2,4-oxadiazol-5-yl)-1H-benzimidazol-2-yl]amino}pyridin-4-yl)methyl]piperazin-1-yl}(cyclopropyl)methanone

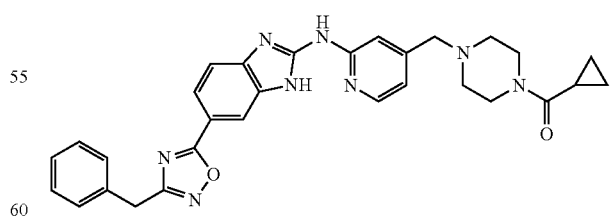

A mixture of N-[({2-[(4-{[4-(cyclopropylcarbonyl)piperazin-1-yl]methyl}pyridin-2-yl)amino]-1H-benzimidazol-6-yl}carbonyl)oxy]-2-phenylethanimidamide (235 mg, 425 μmol) and sodium acetate (38.4 mg, 468 μmol) in 1-propanol (11 mL) and water (5.5 mL) was heated to 100° C. for 70 h. The solvent was removed in vacuum. Silicagel chromatography gave a solid that was triturated with a mixture of ethanol and water (1:1) to give 25.0 mg (10% yield) of the title compound.

LC-MS (Method 2): R$_t$=1.28 min; MS (ESIpos): m/z=535 [M+H]$^+$.

$^1$H-NMR (400 MHz, DMSO-d6) δ [ppm]: 0.665 (0.79), 0.676 (2.49), 0.684 (5.84), 0.689 (3.72), 0.697 (2.96), 0.704 (6.98), 0.708 (6.19), 0.713 (6.46), 0.721 (5.97), 0.725 (6.90), 0.732 (3.20), 0.745 (0.74), 1.232 (0.86), 1.931 (0.67), 1.944 (1.38), 1.950 (1.55), 1.963 (2.47), 1.975 (1.45), 1.982 (1.33), 1.994 (0.57), 2.323 (1.38), 2.327 (1.90), 2.331 (1.60), 2.337 (1.26), 2.365 (2.81), 2.445 (2.98), 2.523 (4.24), 2.660 (0.57), 2.665 (1.16), 2.669 (1.58), 2.673 (1.16), 2.678 (0.59), 3.495 (2.66), 3.530 (12.77), 3.702 (2.61), 4.146 (15.53), 6.972 (3.03), 6.984 (3.06), 7.201 (3.77), 7.250 (0.64), 7.255 (1.21), 7.259 (0.84), 7.265 (0.99), 7.271 (2.88), 7.278 (1.41), 7.283 (1.31), 7.288 (2.49), 7.293 (1.63), 7.332 (2.86), 7.338 (1.75), 7.348 (2.84), 7.352 (8.55), 7.370 (16.00), 7.375 (11.19), 7.391 (2.74), 7.396 (1.75), 7.474 (0.57), 7.769 (2.22), 7.790 (1.82), 8.228 (0.54), 8.280 (4.93), 8.294 (4.71), 10.896 (0.69), 12.473 (1.65).

Example 22.01

N-(4-{[4-(2-chlorophenyl)piperazin-1-yl]methyl}pyridin-2-yl)-6-(5-cyclopropyl-1,2,4-oxadiazol-3-yl)-1H-benzimidazol-2-amine

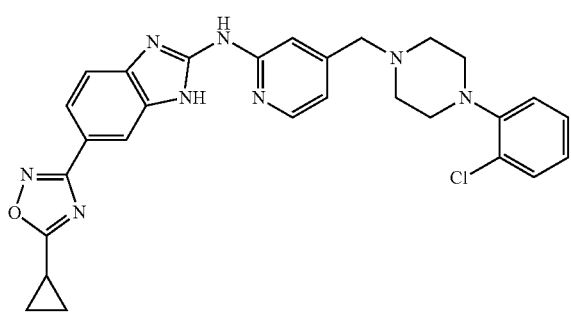 [SMILES: Clc1ccccc1N1CCN(Cc2ccnc(Nc3nc4ccc(-c5noc(C6CC6)n5)cc4[nH]3)c2)CC1]

A mixture of 2-[(4-{[4-(2-chlorophenyl)piperazin-1-yl]methyl}pyridin-2-yl)amino]-N'-[(cyclopropylcarbonyl)oxy]-1H-benzimidazole-6-carboximidamide (160 mg, 294 μmol) and sodium acetate (26.5 mg, 323 μmol) in 1-propanol (10 mL), water (4 mL) and DMA (1.0 mL) was heated to 100° C. 14 h. Water was added and the mixture was extracted with dichloromethane/methanol (20:1). The organic phase was dried (sodium sulfate), filtered and the solvent was removed in vacuum. Silicagel chromatography gave a solid that was triturated with a mixture of warm ethanol and ethyl acetate (3:1) to give 70 mg (37% yield) of the title compound.

LC-MS (Method 2): R$_t$=1.51 min; MS (ESIpos): m/z=527 [M+H]$^+$.

$^1$H-NMR (400 MHz, DMSO-d6) δ [ppm]: 1.167 (0.71), 1.179 (2.54), 1.186 (3.28), 1.191 (2.72), 1.198 (2.94), 1.206 (1.22), 1.254 (1.18), 1.263 (2.73), 1.271 (2.08), 1.275 (2.03), 1.284 (3.38), 1.291 (2.07), 1.304 (0.74), 2.350 (0.54), 2.362 (1.04), 2.370 (1.15), 2.382 (1.95), 2.391 (0.84), 2.394 (1.09), 2.403 (0.98), 2.595 (3.90), 3.019 (4.71), 3.313 (16.00), 6.969 (2.14), 6.982 (2.15), 7.013 (1.23), 7.017 (1.31), 7.033 (2.30), 7.036 (2.27), 7.051 (1.54), 7.055 (1.54), 7.154 (1.97), 7.158 (1.98), 7.174 (2.79), 7.178 (2.46), 7.207 (4.19), 7.274 (1.60), 7.278 (1.70), 7.293 (2.00), 7.297 (2.20), 7.313 (1.06), 7.317 (1.09), 7.386 (2.97), 7.389 (2.93), 7.406 (2.98), 7.410 (2.76), 7.683 (0.83), 8.276 (3.51), 8.288 (3.36), 10.789 (1.70), 12.362 (0.92).

Example 22.02

N-(4-{[4-(2-chlorophenyl)piperazin-1-yl]methyl}pyridin-2-yl)-6-[5-(2,2-dimethylpropyl)-1,2,4-oxadiazol-3-yl]-1H-benzimidazol-2-amine

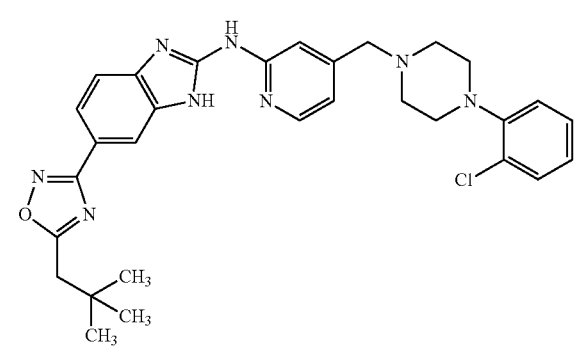 [SMILES: CC(C)(C)Cc1nc(-c2ccc3nc(Nc4cc(CN5CCN(c6ccccc6Cl)CC5)ccn4)[nH]c3c2)no1]

A mixture of 2-[(4-{[4-(2-chlorophenyl)piperazin-1-yl]methyl}pyridin-2-yl)amino]-N'-[(3,3-dimethylbutanoyl)oxy]-1H-benzimidazole-6-carboximidamide (130 mg, 226 μmol) and sodium acetate (20.4 mg, 249 μmol) in 1-propanol (8 mL), water (3 mL) and DMA (770 μl) was heated to 100° C. 14 h. Water was added and the mixture was extracted with dichloromethane/methanol (20:1). The organic phase was dried (sodium sulfate), filtered and the solvent was removed in vacuum. Silicagel chromatography gave a solid that was triturated with warm ethyl acetate to give 80 mg (64% yield) of the title compound.

LC-MS (Method 2): R$_t$=1.65 min; MS (ESIpos): m/z=557 [M+H]$^+$.

$^1$H-NMR (400 MHz, DMSO-d6) δ[ppm]: 1.059 (16.00), 2.904 (3.28), 3.024 (1.35), 3.572 (2.30), 6.975 (0.61), 6.988 (0.62), 7.021 (0.42), 7.036 (0.67), 7.039 (0.71), 7.055 (0.49), 7.058 (0.51), 7.160 (0.59), 7.164 (0.61), 7.180 (0.85), 7.184 (0.77), 7.209 (1.23), 7.279 (0.50), 7.283 (0.53), 7.298 (0.59), 7.302 (0.66), 7.389 (0.91), 7.393 (0.89), 7.409 (0.91), 7.413 (0.83), 8.279 (1.03), 8.293 (1.00), 10.787 (0.59).

Example 23.01.01

2-cyclopropyl-1-{4-[(2-{[6-(pyrimidin-4-yl)-1H-benzimidazol-2-yl]amino}pyridin-4-yl)methyl]piperazin-1-yl}ethanone

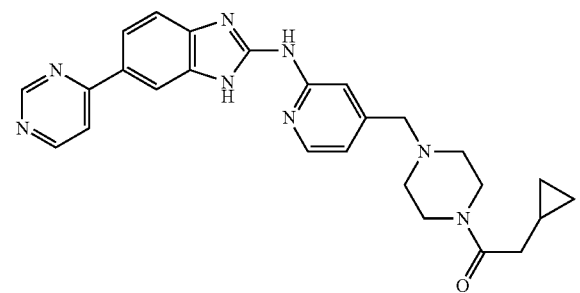 [SMILES: O=C(CC1CC1)N1CCN(Cc2ccnc(Nc3nc4ccc(-c5ccncn5)cc4[nH]3)c2)CC1]

Starting with crude N-[4-(piperazin-1-ylmethyl)pyridin-2-yl]-6-(pyrimidin-4-yl)-1H-benzimidazol-2-amine hydrochloride (144 mg) and cyclopropylacetic acid (25.6 mg, 255 μmol), Example 23.01.01 was prepared analogously to the procedure for the preparation of Example 01.02.

Yield: 12.0 mg of the title compound.

LC-MS (Method 2): $R_t$=0.96 min; MS (ESIpos): m/z=469 [M+H]$^+$.

$^1$H-NMR (400 MHz, DMSO-d6) δ[ppm]: 0.011 (2.89), 0.014 (2.74), 0.023 (2.95), 0.026 (2.84), 0.037 (1.04), 0.330 (1.02), 0.340 (2.57), 0.345 (2.69), 0.350 (1.49), 0.355 (1.34), 0.360 (2.74), 0.365 (2.65), 0.375 (1.04), 0.854 (0.98), 1.022 (16.00), 2.154 (4.65), 2.171 (4.52), 2.242 (1.38), 2.247 (1.08), 2.279 (2.12), 2.291 (1.99), 2.311 (2.19), 2.434 (7.87), 2.438 (5.62), 2.584 (1.27), 2.608 (1.72), 3.373 (2.10), 3.407 (2.08), 3.431 (5.71), 4.110 (1.36), 6.864 (1.34), 6.877 (1.38), 7.118 (2.48), 8.189 (2.27), 8.202 (2.21), 8.668 (3.44), 8.682 (3.25), 9.080 (3.06), 9.083 (3.23).

Example 23.01.02 cyclopropyl{4-[(2-{[6-(pyrimidin-4-yl)-1H-benzimidazol-2-yl]amino}pyridin-4-yl)methyl]piperazin-1-yl}methanone

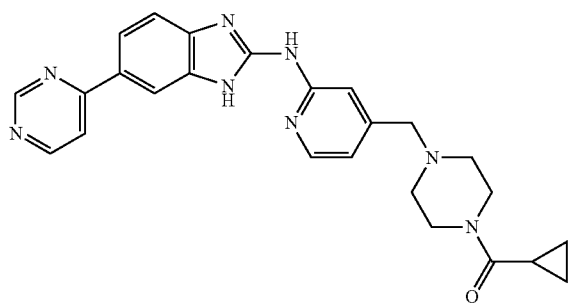 [SMILES: O=C(C1CC1)N1CCN(Cc2ccnc(Nc3nc4ccc(-c5ccncn5)cc4[nH]3)c2)CC1]

Starting with crude N-[4-(piperazin-1-ylmethyl)pyridin-2-yl]-6-(pyrimidin-4-yl)-1H-benzimidazol-2-amine hydrochloride (144 mg) and cyclopropanecarboxylic acid (22.0 mg, 255 μmol), Example 23.01.02 was prepared analogously to the procedure for the preparation of Example 01.02.

Yield: 30.0 mg of the title compound.

LC-MS (Method 2): $R_t$=0.93 min; MS (ESIpos): m/z=455 [M+H]$^+$.

$^1$H-NMR (400 MHz, DMSO-d6) δ [ppm]: 0.686 (2.19), 0.691 (1.38), 0.706 (2.81), 0.710 (2.27), 0.714 (2.50), 0.722 (2.31), 0.726 (2.65), 0.733 (1.19), 1.107 (16.00), 2.323 (1.69), 2.327 (2.42), 2.332 (1.77), 2.518 (13.54), 2.523 (9.46), 2.665 (1.65), 2.669 (2.31), 2.674 (1.65), 3.530 (4.00), 4.194 (1.50), 7.200 (1.65), 8.754 (2.58), 8.768 (2.42), 9.167 (1.69).

Example 23.02.01

3,3,3-trifluoro-1-{4-[(2-methyl-6-{[6-(pyrimidin-4-yl)-1H-benzimidazol-2-yl]amino}pyridin-4-yl)methyl]piperazin-1-yl}propan-1-one

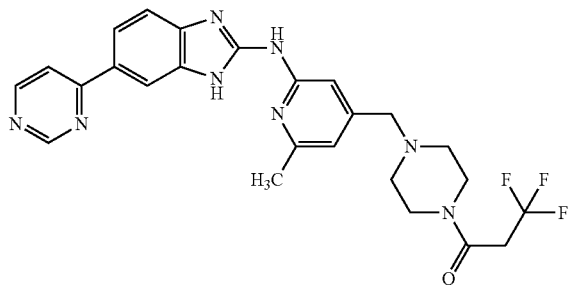 [SMILES: Cc1cc(CN2CCN(C(=O)CC(F)(F)F)CC2)cc(Nc2nc3ccc(-c4ccncn4)cc3[nH]2)n1]

Starting with N-[6-methyl-4-(piperazin-1-ylmethyl)pyridin-2-yl]-6-(pyrimidin-4-yl)-1H-benzimidazol-2-amine (68.0 mg, 170 μmol) and 3,3,3-trifluoropropanoic acid (32.6 mg, 255 μmol), Example 23.02.01 was prepared analogously to the procedure for the preparation of Example 01.02.

Yield: 33.0 mg (34%) of the title compound.

LC-MS (Method 4): $R_t$=1.04 min; MS (ESIpos): m/z=511 [M+H]$^+$.

$^1$H-NMR (400 MHz, CHLOROFORM-d) δ [ppm]: 1.260 (0.99), 2.397 (2.13), 2.410 (2.53), 2.423 (1.87), 2.632 (16.00), 3.157 (1.05), 3.183 (3.12), 3.208 (3.02), 3.233 (0.95), 3.373 (1.58), 3.433 (2.72), 3.478 (5.58), 3.573 (1.43), 6.796 (1.09), 6.808 (1.65), 6.897 (2.03), 7.681 (0.99), 7.701 (1.12), 7.783 (1.86), 7.786 (1.75), 7.797 (1.91), 7.800 (1.71), 7.956 (1.01), 7.960 (1.19), 7.977 (0.81), 7.981 (0.82), 8.345 (1.73), 8.349 (1.68), 8.737 (0.83), 8.745 (1.85), 8.751 (0.94), 8.759 (1.68), 9.243 (1.22), 9.251 (2.33), 9.254 (2.10).

Example 23.02.02 cyclopropyl{4-[(2-methyl-6-{[6-(pyrimidin-4-yl)-1H-benzimidazol-2-yl]amino}pyridin-4-yl)methyl]piperazin-1-yl}methanone

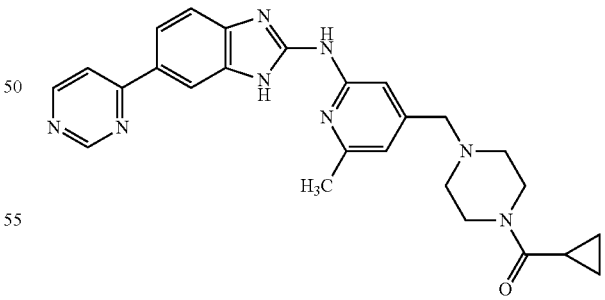

Starting with N-[6-methyl-4-(piperazin-1-ylmethyl)pyridin-2-yl]-6-(pyrimidin-4-yl)-1H-benzimidazol-2-amine (68.0 mg, 170 μmol) and cyclopropanecarboxylic acid (21.9 mg, 255 μmol), Example 23.02.02 was prepared analogously to the procedure for the preparation of Example 01.02.

Yield: 33.0 mg (37%) of the title compound.

LC-MS (Method 4): $R_t$=1.00 min; MS (ESIpos): m/z=469 [M+H]$^+$.

¹H-NMR (400 MHz, CHLOROFORM-d) δ [ppm]: 0.725 (2.01), 0.732 (2.27), 0.745 (2.17), 0.752 (2.30), 0.762 (0.85), 0.944 (0.81), 0.953 (2.28), 0.961 (2.27), 0.965 (2.61), 0.972 (2.35), 1.630 (3.34), 1.648 (1.70), 1.656 (1.31), 1.660 (1.18), 1.667 (1.42), 1.671 (1.04), 1.679 (0.92), 2.383 (1.40), 2.443 (1.40), 2.632 (16.00), 3.476 (5.52), 3.595 (1.69), 6.816 (1.34), 6.830 (2.48), 6.934 (3.02), 7.561 (1.07), 7.582 (1.18), 7.699 (1.60), 7.720 (1.84), 7.782 (0.83), 7.785 (1.03), 7.788 (1.65), 7.791 (1.65), 7.795 (1.00), 7.799 (1.08), 7.801 (1.69), 7.805 (1.62), 7.941 (0.78), 7.946 (0.77), 7.958 (1.49), 7.962 (2.05), 7.967 (0.80), 7.979 (1.25), 7.983 (1.26), 8.351 (2.33), 8.355 (2.27), 8.426 (1.03), 8.727 (1.42), 8.739 (2.97), 8.752 (2.54), 9.240 (1.53), 9.243 (1.64), 9.248 (2.89), 9.251 (2.93), 12.629 (1.28).

Example 23.03.01 cyclopropyl(4-{[2-{[6-(pyrimidin-4-yl)-1H-benzimidazol-2-yl]amino}-6-(trifluoromethyl)pyridin-4-yl]methyl}piperazin-1-yl)methanone

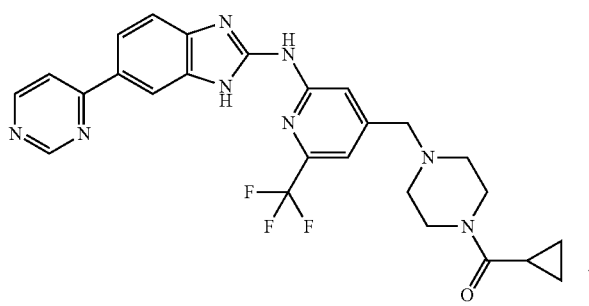

Starting with cyclopropyl(4-{[2-{[6-(4,4,5,5-tetramethyl-1,3,2-dioxaborolan-2-yl)-1H-benzimidazol-2-yl]amino}-6-(trifluoromethyl)pyridin-4-yl]methyl}piperazin-1-yl)methanone (169 mg, 297 µmol) and 4-bromopyrimidine hydrochloride (1:1) (104 mg, 535 µmol), Example 23.03.01 was prepared analogously to the procedure for the preparation of Example 01.01.

Yield: 9.00 mg (6%) of the title compound.

LC-MS (Method 2): $R_t$=1.09 min; MS (ESIpos): m/z=523 [M+H]⁺.

¹H-NMR (400 MHz, DMSO-d6) δ[ppm]: 0.682 (2.62), 0.702 (3.08), 0.715 (2.62), 0.722 (2.62), 0.727 (3.08), 0.734 (1.54), 1.230 (0.92), 1.972 (1.08), 2.318 (1.54), 2.323 (3.54), 2.327 (4.92), 2.332 (3.54), 2.337 (1.38), 2.410 (1.38), 2.518 (16.00), 2.523 (11.85), 2.660 (1.54), 2.665 (3.54), 2.669 (5.08), 2.673 (3.38), 2.679 (1.54), 3.523 (1.38), 3.634 (4.92), 3.732 (1.23), 7.219 (1.38), 7.982 (1.23), 8.180 (1.38), 8.540 (3.69), 8.640 (1.54), 8.654 (1.38), 9.075 (2.46).

Example 23.04.01

(rac)-cyclobutyl{4-[1-(2-{[6-(pyrimidin-4-yl)-1H-benzimidazol-2-yl]amino}pyridin-4-yl)ethyl]piperazin-1-yl}methanone

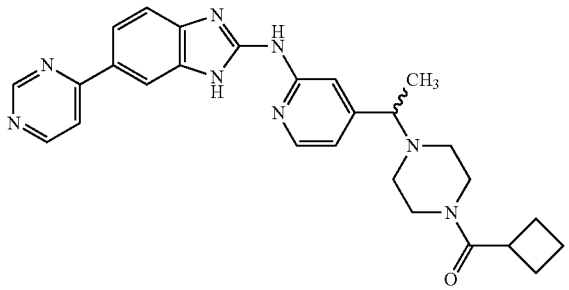

Starting with (rac)-N-{4-[(1-(piperazin-1-yl)ethyl]pyridin-2-yl}-6-(pyrimidin-4-yl)-1H-benzimidazol-2-amine (210 mg, 524 µmol) and cyclobutanecarboxylic acid (78.7 mg, 787 µmol), Example 23.04.01 was prepared analogously to the procedure for the preparation of Example 01.02.

Yield: 30.0 mg (11%) of the title compound.

LC-MS (Method 2): $R_t$=1.07 min; MS (ESIpos): m/z=483 [M+H]⁺.

¹H-NMR (400 MHz, DMSO-d6) δ [ppm]: 1.276 (3.36), 1.293 (3.26), 1.844 (0.78), 2.031 (0.98), 2.052 (1.13), 2.061 (0.94), 2.099 (1.13), 2.121 (1.11), 2.430 (1.18), 3.275 (1.16), 3.294 (1.93), 3.307 (1.71), 3.318 (1.78), 3.336 (16.00), 3.429 (1.39), 3.445 (1.58), 7.173 (1.78), 8.274 (1.18), 8.286 (1.09), 8.753 (2.06), 8.766 (1.91), 9.167 (1.57).

Example 23.04.02

(rac)-cyclopropyl{4-[1-(2-{[6-(pyrimidin-4-yl)-1H-benzimidazol-2-yl]amino}pyridin-4-yl)ethyl]piperazin-1-yl}methanone

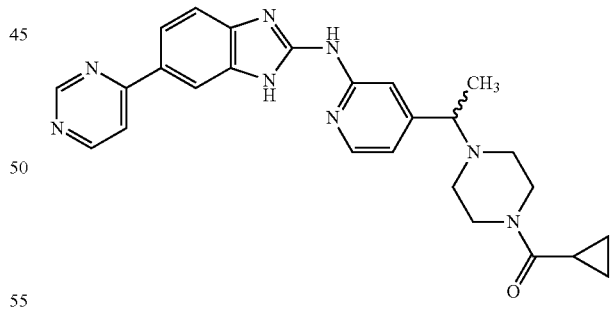

Starting with (rac)-N-{4-[(1-(piperazin-1-yl)ethyl]pyridin-2-yl}-6-(pyrimidin-4-yl)-1H-benzimidazol-2-amine (210 mg, 524 µmol) and cyclopropanecarboxylic acid (67.7 mg, 787 µmol), Example 23.04.02 was prepared analogously to the procedure for the preparation of Example 01.02.

Yield: 33.5 mg (13%) of the title compound.

LC-MS (Method 4): $R_t$=0.97 min; MS (ESIpos): m/z=469 [M+H]⁺.

¹H-NMR (400 MHz, DMSO-d6) δ[ppm]: 0.656 (4.11), 0.663 (8.74), 0.669 (6.30), 0.676 (5.23), 0.683 (10.92), 0.691 (10.79), 0.699 (9.15), 0.703 (10.07), 0.710 (4.93), 1.295 (15.98), 1.312 (16.00), 1.917 (2.10), 1.924 (2.36), 1.936 (3.58), 1.948 (2.14), 1.955 (1.91), 2.326 (2.74), 2.397 (3.32), 2.668 (1.13), 3.455 (6.73), 3.471 (8.23), 3.674 (4.60), 6.970 (3.83), 6.983 (3.92), 7.187 (9.13), 7.454 (1.31), 7.953 (2.94), 7.974 (3.25), 8.227 (1.29), 8.282 (6.17), 8.295 (5.93), 8.407 (1.95), 8.753 (8.97), 8.766 (8.48), 9.167 (8.65), 10.792 (1.22), 12.358 (1.84).

Example 23.04.03

(rac)-3,3,3-trifluoro-1-{4-[1-(2-{[6-(pyrimidin-4-yl)-1H-benzimidazol-2-yl]amino}pyridin-4-yl)ethyl]piperazin-1-yl}propan-1-one

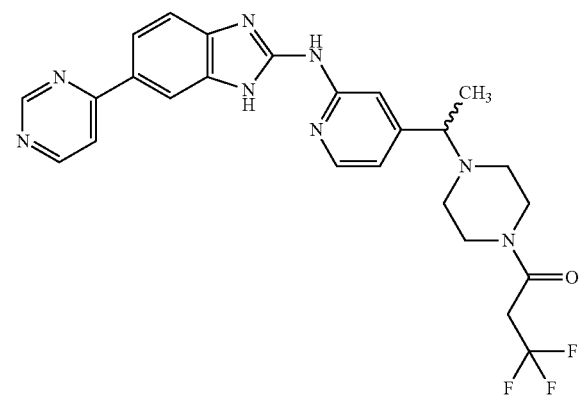 [SMILES: CC(c1ccnc(Nc2nc3ccc(-c4ccncn4)cc3[nH]2)c1)N1CCN(C(=O)CC(F)(F)F)CC1]

Starting with crude (rac)-N-{4-[1-(piperazin-1-yl)ethyl]pyridin-2-yl}-6-(pyrimidin-4-yl)-1H-benzimidazol-2-amine hydrochloride (212 mg) and 3,3,3-trifluoropropanoic acid (66.2 mg, 517 μmol), Example 23.04.03 was prepared analogously to the procedure for the preparation of Example 01.02.

Yield: 63 mg of the title compound.

LC-MS (Method 2): $R_t$=1.02 min; MS (ESIpos): m/z=511 [M+H]$^+$.

$^1$H-NMR (400 MHz, CHLOROFORM-d) δ [ppm]: 1.260 (1.92), 1.330 (15.82), 1.346 (16.00), 1.640 (3.19), 2.339 (4.95), 2.384 (2.75), 2.422 (2.52), 3.128 (3.35), 3.153 (9.73), 3.178 (9.41), 3.203 (3.24), 3.297 (6.15), 3.354 (1.46), 3.373 (3.82), 3.390 (3.75), 3.404 (2.03), 3.492 (3.63), 6.933 (2.82), 6.947 (5.43), 6.962 (3.93), 6.964 (3.75), 7.006 (1.11), 7.090 (10.52), 7.529 (1.25), 7.573 (4.09), 7.594 (4.60), 7.708 (4.97), 7.729 (5.60), 7.770 (4.21), 7.774 (4.53), 7.780 (4.14), 7.784 (6.91), 7.787 (5.09), 7.794 (3.56), 7.797 (2.98), 7.925 (2.94), 7.929 (2.96), 7.945 (2.50), 7.950 (2.61), 7.997 (3.98), 8.002 (3.86), 8.018 (3.40), 8.023 (3.40), 8.306 (4.62), 8.314 (8.62), 8.318 (15.56), 8.332 (5.73), 8.467 (4.72), 8.471 (4.60), 8.736 (5.02), 8.748 (9.69), 8.762 (6.68), 9.230 (5.71), 9.234 (5.64), 9.254 (8.12), 9.257 (7.79), 12.512 (2.96).

Example 23.05.01.A cyclopropyl{4-[(1R or 1S)-1-(2-{[6-(pyrimidin-4-yl)-1H-benzimidazol-2-yl]amino}pyridin-4-yl)ethyl]piperazin-1-yl}methanone (single stereoisomer A)

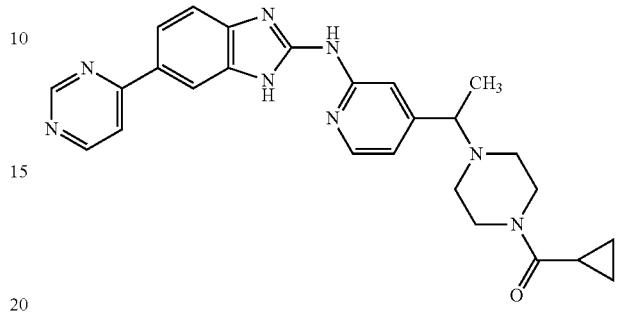

Example 23.05.01.B cyclopropyl{4-[(1S or 1R)-1-(2-{[6-(pyrimidin-4-yl)-1H-benzimidazol-2-yl]amino}pyridin-4-yl)ethyl]piperazin-1-yl}methanone (single stereoisomer B)

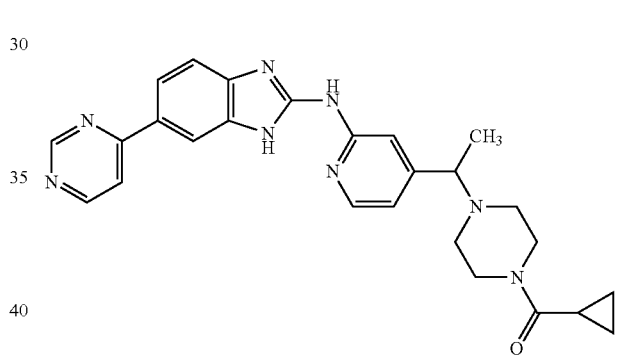

30 mg of (rac)-cyclopropyl{4-[1-(2-{[6-(pyrimidin-4-yl)-1H-benzimidazol-2-yl]amino}pyridin-4-yl)ethyl]piperazin-1-yl}methanone was separated into the single stereoisomers (Example 23.05.01.A and Example 23.05.01.B) via preparative, chiral HPLC.

Instrument: Labomatic HD5000, Labocord-5000; Gilson GX-241, Labcol Vario 4000;
Column: IB 5μ 250×30 mm;
Eluent A: hexane+0.2 Vol-% diethylamine (99%); Eluent B: ethanol; isocratic: 70% A+30% B;
Flow 30 mL/min;
Solution: 30 mg/2 mL ethanol
Injection: 4×0.5 mL
Detection: DAD @ 325 nm

| | Retention time in min | purity in % | yield | Optical rotation [α]$_D$ |
|---|---|---|---|---|
| Example 23.05.01.A Stereoisomer A | 9.5-11.0 | >99% | 8 mg | −36.8° (from solution in DMSO, c = 2.7 mg/mL) |
| Example 23.05.01.B | 11.2-13.5 | 94% | 8 mg | +27.1° (from solution |

| | Retention time in min | purity in % | yield | Optical rotation $[\alpha]_D$ |
|---|---|---|---|---|
| Stereoisomer B | | | | in DMSO, c = 2.6 mg/mL) |

Example 23.05.01.A

¹H-NMR (400 MHz, DMSO-d6) δ[ppm]: 0.658 (3.31), 0.666 (7.60), 0.671 (4.94), 0.685 (10.02), 0.692 (9.53), 0.700 (7.95), 0.704 (8.84), 0.711 (4.25), 1.107 (16.00), 1.231 (6.32), 1.298 (14.67), 1.314 (14.52), 1.919 (1.88), 1.926 (2.07), 1.938 (3.21), 1.951 (1.98), 1.957 (1.83), 2.323 (3.60), 2.327 (4.25), 2.331 (3.41), 2.399 (2.91), 2.523 (9.93), 2.665 (2.22), 2.669 (2.96), 2.673 (2.22), 3.458 (5.68), 3.474 (6.81), 3.678 (3.75), 4.191 (1.48), 6.975 (3.16), 7.184 (7.46), 7.433 (1.53), 7.453 (1.63), 7.619 (1.04), 7.958 (2.62), 7.980 (3.01), 8.091 (1.14), 8.225 (1.68), 8.283 (4.35), 8.296 (4.15), 8.407 (2.52), 8.753 (7.90), 8.767 (7.56), 9.166 (6.62), 10.789 (1.98), 12.306 (1.73), 12.344 (2.57).

Example 23.05.01.B

¹H-NMR (400 MHz, DMSO-d6) δ[ppm]: 0.646 (0.67), 0.658 (2.13), 0.666 (5.11), 0.671 (3.17), 0.678 (2.57), 0.685 (6.60), 0.692 (6.27), 0.700 (5.07), 0.704 (5.82), 0.711 (2.69), 0.851 (0.78), 1.107 (16.00), 1.146 (0.63), 1.195 (0.71), 1.212 (0.90), 1.232 (4.25), 1.256 (1.04), 1.259 (1.08), 1.277 (0.97), 1.298 (10.14), 1.315 (9.85), 1.348 (0.63), 1.907 (0.63), 1.920 (1.23), 1.926 (1.38), 1.939 (2.16), 1.945 (1.12), 1.951 (1.31), 1.958 (1.19), 1.970 (0.63), 2.318 (1.79), 2.323 (2.54), 2.327 (3.10), 2.331 (2.39), 2.337 (1.38), 2.399 (1.86), 2.523 (5.15), 2.659 (0.71), 2.665 (1.60), 2.669 (2.20), 2.673 (1.60), 2.678 (0.75), 3.443 (1.38), 3.458 (3.80), 3.475 (4.44), 3.504 (1.08), 3.511 (0.86), 3.678 (2.39), 4.191 (1.53), 6.977 (2.05), 7.185 (5.07), 7.433 (0.97), 7.454 (1.04), 7.619 (0.71), 7.958 (1.72), 7.980 (1.90), 7.995 (1.12), 8.102 (0.71), 8.225 (1.12), 8.283 (2.98), 8.296 (2.80), 8.407 (1.68), 8.753 (5.74), 8.767 (5.30), 9.166 (4.44), 10.744 (0.75), 10.790 (1.12), 12.307 (0.97), 12.345 (1.45).

Example 23.05.02.A 3,3,3-trifluoro-1-{4-[(1R or 1S)-1-(2-{[6-(pyrimidin-4-yl)-1H-benzimidazol-2-yl]amino}pyridin-4-yl)ethyl]piperazin-1-yl}propan-1-one (single stereoisomer A)

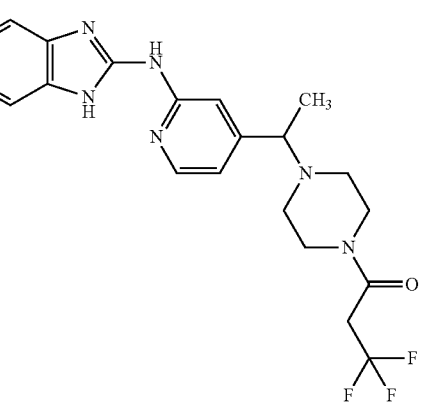

Example 23.05.02.B 3,3,3-trifluoro-1-{4-[(1S or 1R)-1-(2-{[6-(pyrimidin-4-yl)-1H-benzimidazol-2-yl]amino}pyridin-4-yl)ethyl]piperazin-1-yl}propan-1-one (single stereoisomer B)

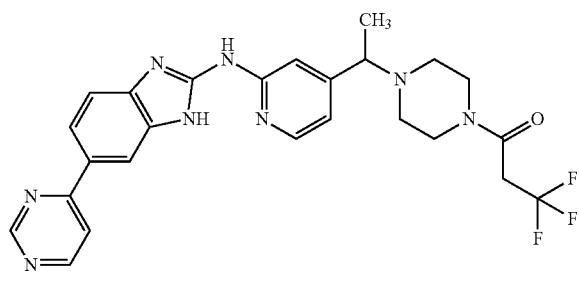 [SMILES: CC(c1ccnc(Nc2nc3ccc(-c4ccncn4)cc3[nH]2)c1)N1CCN(C(=O)CC(F)(F)F)CC1]

63 mg of (rac)-3,3,3-trifluoro-1-{4-[1-(2-{[6-(pyrimidin-4-yl)-1H-benzimidazol-2-yl]amino}pyridin-4-yl)ethyl]piperazin-1-yl}propan-1-one was separated into the single stereoisomers (Example 23.05.02.A and Example 23.05.02.B) via preparative, chiral HPLC.

Instrument: Labomatic HD5000, Labocord-5000; Gilson GX-241, Labcol Vario 4000,

Column: Chiralpak ID 5µ 250×30 mm;

Eluent A: ethanol+0.1 Vol-% diethylamine (99%); Eluent B: tert.butylmethyl ether; isocratic: 20% A+80% B;

Flow: 50.0 mL/min;

Solution: 54 mg/4.5 mL ethanol

Injection: 2×2.25 mL

Detection: UV 325 nm

| | Retention time in min | purity in % | yield | Optical rotation $[\alpha]_D$ |
|---|---|---|---|---|
| Example 23.05.02.A Stereoisomer A | 5.6-7.4 | 99.8% | 23 mg | +10.0° (from solution in DMSO, c = 2.4 mg/mL) |
| Example 23.05.02.B Stereoisomer B | 8.0-10.0 | 99.0% | 23 mg | −35.6° (from solution in DMSO, c = 2.6 mg/mL) |

Example 23.05.02.A

¹H-NMR (400 MHz, DMSO-d6) δ[ppm]: 1.107 (16.00), 1.295 (8.58), 1.312 (8.66), 2.323 (1.97), 2.327 (2.69), 2.332 (2.61), 2.431 (2.31), 2.523 (8.19), 2.540 (4.38), 2.665 (1.14), 2.669 (1.57), 2.674 (1.14), 3.438 (4.60), 3.476 (4.75), 3.492 (4.30), 3.582 (1.82), 3.610 (5.10), 3.637 (4.88), 3.665 (1.64), 4.195 (1.12), 6.965 (2.49), 6.977 (2.56), 7.178 (5.05), 7.951 (1.97), 7.973 (2.09), 8.283 (4.13), 8.296 (3.98), 8.754 (6.32), 8.768 (6.12), 9.166 (5.72), 9.169 (5.95).

Example 23.05.02.B

¹H-NMR (400 MHz, DMSO-d6) δ[ppm]: 1.107 (16.00), 1.295 (7.48), 1.311 (7.66), 2.323 (1.64), 2.327 (2.19), 2.332 (2.21), 2.431 (2.23), 2.523 (6.97), 2.540 (4.44), 2.669 (1.06), 3.354 (2.07), 3.438 (4.05), 3.475 (4.14), 3.582 (1.56), 3.610 (4.47), 3.637 (4.23), 3.664 (1.36), 4.194 (1.06), 6.964 (2.39), 6.978 (2.40), 7.178 (4.60), 7.951 (2.00), 7.974 (2.00), 8.283 (3.80), 8.296 (3.64), 8.754 (5.64), 8.768 (5.30), 9.166 (5.36), 9.169 (5.48).

Example 23.05.03.A cyclobutyl{4-[(1R or 1S)-1-(2-{[6-(pyrimidin-4-yl)-1H-benzimidazol-2-yl]amino}pyridin-4-yl)ethyl]piperazin-1-yl}methanone (single stereoisomer A)

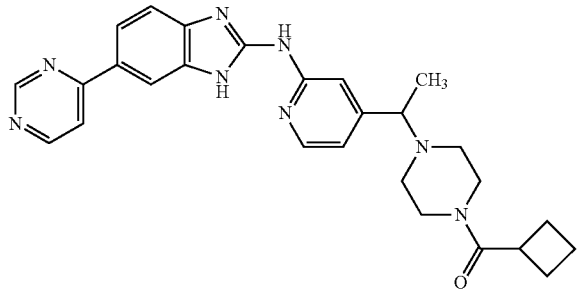 [SMILES: CC(c1ccnc(Nc2nc3ccc(-c4ccncn4)cc3[nH]2)c1)N1CCN(C(=O)C2CCC2)CC1]

Example 23.05.03.B cyclobutyl{4-[(1S or 1R)-1-(2-{[6-(pyrimidin-4-yl)-1H-benzimidazol-2-yl]amino}pyridin-4-yl)ethyl]piperazin-1-yl}methanone (single stereoisomer B)

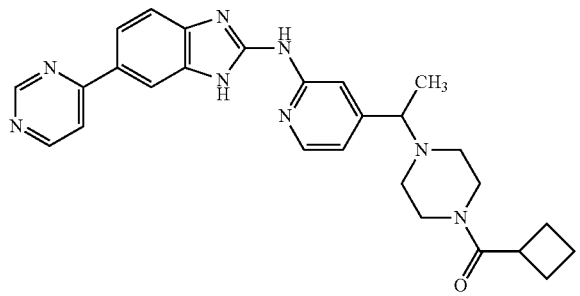 [SMILES: CC(c1ccnc(Nc2nc3ccc(-c4ccncn4)cc3[nH]2)c1)N1CCN(C(=O)C2CCC2)CC1]

30 mg of (rac)-cyclobutyl{4-[1-(2-{[6-(pyrimidin-4-yl)-1H-benzimidazol-2-yl]amino}pyridin-4-yl)ethyl]piperazin-1-yl}methanone was separated into the single stereoisomers (Example 23.05.03.A and Example 23.05.03.B) via preparative, chiral HPLC.
Instrument: Labomatic HD5000, Labocord-5000; Gilson GX-241, Labcol Vario 4000,
Column: Chiralpak IB 5µ 250×30 mm;
Eluent A: hexane+0.2 Vol-% diethylamine (99%); Eluent B: ethanol; isocratic: 70% A+30% B;
Flow: 30.0 mL/min;
Solution: 30 mg/2.0 mL ethanol
Injection: 4×0.5 mL
Detection: UV 325 nm

| | Retention time in min | purity in % | yield | Optical rotation $[\alpha]_D$ |
|---|---|---|---|---|
| Example 23.05.03.A | 8.5-10.0 | >99.0% | 10 mg | −36.1° (from solution in DMSO, c = 3.0 mg/mL) |
| Example 23.05.03.B Stereoisomer B | 10.2-12.5 | 97.5% | 9 mg | +35.6° (from solution in DMSO, c = 2.8 mg/mL) |

Example 23.05.03.A $^1$H-NMR (400 MHz, DMSO-d6) δ[ppm]: 1.108 (16.00), 1.231 (2.47), 1.279 (7.41), 1.296 (7.52), 1.847 (1.63), 1.873 (1.29), 2.033 (1.94), 2.055 (2.20), 2.064 (1.71), 2.077 (1.56), 2.084 (1.52), 2.101 (2.36), 2.123 (2.43), 2.151 (1.29), 2.285 (1.67), 2.299 (1.90), 2.323 (2.32), 2.327 (2.70), 2.331 (1.86), 2.523 (5.09), 2.665 (1.56), 2.669 (2.13), 2.674 (1.48), 3.277 (1.75), 3.297 (4.03), 3.309 (3.84), 3.432 (2.74), 3.449 (3.46), 4.191 (1.56), 6.960 (1.56), 7.173 (4.03), 7.978 (1.48), 8.275 (2.36), 8.287 (2.24), 8.406 (1.25), 8.753 (4.60), 8.767 (4.37), 9.166 (3.76), 12.340 (1.29).

Example 23.05.03.B $^1$H-NMR (400 MHz, DMSO-d6) δ[ppm]: 0.851 (0.99), 0.967 (0.52), 1.107 (16.00), 1.135 (1.04), 1.154 (1.25), 1.172 (0.78), 1.231 (4.99), 1.259 (2.03), 1.279 (14.39), 1.295 (14.70), 1.347 (0.94), 1.694 (1.66), 1.719 (2.13), 1.742 (1.04), 1.825 (1.61), 1.846 (3.17), 1.868 (2.49), 1.873 (2.49), 1.896 (1.61), 1.918 (0.73), 2.033 (3.74), 2.041 (2.81), 2.054 (4.36), 2.064 (3.38), 2.078 (3.06), 2.084 (2.44), 2.101 (4.62), 2.123 (4.88), 2.152 (2.55), 2.175 (0.83), 2.284 (3.32), 2.297 (3.74), 2.312 (3.48), 2.323 (3.79), 2.327 (4.16), 2.331 (2.91), 2.364 (2.29), 2.403 (2.75), 2.523 (7.48), 2.665 (2.18), 2.669 (2.96), 2.673 (2.18), 2.678 (1.09), 3.256 (0.88), 3.276 (3.38), 3.297 (7.95), 3.308 (7.43), 3.432 (5.51), 3.449 (6.86), 3.504 (0.94), 3.511 (0.78), 4.191 (1.45), 6.958 (3.12), 6.969 (3.12), 7.172 (8.00), 7.431 (1.14), 7.453 (1.30), 7.619 (0.83), 7.955 (2.39), 7.978 (2.70), 8.101 (0.99), 8.224 (1.35), 8.275 (4.94), 8.287 (4.78), 8.407 (2.03), 8.753 (8.62), 8.767 (8.26), 9.166 (7.79), 10.785 (1.71), 12.301 (1.45), 12.340 (2.29).

Example 24.01.01

3,3,3-trifluoro-1-{4-[(2-{[6-(2-methylpyrimidin-4-yl)-1H-benzimidazol-2-yl]amino}pyridin-4-yl)methyl]piperazin-1-yl}propan-1-one

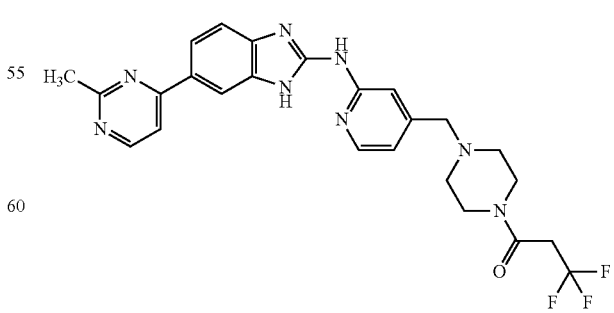

Starting with crude 6-(2-methylpyrimidin-4-yl)-N-[4-(piperazin-1-ylmethyl)pyridin-2-yl]-1H-benzimidazol-2-

571 amine hydrochloride (140 mg, approx. 252 µmol) and 3,3,3-trifluoropropanoic acid (48.3 mg, 377 µmol), Example 24.01.01 was prepared analogously to the procedure for the preparation of Example 01.02.

Yield: 31 mg of the title compound.

LC-MS (Method 4): $R_f$=1.00 min; MS (ESIpos): m/z=511 [M+H]$^+$.

$^1$H-NMR (400 MHz, CHLOROFORM-d) δ [ppm]: 0.077 (0.53), 0.102 (1.32), 0.180 (1.82), 1.466 (8.21), 2.404 (3.20), 2.416 (3.53), 2.438 (1.94), 2.811 (16.00), 3.160 (1.38), 3.185 (3.91), 3.210 (3.84), 3.235 (1.32), 3.366 (1.68), 3.381 (2.08), 3.390 (1.57), 3.427 (1.17), 3.439 (1.77), 3.516 (6.44), 3.589 (1.87), 6.974 (1.83), 6.984 (1.75), 6.987 (1.73), 7.006 (0.50), 7.137 (3.18), 7.529 (0.46), 7.548 (2.47), 7.562 (2.54), 7.642 (0.70), 7.969 (1.63), 7.972 (1.65), 7.989 (1.48), 7.993 (1.51), 8.310 (3.01), 8.323 (3.03), 8.335 (3.05), 8.339 (2.97), 8.650 (3.38), 8.664 (3.20).

Example 24.01.02 cyclobutyl{4-[(2-{[6-(2-methylpyrimidin-4-yl)-1H-benzimidazol-2-yl]amino}pyridin-4-yl)methyl]piperazin-1-yl}methanone

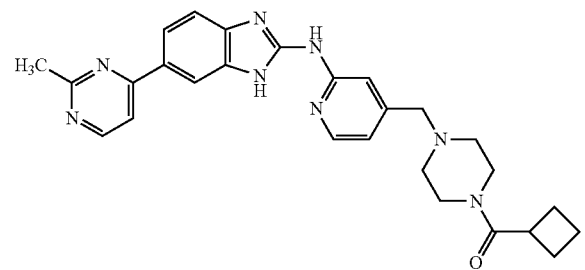 [SMILES: Cc1nccc(-c2ccc3nc(Nc4cc(CN5CCN(C(=O)C6CCC6)CC5)ccn4)[nH]c3c2)n1]

Starting with crude 6-(2-methylpyrimidin-4-yl)-N-[4-(piperazin-1-ylmethyl)pyridin-2-yl]-1H-benzimidazol-2-amine hydrochloride (140 mg, approx. 252 µmol) and cyclobutanecarboxylic acid (37.8 mg, 377 µmol), Example 24.01.02 was prepared analogously to the procedure for the preparation of Example 01.02.

Yield: 60 mg of the title compound.

LC-MS (Method 4): $R_f$=1.03 min; MS (ESIpos): m/z=483 [M+H]$^+$.

$^1$H-NMR (400 MHz, CHLOROFORM-d) δ [ppm]: 0.077 (0.40), 0.102 (1.02), 0.180 (1.38), 1.831 (0.78), 1.855 (1.07), 1.878 (0.80), 1.900 (0.99), 1.922 (1.63), 1.943 (1.22), 1.949 (1.08), 1.966 (0.70), 1.971 (0.76), 1.993 (0.45), 2.062 (0.70), 2.071 (0.77), 2.092 (1.79), 2.101 (1.32), 2.113 (1.83), 2.123 (1.41), 2.137 (0.87), 2.144 (0.77), 2.265 (0.84), 2.271 (0.71), 2.287 (1.95), 2.293 (1.49), 2.309 (2.35), 2.318 (2.18), 2.339 (4.11), 2.350 (3.69), 2.362 (3.44), 2.374 (2.07), 2.812 (16.00), 3.164 (1.10), 3.185 (1.62), 3.207 (1.08), 3.249 (1.74), 3.261 (2.31), 3.273 (1.67), 3.485 (6.73), 3.542 (2.04), 6.978 (1.87), 6.981 (1.85), 6.994 (1.89), 7.006 (0.49), 7.140 (3.18), 7.529 (0.42), 7.549 (2.39), 7.562 (2.48), 7.641 (0.68), 7.971 (1.32), 7.988 (1.18), 8.298 (3.03), 8.311 (2.98), 8.336 (2.71), 8.647 (3.18), 8.661 (3.11).

572

Example 24.01.03 cyclopropyl{4-[(2-{[6-(2-methylpyrimidin-4-yl)-1H-benzimidazol-2-yl]amino}pyridin-4-yl)methyl]piperazin-1-yl}methanone

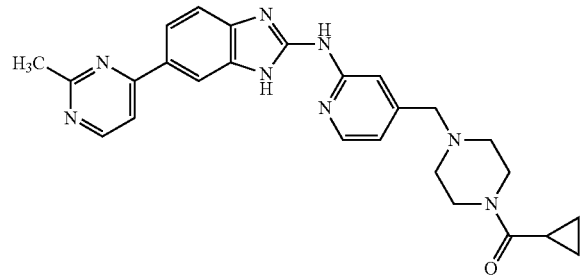 [SMILES: Cc1nccc(-c2ccc3nc(Nc4cc(CN5CCN(C(=O)C6CC6)CC5)ccn4)[nH]c3c2)n1]

Starting with crude 6-(2-methylpyrimidin-4-yl)-N-[4-(piperazin-1-ylmethyl)pyridin-2-yl]-1H-benzimidazol-2-amine hydrochloride (140 mg, approx. 252 µmol) and cyclopropanecarboxylic acid (32.5 mg, 377 µmol), Example 24.01.03 was prepared analogously to the procedure for the preparation of Example 01.02.

Yield: 71 mg of the title compound.

LC-MS (Method 4): $R_f$=0.97 min; MS (ESIneg): m/z=467 [M−H]$^+$.

$^1$H-NMR (400 MHz, CHLOROFORM-d) δ [ppm]: 0.102 (0.74), 0.180 (1.00), 0.717 (0.85), 0.727 (2.38), 0.734 (2.65), 0.744 (1.83), 0.747 (2.57), 0.755 (2.84), 0.764 (1.16), 0.948 (1.04), 0.957 (2.89), 0.964 (2.83), 0.969 (3.06), 0.976 (2.74), 0.986 (1.04), 1.466 (1.06), 1.639 (0.49), 1.651 (0.85), 1.658 (0.97), 1.670 (1.59), 1.682 (0.91), 1.691 (0.82), 2.383 (1.84), 2.435 (1.87), 2.812 (16.00), 3.509 (7.01), 3.539 (1.02), 3.591 (2.30), 6.988 (1.88), 6.991 (1.85), 7.001 (1.93), 7.005 (1.93), 7.152 (3.31), 7.553 (2.54), 7.567 (2.58), 7.644 (0.58), 7.969 (1.73), 7.973 (1.72), 7.989 (1.52), 7.994 (1.56), 8.306 (3.13), 8.319 (3.08), 8.342 (3.41), 8.345 (3.37), 8.643 (3.27), 8.657 (3.12).

Example 24.01.04

2-cyclopropyl-1-{4-[(2-{[6-(2-methylpyrimidin-4-yl)-1H-benzimidazol-2-yl]amino}pyridin-4-yl)methyl]piperazin-1-yl}ethanone

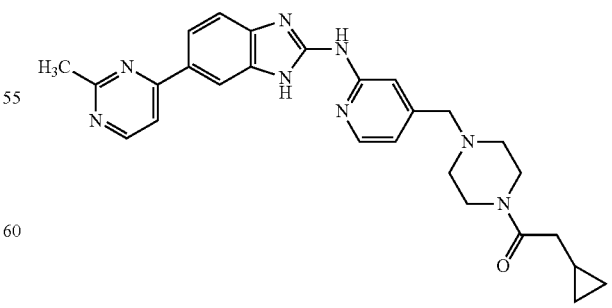

Starting with crude 6-(2-methylpyrimidin-4-yl)-N-[4-(piperazin-1-ylmethyl)pyridin-2-yl]-1H-benzimidazol-2-amine hydrochloride (140 mg, approx. 252 µmol) and cyclopropylacetic acid (37.8 mg, 377 µmol), Example 24.01.04 was prepared analogously to the procedure for the preparation of Example 01.02.

Yield: 81 mg of the title compound.

LC-MS (Method 4): $R_t$=1.00 min; MS (ESIpos): m/z=483 [M+H]$^+$.

$^1$H-NMR (400 MHz, CHLOROFORM-d) δ [ppm]: 0.127 (1.18), 0.139 (4.30), 0.142 (3.48), 0.151 (3.83), 0.154 (4.24), 0.166 (1.49), 0.180 (0.51), 0.183 (0.50), 0.522 (1.44), 0.533 (3.27), 0.536 (3.52), 0.542 (1.92), 0.548 (1.95), 0.551 (2.40), 0.553 (3.71), 0.556 (3.60), 0.568 (1.53), 0.577 (0.47), 0.963 (0.45), 0.975 (0.76), 0.979 (0.78), 0.983 (0.74), 0.988 (0.65), 0.995 (1.27), 0.999 (0.70), 1.003 (0.65), 1.007 (0.76), 1.012 (0.78), 1.015 (0.72), 1.041 (0.61), 1.060 (1.11), 1.079 (0.52), 2.204 (6.67), 2.221 (6.57), 2.263 (0.73), 2.280 (0.70), 2.373 (5.17), 2.456 (0.58), 2.811 (16.00), 3.335 (1.87), 3.346 (2.51), 3.494 (8.02), 3.545 (2.48), 6.962 (2.23), 6.965 (2.22), 6.978 (2.27), 7.007 (0.41), 7.151 (4.02), 7.554 (3.31), 7.567 (3.40), 7.960 (2.58), 7.965 (2.60), 7.981 (2.27), 7.985 (2.37), 8.303 (4.01), 8.316 (3.93), 8.341 (3.78), 8.344 (3.77), 8.643 (3.58), 8.656 (3.45).

Example 24.02.01 cyclopropyl{4-[(2-methyl-6-{[6-(2-methylpyrimidin-4-yl)-1H-benzimidazol-2-yl]amino}pyridin-4-yl)methyl]piperazin-1-yl}methanone

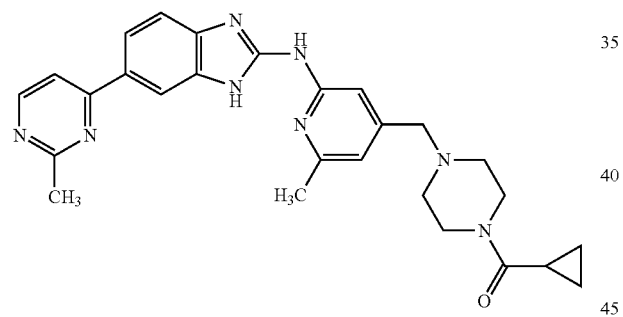

Starting with N-[6-methyl-4-(piperazin-1-ylmethyl)pyridin-2-yl]-6-(2-methylpyrimidin-4-yl)-1H-benzimidazol-2-amine (75.0 mg, 181 µmol) and cyclopropanecarboxylic acid (23.4 mg, 271 µmol), Example 24.02.01 was prepared analogously to the procedure for the preparation of Example 01.02.

Yield: 30.0 mg (32%) of the title compound.

LC-MS (Method 4): $R_t$=1.03 min; MS (ESIpos): m/z=483 [M+H]$^+$.

$^1$H-NMR (400 MHz, DMSO-d6) δ[ppm]: 0.676 (1.26), 0.683 (2.91), 0.689 (1.83), 0.696 (1.47), 0.703 (3.59), 0.707 (3.09), 0.712 (3.33), 0.719 (2.93), 0.724 (3.46), 0.731 (1.57), 1.945 (0.71), 1.964 (1.26), 2.323 (1.41), 2.327 (2.04), 2.331 (1.83), 2.337 (1.41), 2.349 (1.39), 2.432 (1.47), 2.518 (7.54), 2.523 (5.05), 2.539 (2.28), 2.549 (2.30), 2.573 (5.16), 2.659 (1.49), 2.667 (16.00), 2.673 (2.57), 3.472 (6.36), 3.704 (1.31), 6.805 (2.44), 7.015 (1.39), 7.411 (0.97), 7.432 (1.05), 7.797 (0.94), 7.811 (1.00), 7.924 (0.92), 7.945 (0.92), 8.483 (1.34), 8.641 (3.35), 8.655 (3.25), 10.726 (1.05).

Example 24.02.02

3,3,3-trifluoro-1-{4-[(2-methyl-6-{[6-(2-methylpyrimidin-4-yl)-1H-benzimidazol-2-yl]amino}pyridin-4-yl)methyl]piperazin-1-yl}propan-1-one

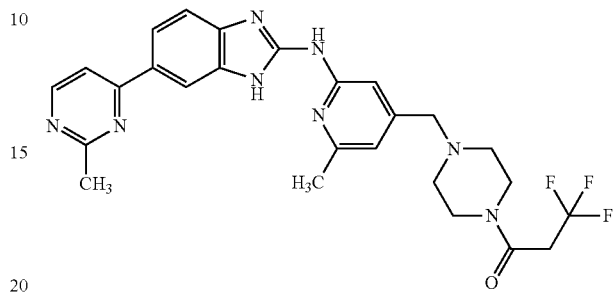

Starting with N-[6-methyl-4-(piperazin-1-ylmethyl)pyridin-2-yl]-6-(2-methylpyrimidin-4-yl)-1H-benzimidazol-2-amine (75.0 mg, 181 µmol) and 3,3,3-trifluoropropanoic acid (34.8 mg, 271 µmol), Example 24.02.02 was prepared analogously to the procedure for the preparation of Example 01.02.

Yield: 30.0 mg (29%) of the title compound.

LC-MS (Method 4): $R_t$=1.07 min; MS (ESIpos): m/z=525 [M+H]$^+$.

$^1$H-NMR (400 MHz, DMSO-d6) δ[ppm]: 2.323 (1.29), 2.327 (1.77), 2.331 (1.29), 2.357 (1.48), 2.369 (2.17), 2.382 (1.64), 2.409 (2.09), 2.518 (7.60), 2.523 (4.99), 2.540 (1.64), 2.546 (2.38), 2.571 (5.10), 2.667 (16.00), 2.674 (2.22), 3.474 (7.16), 3.502 (1.98), 3.608 (0.92), 3.635 (2.59), 3.662 (2.46), 3.690 (0.77), 4.045 (1.21), 6.796 (2.30), 7.010 (1.35), 7.410 (0.95), 7.432 (1.03), 7.797 (0.95), 7.811 (1.00), 7.924 (0.92), 7.945 (0.92), 8.480 (1.40), 8.641 (3.51), 8.655 (3.17), 10.724 (1.19), 12.094 (1.08).

Example 24.03.01 cyclopropyl(4-{[2-{[6-(2-methylpyrimidin-4-yl)-1H-benzimidazol-2-yl]amino}-6-(trifluoromethyl)pyridin-4-yl]methyl}piperazin-1-yl)methanone

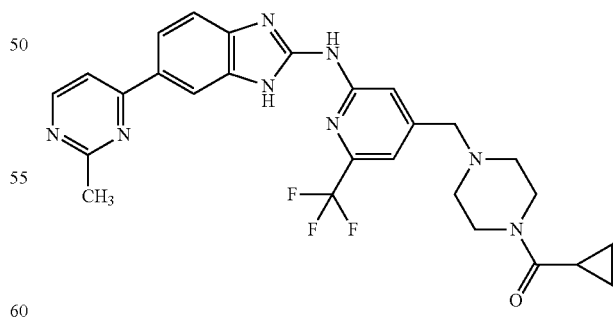

To a stirred solution of 4-chloro-2-methylpyrimidine (81.1 mg, 631 µmol), and cyclopropyl(4-{[2-{[6-(4,4,5,5-tetramethyl-1,3,2-dioxaborolan-2-yl)-1H-benzimidazol-2-yl]amino}-6-(trifluoromethyl)pyridin-4-yl]methyl}piperazin-1-yl)methanone (200 mg, 351 µmol) in Dioxane (1.7 mL) and water (340 µl) was added sodium carbonate (111 mg, 1.05 mmol) and Pd(dppf)Cl$_2$. CH$_2$Cl$_2$ (42.9 mg, 52.6 µmol). The mixture was heated to reflux for 19 h. Dichloromethane was added, the mixture was filtered and, the solvent was removed in vacuum. Preparative reverse phase HPLC (gradient of water and acetonitrile containing ammonia as additive) gave 20.0 mg (10% yield) of the title compound.

LC-MS (Method 2): R$_t$=1.16 min; MS (ESIpos): m/z=537 [M+H]$^+$.

$^1$H-NMR (400 MHz, CHLOROFORM-d) δ [ppm]: 0.725 (4.36), 0.951 (5.34), 1.261 (1.93), 1.284 (6.51), 1.648 (2.11), 2.388 (3.45), 2.793 (3.68), 2.845 (16.00), 3.560 (7.24), 7.582 (2.62), 7.985 (1.62), 8.348 (0.99), 8.675 (3.91), 8.688 (3.75), 11.977 (2.41).

Example 24.04.01

(rac)-cyclopropyl{4-[1-(2-{[6-(2-methylpyrimidin-4-yl)-1H-benzimidazol-2-yl]amino}pyridin-4-yl)ethyl]piperazin-1-yl}methanone

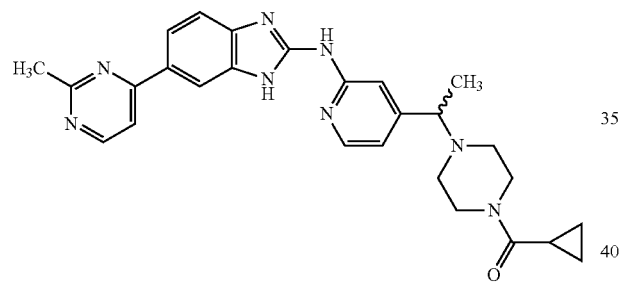

Starting with 6-(2-methylpyrimidin-4-yl)-N-{4-[(1R)-1-(piperazin-1-yl)ethyl]pyridin-2-yl}-1H-benzimidazol-2-amine (207 mg, 499 µmol) and cyclopropanecarboxylic acid (64.5 mg, 749 µmol), Example 24.04.01 was prepared analogously to the procedure for the preparation of Example 01.02.

Yield: 53.0 mg (22%) of the title compound.

LC-MS (Method 4): R$_t$=1.01 min; MS (ESIpos): m/z=483 [M+H]$^+$.

$^1$H-NMR (400 MHz, DMSO-d6) δ[ppm]: 0.656 (1.22), 0.664 (2.91), 0.669 (1.82), 0.676 (1.42), 0.683 (3.51), 0.687 (3.01), 0.691 (3.35), 0.698 (2.83), 0.704 (3.29), 0.711 (1.55), 1.296 (5.42), 1.312 (5.54), 1.936 (1.21), 2.083 (0.77), 2.327 (0.91), 2.665 (16.00), 3.453 (2.09), 3.469 (2.63), 3.676 (1.35), 6.966 (1.55), 6.980 (1.59), 7.196 (1.71), 7.920 (1.57), 7.924 (1.67), 7.941 (1.45), 7.945 (1.50), 8.271 (2.87), 8.284 (2.76), 8.639 (3.72), 8.653 (3.53).

Example 24.04.02

(rac)-cyclobutyl{4-[1-(2-{[6-(2-methylpyrimidin-4-yl)-1H-benzimidazol-2-yl]amino}pyridin-4-yl)ethyl]piperazin-1-yl}methanone

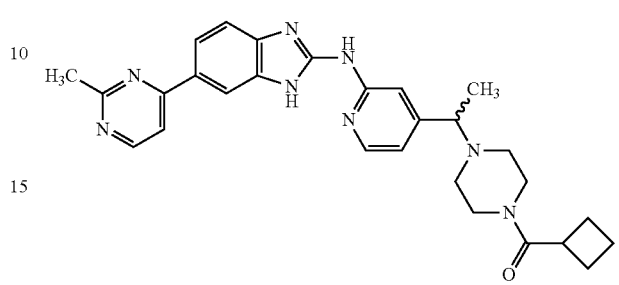

Starting with 6-(2-methylpyrimidin-4-yl)-N-{4-[(1R)-1-(piperazin-1-yl)ethyl]pyridin-2-yl}-1H-benzimidazol-2-amine (207 mg, 499 µmol) and cyclobutanecarboxylic acid (75.0 mg, 749 µmol), Example 24.04.02 was prepared analogously to the procedure for the preparation of Example 01.02.

Yield: 56.5 mg (22%) of the title compound.

LC-MS (Method 4): R$_t$=1.08 min; MS (ESIpos): m/z=497 [M+H]$^+$.

$^1$H-NMR (400 MHz, DMSO-d6) δ[ppm]: 1.274 (5.70), 1.291 (5.90), 1.843 (1.23), 1.865 (0.93), 1.870 (0.97), 2.029 (1.44), 2.038 (1.07), 2.051 (1.67), 2.060 (1.29), 2.075 (1.12), 2.081 (0.96), 2.099 (1.80), 2.120 (1.86), 2.150 (0.97), 2.279 (1.27), 2.293 (1.44), 2.307 (1.40), 2.397 (1.03), 2.665 (16.00), 3.271 (1.23), 3.293 (2.89), 3.304 (2.46), 3.314 (2.50), 3.424 (2.30), 3.442 (2.95), 6.950 (1.33), 6.963 (1.36), 7.167 (1.66), 7.922 (1.32), 7.943 (1.22), 8.264 (2.98), 8.277 (2.83), 8.639 (4.06), 8.653 (3.78).

Example 24.04.03

(rac)-3,3,3-trifluoro-1-{4-[1-(2-{[6-(2-methylpyrimidin-4-yl)-1H-benzimidazol-2-yl]amino}pyridin-4-yl)ethyl]piperazin-1-yl}propan-1-one

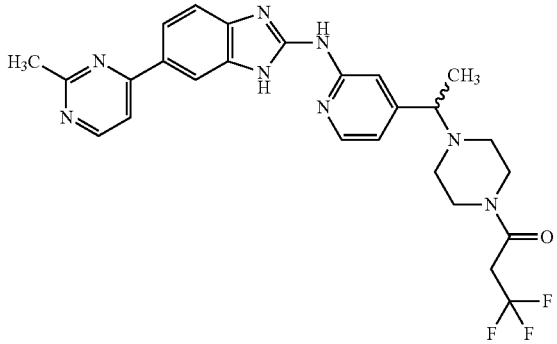 [SMILES: Cc1nccc(-c2ccc3nc(Nc4cc(C(C)N5CCN(C(=O)CC(F)(F)F)CC5)ccn4)[nH]c3c2)n1]

Starting with 6-(2-methylpyrimidin-4-yl)-N-{4-[(1R)-1-(piperazin-1-yl)ethyl]pyridin-2-yl}-1H-benzimidazol-2-amine (207 mg, 499 µmol) and 3,3,3-trifluoropropanoic acid (95.9 mg, 749 µmol), Example 24.04.03 was prepared analogously to the procedure for the preparation of Example 01.02.

Yield: 115 mg (41%) of the title compound.

LC-MS (Method 4): $R_t$=1.05 min; MS (ESIpos): m/z=525 [M+H]$^+$.

$^1$H-NMR (400 MHz, DMSO-d6) δ[ppm]: 1.293 (5.27), 1.309 (5.41), 2.327 (1.20), 2.343 (1.21), 2.366 (0.97), 2.417 (1.27), 2.429 (1.45), 2.665 (16.00), 3.424 (1.41), 3.436 (2.49), 3.449 (1.67), 3.470 (2.84), 3.487 (2.83), 3.580 (0.95), 3.608 (2.71), 3.635 (2.57), 3.662 (0.90), 6.960 (1.47), 6.973 (1.50), 7.174 (2.46), 7.922 (1.56), 7.926 (1.63), 7.943 (1.43), 7.947 (1.47), 8.272 (2.73), 8.285 (2.58), 8.640 (3.83), 8.654 (3.63).

Example 24.04.04

(rac)-2-cyclopropyl-1-{4-[1-(2-{[6-(2-methylpyrimidin-4-yl)-1H-benzimidazol-2-yl]amino}pyridin-4-yl)ethyl]piperazin-1-yl}ethanone

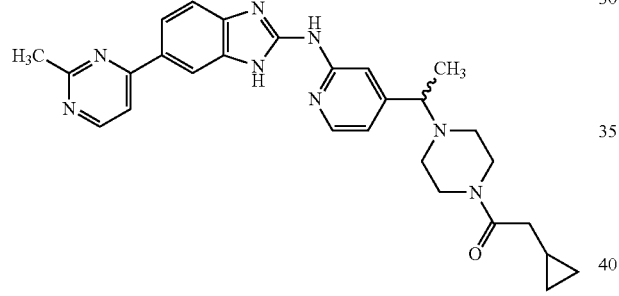

Starting with (rac)-6-(2-methylpyrimidin-4-yl)-N-{4-[1-(piperazin-1-yl)ethyl]pyridin-2-yl}-1H-benzimidazol-2-amine (207 mg, 499 μmol) and cyclopropylacetic acid (75.0 mg, 749 μmol), Example 24.04.04 was prepared analogously to the procedure for the preparation of Example 01.02.

Yield: 40.4 mg (16%) of the title compound.

LC-MS (Method 4): $R_t$=1.05 min; MS (ESIpos): m/z=497 [M+H]$^+$.

$^1$H-NMR (400 MHz, DMSO-d6) δ[ppm]: 0.000 (0.93), 0.011 (3.18), 0.014 (2.97), 0.023 (3.21), 0.026 (3.07), 0.037 (1.01), 0.331 (1.07), 0.341 (2.69), 0.345 (2.83), 0.351 (1.42), 0.356 (1.36), 0.361 (2.93), 0.365 (2.82), 0.376 (1.02), 0.851 (1.04), 1.220 (5.74), 1.237 (5.79), 2.145 (5.05), 2.162 (4.94), 2.262 (1.81), 2.266 (1.58), 2.338 (1.68), 2.457 (1.95), 2.599 (16.00), 3.358 (2.86), 3.375 (2.97), 3.392 (3.10), 6.895 (1.23), 7.108 (1.56), 7.858 (1.19), 7.878 (1.05), 8.202 (2.97), 8.216 (2.85), 8.353 (1.01), 8.575 (4.14), 8.589 (3.90).

Example 24.05.01.A 3,3,3-trifluoro-1-{4-[(1R or 1S)-1-(2-{[6-(2-methylpyrimidin-4-yl)-1H-benzimidazol-2-yl]amino}pyridin-4-yl)ethyl]piperazin-1-yl}propan-1-one (single stereoisomer A)

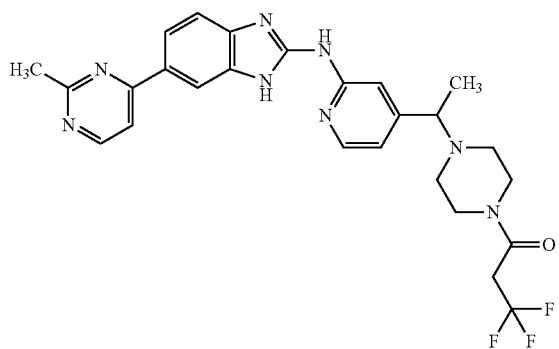 [SMILES: Cc1nccc(-c2ccc3nc(Nc4cc(C(C)N5CCN(C(=O)CC(F)(F)F)CC5)ccn4)[nH]c3c2)n1]

Example 24.05.01.B 3,3,3-trifluoro-1-{4-[(1S or 1R)-1-(2-{[6-(2-methylpyrimidin-4-yl)-1H-benzimidazol-2-yl]amino}pyridin-4-yl)ethyl]piperazin-1-yl}propan-1-one (single stereoisomer B)

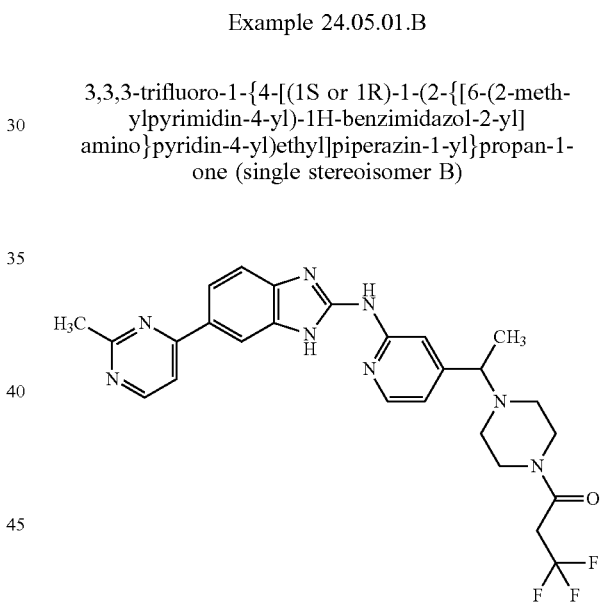

110 mg of (rac)-3,3,3-trifluoro-1-{4-[1-(2-{[6-(2-methylpyrimidin-4-yl)-1H-benzimidazol-2-yl]amino}pyridin-4-yl)ethyl]piperazin-1-yl}propan-1-one was separated into the single stereoisomers (Example 24.05.01.A and Example 23.05.01.B) via preparative, chiral HPLC.

Instrument: Sepiatec: Prep SFC100,

Column: Chiralpak IC 5μ 250×30 mm;

Eluent A CO$_2$, Eluent B: methanol+0.4 Vol-% diethylamine (99%); isocratic: 53% B;

Flow 100.0 mL/min;

Temperature: 40° C.;

Backpressure: 150 bar;

Solution: 110 mg/2 mL dichloromethane/methanol 1:1

Injection: 9×0.25 mL

Detection: MWD @ 254 nm

| | Retention time in min | purity in % | yield | Optical rotation [α]_D |
|---|---|---|---|---|
| Example 24.05.01.A Stereoisomer A | 6.0-7.5 | >99.9% | 35 mg | +31.5° (from solution in DMSO, c = 2.6 mg/mL) |
| Example 24.05.01.B Stereoisomer B | 7.5-10.0 | 99.43% | 35 mg | -38.7° (from solution in DMSO, c = 2.8 mg/mL) |

Example 24.05.01.A $^1$H-NMR (400 MHz, DMSO-d6) δ[ppm]: 1.107 (12.79), 1.133 (0.93), 1.143 (0.81), 1.151 (1.79), 1.161 (1.09), 1.169 (0.89), 1.293 (5.46), 1.309 (5.51), 2.250 (1.99), 2.323 (1.04), 2.327 (1.52), 2.332 (1.39), 2.337 (1.23), 2.417 (1.33), 2.429 (1.52), 2.523 (1.58), 2.665 (16.00), 2.673 (1.39), 3.437 (2.72), 3.447 (2.03), 3.470 (2.92), 3.487 (2.98), 3.503 (1.02), 3.582 (1.04), 3.609 (2.87), 3.637 (2.70), 3.664 (0.87), 6.958 (1.31), 6.972 (1.34), 7.182 (1.82), 7.925 (1.31), 7.946 (1.16), 8.271 (2.85), 8.285 (2.71), 8.640 (3.90), 8.654 (3.57).

Example 24.05.01.B $^1$H-NMR (400 MHz, DMSO-d6) δ[ppm]: 0.966 (0.53), 1.107 (14.94), 1.143 (0.62), 1.293 (6.06), 1.309 (6.15), 2.318 (0.98), 2.323 (1.39), 2.327 (2.01), 2.332 (1.82), 2.337 (1.51), 2.344 (1.46), 2.366 (1.18), 2.417 (1.58), 2.429 (1.84), 2.442 (1.32), 2.458 (1.18), 2.523 (2.99), 2.665 (16.00), 2.673 (1.99), 3.424 (1.72), 3.437 (3.02), 3.449 (2.01), 3.470 (3.26), 3.487 (3.36), 3.503 (1.29), 3.582 (1.13), 3.609 (3.16), 3.637 (2.99), 3.664 (0.94), 4.194 (1.29), 6.965 (1.37), 7.167 (1.87), 7.414 (0.76), 7.435 (0.79), 7.771 (0.79), 7.785 (0.82), 7.925 (1.22), 7.946 (1.08), 8.203 (0.69), 8.272 (3.09), 8.285 (2.94), 8.421 (1.24), 8.641 (4.26), 8.654 (3.86), 10.787 (0.91), 12.368 (0.98).

Example 24.05.02.A cyclobutyl{4-[(1R or 1S)-1-(2-{[6-(2-methylpyrimidin-4-yl)-1H-benzimidazol-2-yl]amino}pyridin-4-yl)ethyl]piperazin-1-yl}methanone (single stereoisomer A)

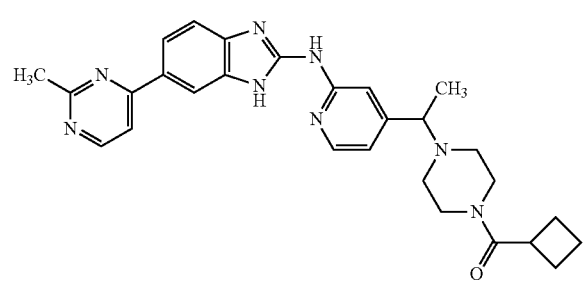 [SMILES: Cc1nccc(-c2ccc3nc(Nc4cc(C(C)N5CCN(C(=O)C6CCC6)CC5)ccn4)[nH]c3c2)n1]

Example 24.05.02.B cyclobutyl{4-[(1S or 1R)-1-(2-{[6-(2-methylpyrimidin-4-yl)-1H-benzimidazol-2-yl]amino}pyridin-4-yl)ethyl]piperazin-1-yl}methanone (single stereoisomer B)

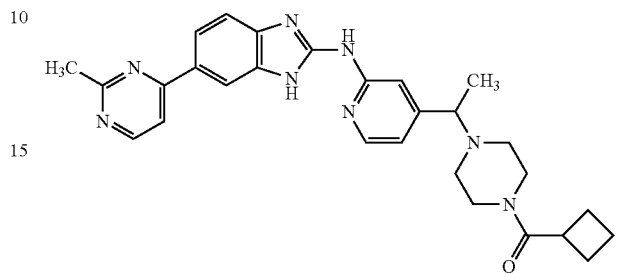

61.9 mg of (rac)-cyclobutyl{4-[1-(2-{[6-(2-methylpyrimidin-4-yl)-1H-benzimidazol-2-yl]amino}pyridin-4-yl)ethyl]piperazin-1-yl}methanone was separated into the single stereoisomers (Example 24.05.02.A and Example 23.05.02.B) via preparative, chiral HPLC.
Instrument: Labomatic HD5000, Labocord-5000; Gilson GX-241, Labcol Vario 4000,
Column: Chiralpak IB 5µ 250×30 mm;
Eluent A: hexane+0.2 Vol-% diethylamine (99%); Eluent B: ethanol; isocratic: 70% A+30% B;
Flow 30.0 mL/min;
Solution: 61 mg/2.5 mL ethanol
Injection: 5×0.5 mL
Detection: UV @ 325 nm

| | Retention time in min | purity in % | yield | Optical rotation [α]_D |
|---|---|---|---|---|
| Example 24.05.02.A Stereoisomer A | 10.1-12.0 | >99.0% | 25 mg | -38.5° (from solution in DMSO, c = 2.6 mg/mL) |
| Example 24.05.02.6 Stereoisomer B | 12.1-14.9 | 93.7% | 27 mg | +26.7° (from solution in DMSO, c = 2.6 mg/mL) |

Example 24.05.02.A $^1$H-NMR (400 MHz, DMSO-d6) δ[ppm]: 1.107 (12.20), 1.232 (1.31), 1.277 (5.97), 1.294 (6.07), 1.846 (1.28), 1.873 (0.98), 2.032 (1.48), 2.054 (1.74), 2.063 (1.31), 2.076 (1.18), 2.100 (1.80), 2.122 (1.90), 2.152 (0.95), 2.282 (1.34), 2.297 (1.51), 2.323 (1.38), 2.327 (1.44), 2.331 (0.98), 2.393 (1.08), 2.523 (2.79), 2.665 (16.00), 2.673 (1.77), 3.276 (1.31), 3.296 (3.15), 3.308 (3.05), 3.319 (3.93), 3.428 (2.36), 3.445 (2.92), 4.193 (1.21), 6.957 (1.28), 7.162 (1.54), 7.924 (1.08), 7.945 (0.95), 8.264 (3.02), 8.278 (2.89), 8.418 (1.15), 8.641 (4.26), 8.654 (4.00), 12.364 (1.11).

Example 24.05.02.B $^1$H-NMR (400 MHz, DMSO-d6) δ[ppm]: 1.107 (8.76), 1.231 (1.53), 1.258 (0.70), 1.276 (6.00), 1.293 (6.28), 1.693 (0.76), 1.719 (0.93), 1.824 (0.67), 1.845 (1.26), 1.872 (1.15), 1.895 (0.71), 2.031 (1.66), 2.040 (1.31), 2.053 (1.92), 2.062

(1.57), 2.078 (1.38), 2.083 (1.15), 2.100 (2.01), 2.121 (2.05), 2.151 (1.16), 2.283 (1.51), 2.296 (1.74), 2.310 (1.63), 2.322 (1.24), 2.326 (1.19), 2.362 (1.08), 2.377 (1.08), 2.399 (1.32), 2.522 (2.92), 2.665 (16.00), 3.275 (1.42), 3.296 (3.52), 3.307 (3.28), 3.317 (3.85), 3.410 (0.80), 3.428 (2.53), 3.445 (3.27), 4.192 (0.93), 6.953 (1.53), 6.965 (1.58), 7.164 (1.90), 7.414 (0.55), 7.434 (0.62), 7.783 (0.71), 7.925 (1.47), 7.945 (1.32), 8.264 (2.95), 8.278 (2.89), 8.421 (0.94), 8.640 (3.66), 8.653 (3.42), 10.773 (0.76), 12.283 (0.54), 12.365 (0.99).

Example 24.05.03.A 2-cyclopropyl-1-{4-[(1R or 1S)-1-(2-{[6-(2-methylpyrimidin-4-yl)-1H-benzimidazol-2-yl]amino}pyridin-4-yl)ethyl]piperazin-1-yl}ethanone (single stereoisomer A)

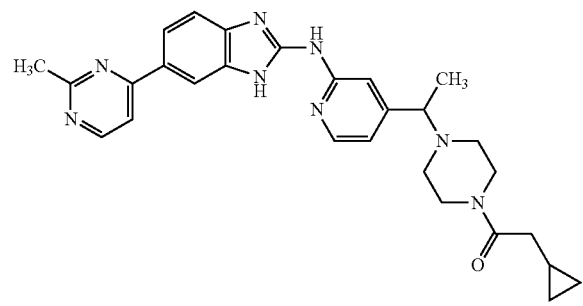 [SMILES: Cc1nccc(-c2ccc3nc(Nc4cc(C(C)N5CCN(C(=O)CC6CC6)CC5)ccn4)[nH]c3c2)n1]

Example 24.05.03.B 2-cyclopropyl-1-{4-[(1S or 1R)-1-(2-{[6-(2-methylpyrimidin-4-yl)-1H-benzimidazol-2-yl]amino}pyridin-4-yl)ethyl]piperazin-1-yl}ethanone (single stereoisomer B)

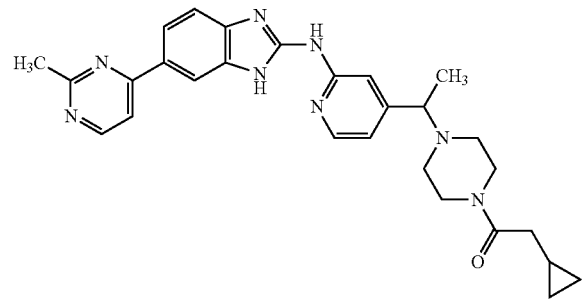 [SMILES: Cc1nccc(-c2ccc3nc(Nc4cc(C(C)N5CCN(C(=O)CC6CC6)CC5)ccn4)[nH]c3c2)n1]

72 mg of (rac)-2-cyclopropyl-1-{4-[1-(2-{[6-(2-methylpyrimidin-4-yl)-1H-benzimidazol-2-yl]amino}pyridin-4-yl)ethyl]piperazin-1-yl}ethanone was separated into the single stereoisomers (Example 24.05.03.A and Example 23.05.03.B) via preparative, chiral HPLC.

Instrument: Labomatic HD5000, Labocord-5000; Gilson GX-241, Labcol Vario 4000,

Column: Chiralpak IC 5µ 250×30 mm;

Eluent A: methanol+0.1 Vol-% diethylamine (99%); Eluent B: ethanol; isocratic: 50% A+50% B;

Flow 50.0 mL/min;

Solution: 72 mg/4.0 mL dichloromethane/methanol 1:1

Injection: 4×1.0 mL

Detection: UV @ 325 nm

| | Retention time in min | purity in % | yield | Optical rotation $[\alpha]_D$ |
|---|---|---|---|---|
| Example 24.05.03.A Stereoisomer A | 10.5-11.5 | >99.0% | 34 mg | +42.2° (from solution in DMSO, c = 2.8 mg/mL) |
| Example 24.05.03.B Stereoisomer B | 11.5-12.5 | 95.0% | 24 mg | −40.1° (from solution in DMSO, c = 3.0 mg/mL) |

Example 24.05.03.A $^1$H-NMR (400 MHz, DMSO-d6) δ[ppm]: 0.000 (0.89), 0.011 (3.11), 0.014 (2.93), 0.023 (3.20), 0.026 (3.02), 0.037 (1.07), 0.331 (1.07), 0.341 (2.76), 0.345 (2.84), 0.352 (1.42), 0.356 (1.42), 0.362 (2.93), 0.366 (2.84), 0.376 (1.07), 0.830 (0.98), 0.846 (0.98), 0.851 (1.16), 1.042 (8.00), 1.165 (0.89), 1.220 (5.69), 1.237 (5.78), 1.982 (1.42), 2.145 (5.16), 2.162 (4.98), 2.183 (0.89), 2.253 (1.42), 2.257 (1.87), 2.262 (2.22), 2.267 (1.87), 2.271 (1.16), 2.338 (1.60), 2.353 (1.42), 2.367 (1.07), 2.453 (5.16), 2.458 (3.29), 2.584 (0.80), 2.600 (16.00), 2.608 (1.87), 3.346 (1.69), 3.358 (3.02), 3.375 (2.93), 3.392 (3.02), 3.405 (1.87), 3.450 (1.51), 3.756 (1.24), 4.134 (0.71), 6.898 (1.24), 7.099 (1.51), 7.347 (0.71), 7.369 (0.80), 7.705 (0.80), 7.719 (0.80), 7.860 (1.07), 7.882 (0.89), 8.204 (2.93), 8.216 (2.76), 8.353 (1.16), 8.576 (4.62), 8.589 (4.18), 10.716 (0.89), 12.304 (0.98).

Example 24.05.03.B $^1$H-NMR (400 MHz, DMSO-d6) δ[ppm]: 0.000 (0.85), 0.011 (3.08), 0.014 (2.83), 0.023 (3.18), 0.026 (2.95), 0.037 (1.05), 0.331 (1.03), 0.341 (2.72), 0.345 (2.80), 0.351 (1.46), 0.356 (1.34), 0.361 (2.88), 0.366 (2.77), 0.376 (1.00), 0.830 (0.67), 0.834 (0.67), 0.838 (0.64), 0.851 (1.05), 0.862 (0.57), 0.867 (0.62), 0.871 (0.54), 0.901 (0.62), 1.042 (3.78), 1.078 (0.46), 1.165 (0.95), 1.220 (5.57), 1.236 (5.62), 2.144 (4.91), 2.161 (4.83), 2.183 (0.69), 2.253 (1.18), 2.257 (1.34), 2.262 (1.54), 2.267 (1.31), 2.279 (0.85), 2.337 (1.59), 2.351 (1.44), 2.365 (1.03), 2.458 (2.05), 2.600 (16.00), 2.608 (1.39), 3.358 (2.88), 3.374 (2.98), 3.391 (3.08), 6.895 (1.21), 6.905 (1.18), 7.102 (1.62), 7.349 (0.54), 7.369 (0.62), 7.719 (0.64), 7.858 (1.16), 7.879 (1.03), 8.203 (2.95), 8.216 (2.77), 8.353 (0.95), 8.575 (4.24), 8.589 (4.03), 10.717 (0.69), 12.308 (0.74).

Example 24.05.04.A cyclopropyl{4-[(1R or 1S)-1-(2-{[6-(2-methylpyrimidin-4-yl)-1H-benzimidazol-2-yl]amino}pyridin-4-yl)ethyl]piperazin-1-yl}methanone (single stereoisomer A)

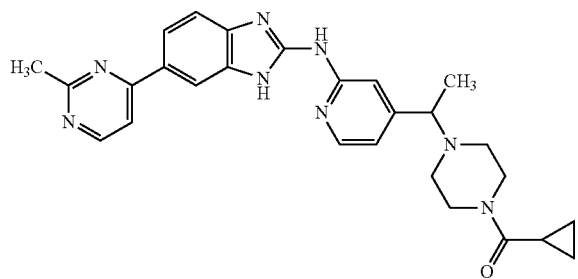 [SMILES: Cc1nccc(-c2ccc3nc(Nc4cc(C(C)N5CCN(C(=O)C6CC6)CC5)ccn4)[nH]c3c2)n1]

Example 24.05.04.B cyclopropyl{4-[(1S or 1R)-1-(2-{[6-(2-methylpyrimidin-4-yl)-1H-benzimidazol-2-yl]amino}pyridin-4-yl)ethyl]piperazin-1-yl}methanone (single stereoisomer B)

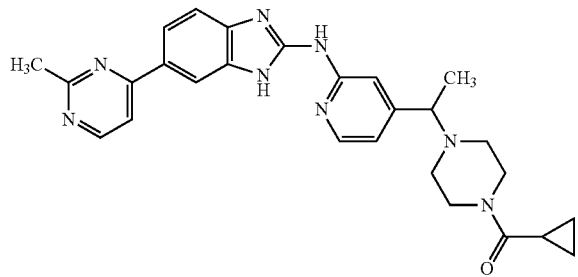 [SMILES: Cc1nccc(-c2ccc3nc(Nc4cc(C(C)N5CCN(C(=O)C6CC6)CC5)ccn4)[nH]c3c2)n1]

49.6 mg of (rac)-cyclopropyl{4-[1-(2-{[6-(2-methylpyrimidin-4-yl)-1H-benzimidazol-2-yl]amino}pyridin-4-yl)ethyl]piperazin-1-yl}methanone was separated into the single stereoisomers (Example 24.05.04.A and Example 23.05.04.B) via preparative, chiral HPLC.

Instrument: Labomatic HD5000, Labocord-5000; Gilson GX-241, Labcol Vario 4000,
Column: Chiralpak IB 5µ 250×30 mm;
Eluent A: hexane+0.2 Vol-% diethylamine (99%); Eluent B: ethanol; isocratic: 80% A+20% B;
Flow 30.0 mL/min;
Solution: 49 mg/2.5 mL ethanol
Injection: 5×0.5 mL
Detection: UV @ 325 nm

|  | Retention time in min | purity in % | yield | Optical rotation $[\alpha]_D$ |
|---|---|---|---|---|
| Example 24.05.04.A Stereoisomer A | 10.8-12.3 | >99.0% | 18 mg | -43.7° (from solution in DMSO, c = 3.0 mg/mL) |
| Example 24.05.04.B | 12.5-14.9 | 95.9% | 16 mg | +45.3° (from solution in DMSO, c = 2.8 mg/mL) |
| Stereoisomer B |  |  |  |  |

Example 24.05.04.A $^1$H-NMR (400 MHz, DMSO-d6) δ[ppm]: 0.664 (3.07), 0.684 (3.95), 0.691 (3.88), 0.698 (3.14), 0.703 (3.51), 0.710 (1.66), 1.106 (8.08), 1.228 (1.06), 1.295 (5.73), 1.312 (5.73), 1.917 (0.74), 1.937 (1.29), 2.326 (1.09), 2.394 (1.11), 2.462 (1.22), 2.522 (2.05), 2.665 (16.00), 3.304 (1.04), 3.326 (2.42), 3.377 (0.83), 3.382 (0.74), 3.454 (2.24), 3.469 (2.82), 3.677 (1.57), 4.198 (0.85), 6.968 (1.45), 6.980 (1.45), 7.175 (2.03), 7.925 (1.41), 7.944 (1.27), 8.273 (2.91), 8.286 (2.77), 8.640 (3.74), 8.654 (3.53).

Example 24.05.04.B $^1$H-NMR (400 MHz, DMSO-d6) δ[ppm]: 0.657 (1.37), 0.665 (3.23), 0.670 (2.11), 0.677 (1.69), 0.684 (4.20), 0.691 (4.03), 0.699 (3.26), 0.703 (3.69), 0.711 (1.66), 0.966 (0.51), 1.107 (10.23), 1.143 (0.40), 1.149 (0.40), 1.230 (0.89), 1.258 (0.69), 1.295 (6.09), 1.312 (6.03), 1.919 (0.74), 1.926 (0.86), 1.938 (1.31), 1.950 (0.80), 1.957 (0.69), 2.322 (1.29), 2.327 (1.46), 2.332 (1.11), 2.397 (1.20), 2.523 (2.83), 2.665 (16.00), 3.454 (2.43), 3.470 (3.09), 3.677 (1.63), 4.197 (1.06), 6.970 (1.31), 7.172 (1.74), 7.414 (0.69), 7.435 (0.74), 7.772 (0.74), 7.785 (0.77), 7.925 (1.20), 7.946 (1.06), 8.202 (0.63), 8.273 (3.09), 8.286 (2.91), 8.420 (1.17), 8.640 (4.11), 8.654 (3.83), 10.739 (0.49), 10.785 (0.91), 12.290 (0.60), 12.373 (1.11).

Example 25.01.01 tert-butyl 4-[(2-{[6-(2-methoxypyrimidin-4-yl)-1H-benzimidazol-2-yl]amino}pyridin-4-yl)methyl]piperazine-1-carboxylate

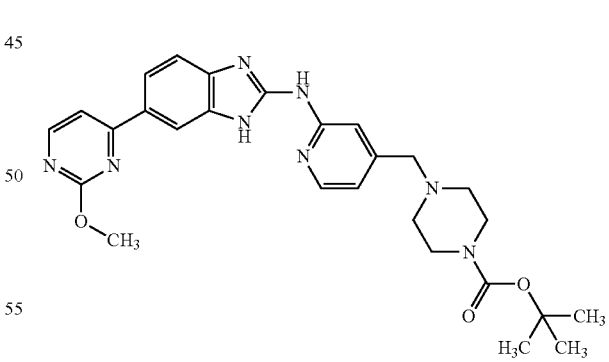

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-bromo-2-methoxypyrimidine (248 mg, 1.31 mmol), Example 25.01.01 was prepared analogously to the procedure for the preparation of Example 01.01.

Yield: 19.0 mg (4%) of the title compound.

LC-MS (Method 2): $R_t$=1.25 min; MS (ESIpos): m/z=517 [M+H]$^+$.

¹H-NMR (400 MHz, DMSO-d6) δ[ppm]: 1.396 (16.00), 2.360 (1.40), 2.372 (1.01), 2.523 (2.96), 3.349 (1.41), 3.506 (1.68), 4.006 (2.25), 8.561 (1.33), 8.575 (1.21).

Example 25.01.02 cyclobutyl{4-[(2-{[6-(2-methoxypyrimidin-4-yl)-1H-benzimidazol-2-yl]amino}pyridin-4-yl)methyl]piperazin-1-yl}methanone

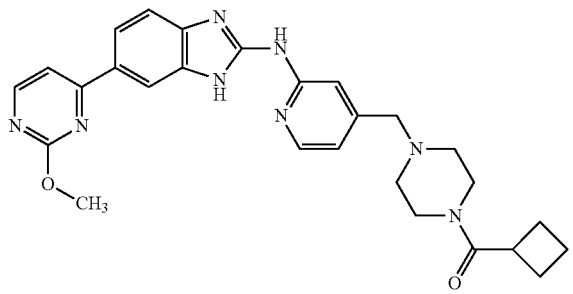 [SMILES: COc1nccc(-c2ccc3nc(Nc4cc(CN5CCN(C(=O)C6CCC6)CC5)ccn4)[nH]c3c2)n1]

Starting with crude 6-(2-methoxypyrimidin-4-yl)-N-[4-(piperazin-1-ylmethyl)pyridin-2-yl]-1H-benzimidazol-2-amine hydrochloride (115 mg) and cyclobutanecarboxylic acid (38.1 mg, 381 µmol), Example 25.01.02 was prepared analogously to the procedure for the preparation of Example 01.02.
Yield: 2.50 mg of the title compound.
LC-MS (Method 4): $R_t$=1.08 min; MS (ESIpos): m/z=499 [M+H]⁺.
¹H-NMR (400 MHz, DMSO-d6) δ[ppm]: 1.230 (0.96), 1.734 (1.42), 1.840 (0.92), 1.862 (1.82), 1.884 (1.63), 1.912 (1.02), 2.052 (2.56), 2.074 (3.02), 2.100 (2.44), 2.123 (3.39), 2.144 (3.36), 2.173 (1.82), 2.323 (2.16), 2.327 (2.99), 2.332 (3.05), 2.355 (6.10), 2.523 (10.76), 2.539 (3.39), 2.665 (1.39), 2.669 (1.88), 2.673 (1.45), 3.169 (1.11), 3.304 (2.71), 3.477 (3.73), 3.506 (7.00), 3.896 (0.83), 3.955 (1.02), 3.973 (1.26), 4.003 (16.00), 6.548 (0.65), 6.943 (1.88), 6.955 (2.03), 7.189 (3.08), 7.617 (0.92), 7.937 (1.66), 7.955 (1.57), 8.271 (2.47), 8.284 (2.47), 8.561 (4.47), 8.574 (4.32).

Example 25.01.03

2-cyclopropyl-1-{4-[(2-{[6-(2-methoxypyrimidin-4-yl)-1H-benzimidazol-2-yl]amino}pyridin-4-yl)methyl]piperazin-1-yl}ethanone

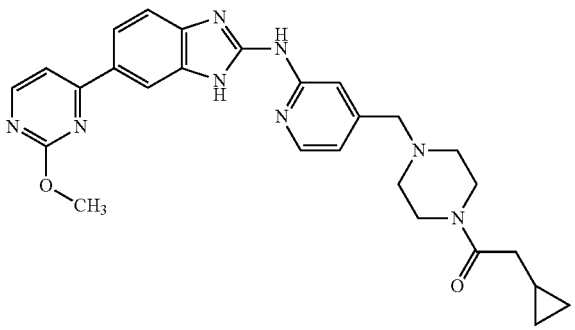 [SMILES: COc1nccc(-c2ccc3nc(Nc4cc(CN5CCN(C(=O)CC6CC6)CC5)ccn4)[nH]c3c2)n1]

Starting with crude 6-(2-methoxypyrimidin-4-yl)-N-[4-(piperazin-1-ylmethyl)pyridin-2-yl]-1H-benzimidazol-2-amine hydrochloride (115 mg) and cyclopropylacetic acid (38.1 mg, 381 µmol), Example 25.01.03 was prepared analogously to the procedure for the preparation of Example 01.02.
Yield: 15.0 mg of the title compound.
LC-MS (Method 4): $R_t$=1.05 min; MS (ESIpos): m/z=499 [M+H]⁺.
¹H-NMR (400 MHz, DMSO-d6) δ[ppm]: 0.000 (1.65), 0.011 (5.58), 0.014 (5.26), 0.023 (5.66), 0.027 (5.23), 0.037 (2.05), 0.331 (2.05), 0.340 (4.93), 0.345 (5.38), 0.351 (2.75), 0.355 (2.65), 0.361 (5.38), 0.365 (5.23), 0.376 (2.13), 0.834 (1.10), 0.838 (1.10), 0.842 (1.08), 0.847 (0.88), 0.854 (1.90), 0.858 (1.00), 0.862 (0.88), 0.867 (1.03), 0.871 (1.08), 0.874 (1.03), 2.154 (8.99), 2.171 (8.91), 2.239 (1.15), 2.243 (1.68), 2.248 (1.33), 2.253 (0.90), 2.279 (3.76), 2.291 (3.46), 2.311 (3.81), 2.434 (8.39), 2.439 (5.93), 2.455 (1.28), 2.581 (1.08), 2.585 (1.55), 2.589 (1.13), 3.372 (3.71), 3.384 (3.36), 3.407 (3.68), 3.431 (10.17), 3.920 (16.00), 6.868 (1.90), 7.109 (3.08), 7.334 (0.88), 7.356 (0.98), 7.526 (1.40), 7.853 (1.60), 7.873 (1.43), 8.125 (0.80), 8.192 (2.23), 8.204 (2.15), 8.325 (1.48), 8.477 (8.36), 8.491 (7.46), 10.731 (0.90), 12.218 (0.88), 12.260 (1.53).

Example 25.01.04

3,3,3-trifluoro-1-{4-[(2-{[6-(2-methoxypyrimidin-4-yl)-1H-benzimidazol-2-yl]amino}pyridin-4-yl)methyl]piperazin-1-yl}propan-1-one

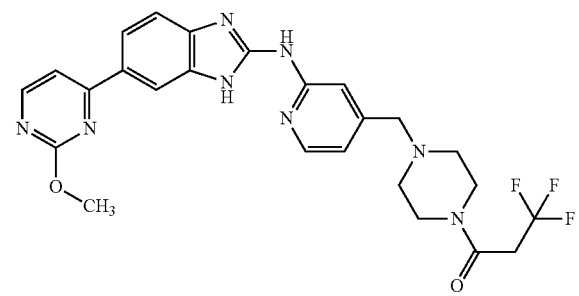 [SMILES: COc1nccc(-c2ccc3nc(Nc4cc(CN5CCN(C(=O)CC(F)(F)F)CC5)ccn4)[nH]c3c2)n1]

Starting with crude 6-(2-methoxypyrimidin-4-yl)-N-[4-(piperazin-1-ylmethyl)pyridin-2-yl]-1H-benzimidazol-2-amine hydrochloride (115 mg) and 3,3,3-trifluoropropanoic acid (48.8 mg, 381 µmol), Example 25.01.04 was prepared analogously to the procedure for the preparation of Example 01.02.
Yield: 30.0 mg of the title compound.
LC-MS (Method 4): $R_t$=1.05 min; MS (ESIpos): m/z=527 [M+H]⁺.
¹H-NMR (400 MHz, DMSO-d6) δ [ppm]: 2.075 (4.09), 2.322 (1.23), 2.327 (1.83), 2.332 (1.35), 2.336 (0.66), 2.371 (2.58), 2.383 (4.06), 2.396 (3.02), 2.425 (3.75), 2.437 (3.06), 2.518 (10.58), 2.523 (7.72), 2.539 (2.02), 2.665 (1.29), 2.669 (1.86), 2.673 (1.35), 3.473 (3.50), 3.484 (3.24), 3.510 (3.91), 3.530 (10.90), 3.613 (1.67), 3.640 (4.79), 3.667 (4.54), 3.695 (1.45), 4.005 (16.00), 4.050 (3.15), 6.953 (1.98), 7.196 (3.40), 7.419 (0.98), 7.441 (1.07), 7.610 (1.57), 7.937 (1.67), 7.958 (1.45), 8.209 (0.94), 8.278 (2.27), 8.290 (2.14), 8.409 (1.64), 8.561 (8.79), 8.575 (8.16), 10.817 (1.07), 12.342 (1.29).

Example 25.01.05 cyclopropyl{4-[(2-{[6-(2-methoxypyrimidin-4-yl)-1H-benzimidazol-2-yl]amino}pyridin-4-yl)methyl]piperazin-1-yl}methanone

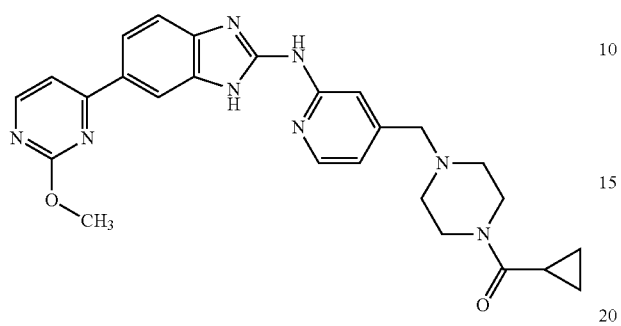

Starting with crude 6-(2-methoxypyrimidin-4-yl)-N-[4-(piperazin-1-ylmethyl)pyridin-2-yl]-1H-benzimidazol-2-amine hydrochloride (115 mg) and cyclopropanecarboxylic acid (32.8 mg, 381 µmol), Example 25.01.05 was prepared analogously to the procedure for the preparation of Example 01.02.

Yield: 27.0 mg of the title compound.

LC-MS (Method 4): $R_t$=1.01 min; MS (ESIpos): m/z=485 [M+H]$^+$.

$^1$H-NMR (400 MHz, DMSO-d6) δ[ppm]: 0.665 (0.77), 0.677 (2.26), 0.684 (5.32), 0.690 (3.32), 0.697 (2.64), 0.704 (6.64), 0.708 (5.56), 0.713 (5.96), 0.720 (5.63), 0.726 (6.46), 0.733 (3.03), 0.745 (0.81), 1.948 (1.25), 1.955 (1.32), 1.967 (2.29), 1.973 (1.08), 1.979 (1.30), 1.986 (1.19), 2.323 (1.08), 2.327 (1.54), 2.332 (1.30), 2.337 (0.92), 2.366 (2.46), 2.447 (2.51), 2.518 (7.78), 2.523 (5.67), 2.539 (3.19), 2.665 (0.95), 2.669 (1.36), 2.673 (0.97), 3.510 (2.57), 3.528 (10.70), 3.709 (2.42), 3.950 (0.84), 4.004 (16.00), 6.959 (1.85), 7.202 (3.05), 7.420 (0.84), 7.441 (0.95), 7.611 (1.36), 7.938 (1.60), 7.958 (1.47), 8.211 (0.79), 8.279 (2.29), 8.292 (2.20), 8.411 (1.41), 8.561 (8.92), 8.575 (8.04), 10.821 (0.79), 12.305 (0.81), 12.347 (1.41).

Example 25.02.01 cyclopropyl(4-{[2-{[6-(2-methoxypyrimidin-4-yl)-1H-benzimidazol-2-yl]amino}-6-(trifluoromethyl)pyridin-4-yl]methyl}piperazin-1-yl)methanone

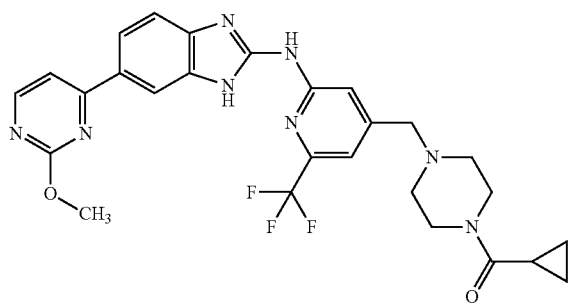 [SMILES: COc1nccc(-c2ccc3nc(Nc4cc(CN5CCN(C(=O)C6CC6)CC5)cc(C(F)(F)F)n4)[nH]c3c2)n1]

Starting with cyclopropyl(4-{[2-{[6-(4,4,5,5-tetramethyl-1,3,2-dioxaborolan-2-yl)-1H-benzimidazol-2-yl]amino}-6-(trifluoromethyl)pyridin-4-yl]methyl}piperazin-1-yl)methanone (200 mg, 351 µmol) and 4-bromo-2-methoxypyrimidine (119 mg, 631 µmol), Example 25.02.01 was prepared analogously to the procedure for the preparation of Example 24.03.01.

Yield: 33.0 mg (15%) of the title compound.

LC-MS (Method 4): $R_t$=1.18 min; MS (ESIpos): m/z=553 [M+H]$^+$.

$^1$H-NMR (400 MHz, CHLOROFORM-d) [ppm]: 0.738 (2.47), 0.951 (2.97), 1.622 (1.97), 2.397 (1.97), 3.565 (4.59), 4.083 (1.72), 4.147 (16.00), 4.263 (0.69), 7.006 (0.87), 7.292 (1.72), 7.428 (1.37), 7.529 (1.14), 7.571 (0.95), 7.601 (0.94), 8.560 (3.36), 8.573 (3.20), 11.967 (2.47).

Example 26.01.01 tert-butyl 4-[(2-{[6-(2-ethoxypyrimidin-4-yl)-1H-benzimidazol-2-yl]amino}pyridin-4-yl)methyl]piperazine-1-carboxylate

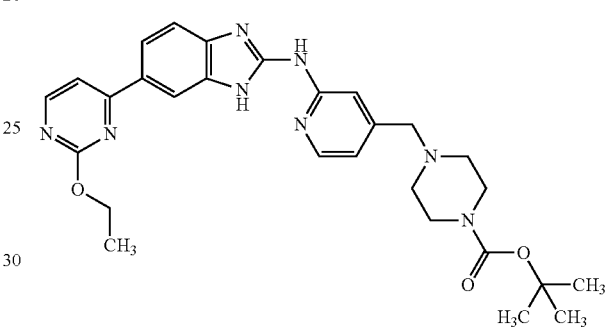

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-2-ethoxypyrimidine (267 mg, 1.68 mmol), Example 26.01.01 was prepared analogously to the procedure for the preparation of Example 01.01.

Yield: 16.5 mg (3%) of the title compound.

LC-MS (Method 4): $R_t$=1.31 min; MS (ESIpos): m/z=531 [M+H]$^+$.

$^1$H-NMR (400 MHz, DMSO-d6) δ[ppm]: 1.377 (0.99), 1.396 (16.00), 1.412 (1.11), 2.360 (1.23), 2.518 (1.68), 3.506 (1.45), 8.545 (1.22), 8.558 (1.11).

Example 26.01.02 cyclopropyl{4-[(2-{[6-(2-ethoxypyrimidin-4-yl)-1H-benzimidazol-2-yl]amino}pyridin-4-yl)methyl]piperazin-1-yl}methanone

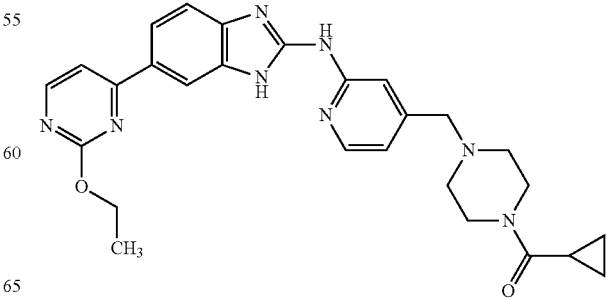

Starting with crude 6-(2-ethoxypyrimidin-4-yl)-N-[4-(piperazin-1-ylmethyl)pyridin-2-yl]-1H-benzimidazol-2-amine hydrochloride (120 mg) and cyclopropanecarboxylic acid (26.5 mg, 308 μmol), Example 26.01.02 was prepared analogously to the procedure for the preparation of Example 01.02.

Yield: 28.0 mg of the title compound.

LC-MS (Method 4): $R_t$=1.09 min; MS (ESIpos): m/z=499 [M+H]$^+$.

$^1$H-NMR (400 MHz, DMSO-d6) δ [ppm]: 0.667 (0.93), 0.678 (2.78), 0.686 (6.61), 0.691 (3.92), 0.698 (3.26), 0.705 (8.15), 0.710 (6.83), 0.715 (7.23), 0.722 (6.74), 0.727 (7.67), 0.734 (3.44), 1.244 (1.10), 1.377 (7.54), 1.395 (16.00), 1.412 (7.67), 1.948 (1.54), 1.955 (1.63), 1.968 (2.78), 1.980 (1.54), 1.987 (1.41), 2.322 (2.07), 2.327 (2.87), 2.332 (2.12), 2.336 (1.37), 2.365 (3.00), 2.444 (2.95), 2.518 (11.11), 2.523 (7.36), 2.660 (0.79), 2.665 (1.85), 2.669 (2.64), 2.674 (1.85), 2.679 (0.84), 3.529 (13.18), 3.709 (2.82), 4.448 (3.88), 4.466 (3.79), 6.962 (2.34), 7.204 (3.39), 7.437 (1.28), 7.599 (1.90), 7.923 (1.72), 8.194 (1.15), 8.282 (2.56), 8.399 (1.98), 8.545 (10.27), 8.559 (9.26), 10.811 (1.19), 12.334 (1.23).

Example 26.01.03

1-{4-[(2-{[6-(2-ethoxypyrimidin-4-yl)-1H-benzimidazol-2-yl]amino}pyridin-4-yl)methyl]piperazin-1-yl}-3,3,3-trifluoropropan-1-one

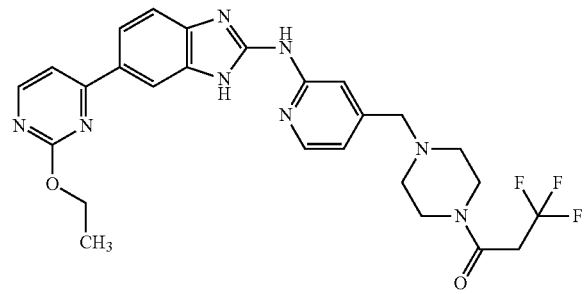 [SMILES: CCOc1nccc(-c2ccc3nc(Nc4cc(CN5CCN(C(=O)CC(F)(F)F)CC5)ccn4)[nH]c3c2)n1]

Starting with crude 6-(2-ethoxypyrimidin-4-yl)-N-[4-(piperazin-1-ylmethyl)pyridin-2-yl]-1H-benzimidazol-2-amine hydrochloride (120 mg) and 3,3,3-trifluoropropanoic acid (39.5 mg, 308 μmol), Example 26.01.03 was prepared analogously to the procedure for the preparation of Example 01.02.

Yield: 26.7 mg of the title compound.

LC-MS (Method 4): $R_t$=1.12 min; MS (ESIpos): m/z=541 [M+H]$^+$.

$^1$H-NMR (400 MHz, DMSO-d6) δ[ppm]: 1.244 (0.91), 1.377 (7.64), 1.395 (16.00), 1.412 (7.76), 2.322 (1.70), 2.327 (2.34), 2.332 (1.66), 2.336 (0.83), 2.372 (3.21), 2.385 (4.91), 2.396 (3.68), 2.426 (4.67), 2.518 (10.10), 2.523 (6.69), 2.660 (0.71), 2.665 (1.66), 2.669 (2.34), 2.674 (1.62), 2.679 (0.75), 3.473 (4.44), 3.485 (3.96), 3.510 (4.75), 3.530 (13.19), 3.611 (2.18), 3.638 (6.26), 3.666 (5.86), 3.693 (1.90), 4.048 (2.46), 4.448 (3.92), 4.466 (3.84), 6.955 (2.46), 7.198 (4.51), 7.415 (1.27), 7.436 (1.43), 7.584 (2.06), 7.599 (2.10), 7.690 (0.87), 7.925 (1.90), 8.193 (1.27), 8.280 (2.69), 8.398 (2.18), 8.545 (10.85), 8.559 (9.82), 10.807 (1.39), 12.327 (1.47).

Example 26.01.04 cyclobutyl{4-[(2-{[6-(2-ethoxypyrimidin-4-yl)-1H-benzimidazol-2-yl]amino}pyridin-4-yl)methyl]piperazin-1-yl}methanone

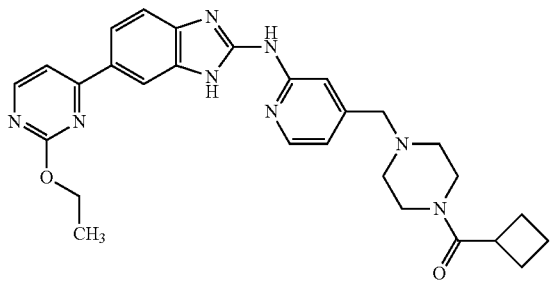 [SMILES: CCOc1nccc(-c2ccc3nc(Nc4cc(CN5CCN(C(=O)C6CCC6)CC5)ccn4)[nH]c3c2)n1]

Starting with crude 6-(2-ethoxypyrimidin-4-yl)-N-[4-(piperazin-1-ylmethyl)pyridin-2-yl]-1H-benzimidazol-2-amine hydrochloride (120 mg) and cyclobutanecarboxylic acid (30.9 mg, 308 μmol), Example 26.01.04 was prepared analogously to the procedure for the preparation of Example 01.02.

Yield: 12.0 mg of the title compound.

LC-MS (Method 4): $R_t$=1.15 min; MS (ESIpos): m/z=513 [M+H]$^+$.

$^1$H-NMR (400 MHz, DMSO-d6) δ[ppm]: 1.244 (1.18), 1.377 (5.97), 1.395 (12.39), 1.412 (6.03), 1.736 (1.51), 1.841 (1.25), 1.863 (2.49), 1.889 (1.84), 1.913 (1.11), 2.054 (2.75), 2.076 (3.15), 2.085 (2.49), 2.101 (2.03), 2.124 (3.67), 2.146 (3.93), 2.176 (2.03), 2.322 (3.08), 2.327 (4.39), 2.332 (3.74), 2.354 (7.61), 2.518 (16.00), 2.523 (10.56), 2.660 (1.31), 2.665 (2.82), 2.669 (4.00), 2.674 (2.62), 2.679 (1.25), 3.304 (3.02), 3.346 (5.77), 3.477 (3.80), 3.505 (11.41), 4.450 (3.34), 4.467 (3.21), 6.948 (2.43), 7.187 (3.08), 7.434 (1.51), 7.584 (2.16), 7.599 (2.30), 7.928 (1.90), 8.192 (1.44), 8.275 (2.62), 8.398 (2.36), 8.545 (8.92), 8.558 (8.26), 10.801 (1.77), 12.326 (2.23).

Example 26.01.05

2-cyclopropyl-1-{4-[(2-{[6-(2-ethoxypyrimidin-4-yl)-1H-benzimidazol-2-yl]amino}pyridin-4-yl)methyl]piperazin-1-yl}ethanone

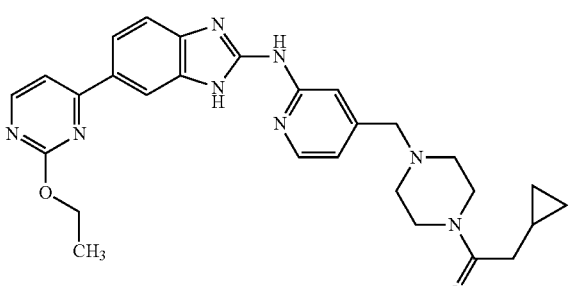

Starting with crude 6-(2-ethoxypyrimidin-4-yl)-N-[4-(piperazin-1-ylmethyl)pyridin-2-yl]-1H-benzimidazol-2-amine hydrochloride (120 mg) and cyclopropylacetic acid (30.9 mg, 308 μmol), Example 26.01.05 was prepared analogously to the procedure for the preparation of Example 01.02.

Yield: 30.0 mg of the title compound.

LC-MS (Method 4): $R_t$=1.12 min; MS (ESIpos): m/z=513 [M+H]$^+$.

$^1$H-NMR (400 MHz, DMSO-d6) δ [ppm]: 0.001 (1.95), 0.011 (6.92), 0.015 (6.18), 0.023 (7.13), 0.027 (6.39), 0.037 (2.29), 0.330 (2.42), 0.340 (6.18), 0.345 (6.32), 0.350 (3.23), 0.355 (2.96), 0.361 (6.39), 0.365 (6.12), 0.376 (2.29), 0.855 (2.22), 1.159 (1.28), 1.292 (6.72), 1.310 (13.98), 1.327 (6.79), 2.154 (11.09), 2.171 (10.69), 2.238 (3.09), 2.242 (4.17), 2.247 (2.96), 2.252 (1.68), 2.278 (4.71), 2.433 (16.00), 2.438 (10.69), 2.580 (2.89), 2.584 (3.97), 2.589 (2.76), 3.430 (12.44), 4.365 (3.63), 4.382 (3.50), 6.869 (2.55), 7.109 (3.50), 7.329 (1.55), 7.350 (1.68), 7.500 (2.35), 7.514 (2.42), 7.845 (1.95), 8.109 (1.55), 8.194 (2.82), 8.314 (2.55), 8.460 (9.82), 8.473 (8.94), 10.721 (1.75), 12.245 (2.02).

Example 26.02.01

(rac)-1-{4-[1-(2-{[6-(2-ethoxypyrimidin-4-yl)-1H-benzimidazol-2-yl]amino}pyridin-4-yl)ethyl]piperazin-1-yl}-3,3,3-trifluoropropan-1-one

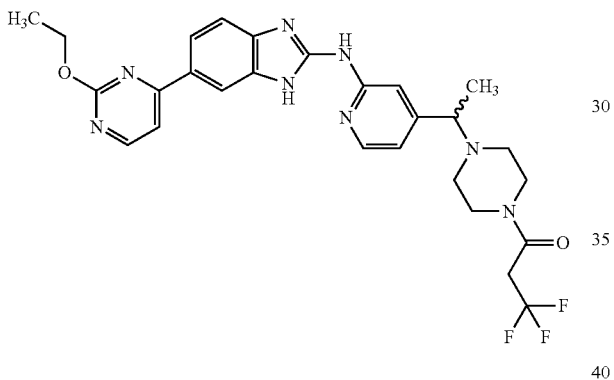

Starting with crude (rac)-6-(2-ethoxypyrimidin-4-yl)-N-{4-[(1-(piperazin-1-yl)ethyl]pyridin-2-yl}-1H-benzimidazol-2-amine hydrochloride (370 mg) and 3,3,3-trifluoropropanoic acid (70.5 mg, 551 µmol), Example 26.02.01 was prepared analogously to the procedure for the preparation of Example 01.02.

Yield: 105 mg of the title compound.

LC-MS (Method 4): $R_t$=1.15 min; MS (ESIpos): m/z=555 [M+H]$^+$.

$^1$H-NMR (400 MHz, CHLOROFORM-d) δ [ppm]: 1.297 (6.52), 1.305 (10.05), 1.314 (7.71), 1.322 (9.47), 1.356 (1.44), 1.373 (1.40), 1.466 (4.21), 1.484 (8.88), 1.502 (5.01), 1.508 (8.01), 1.526 (16.00), 1.543 (7.78), 1.624 (2.03), 2.320 (3.70), 2.409 (2.30), 3.126 (2.47), 3.150 (7.30), 3.176 (7.13), 3.201 (2.38), 3.211 (1.14), 3.236 (0.99), 3.293 (4.83), 3.338 (2.90), 3.354 (2.50), 3.475 (3.16), 4.261 (0.72), 4.266 (0.72), 4.502 (1.26), 4.520 (4.03), 4.538 (5.49), 4.557 (7.95), 4.575 (6.97), 4.592 (2.14), 4.725 (0.74), 4.730 (0.77), 6.909 (1.79), 6.922 (2.08), 6.929 (3.10), 6.946 (2.87), 7.006 (1.13), 7.018 (3.13), 7.053 (5.00), 7.397 (8.94), 7.411 (9.45), 7.528 (0.99), 7.544 (2.59), 7.565 (2.98), 7.679 (3.57), 7.700 (4.03), 7.987 (1.73), 7.991 (1.84), 8.008 (4.40), 8.012 (4.55), 8.029 (2.54), 8.034 (2.53), 8.292 (2.57), 8.305 (3.28), 8.310 (6.26), 8.314 (6.73), 8.318 (6.31), 8.324 (5.52), 8.401 (2.92), 8.509 (3.15), 8.523 (3.54), 8.528 (6.02), 8.540 (5.45), 12.465 (2.26).

Example 26.03.01.A

1-{4-[(1R or 1S)-1-(2-{[6-(2-ethoxypyrimidin-4-yl)-1H-benzimidazol-2-yl]amino}pyridin-4-yl)ethyl] piperazin-1-yl}-3,3,3-trifluoropropan-1-one (single stereoisomer A)

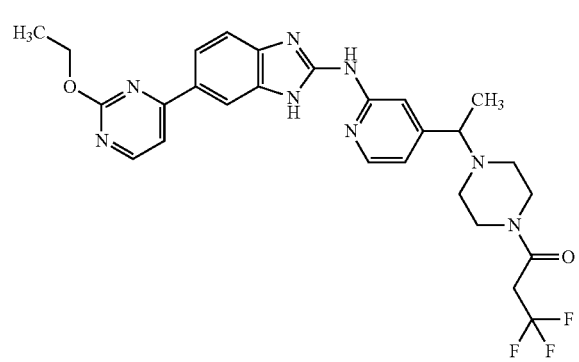 [SMILES: CCOc1nccc(-c2ccc3nc(Nc4cc(C(C)N5CCN(C(=O)CC(F)(F)F)CC5)ccn4)[nH]c3c2)n1]

Example 26.03.01.B

1-{4-[(1S or 1R)-1-(2-{[6-(2-ethoxypyrimidin-4-yl)-1H-benzimidazol-2-yl]amino}pyridin-4-yl)ethyl] piperazin-1-yl}-3,3,3-trifluoropropan-1-one (single stereoisomer B)

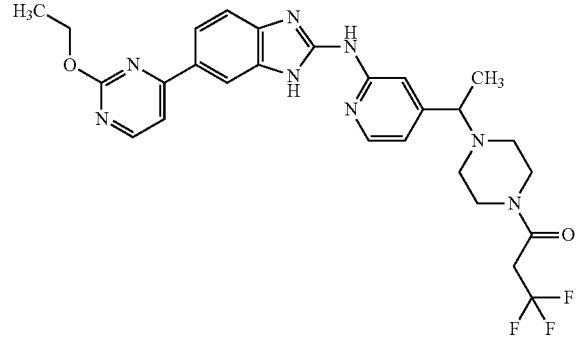 [SMILES: CCOc1nccc(-c2ccc3nc(Nc4cc(C(C)N5CCN(C(=O)CC(F)(F)F)CC5)ccn4)[nH]c3c2)n1]

105 mg of (rac)-1-{4-[1-(2-{[6-(2-ethoxypyrimidin-4-yl)-1H-benzimidazol-2-yl]amino}pyridin-4-yl)ethyl]piperazin-1-yl}-3,3,3-trifluoropropan-1-one was separated into the single stereoisomers (Example 26.03.01.A and Example 26.03.01.B) via preparative, chiral HPLC.

Instrument: Labomatic HD5000, Labocord-5000; Gilson GX-241, Labcol Vario 4000,

Column: Chiralpak IE 5µ 250×30 mm;

Eluent A: tert.-butyl methyl ether+0.1 Vol-% diethylamine (99%);

Eluent B: methanol; isocratic: 90% A+10% B;

Flow: 50.0 mL/min;

Solution: 105 mg/3.0 mL ethanol

Injection: 3×1.0 mL

Detection: UV 325 nm

| | Retention time in min | purity in % | yield | Optical rotation [α]$_D$ |
|---|---|---|---|---|
| Example 26.03.01.A Stereoisomer A | 5.5-7.6 | >99.0% | 39 mg | −37.3° (from solution in DMSO, c = 2.5 mg/mL) |
| Example 26.03.01.B Stereoisomer B | 8.5-11.8 | 97.1% | 38 mg | +29.9° (from solution in DMSO, c = 3.8 mg/mL) |

Example 26.03.01.A $^1$H-NMR (400 MHz, DMSO-d6) δ[ppm]: 0.967 (0.77), 1.107 (12.34), 1.230 (1.74), 1.294 (12.58), 1.310 (12.42), 1.376 (7.64), 1.394 (16.00), 1.411 (7.80), 2.318 (1.84), 2.323 (2.32), 2.327 (3.31), 2.331 (3.31), 2.345 (2.75), 2.367 (2.19), 2.419 (3.05), 2.430 (3.42), 2.444 (2.46), 2.458 (2.00), 2.523 (3.55), 2.665 (1.15), 2.669 (1.60), 2.674 (1.12), 3.424 (3.31), 3.437 (5.88), 3.449 (3.79), 3.473 (6.14), 3.490 (5.88), 3.581 (2.27), 3.608 (6.46), 3.636 (6.09), 3.663 (1.92), 4.192 (1.18), 4.448 (4.01), 4.465 (3.87), 6.967 (2.64), 7.177 (4.94), 7.414 (1.42), 7.434 (1.50), 7.586 (2.30), 7.599 (2.19), 7.690 (0.99), 7.927 (2.03), 7.945 (1.58), 8.192 (1.36), 8.284 (2.78), 8.400 (2.32), 8.545 (9.24), 8.558 (8.65), 10.797 (1.71), 12.301 (1.42), 12.335 (2.38).

Example 26.03.01.B $^1$H-NMR (400 MHz, DMSO-d6) δ[ppm]: 0.962 (0.65), 1.103 (8.33), 1.148 (0.78), 1.178 (0.86), 1.225 (2.61), 1.289 (12.10), 1.305 (12.06), 1.372 (7.80), 1.389 (16.00), 1.407 (7.84), 2.323 (3.04), 2.327 (3.12), 2.340 (2.86), 2.363 (2.31), 2.414 (3.10), 2.425 (3.53), 2.439 (2.61), 2.454 (2.20), 2.660 (0.94), 2.665 (1.27), 2.669 (0.92), 3.421 (3.41), 3.433 (6.04), 3.445 (3.88), 3.468 (6.27), 3.485 (6.16), 3.576 (2.18), 3.604 (6.25), 3.631 (5.92), 3.658 (1.90), 4.187 (0.78), 4.426 (1.59), 4.443 (4.35), 4.460 (4.24), 4.477 (1.47), 6.963 (2.67), 7.173 (5.25), 7.410 (1.25), 7.430 (1.37), 7.581 (2.10), 7.595 (2.08), 7.684 (0.86), 7.920 (2.04), 8.187 (1.24), 8.278 (2.94), 8.290 (2.67), 8.396 (2.16), 8.540 (8.18), 8.553 (7.59), 10.793 (1.43), 12.298 (1.31), 12.330 (2.20).

Example 27.01 cyclopropyl(4-{[2-({6-[2-(trifluoromethyl)pyrimidin-4-yl]-1H-benzimidazol-2-yl}amino)pyridin-4-yl]methyl}piperazin-1-yl)methanone

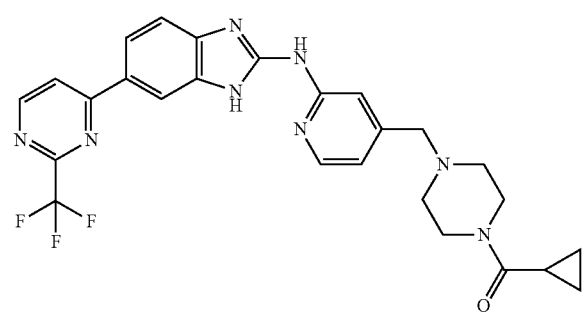 [SMILES: O=C(C1CC1)N1CCN(Cc2ccnc(Nc3nc4ccc(-c5ccnc(C(F)(F)F)n5)cc4[nH]3)c2)CC1]

Starting with crude N-[4-(piperazin-1-ylmethyl)pyridin-2-yl]-6-[2-(trifluoromethyl)pyrimidin-4-yl]-1H-benzimidazol-2-amine hydrochloride (140 mg, approx. 246 μmol) and cyclopropanecarboxylic acid (31.8 mg, 370 μmol), Example 27.01 was prepared analogously to the procedure for the preparation of Example 01.02.

Yield: 39.0 mg of the title compound.

LC-MS (Method 4): R$_t$=1.16 min; MS (ESIpos): m/z=523 [M+H]$^+$.

$^1$H-NMR (400 MHz, DMSO-d6) δ[ppm]: 0.678 (3.61), 0.686 (8.07), 0.691 (5.25), 0.698 (4.46), 0.705 (9.77), 0.709 (8.92), 0.714 (9.25), 0.721 (8.26), 0.726 (9.31), 0.733 (4.39), 1.950 (1.84), 1.957 (2.03), 1.969 (3.28), 1.981 (1.97), 1.988 (1.70), 2.322 (3.15), 2.327 (4.39), 2.331 (3.54), 2.336 (2.30), 2.364 (4.13), 2.447 (4.85), 2.523 (15.21), 2.539 (3.34), 2.659 (1.44), 2.665 (3.02), 2.669 (4.20), 2.673 (3.15), 3.307 (1.70), 3.501 (4.13), 3.532 (16.00), 3.709 (3.93), 6.976 (3.67), 6.989 (2.49), 7.186 (4.20), 7.216 (1.77), 7.467 (2.69), 7.488 (3.15), 7.552 (1.31), 7.646 (1.31), 7.666 (1.31), 8.013 (3.80), 8.035 (3.48), 8.280 (8.13), 8.292 (9.70), 8.413 (1.18), 8.515 (3.67), 8.961 (2.89), 8.975 (3.67), 10.809 (1.44), 10.896 (3.15), 12.394 (1.51), 12.491 (3.54).

Example 27.02 cyclobutyl(4-{[2-({6-[2-(trifluoromethyl)pyrimidin-4-yl]-1H-benzimidazol-2-yl}amino)pyridin-4-yl]methyl}piperazin-1-yl)methanone

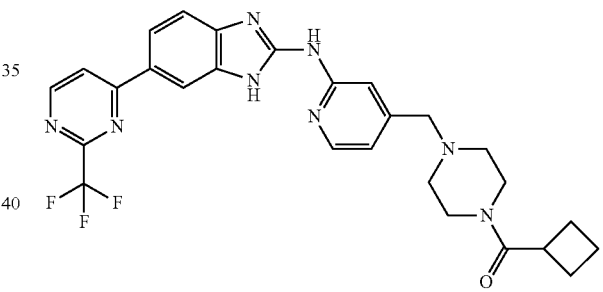

Starting with crude N-[4-(piperazin-1-ylmethyl)pyridin-2-yl]-6-[2-(trifluoromethyl)pyrimidin-4-yl]-1H-benzimidazol-2-amine hydrochloride (140 mg, approx. 246 μmol) and cyclobutanecarboxylic acid (37.0 mg, 370 μmol), Example 27.02 was prepared analogously to the procedure for the preparation of Example 01.02.

Yield: 45.0 mg of the title compound.

LC-MS (Method 4): R$_t$=1.22 min; MS (ESIpos): m/z=537 [M+H]$^+$.

$^1$H-NMR (400 MHz, DMSO-d6) δ[ppm]: 1.065 (0.90), 1.299 (2.85), 1.710 (1.45), 1.734 (1.80), 1.758 (0.85), 1.841 (1.40), 1.862 (2.75), 1.885 (2.30), 1.912 (1.35), 2.053 (3.30), 2.062 (2.50), 2.074 (3.85), 2.083 (2.95), 2.100 (2.40), 2.124 (4.20), 2.145 (4.55), 2.175 (2.30), 2.197 (0.70), 2.318 (1.45), 2.322 (2.85), 2.327 (4.25), 2.331 (4.35), 2.354 (9.25), 2.518 (16.00), 2.523 (10.35), 2.659 (1.10), 2.665 (2.35), 2.669 (3.20), 2.673 (2.35), 2.678 (1.10), 3.306 (3.20), 3.473 (5.00), 3.487 (4.95), 3.507 (12.80), 4.089 (0.80), 4.095 (2.60), 6.955 (2.60), 6.967 (2.65), 7.184 (2.00), 7.486 (1.00), 8.011 (3.50), 8.015 (3.50), 8.032 (3.15), 8.036 (3.25), 8.270 (6.00), 8.283 (6.45), 8.510 (1.25), 8.965 (2.85), 8.979 (2.85), 10.883 (0.75).

Example 27.03

2-cyclopropyl-1-(4-{[2-({6-[2-(trifluoromethyl)py-rimidin-4-yl]-1H-benzimidazol-2-yl}amino)pyridin-4-yl]methyl}piperazin-1-yl)ethanone

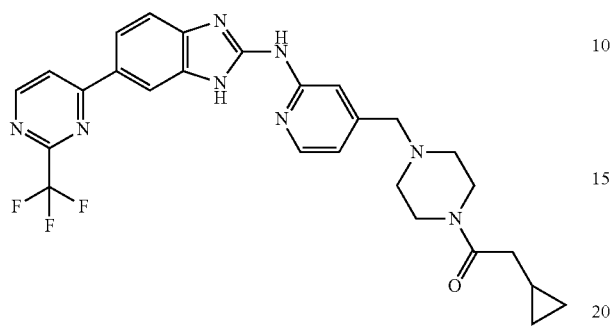

Starting with crude N-[4-(piperazin-1-ylmethyl)pyridin-2-yl]-6-[2-(trifluoromethyl)pyrimidin-4-yl]-1H-benzimidazol-2-amine hydrochloride (140 mg, approx. 246 µmol) and cyclopropylacetic acid (37.0 mg, 370 µmol), Example 27.03 was prepared analogously to the procedure for the preparation of Example 01.02.

Yield: 38.0 mg of the title compound.

LC-MS (Method 4): $R_t$=1.19 min; MS (ESIpos): m/z=537 [M+H]$^+$.

$^1$H-NMR (400 MHz, DMSO-d6) δ[ppm]: −0.001 (2.39), 0.011 (8.24), 0.023 (8.54), 0.037 (2.54), 0.330 (2.54), 0.340 (6.78), 0.344 (6.93), 0.350 (4.10), 0.354 (4.15), 0.360 (7.32), 0.364 (6.93), 0.375 (2.24), 0.754 (1.02), 0.854 (2.49), 0.921 (0.98), 0.980 (0.93), 2.153 (11.41), 2.171 (11.17), 2.242 (3.51), 2.278 (6.83), 2.311 (7.22), 2.437 (16.00), 2.584 (3.22), 3.371 (6.63), 3.406 (6.68), 3.433 (15.46), 4.004 (0.93), 6.882 (3.71), 7.093 (4.20), 7.123 (1.80), 7.380 (2.49), 7.401 (2.93), 7.467 (1.32), 7.560 (1.32), 7.928 (3.85), 7.948 (3.51), 8.190 (7.80), 8.204 (8.78), 8.326 (1.12), 8.428 (3.66), 8.876 (2.78), 8.890 (3.71), 10.721 (1.27), 10.807 (2.83), 12.307 (1.46), 12.404 (3.32).

Example 27.04

3,3,3-trifluoro-1-(4-{[2-({6-[2-(trifluoromethyl)py-rimidin-4-yl]-1H-benzimidazol-2-yl}amino)pyridin-4-yl]methyl}piperazin-1-yl)propan-1-one

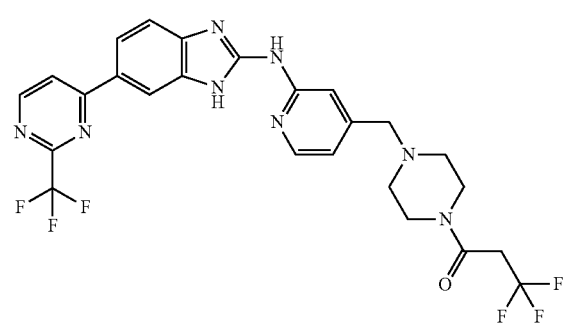 [SMILES: O=C(CC(F)(F)F)N1CCN(Cc2ccnc(Nc3nc4ccc(-c5ccnc(C(F)(F)F)n5)cc4[nH]3)c2)CC1]

Starting with crude N-[4-(piperazin-1-ylmethyl)pyridin-2-yl]-6-[2-(trifluoromethyl)pyrimidin-4-yl]-1H-benzimidazol-2-amine hydrochloride (140 mg, approx. 246 µmol) and 3,3,3-trifluoropropanoic acid (47.3 mg, 370 µmol), Example 27.04 was prepared analogously to the procedure for the preparation of Example 01.02.

Yield: 28.0 mg of the title compound.

LC-MS (Method 1): $R_t$=0.91 min; MS (ESIneg): m/z=563 [M−H]$^+$.

$^1$H-NMR (400 MHz, CHLOROFORM-d) δ [ppm]: 1.284 (16.00), 2.628 (1.29), 3.190 (1.01), 3.215 (0.98), 3.525 (1.65).

Example 28.01 tert-butyl 4-[(2-{[6-(2-ethylpyrimidin-4-yl)-1H-benzimidazol-2-yl]amino}pyridin-4-yl)methyl]piperazine-1-carboxylate

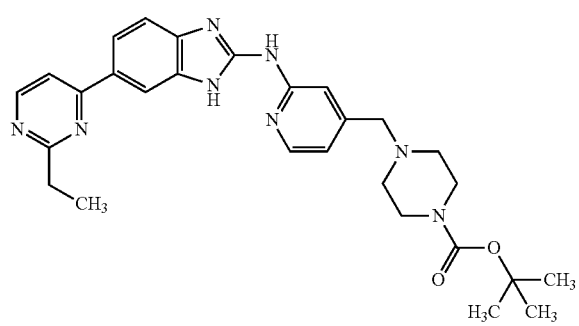

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-2-ethylpyrimidine (240 mg, 1.68 mmol), Example 28.01 was prepared analogously to the procedure for the preparation of Example 01.01.

Yield: 10.0 mg (2%) of the title compound.

LC-MS (Method 2): $R_t$=1.28 min; MS (ESIpos): m/z=515 [M+H]$^+$.

$^1$H-NMR (400 MHz, DMSO-d6) δ[ppm]: 1.107 (6.94), 1.356 (1.64), 1.396 (16.00), 2.327 (0.77), 2.347 (0.97), 2.360 (1.46), 2.373 (1.01), 2.518 (3.41), 2.523 (2.10), 2.669 (0.75), 2.928 (1.03), 2.947 (1.01), 3.352 (1.34), 3.505 (1.83), 8.668 (1.13), 8.682 (1.08).

Example 29.01.01

(rac)-3,3,3-trifluoro-1-(4-{1-[2-({6-[6-(trifluorom-ethyl)pyrimidin-4-yl]-1H-benzimidazol-2-yl}amino)pyridin-4-yl]ethyl}piperazin-1-yl)propan-1-one

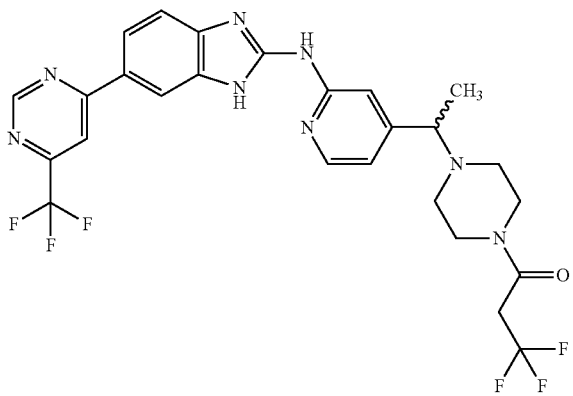 [SMILES: CC(c1ccnc(Nc2nc3ccc(-c4cc(C(F)(F)F)ncn4)cc3[nH]2)c1)N1CCN(C(=O)CC(F)(F)F)CC1]

Starting with N-{4-[(1R)-1-(piperazin-1-yl)ethyl]pyridin-2-yl}-6-[6-(trifluoromethyl)pyrimidin-4-yl]-1H-benzimidazol-2-amine (185 mg, 395 µmol) and 3,3,3-trifluoropropanoic acid (75.8 mg, 592 µmol), Example 29.01.01 was prepared analogously to the procedure for the preparation of Example 01.02.

Yield: 76.2 mg (32%) of the title compound.

LC-MS (Method 4): $R_t$=1.26 min; MS (ESIpos): m/z=579 [M+H]$^+$.

$^1$H-NMR (400 MHz, DMSO-d6) δ[ppm]: 1.065 (1.67), 1.295 (16.00), 1.311 (15.14), 2.318 (2.27), 2.322 (2.76), 2.327 (3.91), 2.332 (4.05), 2.337 (3.36), 2.345 (3.53), 2.367 (2.82), 2.418 (3.85), 2.431 (4.45), 2.445 (3.42), 2.460 (2.61), 2.518 (5.14), 2.523 (3.59), 2.539 (1.52), 2.665 (1.24), 2.669 (1.72), 2.673 (1.24), 2.685 (0.72), 2.729 (0.60), 2.888 (0.78), 3.426 (4.22), 3.438 (7.24), 3.450 (4.60), 3.480 (8.82), 3.495 (6.18), 3.582 (2.73), 3.609 (7.70), 3.637 (7.30), 3.664 (2.27), 4.019 (1.55), 6.982 (2.84), 6.996 (1.87), 7.184 (7.61), 7.459 (1.78), 7.480 (1.92), 7.630 (1.06), 7.652 (1.12), 8.095 (1.12), 8.118 (2.53), 8.140 (1.55), 8.286 (4.80), 8.300 (4.54), 8.391 (1.81), 8.426 (3.04), 8.541 (2.87), 8.573 (1.87), 9.373 (4.83), 10.808 (1.12), 10.884 (1.78), 12.377 (1.61), 12.419 (2.61).

Example 29.01.02

(rac)-cyclopropyl(4-{1-[2-({6-[6-(trifluoromethyl)pyrimidin-4-yl]-1H-benzimidazol-2-yl}amino)pyridin-4-yl]ethyl}piperazin-1-yl)methanone

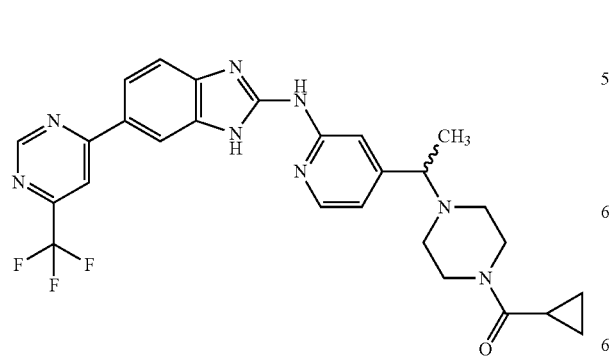

Starting with (rac)-N-{4-[1-(piperazin-1-yl)ethyl]pyridin-2-yl}-6-[6-(trifluoromethyl)pyrimidin-4-yl]-1H-benzimidazol-2-amine (185 mg, 395 µmol) and cyclopropanecarboxylic acid (51.0 mg, 592 µmol), Example 29.01.02 was prepared analogously to the procedure for the preparation of Example 01.02.

Yield: 63.0 mg (28%) of the title compound.

LC-MS (Method 4): $R_t$=1.23 min; MS (ESIpos): m/z=537 [M+H]$^+$.

$^1$H-NMR (400 MHz, DMSO-d6) δ [ppm]: 0.665 (6.69), 0.687 (10.35), 1.064 (1.12), 1.298 (16.00), 1.313 (10.32), 1.938 (2.52), 2.326 (3.08), 2.399 (3.94), 2.672 (1.51), 3.462 (6.88), 3.673 (4.59), 6.989 (2.66), 7.191 (5.06), 7.481 (1.59), 7.630 (1.01), 8.117 (2.13), 8.287 (3.30), 8.300 (3.22), 8.387 (1.34), 8.428 (2.21), 8.538 (2.15), 9.374 (3.86), 10.887 (1.12), 12.433 (1.20).

Example 29.02.01.A 3,3,3-trifluoro-1-(4-{(1R or 1S)-1-[2-({6-[6-(trifluoromethyl)pyrimidin-4-yl]-1H-benzimidazol-2-yl}amino)pyridin-4-yl]ethyl}piperazin-1-yl)propan-1-one (single stereoisomer A)

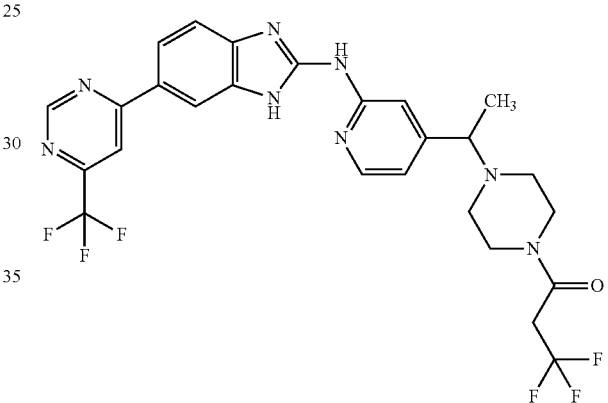

Example 29.02.01.B 3,3,3-trifluoro-1-(4-{(1S or 1R)-1-[2-({6-[6-(trifluoromethyl)pyrimidin-4-yl]-1H-benzimidazol-2-yl}amino)pyridin-4-yl]ethyl}piperazin-1-yl)propan-1-one (single stereoisomer B)

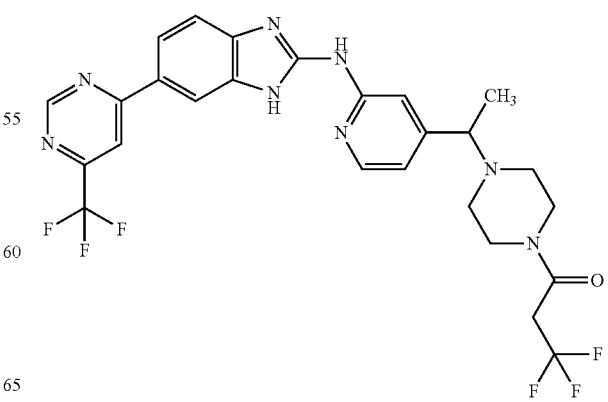

73 mg of (rac)-3,3,3-trifluoro-1-(4-{1-[2-({6-[6-(trifluoromethyl)pyrimidin-4-yl]-1H-benzimidazol-2-yl}amino)pyridin-4-yl]ethyl}piperazin-1-yl)propan-1-one was separated into the single stereoisomers (Example 29.02.01.A and Example 29.02.01.B) via preparative, chiral HPLC.

Instrument: Labomatic HD5000, Labocord-5000; Gilson GX-241, Labcol Vario 4000,

Column: Chiralpak IA 5μ 250×30 mm;

Eluent A: tert.-butyl methyl ether+0.1 Vol-% diethylamine (99%);

Eluent B: acetonitrile; isocratic: 70% A+30% B;

Flow: 50.0 mL/min;

Solution: 73 mg/2 mL dichloromethane/methanol 1:1

Injection: 2×1.0 mL

Detection: UV 325 nm

|  | Retention time in min | purity in % | yield | Optical rotation $[\alpha]_D$ |
|---|---|---|---|---|
| Example 29.02.01.A Stereoisomer A | 6.4-7.7 | >99.0% | 27 mg | +31.0° (from solution in DMSO, c = 2.0 mg/mL) |
| Example 29.02.01.B Stereoisomer B | 8.70-10.50 | 98.0% | 27 mg | −28.2° (from solution in DMSO, c = 2.0 mg/mL) |

Example 29.02.01.A $^1$H-NMR (400 MHz, DMSO-d6) δ[ppm]: 1.107 (3.24), 1.154 (0.90), 1.172 (1.62), 1.190 (0.72), 1.231 (1.80), 1.295 (7.91), 1.312 (7.37), 1.988 (2.34), 2.084 (16.00), 2.318 (1.98), 2.323 (3.42), 2.327 (4.67), 2.332 (3.96), 2.337 (2.34), 2.345 (1.62), 2.366 (1.26), 2.419 (1.80), 2.432 (2.16), 2.518 (11.51), 2.523 (7.73), 2.660 (1.26), 2.665 (2.70), 2.669 (3.60), 2.673 (2.52), 2.679 (1.08), 3.426 (2.16), 3.438 (3.60), 3.450 (2.16), 3.482 (4.13), 3.493 (2.70), 3.582 (1.26), 3.609 (3.96), 3.637 (3.60), 3.664 (1.08), 6.986 (1.44), 7.000 (1.08), 7.183 (3.24), 7.459 (1.44), 7.480 (1.44), 7.631 (0.90), 7.652 (0.90), 8.119 (1.44), 8.123 (1.08), 8.145 (0.90), 8.290 (1.80), 8.304 (1.62), 8.388 (1.44), 8.428 (2.16), 8.537 (1.80), 8.573 (1.44), 9.371 (2.52), 9.382 (1.80), 10.804 (1.26), 10.882 (1.98), 12.376 (1.26), 12.420 (1.80).

Example 29.02.01.B $^1$H-NMR (400 MHz, DMSO-d6) δ[ppm]: 1.107 (0.76), 1.295 (1.48), 1.312 (1.44), 2.084 (16.00), 3.609 (0.82), 3.636 (0.76), 7.184 (0.82).

Example 30.01.01

3,3,3-trifluoro-1-{4-[(2-{[6-(6-methylpyrimidin-4-yl)-1H-benzimidazol-2-yl]amino}pyridin-4-yl)methyl]piperazin-1-yl}propan-1-one

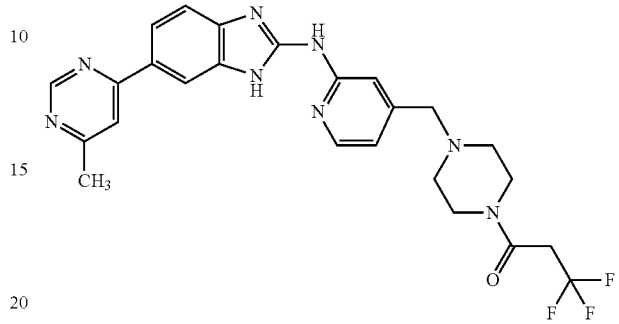

Starting with crude 6-(6-methylpyrimidin-4-yl)-N-[4-(piperazin-1-ylmethyl)pyridin-2-yl]-1H-benzimidazol-2-amine hydrochloride (150 mg, approx. 300 μmol) and 3,3,3-trifluoropropanoic acid (57.6 mg, 449 μmol), Example 30.01.01 was prepared analogously to the procedure for the preparation of Example 01.02.

Yield: 60.0 mg of the title compound.

LC-MS (Method 4): $R_t$=1.00 min; MS (ESIpos): m/z=511 [M+H]$^+$.

$^1$H-NMR (400 MHz, DMSO-d6) δ [ppm]: 1.711 (1.37), 1.734 (1.67), 1.758 (0.82), 1.841 (1.42), 1.862 (2.66), 1.868 (1.20), 1.885 (2.10), 1.889 (2.06), 1.912 (1.29), 2.053 (3.09), 2.062 (2.36), 2.069 (2.27), 2.075 (3.56), 2.084 (2.87), 2.101 (2.23), 2.106 (2.06), 2.124 (4.03), 2.129 (2.79), 2.145 (4.33), 2.169 (2.02), 2.175 (2.27), 2.197 (0.73), 2.318 (1.20), 2.323 (2.45), 2.327 (3.52), 2.331 (3.52), 2.354 (8.62), 2.518 (16.00), 2.523 (9.69), 2.659 (0.94), 2.665 (2.10), 2.669 (2.92), 2.673 (2.06), 2.678 (0.99), 2.848 (0.86), 3.284 (0.77), 3.306 (3.05), 3.346 (6.82), 3.474 (4.50), 3.503 (12.31), 6.948 (2.49), 7.187 (4.46), 7.421 (1.12), 7.442 (1.24), 7.600 (0.90), 7.884 (1.97), 7.925 (3.13), 7.945 (2.83), 7.998 (1.46), 8.201 (1.46), 8.266 (5.19), 8.280 (5.06), 8.395 (1.89), 9.015 (7.55), 9.018 (7.72), 10.779 (1.54), 12.313 (0.94).

Example 30.01.02 cyclobutyl{4-[(2-{[6-(6-methylpyrimidin-4-yl)-1H-benzimidazol-2-yl]amino}pyridin-4-yl)methyl]piperazin-1-yl}methanone

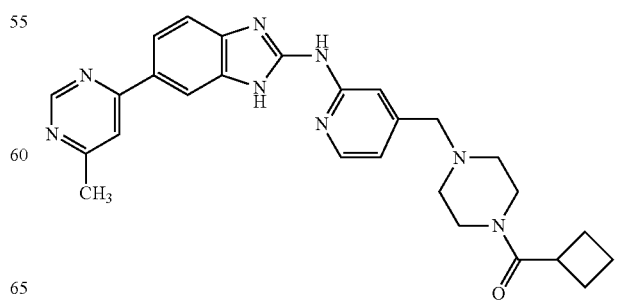

Starting with crude 6-(6-methylpyrimidin-4-yl)-N-[4-(piperazin-1-ylmethyl)pyridin-2-yl]-1H-benzimidazol-2-amine hydrochloride (150 mg, approx. 300 µmol) and cyclobutanecarboxylic acid (45.0 mg, 449 µmol), Example 30.01.02 was prepared analogously to the procedure for the preparation of Example 01.02.

Yield: 46.0 mg of the title compound.

LC-MS (Method 4): R$_t$=1.03 min; MS (ESIpos): m/z=483 [M+H]$^+$.

$^1$H-NMR (400 MHz, DMSO-d6) δ [ppm]: 1.065 (1.08), 1.231 (0.77), 2.318 (0.95), 2.323 (2.12), 2.327 (2.98), 2.331 (2.26), 2.337 (1.08), 2.371 (3.66), 2.384 (5.51), 2.396 (4.20), 2.413 (3.71), 2.426 (5.24), 2.437 (4.20), 2.518 (16.00), 2.523 (9.72), 2.659 (0.99), 2.665 (2.26), 2.669 (3.16), 2.673 (2.21), 2.678 (1.04), 2.848 (8.41), 3.474 (5.11), 3.485 (4.70), 3.497 (4.84), 3.510 (5.42), 3.529 (15.23), 3.612 (2.40), 3.640 (6.64), 3.667 (6.33), 3.694 (2.08), 4.049 (2.85), 6.663 (2.35), 6.667 (2.62), 6.721 (0.86), 6.726 (1.36), 6.730 (0.68), 6.944 (3.53), 6.956 (3.57), 7.090 (0.81), 7.207 (4.84), 7.924 (4.97), 7.928 (4.97), 7.945 (4.34), 7.949 (4.56), 8.271 (6.37), 8.285 (6.10), 9.015 (9.40), 9.018 (9.36).

Example 30.01.03

2-cyclopropyl-1-{4-[(2-{[6-(6-methylpyrimidin-4-yl)-1H-benzimidazol-2-yl]amino}pyridin-4-yl)methyl]piperazin-1-yl}ethanone

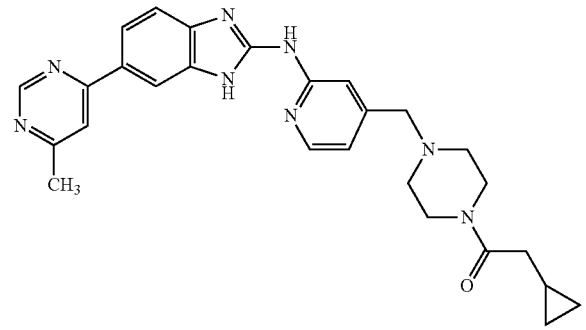 [SMILES: Cc1cc(-c2ccc3nc(Nc4cc(CN5CCN(C(=O)CC6CC6)CC5)ccn4)[nH]c3c2)ncn1]

Starting with crude 6-(6-methylpyrimidin-4-yl)-N-[4-(piperazin-1-ylmethyl)pyridin-2-yl]-1H-benzimidazol-2-amine hydrochloride (150 mg, approx. 300 µmol) and cyclopropylacetic acid (45.0 mg, 449 µmol), Example 30.01.03 was prepared analogously to the procedure for the preparation of Example 01.02.

Yield: 37.0 mg of the title compound.

LC-MS (Method 4): R$_t$=0.99 min; MS (ESIpos): m/z=483 [M+H]$^+$.

$^1$H-NMR (400 MHz, DMSO-d6) δ[ppm]: 0.000 (1.65), 0.011 (5.50), 0.014 (5.20), 0.023 (5.65), 0.026 (5.35), 0.037 (1.90), 0.330 (2.00), 0.340 (4.90), 0.344 (5.10), 0.350 (2.85), 0.354 (2.50), 0.360 (5.30), 0.365 (4.95), 0.375 (1.90), 0.834 (1.05), 0.842 (1.05), 0.854 (1.85), 0.867 (1.05), 0.871 (1.10), 0.921 (1.00), 2.154 (8.80), 2.171 (8.55), 2.233 (1.10), 2.238 (2.30), 2.242 (3.30), 2.247 (2.55), 2.251 (1.50), 2.277 (3.95), 2.311 (4.10), 2.433 (16.00), 2.438 (9.95), 2.575 (1.00), 2.580 (2.30), 2.584 (3.30), 2.589 (2.35), 2.594 (1.05), 3.222 (1.10), 3.374 (3.90), 3.429 (9.90), 6.866 (2.15), 7.106 (3.00), 7.337 (1.20), 7.358 (1.30), 7.517 (0.90), 7.799 (2.00), 7.841 (2.55), 7.862 (2.35), 7.912 (1.50), 8.117 (1.50), 8.186 (4.10), 8.199 (3.95), 8.311 (1.85), 8.930 (5.90), 8.933 (6.45), 10.698 (1.40), 12.230 (0.95).

Example 30.01.04 cyclopropyl{4-[(2-{[6-(6-methylpyrimidin-4-yl)-1H-benzimidazol-2-yl]amino}pyridin-4-yl)methyl]piperazin-1-yl}methanone

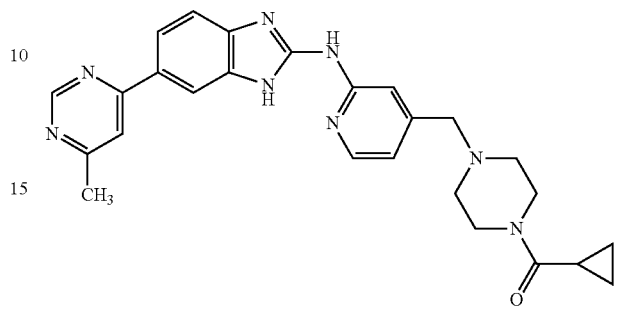

Starting with crude 6-(6-methylpyrimidin-4-yl)-N-[4-(piperazin-1-ylmethyl)pyridin-2-yl]-1H-benzimidazol-2-amine hydrochloride (150 mg, approx. 300 µmol) and cyclopropanecarboxylic acid (38.7 mg, 449 µmol), Example 30.01.04 was prepared analogously to the procedure for the preparation of Example 01.02.

Yield: 38.0 mg of the title compound.

LC-MS (Method 4): R$_t$=0.96 min; MS (ESIpos): m/z=469 [M+H]$^+$.

$^1$H-NMR (400 MHz, DMSO-d6) δ[ppm]: 0.666 (1.22), 0.678 (3.61), 0.685 (7.92), 0.690 (5.08), 0.698 (4.32), 0.705 (9.75), 0.709 (8.43), 0.714 (8.99), 0.721 (8.03), 0.726 (9.19), 0.733 (4.27), 0.745 (1.07), 1.065 (1.17), 1.937 (0.91), 1.949 (1.88), 1.956 (1.98), 1.969 (3.35), 1.981 (1.88), 1.988 (1.73), 2.000 (0.76), 2.318 (1.27), 2.323 (2.69), 2.327 (3.81), 2.331 (3.00), 2.337 (1.93), 2.364 (3.81), 2.446 (4.01), 2.518 (16.00), 2.523 (10.41), 2.659 (1.17), 2.665 (2.64), 2.669 (3.71), 2.673 (2.59), 2.678 (1.22), 3.308 (1.22), 3.503 (3.96), 3.528 (15.54), 3.711 (3.50), 6.954 (3.30), 6.967 (3.40), 7.204 (5.13), 7.445 (1.07), 7.887 (1.47), 7.925 (4.22), 7.930 (4.27), 7.946 (3.76), 7.950 (3.86), 7.997 (1.07), 8.205 (1.07), 8.275 (6.55), 8.288 (6.30), 8.396 (1.42), 9.015 (8.79), 9.019 (8.99), 10.780 (1.37).

Example 30.02.01

(rac)-3,3,3-trifluoro-1-{4-[1-(2-{[6-(6-methylpyrimidin-4-yl)-1H-benzimidazol-2-yl]amino}pyridin-4-yl)ethyl]piperazin-1-yl}propan-1-one

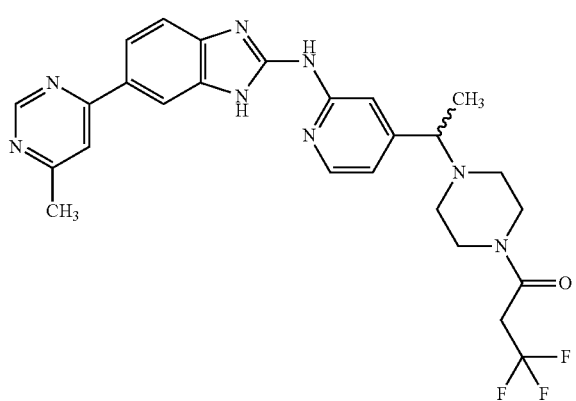 [SMILES: Cc1cc(-c2ccc3nc(Nc4cc(C(C)N5CCN(C(=O)CC(F)(F)F)CC5)ccn4)[nH]c3c2)ncn1]

Starting with (rac)-6-(6-methyl pyrimidin-4-yl)-N-{4-[1-(piperazin-1-yl)ethyl]pyridin-2-yl}-1H-benzimidazol-2-amine (200 mg, 482 µmol) and 3,3,3-trifluoropropanoic acid (92.7 mg, 724 µmol), Example 30.02.01 was prepared analogously to the procedure for the preparation of Example 01.02.

Yield: 9.00 mg (3%) of the title compound.

LC-MS (Method 2): $R_t$=1.05 min; MS (ESIpos): m/z=525 [M+H]$^+$.

$^1$H-NMR (500 MHz, DMSO-d6) δ[ppm]: 1.228 (16.00), 1.294 (13.99), 1.517 (10.40), 2.361 (13.20), 2.539 (13.55), 2.691 (9.27), 3.006 (6.30), 3.471 (14.86), 3.636 (11.89), 5.758 (6.03), 7.622 (5.60).

Example 30.02.02

(rac)-cyclobutyl{4-[1-(2-{[6-(6-methylpyrimidin-4-yl)-1H-benzimidazol-2-yl]amino}pyridin-4-yl)ethyl]piperazin-1-yl}methanone

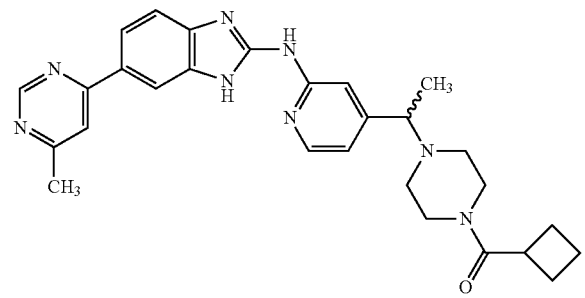 [SMILES: Cc1cc(-c2ccc3nc(Nc4cc(C(C)N5CCN(C(=O)C6CCC6)CC5)ccn4)[nH]c3c2)ncn1]

Starting with (rac)-6-(6-methylpyrimidin-4-yl)-N-{4-[1-(piperazin-1-yl)ethyl]pyridin-2-yl}-1H-benzimidazol-2-amine (200 mg, 482 µmol) and cyclobutanecarboxylic acid (72.5 mg, 724 µmol), Example 30.02.02 was prepared analogously to the procedure for the preparation of Example 01.02.

Yield: 67.8 mg (28%) of the title compound.

LC-MS (Method 4): $R_t$=1.07 min; MS (ESIpos): m/z=497 [M+H]$^+$.

$^1$H-NMR (400 MHz, DMSO-d6) δ[ppm]: 1.275 (15.87), 1.292 (16.00), 1.717 (2.29), 1.822 (1.76), 1.844 (3.49), 1.866 (2.74), 1.893 (1.73), 2.030 (4.12), 2.052 (4.77), 2.061 (3.77), 2.076 (3.34), 2.099 (5.07), 2.121 (5.27), 2.151 (2.69), 2.281 (3.72), 2.295 (4.12), 2.326 (2.49), 2.401 (2.91), 2.522 (9.24), 2.668 (1.66), 3.274 (3.59), 3.294 (8.11), 3.307 (7.28), 3.317 (7.69), 3.427 (6.28), 3.443 (7.91), 6.950 (3.52), 6.963 (3.62), 7.172 (8.97), 7.441 (1.23), 7.883 (1.91), 7.924 (4.57), 7.927 (4.52), 7.944 (4.04), 8.198 (1.38), 8.269 (7.26), 8.282 (6.96), 8.395 (1.86), 9.014 (10.78), 9.017 (10.55), 10.766 (1.53), 12.322 (1.91).

Example 30.02.03

(rac)-cyclopropyl{4-[1-(2-{[6-(6-methylpyrimidin-4-yl)-1H-benzimidazol-2-yl]amino}pyridin-4-yl)ethyl]piperazin-1-yl}methanone

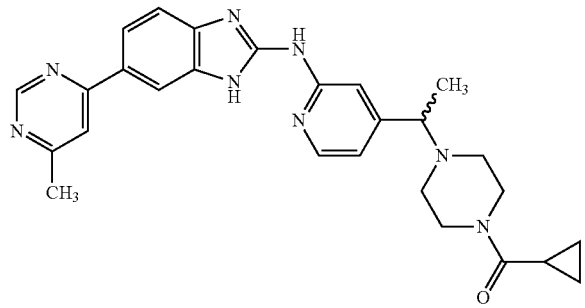 [SMILES: Cc1cc(-c2ccc3nc(Nc4cc(C(C)N5CCN(C(=O)C6CC6)CC5)ccn4)[nH]c3c2)ncn1]

Starting with (rac)-6-(6-methylpyrimidin-4-yl)-N-{4-[1-(piperazin-1-yl)ethyl]pyridin-2-yl}-1H-benzimidazol-2-amine (200 mg, 482 µmol) and cyclopropanecarboxylic acid (62.3 mg, 724 µmol), Example 30.02.03 was prepared analogously to the procedure for the preparation of Example 01.02.

Yield: 58.7 mg (25%) of the title compound.

LC-MS (Method 4): $R_t$=1.00 min; MS (ESIpos): m/z=483 [M+H]$^+$.

$^1$H-NMR (400 MHz, DMSO-d6) δ[ppm]: 0.656 (3.77), 0.664 (8.60), 0.669 (5.44), 0.677 (4.50), 0.684 (10.94), 0.691 (10.30), 0.698 (8.39), 0.703 (9.48), 0.710 (4.42), 1.295 (15.94), 1.312 (16.00), 1.918 (1.96), 1.924 (2.14), 1.937 (3.66), 1.949 (1.99), 1.956 (1.84), 2.322 (2.69), 2.326 (3.07), 2.402 (2.75), 2.522 (5.73), 2.668 (1.93), 3.454 (6.26), 3.470 (7.55), 3.676 (4.07), 6.979 (3.54), 7.186 (8.31), 7.885 (1.87), 7.924 (4.30), 7.929 (4.33), 7.950 (3.98), 8.278 (7.22), 8.290 (6.96), 8.397 (1.78), 9.014 (10.12), 9.017 (11.06), 10.770 (1.49), 12.338 (1.61).

Example 30.02.04

(rac)-2-cyclopropyl-1-{4-[1-(2-{[6-(6-methylpyrimidin-4-yl)-1H-benzimidazol-2-yl]amino}pyridin-4-yl)ethyl]piperazin-1-yl}ethanone

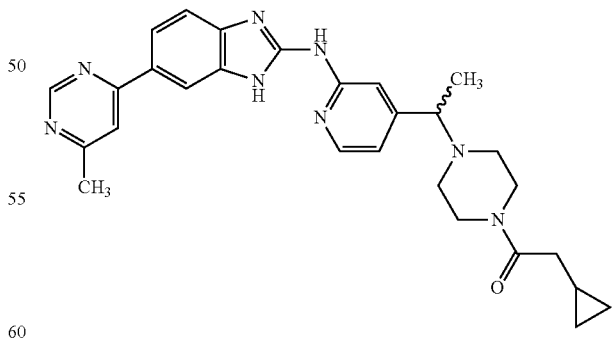

Starting with (rac)-6-(6-methylpyrimidin-4-yl)-N-{4-[1-(piperazin-1-yl)ethyl]pyridin-2-yl}-1H-benzimidazol-2-amine (300 mg, 724 µmol) and cyclopropylacetic acid (109 mg, 1.09 mmol), Example 30.02.04 was prepared analogously to the procedure for the preparation of Example 01.02.

Yield: 63.0 mg (17%) of the title compound.

LC-MS (Method 4): $R_t$=1.05 min; MS (ESIpos): m/z=497 [M+H]$^+$.

$^1$H-NMR (400 MHz, DMSO-d6) δ[ppm]: 0.000 (2.56), 0.011 (9.36), 0.014 (8.28), 0.023 (9.52), 0.026 (8.36), 0.037 (2.76), 0.331 (2.88), 0.341 (7.88), 0.345 (7.72), 0.351 (3.84), 0.356 (3.72), 0.361 (8.16), 0.365 (7.68), 0.375 (2.60), 0.814 (0.76), 0.819 (1.00), 0.831 (1.76), 0.838 (1.76), 0.851 (2.80), 0.863 (1.60), 0.868 (1.68), 0.880 (0.80), 0.888 (0.64), 1.164 (0.76), 1.220 (16.00), 1.237 (15.92), 2.145 (14.24), 2.162 (13.68), 2.231 (2.40), 2.252 (3.80), 2.257 (4.28), 2.261 (4.88), 2.266 (4.24), 2.283 (2.52), 2.338 (5.24), 2.352 (4.20), 2.366 (3.08), 2.457 (4.88), 2.594 (0.88), 2.599 (1.88), 2.604 (2.56), 2.608 (1.80), 2.613 (0.80), 3.358 (8.28), 3.375 (8.08), 3.393 (8.64), 6.904 (3.44), 7.111 (8.72), 7.354 (1.44), 7.376 (1.52), 7.515 (1.04), 7.535 (1.08), 7.817 (2.48), 7.858 (4.20), 7.862 (4.36), 7.883 (3.88), 7.931 (1.80), 8.133 (1.72), 8.207 (7.20), 8.220 (6.88), 8.330 (2.36), 8.949 (10.88), 8.951 (11.16), 10.700 (1.96), 12.211 (1.72), 12.255 (2.48).

Example 30.03.01.A 3,3,3-trifluoro-1-{4-[(1R or 1S)-1-(2-{[6-(6-methylpyrimidin-4-yl)-1H-benzimidazol-2-yl]amino}pyridin-4-yl)ethyl]piperazin-1-yl}propan-1-one (single stereoisomer A)

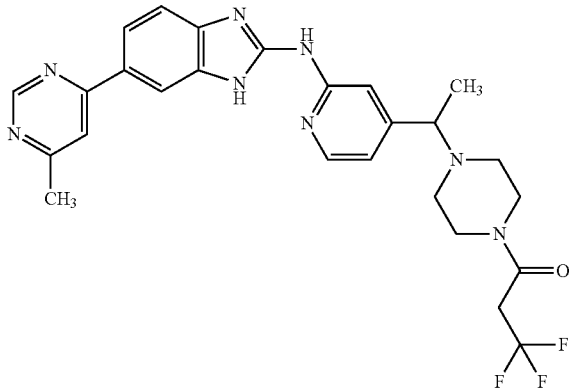 [SMILES: Cc1cc(-c2ccc3nc(Nc4cc(C(C)N5CCN(C(=O)CC(F)(F)F)CC5)ccn4)[nH]c3c2)ncn1]

Example 30.03.01.B 3,3,3-trifluoro-1-{4-[(1S or 1R)-1-(2-{[6-(6-methylpyrimidin-4-yl)-1H-benzimidazol-2-yl]amino}pyridin-4-yl)ethyl]piperazin-1-yl}propan-1-one (single stereoisomer B)

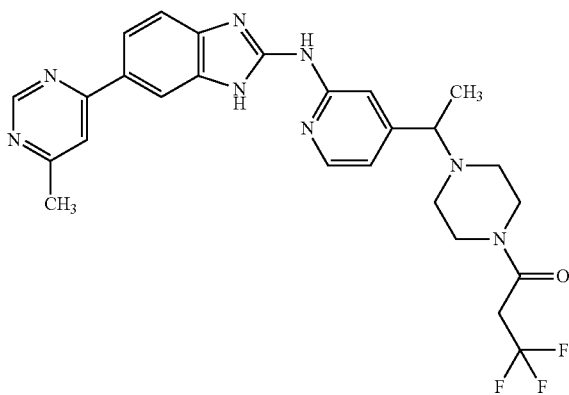 [SMILES: Cc1cc(-c2ccc3nc(Nc4cc(C(C)N5CCN(C(=O)CC(F)(F)F)CC5)ccn4)[nH]c3c2)ncn1]

55 mg of (rac)-3,3,3-trifluoro-1-{4-[1-(2-{[6-(6-methylpyrimidin-4-yl)-1H-benzimidazol-2-yl]amino}pyridin-4-yl)ethyl]piperazin-1-yl}propan-1-one was separated into the single stereoisomers (Example 30.03.01.A and Example 30.03.01.B) via preparative, chiral HPLC.

Instrument: Labomatic HD5000, Labocord-5000; Gilson GX-241, Labcol Vario 4000,

Column: Chiralpak IA 5μ 250×30 mm;

Eluent A: tert.-butyl methyl ether+0.1 Vol-% diethylamine (99%);

Eluent B: acetonitrile; isocratic: 50% A+50% B;

Flow: 60.0 mL/min;

Solution: 55 mg/1.5 mL dichloromethane/methanol 1:1

Injection: 3×0.5 mL

Detection: UV 325 nm

| | Retention time in min | purity in % | yield | Optical rotation [α]$_D$ |
|---|---|---|---|---|
| Example 30.03.01.A Stereoisomer A | 7.00-8.80 | >99.0% | 16 mg | +35.2° (from solution in DMSO, c = 2.0 mg/mL) |
| Example 30.03.01.B Stereoisomer B | 9.60-12.00 | 97.8% | 16 mg | −26.4° (from solution in DMSO, c = 2.2 mg/mL) |

Example 30.03.01.A $^1$H-NMR (400 MHz, DMSO-d6) δ[ppm]: 1.107 (16.00), 1.293 (4.06), 1.310 (3.94), 2.083 (0.65), 2.327 (1.20), 2.332 (1.11), 3.437 (1.91), 3.449 (1.23), 3.471 (2.00), 3.488 (1.94), 3.608 (2.09), 3.635 (1.97), 4.199 (1.48), 7.176 (1.97), 7.925 (1.08), 7.929 (1.05), 8.277 (1.75), 8.290 (1.66), 9.014 (2.58), 9.017 (2.74).

Example 30.03.01.B $^1$H-NMR (400 MHz, DMSO-d6) δ[ppm]: 0.803 (0.41), 0.850 (1.01), 0.859 (0.71), 0.966 (0.61), 1.107 (10.43), 1.135 (0.71), 1.143 (0.61), 1.152 (0.81), 1.171 (0.71), 1.182 (1.11), 1.230 (4.86), 1.254 (1.22), 1.279 (1.82), 1.293 (15.90), 1.310 (16.00), 1.347 (1.11), 2.083 (4.05), 2.318 (2.33), 2.322 (3.14), 2.327 (4.56), 2.332 (4.35), 2.337 (3.44), 2.344 (3.54), 2.366 (2.84), 2.418 (3.85), 2.430 (4.35), 2.444 (3.34), 2.458 (2.94), 2.523 (5.97), 2.660 (0.71), 2.665 (1.62), 2.669 (2.33), 2.673 (1.62), 2.679 (0.71), 3.380 (1.32), 3.425 (4.35), 3.437 (7.70), 3.449 (4.96), 3.472 (7.80), 3.482 (7.59), 3.488 (7.59), 3.503 (2.63), 3.509 (1.72), 3.580 (2.94), 3.608 (8.41), 3.635 (7.90), 3.663 (2.43), 4.197 (0.91), 6.959 (3.75), 6.972 (3.85), 7.176 (8.20), 7.444 (1.01), 7.582 (0.81), 7.885 (1.62), 7.925 (4.76), 7.929 (4.56), 7.946 (4.15), 7.950 (4.15), 7.993 (1.11), 8.201 (1.11), 8.278 (7.49), 8.291 (7.09), 8.396 (1.52), 9.015 (11.44), 9.018 (11.14), 10.770 (2.33), 12.284 (1.32), 12.323 (1.82).

Example 30.03.02.A cyclobutyl{4-[(1R or 1S)-1-(2-{[6-(6-methylpyrimidin-4-yl)-1H-benzimidazol-2-yl]amino}pyridin-4-yl)ethyl]piperazin-1-yl}methanone (single stereoisomer A)

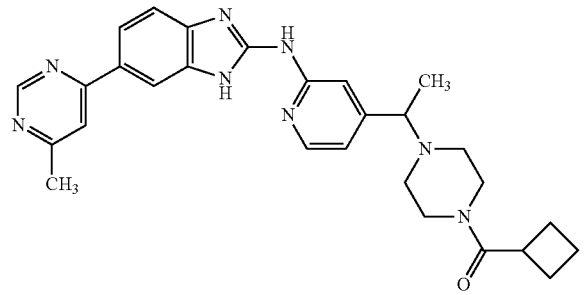 [SMILES: Cc1cc(-c2ccc3nc(Nc4cc(C(C)N5CCN(C(=O)C6CCC6)CC5)ccn4)[nH]c3c2)ncn1]

Example 30.03.02.B cyclobutyl{4-[(1S or 1R)-1-(2-{[6-(6-methylpyrimidin-4-yl)-1H-benzimidazol-2-yl]amino}pyridin-4-yl)ethyl]piperazin-1-yl}methanone (single stereoisomer B)

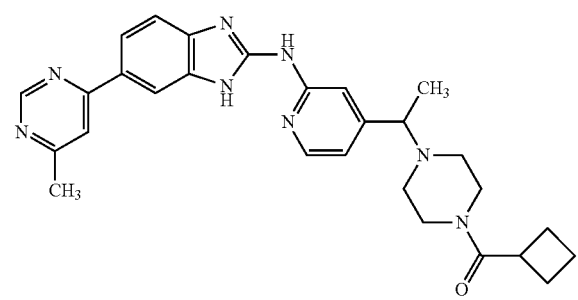 [SMILES: Cc1cc(-c2ccc3nc(Nc4cc(C(C)N5CCN(C(=O)C6CCC6)CC5)ccn4)[nH]c3c2)ncn1]

64.1 mg of (rac)-cyclobutyl{4-[1-(2-{[6-(6-methylpyrimidin-4-yl)-1H-benzimidazol-2-yl]amino}pyridin-4-yl)ethyl]piperazin-1-yl}methanone was separated into the single stereoisomers (Example 30.03.02.A and Example 30.03.02.B) via preparative, chiral HPLC.
Instrument: Labomatic HD5000, Labocord-5000; Gilson GX-241, Labcol Vario 4000,
Column: Chiralpak IB 5µ 250×30 mm;
Eluent A: hexane+0.2 Vol-% diethylamine (99%); Eluent B: ethanol; isocratic: 70% A+30% B;
Flow: 30.0 mL/min;
Solution: 64 mg/2.5 mL ethanol
Injection: 5×0.5 mL
Detection: UV 325 nm

| | Retention time in min | purity in % | yield | Optical rotation [α]$_D$ |
|---|---|---|---|---|
| Example 30.03.02.A Stereoisomer A | 9.05-10.10 | >99.0% | 26 mg | -43.1° (from solution in DMSO, c = 2.6 mg/mL) |
| Example 30.03.02.B Stereoisomer B | 10.20-12.50 | 94.3% | 27 mg | +36.0° (from solution in DMSO, c = 2.9 mg/mL) |

Example 30.03.02.A $^1$H-NMR (400 MHz, DMSO-d6) δ[ppm]: 1.106 (16.00), 1.275 (5.58), 1.292 (5.58), 1.844 (1.20), 2.031 (1.37), 2.052 (1.58), 2.061 (1.20), 2.099 (1.64), 2.121 (1.76), 2.294 (1.37), 3.272 (1.16), 3.294 (2.80), 3.307 (2.44), 3.316 (2.70), 3.427 (2.13), 3.444 (2.65), 4.193 (1.58), 7.172 (3.11), 7.923 (1.46), 7.928 (1.40), 7.945 (1.32), 7.949 (1.27), 8.268 (2.47), 8.282 (2.34), 9.014 (3.78), 9.017 (3.69).

Example 30.03.02.B $^1$H-NMR (400 MHz, DMSO-d6) δ[ppm]: 0.967 (0.76), 1.107 (16.00), 1.144 (0.52), 1.230 (1.08), 1.258 (0.84), 1.276 (10.31), 1.293 (10.47), 1.693 (1.16), 1.707 (1.00), 1.717 (1.40), 1.728 (0.84), 1.741 (0.68), 1.823 (1.12), 1.845 (2.21), 1.850 (1.04), 1.867 (1.72), 1.872 (1.68), 1.889 (0.84), 1.894 (1.08), 2.031 (2.57), 2.040 (1.88), 2.047 (1.88), 2.053 (2.97), 2.062 (2.29), 2.076 (2.01), 2.083 (1.64), 2.100 (3.09), 2.121 (3.29), 2.150 (1.72), 2.282 (2.33), 2.296 (2.57), 2.310 (2.37), 2.323 (1.64), 2.327 (1.48), 2.331 (1.00), 2.361 (1.56), 2.376 (1.52), 2.399 (1.88), 2.413 (1.52), 2.523 (2.93), 2.665 (0.80), 2.669 (1.08), 2.673 (0.72), 3.273 (2.29), 3.294 (5.37), 3.307 (4.81), 3.318 (5.29), 3.410 (1.20), 3.428 (3.93), 3.445 (4.93), 4.194 (1.48), 6.952 (2.17), 6.964 (2.17), 7.172 (5.73), 7.420 (0.84), 7.441 (0.88), 7.883 (1.48), 7.924 (2.73), 7.945 (2.41), 7.994 (1.00), 8.201 (1.04), 8.269 (4.53), 8.282 (4.33), 8.395 (1.40), 9.014 (7.14), 9.017 (6.78), 10.759 (1.44), 12.278 (1.08), 12.321 (1.48).

Example 30.03.03.A cyclopropyl{4-[(1R or 1S)-1-(2-{[6-(6-methylpyrimidin-4-yl)-1H-benzimidazol-2-yl]amino}pyridin-4-yl)ethyl]piperazin-1-yl}methanone (single stereoisomer A)

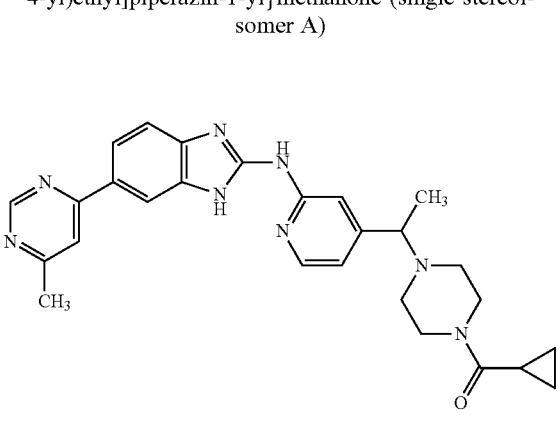

Example 30.03.03.B cyclopropyl{4-[(1S or 1R)-1-(2-{[6-(6-methylpyrimidin-4-yl)-1H-benzimidazol-2-yl]amino}pyridin-4-yl)ethyl]piperazin-1-yl}methanone (single stereoisomer B)

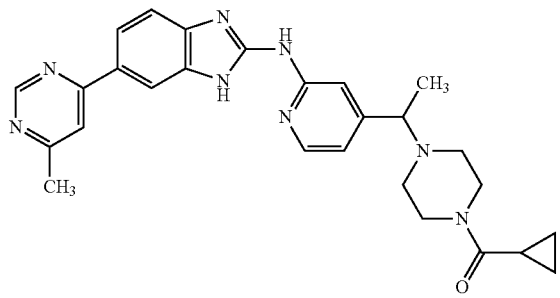

55.4 mg of (rac)-cyclopropyl{4-[1-(2-{[6-(6-methylpyrimidin-4-yl)-1H-benzimidazol-2-yl]amino}pyridin-4-yl)ethyl]piperazin-1-yl}methanone was separated into the single stereoisomers (Example 30.03.03.A and Example 30.03.03.B) via preparative, chiral HPLC.

Instrument: Labomatic HD5000, Labocord-5000; Gilson GX-241, Labcol Vario 4000,

Column: Chiralpak IB 5µ 250×30 mm;

Eluent A: hexane+0.2 Vol-% diethylamine (99%); Eluent B: ethanol; isocratic: 70% A+30% B;

Flow: 30.0 mL/min;

Solution: 55 mg/2.0 mL ethanol

Injection: 4×0.5 mL

Detection: UV 325 nm

| | Retention time in min | purity in % | yield | Optical rotation [α]$_D$ |
|---|---|---|---|---|
| Example 30.03.03.A Stereoisomer A | 12.00-13.55 | 95.2% | 23 mg | −39.5° (from solution in DMSO, c = 2.7 mg/mL) |
| Example 30.03.03.B Stereoisomer B | 13.55-16.00 | 93.3% | 22 mg | +35.4° (from solution in DMSO, c = 3.2 mg/mL) |

Example 30.03.03.A $^1$H-NMR (400 MHz, DMSO-d6) δ[ppm]: 0.657 (1.82), 0.665 (4.32), 0.670 (2.73), 0.677 (2.20), 0.684 (5.57), 0.691 (5.31), 0.699 (4.32), 0.703 (4.97), 0.710 (2.35), 1.106 (16.00), 1.230 (1.40), 1.295 (8.34), 1.312 (8.23), 1.919 (1.02), 1.938 (1.82), 2.318 (1.29), 2.322 (1.67), 2.326 (1.93), 2.332 (1.52), 2.398 (1.59), 2.522 (4.59), 2.664 (2.27), 2.668 (1.71), 2.673 (1.02), 3.455 (3.22), 3.471 (3.91), 3.677 (2.12), 4.195 (1.59), 6.971 (1.74), 7.183 (4.17), 7.884 (1.44), 7.925 (2.12), 7.946 (1.93), 8.278 (3.60), 8.291 (3.22), 8.397 (1.33), 9.015 (5.16), 9.017 (5.35), 10.773 (1.29), 12.326 (1.36).

Example 30.03.03.B $^1$H-NMR (400 MHz, DMSO-d6) δ[ppm]: 0.645 (0.98), 0.657 (2.94), 0.665 (7.35), 0.670 (4.57), 0.677 (3.59), 0.684 (9.63), 0.691 (9.14), 0.699 (7.18), 0.703 (8.33), 0.710 (3.76), 0.723 (0.98), 0.859 (0.49), 0.965 (0.65), 1.052 (0.49), 1.106 (16.00), 1.143 (0.65), 1.153 (0.49), 1.171 (0.82), 1.189 (0.49), 1.230 (2.94), 1.296 (13.88), 1.312 (14.04), 1.907 (0.82), 1.919 (1.80), 1.926 (1.80), 1.938 (3.10), 1.944 (1.47), 1.950 (1.80), 1.957 (1.63), 1.969 (0.82), 1.986 (1.47), 2.318 (2.12), 2.322 (2.78), 2.327 (3.27), 2.332 (2.61), 2.336 (1.47), 2.397 (2.45), 2.456 (2.45), 2.523 (5.88), 2.660 (0.82), 2.664 (1.96), 2.669 (2.45), 2.673 (1.63), 2.678 (0.82), 3.439 (1.80), 3.455 (5.06), 3.471 (6.20), 3.676 (3.43), 4.200 (1.47), 6.973 (2.78), 7.181 (6.86), 7.421 (1.31), 7.443 (1.47), 7.582 (0.98), 7.604 (0.98), 7.884 (2.29), 7.925 (3.43), 7.947 (2.94), 7.996 (1.63), 8.201 (1.63), 8.278 (5.71), 8.291 (5.39), 8.397 (2.12), 9.014 (8.65), 9.017 (8.65), 10.747 (1.47), 10.771 (1.96), 12.285 (1.47), 12.328 (2.12).

Example 31.01

1-{4-[(2-{[6-(2,6-dimethylpyrimidin-4-yl)-1H-benzimidazol-2-yl]amino}pyridin-4-yl)methyl]piperazin-1-yl}-3,3,3-trifluoropropan-1-one

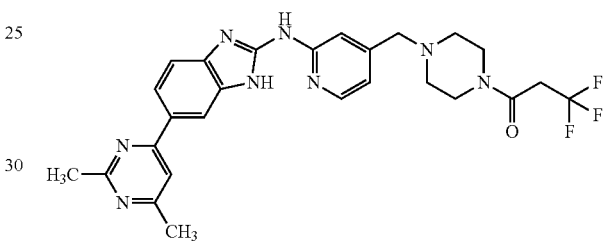

Starting with crude 6-(2,6-dimethylpyrimidin-4-yl)-N-[4-(piperazin-1-ylmethyl)pyridin-2-yl]-1H-benzimidazol-2-amine hydrochloride (150 mg, approx. 176 µmol) and 3,3,3-trifluoropropanoic acid (24 µl, 98% purity, 260 µmol), Example 31.01 was prepared analogously to the procedure for the preparation of Example 05.01.

Yield: 30 mg of the title compound.

LC-MS (Method 2): R$_t$=1.04 min; MS (ESIpos): m/z=525 [M+H]$^+$.

$^1$H-NMR (400 MHz, DMSO-d$_6$): δ [ppm]=2.35-2.44 (m, 4H), 2.46 (s, 3H), 2.62 (s, 3H), 3.45-3.55 (m, 6H), 3.65 (q, 2H), 7.19 (s, 1H), 7.33-7.82 (m, 2H), 7.91 (dd, 1H), 8.27 (d, 2H), 10.78 (br s, 1H), 12.17-12.42 (m, 1H).

Example 31.02 cyclopropyl{4-[(2-{[6-(2,6-dimethylpyrimidin-4-yl)-1H-benzimidazol-2-yl]amino}pyridin-4-yl)methyl]piperazin-1-yl}methanone

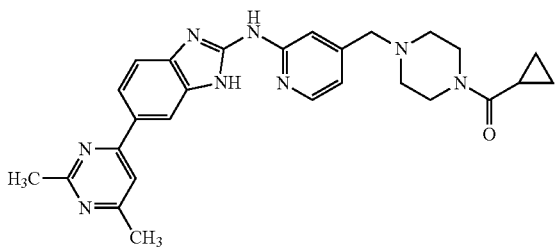 [SMILES: Cc1cc(-c2ccc3nc(Nc4cc(CN5CCN(C(=O)C6CC6)CC5)ccn4)[nH]c3c2)nc(C)n1]

Starting with crude 6-(2,6-dimethylpyrimidin-4-yl)-N-[4-(piperazin-1-ylmethyl)pyridin-2-yl]-1H-benzimidazol-2-amine hydrochloride (150 mg, approx. 176 μmol) and cyclopropanecarboxylic acid (22 μl, 95% purity, 260 μmol), Example 31.02 was prepared analogously to the procedure for the preparation of Example 01.02.

Yield: 75 mg of the title compound.

LC-MS (Method 2): $R_t$=1.00 min; MS (ESIneg): m/z=481 [M−H]$^+$.

$^1$H-NMR (400 MHz, DMSO-d6): δ [ppm]=0.63-0.73 (m, 4H), 1.93 (tt, 1H), 2.44 (s, 7H), 2.59 (s, 3H), 3.50 (s, 4H), 3.68 (br s, 2H), 6.93 (d, 1H), 7.17 (s, 1H), 7.31-7.80 (m, 2H), 7.89 (dd, 1H), 8.25 (d, 2H), 10.63-10.88 (m, 1H), 12.15-12.41 (m, 1H).

Example 32.01 cyclopropyl{4-[(2-{[6-(5,6-dimethylpyrimidin-4-yl)-1H-benzimidazol-2-yl]amino}pyridin-4-yl)methyl]piperazin-1-yl}methanone

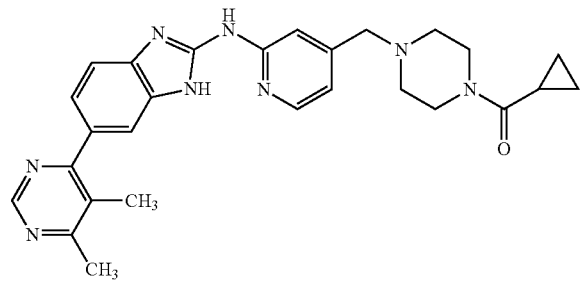 [SMILES: Cc1ncnc(-c2ccc3nc(Nc4cc(CN5CCN(C(=O)C6CC6)CC5)ccn4)[nH]c3c2)c1C]

Starting with crude 6-(5,6-dimethylpyrimidin-4-yl)-N-[4-(piperazin-1-ylmethyl)pyridin-2-yl]-1H-benzimidazol-2-amine hydrochloride (90.0 mg, approx. 200 μmol) and cyclopropanecarboxylic acid (25 μl, 95% purity, 300 μmol), Example 32.01 was prepared analogously to the procedure for the preparation of Example 01.02.

Yield: 30 mg of the title compound.

LC-MS (Method 2): $R_t$=0.97 min; MS (ESIpos): m/z=483 [M+H]$^+$.

$^1$H-NMR (400 MHz, DMSO-d$_6$): δ [ppm]=0.66-0.75 (m, 4H), 1.97 (tt, 1H), 2.31-2.39 (m, 5H), 2.41-2.47 (m, 2H), 2.52-2.54 (m, 3H), 3.44-3.58 (m, 4H), 3.61-3.76 (m, 2H), 6.95 (dd, 1H), 7.14-7.90 (m, 4H), 8.28 (d, 1H), 8.86 (s, 1H), 10.61-10.79 (m, 1H), 12.15-12.33 (m, 1H).

Example 32.02

1-{4-[(2-{[6-(5,6-dimethylpyrimidin-4-yl)-1H-benzimidazol-2-yl]amino}pyridin-4-yl)methyl]piperazin-1-yl}-3,3,3-trifluoropropan-1-one

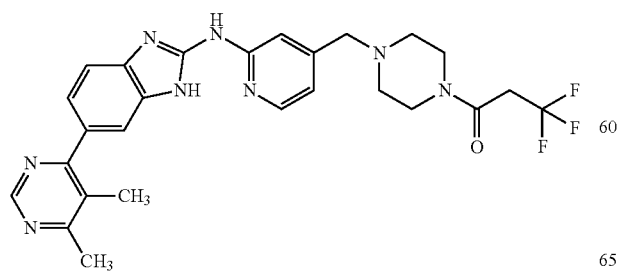

Starting with crude 6-(5,6-dimethylpyrimidin-4-yl)-N-[4-(piperazin-1-ylmethyl)pyridin-2-yl]-1H-benzimidazol-2-amine hydrochloride (90.0 mg, approx. 200 μmol) and 3,3,3-trifluoropropanoic acid (27 μl, 98% purity, 300 μmol), Example 32.02 was prepared analogously to the procedure for the preparation of Example 01.02.

Yield: 30 mg of the title compound.

LC-MS (Method 2): $R_t$=1.01 min; MS (ESIpos): m/z=525 [M+H]$^+$.

$^1$H-NMR (400 MHz, DMSO-d$_6$): δ [ppm]=2.31-2.45 (m, 7H), 2.52 (s, 3H), 3.42-3.58 (m, 6H), 3.65 (q, 2H), 6.94 (dd, 1H), 7.13-7.84 (m, 4H), 8.28 (d, 1H), 8.87 (s, 1H), 10.70 (br dd, 1H), 12.23 (br s, 1H).

Example 32.03

1-{4-[(2-{[6-(5,6-dimethylpyrimidin-4-yl)-1H-benzimidazol-2-yl]amino}pyridin-4-yl)methyl]piperazin-1-yl}ethanone

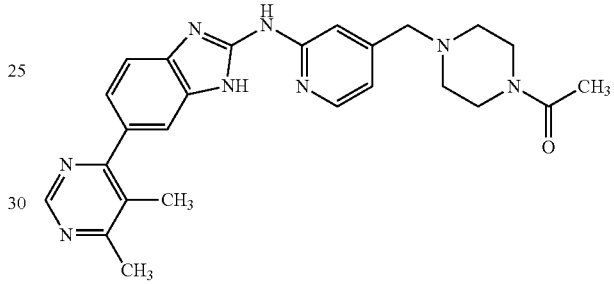

Starting with crude 6-(5,6-dimethylpyrimidin-4-yl)-N-[4-(piperazin-1-ylmethyl)pyridin-2-yl]-1H-benzimidazol-2-amine hydrochloride (90.0 mg, approx. 200 μmol) and acetic acid (17 μl, 300 μmol), Example 32.03 was prepared analogously to the procedure for the preparation of Example 01.02.

Yield: 30 mg of the title compound.

LC-MS (Method 2): $R_t$=0.89 min; MS (ESIpos): m/z=457 [M+H]$^+$.

$^1$H-NMR (400 MHz, DMSO-d$_6$): δ [ppm]=1.99 (s, 3H), 2.31-2.43 (m, 7H), 2.52-2.54 (m, 3H), 3.42-3.53 (m, 6H), 6.94 (dd, 1H), 7.12-7.86 (m, 4H), 8.27 (d, 1H), 8.87 (s, 1H), 10.71 (br s, 1H), 12.23 (s, 1H).

Example 33.01 tert-butyl 4-[(2-{[6-(2,5-dimethylpyrimidin-4-yl)-1H-benzimidazol-2-yl]amino}pyridin-4-yl)methyl]piperazine-1-carboxylate

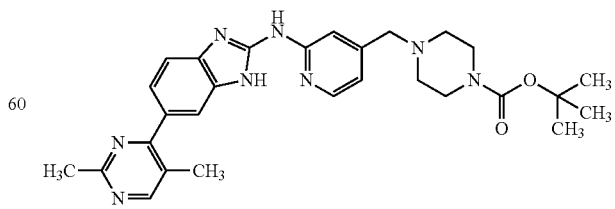

To a stirred solution of tert-butyl 4-[(2-{[6-(4,4,5,5-tetramethyl-1,3,2-dioxaborolan-2-yl)-1H-benzimidazol-2-yl]

amino}pyridin-4-yl)methyl]piperazine-1-carboxylate (600 mg, 1.12 mmol) in 1-propanol (12 mL) was added an aqueous potassium carbonate solution (1.7 mL, 2.0 M, 3.4 mmol), 4-chloro-2,5-dimethylpyrimidine (320 mg, 2.25 mmol), triphenylphosphine (24.7 mg, 225 µmol) and PdCl$_2$(PPh$_3$)$_2$ (158 mg, 225 µmol). The mixture was heated to 120° C. in a sealed tube for 10 h. The solvent was removed in vacuum. Silicagel chromatography followed by amino-phase-silicagel chromatography gave 390 mg (61% yield) of the title compound.

LC-MS (Method 2): R$_t$=1.20 min; MS (ESIpos): m/z=515 [M+H]$^+$.

$^1$H-NMR (400 MHz, DMSO-d6) δ[ppm]: 1.395 (16.00), 2.347 (1.07), 2.360 (1.81), 2.372 (1.49), 2.615 (4.61), 3.331 (9.11), 3.351 (1.10), 5.759 (12.83), 8.259 (0.79), 8.271 (0.75), 8.550 (1.42).

Example 33.02

1-{4-[(2-{[6-(2,5-dimethylpyrimidin-4-yl)-1H-benzimidazol-2-yl]amino}pyridin-4-yl)methyl]piperazin-1-yl}-3,3,3-trifluoropropan-1-one

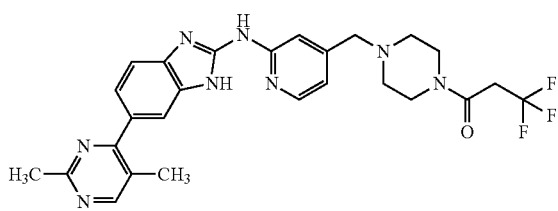 [SMILES: Cc1ncc(C)c(-c2ccc3nc(Nc4cc(CN5CCN(C(=O)CC(F)(F)F)CC5)ccn4)[nH]c3c2)n1]

Starting with crude 6-(2,5-dimethylpyrimidin-4-yl)-N-[4-(piperazin-1-ylmethyl)pyridin-2-yl]-1H-benzimidazol-2-amine hydrochloride (100 mg, approx. 177 µmol) and 3,3,3-trifluoropropanoic acid (24 µl, 98% purity, 270 µmol), Example 33.02 was prepared analogously to the procedure for the preparation of Example 05.01.

Yield: 60 mg of the title compound.

LC-MS (Method 2): R$_t$=1.01 min; MS (ESIpos): m/z=525 [M+H]$^+$.

$^1$H-NMR (400 MHz, DMSO-d6) δ[ppm]: 1.394 (16.00), 2.380 (1.31), 2.615 (2.35), 3.528 (0.85), 5.759 (1.28), 8.550 (0.75).

Example 33.03 cyclopropyl{4-[(2-{[6-(2,5-dimethylpyrimidin-4-yl)-1H-benzimidazol-2-yl]amino}pyridin-4-yl)methyl]piperazin-1-yl}methanone

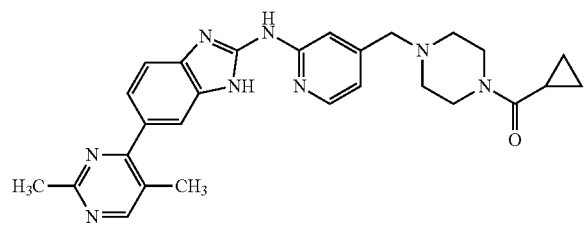 [SMILES: Cc1ncc(C)c(-c2ccc3nc(Nc4cc(CN5CCN(C(=O)C6CC6)CC5)ccn4)[nH]c3c2)n1]

Starting with crude 6-(2,5-dimethylpyrimidin-4-yl)-N-[4-(piperazin-1-ylmethyl)pyridin-2-yl]-1H-benzimidazol-2-amine hydrochloride (100 mg, approx. 177 µmol) and cyclopropanecarboxylic acid (22 µl, 95% purity, 270 µmol), Example 33.03 was prepared analogously to the procedure for the preparation of Example 01.02.

Yield: 45 mg of the title compound.

LC-MS (Method 2): R$_t$=0.97 min; MS (ESIneg): m/z=481 [M−H]$^+$.

$^1$H-NMR (400 MHz, DMSO-d6) δ [ppm]: 0.664 (0.42), 0.676 (1.29), 0.683 (2.96), 0.689 (1.87), 0.696 (1.42), 0.703 (3.63), 0.708 (2.98), 0.713 (3.17), 0.720 (3.05), 0.726 (3.64), 0.733 (1.66), 0.745 (0.41), 1.945 (0.74), 1.952 (0.77), 1.956 (0.57), 1.964 (1.34), 1.971 (0.60), 1.976 (0.75), 1.983 (0.68), 2.327 (0.47), 2.386 (3.33), 2.446 (1.39), 2.518 (0.90), 2.523 (0.66), 2.615 (16.00), 3.499 (1.36), 3.523 (6.71), 3.705 (1.28), 6.941 (1.72), 6.944 (1.74), 6.955 (1.75), 6.958 (1.76), 7.197 (2.25), 7.428 (0.63), 7.446 (0.61), 7.894 (0.55), 8.268 (2.73), 8.281 (2.58), 8.549 (4.87), 12.266 (0.76).

Example 33.04 cyclobutyl{4-[(2-{[6-(2,5-dimethylpyrimidin-4-yl)-1H-benzimidazol-2-yl]amino}pyridin-4-yl)methyl]piperazin-1-yl}methanone

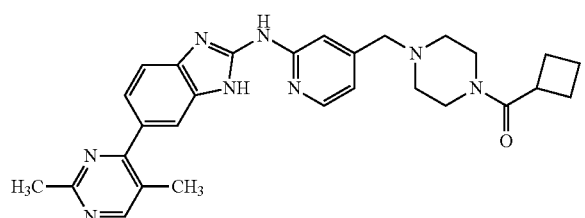

Starting with crude 6-(2,5-dimethylpyrimidin-4-yl)-N-[4-(piperazin-1-ylmethyl)pyridin-2-yl]-1H-benzimidazol-2-amine hydrochloride (100 mg, approx. 177 µmol) and cyclobutanecarboxylic acid (27 µl, 95% purity, 270 µmol), Example 33.04 was prepared analogously to the procedure for the preparation of Example 01.02.

Yield: 41 mg of the title compound.

LC-MS (Method 2): R$_t$=1.04 min; MS (ESIpos): m/z=497 [M+H]$^+$.

$^1$H-NMR (400 MHz, DMSO-d6) δ [ppm]: 1.702 (0.54), 1.705 (0.62), 1.715 (0.51), 1.718 (0.53), 1.729 (0.77), 1.731 (0.72), 1.833 (0.65), 1.855 (1.26), 1.860 (0.56), 1.877 (0.96), 1.881 (0.95), 1.899 (0.47), 1.905 (0.59), 2.036 (0.77), 2.045 (1.39), 2.049 (1.01), 2.054 (1.02), 2.058 (0.88), 2.061 (0.98), 2.067 (1.60), 2.076 (1.24), 2.082 (0.58), 2.088 (0.70), 2.092 (0.76), 2.097 (1.07), 2.102 (0.59), 2.119 (1.81), 2.124 (1.21), 2.140 (1.96), 2.145 (1.51), 2.148 (1.36), 2.164 (0.92), 2.169 (1.04), 2.334 (3.00), 2.346 (4.68), 2.358 (4.00), 2.380 (3.20), 2.613 (16.00), 3.291 (1.04), 3.294 (1.13), 3.315 (2.74), 3.457 (1.44), 3.471 (2.01), 3.491 (6.45), 6.921 (1.76), 6.924 (1.75), 6.934 (1.79), 6.937 (1.75), 7.183 (2.27), 7.432 (0.61), 8.258 (2.84), 8.271 (2.71), 8.545 (4.84), 10.734 (0.58), 12.266 (0.67).

Example 34.01.01 tert-butyl 4-[(2-{[6-(6-methoxypyrimidin-4-yl)-1H-benzimidazol-2-yl]amino}pyridin-4-yl)methyl]piperazine-1-carboxylate

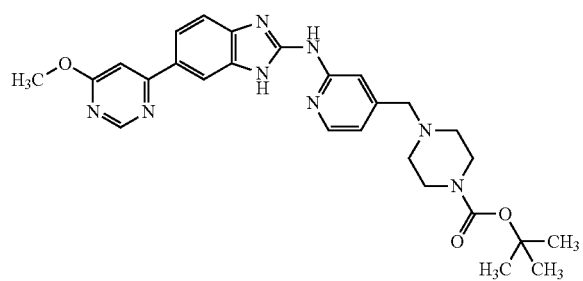 [SMILES: COc1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol) and 4-chloro-6-methoxypyrimidine (189 mg, 1.31 mmol), Example 34.01.01 was prepared analogously to the procedure for the preparation of Example 01.01.

Yield: 20.0 mg (4%) of the title compound.
LC-MS (Method 4): $R_t$=1.27 min; MS (ESIpos): m/z=517 [M+H]$^+$.
$^1$H-NMR (400 MHz, CHLOROFORM-d) δ [ppm]: 1.452 (16.00), 4.046 (2.13), 4.059 (3.07), 7.165 (0.74), 7.167 (0.75), 8.850 (0.89), 8.853 (0.81).

Example 34.02.01

(rac)-3,3,3-trifluoro-1-{4-[1-(2-{[6-(6-methoxypyrimidin-4-yl)-1H-benzimidazol-2-yl]amino}pyridin-4-yl)ethyl]piperazin-1-yl}propan-1-one

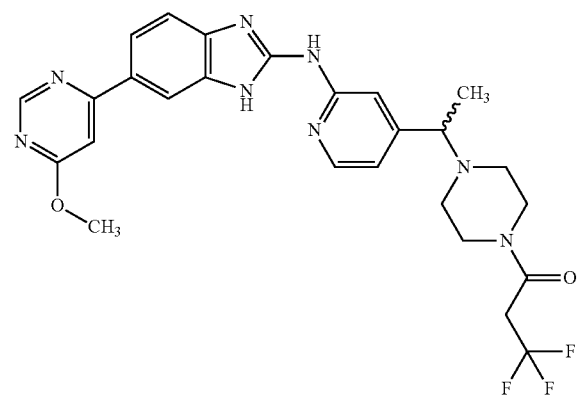 [SMILES: COc1cc(-c2ccc3nc(Nc4cc(C(C)N5CCN(C(=O)CC(F)(F)F)CC5)ccn4)[nH]c3c2)ncn1]

Starting with (rac)-6-(6-methoxypyrimidin-4-yl)-N-{4-[1-(piperazin-1-yl)ethyl]pyridin-2-yl}-1H-benzimidazol-2-amine (265 mg, 616 µmol) and 3,3,3-trifluoropropanoic acid (118 mg, 923 µmol), Example 34.02.01 was prepared analogously to the procedure for the preparation of Example 01.02.

Yield: 46.5 mg (13%) of the title compound.
LC-MS (Method 4): $R_t$=1.12 min; MS (ESIpos): m/z=541 [M+H]$^+$.

$^1$H-NMR (400 MHz, DMSO-d6) δ[ppm]: 1.291 (4.49), 1.308 (4.44), 2.326 (1.50), 2.428 (2.35), 2.522 (3.91), 3.436 (2.38), 3.469 (2.52), 3.485 (2.60), 3.608 (2.32), 3.635 (2.21), 3.969 (16.00), 7.174 (1.86), 8.274 (1.92), 8.288 (1.90), 8.803 (4.06), 8.806 (4.26).

Example 34.02.02

(rac)-cyclopropyl{4-[1-(2-{[6-(6-methoxypyrimidin-4-yl)-1H-benzimidazol-2-yl]amino}pyridin-4-yl)ethyl]piperazin-1-yl}methanone

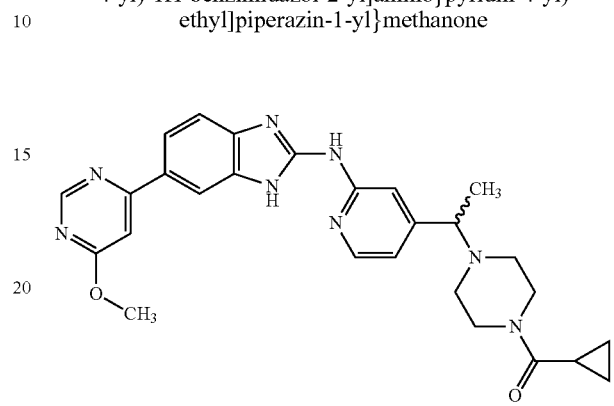

Starting with (rac)-6-(6-methoxypyrimidin-4-yl)-N-{4-[1-(piperazin-1-yl)ethyl]pyridin-2-yl}-1H-benzimidazol-2-amine (265 mg, 616 µmol) and cyclopropanecarboxylic acid (79.5 mg, 923 µmol), Example 34.02.02 was prepared analogously to the procedure for the preparation of Example 01.02.

Yield: 49.7 mg (16%) of the title compound.
LC-MS (Method 4): $R_t$=1.08 min; MS (ESIpos): m/z=499 [M+H]$^+$.
$^1$H-NMR (400 MHz, DMSO-d6) δ[ppm]: 0.656 (1.28), 0.662 (2.84), 0.667 (1.82), 0.675 (1.49), 0.682 (3.47), 0.686 (3.09), 0.691 (3.24), 0.698 (2.91), 0.703 (3.24), 0.710 (1.53), 1.293 (5.37), 1.310 (5.33), 1.934 (1.19), 3.451 (2.02), 3.468 (2.58), 3.674 (1.41), 3.970 (16.00), 6.963 (1.27), 6.975 (1.31), 7.182 (2.78), 8.275 (2.36), 8.289 (2.26), 8.803 (3.94), 8.806 (4.22).

Example 34.03.01.A 3,3,3-trifluoro-1-{4-[(1R or 1S)-1-(2-{[6-(6-methoxypyrimidin-4-yl)-1H-benzimidazol-2-yl]amino}pyridin-4-yl)ethyl]piperazin-1-yl}propan-1-one (single stereoisomer A)

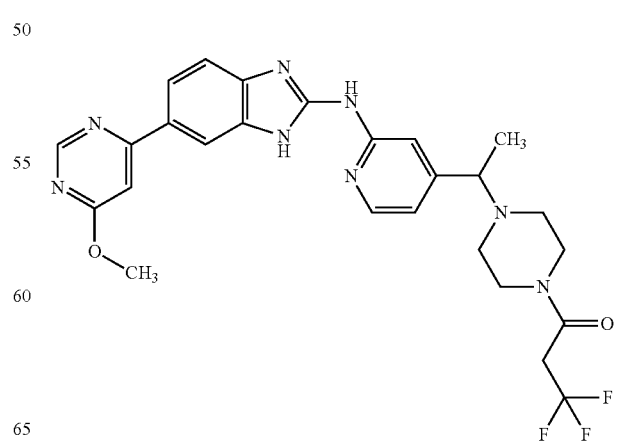

Example 34.03.01.B 3,3,3-trifluoro-1-{4-[(1S or 1R)-1-(2-{[6-(6-methoxypyrimidin-4-yl)-1H-benzimidazol-2-yl]amino}pyridin-4-yl)ethyl]piperazin-1-yl}propan-1-one (single stereoisomer B)

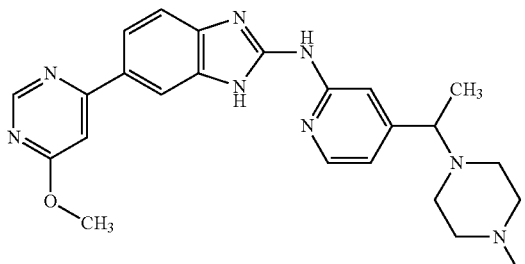

60 mg of (rac)-3,3,3-trifluoro-1-{4-[1-(2-{[6-(6-methoxypyrimidin-4-yl)-1H-benzimidazol-2-yl]amino}pyridin-4-yl)ethyl]piperazin-1-yl}propan-1-one was separated into the single stereoisomers (Example 34.03.01.A and Example 34.03.01.B) via preparative, chiral HPLC.

Instrument: Labomatic HD5000, Labocord-5000; Gilson GX-241, Labcol Vario 4000,
Column: Chiralpak IB 5μ 250×30 mm;
Eluent A: hexane+0.2 Vol-% diethylamine (99%); Eluent B: ethanol; isocratic: 80% A+20%;
Flow: 30.0 mL/min;
Solution: 60 mg/3 mL ethanol
Injection: 6×0.5 mL
Detection: UV 325 nm

|  | Retention time in min | purity in % | yield | Optical rotation [α]$_D$ |
|---|---|---|---|---|
| Example 34.03.01.A Stereoisomer A | 10.50-12.10 | >99.0% | 21 mg | −32.0° (from solution in DMSO, c = 2.6 mg/mL) |
| Example 34.03.01.B Stereoisomer B | 12.20-14.50 | 98.3% | 16 mg | +32.9° (from solution in DMSO, c = 2.7 mg/mL) |

Example 34.03.01.A $^1$H-NMR (400 MHz, DMSO-d6) δ [ppm]: 1.107 (6.75), 1.292 (4.60), 1.309 (4.65), 2.327 (1.36), 2.429 (1.26), 2.523 (1.69), 3.436 (2.22), 3.469 (2.24), 3.486 (2.31), 3.581 (0.86), 3.608 (2.42), 3.636 (2.28), 3.970 (16.00), 6.970 (1.02), 7.173 (1.94), 8.275 (2.02), 8.288 (1.93), 8.804 (4.35), 8.806 (4.43).

Example 34.03.01.B $^1$H-NMR (400 MHz, DMSO-d6) δ[ppm]: 0.966 (0.46), 1.107 (6.66), 1.230 (1.08), 1.291 (6.24), 1.308 (6.30), 2.328 (1.87), 2.342 (1.91), 2.364 (1.57), 2.418 (2.09), 2.427 (2.34), 2.456 (1.79), 3.436 (3.72), 3.468 (3.89), 3.484 (4.40), 3.581 (1.18), 3.608 (3.20), 3.635 (3.10), 3.663 (1.06), 3.969 (16.00), 4.195 (0.70), 6.956 (1.72), 6.968 (1.77), 7.174 (3.09), 7.346 (0.99), 7.421 (0.76), 7.458 (0.74), 7.912 (1.21), 8.192 (0.64), 8.275 (2.68), 8.288 (2.61), 8.358 (0.92), 8.804 (4.71), 8.806 (4.80), 10.759 (0.94), 12.271 (0.83), 12.300 (1.12).

Example 34.03.02.A cyclopropyl{4-[(1R or 1S)-1-(2-{[6-(6-methoxypyrimidin-4-yl)-1H-benzimidazol-2-yl]amino}pyridin-4-yl)ethyl]piperazin-1-yl}methanone (single stereoisomer A)

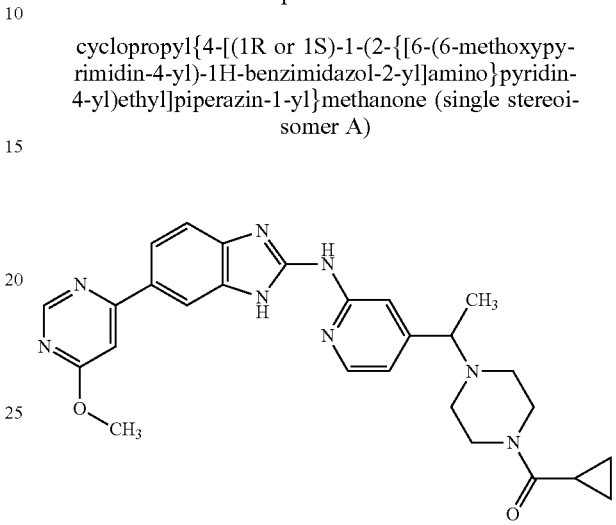

Example 34.03.02.B cyclopropyl{4-[(1S or 1R)-1-(2-{[6-(6-methoxypyrimidin-4-yl)-1H-benzimidazol-2-yl]amino}pyridin-4-yl)ethyl]piperazin-1-yl}methanone (single stereoisomer B)

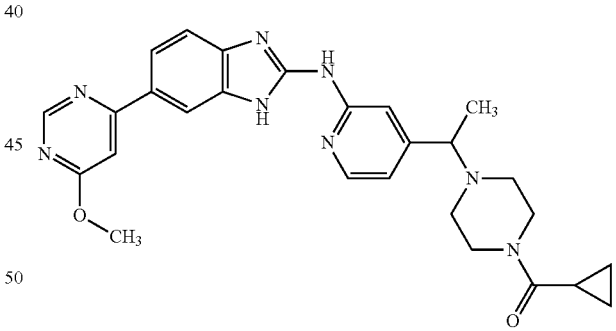

44.7 mg of (rac)-cyclopropyl{4-[1-(2-{[6-(6-methoxypyrimidin-4-yl)-1H-benzimidazol-2-yl]amino}pyridin-4-yl)ethyl]piperazin-1-yl}methanone was separated into the single stereoisomers (Example 34.03.02.A and Example 34.03.02.B) via preparative, chiral HPLC.

Instrument: Labomatic HD5000, Labocord-5000; Gilson GX-241, Labcol Vario 4000,
Column: Chiralpak IA 5μ 250×30 mm;
Eluent A: tert.-butyl methyl ether+0.1 Vol-% diethylamine (99%); Eluent B: methanol; isocratic: 50% A+50% B;
Flow: 50.0 mL/min;
Solution: 44 mg/2 mL dichloromethane/methanol 1:1
Injection: 4×0.5 mL
Detection: UV 325 nm

| | Retention time in min | purity in % | yield | Optical rotation [α]$_D$ |
|---|---|---|---|---|
| Example 34.03.02.A Stereoisomer A | 7.50-8.50 | 99.1% | 15 mg | +42.2° (from solution in DMSO. c = 2.6 mg/mL) |
| Example 34.03.02.B Stereoisomer B | 9.00-12.50 | 98.7% | 7 mg | −43.7° (from solution in DMSO, c = 2.8 mg/mL) |

Example 34.03.02.A $^1$H-NMR (400 MHz, DMSO-d6) δ[ppm]: 0.658 (1.04), 0.665 (2.54), 0.670 (1.53), 0.678 (1.21), 0.685 (3.23), 0.692 (3.06), 0.699 (2.48), 0.704 (2.77), 0.711 (1.24), 1.108 (3.85), 1.231 (1.17), 1.296 (4.89), 1.313 (4.86), 1.938 (1.08), 2.323 (1.17), 2.327 (1.43), 2.331 (1.08), 2.523 (2.15), 2.669 (1.04), 3.455 (1.73), 3.471 (2.15), 3.678 (1.14), 3.970 (16.00), 7.181 (2.15), 7.344 (0.95), 8.276 (1.76), 8.289 (1.69), 8.803 (4.07), 8.806 (4.07).

Example 34.03.02.B $^1$H-NMR (400 MHz, DMSO-d6) δ [ppm]: 0.666 (3.17), 0.685 (4.42), 0.692 (4.20), 0.704 (3.66), 0.711 (1.74), 0.851 (0.49), 1.108 (3.44), 1.153 (0.54), 1.232 (2.55), 1.296 (6.12), 1.314 (5.99), 1.919 (0.80), 1.926 (0.85), 1.938 (1.30), 1.950 (0.80), 2.323 (2.23), 2.327 (2.68), 2.331 (2.10), 2.397 (1.34), 2.523 (8.13), 2.665 (1.65), 2.669 (2.15), 2.673 (1.65), 3.455 (2.46), 3.473 (2.99), 3.676 (1.74), 3.971 (16.00), 6.971 (1.52), 7.182 (2.68), 7.344 (1.52), 7.399 (0.80), 7.421 (0.89), 7.458 (1.07), 7.562 (0.54), 7.583 (0.58), 7.893 (0.63), 7.913 (1.30), 7.934 (0.76), 8.187 (0.98), 8.276 (2.06), 8.289 (2.01), 8.357 (1.30), 8.804 (4.87), 10.715 (0.80), 10.755 (1.16), 12.266 (0.89), 12.301 (1.30).

Example 35.01.01

3,3,3-trifluoro-1-{4-[(2-{[6-(5-methoxypyrimidin-4-yl)-1H-benzimidazol-2-yl]amino}pyridin-4-yl)methyl]piperazin-1-yl}propan-1-one

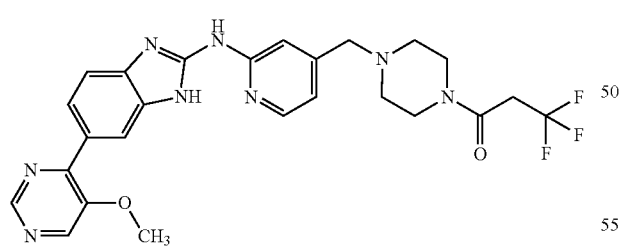

Starting with 6-(5-methoxypyrimidin-4-yl)-N-[4-(piperazin-1-ylmethyl)pyridin-2-yl]-1H-benzimidazol-2-amine (85.0 mg, 204 μmol) and 3,3,3-trifluoropropanoic acid (27 μl, 310 μmol), Example 35.01.01 was prepared analogously to the procedure for the preparation of Example 05.01.
Yield: 40.0 mg (34%) of the title compound.
LC-MS (Method 2): R$_t$=0.99 min; MS (ESIpos): m/z=527 [M+H]$^+$.
$^1$H-NMR (400 MHz, DMSO-d6) δ[ppm]: 1.394 (16.00), 2.374 (1.24), 2.387 (1.87), 2.399 (1.43), 2.415 (1.38), 2.428 (1.82), 2.439 (1.33), 3.462 (1.34), 3.475 (1.85), 3.487 (1.51), 3.499 (1.48), 3.513 (1.97), 3.528 (5.59), 3.607 (0.88), 3.634 (2.53), 3.661 (2.38), 4.023 (8.76), 5.755 (0.72), 6.939 (1.32), 6.952 (1.32), 7.196 (1.78), 8.271 (2.12), 8.284 (2.03), 8.631 (4.78), 8.828 (4.15).

Example 35.01.02 cyclopropyl{4-[(2-{[6-(5-methoxypyrimidin-4-yl)-1H-benzimidazol-2-yl]amino}pyridin-4-yl)methyl]piperazin-1-yl}methanone

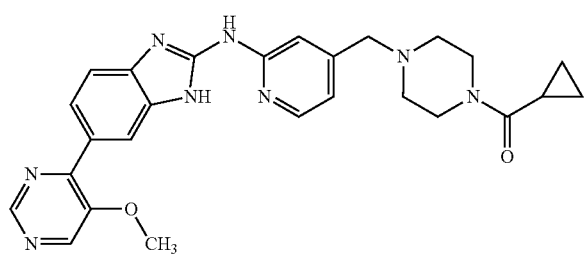 [SMILES: COc1cncnc1-c1ccc2nc(Nc3cc(CN4CCN(C(=O)C5CC5)CC4)ccn3)[nH]c2c1]

Starting with 6-(5-methoxypyrimidin-4-yl)-N-[4-(piperazin-1-ylmethyl)pyridin-2-yl]-1H-benzimidazol-2-amine (85.0 mg, 204 μmol) and cyclopropanecarboxylic acid (24 μl, 310 μmol), Example 35.01.02 was prepared analogously to the procedure for the preparation of Example 05.01.
Yield: 16.0 mg (16%) of the title compound.
LC-MS (Method 2): R$_t$=0.98 min; MS (ESIpos): m/z=485 [M+H]$^+$.
$^1$H-NMR (400 MHz, DMSO-d6) δ [ppm]: 0.685 (2.55), 0.704 (3.12), 0.708 (2.97), 0.713 (3.01), 0.721 (2.74), 0.726 (2.99), 1.394 (16.00), 1.967 (1.06), 2.374 (1.42), 3.527 (4.21), 3.708 (1.34), 4.022 (10.40), 6.948 (1.47), 6.961 (1.50), 7.196 (1.94), 8.274 (2.09), 8.286 (2.02), 8.633 (4.64), 8.829 (4.41).

Example 35.01.03

4-[(2-{[6-(5-methoxypyrimidin-4-yl)-1H-benzimidazol-2-yl]amino}pyridin-4-yl)methyl]-N,N-dimethylpiperazine-1-carboxamide

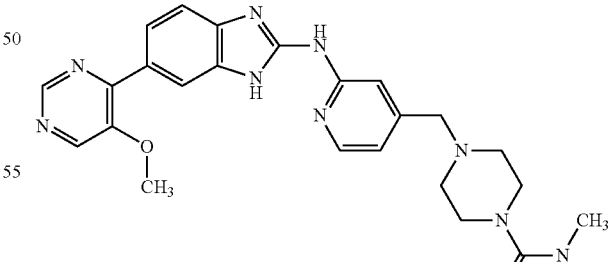

To a stirred solution of crude 6-(5-methoxypyrimidin-4-yl)-N-[4-(piperazin-1-ylmethyl)pyridin-2-yl]-1H-benzimidazol-2-amine hydrochloride (150 mg, approx. 216 μmol) in dichloromethane (3.0 mL, 47 mmol) was added DIPEA (1.0 mL, 5.7 mmol) and dimethylcarbamic chloride (CAS-RN: 79-44-7) (20 μl, 220 μmol). The mixture was stirred at r.t. for 14 h. Water was added and the mixture was extracted with dichloromethane. The organic phase was dried (sodium sulfate) and the solvent was removed in vacuum. Preparative reverse phase HPLC (gradient of water and acetonitrile containing ammonia as additive) gave 57.0 mg of the title compound.

LC-MS (Method 2): $R_t$=0.96 min; MS (ESIpos): m/z=488 [M+H]$^+$.

$^1$H-NMR (400 MHz, DMSO-d6) δ[ppm]: 1.107 (3.40), 2.405 (1.67), 2.416 (1.23), 2.727 (16.00), 3.127 (1.23), 3.140 (1.63), 3.150 (1.19), 3.504 (2.47), 4.024 (2.57), 8.265 (0.85), 8.631 (1.58), 8.827 (1.19).

Example 35.01.04

N,N-diethyl-4-[(2-{[6-(5-methoxypyrimidin-4-yl)-1H-benzimidazol-2-yl]amino}pyridin-4-yl)methyl]piperazine-1-carboxamide

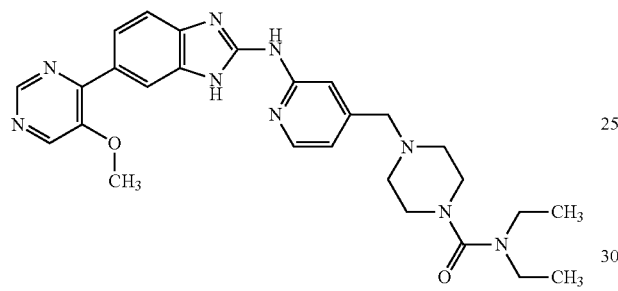

Starting with crude 6-(5-methoxypyrimidin-4-yl)-N-[4-(piperazin-1-ylmethyl)pyridin-2-yl]-1H-benzimidazol-2-amine hydrochloride (150 mg, approx. 216 μmol) and diethylcarbamic chloride (CAS-RN: 88-10-8) (27 μl, 220 μmol), Example 35.01.04 was prepared analogously to the procedure for the preparation of Example 35.01.03.

Yield: 63.0 mg (53%) of the title compound.

LC-MS (Method 2): $R_t$=1.09 min; MS (ESIpos): m/z=516 [M+H]$^+$.

$^1$H-NMR (400 MHz, DMSO-d6) δ[ppm]: 1.014 (3.43), 1.032 (7.93), 1.049 (3.50), 1.107 (16.00), 2.405 (1.69), 3.100 (3.53), 3.118 (4.60), 3.502 (2.01), 4.022 (4.79), 4.194 (1.33), 8.265 (1.14), 8.278 (1.08), 8.632 (2.72), 8.827 (2.45).

Example 35.01.05

{4-[(2-{[6-(5-methoxypyrimidin-4-yl)-1H-benzimidazol-2-yl]amino}pyridin-4-yl)methyl]piperazin-1-yl}(pyrrolidin-1-yl)methanone

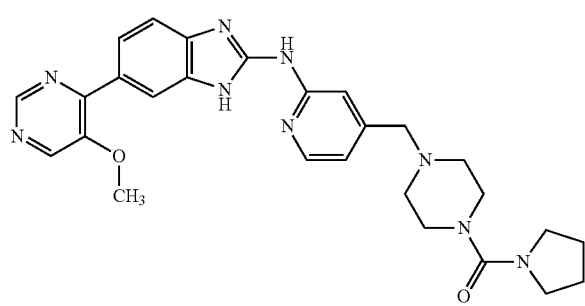 [SMILES: COc1cncnc1-c1ccc2nc(Nc3cc(CN4CCN(C(=O)N5CCCC5)CC4)ccn3)[nH]c2c1]

Starting with crude 6-(5-methoxypyrimidin-4-yl)-N-[4-(piperazin-1-ylmethyl)pyridin-2-yl]-1H-benzimidazol-2-amine hydrochloride (150 mg, approx. 216 μmol) and pyrrolidine-1-carbonyl chloride (CAS-RN: 1192-63-8) (24 μl, 220 μmol), Example 35.01.05 was prepared analogously to the procedure for the preparation of Example 35.01.03.

Yield: 35.0 mg of the title compound.

LC-MS (Method 2): $R_t$=1.03 min; MS (ESIpos): m/z=514 [M+H]$^+$.

$^1$H-NMR (400 MHz, DMSO-d6) δ[ppm]: 1.107 (16.00), 1.715 (4.50), 1.731 (12.03), 1.748 (4.54), 2.322 (1.41), 2.327 (1.98), 2.332 (1.48), 2.401 (8.44), 2.411 (6.18), 2.518 (7.43), 2.523 (4.94), 2.664 (1.38), 2.669 (1.98), 2.673 (1.41), 3.193 (8.00), 3.232 (5.24), 3.249 (13.04), 3.265 (4.71), 3.502 (11.66), 4.022 (15.70), 4.194 (1.55), 6.932 (2.92), 6.946 (2.96), 7.180 (2.72), 8.265 (4.61), 8.278 (4.40), 8.375 (1.38), 8.632 (9.24), 8.827 (7.60).

Example 35.01.06

{4-[(2-{[6-(5-methoxypyrimidin-4-yl)-1H-benzimidazol-2-yl]amino}pyridin-4-yl)methyl]piperazin-1-yl}(piperidin-1-yl)methanone

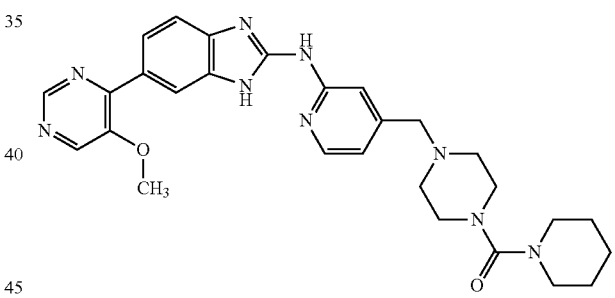

Starting with crude 6-(5-methoxypyrimidin-4-yl)-N-[4-(piperazin-1-ylmethyl)pyridin-2-yl]-1H-benzimidazol-2-amine hydrochloride (150 mg, approx. 216 μmol) and piperidine-1-carbonyl chloride (CAS-RN: 13939-69-0) (27 μl, 220 μmol), Example 35.01.06 was prepared analogously to the procedure for the preparation of Example 35.01.03.

Yield: 75.0 mg of the title compound.

LC-MS (Method 2): $R_t$=1.10 min; MS (ESIpos): m/z=528 [M+H]$^+$.

$^1$H-NMR (400 MHz, DMSO-d6) δ [ppm]: 1.107 (16.00), 1.461 (2.28), 2.396 (2.77), 2.518 (3.17), 2.523 (2.07), 3.100 (3.12), 3.112 (2.31), 3.148 (2.72), 3.501 (3.90), 4.024 (4.49), 4.194 (1.51), 8.264 (1.42), 8.276 (1.34), 8.631 (2.63), 8.827 (2.07).

Example 35.01.07

{4-[(2-{[6-(5-methoxypyrimidin-4-yl)-1H-benzimidazol-2-yl]amino}pyridin-4-yl)methyl]piperazin-1-yl}(morpholin-4-yl)methanone

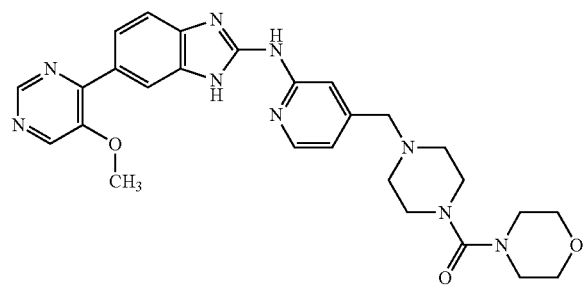 [SMILES: COc1cncnc1-c1ccc2nc(Nc3cc(CN4CCN(C(=O)N5CCOCC5)CC4)ccn3)[nH]c2c1]

To a stirred solution of crude 6-(5-methoxypyrimidin-4-yl)-N-[4-(piperazin-1-ylmethyl)pyridin-2-yl]-1H-benzimidazol-2-amine hydrochloride (200 mg, approx. 288 µmol) in dichloromethane (4.0 mL, 62 mmol) was added pyridine (1.0 mL, 12 mmol) and morpholine-4-carbonyl chloride (CAS-RN: 15159-40-7) (43 µl, 370 µmol). The mixture was stirred at r.t. for 14 h. Further pyridine (1.0 mL, 12 mmol) and morpholine-4-carbonyl chloride (43 µl, 370 µmol) were added and the mixture was stirred at reflux for 14 h. Further morpholine-4-carbonyl chloride (43 µl, 370 µmol) and DIPEA (0.5 mL) were added and the mixture was stirred at reflux for 14 h. Sodium bicarbonate solution was added and the mixture was extracted with dichloromethane. The organic phase was dried (sodium sulfate) and the solvent was removed in vacuum. Aminophase-silicagel chromatography followed by preparative reverse phase HPLC (gradient of water and acetonitrile containing ammonia as additive) gave 15.0 mg of the title compound.

LC-MS (Method 2): $R_t$=0.94 min; MS (ESIpos): m/z=530 [M+H]$^+$.

$^1$H-NMR (400 MHz, DMSO-d6) δ[ppm]: 1.107 (3.48), 2.318 (1.81), 2.322 (3.90), 2.327 (5.57), 2.332 (4.03), 2.336 (1.81), 2.397 (6.40), 2.518 (16.00), 2.523 (11.55), 2.660 (1.67), 2.665 (4.03), 2.669 (5.70), 2.673 (3.90), 2.679 (1.67), 3.109 (5.84), 3.120 (8.07), 3.131 (6.26), 3.200 (6.26), 3.313 (4.17), 3.506 (9.46), 3.539 (7.10), 3.552 (8.21), 3.562 (6.12), 4.022 (13.08), 6.928 (2.23), 6.942 (2.37), 7.182 (1.67), 8.264 (3.62), 8.276 (3.34), 8.371 (1.11), 8.631 (8.07), 8.827 (6.54).

Example 35.01.08

N-(4-{[4-(ethylsulfonyl)piperazin-1-yl]methyl}pyridin-2-yl)-6-(5-methoxypyrimidin-4-yl)-1H-benzimidazol-2-amine

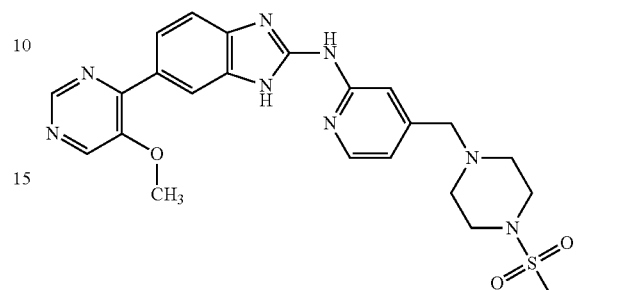

Starting with crude 6-(5-methoxypyrimidin-4-yl)-N-[4-(piperazin-1-ylmethyl)pyridin-2-yl]-1H-benzimidazol-2-amine hydrochloride (130 mg, approx. 187 µmol) and ethanesulfonyl chloride (CAS-RN: 594-44-5) (18 µl, 190 µmol), Example 35.01.08 was prepared analogously to the procedure for the preparation of Example 35.01.03.

Yield: 44.0 mg of the title compound.

LC-MS (Method 4): $R_t$=0.96 min; MS (ESIpos): m/z=509 [M+H]$^+$.

$^1$H-NMR (400 MHz, DMSO-d6) δ[ppm]: 1.200 (6.97), 1.218 (16.00), 1.237 (7.23), 2.327 (0.91), 2.518 (3.79), 2.523 (2.66), 2.539 (0.97), 2.669 (0.90), 3.046 (2.14), 3.065 (6.94), 3.083 (6.76), 3.102 (1.97), 3.203 (4.71), 3.215 (6.51), 3.226 (4.64), 3.545 (9.43), 4.022 (13.11), 6.935 (2.26), 6.947 (2.31), 7.179 (1.80), 8.269 (3.54), 8.282 (3.37), 8.375 (1.04), 8.632 (7.01), 8.828 (5.89), 12.284 (1.19).

Example 35.01.09

6-(5-methoxypyrimidin-4-yl)-N-[4-({4-[(3,3,3-trifluoropropyl)sulfonyl]piperazin-1-yl}methyl)pyridin-2-yl]-1H-benzimidazol-2-amine

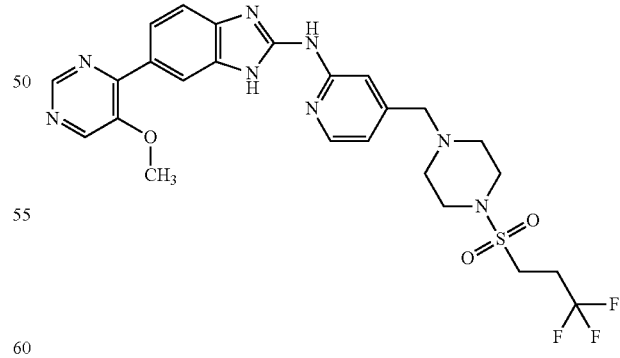

To a stirred solution of crude 6-(5-methoxypyrimidin-4-yl)-N-[4-(piperazin-1-ylmethyl)pyridin-2-yl]-1H-benzimidazol-2-amine hydrochloride (130 mg, approx. 187 µmol) in dichloromethane was added DIPEA and 3,3,3-trifluoropropane-1-sulfonyl chloride (CAS-RN: 845866-80-0) (24 µl, 190 µmol). The mixture was stirred at r.t. for 14 h. Further 3,3,3-trifluoropropane-1-sulfonyl chloride (12 µl, 95 µmol) was added and the mixture was heated to reflux for 6 h. Water was added and the mixture was extracted with dichloromethane. The organic phase was dried (sodium sulfate) and the solvent was removed in vacuum. Preparative reverse phase HPLC (gradient of water and acetonitrile containing ammonia as additive) gave 28.0 mg of the title compound.

LC-MS (Method 4): $R_t$=1.09 min; MS (ESIpos): m/z=577 [M+H]$^+$.

$^1$H-NMR (400 MHz, DMSO-d6) δ[ppm]: 1.065 (0.70), 2.322 (1.15), 2.327 (1.60), 2.331 (1.23), 2.523 (5.51), 2.651 (0.70), 2.665 (1.70), 2.669 (2.23), 2.673 (2.03), 2.678 (2.50), 2.692 (1.90), 2.698 (2.05), 2.706 (2.68), 2.718 (2.98), 2.725 (2.05), 2.733 (1.70), 2.746 (2.20), 3.260 (6.74), 3.273 (9.26), 3.283 (6.71), 3.347 (5.98), 3.354 (3.81), 3.367 (4.46), 3.554 (12.04), 4.023 (16.00), 6.941 (3.18), 6.954 (3.21), 7.178 (4.21), 7.417 (1.33), 7.572 (0.70), 7.833 (0.68), 7.933 (1.15), 8.118 (0.85), 8.272 (4.71), 8.285 (4.61), 8.375 (1.80), 8.632 (8.96), 8.828 (7.24), 10.765 (1.25), 12.236 (0.98), 12.278 (1.90).

Example 35.01.10

N-[4-({4-[(3-methoxypropyl)sulfonyl]piperazin-1-yl}methyl)pyridin-2-yl]-6-(5-methoxypyrimidin-4-yl)-1H-benzimidazol-2-amine

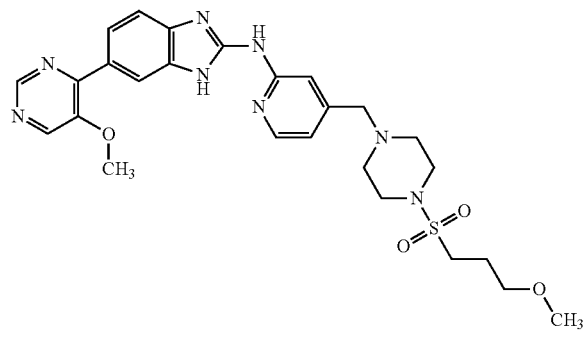 [SMILES: COCCCS(=O)(=O)N1CCN(Cc2ccnc(Nc3nc4ccc(-c5ncncc5OC)cc4[nH]3)c2)CC1]

Starting with crude 6-(5-methoxypyrimidin-4-yl)-N-[4-(piperazin-1-ylmethyl)pyridin-2-yl]-1H-benzimidazol-2-amine hydrochloride (100 mg, approx. 144 µmol) and 3-methoxypropane-1-sulfonyl chloride (CAS-RN: 64297-55-8) (24.9 mg, 144 µmol), Example 35.01.10 was prepared analogously to the procedure for the preparation of Example 35.01.09.

Yield: 18.0 mg of the title compound.

LC-MS (Method 4): $R_t$=0.99 min; MS (ESIpos): m/z=553 [M+H]$^+$.

$^1$H-NMR (400 MHz, DMSO-d6) δ[ppm]: 1.874 (1.54), 1.893 (1.63), 1.914 (1.57), 2.322 (1.30), 2.327 (1.84), 2.331 (1.42), 2.518 (6.99), 2.523 (4.69), 2.665 (1.33), 2.669 (1.84), 2.673 (1.39), 3.058 (2.36), 3.072 (1.81), 3.078 (2.36), 3.084 (1.84), 3.098 (2.18), 3.212 (4.33), 3.223 (3.42), 3.240 (16.00), 3.395 (2.21), 3.410 (4.29), 3.426 (2.15), 3.551 (5.90), 4.026 (7.02), 6.936 (1.36), 6.949 (1.36), 7.184 (1.66), 7.415 (0.79), 8.268 (2.09), 8.281 (2.00), 8.375 (1.15), 8.632 (3.48), 8.826 (2.66), 12.283 (0.94).

Example 35.01.11

N-{4-[(4-{[2-(2-methoxyethoxy)ethyl]sulfonyl}piperazin-1-yl)methyl]pyridin-2-yl}-6-(5-methoxypyrimidin-4-yl)-1H-benzimidazol-2-amine

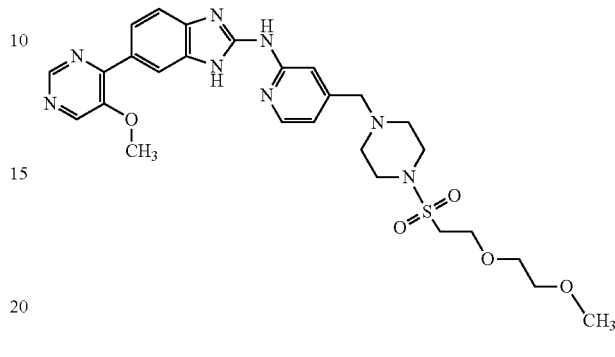

Starting with crude 6-(5-methoxypyrimidin-4-yl)-N-[4-(piperazin-1-ylmethyl)pyridin-2-yl]-1H-benzimidazol-2-amine hydrochloride (130 mg, approx. 187 µmol) and 2-(2-methoxyethoxy)ethanesulfonyl chloride (Uhlenbroek et al. Recueil des Travaux Chimiques des Pays-Bas, 1957, vol. 76, p. 129, 138, 145) (38.0 mg, 187 µmol), Example 35.01.11 was prepared analogously to the procedure for the preparation of Example 35.01.09.

Yield: 41.0 mg of the title compound.

LC-MS (Method 4): $R_t$=0.97 min; MS (ESIpos): m/z=583 [M+H]$^+$.

$^1$H-NMR (400 MHz, DMSO-d6) δ[ppm]: 2.539 (1.76), 3.201 (1.81), 3.214 (2.52), 3.224 (1.83), 3.251 (16.00), 3.320 (1.44), 3.350 (1.57), 3.449 (1.31), 3.459 (2.00), 3.464 (1.59), 3.471 (2.34), 3.542 (5.64), 3.549 (2.23), 3.554 (2.20), 3.566 (1.37), 3.718 (1.53), 3.733 (3.05), 3.748 (1.31), 4.023 (4.75), 8.268 (1.33), 8.282 (1.27), 8.632 (2.68), 8.828 (2.01).

Example 35.01.12

N-(4-{[4-(cyclopropylsulfonyl)piperazin-1-yl]methyl}pyridin-2-yl)-6-(5-methoxypyrimidin-4-yl)-1H-benzimidazol-2-amine

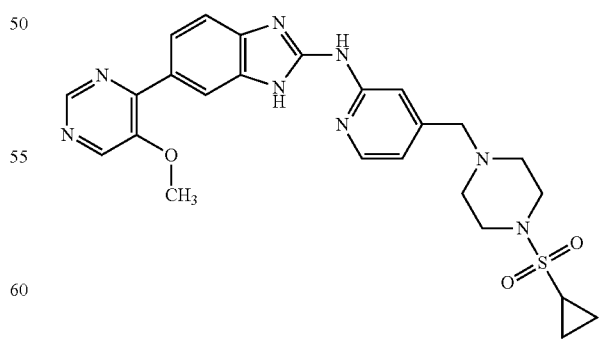

Starting with crude 6-(5-methoxypyrimidin-4-yl)-N-[4-(piperazin-1-ylmethyl)pyridin-2-yl]-1H-benzimidazol-2-amine hydrochloride (100 mg, approx. 144 µmol) and cyclopropanesulfonyl chloride (CAS-RN: 139631-62-2) (15 µl, 140 µmol), Example 35.01.12 was prepared analogously to the procedure for the preparation of Example 35.01.03.

Yield: 21.0 mg of the title compound.

LC-MS (Method 4): $R_t$=0.98 min; MS (ESIpos): m/z=521 [M+H]$^+$.

$^1$H-NMR (400 MHz, DMSO-d6) δ[ppm]: 0.908 (1.30), 0.920 (4.26), 0.927 (5.49), 0.934 (5.36), 0.937 (5.70), 0.947 (3.12), 0.969 (1.41), 0.980 (2.40), 0.990 (4.64), 0.995 (3.81), 1.010 (5.29), 1.015 (3.64), 1.030 (1.17), 1.065 (0.79), 2.318 (0.65), 2.322 (1.41), 2.327 (2.03), 2.331 (1.51), 2.337 (0.72), 2.518 (14.11), 2.523 (9.24), 2.539 (3.47), 2.598 (0.96), 2.610 (1.75), 2.617 (1.92), 2.629 (3.12), 2.638 (1.41), 2.642 (1.79), 2.649 (1.65), 2.665 (1.75), 2.669 (2.20), 2.673 (1.61), 2.678 (0.79), 2.772 (1.34), 3.224 (6.70), 3.236 (9.41), 3.248 (6.63), 3.551 (13.29), 4.023 (16.00), 6.939 (3.09), 6.951 (3.16), 7.188 (2.64), 7.395 (1.13), 7.417 (1.24), 7.935 (1.17), 7.954 (1.06), 8.115 (0.93), 8.270 (4.77), 8.283 (4.53), 8.375 (1.85), 8.632 (9.41), 8.827 (8.38), 10.756 (1.20), 12.235 (0.96), 12.287 (1.85).

Example 35.01.13

N-(4-{[4-(cyclohexylsulfonyl)piperazin-1-yl]methyl}pyridin-2-yl)-6-(5-methoxypyrimidin-4-yl)-1H-benzimidazol-2-amine

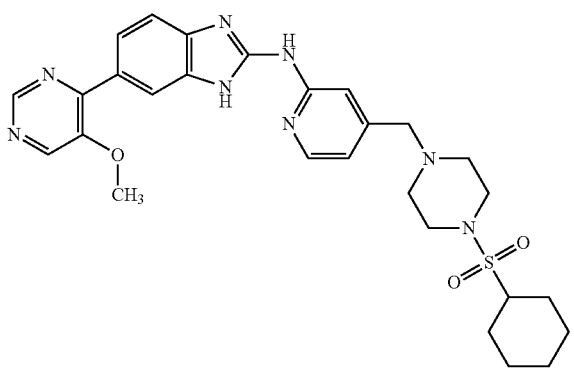 [SMILES: COc1cncnc1-c1ccc2nc(Nc3cc(CN4CCN(S(=O)(=O)C5CCCCC5)CC4)ccn3)[nH]c2c1]

Starting with crude 6-(5-methoxypyrimidin-4-yl)-N-[4-(piperazin-1-ylmethyl)pyridin-2-yl]-1H-benzimidazol-2-amine hydrochloride (145 mg, approx. 209 µmol) and cyclohexanesulfonyl chloride (CAS-RN: 4837-38-1) (30 µl, 210 µmol), Example 35.01.13 was prepared analogously to the procedure for the preparation of Example 35.01.03.

Yield: 34.0 mg of the title compound.

LC-MS (Method 4): $R_t$=1.16 min; MS (ESIpos): m/z=563 [M+H]$^+$.

$^1$H-NMR (400 MHz, DMSO-d6) δ[ppm]: 0.966 (0.99), 1.065 (0.78), 1.143 (1.53), 1.230 (1.48), 1.260 (2.50), 1.292 (2.85), 1.320 (3.60), 1.348 (3.30), 1.380 (2.63), 1.599 (1.66), 1.632 (1.48), 1.755 (2.93), 1.787 (2.93), 1.973 (3.62), 2.003 (2.85), 2.326 (1.66), 2.522 (7.87), 2.669 (1.66), 2.813 (0.78), 3.127 (2.04), 3.281 (9.66), 3.542 (11.65), 4.022 (16.00), 4.208 (1.77), 4.213 (1.83), 4.491 (1.77), 4.495 (1.77), 6.932 (3.14), 6.944 (3.14), 7.191 (2.98), 7.414 (1.40), 7.480 (1.77), 7.489 (1.72), 7.498 (1.83), 7.506 (1.69), 7.524 (2.20), 7.551 (3.49), 7.569 (2.55), 7.932 (1.21), 8.113 (0.91), 8.263 (4.27), 8.276 (4.05), 8.375 (1.85), 8.632 (7.49), 8.827 (6.82), 10.747 (1.18), 12.280 (1.72).

Example 35.01.14

6-(5-methoxypyrimidin-4-yl)-N-(4-{[4-(tetrahydro-2H-pyran-4-ylsulfonyl)piperazin-1-yl]methyl}pyridin-2-yl)-1H-benzimidazol-2-amine

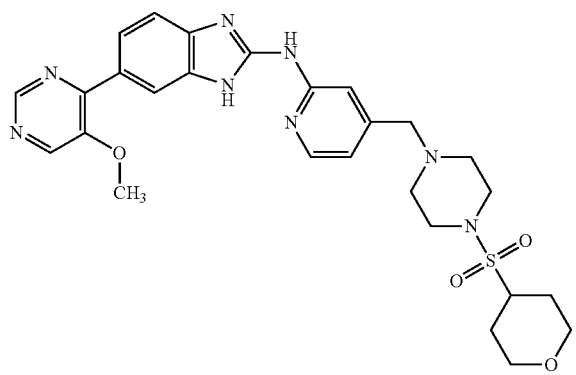 [SMILES: COc1cncnc1-c1ccc2nc(Nc3cc(CN4CCN(S(=O)(=O)C5CCOCC5)CC4)ccn3)[nH]c2c1]

Starting with crude 6-(5-methoxypyrimidin-4-yl)-N-[4-(piperazin-1-ylmethyl)pyridin-2-yl]-1H-benzimidazol-2-amine hydrochloride (100 mg, approx. 144 µmol) and tetrahydro-2H-pyran-4-sulfonyl chloride (CAS-RN: 338453-21-7) (26.6 mg, 144 µmol), Example 35.01.14 was prepared analogously to the procedure for the preparation of Example 35.01.09.

Yield: 15.0 mg of the title compound.

LC-MS (Method 4): $R_t$=0.96 min; MS (ESIpos): m/z=565 [M+H]$^+$.

$^1$H-NMR (400 MHz, DMSO-d6) δ[ppm]: 1.595 (1.59), 1.607 (1.79), 1.627 (1.93), 1.638 (1.79), 1.836 (2.48), 1.862 (1.86), 2.166 (0.97), 2.318 (1.52), 2.323 (3.24), 2.327 (4.48), 2.331 (3.31), 2.336 (1.66), 2.463 (6.00), 2.518 (16.00), 2.523 (10.69), 2.540 (2.62), 2.659 (1.38), 2.665 (3.24), 2.669 (4.48), 2.673 (3.31), 2.678 (1.52), 3.127 (1.38), 3.303 (7.45), 3.362 (2.28), 3.467 (2.00), 3.545 (7.93), 3.909 (2.28), 3.927 (2.00), 4.026 (11.17), 6.934 (1.86), 7.183 (2.21), 7.393 (1.10), 7.414 (1.24), 7.935 (1.03), 8.266 (2.90), 8.279 (2.62), 8.372 (1.72), 8.631 (4.55), 8.826 (3.59), 10.753 (1.03), 12.278 (1.31).

Example 35.01.15

4-[(2-{[6-(5-methoxypyrimidin-4-yl)-1H-benzimidazol-2-yl]amino}pyridin-4-yl)methyl]-N,N-dimethylpiperazine-1-sulfonamide

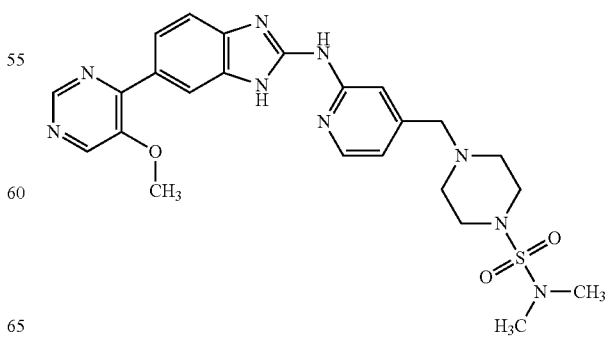

Starting with crude 6-(5-methoxypyrimidin-4-yl)-N-[4-(piperazin-1-ylmethyl)pyridin-2-yl]-1H-benzimidazol-2-amine hydrochloride (130 mg, approx. 187 μmol) and dimethylsulfamyl chloride (CAS-RN: 13360-57-1) (20 μl, 190 μmol), Example 35.01.15 was prepared analogously to the procedure for the preparation of Example 35.01.03.

Yield: 50.0 mg of the title compound.

LC-MS (Method 4): $R_t$=1.00 min; MS (ESIpos): m/z=524 [M+H]$^+$.

$^1$H-NMR (400 MHz, DMSO-d6) δ [ppm]: 2.772 (16.00), 3.538 (1.67), 4.023 (1.84), 8.632 (1.03).

Example 35.01.16

N-{4-[(4-{[4-(methoxymethyl)piperidin-1-yl]sulfonyl}piperazin-1-yl)methyl]pyridin-2-yl}-6-(5-methoxypyrimidin-4-yl)-1H-benzimidazol-2-amine

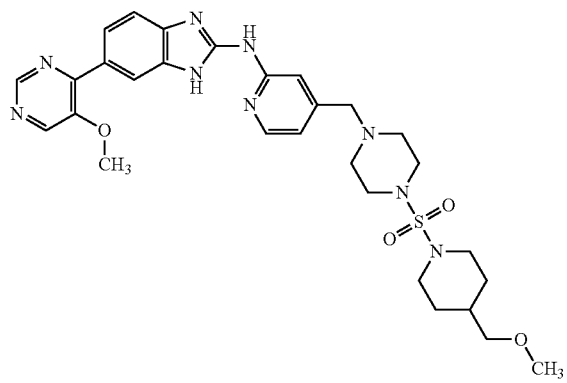 [SMILES: COCC1CCN(S(=O)(=O)N2CCN(Cc3ccnc(Nc4nc5ccc(-c6ncncc6OC)cc5[nH]4)c3)CC2)CC1]

Starting with crude 6-(5-methoxypyrimidin-4-yl)-N-[4-(piperazin-1-ylmethyl)pyridin-2-yl]-1H-benzimidazol-2-amine hydrochloride (130 mg, approx. 187 μmol) and 4-(methoxymethyl)piperidine-1-sulfonyl chloride (CAS-RN: 1243250-01-2) (42.6 mg, 187 μmol), Example 35.01.16 was prepared analogously to the procedure for the preparation of Example 35.01.03.

Yield: 64.0 mg of the title compound.

LC-MS (Method 4): $R_t$=1.11 min; MS (ESIpos): m/z=608 [M+H]$^+$.

$^1$H-NMR (400 MHz, DMSO-d6) δ[ppm]: 1.675 (1.51), 2.465 (2.44), 2.518 (2.07), 2.523 (1.29), 2.799 (1.30), 2.804 (1.33), 3.170 (4.62), 3.178 (3.11), 3.185 (2.94), 3.220 (3.98), 3.224 (16.00), 3.533 (3.65), 3.557 (1.19), 4.023 (4.68), 8.264 (1.43), 8.277 (1.38), 8.632 (2.67), 8.827 (2.07).

Example 35.01.17

N-[4-({4-[(4-methoxypiperidin-1-yl)sulfonyl]piperazin-1-yl}methyl)pyridin-2-yl]-6-(5-methoxypyrimidin-4-yl)-1H-benzimidazol-2-amine

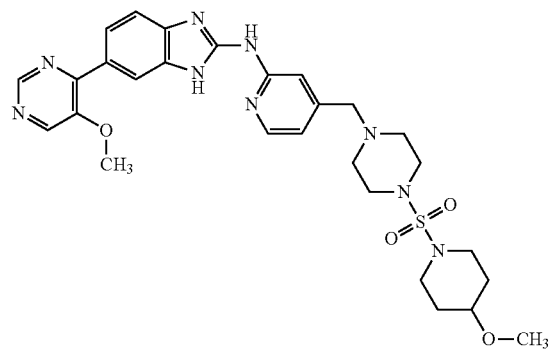 [SMILES: COc1cncnc1-c1ccc2nc(Nc3cc(CN4CCN(S(=O)(=O)N5CCC(OC)CC5)CC4)ccn3)[nH]c2c1]

Starting with crude 6-(5-methoxypyrimidin-4-yl)-N-[4-(piperazin-1-ylmethyl)pyridin-2-yl]-1H-benzimidazol-2-amine hydrochloride (130 mg, approx. 187 μmol) and 4-methoxypiperidine-1-sulfonyl chloride (CAS-RN: 355849-73-9) (40.0 mg, 187 μmol), Example 35.01.17 was prepared analogously to the procedure for the preparation of Example 35.01.03.

Yield: 63.0 mg of the title compound.

LC-MS (Method 4): $R_t$=1.06 min; MS (ESIpos): m/z=594 [M+H]$^+$.

$^1$H-NMR (400 MHz, DMSO-d6) δ [ppm]: 1.465 (1.18), 1.476 (1.01), 1.486 (1.24), 1.833 (1.10), 2.322 (0.83), 2.327 (1.20), 2.331 (0.91), 2.466 (3.97), 2.518 (4.81), 2.523 (3.27), 2.665 (0.87), 2.669 (1.22), 2.673 (0.89), 3.001 (0.89), 3.010 (1.05), 3.031 (1.89), 3.040 (1.20), 3.054 (1.14), 3.062 (1.01), 3.171 (3.97), 3.242 (16.00), 3.359 (1.74), 3.537 (5.46), 4.024 (6.47), 6.928 (1.32), 6.941 (1.32), 7.186 (1.44), 8.264 (2.01), 8.277 (1.93), 8.375 (0.95), 8.632 (3.41), 8.826 (2.60), 12.281 (0.93).

Example 35.01.18

N-[4-({4-[(2,6-dimethylmorpholin-4-yl)sulfonyl]piperazin-1-yl}methyl)pyridin-2-yl]-6-(5-methoxypyrimidin-4-yl)-1H-benzimidazol-2-amine

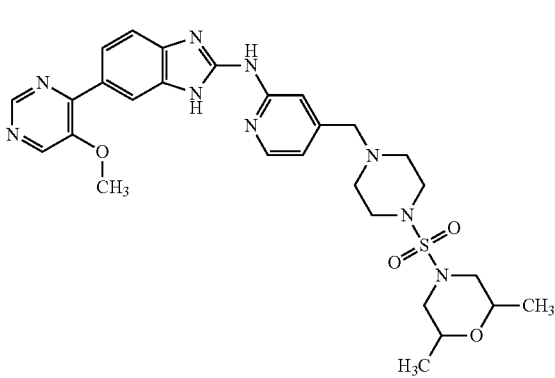 [SMILES: COc1cncnc1-c1ccc2nc(Nc3cc(CN4CCN(S(=O)(=O)N5CC(C)OC(C)C5)CC4)ccn3)[nH]c2c1]

Starting with crude 6-(5-methoxypyrimidin-4-yl)-N-[4-(piperazin-1-ylmethyl)pyridin-2-yl]-1H-benzimidazol-2- amine hydrochloride (150 mg, approx. 216 µmol) and 2,6-dimethylmorpholine-4-sulfonyl chloride (CAS-RN: 919026-20-3) (46.2 mg, 216 µmol), Example 35.01.18 was prepared analogously to the procedure for the preparation of Example 35.01.03.

Yield: 75.0 mg of the title compound.

LC-MS (Method 2): $R_t$=1.14 min; MS (ESIpos): m/z=594 [M+H]$^+$.

$^1$H-NMR (400 MHz, DMSO-d6) δ[ppm]: 1.086 (10.24), 1.102 (12.46), 1.107 (16.00), 2.327 (1.39), 2.669 (1.44), 3.212 (3.98), 3.389 (2.63), 3.416 (2.17), 3.547 (4.32), 4.022 (9.69), 4.194 (0.85), 6.952 (1.37), 7.193 (2.13), 8.270 (1.71), 8.283 (1.76), 8.635 (3.43), 8.829 (3.54).

Example 35.02.01

(rac)-3,3,3-trifluoro-1-{4-[1-(2-{[6-(5-methoxypy-rimidin-4-yl)-1H-benzimidazol-2-yl]amino}pyridin-4-yl)ethyl]piperazin-1-yl}propan-1-one

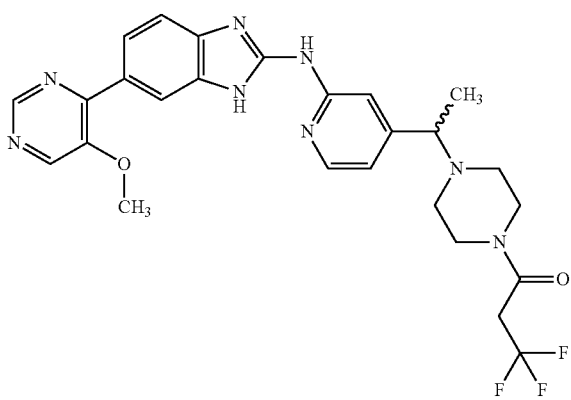 [SMILES: COc1cncnc1-c1ccc2nc(Nc3cc(C(C)N4CCN(C(=O)CC(F)(F)F)CC4)ccn3)[nH]c2c1]

Starting with crude (rac)-6-(5-methoxypyrimidin-4-yl)-N-{4-[1-(piperazin-1-yl)ethyl]pyridin-2-yl}-1H-benzimidazol-2-amine hydrochloride (900 mg, approx. 1.79 mmol) and 3,3,3-trifluoropropanoic acid (320 mg, 2.50 mmol), Example 35.02.01 was prepared analogously to the procedure for the preparation of Example 01.02.

Yield: 990 mg of the title compound.

LC-MS (Method 2): $R_t$=1.04 min; MS (ESIpos): m/z=541 [M+H]$^+$.

$^1$H-NMR (400 MHz, DMSO-d6) δ[ppm]: 1.035 (7.87), 1.052 (16.00), 1.070 (8.19), 1.232 (0.63), 1.298 (3.10), 1.314 (3.04), 2.323 (1.33), 2.327 (1.67), 2.332 (1.43), 2.434 (1.06), 2.523 (2.58), 2.665 (0.82), 2.669 (1.12), 2.673 (0.84), 3.405 (1.03), 3.423 (3.02), 3.435 (3.78), 3.440 (4.12), 3.452 (3.50), 3.469 (2.15), 3.485 (2.09), 3.513 (1.24), 3.540 (0.86), 3.582 (0.82), 3.609 (2.55), 3.636 (2.15), 3.664 (0.68), 4.023 (11.63), 4.344 (1.01), 4.356 (1.77), 4.368 (0.97), 6.960 (1.25), 6.973 (1.27), 7.174 (2.05), 8.280 (1.81), 8.294 (1.73), 8.635 (4.69), 8.829 (5.00).

Example 35.02.02

(rac)-2-cyclopropyl-1-{4-[1-(2-{[6-(5-methoxypy-rimidin-4-yl)-1H-benzimidazol-2-yl]amino}pyridin-4-yl)ethyl]piperazin-1-yl}ethanone

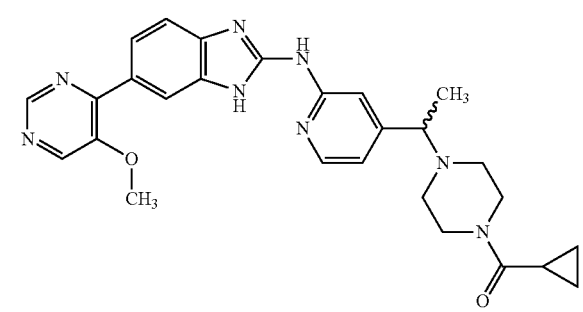 [SMILES: COc1cncnc1-c1ccc2nc(Nc3cc(C(C)N4CCN(C(=O)C5CC5)CC4)ccn3)[nH]c2c1]

Starting with crude (rac)-6-(5-methoxypyrimidin-4-yl)-N-{4-[1-(piperazin-1-yl)ethyl]pyridin-2-yl}-1H-benzimidazol-2-amine (233 mg, 541 µmol) and cyclopropylacetic acid (81.3 mg, 812 µmol), Example 35.02.02 was prepared analogously to the procedure for the preparation of Example 01.02.

Yield: 35.2 mg (12%) of the title compound.

LC-MS (Method 4): $R_t$=1.02 min; MS (ESIpos): m/z=513 [M+H]$^+$.

$^1$H-NMR (400 MHz, DMSO-d6) δ [ppm]: 0.000 (1.63), 0.011 (5.34), 0.014 (4.98), 0.023 (5.34), 0.037 (1.71), 0.331 (1.74), 0.341 (4.45), 0.345 (4.57), 0.351 (2.45), 0.356 (2.36), 0.361 (4.77), 0.366 (4.52), 0.376 (1.60), 0.851 (1.68), 1.219 (8.92), 1.236 (9.25), 2.144 (7.89), 2.161 (7.78), 2.262 (2.45), 2.339 (2.74), 2.458 (5.07), 2.604 (0.81), 3.358 (4.84), 3.372 (5.35), 3.390 (5.07), 3.957 (16.00), 6.886 (2.70), 6.900 (2.73), 7.103 (3.23), 7.350 (0.73), 7.864 (0.73), 8.206 (4.20), 8.219 (4.12), 8.310 (0.96), 8.567 (9.18), 8.762 (8.09), 12.232 (1.17).

Example 35.02.03

(rac)-cyclopropyl{4-[1-(2-{[6-(5-methoxypyrimidin-4-yl)-1H-benzimidazol-2-yl]amino}pyridin-4-yl)ethyl]piperazin-1-yl}methanone Starting with crude (rac)-6-(5-methoxypyrimidin-4-yl)-N-{4-[1-(piperazin-1-yl)ethyl]pyridin-2-yl}-1H-benzimidazol-2-amine (233 mg, 541 µmol) and cyclopropanecarboxylic acid (69.9 mg, 812 µmol), Example 35.02.03 was prepared analogously to the procedure for the preparation of Example 01.02.

Yield: 59.6 mg (22%) of the title compound.

LC-MS (Method 4): $R_t$=0.99 min; MS (ESIpos): m/z=499 [M+H]$^+$.

$^1$H-NMR (400 MHz, DMSO-d6) δ [ppm]: 0.664 (6.36), 0.684 (7.92), 0.691 (7.41), 0.699 (6.29), 0.703 (6.76), 0.710 (3.18), 1.295 (11.02), 1.311 (10.82), 1.937 (2.47), 2.327 (2.51), 2.523 (3.46), 2.669 (0.98), 3.451 (4.64), 3.468 (5.79), 3.675 (3.24), 4.022 (16.00), 6.959 (3.20), 6.972 (3.17), 7.176 (3.41), 7.413 (0.97), 7.934 (0.98), 8.275 (4.76), 8.288 (4.52), 8.379 (1.32), 8.632 (9.56), 8.827 (7.81), 12.304 (1.38).

Example 35.02.04

(rac)-cyclobutyl{4-[1-(2-{[6-(5-methoxypyrimidin-4-yl)-1H-benzimidazol-2-yl]amino}pyridin-4-yl)ethyl]piperazin-1-yl}methanone Starting with crude (rac)-6-(5-methoxypyrimidin-4-yl)-N-{4-[1-(piperazin-1-yl)ethyl]pyridin-2-yl}-1H-benzimidazol-2-amine (233 mg, 541 µmol) and cyclobutanecarboxylic acid (81.3 mg, 812 µmol), Example 35.02.04 was prepared analogously to the procedure for the preparation of Example 01.02.

Yield: 78.2 mg (28%) of the title compound.

LC-MS (Method 4): $R_t$=1.05 min; MS (ESIpos): m/z=513 [M+H]$^+$.

$^1$H-NMR (400 MHz, DMSO-d6) δ[ppm]: 1.274 (4.42), 1.290 (4.49), 1.843 (0.97), 2.030 (1.13), 2.051 (1.33), 2.060 (1.05), 2.075 (0.91), 2.099 (1.39), 2.120 (1.44), 2.280 (1.01), 2.294 (1.14), 2.308 (1.10), 2.523 (1.41), 3.272 (0.98), 3.293 (2.29), 3.305 (1.93), 3.315 (1.99), 3.337 (16.00), 3.423 (1.73), 3.440 (2.32), 4.022 (7.27), 6.943 (1.24), 6.956 (1.30), 7.164 (1.34), 8.267 (2.02), 8.280 (1.95), 8.632 (4.38), 8.827 (3.67).

Example 35.03.01.A 3,3,3-trifluoro-1-{4-[(1R or 1S)-1-(2-{[6-(5-methoxypyrimidin-4-yl)-1H-benzimidazol-2-yl]amino}pyridin-4-yl)ethyl]piperazin-1-yl}propan-1-one (single stereoisomer A)

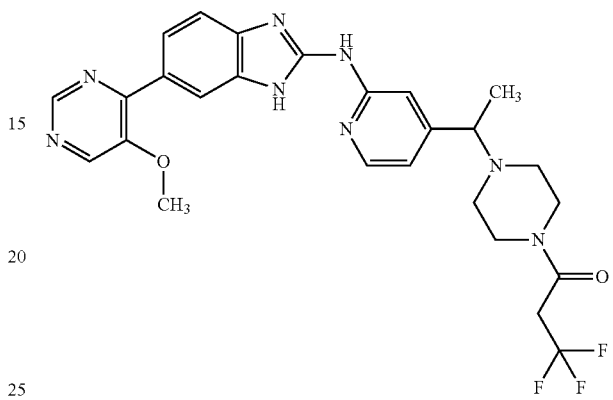

Example 35.03.01.B 3,3,3-trifluoro-1-{4-[(1S or 1R)-1-(2-{[6-(5-methoxypyrimidin-4-yl)-1H-benzimidazol-2-yl]amino}pyridin-4-yl)ethyl]piperazin-1-yl}propan-1-one (single stereoisomer B)

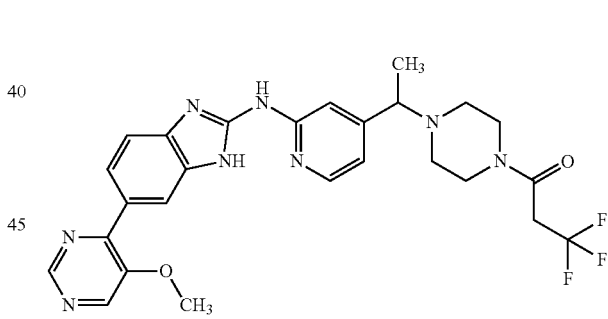

97 mg of (rac)-3,3,3-trifluoro-1-{4-[1-(2-{[6-(5-methoxypyrimidin-4-yl)-1H-benzimidazol-2-yl]amino}pyridin-4-yl)ethyl]piperazin-1-yl}propan-1-one was separated into the single stereoisomers (Example 35.03.01.A and Example 35.03.01.B) via preparative, chiral HPLC.

Instrument: Labomatic HD5000, Labocord-5000; Gilson GX-241, Labcol Vario 4000,

Column: Chiralpak IB 5µ 250×30 mm;

Eluent A: hexane+0.1 Vol-% diethylamine (99%);

Eluent B: ethanol; isocratic: 70% A+30% B;

Flow: 60.0 mL/min;

Solution: 97 mg/4.8 mL dichloromethane/methanol 1:1

Injection: 3×1.6 mL

Detection: UV 325 nm

|  | Retention time in min | purity in % | yield | Optical rotation [α]$_D$ |
|---|---|---|---|---|
| Example 35.03.01.A Stereoisomer A | 7.9-13.5 | >99.9% | 27 mg | −39.1° (from solution in DMSO, c = 2.4 mg/mL) |
| Example 35.03.01.B Stereoisomer B | 15.2-21.3 | >99.9% | 32 mg | +33.2° (from solution in DMSO, c = 3.2 mg/mL) |

Example 35.03.01.A $^1$H-NMR (400 MHz, DMSO-d6) δ[ppm]: 1.107 (9.20), 1.233 (1.29), 1.294 (7.37), 1.311 (7.43), 2.322 (1.66), 2.326 (2.14), 2.331 (2.16), 2.432 (1.92), 2.523 (3.10), 2.664 (0.98), 2.669 (1.33), 2.674 (0.94), 3.438 (3.71), 3.472 (3.64), 3.487 (3.86), 3.580 (1.50), 3.607 (4.23), 3.635 (4.05), 3.662 (1.26), 4.022 (16.00), 4.188 (0.72), 6.954 (2.25), 6.967 (2.29), 7.171 (3.12), 8.276 (3.75), 8.289 (3.57), 8.632 (9.09), 8.827 (8.39), 12.289 (0.92).

Example 35.03.01.B $^1$H-NMR (400 MHz, DMSO-d6) δ[ppm]: 1.107 (8.52), 1.234 (1.38), 1.295 (6.45), 1.311 (6.45), 2.322 (1.92), 2.326 (2.52), 2.331 (2.35), 2.432 (1.81), 2.518 (6.48), 2.522 (4.22), 2.664 (1.26), 2.669 (1.75), 2.674 (1.20), 3.438 (3.38), 3.489 (3.30), 3.580 (1.38), 3.607 (3.93), 3.635 (3.76), 3.662 (1.18), 4.022 (16.00), 6.955 (2.04), 6.969 (2.04), 7.171 (2.87), 8.276 (3.35), 8.290 (3.27), 8.632 (8.66), 8.828 (8.40).

Example 35.03.02.A 2-cyclopropyl-1-{4-[(1R or 1S)-1-(2-{[6-(5-methoxypyrimidin-4-yl)-1H-benzimidazol-2-yl]amino}pyridin-4-yl)ethyl]piperazin-1-yl}ethanone (single stereoisomer A)

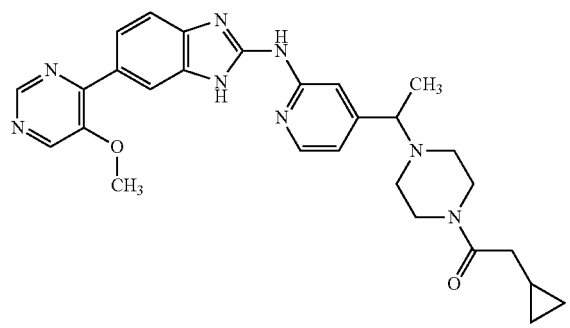 [SMILES: COc1cncnc1-c1ccc2nc(Nc3cc(C(C)N4CCN(C(=O)CC5CC5)CC4)ccn3)[nH]c2c1]

Example 35.03.02.B 2-cyclopropyl-1-{4-[(1S or 1R)-1-(2-{[6-(5-methoxypyrimidin-4-yl)-1H-benzimidazol-2-yl]amino}pyridin-4-yl)ethyl]piperazin-1-yl}ethanone (single stereoisomer B)

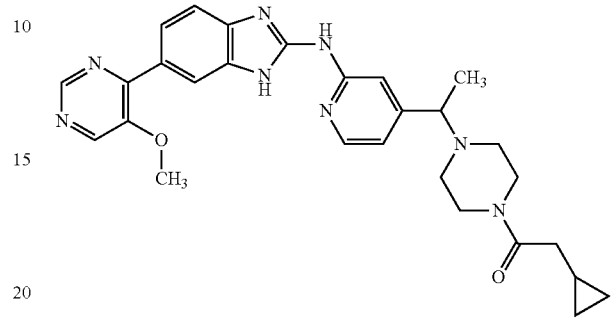

40 mg of (rac)-2-cyclopropyl-1-{4-[1-(2-{[6-(5-methoxy-pyrimidin-4-yl)-1H-benzimidazol-2-yl]amino}pyridin-4-yl)ethyl]piperazin-1-yl}ethanone was separated into the single stereoisomers (Example 35.03.02.A and Example 35.03.02.B) via preparative, chiral HPLC.
Instrument: Labomatic HD5000, Labocord-5000; Gilson GX-241, Labcol Vario 4000,
Column: Chiralpak IB 5μ 250×30 mm;
Eluent A: hexane+0.2 Vol-% diethylamine (99%); Eluent B: ethanol; isocratic: 70% A+30% B;
Flow: 30.0 mL/min;
Solution: 40 mg/2 mL ethanol
Injection: 4×0.5 mL
Detection: UV 325 nm

|  | Retention time in min | purity in % | yield | Optical rotation [α]$_D$ |
|---|---|---|---|---|
| Example 35.03.02.A Stereoisomer A | 9.50-11.10 | 99.6% | 15 mg | −36.4° (from solution in DMSO, c = 2.9 mg/mL) |
| Example 35.03.02.B Stereoisomer B | 11.20-12.50 | 95.1% | 15 mg | +32.4° (from solution in DMSO, c = 2.6 mg/mL) |

Example 35.03.02.A $^1$H-NMR (400 MHz, DMSO-d6) δ[ppm]: 0.000 (2.36), 0.011 (7.87), 0.014 (7.61), 0.023 (8.26), 0.026 (7.87), 0.037 (2.62), 0.331 (2.75), 0.341 (6.69), 0.345 (7.21), 0.352 (3.80), 0.356 (3.67), 0.362 (7.34), 0.366 (7.08), 0.376 (2.62), 0.851 (2.75), 1.042 (14.95), 1.166 (4.98), 1.220 (14.56), 1.238 (14.69), 2.146 (12.46), 2.162 (12.33), 2.257 (4.98), 2.262 (5.90), 2.267 (4.98), 2.339 (4.20), 2.458 (11.28), 2.599 (2.75), 2.604 (3.80), 2.608 (2.75), 3.358 (7.34), 3.374 (8.39), 3.391 (7.87), 3.960 (16.00), 4.132 (1.57), 6.886 (3.41), 7.097 (3.93), 7.327 (1.84), 7.347 (2.10), 7.866 (1.84), 8.049 (1.57), 8.206 (5.38), 8.219 (5.11), 8.310 (3.02), 8.566 (9.70), 8.760 (7.08), 10.675 (2.36), 12.229 (3.02).

Example 35.03.02.B $^1$H-NMR (400 MHz, DMSO-d6) δ[ppm]: 0.000 (1.04), 0.011 (3.49), 0.014 (3.28), 0.023 (3.44), 0.026 (3.39), 0.037

(1.20), 0.331 (1.20), 0.341 (3.00), 0.345 (3.22), 0.352 (1.58), 0.356 (1.53), 0.362 (3.22), 0.366 (3.17), 0.376 (1.20), 0.831 (0.71), 0.834 (0.71), 0.839 (0.71), 0.851 (1.20), 0.868 (0.71), 0.871 (0.66), 0.901 (0.55), 1.042 (16.00), 1.165 (2.02), 1.220 (6.33), 1.237 (6.39), 2.145 (5.62), 2.162 (5.46), 2.253 (1.53), 2.257 (1.91), 2.262 (2.18), 2.267 (1.91), 2.338 (1.69), 2.353 (1.53), 2.367 (1.15), 2.458 (3.33), 2.600 (0.93), 2.604 (1.31), 2.608 (0.98), 3.358 (3.00), 3.373 (3.49), 3.390 (3.28), 3.405 (2.13), 3.959 (6.77), 4.132 (1.47), 6.886 (1.47), 6.899 (1.53), 7.098 (1.64), 7.347 (0.76), 8.206 (2.40), 8.219 (2.29), 8.310 (1.15), 8.566 (4.53), 8.760 (3.22), 10.676 (0.82), 12.230 (1.15).

Example 35.03.03.A cyclopropyl{4-[(1R or 1S)-1-(2-{[6-(5-methoxypyrimidin-4-yl)-1H-benzimidazol-2-yl]amino}pyridin-4-yl)ethyl]piperazin-1-yl}methanone (single stereoisomer A)

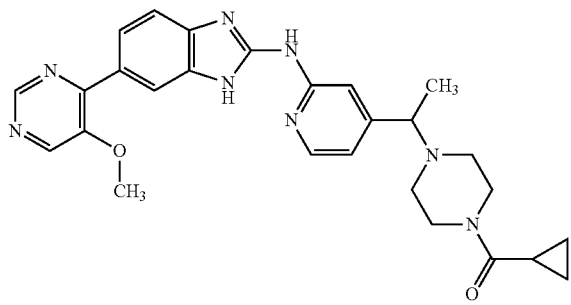 [SMILES: COc1cncnc1-c1ccc2nc(Nc3cc(C(C)N4CCN(C(=O)C5CC5)CC4)ccn3)[nH]c2c1]

Example 35.03.03.B cyclopropyl{4-[(1S or 1R)-1-(2-{[6-(5-methoxypyrimidin-4-yl)-1H-benzimidazol-2-yl]amino}pyridin-4-yl)ethyl]piperazin-1-yl}methanone (single stereoisomer B)

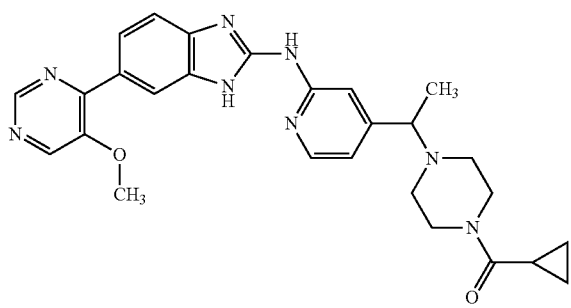 [SMILES: COc1cncnc1-c1ccc2nc(Nc3cc(C(C)N4CCN(C(=O)C5CC5)CC4)ccn3)[nH]c2c1]

40 mg of (rac)-cyclopropyl{4-[1-(2-{[6-(5-methoxypyrimidin-4-yl)-1H-benzimidazol-2-yl]amino}pyridin-4-yl)ethyl]piperazin-1-yl}methanone was separated into the single stereoisomers (Example 35.03.03.A and Example 35.03.03.B) via preparative, chiral HPLC.

Instrument: Labomatic HD5000, Labocord-5000; Gilson GX-241, Labcol Vario 4000,

Column: Chiralpak IB 5μ 250×30 mm;

Eluent A: hexane+0.2 Vol-% diethylamine (99%); Eluent B: ethanol; isocratic: 70% A+30% B;

Flow: 30.0 mL/min;

Solution: 40 mg/2.0 mL ethanol

Injection: 4×0.5 mL

Detection: UV 325 nm

| | Retention time in min | purity in % | yield | Optical rotation $[\alpha]_D$ |
|---|---|---|---|---|
| Example 35.03.03.A Stereoisomer A | 11.00-12.25 | >99.0% | 20 mg | −41.9° (from solution in DMSO, c = 2.8 mg/mL) |
| Example 35.03.03.B Stereoisomer B | 12.25-15.25 | 97.5% | 20 mg | +37.7° (from solution in DMSO, c = 2.7 mg/mL) |

Example 35.03.03.A

¹H-NMR (400 MHz, DMSO-d6) δ[ppm]: 0.658 (2.70), 0.665 (6.49), 0.670 (4.05), 0.678 (3.21), 0.685 (8.29), 0.692 (7.90), 0.699 (6.30), 0.704 (7.33), 0.711 (3.41), 0.967 (0.84), 1.107 (16.00), 1.231 (1.99), 1.296 (12.40), 1.313 (12.40), 1.918 (1.54), 1.925 (1.67), 1.938 (2.76), 1.950 (1.54), 1.957 (1.41), 2.323 (2.44), 2.327 (2.83), 2.331 (2.25), 2.397 (2.18), 2.523 (4.31), 2.665 (1.35), 2.669 (1.86), 2.673 (1.35), 3.453 (4.63), 3.470 (5.85), 3.678 (3.02), 4.023 (14.20), 4.193 (1.54), 6.959 (3.08), 6.973 (3.08), 7.174 (3.15), 7.415 (1.22), 7.932 (1.22), 8.276 (5.01), 8.289 (4.76), 8.377 (1.86), 8.631 (9.77), 8.827 (7.33), 10.740 (1.41), 12.295 (2.06).

Example 35.03.03.B

¹H-NMR (400 MHz, DMSO-d6) δ[ppm]: 0.646 (0.81), 0.658 (2.55), 0.665 (5.98), 0.671 (3.55), 0.678 (2.93), 0.685 (7.66), 0.692 (7.10), 0.700 (5.91), 0.704 (6.72), 0.711 (3.11), 0.724 (0.75), 0.967 (0.44), 1.107 (13.01), 1.153 (0.50), 1.231 (2.43), 1.259 (1.00), 1.296 (11.52), 1.314 (11.33), 1.906 (0.68), 1.919 (1.49), 1.925 (1.49), 1.938 (2.55), 1.944 (1.25), 1.950 (1.43), 1.957 (1.37), 1.969 (0.62), 2.084 (1.12), 2.318 (1.68), 2.323 (2.24), 2.327 (2.55), 2.331 (1.99), 2.337 (1.31), 2.401 (1.99), 2.523 (3.36), 2.665 (1.18), 2.669 (1.56), 2.674 (1.12), 3.437 (1.37), 3.454 (4.11), 3.470 (5.23), 3.504 (1.00), 3.510 (0.87), 3.676 (2.74), 4.022 (16.00), 4.194 (1.25), 6.959 (2.99), 6.973 (3.05), 7.175 (3.18), 7.397 (0.81), 7.415 (0.87), 7.932 (0.93), 8.117 (0.62), 8.276 (4.98), 8.289 (4.73), 8.379 (1.31), 8.631 (10.52), 8.827 (8.53), 10.740 (1.06), 12.252 (0.81), 12.296 (1.56).

Example 35.03.04.A cyclobutyl{4-[(1R or 1S)-1-(2-{[6-(5-methoxypy-rimidin-4-yl)-1H-benzimidazol-2-yl]amino}pyridin-4-yl)ethyl]piperazin-1-yl}methanone (single stereoisomer A)

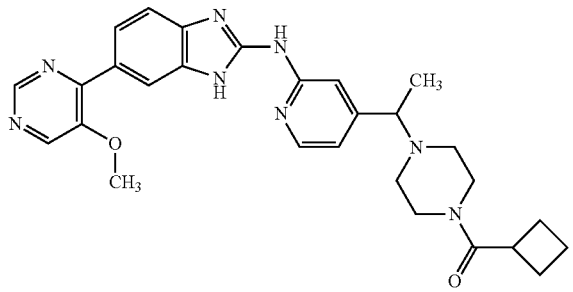 [SMILES: COc1cncnc1-c1ccc2nc(Nc3cc(C(C)N4CCN(C(=O)C5CCC5)CC4)ccn3)[nH]c2c1]

Example 35.03.04.B cyclobutyl{4-[(1R or 1S)-1-(2-{[6-(5-methoxypy-rimidin-4-yl)-1H-benzimidazol-2-yl]amino}pyridin-4-yl)ethyl]piperazin-1-yl}methanone (single stereoisomer B)

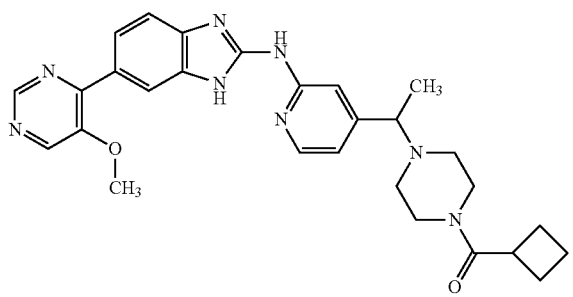 [SMILES: COc1cncnc1-c1ccc2nc(Nc3cc(C(C)N4CCN(C(=O)C5CCC5)CC4)ccn3)[nH]c2c1]

73 mg of (rac)-cyclobutyl{4-[1-(2-{[6-(5-methoxy-pyrimidin-4-yl)-1H-benzimidazol-2-yl]amino}pyridin-4-yl)ethyl]piperazin-1-yl}methanone was separated into the single stereoisomers (Example 35.03.04.A and Example 35.03.04.B) via preparative, chiral HPLC.

Instrument: Labomatic HD5000, Labocord-5000; Gilson GX-241, Labcol Vario 4000,
Column: Chiralpak IB 5µ 250×30 mm;
Eluent A: hexane+0.2 Vol-% diethylamine (99%); Eluent B: ethanol; isocratic: 70% A+30% B;
Flow: 30.0 mL/min;
Solution: 73 mg/2 mL ethanol
Injection: 4×0.5 mL
Detection: UV 325 nm

| | Retention time in min | purity in % | yield | Optical rotation [α]$_D$ |
|---|---|---|---|---|
| Example 35.03.04.A Stereoisomer A | 7.50-8.80 | >99.0% | 30 mg | −35.0° (from solution in DMSO, c = 3.9 mg/mL) |
| Example 35.03.04.B Stereoisomer B | 8.90-11.50 | 95.0% | 32 mg | +32.3° (from solution in DMSO, c = 3.2 mg/mL) |

Example 35.03.04.A $^1$H-NMR (400 MHz, DMSO-d6) δ[ppm]: 1.107 (16.00), 1.277 (6.54), 1.294 (6.69), 1.846 (1.33), 1.873 (1.07), 2.054 (1.92), 2.100 (1.96), 2.122 (2.07), 2.327 (1.88), 2.523 (4.47), 2.669 (1.48), 3.277 (1.48), 3.297 (3.70), 3.427 (2.62), 3.443 (3.40), 4.024 (7.24), 4.192 (1.48), 6.945 (1.59), 7.160 (1.66), 8.268 (2.44), 8.281 (2.33), 8.374 (1.22), 8.630 (4.55), 8.826 (3.55), 12.290 (1.26).

Example 35.03.04.B $^1$H-NMR (400 MHz, DMSO-d6) δ[ppm]: 1.108 (16.00), 1.277 (2.51), 1.295 (2.57), 2.055 (0.72), 2.101 (0.76), 2.122 (0.78), 2.323 (0.80), 2.327 (0.95), 2.331 (0.66), 2.523 (1.71), 2.669 (0.76), 3.297 (1.36), 3.309 (1.38), 3.427 (0.97), 3.444 (1.27), 4.025 (2.61), 4.192 (1.60), 8.267 (0.86), 8.281 (0.84), 8.630 (1.58), 8.825 (1.21).

Example 36.01 tert-butyl 4-{(1R or 1S)-1-[2-({6-[5-(propan-2-yloxy)pyrimidin-4-yl]-1H-benzimidazol-2-yl}amino)pyridin-4-yl]ethyl}piperazine-1-carboxylate (single stereoisomer A)

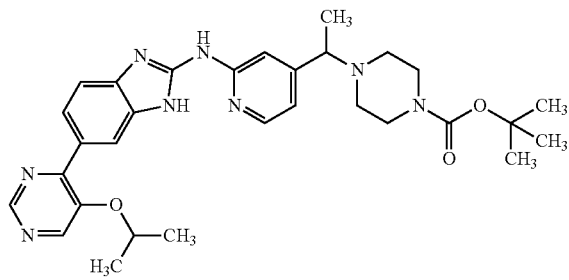 [SMILES: CC(C)Oc1cncnc1-c1ccc2nc(Nc3cc(C(C)N4CCN(C(=O)OC(C)(C)C)CC4)ccn3)[nH]c2c1]

To a stirred solution of 1H-imidazole (33.6 mg, 493 µmol) and di-1H-imidazol-1-ylmethanethione (586 mg, 90% purity, 2.96 mmol) in dichloromethane (10 mL) was added tert-butyl 4-[(1R or 1S)-1-(2-aminopyridin-4-yl)ethyl]piperazine-1-carboxylate (755 mg, 2.47 mmol), dissolved in dichloromethane (20 mL) at 0° C. The mixture was stirred at r.t. for 14 h. 4-[5-(propan-2-yloxy)pyrimidin-4-yl]benzene-1,2-diamine (745 mg, 97% purity, 2.96 mmol), dissolved in dichloromethane (18 mL) was added and the mixture was stirred at r.t. for 2 h. Water was added and the mixture was extracted with dichloromethane. The organic phase was dried (sodium sulfate) and filtered. N,N'-dipropan-2-ylcarbodiimide (0.55 mL, 3.45 mmol) was added. The mixture was stirred at r.t. for 4 h. Further N,N'-dipropan-2-ylcarbodiimide (0.55 mL, 3.45 mmol) was added and the mixture was stirred at 40° C. for 2 h and at r.t. for 14 h. Water was added, the mixture was stirred for 30 minutes. The mixture was extracted with dichloromethane, dried (sodium sulfate) and the solvent was removed in vacuum.

Aminophase-silicagel chromatography gave 470 mg of the title compound.

LC-MS (Method 2): $R_t$=1.31 min; MS (ESIpos): m/z=559 [M+H]$^+$.

$^1$H-NMR (400 MHz, DMSO-d6) δ[ppm]: 1.171 (1.05), 1.279 (1.72), 1.295 (1.76), 1.307 (0.93), 1.323 (0.90), 1.349 (2.19), 1.364 (2.66), 1.369 (4.04), 1.376 (16.00), 1.987 (1.78), 5.758 (2.03), 7.171 (0.86), 8.622 (1.34), 8.801 (1.46).

Example 36.02

3,3,3-trifluoro-1-(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)propan-1-one (single stereoisomer A)

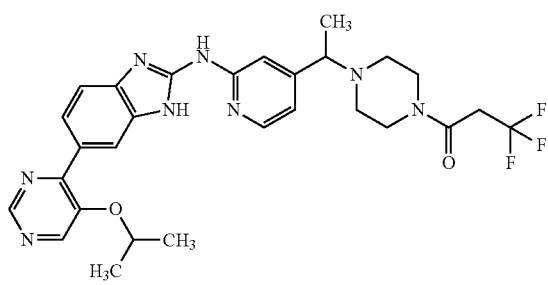 [SMILES: CC(C)Oc1cncnc1-c1ccc2nc(Nc3cc(C(C)N4CCN(C(=O)CC(F)(F)F)CC4)ccn3)[nH]c2c1]

Starting with crude N-{4-[(1R or 1S)-1-(piperazin-1-yl)ethyl]pyridin-2-yl}-6-[5-(propan-2-yloxy)pyrimidin-4-yl]-1H-benzimidazol-2-amine hydrochloride (single stereoisomer A) (160 mg, approx. 200 μmol) and 3,3,3-trifluoropropanoic acid (77.0 mg, 601 μmol), Example 36.02 was prepared analogously to the procedure for the preparation of Example 16.05.02.

Yield: 53.0 mg of the title compound.

Optical rotation [α]$_D$+30.1° (from solution in DMSO, c=2.12 mg/mL)

LC-MS (Method 2): $R_t$=1.13 min; MS (ESIpos): m/z=569 [M+H]$^+$.

$^1$H-NMR (400 MHz, DMSO-d6) δ [ppm]: 1.154 (1.10), 1.172 (2.36), 1.189 (1.29), 1.293 (5.93), 1.309 (6.05), 1.349 (8.44), 1.363 (8.47), 1.987 (4.40), 2.327 (1.16), 2.331 (1.33), 2.345 (1.33), 2.427 (1.53), 2.518 (2.74), 2.523 (1.84), 3.425 (1.56), 3.438 (2.82), 3.450 (2.04), 3.469 (3.01), 3.486 (3.49), 3.580 (1.08), 3.608 (3.07), 3.635 (2.93), 4.016 (0.97), 4.034 (0.96), 4.830 (1.28), 4.845 (1.74), 4.861 (1.31), 5.759 (16.00), 6.946 (1.69), 6.949 (1.70), 6.959 (1.75), 6.962 (1.75), 7.179 (2.34), 8.282 (1.88), 8.296 (1.84), 8.623 (5.39), 8.802 (6.53).

Example 36.03 cyclopropyl(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)methanone (single stereoisomer A)

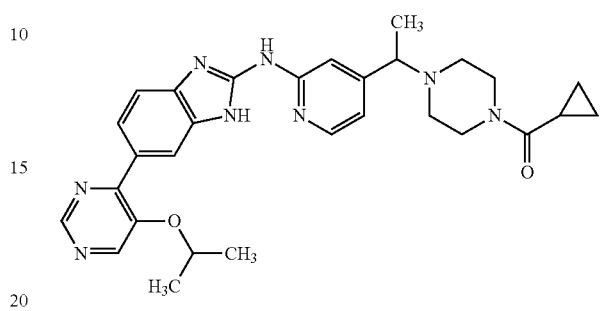

Starting with crude N-{4-[(1R or 1S)-1-(piperazin-1-yl)ethyl]pyridin-2-yl}-6-[5-(propan-2-yloxy)pyrimidin-4-yl]-1H-benzimidazol-2-amine hydrochloride (single stereoisomer A) (160 mg, approx. 200 μmol) and cyclopropanecarboxylic acid (51.8 mg, 601 μmol), Example 36.03 was prepared analogously to the procedure for the preparation of Example 16.05.02.

Yield: 67.0 mg of the title compound.

Optical rotation [α]$_D$+45.2° (from solution in DMSO, c=2.66 mg/mL)

LC-MS (Method 2): $R_t$=1.09 min; MS (ESIpos): m/z=527 [M+H]$^+$.

$^1$H-NMR (400 MHz, DMSO-d6) δ[ppm]: 0.656 (2.31), 0.663 (5.33), 0.668 (3.36), 0.676 (2.68), 0.683 (6.46), 0.687 (5.50), 0.692 (5.97), 0.699 (5.32), 0.704 (6.15), 0.711 (2.91), 1.154 (2.05), 1.172 (4.27), 1.189 (2.26), 1.295 (10.30), 1.312 (10.64), 1.349 (15.35), 1.363 (15.27), 1.916 (1.28), 1.922 (1.36), 1.935 (2.28), 1.947 (1.30), 1.954 (1.19), 1.987 (7.74), 2.318 (1.26), 2.323 (1.39), 2.327 (1.49), 2.331 (1.22), 2.397 (1.80), 2.456 (1.55), 2.518 (2.36), 2.685 (1.03), 3.436 (1.19), 3.452 (3.77), 3.469 (4.81), 3.485 (2.42), 3.675 (2.47), 4.016 (1.68), 4.034 (1.63), 4.830 (2.22), 4.845 (3.02), 4.861 (2.24), 4.876 (0.85), 5.759 (16.00), 6.953 (3.00), 6.956 (2.93), 6.966 (3.02), 6.970 (2.92), 7.187 (5.09), 8.283 (3.40), 8.296 (3.23), 8.623 (9.76), 8.803 (11.46), 12.247 (1.48).

Example 36.04 cyclobutyl(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)methanone (single stereoisomer A)

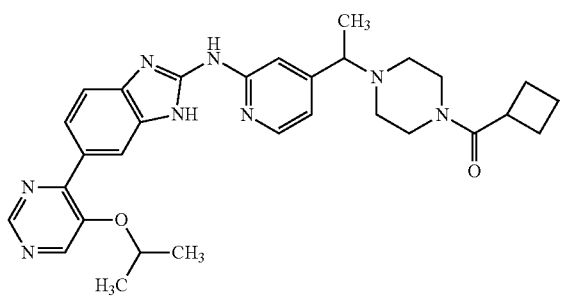 [SMILES: CC(C)Oc1cncnc1-c1ccc2nc(Nc3cc(C(C)N4CCN(C(=O)C5CCC5)CC4)ccn3)[nH]c2c1]

Starting with crude N-{4-[(1R or 1S)-1-(piperazin-1-yl)ethyl]pyridin-2-yl}-6-[5-(propan-2-yloxy)pyrimidin-4-yl]-1H-benzimidazol-2-amine hydrochloride (single stereoisomer A) (160 mg, approx. 200 μmol) and cyclobutanecarboxylic acid (60.2 mg, 601 μmol), Example 36.04 was prepared analogously to the procedure for the preparation of Example 16.05.02.

Yield: 53.0 mg of the title compound.

Optical rotation [α]$_D$+40.6° (from solution in DMSO, c=2.15 mg/mL)

LC-MS (Method 2): R$_t$=1.16 min; MS (ESIpos): m/z=541 [M+H]$^+$.

$^1$H-NMR (400 MHz, DMSO-d6) δ[ppm]: 1.153 (1.45), 1.171 (2.93), 1.189 (1.50), 1.275 (7.99), 1.292 (8.05), 1.347 (10.61), 1.362 (10.36), 1.716 (1.07), 1.822 (0.91), 1.843 (1.75), 1.865 (1.30), 1.870 (1.31), 1.986 (5.35), 2.029 (1.97), 2.039 (1.44), 2.046 (1.44), 2.052 (2.26), 2.060 (1.70), 2.076 (1.48), 2.081 (1.27), 2.099 (2.32), 2.120 (2.44), 2.124 (2.31), 2.149 (1.29), 2.282 (1.76), 2.296 (1.95), 2.311 (1.78), 2.322 (1.17), 2.388 (1.32), 2.401 (1.36), 3.271 (1.68), 3.294 (3.97), 3.307 (3.41), 3.314 (3.52), 3.426 (3.12), 3.442 (3.92), 4.016 (1.21), 4.034 (1.20), 4.829 (1.71), 4.844 (2.32), 4.859 (1.71), 5.758 (16.00), 6.938 (2.29), 6.951 (2.30), 6.953 (2.29), 7.172 (3.82), 8.275 (2.42), 8.287 (2.28), 8.622 (7.20), 8.802 (8.36), 12.243 (1.32).

Example 37.01

3,3,3-trifluoro-1-{4-[(2-{[6-(1-methyl-1H-pyrazol-4-yl)-1H-benzimidazol-2-yl]amino}pyridin-4-yl)methyl]piperazin-1-yl}propan-1-one

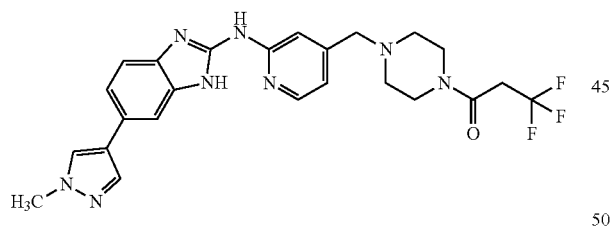

Starting with crude 6-(1-methyl-1H-pyrazol-4-yl)-N-[4-(piperazin-1-ylmethyl)pyridin-2-yl]-1H-benzimidazol-2-amine hydrochloride (120 mg, approx. 208 μmol) and 3,3,3-trifluoropropanoic acid (28 μl, 98% purity, 310 μmol), Example 37.01 was prepared analogously to the procedure for the preparation of Example 05.01.

Yield: 46.0 mg of the title compound.

LC-MS (Method 1): R$_t$=0.66 min; MS (ESIpos): m/z=499 [M+H]$^+$.

$^1$H-NMR (400 MHz, DMSO-d$_6$): δ [ppm]=2.37-2.44 (m, 4H), 3.43-3.56 (m, 6H), 3.66 (q, 2H), 3.87 (s, 3H), 6.92 (d, 1H), 7.13-7.67 (m, 4H), 7.78 (br s, 1H), 8.03 (br s, 1H), 8.26 (d, 1H), 10.59 (br s, 1H), 12.04 (br s, 1H).

Example 37.02

2-cyclopropyl-1-{4-[(2-{[6-(1-methyl-1H-pyrazol-4-yl)-1H-benzimidazol-2-yl]amino}pyridin-4-yl)methyl]piperazin-1-yl}ethanone

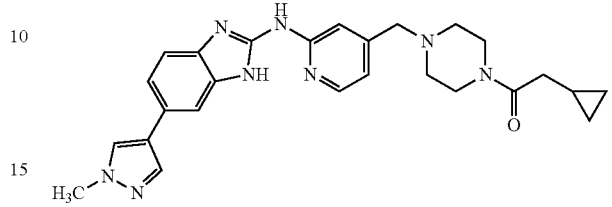

Starting with crude 6-(1-methyl-1H-pyrazol-4-yl)-N-[4-(piperazin-1-ylmethyl)pyridin-2-yl]-1H-benzimidazol-2-amine hydrochloride (120 mg, approx. 208 μmol) and cyclopropylacetic acid (30 μl, 98% purity, 310 μmol), Example 37.02 was prepared analogously to the procedure for the preparation of Example 05.01.

Yield: 70.0 mg of the title compound.

LC-MS (Method 1): R$_t$=0.62 min; MS (ESIneg): m/z=469 [M−H]$^+$.

$^1$H-NMR (400 MHz, DMSO-d6) δ[ppm]: 0.000 (0.96), 0.011 (3.51), 0.014 (3.21), 0.023 (3.61), 0.026 (3.23), 0.037 (1.08), 0.330 (1.08), 0.340 (3.06), 0.344 (3.06), 0.350 (1.62), 0.355 (1.72), 0.360 (3.23), 0.364 (2.97), 0.375 (1.08), 0.834 (0.69), 0.837 (0.70), 0.842 (0.69), 0.854 (1.08), 2.153 (5.45), 2.169 (5.26), 2.238 (0.98), 2.243 (1.34), 2.248 (1.15), 2.273 (2.66), 2.292 (2.54), 2.305 (2.60), 2.438 (3.88), 2.580 (0.74), 2.585 (1.00), 2.590 (0.74), 3.368 (2.58), 3.415 (8.30), 3.776 (9.26), 5.675 (16.00), 6.821 (1.99), 6.824 (1.98), 6.837 (1.99), 7.102 (2.42), 8.157 (3.11), 8.169 (2.97), 10.485 (1.07), 11.935 (1.46).

Example 37.03 cyclopropyl{4-[(2-{[6-(1-methyl-1H-pyrazol-4-yl)-1H-benzimidazol-2-yl]amino}pyridin-4-yl)methyl]piperazin-1-yl}methanone

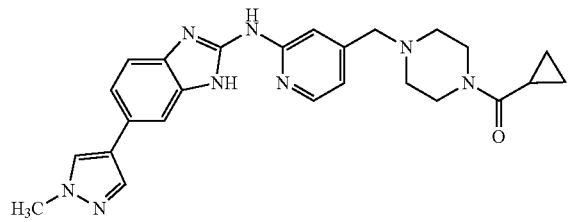 [SMILES: Cn1cc(-c2ccc3nc(Nc4cc(CN5CCN(C(=O)C6CC6)CC5)ccn4)[nH]c3c2)cn1]

Starting with crude 6-(1-methyl-1H-pyrazol-4-yl)-N-[4-(piperazin-1-ylmethyl)pyridin-2-yl]-1H-benzimidazol-2-amine hydrochloride (120 mg, approx. 208 μmol) and cyclopropanecarboxylic acid (25 μl, 98% purity, 310 μmol), Example 37.03 was prepared analogously to the procedure for the preparation of Example 05.01.

Yield: 65.0 mg of the title compound.

LC-MS (Method 2): R$_t$=0.95 min; MS (ESIpos): m/z=457 [M+H]$^+$.

$^1$H-NMR (400 MHz, DMSO-d$_6$): δ [ppm]=0.65-0.76 (m, 4H), 1.92-2.02 (m, 1H), 2.34-2.45 (m, 4H), 3.51 (s, 4H), 3.70 (br s, 2H), 3.86 (s, 3H), 6.89-6.96 (m, 1H), 7.14-7.65 (m, 4H), 7.71-7.84 (m, 1H), 7.94-8.12 (m, 1H), 8.25 (d, 1H), 10.57 (br s, 1H), 12.02 (br s, 1H).

Example 37.04 cyclobutyl{4-[(2-{[6-(1-methyl-1H-pyrazol-4-yl)-1H-benzimidazol-2-yl]amino}pyridin-4-yl)methyl]piperazin-1-yl}methanone

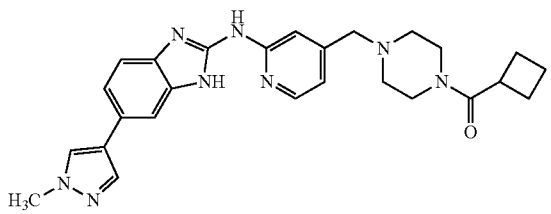 [SMILES: Cn1cc(-c2ccc3nc(Nc4cc(CN5CCN(C(=O)C6CCC6)CC5)ccn4)[nH]c3c2)cn1]

Starting with crude 6-(1-methyl-1H-pyrazol-4-yl)-N-[4-(piperazin-1-ylmethyl)pyridin-2-yl]-1H-benzimidazol-2-amine hydrochloride (120 mg, approx. 208 µmol) and cyclobutanecarboxylic acid (30 µl, 98% purity, 310 µmol), Example 37.04 was prepared analogously to the procedure for the preparation of Example 05.01.

Yield: 48.0 mg of the title compound.

LC-MS (Method 2): $R_t$=1.02 min; MS (ESIpos): m/z=471 [M+H]$^+$.

$^1$H-NMR (400 MHz, DMSO-d$_6$): δ [ppm]=1.67-1.79 (m, 1H), 1.82-1.95 (m, 1H), 2.01-2.22 (m, 4H), 2.35 (br s, 4H), 3.43-3.56 (m, 4H), 3.87 (s, 3H), 6.91 (d, 1H), 6.99-7.03 (m, 1H), 7.09-7.67 (m, 4H), 7.78 (br d, 1H), 7.94-8.12 (m, 1H), 8.19-8.30 (m, 1H), 10.57 (br s, 1H), 12.03 (br s, 1H).

Example 38.01 tert-butyl 4-[(2-{[6-(1-ethyl-1H-pyrazol-4-yl)-1H-benzimidazol-2-yl]amino}pyridin-4-yl)methyl]piperazine-1-carboxylate

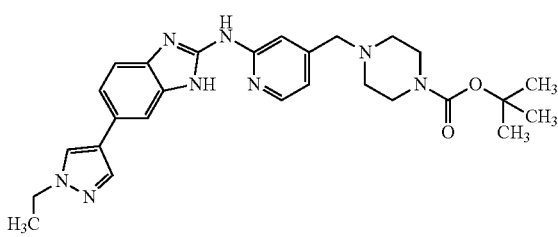 [SMILES: CCn1cc(-c2ccc3nc(Nc4cc(CN5CCN(C(=O)OC(C)(C)C)CC5)ccn4)[nH]c3c2)cn1]

To a stirred solution of 1H-imidazole (39.6 mg, 581 µmol) and di-1H-imidazol-1-ylmethanethione (654 mg, 95% purity, 3.49 mmol) in dichloromethane (60 mL) was added tert-butyl 4-[(2-aminopyridin-4-yl)methyl]piperazine-1-carboxylate (850 mg, 2.91 mmol) dissolved in dichloromethane (30 mL) at 0° C. The mixture was stirred at r.t. for 14 h. 4-(1-ethyl-1H-pyrazol-4-yl)benzene-1,2-diamine (706 mg, 3.49 mmol), dissolved in dichloromethane (30 mL) was added and the mixture was stirred at r.t. for 56 h. Water was added and the mixture was extracted with dichloromethane. The organic phase was dried (sodium sulfate) and filtered. N,N'-dipropan-2-ylcarbodiimide (0.64 mL, 4.0 mmol) was added. The mixture was stirred at r.t. for 4 h. Further N,N'-dipropan-2-ylcarbodiimide (0.32 mL, 2.0 mmol) was added and the mixture was stirred at r.t. for 14 h. Further N,N'-dipropan-2-ylcarbodiimide (0.32 mL, 2.0 mmol) was added and the mixture was stirred at r.t. for 14 h. Saturated sodium chloride solution was added, the mixture was stirred for 30 minutes and was extracted with dichloromethane, dried (sodium sulfate) and the solvent was removed in vacuum. Aminophase-silicagel chromatography followed by silicagel chromatography gave a solid that was triturated with ethanol to give 151 mg of the title compound.

LC-MS (Method 2): $R_t$=1.25 min; MS (ESIpos): m/z=503 [M+H]$^+$.

$^1$H-NMR (400 MHz, DMSO-d6) δ [ppm]: 1.388 (3.11), 1.392 (6.25), 1.394 (16.00), 1.410 (4.28), 1.428 (1.86), 1.987 (0.85), 2.354 (1.26), 3.333 (10.47), 3.347 (1.12), 3.488 (1.61), 5.760 (1.46), 8.235 (0.79), 8.249 (0.76).

Example 38.02

1-{4-[(2-{[6-(1-ethyl-1H-pyrazol-4-yl)-1H-benzimidazol-2-yl]amino}pyridin-4-yl)methyl]piperazin-1-yl}-3,3,3-trifluoropropan-1-one

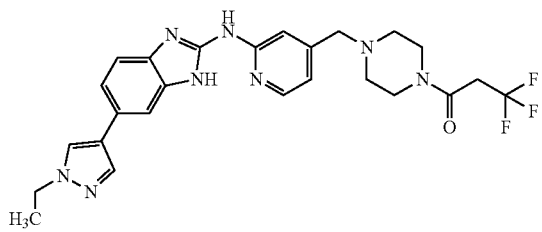 [SMILES: CCn1cc(-c2ccc3nc(Nc4cc(CN5CCN(C(=O)CC(F)(F)F)CC5)ccn4)[nH]c3c2)cn1]

Starting with crude 6-(1-ethyl-1H-pyrazol-4-yl)-N-[4-(piperazin-1-ylmethyl)pyridin-2-yl]-1H-benzimidazol-2-amine hydrochloride (135 mg, approx. 246 µmol) and 3,3,3-trifluoropropanoic acid (33 µl, 370 µmol) Example 38.02. was prepared analogously to the procedure for the preparation of Example 16.01.02.

Yield: 80.0 mg of the title compound.

LC-MS (Method 2): $R_t$=1.04 min; MS (ESIpos): m/z=513 [M+H]$^+$.

$^1$H-NMR (400 MHz, DMSO-d6) δ[ppm]: 1.392 (6.95), 1.410 (16.00), 1.428 (6.76), 2.327 (0.67), 2.365 (1.54), 2.378 (2.43), 2.390 (1.84), 2.406 (1.72), 2.419 (2.37), 2.431 (1.76), 2.518 (3.87), 2.523 (2.64), 2.669 (0.68), 3.456 (1.71), 3.469 (2.41), 3.481 (2.01), 3.493 (1.98), 3.514 (8.15), 3.610 (1.20), 3.638 (3.51), 3.665 (3.30), 3.693 (1.02), 4.117 (0.83), 4.135 (2.41), 4.154 (2.40), 4.171 (0.85), 6.906 (1.98), 6.910 (1.93), 6.919 (2.03), 6.922 (2.11), 7.190 (2.08), 8.243 (3.22), 8.257 (3.12), 10.580 (0.97), 12.021 (1.29).

Example 38.03 cyclopropyl{4-[(2-{[6-(1-ethyl-1H-pyrazol-4-yl)-1H-benzimidazol-2-yl]amino}pyridin-4-yl)methyl]piperazin-1-yl}methanone

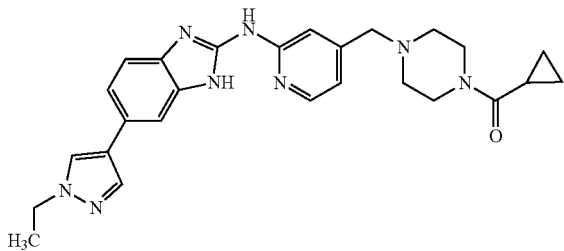 [SMILES: CCn1cc(-c2ccc3nc(Nc4cc(CN5CCN(C(=O)C6CC6)CC5)ccn4)[nH]c3c2)cn1]

Starting with crude 6-(1-ethyl-1H-pyrazol-4-yl)-N-[4-(piperazin-1-ylmethyl)pyridin-2-yl]-1H-benzimidazol-2-amine hydrochloride (135 mg, approx. 246 µmol) and cyclopropanecarboxylic acid (31 µl, 95% purity, 370 µmol) Example 38.03. was prepared analogously to the procedure for the preparation of Example 16.01.02.

Yield: 65.0 mg of the title compound.

LC-MS (Method 2): $R_t$=1.00 min; MS (ESIpos): m/z=471 [M+H]$^+$.

$^1$H-NMR (400 MHz, DMSO-d6) δ[ppm]: 0.674 (1.54), 0.682 (3.51), 0.688 (2.19), 0.695 (1.75), 0.702 (4.26), 0.707 (3.02), 0.714 (3.62), 0.721 (3.60), 0.726 (4.27), 0.733 (1.98), 1.393 (7.22), 1.411 (16.00), 1.429 (7.04), 1.958 (1.58), 2.361 (1.58), 3.511 (8.63), 3.698 (1.46), 4.118 (1.24), 4.136 (3.72), 4.154 (3.71), 4.172 (1.20), 5.756 (1.59), 6.913 (2.21), 6.917 (2.15), 6.926 (2.25), 6.929 (2.28), 7.198 (3.37), 8.245 (3.58), 8.259 (3.39), 10.567 (1.36), 12.010 (1.38).

Example 39.01.01 tert-butyl 4-{[2-({6-[1-(cyclopropylmethyl)-1H-pyrazol-4-yl]-1H-benzimidazol-2-yl}amino)pyridin-4-yl]methyl}piperazine-1-carboxylate

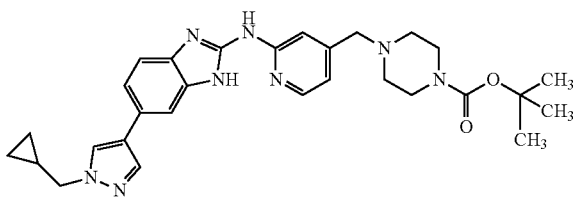 [SMILES: CC(C)(C)OC(=O)N1CCN(Cc2ccnc(Nc3nc4ccc(-c5cnn(CC6CC6)c5)cc4[nH]3)c2)CC1]

To a stirred solution of 1H-imidazole (53.0 mg, 779 µmol) and di-1H-imidazol-1-ylmethanethione (925 mg, 90% purity, 4.67 mmol) in dichloromethane (30 mL) was added tert-butyl 4-[(2-aminopyridin-4-yl)methyl]piperazine-1-carboxylate (1.14 g, 3.89 mmol), dissolved in dichloromethane (45 mL) at 0° C. The mixture was stirred at r.t. for 14 h. 4-[1-(cyclopropylmethyl)-1H-pyrazol-4-yl]benzene-1,2-diamine (1.10 g, 97% purity, 4.67 mmol), dissolved in dichloromethane (15 mL) was added and the mixture was stirred at r.t. for 2 h.

Water was added and the mixture was extracted with dichloromethane. The organic phase was dried (sodium sulfate) and filtered. N,N'-dipropan-2-ylcarbodiimide (0.87 mL, 5.5 mmol) was added. The mixture was stirred at r.t. for 4 h. Further N,N'-dipropan-2-ylcarbodiimide (0.87 mL, 5.5 mmol) was added and the mixture was stirred at 40° C. for 4 h. Saturated sodium chloride solution was added, the mixture was stirred for 30 minutes and was extracted with dichloromethane, dried (sodium sulfate) and the solvent was removed in vacuum.

Aminophase-silicagel chromatography gave 362 mg of the title compound.

LC-MS (Method 2): $R_t$=1.28 min; MS (ESIpos): m/z=529 [M+H]$^+$.

$^1$H-NMR (400 MHz, DMSO-d6) [ppm]: 0.389 (0.88), 0.393 (0.77), 0.402 (0.87), 0.405 (0.84), 0.537 (0.73), 0.541 (0.72), 0.557 (0.80), 1.394 (16.00), 1.987 (0.91), 2.342 (0.94), 2.354 (1.41), 2.366 (1.03), 3.331 (9.00), 3.348 (1.14), 3.967 (0.82), 3.984 (0.81), 5.759 (1.12), 7.172 (0.81), 8.235 (0.88), 8.248 (0.83).

Example 39.01.02

1-(4-{[2-({6-[1-(cyclopropylmethyl)-1H-pyrazol-4-yl]-1H-benzimidazol-2-yl}amino)pyridin-4-yl]methyl}piperazin-1-yl)-3,3,3-trifluoropropan-1-one

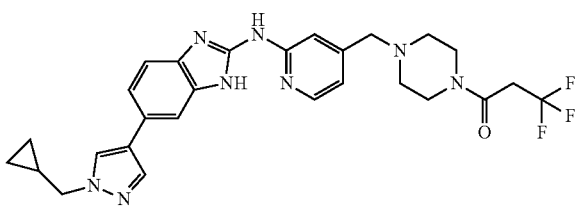 [SMILES: O=C(CC(F)(F)F)N1CCN(Cc2ccnc(Nc3nc4ccc(-c5cnn(CC6CC6)c5)cc4[nH]3)c2)CC1]

Starting with crude 6-[1-(cyclopropylmethyl)-1H-pyrazol-4-yl]-N-[4-(piperazin-1-ylmethyl)pyridin-2-yl]-1H-benzimidazol-2-amine hydrochloride (160 mg, approx. 344 µmol) and 3,3,3-trifluoropropanoic acid (132 mg, 1.03 mmol), Example 39.01.02 was prepared analogously to the procedure for the preparation of Example 16.05.02.

Yield: 104 mg of the title compound.

LC-MS (Method 2): $R_t$=1.11 min; MS (ESIpos): m/z=539 [M+H]$^+$.

$^1$H-NMR (400 MHz, DMSO-d6) δ[ppm]: 0.379 (1.53), 0.390 (6.33), 0.394 (5.52), 0.402 (6.13), 0.406 (6.11), 0.416 (2.29), 0.527 (2.28), 0.536 (5.22), 0.541 (5.32), 0.546 (2.93), 0.553 (2.91), 0.557 (5.80), 0.561 (5.00), 0.572 (1.75), 1.235 (0.70), 1.241 (0.91), 1.253 (1.50), 1.261 (1.40), 1.265 (1.10), 1.273 (2.36), 1.281 (1.10), 1.285 (1.35), 1.293 (1.40), 1.305 (0.71), 2.322 (0.64), 2.327 (0.92), 2.332 (0.70), 2.365 (3.21), 2.378 (4.92), 2.390 (3.78), 2.406 (3.55), 2.420 (4.73), 2.431 (3.48), 2.518 (3.14), 2.523 (1.92), 2.664 (0.59), 2.669 (0.85), 2.673 (0.61), 3.456 (3.60), 3.469 (4.89), 3.481 (4.06), 3.493 (4.00), 3.514 (16.00), 3.610 (2.44), 3.638 (6.87), 3.665 (6.48), 3.693 (1.99), 3.967 (5.70), 3.984 (5.65), 6.907 (4.01), 6.914 (3.91), 6.920 (3.88), 6.924 (3.96), 7.188 (5.22), 7.249 (1.25), 7.535 (0.77), 7.626 (0.65), 7.806 (1.00), 8.079 (0.88), 8.120 (0.92), 8.243 (6.26), 8.257 (6.04), 10.584 (2.42), 12.021 (2.56).

Example 39.01.03 cyclopropyl(4-{[2-({6-[1-(cyclopropylmethyl)-1H-pyrazol-4-yl]-1H-benzimidazol-2-yl}amino)pyridin-4-yl]methyl}piperazin-1-yl)methanone

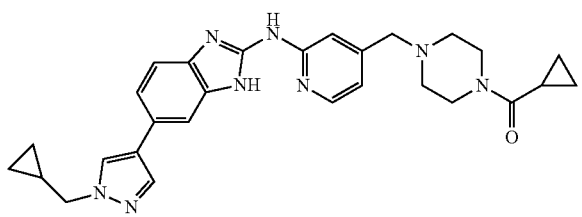 [SMILES: O=C(C1CC1)N1CCN(Cc2ccnc(Nc3nc4ccc(-c5cnn(CC6CC6)c5)cc4[nH]3)c2)CC1]

Starting with crude 6-[1-(cyclopropylmethyl)-1H-pyrazol-4-yl]-N-[4-(piperazin-1-ylmethyl)pyridin-2-yl]-1H-benzimidazol-2-amine hydrochloride (160 mg, approx. 344 µmol) and cyclopropanecarboxylic acid (88.9 mg, 1.03 mmol), Example 39.01.03 was prepared analogously to the procedure for the preparation of Example 16.05.02.

Yield: 115 mg of the title compound.

LC-MS (Method 2): $R_t$=1.08 min; MS (ESIpos): m/z=497 [M+H]$^+$.

$^1$H-NMR (400 MHz, DMSO-d6) δ[ppm]: 0.390 (1.58), 0.394 (1.38), 0.402 (1.52), 0.406 (1.51), 0.536 (1.33), 0.541 (1.31), 0.556 (1.45), 0.561 (1.24), 0.682 (1.61), 0.688 (0.99), 0.702 (1.97), 0.707 (1.64), 0.712 (1.74), 0.719 (1.60), 0.724 (1.95), 0.731 (0.89), 3.335 (16.00), 3.966 (1.50), 3.984 (1.49), 6.915 (1.00), 6.918 (0.99), 6.927 (0.97), 6.931 (0.99), 7.192 (1.47), 8.246 (1.57), 8.259 (1.54).

Example 39.02.01 tert-butyl 4-{(1R or 1S)-1-[2-({6-[1-(cyclopropylmethyl)-1H-pyrazol-4-yl]-1H-benzimidazol-2-yl}amino)pyridin-4-yl]ethyl}piperazine-1-carboxylate (single stereoisomer A)

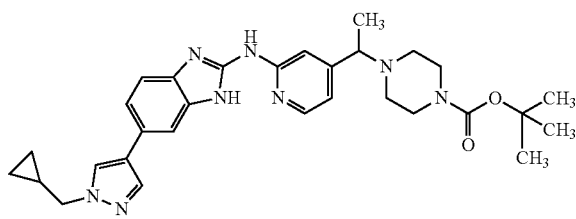 [SMILES: CC(c1ccnc(Nc2nc3ccc(-c4cnn(CC5CC5)c4)cc3[nH]2)c1)N1CCN(C(=O)OC(C)(C)C)CC1]

To a stirred solution of 1H-imidazole (55.1 mg, 809 µmol) and di-1H-imidazol-1-ylmethanethione (962 mg, 90% purity, 4.86 mmol) in dichloromethane (30 mL) was added tert-butyl 4-[(1R or 1S)-1-(2-aminopyridin-4-yl)ethyl]piperazine-1-carboxylate (1.24 g, 4.05 mmol), dissolved in dichloromethane (45 mL) at 0° C. The mixture was stirred at r.t. for 14 h. 4-[1-(cyclopropylmethyl)-1H-pyrazol-4-yl]benzene-1,2-diamine (1.14 g, 97% purity, 4.86 mmol), dissolved in dichloromethane (15 mL) was added and the mixture was stirred at r.t. for 2 h. Water was added and the mixture was extracted with dichloromethane. The organic phase was dried (sodium sulfate) and filtered. N,N'-dipropan-2-ylcarbodiimide (0.88 mL, 5.6 mmol) was added. The mixture was stirred at r.t. for 4 h. Further N,N'-dipropan-2-ylcarbodiimide (0.88 mL, 5.6 mmol) was added and the mixture was stirred at 40° C. for 4 h. The solvent was removed in vacuum. Ethyl acetate and water were added and the mixture was stirred at r.t. for 30 minutes. The mixture was extracted with ethyl acetate, dried (sodium sulfate) and the solvent was removed in vacuum. Aminophase-silicagel chromatography followed by silicagel chromatography gave 391 mg of the title compound.

LC-MS (Method 2): $R_t$=1.32 min; MS (ESIpos): m/z=543 [M+H]$^+$.

$^1$H-NMR (400 MHz, DMSO-d6) δ[ppm]: 0.390 (0.92), 0.394 (0.80), 0.402 (0.91), 0.405 (0.90), 0.537 (0.76), 0.541 (0.75), 0.557 (0.82), 0.561 (0.72), 1.274 (2.01), 1.290 (1.91), 1.376 (16.00), 2.083 (1.81), 3.320 (1.26), 3.967 (0.87), 3.984 (0.87), 5.758 (4.92), 7.158 (0.88), 8.238 (0.96), 8.251 (0.89).

Example 39.02.02

1-(4-{(1R or 1S)-1-[2-({6-[1-(cyclopropylmethyl)-1H-pyrazol-4-yl]-1H-benzimidazol-2-yl}amino)pyridin-4-yl]ethyl}piperazin-1-yl)-3,3,3-trifluoropropan-1-one (single stereoisomer A)

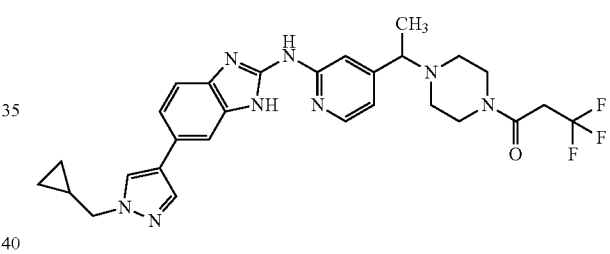

Starting with crude 6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride (single stereoisomer A) (120 mg, approx. 251 µmol) and 3,3,3-trifluoropropanoic acid (96.2 mg, 752 µmol), Example 39.02.02 was prepared analogously to the procedure for the preparation of Example 16.05.02.

Yield: 61.0 mg of the title compound.

Optical rotation $[α]_D$+30.4° (from solution in DMSO, c=2.25 mg/mL)

LC-MS (Method 2): $R_t$=1.15 min; MS (ESIpos): m/z=553 [M+H]$^+$.

$^1$H-NMR (400 MHz, DMSO-d6) δ [ppm]: 0.379 (1.00), 0.390 (3.98), 0.394 (3.43), 0.402 (3.84), 0.406 (3.81), 0.416 (1.36), 0.527 (1.41), 0.537 (3.36), 0.542 (3.28), 0.547 (1.78), 0.553 (1.83), 0.558 (3.59), 0.562 (3.06), 0.573 (1.06), 1.273 (1.85), 1.288 (8.10), 1.305 (8.07), 1.987 (0.92), 2.323 (1.49), 2.327 (1.80), 2.332 (1.50), 2.337 (1.68), 2.351 (1.49), 2.364 (1.27), 2.416 (1.80), 2.423 (1.82), 3.422 (2.02), 3.435 (3.89), 3.447 (2.47), 3.453 (2.92), 3.470 (3.84), 3.480 (3.18), 3.578 (1.40), 3.606 (4.04), 3.633 (3.75), 3.661 (1.16), 3.967 (3.75), 3.984 (3.71), 5.759 (16.00), 6.918 (2.49), 6.922 (2.48), 6.932 (2.48), 6.935 (2.50), 7.172 (3.44), 8.247 (4.15), 8.260 (3.89), 10.571 (1.34).

Example 39.02.03 cyclopropyl(4-{(1R or 1S)-1-[2-({6-[1-(cyclopropylmethyl)-1H-pyrazol-4-yl]-1H-benzimidazol-2-yl}amino)pyridin-4-yl]ethyl}piperazin-1-yl)methanone (single stereoisomer A)

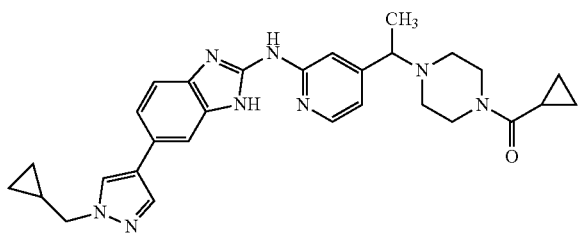 [SMILES: CC(c1ccnc(Nc2nc3ccc(-c4cnn(CC5CC5)c4)cc3[nH]2)c1)N1CCN(C(=O)C2CC2)CC1]

Starting with crude 6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride (single stereoisomer A) (120 mg, approx. 251 µmol) and cyclopropanecarboxylic acid (64.7 mg, 752 µmol), Example 39.02.03 was prepared analogously to the procedure for the preparation of Example 16.05.02.

Yield: 58.0 mg of the title compound.

Optical rotation $[\alpha]_D$+37.10 (from solution in DMSO, c=2.66 mg/mL)

LC-MS (Method 2): $R_t$=1.11 min; MS (ESIpos): m/z=511 [M+H]$^+$.

$^1$H-NMR (400 MHz, DMSO-d6) δ[ppm]: 0.390 (3.29), 0.394 (2.88), 0.402 (3.18), 0.406 (3.23), 0.416 (1.18), 0.527 (1.17), 0.537 (2.74), 0.542 (2.77), 0.547 (1.53), 0.553 (1.51), 0.557 (3.00), 0.562 (2.62), 0.573 (0.93), 0.656 (1.42), 0.663 (3.37), 0.669 (2.05), 0.676 (1.62), 0.683 (4.14), 0.687 (3.40), 0.691 (3.84), 0.698 (3.29), 0.703 (3.81), 0.710 (1.77), 1.172 (0.96), 1.273 (1.45), 1.291 (7.14), 1.308 (6.65), 1.935 (1.44), 1.987 (1.49), 2.327 (1.00), 2.523 (1.43), 3.437 (1.94), 3.453 (2.49), 3.469 (1.84), 3.672 (1.50), 3.967 (3.30), 3.984 (3.27), 5.759 (16.00), 6.927 (2.04), 6.930 (2.08), 6.940 (2.04), 6.944 (2.06), 7.181 (2.92), 8.247 (3.46), 8.260 (3.26).

Example 40.01

3,3,3-trifluoro-1-{4-[(2-{[6-(1-methyl-1H-pyrazol-3-yl)-1H-benzimidazol-2-yl]amino}pyridin-4-yl)methyl]piperazin-1-yl}propan-1-one

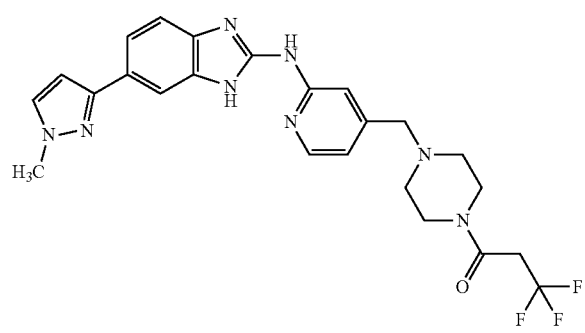 [SMILES: Cn1ccc(-c2ccc3nc(Nc4cc(CN5CCN(C(=O)CC(F)(F)F)CC5)ccn4)[nH]c3c2)n1]

Starting with crude 6-(1-methyl-1H-pyrazol-3-yl)-N-[4-(piperazin-1-ylmethyl)pyridin-2-yl]-1H-benzimidazol-2-amine hydrochloride (150 mg, approx. 282 µmol) and 3,3,3-trifluoropropanoic acid (54.1 mg, 423 µmol), Example 40.01 was prepared analogously to the procedure for the preparation of Example 01.02.

Yield: 39 mg of the title compound.

LC-MS (Method 2): $R_t$=1.02 min; MS (ESIpos): m/z=499 [M+H]$^+$.

$^1$H-NMR (400 MHz, CHLOROFORM-d) [ppm]: 1.146 (1.00), 1.163 (0.99), 1.262 (0.58), 2.019 (1.32), 2.347 (3.85), 2.359 (7.41), 2.370 (7.02), 2.465 (0.83), 2.476 (1.43), 2.489 (1.34), 3.099 (2.51), 3.124 (7.42), 3.149 (7.37), 3.175 (2.52), 3.204 (0.70), 3.229 (1.73), 3.247 (3.23), 3.254 (4.62), 3.260 (4.35), 3.271 (3.22), 3.460 (11.58), 3.491 (3.85), 3.502 (4.66), 3.515 (3.20), 3.540 (2.72), 3.598 (0.45), 3.681 (0.56), 3.694 (0.72), 3.706 (0.61), 3.968 (16.00), 6.550 (4.25), 6.555 (4.30), 6.861 (3.34), 6.864 (3.30), 6.874 (3.44), 6.877 (3.37), 7.007 (0.79), 7.017 (0.55), 7.102 (4.89), 7.397 (3.48), 7.529 (0.73), 7.675 (1.77), 7.909 (0.57), 8.263 (5.60), 8.276 (5.42), 8.311 (0.95), 8.324 (0.88).

Example 40.02

2-cyclopropyl-1-{4-[(2-{[6-(1-methyl-1H-pyrazol-3-yl)-1H-benzimidazol-2-yl]amino}pyridin-4-yl)methyl]piperazin-1-yl}ethanone

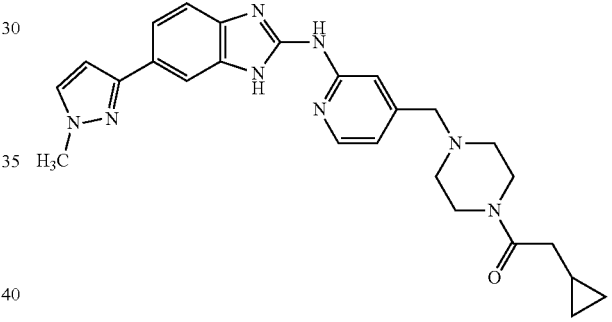

Starting with crude 6-(1-methyl-1H-pyrazol-3-yl)-N-[4-(piperazin-1-ylmethyl)pyridin-2-yl]-1H-benzimidazol-2-amine hydrochloride (150 mg, approx. 282 µmol) and cyclopropylacetic acid (42.3 mg, 423 µmol), Example 40.02 was prepared analogously to the procedure for the preparation of Example 01.02.

Yield: 55 mg of the title compound.

LC-MS (Method 2): $R_t$=1.01 min; MS (ESIpos): m/z=471 [M+H]$^+$.

$^1$H-NMR (400 MHz, CHLOROFORM-d) [ppm]: 0.133 (2.01), 0.145 (7.40), 0.148 (6.12), 0.157 (7.30), 0.160 (7.78), 0.171 (4.38), 0.182 (2.21), 0.185 (2.50), 0.197 (0.92), 0.527 (2.66), 0.538 (5.87), 0.541 (6.24), 0.547 (3.95), 0.553 (3.39), 0.558 (8.32), 0.561 (7.73), 0.568 (1.69), 0.573 (3.31), 0.577 (1.53), 0.579 (2.35), 0.582 (2.08), 0.594 (0.86), 0.968 (0.68), 0.973 (0.81), 0.976 (0.70), 0.981 (0.52), 0.985 (1.47), 0.988 (1.35), 0.992 (1.39), 0.997 (1.09), 1.001 (1.26), 1.005 (2.50), 1.010 (1.28), 1.013 (1.28), 1.017 (1.39), 1.022 (1.76), 1.025 (1.60), 1.030 (0.89), 1.034 (0.96), 1.037 (0.96), 1.042 (1.29), 1.048 (1.10), 1.055 (0.77), 1.060 (0.61), 1.063 (0.57), 1.067 (1.94), 1.075 (0.98), 1.086 (0.92), 1.093 (0.44), 1.259 (0.49), 2.203 (12.70), 2.220 (12.47), 2.239 (0.50), 2.264 (4.29), 2.274 (0.74), 2.281 (4.14), 2.291 (0.50), 2.345 (3.59), 2.360 (7.87), 2.371 (8.10), 2.385 (4.12), 2.432 (1.34), 2.444 (2.80), 2.456 (3.07), 2.469 (1.58), 3.313 (3.36), 3.325 (4.51), 3.337

(3.26), 3.467 (14.60), 3.487 (1.71), 3.528 (7.00), 3.545 (4.34), 3.556 (3.11), 3.582 (0.75), 3.656 (1.06), 3.669 (1.41), 3.680 (1.08), 3.951 (0.84), 3.973 (16.00), 6.553 (4.22), 6.557 (4.16), 6.900 (3.71), 6.903 (3.90), 6.914 (4.01), 6.917 (3.96), 7.007 (1.60), 7.010 (1.10), 7.023 (1.10), 7.128 (7.10), 7.395 (4.33), 7.399 (4.26), 7.454 (0.57), 7.529 (0.78), 7.671 (1.84), 7.901 (0.87), 8.013 (0.54), 8.266 (6.85), 8.279 (6.59), 8.304 (2.03), 8.317 (1.91).

Example 40.03 cyclopropyl{4-[(2-{[6-(1-methyl-1H-pyrazol-3-yl)-1H-benzimidazol-2-yl]amino}pyridin-4-yl)methyl]piperazin-1-yl}methanone

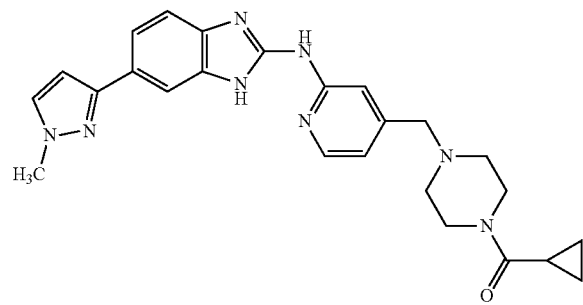 [SMILES: Cn1ccc(-c2ccc3nc(Nc4cc(CN5CCN(C(=O)C6CC6)CC5)ccn4)[nH]c3c2)n1]

Starting with crude 6-(1-methyl-1H-pyrazol-3-yl)-N-[4-(piperazin-1-ylmethyl)pyridin-2-yl]-1H-benzimidazol-2-amine hydrochloride (150 mg, approx. 282 µmol) and cyclopropanecarboxylic acid (36.4 mg, 423 µmol), Example 40.03 was prepared analogously to the procedure for the preparation of Example 01.02.

Yield: 30 mg of the title compound.

LC-MS (Method 2): $R_t$=0.98 min; MS (ESIpos): m/z=457 [M+H]$^+$.

$^1$H-NMR (400 MHz, CHLOROFORM-d) δ [ppm]: 0.716 (1.84), 0.726 (5.51), 0.733 (6.37), 0.742 (3.99), 0.746 (6.10), 0.751 (3.91), 0.754 (6.99), 0.758 (2.88), 0.763 (2.89), 0.767 (1.45), 0.771 (1.87), 0.778 (2.14), 0.787 (0.73), 0.951 (2.35), 0.960 (6.88), 0.963 (4.71), 0.967 (6.40), 0.972 (7.55), 0.979 (6.56), 0.983 (3.24), 0.986 (2.06), 0.989 (3.47), 0.995 (2.39), 1.002 (1.99), 1.012 (0.78), 1.648 (1.11), 1.659 (2.03), 1.667 (2.26), 1.671 (1.67), 1.679 (3.86), 1.688 (1.65), 1.691 (2.17), 1.699 (1.97), 1.706 (1.01), 1.711 (1.15), 1.714 (1.04), 1.718 (0.69), 1.726 (1.34), 1.735 (0.69), 1.738 (0.78), 1.746 (0.76), 1.758 (0.45), 2.038 (0.45), 2.401 (5.70), 2.462 (1.27), 3.481 (15.71), 3.540 (4.79), 3.576 (8.71), 3.690 (1.32), 3.972 (16.00), 6.556 (4.82), 6.562 (4.78), 6.928 (4.13), 6.931 (3.97), 6.941 (4.19), 6.944 (3.96), 7.007 (1.02), 7.023 (0.95), 7.036 (0.95), 7.131 (7.55), 7.394 (4.07), 7.460 (0.50), 7.529 (1.24), 7.675 (2.01), 7.916 (0.72), 8.273 (7.01), 8.286 (6.73), 8.309 (1.74), 8.324 (1.65).

Example 40.04 cyclobutyl{4-[(2-{[6-(1-methyl-1H-pyrazol-3-yl)-1H-benzimidazol-2-yl]amino}pyridin-4-yl)methyl]piperazin-1-yl}methanone

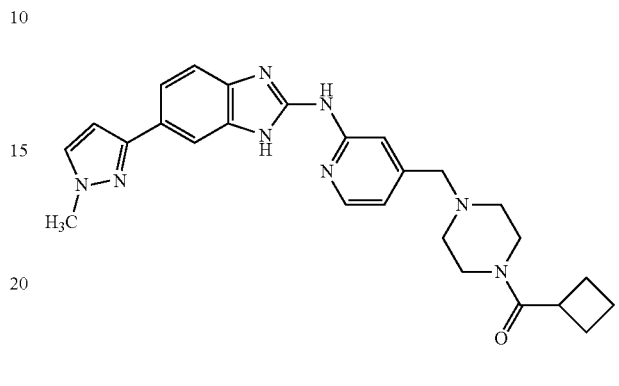

Starting with crude 6-(1-methyl-1H-pyrazol-3-yl)-N-[4-(piperazin-1-ylmethyl)pyridin-2-yl]-1H-benzimidazol-2-amine hydrochloride (150 mg, approx. 282 µmol) and cyclobutanecarboxylic acid (42.3 mg, 423 µmol), Example 40.04 was prepared analogously to the procedure for the preparation of Example 01.02.

Yield: 50 mg of the title compound.

LC-MS (Method 2): $R_t$=1.04 min; MS (ESIpos): m/z=471 [M+H]$^+$.

$^1$H-NMR (400 MHz, CHLOROFORM-d) δ [ppm]: 1.252 (0.50), 1.299 (1.03), 1.804 (0.58), 1.820 (0.81), 1.826 (1.25), 1.828 (1.34), 1.832 (1.16), 1.839 (1.22), 1.842 (1.30), 1.849 (1.37), 1.853 (2.01), 1.856 (1.86), 1.863 (1.38), 1.877 (1.57), 1.888 (0.96), 1.897 (1.96), 1.918 (3.52), 1.925 (1.30), 1.940 (3.09), 1.946 (2.14), 1.963 (1.67), 1.967 (1.66), 1.983 (0.48), 1.990 (0.96), 1.993 (0.71), 2.015 (0.93), 2.021 (0.41), 2.037 (0.77), 2.043 (0.62), 2.057 (1.04), 2.066 (1.32), 2.072 (1.02), 2.077 (1.61), 2.087 (3.04), 2.093 (1.99), 2.097 (2.10), 2.099 (1.99), 2.102 (2.07), 2.109 (3.11), 2.118 (2.47), 2.123 (1.74), 2.130 (1.59), 2.132 (1.62), 2.139 (1.38), 2.154 (0.72), 2.166 (0.42), 2.229 (0.55), 2.236 (0.63), 2.239 (0.93), 2.244 (0.57), 2.248 (0.65), 2.251 (0.65), 2.254 (0.65), 2.260 (1.24), 2.263 (1.26), 2.267 (1.54), 2.272 (1.16), 2.289 (3.63), 2.294 (2.98), 2.301 (3.75), 2.311 (7.30), 2.313 (7.01), 2.323 (4.51), 2.334 (3.04), 2.340 (3.55), 2.346 (3.51), 2.350 (4.14), 2.354 (3.93), 2.363 (5.38), 2.375 (4.46), 2.382 (2.29), 2.398 (2.61), 2.404 (1.65), 2.407 (1.87), 2.420 (1.54), 2.431 (1.80), 2.446 (1.18), 2.451 (0.49), 3.141 (0.55), 3.160 (1.92), 3.163 (1.99), 3.182 (2.86), 3.184 (2.88), 3.190 (0.96), 3.206 (2.83), 3.211 (4.00), 3.225 (4.69), 3.236 (3.47), 3.261 (0.61), 3.354 (1.16), 3.366 (1.36), 3.379 (1.12), 3.456 (12.07), 3.520 (7.21), 3.527 (3.83), 3.541 (2.56), 3.567 (0.44), 3.629 (0.88), 3.641 (1.15), 3.653 (0.88), 3.973 (16.00), 6.553 (4.07), 6.558 (4.02), 6.898 (3.24), 6.902 (3.37), 6.912 (3.44), 6.915 (3.38), 7.006 (0.70), 7.048 (0.93), 7.052 (0.86), 7.060 (0.96), 7.064 (0.91), 7.109 (5.86), 7.395 (3.42), 7.399 (3.37), 7.528 (0.83), 7.621 (0.53), 7.667 (2.03), 7.688 (1.36), 7.860 (0.82), 7.909 (0.61), 8.191 (1.36), 8.193 (1.39), 8.203 (1.32), 8.205 (1.41), 8.222 (1.31), 8.261 (5.52), 8.274 (5.27).

Example 41.01 tert-butyl 4-[(2-{[6-(1-methyl-1H-1,2,4-triazol-5-yl)-1H-benzimidazol-2-yl]amino}pyridin-4-yl)methyl]piperazine-1-carboxylate

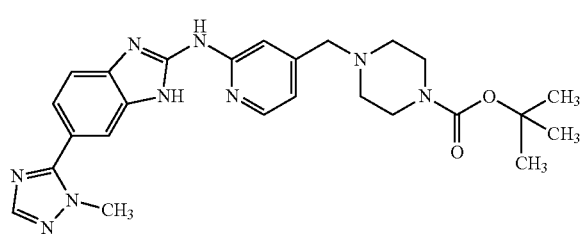 [SMILES: Cn1ncnc1-c1ccc2nc(Nc3cc(CN4CCN(C(=O)OC(C)(C)C)CC4)ccn3)[nH]c2c1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (800 mg, 1.50 mmol) in 1-propanol (17 mL) was added a potassium carbonate solution (2.2 mL, 2.0 M, 4.5 mmol), 5-bromo-1-methyl-1H-1,2,4-triazole (375 mg, 97% purity, 2.25 mmol), triphenylphosphine (39.3 mg, 150 µmol) and PdCl$_2$(PPh$_3$)$_2$ (105 mg, 150 µmol). The mixture was heated to 110° C. in a sealed tube for 14 h. Water was added and the mixture was extracted with dichloromethane.

The organic phase was dried (sodium sulfate), filtered and the solvent was removed in vacuum. Aminophase-silicagel chromatography followed by silicagel chromatography gave 196.0 mg (26% yield) of the title compound.

LC-MS (Method 2): R$_t$=1.12 min; MS (ESIpos): m/z=490 [M+H]$^+$.

$^1$H-NMR (400 MHz, DMSO-d6) δ[ppm]: 1.066 (15.61), 1.396 (16.00), 1.988 (0.58), 2.361 (1.27), 3.506 (1.73), 3.939 (2.53), 3.995 (1.60), 5.759 (2.17), 7.954 (1.49), 8.269 (0.80).

Example 41.02

3,3,3-trifluoro-1-{4-[(2-{[6-(1-methyl-1H-1,2,4-triazol-5-yl)-1H-benzimidazol-2-yl]amino}pyridin-4-yl)methyl]piperazin-1-yl}propan-1-one

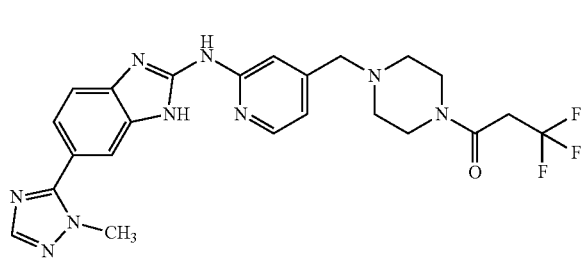 [SMILES: Cn1ncnc1-c1ccc2nc(Nc3cc(CN4CCN(C(=O)CC(F)(F)F)CC4)ccn3)[nH]c2c1]

Starting with crude 6-(1-methyl-1H-1,2,4-triazol-5-yl)-N-[4-(piperazin-1-ylmethyl)pyridin-2-yl]-1H-benzimidazol-2-amine hydrochloride (111 mg, approx. 261 µmol) and 3,3,3-trifluoropropanoic acid (69 µl, 780 µmol), Example 41.02 was prepared analogously to the procedure for the preparation of Example 16.05.02.

Yield: 56.0 mg of the title compound.

LC-MS (Method 2): R$_t$=0.90 min; MS (ESIpos): m/z=500 [M+H]$^+$.

$^1$H-NMR (400 MHz, DMSO-d$_6$): δ [ppm]=2.41 (dt, 4H), 3.44-3.57 (m, 6H), 3.66 (q, 2H), 4.00 (br s, 3H), 6.96 (d, 1H), 7.20 (s, 1H), 7.31-8.03 (m, 4H), 8.29 (d, 1H), 10.65-10.89 (m, 1H), 12.31 (s, 1H).

Example 41.03 cyclopropyl{4-[(2-{[6-(1-methyl-1H-1,2,4-triazol-5-yl)-1H-benzimidazol-2-yl]amino}pyridin-4-yl)methyl]piperazin-1-yl}methanone

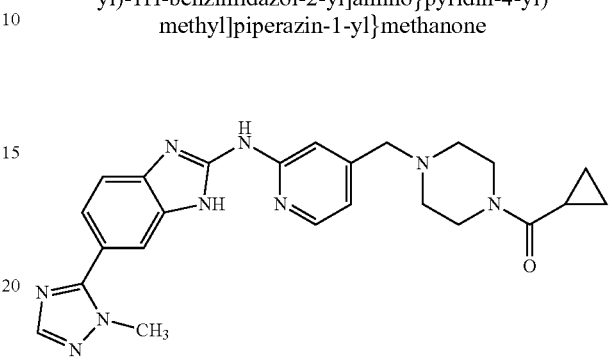

Starting with crude 6-(1-methyl-1H-1,2,4-triazol-5-yl)-N-[4-(piperazin-1-ylmethyl)pyridin-2-yl]-1H-benzimidazol-2-amine hydrochloride (97.6 mg, approx. 229 µmol) and cyclopropanecarboxylic acid (54 µl, 690 µmol), Example 41.03 was prepared analogously to the procedure for the preparation of Example 16.05.02.

Yield: 39.0 mg of the title compound.

LC-MS (Method 2): R$_t$=0.86 min; MS (ESIpos): m/z=458 [M+H]$^+$.

$^1$H-NMR (400 MHz, DMSO-d$_6$): δ [ppm]=0.66-0.76 (m, 4H), 1.93-2.02 (m, 1H), 2.34-2.48 (m, 4H), 3.45-3.77 (m, 6H), 4.00 (s, 3H), 6.97 (d, 1H), 7.21 (s, 1H), 7.32-8.04 (m, 4H), 8.29 (d, 1H), 10.64-10.87 (m, 1H), 12.32 (s, 1H).

Example 42.01 tert-butyl 4-{[2-({6-[1-methyl-3-(2-methylpropyl)-1H-1,2,4-triazol-5-yl]-1H-benzimidazol-2-yl}amino)pyridin-4-yl]methyl}piperazine-1-carboxylate

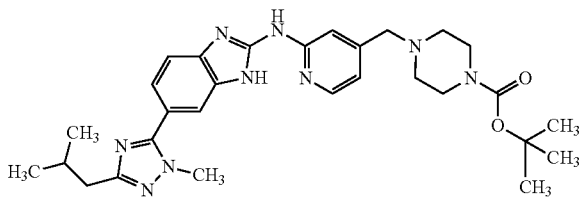 [SMILES: CC(C)Cc1nc(-c2ccc3nc(Nc4cc(CN5CCN(C(=O)OC(C)(C)C)CC5)ccn4)[nH]c3c2)n(C)n1]

A mixture of tert-butyl 4-({2-[(6-{[1-methyl-2-(3-methylbutanimidoyl)hydrazinyl]carbonyl}-1H-benzimidazol-2-yl)amino]pyridin-4-yl}methyl)piperazine-1-carboxylate (125 mg, 222 µmol) and sodium acetate (20.0 mg, 244 µmol) in 1-propanol 6 mL) and water (3 mL) was heated to 100° C. for 14 h. The solvent was removed in vacuum. Aminophase-silicagel chromatography gave 35.0 mg (26% yield) of the title compound.

LC-MS (Method 2): R$_t$=1.25 min; MS (ESIpos): m/z=546 [M+H]$^+$.

$^1$H-NMR (400 MHz, DMSO-d6) δ[ppm]: 0.946 (5.75), 0.963 (5.95), 1.397 (16.00), 2.350 (0.90), 2.363 (1.32), 2.375 (0.95), 2.475 (1.77), 3.352 (1.12), 3.505 (1.76), 3.922 (3.87), 5.752 (1.30), 7.199 (0.73), 8.260 (0.82), 8.273 (0.78).

Example 42.02

3,3,3-trifluoro-1-(4-{[2-({6-[1-methyl-3-(2-methylpropyl)-1H-1,2,4-triazol-5-yl]-1H-benzimidazol-2-yl}amino)pyridin-4-yl]methyl}piperazin-1-yl)propan-1-one

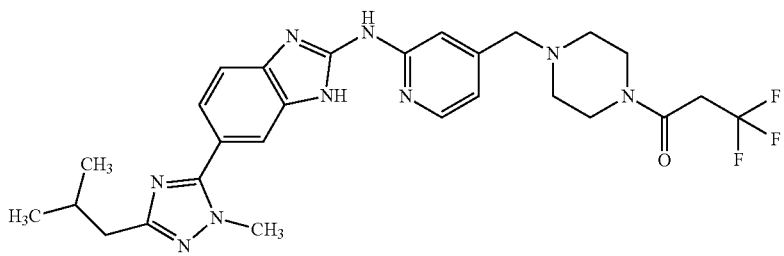 [SMILES: CC(C)Cc1nc(-c2ccc3nc(Nc4cc(CN5CCN(C(=O)CC(F)(F)F)CC5)ccn4)[nH]c3c2)n(C)n1]

Starting with crude 6-[1-methyl-3-(2-methylpropyl)-1H-1,2,4-triazol-5-yl]-N-[4-(piperazin-1-ylmethyl)pyridin-2-yl]-1H-benzimidazol-2-amine hydrochloride (23.0 mg, approx. 44.4 μmol) and 3,3,3-trifluoropropanoic acid (17.0 mg, 133 μmol) Example 42.2. was prepared analogously to the procedure for the preparation of Example 02.02.

Yield: 16.0 mg of the title compound.

LC-MS (Method 2): $R_t$=1.09 min; MS (ESIpos): m/z=556 [M+H]$^+$.

$^1$H-NMR (400 MHz, DMSO-d6) δ[ppm]: 0.832 (0.46), 0.947 (15.70), 0.963 (16.00), 2.040 (0.84), 2.057 (1.06), 2.073 (0.84), 2.327 (0.53), 2.375 (1.28), 2.388 (1.97), 2.400 (1.49), 2.417 (1.45), 2.429 (1.93), 2.441 (1.41), 2.476 (5.53), 2.523 (1.34), 2.669 (0.50), 3.463 (1.38), 3.477 (1.93), 3.489 (1.59), 3.499 (1.55), 3.513 (1.94), 3.530 (5.81), 3.601 (0.99), 3.629 (2.83), 3.656 (2.69), 3.683 (0.84), 3.924 (5.17), 6.941 (1.42), 6.957 (1.44), 7.204 (2.57), 7.449 (0.91), 8.271 (2.45), 8.283 (2.34), 12.273 (1.27).

Example 43.01 cyclopropyl{4-[(2-{[6-(1H-imidazol-2-yl)-1H-benzimidazol-2-yl]amino}pyridin-4-yl)methyl]piperazin-1-yl}methanone

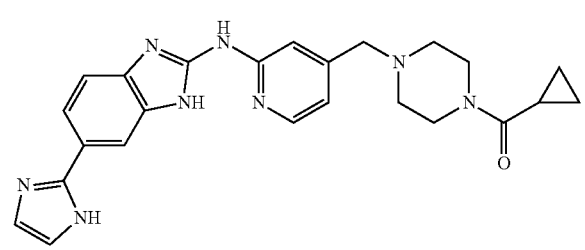 [SMILES: O=C(C1CC1)N1CCN(Cc2ccnc(Nc3nc4ccc(-c5ncc[nH]5)cc4[nH]3)c2)CC1]

To a stirred solution of 2-iodo-1H-imidazole (174 mg, 896 μmol) and cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (150 mg, 299 μmol) in dioxane (2.0 mL) and water (0.5 mL) was added sodium carbonate (130 mg, 1.22 mmol) and Pd(dppf)C$_2$. CH$_2$Cl$_2$ (48.8 mg, 59.7 μmol) and Tetrakis(triphenylphosphin)palladium (69.0 mg, 59.7 μmol). The mixture was heated to reflux for 36 h. Further 2-iodo-1H-imidazole (174 mg, 896 μmol) Pd(dppf)Cl$_2$. CH$_2$Cl$_2$ (48.8 mg, 59.7 μmol) and Tetrakis(triphenylphosphin)palladium (69.0 mg, 59.7 μmol). were added and the mixture was heated to reflux for 7 h. Methanol was added, the mixture was filtered and the solvent was removed in vacuum. Silicagel chromatography gave a solid that was crystallized from ethanol to give 20.0 mg (14% yield) of the title compound.

LC-MS (Method 5): $R_t$=2.17 min; MS (ESIpos): m/z=443 [M+H]$^+$.

$^1$H-NMR (400 MHz, DMSO-d6) δ [ppm]: 2.490 (1.57), 2.495 (3.44), 2.500 (4.85), 2.505 (3.44), 2.509 (1.55), 3.303 (16.00).

Example 43.02 cyclopropyl{4-[(2-{[6-(4-methyl-1H-imidazol-2-yl)-1H-benzimidazol-2-yl]amino}pyridin-4-yl)methyl]piperazin-1-yl}methanone

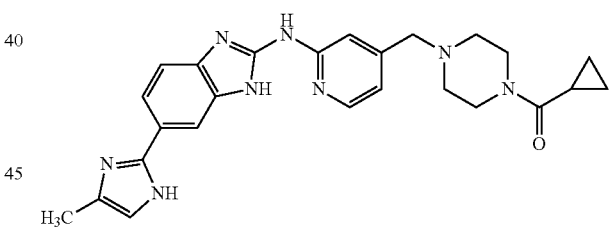

To a stirred solution of 2-bromo-4-methyl-1H-imidazole (240 mg, 1.49 mmol) and cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (150 mg, 299 μmol) in dioxane (2.0 mL) and water (0.5 mL) was added sodium carbonate (130 mg, 1.22 mmol) and Pd(dppf)C$_2$. CH$_2$Cl$_2$ (48.8 mg, 59.7 μmol) and Tetrakis (triphenylphosphin)palladium (69.0 mg, 59.7 μmol). The mixture was heated to reflux for 24 h. Methanol was added, the mixture was filtered and the solvent was removed in vacuum. Silicagel chromatography gave 19.0 mg (13% yield) of the title compound.

LC-MS (Method 5): $R_t$=2.31 min; MS (ESIpos): m/z=457 [M+H]$^+$.

$^1$H-NMR (400 MHz, DMSO-d6) δ[ppm]: 0.691 (1.89), 0.711 (2.62), 0.718 (2.69), 0.731 (2.52), 1.234 (0.47), 1.952 (0.59), 1.964 (0.84), 2.341 (6.66), 2.395 (0.88), 2.495 (10.55), 2.500 (13.36), 2.504 (11.34), 3.169 (0.43), 3.309

(16.00), 3.565 (1.65), 3.718 (0.95), 6.986 (1.09), 6.999 (1.14), 7.227 (1.50), 7.408 (1.77), 7.639 (1.33), 7.997 (2.12), 8.299 (1.25), 8.312 (1.25).

Example 43.03 cyclopropyl{4-[(2-{[6-(4-cyclopropyl-1H-imidazol-2-yl)-1H-benzimidazol-2-yl]amino}pyridin-4-yl)methyl]piperazin-1-yl}methanone

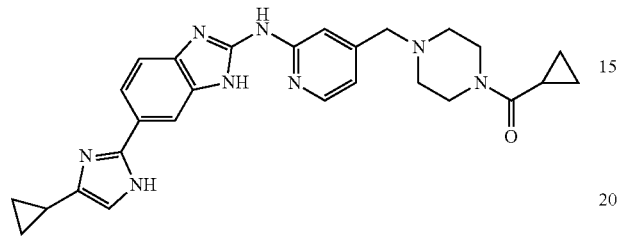

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (200 mg, 398 μmol) and 4-cyclopropyl-2-iodo-1H-imidazole (200 mg, 855 μmol), Example 43.03 was prepared analogously to the procedure for the preparation of Example 43.02.

Yield: 8 mg (4%) of the title compound.

LC-MS (Method 5): $R_t$=2.46 min; MS (ESIpos): m/z=483 [M+H]$^+$.

$^1$H-NMR (400 MHz, DMSO-d6): δ [ppm]=0.61-0.77 (m, 6H), 0.77-0.93 (m, 2H), 1.85 (m, 1H), 1.96 (m, 1H), 2.41 (m, 4H), 3.52 (m, 4H), 3.70 (s, 1H), 6.87 (s, 1H), 6.94 (m, 1H), 7.21 (s, 1H), 7.43 (bs, 1H), 7.60 (m, 1H), 7.94 (bs, 1H), 8.26 (d, 1H), 10.85 (bs, 1H), 12.18 (bs, 1H).

13C-NMR (101 MHz, DMSO-d6): δ [ppm]=6.86, 6.89, 10.1, 40.3, 44.8, 52.4, 53.1, 60.6, 110.4, 116.4, 145.9, 146.9, 149.4, 150.4, 153.6, 170.9.

Example 44.01

1-(cyclopropylmethyl)-4-{2-[(4-{[4-(3,3,3-trifluoropropanoyl)piperazin-1-yl]methyl}pyridin-2-yl)amino]-1H-benzimidazol-6-yl}pyridin-2(1H)-one

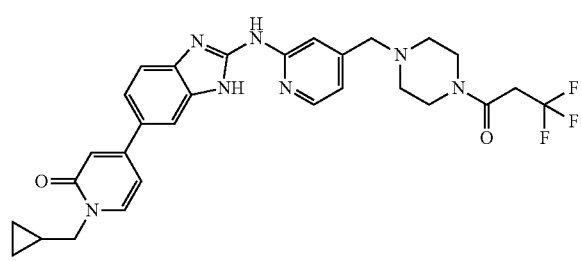 [SMILES: O=C(CC(F)(F)F)N1CCN(Cc2ccnc(Nc3nc4ccc(-c5ccn(CC6CC6)c(=O)c5)cc4[nH]3)c2)CC1]

Starting with crude 1-(cyclopropylmethyl)-4-(2-{[4-(piperazin-1-ylmethyl)pyridin-2-yl]amino}-1H-benzimidazol-6-yl)pyridin-2(1H)-one hydrochloride (150 mg, approx. 241 μmol) and 3,3,3-trifluoropropanoic acid (33 μl, 98% purity, 360 μmol), Example 44.01 was prepared analogously to the procedure for the preparation of Example 01.02.

Yield: 55.0 mg of the title compound.

LC-MS (Method 2): $R_t$=1.06 min; MS (ESIpos): m/z=566 [M+H]$^+$.

$^1$H-NMR (400 MHz, DMSO-d$_6$): δ [ppm]=0.36-0.44 (m, 2H), 0.46-0.55 (m, 2H), 1.16-1.35 (m, 1H), 2.41 (dt, 4H), 3.45-3.58 (m, 6H), 3.66 (q, 2H), 3.76 (d, 2H), 6.63 (br d, 2H), 6.95 (br d, 1H), 7.20 (s, 1H), 7.34-7.91 (m, 4H), 8.24-8.33 (m, 1H), 10.72 (br s, 1H), 11.45-12.91 (m, 1H).

Example 44.02

4-{2-[(4-{[4-(cyclopropylcarbonyl)piperazin-1-yl]methyl}pyridin-2-yl)amino]-1H-benzimidazol-6-yl}-1-(cyclopropylmethyl)pyridin-2(1H)-one

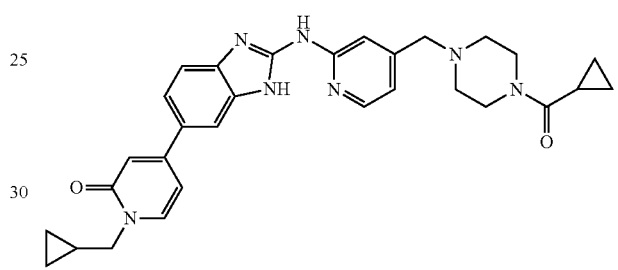

Starting with crude 1-(cyclopropylmethyl)-4-(2-{[4-(piperazin-1-ylmethyl)pyridin-2-yl]amino}-1H-benzimidazol-6-yl)pyridin-2(1H)-one hydrochloride (150 mg, approx. 241 μmol) and cyclopropanecarboxylic acid (29 μl, 98% purity, 360 μmol), Example 44.02 was prepared analogously to the procedure for the preparation of Example 01.02.

Yield: 57.0 mg of the title compound.

LC-MS (Method 2): $R_t$=1.02 min; MS (ESIpos): m/z=524 [M+H]$^+$.

$^1$H-NMR (400 MHz, DMSO-d6) δ [ppm]: 0.383 (1.46), 0.395 (5.79), 0.398 (5.62), 0.407 (6.77), 0.410 (5.92), 0.419 (2.66), 0.435 (0.71), 0.443 (0.65), 0.455 (0.82), 0.471 (2.38), 0.479 (5.34), 0.484 (4.49), 0.490 (3.34), 0.500 (5.86), 0.504 (4.63), 0.516 (1.70), 0.666 (0.95), 0.677 (3.00), 0.685 (7.08), 0.690 (4.29), 0.697 (3.54), 0.704 (8.75), 0.709 (7.32), 0.713 (7.97), 0.721 (7.25), 0.725 (8.51), 0.732 (4.05), 0.745 (1.12), 1.211 (0.82), 1.224 (1.77), 1.231 (2.14), 1.243 (2.69), 1.255 (1.57), 1.263 (1.60), 1.275 (0.89), 1.935 (0.78), 1.948 (1.70), 1.955 (1.80), 1.967 (3.10), 1.973 (1.50), 1.980 (1.77), 1.986 (1.70), 1.998 (0.78), 2.074 (0.75), 2.318 (0.89), 2.323 (1.80), 2.327 (2.55), 2.331 (2.08), 2.337 (1.43), 2.363 (3.34), 2.446 (3.47), 2.518 (16.00), 2.523 (13.07), 2.659 (0.75), 2.665 (1.63), 2.669 (2.28), 2.673 (1.63), 2.678 (0.75), 3.525 (14.84), 3.709 (3.20), 3.746 (10.08), 3.764 (9.94), 6.618 (6.16), 6.941 (3.71), 6.944 (3.78), 6.954 (3.88), 6.957 (3.91), 7.228 (2.86), 7.411 (2.42), 7.757 (4.83), 7.776 (4.83), 8.268 (5.99), 8.282 (5.79), 12.235 (0.75).

Example 44.03

4-{2-[(4-{[4-(cyclobutylcarbonyl)piperazin-1-yl]methyl}pyridin-2-yl)amino]-1H-benzimidazol-6-yl}-1-(cyclopropylmethyl)pyridin-2(1H)-one

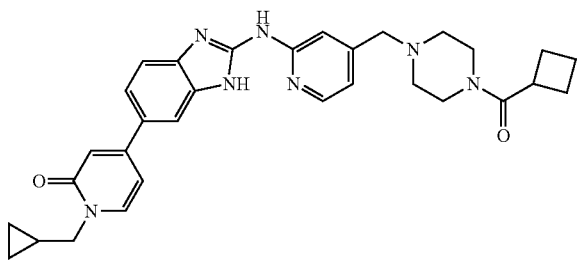 [SMILES: O=C(C1CCC1)N1CCN(Cc2ccnc(Nc3nc4ccc(-c5ccn(CC6CC6)c(=O)c5)cc4[nH]3)c2)CC1]

Starting with crude 1-(cyclopropylmethyl)-4-(2-{[4-(piperazin-1-ylmethyl)pyridin-2-yl]amino}-1H-benzimidazol-6-yl)pyridin-2(1H)-one hydrochloride (150 mg, approx. 241 µmol) and cyclobutanecarboxylic acid (35 µl, 98% purity, 360 µmol), Example 44.03 was prepared analogously to the procedure for the preparation of Example 01.02.

Yield: 30.0 mg of the title compound.

LC-MS (Method 2): $R_t$=1.08 min; MS (ESIneg): m/z=536 [M−H]⁺.

¹H-NMR (400 MHz, DMSO-d₆): δ [ppm]=0.36-0.44 (m, 2H), 0.46-0.56 (m, 2H), 1.17-1.33 (m, 1H), 1.67-1.80 (m, 1H), 1.81-1.95 (m, 1H), 1.99-2.22 (m, 4H), 2.28-2.42 (m, 4H), 3.43-3.59 (m, 4H), 3.76 (d, 2H), 6.62 (br s, 2H), 6.94 (d, 1H), 7.20 (s, 1H), 7.32-7.91 (m, 4H), 8.28 (d, 1H), 10.72 (br s, 1H), 12.24 (br s, 1H).

Example 45.01.01

3,3,3-trifluoro-1-{4-[(2-{[6-(pyrimidin-5-yl)-1H-benzimidazol-2-yl]amino}pyridin-4-yl)methyl]piperazin-1-yl}propan-1-one

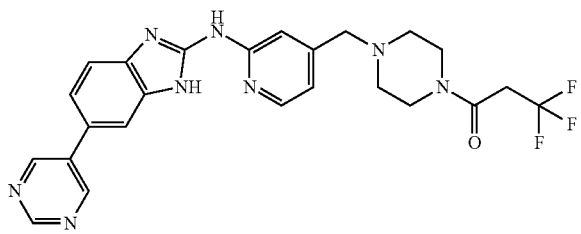 [SMILES: O=C(CC(F)(F)F)N1CCN(Cc2ccnc(Nc3nc4ccc(-c5cncnc5)cc4[nH]3)c2)CC1]

Crude N-[4-(piperazin-1-ylmethyl)pyridin-2-yl]-6-(pyrimidin-5-yl)-1H-benzimidazol-2-amine hydrochloride (211 mg, approx. 426 µmol), 3,3,3-trifluoropropanoic acid (75 µl, 850 µmol), T3P (450 µl, 50% solution in DMF, 770 µmol) and DIPEA (370 µl, 2.1 mmol) were solubilized in DMF (21 mL) and the reaction was stirred at r.t. for 2 days. The reaction mixture was then diluted with water and extracted with dichloromethane. The aqueous phase was then basified with saturated sodium bicarbonate solution and extracted with a mixture of dichloromethane/isopropanol (8/2). The organic phase was dried (magnesium sulfate) filtered and concentrated under reduced pressure. The crude mixture was purified by preparative HPLC (water/acetonitrile with ammonia as additive) and 8 mg of the title compound were obtained.

LC-MS (Method 2): $R_t$=0.95 min; MS (ESIpos): m/z=497 [M+H]⁺

¹H-NMR (400 MHz, DMSO-d6) δ[ppm]: 1.064 (1.39), 1.176 (0.67), 1.192 (0.63), 1.228 (1.79), 1.239 (1.84), 1.254 (2.33), 1.272 (1.21), 2.072 (5.65), 2.082 (0.90), 2.322 (1.79), 2.327 (2.42), 2.332 (1.93), 2.336 (1.17), 2.383 (7.39), 2.425 (7.31), 2.523 (6.45), 2.539 (1.48), 2.660 (0.81), 2.664 (1.57), 2.669 (2.24), 2.673 (1.61), 3.471 (7.84), 3.483 (7.53), 3.509 (8.87), 3.527 (16.00), 3.609 (2.91), 3.636 (7.26), 3.663 (6.90), 3.691 (2.51), 4.047 (3.41), 6.939 (4.48), 6.951 (4.57), 7.204 (4.62), 7.464 (2.69), 7.811 (1.03), 8.271 (5.38), 8.283 (5.15), 9.141 (13.45), 10.715 (1.48), 12.259 (1.17).

Example 45.01.02

2-cyclopropyl-1-{4-[(2-{[6-(pyrimidin-5-yl)-1H-benzimidazol-2-yl]amino}pyridin-4-yl)methyl]piperazin-1-yl}ethanone

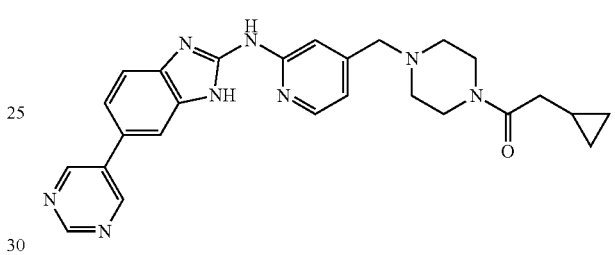

Starting with crude N-[4-(piperazin-1-ylmethyl)pyridin-2-yl]-6-(pyrimidin-5-yl)-1H-benzimidazol-2-amine hydrochloride (130 mg, approx. 262 µmol) and cyclopropylacetic acid (78.7 mg, 787 µmol), Example 45.01.02 was prepared analogously to the procedure for the preparation of Example 01.02.

Yield: 4 mg of the title compound.

LC-MS (Method 4): $R_t$=0.94 min; MS (ESIpos): m/z=469 [M+H]⁺.

¹H-NMR (400 MHz, DMSO-d6): δ [ppm]=0.05-0.16 (m, 2H), 0.39-0.48 (m, 2H), 0.88-1.00 (m, 1H), 2.25 (d, 2H), 2.34-2.43 (m, 4H), 3.40-3.55 (m, 6H), 6.95 (d, 1H), 7.21 (s, 1H), 7.39-7.52 (m, 1.5H), 7.62 (br d, 0.5H), 7.75-7.90 (m, 1H), 8.28 (d, 1H), 9.06-9.23 (m, 3H), 10.71 (br d, 1H), 12.25 (br d, 1H).

Example 45.01.03 cyclopropyl{4-[(2-{[6-(pyrimidin-5-yl)-1H-benzimidazol-2-yl]amino}pyridin-4-yl)methyl]piperazin-1-yl}methanone

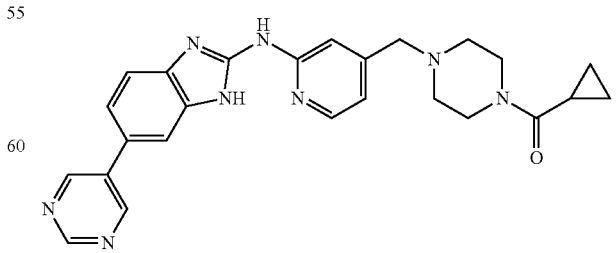

Starting with crude N-[4-(piperazin-1-ylmethyl)pyridin-2-yl]-6-(pyrimidin-5-yl)-1H-benzimidazol-2-amine hydrochloride (211 mg, approx. 426 µmol) and cyclopropanecarboxylic acid (68 µl, 850 µmol) Example 45.01.03 was prepared analogously to the procedure for the preparation of Example 45.01.01.

Yield: 20.0 mg of the title compound.

LC-MS (Method 2): R$_t$=0.92 min; MS (ESIpos): m/z=455 [M+H]$^+$.

$^1$H-NMR (400 MHz, DMSO-d6) δ[ppm]: 0.662 (0.84), 0.674 (2.41), 0.682 (5.23), 0.687 (3.43), 0.694 (2.76), 0.701 (6.28), 0.707 (5.04), 0.713 (5.61), 0.720 (5.52), 0.724 (6.48), 0.731 (3.25), 0.744 (0.80), 1.928 (0.66), 1.941 (1.33), 1.948 (1.40), 1.952 (1.07), 1.960 (2.25), 1.966 (1.14), 1.972 (1.30), 1.979 (1.16), 2.073 (0.52), 2.327 (0.64), 2.332 (0.71), 2.361 (2.57), 2.467 (0.85), 3.385 (0.92), 3.502 (2.67), 3.521 (11.47), 3.703 (2.40), 5.756 (0.40), 6.943 (2.91), 6.946 (2.91), 6.956 (3.02), 6.959 (2.95), 7.212 (5.51), 7.481 (1.32), 7.789 (0.77), 8.273 (4.78), 8.286 (4.56), 8.780 (0.56), 9.062 (0.50), 9.094 (1.03), 9.114 (1.92), 9.120 (2.39), 9.126 (16.00), 9.137 (2.25), 9.143 (2.11), 10.727 (0.80), 12.245 (0.80).

Example 45.02.01

1-{4-[(2-{[6-(2-chloropyrimidin-5-yl)-1H-benzimidazol-2-yl]amino}pyridin-4-yl)methyl]piperazin-1-yl}-3,3,3-trifluoropropan-1-one

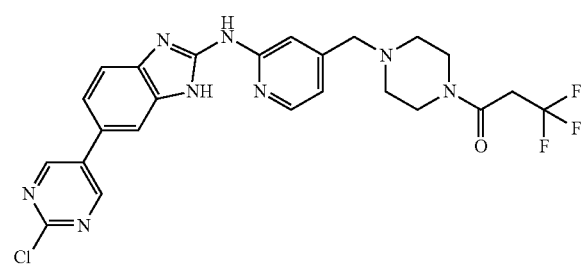 [SMILES: O=C(CC(F)(F)F)N1CCN(Cc2ccnc(Nc3nc4ccc(-c5cnc(Cl)nc5)cc4[nH]3)c2)CC1]

Starting with crude 6-(2-chloropyrimidin-5-yl)-N-[4-(piperazin-1-ylmethyl)pyridin-2-yl]-1H-benzimidazol-2-amine hydrochloride (305 mg, approx. 575 µmol) and 3,3,3-trifluoropropanoic acid (150 µl, 1.7 mmol), Example 45.02.01 was prepared analogously to the procedure for the preparation of Example 01.02.

Yield: 5.30 mg of the title compound.

LC-MS (Method 2): R$_t$=1.11 min; MS (ESIpos): m/z=531 [M+H]$^+$.

1H-NMR (400 MHz, DMSO-d6) δ[ppm]: 1.232 (1.88), 2.318 (1.18), 2.322 (2.59), 2.326 (3.59), 2.332 (2.59), 2.336 (1.24), 2.370 (2.35), 2.382 (3.53), 2.394 (2.65), 2.412 (2.59), 2.425 (3.59), 2.437 (2.65), 2.518 (16.00), 2.522 (10.71), 2.660 (1.18), 2.664 (2.59), 2.669 (3.47), 2.673 (2.53), 2.678 (1.18), 3.395 (1.06), 3.459 (2.71), 3.473 (3.65), 3.484 (3.06), 3.495 (2.94), 3.510 (3.65), 3.528 (9.24), 3.610 (1.82), 3.638 (5.00), 3.653 (0.88), 3.665 (4.94), 3.679 (0.71), 3.693 (1.94), 3.700 (0.82), 6.944 (2.41), 6.955 (2.29), 7.206 (4.00), 7.458 (1.00), 7.482 (1.12), 7.607 (0.88), 7.627 (0.71), 7.810 (1.12), 7.868 (0.82), 8.271 (4.12), 8.284 (3.88), 9.075 (1.71), 9.131 (2.29), 10.732 (1.06), 12.254 (1.00), 12.285 (0.76).

Example 45.02.02

{4-[(2-{[6-(2-chloropyrimidin-5-yl)-1H-benzimidazol-2-yl]amino}pyridin-4-yl)methyl]piperazin-1-yl}(cyclopropyl)methanone

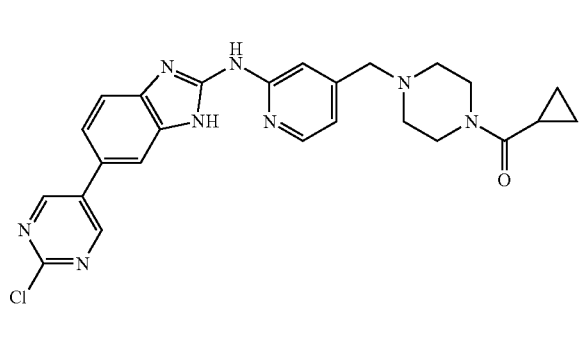 [SMILES: O=C(C1CC1)N1CCN(Cc2ccnc(Nc3nc4ccc(-c5cnc(Cl)nc5)cc4[nH]3)c2)CC1]

Starting with crude 6-(2-chloropyrimidin-5-yl)-N-[4-(piperazin-1-ylmethyl)pyridin-2-yl]-1H-benzimidazol-2-amine hydrochloride (305 mg, approx. 575 µmol) and cyclopropanecarboxylic acid (140 µl, 1.7 mmol), Example 45.02.02 was prepared analogously to the procedure for the preparation of Example 01.02.

Yield: 9.14 mg of the title compound.

LC-MS (Method 2): R$_t$=1.06 min; MS (ESIpos): m/z=489 [M+H]$^+$

1H-NMR (400 MHz, DMSO-d6) δ[ppm]: 0.677 (1.61), 0.685 (3.36), 0.690 (2.09), 0.698 (2.02), 0.705 (4.30), 0.709 (3.59), 0.713 (3.81), 0.720 (3.44), 0.726 (3.70), 0.733 (1.76), 1.907 (0.90), 1.968 (1.38), 2.084 (2.39), 2.322 (1.79), 2.326 (2.50), 2.332 (1.83), 2.336 (1.12), 2.363 (1.50), 2.518 (9.46), 2.522 (6.62), 2.664 (1.68), 2.668 (2.32), 2.673 (1.64), 2.727 (2.54), 2.729 (2.24), 2.888 (3.10), 3.257 (0.67), 3.511 (2.09), 3.527 (5.53), 3.707 (1.46), 3.965 (1.12), 5.759 (16.00), 6.951 (1.27), 6.963 (1.16), 7.212 (2.58), 8.272 (2.36), 8.285 (2.21), 8.496 (1.12), 9.074 (1.42), 9.132 (2.02).

Example 45.03.01

3,3,3-trifluoro-1-{4-[(2-{[6-(2-methylpyrimidin-5-yl)-1H-benzimidazol-2-yl]amino}pyridin-4-yl)methyl]piperazin-1-yl}propan-1-one

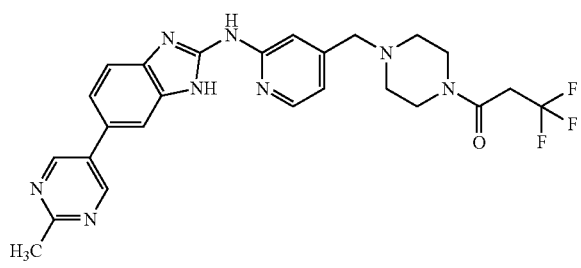 [SMILES: Cc1ncc(-c2ccc3nc(Nc4cc(CN5CCN(C(=O)CC(F)(F)F)CC5)ccn4)[nH]c3c2)cn1]

Starting with crude 6-(2-methylpyrimidin-5-yl)-N-[4-(piperazin-1-ylmethyl)pyridin-2-yl]-1H-benzimidazol-2-amine hydrochloride (204 mg, approx. 400 µmol) and 3,3,3-trifluoropropanoic acid (110 µl, 1.2 mmol), Example 45.03.01 was prepared analogously to the procedure for the preparation of Example 01.02.

Yield: 20.5 mg of the title compound.

LC-MS (Method 2): $R_t$=0.99 min; MS (ESIpos): m/z=511 [M+H]$^+$.

1H-NMR (400 MHz, DMSO-d6) δ [ppm]: 2.323 (0.94), 2.327 (1.28), 2.331 (0.94), 2.369 (1.71), 2.383 (2.63), 2.395 (1.97), 2.413 (1.95), 2.425 (2.65), 2.437 (1.99), 2.518 (5.72), 2.523 (3.89), 2.657 (16.00), 2.665 (2.26), 2.669 (1.79), 2.674 (1.12), 3.159 (2.48), 3.172 (2.71), 3.459 (1.83), 3.473 (2.54), 3.485 (2.10), 3.495 (2.04), 3.510 (2.59), 3.526 (7.37), 3.611 (1.20), 3.638 (3.50), 3.666 (3.28), 3.693 (1.04), 4.097 (0.67), 4.110 (0.63), 5.760 (1.81), 6.935 (1.89), 6.938 (1.89), 6.947 (1.85), 6.951 (1.89), 7.208 (3.22), 7.451 (0.94), 8.266 (3.20), 8.280 (3.11), 8.977 (1.32), 9.010 (1.47), 10.702 (1.36).

Example 45.03.02 cyclopropyl{4-[(2-{[6-(2-methylpyrimidin-5-yl)-1H-benzimidazol-2-yl]amino}pyridin-4-yl)methyl]piperazin-1-yl}methanone

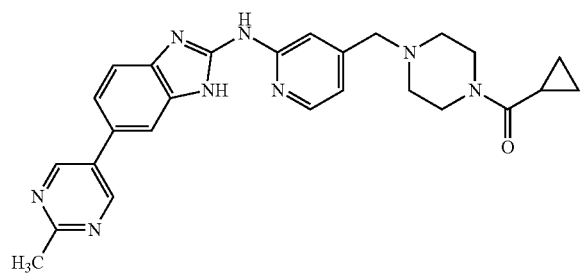 [SMILES: Cc1ncc(-c2ccc3nc(Nc4cc(CN5CCN(C(=O)C6CC6)CC5)ccn4)[nH]c3c2)cn1]

Starting with crude 6-(2-methylpyrimidin-5-yl)-N-[4-(piperazin-1-ylmethyl)pyridin-2-yl]-1H-benzimidazol-2-amine hydrochloride (204 mg, approx. 400 μmol) and cyclopropanecarboxylic acid (96 μl, 1.2 mmol), Example 45.03.02 was prepared analogously to the procedure for the preparation of Example 01.02.

Yield: 23.6 mg of the title compound.

LC-MS (Method 2): $R_t$=0.95 min; MS (ESIpos): m/z=469 [M+H]$^+$.

1H-NMR (400 MHz, DMSO-d6) δ[ppm]: 0.677 (1.69), 0.685 (3.76), 0.691 (2.29), 0.698 (2.03), 0.705 (4.66), 0.709 (3.83), 0.713 (4.09), 0.720 (3.61), 0.726 (4.17), 0.733 (1.84), 1.065 (0.60), 1.751 (0.68), 1.948 (0.94), 1.955 (0.94), 1.967 (1.58), 1.979 (0.86), 1.986 (0.79), 2.318 (0.86), 2.322 (1.80), 2.326 (2.48), 2.332 (1.92), 2.336 (1.13), 2.364 (1.62), 2.446 (1.69), 2.518 (9.16), 2.522 (6.31), 2.656 (16.00), 2.664 (2.93), 2.668 (2.70), 2.673 (1.84), 2.678 (0.86), 3.504 (1.80), 3.511 (1.88), 3.525 (7.14), 3.709 (1.58), 6.943 (1.77), 6.946 (1.80), 6.956 (1.80), 6.959 (1.77), 7.209 (3.38), 7.452 (1.09), 8.268 (3.12), 8.283 (3.08), 8.975 (1.31), 9.013 (1.54).

Example 45.04.01 cyclopropyl{4-[(2-{[6-(2-cyclopropylpyrimidin-5-yl)-1H-benzimidazol-2-yl]amino}pyridin-4-yl)methyl]piperazin-1-yl}methanone

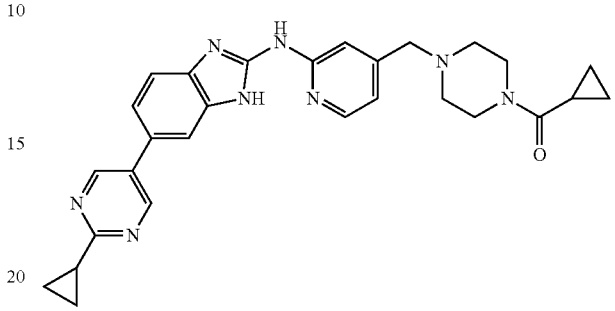

Starting with crude 6-(2-cyclopropylpyrimidin-5-yl)-N-[4-(piperazin-1-ylmethyl)pyridin-2-yl]-1H-benzimidazol-2-amine hydrochloride (366 mg, approx. 683 μmol) and cyclopropanecarboxylic acid (160 μl, 2.0 mmol), Example 45.04.01 was prepared analogously to the procedure for the preparation of Example 01.02.

Yield: 24.4 mg of the title compound.

LC-MS (Method 2): $R_t$=1.09 min; MS (ESIneg): m/z=493 [M−H]$^+$.

1H-NMR (400 MHz, DMSO-d6) δ[ppm]: 0.665 (0.90), 0.677 (2.52), 0.685 (5.61), 0.690 (3.48), 0.698 (2.90), 0.704 (6.84), 0.708 (5.87), 0.713 (6.32), 0.720 (5.61), 0.725 (6.52), 0.732 (3.03), 0.745 (0.77), 0.821 (0.65), 0.829 (0.90), 0.833 (0.77), 0.835 (0.77), 0.840 (0.90), 0.863 (0.58), 0.870 (0.71), 0.883 (0.58), 0.889 (1.10), 0.897 (0.58), 0.999 (0.65), 1.013 (0.90), 1.026 (3.03), 1.033 (6.06), 1.038 (5.16), 1.045 (6.00), 1.053 (6.52), 1.060 (2.58), 1.067 (2.84), 1.073 (5.61), 1.080 (2.52), 1.093 (0.71), 1.230 (0.71), 1.907 (0.65), 1.936 (0.65), 1.948 (1.35), 1.955 (1.42), 1.959 (1.03), 1.967 (2.45), 1.973 (1.10), 1.979 (1.35), 1.986 (1.23), 2.207 (0.77), 2.220 (1.42), 2.227 (1.48), 2.233 (1.03), 2.240 (2.71), 2.248 (1.03), 2.252 (1.42), 2.259 (1.29), 2.271 (0.71), 2.318 (1.42), 2.322 (3.03), 2.326 (4.19), 2.332 (3.10), 2.336 (1.74), 2.364 (2.39), 2.444 (2.52), 2.518 (16.00), 2.522 (11.10), 2.539 (1.35), 2.660 (1.29), 2.664 (2.90), 2.668 (3.94), 2.673 (2.77), 2.678 (1.23), 3.525 (8.77), 3.632 (1.10), 3.641 (0.71), 3.644 (1.10), 3.648 (0.71), 3.656 (1.23), 3.665 (0.65), 3.670 (0.77), 3.675 (0.97), 3.681 (1.42), 3.685 (1.68), 3.692 (2.58), 3.694 (2.90), 3.709 (3.42), 3.712 (3.10), 3.718 (2.52), 3.723 (2.06), 3.728 (1.35), 3.733 (0.97), 3.738 (0.71), 4.124 (0.84), 4.136 (0.84), 4.149 (0.77), 4.214 (1.42), 6.941 (2.77), 6.944 (2.84), 6.954 (2.84), 6.957 (2.84), 7.209 (4.90), 7.377 (0.77), 7.573 (0.65), 7.582 (0.71), 7.593 (0.65), 7.601 (0.58), 7.706 (0.84), 7.710 (0.84), 8.269 (4.65), 8.281 (4.45), 8.898 (0.71), 8.939 (2.13), 10.690 (1.16), 12.222 (0.77).

Example 45.05.01

3,3,3-trifluoro-1-(4-{[2-({6-[2-(methylsulfanyl)pyrimidin-5-yl]-1H-benzimidazol-2-yl}amino)pyridin-4-yl]methyl}piperazin-1-yl)propan-1-one

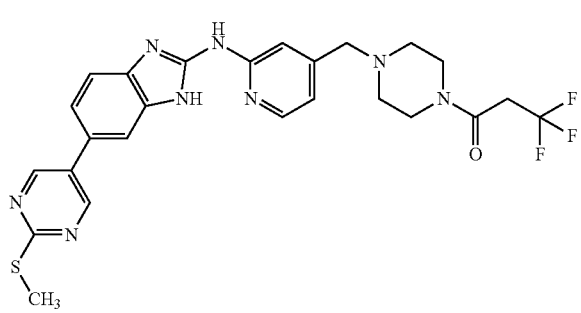 [SMILES: CSc1ncc(-c2ccc3nc(Nc4cc(CN5CCN(C(=O)CC(F)(F)F)CC5)ccn4)[nH]c3c2)cn1]

Starting with crude 6-[2-(methylsulfanyl)pyrimidin-5-yl]-N-[4-(piperazin-1-ylmethyl)pyridin-2-yl]-1H-benzimidazol-2-amine hydrochloride (183 mg, approx. 338 µmol) and 3,3,3-trifluoropropanoic acid (60 µl, 680 µmol) Example 45.05.01 was prepared analogously to the procedure for the preparation of Example 45.01.01.

Yield: 4.0 mg of the title compound.

LC-MS (Method 2): R$_t$=1.14 min; MS (ESIpos): m/z=543 [M+H]$^+$

1H-NMR (400 MHz, DMSO-d6) δ[ppm]: 1.229 (4.12), 2.390 (1.33), 2.433 (1.28), 2.569 (16.00), 3.475 (1.49), 3.485 (1.31), 3.508 (1.40), 3.533 (2.78), 3.638 (1.88), 3.665 (1.77), 6.942 (1.25), 6.955 (1.46), 7.208 (2.37), 8.271 (1.73), 8.284 (1.62), 8.965 (3.13).

Example 45.05.02

2-cyclopropyl-1-(4-{[2-({6-[2-(methylsulfanyl)pyrimidin-5-yl]-1H-benzimidazol-2-yl}amino)pyridin-4-yl]methyl}piperazin-1-yl)ethanone

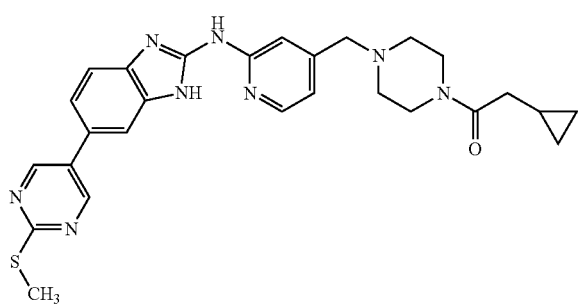 [SMILES: CSc1ncc(-c2ccc3nc(Nc4cc(CN5CCN(C(=O)CC6CC6)CC5)ccn4)[nH]c3c2)cn1]

Starting with crude 6-[2-(methylsulfanyl)pyrimidin-5-yl]-N-[4-(piperazin-1-ylmethyl)pyridin-2-yl]-1H-benzimidazol-2-amine hydrochloride (130 mg, approx. 240 µmol) and cyclopropylacetic acid (72.0 mg, 720 µmol), Example 45.05.02 was prepared analogously to the procedure for the preparation of Example 01.02.

Yield: 9 mg of the title compound.

LC-MS (Method 4): R$_t$=1.13 min; MS (ESIpos): m/z=515 [M+H]$^+$.

$^1$H-NMR (400 MHz, DMSO-d6): δ [ppm]=0.06-0.14 (m, 2H), 0.39-0.48 (m, 2H), 0.88-0.99 (m, 1H), 2.25 (d, 2H), 2.34-2.42 (m, 4H), 2.57 (s, 3H), 3.40-3.56 (m, 6H), 6.94 (d, 1H), 7.20 (s, 1H), 7.38 (br d, 0.5H), 7.44 (br s, 1H), 7.59 (br d, 0.5H), 7.70-7.84 (m, 1H), 8.27 (d, 1H), 8.94 (s, 1H), 8.99 (s, 1H), 10.69 (br s, 1H), 12.22 (br d, 1H).

Example 45.05.03 cyclopropyl(4-{[2-({6-[2-(methylsulfanyl)pyrimidin-5-yl]-1H-benzimidazol-2-yl}amino)pyridin-4-yl]methyl}piperazin-1-yl)methanone

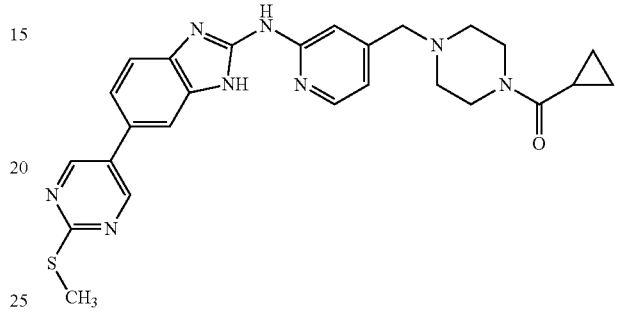

Starting with crude 6-[2-(methylsulfanyl)pyrimidin-5-yl]-N-[4-(piperazin-1-ylmethyl)pyridin-2-yl]-1H-benzimidazol-2-amine hydrochloride (183 mg, approx. 338 µmol) and cyclopropanecarboxylic acid (54 µl, 680 µmol) Example 45.05.03 was prepared analogously to the procedure for the preparation of Example 45.01.01.

Yield: 17.0 mg of the title compound.

LC-MS (Method 2): R$_t$=1.11 min; MS (ESIpos): m/z=501 [M+H]$^+$.

1H-NMR (400 MHz, DMSO-d6) δ[ppm]: 0.677 (1.09), 0.684 (2.44), 0.689 (1.59), 0.696 (1.30), 0.703 (2.96), 0.708 (2.67), 0.712 (2.82), 0.720 (2.52), 0.724 (2.86), 0.731 (1.36), 1.964 (0.98), 2.363 (1.22), 2.446 (1.27), 2.568 (16.00), 3.499 (1.33), 3.523 (4.62), 3.706 (1.17), 6.941 (1.32), 6.956 (1.35), 7.210 (1.94), 8.268 (1.87), 8.281 (1.78), 8.965 (1.50).

Example 46.01 cyclopropyl{4-[(2-{[6-(3-methoxypyridazin-4-yl)-1H-benzimidazol-2-yl]amino}pyridin-4-yl)methyl]piperazin-1-yl}methanone

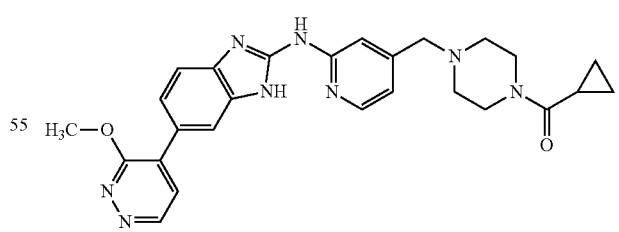

To a stirred solution of {4-[(2-{[6-(6-chloro-3-methoxypyridazin-4-yl)-1H-benzimidazol-2-yl]amino}pyridin-4-yl)methyl]piperazin-1-yl}(cyclopropyl) methanone (190 mg, 366 µmol) in methanol (2 mL) was added palladium on carbon (10% w/w palladium, 200 mg) and the mixture was hydrogenated at 40° C. at 4 bar hydrogen atmosphere for 2 h. Methanol was added, the mixture was filtered through celite and the solution was concentrated in vacuum. A saturated solution of sodium bicarbonate was added and the mixture was extracted with ethyl acetate. The organic phase was dried (magnesium sulfate) and the solvent was removed in vacuum. Silicagel chromatography gave 37 mg (21% yield) of the title compound.

LC-MS (Method 5): $R_t$=2.52 min; MS (ESIpos): m/z=485 [M+H]$^+$.

$^1$H-NMR (400 MHz, DMSO-d6): δ [ppm]=0.70 (m, 4H), 1.95 (m, 1H), 2.41 (m, 4H), 3.52 (s, 4H), 3.70 (s, 2H), 4.11 (s, 3H), 6.95 (d, 1H), 7.22 (s, 1H), 7.30-8.05 (m, 4H), 8.28 (d, 1H), 8.90 (d, 1H), 10.69 (s, 1H), 12.26 (s, 1H). 13C-NMR (101 MHz, DMSO-d6): δ [ppm]=6.9, 10.2, 41.6, 44.8, 52.4, 53.1, 54.5, 60.6, 110.5, 116.6, 127.4, 130.1, 146.9, 148.0, 149.5, 153.5, 162.0, 170.9.

Example 46.02

{4-[(2-{[6-(6-chloro-3-methoxypyridazin-4-yl)-1H-benzimidazol-2-yl]amino}pyridin-4-yl)methyl]piperazin-1-yl}(cyclopropyl)methanone

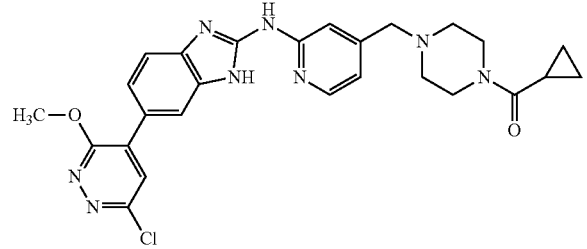 [SMILES: COc1nnc(Cl)cc1-c1ccc2nc(Nc3cc(CN4CCN(C(=O)C5CC5)CC4)ccn3)[nH]c2c1]

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (300 mg, 597 μmol) and 6-chloro-4-iodo-3-methoxypyridazine (300 mg, 1.11 mmol) Example 46.02 was prepared analogously to the procedure for the preparation of Example 08.01.

Yield: 242 mg (74%) of the title compound.

LC-MS (Method 5): $R_t$=2.81 min; MS (ESIpos): m/z=519 [M+H]$^+$.

$^1$H-NMR (400 MHz, DMSO-d6): δ [ppm]=0.70 (m, 4H), 1.95 (m, 1H), 2.40 (m, 4H), 3.52 (s, 4H), 3.69 (s, 2H), 4.10 (s, 3H), 6.95 (d, 1H), 7.21 (s, 1H), 7.28-7.69 (m, 3H), 7.82 (d, 1H), 8.28 (d, 1H), 10.71 (s, 1H), 12.30 (s, 1H).

$^{13}$C-NMR (101 MHz, DMSO-d6): δ [ppm]=7.0, 10.2, 41.6, 44.9, 52.4, 53.1, 55.2, 60.6, 110.6, 116.7, 128.2, 133.7, 147.0, 149.6, 151.0, 153.5, 161.8, 171.1.

Example 47.01 cyclopropyl{4-[(2-{[6-(6-methoxypyridazin-3-yl)-1H-benzimidazol-2-yl]amino}pyridin-4-yl)methyl]piperazin-1-yl}methanone

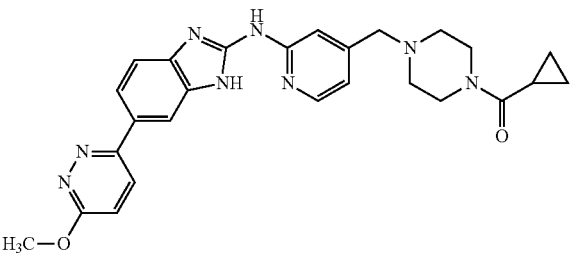 [SMILES: COc1ccc(-c2ccc3nc(Nc4cc(CN5CCN(C(=O)C6CC6)CC5)ccn4)[nH]c3c2)nn1]

To a stirred solution of 3-chloro-6-methoxypyridazine (216 mg, 1.49 mmol) and cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (150 mg, 299 μmol) in ioxane (1.9 mL) and water (380 μl) was added sodium carbonate (130 mg, 1.22 mmol) and Pd(dppf)Cl$_2$. CH$_2$Cl$_2$ (48.8 mg, 59.7 μmol) and PdCl$_2$(PPh$_3$)$_2$ (41.9 mg, 59.7 μmol). The mixture was heated to reflux for 42 h. Methanol was added, the mixture was filtered and the solvent was removed in vacuum. Silicagel chromatography gave 29.0 mg (19% yield) of the title compound.

LC-MS (Method 5): $R_t$=2.72 min; MS (ESIpos): m/z=485 [M+H]$^+$.

$^1$H-NMR (400 MHz, DMSO-d6) δ[ppm]: 2.490 (0.58), 2.495 (1.24), 2.500 (1.74), 2.505 (1.24), 2.509 (0.58), 3.305 (16.00), 4.077 (2.13).

Example 47.02 cyclopropyl{4-[(2-{[6-(5-methoxypyridazin-3-yl)-1H-benzimidazol-2-yl]amino}pyridin-4-yl)methyl]piperazin-1-yl}methanone

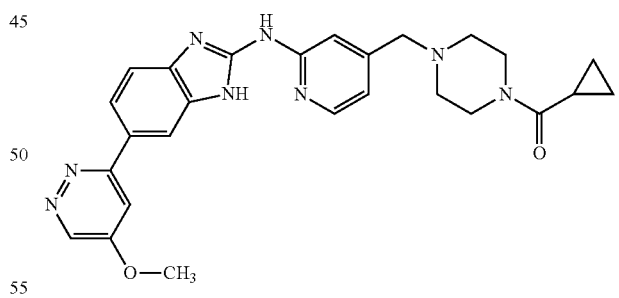

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (150 mg, 299 μmol) and 3-chloro-5-methoxypyridazine (115 mg, 796 μmol) Example 47.02 was prepared analogously to the procedure for the preparation of Example 08.01.

Yield: 16 mg (11% Yield) of the title compound.

LC-MS (Method 5): $R_t$=2.53 min; MS (ESIpos): m/z=485 [M+H]$^+$.

$^1$H-NMR (400 MHz, DMSO-d6): δ [ppm]=0.71 (m, 4H), 1.96 (m, 1H), 2.41 (m, 4H), 3.53 (m, 4H), 3.70 (s, 2H), 4.02

(s, 3H), 6.95 (d, 1H), 7.23 (s, 1H), 7.36-7.72 (m, 2H), 7.90 (d, 1H), 8.07-8.46 (m, 2H), 8.88 (d, 1H), 10.71 (s, 1H), 12.61 (s, 1H).

$^{13}$C-NMR (101 MHz, DMSO-d6): δ [ppm]=6.9, 10.2, 41.6, 44.8, 52.4, 53.1, 60.6, 67.4, 110.5, 116.6, 141.5, 146.9, 149.5, 153.5, 158.2, 160.2, 170.9.

Example 48.01 cyclopropyl{4-[(2-{[6-(6-methoxypyrazin-2-yl)-1H-benzimidazol-2-yl]amino}pyridin-4-yl)methyl]piperazin-1-yl}methanone

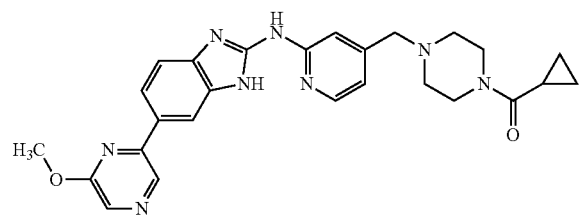 [SMILES: COc1cncc(-c2ccc3nc(Nc4cc(CN5CCN(C(=O)C6CC6)CC5)ccn4)[nH]c3c2)n1]

Starting with cyclopropyl{4-[(2-{[6-(4,4,5,5-tetramethyl-1,3,2-dioxaborolan-2-yl)-1H-benzimidazol-2-yl]amino}pyridin-4-yl)methyl]piperazin-1-yl}methanone (200 mg, 398 μmol) and 2-chloro-6-methoxypyrazine (70.0 mg, 484 μmol), Example 48.01 was prepared analogously to the procedure for the preparation of Example 08.01.

Yield: 117 mg (58%) of the title compound.

LC-MS (Method 5): $R_t$=2.84 min; MS (ESIpos): m/z=485 [M+H]$^+$.

$^1$H-NMR (400 MHz, DMSO-d6): δ [ppm]=0.70 (m, 4H), 1.94 (m, 1H), 2.40 (m, 4H), 3.52 (m, 4H), 3.69 (s, 2H), 4.04 (s, 3H), 6.95 (d, 1H), 7.22 (s, 1H), 7.34-7.45 (m, 1H), 7.87 (d, 1H), 8.16 (s, 1H), 8.27 (d, 1H), 8.77 (s, 1H), 10.71 (s, 1H), 12.27 (s, 1H).

$^{13}$C-NMR (101 MHz, DMSO-d6): δ [ppm]=6.9, 10.2, 41.6, 44.8, 52.4, 53.1, 60.6, 110.5, 116.6, 132.5, 146.9, 149.47, 149.51, 153.5, 159.2, 170.9.

Example 49.01 cyclopropyl{4-[(2-{[6-(2-methoxypyridin-4-yl)-7-(2-methylpropoxy)-1H-benzimidazol-2-yl]amino}pyridin-4-yl)methyl]piperazin-1-yl}methanone

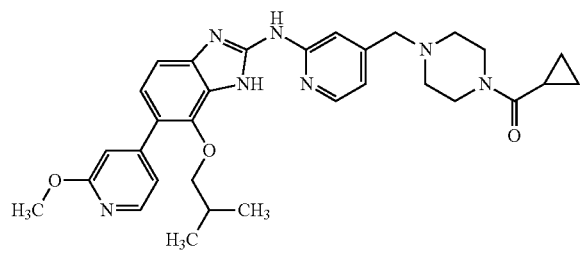 [SMILES: COc1cc(-c2ccc3nc(Nc4cc(CN5CCN(C(=O)C6CC6)CC5)ccn4)[nH]c3c2OCC(C)C)ccn1]

To a stirred solution of cyclopropyl{4-[(2-{[7-(2-methylpropoxy)-6-(4,4,5,5-tetramethyl-1,3,2-dioxaborolan-2-yl)-1H-benzimidazol-2-yl]amino}pyridin-4-yl)methyl]piperazin-1-yl}methanone (160 mg, 278 μmol) in dioxane (5 mL) and water (0.5 mL) was added sodium bicarbonate (88.5 mg, 835 μmol), 4-bromo-2-methoxypyridine (78.5 mg, 418 μmol), and Pd(dppf)Cl$_2$. CH$_2$Cl$_2$ (34.1 mg, 41.8 μmol). The mixture was heated to 120° C. in a sealed tube for 14 h. Ethyl acetate was added, the mixture was filtered through celite and the solvent was removed in vacuum. Aminophase-silicagel chromatography followed by silicagel chromatography gave a residue that was dissolved in dichloromethane and acidified with aqueous 2N hydrochloric acid. The organic phase was removed and saturated potassium carbonate solution was added to the aqueous phase until basic pH was reached. The aqueous phase was extracted with dichloromethane/methanol (10:1). The organic phase was dried (sodium sulfate), filtered and the solvent was removed in vacuum. Aminophase-silicagel chromatography followed by preparative reverse phase HPLC (gradient of water and acetonitrile containing ammonia as additive) gave 35.0 mg (20% yield) of the title compound.

LC-MS (Method 2): $R_t$=1.35 min; MS (ESIpos): m/z=556 [M+H]$^+$.

$^1$H-NMR (400 MHz, DMSO-d6) δ[ppm]: 0.683 (3.26), 0.688 (2.16), 0.703 (4.05), 0.711 (3.89), 0.719 (3.35), 0.723 (3.77), 0.730 (1.84), 0.814 (1.49), 0.830 (3.28), 0.836 (1.82), 0.851 (16.00), 0.858 (6.12), 0.867 (15.82), 0.894 (1.28), 0.910 (1.21), 0.936 (1.65), 0.953 (1.68), 1.237 (2.80), 1.394 (0.74), 1.873 (0.96), 1.889 (1.16), 1.905 (0.96), 1.965 (1.40), 2.327 (1.44), 2.356 (1.68), 2.435 (1.79), 2.523 (4.01), 2.669 (1.12), 3.512 (6.15), 3.705 (1.58), 3.875 (12.99), 4.296 (4.71), 4.312 (4.54), 6.926 (3.31), 6.932 (2.02), 6.946 (1.89), 7.005 (2.54), 7.025 (2.68), 7.136 (1.65), 7.140 (1.66), 7.150 (1.65), 7.153 (1.72), 7.227 (2.84), 7.260 (2.84), 7.280 (2.31), 8.130 (2.26), 8.143 (2.16), 8.258 (2.23), 8.271 (2.09), 10.719 (2.72), 12.187 (2.40).

Example 50.01

3,3,3-trifluoro-1-{4-[(2-{[6-(3-methoxypyridin-4-yl)-7-(2-methylpropoxy)-1H-benzimidazol-2-yl]amino}pyridin-4-yl)methyl]piperazin-1-yl}propan-1-one

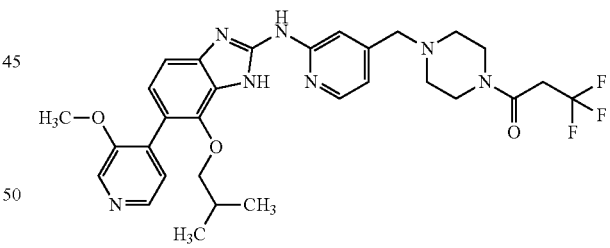

Starting with crude 6-(3-methoxypyridin-4-yl)-7-(2-methylpropoxy)-N-[4-(piperazin-1-ylmethyl)pyridin-2-yl]-1H-benzimidazol-2-amine hydrochloride (120 mg, approx. 171 μmol) and 3,3,3-trifluoropropanoic acid (23 μl, 98% purity, 260 μmol), Example 50.01 was prepared analogously to the procedure for the preparation of Example 05.01.

Yield: 58.0 mg of the title compound.

LC-MS (Method 2): $R_t$=1.20 min; MS (ESIpos): m/z=598 [M+H]$^+$.

$^1$H-NMR (400 MHz, DMSO-d$_6$): δ [ppm]=0.75 (d, 6H), 1.70-1.87 (m, 1H), 2.41 (br dd, 4H), 3.43-3.57 (m, 6H), 3.59-3.71 (m, 2H), 3.81 (s, 3H), 4.25 (d, 2H), 6.80 (d, 1H), 6.94 (d, 1H), 7.17-7.25 (m, 3H), 8.21 (d, 1H), 8.27 (d, 1H), 8.38 (s, 1H), 10.70 (s, 1H), 12.15 (s, 1H).

Example 50.02 cyclopropyl{4-[(2-{[6-(3-methoxypyridin-4-yl)-7-(2-methylpropoxy)-1H-benzimidazol-2-yl]amino}pyridin-4-yl)methyl]piperazin-1-yl}methanone

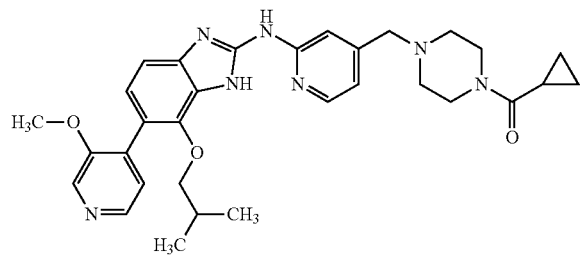 [SMILES: COc1cnccc1-c1ccc2nc(Nc3cc(CN4CCN(C(=O)C5CC5)CC4)ccn3)[nH]c2c1OCC(C)C]

Starting with crude 6-(3-methoxypyridin-4-yl)-7-(2-methylpropoxy)-N-[4-(piperazin-1-ylmethyl)pyridin-2-yl]-1H-benzimidazol-2-amine hydrochloride (120 mg, approx. 171 µmol) and cyclopropanecarboxylic acid (21 µl, 98% purity, 260 µmol), Example 50.02 was prepared analogously to the procedure for the preparation of Example 05.01.
Yield: 62.0 mg of the title compound.
LC-MS (Method 2): $R_t$=1.17 min; MS (ESIpos): m/z=556 [M+H]$^+$.
$^1$H-NMR (400 MHz, DMSO-d$_6$): δ [ppm]=0.66-0.80 (m, 10H), 1.78 (dt, 1H), 1.90-2.03 (m, 1H), 2.32-2.48 (m, 4H), 3.52 (s, 4H), 3.71 (br s, 2H), 3.81 (s, 3H), 4.25 (d, 2H), 6.80 (d, 1H), 6.94 (br d, 1H), 7.21 (dt, 3H), 8.21 (d, 1H), 8.27 (d, 1H), 8.38 (s, 1H), 10.71 (s, 1H), 12.16 (s, 1H).

Example 50.03 cyclobutyl{4-[(2-{[6-(3-methoxypyridin-4-yl)-7-(2-methylpropoxy)-1H-benzimidazol-2-yl]amino}pyridin-4-yl)methyl]piperazin-1-yl}methanone

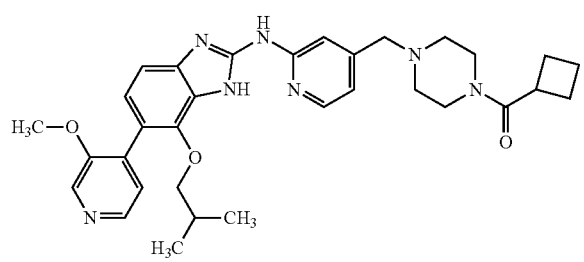 [SMILES: COc1cnccc1-c1ccc2nc(Nc3cc(CN4CCN(C(=O)C5CCC5)CC4)ccn3)[nH]c2c1OCC(C)C]

Starting with crude 6-(3-methoxypyridin-4-yl)-7-(2-methylpropoxy)-N-[4-(piperazin-1-ylmethyl)pyridin-2-yl]-1H-benzimidazol-2-amine hydrochloride (120 mg, approx. 171 µmol) and cyclobutanecarboxylic acid (25 µl, 98% purity, 260 µmol), Example 50.03 was prepared analogously to the procedure for the preparation of Example 05.01.
Yield: 88.0 mg of the title compound.
LC-MS (Method 2): $R_t$=1.23 min; MS (ESIpos): m/z=570 [M+H]$^+$
$^1$H-NMR (400 MHz, DMSO-d$_6$): δ [ppm]=0.75 (d, 6H), 1.67-1.81 (m, 2H), 1.82-1.96 (m, 1H), 1.99-2.22 (m, 4H), 2.35 (br d, 4H), 3.49 (s, 4H), 3.81 (s, 3H), 4.25 (d, 2H), 6.80 (d, 1H), 6.93 (d, 1H), 7.16-7.25 (m, 3H), 8.21 (d, 1H), 8.26 (d, 1H), 8.38 (s, 1H), 10.70 (s, 1H), 12.15 (s, 1H).

Example 51.01

1-{4-[(2-{[7-ethoxy-6-(3-methoxypyridin-4-yl)-1H-benzimidazol-2-yl]amino}pyridin-4-yl)methyl]piperazin-1-yl}-3,3,3-trifluoropropan-1-one

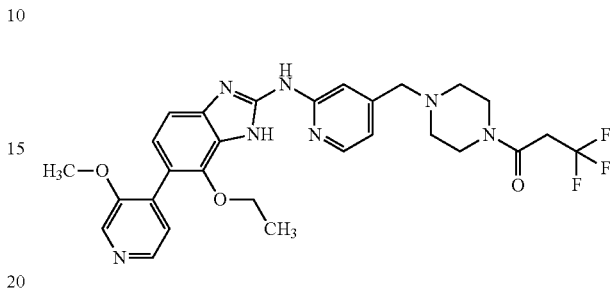

Starting with crude 7-ethoxy-6-(3-methoxypyridin-4-yl)-N-[4-(piperazin-1-ylmethyl)pyridin-2-yl]-1H-benzimidazol-2-amine hydrochloride (250 mg, approx. 378 µmol) and 3,3,3-trifluoropropanoic acid (50 µl, 570 µmol), Example 51.01. was prepared analogously to the procedure for the preparation of Example 16.01.02.
Yield: 100.0 mg of the title compound.
LC-MS (Method 2): $R_t$=1.10 min; MS (ESIpos): m/z=570 [M+H]$^+$.
$^1$H-NMR (400 MHz, DMSO-d6) δ[ppm]: 1.131 (5.68), 1.149 (12.32), 1.154 (1.75), 1.167 (5.91), 1.172 (2.35), 1.190 (1.05), 1.986 (3.46), 2.366 (1.53), 2.378 (2.32), 2.390 (1.80), 2.408 (1.73), 2.420 (2.32), 2.432 (1.69), 2.522 (1.37), 3.456 (1.70), 3.469 (2.35), 3.480 (2.00), 3.492 (2.04), 3.513 (6.88), 3.604 (1.16), 3.631 (3.33), 3.659 (3.13), 3.686 (1.00), 3.820 (16.00), 4.018 (0.77), 4.036 (0.74), 4.533 (1.15), 4.550 (3.62), 4.568 (3.57), 4.585 (1.15), 5.755 (3.03), 6.792 (2.86), 6.812 (2.99), 6.915 (1.62), 6.919 (1.68), 6.929 (1.76), 6.932 (1.72), 7.180 (2.88), 7.192 (4.57), 7.213 (3.26), 7.233 (2.70), 8.206 (3.20), 8.218 (2.92), 8.257 (2.75), 8.270 (2.62), 8.384 (4.97), 10.689 (3.24), 12.132 (2.74).

Example 51.02

2-cyclopropyl-1-{4-[(2-{[7-ethoxy-6-(3-methoxypyridin-4-yl)-1H-benzimidazol-2-yl]amino}pyridin-4-yl)methyl]piperazin-1-yl}ethanone

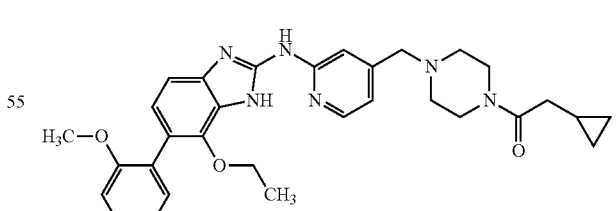

Starting with crude 7-ethoxy-6-(3-methoxypyridin-4-yl)-N-[4-(piperazin-1-ylmethyl)pyridin-2-yl]-1H-benzimidazol-2-amine hydrochloride (200 mg, approx. 302 µmol) and cyclopropylacetic acid (42 µl, 450 µmol), Example 51.02 was prepared analogously to the procedure for the preparation of Example 01.02.

Yield: 50.0 mg of the title compound.

LC-MS (Method 2): $R_t$=1.09 min; MS (ESIpos): m/z=542 [M+H]⁺.

¹H-NMR (400 MHz, DMSO-d6) δ [ppm]: 0.000 (0.94), 0.011 (3.25), 0.014 (2.94), 0.023 (3.26), 0.026 (3.00), 0.037 (1.07), 0.330 (1.16), 0.339 (2.82), 0.344 (2.96), 0.350 (1.48), 0.354 (1.44), 0.360 (3.01), 0.364 (2.87), 0.375 (1.09), 0.854 (1.06), 1.047 (5.83), 1.064 (12.53), 1.071 (4.46), 1.082 (5.79), 1.089 (8.19), 1.107 (3.86), 1.905 (13.05), 2.153 (5.25), 2.170 (5.09), 2.273 (2.18), 2.293 (1.97), 2.306 (2.17), 3.368 (2.13), 3.380 (1.94), 3.413 (6.49), 3.738 (16.00), 3.916 (1.04), 3.935 (2.95), 3.952 (2.96), 3.970 (0.98), 4.449 (1.14), 4.467 (3.67), 4.485 (3.64), 4.503 (1.11), 6.707 (2.95), 6.728 (3.14), 6.832 (1.60), 6.835 (1.64), 6.845 (1.69), 6.848 (1.68), 7.097 (3.08), 7.109 (5.16), 7.131 (3.18), 7.151 (2.78), 8.124 (3.28), 8.135 (3.01), 8.172 (2.67), 8.185 (2.51), 8.301 (5.03), 10.620 (3.23), 12.056 (2.74).

Example 51.03 cyclopropyl{4-[(2-{[7-ethoxy-6-(3-methoxypyridin-4-yl)-1H-benzimidazol-2-yl]amino}pyridin-4-yl)methyl]piperazin-1-yl}methanone

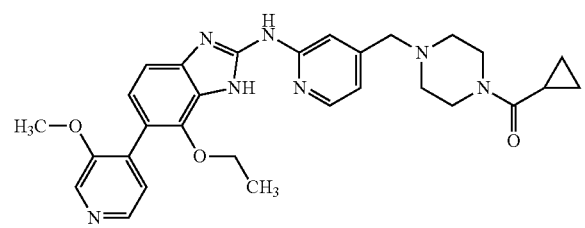 [SMILES: CCOc1c(-c2ccncc2OC)ccc2nc(Nc3cc(CN4CCN(C(=O)C5CC5)CC4)ccn3)[nH]c12]

Starting with crude 7-ethoxy-6-(3-methoxypyridin-4-yl)-N-[4-(piperazin-1-ylmethyl)pyridin-2-yl]-1H-benzimidazol-2-amine hydrochloride (150 mg, approx. 227 μmol) and cyclopropanecarboxylic acid (28 μl, 95% purity, 340 μmol) Example 51.03. was prepared analogously to the procedure for the preparation of Example 16.01.02.

Yield: 30.0 mg of the title compound.

LC-MS (Method 2): $R_t$=1.06 min; MS (ESIpos): m/z=528 [M+H]⁺.

¹H-NMR (400 MHz, DMSO-d6) δ [ppm]: 0.676 (1.50), 0.683 (3.35), 0.689 (2.09), 0.696 (1.72), 0.703 (4.06), 0.708 (3.54), 0.713 (3.68), 0.720 (3.43), 0.725 (3.98), 0.732 (1.83), 1.132 (5.83), 1.149 (12.24), 1.155 (2.06), 1.167 (6.01), 1.173 (2.60), 1.191 (1.16), 1.942 (0.80), 1.949 (0.87), 1.961 (1.47), 1.973 (0.87), 1.980 (0.86), 1.988 (4.23), 2.085 (4.51), 2.361 (1.58), 2.440 (1.62), 3.513 (6.33), 3.700 (1.46), 3.821 (16.00), 4.019 (0.95), 4.037 (0.95), 4.533 (0.99), 4.551 (2.93), 4.569 (2.89), 4.586 (0.97), 5.756 (5.66), 6.792 (2.10), 6.812 (2.27), 6.927 (1.82), 6.940 (1.87), 7.181 (2.34), 7.193 (2.98), 7.201 (3.06), 7.212 (2.81), 7.233 (2.22), 8.208 (2.63), 8.219 (2.57), 8.260 (2.94), 8.273 (2.77), 8.385 (4.23), 10.691 (2.87), 12.133 (2.64).

Example 51.04 cyclobutyl{4-[(2-{[7-ethoxy-6-(3-methoxypyridin-4-yl)-1H-benzimidazol-2-yl]amino}pyridin-4-yl)methyl]piperazin-1-yl}methanone

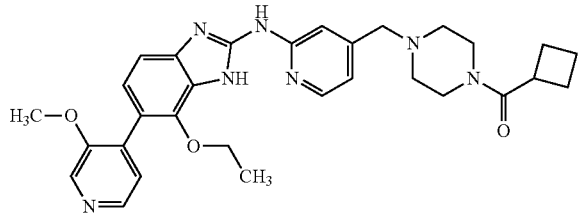 [SMILES: CCOc1c(-c2ccncc2OC)ccc2nc(Nc3cc(CN4CCN(C(=O)C5CCC5)CC4)ccn3)[nH]c12]

Starting with crude 7-ethoxy-6-(3-methoxypyridin-4-yl)-N-[4-(piperazin-1-ylmethyl)pyridin-2-yl]-1H-benzimidazol-2-amine hydrochloride (200 mg, approx. 302 μmol) and cyclobutanecarboxylic acid (43 μl, 450 μmol), Example 51.04 was prepared analogously to the procedure for the preparation of Example 01.02.

Yield: 50.0 mg of the title compound.

LC-MS (Method 2): $R_t$=1.12 min; MS (ESIpos): m/z=542 [M+H]⁺.

¹H-NMR (400 MHz, DMSO-d6) δ[ppm]: 1.128 (5.83), 1.146 (12.86), 1.154 (3.59), 1.163 (6.14), 1.172 (6.76), 1.189 (3.34), 1.838 (0.69), 1.859 (1.33), 1.882 (1.02), 1.886 (0.99), 1.987 (11.56), 2.049 (1.46), 2.058 (1.08), 2.065 (1.05), 2.071 (1.67), 2.080 (1.29), 2.097 (1.03), 2.102 (0.92), 2.120 (1.90), 2.125 (1.26), 2.142 (2.06), 2.147 (1.66), 2.165 (0.95), 2.171 (1.07), 2.345 (4.13), 3.300 (1.17), 3.319 (3.19), 3.468 (2.22), 3.485 (6.10), 3.820 (16.00), 3.999 (0.93), 4.016 (2.55), 4.034 (2.47), 4.053 (0.79), 4.531 (1.16), 4.549 (3.63), 4.566 (3.56), 4.584 (1.12), 6.790 (2.87), 6.810 (3.00), 6.907 (1.65), 6.923 (1.78), 7.179 (4.15), 7.191 (3.45), 7.213 (3.17), 7.233 (2.70), 8.206 (3.18), 8.218 (3.04), 8.251 (2.77), 8.263 (2.63), 8.384 (5.09), 10.699 (3.23), 12.137 (2.81).

Example 52.01

1-{4-[(2-{[6-(1-ethyl-1H-pyrazol-4-yl)-7-(2-methylpropoxy)-1H-benzimidazol-2-yl]amino}pyridin-4-yl)methyl]piperazin-1-yl}-3,3,3-trifluoropropan-1-one

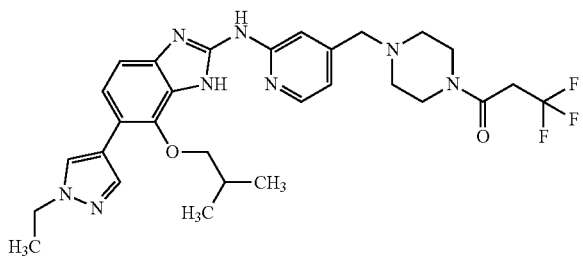 [SMILES: CCn1cc(-c2ccc3nc(Nc4cc(CN5CCN(C(=O)CC(F)(F)F)CC5)ccn4)[nH]c3c2OCC(C)C)cn1]

Starting with crude 6-(1-ethyl-1H-pyrazol-4-yl)-7-(2-methylpropoxy)-N-[4-(piperazin-1-ylmethyl)pyridin-2-yl]-1H-benzimidazol-2-amine hydrochloride (248 mg, approx. 453 μmol) and 3,3,3-trifluoropropanoic acid (61 μl, 98% purity, 680 μmol), Example 52.01 was prepared analogously to the procedure for the preparation of Example 01.02.

Yield: 24.0 mg of the title compound.

LC-MS (Method 2): $R_t$=1.26 min; MS (ESIpos): m/z=585 [M+H]$^+$.

$^1$H-NMR (400 MHz, DMSO-d$_6$): δ [ppm]=1.00 (d, 6H), 1.41 (t, 3H), 2.07 (dt, 1H), 2.35-2.45 (m, 4H), 3.44-3.57 (m, 6H), 3.66 (q, 2H), 3.78 (br d, 1H), 4.16 (q, 2H), 4.36 (d, 2H), 6.92 (d, 1H), 7.10-7.32 (m, 3H), 7.81 (s, 1H), 8.02 (s, 1H), 8.25 (d, 1H), 10.61 (s, 1H), 12.02 (s, 1H), 12.11-12.20 (m, 1H).

Example 52.02 cyclopropyl{4-[(2-{[6-(1-ethyl-1H-pyrazol-4-yl)-7-(2-methylpropoxy)-1H-benzimidazol-2-yl]amino}pyridin-4-yl)methyl]piperazin-1-yl}methanone

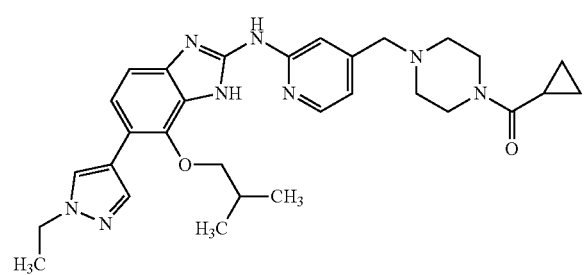 [SMILES: CCn1cc(-c2ccc3nc(Nc4cc(CN5CCN(C(=O)C6CC6)CC5)ccn4)[nH]c3c2OCC(C)C)cn1]

Starting with crude 6-(1-ethyl-1H-pyrazol-4-yl)-7-(2-methylpropoxy)-N-[4-(piperazin-1-ylmethyl)pyridin-2-yl]-1H-benzimidazol-2-amine hydrochloride (248 mg, approx. 453 μmol) and cyclopropanecarboxylic acid (55 μl, 98% purity, 680 μmol), Example 52.02 was prepared analogously to the procedure for the preparation of Example 01.02.

Yield: 49.0 mg of the title compound.

LC-MS (Method 2): $R_t$=1.23 min; MS (ESIpos): m/z=543 [M+H]$^+$.

$^1$H-NMR (400 MHz, DMSO-d$_6$): δ [ppm]=0.65-0.78 (m, 4H), 1.00 (d, 6H), 1.37-1.45 (m, 3H), 1.92-2.13 (m, 2H), 2.32-2.47 (m, 4H), 3.51 (s, 4H), 3.71 (br s, 2H), 4.16 (q, 2H), 4.36 (d, 2H), 6.93 (d, 1H), 7.10-7.31 (m, 3H), 7.81 (s, 1H), 8.02 (s, 1H), 8.25 (d, 1H), 10.61 (s, 1H), 12.02 (s, 1H), 12.16 (br s, 1H).

Example 53.01

1-{4-[(2-{[7-ethoxy-6-(1-ethyl-1H-pyrazol-4-yl)-1H-benzimidazol-2-yl]amino}pyridin-4-yl)methyl]piperazin-1-yl}-3,3,3-trifluoropropan-1-one

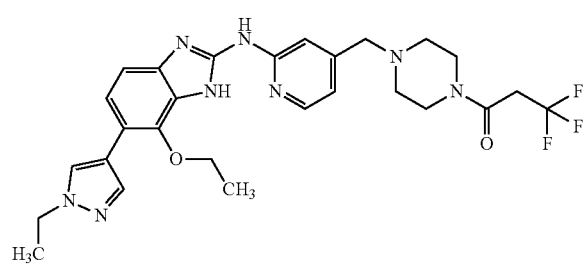 [SMILES: CCOc1c(-c2cnn(CC)c2)ccc2nc(Nc3cc(CN4CCN(C(=O)CC(F)(F)F)CC4)ccn3)[nH]c12]

Starting with crude 7-ethoxy-6-(1-ethyl-1H-pyrazol-4-yl)-N-[4-(piperazin-1-ylmethyl)pyridin-2-yl]-1H-benzimidazol-2-amine hydrochloride (200 mg, approx. 311 μmol) and 3,3,3-trifluoropropanoic acid (41 μl, 470 μmol) Example 53.01. was prepared analogously to the procedure for the preparation of Example 16.01.02.

Yield: 7.0 mg of the title compound.

LC-MS (Method 2): $R_t$=1.13 min; MS (ESIpos): m/z=557 [M+H]$^+$.

$^1$H-NMR (400 MHz, DMSO-d6) δ[ppm]: 1.006 (0.46), 1.232 (1.56), 1.347 (2.97), 1.365 (6.15), 1.383 (3.61), 1.389 (4.80), 1.407 (9.24), 1.425 (4.34), 2.318 (0.67), 2.323 (1.47), 2.327 (2.02), 2.331 (1.47), 2.337 (0.76), 2.376 (2.05), 2.387 (1.77), 2.403 (1.84), 2.416 (2.26), 2.518 (16.00), 2.523 (13.37), 2.529 (8.84), 2.540 (10.68), 2.660 (0.80), 2.665 (1.56), 2.669 (2.05), 2.674 (1.44), 2.678 (0.70), 3.308 (1.07), 3.455 (1.80), 3.468 (2.29), 3.479 (2.02), 3.507 (5.78), 3.610 (0.98), 3.628 (0.73), 3.637 (2.69), 3.655 (0.83), 3.664 (2.51), 3.692 (0.83), 4.135 (0.92), 4.153 (2.72), 4.171 (2.78), 4.189 (0.98), 4.543 (0.86), 4.560 (2.57), 4.578 (2.57), 4.595 (0.86), 6.903 (1.25), 6.919 (1.28), 7.159 (1.99), 7.164 (2.23), 7.179 (3.03), 7.196 (3.06), 7.217 (1.01), 7.837 (3.73), 8.059 (3.37), 8.223 (0.46), 8.239 (1.87), 8.252 (1.71), 10.678 (1.93), 12.039 (1.90).

Example 53.02 cyclopropyl{4-[(2-{[7-ethoxy-6-(1-ethyl-1H-pyrazol-4-yl)-1H-benzimidazol-2-yl]amino}pyridin-4-yl)methyl]piperazin-1-yl}methanone

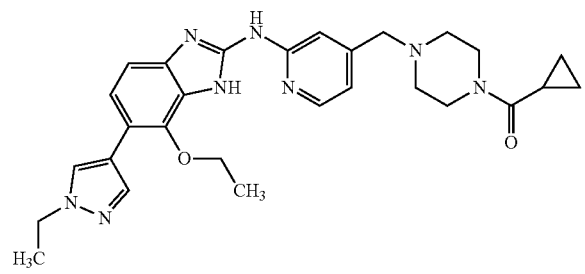 [SMILES: CCOc1c(-c2cnn(CC)c2)ccc2nc(Nc3cc(CN4CCN(C(=O)C5CC5)CC4)ccn3)[nH]c12]

Starting with crude 7-ethoxy-6-(1-ethyl-1H-pyrazol-4-yl)-N-[4-(piperazin-1-ylmethyl)pyridin-2-yl]-1H-benzimidazol-2-amine hydrochloride (200 mg, approx. 311 μmol) and cyclopropanecarboxylic acid (39 μl, 95% purity, 470 μmol) Example 53.02. was prepared analogously to the procedure for the preparation of Example 16.01.02.

Yield: 30.0 mg of the title compound.

LC-MS (Method 2): $R_t$=1.10 min; MS (ESIpos): m/z=515 [M+H]$^+$.

$^1$H-NMR (400 MHz, DMSO-d6) δ[ppm]: 0.682 (3.37), 0.702 (4.15), 0.706 (4.08), 0.711 (4.11), 0.723 (4.06), 1.348 (3.15), 1.366 (6.16), 1.389 (5.71), 1.407 (8.40), 1.425 (4.20), 1.950 (1.00), 1.962 (1.40), 1.973 (0.94), 1.980 (0.80), 2.356 (2.28), 3.334 (16.00), 3.699 (2.08), 4.135 (1.19), 4.153 (3.23), 4.172 (3.22), 4.189 (1.20), 4.544 (1.04), 4.562 (2.74), 4.579 (2.71), 4.597 (1.00), 6.910 (1.80), 6.924 (1.89), 7.171 (3.40), 7.181 (3.78), 7.197 (3.07), 7.218 (1.03), 7.839 (4.28), 8.060 (3.71), 8.240 (2.08), 8.253 (2.11), 10.682 (2.57), 12.043 (2.50).

Example 54.01

3,3,3-trifluoro-1-{4-[(2-{[7-methyl-6-(3-methyl-1,2,4-oxadiazol-5-yl)-1H-benzimidazol-2-yl]amino}pyridin-4-yl)methyl]piperazin-1-yl}propan-1-one

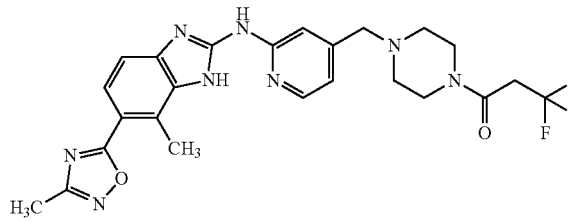

Starting with crude 7-methyl-6-(3-methyl-1,2,4-oxadiazol-5-yl)-N-[4-(piperazin-1-ylmethyl)pyridin-2-yl]-1H-benzimidazol-2-amine hydrochloride (235 mg, approx. 457 µmol) and 3,3,3-trifluoropropanoic acid (120 µl, 1.4 mmol), Example 54.01 was prepared analogously to the procedure for the preparation of Example 01.02.

Yield: 100 mg of the title compound.

LC-MS (Method 2): $R_t$=1.13 min; MS (ESIpos): m/z=515 [M+H]$^+$.

$^1$H-NMR (400 MHz, DMSO-d6): δ [ppm]=2.42 (s, 3H), 2.85 (s, 3H), 3.38 (br. s., 8H), 3.61-3.82 (m, 4H), 7.09 (d, 1H), 7.29 (br. s., 1H), 7.52 (d, 1H), 7.80 (d, 1H), 8.44 (d, 1H), 11.26 (br. s., 1H), 12.50 (br. s., 1H).

Example 54.02 cyclopropyl{4-[(2-{[7-methyl-6-(3-methyl-1,2,4-oxadiazol-5-yl)-1H-benzimidazol-2-yl]amino}pyridin-4-yl)methyl]piperazin-1-yl}methanone

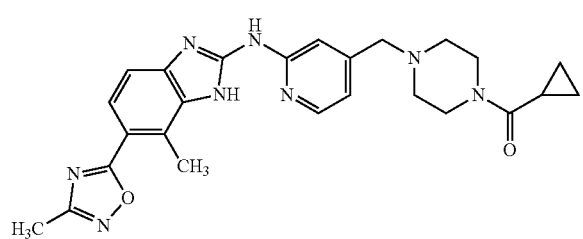 [SMILES: Cc1noc(-c2ccc3nc(Nc4cc(CN5CCN(C(=O)C6CC6)CC5)ccn4)[nH]c3c2C)n1]

Starting with crude 7-methyl-6-(3-methyl-1,2,4-azol-5-yl)-N-[4-(piperazin-1-ylmethyl)pyridin-2-yl]-1H-oxadibenzimidazol-2-amine hydrochloride (235 mg, approx. 457 µmol) and cyclopropanecarboxylic acid (110 µl, 1.4 mmol), Example 54.02 was prepared analogously to the procedure for the preparation of Example 01.02.

Yield: 43 mg of the title compound.

LC-MS (Method 2): $R_t$=1.10 min; MS (ESIpos): m/z=473 [M+H]$^+$.

$^1$H-NMR (400 MHz, DMSO-d6): δ [ppm]=0.66-0.74 (m, 4H), 1.90-2.00 (m, 1H), 2.36 (br. s., 2H), 2.41 (s, 3H), 2.43 (br. s., 2H), 2.83 (s, 3H), 3.52 (br. s., 4H), 3.70 (br. s., 2H), 6.95 (d, 1H), 7.17 (br. s., 1H), 7.50 (d, 1H), 7.73 (d, 1H), 8.28 (d, 1H), 10.89 (br. s., 1H), 12.41 (br. s., 1H).

Example 55.01 tert-butyl 4-[(1R or 1S)-1-(2-{[6-(1-{[(1RS)-2,2-difluorocyclopropyl]methyl}-1H-pyrazol-4-yl)-1H-benzimidazol-2-yl]amino}pyridin-4-yl)ethyl]piperazine-1-carboxylate

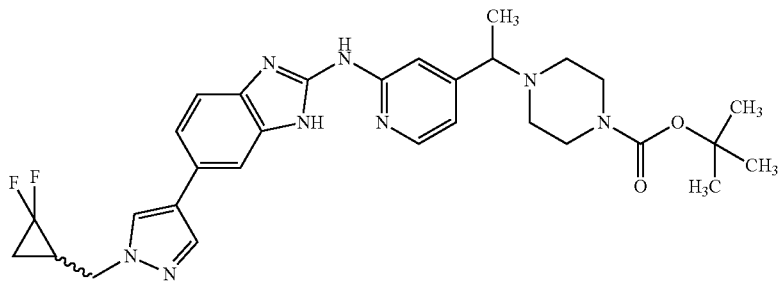 [SMILES: CC(c1ccnc(Nc2nc3ccc(-c4cnn(CC5CC5(F)F)c4)cc3[nH]2)c1)N1CCN(C(=O)OC(C)(C)C)CC1]

Starting with crude 4-(1-{[(1RS)-2,2-difluorocyclopropyl]methyl}-1H-pyrazol-4-yl)benzene-1,2-diamine (360 mg, 1.36 mmol) Compound 55.03, Example 55.01 was prepared analogously to the procedure for the preparation of Example 39.02.01.

Yield: 369 mg of the 90% pure title compound.

LC-MS (Method 2): $R_t$=1.31 min; MS (ESIpos): m/z=579 [M+H]$^+$.

$^1$H-NMR (400 MHz, DMSO-d6): δ [ppm]=1.28 (d, 3H), 1.38 (s, 9H), 1.47-1.59 (m, 1H), 1.64-1.78 (m, 1H), 2.20-2.34 (m, 3H), 2.35-2.44 (m, 2H), 2.51-2.53 (m, 2H), 3.32 (br s, 2H), 3.44 (q, 1H), 4.16-4.33 (m, 2H), 6.92 (dd, 1H), 7.16 (s, 1H), 7.24 (br s, 1H), 7.39-7.67 (m, 2H), 7.77-7.91 (m, 1H), 8.10 (br d, 1H), 8.25 (d, 1H), 10.56 (br s, 1H), 12.04 (br s, 1H).—contains ethanol.

Example 55.01.01 tert-butyl 4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazine-1-carboxylate

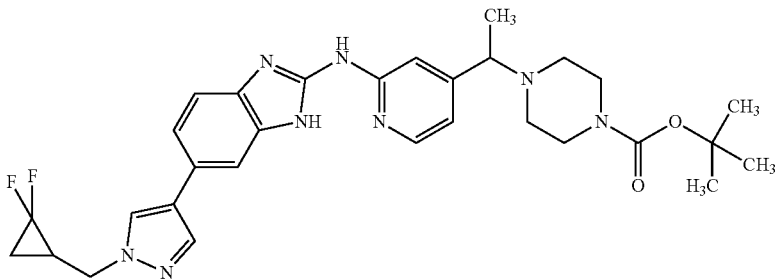 [SMILES: CC(c1ccnc(Nc2nc3ccc(-c4cnn(CC5CC5(F)F)c4)cc3[nH]2)c1)N1CCN(C(=O)OC(C)(C)C)CC1]

Starting with 4-(1-{[(1R or 1S)-2,2-difluorocyclopropyl]methyl}-1H-pyrazol-4-yl)benzene-1,2-diamine (160 mg, see Compound 55.03.01), Example 55.01.01 was prepared analogously to the procedure for the preparation of Example 39.02.01.

Yield: 74 mg of the 86% pure title compound.

LC-MS (Method 2): $R_t$=1.33 min; MS (ESIpos): m/z=579 [M+H]$^+$.

$^1$H-NMR (400 MHz, DMSO-d6): δ [ppm]=1.28 (d, 3H), 1.38 (s, 9H), 1.48-1.59 (m, 1H), 1.64-1.77 (m, 1H), 2.25-2.44 (m, 5H), 3.24-3.32 (m, 4H), 3.43 (q, 1H), 4.17-4.36 (m, 2H), 6.92 (d, 1H), 7.16 (s, 1H), 7.18-7.48 (m, 2H), 7.50-7.68 (m, 1H), 7.85 (br d, 1H), 8.04-8.16 (m, 1H), 8.25 (d, 1H), 10.56 (br s, 1H), 12.03 (br s, 1H).

Example 55.01.02 tert-butyl 4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazine-1-carboxylate

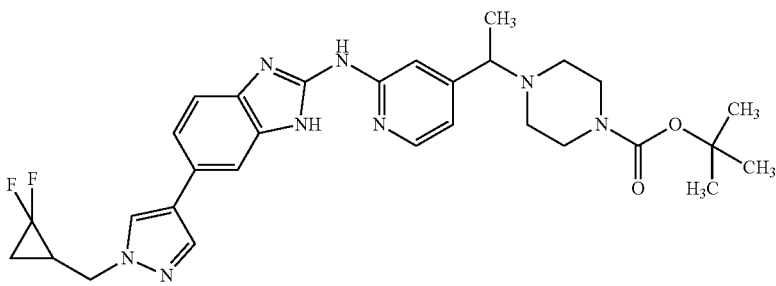 [SMILES: CC(c1ccnc(Nc2nc3ccc(-c4cnn(CC5CC5(F)F)c4)cc3[nH]2)c1)N1CCN(C(=O)OC(C)(C)C)CC1]

Starting with 4-(1-{[(1R or 1S)-2,2-difluorocyclopropyl]methyl}-1H-pyrazol-4-yl)benzene-1,2-diamine (140 mg, see Compound 55.03.02), Example 55.01.02 was prepared analogously to the procedure for the preparation of Example 39.02.01.

Yield: 85 mg of the 88% pure title compound.

LC-MS (Method 2): $R_t$=1.33 min; MS (ESIpos): m/z=579 [M+H]$^+$.

$^1$H-NMR (400 MHz, DMSO-d6): δ [ppm]=1.28 (d, 3H), 1.38 (s, 9H), 1.50-1.59 (m, 1H), 1.70 (tdd, 1H), 2.20-2.44 (m, 5H), 3.24-3.32 (m, 4H), 3.39-3.48 (m, 1H), 4.18-4.34 (m, 2H), 6.92 (d, 1H), 7.16 (s, 1H), 7.25 (br d, 1H), 7.32-7.45 (m, 1H), 7.58 (br s, 1H), 7.85 (s, 1H), 8.10 (s, 1H), 8.25 (d, 1H), 10.58 (br s, 1H), 12.06 (br s, 1H).

Example 55.02

1-{4-[(1R or 1S)-1-(2-{[6-(1-{[(1RS)-2,2-difluorocyclopropyl]methyl}-1H-pyrazol-4-yl)-1H-benzimidazol-2-yl]amino}pyridin-4-yl)ethyl]piperazin-1-yl}-3,3,3-trifluoropropan-1-one

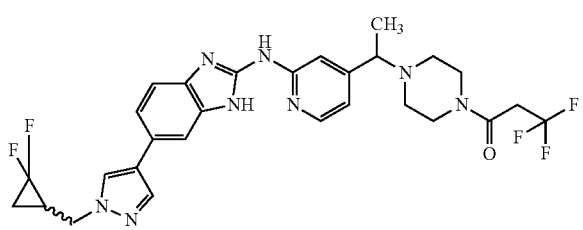 [SMILES: CC(c1ccnc(Nc2nc3ccc(-c4cnn(CC5CC5(F)F)c4)cc3[nH]2)c1)N1CCN(C(=O)CC(F)(F)F)CC1]

Starting with 6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt (210 mg, Compound 55.04), Example 55.02 was prepared analogously to the procedure for the preparation of Example 39.02.02.

Yield: 127 mg of the 94% pure title compound.

LC-MS (Method 2): $R_t$=1.16 min; MS (ESIpos): m/z=590 [M+H]$^+$.

$^1$H-NMR (400 MHz, DMSO-d6): δ [ppm]=1.39 (br s, 4H), 1.48-1.60 (m, 1H), 1.64-1.78 (m, 1H), 2.22-2.32 (m, 1H), 3.17-3.57 (m, 7H), 3.64 (q, 2H), 4.29 (br d, 2H), 7.18

(br d, 1H), 7.22 (s, 1H), 7.46-7.60 (m, 3H), 7.70 (s, 1H), 7.92 (s, 1H), 8.20 (s, 1H), 8.43 (br d, 1H), 8.54 (dd, 1H), 8.77 (dd, 1H).

Example 55.02.01

1-{4-[(1R or 1S)-1-(2-{[6-(1-{[(1R or lS)-2,2-difluorocyclopropyl]methyl}-1H-pyrazol-4-yl)-1H-benzimidazol-2-yl]amino}pyridin-4-yl)ethyl]piperazin-1-yl}-3,3,3-trifluoropropan-1-one

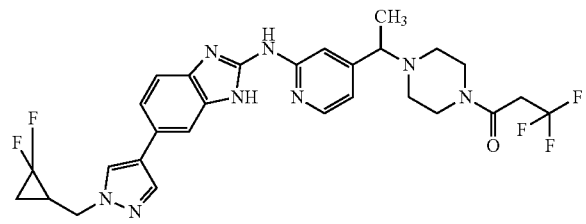 [SMILES: CC(c1ccnc(Nc2nc3ccc(-c4cnn(CC5CC5(F)F)c4)cc3[nH]2)c1)N1CCN(C(=O)CC(F)(F)F)CC1]

Starting with 6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (45 mg, see Compound 55.04.01), Example 55.02.01 was prepared analogously to the procedure for the preparation of Example 39.02.02.

Yield: 18 mg of the 92% pure title compound.

LC-MS (Method 2): $R_t$=1.17 min; MS (ESIpos): m/z=589 [M+H]$^+$.

$^1$H-NMR (400 MHz, DMSO-d6): δ [ppm]=1.30 (d, 3H), 1.47-1.59 (m, 1H), 1.64-1.77 (m, 1H), 2.22-2.47 (m, 5H), 3.39-3.52 (m, 5H), 3.62 (q, 2H), 4.17-4.34 (m, 2H), 6.93 (d, 1H), 7.17 (s, 1H), 7.21-7.67 (m, 3H), 7.78-7.90 (m, 1H), 8.04-8.16 (m, 1H), 8.25 (d, 1H), 10.57 (br s, 1H), 12.04 (br d, 1H).

Example 55.02.02

1-{4-[(1R or 1S)-1-(2-{[6-(1-{[(1R or lS)-2,2-difluorocyclopropyl]methyl}-1H-pyrazol-4-yl)-1H-benzimidazol-2-yl]amino}pyridin-4-yl)ethyl]piperazin-1-yl}-3,3,3-trifluoropropan-1-one

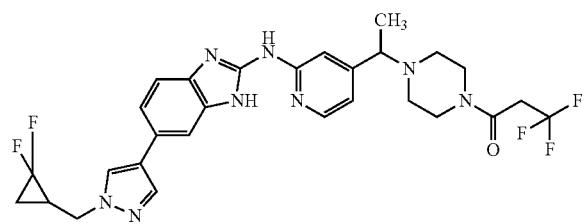 [SMILES: CC(c1ccnc(Nc2nc3ccc(-c4cnn(CC5CC5(F)F)c4)cc3[nH]2)c1)N1CCN(C(=O)CC(F)(F)F)CC1]

Starting with 6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (37 mg, see Compound 55.04.02), Example 55.02.02 was prepared analogously to the procedure for the preparation of Example 39.02.02.

Yield: 19 mg of the 93% pure title compound.

LC-MS (Method 2): $R_t$=1.17 min; MS (ESIpos): m/z=589 [M+H]$^+$.

$^1$H-NMR (400 MHz, DMSO-d6): δ [ppm]=1.30 (d, 3H), 1.48-1.59 (m, 1H), 1.70 (tdd, 1H), 2.23-2.47 (m, 5H), 3.39-3.53 (m, 5H), 3.62 (q, 2H), 4.14-4.34 (m, 2H), 6.93 (dd, 1H), 7.17 (s, 1H), 7.20-7.48 (m, 2H), 7.51-7.67 (m, 1H), 7.79-7.90 (m, 1H), 8.04-8.17 (m, 1H), 8.25 (d, 1H), 10.57 (br s, 1H), 12.04 (br d, 1H).

Example 55.03 cyclopropyl{4-[(1R or 1S)-1-(2-{[6-(1-{[(1RS)-2,2-difluorocyclopropyl]methyl}-1H-pyrazol-4-yl)-1H-benzimidazol-2-yl]amino}pyridin-4-yl)ethyl]piperazin-1-yl}methanone

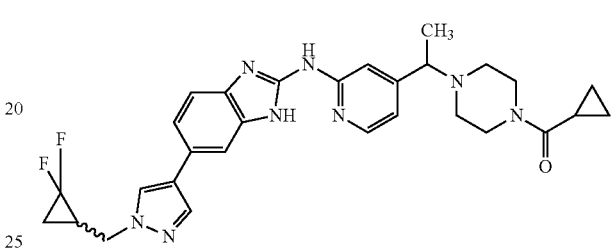

Starting with 6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt (210 mg, Compound 55.04), Example 55.03 was prepared analogously to the procedure for the preparation of Example 39.02.03.

Yield: 112 mg of the 94% pure title compound.

LC-MS (Method 2): $R_t$=1.12 min; MS (ESIpos): m/z=548 [M+H]$^+$.

$^1$H-NMR (400 MHz, DMSO-d6): δ [ppm]=0.64-0.75 (m, 4H), 1.38 (br d, 2H), 1.45-1.60 (m, 1H), 1.71 (tdd, 1H), 1.87-2.01 (m, 1H), 2.21-2.32 (m, 1H), 3.13-3.87 (m, 9H), 4.20-4.36 (m, 2H), 7.12 (d, 1H), 7.22 (s, 1H), 7.40-7.56 (m, 3H), 7.66 (d, 1H), 7.90 (s, 1H), 8.17 (s, 1H), 8.38 (d, 1H), 8.54 (dd, 1H), 8.77 (dd, 1H).

Example 55.03.01 cyclopropyl{4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazin-1-yl}methanone

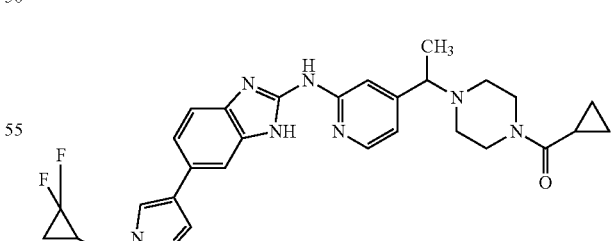

Starting with 6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (45 mg, see Compound 55.04.01), Example 55.03.01 was prepared analogously to the procedure for the preparation of Example 39.02.03.

Yield: 19 mg of the 90% pure title compound.

LC-MS (Method 2): $R_t$=1.13 min; MS (ESIpos): m/z=547 [M+H]$^+$.

$^1$H-NMR (400 MHz, DMSO-d6): δ [ppm]=0.61-0.75 (m, 4H), 1.28-1.33 (m, 3H), 1.53 (ddt, 1H), 1.65-1.78 (m, 1H), 1.89-1.97 (m, 1H), 2.20-2.45 (m, 5H), 3.40-3.53 (m, 3H), 3.60-3.75 (m, 2H), 4.19-4.34 (m, 2H), 6.94 (dd, 1H), 7.17 (s, 1H), 7.20-7.48 (m, 2H), 7.50-7.68 (m, 1H), 7.77-7.90 (m, 1H), 8.04-8.16 (m, 1H), 8.26 (d, 1H), 10.57 (br s, 1H), 12.03 (br s, 1H).

Example 55.03.02 cyclopropyl{4-[(1R or 1S)-1-(2-{[6-(1-{[(1R or 1S)-2,2-difluorocyclopropyl]methyl}-1H-pyrazol-4-yl)-1H-benzimidazol-2-yl]amino}pyridin-4-yl)ethyl]piperazin-1-yl}methanone

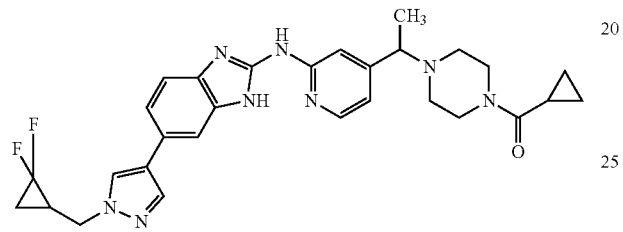

Starting with 6-(1-{[(1R or 1S)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (37 mg, see Compound 55.04.02), Example 55.03.02 was prepared analogously to the procedure for the preparation of Example 39.02.03.

Yield: 18 mg of the 93% pure title compound.

LC-MS (Method 2): $R_t$=1.13 min; MS (ESIpos): m/z=547 [M+H]$^+$.

$^1$H-NMR (400 MHz, DMSO-d6): δ [ppm]=0.60-0.75 (m, 4H), 1.30 (d, 3H), 1.47-1.58 (m, 1H), 1.70 (tdd, 1H), 1.87-1.99 (m, 1H), 2.19-2.43 (m, 5H), 3.39-3.55 (m, 3H), 3.67 (br s, 2H), 4.17-4.36 (m, 2H), 6.94 (dd, 1H), 7.17 (s, 1H), 7.20-7.48 (m, 2H), 7.49-7.68 (m, 1H), 7.77-7.92 (m, 1H), 8.02-8.17 (m, 1H), 8.26 (d, 1H), 10.57 (br s, 1H), 12.04 (br d, 1H).

Example 56.01 tert-butyl 4-[(1R or 1S)-1-(2-{[6-(1-{[(1RS,2RS)-2-methylcyclopropyl]methyl}-1H-pyrazol-4-yl)-1H-benzimidazol-2-yl]amino}pyridin-4-yl)ethyl]piperazine-1-carboxylate

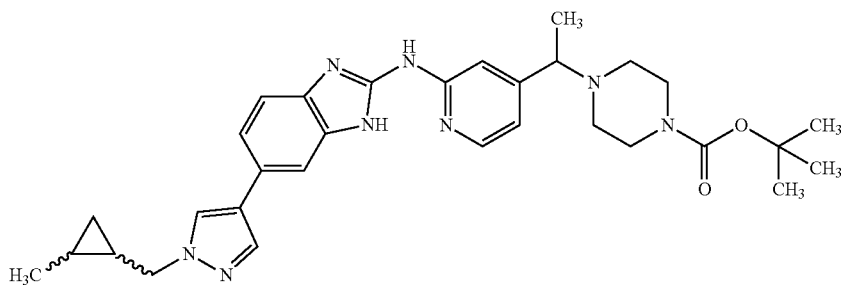 [SMILES: CC1CC1Cn1cc(-c2ccc3nc(Nc4cc(C(C)N5CCN(C(=O)OC(C)(C)C)CC5)ccn4)[nH]c3c2)cn1]

Starting with 4-(1-{[(1RS,2RS)-2-methylcyclopropyl]methyl}-1H-pyrazol-4-yl)benzene-1,2-diamine (350 mg, 1.44 mmol, Compound 56.03), Example 56.01 was prepared analogously to the procedure for the preparation of Example 39.02.01.

Yield: 188 mg of the 83% pure title compound.

LC-MS (Method 2): $R_t$=1.38 min; MS (ESIpos): m/z=557 [M+H]$^+$.

$^1$H-NMR (400 MHz, DMSO-d6): δ [ppm]=0.22-0.35 (m, 1H), 0.55 (dt, 1H), 0.77-0.89 (m, 1H), 0.94-1.00 (m, 1H), 0.99-1.05 (m, 3H), 1.28 (d, 3H), 1.38 (s, 9H), 2.24-2.34 (m, 2H), 2.34-2.44 (m, 2H), 3.32 (br s, 4H), 3.43 (q, 1H), 3.88-4.20 (m, 2H), 6.92 (dd, 1H), 7.16 (s, 1H), 7.18-7.48 (m, 2H), 7.49-7.67 (m, 1H), 7.79 (br s, 1H), 8.08 (br s, 1H), 8.24 (d, 1H), 10.56 (br s, 1H), 12.02 (br s, 1H).

Example 56.02

3,3,3-trifluoro-1-{4-[(1R or 1S)-1-(2-{[6-(1-{[(1RS,2RS)-2-methylcyclopropyl]methyl}-1H-pyrazol-4-yl)-1H-benzimidazol-2-yl]amino}pyridin-4-yl)ethyl]piperazin-1-yl}propan-1-one

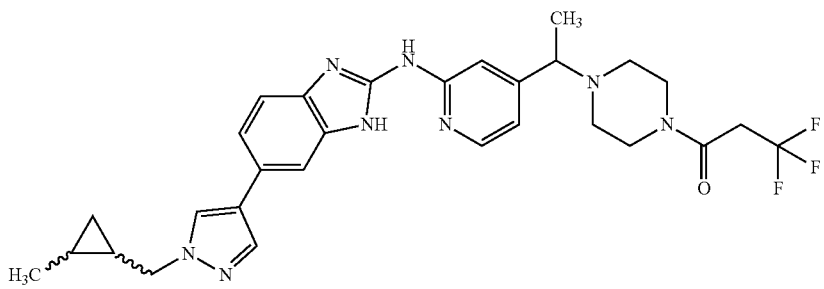 [SMILES: CC1CC1Cn1cc(-c2ccc3nc(Nc4cc(C(C)N5CCN(C(=O)CC(F)(F)F)CC5)ccn4)[nH]c3c2)cn1]

Starting with 6-(1-{[(1RS,2RS)-2-methylcyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt (310 mg, Compound 56.04), Example 56.02 was prepared analogously to the procedure for the preparation of Example 39.02.02.

Yield: 101 mg of the 93% pure title compound.

LC-MS (Method 2): $R_t$=1.22 min; MS (ESIpos): m/z=568 [M+H]$^+$.

$^1$H-NMR (400 MHz, DMSO-d6): δ [ppm]=0.26-0.35 (m, 1H), 0.55 (dt, 1H), 0.77-0.89 (m, 1H), 0.92-1.00 (m, 1H), 0.99-1.06 (m, 3H), 1.30 (d, 3H), 2.27-2.46 (m, 4H), 3.40-3.52 (m, 5H), 3.62 (q, 2H), 3.86-4.19 (m, 2H), 6.93 (dd, 1H), 7.17 (s, 1H), 7.20-7.47 (m, 2H), 7.49-7.67 (m, 1H), 7.78 (br d, 1H), 8.06 (br d, 1H), 8.25 (d, 1H), 10.56 (br s, 1H), 12.03 (br s, 1H).

Example 57.01 tert-butyl 4-[(1R or 1S)-1-(2-{[6-(1H-pyrazol-4-yl)-1H-benzimidazol-2-yl]amino}pyridin-4-yl)ethyl]piperazine-1-carboxylate

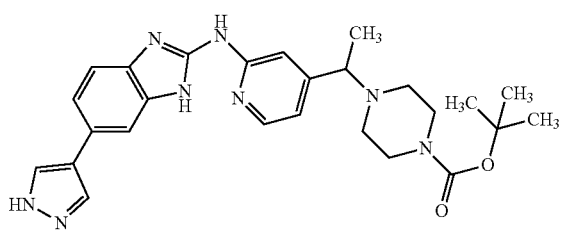 [SMILES: CC(c1ccnc(Nc2nc3ccc(-c4cn[nH]c4)cc3[nH]2)c1)N1CCN(C(=O)OC(C)(C)C)CC1]

tert-butyl 4-[(1R or 1S)-1-(2-{[6-(1-{[2-(trimethylsilyl)ethoxy]methyl}-1H-pyrazol-4-yl)-1H-benzimidazol-2-yl]amino}pyridin-4-yl)ethyl]piperazine-1-carboxylate (500 mg, 808 µmol) Compound 57.03 was solved in 13 mL THF and tetrabutylammonium fluoride (8.1 ml, 1.0 M, 8.1 mmol) was added. This mixture was stirred at 70° C. for 3 hours. The THF was removed under reduced pressure. The residue was diluted with ethyl acetate and water. The layers were separated and the aqueous layer was extracted with dichloromethane/isopropanol (7:3) twice. The combined organic layers were dried using a water resistant filter and the clear filtrate was concentrated under reduced pressure. The crude product was purified by flash chromatography. The residue was diluted with water. A beige solid precipitated. It was filtered off under vacuo. The filter cake was dried at 50° C. overnight.

Yield: 276 mg (64%) of the 91% pure title compound.

LC-MS (Method 2): $R_t$=1.22 min; MS (ESIpos): m/z=489 [M+H]$^+$.

$^1$H-NMR (400 MHz, DMSO-d6): δ [ppm]=1.28 (d, 3H), 1.38 (s, 9H), 1.48-1.68 (m, 2H), 2.20-2.34 (m, 2H), 2.34-2.43 (m, 2H), 3.09-3.21 (m, 2H), 3.43 (q, 1H), 6.92 (dd, 1H), 7.16 (s, 1H), 7.20-7.48 (m, 2H), 7.51-7.70 (m, 1H), 7.73-8.16 (m, 2H), 8.24 (d, 1H), 10.54 (br s, 1H), 12.02 (br s, 1H), 12.81 (br s, 1H)

Example 58.01.01 cyclobutyl(4-{[2-({6-[1-(2,2,2-trifluoroethyl)-1H-pyrazol-4-yl]-1H-benzimidazol-2-yl}amino)pyridin-4-yl]methyl}piperazin-1-yl)methanone

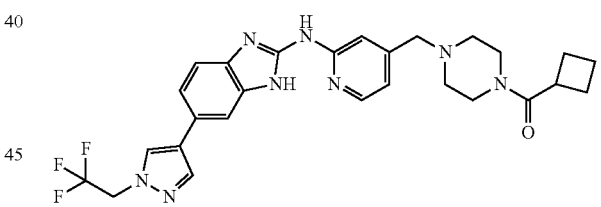

Starting with crude N-[4-(piperazin-1-ylmethyl)pyridin-2-yl]-6-[1-(2,2,2-trifluoroethyl)-1H-pyrazol-4-yl]-1H-benzimidazol-2-amine hydrochloride (150 mg) and cyclobutanecarboxylic acid (36 µl, 360 µmol), Example 58.01.01 was prepared analogously to the procedure for the preparation of Example 16.05.02.

Yield: 60 mg of the title compound.

LC-MS (Method 2): $R_t$=1.13 min; MS (ESIpos): m/z=539 [M+H]$^+$.

$^1$H-NMR (400 MHz, DMSO-d6) δ[ppm]: 1.036 (0.50), 1.053 (1.05), 1.071 (0.53), 1.708 (0.47), 1.722 (0.42), 1.732 (0.58), 1.837 (0.42), 1.858 (0.83), 1.882 (0.70), 1.908 (0.42), 2.049 (1.04), 2.058 (0.81), 2.074 (3.06), 2.099 (0.75), 2.121 (1.30), 2.143 (1.40), 2.167 (0.70), 2.172 (0.75), 2.346 (3.31), 3.297 (0.83), 3.320 (2.36), 3.334 (16.00), 3.436 (0.41), 3.441 (0.46), 3.471 (1.81), 3.487 (4.84), 5.133 (0.95), 5.155 (0.95), 5.758 (0.87), 6.903 (1.34), 6.917 (1.36), 7.180 (1.86), 7.271 (0.49), 8.241 (1.99), 8.254 (1.89), 10.599 (1.21), 12.056 (1.14).

Example 58.01.02

3,3,3-trifluoro-1-(4-{[2-({6-[1-(2,2,2-trifluoroethyl)-1H-pyrazol-4-yl]-1H-benzimidazol-2-yl}amino)pyridin-4-yl]methyl}piperazin-1-yl)propan-1-one

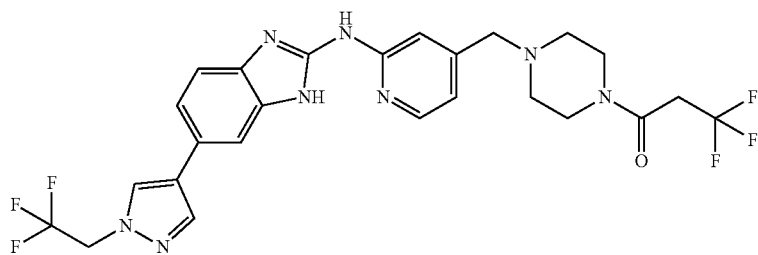 [SMILES: O=C(CC(F)(F)F)N1CCN(Cc2ccnc(Nc3nc4ccc(-c5cnn(CC(F)(F)F)c5)cc4[nH]3)c2)CC1]

Starting with crude N-[4-(piperazin-1-ylmethyl)pyridin-2-yl]-6-[1-(2,2,2-trifluoroethyl)-1H-pyrazol-4-yl]-1H-benzimidazol-2-amine hydrochloride (150 mg) and 3,3,3-trifluoropropanoic acid (32 μl, 360 μmol), Example 58.01.02 was prepared analogously to the procedure for the preparation of Example 01.02.

Yield: 30 mg of the title compound.

LC-MS (Method 2): $R_t$=1.11 min; MS (ESIneg): m/z=565 [M−H]⁻

¹H-NMR (400 MHz, DMSO-d6) δ[ppm]: 2.368 (3.26), 2.380 (4.90), 2.392 (3.68), 2.409 (3.28), 2.421 (4.57), 2.432 (3.52), 2.461 (1.23), 2.465 (1.31), 2.470 (1.18), 2.518 (4.12), 2.523 (2.80), 3.382 (0.42), 3.457 (3.28), 3.471 (4.53), 3.482 (3.96), 3.494 (3.96), 3.517 (16.00), 3.609 (2.28), 3.637 (6.68), 3.664 (6.22), 3.692 (1.90), 4.047 (1.86), 5.135 (2.15), 5.155 (2.15), 6.913 (4.05), 6.916 (3.85), 6.926 (4.03), 6.929 (3.90), 7.189 (4.18), 7.266 (1.12), 7.323 (0.72), 7.449 (0.66), 7.565 (0.92), 7.659 (0.77), 7.943 (0.88), 8.001 (0.98), 8.146 (0.94), 8.195 (1.03), 8.248 (6.52), 8.262 (6.15), 10.601 (3.15), 12.055 (3.92).

Example 58.01.03 cyclopropyl(4-{[2-({6-[1-(2,2,2-trifluoroethyl)-1H-pyrazol-4-yl]-1H-benzimidazol-2-yl}amino)pyridin-4-yl]methyl}piperazin-1-yl)methanone

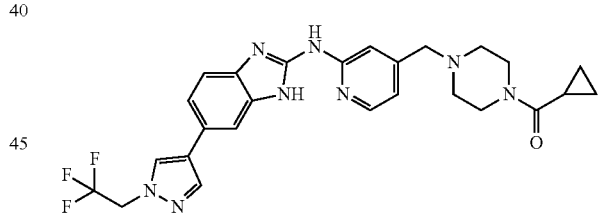

Starting with crude N-[4-(piperazin-1-ylmethyl)pyridin-2-yl]-6-[1-(2,2,2-trifluoroethyl)-1H-pyrazol-4-yl]-1H-benzimidazol-2-amine hydrochloride (150 mg) and cyclopropanecarboxylic acid (30 μl, 360 μmol), Example 58.01.03 was prepared analogously to the procedure for the preparation of Example 01.02.

Yield: 60.0 mg of the title compound.

LC-MS (Method 2): $R_t$=1.07 min; MS (ESIpos): m/z=524 [M+H]⁺.

¹H-NMR (400 MHz, DMSO-d6) δ[ppm]: 0.675 (0.67), 0.682 (1.52), 0.687 (0.95), 0.694 (0.75), 0.701 (1.83), 0.707 (1.47), 0.712 (1.61), 0.720 (1.53), 0.724 (1.84), 0.731 (0.85), 1.962 (0.67), 2.074 (0.70), 2.359 (0.74), 2.441 (0.76), 2.518 (0.75), 2.522 (0.51), 3.333 (16.00), 3.701 (0.70), 5.133 (0.63), 5.154 (0.62), 6.919 (0.96), 6.922 (0.95), 6.932 (0.96), 6.935 (0.98), 7.194 (1.32), 8.250 (1.54), 8.263 (1.46), 10.606 (0.78), 12.060 (0.73).

Example 59.01.01 tert-butyl 4-{(1R or 1S)-1-[2-({6-[1-(cyclobutylmethyl)-1H-pyrazol-4-yl]-1H-benzimidazol-2-yl}amino)pyridin-4-yl]ethyl}piperazine-1-carboxylate (Single Stereoisomer A)

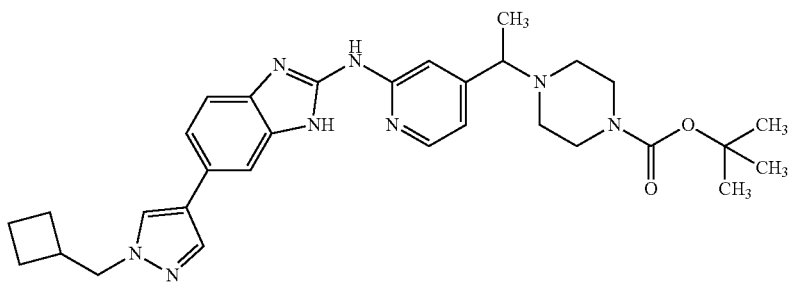 [SMILES: CC(c1ccnc(Nc2nc3ccc(-c4cnn(CC5CCC5)c4)cc3[nH]2)c1)N1CCN(C(=O)OC(C)(C)C)CC1]

To a stirred solution of 1H-imidazole (24.4 mg, 359 µmol) and di-1H-imidazol-1-ylmethanethione (427 mg, 90% purity, 2.15 mmol) in dichloromethane (5 mL) was added tert-butyl 4-[(1R or 1S)-1-(2-aminopyridin-4-yl)ethyl]piperazine-1-carboxylate (Single Stereoisomer A) (Compound 36.05) (550 mg, 1.79 mmol), dissolved in dichloromethane (10 mL) at r.t. The mixture was stirred at r.t. for 14 h. 4-[1-(Cyclobutylmethyl)-1H-pyrazol-4-yl]benzene-1,2-diamine (538 mg, 2.15 mmol, Compound 59.03), dissolved in dichloromethane (10 mL) was added and the mixture was stirred at r.t. for 14 h. Silicagel chromatography of the crude reaction mixture gave 1.80 g of a solid that was dissolved in dichloromethane (22 mL). EDC (385 mg, 2.01 mmol) was added and the mixture was stirred for 62 h. Further EDC (385 mg, 2.01 mmol) was added and the mixture was stirred for 4 h. Dichloromethane and methanol (10:1 mixture) and water were added, the mixture was stirred for 30 minutes. Saturated ammonium chloride solution was added and the mixture was extracted with dichloromethane. Aminophase-silicagel chromatography followed by silicagel chromatography gave 680 mg of the title compound.

LC-MS (Method 2): $R_t$=1.40 min; MS (ESIpos): m/z=557 [M+H]$^+$.

$^1$H-NMR (400 MHz, DMSO-d6) δ[ppm]: 1.273 (1.79), 1.290 (1.76), 1.376 (16.00), 1.793 (0.43), 1.811 (0.67), 1.822 (0.74), 1.826 (0.69), 1.831 (0.80), 1.840 (0.47), 1.991 (0.50), 2.000 (0.45), 2.004 (0.40), 2.012 (0.46), 2.292 (0.42), 2.305 (0.50), 2.378 (0.50), 2.390 (0.44), 2.518 (0.84), 2.523 (0.57), 3.421 (0.46), 3.437 (0.45), 4.120 (0.81), 4.138 (0.79), 6.908 (0.56), 6.911 (0.57), 6.922 (0.57), 6.924 (0.57), 7.155 (0.85), 8.237 (0.95), 8.250 (0.89).

Example 59.01.02

1-(4-{(1R or 1S)-1-[2-({6-[1-(cyclobutylmethyl)-1H-pyrazol-4-yl]-1H-benzimidazol-2-yl}amino)pyridin-4-yl]ethyl}piperazin-1-yl)-3,3,3-trifluoropropan-1-one (Single Stereoisomer A)

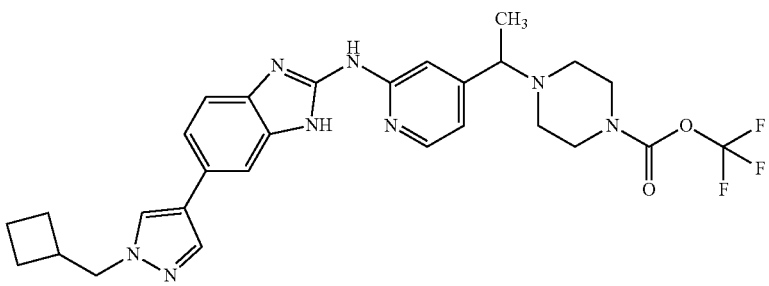 [SMILES: CC(c1ccnc(Nc2nc3ccc(-c4cnn(CC5CCC5)c4)cc3[nH]2)c1)N1CCN(C(=O)OC(F)(F)F)CC1]

Starting with crude 6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride (single stereoisomer A) (150 mg, Compound 59.04) and 3,3,3-trifluoropropanoic acid (22 µl, 240 µmol), Example 59.01.02 was prepared analogously to the procedure for the preparation of Example 16.05.02.

Yield: 35.0 mg of the title compound.

LC-MS (Method 2): $R_f$=1.24 min; MS (ESIpos): m/z=567 [M+H]$^+$.

$^1$H-NMR (400 MHz, DMSO-d6) δ[ppm]: 1.070 (0.67), 1.087 (1.34), 1.105 (0.71), 1.230 (0.78), 1.287 (15.71), 1.303 (16.00), 1.353 (0.80), 1.771 (2.90), 1.791 (4.72), 1.811 (7.62), 1.822 (8.44), 1.831 (8.92), 1.858 (4.62), 1.880 (2.75), 1.897 (1.18), 1.969 (2.58), 1.983 (4.09), 1.991 (5.21), 1.999 (5.33), 2.012 (5.19), 2.326 (4.98), 2.336 (5.27), 2.423 (5.94), 2.668 (1.34), 2.741 (1.20), 2.758 (2.56), 2.777 (3.32), 2.795 (2.71), 2.815 (1.26), 3.144 (0.40), 3.370 (1.47), 3.388 (1.41), 3.434 (10.48), 3.452 (8.21), 3.470 (10.58), 3.578 (3.07), 3.605 (8.29), 3.632 (7.96), 3.660 (2.79), 4.120 (11.04), 4.138 (10.84), 6.920 (5.71), 6.934 (5.90), 7.167 (9.07), 7.226 (3.00), 7.245 (3.89), 7.372 (1.34), 7.566 (1.93), 7.776 (4.87), 8.037 (4.16), 8.246 (7.48), 8.260 (7.24), 10.570 (3.93), 12.030 (3.21).

$^1$H-NMR (400 MHz, DMSO-d6) δ[ppm]: 0.661 (8.93), 0.689 (11.46), 0.700 (11.20), 0.768 (0.88), 0.849 (0.68), 1.006 (0.43), 1.070 (3.51), 1.087 (6.63), 1.105 (3.67), 1.178 (1.68), 1.232 (2.87), 1.288 (15.91), 1.304 (16.00), 1.770 (2.99), 1.791 (4.82), 1.810 (7.73), 1.829 (8.97), 1.857 (4.72), 1.878 (2.86), 1.898 (2.27), 1.918 (3.12), 1.930 (4.02), 1.967 (2.98), 1.982 (4.24), 1.990 (5.35), 1.998 (5.46), 2.010 (5.26), 2.324 (2.74), 2.389 (4.27), 2.670 (0.95), 2.739 (1.16), 2.758 (2.54), 2.776 (3.26), 2.795 (2.66), 2.814 (1.23), 3.144 (0.41), 3.370 (3.87), 3.387 (3.66), 3.405 (1.96), 3.433 (5.55), 3.450 (7.55), 3.466 (6.74), 3.666 (5.60), 4.119 (9.58), 4.137 (9.41), 6.926 (5.82), 6.939 (5.94), 7.176 (9.15), 7.241 (2.87), 7.297 (1.03), 7.413 (1.05), 7.533 (1.32), 7.607 (1.11), 7.778 (2.55), 8.037 (2.08), 8.246 (7.18), 8.260 (6.82), 10.573 (3.64), 12.031 (3.43).

Example 59.02.01

1-(4-{[2-({6-[1-(cyclobutylmethyl)-1H-pyrazol-4-yl]-1H-benzimidazol-2-yl}amino)pyridin-4-yl]methyl}piperazin-1-yl)-3,3,3-trifluoropropan-1-one

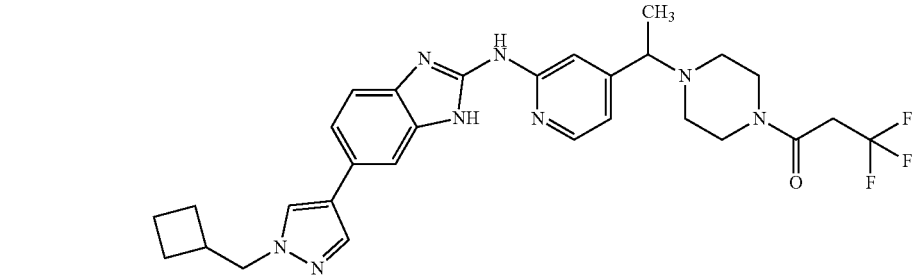

Starting with crude 6-[1-(cyclobutylmethyl)-1H-pyrazol-4-yl]-N-[4-(piperazin-1-ylmethyl)pyridin-2-yl]-1H-benzimidazol-2-amine hydrochloride (125 mg Compound 59.06) and 3,3,3-trifluoropropanoic acid (24 µl, 260 µmol), Example 59.02.01 was prepared analogously to the procedure for the preparation of Example 01.02.

Yield: 30.0 mg of the title compound.

LC-MS (Method 2): $R_f$=1.20 min; MS (ESIpos): m/z=553 [M+H]$^+$.

$^1$H-NMR (400 MHz, DMSO-d6) δ[ppm]: 1.753 (0.47), 1.772 (1.89), 1.793 (3.00), 1.811 (4.58), 1.819 (3.81), 1.822 (5.20), 1.826 (4.74), 1.831 (5.51), 1.840 (3.21), 1.849 (2.15), 1.859 (2.64), 1.874 (1.22), 1.881 (1.73), 1.898 (0.67), 1.969 (1.71), 1.983 (2.59), 1.991 (3.44), 2.000 (3.00), 2.004 (2.74), 2.012 (3.21), 2.030 (1.32), 2.336 (0.62), 2.365 (3.34), 2.378 (4.94), 2.390 (3.73), 2.406 (3.60), 2.419 (4.89), 2.430 (3.68), 2.518 (6.42), 2.522 (4.27), 2.539 (0.60), 2.740 (0.78), 2.759 (1.71), 2.777 (2.20), 2.796 (1.84), 2.815 (0.80), 3.456 (3.55), 3.469 (4.76), 3.481 (4.04), 3.513 (16.00), 3.608 (2.36), 3.636 (6.76), 3.663 (6.34), 3.690 (1.97), 4.046 (0.54), 4.120 (5.46), 4.139 (5.28), 6.906 (3.99), 6.908 (3.86), 6.919 (4.01), 6.922 (3.94), 7.187 (4.58), 7.234 (1.22), 7.293 (0.67), 7.414 (0.80), 7.522 (0.96), 7.615 (0.78), 7.752 (0.98), 7.800 (1.11), 8.013 (0.93), 8.060 (1.06), 8.241 (6.45), 8.255 (6.06), 10.571 (1.99), 12.010 (2.77).

Example 59.01.03

(4-{(1R or 1S)-1-[2-({6-[1-(cyclobutylmethyl)-1H-pyrazol-4-yl]-1H-benzimidazol-2-yl}amino)pyridin-4-yl]ethyl}piperazin-1-yl)(cyclopropyl)methanone (Single Stereoisomer A)

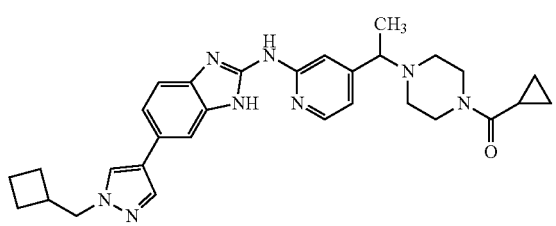 [SMILES: CC(c1ccnc(Nc2nc3ccc(-c4cnn(CC5CCC5)c4)cc3[nH]2)c1)N1CCN(C(=O)C2CC2)CC1]

Starting with crude 6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride (single stereoisomer A) (150 mg, Compound 59.04) and cyclopropanecarboxylic acid (20 µl, 240 µmol), Example 59.01.03 was prepared analogously to the procedure for the preparation of Example 16.05.02.

Yield: 40.0 mg of the title compound.

LC-MS (Method 2): $R_f$=1.20 min; MS (ESIpos): m/z=525 [M+H]$^+$.

Example 59.02.02

(4-{[2-({6-[1-(cyclobutylmethyl)-1H-pyrazol-4-yl]-1H-benzimidazol-2-yl}amino)pyridin-4-yl]methyl}piperazin-1-yl)(cyclopropyl)methanone

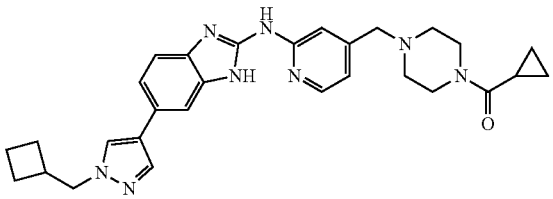 [SMILES: O=C(C1CC1)N1CCN(Cc2ccnc(Nc3nc4ccc(-c5cnn(CC6CCC6)c5)cc4[nH]3)c2)CC1]

Starting with crude 6-[1-(cyclobutylmethyl)-1H-pyrazol-4-yl]-N-[4-(piperazin-1-ylmethyl)pyridin-2-yl]-1H-benzimidazol-2-amine hydrochloride (125 mg, Compound 59.06) and cyclopropanecarboxylic acid (22 μl, 260 μmol), Example 59.02.02 was prepared analogously to the procedure for the preparation of Example 01.02.

Yield: 30.0 mg of the title compound.

LC-MS (Method 2): $R_t$=1.16 min; MS (ESIpos): m/z=511 [M+H]$^+$.

$^1$H-NMR (400 MHz, DMSO-d6) δ[ppm]: 0.663 (1.08), 0.675 (3.17), 0.682 (7.25), 0.688 (4.33), 0.695 (3.51), 0.702 (8.75), 0.707 (7.13), 0.712 (7.52), 0.719 (7.03), 0.724 (8.45), 0.731 (3.81), 0.743 (0.93), 1.752 (0.49), 1.772 (2.02), 1.792 (3.22), 1.798 (1.99), 1.811 (4.94), 1.818 (4.01), 1.822 (5.70), 1.826 (5.24), 1.831 (6.05), 1.840 (3.47), 1.849 (2.26), 1.859 (2.85), 1.874 (1.33), 1.881 (1.89), 1.898 (0.76), 1.931 (0.93), 1.944 (1.94), 1.951 (2.02), 1.955 (1.67), 1.963 (4.13), 1.969 (3.12), 1.983 (4.25), 1.991 (3.96), 1.996 (3.22), 2.000 (3.32), 2.004 (2.92), 2.012 (3.49), 2.030 (1.40), 2.322 (1.40), 2.326 (1.89), 2.331 (1.72), 2.361 (3.29), 2.442 (3.59), 2.518 (5.73), 2.522 (3.96), 2.539 (0.91), 2.659 (0.54), 2.664 (1.08), 2.668 (1.45), 2.673 (1.03), 2.678 (0.47), 2.740 (0.79), 2.759 (1.82), 2.777 (2.33), 2.796 (1.99), 2.815 (0.91), 3.513 (16.00), 3.701 (3.07), 4.120 (10.37), 4.138 (10.10), 6.912 (4.45), 6.914 (4.28), 6.925 (4.40), 6.927 (4.37), 7.221 (3.32), 7.238 (3.96), 7.363 (1.11), 7.571 (1.89), 7.774 (5.46), 8.036 (4.60), 8.239 (6.69), 8.252 (6.32).

Example 60.01

1-{4-[(2-{[6-(6-chloro-5-methoxypyrimidin-4-yl)-1H-benzimidazol-2-yl]amino}pyridin-4-yl)methyl]piperazin-1-yl}-3,3,3-trifluoropropan-1-one

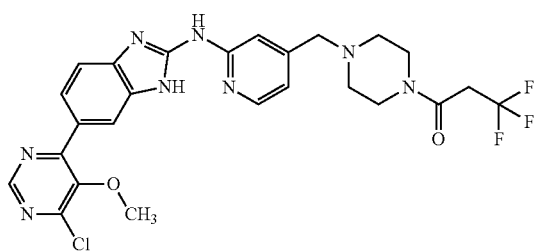 [SMILES: COc1c(Cl)ncnc1-c1ccc2nc(Nc3cc(CN4CCN(C(=O)CC(F)(F)F)CC4)ccn3)[nH]c2c1]

Starting with crude 6-(6-chloro-5-methoxypyrimidin-4-yl)-N-[4-(piperazin-1-ylmethyl)pyridin-2-yl]-1H-benzimidazol-2-amine hydrochloride (150 mg, Compound 60.02) and 3,3,3-trifluoropropanoic acid (82 μl, 920 μmol), Example 60.01 was prepared analogously to the procedure for the preparation of Example 01.02.

Yield: 12.2 mg of the title compound.

LC-MS (Method 2): $R_t$=1.14 min; MS (ESIpos): m/z=561 [M+H]$^+$.

$^1$H-NMR (500 MHz, DMSO-d6) δ[ppm]: 2.354 (0.60), 2.358 (1.33), 2.361 (1.91), 2.365 (1.73), 2.375 (4.08), 2.385 (6.04), 2.395 (4.26), 2.417 (4.05), 2.427 (5.80), 2.436 (4.31), 2.515 (5.86), 2.518 (5.57), 2.522 (4.29), 2.540 (1.41), 2.631 (1.05), 2.635 (1.57), 2.639 (1.20), 3.464 (4.16), 3.474 (5.54), 3.484 (4.29), 3.500 (4.21), 3.510 (5.33), 3.519 (4.89), 3.531 (16.00), 3.619 (2.64), 3.642 (7.35), 3.663 (7.08), 3.685 (3.24), 3.694 (3.01), 3.737 (8.08), 4.024 (3.74), 4.048 (1.65), 6.954 (2.85), 6.964 (2.67), 7.187 (5.12), 7.446 (1.28), 7.462 (1.39), 7.958 (1.28), 7.975 (1.15), 8.117 (0.84), 8.284 (4.63), 8.294 (4.37), 8.410 (2.17), 8.795 (3.40), 10.836 (1.12), 12.329 (0.92), 12.368 (2.12).

Example 61.01.01

3,3,3-trifluoro-1-{4-[(2-{[6-(5-methoxy-6-methylpyrimidin-4-yl)-1H-benzimidazol-2-yl]amino}pyridin-4-yl)methyl]piperazin-1-yl}propan-1-one

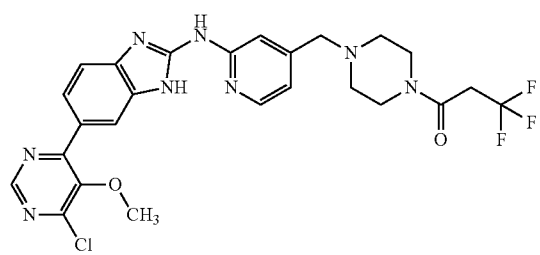 [SMILES: COc1c(Cl)ncnc1-c1ccc2nc(Nc3cc(CN4CCN(C(=O)CC(F)(F)F)CC4)ccn3)[nH]c2c1]

Starting with crude 6-(5-methoxy-6-methylpyrimidin-4-yl)-N-[4-(piperazin-1-ylmethyl)pyridin-2-yl]-1H-benzimidazol-2-amine hydrochloride (90.0 mg, Compound 61.02) and 3,3,3-trifluoropropanoic acid (24 μl, 270 μmol), Example 61.01.01 was prepared analogously to the procedure for the preparation of Example 16.05.02.

Yield: 40.0 mg of the title compound.

LC-MS (Method 2): $R_t$=1.04 min; MS (ESIneg): m/z=539 [M–H]$^-$.

$^1$H-NMR (400 MHz, DMSO-d6) δ[ppm]: 1.394 (16.00), 2.373 (0.58), 2.385 (0.87), 2.397 (0.64), 2.415 (0.64), 2.427 (0.86), 2.513 (8.64), 2.523 (0.80), 3.462 (0.64), 3.474 (0.86), 3.486 (0.71), 3.498 (0.70), 3.512 (0.89), 3.528 (2.45), 3.556 (0.56), 3.587 (1.11), 3.611 (0.45), 3.638 (1.15), 3.666 (1.08), 5.759 (1.93), 6.941 (0.58), 6.954 (0.58), 7.188 (1.06), 8.274 (1.06), 8.287 (1.00), 8.800 (1.09).

Example 61.01.02 cyclopropyl{4-[(2-{[6-(5-methoxy-6-methylpyrimidin-4-yl)-1H-benzimidazol-2-yl]amino}pyridin-4-yl)methyl]piperazin-1-yl}methanone

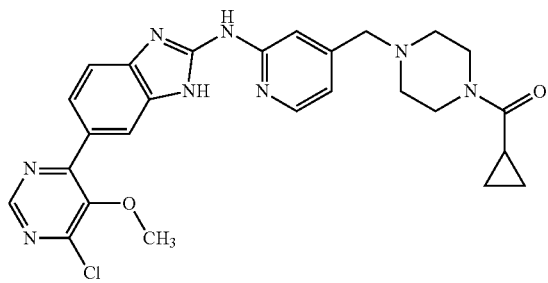 [SMILES: COc1c(Cl)ncnc1-c1ccc2nc(Nc3cc(CN4CCN(C(=O)C5CC5)CC4)ccn3)[nH]c2c1]

Starting with crude 6-(5-methoxy-6-methylpyrimidin-4-yl)-N-[4-(piperazin-1-ylmethyl)pyridin-2-yl]-1H-benzimidazol-2-amine hydrochloride (51.5 mg, Compound 61.02) and cyclopropanecarboxylic acid (28 µl, 360 µmol), Example 61.01.02 was prepared analogously to the procedure for the preparation of Example 16.05.02.

Yield: 16.0 mg of the title compound.

LC-MS (Method 2): $R_t$=0.98 min; MS (ESIpos): m/z=499 [M+H]$^+$.

$^1$H-NMR (400 MHz, DMSO-d6) δ [ppm]: 0.678 (0.74), 0.686 (1.72), 0.691 (1.06), 0.698 (0.84), 0.705 (2.05), 0.710 (1.71), 0.714 (1.80), 0.722 (1.64), 0.726 (1.90), 0.733 (0.84), 1.232 (1.03), 1.969 (0.74), 2.366 (0.77), 2.434 (0.81), 2.451 (1.12), 2.514 (16.00), 2.518 (4.36), 2.523 (2.64), 2.674 (0.62), 3.159 (3.61), 3.172 (3.99), 3.528 (3.48), 3.551 (1.05), 3.589 (1.84), 3.711 (0.72), 4.096 (0.83), 4.110 (0.80), 6.949 (0.77), 6.963 (0.77), 7.196 (1.22), 8.276 (1.55), 8.289 (1.43), 8.799 (1.36).

Example 62.01.01 tert-butyl 4-{[2-({6-[2-(cyclopropylmethoxy)pyrimidin-4-yl]-1H-benzimidazol-2-yl}amino)pyridin-4-yl]methyl}piperazine-1-carboxylate

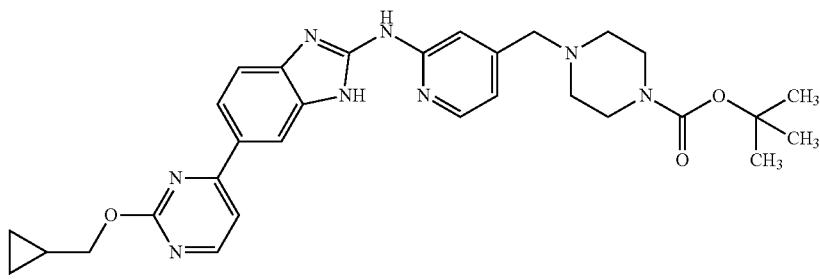 [SMILES: CC(C)(C)OC(=O)N1CCN(Cc2ccnc(Nc3nc4ccc(-c5ccnc(OCC6CC6)n5)cc4[nH]3)c2)CC1]

To a stirred solution of cyclopropylmethanol (1000 µl, 12 mmol) in NMP (1 mL) was added sodium hydride (55% w/w in oil; 33.5 mg, 768 µmol) at r.t. and the mixture was stirred for 10 minutes. Tert-butyl 4-[(2-{[6-(2-chloropyrimidin-4-yl)-1H-benzimidazol-2-yl]amino}pyridin-4-yl)methyl]piperazine-1-carboxylate (100 mg, 192 µmol) was added and the mixture was stirred at 80° C. for 1 h. Water was added and the mixture was extracted with ethyl acetate. The organic phase was dried (sodium sulfate), filtered and the solvent was removed in vacuum.

Silicagel chromatography followed by aminophase-silicagel chromatography gave a solid that was triturated with ethanol to give 70.0 mg of the title compound.

LC-MS (Method 2): $R_t$=1.39 min; MS (ESIpos): m/z=557 [M+H]$^+$.

$^1$H-NMR (400 MHz, DMSO-d6) δ [ppm]: 0.385 (0.84), 0.397 (0.81), 0.401 (0.80), 1.395 (16.00), 2.359 (1.29), 2.371 (0.92), 3.331 (9.28), 3.351 (1.01), 8.537 (1.31), 8.551 (1.20).

Example 62.01.02 cyclobutyl(4-{[2-({6-[2-(cyclopropylmethoxy)pyrimidin-4-yl]-1H-benzimidazol-2-yl}amino)pyridin-4-yl]methyl}piperazin-1-yl)methanone

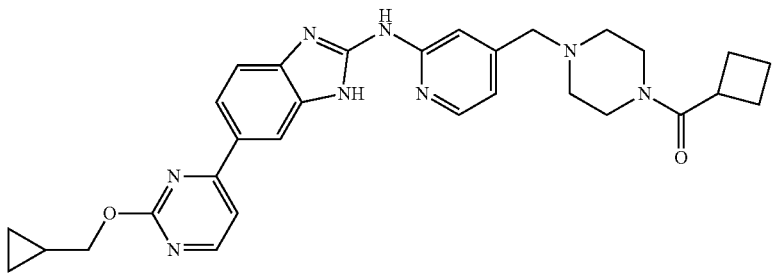 [SMILES: O=C(C1CCC1)N1CCN(Cc2ccnc(Nc3nc4ccc(-c5ccnc(OCC6CC6)n5)cc4[nH]3)c2)CC1]

Starting with crude 6-[2-(cyclopropylmethoxy)pyrimidin-4-yl]-N-[4-(piperazin-1-ylmethyl)pyridin-2-yl]-1H-benzimidazol-2-amine hydrochloride (200 mg, Compound 62.02) and cyclobutanecarboxylic acid (37 µl, 370 µmol), Example 62.01.02 was prepared analogously to the procedure for the preparation of Example 16.05.02.

Yield: 55.0 mg of the title compound.

LC-MS (Method 2): $R_t$=1.23 min; MS (ESIpos): m/z=539 [M+H]$^+$.

$^1$H-NMR (400 MHz, DMSO-d6) δ[ppm]: 0.374 (2.07), 0.385 (8.20), 0.389 (7.07), 0.396 (7.67), 0.401 (7.39), 0.411 (2.77), 0.570 (1.98), 0.580 (5.44), 0.585 (5.50), 0.590 (3.27), 0.601 (6.10), 0.605 (5.38), 0.617 (1.89), 1.035 (0.88), 1.052 (2.01), 1.070 (0.88), 1.291 (0.60), 1.297 (0.88), 1.309 (1.67), 1.317 (1.54), 1.329 (2.45), 1.341 (1.57), 1.348 (1.60), 1.361 (0.85), 1.684 (0.60), 1.702 (0.94), 1.710 (1.70), 1.720 (1.48), 1.723 (1.51), 1.734 (2.14), 1.744 (1.26), 1.756 (0.97), 1.767 (0.53), 1.816 (0.44), 1.839 (1.79), 1.860 (3.49), 1.866 (1.51), 1.883 (2.67), 1.888 (2.55), 1.905 (1.32), 1.910 (1.60), 1.931 (0.69), 2.022 (0.97), 2.031 (1.10), 2.036 (1.07), 2.051 (3.87), 2.061 (2.80), 2.067 (2.80), 2.073 (4.43), 2.082 (3.33), 2.088 (1.54), 2.100 (2.55), 2.123 (5.06), 2.128 (3.36), 2.144 (5.53), 2.149 (4.18), 2.152 (3.68), 2.168 (2.51), 2.173 (2.80), 2.191 (0.63), 2.197 (0.85), 2.318 (1.07), 2.322 (2.01), 2.326 (2.95), 2.332 (3.61), 2.352 (11.10), 2.518 (7.23), 2.522 (5.06), 2.660 (0.72), 2.664 (1.41), 2.668 (1.89), 2.673 (1.35), 2.678 (0.63), 3.279 (0.82), 3.303 (3.27), 3.344 (7.92), 3.366 (1.26), 3.422 (0.63), 3.435 (0.79), 3.439 (0.88), 3.452 (1.89), 3.474 (5.50), 3.502 (16.00), 4.240 (5.06), 4.257 (4.31), 4.343 (0.85), 4.355 (0.97), 6.942 (3.21), 7.188 (6.54), 7.412 (1.29), 7.433 (1.38), 7.580 (2.23), 7.593 (2.11), 7.686 (0.94), 7.917 (2.39), 7.939 (2.14), 8.191 (1.38), 8.274 (3.36), 8.391 (2.23), 8.538 (13.86), 8.551 (12.23), 10.729 (0.88), 10.801 (1.38), 12.293 (1.70), 12.323 (2.51).

Example 62.01.03

1-(4-{[2-({6-[2-(cyclopropylmethoxy)pyrimidin-4-yl]-1H-benzimidazol-2-yl}amino)pyridin-4-yl]methyl}piperazin-1-yl)-3,3,3-trifluoropropan-1-one

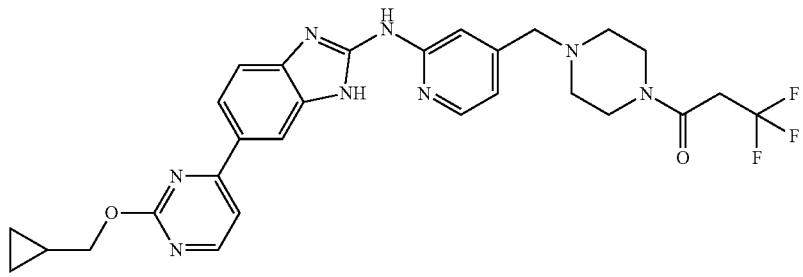 [SMILES: O=C(CC(F)(F)F)N1CCN(Cc2ccnc(Nc3nc4ccc(-c5ccnc(OCC6CC6)n5)cc4[nH]3)c2)CC1]

Starting with crude 6-[2-(cyclopropylmethoxy)pyrimidin-4-yl]-N-[4-(piperazin-1-ylmethyl)pyridin-2-yl]-1H-benzimidazol-2-amine hydrochloride (200 mg, Compound 62.02) and 3,3,3-trifluoropropanoic acid (33 µl, 370 µmol), Example 62.01.03 was prepared analogously to the procedure for the preparation of Example 16.05.02.

Yield: 65.0 mg of the title compound.

LC-MS (Method 2): $R_t$=1.20 min; MS (ESIpos): m/z=567 [M+H]$^+$.

$^1$H-NMR (400 MHz, DMSO-d6) δ [ppm]: 0.374 (1.95), 0.384 (7.72), 0.389 (6.82), 0.396 (7.43), 0.401 (7.15), 0.410 (2.62), 0.570 (2.00), 0.580 (5.48), 0.585 (5.45), 0.590 (3.05), 0.596 (3.35), 0.601 (5.99), 0.605 (5.45), 0.616 (1.79), 1.035 (0.43), 1.053 (0.77), 1.070 (0.44), 1.291 (0.58), 1.297 (0.85), 1.309 (1.60), 1.317 (1.49), 1.321 (1.20), 1.329 (2.50), 1.337 (1.22), 1.341 (1.46), 1.349 (1.52), 1.361 (0.81), 2.323 (0.62), 2.327 (0.87), 2.332 (0.66), 2.370 (3.83), 2.383 (5.79), 2.396 (4.35), 2.412 (4.20), 2.424 (5.62), 2.436 (4.14), 2.518 (2.66), 2.523 (2.02), 2.665 (0.55), 2.669 (0.79), 2.673 (0.52), 3.460 (4.19), 3.473 (5.67), 3.484 (4.58), 3.497 (4.46), 3.510 (5.70), 3.528 (16.00), 3.610 (2.90), 3.637 (8.21), 3.665 (7.78), 3.693 (2.46), 4.239 (5.05), 4.256 (4.70), 4.357 (0.52), 6.949 (3.16), 6.961 (2.93), 7.198 (7.60), 7.416 (1.05), 7.438 (1.12), 7.584 (1.79), 7.687 (0.75), 7.918 (2.69), 7.939 (2.35), 8.193 (0.99), 8.278 (3.60), 8.291 (3.36), 8.393 (1.73), 8.538 (13.90), 8.551 (12.12), 10.801 (1.05), 12.300 (1.54), 12.325 (2.19).

Example 62.01.04 cyclopropyl(4-{[2-({6-[2-(cyclopropylmethoxy)pyrimidin-4-yl]-1H-benzimidazol-2-yl}amino)pyridin-4-yl]methyl}piperazin-1-yl)methanone

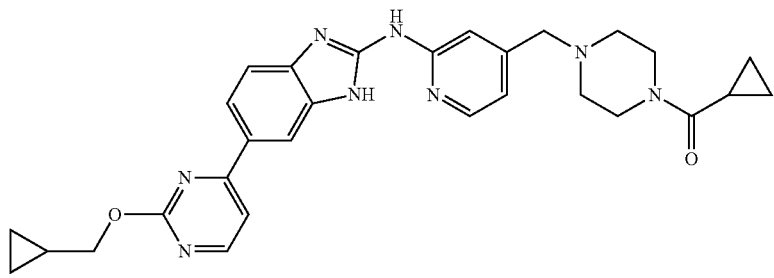 [SMILES: O=C(C1CC1)N1CCN(Cc2ccnc(Nc3nc4ccc(-c5ccnc(OCC6CC6)n5)cc4[nH]3)c2)CC1]

Starting with crude 6-[2-(cyclopropylmethoxy)pyrimidin-4-yl]-N-[4-(piperazin-1-ylmethyl)pyridin-2-yl]-1H-benzimidazol-2-amine hydrochloride (200 mg, Compound 62.02) and cyclopropanecarboxylic acid (31 μl, 370 μmol), Example 62.01.04 was prepared analogously to the procedure for the preparation of Example 16.05.02.

Yield: 65.0 mg of the title compound.

LC-MS (Method 2): $R_t$=1.16 min; MS (ESIpos): m/z=525 [M+H]$^+$.

$^1$H-NMR (400 MHz, DMSO-d6) δ[ppm]: 0.375 (1.91), 0.386 (7.71), 0.389 (6.73), 0.398 (7.42), 0.401 (7.36), 0.411 (2.71), 0.571 (1.79), 0.581 (5.05), 0.585 (5.23), 0.591 (3.00), 0.601 (5.72), 0.606 (5.23), 0.617 (1.70), 0.665 (1.10), 0.677 (3.21), 0.684 (7.86), 0.690 (4.79), 0.697 (3.67), 0.704 (9.44), 0.709 (7.88), 0.713 (8.43), 0.721 (7.83), 0.726 (9.27), 0.733 (4.16), 0.745 (1.01), 1.292 (0.55), 1.297 (0.81), 1.311 (1.56), 1.318 (1.44), 1.330 (2.43), 1.342 (1.44), 1.349 (1.47), 1.361 (0.81), 1.368 (0.49), 1.934 (0.87), 1.946 (1.85), 1.953 (2.02), 1.966 (3.41), 1.972 (1.56), 1.978 (1.91), 1.985 (1.76), 1.997 (0.78), 2.318 (0.66), 2.322 (1.36), 2.327 (2.02), 2.332 (1.65), 2.337 (1.21), 2.363 (3.52), 2.449 (4.30), 2.454 (4.30), 2.459 (3.61), 2.463 (2.77), 2.518 (6.56), 2.523 (4.62), 2.660 (0.55), 2.665 (1.21), 2.669 (1.76), 2.673 (1.24), 2.678 (0.55), 3.286 (0.72), 3.499 (3.52), 3.528 (16.00), 3.707 (3.35), 4.241 (4.79), 4.258 (4.16), 6.958 (2.92), 7.204 (6.24), 7.416 (1.24), 7.437 (1.30), 7.582 (2.05), 7.595 (1.94), 7.698 (0.84), 7.919 (2.34), 7.941 (2.02), 8.193 (1.21), 8.283 (3.15), 8.293 (2.86), 8.392 (2.08), 8.539 (12.51), 8.552 (11.44), 10.745 (0.81), 10.806 (1.36), 12.298 (1.59), 12.328 (2.40).

Example 63.01.01 tert-butyl 4-[(2-{[6-(2-chloro-5-methoxypyrimidin-4-yl)-1H-benzimidazol-2-yl]amino}pyridin-4-yl)methyl]piperazine-1-carboxylate

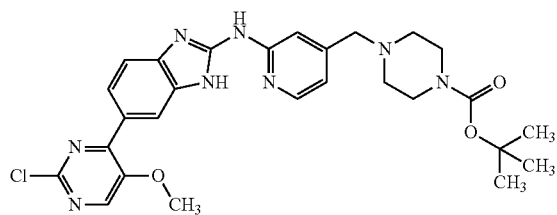 [SMILES: COc1cnc(Cl)nc1-c1ccc2nc(Nc3cc(CN4CCN(C(=O)OC(C)(C)C)CC4)ccn3)[nH]c2c1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (2.50 g, 4.68 mmol, Compound 01.04) in 1-propanol (75 ml) was added a sodium carbonate solution (7.0 ml, 2.0 M, 14 mmol), 2,4-dichloro-5-methoxypyrimidine (2.59 g, 14.0 mmol), triphenylphosphine (123 mg, 468 μmol) and PdCl$_2$(PPh$_3$)$_2$ (382 mg, 468 μmol). The mixture was heated to 110° C. in a sealed tube for 14 h. Water was added and the mixture was extracted with ethyl acetate. The organic phase was dried (sodium sulfate), filtered and the solvent was removed in vacuum. Silicagel chromatography gave a solid that was triturated with cyclopentylmethylether to give 900 mg (35% yield) of the title compound.

LC-MS (Method 2): $R_t$=1.30 min; MS (ESIpos): m/z=551 [M+H]$^+$.

$^1$H-NMR (400 MHz, DMSO-d6) δ[ppm]: 1.066 (1.06), 1.298 (1.65), 1.394 (16.00), 2.344 (0.87), 2.357 (1.21), 2.369 (0.81), 3.333 (4.46), 3.349 (0.97), 4.039 (2.24), 8.262 (0.67), 8.275 (0.62), 8.576 (0.71).

Example 64.01.01 tert-butyl 4-{[2-({6-[2-(cyclopropylmethoxy)-5-methoxypyrimidin-4-yl]-1H-benzimidazol-2-yl}amino)pyridin-4-yl]methyl}piperazine-1-carboxylate

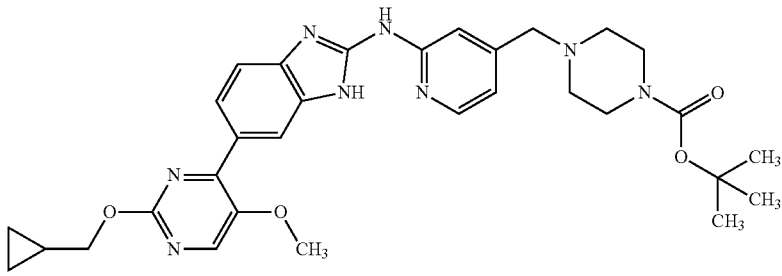 [SMILES: COc1cnc(OCC2CC2)nc1-c1ccc2nc(Nc3cc(CN4CCN(C(=O)OC(C)(C)C)CC4)ccn3)[nH]c2c1]

To a stirred solution of cyclopropylmethanol (500 µl, 6.3 mmol) in N-methylpyrrolidone (1 mL) was added sodium hydride (55% w/w in oil; 31.7 mg, 726 µmol) at r.t. and the mixture was stirred for 10 minutes. tert-Butyl 4-[(2-{[6-(2-chloro-5-methoxypyrimidin-4-yl)-1H-benzimidazol-2-yl]amino}pyridin-4-yl)methyl]piperazine-1-carboxylate (100 mg, 181 µmol) was added and the mixture was stirred at 80° C. for 1 h. Water was added and the mixture was extracted with ethyl acetate. The organic phase was dried (sodium sulfate), filtered and the solvent was removed in vacuum. Aminophase-silicagel chromatography gave a solid that was triturated with ethanol to give 65.0 mg of the title compound.

LC-MS (Method 2): $R_t$=1.37 min; MS (ESIpos): m/z=587 [M+H]$^+$.

$^1$H-NMR (400 MHz, DMSO-d6) δ[ppm]: 0.356 (0.91), 0.360 (0.78), 0.368 (0.87), 0.371 (0.82), 0.560 (0.71), 0.564 (0.71), 0.580 (0.74), 0.584 (0.67), 1.395 (16.00), 2.347 (0.92), 2.359 (1.33), 2.371 (0.94), 2.518 (0.57), 2.522 (0.41), 3.330 (10.26), 3.351 (1.05), 3.928 (2.47), 4.149 (1.02), 4.166 (0.99), 6.928 (0.42), 6.941 (0.41), 8.264 (0.52), 8.277 (0.49), 8.418 (1.69).

Example 64.01.02 cyclopropyl(4-{[2-({6-[2-(cyclopropylmethoxy)-5-methoxypyrimidin-4-yl]-1H-benzimidazol-2-yl}amino)pyridin-4-yl]methyl}piperazin-1-yl)methanone Starting with crude 6-[2-(cyclopropylmethoxy)-5-methoxypyrimidin-4-yl]-N-[4-(piperazin-1-ylmethyl)pyridin-2-yl]-1H-benzimidazol-2-amine hydrochloride (110 mg, Compound 64.01) and cyclopropanecarboxylic acid (23 µl, 280 µmol), Example 64.01.02 was prepared analogously to the procedure for the preparation of Example 01.02.

Yield: 65.0 mg of the title compound.

LC-MS (Method 2): $R_t$=1.19 min; MS (ESIpos): m/z=555 [M+H]$^+$.

$^1$H-NMR (400 MHz, DMSO-d6) δ[ppm]: 0.346 (1.69), 0.357 (6.65), 0.361 (5.76), 0.369 (6.38), 0.372 (6.31), 0.382 (2.24), 0.551 (1.96), 0.561 (5.24), 0.565 (5.27), 0.571 (2.57), 0.581 (5.52), 0.585 (5.06), 0.596 (1.59), 0.665 (0.98), 0.677 (2.91), 0.685 (6.93), 0.690 (4.14), 0.698 (3.16), 0.705 (8.31), 0.709 (6.87), 0.714 (7.26), 0.721 (6.74), 0.726 (8.03), 0.733 (3.59), 0.746 (0.89), 0.983 (0.43), 1.002 (0.98), 1.020 (0.52), 1.230 (0.61), 1.259 (0.58), 1.265 (0.83), 1.277 (1.47), 1.285 (1.38), 1.297 (2.39), 1.309 (1.29), 1.317 (1.38), 1.329 (0.70), 1.335 (0.46), 1.935 (0.80), 1.947 (1.69), 1.954 (1.72), 1.967 (3.00), 1.979 (1.66), 1.986 (1.53), 1.998 (0.70), 2.323 (1.47), 2.327 (2.05), 2.332 (1.59), 2.337 (1.10), 2.366 (2.97), 2.449 (3.16), 2.518 (6.68), 2.523 (4.87), 2.540 (2.27), 2.660 (0.58), 2.665 (1.32), 2.669 (1.84), 2.673 (1.26), 2.679 (0.55), 3.501 (3.00), 3.526 (14.53), 3.710 (2.85), 3.897 (0.58), 3.930 (16.00), 4.150 (6.93), 4.168 (6.80), 4.274 (0.49), 6.948 (3.03), 6.960 (3.00), 7.191 (2.30), 7.388 (1.01), 7.409 (1.10), 7.550 (0.49), 7.866 (0.52), 7.951 (1.07), 7.972 (0.95), 8.130 (0.70), 8.275 (3.71), 8.288 (3.56), 8.400 (1.78), 8.419 (12.81), 10.681 (0.43), 10.767 (0.98), 12.250 (0.89), 12.290 (1.87).

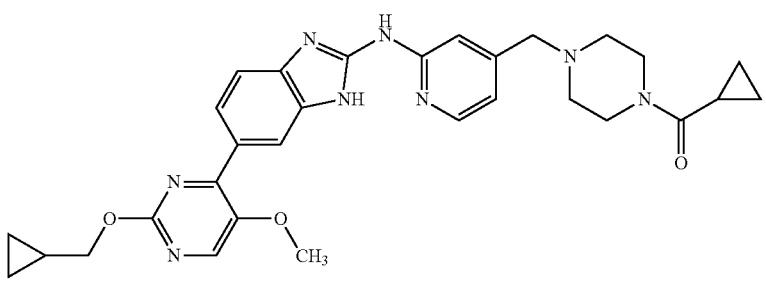 [SMILES: COc1cnc(OCC2CC2)nc1-c1ccc2nc(Nc3cc(CN4CCN(C(=O)C5CC5)CC4)ccn3)[nH]c2c1]

Example 64.01.03

1-(4-{[2-({6-[2-(cyclopropylmethoxy)-5-methoxy-pyrimidin-4-yl]-1H-benzimidazol-2-yl}amino)pyridin-4-yl]methyl}piperazin-1-yl)-3,3,3-trifluoropropan-1-one

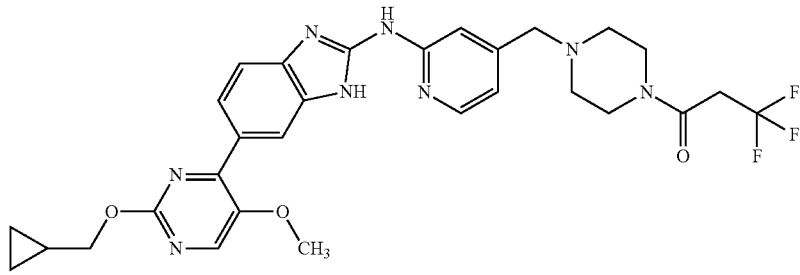 [SMILES: COc1cnc(OCC2CC2)nc1-c1ccc2nc(Nc3cc(CN4CCN(C(=O)CC(F)(F)F)CC4)ccn3)[nH]c2c1]

Starting with crude 6-[2-(cyclopropylmethoxy)-5-methoxypyrimidin-4-yl]-N-[4-(piperazin-1-ylmethyl)pyridin-2-yl]-1H-benzimidazol-2-amine hydrochloride (110 mg, Compound 64.01) and 3,3,3-trifluoropropanoic acid (25 µl, 280 µmol), Example 64.01.03 was prepared analogously to the procedure for the preparation of Example 01.02.

Yield: 55.0 mg of the title compound.

LC-MS (Method 2): $R_t$=1.22 min; MS (ESIpos): m/z=597 [M+H]$^+$.

$^1$H-NMR (400 MHz, DMSO-d6) δ[ppm]: 0.346 (1.60), 0.356 (6.61), 0.360 (5.71), 0.368 (6.29), 0.372 (6.16), 0.382 (2.27), 0.551 (1.92), 0.561 (5.07), 0.565 (5.20), 0.570 (2.61), 0.577 (2.53), 0.581 (5.39), 0.585 (4.96), 0.596 (1.63), 0.983 (0.40), 1.001 (0.99), 1.019 (0.48), 1.027 (0.56), 1.042 (0.40), 1.259 (0.56), 1.265 (0.77), 1.277 (1.39), 1.285 (1.33), 1.297 (2.43), 1.304 (0.99), 1.309 (1.25), 1.316 (1.36), 1.328 (0.67), 1.335 (0.48), 2.337 (0.40), 2.372 (3.17), 2.384 (4.80), 2.396 (3.60), 2.413 (3.23), 2.425 (4.61), 2.437 (3.55), 2.518 (4.48), 2.523 (3.33), 3.144 (1.20), 3.159 (0.83), 3.173 (0.83), 3.319 (0.85), 3.349 (0.85), 3.360 (0.48), 3.370 (0.64), 3.384 (0.48), 3.460 (3.17), 3.473 (4.37), 3.484 (3.81), 3.497 (3.76), 3.510 (4.67), 3.527 (14.24), 3.565 (0.56), 3.610 (2.21), 3.637 (6.37), 3.665 (6.05), 3.693 (1.89), 3.896 (0.61), 3.905 (0.61), 3.929 (16.00), 4.048 (2.16), 4.149 (6.83), 4.167 (6.64), 4.273 (0.43), 6.940 (3.01), 6.953 (2.93), 7.188 (2.69), 7.388 (0.99), 7.408 (1.07), 7.549 (0.45), 7.866 (0.45), 7.953 (1.04), 7.974 (0.91), 8.130 (0.69), 8.273 (3.84), 8.286 (3.73), 8.399 (1.71), 8.419 (13.23), 10.684 (0.45), 10.763 (1.07), 12.247 (1.01), 12.284 (1.97).

Example 65.01.01 tert-butyl 4-{[2-({6-[6-(cyclopropylmethoxy)-5-methoxypyrimidin-4-yl]-1H-benzimidazol-2-yl}amino)pyridin-4-yl]methyl}piperazine-1-carboxylate

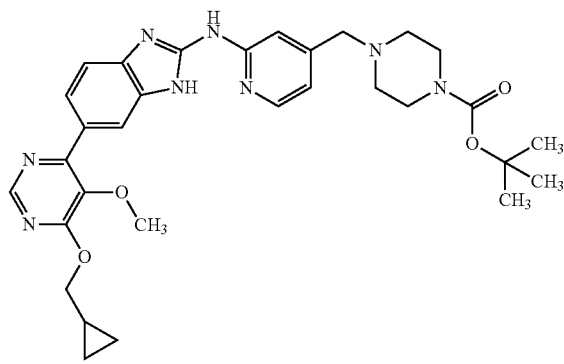 [SMILES: COc1c(OCC2CC2)ncnc1-c1ccc2nc(Nc3cc(CN4CCN(C(=O)OC(C)(C)C)CC4)ccn3)[nH]c2c1]

To a stirred solution of cyclopropylmethanol (290 µl, 3.7 mmol) in N-methylpyrrolidone NMP (1 mL) was added sodium hydride (55% w/w in oil; 108 mg, 2.47 mmol) at r.t. and the mixture was stirred for 10 minutes. tert-Butyl 4-[(2-{[6-(6-chloro-5-methoxypyrimidin-4-yl)-1H-benzimidazol-2-yl]amino}pyridin-4-yl)methyl]piperazine-1-carboxylate (340 mg, 617 µmol) dissolved in NMP (1 mL), was added and the mixture was stirred at 80° C. for 1 h. Water was added and the mixture was extracted with ethyl acetate. The organic phase was dried (sodium sulfate), filtered and the solvent was removed in vacuum. Silicagel chromatography followed by aminophase-silicagel chromatography gave a solid that was triturated with ethanol to give 160 mg of the title compound.

LC-MS (Method 2): $R_t$=1.43 min; MS (ESIpos): m/z=587 [M+H]$^+$.

$^1$H-NMR (400 MHz, DMSO-d6) δ[ppm]: 0.399 (0.84), 0.403 (0.72), 0.411 (0.79), 0.415 (0.78), 0.591 (0.70), 0.596 (0.71), 0.611 (0.74), 0.616 (0.67), 1.396 (16.00), 2.349 (0.80), 2.361 (1.18), 2.373 (0.83), 2.518 (0.66), 2.523 (0.47), 3.352 (0.92), 3.502 (1.56), 3.789 (0.86), 4.278 (1.56), 4.296 (1.56), 6.938 (0.40), 8.266 (0.55), 8.279 (0.52), 8.505 (1.37).

Example 65.01.02

1-(4-{[2-({6-[6-(cyclopropylmethoxy)-5-methoxy-pyrimidin-4-yl]-1H-benzimidazol-2-yl}amino)pyridin-4-yl]methyl}piperazin-1-yl)-3,3,3-trifluoropropan-1-one

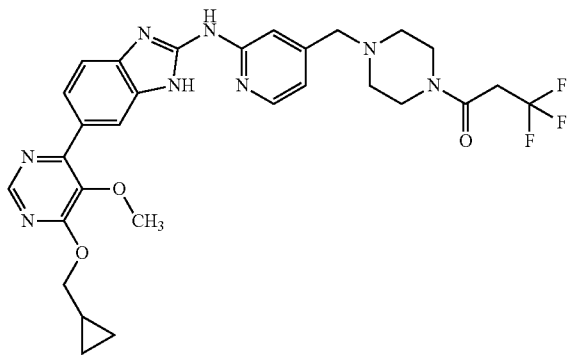 [SMILES: COc1c(OCC2CC2)ncnc1-c1ccc2nc(Nc3cc(CN4CCN(C(=O)CC(F)(F)F)CC4)ccn3)[nH]c2c1]

Starting with crude 6-[6-(cyclopropylmethoxy)-5-methoxypyrimidin-4-yl]-N-[4-(piperazin-1-ylmethyl)pyridin-2-yl]-1H-benzimidazol-2-amine hydrochloride (200 mg, Compound 65.01) and 3,3,3-trifluoropropanoic acid (68 µl, 770 µmol), Example 65.01.02 was prepared analogously to the procedure for the preparation of Example 16.05.02.

Yield: 6.00 mg of the title compound.

LC-MS (Method 2): $R_t$=1.27 min; MS (ESIpos): m/z=597 [M+H]$^+$.

$^1$H-NMR (400 MHz, DMSO-d6) δ[ppm]: 0.389 (1.68), 0.399 (6.85), 0.403 (6.01), 0.411 (6.57), 0.415 (6.36), 0.425 (2.17), 0.582 (2.10), 0.592 (5.80), 0.597 (5.66), 0.602 (2.93), 0.612 (6.08), 0.617 (5.45), 0.628 (1.75), 1.232 (0.84), 1.305 (0.63), 1.311 (0.84), 1.323 (1.54), 1.331 (1.40), 1.343 (1.23), 1.355 (1.40), 1.363 (1.47), 1.375 (0.70), 1.382 (0.49), 1.955 (0.49), 2.332 (2.93), 2.336 (1.40), 2.385 (6.01), 2.397 (4.68), 2.415 (4.33), 2.427 (5.80), 2.438 (4.40), 2.518 (16.00), 2.522 (10.76), 2.673 (2.93), 2.678 (1.33), 2.897 (0.56), 2.941 (0.56), 3.461 (4.33), 3.474 (5.66), 3.485 (4.68), 3.513 (6.85), 3.527 (16.00), 3.611 (2.79), 3.638 (7.76), 3.666 (7.34), 3.693 (2.38), 3.762 (4.82), 3.793 (10.41), 3.829 (0.91), 3.847 (0.77), 4.025 (0.98), 4.279 (12.44), 4.297 (12.51), 6.937 (3.70), 6.949 (3.63), 7.189 (4.68), 7.394 (1.61), 7.416 (1.75), 7.552 (0.77), 7.572 (0.84), 7.773 (0.84), 7.794 (0.70), 7.881 (1.54), 7.903 (1.33), 8.052 (1.26), 8.274 (4.54), 8.287 (4.26), 8.318 (2.45), 8.505 (7.97), 10.680 (0.98), 10.742 (1.96), 12.229 (1.40), 12.271 (2.72).

Example 66.01.01 tert-butyl 4-[(2-{[6-(5-methyl-1,3,4-oxadiazol-2-yl)-1H-benzimidazol-2-yl]amino}pyridin-4-yl)methyl]piperazine-1-carboxylate

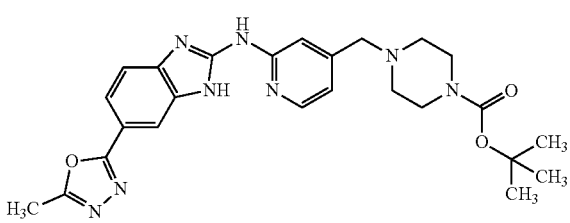 [SMILES: Cc1nnc(-c2ccc3nc(Nc4cc(CN5CCN(C(=O)OC(C)(C)C)CC5)ccn4)[nH]c3c2)o1]

To a stirred solution of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (500 mg, 936 µmol, Compound 01.04) in 1-propanol (11 ml, 150 mmol) in a microwave tube was added a sodium carbonate solution (1.4 ml, 2.0 M, 2.8 mmol), 2-bromo-5-methyl-1,3,4-oxadiazole (236 mg, 1.40 mmol), triphenylphosphine (24.5 mg, 93.6 µmol) and PdCl$_2$(PPh$_3$)$_2$ (115 mg, 140 µmol). The mixture was heated to 110° C. for 14 h. Further 2-bromo-5-methyl-1,3,4-oxadiazole (157 mg), triphenylphosphine (24.5 mg, 93.6 µmol) and PdCl$_2$(PPh$_3$)$_2$ (115 mg, 140 µmol) were added and the mixture was heated to 110° C. for 14 h. The crude reaction mixture was filtered through aminophase-silicagel and the solvent was removed in vacuum. Silicagel chromatography gave 54.0 mg (11% yield) of the title compound.

LC-MS (Method 2): $R_t$=1.14 min; MS (ESIpos): m/z=491 [M−H]$^+$.

$^1$H-NMR (400 MHz, DMSO-d6) δ[ppm]: 1.172 (0.62), 1.394 (16.00), 1.987 (1.19), 2.309 (1.73), 2.345 (0.94), 2.357 (1.39), 2.369 (0.98), 2.574 (5.80), 2.939 (3.74), 3.333 (7.54), 3.349 (1.13), 5.759 (0.80).

Example 66.01.02 cyclopropyl{4-[(2-{[6-(5-methyl-1,3,4-oxadiazol-2-yl)-1H-benzimidazol-2-yl]amino}pyridin-4-yl)methyl]piperazin-1-yl}methanone

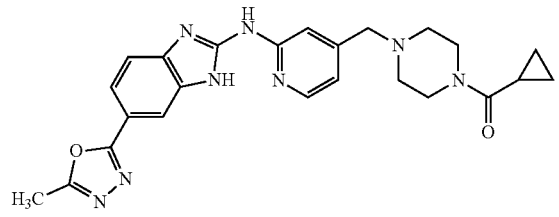 [SMILES: Cc1nnc(-c2ccc3nc(Nc4cc(CN5CCN(C(=O)C6CC6)CC5)ccn4)[nH]c3c2)o1]

Starting with crude 6-(5-methyl-1,3,4-oxadiazol-2-yl)-N-[4-(piperazin-1-ylmethyl)pyridin-2-yl]-1H-benzimidazol-2-amine hydrochloride (20.0 mg, Compound 66.01) and cyclopropanecarboxylic acid (11 µl, 140 µmol), Example 66.01.02 was prepared analogously to the procedure for the preparation of Example 16.05.02.

Yield: 2.00 mg of the title compound.

LC-MS (Method 2): $R_t$=0.90 min; MS (ESIpos): m/z=459 [M+H]$^+$.

$^1$H-NMR (400 MHz, DMSO-d6) δ[ppm]: 0.677 (1.14), 0.685 (2.68), 0.690 (1.63), 0.697 (1.35), 0.704 (3.15), 0.709 (2.71), 0.713 (2.86), 0.721 (2.60), 0.725 (3.07), 0.733 (1.47), 0.757 (1.73), 0.765 (3.72), 0.769 (2.75), 0.776 (3.23), 0.779 (1.58), 0.782 (2.04), 0.784 (2.10), 0.789 (3.30), 0.797 (1.44), 0.803 (1.53), 0.807 (1.46), 0.809 (3.54), 0.817 (1.65), 1.467 (1.02), 1.475 (0.79), 1.481 (0.63), 1.487 (1.58), 1.495 (0.64), 1.499 (0.96), 1.506 (0.78), 1.967 (1.09), 2.327 (0.88), 2.331 (1.03), 2.363 (1.18), 2.446 (1.27), 2.518 (3.16), 2.523 (2.23), 2.575 (16.00), 2.669 (0.70), 3.504 (1.33), 3.528 (4.91), 3.707 (1.11), 5.759 (3.22), 6.965 (1.16), 6.978 (1.14), 7.185 (1.40), 8.284 (1.86), 8.297 (1.70).

Example 66.01.03

3,3,3-trifluoro-1-{4-[(2-{[6-(5-methyl-1,3,4-oxadiazol-2-yl)-1H-benzimidazol-2-yl]amino}pyridin-4-yl)methyl]piperazin-1-yl}propan-1-one

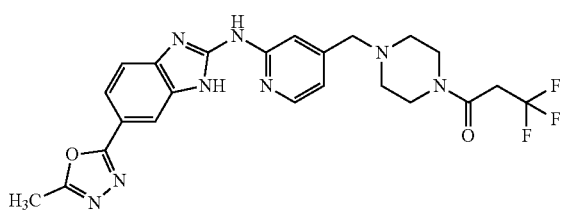 [SMILES: Cc1nnc(-c2ccc3nc(Nc4cc(CN5CCN(C(=O)CC(F)(F)F)CC5)ccn4)[nH]c3c2)o1]

Starting with crude 6-(5-methyl-1,3,4-oxadiazol-2-yl)-N-[4-(piperazin-1-ylmethyl)pyridin-2-yl]-1H-benzimidazol-2-amine hydrochloride (26.0 mg, Compound 66.01) and 3,3,3-trifluoropropanoic acid (16 μl, 180 μmol), Example 66.01.03 was prepared analogously to the procedure for the preparation of Example 16.05.02.

Yield: 10.0 mg of the title compound.

LC-MS (Method 2): $R_t$=0.94 min; MS (ESIpos): m/z=501 [M+H]$^+$.

$^1$H-NMR (400 MHz, DMSO-d6) δ[ppm]: 0.858 (0.75), 1.231 (0.94), 1.395 (0.78), 2.370 (1.25), 2.382 (1.87), 2.395 (1.40), 2.411 (1.40), 2.424 (1.90), 2.436 (1.32), 2.518 (6.78), 2.523 (4.78), 2.575 (16.00), 3.459 (1.40), 3.473 (1.92), 3.483 (1.56), 3.495 (1.56), 3.505 (1.92), 3.530 (4.75), 3.610 (0.91), 3.637 (2.57), 3.665 (2.42), 3.693 (0.78), 6.958 (0.99), 6.972 (0.91), 7.185 (1.14), 7.652 (0.91), 8.129 (0.99), 8.283 (1.45), 8.296 (1.35), 12.407 (1.53).

Example 67.01 tert-butyl 4-[(1R or 1S)-1-(2-{[6-(1-{[(1RS)-2,2-dimethylcyclopropyl]methyl}-1H-pyrazol-4-yl)-1H-benzimidazol-2-yl]amino}pyridin-4-yl)ethyl]piperazine-1-carboxylate

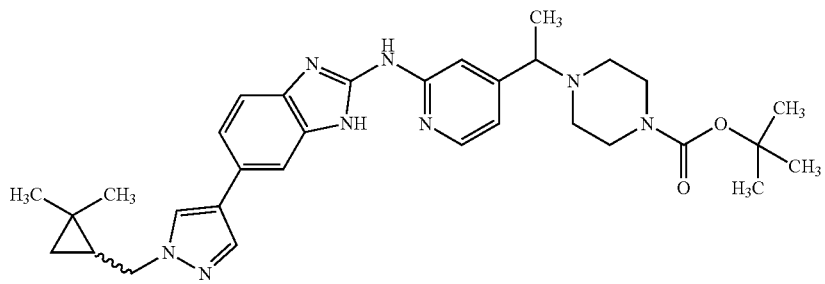 [SMILES: CC(c1ccnc(Nc2nc3ccc(-c4cnn(CC5CC5(C)C)c4)cc3[nH]2)c1)N1CCN(C(=O)OC(C)(C)C)CC1]

Starting with 4-{1-[((1RS)-2,2-dimethylcyclopropyl)methyl]-1H-pyrazol-4-yl}benzene-1,2-diamine (147 mg, 85% pure; see Compound 67.02), Example 67.01 was prepared analogously to the procedure for the preparation of Example 39.02.01. The intermediate thiourea was purified by flash chromatography.

Yield: 105 mg of the 94% pure title compound.

LC-MS (Method 2): $R_t$=1.44 min; MS (ESIpos): m/z=571 [M+H]$^+$.

$^1$H-NMR (400 MHz, DMSO-d6): δ [ppm]=0.33 (t, 1H), 0.53 (dd, 1H), 1.04-1.08 (m, 3H), 1.08-1.13 (m, 1H), 1.14-1.17 (m, 3H), 1.28 (d, 3H), 1.38 (s, 9H), 2.23-2.44 (m, 4H), 3.27-3.33 (m, 4H), 3.43 (q, 1H), 4.12 (br d, 2H), 6.92 (dd, 1H), 7.16 (s, 1H), 7.18-7.47 (m, 2H), 7.50-7.68 (m, 1H), 7.72-7.84 (m, 1H), 7.95-8.11 (m, 1H), 8.24 (d, 1H), 10.55 (br s, 1H), 12.02 (br s, 1H).

Example 67.02

1-{4-[(1R or 1S)-1-(2-{[6-(1-{[(1RS)-2,2-dimethyl-cyclopropyl]methyl}-1H-pyrazol-4-yl)-1H-benzimi-dazol-2-yl]amino}pyridin-4-yl)ethyl]piperazin-1-yl}-3,3,3-trifluoropropan-1-one

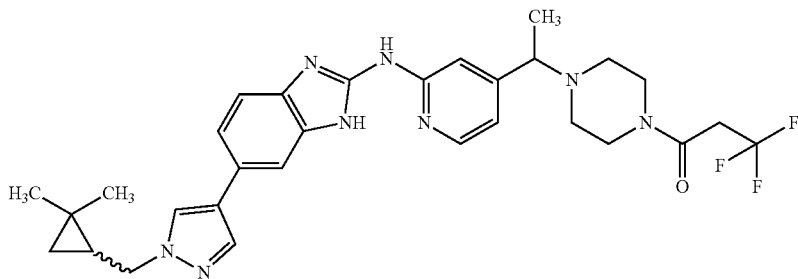 [SMILES: CC(c1ccnc(Nc2nc3ccc(-c4cnn(CC5CC5(C)C)c4)cc3[nH]2)c1)N1CCN(C(=O)CC(F)(F)F)CC1]

Starting with 6-(1-{[(1RS)-2,2-dimethylcyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride salt (62.5 mg, see Compound 67.03), Example 67.02 was prepared analogously to the procedure for the preparation of Example 39.02.02.

Yield: 16 mg of the 88% pure title compound.

LC-MS (Method 2): $R_t$=1.29 min; MS (ESIpos): m/z=581 [M+H]$^+$.

$^1$H-NMR (400 MHz, DMSO-d6): δ [ppm]=0.33 (t, 1H), 0.53 (dd, 1H), 1.07 (s, 3H), 1.10-1.15 (m, 1H), 1.16 (s, 3H), 1.30 (d, 3H), 2.27-2.47 (m, 4H), 3.39-3.53 (m, 5H), 3.62 (q, 2H), 4.12 (br d, 2H), 6.93 (dd, 1H), 7.17 (s, 1H), 7.20-7.46 (m, 2H), 7.49-7.67 (m, 1H), 7.79 (br d, 1H), 7.96-8.11 (m, 1H), 8.25 (d, 1H), 10.56 (br s, 1H), 12.02 (br s, 1H).

Example 67.03 cyclopropyl{4-[(1R or 1S)-1-(2-{[6-(1-{[(1RS)-2,2-dimethylcyclopropyl]methyl}-1H-pyrazol-4-yl)-1H-benzimidazol-2-yl]amino}pyridin-4-yl)ethyl]piperazin-1-yl}methanone Starting with 6-(1-{[(1RS)-2,2-dimethylcyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (62.5 mg, see Compound 67.03), Example 67.03 was prepared analogously to the procedure for the preparation of Example 39.02.03.

Yield: 16 mg of the 76% pure title compound.

LC-MS (Method 2): $R_t$=1.26 min; MS (ESIpos): m/z=539 [M+H]$^+$.

$^1$H-NMR (400 MHz, DMSO-d6): δ [ppm]=0.33 (t, 1H), 0.53 (dd, 1H), 0.62-0.73 (m, 4H), 1.07 (s, 3H), 1.11-1.14 (m, 1H), 1.16 (s, 3H), 1.30 (d, 3H), 1.88-1.99 (m, 1H), 2.24-2.45 (m, 4H), 3.39-3.53 (m, 3H), 3.67 (br s, 2H), 4.12 (br d, 2H), 6.94 (dd, 1H), 7.17 (s, 1H), 7.20-7.47 (m, 2H), 7.50-7.69 (m, 1H), 7.79 (br s, 1H), 8.05 (br s, 1H), 8.25 (d, 1H), 10.56 (br s, 1H), 12.03 (br s, 1H).

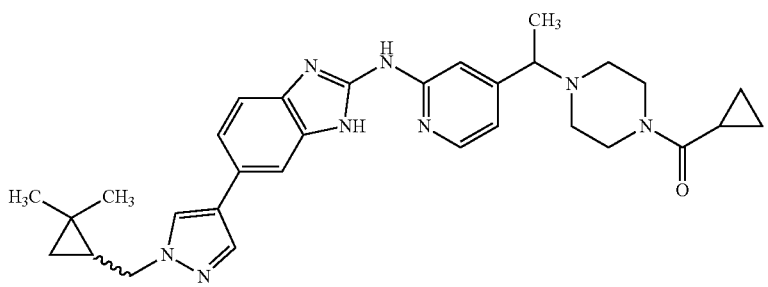 [SMILES: CC(c1ccnc(Nc2nc3ccc(-c4cnn(CC5CC5(C)C)c4)cc3[nH]2)c1)N1CCN(C(=O)C2CC2)CC1]

Example 68.01 tert-butyl 4-[(1R or 1S)-1-{2-[(6-{1-[(1-methylcyclopropyl)methyl]-1H-pyrazol-4-yl}-1H-benzimidazol-2-yl)amino]pyridin-4-yl}ethyl]piperazine-1-carboxylate

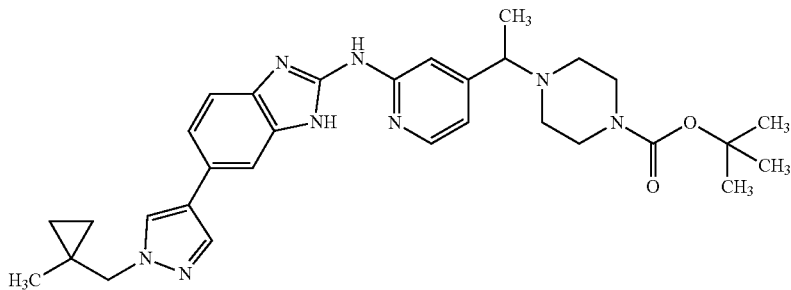 [SMILES: CC(c1ccnc(Nc2nc3ccc(-c4cnn(CC5(C)CC5)c4)cc3[nH]2)c1)N1CCN(C(=O)OC(C)(C)C)CC1]

Starting with 4-{1-[(1-methylcyclopropyl)methyl]-1H-pyrazol-4-yl}benzene-1,2-diamine (158 mg, see Compound 68.02), Example 68.01 was prepared analogously to the procedure for the preparation of Example 39.02.01. The intermediate thiourea was purified by flash chromatography.

Yield: 89 mg of the 72% pure title compound.

LC-MS (Method 2): $R_t$=1.75 min; MS (ESIpos): m/z=558 [M+H]$^+$.

$^1$H-NMR (400 MHz, DMSO-d6): δ [ppm]=0.34-0.40 (m, 2H), 0.63-0.70 (m, 2H), 1.00 (s, 3H), 1.26-1.31 (m, 3H), 1.38 (s, 9H), 2.24-2.44 (m, 4H), 3.25-3.32 (m, 4H), 3.43 (q, 1H), 3.96 (br s, 2H), 6.92 (d, 1H), 7.18 (br s, 1H), 7.21-7.46 (m, 2H), 7.51-7.68 (m, 1H), 7.73-7.87 (m, 1H), 8.01-8.15 (m, 1H), 8.24 (d, 1H), 10.57 (br s, 1H), 12.09 (br d, 1H).

Example 68.02

3,3,3-trifluoro-1-{4-[(1R or 1S)-1-{2-[(6-{1-[(1-methylcyclopropyl)methyl]-1H-pyrazol-4-yl}-1H-benzimidazol-2-yl)amino]pyridin-4-yl}ethyl]piperazin-1-yl}propan-1-one

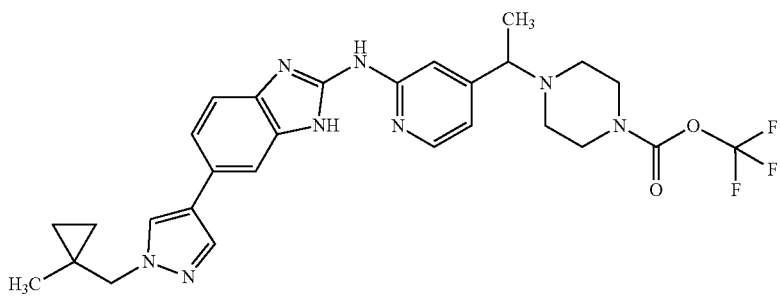 [SMILES: CC(c1ccnc(Nc2nc3ccc(-c4cnn(CC5(C)CC5)c4)cc3[nH]2)c1)N1CCN(C(=O)OC(F)(F)F)CC1]

Starting with 6-{1-[(1-methylcyclopropyl)methyl]-1H-pyrazol-4-yl}-N-{4-[(1R or 1S)-1-(piperazin-1-yl)ethyl]pyridin-2-yl}-1H-benzimidazol-2-amine hydrochloride (86.0 mg, see Compound 68.03), Example 68.02 was prepared analogously to the procedure for the preparation of Example 39.02.02.

Yield: 33 mg of the 92% pure title compound.

LC-MS (Method 2): $R_t$=1.17 min; MS (ESIpos): m/z=567 [M+H]$^+$.

$^1$H-NMR (400 MHz, DMSO-d6): δ [ppm]=0.31-0.41 (m, 2H), 0.62-0.72 (m, 2H), 1.00 (s, 3H), 1.30 (d, 3H), 2.26-2.47 (m, 4H), 3.39-3.52 (m, 5H), 3.62 (q, 2H), 3.97 (br s, 2H), 6.86-6.98 (m, 1H), 7.14-7.19 (m, 1H), 7.20-7.48 (m, 2H), 7.50-7.68 (m, 1H), 7.72-7.87 (m, 1H), 7.98-8.14 (m, 1H), 8.20-8.29 (m, 1H), 10.57 (br s, 1H), 12.02 (br d, 1H).

Example 69.01 tert-butyl 4-[(1R or 1S)-1-{2-[(6-{1-[(1-chlorocyclopropyl)methyl]-1H-pyrazol-4-yl}-1H-benzimidazol-2-yl)amino]pyridin-4-yl}ethyl]piperazine-1-carboxylate

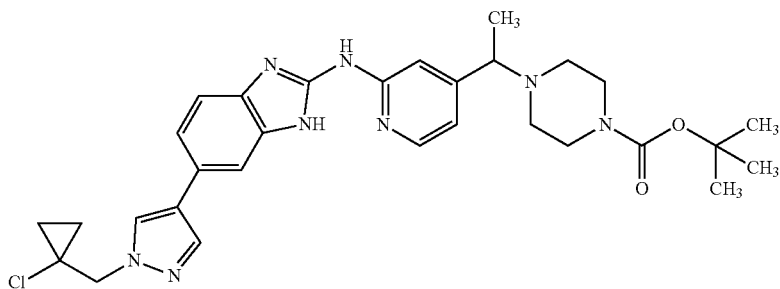 [SMILES: CC(c1ccnc(Nc2nc3ccc(-c4cnn(CC5(Cl)CC5)c4)cc3[nH]2)c1)N1CCN(C(=O)OC(C)(C)C)CC1]

Starting with 4-{1-[(1-chlorocyclopropyl)methyl]-1H-pyrazol-4-yl}benzene-1,2-diamine (65.0 mg, 85% purity, see Compound 69.03), Example 69.01 was prepared analogously to the procedure for the preparation of Example 39.02.01. The intermediate thiourea was purified by flash chromatography.

Yield: 51 mg of the 87% pure title compound.

LC-MS (Method 2): $R_t$=1.37 min; MS (ESIpos): m/z=577 [M+H]$^+$.

$^1$H-NMR (400 MHz, DMSO-d6): δ [ppm] 1.10-1.16 (m, 2H), 1.23-1.32 (m, 5H), 1.38 (s, 9H), 2.23-2.44 (m, 4H), 3.21-3.32 (m, 4H), 3.43 (q, 1H), 4.40 (s, 2H), 6.92 (dd, 1H), 7.16 (s, 1H), 7.22-7.49 (m, 2H), 7.52-7.72 (m, 1H), 7.79-7.93 (m, 1H), 8.13 (br s, 1H), 8.25 (d, 1H), 10.56 (br s, 1H), 12.04 (br s, 1H).

Example 69.02

1-{4-[(1R or 1S)-1-{2-[(6-{1-[(1-chlorocyclopropyl)methyl]-1H-pyrazol-4-yl}-1H-benzimidazol-2-yl)amino]pyridin-4-yl}ethyl]piperazin-1-yl}-3,3,3-trifluoropropan-1-one Starting with 6-{1-[(1-chlorocyclopropyl)methyl]-1H-pyrazol-4-yl}-N-{4-[(1R or 1S)-1-(piperazin-1-yl)ethyl]pyridin-2-yl}-1H-benzimidazol-2-amine hydrochloride (45 mg, Compound 69.04), Example 69.02 was prepared analogously to the procedure for the preparation of Example 39.02.02.

Yield: 16 mg of the 97% pure title compound.

LC-MS (Method 2): $R_t$=1.20 min; MS (ESIpos): m/z=587 [M+H]$^+$.

$^1$H-NMR (400 MHz, DMSO-d6): δ [ppm]=1.06-1.17 (m, 2H), 1.21-1.36 (m, 5H), 2.25-2.48 (m, 4H), 3.46 (br d, 5H), 3.62 (q, 2H), 4.41 (s, 2H), 6.94 (d, 1H), 7.17 (s, 1H), 7.28 (br d, 1H), 7.37 (br d, 1H), 7.61 (br s, 1H), 7.86 (s, 1H), 8.15 (br s, 1H), 8.26 (d, 1H), 10.60 (br s, 1H), 12.08 (br s, 1H).

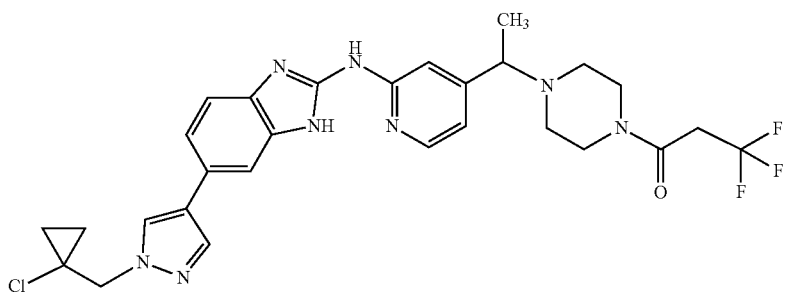 [SMILES: CC(c1ccnc(Nc2nc3ccc(-c4cnn(CC5(Cl)CC5)c4)cc3[nH]2)c1)N1CCN(C(=O)CC(F)(F)F)CC1]

Example 70.01

1-{4-[(1R or 1S)-1-(2-{[7-chloro-6-(1-{[(1RS)-2,2-difluorocyclopropyl]methyl}-1H-pyrazol-4-yl)-1H-benzimidazol-2-yl]amino}pyridin-4-yl)ethyl]piperazin-1-yl}-3,3,3-trifluoropropan-1-one

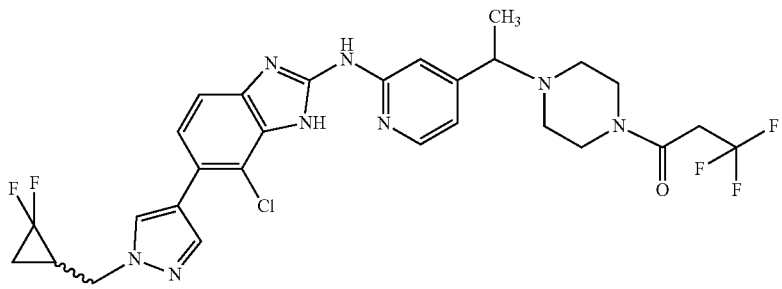 [SMILES: CC(c1ccnc(Nc2nc3ccc(-c4cnn(CC5CC5(F)F)c4)c(Cl)c3[nH]2)c1)N1CCN(C(=O)CC(F)(F)F)CC1]

Starting with 7-chloro-6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (100 mg, see Compound 70.03), Example 70.01 was prepared analogously to the procedure for the preparation of Example 39.02.02.

Yield: 37 mg of the 96% pure title compound.

LC-MS (Method 2): $R_t$=1.24 min; MS (ESIpos): m/z=623 [M+H]$^+$.

$^1$H-NMR (400 MHz, DMSO-d6): δ [ppm]=1.30 (d, 3H), 1.48-1.59 (m, 1H), 1.64-1.77 (m, 1H), 2.23-2.48 (m, 5H), 3.40-3.53 (m, 5H), 3.62 (q, 2H), 4.21-4.39 (m, 2H), 6.96 (d, 1H), 7.08 (s, 1H), 7.19 (d, 1H), 7.45 (d, 1H), 7.83 (s, 1H), 8.15 (s, 1H), 8.28 (d, 1H), 10.98 (s, 1H), 12.31 (s, 1H).

Example 70.02

{4-[(1R or 1S)-1-(2-{[7-chloro-6-(1-{[(1RS)-2,2-difluorocyclopropyl]methyl}-1H-pyrazol-4-yl)-1H-benzimidazol-2-yl]amino}pyridin-4-yl)ethyl]piperazin-1-yl}(cyclopropyl)methanone

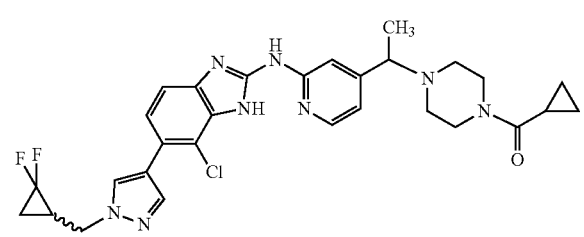 [SMILES: CC(c1ccnc(Nc2nc3ccc(-c4cnn(CC5CC5(F)F)c4)c(Cl)c3[nH]2)c1)N1CCN(C(=O)C2CC2)CC1]

Starting with 7-chloro-6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (100 mg, see Compound 70.03), Example 70.02 was prepared analogously to the procedure for the preparation of Example 39.02.03.

Yield: 61 mg of the 95% pure title compound.

LC-MS (Method 2): $R_t$=1.21 min; MS (ESIpos): m/z=581 [M+H]$^+$.

$^1$H-NMR (400 MHz, DMSO-d6): δ [ppm]=0.61-0.74 (m, 4H), 1.30 (br d, 3H), 1.48-1.60 (m, 1H), 1.71 (tdd, 1H), 1.88-1.97 (m, 1H), 2.21-2.45 (m, 5H), 3.47 (br s, 3H), 3.67 (br s, 2H), 4.21-4.39 (m, 2H), 6.97 (br d, 1H), 7.08 (s, 1H), 7.19 (d, 1H), 7.45 (d, 1H), 7.83 (s, 1H), 8.16 (s, 1H), 8.28 (d, 1H), 10.98 (br s, 1H), 12.32 (s, 1H).

Example 71.01 tert-butyl 4-{(1R or 1S)-1-[2-({6-[1-(cyclopentylmethyl)-1H-pyrazol-4-yl]-1H-benzimidazol-2-yl}amino)pyridin-4-yl]ethyl}piperazine-1-carboxylate

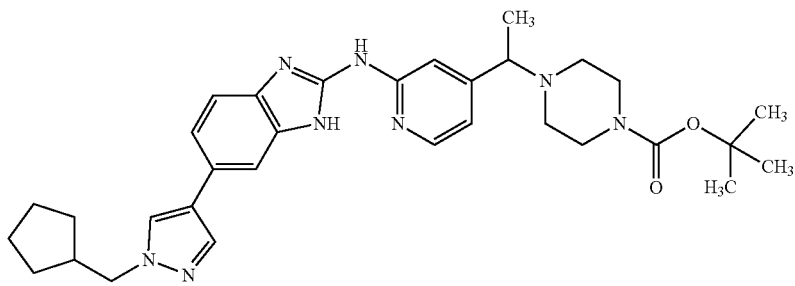 [SMILES: CC(c1ccnc(Nc2nc3ccc(-c4cnn(CC5CCCC5)c4)cc3[nH]2)c1)N1CCN(C(=O)OC(C)(C)C)CC1]

Starting with 4-[1-(cyclopentylmethyl)-1H-pyrazol-4-yl]benzene-1,2-diamine (62.5 mg, see Compound 71.03), Example 71.01 was prepared analogously to the procedure for the preparation of Example 39.02.01. The intermediate thiourea was purified by flash chromatography.

Yield: 41 mg of the 96% pure title compound.

LC-MS (Method 2): $R_t$=1.45 min; MS (ESIpos): m/z=571 [M+H]$^+$.

$^1$H-NMR (400 MHz, DMSO-d6): δ [ppm]=1.22-1.33 (m, 5H), 1.38 (s, 9H), 1.47-1.69 (m, 6H), 2.22-2.45 (m, 5H), 3.24-3.33 (m, 4H), 3.43 (q, 1H), 3.97-4.07 (m, 2H), 6.92 (dd, 1H), 7.16 (s, 1H), 7.18-7.47 (m, 2H), 7.49-7.67 (m, 1H), 7.78 (br d, 1H), 8.07 (br d, 1H), 8.24 (d, 1H), 10.55 (br s, 1H), 12.02 (br s, 1H).

Example 71.02

1-(4-{(1R or 1S)-1-[2-({6-[1-(cyclopentylmethyl)-1H-pyrazol-4-yl]-1H-benzimidazol-2-yl}amino)pyridin-4-yl]ethyl}piperazin-1-yl)-3,3,3-trifluoropropan-1-one

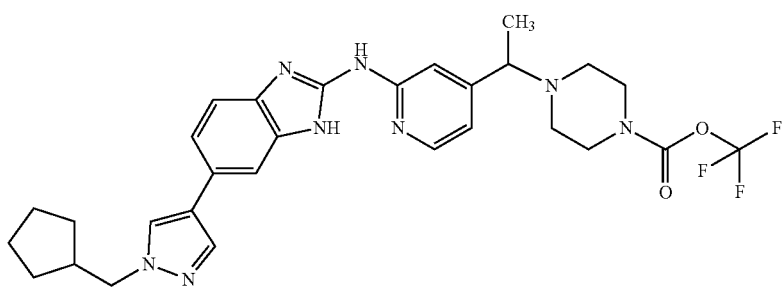 [SMILES: CC(c1ccnc(Nc2nc3ccc(-c4cnn(CC5CCCC5)c4)cc3[nH]2)c1)N1CCN(C(=O)OC(F)(F)F)CC1]

Starting with 6-[1-(cyclopentylmethyl)-1H-pyrazol-4-yl]-N-{4-[(1R or 1S)-1-(piperazin-1-yl)ethyl]pyridin-2-yl}-1H-benzimidazol-2-amine hydrochloride (37 mg, see Compound 70.04), Example 71.02 was prepared analogously to the procedure for the preparation of Example 39.02.02.

Yield: 15 mg of the 90% pure title compound.

LC-MS (Method 2): $R_t$=1.30 min; MS (ESIpos): m/z=581 [M+H]$^+$.

$^1$H-NMR (400 MHz, DMSO-d6): δ [ppm]=1.21-1.69 (m, 11H), 2.37-2.45 (m, 1H), 3.22-3.56 (m, 9H), 3.65 (q, 2H), 4.04 (d, 2H), 7.11-7.24 (m, 1H), 7.26 (br s, 1H), 7.40-7.47 (m, 1H), 7.49-7.55 (m, 1H), 7.67 (s, 1H), 7.83 (s, 1H), 8.15 (s, 1H), 8.39 (br d, 1H), 11.75 (br d, 1H), 12.90 (br s, 1H).

Example 72.01 tert-butyl 4-{(1R or 1S)-1-[2-({6-[1-(propan-2-yl)-1H-pyrazol-5-yl]-1H-benzimidazol-2-yl}amino)pyridin-4-yl]ethyl}piperazine-1-carboxylate

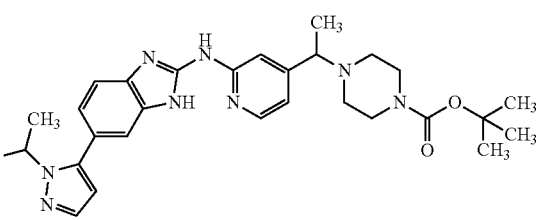

Starting with 4-[1-(propan-2-yl)-1H-pyrazol-5-yl]benzene-1,2-diamine (550 mg, see Compound 72.01), Example 72.01 was prepared analogously to the procedure for the preparation of Example 39.02.01. The intermediate thiourea was purified by flash chromatography.

Yield: 400 mg of the 97% pure title compound.

LC-MS (Method 2): $R_t$=1.34 min; MS (ESIpos): m/z=531 [M+H]$^+$.

$^1$H-NMR (400 MHz, DMSO-d6): δ [ppm]=1.28 (d, 3H), 1.32-1.43 (m, 15H), 2.22-2.44 (m, 4H), 3.25-3.32 (m, 4H), 3.44 (q, 1H), 4.53-4.71 (m, 1H), 6.23 (s, 1H), 6.94 (d, 1H), 6.98-7.61 (m, 5H), 8.18-8.30 (m, 1H), 10.66 (br d, 1H), 12.22 (br d, 1H).

Example 72.02

3,3,3-trifluoro-1-(4-{(1R or 1S)-1-[2-({6-[1-(propan-2-yl)-1H-pyrazol-5-yl]-1H-benzimidazol-2-yl}amino)pyridin-4-yl]ethyl}piperazin-1-yl)propan-1-one

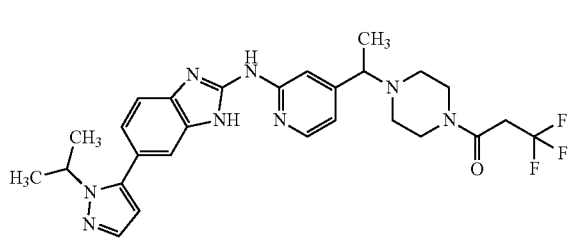 [SMILES: CC(c1ccnc(Nc2nc3ccc(-c4ccnn4C(C)C)cc3[nH]2)c1)N1CCN(C(=O)CC(F)(F)F)CC1]

Starting with N-{4-[(1R or 1S)-1-(piperazin-1-yl)ethyl]pyridin-2-yl}-6-[1-(propan-2-yl)-1H-pyrazol-5-yl]-1H-benzimidazol-2-amine hydrochloride (126 mg, see Compound 72.02), Example 72.02 was prepared analogously to the procedure for the preparation of Example 39.02.02.

Yield: 50 mg of the 100% pure title compound.

LC-MS (Method 2): $R_t$=1.18 min; MS (ESIpos): m/z=541 [M+H]$^+$.

$^1$H-NMR (400 MHz, DMSO-d6): δ [ppm]=1.30 (br d, 3H), 1.38 (d, 6H), 2.27-2.47 (m, 4H), 3.38-3.54 (m, 5H), 3.62 (q, 2H), 4.54-4.68 (m, 1H), 6.24 (d, 1H), 6.96 (d, 1H), 7.06 (br d, 1H), 7.17 (s, 1H), 7.49 (d, 3H), 8.28 (d, 1H), 10.70 (br s, 1H), 12.25 (br s, 1H).

Example 72.03 cyclopropyl(4-{(1R or 1S)-1-[2-({6-[1-(propan-2-yl)-1H-pyrazol-5-yl]-1H-benzimidazol-2-yl}amino)pyridin-4-yl]ethyl}piperazin-1-yl)methanone

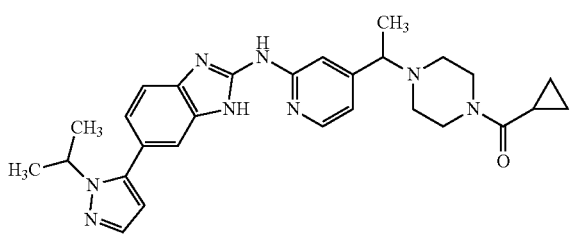 [SMILES: CC(c1ccnc(Nc2nc3ccc(-c4ccnn4C(C)C)cc3[nH]2)c1)N1CCN(C(=O)C2CC2)CC1]

Starting with N-{4-[(1R or 1S)-1-(piperazin-1-yl)ethyl]pyridin-2-yl}-6-[1-(propan-2-yl)-1H-pyrazol-5-yl]-1H-benzimidazol-2-amine hydrochloride (126 mg, see Compound 72.02), Example 72.03 was prepared analogously to the procedure for the preparation of Example 39.02.03.

Yield: 46 mg of the 100% pure title compound.

LC-MS (Method 2): $R_t$=1.14 min; MS (ESIpos): m/z=499 [M+H]$^+$.

$^1$H-NMR (400 MHz, DMSO-d6): δ [ppm]=0.62-0.75 (m, 4H), 1.30 (d, 3H), 1.38 (br d, 6H), 1.89-1.98 (m, 1H), 2.23-2.45 (m, 4H), 3.40-3.54 (m, 3H), 3.68 (br s, 2H), 4.53-4.70 (m, 1H), 6.24 (s, 1H), 6.96 (dd, 1H), 6.99-7.12 (m, 1H), 7.18 (br s, 1H), 7.27-7.62 (m, 3H), 8.28 (d, 1H), 10.67 (br d, 1H), 12.22 (br d, 1H).

Example 73.01

1-{4-[(1R or 1S)-1-(2-{[6-(1,4-dimethyl-1H-pyrazol-5-yl)-1H-benzimidazol-2-yl]amino}pyridin-4-yl)ethyl]piperazin-1-yl}-3,3,3-trifluoropropan-1-one

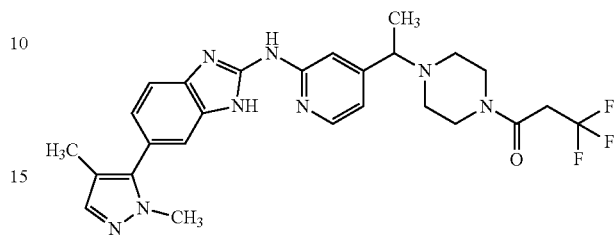

Starting with 6-(1,4-dimethyl-1H-pyrazol-5-yl)-N-{4-[(1R or 1S)-1-(piperazin-1-yl)ethyl]pyridin-2-yl}-1H-benzimidazol-2-amine hydrochloride (33 mg, see Compound 73.03), Example 73.01 was prepared analogously to the procedure for the preparation of Example 39.02.02.

Yield: 17 mg of the 90% pure title compound.

LC-MS (Method 2): $R_t$=1.11 min; MS (ESIpos): m/z=527 [M+H]$^+$.

$^1$H-NMR (400 MHz, DMSO-d6): δ [ppm]=1.30 (d, 3H), 1.98 (s, 3H), 2.31-2.46 (m, 4H), 3.40-3.52 (m, 5H), 3.56-3.67 (m, 2H), 3.71 (s, 3H), 6.36-6.65 (m, 1H), 6.96 (d, 1H), 7.03 (br d, 1H), 7.14-7.21 (m, 1H), 7.31 (s, 1H), 7.42-7.58 (m, 1H), 8.28 (d, 1H), 10.69 (br s, 1H), 12.21 (br s, 1H).

Example 74.01 tert-butyl 4-[(1R or 1S)-1-{2-[(6-{1-[(1RS)-1-cyclopropylethyl]-1H-pyrazol-4-yl}-1H-benzimidazol-2-yl)amino]pyridin-4-yl}ethyl]piperazine-1-carboxylate

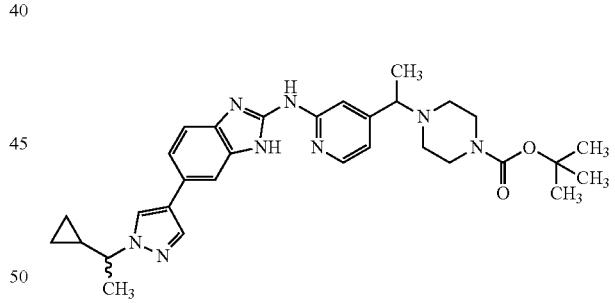

Starting with 4-{1-[(1RS)-1-cyclopropylethyl]-1H-pyrazol-4-yl}benzene-1,2-diamine (80.0 mg, see Compound 74.02), Example 74.01 was prepared analogously to the procedure for the preparation of Example 39.02.01. The intermediate thiourea was purified by flash chromatography.

Yield: 84 mg of the 90% pure title compound.

LC-MS (Method 2): $R_t$=1.37 min; MS (ESIpos): m/z=557 [M+H]$^+$.

$^1$H-NMR (400 MHz, DMSO-d6): δ [ppm]=0.29-0.40 (m, 2H), 0.42-0.51 (m, 1H), 0.56-0.65 (m, 1H), 1.22-1.31 (m, 4H), 1.38 (s, 9H), 1.54 (d, 3H), 2.23-2.44 (m, 4H), 3.24-3.33 (m, 4H), 3.43 (q, 1H), 3.59-3.70 (m, 1H), 6.92 (dd, 1H), 7.16 (s, 1H), 7.20-7.48 (m, 2H), 7.50-7.68 (m, 1H), 7.80 (br s, 1H), 8.13 (br d, 1H), 8.24 (d, 1H), 10.55 (br s, 1H), 12.02 (br s, 1H).

Example 74.02

1-{4-[(1R or 1S)-1-{2-[(6-{1-[(1RS)-1-cyclopropyl-ethyl]-1H-pyrazol-4-yl}-1H-benzimidazol-2-yl)amino]pyridin-4-yl}ethyl]piperazin-1-yl}-3,3,3-trifluoropropan-1-one

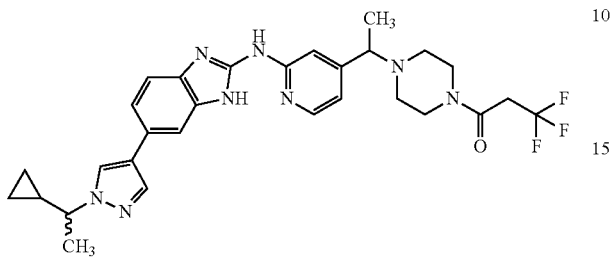

Starting with 6-{1-[(1RS)-1-cyclopropylethyl]-1H-pyrazol-4-yl}-N-{4-[(1R or 1S)-1-(piperazin-1-yl)ethyl]pyridin-2-yl}-1H-benzimidazol-2-amine hydrochloride (83.0 mg, see Compound 74.03), Example 74.02 was prepared analogously to the procedure for the preparation of Example 39.02.02.

Yield: 42 mg of the 86% pure title compound.

LC-MS (Method 2): $R_t$=1.22 min; MS (ESIpos): m/z=567 [M+H]$^+$.

$^1$H-NMR (400 MHz, DMSO-d6): δ [ppm]=0.29-0.40 (m, 2H), 0.41-0.50 (m, 1H), 0.55-0.65 (m, 1H), 1.20-1.34 (m, 4H), 1.54 (d, 3H), 2.29-2.47 (m, 4H), 3.39-3.52 (m, 5H), 3.62 (q, 3H), 6.93 (dd, 1H), 7.17 (s, 1H), 7.20-7.47 (m, 2H), 7.50-7.67 (m, 1H), 7.78 (br d, 1H), 8.07-8.19 (m, 1H), 8.25 (d, 1H), 10.57 (br s, 1H), 12.02 (br s, 1H).

Example 75.01 tert-butyl 4-{(1R or 1S)-1-[2-({7-chloro-6-[1-(cyclobutylmethyl)-1H-pyrazol-4-yl]-1H-benzimidazol-2-yl}amino)pyridin-4-yl]ethyl}piperazine-1-carboxylate

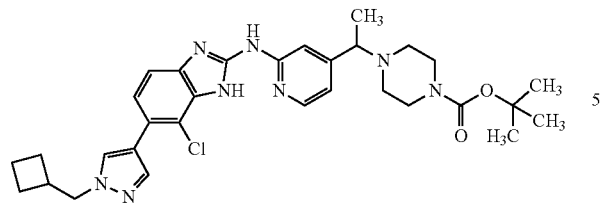

Starting with 3-chloro-4-[1-(cyclobutylmethyl)-1H-pyrazol-4-yl]benzene-1,2-diamine (171 mg, 86% purity; see Compound 75.02), Example 75.01 was prepared analogously to the procedure for the preparation of Example 39.02.01. The intermediate thiourea was purified by flash chromatography.

Yield: 117 mg of the 94% pure title compound.

LC-MS (Method 2): $R_t$=1.49 min; MS (ESIpos): m/z=591 [M+H]$^+$.

$^1$H-NMR (400 MHz, DMSO-d6): δ [ppm]=1.28 (d, 3H), 1.38 (s, 9H), 1.74-1.91 (m, 4H), 1.95-2.06 (m, 2H), 2.25-2.45 (m, 4H), 2.73-2.85 (m, 1H), 3.24-3.33 (m, 4H), 3.40-3.51 (m, 1H), 4.17 (d, 2H), 6.95 (d, 1H), 7.08 (s, 1H), 7.17 (d, 1H), 7.44 (d, 1H), 7.76 (s, 1H), 8.07 (s, 1H), 8.27 (d, 1H), 10.96 (s, 1H), 12.29 (s, 1H).

Example 75.02

1-(4-{(1R or 1S)-1-[2-({7-chloro-6-[1-(cyclobutylmethyl)-1H-pyrazol-4-yl]-1H-benzimidazol-2-yl}amino)pyridin-4-yl]ethyl}piperazin-1-yl)-3,3,3-trifluoropropan-1-one Starting with 7-chloro-6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride (59 mg, see Compound 75.03), Example 75.02 was prepared analogously to the procedure for the preparation of Example 39.02.02.

Yield: 42 mg of the 96% pure title compound.

LC-MS (Method 2): $R_t$=1.33 min; MS (ESIpos): m/z=601 [M+H]$^+$.

$^1$H-NMR (400 MHz, DMSO-d6): δ [ppm]=1.29 (d, 3H), 1.72-1.92 (m, 4H), 1.95-2.07 (m, 2H), 2.28-2.46 (m, 4H), 2.73-2.85 (m, 1H), 3.40-3.52 (m, 5H), 3.62 (q, 2H), 4.13-4.22 (m, 2H), 6.96 (d, 1H), 7.08 (s, 1H), 7.17 (d, 1H), 7.44 (d, 1H), 7.76 (s, 1H), 8.07 (s, 1H), 8.28 (d, 1H), 10.97 (s, 1H), 12.30 (s, 1H).

Example 75.03

(4-{(1R or 1S)-1-[2-({7-chloro-6-[1-(cyclobutylmethyl)-1H-pyrazol-4-yl]-1H-benzimidazol-2-yl}amino)pyridin-4-yl]ethyl}piperazin-1-yl)(cyclopropyl)methanone Starting with 7-chloro-6-[1-(cyclobutylmethyl)-1H-pyrazol-4-yl]-N-{4-[(1R or 1S)-1-(piperazin-1-yl)ethyl]pyridin-2-yl}-1H-benzimidazol-2-amine hydrochloride (59 mg, see Compound 75.03), Example 75.03 was prepared analogously to the procedure for the preparation of Example 39.02.03.

Yield: 36 mg of the 91% pure title compound.

LC-MS (Method 2): $R_t$=1.30 min; MS (ESIpos): m/z=559 [M+H]$^+$.

¹H-NMR (400 MHz, DMSO-d6): δ [ppm]=0.62-0.74 (m, 4H), 1.30 (d, 3H), 1.74-2.06 (m, 7H), 2.24-2.45 (m, 4H), 2.72-2.85 (m, 1H), 3.40-3.54 (m, 3H), 3.67 (br s, 2H), 4.11-4.22 (m, 2H), 6.97 (d, 1H), 7.08 (s, 1H), 7.17 (d, 1H), 7.44 (d, 1H), 7.76 (s, 1H), 8.07 (s, 1H), 8.28 (d, 1H), 10.97 (s, 1H), 12.30 (s, 1H).

Example 76.01

1-{4-[(2-{[6-(6-cyclopropylpyrimidin-4-yl)-1H-benzimidazol-2-yl]amino}pyridin-4-yl)methyl]piperazin-1-yl}-3,3,3-trifluoropropan-1-one

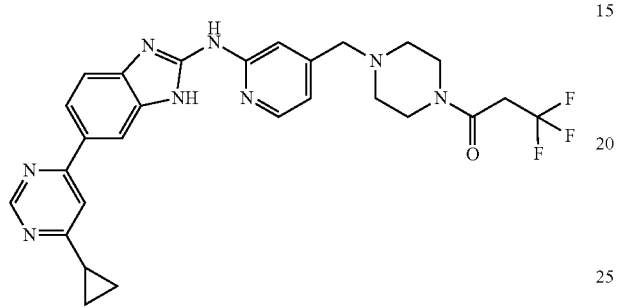

Starting with 6-(6-cyclopropylpyrimidin-4-yl)-N-[4-(piperazin-1-ylmethyl)pyridin-2-yl]-1H-benzimidazol-2-amine hydrochloride (100 mg, see Compound 76.02), Example 76.01 was prepared analogously to the procedure for the preparation of Example 39.02.02.

Yield: 50 mg of the 91% pure title compound.

LC-MS (Method 2): $R_t$=1.14 min; MS (ESIpos): m/z=537 [M+H]⁺.

¹H-NMR (400 MHz, DMSO-d6): δ [ppm]=1.03-1.15 (m, 4H), 2.18 (quin, 1H), 2.35-2.45 (m, 4H), 3.44-3.55 (m, 6H), 3.65 (q, 2H), 6.95 (br d, 1H), 7.20 (s, 1H), 7.38-7.65 (m, 1H), 7.87-8.08 (m, 2H), 8.18-8.47 (m, 2H), 8.93 (d, 1H), 10.70-10.86 (m, 1H), 12.29 (br d, 1H).

Example 76.02 cyclopropyl{4-[(2-{[6-(6-cyclopropylpyrimidin-4-yl)-1H-benzimidazol-2-yl]amino}pyridin-4-yl)methyl]piperazin-1-yl}methanone

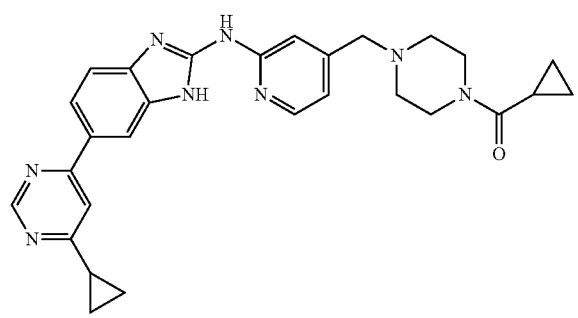 [SMILES: O=C(C1CC1)N1CCN(Cc2ccnc(Nc3nc4ccc(-c5cc(C6CC6)ncn5)cc4[nH]3)c2)CC1]

Starting with 6-(6-cyclopropylpyrimidin-4-yl)-N-[4-(piperazin-1-ylmethyl)pyridin-2-yl]-1H-benzimidazol-2-amine hydrochloride (100 mg, see Compound 76.02), Example 76.02 was prepared analogously to the procedure for the preparation of Example 39.02.03.

Yield: 38 mg of the 97% pure title compound.

LC-MS (Method 4): $R_t$=1.07 min; MS (ESIpos): m/z=495 [M+H]⁺.

¹H-NMR (400 MHz, DMSO-d6): δ [ppm]=0.64-0.76 (m, 4H), 1.02-1.13 (m, 4H), 1.91-2.03 (m, 1H), 2.18 (quin, 1H), 2.34-2.47 (m, 4H), 3.44-3.57 (m, 4H), 3.71 (br s, 2H), 6.96 (d, 1H), 7.22 (s, 1H), 7.39-7.66 (m, 1H), 7.88-8.08 (m, 2H), 8.17-8.46 (m, 2H), 8.93 (d, 1H), 10.78 (br s, 1H), 12.34 (br s, 1H).

Example 77.01

6-{2-[(4-{[4-(3,3,3-trifluoropropanoyl)piperazin-1-yl]methyl}pyridin-2-yl)amino]-1H-benzimidazol-6-yl}pyrimidine-4-carbonitrile

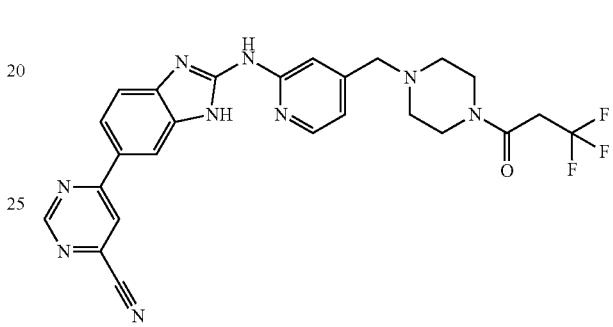

Starting with 6-(2-{[4-(piperazin-1-ylmethyl)pyridin-2-yl]amino}-1H-benzimidazol-6-yl)pyrimidine-4-carbonitrile hydrochloride (120 mg, see Compound 77.02), Example 77.01 was prepared analogously to the procedure for the preparation of Example 39.02.02.

Yield: 12 mg of the 90% pure title compound.

LC-MS (Method 4): $R_t$=1.07 min; MS (ESIpos): m/z=522 [M+H]⁺.

¹H-NMR (400 MHz, DMSO-d6): δ [ppm]=2.35-2.46 (m, 4H), 3.42-3.57 (m, 6H), 3.65 (q, 2H), 6.92-7.03 (m, 1H), 7.20 (br s, 1H), 7.42-7.68 (m, 1H), 8.05 (dd, 1H), 8.23-8.55 (m, 2H), 8.63-8.85 (m, 1H), 9.31 (br s, 1H), 10.76-10.96 (m, 1H), 12.40 (br s, 1H).

Example 78.01

3,3,3-trifluoro-1-(4-{[2-({6-[6-(propan-2-yl)pyrimidin-4-yl]-1H-benzimidazol-2-yl}amino)pyridin-4-yl]methyl}piperazin-1-yl)propan-1-one

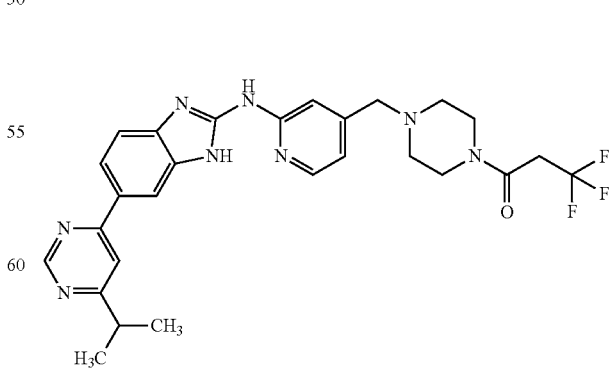

Starting with N-[4-(piperazin-1-ylmethyl)pyridin-2-yl]-6-[6-(propan-2-yl)pyrimidin-4-yl]-1H-benzimidazol-2-amine hydrochloride (110 mg, see Compound 78.02), Example 78.01 was prepared analogously to the procedure for the preparation of Example 39.02.02.

Yield: 17 mg of the 85% pure title compound.

LC-MS (Method 2): $R_t$=1.16 min; MS (ESIpos): m/z=539 [M+H]$^+$.

$^1$H-NMR (400 MHz, DMSO-d6): δ [ppm]=1.30 (d, 6H), 2.41 (dt, 4H), 3.05 (dt, 1H), 3.42-3.56 (m, 6H), 3.65 (q, 2H), 6.95 (br d, 1H), 7.20 (s, 1H), 7.39-7.65 (m, 1H), 7.83-8.03 (m, 2H), 8.19-8.45 (m, 2H), 9.06 (d, 1H), 10.79 (d, 1H), 12.23-12.37 (m, 1H).

Example 78.02 cyclopropyl(4-{[2-({6-[6-(propan-2-yl)pyrimidin-4-yl]-1H-benzimidazol-2-yl}amino)pyridin-4-yl]methyl}piperazin-1-yl)methanone

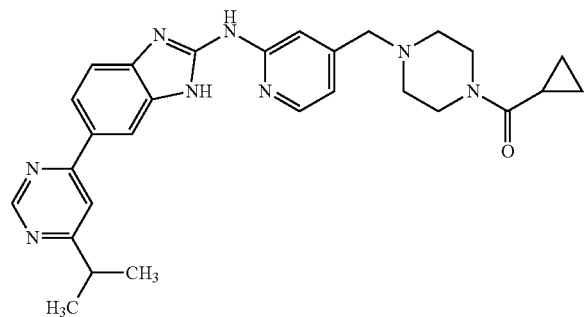 [SMILES: CC(C)c1cc(-c2ccc3nc(Nc4cc(CN5CCN(C(=O)C6CC6)CC5)ccn4)[nH]c3c2)ncn1]

Starting with N-[4-(piperazin-1-ylmethyl)pyridin-2-yl]-6-[6-(propan-2-yl)pyrimidin-4-yl]-1H-benzimidazol-2-amine hydrochloride (110 mg, see Compound 78.02), Example 78.02 was prepared analogously to the procedure for the preparation of Example 39.02.03.

Yield: 20 mg of the 88% pure title compound.

LC-MS (Method 2): $R_t$=1.13 min; MS (ESIpos): m/z=497 [M+H]$^+$.

$^1$H-NMR (400 MHz, DMSO-d6): δ [ppm]=0.64-0.78 (m, 4H), 1.30 (d, 6H), 1.93-2.01 (m, 1H), 2.34-2.47 (m, 4H), 2.97-3.13 (m, 1H), 3.44-3.58 (m, 4H), 3.71 (br s, 2H), 6.90-6.99 (m, 1H), 7.14-7.25 (m, 1H), 7.35-7.64 (m, 1H), 7.83-8.01 (m, 2H), 8.19-8.45 (m, 2H), 9.06 (d, 1H), 10.68-10.86 (m, 1H), 12.23-12.37 (m, 1H).

Example 79.01

3,3,3-trifluoro-1-(4-{[2-({6-[6-(methoxymethyl)pyrimidin-4-yl]-1H-benzimidazol-2-yl}amino)pyridin-4-yl]methyl}piperazin-1-yl)propan-1-one

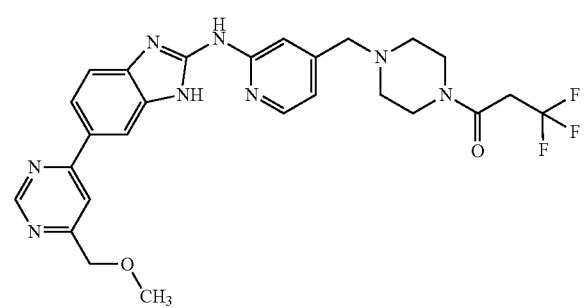 [SMILES: COCc1cc(-c2ccc3nc(Nc4cc(CN5CCN(C(=O)CC(F)(F)F)CC5)ccn4)[nH]c3c2)ncn1]

Starting with 6-[6-(methoxymethyl)pyrimidin-4-yl]-N-[4-(piperazin-1-ylmethyl)pyridin-2-yl]-1H-benzimidazol-2-amine hydrochloride (200 mg, see Compound 79.02), Example 79.01 was prepared analogously to the procedure for the preparation of Example 39.02.02.

Yield: 40 mg of the 79% pure title compound.

LC-MS (Method 2): $R_t$=1.03 min; MS (ESIpos): m/z=541 [M+H]$^+$.

$^1$H-NMR (400 MHz, DMSO-d6): δ [ppm]=2.34-2.45 (m, 4H), 3.39 (s, 2H), 3.43-3.56 (m, 7H), 3.65 (q, 2H), 4.55 (s, 2H), 6.86-7.04 (m, 1H), 7.19 (s, 1H), 7.32-8.08 (m, 3H), 8.14-8.52 (m, 2H), 9.01-9.34 (m, 1H), 10.82 (br s, 1H), 12.35 (br s, 1H).

Example 79.02 cyclopropyl(4-{[2-({6-[6-(methoxymethyl)pyrimidin-4-yl]-1H-benzimidazol-2-yl}amino)pyridin-4-yl]methyl}piperazin-1-yl)methanone

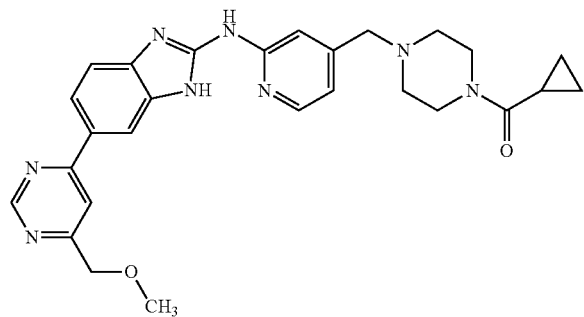 [SMILES: COCc1cc(-c2ccc3nc(Nc4cc(CN5CCN(C(=O)C6CC6)CC5)ccn4)[nH]c3c2)ncn1]

Starting with 6-[6-(methoxymethyl)pyrimidin-4-yl]-N-[4-(piperazin-1-ylmethyl)pyridin-2-yl]-1H-benzimidazol-2-amine hydrochloride (200 mg, see Compound 79.02), Example 79.02 was prepared analogously to the procedure for the preparation of Example 39.02.03.

Yield: 38 mg of the 89% pure title compound.

LC-MS (Method 2): $R_t$=0.99 min; MS (ESIpos): m/z=499 [M+H]$^+$.

$^1$H-NMR (400 MHz, DMSO-d6): δ [ppm]=0.65-0.75 (m, 4H), 1.92-2.01 (m, 1H), 2.34-2.47 (m, 4H), 3.44-3.56 (m, 7H), 3.71 (br s, 2H), 4.55 (s, 2H), 6.89-7.00 (m, 1H), 7.19 (s, 1H), 7.40-8.05 (m, 3H), 8.15-8.50 (m, 2H), 9.09 (s, 1H), 10.82 (br s, 1H), 12.35 (br s, 1H).

Example 79.03

(4-{[2-({6-[6-(methoxymethyl)pyrimidin-4-yl]-1H-benzimidazol-2-yl}amino)pyridin-4-yl]methyl}piperazin-1-yl)[1-(trifluoromethyl)cyclopropyl]methanone

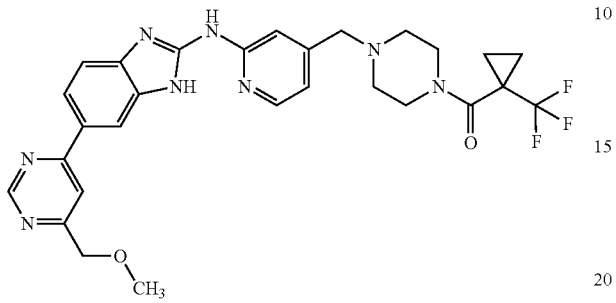

Starting with 6-[6-(methoxymethyl)pyrimidin-4-yl]-N-[4-(piperazin-1-ylmethyl)pyridin-2-yl]-1H-benzimidazol-2-amine hydrochloride (107 mg, see Compound 79.02), Example 79.03 was prepared analogously to the procedure for the preparation of Example 83.05.

Yield: 8 mg of the 86% pure title compound.

LC-MS (Method 4): $R_t$=1.08 min; MS (ESIpos): m/z=567 [M+H]$^+$.

$^1$H-NMR (400 MHz, DMSO-d6): δ [ppm]=1.12-1.22 (m, 2H), 1.25-1.33 (m, 2H), 2.42 (br s, 4H), 3.42-3.72 (m, 9H), 4.55 (s, 2H), 6.96 (br d, 1H), 7.19 (s, 1H), 7.38-7.70 (m, 1H), 7.86-8.02 (m, 2H), 8.14-8.46 (m, 2H), 9.09 (s, 1H), 10.82 (br s, 1H), 12.19-12.46 (m, 1H).

Example 80.01 tert-butyl 4-{[2-({6-[6-(cyclopropylmethoxy)pyrimidin-4-yl]-1H-benzimidazol-2-yl}amino)pyridin-4-yl]methyl}piperazine-1-carboxylate

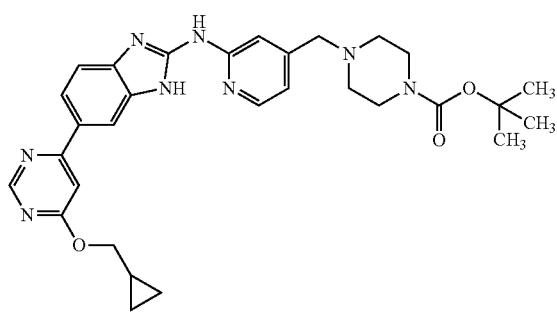 [SMILES: CC(C)(C)OC(=O)N1CCN(Cc2ccnc(Nc3nc4ccc(-c5cc(OCC6CC6)ncn5)cc4[nH]3)c2)CC1]

tert-butyl 4-[(2-{[6-(6-chloropyrimidin-4-yl)-1H-benzimidazol-2-yl]amino}pyridin-4-yl)methyl]piperazine-1-carboxylate (608 mg, see Compound 80.01) was dissolved in 8 mL dioxane and treated with sodium hydride (280 mg, 60% purity). Then, cyclopropylmethanol (504 mg) was added and the reaction mixture was stirred at rt for 30 min and afterwards concentrated under reduced pressure. The crude product was purified by flash chromatography.

Yield: 312 mg of the title compound with 96% purity.

LC-MS (Method 2): $R_t$=1.41 min; MS (ESIpos): m/z=558 [M+H]$^+$.

$^1$H-NMR (400 MHz, DMSO-d6) δ[ppm]=0.31-0.41 (m, 2H), 0.53-0.63 (m, 2H), 1.23-1.33 (m, 1H), 1.39 (s, 9H), 2.29-2.41 (m, 4H), 3.34 (s, 4H), 3.50 (s, 2H), 4.22 (d, 2H), 6.94 (br d, 1H), 7.18 (br s, 1H), 7.30-7.61 (m, 2H), 7.91 (br s, 1H), 8.12-8.40 (m, 2H), 8.77 (d, 1H), 10.76 (br s, 1H), 12.27 (br d, 1H).

Example 80.02

1-(4-{[2-({6-[6-(cyclopropylmethoxy)pyrimidin-4-yl]-1H-benzimidazol-2-yl}amino)pyridin-4-yl]methyl}piperazin-1-yl)-3,3,3-trifluoropropan-1-one

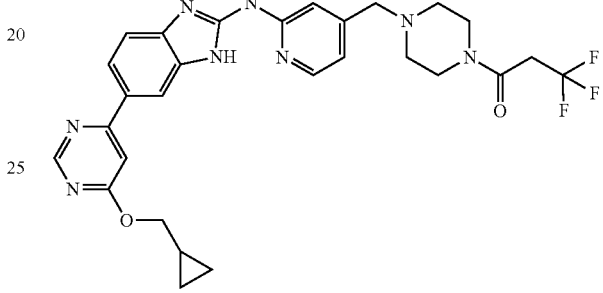

Starting with 6-[6-(cyclopropylmethoxy)pyrimidin-4-yl]-N-[4-(piperazin-1-ylmethyl)pyridin-2-yl]-1H-benzimidazol-2-amine hydrochloride (100 mg, see Compound 80.02), Example 80.02 was prepared analogously to the procedure for the preparation of Example 39.02.02.

Yield: 35 mg of the 89% pure title compound.

LC-MS (Method 2): $R_t$=1.25 min; MS (ESIpos): m/z=567 [M+H]$^+$.

$^1$H-NMR (400 MHz, DMSO-d6): δ [ppm]=0.33-0.44 (m, 2H), 0.53-0.62 (m, 2H), 1.21-1.37 (m, 1H), 2.40 (dt, 4H), 3.41-3.56 (m, 6H), 3.65 (q, 2H), 4.23 (d, 2H), 6.95 (br d, 1H), 7.13-7.61 (m, 3H), 7.92 (br d, 1H), 8.11-8.41 (m, 2H), 8.77 (d, 1H), 10.74 (br s, 1H), 12.25 (br s, 1H).

Example 80.03 cyclopropyl(4-{[2-({6-[6-(cyclopropylmethoxy)pyrimidin-4-yl]-1H-benzimidazol-2-yl}amino)pyridin-4-yl]methyl}piperazin-1-yl)methanone

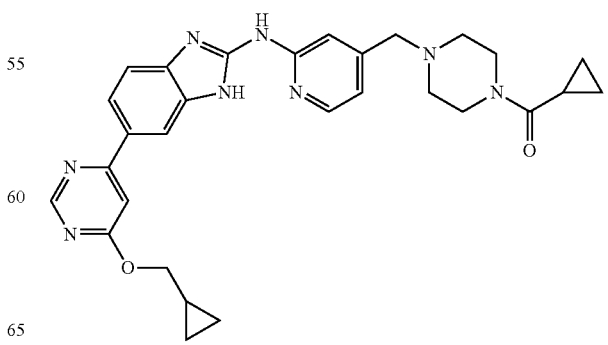

Starting with 6-[6-(cyclopropylmethoxy)pyrimidin-4-yl]-N-[4-(piperazin-1-ylmethyl)pyridin-2-yl]-1H-benzimidazol-2-amine hydrochloride (100 mg, see Compound 80.02), Example 80.03 was prepared analogously to the procedure for the preparation of Example 39.02.03.

Yield: 30 mg of the 98% pure title compound.

LC-MS (Method 2): R$_t$=1.22 min; MS (ESIpos): m/z=525 [M+H]$^+$.

$^1$H-NMR (400 MHz, DMSO-d6): δ [ppm]=0.33-0.42 (m, 2H), 0.53-0.63 (m, 2H), 0.65-0.76 (m, 4H), 1.22-1.36 (m, 1H), 1.92-2.04 (m, 1H), 2.33-2.46 (m, 4H), 3.44-3.57 (m, 4H), 3.71 (br s, 2H), 4.23 (d, 2H), 6.96 (br d, 1H), 7.20 (br s, 1H), 7.32-7.63 (m, 2H), 7.92 (br d, 1H), 8.13-8.40 (m, 2H), 8.77 (d, 1H), 10.75 (br s, 1H), 12.27 (br s, 1H).

Example 81.01 tert-butyl 4-({2-[(6-{6-[(2-hydroxyethyl)amino]pyrimidin-4-yl}-1H-benzimidazol-2-yl)amino]pyridin-4-yl}methyl)piperazine-1-carboxylate

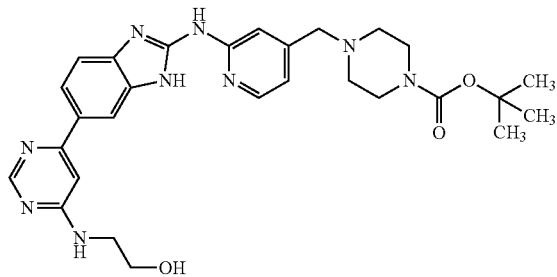 [SMILES: CC(C)(C)OC(=O)N1CCN(Cc2ccnc(Nc3nc4ccc(-c5cc(NCCO)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (100 mg, see Compound 01.04), Example 81.01 was prepared analogously to the procedure for the preparation of Compound 76.01.

Yield: 40 mg of the title compound with 97% purity.

LC-MS (Method 4): R$_t$=1.04 min; MS (ESIpos): m/z=546 [M+H]$^+$.

$^1$H-NMR (400 MHz, DMSO-d6): δ [ppm]=1.40 (s, 9H), 2.29-2.40 (m, 4H), 3.34-3.38 (m, 4H), 3.42 (br d, 2H), 3.50 (s, 2H), 3.56 (q, 2H), 4.79 (t, 1H), 6.87-7.02 (m, 2H), 7.10-7.60 (m, 3H), 7.73 (br s, 1H), 7.92-8.22 (m, 1H), 8.26 (d, 1H), 8.45 (s, 1H), 10.70 (br s, 1H), 12.22 (br d, 1H).

Example 82.01 tert-butyl 4-{[2-({6-[6-(cyclopropylamino)pyrimidin-4-yl]-1H-benzimidazol-2-yl}amino)pyridin-4-yl]methyl}piperazine-1-carboxylate

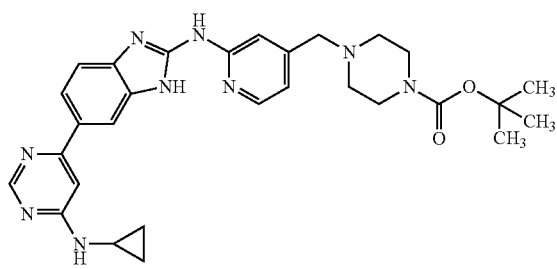 [SMILES: CC(C)(C)OC(=O)N1CCN(Cc2ccnc(Nc3nc4ccc(-c5cc(NC6CC6)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (100 mg, see Compound 01.04), Example 82.01 was prepared analogously to the procedure for the preparation of Compound 76.01.

Yield: 6 mg of the title compound with 95% purity.

LC-MS (Method 2): R$_t$=1.18 min; MS (ESIpos): m/z=542 [M+H]$^+$.

$^1$H-NMR (400 MHz, DMSO-d6): δ [ppm]=0.52 (br s, 2H), 0.71-0.89 (m, 2H), 1.13-1.27 (m, 1H), 1.40 (s, 9H), 2.27-2.41 (m, 4H), 3.34-3.40 (m, 4H), 3.50 (s, 2H), 6.87-7.62 (m, 6H), 7.80 (br s, 1H), 8.26 (br d, 1H), 8.47 (s, 1H), 10.72 (br s, 1H), 12.26 (br s, 1H).

Example 83.01 tert-butyl 4-[(1R or 1S)-1-(2-{[6-(6-chloro-5-methoxypyrimidin-4-yl)-1H-benzimidazol-2-yl]amino}pyridin-4-yl)ethyl]piperazine-1-carboxylate

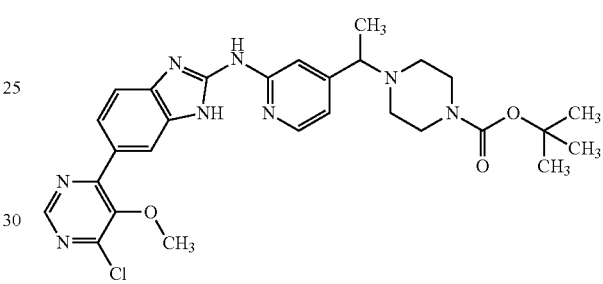

Starting with 4-(6-chloro-5-methoxypyrimidin-4-yl)benzene-1,2-diamine (1.07 g, see Compound 83.02), Example 83.01 was prepared analogously to the procedure for the preparation of Example 39.02.01.

Yield: 1.16 g of the title compound with 88% purity.

LC-MS (Method 2): R$_t$=1.38 min; MS (ESIpos): m/z=566 [M+H]$^+$.

$^1$H-NMR (400 MHz, DMSO-d6): δ [ppm]=1.29 (d, 3H), 1.38 (s, 9H), 2.24-2.45 (m, 4H), 3.23-3.32 (m, 4H), 3.45 (q, 1H), 3.65-3.78 (m, 3H), 6.96 (br d, 1H), 7.09-7.26 (m, 1H), 7.40-7.66 (m, 1H), 7.80-8.00 (m, 1H), 8.24-8.33 (m, 1H), 8.41 (br s, 1H), 8.80 (s, 1H), 10.63-10.87 (m, 1H), 12.16-12.45 (m, 1H).

Example 83.02 tert-butyl 4-[(1R or 1S)-1-(2-{[6-(5-methoxy-6-methylpyrimidin-4-yl)-1H-benzimidazol-2-yl]amino}pyridin-4-yl)ethyl]piperazine-1-carboxylate

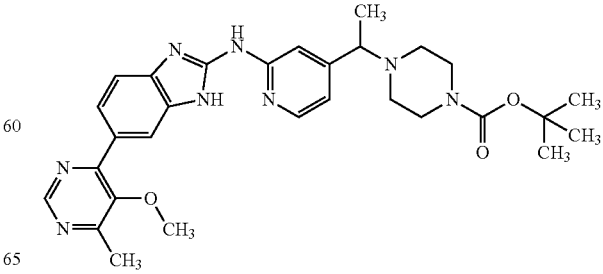

Starting with tert-butyl 4-[(1R or 1S)-1-(2-{[6-(6-chloro-5-methoxypyrimidin-4-yl)-1H-benzimidazol-2-yl]amino}pyridin-4-yl)ethyl]piperazine-1-carboxylate (958 mg, see Example 83.01), Example 83.02 was prepared analogously to the procedure for the preparation of Compound 61.01.

Yield: 635 mg of the title compound with 100% purity.

LC-MS (Method 2): $R_t$=1.28 min; MS (ESIpos): m/z=546 [M+H]$^+$.

$^1$H-NMR (400 MHz, DMSO-d6): δ [ppm]=1.29 (d, 3H), 1.38 (s, 9H), 2.24-2.45 (m, 4H), 2.51-2.52 (m, 3H), 3.21-3.32 (m, 4H), 3.40-3.50 (m, 1H), 3.51-3.69 (m, 3H), 6.95 (d, 1H), 7.16 (br s, 1H), 7.34-7.66 (m, 1H), 7.75-7.97 (m, 1H), 8.04-8.40 (m, 2H), 8.80 (s, 1H), 10.59-10.82 (m, 1H), 12.16-12.37 (m, 1H).

Example 83.03

3,3,3-trifluoro-1-{4-[(1R or 1S)-1-(2-{[6-(5-methoxy-6-methyl pyrimidin-4-yl)-1H-benzimidazol-2-yl]amino}pyridin-4-yl)ethyl]piperazin-1-yl}propan-1-one

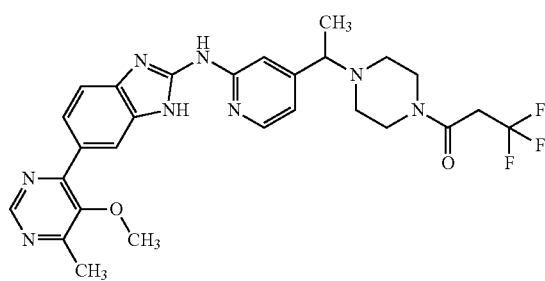 [SMILES: COc1c(C)ncnc1-c1ccc2nc(Nc3cc(C(C)N4CCN(C(=O)CC(F)(F)F)CC4)ccn3)[nH]c2c1]

Starting with 6-(5-methoxy-6-methylpyrimidin-4-yl)-N-{4-[(1R or 1S)-1-(piperazin-1-yl)ethyl]pyridin-2-yl}-1H-benzimidazol-2-amine hydrochloride (200 mg, see Compound 83.03), Example 83.03 was prepared analogously to the procedure for the preparation of Example 39.02.02.

Yield: 98 mg of the 97% pure title compound.

LC-MS (Method 2): $R_t$=1.10 min; MS (ESIpos): m/z=555 [M+H]$^+$.

$^1$H-NMR (400 MHz, DMSO-d6): δ [ppm]=1.30 (d, 3H), 2.26-2.48 (m, 4H), 2.51 (s, 3H), 3.38-3.68 (m, 10H), 6.96 (d, 1H), 7.17 (s, 1H), 7.36-7.64 (m, 1H), 7.75-7.97 (m, 1H), 8.02-8.40 (m, 2H), 8.80 (s, 1H), 10.75 (d, 1H), 12.13-12.41 (m, 1H).

Example 83.04 cyclopropyl{4-[(1R or 1S)-1-(2-{[6-(5-methoxy-6-methylpyrimidin-4-yl)-1H-benzimidazol-2-yl]amino}pyridin-4-yl)ethyl]piperazin-1-yl}methanone

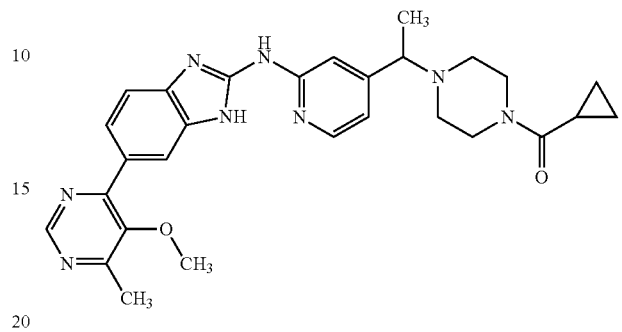

Starting with 6-(5-methoxy-6-methylpyrimidin-4-yl)-N-{4-[(1R or 1S)-1-(piperazin-1-yl)ethyl]pyridin-2-yl}-1H-benzimidazol-2-amine hydrochloride (200 mg, see Compound 83.03), Example 83.04 was prepared analogously to the procedure for the preparation of Example 39.02.03.

Yield: 115 mg of the 100% pure title compound.

LC-MS (Method 2): $R_t$=1.06 min; MS (ESIpos): m/z=513 [M+H]$^+$.

$^1$H-NMR (400 MHz, DMSO-d6): δ [ppm]=0.61-0.74 (m, 4H), 1.30 (d, 3H), 1.86-2.00 (m, 1H), 2.24-2.47 (m, 4H), 2.51 (s, 3H), 3.46 (q, 3H), 3.53-3.62 (m, 3H), 3.63-3.73 (m, 2H), 6.97 (d, 1H), 7.18 (s, 1H), 7.37-7.62 (m, 1H), 7.74-7.95 (m, 1H), 8.03-8.40 (m, 2H), 8.80 (s, 1H), 10.63-10.82 (m, 1H), 12.21-12.41 (m, 1H).

Example 83.05

{4-[(1R or IS)-1-(2-{[6-(5-methoxy-6-methylpyrimidin-4-yl)-1H-benzimidazol-2-yl]amino}pyridin-4-yl)ethyl]piperazin-1-yl}[1-(trifluoromethyl)cyclopropyl]methanone

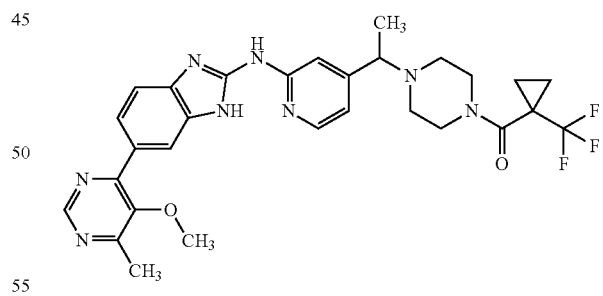

6-(5-methoxy-6-methylpyrimidin-4-yl)-N-{4-[(1R or 1S)-1-(piperazin-1-yl)ethyl]pyridin-2-yl}-1H-benzimidazol-2-amine hydrochloride (150 mg, Compound 83.03), 1-(trifluoromethyl)cyclopropanecarboxylic acid (79 μl), 1-[Bis(dimethylamino)methylene]-1H-1,2,3-triazolo[4,5-b]pyridinium 3-oxide hexafluorophosphate (309 mg) and sodium bicarbonate (136 mg) were combined in 2.1 mL DMF and stirred at room temperature overnight. The reaction mixture was filtrated and given to standard reversed-phased preparative HPLC purification to provide the target compound.

Yield: 92 mg of the title compound with 95% purity.

LC-MS (Method 4): $R_t$=1.14 min; MS (ESIpos): m/z=581 [M+H]⁺.

¹H-NMR (400 MHz, DMSO-d6): δ [ppm]=1.10-1.20 (m, 2H), 1.23-1.37 (m, 5H), 2.28-2.48 (m, 4H), 2.51 (br s, 3H), 3.46 (q, 1H), 3.59 (br s, 7H), 6.96 (d, 1H), 7.17 (s, 1H), 7.38-7.65 (m, 1H), 7.76-7.96 (m, 1H), 8.03-8.39 (m, 2H), 8.80 (s, 1H), 10.75 (d, 1H), 12.30 (br d, 1H).

Example 84.01 tert-butyl 4-{(1R or 1S)-1-[2-({6-[6-(methoxymethyl)pyrimidin-4-yl]-1H-benzimidazol-2-yl}amino)pyridin-4-yl]ethyl}piperazine-1-carboxylate

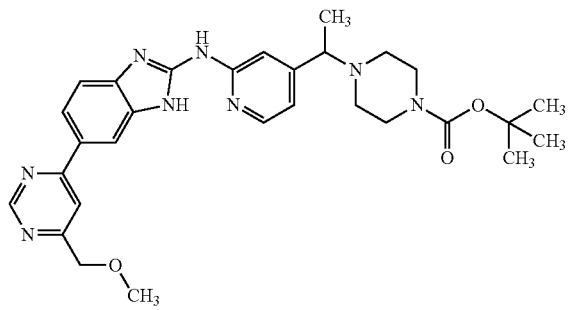 [SMILES: COCc1cc(-c2ccc3nc(Nc4cc(C(C)N5CCN(C(=O)OC(C)(C)C)CC5)ccn4)[nH]c3c2)ncn1]

Starting with tert-butyl 4-[(1R or 1S)-1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (1.56 g, 85% purity; see Compound 23.15.01), Example 84.01 was prepared analogously to the procedure for the preparation of Compound 60.01.

Yield: 327 mg of the title compound with 90% purity.

LC-MS (Method 4): $R_t$=1.27 min; MS (ESIpos): m/z=545 [M+H]⁺.

¹H-NMR (400 MHz, DMSO-d6): δ [ppm]=1.29 (d, 3H), 1.38 (s, 9H), 2.22-2.44 (m, 4H), 3.32 (br s, 3H), 3.39-3.50 (m, 5H), 4.55 (s, 2H), 6.96 (br s, 1H), 7.16 (s, 1H), 7.20-7.29 (m, 1H); 7.59-7.68 (m, 1H), 7.86-8.05 (m, 2H), 8.24-8.30 (m, 1H), 9.09 (s, 1H), 10.79 (br s, 1H), 12.22-12.41 (m, 1H).

Example 84.02

3,3,3-trifluoro-1-(4-{(1R or 1S)-1-[2-({6-[6-(methoxymethyl)pyrimidin-4-yl]-1H-benzimidazol-2-yl}amino)pyridin-4-yl]ethyl}piperazin-1-yl)propan-1-one

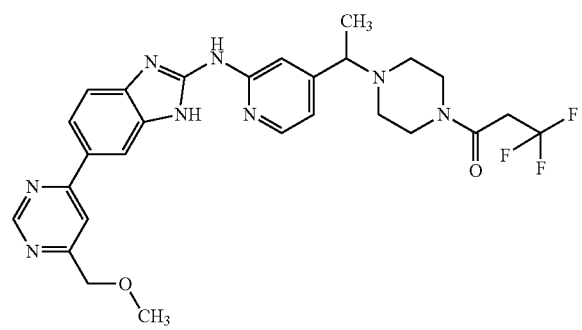 [SMILES: COCc1cc(-c2ccc3nc(Nc4cc(C(C)N5CCN(C(=O)CC(F)(F)F)CC5)ccn4)[nH]c3c2)ncn1]

Starting with 6-[6-(methoxymethyl)pyrimidin-4-yl]-N-{4-[(1R or 1S)-1-(piperazin-1-yl)ethyl]pyridin-2-yl}-1H-benzimidazol-2-amine hydrochloride (184 mg, see Compound 84.01), Example 84.02 was prepared analogously to the procedure for the preparation of Example 39.02.02.

Yield: 67 mg of the 98% pure title compound.

LC-MS (Method 2): $R_t$=1.07 min; MS (ESIpos): m/z=555 [M+H]⁺.

¹H-NMR (400 MHz, DMSO-d6): δ [ppm]=1.30 (d, 3H), 2.25-2.46 (m, 4H), 3.38-3.53 (m, 8H), 3.62 (q, 2H), 4.55 (s, 2H), 6.97 (br s, 1H), 7.17 (s, 1H), 7.36-7.50 (m, 1H), 7.84-8.02 (m, 2H), 8.15-8.44 (m, 2H), 9.09 (br s, 1H), 10.81 (br s, 1H), 12.22-12.43 (m, 1H).

Example 84.03 cyclopropyl(4-{(1R or 1S)-1-[2-({6-[6-(methoxymethyl)pyrimidin-4-yl]-1H-benzimidazol-2-yl}amino)pyridin-4-yl]ethyl}piperazin-1-yl)methanone

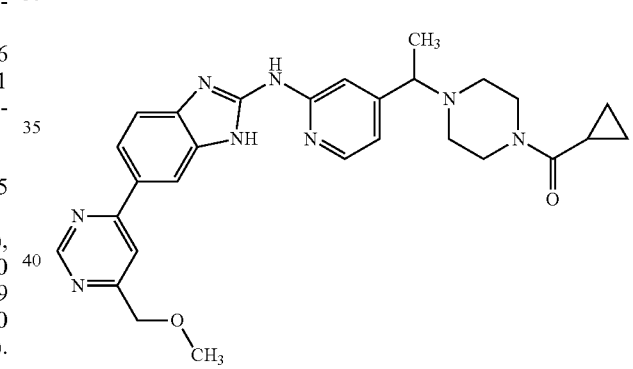

Starting with 6-[6-(methoxymethyl)pyrimidin-4-yl]-N-{4-[(1R or 1S)-1-(piperazin-1-yl)ethyl]pyridin-2-yl}-1H-benzimidazol-2-amine hydrochloride (184 mg, see Compound 84.01), Example 84.03 was prepared analogously to the procedure for the preparation of Example 39.02.03.

Yield: 57 mg of the 97% pure title compound.

LC-MS (Method 2): $R_t$=1.03 min; MS (ESIpos): m/z=513 [M+H]⁺.

¹H-NMR (400 MHz, DMSO-d6): δ [ppm]=0.59-0.75 (m, 4H), 1.30 (d, 3H), 1.86-1.99 (m, 1H), 2.21-2.44 (m, 4H), 3.38-3.54 (m, 6H), 3.67 (br s, 2H), 4.55 (s, 2H), 6.97 (br s, 1H), 7.18 (s, 1H), 7.36-7.50 (m, 1H), 7.86-8.03 (m, 2H), 8.15-8.46 (m, 2H), 9.09 (br s, 1H), 10.80 (br s, 1H), 12.24-12.46 (m, 1H).

Example 85.01 tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate

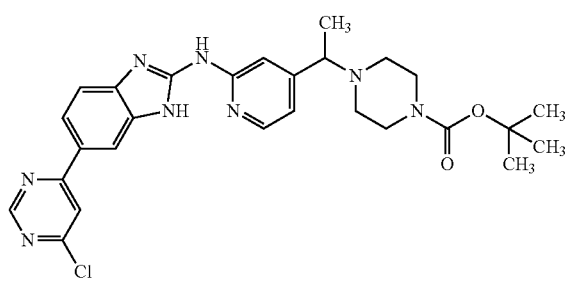 [SMILES: CC(c1ccnc(Nc2nc3ccc(-c4cc(Cl)ncn4)cc3[nH]2)c1)N1CCN(C(=O)OC(C)(C)C)CC1]

Starting with tert-butyl 4-[(1R or 1S)-1-(2-{[6-(4,4,5,5-tetramethyl-1,3,2-dioxaborolan-2-yl)-1H-benzimidazol-2-yl]amino}pyridin-4-yl)ethyl]piperazine-1-carboxylate (3.23 g, 85% purity, see Compound 23.15.01), Example 85.01 was prepared analogously to the procedure for the preparation of Compound 76.01.

Yield: 89 mg of the title compound with 100% purity.
LC-MS (Method 4): $R_t$=1.38 min; MS (ESIpos): m/z=535 [M+H]$^+$.
$^1$H-NMR (400 MHz, DMSO-d6): δ [ppm]=1.29 (d, 3H), 1.38 (s, 9H), 2.23-2.44 (m, 4H), 3.26-3.32 (m, 4H), 3.45 (q, 1H), 6.90-7.03 (m, 1H), 7.17 (s, 1H), 7.37-7.66 (m, 1H), 8.00 (br d, 1H), 8.13-8.50 (m, 3H), 9.01 (s, 1H), 10.80 (br d, 1H), 12.37 (d, 1H).

Example 85.01 Alternative Procedure tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate

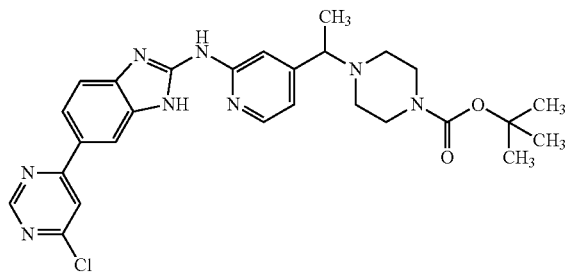 [SMILES: CC(c1ccnc(Nc2nc3ccc(-c4cc(Cl)ncn4)cc3[nH]2)c1)N1CCN(C(=O)OC(C)(C)C)CC1]

To a stirred solution of 1H-imidazole (21 mg) and di-1H-imidazol-1-ylmethanethione (391 mg, 90% purity) in THF (10 mL) was added tert-butyl 4-[(1R or 1S)-1-(2-aminopyridin-4-yl)ethyl]piperazine-1-carboxylate (500 mg, 93% purity, see Compound 36.05.), dissolved in THF (10 mL) at r.t. The mixture was stirred at 60° C. for 2 h. Further di-1H-imidazol-1-ylmethanethione (60 mg) was added and the mixture was stirred at 60° C. for 1 h. 4-(6-chloropyrimidin-4-yl)benzene-1,2-diamine (718 mg, 70% purity see Compound 85.02), dissolved in THF (3 mL) was added and the mixture was stirred at r.t. for 16 h. The mixture was filtered and N,N'-dipropan-2-ylcarbodiimide (510 µl) was added to the solution at r.t. The mixture was stirred at r.t. for 65 h. The crude reaction mixture was filtered and the solution was concentrated in vacuum. Silicagel chromatography gave 600 mg of the title compound.

LC-MS (Method 2): $R_t$=1.36 min; MS (ESIpos): m/z=535 [M+H]$^+$.
$^1$H-NMR (400 MHz, DMSO-d6) δ[ppm]: 0.990 (0.48), 1.006 (0.43), 1.153 (1.95), 1.172 (4.04), 1.189 (2.08), 1.279 (1.73), 1.296 (1.75), 1.376 (16.00), 1.987 (7.35), 2.296 (0.41), 2.309 (0.49), 2.383 (0.47), 2.518 (0.62), 2.523 (0.43), 3.999 (0.59), 4.016 (1.76), 4.034 (1.72), 4.052 (0.55), 5.758 (0.93), 6.977 (0.56), 6.979 (0.67), 7.011 (3.00), 7.170 (0.89), 7.233 (0.42), 7.637 (1.85), 8.273 (0.79), 8.286 (0.80), 9.009 (1.07).

Example 85.02 tert-butyl 4-{(1R or 1S)-1-[2-({6-[6-(cyclopropylmethoxy)pyrimidin-4-yl]-1H-benzimidazol-2-yl}amino)pyridin-4-yl]ethyl}piperazine-1-carboxylate

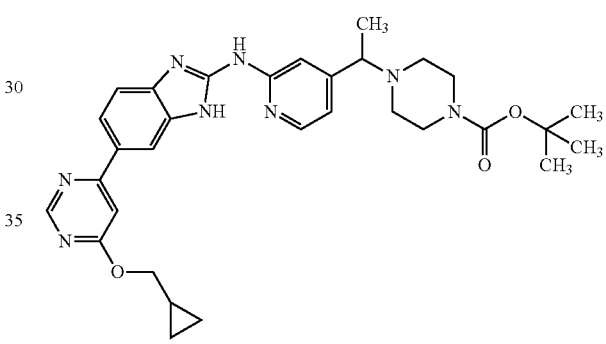

tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (60.0 mg, see Example 85.01), was dissolved in 0.77 mL dioxane and sodium hydride (26.9 mg, 60% purity) was added portionwise. cyclopropylmethanol (53 µl) was added into the reaction mixture. It was stirred for 30 min at rt. The reaction mixture was diluted with ethyl acetate and the reaction was stopped by the addition of water. The layers were separated and the aqueous layer was extracted with ethyl acetate twice. The combined organic layers were washed with brine and dried using a water resistant filter. The clear filtrate was concentrated under reduced pressure.

Yield: 64 mg of the title compound with 92% purity.
LC-MS (Method 4): $R_t$=1.47 min; MS (ESIpos): m/z=571 [M+H]$^+$.
$^1$H-NMR (400 MHz, DMSO-d6): δ [ppm]=0.33-0.41 (m, 2H), 0.55-0.63 (m, 2H), 0.77-0.88 (m, 1H), 1.26-1.33 (m, 3H), 1.38 (s, 9H), 2.24-2.44 (m, 4H), 3.25-3.33 (m, 4H), 3.45 (q, 1H), 4.23 (d, 2H), 6.95 (br d, 1H), 7.17 (br s, 1H), 7.31-7.60 (m, 2H), 7.91 (br s, 1H), 8.14-8.40 (m, 2H), 8.73-8.79 (m, 1H), 10.73 (br s, 1H), 12.29 (br s, 1H).

Example 85.03

1-(4-{(1R or 1S)-1-[2-({6-[6-(cyclopropylmethoxy)pyrimidin-4-yl]-1H-benzimidazol-2-yl}amino)pyridin-4-yl]ethyl}piperazin-1-yl)-3,3,3-trifluoropropan-1-one

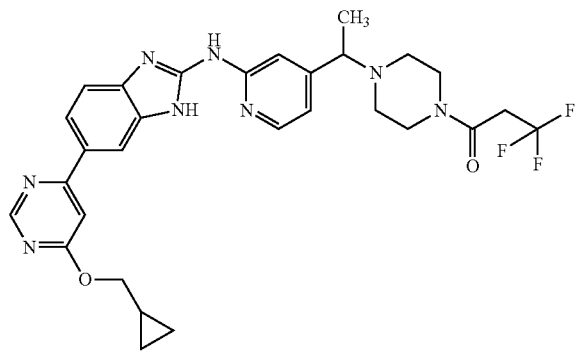 [SMILES: CC(c1ccnc(Nc2nc3ccc(-c4cc(OCC5CC5)ncn4)cc3[nH]2)c1)N1CCN(C(=O)CC(F)(F)F)CC1]

Starting with 6-[6-(cyclopropylmethoxy)pyrimidin-4-yl]-N-{4-[(1R or 1S)-1-(piperazin-1-yl)ethyl]pyridin-2-yl}-1H-benzimidazol-2-amine hydrochloride (184 mg, see Compound 85.03), Example 85.03 was prepared analogously to the procedure for the preparation of Example 39.02.02.

Yield: 18 mg of the 95% pure title compound.

LC-MS (Method 2): $R_t$=1.30 min; MS (ESIpos): m/z=581 [M+H]$^+$.

$^1$H-NMR (400 MHz, DMSO-d6): δ [ppm]=0.34-0.42 (m, 2H), 0.54-0.64 (m, 2H), 1.20-1.36 (m, 4H), 2.29-2.47 (m, 4H), 3.40-3.52 (m, 5H), 3.62 (q, 2H), 4.23 (d, 2H), 6.96 (br s, 1H), 7.17 (br d, 1H), 7.33-7.61 (m, 2H), 7.86-7.96 (m, 1H), 8.16-8.42 (m, 2H), 8.77 (d, 1H), 10.66-10.81 (m, 1H), 12.21-12.33 (m, 1H).

Example 86.01 tert-butyl 4-[(1R or 1S)-1-(2-{[6-(1-{[(1RS)-2,2-difluorocyclopropyl]methyl}-1H-pyrazol-4-yl)-7-fluoro-1H-benzimidazol-2-yl]amino}pyridin-4-yl)ethyl]piperazine-1-carboxylate

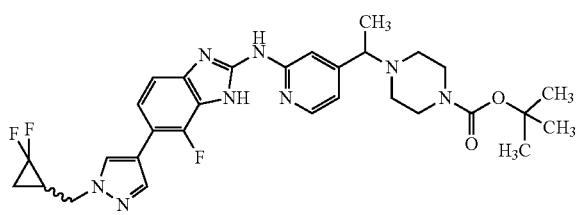 [SMILES: CC(c1ccnc(Nc2nc3ccc(-c4cnn(CC5CC5(F)F)c4)c(F)c3[nH]2)c1)N1CCN(C(=O)OC(C)(C)C)CC1]

Starting with 4-(1-{[(1RS)-2,2-difluorocyclopropyl]methyl}-1H-pyrazol-4-yl)-3-fluorobenzene-1,2-diamine (1.65 g, 90% purity, see Compound 86.01), Example 86.01 was prepared analogously to the procedure for the preparation of Example 39.02.01. The intermediate thiourea was purified by flash chromatography.

Yield: 1.5 g of the 92% pure title compound.

LC-MS (Method 2): $R_t$=1.38 min; MS (ESIpos): m/z=597 [M+H]$^+$.

$^1$H-NMR (400 MHz, DMSO-d6): δ [ppm]=1.28 (d, 3H), 1.38 (s, 9H), 1.46-1.60 (m, 1H), 1.70 (tdd, 1H), 2.19-2.44 (m, 5H), 3.25-3.33 (m, 4H), 3.39-3.50 (m, 1H), 4.21-4.38 (m, 2H), 6.94 (d, 1H), 7.10 (s, 1H), 7.21-7.38 (m, 2H), 7.85-7.95 (m, 1H), 8.14 (d, 1H), 8.26 (d, 1H), 10.79 (s, 1H), 12.29 (s, 1H)

Example 86.02

1-{4-[(1R or 1S)-1-(2-{[6-(1-{[(1RS)-2,2-difluorocyclopropyl]methyl}-1H-pyrazol-4-yl)-7-fluoro-1H-benzimidazol-2-yl]amino}pyridin-4-yl)ethyl]piperazin-1-yl}-3,3,3-trifluoropropan-1-one

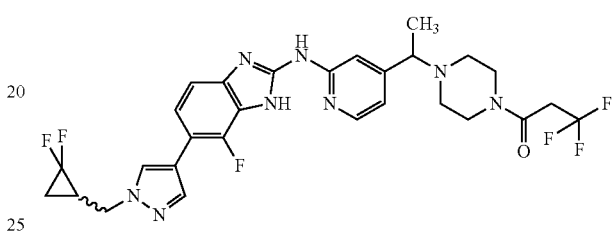

Starting with 6-(1-{[(1RS)-2,2-difluorocyclopropyl]methyl}-1H-pyrazol-4-yl)-7-fluoro-N-{4-[(1R or 1S)-1-(piperazin-1-yl)ethyl]pyridin-2-yl}-1H-benzimidazol-2-amine hydrochloride (250 mg, see Compound 86.02), Example 86.02 was prepared analogously to the procedure for the preparation of Example 39.02.02.

Yield: 74 mg of the 99% pure title compound.

LC-MS (Method 2): $R_t$=1.21 min; MS (ESIpos): m/z=607 [M+H]$^+$.

$^1$H-NMR (400 MHz, DMSO-d6): δ [ppm]=1.30 (br d, 3H), 1.47-1.60 (m, 1H), 1.63-1.78 (m, 1H), 2.22-2.47 (m, 5H), 3.39-3.53 (m, 5H), 3.62 (q, 2H), 4.22-4.40 (m, 2H), 6.96 (d, 1H), 7.11 (s, 1H), 7.23-7.37 (m, 2H), 7.90 (s, 1H), 8.14 (s, 1H), 8.27 (d, 1H), 10.80 (s, 1H), 12.29 (br s, 1H).

Example 86.03 cyclopropyl{4-[(1R or 1S)-1-(2-{[6-(1-{[(1RS)-2,2-difluorocyclopropyl]methyl}-1H-pyrazol-4-yl)-7-fluoro-1H-benzimidazol-2-yl]amino}pyridin-4-yl)ethyl]piperazin-1-yl}methanone

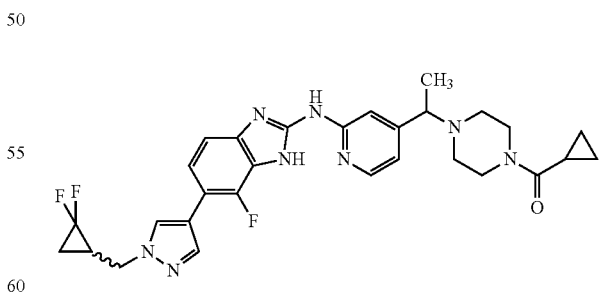

Starting with 7-chloro-6-(1-{[(1RS)-2,2-difluorocyclopropyl]methyl}-1H-pyrazol-4-yl)-N-{4-[(1R or 1S)-1-(piperazin-1-yl)ethyl]pyridin-2-yl}-1H-benzimidazol-2-amine hydrochloride (250 mg, see Compound 86.02), Example 86.03 was prepared analogously to the procedure for the preparation of Example 39.02.03.

Yield: 100 mg of the 96% pure title compound.

LC-MS (Method 2): R$_t$=1.18 min; MS (ESIpos): m/z=565 [M+H]$^+$.

$^1$H-NMR (400 MHz, DMSO-d6): δ [ppm]=0.62-0.76 (m, 4H), 1.30 (d, 3H), 1.48-1.60 (m, 1H), 1.62-1.77 (m, 1H), 1.89-1.98 (m, 1H), 2.20-2.47 (m, 5H), 3.40-3.55 (m, 3H), 3.67 (br s, 2H), 4.22-4.39 (m, 2H), 6.96 (d, 1H), 7.11 (s, 1H), 7.23-7.36 (m, 2H), 7.89 (s, 1H), 8.14 (d, 1H), 8.27 (d, 1H), 10.80 (s, 1H), 12.29 (s, 1H)

Example 87.01

1-(4-{(1R or 1S)-1-[2-({6-[1-(2,2-difluoroethyl)-1H-pyrazol-4-yl]-1H-benzimidazol-2-yl}amino)pyridin-4-yl]ethyl}piperazin-1-yl)-3,3,3-trifluoropropan-1-one

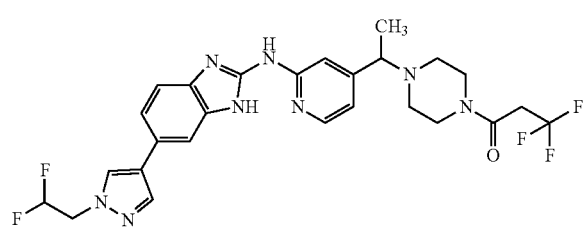 [SMILES: CC(c1ccnc(Nc2nc3ccc(-c4cnn(CC(F)F)c4)cc3[nH]2)c1)N1CCN(C(=O)CC(F)(F)F)CC1]

Starting with 6-[1-(2,2-difluoroethyl)-1H-pyrazol-4-yl]-N-{4-[(1R or 1S)-1-(piperazin-1-yl)ethyl]pyridin-2-yl}-1H-benzimidazol-2-amine hydrochloride (232 mg, see Compound 87.04), Example 87.01 was prepared analogously to the procedure for the preparation of Example 39.02.02.

Yield: 85 mg of the 98% pure title compound.

LC-MS (Method 2): R$_t$=1.11 min; MS (ESIpos): m/z=563 [M+H]$^+$.

$^1$H-NMR (400 MHz, DMSO-d6): δ [ppm]=1.30 (d, 3H), 2.26-2.47 (m, 4H), 3.37-3.52 (m, 5H), 3.56-3.69 (m, 2H), 4.64 (br t, 2H), 6.17-6.58 (m, 1H), 6.93 (dd, 1H), 7.17 (s, 1H), 7.20-7.48 (m, 2H), 7.51-7.68 (m, 1H), 7.85-7.97 (m, 1H), 8.06-8.17 (m, 1H), 8.26 (d, 1H), 10.58 (br s, 1H), 12.05 (br s, 1H).—contains ethyl acetate Example 87.02 cyclopropyl(4-{(1R or 1S)-1-[2-({6-[1-(2,2-difluoroethyl)-1H-pyrazol-4-yl]-1H-benzimidazol-2-yl}amino)pyridin-4-yl]ethyl}piperazin-1-yl)methanone

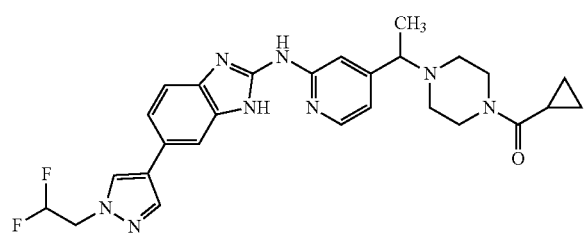 [SMILES: CC(c1ccnc(Nc2nc3ccc(-c4cnn(CC(F)F)c4)cc3[nH]2)c1)N1CCN(C(=O)C2CC2)CC1]

Starting with 6-[1-(2,2-difluoroethyl)-1H-pyrazol-4-yl]-N-{4-[(1R or 1S)-1-(piperazin-1-yl)ethyl]pyridin-2-yl}-1H-benzimidazol-2-amine hydrochloride (232 mg, see Compound 87.04), Example 87.02 was prepared analogously to the procedure for the preparation of Example 39.02.03.

Yield: 73 mg of the 95% pure title compound.

LC-MS (Method 2): R$_t$=1.07 min; MS (ESIpos): m/z=521 [M+H]$^+$.

$^1$H-NMR (400 MHz, DMSO-d6): δ [ppm]=0.59-0.75 (m, 4H), 1.30 (d, 3H), 1.87-1.97 (m, 1H), 2.21-2.47 (m, 4H), 3.39-3.54 (m, 3H), 3.67 (br s, 2H), 4.64 (td, 2H), 6.21-6.59 (m, 1H), 6.94 (dd, 1H), 7.17 (s, 1H), 7.25 (br d, 1H), 7.43 (br s, 1H), 7.51-7.69 (m, 1H), 7.85-7.97 (m, 1H), 8.12 (br s, 1H), 8.26 (d, 1H), 10.58 (br s, 1H), 12.06 (br s, 1H).

Example 88.01 tert-butyl 4-{(1R or 1S)-1-[2-({5-[1-methyl-3-(trifluoromethyl)-1H-pyrazol-5-yl]-1H-benzimidazol-2-yl}amino)pyridin-4-yl]ethyl}piperazine-1-carboxylate

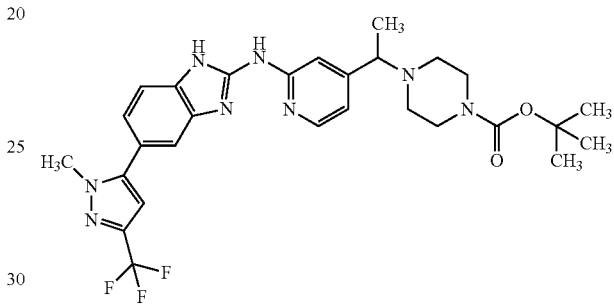

Starting with 4-[1-methyl-3-(trifluoromethyl)-1H-pyrazol-5-yl]benzene-1,2-diamine (590 mg, see Compound 88.01), Example 88.01 was prepared analogously to the procedure for the preparation of Example 39.02.01. The intermediate was purified by flash chromatography.

Yield: 250 mg of the 94% pure title compound.

LC-MS (Method 2): R$_t$=1.44 min; MS (ESIpos): m/z=571 [M+H]$^+$.

$^1$H-NMR (400 MHz, DMSO-d6): δ [ppm]=1.29 (d, 3H), 1.38 (s, 9H), 2.23-2.45 (m, 4H), 3.24-3.33 (m, 4H), 3.45 (q, 1H), 3.94 (s, 3H), 6.83 (br s, 1H), 6.95 (d, 1H), 7.13-7.29 (m, 2H), 7.41-7.71 (m, 2H), 8.28 (d, 1H), 10.70 (br d, 1H), 12.28 (s, 1H).

Example 88.02

3,3,3-trifluoro-1-(4-{(1R or 1S)-1-[2-({6-[1-methyl-3-(trifluoromethyl)-1H-pyrazol-5-yl]-1H-benzimidazol-2-yl}amino)pyridin-4-yl]ethyl}piperazin-1-yl)propan-1-one

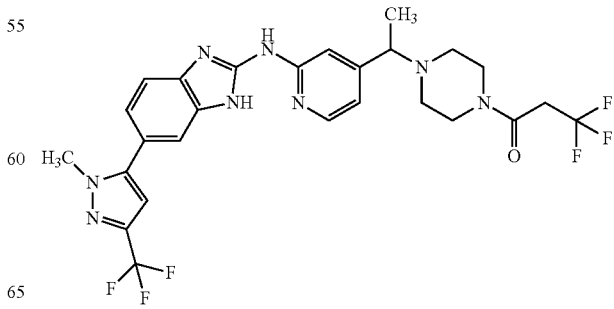

Starting 6-[1-methyl-3-(trifluoromethyl)-1H-pyrazol-5-yl]-N-{4-[(1R or 1S)-1-(piperazin-1-yl)ethyl]pyridin-2-yl}-1H-benzimidazol-2-amine hydrochloride (100 mg, see Compound 88.02), Example 88.02 was prepared analogously to the procedure for the preparation of Example 39.02.02.

Yield: 76 mg of the 95% pure title compound.

LC-MS (Method 2): $R_t$=1.28 min; MS (ESIpos): m/z=581 [M+H]$^+$.

$^1$H-NMR (400 MHz, DMSO-d6): δ [ppm]=1.30 (d, 3H), 2.25-2.47 (m, 4H), 3.38-3.54 (m, 5H), 3.62 (q, 2H), 3.94 (s, 3H), 6.83 (br s, 1H), 6.96 (d, 1H), 7.14-7.29 (m, 2H), 7.41-7.72 (m, 2H), 8.28 (d, 1H), 10.72 (br d, 1H), 12.27 (br s, 1H).—contains ethyl acetate Example 88.03 cyclopropyl(4-{(1R or 1S)-1-[2-({6-[1-methyl-3-(trifluoromethyl)-1H-pyrazol-5-yl]-1H-benzimidazol-2-yl}amino)pyridin-4-yl]ethyl}piperazin-1-yl)methanone

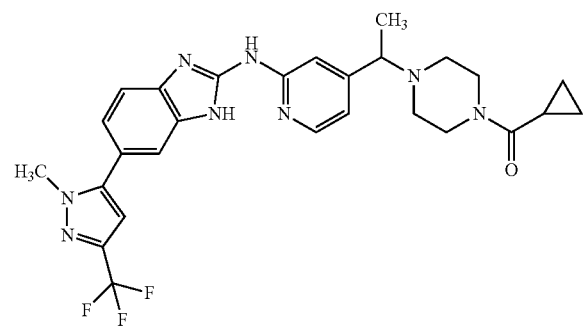 [SMILES: CC(c1ccnc(Nc2nc3ccc(-c4cc(C(F)(F)F)nn4C)cc3[nH]2)c1)N1CCN(C(=O)C2CC2)CC1]

Starting with 6-[1-methyl-3-(trifluoromethyl)-1H-pyrazol-5-yl]-N-{4-[(1R or 1S)-1-(piperazin-1-yl)ethyl]pyridin-2-yl}-1H-benzimidazol-2-amine hydrochloride (100 mg, see Compound 88.02), Example 88.03 was prepared analogously to the procedure for the preparation of Example 39.02.03.

Yield: 40 mg of the 95% pure title compound.

LC-MS (Method 2): $R_t$=1.25 min; MS (ESIpos): m/z=539 [M+H]$^+$.

$^1$H-NMR (400 MHz, DMSO-d6): δ [ppm]=0.59-0.76 (m, 4H), 1.30 (d, 3H), 1.88-1.98 (m, 1H), 2.20-2.45 (m, 4H), 3.38-3.55 (m, 3H), 3.68 (br s, 2H), 3.94 (s, 3H), 6.83 (br s, 1H), 6.97 (d, 1H), 7.14-7.29 (m, 2H), 7.41-7.74 (m, 2H), 8.29 (d, 1H), 10.71 (br d, 1H), 12.28 (br s, 1H).—contains ethyl acetate Example 89.01 tert-butyl 4-[(1R or 1S)-1-(2-{[6-(1,3-dimethyl-1H-pyrazol-5-yl)-1H-benzimidazol-2-yl]amino}pyridin-4-yl)ethyl]piperazine-1-carboxylate

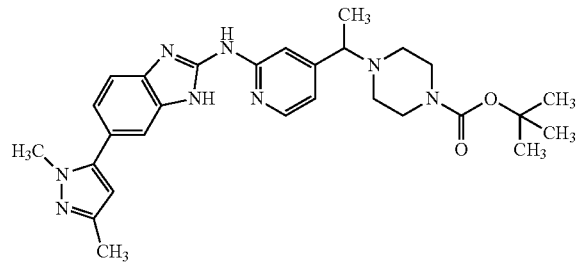 [SMILES: Cc1cc(-c2ccc3nc(Nc4cc(C(C)N5CCN(C(=O)OC(C)(C)C)CC5)ccn4)[nH]c3c2)n(C)n1]

Starting with 4-(1,3-dimethyl-1H-pyrazol-5-yl)benzene-1,2-diamine (350 mg, 95% purity, see Compound 89.01), Example 89.01 was prepared analogously to the procedure for the preparation of Example 39.02.01. The intermediate thiourea was purified by flash chromatography.

Yield: 190 mg of the 95% pure title compound.

LC-MS (Method 2): $R_t$=1.30 min; MS (ESIpos): m/z=517 [M+H]$^+$.

$^1$H-NMR (400 MHz, DMSO-d6): δ [ppm]=1.29 (d, 3H), 1.38 (s, 9H), 2.17 (s, 3H), 2.24-2.44 (m, 4H), 3.24-3.32 (m, 4H), 3.44 (q, 1H), 3.77 (s, 3H), 6.10 (s, 1H), 6.90-6.98 (m, 1H), 7.05-7.21 (m, 2H), 7.39 (br s, 1H), 7.51-7.65 (m, 1H), 8.27 (d, 1H), 10.65 (br d, 1H), 12.20 (br s, 1H).

Example 89.02

1-{4-[(1R or 1S)-1-(2-{[6-(1,3-dimethyl-1H-pyrazol-5-yl)-1H-benzimidazol-2-yl]amino}pyridin-4-yl)ethyl]piperazin-1-yl}-3,3,3-trifluoropropan-1-one

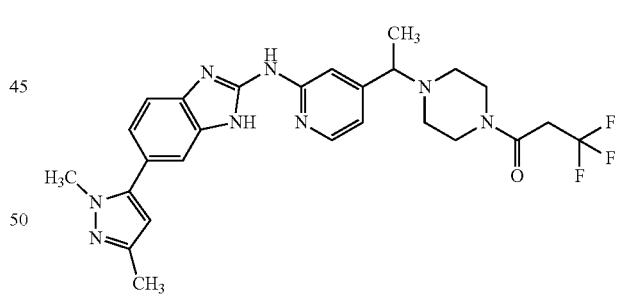

Starting with 6-(1,3-dimethyl-1H-pyrazol-5-yl)-N-{4-[(1R or 1S)-1-(piperazin-1-yl)ethyl]pyridin-2-yl}-1H-benzimidazol-2-amine hydrochloride (82 mg, see Compound 89.02), Example 89.02 was prepared analogously to the procedure for the preparation of Example 39.02.02.

Yield: 54 mg of the 95% pure title compound.

LC-MS (Method 2): $R_t$=1.11 min; MS (ESIpos): m/z=527 [M+H]$^+$.

$^1$H-NMR (400 MHz, DMSO-d6): δ [ppm]=1.30 (d, 3H), 2.17 (s, 3H), 2.28-2.47 (m, 4H), 3.39-3.53 (m, 5H), 3.62 (q, 2H), 3.77 (s, 3H), 6.10 (s, 1H), 6.95 (d, 1H), 7.08-7.21 (m, 2H), 7.33-7.65 (m, 2H), 8.28 (d, 1H), 10.67 (br s, 1H), 12.21 (br s, 1H).

Example 89.03 cyclopropyl{4-[(1R or 1S)-1-(2-{[6-(1,3-dimethyl-1H-pyrazol-5-yl)-1H-benzimidazol-2-yl]amino}pyridin-4-yl)ethyl]piperazin-1-yl}methanone

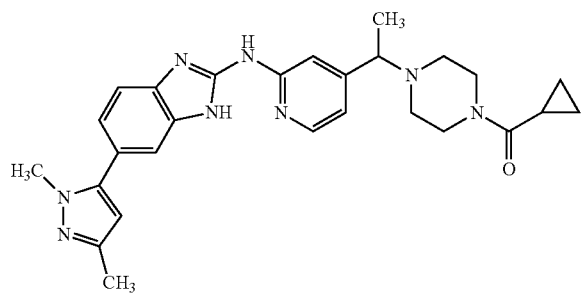 [SMILES: Cc1cc(-c2ccc3nc(Nc4cc(C(C)N5CCN(C(=O)C6CC6)CC5)ccn4)[nH]c3c2)n(C)n1]

Starting with 6-(1,3-dimethyl-1H-pyrazol-5-yl)-N-{4-[(1R or 1S)-1-(piperazin-1-yl)ethyl]pyridin-2-yl}-1H-benzimidazol-2-amine hydrochloride (82 mg, see Compound 89.02), Example 89.03 was prepared analogously to the procedure for the preparation of Example 39.02.03.

Yield: 20 mg of the 92% pure title compound.

LC-MS (Method 2): $R_t$=1.08 min; MS (ESIpos): m/z=485 [M+H]$^+$.

$^1$H-NMR (400 MHz, DMSO-d6): δ [ppm]=0.60-0.75 (m, 4H), 1.30 (d, 3H), 1.88-1.99 (m, 1H), 2.17 (s, 3H), 2.24-2.43 (m, 4H), 3.40-3.53 (m, 3H), 3.68 (br s, 2H), 3.77 (s, 3H), 6.10 (s, 1H), 6.96 (d, 1H), 7.05-7.23 (m, 2H), 7.39 (br s, 1H), 7.51-7.65 (m, 1H), 8.28 (d, 1H), 10.66 (br d, 1H), 12.20 (br s, 1H).

Example 90.01 tert-butyl 4-({2-[(6-{6-[(3-methoxypropyl)amino]pyrimidin-4-yl}-1H-benzimidazol-2-yl)amino]pyridin-4-yl}methyl)piperazine-1-carboxylate

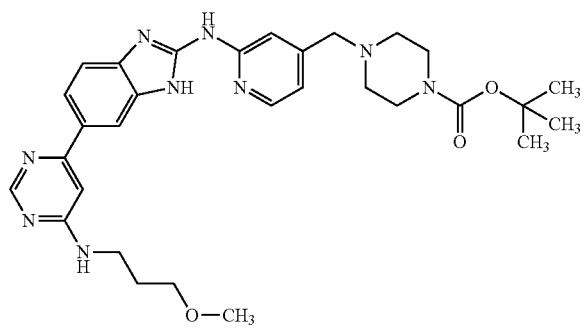 [SMILES: COCCCNc1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (150 mg, see Compound 01.04), Example 90.01 was prepared analogously to the procedure for the preparation of Compound 60.01.

Yield: 92 mg of the title compound with 77% purity.

LC-MS (Method 4): $R_t$=1.23 min; MS (ESIpos): m/z=575 [M+H]$^+$.

$^1$H-NMR (400 MHz, DMSO-d6): δ [ppm]: 1.396 (13.67), 1.773 (0.50), 1.790 (0.72), 1.806 (0.50), 2.327 (0.42), 2.346 (1.07), 2.358 (1.54), 2.369 (1.10), 3.159 (7.95), 3.172 (8.00), 3.221 (0.71), 3.331 (16.00), 3.350 (1.75), 3.394 (1.06), 3.410 (1.66), 3.426 (0.80), 3.499 (1.70), 4.082 (0.72), 4.096 (2.07), 4.109 (2.02), 4.122 (0.67), 5.759 (0.95), 6.922 (0.65), 6.935 (0.56), 8.257 (0.78), 8.270 (0.75), 8.452 (0.65), 10.709 (0.51).

Example 90.02

3,3,3-trifluoro-1-[4-({2-[(6-{6-[(3-methoxypropyl)amino]pyrimidin-4-yl}-1H-benzimidazol-2-yl)amino]pyridin-4-yl}methyl)piperazin-1-yl]propan-1-one

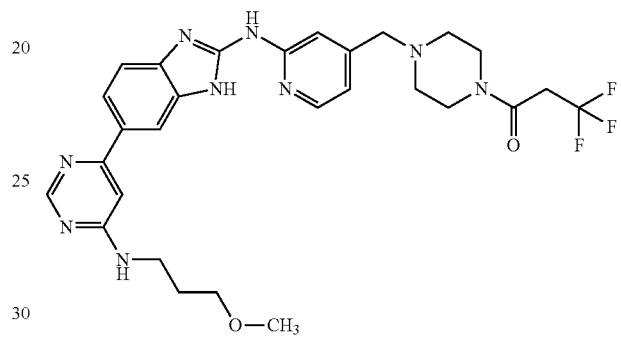

Starting with 6-{6-[(3-methoxypropyl)amino]pyrimidin-4-yl}-N-[4-(piperazin-1-ylmethyl)pyridin-2-yl]-1H-benzimidazol-2-amine hydrochloride (80 mg, see Compound 90.01), Example 90.02 was prepared analogously to the procedure for the preparation of Example 39.02.02.

Yield: 52 mg of the 74% pure title compound.

LC-MS (Method 2): $R_t$=1.02 min; MS (ESIpos): m/z=584 [M+H]$^+$.

$^1$H-NMR (500 MHz, DMSO-d6): δ [ppm]=1.79 (quin, 2H), 2.31-2.46 (m, 4H), 3.25 (s, 3H), 3.35-3.44 (m, 4H), 3.44-3.56 (m, 6H), 3.65 (q, 2H), 6.83-6.98 (m, 2H), 7.18 (br s, 1H), 7.26-7.60 (m, 2H), 7.74 (br s, 1H), 7.91-8.24 (m, 1H), 8.27 (d, 1H), 8.45 (s, 1H), 10.72 (br s, 1H), 12.23 (br s, 1H).

Example 91.01 tert-butyl 4-[(2-{[6-(6-ethylpyrimidin-4-yl)-1H-benzimidazol-2-yl]amino}pyridin-4-yl)methyl]piperazine-1-carboxylate

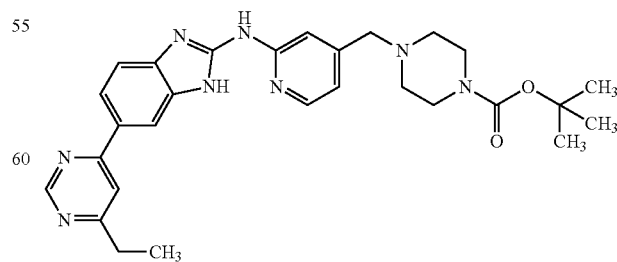

Starting with tert-butyl 4-[(2-{[6-(4,4,5,5-tetramethyl-1,3,2-dioxaborolan-2-yl)-1H-benzimidazol-2-yl]

amino}pyridin-4-yl)methyl]piperazine-1-carboxylate (150 mg, see Compound 01.04), Example 91.01 was prepared analogously to the procedure for the preparation of Compound 60.01.

Yield: 168 mg of the title compound with 78% purity.

LC-MS (Method 2): $R_t$=1.31 min; MS (ESIpos): m/z=516 [M+H]$^+$.

$^1$H-NMR (400 MHz, DMSO-d6): δ [ppm]: 1.109 (0.44), 1.128 (0.89), 1.147 (0.50), 1.274 (1.61), 1.293 (3.33), 1.312 (1.65), 1.363 (0.44), 1.370 (0.57), 1.395 (16.00), 2.358 (2.05), 2.440 (0.43), 2.459 (0.47), 2.763 (0.45), 2.782 (1.29), 2.801 (1.26), 2.819 (0.43), 3.159 (1.28), 3.172 (1.30), 3.333 (6.33), 3.349 (1.75), 3.502 (2.04), 5.758 (8.24), 6.935 (0.53), 6.947 (0.53), 7.181 (1.09), 7.944 (0.50), 7.966 (0.53), 8.237 (0.45), 8.264 (0.90), 8.276 (0.84), 9.047 (1.29).

Example 91.02

1-{4-[(2-{[6-(6-ethylpyrimidin-4-yl)-1H-benzimidazol-2-yl]amino}pyridin-4-yl)methyl]piperazin-1-yl}-3,3,3-trifluoropropan-1-one

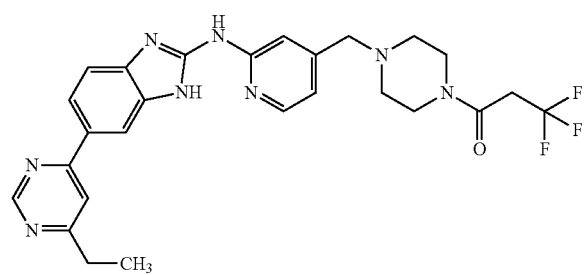 [SMILES: CCc1cc(-c2ccc3nc(Nc4cc(CN5CCN(C(=O)CC(F)(F)F)CC5)ccn4)[nH]c3c2)ncn1]

Starting with 6-(6-ethylpyrimidin-4-yl)-N-[4-(piperazin-1-ylmethyl)pyridin-2-yl]-1H-benzimidazol-2-amine hydrochloride (80 mg, see Compound 91.01), Example 91.02 was prepared analogously to the procedure for the preparation of Example 39.02.02.

Yield: 42 mg of the 79% pure title compound.

LC-MS (Method 4): $R_t$=1.06 min; MS (ESIpos): m/z=525 [M+H]$^+$.

$^1$H-NMR (500 MHz, DMSO-d6): δ [ppm]=1.29 (t, 3H), 2.33-2.46 (m, 4H), 2.79 (q, 2H), 3.42-3.56 (m, 6H), 3.65 (q, 2H), 6.95 (br d, 1H), 7.20 (s, 1H), 7.39-7.67 (m, 1H), 7.82-8.01 (m, 2H), 8.15-8.45 (m, 2H), 9.05 (d, 1H), 10.77 (br s, 1H), 11.62-12.95 (m, 1H).

Example 91.03 cyclopropyl{4-[(2-{[6-(6-ethylpyrimidin-4-yl)-1H-benzimidazol-2-yl]amino}pyridin-4-yl)methyl]piperazin-1-yl}methanone

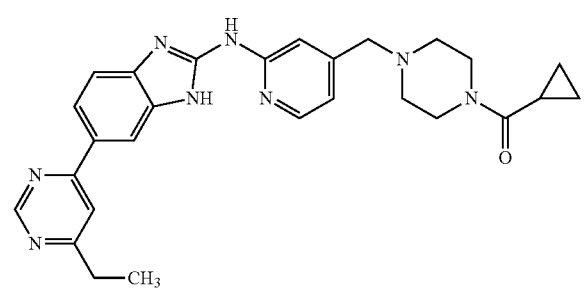

Starting with 6-(6-ethylpyrimidin-4-yl)-N-[4-(piperazin-1-ylmethyl)pyridin-2-yl]-1H-benzimidazol-2-amine hydrochloride (80 mg, see Compound 91.01), Example 91.03 was prepared analogously to the procedure for the preparation of Example 39.02.03.

Yield: 40 mg of the 91% pure title compound.

LC-MS (Method 2): $R_t$=1.06 min; MS (ESIpos): m/z=483 [M+H]$^+$.

$^1$H-NMR (500 MHz, DMSO-d6): δ [ppm]=0.64-0.77 (m, 4H), 1.29 (t, 3H), 1.93-2.03 (m, 1H), 2.31-2.47 (m, 4H), 2.79 (q, 2H), 3.44-3.57 (m, 4H), 3.71 (br s, 2H), 6.96 (br d, 1H), 7.20 (s, 1H), 7.38-7.65 (m, 1H), 7.84-8.02 (m, 2H), 8.19-8.45 (m, 2H), 9.05 (d, 1H), 10.78 (br s, 1H), 12.22-12.40 (m, 1H).

Example 92.01 tert-butyl 4-{[2-({6-[6-(3,5-dimethyl-1,2-oxazol-4-yl)pyrimidin-4-yl]-1H-benzimidazol-2-yl}amino)pyridin-4-yl]methyl}piperazine-1-carboxylate

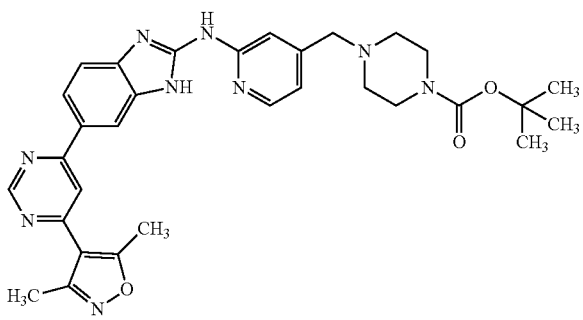 [SMILES: Cc1noc(C)c1-c1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (150 mg, see Compound 01.04 and 4-chloro-6-(3,5-dimethyl-1,2-oxazol-4-yl)pyrimidine, which can be prepared from 4,6-dichloropyrimidine and (3,5-dimethylisoxazol-4-yl)boronic acid, Example 92.01 was prepared analogously to the procedure for the preparation of Compound 60.01.

Yield: 106 mg of the title compound with 84% purity.

LC-MS (Method 2): $R_t$=1.35 min; MS (ESIpos): m/z=582 [M+H]$^+$.

$^1$H-NMR (400 MHz, DMSO-d6): δ [ppm]: 1.365 (0.53), 1.396 (16.00), 2.327 (0.64), 2.363 (2.01), 2.669 (0.65), 2.729 (2.92), 3.159 (3.22), 3.172 (3.35), 3.509 (1.94), 4.095 (0.88), 4.108 (0.85), 6.949 (0.49), 7.193 (0.57), 8.032 (0.59), 8.282 (0.65), 9.214 (0.85).

Example 92.02

1-(4-{[2-({6-[6-(3,5-dimethyl-1,2-oxazol-4-yl)pyrimidin-4-yl]-1H-benzimidazol-2-yl}amino)pyridin-4-yl]methyl}piperazin-1-yl)-3,3,3-trifluoropropan-1-one

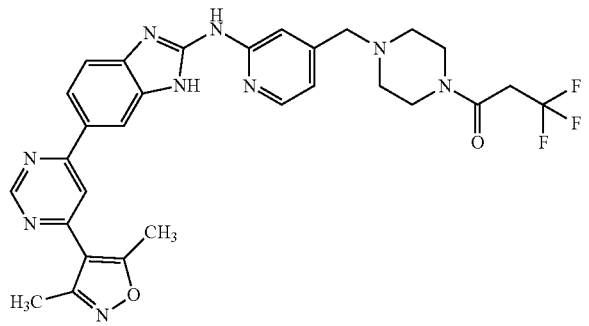 [SMILES: Cc1noc(C)c1-c1cc(-c2ccc3nc(Nc4cc(CN5CCN(C(=O)CC(F)(F)F)CC5)ccn4)[nH]c3c2)ncn1]

Starting with 6-[6-(3,5-dimethyl-1,2-oxazol-4-yl)pyrimidin-4-yl]-N-[4-(piperazin-1-ylmethyl)pyridin-2-yl]-1H-benzimidazol-2-amine hydrochloride (105 mg, see Compound 92.01), Example 92.02 was prepared analogously to the procedure for the preparation of Example 39.02.02.

Yield: 55 mg of the 83% pure title compound.

LC-MS (Method 4): $R_t$=1.14 min; MS (ESIpos): m/z=592 [M+H]$^+$.

$^1$H-NMR (500 MHz, DMSO-d6): δ [ppm]=2.29-2.46 (m, 4H), 2.51 (s, 3H), 2.73 (s, 3H), 3.42-3.56 (m, 6H), 3.65 (q, 2H), 6.96 (br s, 1H), 7.21 (s, 1H), 7.40-7.65 (m, 1H), 7.95-8.14 (m, 2H), 8.22-8.51 (m, 2H), 9.21 (s, 1H), 10.65-10.89 (m, 1H), 12.33 (br s, 1H).

Example 93.01

3,3,3-trifluoro-1-(4-{[2-({6-[6-(pyrrolidin-1-yl)pyrimidin-4-yl]-1H-benzimidazol-2-yl}amino)pyridin-4-yl]methyl}piperazin-1-yl)propan-1-one

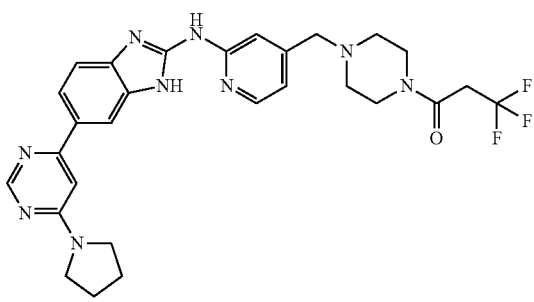 [SMILES: O=C(CC(F)(F)F)N1CCN(Cc2ccnc(Nc3nc4ccc(-c5cc(N6CCCC6)ncn5)cc4[nH]3)c2)CC1]

Starting with N-[4-(piperazin-1-ylmethyl)pyridin-2-yl]-6-[6-(pyrrolidin-1-yl)pyrimidin-4-yl]-1H-benzimidazol-2-amine hydrochloride (100 mg, see Compound 93.02), Example 93.01 was prepared analogously to the procedure for the preparation of Example 39.02.02.

Yield: 33 mg of the 79% pure title compound.

LC-MS (Method 4): $R_t$=1.11 min; MS (ESIpos): m/z=566 [M+H]$^+$.

$^1$H-NMR (400 MHz, DMSO-d6): δ [ppm]=1.85-2.10 (m, 4H), 2.34-2.46 (m, 4H), 3.36-3.58 (m, 10H), 3.65 (q, 2H), 6.79-6.99 (m, 2H), 7.20 (s, 1H), 7.35-7.61 (m, 1H), 7.87 (br d, 1H), 8.07-8.35 (m, 2H), 8.50 (s, 1H), 10.71 (br s, 1H), 12.24 (d, 1H).

Example 94.01

3,3,3-trifluoro-1-(4-{[2-({6-[6-(morpholin-4-yl)pyrimidin-4-yl]-1H-benzimidazol-2-yl}amino)pyridin-4-yl]methyl}piperazin-1-yl)propan-1-one

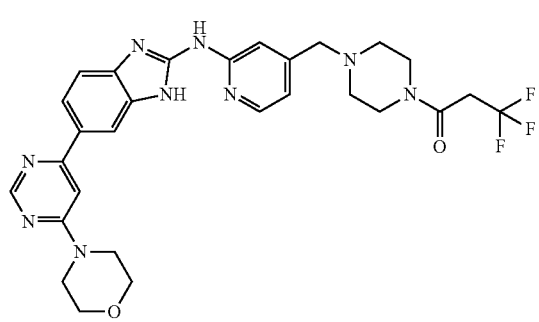 [SMILES: O=C(CC(F)(F)F)N1CCN(Cc2ccnc(Nc3nc4ccc(-c5cc(N6CCOCC6)ncn5)cc4[nH]3)c2)CC1]

Starting with 6-[6-(morpholin-4-yl)pyrimidin-4-yl]-N-[4-(piperazin-1-ylmethyl)pyridin-2-yl]-1H-benzimidazol-2-amine hydrochloride (140 mg, see Compound 94.02), Example 94.01 was prepared analogously to the procedure for the preparation of Example 39.02.02.

Yield: 38 mg of the 77% pure title compound.

LC-MS (Method 4): $R_t$=1.02 min; MS (ESIpos): m/z=582 [M+H]$^+$.

$^1$H-NMR (400 MHz, DMSO-d6): δ [ppm]=2.35-2.45 (m, 4H), 3.43-3.56 (m, 6H), 3.59-3.75 (m, 10H), 6.94 (br d, 1H), 7.20 (s, 1H), 7.23-7.60 (m, 2H), 7.91 (br d, 1H), 8.16-8.38 (m, 2H), 8.57 (s, 1H), 10.73 (br s, 1H), 12.23 (br d, 1H).

Example 95.01

3,3,3-trifluoro-1-(4-{[2-({6-[6-(methylsulfanyl)pyrimidin-4-yl]-1H-benzimidazol-2-yl}amino)pyridin-4-yl]methyl}piperazin-1-yl)propan-1-one

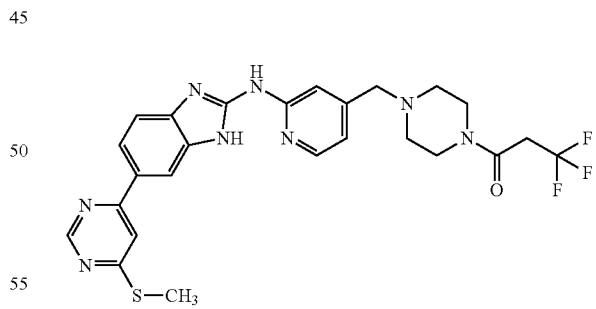

Starting with 6-[6-(methylsulfanyl)pyrimidin-4-yl]-N-[4-(piperazin-1-ylmethyl)pyridin-2-yl]-1H-benzimidazol-2-amine hydrochloride (100 mg, see Compound 95.02), Example 95.01 was prepared analogously to the procedure for the preparation of Example 39.02.02.

Yield: 9 mg of the 86% pure title compound.

LC-MS (Method 4): $R_t$=1.13 min; MS (ESIpos): m/z=543 [M+H]$^+$.

$^1$H-NMR (400 MHz, DMSO-d6): δ [ppm]=2.29-2.46 (m, 4H), 2.61 (s, 3H), 3.41-3.57 (m, 6H), 3.65 (q, 2H), 6.95 (br d, 1H), 7.20 (s, 1H), 7.37-7.65 (m, 1H), 7.79-8.01 (m, 2H), 8.18-8.45 (m, 2H), 8.92 (s, 1H), 10.79 (br s, 1H), 12.13-12.45 (m, 1H).

Example 95.02 cyclopropyl(4-{[2-({6-[6-(methylsulfanyl)pyrimidin-4-yl]-1H-benzimidazol-2-yl}amino)pyridin-4-yl]methyl}piperazin-1-yl)methanone

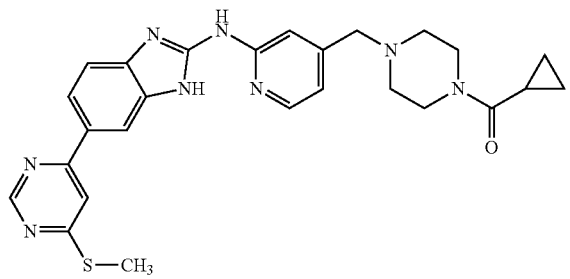

Starting with 6-[6-(methylsulfanyl)pyrimidin-4-yl]-N-[4-(piperazin-1-ylmethyl)pyridin-2-yl]-1H-benzimidazol-2-amine hydrochloride (100 mg, see Compound 95.02), Example 95.02 was prepared analogously to the procedure for the preparation of Example 39.02.03.

Yield: 6 mg of the 52% pure title compound.

LC-MS (Method 4): $R_t$=1.09 min; MS (ESIpos): m/z=501 [M+H]$^+$.

$^1$H-NMR (500 MHz, DMSO-d6): δ [ppm]=0.57-0.82 (m, 4H), 1.88-2.01 (m, 1H), 2.28-2.47 (m, 4H), 2.61 (s, 3H), 3.42-3.58 (m, 4H), 3.71 (br s, 2H), 6.89-7.00 (m, 1H), 7.22 (s, 1H), 7.36-7.70 (m, 1H), 7.82-8.03 (m, 2H), 8.19-8.42 (m, 2H), 8.92 (d, 1H), 10.78 (br s, 1H), 12.32 (br s, 1H).

Example 96.01 tert-butyl 4-{[2-({6-[6-(2-hydroxypropan-2-yl)pyrimidin-4-yl]-1H-benzimidazol-2-yl}amino)pyridin-4-yl]methyl}piperazine-1-carboxylate

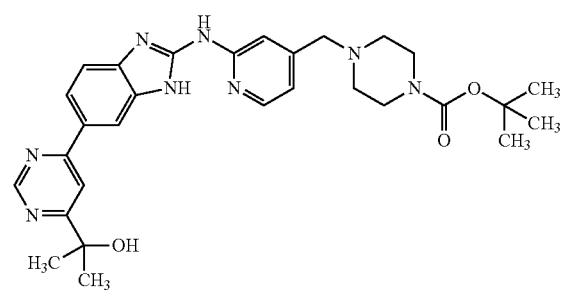 [SMILES: CC(C)(C)OC(=O)N1CCN(Cc2ccnc(Nc3nc4ccc(-c5cc(C(C)(C)O)ncn5)cc4[nH]3)c2)CC1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (186 mg, see Compound 01.04), Example 96.01 was prepared analogously to the procedure for the preparation of Compound 60.01.

Yield: 117 mg of the title compound with 90% purity.

LC-MS (Method 2): $R_t$=1.21 min; MS (ESIpos): m/z=546 [M+H]$^+$.

$^1$H-NMR (500 MHz, DMSO-d6): δ [ppm]=1.40 (s, 9H), 1.46-1.52 (m, 6H), 2.36 (br t, 4H), 3.35 (br s, 4H), 3.50 (s, 2H), 5.49 (br s, 1H), 6.95 (br d, 1H), 7.17 (s, 1H), 7.36-7.64 (m, 1H), 7.85-8.02 (m, 1H), 8.11-8.45 (m, 3H), 9.08 (s, 1H), 10.80 (br s, 1H), 12.22-12.43 (m, 1H).

Example 96.02

3,3,3-trifluoro-1-(4-{[2-({6-[6-(2-hydroxypropan-2-yl)pyrimidin-4-yl]-1H-benzimidazol-2-yl}amino)pyridin-4-yl]methyl}piperazin-1-yl)propan-1-one

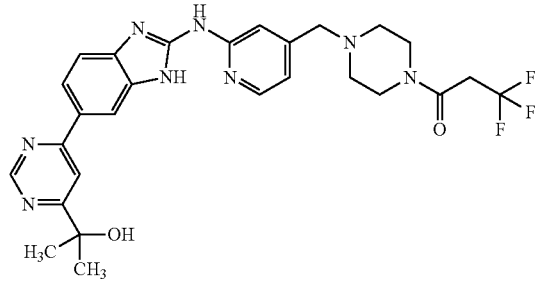 [SMILES: CC(C)(O)c1cc(-c2ccc3nc(Nc4cc(CN5CCN(C(=O)CC(F)(F)F)CC5)ccn4)[nH]c3c2)ncn1]

Starting with 2-[6-(2-{[4-(piperazin-1-ylmethyl)pyridin-2-yl]amino}-1H-benzimidazol-6-yl)pyrimidin-4-yl]propan-2-ol hydrochloride (115 mg, see Compound 96.02), Example 96.02 was prepared analogously to the procedure for the preparation of Example 39.02.02.

Yield: 60 mg of the 83% pure title compound.

LC-MS (Method 4): $R_t$=1.00 min; MS (ESIpos): m/z=555 [M+H]$^+$.

$^1$H-NMR (400 MHz, DMSO-d6): δ [ppm]=1.48 (s, 6H), 2.40 (dt, 4H), 3.44-3.58 (m, 6H), 3.65 (q, 2H), 5.49 (s, 1H), 6.96 (br d, 1H), 7.18 (s, 1H), 7.39-7.67 (m, 1H), 7.86-8.02 (m, 1H), 8.11-8.44 (m, 3H), 9.08 (s, 1H), 10.80 (br s, 1H), 12.32 (br s, 1H).

Example 97.01

(rac)-tert-butyl 4-({2-[(6-{6-[1-hydroxyethyl]pyrimidin-4-yl}-1H-benzimidazol-2-yl)amino]pyridin-4-yl}methyl)piperazine-1-carboxylate

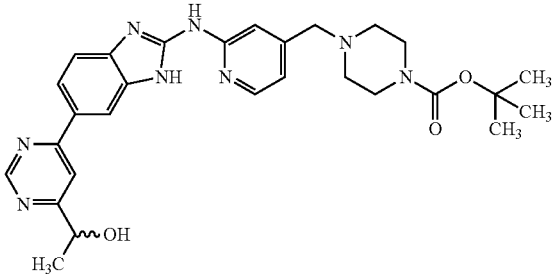 [SMILES: CC(O)c1cc(-c2ccc3nc(Nc4cc(CN5CCN(C(=O)OC(C)(C)C)CC5)ccn4)[nH]c3c2)ncn1]

Starting with tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (200 mg, see Compound 01.04), Example 97.01 was prepared analogously to the procedure for the preparation of Compound 60.01.

Yield: 142 mg of the title compound with 96% purity.

LC-MS (Method 2): $R_t$=1.14 min; MS (ESIpos): m/z=532 [M+H]$^+$.

$^1$H-NMR (400 MHz, DMSO-d6): δ [ppm]=1.40 (s, 9H), 1.43 (d, 3H), 2.30-2.42 (m, 4H), 3.35 (br s, 4H), 3.50 (s, 2H), 4.66-4.78 (m, 1H), 5.64 (br s, 1H), 6.95 (br d, 1H), 7.17 (s, 1H), 7.39-7.66 (m, 1H), 7.87-8.11 (m, 2H), 8.13-8.44 (m, 2H), 9.06 (s, 1H), 10.80 (br s, 1H), 12.35 (br s, 1H).

Example 97.02

(rac)-3,3,3-trifluoro-1-[4-({2-[(6-{6-[1-hydroxy-ethyl]pyrimidin-4-yl}-1H-benzimidazol-2-yl)amino]pyridin-4-yl}methyl)piperazin-1-yl]propan-1-one

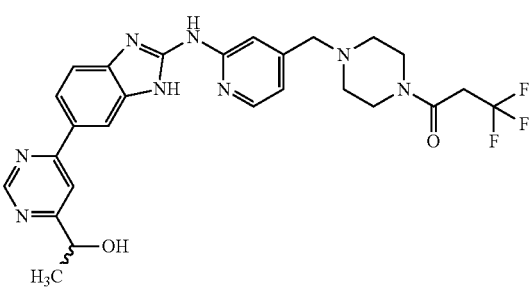 [SMILES: CC(O)c1cc(-c2ccc3nc(Nc4cc(CN5CCN(C(=O)CC(F)(F)F)CC5)ccn4)[nH]c3c2)ncn1]

Starting with (rac)-1-[6-(2-{[4-(piperazin-1-ylmethyl)pyridin-2-yl]amino}-1H-benzimidazol-6-yl)pyrimidin-4-yl]ethanol hydrochloride (155 mg, Compound 97.02), Example 95.02 was prepared analogously to the procedure for the preparation of Example 39.02.02.

Yield: 48 mg of the 99% pure title compound.

LC-MS (Method 2): $R_t$=0.95 min; MS (ESIpos): m/z=541 [M+H]$^+$.

$^1$H-NMR (400 MHz, DMSO-d6): ([ppm]=1.43 (d, 3H), 2.35-2.46 (m, 4H), 3.43-3.58 (m, 6H), 3.65 (q, 2H), 4.67-4.79 (m, 1H), 5.64 (br s, 1H), 6.96 (d, 1H), 7.18 (s, 1H), 7.38-7.70 (m, 1H), 7.95 (br s, 1H), 8.05 (br s, 1H), 8.12-8.46 (m, 2H), 9.06 (s, 1H), 10.72-10.89 (m, 1H), 12.34 (br s, 1H).

Example 97.03

1-{4-[(2-{[6-(6-acetylpyrimidin-4-yl)-1H-benzimidazol-2-yl]amino}pyridin-4-yl)methyl]piperazin-1-yl}-3,3,3-trifluoropropan-1-one

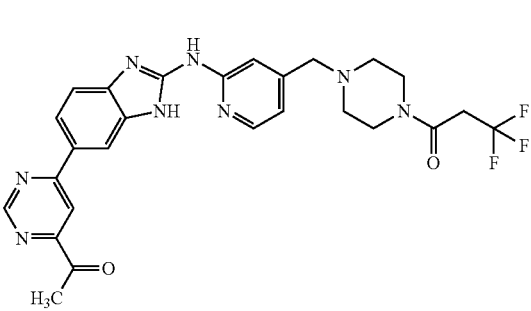 [SMILES: CC(=O)c1cc(-c2ccc3nc(Nc4cc(CN5CCN(C(=O)CC(F)(F)F)CC5)ccn4)[nH]c3c2)ncn1]

As side product Example 97.03 was isolated from the previous reaction Example 97.02.

Yield: 40 mg of the 99% pure title compound.

LC-MS (Method 2): $R_t$=1.10 min; MS (ESIpos): m/z=539 [M+H]$^+$.

$^1$H-NMR (400 MHz, DMSO-d6): δ [ppm]=2.34-2.46 (m, 4H), 2.69 (s, 3H), 3.42-3.58 (m, 6H), 3.65 (q, 2H), 6.96 (br d, 1H), 7.19 (s, 1H), 7.37-7.70 (m, 1H), 8.05 (br d, 1H), 8.23-8.56 (m, 3H), 9.36 (s, 1H), 10.85 (br s, 1H), 12.38 (br s, 1H).

Example 98.01 tert-butyl 4-[(1R or 1S)-1-(2-{[7-chloro-6-(6-methylpyrimidin-4-yl)-1H-benzimidazol-2-yl]amino}pyridin-4-yl)ethyl]piperazine-1-carboxylate

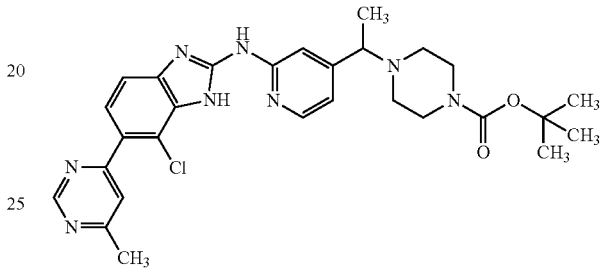

Starting with 3-chloro-4-(6-methylpyrimidin-4-yl)benzene-1,2-diamine (390 mg, see Compound 98.02), Example 98.01 was prepared analogously to the procedure for the preparation of Example 39.02.01.

Yield: 249 mg of the title compound with 91% purity.

LC-MS (Method 2): $R_t$=1.31 min; MS (ESIpos): m/z=549 [M+H]$^+$.

$^1$H-NMR (400 MHz, DMSO-d6): δ [ppm]=1.29 (d, 3H), 1.38 (s, 9H), 2.22-2.45 (m, 4H), 2.54 (s, 3H), 3.24-3.33 (m, 4H), 3.46 (q, 1H), 6.97 (br d, 1H), 7.11 (s, 1H), 7.31 (d, 1H), 7.52-7.61 (m, 1H), 7.74 (s, 1H), 8.29 (d, 1H), 8.96-9.17 (m, 1H), 11.06 (s, 1H), 12.48 (s, 1H).

Example 98.02

1-{4-[(1R or 1S)-1-(2-{[7-chloro-6-(6-methylpyrimidin-4-yl)-1H-benzimidazol-2-yl]amino}pyridin-4-yl)ethyl]piperazin-1-yl}-3,3,3-trifluoropropan-1-one

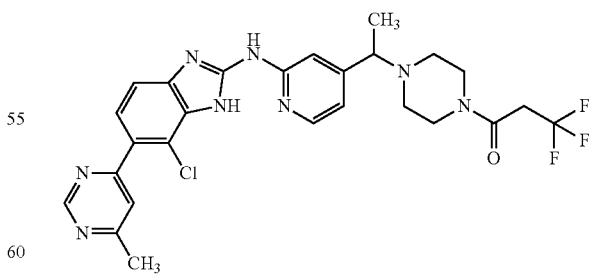

Starting with 7-chloro-6-(6-methylpyrimidin-4-yl)-N-{4-[(1R or 1S)-1-(piperazin-1-yl)ethyl]pyridin-2-yl}-1H-benzimidazol-2-amine hydrochloride (135 mg, see Compound 98.03), Example 98.02 was prepared analogously to the procedure for the preparation of Example 39.02.02.

Yield: 85 mg of the 85% pure title compound.

LC-MS (Method 4): $R_t$=1.08 min; MS (ESIpos): m/z=559 [M+H]$^+$.

$^1$H-NMR (400 MHz, DMSO-d6): δ [ppm]=1.30 (d, 3H), 2.26-2.47 (m, 4H), 2.54 (s, 3H), 3.38-3.53 (m, 5H), 3.62 (q, 2H), 6.99 (d, 1H), 7.11 (s, 1H), 7.31 (d, 1H), 7.57 (d, 1H), 7.74 (s, 1H), 8.30 (d, 1H), 9.12 (d, 1H), 11.08 (s, 1H), 12.48 (br s, 1H).

Example 98.03

{4-[(1R or 1S)-1-(2-{[7-chloro-6-(6-methylpyrimidin-4-yl)-1H-benzimidazol-2-yl]amino}pyridin-4-yl)ethyl]piperazin-1-yl}(cyclopropyl)methanone

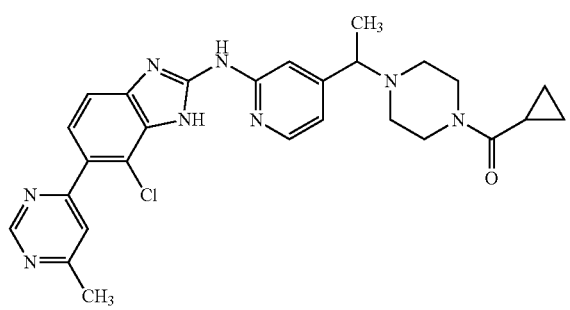 [SMILES: Cc1cc(-c2ccc3nc(Nc4cc(C(C)N5CCN(C(=O)C6CC6)CC5)ccn4)[nH]c3c2Cl)ncn1]

Starting with 7-chloro-6-(6-methylpyrimidin-4-yl)-N-{4-[(1R or 1S)-1-(piperazin-1-yl)ethyl]pyridin-2-yl}-1H-benzimidazol-2-amine hydrochloride (135 mg, see Compound 98.03), Example 98.03 was prepared analogously to the procedure for the preparation of Example 39.02.03.

Yield: 85 mg of the 98% pure title compound.

LC-MS (Method 4): $R_t$=1.04 min; MS (ESIpos): m/z=517 [M+H]$^+$.

$^1$H-NMR (400 MHz, DMSO-d6): δ [ppm]=0.62-0.76 (m, 4H), 1.30 (d, 3H), 1.89-2.00 (m, 1H), 2.25-2.45 (m, 4H), 2.54 (s, 3H), 3.47 (br d, 3H), 3.68 (br s, 2H), 6.99 (d, 1H), 7.12 (br s, 1H), 7.31 (br d, 1H), 7.56 (br d, 1H), 7.74 (d, 1H), 8.30 (d, 1H), 9.12 (d, 1H), 11.06 (br s, 1H), 12.49 (br s, 1H).

Example 99.01

1-(4-{(1R or 1S)-1-[2-({7-chloro-6-[6-(methoxymethyl)pyrimidin-4-yl]-1H-benzimidazol-2-yl}amino)pyridin-4-yl]ethyl}piperazin-1-yl)-3,3,3-trifluoropropan-1-one

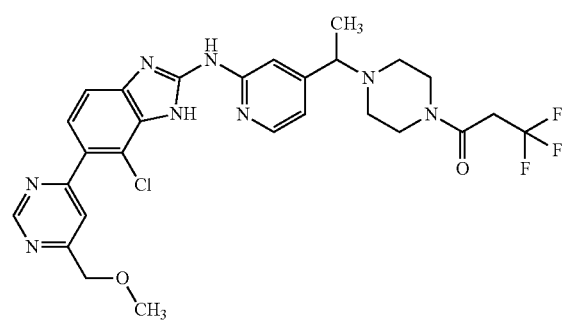 [SMILES: COCc1cc(-c2ccc3nc(Nc4cc(C(C)N5CCN(C(=O)CC(F)(F)F)CC5)ccn4)[nH]c3c2Cl)ncn1]

Starting with 7-chloro-6-[6-(methoxymethyl)pyrimidin-4-yl]-N-{4-[(1R or 1S)-1-(piperazin-1-yl)ethyl]pyridin-2-yl}-1H-benzimidazol-2-amine hydrochloride (150 mg, see Compound 99.03), Example 99.01 was prepared analogously to the procedure for the preparation of Example 39.02.02.

Yield: 22 mg of the 77% pure title compound.

LC-MS (Method 4): $R_t$=1.09 min; MS (ESIpos): m/z=589 [M+H]$^+$.

$^1$H-NMR (400 MHz, DMSO-d6): δ [ppm]=1.30 (br d, 3H), 2.25-2.46 (m, 4H), 3.38-3.55 (m, 8H), 3.62 (q, 2H), 4.60 (s, 2H), 6.99 (br d, 1H), 7.10 (s, 1H), 7.37 (d, 1H), 7.59 (d, 1H), 7.84 (s, 1H), 8.30 (d, 1H), 9.21 (d, 1H), 11.10 (s, 1H), 12.51 (brs, 1H).

Example 100.01

1-(4-{(1R or 1S)-1-[2-({6-[6-(dimethylamino)pyrimidin-4-yl]-1H-benzimidazol-2-yl}amino)pyridin-4-yl]ethyl}piperazin-1-yl)-3,3,3-trifluoropropan-1-one

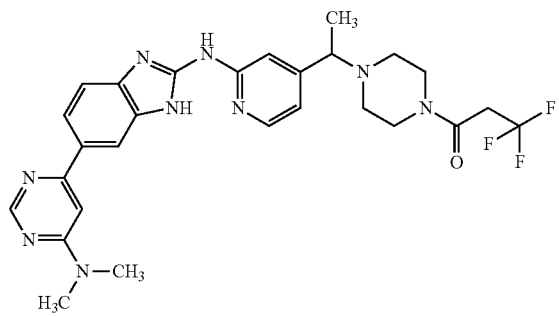 [SMILES: CC(c1ccnc(Nc2nc3ccc(-c4cc(N(C)C)ncn4)cc3[nH]2)c1)N1CCN(C(=O)CC(F)(F)F)CC1]

Starting with 6-[6-(dimethylamino)pyrimidin-4-yl]-N-{4-[(1R or 1S)-1-(piperazin-1-yl)ethyl]pyridin-2-yl}-1H-benzimidazol-2-amine hydrochloride (105 mg, see Compound 100.02), Example 100.01 was prepared analogously to the procedure for the preparation of Example 39.02.02.

Yield: 64 mg of the 90% pure title compound.

LC-MS (Method 2): $R_t$=1.10 min; MS (ESIpos): m/z=554 [M+H]$^+$.

$^1$H-NMR (400 MHz, DMSO-d6): δ [ppm]=1.30 (d, 3H), 2.28-2.47 (m, 4H), 3.15 (s, 6H), 3.39-3.53 (m, 5H), 3.56-3.69 (m, 2H), 6.95 (d, 1H), 7.00-7.14 (m, 1H), 7.18 (s, 1H), 7.34-7.59 (m, 1H), 7.89 (br s, 1H), 8.11-8.35 (m, 2H), 8.52 (d, 1H), 10.71 (br s, 1H), 12.23 (br d, 1H).—contains ethyl acetate

Example 100.03 cyclopropyl(4-{(1R or 1S)-1-[2-({6-[6-(dimethyl-amino)pyrimidin-4-yl]-1H-benzimidazol-2-yl}amino)pyridin-4-yl]ethyl}piperazin-1-yl)methanone

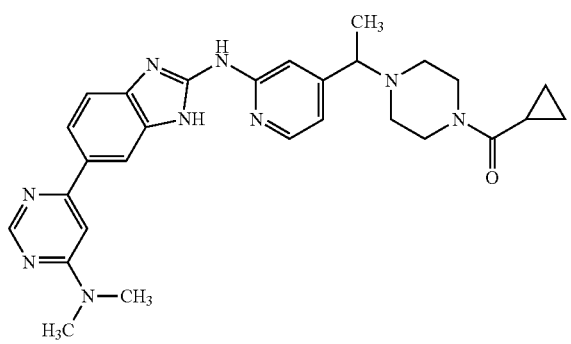 [SMILES: CC(c1ccnc(Nc2nc3ccc(-c4cc(N(C)C)ncn4)cc3[nH]2)c1)N1CCN(C(=O)C2CC2)CC1]

6-[6-(Dimethylamino)pyrimidin-4-yl]-N-{4-[(1R or 1S)-1-(piperazin-1-yl)ethyl]pyridin-2-yl}-1H-benzimidazol-2-amine hydrochloride (150 mg, see Compound 100.02), cyclopropanecarboxylic acid (32 µl), NaHCO₃ (137 mg) and HATU (155 mg) were stirred in DMF (2.7 ml) for 2 h at rt. The reaction mixture was diluted with water and extracted three times with EtOAc. The combined organic layers were washed with brine, dried (silicone filter) and evaporated under reduced pressure. The crude mixture was purified by flash chromatography on silica gel to give 86.5 mg (100% purity) of the title compound.

LC-MS (Method 2): $R_t$=1.04 min; MS (ESIpos): m/z=512 [M+H]⁺. ¹H NMR (400 MHz, DMSO-d6) δ ppm 0.64-0.73 (m, 4H) 1.30 (d, J=6.84 Hz, 3H) 1.90-1.97 (m, 1H) 2.24-2.45 (m, 4H) 3.15 (s, 6H) 3.41-3.53 (m, 3H) 3.67 (br s, 2H) 6.96 (d, J=5.07 Hz, 1H) 7.03-7.14 (m, 1H) 7.18 (s, 1H) 7.35-7.57 (m, 1H) 7.89 (br s, 1H) 8.16 (br s, 0.5H) 8.27 (d, J=5.32 Hz, 1H) 8.31 (br s, 0.5H) 8.52 (d, J=1.01 Hz, 1H) 10.71 (br s, 1H) 12.23 (br d, J=16.98 Hz, 1H)

Example 100.04

(4-{(1R or 1S)-1-[2-({6-[6-(dimethylamino)pyrimidin-4-yl]-1H-benzimidazol-2-yl}amino)pyridin-4-yl]ethyl}piperazin-1-yl)[1-(trifluoromethyl)cyclopropyl]methanone

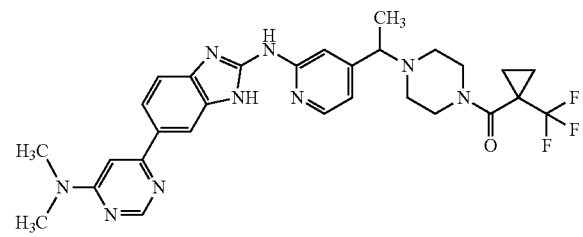 [SMILES: CC(c1ccnc(Nc2nc3ccc(-c4cc(N(C)C)ncn4)cc3[nH]2)c1)N1CCN(C(=O)C2(C(F)(F)F)CC2)CC1]

A mixture of 6-[6-(dimethylamino)pyrimidin-4-yl]-N-{4-[(1R or 1S)-1-(piperazin-1-yl)ethyl]pyridin-2-yl}-1H-benzimidazol-2-amine hydrochloride (190 mg, see Compound 100.02), 1-(trifluoromethyl)cyclopropanecarboxylic acid (159 mg), solid NaHCO₃ (173 mg) and HATU (392 mg) was stirred in DMF (2.1 ml) overnight at rt. The crude mixture was purified by flash chromatography on silica gel to give 40.3 mg (95% purity) of the title compound.

LC-MS (Method 2): $R_t$=1.15 min; MS (ESIpos): m/z=580 [M+H]⁺.

¹H-NMR (400 MHz, DMSO-d6): δ [ppm]=1.16 (br s, 2H), 1.21-1.35 (m, 5H), 2.26-2.48 (m, 4H), 3.06-3.20 (m, 6H), 3.45 (q, 1H), 3.56 (br s, 4H), 6.96 (dd, 1H), 7.07 (s, 1H), 7.18 (s, 1H), 7.36-7.66 (m, 2H), 7.89 (dd, 1H), 8.16-8.33 (m, 2H), 8.52 (d, 1H), 10.71 (br s, 1H), 12.23 (br s, 1H).

Example 101.01

4-[(2-{[6-(3-methyl-1,2,4-oxadiazol-5-yl)-1H-benzimidazol-2-yl]amino}pyridin-4-yl)methyl]piperazine-1-carbaldehyde

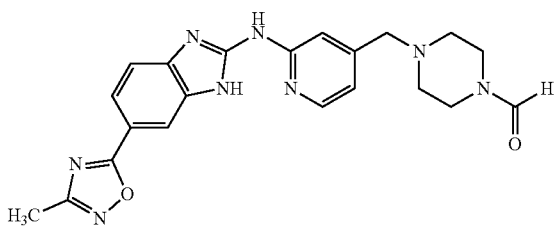 [SMILES: Cc1noc(-c2ccc3nc(Nc4cc(CN5CCN(C=O)CC5)ccn4)[nH]c3c2)n1]

To a mixture of piperazine-1-carbaldehyde (34 mg) in 2 mL DMF was added N-[4-(chloromethyl)pyridin-2-yl]-6-(3-methyl-1,2,4-oxadiazol-5-yl)-1H-benzimidazol-2-amine (51 mg) (see Compound 16.30) in 1 mL DMF. Potassium carbonate was added (104 mg) and the resulting mixture was heated to 40° C. for 16 h.

The precipitate was filtered off. The remaining solution was subjected to standard reversed-phase preparative HPLC purification to give 4 mg of the title compound.

LC-MS (UPLC-MS Method 7): $R_t$=0.64 min; MS (ESIpos): m/z=419 [M+H]⁺.

The examples in the following table 9 were prepared in analogy to example 101.01. UPLC-MS Method 7 was used for determination of retention times and LC-S m/z.

TABLE 9

| Example | Structure | IUPAC Name | Retention time [min] | LC-MS m/z [M + H]+ |
|---|---|---|---|---|
| 101.02 | 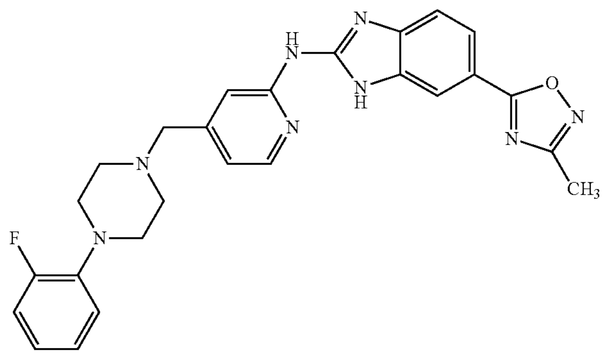 [SMILES: Cc1noc(-c2ccc3nc(Nc4cc(CN5CCN(c6ccccc6F)CC5)ccn4)[nH]c3c2)n1] | N-(4-{[4-(2-fluorophenyl)piperazin-1-yl]methyl}pyridin-2-yl)-6-(3-methyl-1,2,4-oxadiazol-5-yl)-1H-benzimidazol-2-amine | 0.81 | 485 |
| 101.03 | 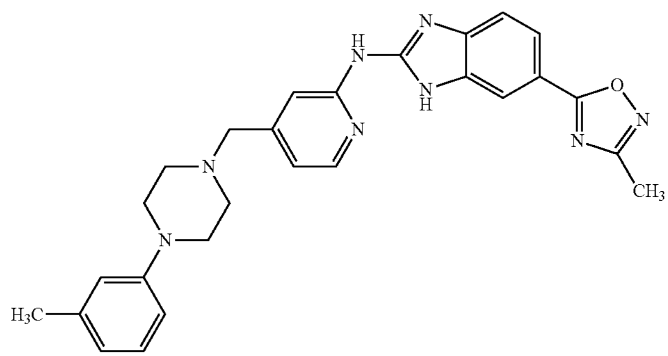 [SMILES: Cc1cccc(N2CCN(Cc3ccnc(Nc4nc5ccc(-c6nc(C)no6)cc5[nH]4)c3)CC2)c1] | 6-(3-methyl-1,2,4-oxadiazol-5-yl)-N-(4-{[4-(3-methylphenyl)piperazin-1-yl]methyl}pyridin-2-yl)-1H-benzimidazol-2-amine | 0.84 | 481 |
| 101.04 | 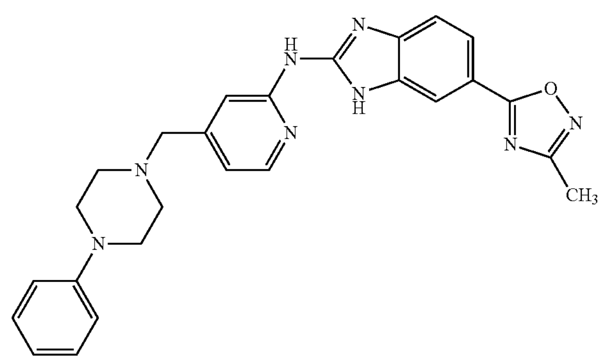 | 6-(3-methyl-1,2,4-oxadiazol-5-yl)-N-{4-[(4-phenylpiperazin-1-yl)methyl]pyridin-2-yl}-1H-benzimidazol-2-amine | 0.79 | 467 |
| 101.05 | 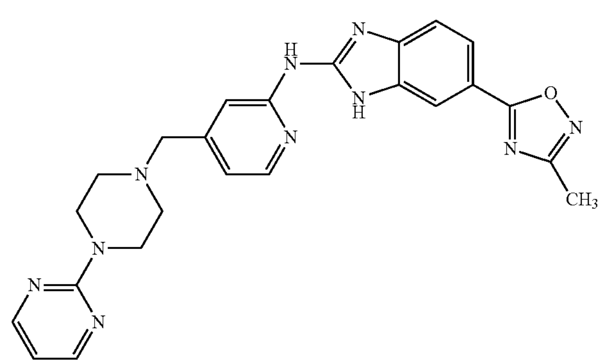 [SMILES: Cc1noc(-c2ccc3nc(Nc4cc(CN5CCN(c6ncccn6)CC5)ccn4)[nH]c3c2)n1] | 6-(3-methyl-1,2,4-oxadiazol-5-yl)-N-(4-{[4-(pyrimidin-2-yl)piperazin-1-yl]methyl}pyridin-2-yl)-1H-benzimidazol-2-amine | 0.70 | 469 |

TABLE 9-continued

| Example | IUPAC Name | Retention time [min] | LC-MS m/z [M + H]+ |
|---|---|---|---|
| 101.06 | 1-{4-[(2-{[6-(3-methyl-1,2,4-oxadiazol-5-yl)-1H-benzimidazol-2-yl]amino}pyridin-4-yl)methyl]piperazin-1-yl}ethanone | 0.63 | 433 |
| 101.07 | N-(4-{[4-(2-methoxyphenyl)piperazin-1-yl]methyl}pyridin-2-yl)-6-(3-methyl-1,2,4-oxadiazol-5-yl)-1H-benzimidazol-2-amine | 0.78 | 497 |
| 101.08 | 6-(3-methyl-1,2,4-oxadiazol-5-yl)-N-[4-({4-[5-(trifluoromethyl)pyridin-2-yl]piperazin-1-yl}methyl)pyridin-2-yl]-1H-benzimidazol-2-amine | 0.92 | 536 |
| 101.09 | N-(4-{[4-(3-fluorophenyl)piperazin-1-yl]methyl}pyridin-2-yl)-6-(3-methyl-1,2,4-oxadiazol-5-yl)-1H-benzimidazol-2-amine | 0.84 | 485 |

TABLE 9-continued

| Example | Structure | IUPAC Name | Retention time [min] | LC-MS m/z [M + H]+ |
|---|---|---|---|---|
| 101.10 | 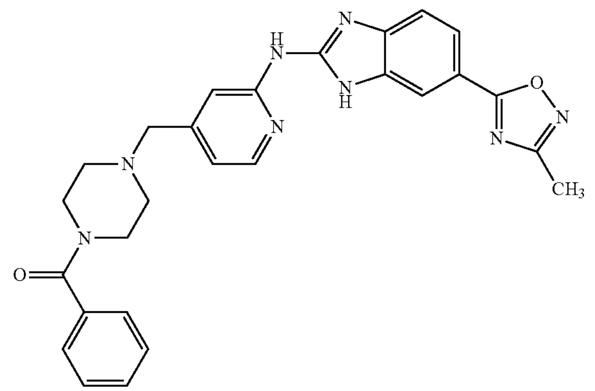 [SMILES: Cc1noc(-c2ccc3nc(Nc4cc(CN5CCN(C(=O)c6ccccc6)CC5)ccn4)[nH]c3c2)n1] | {4-[(2-{[6-(3-methyl-1,2,4-oxadiazol-5-yl)-1H-benzimidazol-2-yl]amino}pyridin-4-yl)methyl]piperazin-1-yl}(phenyl)methanone | 0.78 | 495 |
| 101.11 | 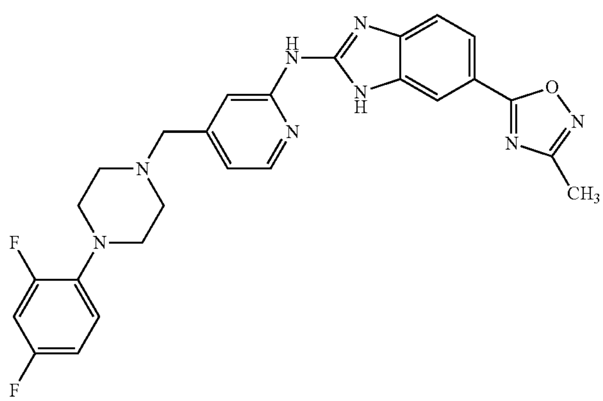 [SMILES: Cc1noc(-c2ccc3nc(Nc4cc(CN5CCN(c6ccc(F)cc6F)CC5)ccn4)[nH]c3c2)n1] | N-(4-{[4-(2,4-difluorophenyl)piperazin-1-yl]methyl}pyridin-2-yl)-6-(3-methyl-1,2,4-oxadiazol-5-yl)-1H-benzimidazol-2-amine | 0.85 | 503 |
| 101.12 | 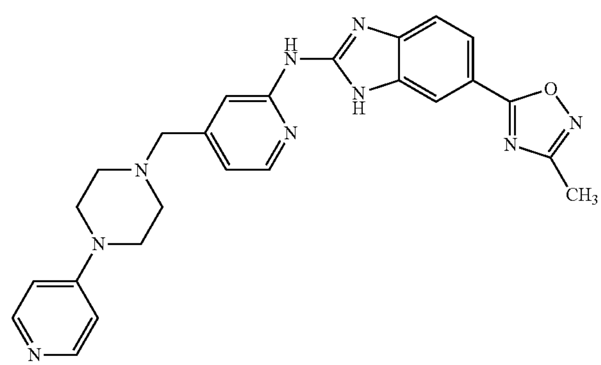 [SMILES: Cc1noc(-c2ccc3nc(Nc4cc(CN5CCN(c6ccncc6)CC5)ccn4)[nH]c3c2)n1] | 6-(3-methyl-1,2,4-oxadiazol-5-yl)-N-(4-{[4-(pyridin-4-yl)piperazin-1-yl]methyl}pyridin-2-yl)-1H-benzimidazol-2-amine | 0.62 | 468 |
| 101.13 | 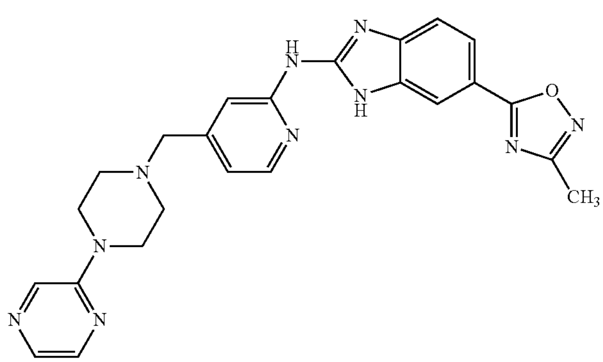 [SMILES: Cc1noc(-c2ccc3nc(Nc4cc(CN5CCN(c6cnccn6)CC5)ccn4)[nH]c3c2)n1] | 6-(3-methyl-1,2,4-oxadiazol-5-yl)-N-(4-{[4-(pyrazin-2-yl)piperazin-1-yl]methyl}pyridin-2-yl)-1H-benzimidazol-2-amine | 0.69 | 469 |

TABLE 9-continued

| Example | Structure | IUPAC Name | Retention time [min] | LC-MS m/z [M + H]+ |
|---|---|---|---|---|
| 101.14 | 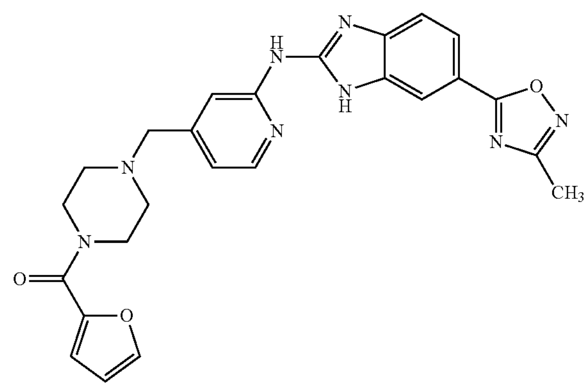 [SMILES: Cc1noc(-c2ccc3nc(Nc4cc(CN5CCN(C(=O)c6ccco6)CC5)ccn4)[nH]c3c2)n1] | furan-2-yl{4-[(2-{[6-(3-methyl-1,2,4-oxadiazol-5-yl)-1H-benzimidazol-2-yl]amino}pyridin-4-yl)methyl]piperazin-1-yl}methanone | 0.72 | 485 |
| 101.15 | 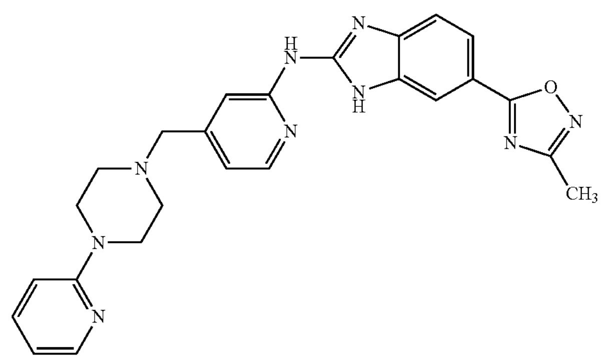 [SMILES: Cc1noc(-c2ccc3nc(Nc4cc(CN5CCN(c6ccccn6)CC5)ccn4)[nH]c3c2)n1] | 6-(3-methyl-1,2,4-oxadiazol-5-yl)-N-(4-{[4-(pyridin-2-yl)piperazin-1-yl]methyl}pyridin-2-yl)-1H-benzimidazol-2-amine | 0.67 | 468 |
| 101.16 | 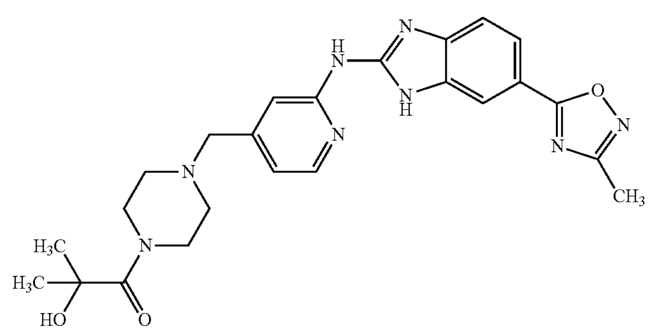 [SMILES: Cc1noc(-c2ccc3nc(Nc4cc(CN5CCN(C(=O)C(C)(C)O)CC5)ccn4)[nH]c3c2)n1] | 2-hydroxy-2-methyl-1-{4-[(2-{[6-(3-methyl-1,2,4-oxadiazol-5-yl)-1H-benzimidazol-2-yl]amino}pyridin-4-yl)methyl]piperazin-1-yl}propan-1-one | 0.65 | 477 |
| 101.17 | 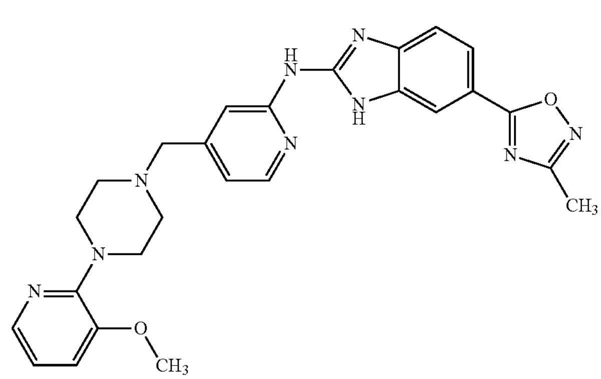 [SMILES: COc1cccnc1N1CCN(Cc2ccnc(Nc3nc4ccc(-c5nc(C)no5)cc4[nH]3)c2)CC1] | N-(4-{[4-(3-methoxypyridin-2-yl)piperazin-1-yl]methyl}pyridin-2-yl)-6-(3-methyl-1,2,4-oxadiazol-5-yl)-1H-benzimidazol-2-amine | 0.72 | 498 |

TABLE 9-continued

| Example | Structure | IUPAC Name | Retention time [min] | LC-MS m/z [M + H]+ |
|---|---|---|---|---|
| 101.18 | 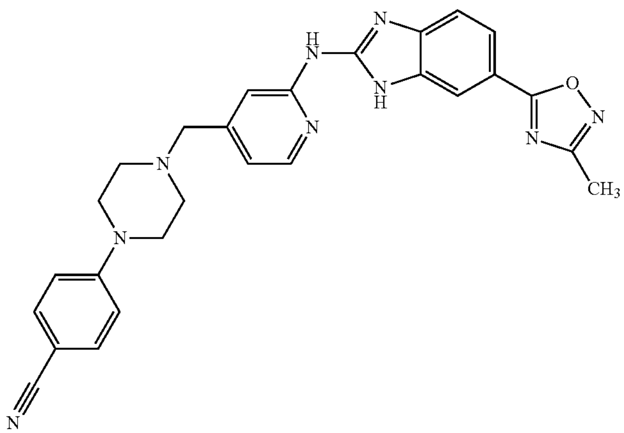 [SMILES: Cc1noc(-c2ccc3nc(Nc4cc(CN5CCN(c6ccc(C#N)cc6)CC5)ccn4)[nH]c3c2)n1] | 4-{4-[(2-{[6-(3-methyl-1,2,4-oxadiazol-5-yl)-1H-benzimidazol-2-yl]amino}pyridin-4-yl)methyl]piperazin-1-yl}benzonitrile | 0.80 | 492 |
| 101.19 | 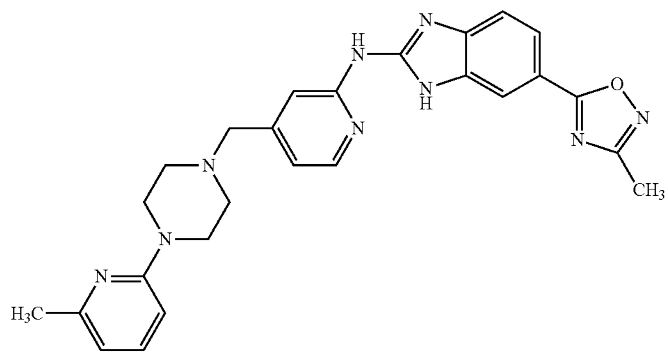 [SMILES: Cc1cccc(N2CCN(Cc3ccnc(Nc4nc5ccc(-c6nc(C)no6)cc5[nH]4)c3)CC2)n1] | 6-(3-methyl-1,2,4-oxadiazol-5-yl)-N-(4-{[4-(6-methylpyridin-2-yl)piperazin-1-yl]methyl}pyridin-2-yl)-1H-benzimidazol-2-amine | 0.70 | 482 |
| 101.20 | 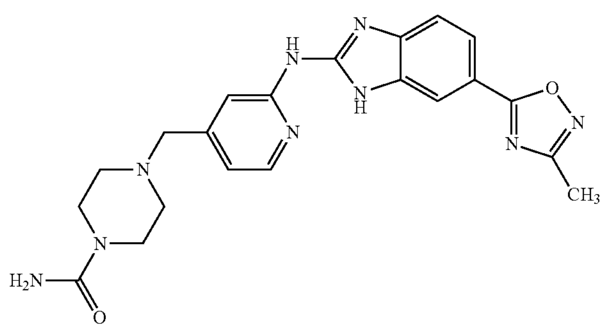 | 4-[(2-{[6-(3-methyl-1,2,4-oxadiazol-5-yl)-1H-benzimidazol-2-yl]amino}pyridin-4-yl)methyl]piperazine-1-carboxamide | 0.60 | 434 |
| 101.21 | 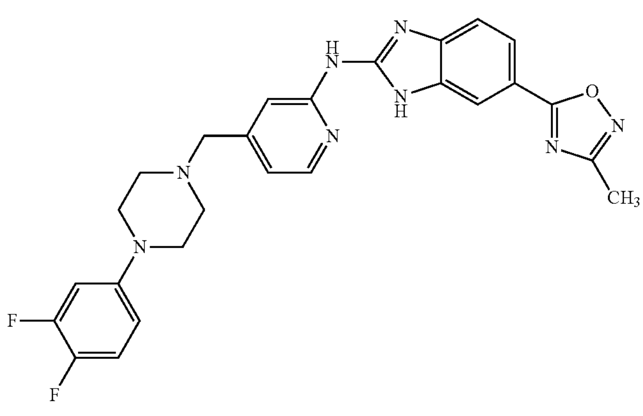 [SMILES: Cc1noc(-c2ccc3nc(Nc4cc(CN5CCN(c6ccc(F)c(F)c6)CC5)ccn4)[nH]c3c2)n1] | N-(4-{[4-(3,4-difluorophenyl)piperazin-1-yl]methyl}pyridin-2-yl)-6-(3-methyl-1,2,4-oxadiazol-5-yl)-1H-benzimidazol-2-amine | 0.86 | 503 |

TABLE 9-continued

| Example | Structure | IUPAC Name | Retention time [min] | LC-MS m/z [M + H]+ |
|---|---|---|---|---|
| 101.22 | 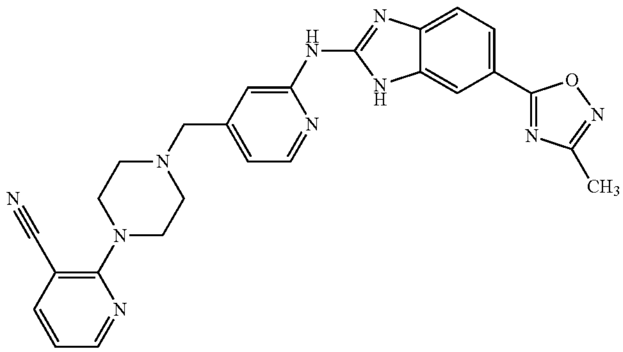 [SMILES: Cc1noc(-c2ccc3nc(Nc4cc(CN5CCN(c6ncccc6C#N)CC5)ccn4)[nH]c3c2)n1] | 2-{4-[(2-{[6-(3-methyl-1,2,4-oxadiazol-5-yl)-1H-benzimidazol-2-yl]amino}pyridin-4-yl)methyl]piperazin-1-yl}pyridine-3-carbonitrile | 0.76 | 493 |
| 101.23 | 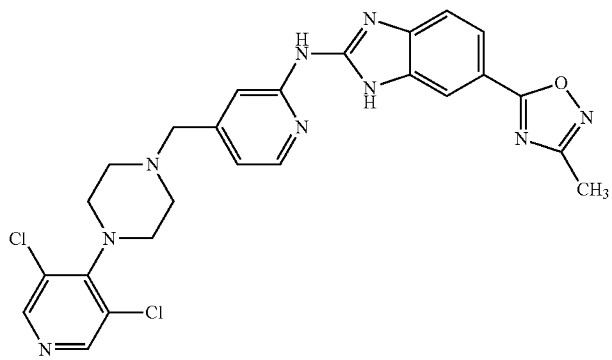 [SMILES: Cc1noc(-c2ccc3nc(Nc4cc(CN5CCN(c6c(Cl)cncc6Cl)CC5)ccn4)[nH]c3c2)n1] | N-(4-{[4-(3,5-dichloropyridin-4-yl)piperazin-1-yl]methyl}pyridin-2-yl)-6-(3-methyl-1,2,4-oxadiazol-5-yl)-1H-benzimidazol-2-amine | 0.81 | 536 |
| 101.24 | 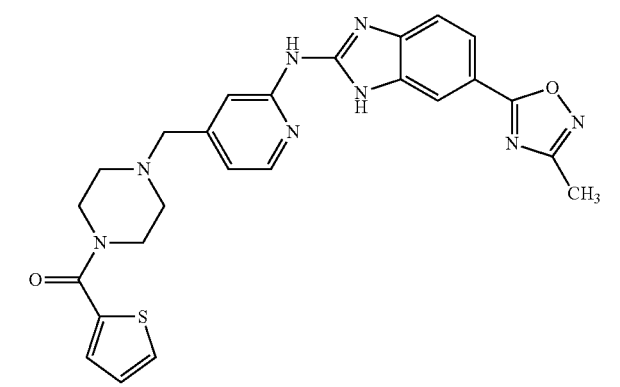 | {4-[(2-{[6-(3-methyl-1,2,4-oxadiazol-5-yl)-1H-benzimidazol-2-yl]amino}pyridin-4-yl)methyl]piperazin-1-yl}(thiophen-2-yl)methanone | 0.76 | 501 |
| 101.26 | 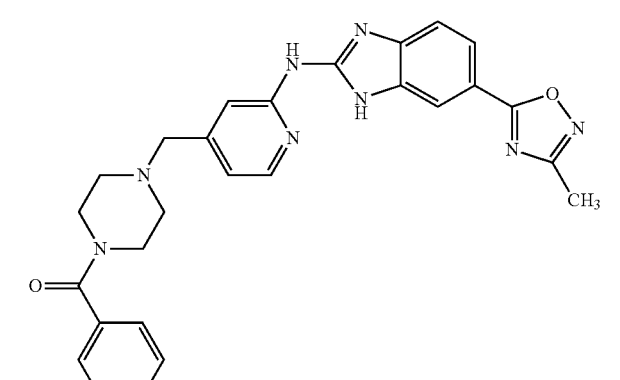 | {4-[(2-{[6-(3-methyl-1,2,4-oxadiazol-5-yl)-1H-benzimidazol-2-yl]amino}pyridin-4-yl)methyl]piperazin-1-yl}(pyridin-3-yl)methanone | 0.68 | 496 |

TABLE 9-continued

| Example | Structure | IUPAC Name | Retention time [min] | LC-MS m/z [M + H]+ |
|---|---|---|---|---|
| 101.27 | 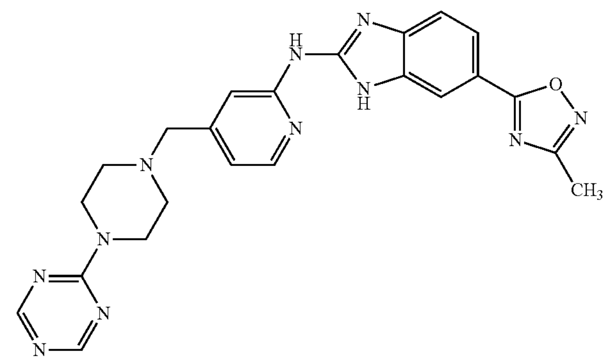 [SMILES: Cc1noc(-c2ccc3nc(Nc4cc(CN5CCN(c6ncncn6)CC5)ccn4)[nH]c3c2)n1] | 6-(3-methyl-1,2,4-oxadiazol-5-yl)-N-(4-{[4-(1,3,5-triazin-2-yl)piperazin-1-yl]methyl}pyridin-2-yl)-1H-benzimidazol-2-amine | 0.69 | 470 |
| 101.28 | 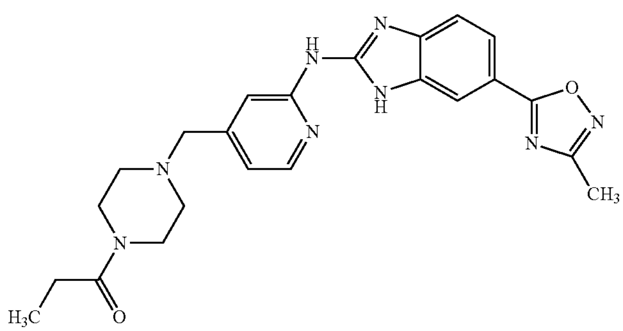 [SMILES: CCC(=O)N1CCN(Cc2ccnc(Nc3nc4ccc(-c5nc(C)no5)cc4[nH]3)c2)CC1] | 1-{4-[(2-{[6-(3-methyl-1,2,4-oxadiazol-5-yl)-1H-benzimidazol-2-yl]amino}pyridin-4-yl)methyl]piperazin-1-yl}propan-1-one | 0.67 | 447 |
| 101.29 | 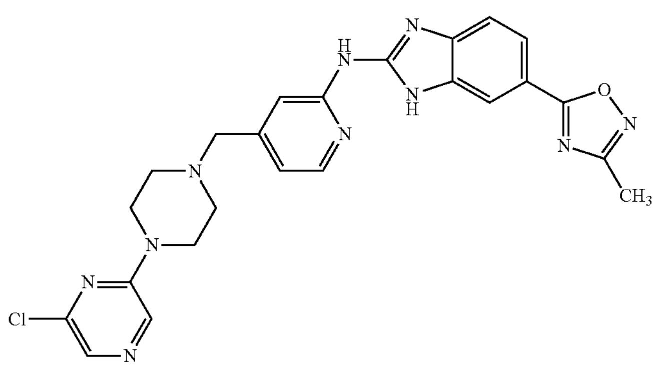 [SMILES: Cc1noc(-c2ccc3nc(Nc4cc(CN5CCN(c6cncc(Cl)n6)CC5)ccn4)[nH]c3c2)n1] | N-(4-{[4-(6-chloropyrazin-2-yl)piperazin-1-yl]methyl}pyridin-2-yl)-6-(3-methyl-1,2,4-oxadiazol-5-yl)-1H-benzimidazol-2-amine | 0.82 | 503 |
| 101.30 | 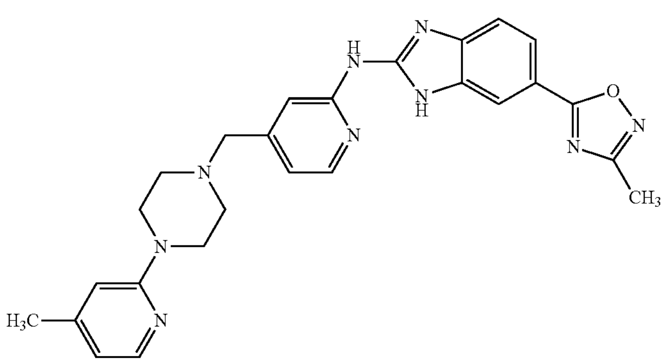 [SMILES: Cc1ccnc(N2CCN(Cc3ccnc(Nc4nc5ccc(-c6nc(C)no6)cc5[nH]4)c3)CC2)c1] | 6-(3-methyl-1,2,4-oxadiazol-5-yl)-N-(4-{[4-(4-methylpyridin-2-yl)piperazin-1-yl]methyl}pyridin-2-yl)-1H-benzimidazol-2-amine | 0.69 | 482 |

TABLE 9-continued

| Example | Structure | IUPAC Name | Retention time [min] | LC-MS m/z [M + H]+ |
|---|---|---|---|---|
| 101.31 | 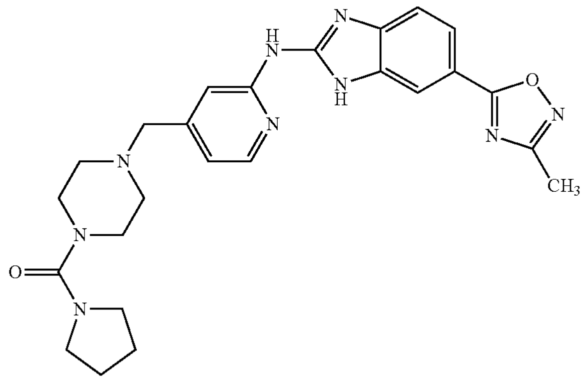 [SMILES: Cc1noc(-c2ccc3nc(Nc4cc(CN5CCN(C(=O)N6CCCC6)CC5)ccn4)[nH]c3c2)n1] | {4-[(2-{[6-(3-methyl-1,2,4-oxadiazol-5-yl)-1H-benzimidazol-2-yl]amino}pyridin-4-yl)methyl]piperazin-1-yl}(pyrrolidin-1-yl)methanone | 0.70 | 488 |

Example 102.01 cyclopropyl{4-[(2-{[6-(2,6-dimethylpyridin-4-yl)-1H-benzimidazol-2-yl]amino}pyridin-4-yl)methyl]piperazin-1-yl}methanone

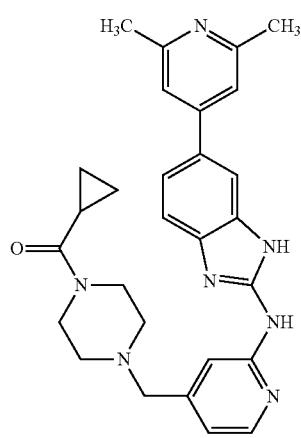 [SMILES: Cc1cc(-c2ccc3nc(Nc4cc(CN5CCN(C(=O)C6CC6)CC5)ccn4)[nH]c3c2)cc(C)n1]

A suspension of tert-butyl 4-[(2-{[6-(4,4,5,5-tetramethyl-1,3,2-dioxaborolan-2-yl)-1H-benzimidazol-2-yl]amino}pyridin-4-yl)methyl]piperazine-1-carboxylate (see Compound 01.04) in dioxane (800 µl, 0.25 M), was added to 75 mg (2 eq) 4-bromo-2,6-dimethylpyridine. 600 µl aqueous potassium carbonate solution (1.0 M, 3 eq) were added and the mixture was shaken at rt for 1 h. A solution of Pd(dppf)Cl$_2$×CH$_2$Cl$_2$ (1.0 ml, 0.040 M in dioxane, 0.2 eq) was added and the mixture was heated overnight at 140° C. in a pressure reactor. After cooling, the mixture was filtered, evaporated and treated with 2 mL TFA/DCM/water (2:1:0.1) for 3 h at rt. After vacuum evaporation the residue was treated with cyclopropanecarboxylic acid (600 µl, 1.0 M in NMP, 3 eq), NMM (400 µl, 3.0 M in NMP, 6 eq) and HATU (1.2 ml, 0.50 M in NMP, 3 eq), shaken overnight at rt, filtered and subjected to standard reversed-phase preparative HPLC to yield 17.8 mg (18%) of the title compound cyclopropyl{4-[(2-{[6-(2,6-dimethylpyridin-4-yl)-1H-benzimidazol-2-yl]amino}pyridin-4-yl)methyl]piperazin-1-yl}methanone.

LC-MS (Method 4): R$_t$=1.1.08 min; MS (ESIpos): m/z=483 [M+H]$^+$.

The following examples shown in Table 10 below were prepared in analogy to example 102.01 using the appropriate aryl bromide and carboxylic acid derivative:

TABLE 10

| Example | Structure IUPAC-Name | LC-MS method Retention time Mass found |
|---|---|---|
| 103.01 | 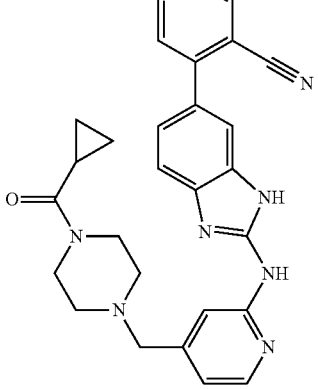<br>4-{2-[(4-{[4-(cyclopropylcarbonyl)piperazin-1-yl]methyl}pyridin-2-yl)amino]-1H-benzimidazol-6-yl}pyridine-3-carbonitrile | Method 4 1.01 480 |

TABLE 10-continued

| Example | Structure IUPAC-Name | LC-MS method Retention time Mass found |
|---|---|---|
| 104.01 | 3,3,3-trifluoro-1-{4-[(2-{[6-(2-methylthieno[2,3-d]pyrimidin-4-yl)-1H-benzimidazol-2-yl]amino}pyridin-4-yl)methyl]piperazin-1-yl}propan-1-one | Method 4 1.16 568 |
| 105.01 | 3,3,3-trifluoro-1-{4-[(2-{[6-(thieno[2,3-d]pyrimidin-4-yl)-1H-benzimidazol-2-yl]amino}pyridin-4-yl)methyl]piperazin-1-yl}propan-1-one | Method 4 1.11 554 |
| 106.01 | 3,3,3-trifluoro-1-(4-{[2-({6-[3-(trifluoromethyl)pyridin-4-yl]-1H-benzimidazol-2-yl}amino)pyridin-4-yl]methyl}piperazin-1-yl)propan-1-one | Method 4 1.16 565 |

Example 107.01.01 tert-butyl 4-{[2-({6-[6-(dimethylamino)-5-methoxy-pyrimidin-4-yl]-1H-benzimidazol-2-yl}amino)pyridin-4-yl]methyl}piperazine-1-carboxylate

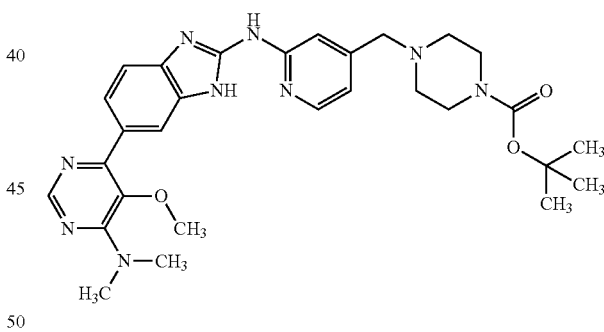

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (300 mg, see Compound 60.01) in 2-propanol (3.0 ml) in a microwave tube was added N-methylmethanamine (1.4 ml, 2.0 M in THF). The mixture was stirred at 100° C. for 30 minutes in a microwave oven. The mixture was concentrated in vacuum. Silicagel chromatography gave a solid that was triturated with warm ethanol to give 210 mg of the title compound.

LC-MS (Method 2): $R_t$=1.27 min; MS (ESIpos): m/z=560 [M+H]$^+$.

$^1$H-NMR (400 MHz, DMSO-d6) δ[ppm]: 1.395 (16.00), 2.345 (0.91), 2.358 (1.35), 2.370 (0.94), 3.197 (10.86), 3.332 (8.15), 3.351 (1.20), 3.371 (1.69), 6.919 (0.52), 6.931 (0.53), 7.169 (0.57), 8.251 (0.74), 8.263 (0.69), 8.325 (3.02).

Example 107.01.02 cyclopropyl(4-{[2-({6-[6-(dimethylamino)-5-methoxypyrimidin-4-yl]-1H-benzimidazol-2-yl}amino)pyridin-4-yl]methyl}piperazin-1-yl)methanone

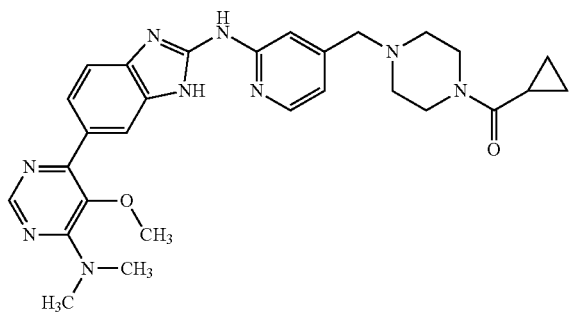 [SMILES: COc1c(-c2ccc3nc(Nc4cc(CN5CCN(C(=O)C6CC6)CC5)ccn4)[nH]c3c2)ncnc1N(C)C]

To a stirred solution of crude 6-[6-(dimethylamino)-5-methoxypyrimidin-4-yl]-N-[4-(piperazin-1-ylmethyl)pyridin-2-yl]-1H-benzimidazol-2-amine hydrochloride (100 mg, see Compound 107.01.01) in DMF (1.7 mL) was added sodium bicarbonate (81.5 mg), cyclopropanecarboxylic acid (20 µl, 95% purity) and HATU (98.4 mg). The mixture was stirred at r.t. for 16 h. An excess of water was added and the mixture was stirred for 15 minutes. A solid precipitated and was collected by filtration. Aminophase-silicagel chromatography gave a solid that was triturated with ether to give 60.0 mg of the title compound.

LC-MS (Method 2): $R_t$=1.07 min; MS (ESIpos): m/z=528 [M+H]$^+$.

$^1$H-NMR (400 MHz, DMSO-d6) δ[ppm]: 0.676 (0.69), 0.683 (1.47), 0.697 (0.81), 0.703 (1.76), 0.708 (1.54), 0.713 (1.61), 0.721 (1.54), 0.725 (1.72), 0.732 (0.80), 1.952 (0.40), 1.964 (0.63), 2.364 (0.80), 2.446 (0.88), 2.523 (0.66), 3.198 (16.00), 3.331 (8.10), 3.521 (3.32), 3.705 (0.74), 6.936 (0.93), 6.948 (0.93), 7.188 (1.16), 8.260 (1.24), 8.273 (1.14), 8.325 (3.92), 10.704 (0.52).

Example 107.01.03

1-(4-{[2-({6-[6-(dimethylamino)-5-methoxypyrimidin-4-yl]-1H-benzimidazol-2-yl}amino)pyridin-4-yl]methyl}piperazin-1-yl)-3,3,3-trifluoropropan-1-one

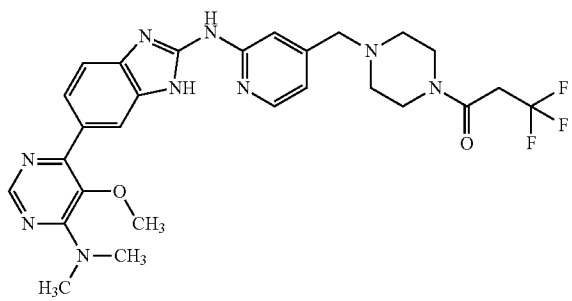 [SMILES: COc1c(-c2ccc3nc(Nc4cc(CN5CCN(C(=O)CC(F)(F)F)CC5)ccn4)[nH]c3c2)ncnc1N(C)C]

To a stirred solution of crude 6-[6-(dimethylamino)-5-methoxypyrimidin-4-yl]-N-[4-(piperazin-1-ylmethyl)pyridin-2-yl]-1H-benzimidazol-2-amine hydrochloride (100 mg, see Compound 107.01.01) in DMF (2.7 mL) was added sodium bicarbonate (109 mg), 3,3,3-trifluoropropanoic acid (21 µl) and HATU (98.4 mg). The mixture was stirred at r.t. for 16 h. An excess of water was added and the mixture was stirred for 15 minutes. A solid precipitated and was collected by filtration. Preparative reverse phase HPLC (gradient of water and acetonitrile containing ammonia as additive) gave 45.0 mg of the title compound.

LC-MS (Method 2): $R_t$=1.09 min; MS (ESIpos): m/z=570 [M+H]$^+$.

$^1$H-NMR (400 MHz, DMSO-d6) δ [ppm]: 2.369 (0.64), 2.382 (0.95), 2.394 (0.71), 2.411 (0.68), 2.423 (0.92), 2.434 (0.69), 2.518 (0.49), 3.197 (16.00), 3.372 (2.11), 3.459 (0.67), 3.472 (0.90), 3.483 (0.76), 3.496 (0.77), 3.521 (2.97), 3.609 (0.43), 3.636 (1.23), 3.664 (1.14), 6.926 (0.74), 6.939 (0.74), 7.183 (0.94), 8.258 (1.00), 8.271 (0.93), 8.325 (4.61).

Example 107.02.01 tert-butyl 4-{(1R or 1S)-1-[2-({6-[6-(dimethylamino)-5-methoxypyrimidin-4-yl]-1H-benzimidazol-2-yl}amino)pyridin-4-yl]ethyl}piperazine-1-carboxylate

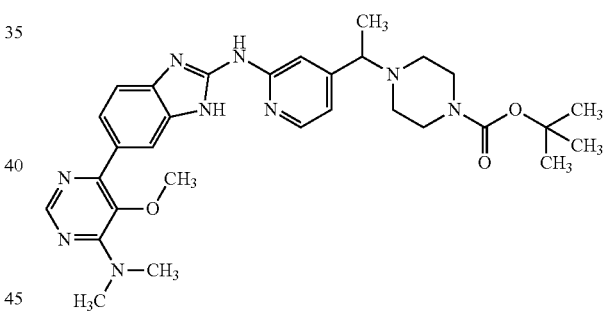

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (140 mg, see Example 83.01) in 2-propanol (5.0 ml) in a microwave tube was added N-methylmethanamine (620 µl, 2.0 M in THF). The mixture was stirred at 100° C. for 30 minutes in a microwave oven. The mixture was concentrated in vacuum. Aminophase-silicagel chromatography gave 135 mg of the title compound.

LC-MS (Method 2): $R_t$=1.31 min; MS (ESIpos): m/z=574 [M+H]$^+$.

$^1$H-NMR (400 MHz, DMSO-d6) δ[ppm]: 1.278 (0.77), 1.295 (0.79), 1.376 (7.45), 1.394 (16.00), 2.518 (0.75), 2.522 (0.48), 3.197 (5.52), 3.377 (0.54), 8.324 (1.84).

Example 107.02.02 cyclopropyl(4-{(1R or 1S)-1-[2-({6-[6-(dimethyl-amino)-5-methoxypyrimidin-4-yl]-1H-benzimidazol-2-yl}amino)pyridin-4-yl]ethyl}piperazin-1-yl)methanone

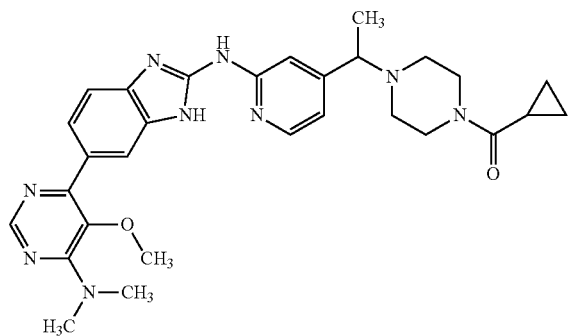 [SMILES: COc1c(-c2ccc3nc(Nc4cc(C(C)N5CCN(C(=O)C6CC6)CC5)ccn4)[nH]c3c2)ncnc1N(C)C]

To a stirred solution of 6-[6-(dimethylamino)-5-methoxypyrimidin-4-yl]-N-{4-[(1R or 1S)-1-(piperazin-1-yl)ethyl]pyridin-2-yl}-1H-benzimidazol-2-amine hydrochloride (90.0 mg, see Compound 107.02.01) in DMF (0.84 mL) was added sodium bicarbonate (77.8 mg), cyclopropanecarboxylic acid (19 µl, 95% purity) and HATU (94 mg). The mixture was stirred at r.t. for 16 h. Water was added, the mixture was stirred for 15 minutes and filtered. Preparative reverse phase HPLC (gradient of water and acetonitrile containing ammonia as additive) gave 50.0 mg of the title compound.

LC-MS (Method 2): $R_t$=1.11 min; MS (ESIpos): m/z=542 [M+H]$^+$.

$^1$H-NMR (400 MHz, DMSO-d6) δ[ppm]: 0.656 (0.51), 0.663 (1.20), 0.667 (0.73), 0.676 (0.57), 0.682 (1.45), 0.686 (1.22), 0.691 (1.33), 0.698 (1.17), 0.703 (1.39), 0.710 (0.64), 1.298 (2.28), 1.315 (2.34), 1.935 (0.52), 2.327 (0.47), 2.518 (1.18), 2.523 (0.81), 3.197 (16.00), 3.371 (7.49), 3.450 (0.81), 3.466 (1.06), 3.676 (0.55), 6.941 (0.72), 6.954 (0.73), 8.251 (1.07), 8.264 (1.02), 8.322 (4.67).

Example 107.02.03

1-(4-{(1R or 1S)-1-[2-({6-[6-(dimethylamino)-5-methoxypyrimidin-4-yl]-1H-benzimidazol-2-yl}amino)pyridin-4-yl]ethyl}piperazin-1-yl)-3,3,3-trifluoropropan-1-one

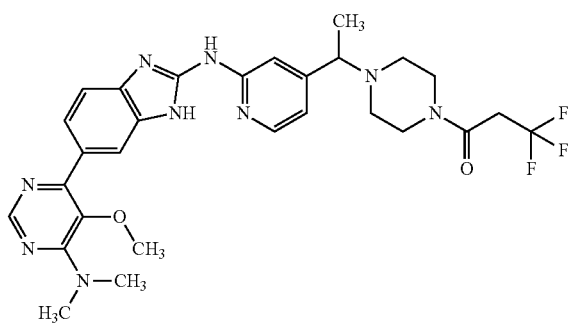 [SMILES: COc1c(-c2ccc3nc(Nc4cc(C(C)N5CCN(C(=O)CC(F)(F)F)CC5)ccn4)[nH]c3c2)ncnc1N(C)C]

To a stirred solution of 6-[6-(dimethylamino)-5-methoxypyrimidin-4-yl]-N-{4-[(1R or 1S)-1-(piperazin-1-yl)ethyl]pyridin-2-yl}-1H-benzimidazol-2-amine hydrochloride (100 mg, see Compound 107.02.01) in DMF (2.9 mL) was added sodium bicarbonate (115 mg), 3,3,3-trifluoropropanoic acid (23 µl) and HATU (104 mg). The mixture was stirred at r.t. for 16 h.

Water was added, the mixture was stirred for 15 minutes and the mixture was extracted with ethyl acetate. The organic phase was washed with saturated sodium chloride solution, dried (sodium sulfate), filtered and the solvent was removed in vacuum. Aminophase-silicagel chromatography gave a solid that was triturated with a mixture of dichloromethane and cyclohexane to give 45 mg of the title compound.

LC-MS (Method 2): $R_t$=1.14 min; MS (ESIpos): m/z=584 [M+H]$^+$.

$^1$H-NMR (400 MHz, DMSO-d6) δ [ppm]: 1.287 (2.69), 1.303 (2.69), 1.389 (12.44), 2.323 (0.69), 2.339 (0.68), 2.349 (0.63), 2.362 (0.55), 2.414 (0.75), 2.424 (0.80), 2.452 (0.50), 3.193 (16.00), 3.327 (7.92), 3.433 (1.44), 3.443 (1.12), 3.461 (1.39), 3.477 (1.87), 3.575 (0.51), 3.602 (1.44), 3.630 (1.36), 3.657 (0.44), 6.938 (0.87), 6.951 (0.89), 7.160 (0.99), 8.258 (1.14), 8.271 (1.11), 8.320 (3.88), 10.685 (0.49).

Example 107.02.04

(4-{(1R or 1S)-1-[2-({6-[6-(dimethylamino)-5-methoxypyrimidin-4-yl]-1H-benzimidazol-2-yl}amino)pyridin-4-yl]ethyl}piperazin-1-yl)[1-(trifluoromethyl)cyclopropyl]methanone

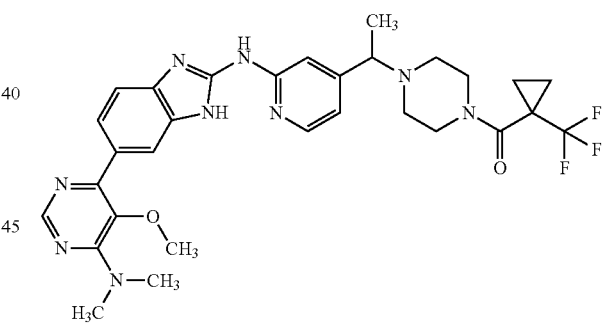

To a stirred solution of 6-[6-(dimethylamino)-5-methoxypyrimidin-4-yl]-N-{4-[(1R or 1S)-1-(piperazin-1-yl)ethyl]pyridin-2-yl}-1H-benzimidazol-2-amine hydrochloride (40.0 mg, see Compound 107.02.01) in DMF (0.4 mL) was added sodium bicarbonate (46.1 mg), 1-(trifluoromethyl)cyclopropanecarboxylic acid (15.9 mg) and HATU (41.7 mg). The mixture was stirred at r.t. for 16 h. An excess of water was added and the mixture was stirred for 15 minutes. A solid precipitated and was collected by filtration. Aminophase-silicagel chromatography gave 20 mg of the title compound.

LC-MS (Method 2): $R_t$=1.20 min; MS (ESIpos): m/z=610 [M+H]$^+$.

$^1$H-NMR (400 MHz, DMSO-d6) δ[ppm]: 1.161 (0.77), 1.255 (0.46), 1.266 (0.96), 1.288 (1.74), 1.305 (1.60), 1.395 (16.00), 2.327 (0.46), 2.332 (0.41), 2.518 (1.52), 2.522 (0.99), 3.198 (12.27), 3.380 (1.06), 3.449 (0.41), 3.466

(0.41), 3.570 (0.51), 5.758 (0.74), 6.946 (0.46), 6.960 (0.47), 8.261 (0.59), 8.274 (0.56), 8.324 (4.03).

Example 108.01 tert-butyl 4-{[2-({6-[6-(cyclopropylamino)-5-methoxypyrimidin-4-yl]-1H-benzimidazol-2-yl}amino)pyridin-4-yl]methyl}piperazine-1-carboxylate

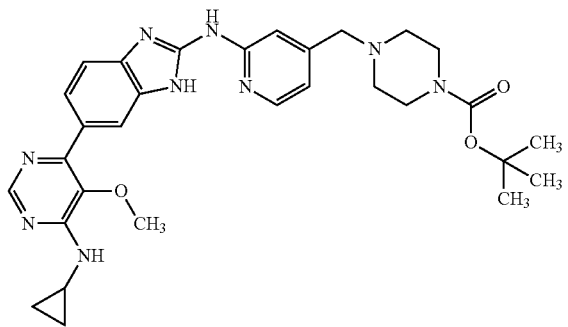 [SMILES: COc1c(NC2CC2)ncnc1-c1ccc2nc(Nc3cc(CN4CCN(C(=O)OC(C)(C)C)CC4)ccn3)[nH]c2c1]

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (300 mg, see Compound 60.01) in 2-propanol (3.0 ml) in a microwave tube was added cyclopropanamine (190 µl). The mixture was stirred at 100° C. for 1 h in a microwave oven. Further cyclopropanamine (95 µl) and the mixture was stirred at 100° C. for 16 h. The mixture was concentrated in vacuum. Aminophase-silicagel chromatography gave 285 mg of the title compound.

LC-MS (Method 2): $R_t$=1.20 min; MS (ESIpos): m/z=572 [M+H]$^+$.

$^1$H-NMR (400 MHz, DMSO-d6) δ[ppm]: 0.609 (0.58), 0.615 (0.74), 0.624 (0.81), 0.712 (0.65), 0.719 (0.68), 0.730 (0.78), 1.394 (16.00), 2.346 (1.02), 2.358 (1.45), 2.369 (1.01), 2.518 (0.73), 2.522 (0.49), 3.428 (0.97), 3.498 (1.76), 5.758 (3.78), 6.916 (0.52), 6.929 (0.54), 7.170 (0.92), 7.310 (0.62), 7.320 (0.59), 8.256 (0.86), 8.268 (0.80), 8.307 (1.86).

Example 108.02

1-(4-{[2-({6-[6-(cyclopropylamino)-5-methoxypyrimidin-4-yl]-1H-benzimidazol-2-yl}amino)pyridin-4-yl]methyl}piperazin-1-yl)-3,3,3-trifluoropropan-1-one

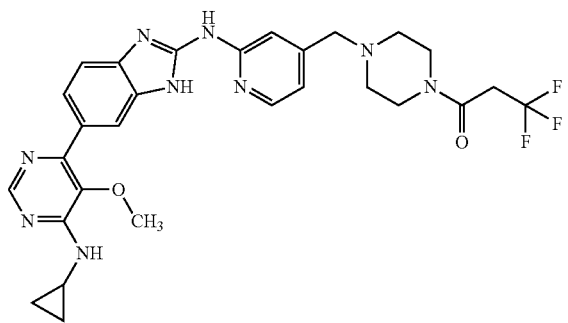 [SMILES: COc1c(NC2CC2)ncnc1-c1ccc2nc(Nc3cc(CN4CCN(C(=O)CC(F)(F)F)CC4)ccn3)[nH]c2c1]

To a stirred solution of crude 6-[6-(cyclopropylamino)-5-methoxypyrimidin-4-yl]-N-[4-(piperazin-1-ylmethyl)pyridin-2-yl]-1H-benzimidazol-2-amine hydrochloride (140 mg, see Compound 108.01) in DMF (4.9 mL) was added sodium bicarbonate (154 mg), 3,3,3-trifluoropropanoic acid (22 µl) and HATU (113 mg). The mixture was stirred at r.t. for 3 h. Water was added, the mixture was stirred for 16 h. A saturated sodium chloride solution was added and the mixture was extracted with ethyl acetate. The organic phase was dried (sodium sulfate) and the solvent was removed in vacuum. Preparative reverse phase HPLC (gradient of water and acetonitrile containing ammonia as additive) gave 50.0 mg of the title compound.

LC-MS (Method 2): $R_t$=1.02 min; MS (ESIpos): m/z=582 [M+H]$^+$.

$^1$H-NMR (400 MHz, DMSO-d6) δ[ppm]: 0.597 (1.37), 0.610 (4.04), 0.616 (5.07), 0.625 (6.22), 0.635 (2.09), 0.664 (0.71), 0.682 (0.40), 0.702 (2.02), 0.713 (4.64), 0.719 (4.92), 0.731 (5.70), 0.735 (3.85), 0.749 (1.50), 1.224 (0.54), 2.327 (0.45), 2.369 (3.03), 2.381 (4.59), 2.393 (3.47), 2.409 (3.01), 2.421 (4.29), 2.432 (3.42), 2.518 (1.60), 2.523 (1.14), 2.810 (0.51), 2.819 (1.38), 2.828 (1.72), 2.837 (2.92), 2.846 (2.89), 2.855 (1.83), 2.864 (1.34), 2.874 (0.47), 3.392 (1.18), 3.427 (9.18), 3.458 (3.28), 3.471 (4.16), 3.482 (3.71), 3.495 (3.80), 3.520 (14.20), 3.608 (1.98), 3.635 (5.49), 3.663 (5.16), 3.691 (1.63), 4.047 (2.97), 6.924 (3.48), 6.927 (3.34), 6.937 (3.49), 6.940 (3.40), 7.186 (6.01), 7.312 (4.55), 7.321 (4.43), 7.399 (0.62), 7.808 (0.69), 8.227 (0.72), 8.262 (5.77), 8.276 (5.37), 8.310 (16.00), 10.699 (0.58).

Example 108.03 cyclopropyl(4-{[2-({6-[6-(cyclopropylamino)-5-methoxypyrimidin-4-yl]-1H-benzimidazol-2-yl}amino)pyridin-4-yl]methyl}piperazin-1-yl)methanone

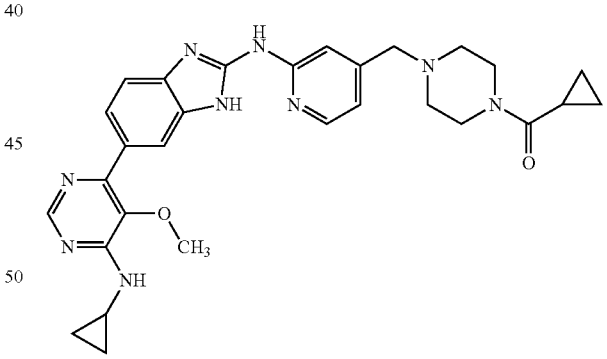

To a stirred solution of crude 6-[6-(cyclopropylamino)-5-methoxypyrimidin-4-yl]-N-[4-(piperazin-1-ylmethyl)pyridin-2-yl]-1H-benzimidazol-2-amine hydrochloride (140 mg, see Compound 108.01) in DMF (1.2 mL) was added sodium bicarbonate (154 mg), cyclopropanecarboxylic acid (21 µl, 95% purity) and HATU (113 mg). The mixture was stirred at r.t. for 16 h. Water was added, the mixture was stirred for 24 h. A saturated sodium chloride solution was added and the mixture was extracted with ethyl acetate. The organic phase was dried (sodium sulfate) and the solvent was removed in vacuum. Preparative reverse phase HPLC (gradient of water and acetonitrile containing ammonia as additive) gave 50.0 mg of the title compound.

LC-MS (Method 2): R$_t$=0.98 min; MS (ESIpos): m/z=540 [M+H]$^+$.

$^1$H-NMR (400 MHz, DMSO-d6) δ[ppm]: 0.597 (0.69), 0.607 (1.57), 0.610 (1.96), 0.615 (2.43), 0.625 (3.04), 0.635 (1.05), 0.658 (0.52), 0.663 (0.61), 0.670 (1.36), 0.677 (2.83), 0.682 (1.94), 0.689 (1.45), 0.697 (3.39), 0.701 (2.71), 0.705 (2.19), 0.711 (4.85), 0.718 (5.09), 0.722 (4.11), 0.730 (4.28), 0.733 (2.25), 0.742 (0.66), 0.748 (0.78), 1.932 (0.70), 1.940 (0.75), 1.952 (1.24), 1.964 (0.70), 1.971 (0.65), 2.359 (1.37), 2.436 (1.38), 2.518 (0.58), 2.523 (0.42), 2.819 (0.61), 2.828 (0.78), 2.837 (1.26), 2.846 (1.25), 2.855 (0.82), 2.864 (0.57), 3.427 (16.00), 3.513 (6.31), 3.696 (1.30), 6.925 (1.79), 6.928 (1.75), 6.939 (1.79), 6.941 (1.79), 7.224 (1.46), 7.311 (2.00), 7.320 (1.93), 7.440 (0.52), 7.459 (0.55), 7.772 (0.86), 7.792 (0.77), 8.260 (2.85), 8.273 (2.69), 8.311 (8.63).

Example 109.01.01 tert-butyl 4-({2-[(6-{6-[(cyclopropylmethyl)amino]-5-methoxypyrimidin-4-yl}-1H-benzimidazol-2-yl)amino]pyridin-4-yl}methyl)piperazine-1-carboxylate

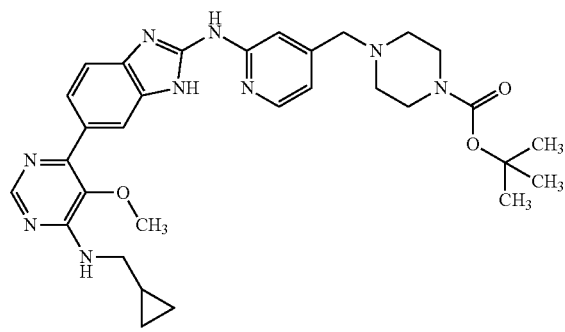 [SMILES: COc1c(NCC2CC2)ncnc1-c1ccc2nc(Nc3cc(CN4CCN(C(=O)OC(C)(C)C)CC4)ccn3)[nH]c2c1]

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (350 mg, see Compound 60.01) in 2-propanol (2.0 ml) in a microwave tube was added 1-cyclopropylmethanamine (280 μl). The mixture was stirred at 100° C. for 1.5 h in a microwave oven. A half-saturated ammonium chloride solution was added and the reaction mixture was extracted with dichloromethane. The organic phase was dried (sodium sulfate) and the solvent was removed in vacuum. Silicagel chromatography gave a solid that was triturated with pentane to give 95 mg of the title compound.

LC-MS (Method 2): R$_t$=1.28 min; MS (ESIpos): m/z=586 [M+H]$^+$.

$^1$H-NMR (400 MHz, DMSO-d6) δ[ppm]: 0.266 (0.80), 0.270 (0.75), 0.279 (0.86), 0.416 (0.70), 0.421 (0.69), 0.436 (0.74), 0.440 (0.67), 0.830 (0.69), 0.836 (0.45), 0.839 (0.42), 0.852 (0.55), 0.857 (1.01), 0.935 (0.47), 0.953 (0.49), 1.237 (0.49), 1.396 (16.00), 2.349 (0.86), 2.361 (1.28), 2.373 (0.91), 2.518 (0.92), 2.523 (0.64), 3.271 (0.58), 3.287 (1.00), 3.302 (0.61), 3.331 (9.86), 3.352 (1.05), 3.500 (1.67), 6.920 (0.50), 6.933 (0.51), 7.172 (0.87), 7.328 (0.55), 8.241 (2.06), 8.259 (0.90), 8.272 (0.81).

Example 109.01.02

1-[4-({2-[(6-{6-[(cyclopropylmethyl)amino]-5-methoxypyrimidin-4-yl}-1H-benzimidazol-2-yl)amino]pyridin-4-yl}methyl)piperazin-1-yl]-3,3,3-trifluoropropan-1-one To a stirred solution of 6-{6-[(cyclopropylmethyl)amino]-5-methoxypyrimidin-4-yl}-N-[4-(piperazin-1-ylmethyl)pyridin-2-yl]-1H-benzimidazol-2-amine hydrochloride (90.0 mg, see Compound 109.01.01) in DMF (3.3 mL) was added sodium bicarbonate (102 mg), 3,3,3-trifluoropropanoic acid (20 μl) and HATU (92.0 mg). The mixture was stirred at r.t. for 65 h. Water was added, the mixture was stirred for 15 minutes and the mixture was extracted with ethyl acetate. The organic phase was dried (sodium sulfate) and the solvent was removed in vacuum. Silicagel chromatography gave a solid that was triturated with ethanol to give 30.0 mg of the title compound.

LC-MS (Method 2): R$_t$=1.12 min; MS (ESIpos): m/z=596 [M+H]$^+$.

$^1$H-NMR (400 MHz, DMSO-d6) δ[ppm]: 0.255 (1.57), 0.267 (6.27), 0.271 (5.81), 0.279 (6.68), 0.292 (2.26), 0.407 (2.14), 0.416 (5.54), 0.421 (5.36), 0.427 (2.96), 0.432 (2.80), 0.436 (5.88), 0.441 (5.33), 0.452 (1.80), 1.122 (0.66), 1.142 (1.46), 1.154 (2.05), 1.166 (1.21), 1.171 (1.25), 1.396 (0.59), 2.373 (3.33), 2.385 (5.04), 2.397 (3.85), 2.414 (3.69), 2.425 (4.95), 2.437 (3.69), 2.518 (7.27), 2.523 (4.92), 3.271 (4.38), 3.287 (7.52), 3.303 (4.49), 3.483 (10.46), 3.512 (5.45), 3.525 (15.13), 3.611 (2.32), 3.638 (6.77), 3.666 (6.40), 3.693 (2.01), 6.931 (3.85), 6.944 (3.92), 7.186 (6.50), 7.312 (2.10), 7.327 (4.44), 7.342 (2.05), 7.378 (0.91), 7.398 (1.05), 7.552 (0.52), 7.747 (0.55), 7.823 (1.00), 7.842 (0.89), 8.000 (0.80), 8.241 (16.00), 8.267 (6.66), 8.280 (6.13), 10.696 (1.64), 12.189 (1.30), 12.213 (2.14).

Example 109.01.03 cyclopropyl[4-({2-[(6-{6-[(cyclopropylmethyl)amino]-5-methoxypyrimidin-4-yl}-1H-benzimidazol-2-yl)amino]pyridin-4-yl}methyl)piperazin-1-yl]methanone

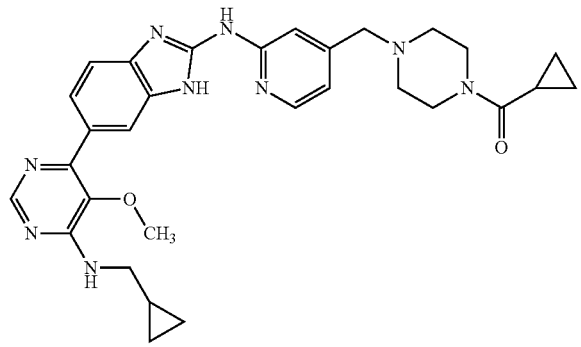 [SMILES: COc1c(NCC2CC2)ncnc1-c1ccc2nc(Nc3cc(CN4CCN(C(=O)C5CC5)CC4)ccn3)[nH]c2c1]

To a stirred solution of crude 6-{6-[(cyclopropylmethyl)amino]-5-methoxypyrimidin-4-yl}-N-[4-(piperazin-1-ylmethyl)pyridin-2-yl]-1H-benzimidazol-2-amine hydrochloride (170 mg, see Compound 109.01.01) in DMF (1.3 mL) was added sodium bicarbonate (125 mg), cyclopropanecarboxylic acid (31 µl, 95% purity) and HATU (151 mg). The mixture was stirred at r.t. for 65 h. An excess of water was added and the mixture was stirred for 15 minutes. A solid precipitated and was collected by filtration. The solid was dissolved in ethyl acetate and the solution was filtered and concentrated in vacuum. Preparative reverse phase HPLC (gradient of water and acetonitrile containing ammonia as additive) gave 55.0 mg of the title compound.

LC-MS (Method 2): $R_t$=1.17 min; MS (ESIpos): m/z=554 [M+H]$^+$.

$^1$H-NMR (400 MHz, DMSO-d6) δ[ppm]: 0.249 (1.58), 0.260 (6.60), 0.264 (6.06), 0.273 (7.18), 0.286 (2.31), 0.399 (2.02), 0.409 (5.61), 0.413 (5.33), 0.419 (3.03), 0.429 (5.98), 0.433 (5.38), 0.444 (1.75), 0.651 (1.09), 0.662 (2.97), 0.670 (5.79), 0.674 (4.49), 0.683 (3.36), 0.690 (6.72), 0.707 (6.01), 0.714 (6.69), 0.718 (7.32), 0.725 (4.00), 0.737 (1.07), 1.112 (0.51), 1.117 (0.71), 1.129 (1.33), 1.132 (1.36), 1.137 (1.40), 1.141 (1.17), 1.149 (2.15), 1.157 (1.18), 1.161 (1.31), 1.166 (1.34), 1.178 (0.66), 1.186 (0.48), 1.909 (0.72), 1.922 (1.51), 1.929 (1.74), 1.942 (2.69), 1.953 (1.61), 1.960 (1.44), 1.972 (0.67), 2.352 (3.50), 2.428 (3.51), 2.518 (0.96), 3.268 (4.48), 3.283 (7.82), 3.299 (4.65), 3.347 (11.60), 3.505 (15.47), 3.687 (3.30), 6.923 (4.21), 6.936 (4.30), 7.195 (6.46), 7.306 (2.18), 7.322 (4.56), 7.336 (2.17), 7.437 (0.69), 7.797 (1.16), 8.229 (0.63), 8.243 (16.00), 8.260 (6.74), 8.273 (6.17), 10.726 (0.62), 12.227 (0.57).

Example 109.02.01 tert-butyl 4-[(1R or 1S)-1-{2-[(6-{6-[(cyclopropylmethyl)amino]-5-methoxypyrimidin-4-yl}-1H-benzimidazol-2-yl)amino]pyridin-4-yl}ethyl]piperazine-1-carboxylate

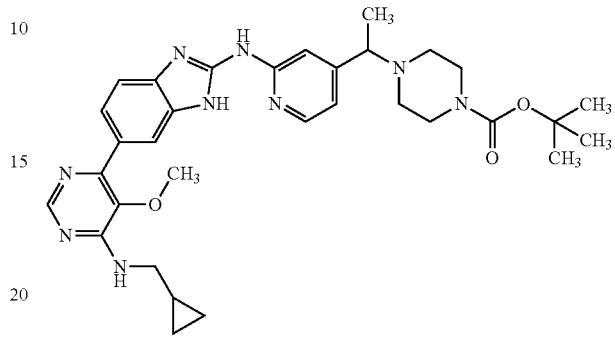

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (250 mg, see Example 83.01) in 2-propanol (10 ml) in a microwave tube was added 1-cyclopropylmethanamine (190 µl). The mixture was stirred at 100° C. for 1.5 h in a microwave oven. Further 1-cyclopropylmethanamine (200 µl) was added and the mixture was stirred at 100° C. for 2.5 h. The mixture was concentrated in vacuum. Silicagel chromatography followed by aminophase-silicagel chromatography gave 200 mg of the title compound.

LC-MS (Method 2): $R_t$=1.33 min; MS (ESIpos): m/z=600 [M+H]$^+$.

$^1$H-NMR (400 MHz, DMSO-d6) δ[ppm]: 0.266 (0.91), 0.270 (0.84), 0.279 (0.96), 0.415 (0.80), 0.420 (0.77), 0.426 (0.41), 0.436 (0.84), 0.440 (0.75), 1.278 (1.76), 1.295 (1.75), 1.376 (16.00), 2.311 (0.47), 2.384 (0.48), 2.518 (0.55), 3.271 (0.71), 3.287 (1.24), 3.303 (1.07), 3.435 (0.51), 3.452 (0.62), 3.475 (1.22), 6.930 (0.55), 6.932 (0.55), 6.946 (0.56), 7.157 (0.98), 7.325 (0.65), 8.241 (2.32), 8.262 (1.01), 8.275 (0.92).

Example 109.02.02 cyclopropyl{4-[(1R or 1S)-1-{2-[(6-{6-[(cyclopropylmethyl)amino]-5-methoxypyrimidin-4-yl}-1H-benzimidazol-2-yl)amino]pyridin-4-yl}ethyl]piperazin-1-yl}methanone

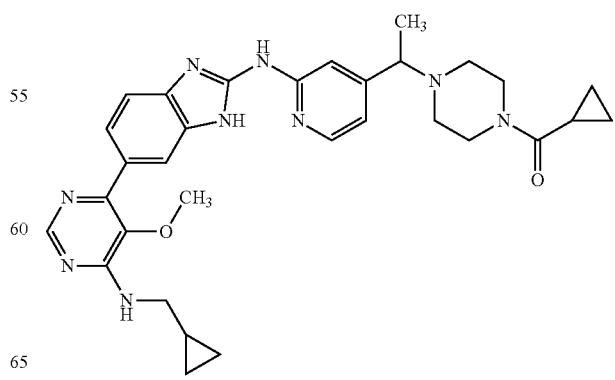

To a stirred solution of crude 6-{6-[(cyclopropylmethyl)amino]-5-methoxypyrimidin-4-yl}-N-{4-[(1R or 1S)-1-(piperazin-1-yl)ethyl]pyridin-2-yl}-1H-benzimidazol-2-amine hydrochloride (90.0 mg, see Compound 109.02.01) in DMF (0.75 mL) was added sodium bicarbonate (68.5 mg), cyclopropanecarboxylic acid (17 µl, 95% purity) and HATU (82.7 mg). The mixture was stirred at r.t. for 16 h. An excess of water was added and the mixture was stirred for 15 minutes. A solid precipitated and was collected by filtration. Preparative reverse phase HPLC (gradient of water and acetonitrile containing ammonia as additive) gave 50.0 mg of the title compound.

LC-MS (Method 2): R$_t$=1.14 min; MS (ESIpos): m/z=568 [M+H]$^+$.

$^1$H-NMR (400 MHz, DMSO-d6) δ[ppm]: 0.255 (1.69), 0.267 (6.34), 0.270 (5.88), 0.279 (6.79), 0.282 (6.29), 0.292 (2.44), 0.407 (2.21), 0.416 (5.60), 0.421 (5.51), 0.426 (3.07), 0.431 (2.90), 0.436 (6.01), 0.441 (5.41), 0.452 (1.90), 0.645 (0.86), 0.657 (2.72), 0.664 (6.36), 0.669 (4.00), 0.677 (3.20), 0.684 (7.78), 0.688 (6.55), 0.692 (7.37), 0.699 (6.36), 0.704 (7.37), 0.711 (3.59), 0.724 (0.91), 1.122 (0.69), 1.137 (1.38), 1.142 (1.54), 1.154 (2.29), 1.166 (1.30), 1.171 (1.30), 1.183 (0.67), 1.296 (12.04), 1.312 (12.35), 1.405 (0.50), 1.422 (0.48), 1.904 (0.76), 1.917 (1.51), 1.924 (1.64), 1.936 (2.75), 1.948 (1.58), 1.955 (1.45), 1.967 (0.67), 2.322 (2.03), 2.327 (2.38), 2.331 (1.92), 2.400 (2.12), 2.518 (10.34), 2.523 (7.35), 2.539 (8.52), 2.616 (0.45), 2.665 (0.95), 2.669 (1.34), 2.673 (0.97), 3.271 (4.50), 3.287 (7.70), 3.302 (4.78), 3.434 (1.64), 3.450 (5.66), 3.468 (10.18), 3.479 (10.05), 3.675 (2.98), 6.951 (3.83), 6.965 (3.98), 7.174 (6.77), 7.312 (2.10), 7.327 (4.50), 7.341 (2.18), 7.399 (0.86), 7.533 (0.45), 7.746 (0.48), 7.821 (0.86), 8.003 (0.58), 8.241 (16.00), 8.271 (6.90), 8.285 (6.42), 10.685 (1.04), 12.229 (1.47).

Example 109.02.03

1-{4-[(1R or 1S)-1-{2-[(6-{6-[(cyclopropylmethyl)amino]-5-methoxypyrimidin-4-yl}-1H-benzimidazol-2-yl)amino]pyridin-4-yl}ethyl]piperazin-1-yl}-3,3,3-trifluoropropan-1-one

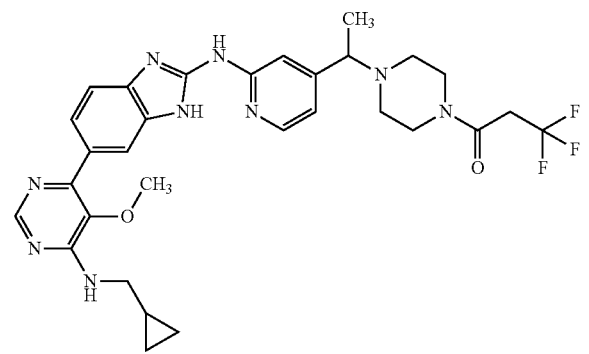 [SMILES: COc1c(NCC2CC2)ncnc1-c1ccc2nc(Nc3cc(C(C)N4CCN(C(=O)CC(F)(F)F)CC4)ccn3)[nH]c2c1]

To a stirred solution of crude 6-{6-[(cyclopropylmethyl)amino]-5-methoxypyrimidin-4-yl}-N-{4-[(1R or 1S)-1-(piperazin-1-yl)ethyl]pyridin-2-yl}-1H-benzimidazol-2-amine hydrochloride (90.0 mg, see Compound 109.02.01) in DMF (2.3 mL) was added sodium bicarbonate (68.5 mg), 3,3,3-trifluoropropanoic acid (18 µl) and HATU (82.7 mg). The mixture was stirred at r.t. for 16 h. An excess of water was added and the mixture was stirred for 15 minutes. A solid precipitated and was collected by filtration. Silicagel chromatography gave 35.0 mg of the title compound.

LC-MS (Method 2): R$_t$=1.17 min; MS (ESIpos): m/z=610 [M+H]$^+$.

$^1$H-NMR (400 MHz, DMSO-d6) δ[ppm]: 0.255 (1.68), 0.267 (6.53), 0.279 (7.04), 0.292 (2.26), 0.407 (2.09), 0.417 (5.47), 0.421 (5.36), 0.427 (3.10), 0.436 (5.86), 0.441 (5.36), 0.452 (1.70), 1.066 (0.45), 1.154 (3.55), 1.172 (4.05), 1.189 (1.87), 1.229 (0.59), 1.294 (12.03), 1.310 (12.01), 1.394 (1.93), 1.987 (5.33), 2.331 (3.63), 2.345 (3.04), 2.369 (2.40), 2.430 (3.55), 2.669 (1.70), 2.728 (1.03), 2.888 (1.12), 3.271 (4.58), 3.287 (8.01), 3.303 (5.11), 3.438 (6.81), 3.451 (5.98), 3.474 (16.00), 3.565 (2.99), 3.580 (2.29), 3.608 (6.31), 3.635 (6.03), 3.662 (1.98), 3.999 (0.42), 4.017 (1.23), 4.035 (1.23), 4.053 (0.42), 5.758 (3.91), 6.944 (4.02), 6.957 (4.08), 7.165 (6.65), 7.316 (1.93), 7.331 (3.94), 7.346 (2.07), 7.398 (0.75), 7.821 (0.87), 8.242 (14.27), 8.271 (6.39), 8.285 (5.84), 10.678 (2.21), 12.222 (1.73).

Example 110.01 tert-butyl 4-({2-[(6-{6-[(cyclopropyl{methyl})(methyl)amino]-5-methoxypyrimidin-4-yl}-1H-benzimidazol-2-yl)amino]pyridin-4-ylmethyl)piperazine-1-carboxylate

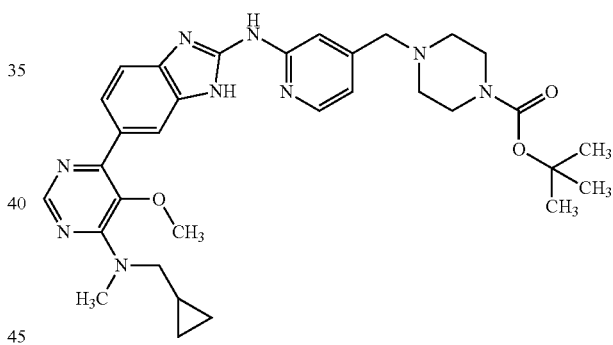

To a stirred solution of tert-butyl 4-[(2-{[6-(6-chloro-5-methoxypyrimidin-4-yl)-1H-benzimidazol-2-yl]amino}pyridin-4-yl)methyl]piperazine-1-carboxylate (350 mg, see Compound 60.01) in 2-propanol (2.0 ml) in a microwave tube was added 1-cyclopropyl-N-methylmethanamine (270 mg). The mixture was stirred at 120° C. for 15 minutes in a microwave oven. The mixture was concentrated in vacuum. Silicagel chromatography gave 340 mg of the title compound.

LC-MS (Method 2): R$_t$=1.42 min; MS (ESIpos): m/z=600 [M+H]$^+$.

$^1$H-NMR (400 MHz, DMSO-d6) δ[ppm]: 0.267 (0.75), 0.271 (0.69), 0.280 (0.78), 0.283 (0.71), 0.469 (0.66), 0.473 (0.65), 0.489 (0.68), 0.493 (0.64), 1.066 (0.61), 1.070 (0.99), 1.088 (2.14), 1.105 (1.13), 1.395 (16.00), 2.347 (0.84), 2.359 (1.20), 2.371 (0.83), 2.518 (0.86), 2.522 (0.63), 3.242 (4.19), 3.353 (2.21), 3.371 (1.33), 3.388 (1.00), 3.499 (1.51), 3.547 (0.90), 3.565 (0.88), 6.917 (0.46), 6.920 (0.45), 6.930 (0.45), 8.250 (0.72), 8.264 (0.63), 8.325 (4.23).

Example 110.02 cyclopropyl[4-({2-[(6-{6-[(cyclopropylmethyl)(methyl)amino]-5-methoxypyrimidin-4-yl}-1H-benzimidazol-2-yl)amino]pyridin-4-yl}methyl)piperazin-1-yl]methanone

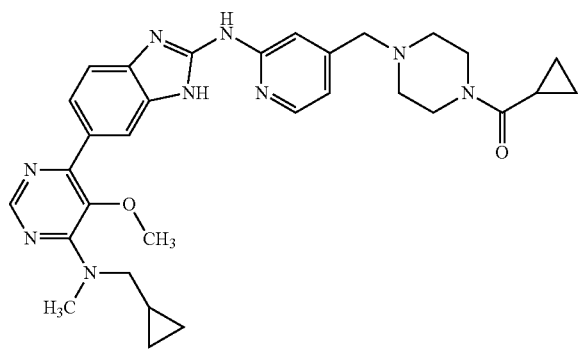 [SMILES: COc1c(-c2ccc3nc(Nc4cc(CN5CCN(C(=O)C6CC6)CC5)ccn4)[nH]c3c2)ncnc1N(C)CC1CC1]

To a stirred solution of crude 6-{6-[(cyclopropylmethyl)(methyl)amino]-5-methoxypyrimidin-4-yl}-N-[4-(piperazin-1-ylmethyl)pyridin-2-yl]-1H-benzimidazol-2-amine hydrochloride (130 mg, see Compound 110.01) in DMF (1.0 mL) was added sodium bicarbonate (93.6 mg), cyclopropanecarboxylic acid (23 µl, 95% purity) and HATU (113 mg). The mixture was stirred at r.t. for 65 h. An excess of water was added and the mixture was stirred for 15 minutes. A solid precipitated and was collected by filtration. The solid was dissolved in ethyl acetate and the solution was filtered and concentrated in vacuum. Preparative reverse phase HPLC (gradient of water and acetonitrile containing ammonia as additive) gave 55.0 mg of the title compound.

LC-MS (Method 2): $R_t$=1.21 min; MS (ESIpos): m/z=568 [M+H]$^+$.

$^1$H-NMR (400 MHz, DMSO-d6) δ[ppm]: 0.266 (1.42), 0.269 (1.34), 0.278 (1.54), 0.292 (0.50), 0.458 (0.46), 0.468 (1.24), 0.472 (1.23), 0.478 (0.65), 0.483 (0.62), 0.488 (1.30), 0.492 (1.24), 0.503 (0.42), 0.675 (0.62), 0.682 (1.45), 0.687 (0.90), 0.695 (0.70), 0.702 (1.72), 0.707 (1.34), 0.712 (1.51), 0.720 (1.47), 0.724 (1.76), 0.731 (0.83), 1.121 (0.47), 1.962 (0.64), 2.364 (0.70), 2.444 (0.72), 2.518 (0.83), 2.523 (0.56), 3.337 (16.00), 3.355 (6.48), 3.519 (3.33), 3.546 (1.85), 3.563 (1.78), 3.704 (0.67), 6.933 (0.91), 6.936 (0.91), 6.946 (0.93), 6.949 (0.92), 7.203 (0.74), 8.259 (1.46), 8.272 (1.38), 8.326 (5.80).

Example 110.03

[4-({2-[(6-{6-[(cyclopropylmethyl)(methyl)amino]-5-methoxypyrimidin-4-yl}-1H-benzimidazol-2-yl)amino]pyridin-4-yl}methyl)piperazin-1-yl][1-(trifluoromethyl)cyclopropyl]methanone

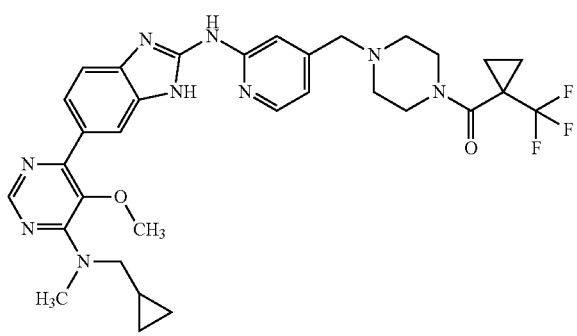 [SMILES: COc1c(-c2ccc3nc(Nc4cc(CN5CCN(C(=O)C6(C(F)(F)F)CC6)CC5)ccn4)[nH]c3c2)ncnc1N(C)CC1CC1]

To a stirred solution of crude 6-{6-[(cyclopropylmethyl)(methyl)amino]-5-methoxypyrimidin-4-yl}-N-[4-(piperazin-1-ylmethyl)pyridin-2-yl]-1H-benzimidazol-2-amine hydrochloride (130 mg, see Compound 110.01) in DMF (1.0 mL) was added sodium bicarbonate (125 mg), 1-(trifluoromethyl)cyclopropanecarboxylic acid (42.9 mg) and HATU (113 mg). The mixture was stirred at r.t. for 65 h. An excess of water was added and the mixture was stirred for 15 minutes. A solid precipitated and was collected by filtration. The solid was dissolved in ethyl acetate and the solution was filtered and concentrated in vacuum. Preparative reverse phase HPLC (gradient of water and acetonitrile containing ammonia as additive) gave 75.0 mg of the title compound.

LC-MS (Method 2): $R_t$=1.29 min; MS (ESIpos): m/z=636 [M+H]$^+$.

$^1$H-NMR (400 MHz, DMSO-d6) δ[ppm]: 0.256 (0.78), 0.267 (2.93), 0.271 (2.68), 0.280 (3.09), 0.293 (0.99), 0.459 (0.94), 0.469 (2.55), 0.473 (2.48), 0.479 (1.31), 0.484 (1.27), 0.489 (2.62), 0.493 (2.43), 0.504 (0.78), 1.105 (0.58), 1.110 (0.60), 1.122 (0.97), 1.135 (0.58), 1.142 (0.62), 1.182 (2.75), 1.237 (0.47), 1.275 (1.62), 1.287 (3.29), 1.307 (1.03), 2.423 (3.36), 2.518 (1.72), 2.523 (1.23), 2.539 (0.70), 3.242 (16.00), 3.358 (4.70), 3.522 (5.97), 3.547 (3.85), 3.565 (4.10), 3.596 (1.85), 6.929 (1.76), 6.945 (1.80), 7.181 (1.24), 7.392 (0.41), 7.744 (0.42), 8.193 (0.57), 8.259 (2.59), 8.272 (2.41), 8.326 (12.94), 10.708 (0.64), 12.253 (0.74).

Example 110.04

1-[4-({2-[(6-{6-[(cyclopropylmethyl)(methyl)amino]-5-methoxypyrimidin-4-yl}-1H-benzimidazol-2-yl)amino]pyridin-4-yl}methyl)piperazin-1-yl]-3,3,3-trifluoropropan-1-one

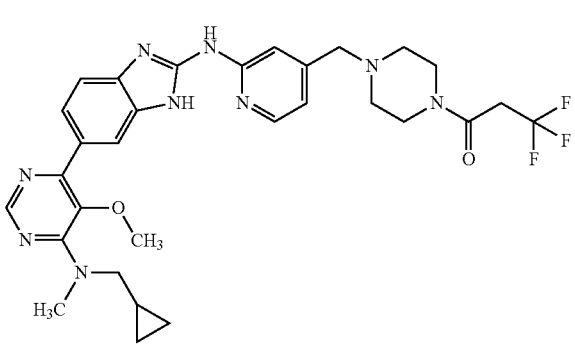 [SMILES: COc1c(-c2ccc3nc(Nc4cc(CN5CCN(C(=O)CC(F)(F)F)CC5)ccn4)[nH]c3c2)ncnc1N(C)CC1CC1]

To a stirred solution of crude 6-{6-[(cyclopropylmethyl)(methyl)amino]-5-methoxypyrimidin-4-yl}-N-[4-(piperazin-1-ylmethyl)pyridin-2-yl]-1H-benzimidazol-2-amine hydrochloride (130 mg, see Compound 110.01) in DMF (4.0 mL) was added sodium bicarbonate (125 mg), 3,3,3-trifluoropropanoic acid (25 µl) and HATU (113 mg). The mixture was stirred at r.t. for 65 h. An excess of water was added and the mixture was stirred for 15 minutes. A solid precipitated and was collected by filtration. The solid was dissolved in ethyl acetate and the solution was filtered and concentrated in vacuum. Preparative reverse phase HPLC (gradient of water and acetonitrile containing ammonia as additive) gave 50.0 mg of the title compound.

LC-MS (Method 2): $R_t$=1.24 min; MS (ESIpos): m/z=610 [M+H]$^+$.

$^1$H-NMR (400 MHz, DMSO-d6) δ[ppm]: 0.250 (0.76), 0.262 (2.99), 0.265 (2.85), 0.274 (3.25), 0.287 (1.03), 0.454 (0.92), 0.464 (2.56), 0.468 (2.54), 0.474 (1.38), 0.479 (1.33), 0.484 (2.71), 0.488 (2.56), 0.499 (0.81), 1.099 (0.60), 1.104 (0.61), 1.117 (0.96), 1.125 (0.51), 1.129 (0.57), 1.134 (0.59), 2.368 (1.56), 2.380 (2.40), 2.392 (1.85), 2.407 (1.70), 2.420 (2.32), 2.431 (1.77), 2.518 (0.67), 2.523 (0.43), 3.237 (16.00), 3.458 (1.65), 3.470 (2.29), 3.481 (1.95), 3.497 (2.01), 3.516 (7.52), 3.542 (3.75), 3.559 (3.57), 3.608 (1.07), 3.635 (2.96), 3.662 (2.82), 3.690 (0.91), 4.046 (0.58), 6.924 (1.83), 6.925 (1.82), 6.939 (1.89), 7.187 (2.13), 8.258 (2.75), 8.271 (2.59), 8.328 (10.84), 10.725 (0.57).

Example 111.01 tert-butyl 4-{(1R or 1S)-1-[2-({6-[6-(azetidin-1-yl)-5-methoxypyrimidin-4-yl]-1H-benzimidazol-2-yl}amino)pyridin-4-yl]ethyl}piperazine-1-carboxylate

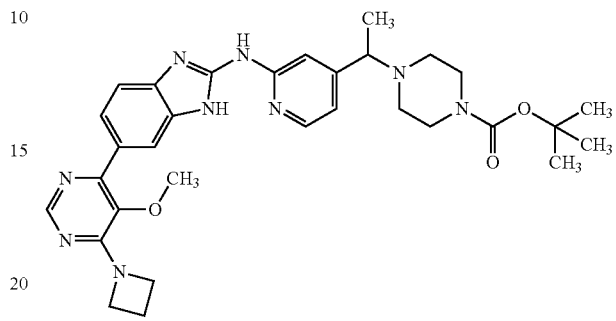

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (250 mg, see Example 83.01) in 2-propanol (3.0 ml) in a microwave tube was added azetidine (126 mg). The mixture was stirred at 100° C. for 30 minutes. The mixture was concentrated in vacuum. Silicagel chromatography gave 180 mg of the title compound.

LC-MS (Method 2): $R_t$=1.29 min; MS (ESIpos): m/z=586 [M+H]$^+$.

$^1$H-NMR (400 MHz, DMSO-d6) δ [ppm]: 1.277 (1.73), 1.294 (1.73), 1.376 (16.00), 2.296 (0.41), 2.311 (0.55), 2.323 (0.50), 2.331 (0.64), 2.351 (0.64), 2.371 (0.70), 2.383 (0.55), 2.518 (0.87), 2.523 (0.60), 3.409 (1.22), 3.433 (0.52), 3.450 (0.46), 4.208 (0.88), 4.227 (1.47), 4.245 (0.85), 5.759 (4.15), 6.932 (0.54), 6.946 (0.55), 7.149 (0.52), 8.252 (0.88), 8.265 (0.75), 8.277 (2.92).

Example 111.02

(4-{(1R or 1S)-1-[2-({6-[6-(azetidin-1-yl)-5-methoxypyrimidin-4-yl]-1H-benzimidazol-2-yl}amino)pyridin-4-yl]ethyl}piperazin-1-yl)(cyclopropyl)methanone

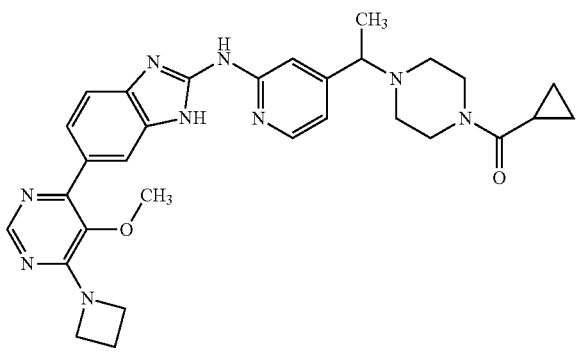 [SMILES: COc1c(-c2ccc3nc(Nc4cc(C(C)N5CCN(C(=O)C6CC6)CC5)ccn4)[nH]c3c2)ncnc1N1CCC1]

To a stirred solution of 6-[6-(azetidin-1-yl)-5-methoxypyrimidin-4-yl]-N-{4-[(1R or 1S)-1-(piperazin-1-yl)ethyl]pyridin-2-yl}-1H-benzimidazol-2-amine hydrochloride (100 mg, see Compound 111.01) in DMF (2.0 mL) was added sodium bicarbonate (76.2 mg), cyclopropanecarboxylic acid (19 μl, 95% purity) and HATU (92.0 mg). The mixture was stirred at r.t. for 16 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40 mg of the title compound.

LC-MS (Method 2): $R_t$=1.11 min; MS (ESIpos): m/z=554 [M+H]$^+$.

$^1$H-NMR (400 MHz, DMSO-d6) δ[ppm]: 0.641 (0:66), 0.653 (1.96), 0.660 (4.31), 0.665 (3.08), 0.673 (2.42), 0.679 (5.21), 0.684 (4.77), 0.689 (5.09), 0.696 (4.68), 0.701 (5.34), 0.708 (2.73), 0.720 (0.67), 1.288 (8.19), 1.305 (8.47), 1.895 (0.52), 1.908 (1.04), 1.914 (1.20), 1.927 (1.89), 1.939 (1.14), 1.946 (1.02), 1.958 (0.48), 2.309 (1.73), 2.327 (3.08), 2.347 (3.87), 2.367 (3.36), 2.385 (2.38), 2.444 (1.31), 2.611 (2.50), 3.402 (10.90), 3.425 (1.65), 3.442 (3.21), 3.459 (4.31), 3.668 (2.33), 4.205 (4.58), 4.224 (7.78), 4.242 (4.57), 6.947 (2.80), 6.960 (2.85), 7.166 (3.38), 7.388 (0.77), 7.397 (0.74), 7.685 (0.41), 7.792 (0.67), 8.247 (0.94), 8.260 (4.27), 8.276 (16.00), 8.281 (2.76), 10.709 (0.73), 12.263 (0.75).

Example 111.03

1-(4-{(1R or 1S)-1-[2-({6-[6-(azetidin-1-yl)-5-methoxypyrimidin-4-yl]-1H-benzimidazol-2-yl}amino)pyridin-4-yl]ethyl}piperazin-1-yl)-3,3,3-trifluoropropan-1-one

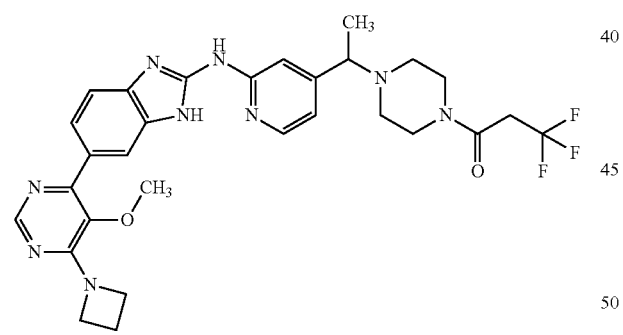

To a stirred solution of 6-[6-(azetidin-1-yl)-5-methoxypyrimidin-4-yl]-N-{4-[(1R or 1S)-1-(piperazin-1-yl)ethyl]pyridin-2-yl}-1H-benzimidazol-2-amine hydrochloride (100 mg, see Compound 111.01) in DMF (2.0 mL) was added sodium bicarbonate (76.2 mg), 3,3,3-trifluoropropanoic acid (20 μl) and HATU (92.0 mg). The mixture was stirred at r.t. for 16 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40 mg of the title compound.

LC-MS (Method 2): $R_t$=1.16 min; MS (ESIpos): m/z=596 [M+H]$^+$.

$^1$H-NMR (400 MHz, DMSO-d6) δ[ppm]: 1.287 (5.08), 1.303 (5.19), 2.327 (2.64), 2.346 (3.39), 2.365 (2.69), 2.426 (1.69), 3.401 (16.00), 3.422 (2.80), 3.434 (3.50), 3.445 (2.77), 3.465 (3.33), 3.480 (3.91), 3.576 (1.00), 3.603 (2.63), 3.630 (2.49), 3.658 (0.86), 4.014 (0.64), 4.206 (2.96), 4.224 (4.97), 4.242 (2.95), 6.943 (1.83), 6.956 (1.86), 7.164 (3.03), 7.436 (0.76), 7.455 (0.85), 7.765 (1.22), 7.785 (1.12), 8.152 (0.55), 8.262 (2.62), 8.279 (7.81).

Example 112.01 tert-butyl 4-{(1R or S)-1-[2-({6-[5-methoxy-6-(pyrrolidin-1-yl)pyrimidin-4-yl]-1H-benzimidazol-2-yl}amino)pyridin-4-yl]ethyl}piperazine-1-carboxylate

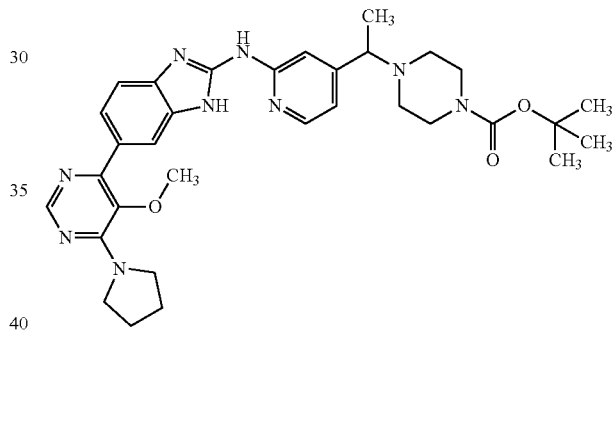

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (250 mg, see Example 83.01) in 2-propanol (10 ml) in a microwave tube was added pyrrolidine (180 μl). The mixture was stirred at 100° C. for 30 minutes. The mixture was concentrated in vacuum. Silicagel chromatography gave 230 mg of the title compound.

LC-MS (Method 2): $R_t$=1.36 min; MS (ESIneg): m/z=598 [M−H]$^-$.

$^1$H-NMR (400 MHz, DMSO-d6) δ[ppm]: 0.814 (1.19), 0.831 (2.77), 0.836 (1.15), 0.840 (1.22), 0.852 (1.59), 0.858 (3.23), 0.870 (0.77), 0.875 (0.98), 0.936 (1.14), 0.953 (1.19), 1.238 (1.71), 1.244 (1.64), 1.279 (2.08), 1.296 (1.91), 1.377 (16.00), 1.395 (1.40), 1.902 (0.69), 1.919 (1.86), 1.935 (0.71), 2.311 (0.48), 2.323 (0.51), 2.327 (0.54), 2.385 (0.46), 2.518 (1.25), 2.523 (0.86), 3.435 (0.45), 3.452 (0.43), 3.657 (0.70), 3.673 (1.69), 3.688 (0.67), 5.759 (0.74), 6.932 (0.54), 6.945 (0.55), 7.154 (0.50), 8.253 (0.68), 8.266 (0.65), 8.276 (3.34).

Example 112.02 cyclopropyl(4-{(1R or 1S)-1-[2-({6-[5-methoxy-6-(pyrrolidin-1-yl)pyrimidin-4-yl]-1H-benzimidazol-2-yl}amino)pyridin-4-yl]ethyl}piperazin-1-yl)methanone

Example 112.03

3,3,3-trifluoro-1-(4-{(1R or 1S)-1-[2-({6-[5-methoxy-6-(pyrrolidin-1-yl)pyrimidin-4-yl]-1H-benzimidazol-2-yl}amino)pyridin-4-yl]ethyl}piperazin-1-yl)propan-1-one

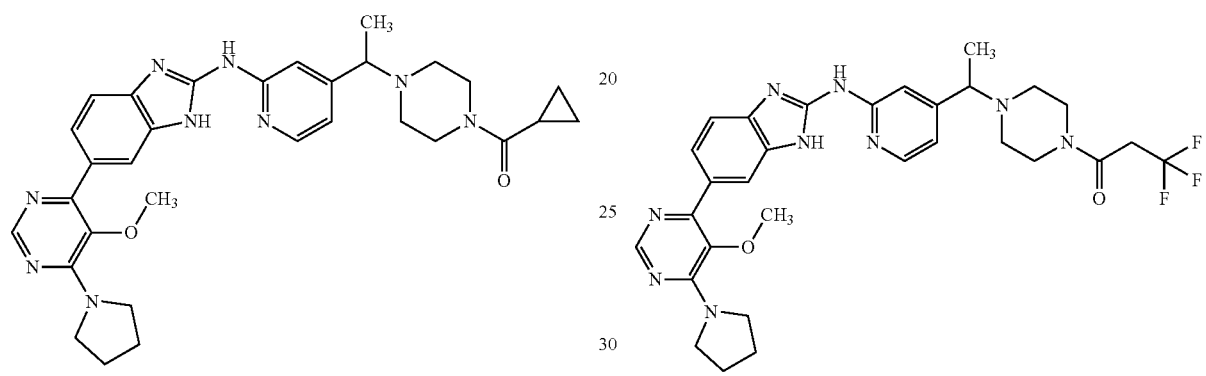

To a stirred solution of 6-[5-methoxy-6-(pyrrolidin-1-yl)pyrimidin-4-yl]-N-{4-[(1R or 1S)-1-(piperazin-1-yl)ethyl]pyridin-2-yl}-1H-benzimidazol-2-amine hydrochloride (120 mg, see compound 112.01) in DMF (2.0 mL) was added sodium bicarbonate (89.4 mg), cyclopropanecarboxylic acid (22 µl, 95% purity) and HATU (108 mg). The mixture was stirred at r.t. for 16 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40.0 mg of the title compound.

LC-MS (Method 2): $R_t$=1.19 min; MS (ESIpos): m/z=568 [M+H]$^+$.

$^1$H-NMR (400 MHz, DMSO-d6) δ[ppm]: 0.630 (0.84), 0.642 (2.34), 0.649 (4.48), 0.662 (2.73), 0.669 (5.28), 0.683 (4.84), 0.690 (5.07), 0.694 (5.71), 0.701 (3.07), 0.714 (0.79), 1.031 (1.03), 1.048 (2.18), 1.066 (1.09), 1.277 (9.35), 1.293 (9.47), 1.903 (11.77), 1.910 (8.24), 1.919 (5.46), 1.941 (0.90), 2.298 (1.16), 2.322 (0.96), 2.327 (0.93), 2.380 (1.82), 2.425 (1.57), 2.605 (0.92), 3.322 (13.30), 3.393 (0.53), 3.412 (1.24), 3.428 (3.32), 3.445 (4.32), 3.460 (3.33), 3.661 (11.85), 6.934 (3.27), 6.948 (3.32), 7.168 (4.01), 7.380 (0.60), 7.392 (0.65), 7.691 (0.50), 7.752 (0.71), 8.196 (0.61), 8.255 (4.53), 8.269 (5.17), 8.272 (16.00), 10.720 (1.21), 12.259 (0.77).

To a stirred solution of 6-[5-methoxy-6-(pyrrolidin-1-yl)pyrimidin-4-yl]-N-{4-[(1R or 1S)-1-(piperazin-1-yl)ethyl]pyridin-2-yl}-1H-benzimidazol-2-amine hydrochloride (120 mg, see Compound 112.01) in DMF (2.0 mL) was added sodium bicarbonate (89.4 mg), 3,3,3-trifluoropropanoic acid (23 µl) and HATU (108 mg). The mixture was stirred at r.t. for 16 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40.0 mg of the title compound.

LC-MS (Method 2): $R_t$=1.22 min; MS (ESIpos): m/z=610 [M+H]$^+$.

$^1$H-NMR (400 MHz, DMSO-d6) δ[ppm]: 1.035 (1.37), 1.052 (2.69), 1.070 (1.43), 1.280 (6.63), 1.297 (6.77), 1.890 (2.99), 1.907 (7.86), 1.922 (3.31), 2.307 (0.78), 2.321 (1.40), 2.333 (1.74), 2.345 (1.62), 2.359 (1.35), 2.414 (2.01), 2.423 (1.79), 2.442 (1.28), 3.326 (16.00), 3.418 (3.12), 3.430 (4.73), 3.450 (3.59), 3.468 (4.27), 3.573 (1.26), 3.601 (3.47), 3.628 (3.53), 3.666 (7.28), 4.012 (0.60), 6.933 (2.35), 6.946 (2.37), 7.167 (3.70), 7.442 (0.45), 7.734 (0.77), 8.260 (3.51), 8.278 (11.47).

Example 113.01 tert-butyl 4-{(1R or 1S)-1-[2-({6-[6-(3,3-difluoro-azetidin-1-yl)-5-methoxypyrimidin-4-yl]-1H-benz-imidazol-2-yl}amino)pyridin-4-yl]ethyl}piperazine-1-carboxylate

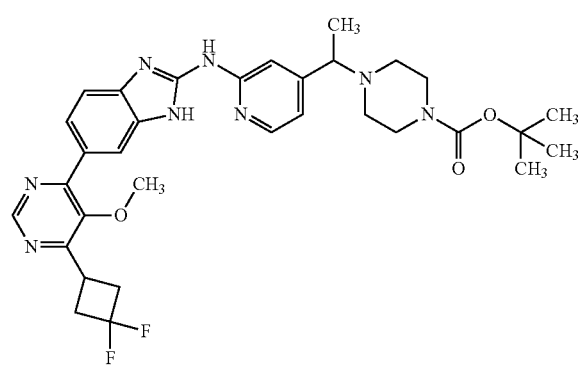 [SMILES: COc1c(-c2ccc3nc(Nc4cc(C(C)N5CCN(C(=O)OC(C)(C)C)CC5)ccn4)[nH]c3c2)ncnc1C1CC(F)(F)C1]

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (225 mg, see Example 83.01) in 2-propanol (9.0 ml) in a microwave tube was added 3,3-difluoroazetidine hydrochloride (516 mg) and N,N-diisopropylethylamine (690 µl). The mixture was stirred at 90° C. for 16 h. The mixture was concentrated in vacuum. Silicagel chromatography followed by aminophase-silicagel chromatography gave 160 mg of the title compound.

LC-MS (Method 2): $R_t$=1.35 min; MS (ESIpos): m/z=622 [M+H]$^+$.

$^1$H-NMR (400 MHz, DMSO-d6) δ[ppm]: 1.154 (2.34), 1.172 (4.64), 1.190 (2.35), 1.278 (1.75), 1.295 (1.79), 1.377 (16.00), 1.987 (9.19), 2.297 (0.41), 2.310 (0.48), 2.322 (0.44), 2.327 (0.43), 2.385 (0.48), 2.396 (0.41), 2.518 (1.76), 2.523 (1.25), 3.437 (0.76), 3.454 (0.99), 3.469 (1.20), 3.999 (0.68), 4.017 (2.08), 4.035 (2.07), 4.053 (0.68), 4.590 (1.02), 4.622 (2.14), 4.653 (0.97), 6.938 (0.52), 6.951 (0.53), 7.149 (0.46), 8.258 (0.86), 8.271 (0.89), 8.404 (2.42).

Example 113.02

1-(4-{(1R or 1S)-1-[2-({6-[6-(3,3-difluoroazetidin-1-yl)-5-methoxypyrimidin-4-yl]-1H-benzimidazol-2-yl}amino)pyridin-4-yl]ethyl}piperazin-1-yl)-3,3,3-trifluoropropan-1-one

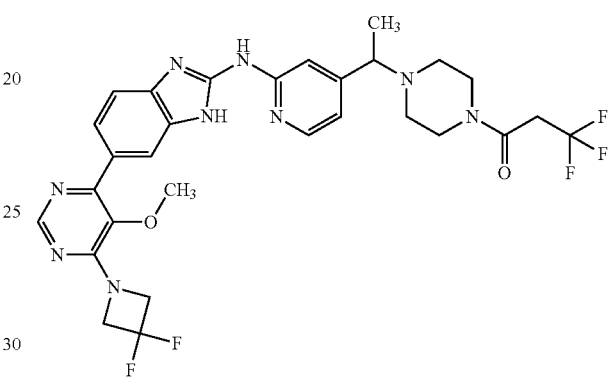

To a stirred solution of 6-[6-(3,3-difluoroazetidin-1-yl)-5-methoxypyrimidin-4-yl]-N-{4-[(1R or 1S)-1-(piperazin-1-yl)ethyl]pyridin-2-yl}-1H-benzimidazol-2-amine hydrochloride (80.0 mg, see Compound 113.01) in DMF (1.5 mL) was added sodium bicarbonate (57.5 mg), 3,3,3-trifluoropropanoic acid (15 µl) and HATU (69.4 mg). The mixture was stirred at r.t. for 3 h. An excess of water was added and the mixture was stirred for 15 minutes. A solid precipitated and was collected by filtration. Silicagel chromatography gave a solid that was triturated with pentane to give 50.0 mg of the title compound.

LC-MS (Method 2): $R_t$=1.19 min; MS (ESIpos): m/z=632 [M+H]$^+$.

$^1$H-NMR (400 MHz, DMSO-d6) δ [ppm]: 0.839 (5.09), 0.857 (11.22), 0.874 (4.50), 1.232 (3.09), 1.237 (3.03), 1.253 (2.75), 1.270 (2.91), 1.295 (9.28), 1.311 (9.09), 1.377 (2.53), 1.395 (10.84), 2.327 (3.09), 2.331 (3.03), 2.433 (2.75), 2.523 (5.81), 2.669 (1.84), 3.439 (6.00), 3.460 (16.00), 3.580 (1.97), 3.608 (5.41), 3.635 (5.19), 3.662 (1.66), 4.591 (6.28), 4.623 (12.75), 4.653 (5.75), 6.953 (3.25), 6.965 (3.22), 7.165 (4.31), 7.433 (0.53), 7.823 (0.75), 8.270 (5.28), 8.283 (5.00), 8.406 (15.00), 10.730 (1.37), 12.298 (0.78).

Example 113.03 cyclopropyl(4-{(1R or 1S)-1-[2-({6-[6-(3,3-difluoroazetidin-1-yl)-5-methoxypyrimidin-4-yl]-1H-benzimidazol-2-yl}amino)pyridin-4-yl]ethyl}piperazin-1-yl)methanone

Example 114.01 tert-butyl 4-{(1R or 1S)-1-[2-({6-[6-(cyclobutylamino)-5-methoxypyrimidin-4-yl]-1H-benzimidazol-2-yl}amino)pyridin-4-yl]ethyl}piperazine-1-carboxylate

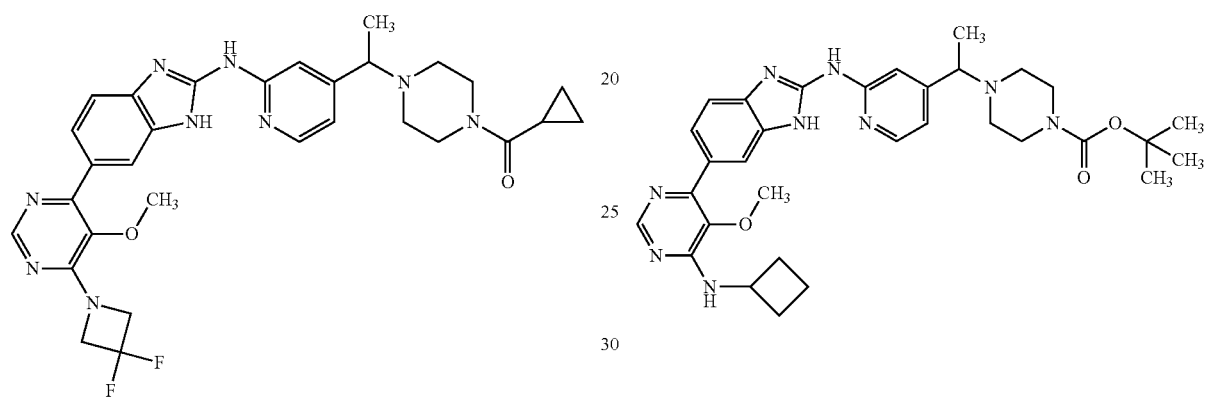

To a stirred solution of 6-[6-(3,3-difluoroazetidin-1-yl)-5-methoxypyrimidin-4-yl]-N-{4-[(1R or 1S)-1-(piperazin-1-yl)ethyl]pyridin-2-yl}-1H-benzimidazol-2-amine hydrochloride (80.0 mg, see Compound 113.01) in DMF (1.5 mL) was added sodium bicarbonate (57.5 mg), cyclopropanecarboxylic acid (14 µl, 95% purity) and HATU (69.4 mg). The mixture was stirred at r.t. for 3 h. Water was added, the mixture was stirred for 15 minutes and the mixture was filtered. The solution was directly used for preparative reverse phase HPLC purification.

Preparative reverse phase HPLC (gradient of water and acetonitrile containing ammonia as additive) gave 40.0 mg of the title compound.

LC-MS (Method 2): $R_t$=1.16 min; MS (ESIpos): m/z=590 [M+H]$^+$.

$^1$H-NMR (400 MHz, DMSO-d6) δ[ppm]: 0.653 (1.04), 0.660 (2.29), 0.665 (1.47), 0.672 (1.17), 0.679 (2.77), 0.684 (2.30), 0.689 (2.50), 0.697 (2.36), 0.701 (2.73), 0.708 (1.32), 1.292 (4.51), 1.309 (4.60), 1.909 (0.57), 1.916 (0.62), 1.928 (1.01), 1.940 (0.58), 1.947 (0.53), 2.318 (0.49), 2.322 (0.52), 2.326 (0.52), 2.331 (0.43), 2.394 (0.77), 2.450 (0.61), 2.518 (0.72), 2.523 (0.45), 3.429 (0.69), 3.446 (1.95), 3.458 (16.00), 3.493 (0.65), 3.668 (1.10), 4.589 (2.68), 4.620 (5.66), 4.651 (2.48), 6.942 (1.47), 6.944 (1.47), 6.955 (1.49), 6.958 (1.50), 7.247 (0.62), 7.449 (0.56), 7.468 (0.61), 7.787 (0.83), 7.807 (0.74), 8.257 (2.41), 8.271 (2.27), 8.402 (9.17).

To a stirred solution of tert-butyl 4-[(1R or S)-1-(2-{[6-(6-chloro-5-methoxypyrimidin-4-yl)-1H-benzimidazol-2-yl]amino}pyridin-4-yl)ethyl]piperazine-1-carboxylate (300 mg, see Example 83.01) in 2-propanol (10 ml) in a microwave tube was added cyclobutanamine (227 mg). The mixture was stirred at 90° C. for 2 h. Further cyclo butanamine (115 mg) was added and the mixture was stirred at 90° C. for 5 h. The mixture was concentrated in vacuum. Silicagel chromatography gave 320 mg of the title compound that was used without further purification.

LC-MS (Method 2): $R_t$=1.37 min; MS (ESIpos): m/z=600 [M+H]$^+$.

$^1$H-NMR (400 MHz, DMSO-d6) δ[ppm]: 0.989 (0.40), 1.005 (0.43), 1.278 (1.52), 1.295 (1.41), 1.370 (5.88), 1.376 (13.86), 2.248 (0.46), 2.269 (0.52), 2.277 (0.45), 2.282 (0.44), 2.295 (0.43), 2.311 (0.43), 2.322 (0.42), 2.326 (0.43), 2.385 (0.44), 2.518 (1.14), 2.522 (0.75), 3.436 (0.53), 3.452 (0.81), 3.468 (0.82), 5.758 (16.00), 6.932 (0.40), 6.946 (0.41), 7.154 (0.69), 7.378 (0.41), 8.237 (1.77), 8.260 (0.73), 8.274 (0.69).

The Example compounds in the following table 11 were synthesized in analogy to the preparation of Example 117.02, followed by purification by preparative reverse phase HPLC or silicagel chromatography.

TABLE 11

Structure
IUPAC-Name
LC-MS (method): Retention time; Mass found
¹H-NMR
Example                Starting materials (SM):

Example 114.02

1-(4-{(1R or 1S)-1-[2-({6-[6-(cyclobutylamino)-5-methoxypyrimidin-4-yl]-
1H-benzimidazol-2-yl}amino)pyridin-4-yl]ethyl}piperazin-1-yl)-3,3,3-
trifluoropropan-1-one
LC-MS (Method 2): R$_t$ = 1.19 min; MS (ESIpos): m/z = 609.7 [M + H]$^+$
¹H-NMR (400 MHz, DMSO-d6) δ [ppm]: 1.292 (12.16), 1.309 (12.33), 1.624 (0.80), 1.643 (1.57), 1.651 (1.31), 1.662 (1.68), 1.669 (2.85), 1.676 (1.77), 1.686 (2.70), 1.706 (1.54), 1.714 (1.51), 2.084 (0.60), 2.112 (1.99), 2.135 (3.10), 2.160 (2.22), 2.183 (0.68), 2.223 (1.17), 2.229 (1.48), 2.249 (3.27), 2.255 (2.45), 2.269 (2.85), 2.288 (1.11), 2.296 (0.91), 2.318 (1.74), 2.323 (2.19), 2.327 (3.30), 2.332 (3.25), 2.345 (2.59), 2.353 (2.42), 2.368 (2.14), 2.419 (2.76), 2.428 (2.88), 2.456 (1.79), 2.469 (1.05), 2.518 (6.95), 2.523 (4.98), 2.533 (0.80), 2.539 (2.76), 2.665 (1.20), 2.669 (1.71), 2.673 (1.22), 2.678 (0.57), 3.345 (0.80), 3.438 (7.35), 3.449 (7.54), 3.468 (11.67), 3.483 (8.97), 3.579 (2.28), 3.607 (6.46), 3.634 (6.12), 3.661 (1.91), 4.017 (0.77), 4.537 (1.08), 4.558 (2.08), 4.578 (2.02), 4.598 (1.08), 6.930 (3.59), 6.943 (3.59), 6.956 (3.67), 7.164 (5.41), 7.359 (3.44), 7.378 (3.81), 7.549 (0.54), 7.712 (0.54), 7.807 (1.02), 7.826 (0.88), 7.990 (0.80), 8.224 (1.79), 8.238 (16.00), 8.270 (6.63), 8.283 (6.23), 10.681 (1.40), 12.217 (1.85).
SM: Compound 114.01 and 3,3,3-trifluoropropanoic acid Example 114.03

(4-{(1R or 1S)-1-[2-({6-[6-(cyclobutylamino)-5-methoxypyrimidin-4-yl]-1H-
benzimidazol-2-yl}amino)pyridin-4-yl]ethyl}piperazin-1-
yl)(cyclopropyl)methanone
LC-MS (Method 2): R$_t$ = 1.15 min; MS (ESIpos): m/z = 567.7 [M + H]$^+$
¹H-NMR (400 MHz, DMSO-d6) δ [ppm]: 0.645 (0.63), 0.656 (1.95), 0.664 (4.70), 0.669 (2.87), 0.677 (2.24), 0.684 (5.73), 0.691 (5.36), 0.699 (4.56), 0.703 (5.25), 0.711 (2.44), 0.724 (0.60), 1.297 (8.86), 1.313 (8.89), 1.624 (0.57), 1.643 (1.15), 1.650 (1.00), 1.662 (1.29), 1.669 (2.15), 1.676 (1.35), 1.686 (2.04), 1.713 (1.15), 1.905 (0.57), 1.917 (1.12), 1.924 (1.20), 1.936

TABLE 11-continued

| Example | Structure<br>IUPAC-Name<br>LC-MS (method): Retention time; Mass found<br>¹H-NMR<br>Starting materials (SM): |
|---|---|
| | (2.01), 1.948 (1.15), 1.955 (1.03), 1.968 (0.49), 2.084 (0.57), 2.107 (1.63), 2.113 (1.66), 2.135 (2.49), 2.160 (1.81), 2.183 (0.60), 2.223 (0.89), 2.229 (1.15), 2.248 (2.52), 2.255 (1.86), 2.269 (2.32), 2.288 (1.35), 2.295 (1.15), 2.318 (1.41), 2.322 (1.95), 2.327 (2.41), 2.332 (1.86), 2.399 (1.43), 2.518 (6.74), 2.523 (4.70), 2.539 (1.81), 2.616 (0.57), 2.665 (1.23), 2.669 (1.78), 2.673 (1.26), 3.461 (16.00), 3.677 (2.06), 4.537 (0.86), 4.557 (1.63), 4.578 (1.61), 4.598 (0.83), 6.946 (2.64), 6.960 (2.67), 7.206 (0.80), 7.355 (2.98), 7.375 (2.98), 7.772 (0.69), 8.236 (12.90), 8.265 (4.30), 8.278 (4.01), 12.230 (0.40).<br>SM: Compound 114.01 and cyclopropanecarboxylic acid |

Example 115.01 tert-butyl 4-{(1R or 1S)-1-[2-({6-[6-(azetidin-1-yl)pyrimidin-4-yl]-1H-benzimidazol-2-yl}amino)pyridin-4-yl]ethyl}piperazine-1-carboxylate

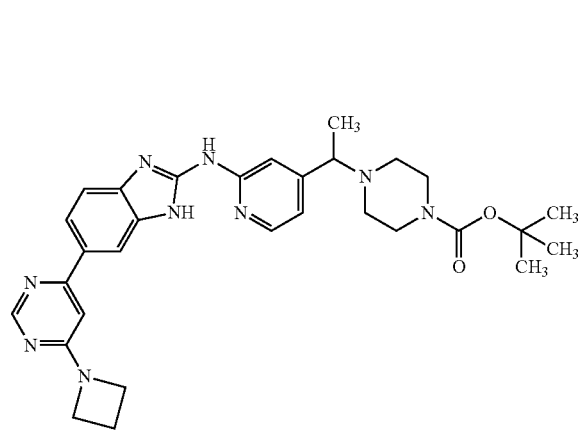 [SMILES: CC(c1ccnc(Nc2nc3ccc(-c4cc(N5CCC5)ncn4)cc3[nH]2)c1)N1CCN(C(=O)OC(C)(C)C)CC1]

To a stirred solution of tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (440 mg, see Example 85.01) in 2-propanol (6.0 ml) in a microwave tube was added azetidine (235 mg). The mixture was stirred at 90° C. for 30 minutes. Upon cooling to r.t. a solid precipitated, was collected by filtration and was washed with ethanol to give 130 mg of the title compound.

LC-MS (Method 2): $R_t$=1.25 min; MS (ESIpos): m/z=556 [M+H]⁺.

¹H-NMR (400 MHz, DMSO-d6) δ [ppm]: 1.277 (1.72), 1.293 (1.76), 1.376 (16.00), 2.308 (0.46), 2.369 (0.63), 2.386 (0.93), 2.406 (0.70), 2.518 (1.32), 2.522 (0.92), 3.433 (0.44), 3.449 (0.43), 4.079 (1.20), 4.098 (1.95), 4.116 (1.18), 6.937 (0.45), 6.950 (0.46), 7.163 (0.85), 8.254 (0.98), 8.266 (0.95), 8.492 (1.56), 8.494 (1.66).

Example 115.02

1-(4-{(1R or 1S)-1-[2-({6-[6-(azetidin-1-yl)pyrimidin-4-yl]-1H-benzimidazol-2-yl}amino)pyridin-4-yl]ethyl}piperazin-1-yl)-3,3,3-trifluoropropan-1-one

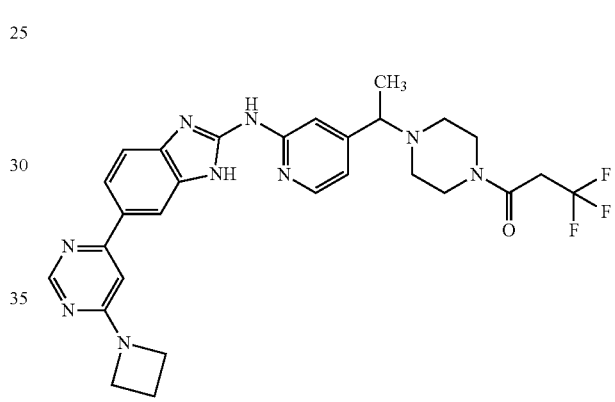

To a stirred solution of 6-[6-(azetidin-1-yl)pyrimidin-4-yl]-N-{4-[(1R or 1S)-1-(piperazin-1-yl)ethyl]pyridin-2-yl}-1H-benzimidazol-2-amine hydrochloride (90.0 mg, see Compound 115.01) in DMF (1.9 mL) was added sodium bicarbonate (72.3 mg), 3,3,3-trifluoropropanoic acid (19 μl) and HATU (87.2 mg). The mixture was stirred at r.t. for 16 h. An excess of water was added and the mixture was stirred for 15 minutes. A solid precipitated and was collected by filtration. Silicagel chromatography gave a solid that was triturated with ethanol to give 55.0 mg of the title compound.

LC-MS (Method 2): $R_t$=1.10 min; MS (ESIpos): m/z=566 [M+H]⁺.

¹H-NMR (400 MHz, DMSO-d6) δ [ppm]: 1.291 (14.31), 1.307 (14.45), 2.327 (4.38), 2.332 (3.76), 2.336 (3.34), 2.350 (3.86), 2.368 (5.17), 2.387 (4.86), 2.407 (4.72), 2.416 (4.21), 2.427 (4.72), 2.456 (2.17), 2.518 (10.00), 2.523 (6.52), 2.548 (0.72), 2.665 (1.48), 2.669 (2.07), 2.673 (1.48), 3.424 (3.76), 3.436 (6.76), 3.448 (4.97), 3.466 (6.93), 3.482 (8.97), 3.579 (2.66), 3.606 (7.62), 3.634 (7.14), 3.661 (2.24), 4.079 (9.93), 4.098 (16.00), 4.116 (9.52), 6.755 (2.24), 6.844 (1.41), 6.947 (3.28), 6.960 (3.34), 7.174 (6.41), 7.373 (1.24), 7.394 (1.38), 7.528 (0.79), 7.547 (0.83), 7.853 (2.21), 7.874 (1.41), 8.114 (1.38), 8.262 (7.93), 8.276 (8.07), 8.492 (13.03), 8.495 (13.86), 10.689 (1.24), 10.722 (1.97), 12.208 (1.66), 12.257 (2.48).

Example 115.03

(4-{(1R or 1S)-1-[2-({6-[6-(azetidin-1-yl)pyrimidin-4-yl]-1H-benzimidazol-2-yl}amino)pyridin-4-yl]ethyl}piperazin-1-yl)(cyclopropyl)methanone

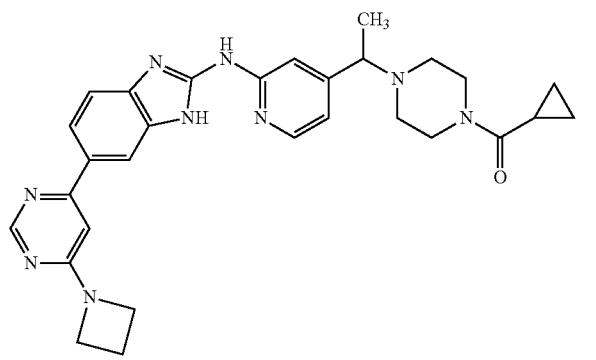 [SMILES: CC(c1ccnc(Nc2nc3ccc(-c4cc(N5CCC5)ncn4)cc3[nH]2)c1)N1CCN(C(=O)C2CC2)CC1]

To a stirred solution of 6-[6-(azetidin-1-yl)pyrimidin-4-yl]-N-{4-[(1R or 1S)-1-(piperazin-1-yl)ethyl]pyridin-2-yl}-1H-benzimidazol-2-amine trihydrochloride (60.0 mg, see Compound 115.01) in DMF (1.2 mL) was added sodium bicarbonate (45.5 mg), cyclopropanecarboxylic acid (11 µl, 95% purity) and HATU (54.9 mg). The mixture was stirred at r.t. for 16 h. Further sodium bicarbonate (45.5 mg), cyclopropanecarboxylic acid (11 µl, 95% purity) and HATU (54.9 mg) were added and the mixture was stirred at r.t. for 24 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 10.0 mg of the title compound.

LC-MS (Method 2): $R_t$=1.03 min; MS (ESIpos): m/z=524 [M+H]$^+$.

$^1$H-NMR (500 MHz, DMSO-d6) δ[ppm]: 0.644 (1.40), 0.653 (3.45), 0.659 (6.53), 0.664 (5.24), 0.669 (3.49), 0.675 (7.33), 0.679 (3.66), 0.686 (4.45), 0.690 (6.54), 0.696 (7.02), 0.700 (7.79), 0.705 (4.58), 0.715 (1.21), 1.053 (0.42), 1.221 (0.45), 1.288 (14.84), 1.302 (15.06), 1.754 (0.77), 1.897 (0.93), 1.907 (1.84), 1.913 (2.01), 1.923 (3.19), 1.932 (1.84), 1.938 (1.71), 1.948 (0.81), 2.303 (1.36), 2.352 (2.23), 2.366 (4.82), 2.382 (6.73), 2.397 (5.27), 2.412 (2.69), 2.448 (1.53), 2.514 (1.28), 2.518 (1.22), 2.522 (0.98), 2.612 (0.45), 2.635 (0.43), 3.428 (1.47), 3.442 (4.50), 3.455 (5.86), 3.468 (3.94), 3.663 (3.26), 4.079 (10.01), 4.094 (16.00), 4.109 (9.56), 6.762 (0.75), 6.827 (0.47), 6.951 (3.96), 6.960 (3.97), 7.179 (7.11), 7.394 (0.58), 7.848 (2.06), 7.864 (1.89), 8.263 (8.19), 8.273 (7.77), 8.493 (13.25), 8.495 (13.53), 10.724 (1.18), 12.269 (0.83).

Example 116.01 tert-butyl 4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazine-1-carboxylate

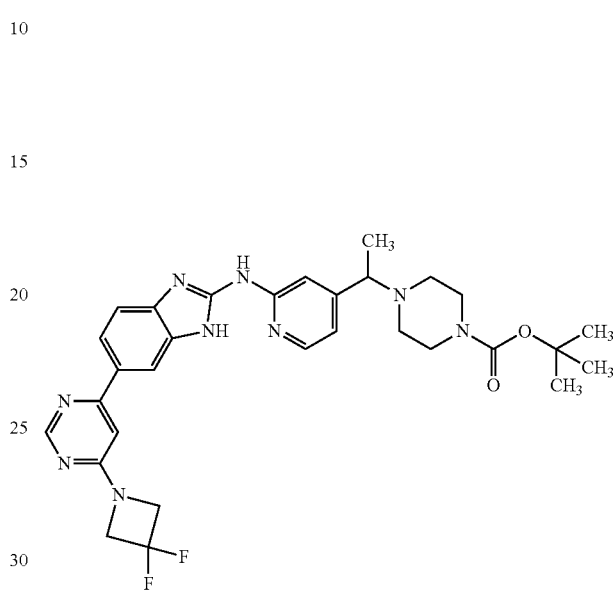

To a stirred solution of tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (270 mg, see Example 85.01) in 2-propanol (10 ml) in a microwave tube was added 3,3-difluoroazetidine hydrochloride (392 mg) and N,N-diisopropylethylamine (880 µl). The mixture was stirred at 90° C. for 16 h. The mixture was concentrated in vacuum. Silicagel chromatography gave 270 mg of the title compound.

LC-MS (Method 2): $R_t$=1.31 min; MS (ESIpos): m/z=592 [M+H]$^+$.

$^1$H-NMR (400 MHz, DMSO-d6) δ[ppm]: 0.990 (1.50), 1.006 (1.45), 1.090 (0.52), 1.106 (0.50), 1.132 (0.48), 1.149 (0.49), 1.229 (0.46), 1.279 (1.69), 1.295 (1.66), 1.377 (16.00), 1.729 (0.46), 1.763 (0.45), 1.979 (0.58), 2.084 (0.42), 2.310 (0.43), 2.384 (0.41), 2.518 (0.72), 2.523 (0.48), 3.436 (0.42), 3.453 (0.41), 3.797 (0.41), 4.529 (1.04), 4.561 (2.23), 4.592 (0.97), 5.759 (2.60), 6.942 (0.41), 6.954 (0.41), 7.170 (0.68), 8.259 (0.89), 8.272 (0.84), 8.618 (1.61), 8.620 (1.61).

807

Example 116.02 cyclopropyl(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)methanone

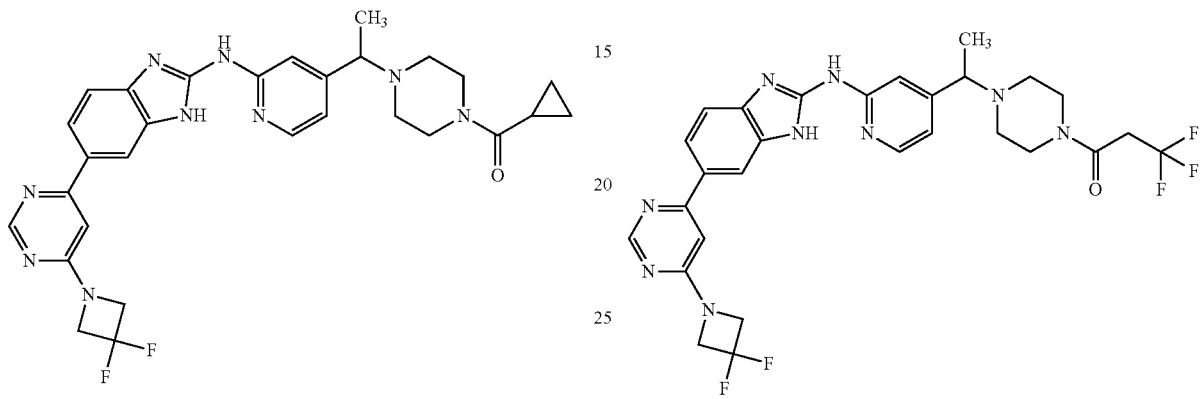

To a stirred solution of 6-[6-(3,3-difluoroazetidin-1-yl)pyrimidin-4-yl]-N-{4-[(1R or 1S)-1-(piperazin-1-yl)ethyl]pyridin-2-yl}-1H-benzimidazol-2-amine trihydrochloride (100 mg, see Compound 116.01) in DMF (2.1 mL) was added sodium bicarbonate (78.8 mg), cyclopropanecarboxylic acid (20 μl, 95% purity) and HATU (95.2 mg). The mixture was stirred at r.t. for 3 h. An excess of water was added and the mixture was stirred for 15 minutes. A solid precipitated and was collected by filtration. Silicagel chromatography gave a solid that was triturated with cyclopentyl methyl ether to give 50.0 mg of the title compound.

LC-MS (Method 2): $R_t$=1.10 min; MS (ESIpos): m/z=560 [M+H]$^+$.

$^1$H-NMR (400 MHz, DMSO-d6) δ[ppm]: 0.644 (0.81), 0.656 (2.79), 0.663 (6.29), 0.683 (7.79), 0.687 (7.07), 0.691 (7.51), 0.699 (6.67), 0.703 (7.48), 0.710 (3.66), 0.723 (0.91), 1.294 (11.64), 1.311 (11.91), 1.903 (0.70), 1.915 (1.48), 1.922 (1.67), 1.934 (2.67), 1.946 (1.58), 1.953 (1.43), 1.966 (0.64), 2.322 (1.88), 2.326 (2.01), 2.395 (2.28), 2.616 (0.68), 2.668 (0.92), 2.673 (0.72), 3.144 (1.45), 3.434 (1.42), 3.450 (4.31), 3.467 (5.75), 3.674 (3.18), 4.530 (7.67), 4.561 (16.00), 4.592 (7.16), 6.960 (3.30), 6.972 (3.34), 7.032 (1.18), 7.134 (0.86), 7.186 (5.09), 7.415 (0.83), 7.554 (0.59), 7.884 (2.83), 7.903 (2.61), 8.164 (0.81), 8.268 (6.18), 8.281 (5.84), 8.330 (1.11), 8.618 (10.05), 8.621 (10.38), 10.739 (1.42), 12.245 (1.10), 12.304 (1.45).

808

Example 116.03

1-(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)-3,3,3-trifluoropropan-1-one To a stirred solution of 6-[6-(3,3-difluoroazetidin-1-yl)pyrimidin-4-yl]-N-{4-[(1R or 1S)-1-(piperazin-1-yl)ethyl]pyridin-2-yl}-1H-benzimidazol-2-amine hydrochloride (100 mg, see Compound 116.01) in DMF (2.1 mL) was added sodium bicarbonate (78.8 mg), 3,3,3-trifluoropropanoic acid (21 μl) and HATU (95.2 mg). The mixture was stirred at r.t. for 3 h. An excess of water was added and the mixture was stirred for 15 minutes. A solid precipitated and was collected by filtration. Silicagel chromatography followed by aminophase-silicagel chromatography gave a solid that was triturated with a mixture of 2-propanol and cyclohexane to give 53.0 mg of the title compound.

LC-MS (Method 2): $R_t$=1.14 min; MS (ESIpos): m/z=602 [M+H]$^+$.

$^1$H-NMR (400 MHz, DMSO-d6) δ [ppm]: 1.027 (0.71), 1.042 (0.71), 1.292 (5.91), 1.308 (6.02), 1.394 (16.00), 2.327 (1.71), 2.343 (1.69), 2.365 (1.35), 2.417 (1.81), 2.428 (2.11), 2.442 (1.67), 2.457 (1.42), 2.669 (0.51), 3.437 (3.34), 3.448 (2.54), 3.468 (3.52), 3.483 (4.27), 3.579 (1.11), 3.606 (3.10), 3.634 (2.96), 3.661 (0.97), 4.530 (3.85), 4.561 (7.84), 4.592 (3.66), 6.951 (1.61), 6.963 (1.62), 7.031 (0.96), 7.137 (0.73), 7.180 (2.33), 7.400 (0.56), 7.419 (0.61), 7.553 (0.42), 7.571 (0.44), 7.882 (1.37), 7.903 (1.24), 8.163 (0.68), 8.267 (2.92), 8.280 (2.77), 8.331 (0.91), 8.620 (4.81), 10.712 (0.63), 10.744 (0.81), 12.240 (0.80), 12.300 (1.03).

Example 116.04

(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)[1-(trifluoromethyl)cyclopropyl]methanone

Example 117.01 tert-butyl 4-{(1R or 1S)-1-[2-({6-[6-(pyrrolidin-1-yl)pyrimidin-4-yl]-1H-benzimidazol-2-yl}amino)pyridin-4-yl]ethyl}piperazine-1-carboxylate

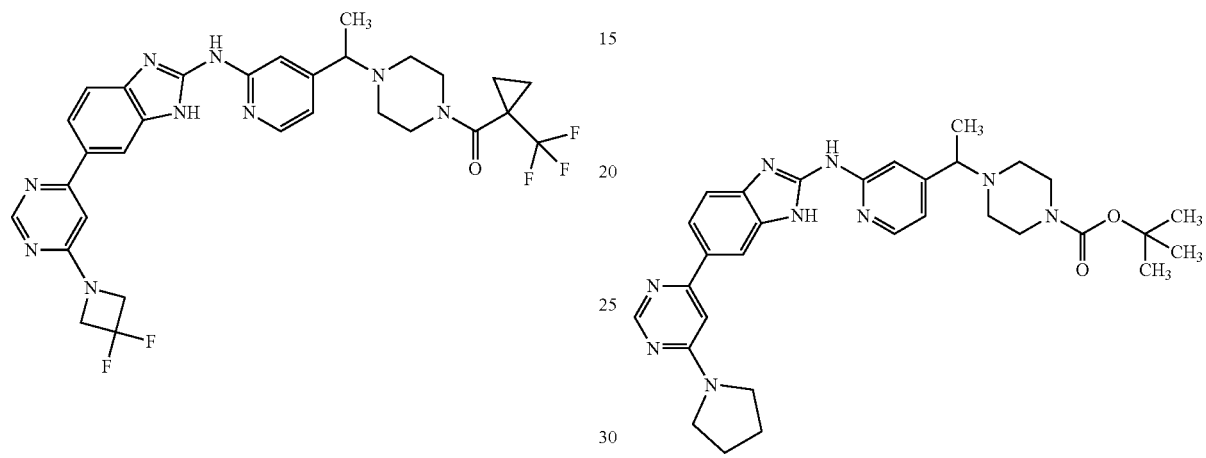

To a stirred solution of 6-[6-(3,3-difluoroazetidin-1-yl)pyrimidin-4-yl]-N-{4-[(1R or 1S)-1-(piperazin-1-yl)ethyl]pyridin-2-yl}-1H-benzimidazol-2-amine hydrochloride (80.0 mg, see Compound 116.01) in DMF (1.7 mL) was added sodium bicarbonate (63.1 mg), 1-(trifluoromethyl)cyclopropanecarboxylic acid (28.9 mg) and HATU (76.1 mg). The mixture was stirred at r.t. for 3 h. An excess of water was added and the mixture was stirred for 15 minutes. A solid precipitated and was collected by filtration. Preparative reverse phase HPLC (gradient of water and acetonitrile containing ammonia as additive) gave 55.0 mg of the title compound.

LC-MS (Method 2): $R_t$=1.19 min; MS (ESIpos): m/z=628 [M+H]$^+$.

$^1$H-NMR (400 MHz, DMSO-d6) δ [ppm]: 1.161 (5.70), 1.215 (0.89), 1.228 (0.54), 1.255 (3.26), 1.267 (7.13), 1.288 (12.83), 1.304 (11.49), 2.323 (1.40), 2.327 (2.16), 2.332 (1.99), 2.342 (1.99), 2.356 (2.40), 2.370 (2.79), 2.453 (2.85), 2.465 (2.61), 2.518 (4.58), 2.523 (3.15), 2.539 (9.98), 2.665 (0.84), 2.669 (1.23), 2.673 (0.89), 3.434 (0.89), 3.451 (2.85), 3.468 (2.83), 3.483 (0.97), 3.568 (3.93), 4.530 (7.51), 4.561 (16.00), 4.592 (6.80), 6.956 (2.55), 6.969 (2.61), 7.031 (1.60), 7.137 (1.14), 7.185 (4.08), 7.398 (0.89), 7.419 (0.95), 7.553 (0.67), 7.574 (0.69), 7.882 (2.18), 7.903 (1.92), 8.161 (1.10), 8.266 (6.11), 8.279 (5.79), 8.332 (1.51), 8.618 (11.90), 8.621 (11.88), 10.708 (0.89), 10.745 (1.17), 12.242 (1.17), 12.300 (1.58).

To a stirred solution of tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (300 mg, 561 μmol, see Example 85.01) in 2-propanol (10 ml) in a microwave tube was added pyrrolidine (280 μl). The mixture was stirred at 90° C. for 2 h. The mixture was concentrated in vacuum. Silicagel chromatography gave 250 mg of the title compound.

LC-MS (Method 2): $R_t$=1.31 min; MS (ESIpos): m/z=570 [M+H]$^+$.

$^1$H-NMR (400 MHz, DMSO-d6) δ[ppm]: 0.814 (0.76), 0.830 (1.79), 0.835 (0.64), 0.849 (0.73), 0.852 (0.77), 0.858 (0.68), 0.935 (0.51), 0.952 (0.54), 1.237 (0.44), 1.278 (1.73), 1.295 (1.72), 1.377 (16.00), 1.394 (0.85), 1.971 (0.59), 2.310 (0.44), 2.383 (0.44), 2.518 (0.64), 2.523 (0.44), 3.434 (0.45), 3.450 (0.47), 3.513 (0.62), 6.936 (0.49), 6.949 (0.44), 7.165 (0.89), 8.255 (0.94), 8.268 (0.89), 8.499 (1.63), 8.501 (1.60).

Example 117.02 cyclopropyl(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)methanone

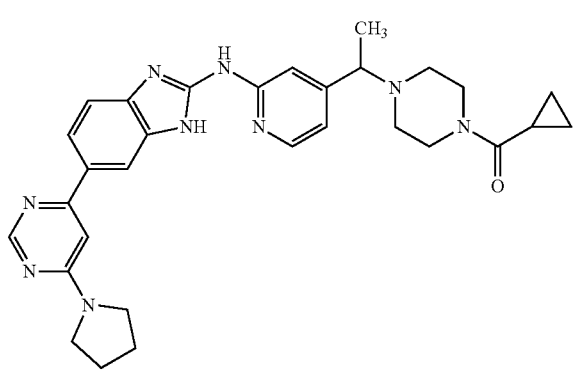 [SMILES: CC(c1ccnc(Nc2nc3ccc(-c4cc(N5CCCC5)ncn4)cc3[nH]2)c1)N1CCN(C(=O)C2CC2)CC1]

To a stirred solution of N-{4-[(1R or 1S)-1-(piperazin-1-yl)ethyl]pyridin-2-yl}-6-[6-(pyrrolidin-1-yl)pyrimidin-4-yl]-1H-benzimidazol-2-amine hydrochloride (100 mg, see Compound 117.01) in DMF (2.3 mL) was added sodium bicarbonate (87.1 mg), cyclopropanecarboxylic acid (22 µl, 95% purity) and HATU (105 mg). The mixture was stirred at r.t. for 16 h. An excess of water was added and the mixture was stirred for 15 minutes. A solid precipitated and was collected by filtration. Preparative reverse phase HPLC (gradient of water and acetonitrile containing ammonia as additive) gave 60.0 mg of the title compound.

LC-MS (Method 2): $R_t$=1.11 min; MS (ESIpos): m/z=538 [M+H]$^+$.

$^1$H-NMR (400 MHz, DMSO-d6) δ[ppm]: 0.642 (1.07), 0.653 (3.40), 0.661 (7.84), 0.666 (4.96), 0.674 (3.83), 0.681 (9.45), 0.686 (7.82), 0.690 (8.55), 0.698 (8.00), 0.702 (9.33), 0.709 (4.53), 0.722 (1.10), 1.069 (0.49), 1.225 (0.98), 1.291 (15.58), 1.307 (15.85), 1.409 (0.48), 1.897 (1.30), 1.909 (2.50), 1.917 (2.83), 1.929 (4.86), 1.934 (3.43), 1.941 (4.36), 1.948 (5.14), 1.960 (5.77), 2.318 (1.58), 2.323 (1.79), 2.327 (1.86), 2.332 (1.50), 2.390 (2.47), 2.450 (1.86), 2.518 (3.62), 2.523 (2.53), 2.540 (0.67), 2.665 (0.60), 2.669 (0.80), 2.674 (0.58), 3.428 (1.92), 3.444 (5.59), 3.461 (7.82), 3.477 (6.05), 3.509 (6.32), 3.669 (3.74), 6.868 (1.30), 6.920 (0.89), 6.952 (4.35), 6.964 (4.35), 7.183 (8.57), 7.403 (0.82), 7.544 (0.55), 7.865 (1.97), 8.137 (0.70), 8.264 (8.82), 8.277 (8.54), 8.299 (1.15), 8.499 (15.76), 8.502 (16.00), 10.710 (1.59), 12.216 (0.91), 12.257 (1.27).

Example 117.03

3,3,3-trifluoro-1-(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)propan-1-one

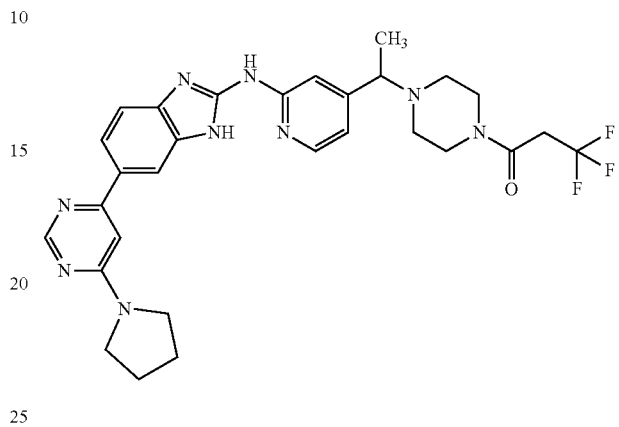

To a stirred solution of N-{4-[(1R or 1S)-1-(piperazin-1-yl)ethyl]pyridin-2-yl}-6-[6-(pyrrolidin-1-yl)pyrimidin-4-yl]-1H-benzimidazol-2-amine hydrochloride (100 mg, see Compound 117.01) in DMF (2.3 mL) was added sodium bicarbonate (87.1 mg), 3,3,3-trifluoropropanoic acid (23 µl) and HATU (105 mg). The mixture was stirred at r.t. for 16 h. An excess of water was added and the mixture was stirred for 15 minutes. A solid precipitated and was collected by filtration.

Preparative reverse phase HPLC (gradient of water and acetonitrile containing ammonia as additive) gave 25.0 mg of the title compound.

LC-MS (Method 2): $R_t$=1.14 min; MS (ESIpos): m/z=580 [M+H]$^+$.

$^1$H-NMR (400 MHz, DMSO-d6) δ[ppm]: 1.225 (0.69), 1.289 (15.12), 1.306 (15.29), 1.908 (0.87), 1.969 (5.59), 2.301 (0.81), 2.327 (3.36), 2.332 (2.84), 2.341 (3.28), 2.351 (3.08), 2.364 (2.67), 2.416 (3.51), 2.426 (3.77), 2.438 (2.86), 2.453 (2.20), 2.518 (3.32), 2.523 (2.30), 2.540 (2.86), 2.665 (0.56), 2.669 (0.80), 2.674 (0.55), 3.423 (4.20), 3.435 (7.28), 3.446 (5.80), 3.463 (7.71), 3.480 (11.72), 3.494 (8.33), 3.578 (3.11), 3.605 (7.94), 3.632 (7.36), 3.660 (2.35), 4.015 (1.68), 6.869 (1.34), 6.919 (0.97), 6.944 (4.34), 6.957 (4.23), 7.178 (8.19), 7.401 (0.85), 7.537 (0.57), 7.865 (2.03), 8.136 (0.74), 8.264 (8.47), 8.277 (8.22), 8.297 (1.16), 8.499 (15.22), 8.502 (16.00), 10.710 (1.55), 12.214 (0.92), 12.251 (1.29).

The Example compounds in the following table 12 were synthesized in analogy to the preparation of Example 117.02, followed by purification by preparative reverse phase HPLC or silicagel chromatography.

TABLE 12

| Example | Structure<br>IUPAC-Name<br>LC-MS (method): Retention time; Mass found<br>¹H-NMR<br>Starting materials (SM): |
|---|---|
| Example 117.04 | (4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)[1-(trifluoromethyl)cyclopropyl]methanone<br>LC-MS (Method 2): R$_t$ = 1.2 min; MS (ESIneg): m/z = 604 [M − H]⁻<br>¹H-NMR (400 MHz, DMSO-d6) δ [ppm]: 1.155 (7.52), 1.210 (1.07), 1.250 (4.04), 1.262 (9.32), 1.280 (16.00), 1.296 (14.34), 1.325 (0.57), 1.963 (5.51), 2.333 (2.75), 2.348 (3.23), 2.361 (3.73), 2.443 (3.77), 2.456 (3.26), 2.472 (2.66), 2.518 (1.25), 2.523 (0.86), 3.419 (2.63), 3.436 (5.06), 3.453 (5.18), 3.470 (3.41), 3.506 (6.35), 3.558 (6.21), 6.886 (7.37), 6.937 (4.90), 6.939 (4.86), 6.950 (4.87), 6.952 (4.86), 7.226 (3.99), 7.450 (1.82), 7.470 (1.92), 7.856 (4.54), 7.861 (4.50), 7.878 (3.94), 7.882 (4.04), 8.230 (2.71), 8.257 (8.34), 8.270 (7.49), 8.499 (12.90), 8.501 (13.02).<br>SM: Compound 117.01 and 1-(trifluoromethyl)cyclopropanecarboxylic acid |
| Example 117.05 | ((1RS)-2,2-difluorocyclopropyl)(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)methanone<br>LC-MS (Method 2): R$_t$ = 1.14 min; MS (ESIpos): m/z = 573.7 [M + H]⁺<br>¹H-NMR (400 MHz, DMSO-d6) δ [ppm]: 1.290 (15.79), 1.307 (16.00), 1.334 (0.60), 1.757 (0.67), 1.777 (1.13), 1.788 (1.66), 1.806 (1.91), 1.818 (1.95), 1.842 (1.47), 1.861 (1.98), 1.875 (2.57), 1.894 (2.64), 1.907 (2.24), 1.963 (6.55), 2.304 (1.63), 2.323 (2.14), 2.331 (2.36), 2.342 (2.15), 2.358 (2.78), 2.368 (2.22), 2.385 (1.33), 2.404 (0.85), 2.437 (3.91), 2.469 (0.87), 2.518 (1.58), 2.523 (1.22), 2.539 (1.31), 2.556 (1.20), 2.575 (0.80), 3.067 (1.53), 3.087 (1.75), 3.095 (2.04), 3.100 (2.05), 3.115 (1.86), 3.121 (2.13), 3.129 (1.79), 3.148 (1.54), 3.359 (4.87), 3.457 (5.15), 3.464 (5.77), 3.474 (6.68), 3.481 (8.06), 3.554 (4.26), 3.615 (2.65), 3.630 (2.19), 3.648 (1.47), 6.886 (8.77), 6.941 (5.56), 6.956 (5.57), 7.267 (2.87), 7.452 (2.29), 7.472 (2.44), 7.856 (5.25), 7.860 (5.18), 7.877 (4.54), 7.881 (4.66), 8.230 (3.55), 8.256 (9.02), 8.270 (8.18), 8.500 (14.73), 8.501 (14.96).<br>SM: Compound 117.01 and (1RS)-2,2-difluorocyclopropanecarboxylic acid |

TABLE 12-continued

Structure
IUPAC-Name
LC-MS (method): Retention time; Mass found
¹H-NMR

Example | Starting materials (SM):

Example 117.06

[(1RS)-2,2-difluoro-1-methylcyclopropyl](4-{(1R or S)-1-[2-({6-[6-(pyrrolidin-1-yl)pyrimidin-4-yl]-1H-benzimidazol-2-yl}amino)pyridin-4-yl]ethyl}piperazin-1-yl)methanone LC-MS (Method 2): R$_t$ = 1.18 min; MS (ESIneg): m/z = 586 [M − H]⁻
¹H-NMR (400 MHz, DMSO-d6) δ [ppm]: 1.285 (13.10), 1.301 (13.44), 1.328 (16.00), 1.495 (0.94), 1.515 (1.54), 1.527 (1.78), 1.545 (1.32), 1.558 (0.95), 1.676 (1.17), 1.687 (1.23), 1.696 (1.31), 1.712 (1.68), 1.723 (1.30), 1.733 (1.13), 1.743 (0.89), 1.964 (5.33), 2.247 (0.85), 2.267 (0.67), 2.322 (1.82), 2.326 (1.80), 2.385 (1.26), 2.404 (1.25), 2.522 (1.52), 2.539 (0.68), 2.615 (0.77), 3.390 (5.16), 3.445 (3.53), 3.454 (4.23), 3.461 (4.69), 3.471 (5.40), 3.503 (6.55), 3.565 (2.16), 6.886 (7.72), 6.939 (4.59), 6.952 (4.58), 7.260 (2.35), 7.449 (2.15), 7.469 (2.30), 7.853 (4.30), 7.857 (4.33), 7.874 (3.75), 7.878 (3.91), 8.229 (3.31), 8.255 (7.11), 8.268 (6.42), 8.500 (12.46).
SM: Compound 117.01 and (1RS)-2,2-difluoro-1-methylcyclopropanecarboxylic acid Example 117.07

2-hydroxy-2-methyl-1-(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)propan-1-one LC-MS (Method 2): R$_t$ = 1.09 min; MS (ESIpos): m/z = 555.7 [M + H]⁺
¹H-NMR (400 MHz, DMSO-d6) δ [ppm]: 1.279 (16.00), 1.293 (3.15), 1.310 (2.70), 1.391 (6.67), 1.446 (0.46), 1.908 (0.59), 1.968 (1.31), 2.331 (0.65), 2.345 (0.73), 2.358 (0.80), 2.430 (0.58), 2.522 (0.52), 3.431 (0.74), 3.448 (0.78), 3.511 (1.57), 5.370 (3.56), 6.893 (1.42), 6.949 (1.01), 6.962 (1.01), 7.172 (1.81), 7.857 (0.98), 7.861 (1.02), 7.878 (0.87), 7.882 (0.92), 8.225 (0.45), 8.263 (1.72), 8.276 (1.58), 8.503 (2.81), 8.505 (2.96).
SM: Compound 117.01 and 2-hydroxy-2-methylpropanoic acid

Example 118.01 tert-butyl 4-{(1R or 1S)-1-[2-({6-[6-(morpholin-4-yl)pyrimidin-4-yl]-1H-benzimidazol-2-yl}amino)pyridin-4-yl]ethyl}piperazine-1-carboxylate

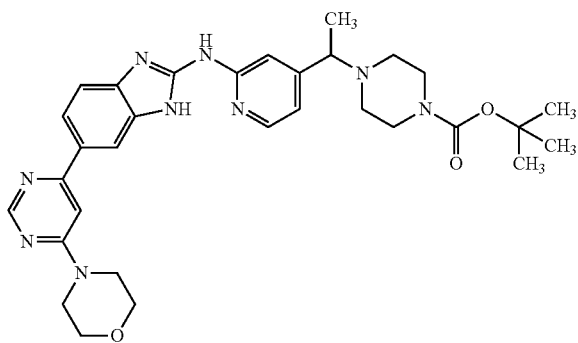 [SMILES: CC(c1ccnc(Nc2nc3ccc(-c4cc(N5CCOCC5)ncn4)cc3[nH]2)c1)N1CCN(C(=O)OC(C)(C)C)CC1]

To a stirred solution of tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (300 mg, see Example 85.01) in 2-propanol (10 ml) in a microwave tube was added morpholine (290 μl). The mixture was stirred at 90° C. for 2 h. The mixture was concentrated in vacuum. Silicagel chromatography gave a solid that was triturated with warm ethanol to give 250 mg of the title compound.

LC-MS (Method 2): $R_t$=1.24 min; MS (ESIpos): m/z=586 [M+H]$^+$.

$^1$H-NMR (400 MHz, DMSO-d6) δ[ppm]: 0.813 (1.12), 0.830 (2.39), 0.835 (0.97), 0.840 (0.56), 0.849 (1.05), 0.852 (1.17), 0.857 (1.41), 0.874 (0.40), 0.935 (0.83), 0.952 (0.90), 1.237 (0.76), 1.239 (0.71), 1.278 (1.85), 1.295 (1.78), 1.377 (16.00), 1.394 (1.23), 2.309 (0.45), 2.383 (0.44), 2.518 (0.70), 2.523 (0.48), 3.331 (11.92), 3.433 (0.41), 3.450 (0.40), 5.759 (1.90), 6.938 (0.41), 6.951 (0.41), 7.169 (0.91), 8.255 (0.91), 8.268 (0.86), 8.568 (1.56), 8.570 (1.53).

Example 118.02 cyclopropyl(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)methanone

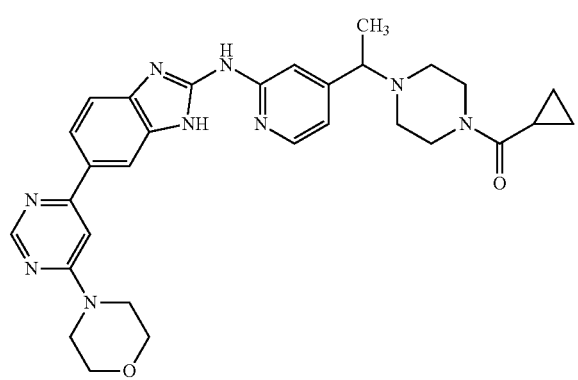 [SMILES: CC(c1ccnc(Nc2nc3ccc(-c4cc(N5CCOCC5)ncn4)cc3[nH]2)c1)N1CCN(C(=O)C2CC2)CC1]

To a stirred solution of 6-[6-(morpholin-4-yl)pyrimidin-4-yl]-N-{4-[(1R or 1S)-1-(piperazin-1-yl)ethyl]pyridin-2-yl}-1H-benzimidazol-2-amine hydrochloride (85.0 mg, see Compound 118.01) in DMF (1.9 mL) was added sodium bicarbonate (72.0 mg), cyclopropanecarboxylic acid (18 μl, 95% purity) and HATU (86.9 mg). The mixture was stirred at r.t. for 3 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40.0 mg of the title compound.

LC-MS (Method 2): $R_t$=1.03 min; MS (ESIpos): m/z=554 [M+H]$^+$.

$^1$H-NMR (400 MHz, DMSO-d6) δ[ppm]: 0.653 (0.81), 0.661 (1.79), 0.666 (1.14), 0.674 (0.93), 0.681 (2.17), 0.685 (1.82), 0.690 (1.97), 0.698 (1.79), 0.702 (2.10), 0.709 (1.01), 1.291 (3.48), 1.308 (3.48), 1.910 (0.45), 1.917 (0.48), 1.929 (0.79), 1.941 (0.44), 1.948 (0.40), 2.083 (1.44), 2.322 (0.43), 2.326 (0.45), 2.393 (0.57), 2.447 (0.42), 2.518 (0.89), 2.522 (0.60), 3.446 (1.16), 3.463 (1.55), 3.702 (16.00), 6.952 (1.01), 6.955 (1.02), 6.965 (1.03), 7.186 (1.94), 7.901 (0.97), 7.905 (0.97), 7.922 (0.87), 7.926 (0.87), 8.263 (1.97), 8.276 (1.86), 8.568 (3.21), 8.570 (3.27).

Example 118.03

3,3,3-trifluoro-1-(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)propan-1-one

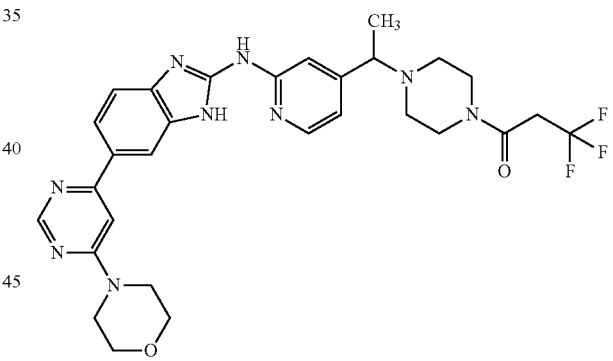

To a stirred solution of 6-[6-(morpholin-4-yl)pyrimidin-4-yl]-N-{4-[(1R or 1S)-1-(piperazin-1-yl)ethyl]pyridin-2-yl}-1H-benzimidazol-2-amine trihydrochloride (85.0 mg, see Compound 118.01) in DMF (1.9 mL) was added sodium bicarbonate (72.0 mg), 3,3,3-trifluoropropanoic acid (19 μl) and HATU (86.9 mg). The mixture was stirred at r.t. for 3 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40 mg of the title compound.

LC-MS (Method 2): $R_t$=1.08 min; MS (ESIpos): m/z=596 [M+H]$^+$.

$^1$H-NMR (400 MHz, DMSO-d6) δ[ppm]: 1.036 (5.01), 1.054 (9.81), 1.071 (5.08), 1.285 (14.20), 1.302 (14.48), 1.334 (0.47), 2.081 (0.78), 2.310 (1.65), 2.323 (2.98), 2.337 (3.61), 2.347 (3.33), 2.361 (2.85), 2.412 (3.72), 2.435 (3.16), 2.449 (2.41), 2.522 (1.23), 3.352 (16.00), 3.433 (8.05), 3.442 (6.71), 3.459 (6.68), 3.476 (9.33), 3.490 (4.87), 3.576 (2.61), 3.603 (7.36), 3.631 (7.02), 3.658 (2.58), 4.014 (1.54), 4.352 (0.53), 4.364 (0.90), 4.376 (0.51), 6.943 (4.42), 6.956 (4.42), 7.183 (8.34), 7.278 (1.17), 7.345 (0.48), 7.411 (0.66), 7.535 (0.53), 7.905 (4.14), 7.908 (4.17), 7.926 (3.71), 7.929 (3.76), 8.212 (0.58), 8.262 (8.01), 8.276 (7.51), 8.333 (0.72), 8.571 (13.14), 10.732 (1.35), 12.252 (1.00).

Example 118.04

(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)[1-(trifluoromethyl)cyclopropyl]methanone

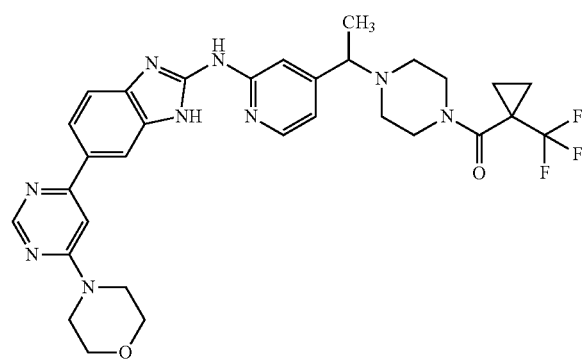 [SMILES: CC(c1ccnc(Nc2nc3ccc(-c4cc(N5CCOCC5)ncn4)cc3[nH]2)c1)N1CCN(C(=O)C2(C(F)(F)F)CC2)CC1]

To a stirred solution of 6-[6-(morpholin-4-yl)pyrimidin-4-yl]-N-{4-[(1R or 1S)-1-(piperazin-1-yl)ethyl]pyridin-2-yl}-1H-benzimidazol-2-amine trihydrochloride (60.0 mg, see Compound 118.01) in DMF (1.3 mL) was added sodium bicarbonate (50.8 mg), 1-(trifluoromethyl)cyclopropanecarboxylic acid (23.3 mg) and HATU (61.4 mg). The mixture was stirred at r.t. for 65 h. Water was added, the mixture was stirred for 15 minutes and the mixture was filtered. The solution was directly used for preparative reverse phase HPLC purification. Preparative reverse phase HPLC (gradient of water and acetonitrile containing ammonia as additive) gave 40.0 mg of the title compound.

LC-MS (Method 2): $R_t$=1.14 min; MS (ESIpos): m/z=622 [M+H]$^+$.

$^1$H-NMR (400 MHz, DMSO-d6) δ[ppm]: 1.159 (1.63), 1.254 (0.94), 1.266 (2.03), 1.289 (3.41), 1.305 (3.28), 2.327 (0.59), 2.332 (0.54), 2.341 (0.55), 2.356 (0.67), 2.370 (0.78), 2.453 (0.82), 2.466 (0.76), 2.518 (1.36), 2.523 (0.97), 3.447 (0.93), 3.463 (0.90), 3.569 (1.12), 3.702 (16.00), 6.941 (1.01), 6.944 (1.02), 6.955 (1.03), 6.958 (1.05), 7.261 (0.48), 7.285 (1.16), 7.891 (1.07), 7.896 (1.05), 7.912 (0.94), 7.917 (0.97), 8.253 (2.03), 8.267 (1.99), 8.565 (3.20), 8.567 (3.29).

Example 119.01 tert-butyl 4-{(1R or 1S)-1-[2-({6-[6-(2,2,2-trifluoroethoxy)pyrimidin-4-yl]-1H-benzimidazol-2-yl}amino)pyridin-4-yl]ethyl}piperazine-1-carboxylate

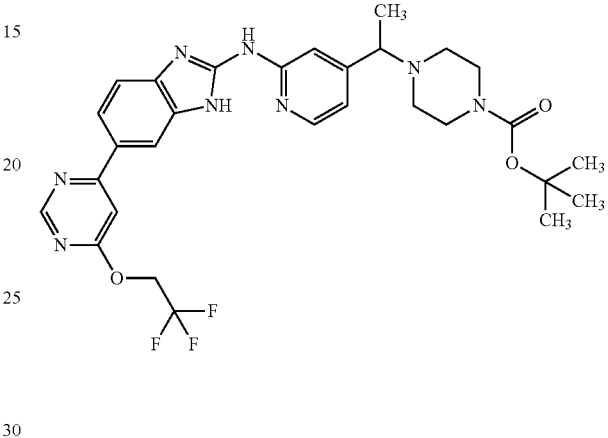

To a stirred solution of 2,2,2-trifluoroethanol (748 mg) in 1,4-dioxane (4.0 ml) was added sodium hydride (196 mg, 55% w/w in oil) and the mixture was stirred for 10 minutes. A solution of tert-butyl 4-[(1R or 1S)-1-(2-{[6-(6-chloropyrimidin-4-yl)-1H-benzimidazol-2-yl]amino}pyridin-4-yl)ethyl]piperazine-1-carboxylate (400 mg, see Example 85.01) in 1,4-dioxane (2.0 ml) was added and the mixture was stirred at r.t. for 1 h and at 60° C. for 2 h. Water was added and the mixture was extracted with ethyl acetate. The organic phase was washed with half-saturated sodium chloride solution, dried (sodium sulfate), filtered and the solvent was removed in vacuum. Silicagel chromatography followed by aminophase-silicagel chromatography gave 250 mg of the title compound.

LC-MS (Method 2): $R_t$=1.46 min; MS (ESIpos): m/z=599 [M+H]$^+$.

$^1$H-NMR (400 MHz, DMSO-d6) δ[ppm]: 1.278 (1.66), 1.295 (1.67), 1.307 (0.42), 1.369 (5.29), 1.375 (16.00), 2.295 (0.43), 2.309 (0.51), 2.322 (0.42), 2.383 (0.49), 2.396 (0.41), 2.518 (0.48), 5.107 (0.41), 5.130 (1.18), 5.152 (1.09), 5.758 (4.36), 7.167 (0.48), 8.269 (0.73), 8.283 (0.67), 8.863 (1.56), 8.865 (1.57).

The Example compounds in the following table 13 were synthesized in analogy to the preparation of Example 117.02, followed by purification by preparative reverse phase HPLC or silicagel chromatography.

TABLE 13

| Example | Structure<br>IUPAC-Name<br>LC-MS (method): Retention time; Mass found<br>¹H-NMR<br>Starting materials (SM): |
|---|---|

Example 119.02

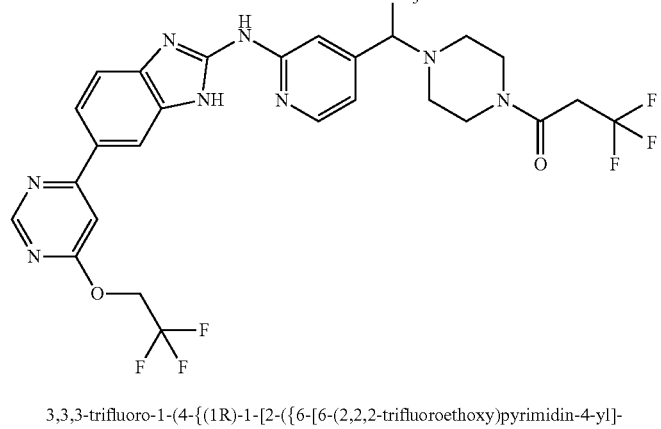

3,3,3-trifluoro-1-(4-{(1R)-1-[2-({6-[6-(2,2,2-trifluoroethoxy)pyrimidin-4-yl]-1H-benzimidazol-2-yl}amino)pyridin-4-yl]ethyl}piperazin-1-yl)propan-1-one
LC-MS (Method 2): $R_t$ = 1.3 min; MS (ESIpos): m/z = 608.6 [M + H]$^+$
¹H-NMR (400 MHz, DMSO-d6) δ [ppm]: 1.291 (15.78), 1.308 (16.00), 2.328 (3.47), 2.342 (3.44), 2.351 (3.18), 2.366 (2.82), 2.417 (3.75), 2.428 (4.08), 2.440 (3.00), 2.455 (2.37), 2.518 (3.28), 2.523 (2.24), 2.540 (1.62), 2.665 (0.59), 2.669 (0.81), 2.673 (0.58), 3.424 (4.23), 3.436 (7.49), 3.449 (4.92), 2.470 (7.89), 3.485 (8.20), 3.578 (2.91), 3.606 (8.26), 3.633 (7.84), 3.660 (2.47), 4.016 (0.65), 5.107 (3.75), 5.130 (11.02), 5.152 (10.55), 5.175 (3.24), 6.958 (3.63), 6.971 (3.63), 7.177 (5.01), 7.410 (0.92), 7.427 (1.00), 7.559 (1.93), 7.674 (1.14), 7.956 (3.18), 7.977 (2.86), 8.249 (1.11), 8.278 (7.78), 8.292 (7.27), 8.410 (1.49), 8.864 (14.75), 8.866 (14.66), 10.769 (2.02), 12.314 (1.79).
SM: Compound 119.01 and 3,3,3-trifluoropropanoic acid Example 119.03 cyclopropyl(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)methanone
LC-MS (Method 2): $R_t$ = 1.28 min; MS (ESIpos): m/z = 567 [M + H]$^+$
¹H-NMR (400 MHz, DMSO-d6) δ [ppm]: 0.643 (1.20), 0.662 (8.20), 0.681 (9.86), 0.686 (9.10), 0.690 (9.63), 0.702 (9.83), 0.709 (4.87), 0.722 (1.17), 1.293 (15.75), 1.310 (16.00), 1.900 (0.97), 1.912 (1.96), 1.919 (2.27), 1.931 (3.52), 1.944 (2.11), 1.950 (1.89), 1.963 (0.87), 2.326 (2.34), 2.394 (3.13), 2.454 (2.57), 2.617 (0.59), 2.669 (0.87), 3.453 (6.29), 3.469 (7.92), 3.671 (4.38), 5.107 (3.44), 5.130 (10.17), 5.152 (9.73), 5.175 (3.16), 6.966 (3.77), 6.978 (3.82), 7.184 (6.24), 7.409 (1.17), 7.428 (1.22), 7.558 (2.32), 7.675 (1.43), 7.957 (3.29), 7.977 (3.03), 8.249 (1.38), 8.279 (7.31), 8.292 (6.85), 8.410 (1.83), 8.865 (14.47), 10.767 (2.55), 12.293 (1.81), 12.318 (2.22).
SM: Compound 119.01 and cyclopropanecarboxylic acid

TABLE 13-continued

| Example | Structure<br>IUPAC-Name<br>LC-MS (method): Retention time; Mass found<br>¹H-NMR<br>Starting materials (SM): |
|---|---|
| Example 119.04 | 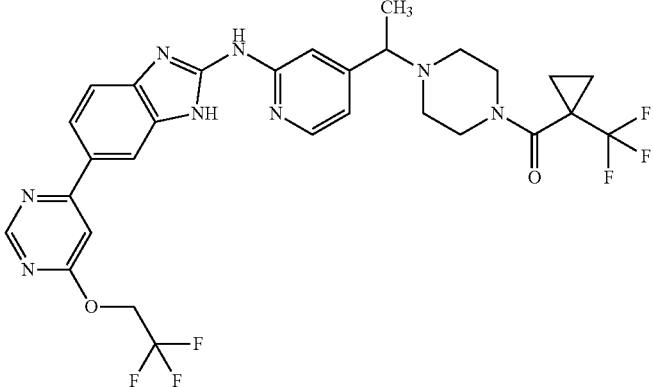 [SMILES: CC(c1ccnc(Nc2nc3ccc(-c4cc(OCC(F)(F)F)ncn4)cc3[nH]2)c1)N1CCN(C(=O)C2(C(F)(F)F)CC2)CC1]<br>(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)[1-(trifluoromethyl)cyclopropyl]methanone<br>LC-MS (Method 2): $R_t$ = 1.34 min; MS (ESIneg): m/z = 633 [M − H]⁻<br>¹H-NMR (400 MHz, DMSO-d6) δ [ppm]: 1.159 (3.34), 1.218 (1.44), 1.283 (5.77), 1.297 (5.31), 1.387 (16.00), 2.364 (2.20), 3.449 (1.61), 3.463 (1.66), 3.565 (3.37), 5.128 (2.17), 5.149 (2.24), 6.968 (1.62), 7.183 (2.12), 7.426 (0.49), 7.565 (0.88), 7.664 (0.48), 7.958 (1.30), 7.976 (1.28), 8.278 (1.90), 8.288 (1.96), 8.410 (0.56), 8.862 (2.42), 10.777 (1.04), 12.312 (0.91).<br>SM: Compound 119.01 and 1-(trifluoromethyl)cyclopropanecarboxylic acid |
| Example 119.05 | 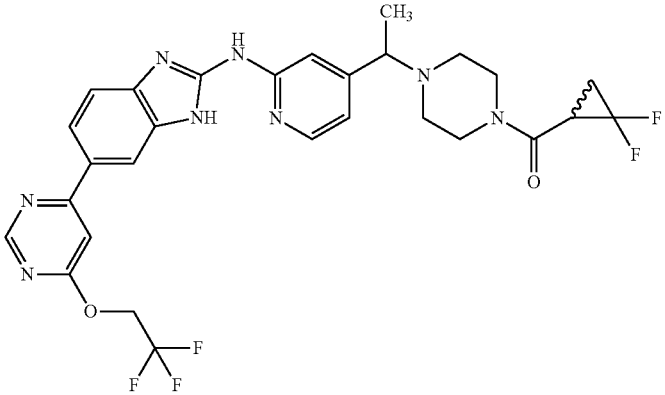 [SMILES: CC(c1ccnc(Nc2nc3ccc(-c4cc(OCC(F)(F)F)ncn4)cc3[nH]2)c1)N1CCN(C(=O)C2CC2(F)F)CC1]<br>((1RS)-2,2-difluorocyclopropyl)(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)methanone<br>LC-MS (Method 2): $R_t$ = 1.29 min; MS (ESIpos): m/z = 603 [M + H]⁺<br>¹H-NMR (400 MHz, DMSO-d6) δ [ppm]: 1.144 (0.50), 1.229 (0.50), 1.297 (15.57), 1.314 (15.64), 1.390 (0.46), 1.418 (1.57), 1.763 (0.50), 1.780 (1.00), 1.792 (1.43), 1.810 (1.61), 1.822 (1.68), 1.839 (1.61), 1.859 (1.71), 1.873 (2.07), 1.892 (1.93), 1.905 (1.25), 2.309 (1.43), 2.322 (3.11), 2.326 (3.71), 2.332 (3.00), 2.335 (2.50), 2.347 (1.71), 2.364 (2.54), 2.373 (2.00), 2.444 (3.18), 2.518 (8.25), 2.522 (5.86), 2.539 (1.00), 2.567 (1.14), 2.664 (1.61), 2.668 (2.21), 2.673 (1.57), 3.076 (1.39), 3.096 (1.54), 3.105 (1.75), 3.110 (1.79), 3.125 (1.54), 3.131 (1.82), 3.138 (1.54), 3.158 (1.25), 3.474 (3.07), 3.482 (3.57), 3.491 (4.07), 3.499 (4.43), 3.509 (3.79), 3.515 (3.82), 3.563 (2.54), 3.621 (1.96), 3.637 (1.68), 3.658 (1.04), 5.108 (3.93), 5.130 (11.54), 5.153 (10.89), 5.175 (3.29), 6.966 (4.29), 6.979 (4.32), 7.203 (4.82), 7.437 (0.54), 7.578 (0.96), 7.951 (4.21), 7.955 (4.21), 7.972 (3.79), 7.976 (3.79), 8.278 (8.25), 8.291 (7.71), 8.862 (16.00), 8.865 (16.00), 10.756 (1.04), 12.311 (0.93).<br>SM: Compound 119.01 and (1RS)-2,2-difluorocyclopropanecarboxylic acid |

Example 120.01 tert-butyl 4-{(1R or 1S)-1-[2-({6-[1-(cyclopropylmethyl)-3,5-dimethyl-1H-pyrazol-4-yl]-1H-benzimidazol-2-yl}amino)pyridin-4-yl]ethyl}piperazine-1-carboxylate

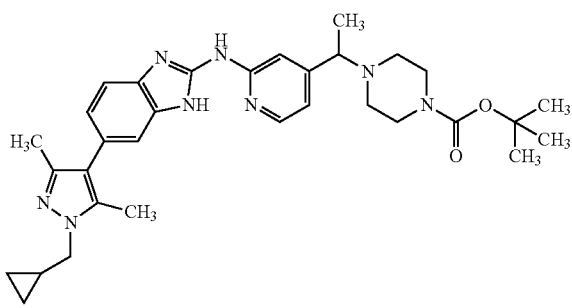 [SMILES: Cc1nn(CC2CC2)c(C)c1-c1ccc2nc(Nc3cc(C(C)N4CCN(C(=O)OC(C)(C)C)CC4)ccn3)[nH]c2c1]

tert-Butyl 4-[(1R or 1S)-1-{2-[({2-amino-4-[1-(cyclopropylmethyl)-3,5-dimethyl-1H-pyrazol-4-yl]phenyl}carbamothioyl)amino]pyridin-4-yl}ethyl]piperazine-1-carboxylate (240 mg, 397 µmol; see Compound 120.02) and EDCI (76.1 mg, 397 µmol) were stirred in dichloromethane (7.2 ml) under argon overnight at rt. The mixture was concentrated under reduced pressure and the crude mixture was purified by flash chromatography on silica gel to give 47 mg (19% yield) of the title compound.

$^1$H-NMR (400 MHz, DMSO-d6) δ[ppm]: 0.353 (0.49), 0.366 (0.48), 0.519 (0.42), 1.035 (3.70), 1.052 (8.44), 1.070 (4.28), 1.266 (1.62), 1.282 (1.83), 1.294 (0.90), 1.319 (0.44), 1.372 (16.00), 1.376 (8.97), 2.126 (0.54), 2.147 (0.80), 2.228 (0.61), 2.247 (1.10), 2.265 (0.48), 2.280 (0.59), 2.292 (0.83), 2.323 (0.67), 2.327 (0.79), 2.331 (0.62), 2.337 (0.48), 2.359 (0.48), 2.372 (0.48), 2.387 (0.51), 2.398 (0.73), 2.518 (1.97), 2.523 (1.41), 2.665 (0.42), 2.669 (0.56), 2.673 (0.41), 3.404 (0.60), 3.417 (0.68), 3.422 (1.84), 3.435 (1.89), 3.440 (1.97), 3.452 (1.73), 3.457 (0.95), 3.469 (0.63), 3.878 (0.48), 3.895 (0.48), 4.344 (1.15), 4.356 (2.21), 4.369 (1.06), 6.999 (0.57), 7.003 (0.56), 7.013 (0.57), 7.016 (0.56), 8.212 (0.75), 8.225 (0.72).

Example 120.02

1-(4-{(1R or 1S)-1-[2-({6-[1-(cyclopropylmethyl)-3,5-dimethyl-1H-pyrazol-4-yl]-1H-benzimidazol-2-yl}amino)pyridin-4-yl]ethyl}piperazin-1-yl)-3,3,3-trifluoropropan-1-one

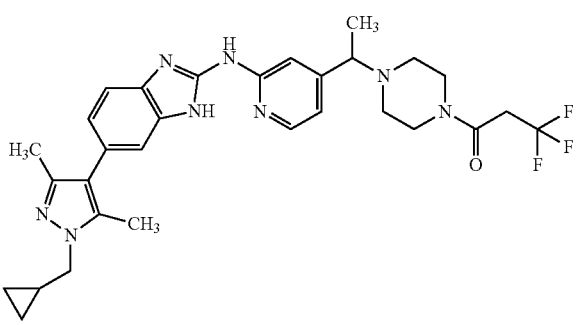 [SMILES: Cc1nn(CC2CC2)c(C)c1-c1ccc2nc(Nc3cc(C(C)N4CCN(C(=O)CC(F)(F)F)CC4)ccn3)[nH]c2c1]

6-[1-(cyclopropylmethyl)-3,5-dimethyl-1H-pyrazol-4-yl]-N-{4-[(1R or 1S)-1-(piperazin-1-yl)ethyl]pyridin-2-yl}-1H-benzimidazol-2-amine hydrochloride (56.0 mg; see Compound 120.03), 3,3,3-trifluoropropanoic acid (26 µl), NaHCO$_3$ (48.7 mg) and HATU (110 mg) were stirred in DMF (740 µl) overnight at rt. The crude mixture was purified without work up by preparative HPLC to give 4 mg (90% purity) of the title compound.

LC-MS (method 2): R$_t$=1.19 min; MS (ESIpos): m/z=851 [M+H]$^+$.

$^1$H-NMR (400 MHz, DMSO-d6): δ [ppm]=0.36 (dd, 2H), 0.47-0.54 (m, 2H), 1.18-1.25 (m, 1H), 1.30 (d, 3H), 2.15 (br s, 3H), 2.25 (br s, 3H), 2.33-2.39 (m, 2H), 2.40-2.46 (m, 2H), 3.42-3.50 (m, 5H), 3.62 (q, 2H), 3.89 (d, 2H), 6.85-6.95 (m, 2H), 7.12-7.52 (m, 3H), 8.26 (d, 1H), 10.55 (br d, 1H), 12.05 (br d, 1H).

Example 121.01 tert-butyl 4-{(1R or 1S)-1-[2-({6-[1-(cyclopropylmethyl)-1H-pyrazol-4-yl]-7-fluoro-1H-benzimidazol-2-yl}amino)pyridin-4-yl]ethyl}piperazine-1-carboxylate

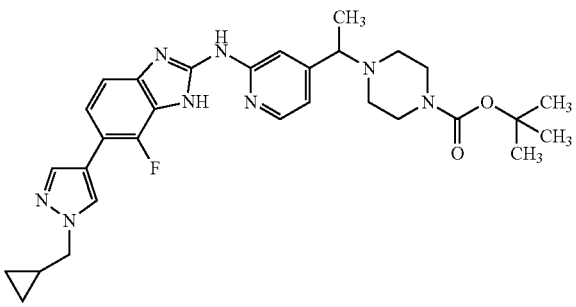 [SMILES: CC(c1ccnc(Nc2nc3ccc(-c4cnn(CC5CC5)c4)c(F)c3[nH]2)c1)N1CCN(C(=O)OC(C)(C)C)CC1]

tert-butyl 4-[(1R or 1S)-1-{2-[({2-amino-4-[1-(cyclopropylmethyl)-1H-pyrazol-4-yl]-3-fluorophenyl}carbamothioyl)amino]pyridin-4-yl}ethyl]piperazine-1-carboxylate (1.30 g; see Compound 121.02) and EDCI (419 mg) were stirred in dichloromethane (39 ml) under argon overnight at rt. The mixture was then concentrated under reduced pressure and the crude mixture was purified by flash chromatography on silica gel to give 728 mg (90% purity) of the title compound.

LC-MS (method 2): R$_t$=1.37 min; MS (ESIpos): m/z=561 [M+H]$^+$.

$^1$H-NMR (400 MHz, DMSO-d6): δ [ppm]=0.37-0.44 (m, 2H), 0.51-0.58 (m, 2H), 1.20-1.33 (m, 4H), 1.38 (s, 9H), 2.24-2.44 (m, 4H), 3.33 (s, 4H), 3.44 (q, 1H), 4.01 (d, 2H), 6.94 (d, 1H), 7.11 (br s, 1H), 7.22-7.35 (m, 2H), 7.83 (s, 1H), 8.12 (d, 1H), 8.25 (s, 1H), 10.77 (br s, 1H), 12.28 (br s, 1H).

Example 121.02

1-(4-{(1R or 1S)-1-[2-({6-[1-(cyclopropylmethyl)-1H-pyrazol-4-yl]-7-fluoro-1H-benzimidazol-2-yl}amino)pyridin-4-yl]ethyl}piperazin-1-yl)-3,3,3-trifluoropropan-1-one

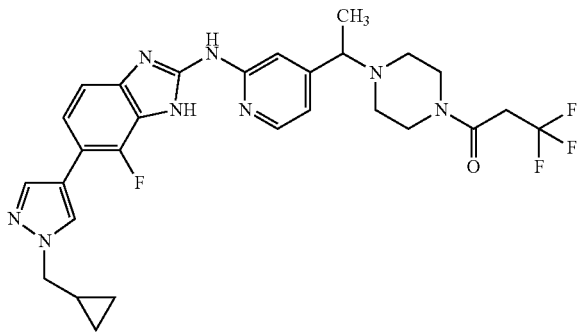 [SMILES: CC(c1ccnc(Nc2nc3ccc(-c4cnn(CC5CC5)c4)c(F)c3[nH]2)c1)N1CCN(C(=O)CC(F)(F)F)CC1]

6-[1-(cyclopropylmethyl)-1H-pyrazol-4-yl]-7-fluoro-N-{4-[(1R or 1S)-1-(piperazin-1-yl)ethyl]pyridin-2-yl}-1H-benzimidazol-2-amine hydrochloride (100 mg; see Compound 121.03), 3,3,3-trifluoropropanoic acid (46 µl), NaHCO₃ (88.4 mg) and HATU (200 mg) were stirred in DMF (2.0 ml) overnight at rt. The crude mixture was purified without work up by preparative HPLC to give 51 mg (95% purity) of the title compound.

LC-MS (method 2): $R_t$=1.20 min; MS (ESIpos): m/z=571 [M+H]⁺.

¹H-NMR (400 MHz, DMSO-d6): δ [ppm]=0.37-0.43 (m, 2H), 0.52-0.59 (m, 2H), 1.21-1.34 (m, 4H), 2.28-2.47 (m, 4H), 3.39-3.53 (m, 5H), 3.62 (d, 2H), 4.01 (d, 2H), 6.92-6.99 (m, 1H), 7.11 (s, 1H), 7.31 (s, 2H), 7.83 (s, 1H), 8.12 (d, 1H), 8.27 (d, 1H), 10.79 (s, 1H), 12.27 (s, 1H).

Example 121.03 cyclopropyl(4-{(1R or 1S)-1-[2-({6-[1-(cyclopropylmethyl)-1H-pyrazol-4-yl]-7-fluoro-1H-benzimidazol-2-yl}amino)pyridin-4-yl]ethyl}piperazin-1-yl)methanone

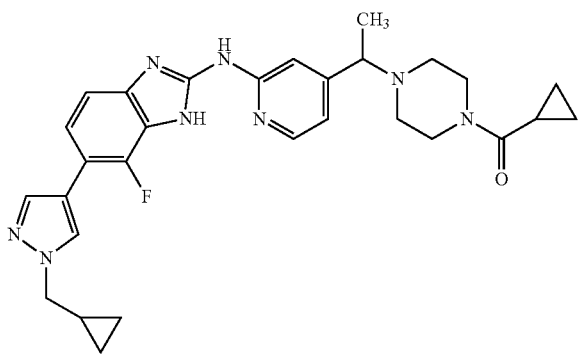 [SMILES: CC(c1ccnc(Nc2nc3ccc(-c4cnn(CC5CC5)c4)c(F)c3[nH]2)c1)N1CCN(C(=O)C2CC2)CC1]

6-[1-(cyclopropylmethyl)-1H-pyrazol-4-yl]-7-fluoro-N-{4-[(1R or 1S)-1-(piperazin-1-yl)ethyl]pyridin-2-yl}-1H-benzimidazol-2-amine hydrochloride (100 mg; see Compound 121.03), cyclopropanecarboxylic acid (42 µl), NaHCO₃ (88.4 mg) and HATU (200 mg) were stirred in DMF (2.0 ml) overnight at rt. The crude mixture was purified without work up by preparative HPLC to give 21.7 mg (92% purity) of the title compound.

LC-MS (method 2): $R_t$=1.16 min; MS (ESIpos): m/z=529 [M+H]⁺.

¹H-NMR (400 MHz, DMSO-d6): δ [ppm]=0.36-0.43 (m, 2H), 0.52-0.58 (m, 2H), 0.63-0.73 (m, 4H), 1.21-1.34 (m, 4H), 1.90-1.98 (m, 1H), 2.24-2.43 (m, 4H), 3.41-3.54 (m, 3H), 3.68 (br s, 2H), 4.01 (d, 2H), 6.93-6.99 (m, 1H), 7.12 (s, 1H), 7.23-7.35 (m, 2H), 7.83 (s, 1H), 8.12 (d, 1H), 8.27 (d, 1H), 10.79 (s, 1H), 12.28 (br s, 1H).

Example 122.01 tert-butyl 4-{(1R or 1S)-1-[2-({7-chloro-6-[1-(cyclopropylmethyl)-1H-pyrazol-4-yl]-1H-benzimidazol-2-yl}amino)pyridin-4-yl]ethyl}piperazine-1-carboxylate

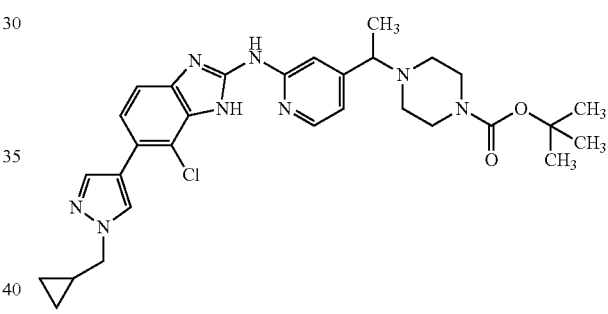

tert-butyl 4-[(1R or 1S)-1-{2-[({2-amino-3-chloro-4-[1-(cyclopropylmethyl)-1H-pyrazol-4-yl]phenyl}carbamothioyl)amino]pyridin-4-yl}ethyl]piperazine-1-carboxylate (1.10 g, see Compound 122.02) and EDCI (345 mg) were stirred in dichloromethane (32 ml) under argon overnight at rt. The mixture was concentrated under reduced pressure and purified by flash chromatography on silica gel to give 554 mg (91% purity) of the title compound.

LC-MS (method 2): $R_t$=1.40 min; MS (ESIpos): m/z=577 [M+H]⁺.

¹H-NMR (400 MHz, DMSO-d6): δ [ppm]=0.37-0.43 (m, 2H), 0.52-0.58 (m, 2H), 1.25-1.31 (m, 4H), 1.38 (s, 9H), 2.25-2.44 (m, 4H), 3.33 (s, 4H), 3.44 (q, 1H), 4.02 (d, 2H), 6.92-6.98 (m, 1H), 7.07 (s, 1H), 7.20 (d, 1H), 7.41-7.47 (m, 1H), 7.78 (s, 1H), 8.13 (s, 1H), 8.27 (d, 1H), 10.96 (s, 1H), 12.30 (s, 1H).

Example 122.02

1-(4-{(1R or 1S)-1-[2-({7-chloro-6-[1-(cyclopropylmethyl)-1H-pyrazol-4-yl]-1H-benzimidazol-2-yl}amino)pyridin-4-yl]ethyl}piperazin-1-yl)-3,3,3-trifluoropropan-1-one

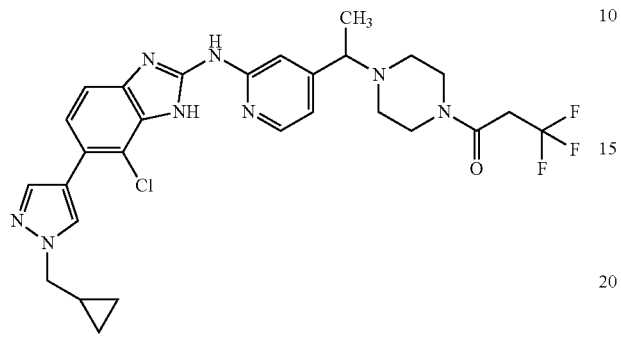

7-chloro-6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride (100 mg; see Compound 122.03), 3,3,3-trifluoropropanoic acid (45 µl), NaHCO₃ (86.0 mg) and HATU (195 mg) were stirred in DMF (2.0 ml) overnight at rt. The crude mixture was purified without work up by preparative HPLC to give 22.0 mg (95% purity) of the title compound.

LC-MS (method 2): $R_t$=1.23 min; MS (ESIpos): m/z=587 [M+H]⁺.

¹H-NMR (400 MHz, DMSO-d6): δ [ppm]=0.37-0.43 (m, 2H), 0.52-0.58 (m, 2H), 1.22-1.34 (m, 4H), 2.29-2.46 (m, 4H), 3.40-3.51 (m, 5H), 3.62 (q, 2H), 4.02 (d, 2H), 6.94-6.98 (m, 1H), 7.08 (s, 1H), 7.19 (d, 1H), 7.44 (d, 1H), 7.78 (s, 1H), 8.13 (s, 1H), 8.28 (d, 1H), 10.98 (s, 1H), 12.30 (s, 1H).

Example 122.03

(4-{(1R or 1S)-1-[2-({7-chloro-6-[1-(cyclopropylmethyl)-1H-pyrazol-4-yl]-1H-benzimidazol-2-yl}amino)pyridin-4-yl]ethyl}piperazin-1-yl)(cyclopropyl)methanone

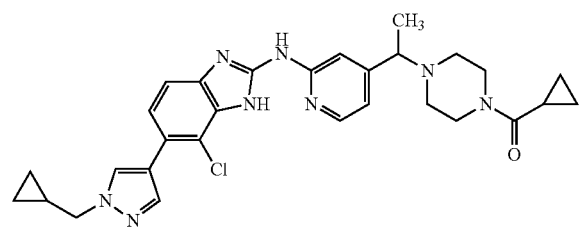 [SMILES: CC(c1ccnc(Nc2nc3ccc(-c4cnn(CC5CC5)c4)c(Cl)c3[nH]2)c1)N1CCN(C(=O)C2CC2)CC1]

7-chloro-6-[1-(cyclopropylmethyl)-1H-pyrazol-4-yl]-N-{4-[(1R or 1S)-1-(piperazin-1-yl)ethyl]pyridin-2-yl}-1H-benzimidazol-2-amine hydrochloride (100 mg; see Compound 122.03), cyclopropanecarboxylic acid (41 µl), NaHCO₃ (86.0 mg) and HATU (195 mg) were stirred in DMF (2.0 ml) overnight at rt. The crude mixture was purified without work up by preparative HPLC to give 44.1 mg (90% purity) of the title compound.

LC-MS (method 2): $R_t$=1.20 min; MS (ESIpos): m/z=545 [M+H]⁺.

¹H-NMR (400 MHz, DMSO-d6): δ [ppm]=0.37-0.43 (m, 2H), 0.52-0.59 (m, 2H), 0.64-0.73 (m, 4H), 1.22-1.35 (m, 4H), 1.88-1.98 (m, 1H), 2.25-2.45 (m, 4H), 3.41-3.53 (m, 3H), 3.68 (br s, 2H), 4.02 (d, 2H), 6.94-7.00 (m, 1H), 7.09 (br s, 1H), 7.19 (d, 1H), 7.44 (d, 1H), 7.78 (s, 1H), 8.13 (s, 1H), 8.25-8.31 (m, 1H), 10.98 (s, 1H), 12.31 (s, 1H).

Example 123.01 tert-butyl 4-[(1R or 1S)-1-(2-{[6-(1-methyl-1H-pyrazol-5-yl)-1H-benzimidazol-2-yl]amino}pyridin-4-yl)ethyl]piperazine-1-carboxylate

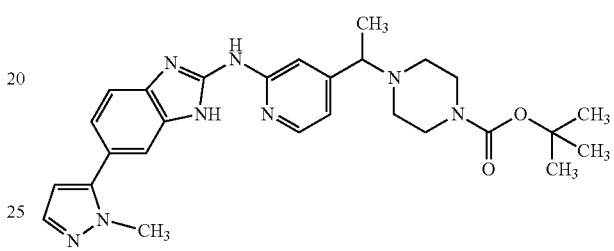

tert-butyl 4-{(1R or 1S)-1-[2-({[2-amino-4-(1-methyl-1H-pyrazol-5-yl)phenyl]carbamothioyl}amino)pyridin-4-yl]ethyl}piperazine-1-carboxylate (466 mg; see Compound 123.02) and EDCI (167 mg) were stirred in dichloromethane (16 ml) under argon overnight at rt. The mixture was concentrated under reduced pressure and purified by flash chromatography on silica gel to give 211 mg (83% purity) of the title compound.

LC-MS (method 2): $R_t$=1.24 min; MS (ESIpos): m/z=503 [M+H]⁺.

¹H-NMR (400 MHz, DMSO-d6): δ [ppm]=1.20-1.32 (m, 4H), 1.38 (s, 9H), 2.25-2.44 (m, 4H), 3.33 (s, 4H), 3.44 (q, 1H), 3.86 (s, 3H), 6.33 (d, 1H), 6.94 (dd, 1H), 7.17 (br s, 2H), 7.44 (d, 2H), 7.52-7.66 (m, 1H), 8.27 (d, 1H), 10.66 (br s, 1H), 12.18-12.30 (m, 1H), 12.24 (br s, 1H).

Example 123.02

3,3,3-trifluoro-1-{4-[(1R or 1S)-1-(2-{[6-(1-methyl-1H-pyrazol-5-yl)-1H-benzimidazol-2-yl]amino}pyridin-4-yl)ethyl]piperazin-1-yl}propan-1-one

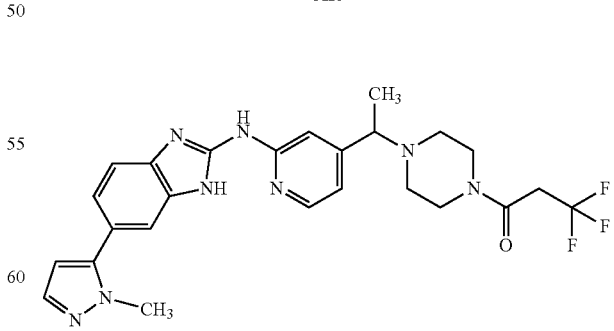

6-(1-Methyl-1H-pyrazol-5-yl)-N-{4-[(1R or 1S)-1-(piperazin-1-yl)ethyl]pyridin-2-yl}-1 h-benzimidazol-2-amine hydrochloride (75.0 mg; see Compound 123.03), 3,3,3-trifluoropropanoic acid (39 µl), NaHCO₃ (73.8 mg) and HATU (167 mg) were stirred in DMF (2.0 ml) overnight at rt. The crude mixture was purified without work up by preparative HPLC to give 7.50 mg (90% purity) of the title compound.

LC-MS (method 2): R$_t$=1.04 min; MS (ESIpos): m/z=513 [M+H]$^+$.

$^1$H-NMR (400 MHz, DMSO-d6): δ [ppm]=1.30 (d, 3H), 2.31-2.39 (m, 2H), 2.43 (dt, 2H), 3.44 (br t, 2H), 3.47 (br d, 3H), 3.62 (q, 2H), 3.86 (s, 3H), 6.33 (d, 1H), 6.95 (dd, 1H), 7.18 (s, 2H), 7.44 (d, 2H), 7.53-7.65 (m, 1H), 8.28 (d, 1H), 10.69 (br s, 1H), 12.23 (br s, 1H).

Example 123.03 cyclopropyl{4-[(1R or 1S)-1-(2-{[6-(1-methyl-1H-pyrazol-5-yl)-1H-benzimidazol-2-yl]amino}pyridin-4-yl)ethyl]piperazin-1-yl}methanone

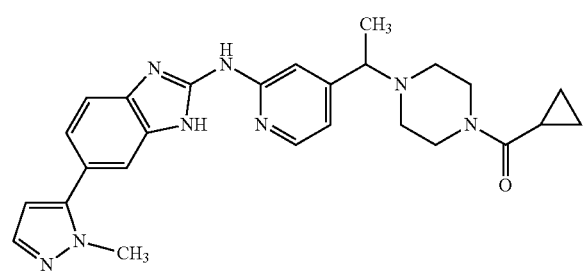 [SMILES: CC(c1ccnc(Nc2nc3ccc(-c4ccnn4C)cc3[nH]2)c1)N1CCN(C(=O)C2CC2)CC1]

6-(1-methyl-1H-pyrazol-5-yl)-N-{4-[(1R or 1S)-1-(piperazin-1-yl)ethyl]pyridin-2-yl}-1H-benzimidazol-2-amine hydrochloride (75.0 mg; see Compound 123.03), cyclopropanecarboxylic acid (35 µl), NaHCO$_3$ (73.8 mg) and HATU (167 mg) were stirred in DMF (2.0 ml) overnight at rt. The crude mixture was purified without work up by preparative HPLC to give 9.00 mg (90% purity) of the title compound.

LC-MS (method 2): R$_t$=1.01 min; MS (ESIpos): m/z=471 [M+H]$^+$.

$^1$H-NMR (400 MHz, DMSO-d6): δ [ppm]=0.63-0.74 (m, 4H), 1.30 (d, 3H), 1.88-1.99 (m, 1H), 2.25-2.46 (m, 4H), 3.41-3.54 (m, 3H), 3.60-3.74 (m, 2H), 3.86 (s, 3H), 6.33 (s, 1H), 6.96 (dd, 1H), 7.10-7.22 (m, 2H), 7.37-7.48 (m, 2H), 7.54-7.66 (m, 1H), 8.28 (d, 1H), 10.67 (br d, 1H), 12.23 (br d, 1H).

Example 124.02

3,3,3-trifluoro-1-{4-[(2-{[6-(1H-pyrazol-5-yl)-1H-benzimidazol-2-yl]amino}pyridin-4-yl)methyl]piperazin-1-yl}propan-1-one

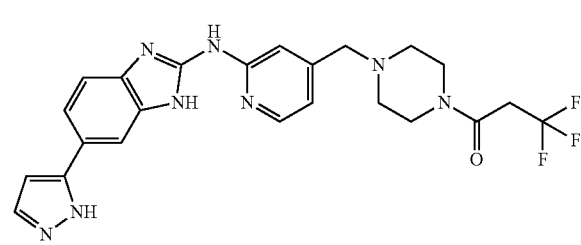 [SMILES: O=C(CC(F)(F)F)N1CCN(Cc2ccnc(Nc3nc4ccc(-c5ccn[nH]5)cc4[nH]3)c2)CC1]

Crude N-[4-(piperazin-1-ylmethyl)pyridin-2-yl]-6-(1H-pyrazol-5-yl)-1H-benzimidazol-2-amine hydrochloride (35.0 mg; see compound 124.04), 3,3,3-trifluoropropanoic acid (19 µl), NaHCO$_3$ (36.5 mg) and HATU (82.5 mg) were stirred in DMF (550 µl) for 2 h at rt. The mixture was diluted with water and stirred for 1 h at rt. The aqueous phase was extracted three times with DCM. The organic layer was filtered (silicone filter) and concentrated under reduced pressure. The crude mixture was purified without work up by preparative HPLC to give 6.00 mg (95% purity) of the title compound.

LC-MS (Method 2): R$_t$=0.95 min; MS (ESIpos): m/z=485 [M+H]$^+$.

$^1$H-NMR (400 MHz, DMSO-d6): δ [ppm]=2.40 (dt, 4H), 3.16 (s, 2H), 3.42-3.55 (m, 6H), 3.65 (q, 2H), 6.55-6.67 (m, 1H), 6.92 (dd, 1H), 7.18-7.55 (m, 3H), 7.57-7.79 (m, 1H), 8.26 (d, 1H), 10.65 (br s, 1H), 12.18 (br s, 1H).

Example 125.01 tert-butyl 4-[(5-bromo-2-{[6-(3-methyl-1,2,4-oxadiazol-5-yl)-1H-benzimidazol-2-yl]amino}pyridin-4-yl)methyl]piperazine-1-carboxylate

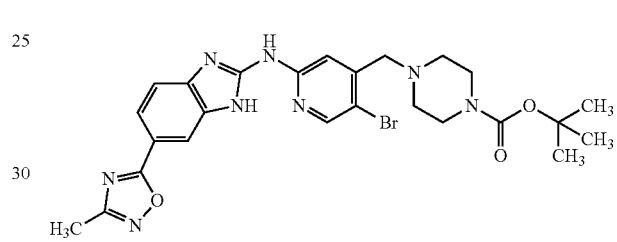

tert-Butyl 4-{[2-({[2-amino-4-(3-methyl-1,2,4-oxadiazol-5-yl)phenyl]carbamothioyl}amino)-5-bromopyridin-4-yl]methyl}piperazine-1-carboxylate (116 mg, see compound 125.04) was stirred with EDCI (73.7 mg) in dichloromethane (4.0 ml) under argon overnight at rt. The mixture was diluted with water and extracted three times with DCM. The organic layer was filtered, dried over a silicone filter and concentrated under reduced pressure. The compound was used without further purification.

LC-MS (Method 2): R$_t$=1.59 min; MS (ESIpos): m/z=541 [M+H]$^+$.

Example 125.02

1-{4-[(5-bromo-2-{[6-(3-methyl-1,2,4-oxadiazol-5-yl)-1H-benzimidazol-2-yl]amino}pyridin-4-yl)methyl]piperazin-1-yl}-3,3,3-trifluoropropan-1-one

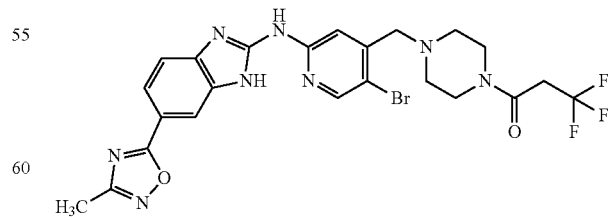

N-[5-Bromo-4-(piperazin-1-ylmethyl)pyridin-2-yl]-6-(3-methyl-1,2,4-oxadiazol-5-yl)-1H-benzimidazol-2-amine hydrochloride (110 mg; see compound 125.05), 3,3,3-trifluoropropanoic acid (50 µl), NaHCO$_3$ (95.8 mg) and HATU (217 mg) were stirred in DMF (1.5 ml) for 2 h at rt. The mixture was diluted with water stirred for 1 h at rt. The reaction mixture was extracted three times with DCM. The organic layer was dried (silicone filter) and concentrated under reduced pressure. The crude mixture was purified by flash chromatography on silica gel to give 5 mg of the title compound.

LC-MS (Method 2): $R_t$=1.20 min; MS (ESIpos): m/z=579 [M+H]$^+$.

1H-NMR (400 MHz, DMSO-d6): δ [ppm]=2.40 (s, 3H), 3.58 (s, 6H), 3.68 (d, 2H), 7.45-7.60 (m, 1.5H), 7.66 (d, 0.5H), 7.74-7.89 (m, 1H), 8.02 (s, 0.5H), 8.21 (s, 0.5H), 8.34-8.43 (m, 1H), 10.94-11.08 (m, 1H), 12.22-12.33 (m, 1H).

Example 126.02

1-(4-{[2-({6-[5-(cyclobutylmethyl)-1,3,4-oxadiazol-2-yl]-1H-benzimidazol-2-yl}amino)pyridin-4-yl]methyl}piperazin-1-yl)-3,3,3-trifluoropropan-1-one

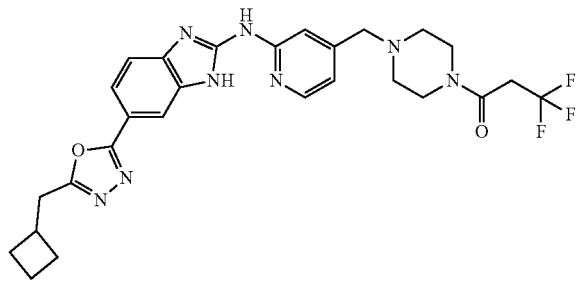 [SMILES: O=C(CC(F)(F)F)N1CCN(Cc2ccnc(Nc3nc4ccc(-c5nnc(CC6CCC6)o5)cc4[nH]3)c2)CC1]

6-[5-(Cyclobutylmethyl)-1,3,4-oxadiazol-2-yl]-N-[4-(piperazin-1-ylmethyl)pyridin-2-yl]-1H-benzimidazol-2-amine (7.00 mg; see compound 126.03), 3,3,3-trifluoropropanoic acid (4.2 μl, 47 μmol), NaHCO$_3$ (7.94 mg) and HATU (18.0 mg) were stirred in DMF (89 μl) overnight at rt. The mixture was concentrated and purified by preparative thin layer chromatography to give 2.00 mg (95% purity) of the title compound.

LC-MS (method 2): $R_t$=1.17 min; MS (ESIpos): m/z=555 [M+H]$^+$.

$^1$H-NMR (400 MHz, DMSO-d6): δ [ppm]=1.77-1.95 (m, 4H), 2.07-2.19 (m, 2H), 2.40 (dt, 4H), 2.72-2.82 (m, 1H), 3.03 (d, 2H), 3.42-3.55 (m, 6H), 3.65 (q, 2H), 6.97 (br d, 1H), 7.19 (s, 1H), 7.47 (br d, 1H), 7.62-7.71 (m, 1H), 7.84-8.15 (m, 1H), 8.29 (d, 1H), 10.80-10.91 (m, 1H), 12.43 (br s, 1H).

The compounds shown in table 14 below were prepared according to the following general procedure:

Compound 01.04 (1 eq.) and the respective heteroaryl halide (1.3 eq) were solubilised in DME and aqueous Na$_2$CO$_3$ (2.5 eq, 2M) was added. The mixture was sparged with argon and 1,1'-bis(diphenylphosphino)ferrocene-palladium(II)dichloride dichloromethane complex (0.1 eq) was added. The reaction mixture was stirred at 150° C. for 2 hours (if the reaction was not complete, 1.3 eq. of heteroaryl halide as well as 0.1 eq. of catalyst were added and the reaction was stirred between 2 and 20 additional hours at 150° C.). The reaction mixture was then filtered through silicone filter and concentrated under reduced pressure. The crude mixture was purified without work up by preparative HPLC to the desired compound.

TABLE 14

| Example | Structure<br>IUPAC-Name<br>LC-MS (method): Retention time; Mass found<br>$^1$H-NMR |
|---|---|
| Example 130.01 | tert-butyl 4-[(2-{[6-(3-chloro-2-methylpyridin-4-yl)-1H-benzimidazol-2-yl]amino}pyridin-4-yl)methyl]piperazine-1-carboxylate<br>LC-MS (Method 4): $R_t$ = 1.33 min; MS (ESpos): m/z = 534 [M + H]$^+$<br>$^1$H-NMR (400 MHz, DMSO-d$_6$): δ [ppm] = 1.39 (s, 9H), 2.36 (br t, 4H), 2.64 (s, 3H), 3.34-3.38 (m, 4H), 3.50 (s, 2H), 6.93 (d, 1H), 7.08-7.16 (m, 1H), 7.18 (br s, 1H), 7.31 (br d, 1H), 7.40-7.45 (m, 1H), 7.55-7.67 (m, 1H), 8.27 (br d, 1H), 8.41 (d, 1H), 10.69 (br d, 1H), 12.24 (br s, 1H). |

TABLE 14-continued

| | Structure<br>IUPAC-Name<br>LC-MS (method): Retention time; Mass found |
|---|---|
| Example | $^1$H-NMR |

Example 131.01 tert-butyl 4-[(2-{[6-(5-fluoro-2-methylpyridin-4-yl)-1H-benzimidazol-2-yl]amino}pyridin-4-yl)methyl]piperazine-1-carboxylate
LC-MS (Method 4): $R_t$ = 1.29 min; MS (ESpos): m/z = 518 [M + H]$^+$
$^1$H-NMR (400 MHz, DMSO-d$_6$): δ [ppm] = 1.39 (s, 9H), 2.36 (br t, 4H), 3.34-3.38 (m, 4H), 3.50 (s, 2H), 6.94 (d, 1H), 7.18 (s, 1H), 7.28-7.40 (m, 1H), 7.42-7.54 (m, 2H), 7.62 (br s, 0,5H), 7.84 (br s, 0,5H), 8.27 (d, 1H), 8.45 (d, 1H), 10.73 (br s, 1H), 12.27 (br s, 1H).

Example 132.01 tert-butyl 4-[(2-{[6-(3-chloro-5-fluoropyridin-4-yl)-1H-benzimidazol-2-yl]amino}pyridin-4-yl)methyl]piperazine-1-carboxylate
LC-MS (Method 4): $R_t$ = 1.32 min; MS (ESpos): m/z = 538 [M + H]$^+$
$^1$H-NMR (400 MHz, DMSO-d$_6$): δ [ppm] = 1.39 (s, 9H), 2.36 (br t, 4H), 3.35 (br d, 4H), 3.50 (s, 2H), 6.92-6.95 (m, 1H), 7.03-7.15 (m, 1H), 7.18 (br s, 1H), 7.39-7.48 (m, 1H), 7.57-7.64 (m, 1H), 8.27 (br s, 1H), 8.67 (br d, 2H), 10.72 (br d, 1H), 12.27 (br s, 1H).

Example 133.01 tert-butyl 4-[(2-{[6-(3-cyanopyridin-4-yl)-1H-benzimidazol-2-yl]amino}pyridin-4-yl)methyl]piperazine-1-carboxylate
LC-MS (Method 4): $R_t$ = 1.21 min; MS (ESpos): m/z = 511 [M + H]$^+$
$^1$H-NMR (400 MHz, DMSO-d$_6$): δ [ppm] = 1.40 (s, 9H), 2.36 (br t, 4H), 3.35-3.38 (m, 4H), 3.51 (s, 2H), 6.95 (d, 1H), 7.20 (br s, 1H), 7.39 (br s, 1H), 7.53 (br s, 1H), 7.65-7.77 (m, 2H), 8.28 (d, 1H), 8.83 (d, 1H), 9.06 (s, 1H), 10.67-10.86 (m, 1H), 12.27-12.47 (m, 1H).

TABLE 14-continued

| Example | Structure<br>IUPAC-Name<br>LC-MS (method): Retention time; Mass found<br>¹H-NMR |
|---|---|
| Example 134.01 | 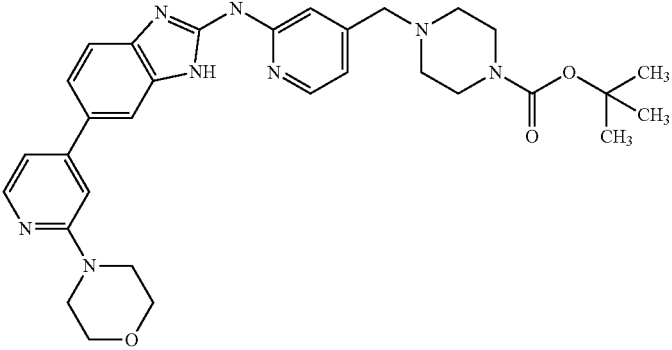<br>tert-butyl 4-{[2-({6-[2-(morpholin-4-yl)pyridin-4-yl]-1H-benzimidazol-2-yl}amino)pyridin-4-yl]methyl}piperazine-1-carboxylate<br>LC-MS (Method 4): $R_t$ = 1.28 min; MS (ESpos): m/z = 571 [M + H]⁺<br>1H-NMR (400 MHz, DMSO-d6): δ [ppm] = 1.40 (s, 9H), 2.36 (br t, 4H), 3.34-3.38 (m, 4H), 3.50 (s, 2H), 3.51-3.56 (m, 4H), 3.69-3.76 (m, 4H), 6.93 (d, 1H), 7.01 (br s, 1H), 7.06 (br s, 1H), 7.20 (br s, 1H), 7.38-7.56 (m, 2H), 7.71-7.90 (m, 1H), 8.15 (d, 1H), 8.26 (d, 1H), 10.68 (br s, 1H), 12.19 (br s, 1H). |
| Example 135.01 | 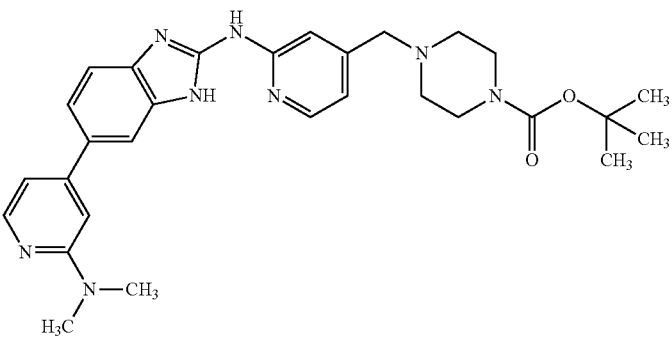 [SMILES: CN(C)c1cc(-c2ccc3nc(Nc4cc(CN5CCN(C(=O)OC(C)(C)C)CC5)ccn4)[nH]c3c2)ccn1]<br>tert-butyl 4-{[2-({6-[2-(dimethylamino)pyridin-4-yl]-1H-benzimidazol-2-yl}amino)pyridin-4-yl]methyl}piperazine-1-carboxylate<br>LC-MS (Method 2): $R_t$ = 1.33 min; MS (ESIpos): m/z = 529 [M + H]⁺<br>¹H-NMR (400 MHz, DMSO-d₆): δ [ppm] = 1.40 (s, 9H), 2.36 (br t, 4H), 3.09 (s, 6H), 3.34 (s, 4H), 3.50 (s, 2H), 6.80-6.90 (m, 2H), 6.90-6.95 (m, 1H), 7.18 (br s, 1H), 7.37-7.58 (m, 2H), 7.68-7.89 (m, 1H), 8.07-8.13 (m, 1H), 8.26 (d, 1H), 10.62-10.73 (m, 1H), 12.14-12.24 (m, 1H). |
| Example 136.01 | 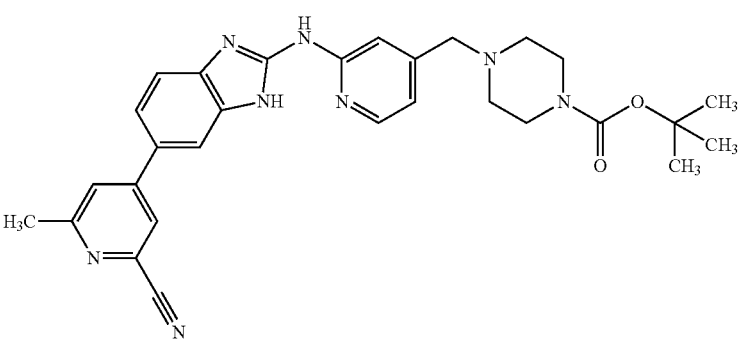 [SMILES: Cc1cc(-c2ccc3nc(Nc4cc(CN5CCN(C(=O)OC(C)(C)C)CC5)ccn4)[nH]c3c2)cc(C#N)n1]<br>tert-butyl 4-[(2-{[6-(2-cyano-6-methylpyridin-4-yl)-1H-benzimidazol-2-yl]amino}pyridin-4-yl)methyl]piperazine-1-carboxylate<br>LC-MS (Method 2): $R_t$ = 1.32 min; MS (ESIpos): m/z = 525 [M + H]⁺<br>¹H-NMR (400 MHz, DMSO-d₆): δ [ppm] = 1.40 (s, 9H), 2.36 (br s, 4H), 2.58 (s, 3H), 3.34 (s, 4H), 3.50 (s, 2H), 6.94 (d, 1H), 7.22 (br s, 1H), |

TABLE 14-continued

| Example | Structure<br>IUPAC-Name<br>LC-MS (method): Retention time; Mass found<br>¹H-NMR |
|---|---|
| | 7.42-7.65 (m, 2H), 7.94 (br s, 2H), 8.20 (br s, 1H), 8.27 (d, 1H), 10.73 (br s, 1H), 12.13-12.44 (m, 1H). |
| Example 137.01 | tert-butyl 4-[(2-{[6-(2-fluoropyridin-4-yl)-1H-benzimidazol-2-yl]amino}pyridin-4-yl)methyl]piperazine-1-carboxylate<br>LC-MS (Method 2): R$_t$ = 1.29 min; MS (ESIpos): m/z = 504 [M + H]⁺<br>¹H-NMR (400 MHz, DMSO-d$_6$): δ [ppm] = 1.39 (s, 9H), 2.36 (br t, 4H), 3.34 (s, 4H), 3.50 (s, 2H), 6.94 (d, 1H), 7.22 (br s, 1H), 7.41-7.60 (m, 3H), 7.64-7.74 (m, 1H), 7.90 (br s, 1H), 8.26 (dd, 2H), 10.59-10.84 (m, 1H), 12.13-12.42 (m, 1H). |
| Example 138.01 | tert-butyl 4-[(2-{[6-(2-aminopyridin-4-yl)-1H-benzimidazol-2-yl]amino}pyridin-4-yl)methyl]piperazine-1-carboxylate<br>LC-MS (Method 2): R$_t$ = 1.14 min; MS (ESIpos): m/z = 501 [M + H]⁺<br>¹H-NMR (400 MHz, DMSO-d$_6$): δ [ppm] = 1.40 (s, 9H), 2.36 (br t, 4H), 3.34 (s, 4H), 3.50 (s, 2H), 5.89 (br s, 2H), 6.68-6.83 (m, 2H), 6.90-6.95 (m, 1H), 7.14-7.84 (m, 4H), 7.93 (d, 1H), 8.25 (s, 1H), 10.60-10.75 (m, 1H), 12.12-12.29 (m, 1H). |
| Example 139.01 | tert-butyl 4-{[2-({6-[2-(difluoromethyl)pyridin-4-yl]-1H-benzimidazol-2-yl}amino)pyridin-4-yl]methyl}piperazine-1-carboxylate<br>LC-MS (Method 4): R$_t$ = 1.29 min; MS (ESpos): m/z = 536 [M + H]⁺<br>¹H-NMR (400 MHz, DMSO-d$_6$): δ [ppm] = 1.39 (s, 9H), 2.33-2.39 (m, 4H), 3.34 (s, 4H), 3.50 (s, 2H), 6.84-7.22 (m, 3H), 7.42-7.66 (m, 2H), 7.81-8.03 (m, 3H), 8.27 (d, 1H), 8.66-8.71 (m, 1H), 10.70-10.82 (m, 1H), 12.17-12.37 (m, 1H). |

TABLE 14-continued

Example | Structure / IUPAC-Name / LC-MS (method): Retention time; Mass found / ¹H-NMR Example 140.01

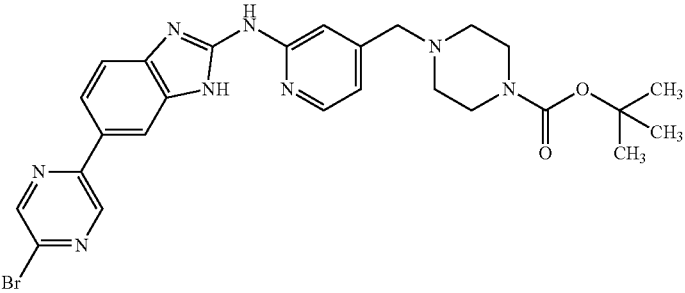 [SMILES: CC(C)(C)OC(=O)N1CCN(Cc2ccnc(Nc3nc4ccc(-c5cnc(Br)cn5)cc4[nH]3)c2)CC1]

tert-butyl 4-[(2-{[6-(5-bromopyrazin-2-yl)-1H-benzimidazol-2-yl]amino}pyridin-4-yl)methyl]piperazine-1-carboxylate
LC-MS (Method 2): $R_t$ = 1.39 min; MS (ESIneg): m/z = 563 [M − H]⁻
¹H-NMR (400 MHz, DMSO-d₆): δ [ppm] = 1.40 (s, 9H), 2.33-2.40 (m, 4H), 3.34-3.39 (m, 4H), 3.51 (s, 2H), 6.94 (d, 1H), 7.18 (s, 1H), 7.40-7.66 (m, 1H), 7.85 (br d, 1H), 8.27 (d, 2H), 8.85 (d, 1H), 9.04 (br s, 1H), 10.77 (br s, 1H), 12.31 (br s, 1H).

Example 141.01

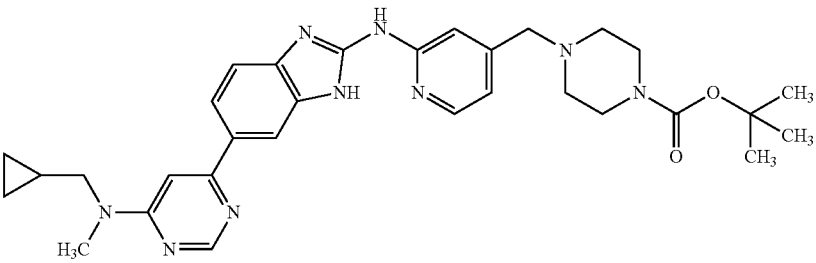 [SMILES: CN(CC1CC1)c1cc(-c2ccc3nc(Nc4cc(CN5CCN(C(=O)OC(C)(C)C)CC5)ccn4)[nH]c3c2)ncn1]

tert-butyl 4-({2-[(6-{6-[(cyclopropylmethyl)(methyl)amino]pyrimidin-4-yl}-1H-benzimidazol-2-yl)amino]pyridin-4-yl}methyl)piperazin-1-carboxylate
LC-MS (Method 2): $R_t$ = 1.33 min; MS (ESIpos): m/z = 570 [M + H]⁺
¹H NMR (400 MHz, DMSO-d₆) δ ppm 0.32 (q, J = 4.90 Hz, 2 H), 0.40-0.51 (m, 2 H) 1.07-1.12 (m, 1 H) 1.40 (s, 9 H) 2.36 (br t, J = 4.69 Hz, 4 H) 3.17 (s, 3 H) 3.35 (br s, 4 H) 3.50 (s, 2 H) 3.54 (br d, J = 6.59 Hz, 2 H) 6.93 (br d, J = 4.31 Hz, 1 H) 7.02-7.13 (m, 1 H), 7.18 (b s, 1 H), 7.35-7.58 (m, 1 H) 7.88 (br dd, J = 15.59, 8.24 Hz, 1 H) 8.15 (s, 0,5 H) 8.26 (d, J = 5.07 Hz, 1 H) 8.30 (s, 0,5 H) 8.51 (s, 1 H) 10.57-10.77 (m, 1 H) 12.22 (br d, J = 18.50 Hz, 1 H)

Example 142.01

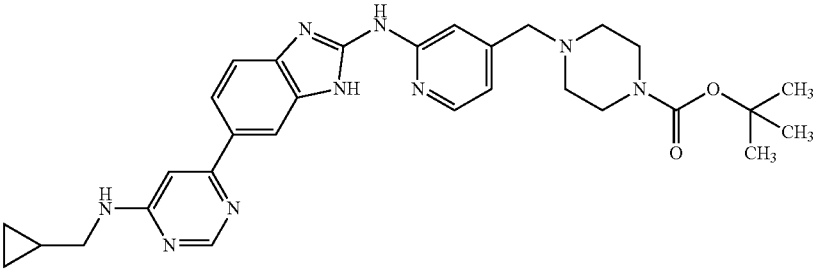 [SMILES: CC(C)(C)OC(=O)N1CCN(Cc2ccnc(Nc3nc4ccc(-c5cc(NCC6CC6)ncn5)cc4[nH]3)c2)CC1]

tert-butyl 4-({2-[(6-{6-[(cyclopropylmethyl)amino]pyrimidin-4-yl}-1H-benzimidazol-2-yl)amino]pyridin-4-yl}methyl)piperazine-1-carboxylate
LC-MS (Method 2): $R_t$ = 1.24 min; MS (ESIpos): m/z = 556 [M + H]⁺
¹H-NMR (400 MHz, DMSO-d₆): δ [ppm] = 0.21-0.28 (m, 2H), 0.44-0.50 (m, 2H), 1.02-1.12 (m, 1H), 1.37-1.42 (m, 9H), 2.35 (t, 4H), 3.22 (t, 2H), 3.34-3.41 (m, 4H), 3.50 (s, 2H), 6.87-6.98 (m, 2H), 7.17 (br s, 1H), 7.33-7.59 (m, 3H), 7.67-7.82 (m, 1H), 8.27 (d, 1H), 8.44 (s, 1H), 10.62-10.80 (m, 1H), 12.15-12.30 (m, 1H).

TABLE 14-continued

| Example | Structure<br>IUPAC-Name<br>LC-MS (method): Retention time; Mass found<br>¹H-NMR |
|---|---|
| Example 143.01 | 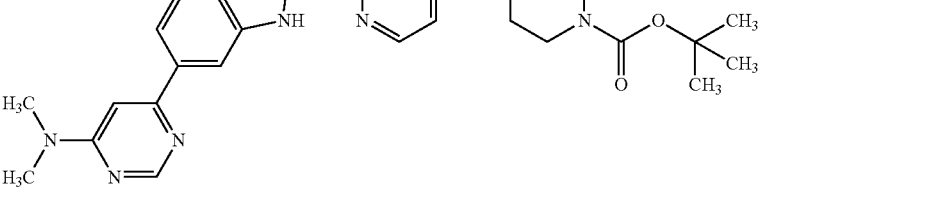<br>tert-butyl 4-{[2-({6-[6-(dimethylamino)pyrimidin-4-yl]-1H-benzimidazol-2-yl}amino)pyridin-4-yl]methyl}piperazine-1-carboxylate<br>LC-MS (Method 2): $R_t$ = 1.2 min; MS (ESIpos): m/z = 530 [M + H]⁺<br>¹H-NMR (400 MHz, DMSO-d₆); δ [ppm] = 1.40 (s, 12H), 2.34-2.38 (m, 4H), 3.15 (s, 6H), 3.35-3.38 (m, 4H), 3.50 (s, 2H), 6.91-6.96 (m, 1H), 7.02-7.15 (m, 1H), 7.17-7.20 (m, 1H), 7.35-7.44 (m, 1H), 7.85-7.93 (m, 1H), 8.16 (br s, 1H), 8.24-8.28 (m, 1H), 8.31 (br s, 1H), 8.52 (d, 1H), 10.65-10.76 (m, 1H), 12.16-12.29 (m, 1H). |

Example 145.01.01

Tert-butyl 4-[(2-{[6-(6-chloropyrimidin-4-yl)-1H-benzimidazol-2-yl]amino}pyridin-4-yl)methyl]piperazine-1-carboxylate

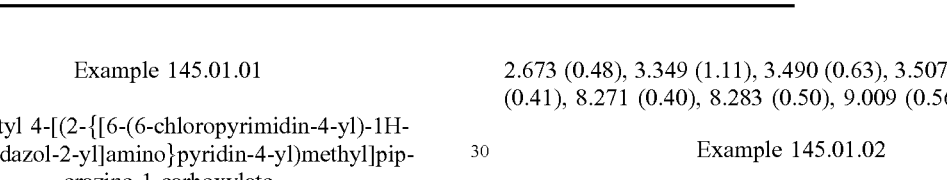

Tert-butyl 4-[(2-{[6-(4,4,5,5-tetramethyl-1,3,2-dioxaborolan-2-yl)-1H-benzimidazol-2-yl]amino}pyridin-4-yl) methyl]piperazine-1-carboxylate (500 mg; see Compound 01.04), 4,6-dichloropyrimidine (418 mg), Na₂CO₃ (1.4 ml, 2.0 M) were solubilised in a mixture of 1,4-dioxane (15 ml) and water (1.5 ml) and the reaction mixture was sparged with argon for 5 min. The 1,1'-bis(diphenylphosphino)ferrocene-palladium(II)dichloride dichloromethane complex (76.4 mg) was added and the mixture was stirred 5 h at 120° C. The mixture was diluted with water and extracted three times with EtOAc. The combined organic layer were washed with brine, dried over a silicone filter and concentrated under reduced pressure. The crude mixture was purified by flash chromatography on silica gel to give 286 mg (71% purity) of the title compound.

LC-MS (method 2): $R_t$=1.32 min; MS (ESIneg): m/z=519 [M−H]⁻.

¹H-NMR (400 MHz, DMSO-d6) δ[ppm]: 0.805 (0.50), 0.814 (1.49), 0.822 (0.56), 0.831 (3.56), 0.836 (2.02), 0.841 (0.67), 0.851 (1.58), 0.853 (2.39), 0.858 (1.79), 0.869 (0.66), 0.875 (0.48), 0.936 (0.92), 0.953 (1.06), 1.066 (1.70), 1.237 (1.03), 1.274 (0.44), 1.299 (4.92), 1.395 (16.00), 1.987 (0.48), 2.332 (0.60), 2.359 (1.23), 2.518 (2.69), 2.522 (1.73), 2.673 (0.48), 3.349 (1.11), 3.490 (0.63), 3.507 (1.01), 7.180 (0.41), 8.271 (0.40), 8.283 (0.50), 9.009 (0.56).

Example 145.01.02 tert-butyl 4-[(2-{[6-(6-chloro-5-fluoropyrimidin-4-yl)-1H-benzimidazol-2-yl]amino}pyridin-4-yl) methyl]piperazine-1-carboxylate

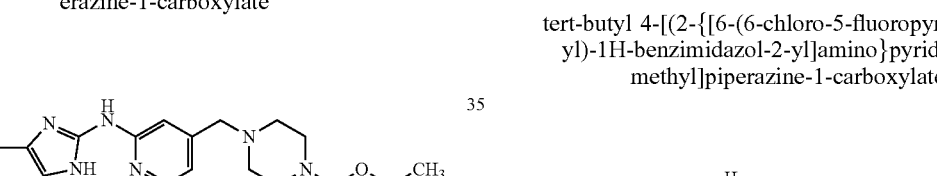

tert-butyl 4-[(2-{[6-(4,4,5,5-tetramethyl-1,3,2-dioxaborolan-2-yl)-1H-benzimidazol-2-yl]amino}pyridin-4-yl) methyl]piperazine-1-carboxylate (500 mg, see Compound 01.04), 4,6-dichloro-5-fluoropyrimidine (469 mg), aqueous Na₂CO₃ (1.4 ml, 2.0 M) and 1,1'-bis(diphenylphosphino) ferrocene-palladium(II)dichloride dichloromethane complex (76.4 mg) were stirred in a sealed tube in a mixture of 1,4-dioxane (10 ml) and water (2.0 ml) overnight at 110'. The mixture was then filtered over a silicon e filter and concentrated under reduced pressure. The crude mixture was purified by flash chromatography on silica gel to give 556 mg (60% purity) of the title compound.

LC-MS (method 2): $R_t$=1.36 min; MS (ESIpos): m/z=537 [M−H]⁺.

¹H-NMR (400 MHz, DMSO-d6) δ [ppm]: 1.065 (16.00), 1.155 (1.74), 1.299 (1.42), 1.393 (2.88), 1.414 (1.32), 2.539 (0.70), 3.334 (0.76), 3.937 (0.68), 8.097 (0.85).

The Example compounds shown in table 15 below were prepared as follows:

The respective chloride (example 145.01.01 or 145.01.02) was solubilised in dioxane and the respective amine (4 to 6 eq) was added. In some cases K$_2$CO$_3$ or DIPEA (4 eq.) was used. The reaction mixture was stirred 16 hours at reflux. The reaction mixture was then filtered, concentrated under reduced pressure and purified by standard reversed-phase preparative HPLC. or The respective chloride (example 145.01.01 or 145.01.02) was solubilised in dioxane and the respective alcohol (2 to 6 eq) and NaH (6 eq.) was added. The reaction was stirred 1 to 3 hours at rt. The reaction was stopped by the addition of water, and the aqueous phase was extracted three times with DCM. The organic phase was dried (silicone filter), concentrated under reduced pressure and purified by standard reversed-phase preparative HPLC.

TABLE 15

| Example | Structure<br>IUPAC-Name<br>LC-MS (method): Retention time; Mass found<br>$^1$H-NMR |
|---|---|
| Example 144.01 | 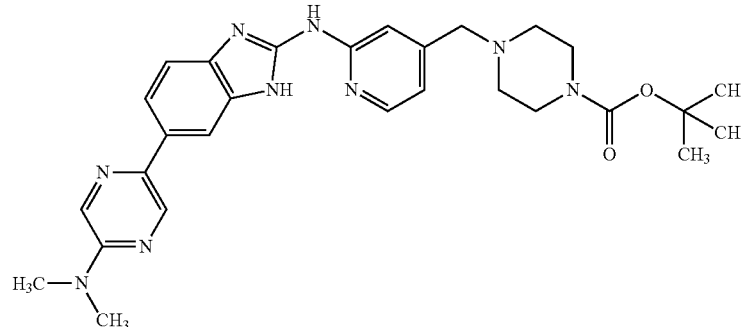<br>tert-butyl 4-{[2-({6-[5-(dimethylamino)pyrazin-2-yl]-1H-benzimidazol-2-yl}amino)pyridin-4-yl]methyl}piperazine-1-carboxylate<br>LC-MS (Method 2): R$_t$ = 1.3 min; MS (ESIpos): m/z = 530 [M + H]$^+$<br>$^1$H NMR (400 MHz, DMSO-d$_6$) δ ppm 1.40 (s, 9 H) 2.36 (br t, J = 4.69 Hz, 4 H) 3.12 (s, 6 H) 3.34-3.39 (m, 4 H) 3.50 (s, 2 H) 6.92 (d, J = 5.83 Hz, 1 H) 7.18 (br s, 1 H) 7.34-7.53 (m, 1 H) 7.65 (br dd, J = 14.32, 8.24 Hz, 1 H) 7.88-8.09 (m, 1 H) 8.21 (s, 1 H) 8.26 (d, J = 5.07 Hz, 1H) 8.57-8.67 (m, 1 H) 10.62 (s, 1 H) 12.11 (br d, J = 11.41 Hz, 1 H) |
| Example 145.01 | tert-butyl 4-{[2-({6-[6-(piperidin-1-yl)pyrimidin-4-yl]-1H-benzimidazol-2-yl}amino)pyridin-4-yl]methyl}piperazine-1-carboxylate<br>LC-MS (Method 4): R$_t$ = 1.35 min; MS (ESIpos): m/z = 570 [M + H]$^+$<br>$^1$H NMR (400 MHz, DMSO-d$_6$) δ ppm 1.40 (s, 9 H) 1.56 (br d, J = 3.80 Hz, 4 H) 1.63-1.70 (m, 2 H) 2.36 (br t, J = 4.94 Hz, 4 H) 3.34-3.39 (m, 4 H) 3.50 (s, 2 H) 3.72 (br s, 4 H) 6.93 (br d, J = 5.32 Hz, 1 H) 7.18 (s, 1 H) 7.20-7.29 (m, 1 H) 7.34-7.56 (m, 1 H) 7.89 (br s, 1H) 8.17 (br s, 0,5 H) 8.26 (d, J = 5.32 Hz, 1 H) 8.31 (br s, 0,5 H) 8.51 (d, J = 1.01 Hz, 1 H) 10.70 (br d, J = 11.66 Hz 1 H) 12.21 (br d, J = 15.71 Hz, 1 H) |

TABLE 15-continued

| Example | Structure<br>IUPAC-Name<br>LC-MS (method): Retention time; Mass found<br>¹H-NMR |
|---|---|
| Example 146.01 | 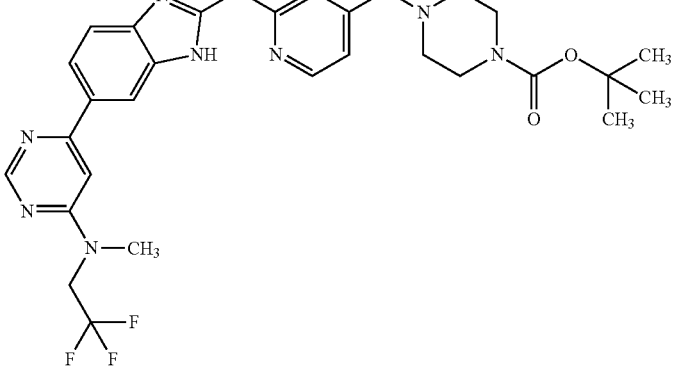<br>tert-butyl 4-({2-[(6-{6-[methyl(2,2,2-trifluoroethyl)amino]pyrimidin-4-yl}-1H-benzimidazol-2-yl)amino]pyridin-4-yl}methyl)piperazine-1-carboxylate<br>LC-MS (Method 2): $R_t$ = 1.32 min; MS (ESIpos): m/z = 598 [M + H]⁺<br>¹H-NMR (400 MHz, DMSO-d₆): δ [ppm] = 1.40 (s, 9H), 2.36 (br t, 4H), 3.24 (s, 3H), 3.35 (br s, 4H), 3.50 (s, 2H), 4.62 (q, 2H), 6.93 (d, 1H), 7.21 (br s, 1H), 7.28 (br s, 1H), 7.44 (br s, 1H), 7.93 (br d, 1H), 8.26 (d, 2H), 8.62 (d, 1H), 10.71 (br s, 1H), 12.27 (br s, 1H). |
| Example 147.01 | 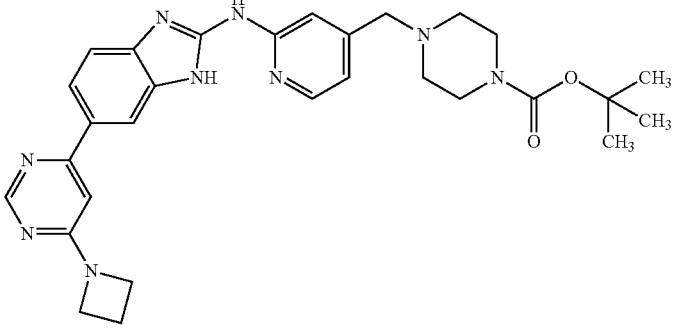<br>tert-butyl 4-{[2-({6-[6-(azetidin-1-yl)pyrimidin-4-yl]-1H-benzimidazol-2-yl}amino)pyridin-4-yl]methyl}piperazine-1-carboxylate<br>LC-MS (Method 2): $R_t$ = 1.18 min; MS (ESIpos): m/z = 542 [M + H]⁺<br>6H), 3.35 (br s, 4H), 3.50 (s, 2H), 4.10 (t, 4H), 6.73-6.87 (m, 1H), 6.91-6.96 (m, 1H), 7.18 (s, 1H), 7.36-7.57 (m, 1H), 7.82-7.88 (m, 1H), 8.09-8.31 (m, 2H), 8.49 (d, 1H), 10.71 (br s, 1H), 12.24 (br s, 1H). |
| Example 148.01 | 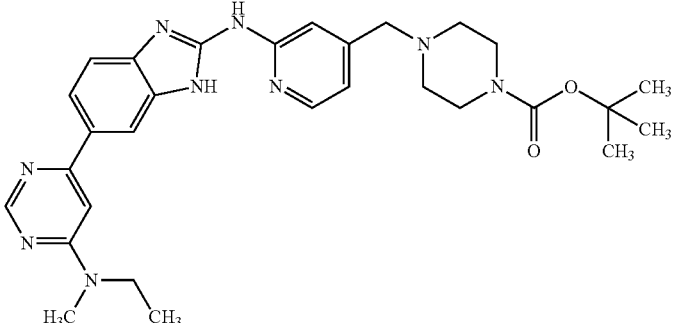<br>tert-butyl 4-({2-[(6-{6-[ethyl(methyl)amino]pyrimidin-4-yl}-1H-benzimidazol-2-yl)amino]pyridin-4-yl}methyl)piperazine-1-carboxylate<br>LC-MS (Method 4): $R_t$ = 1.29 min; MS (ESIpos): m/z = 544 [M + H]⁺<br>¹H NMR (400 MHz, DMSO-d₆) δ ppm 1.07-1.16 (m, 3 H) 1.40 (s, 9 H) |

TABLE 15-continued

| Example | Structure<br>IUPAC-Name<br>LC-MS (method): Retention time; Mass found<br>¹H-NMR |
|---|---|
| | 2.31-2.40 (m, 4 H) 3.10 (s, 3 H) 3.34-3.38 (m, 4 H) 3.43-3.56 (m, 2 H) 3.66 (q, J = 6.84 Hz, 2 H) 6.91-6.95 (m, 1 H) 6.99-7.11 (m, 1 H) 7.15-7.21 (m, 1 H) 7.36-7.57 (m, 1 H) 7.88 (br s, 1 H) 8.15 (br s, 0,5 H) 8.26 (d, J = 5.58 Hz, 1 H) 8.30 (br s, 0,5 H) 8.51 (d, J = 1.01 Hz, 1 H) 10.71 (br s, 1 H) 12.22 (br d, J = 16.98 Hz, 1 H) |
| Example 149.01 | 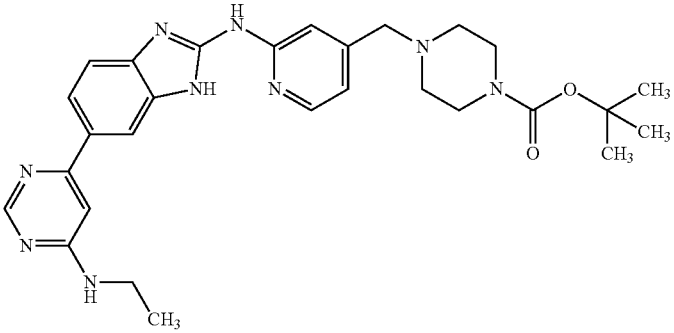<br>tert-butyl 4-{[2-({6-[6-(ethylamino)pyrimidin-4-yl]-1H-benzimidazol-2-yl}amino)pyridin-4-yl]methyl}piperazine-1-carboxylate<br>LC-MS (Method 4): R$_t$ = 1.19 min; MS (ESIpos): m/z = 530 [M + H]⁺<br>¹H NMR (400 MHz, DMSO-d$_6$) δ ppm 1.17 (t, J = 7.10 Hz, 3 H) 1.40 (s, 9 H) 2.36 (br t, J = 4.94 Hz, 4 H) 3.35 (br s, 4 H) 3.50 (s, 2 H) 6.83-6.91 (m, 1 H) 6.93 (d, J = 5.07 Hz, 1 H) 7.17 (br s, 1 H) 7.30 (br s, 1 H) 7.35-7.58 (m, 1 H) 7.74 (br s, 1 H) 7.94-8.23 (m, 1 H) 8.26 (d, J = 5.32 Hz, 1 H) 8.45 (s, 1 H) 10.71 (s, 1 H) 12.22 (br d, J = 8.11 Hz, 1 H) |
| Example 150.01 | 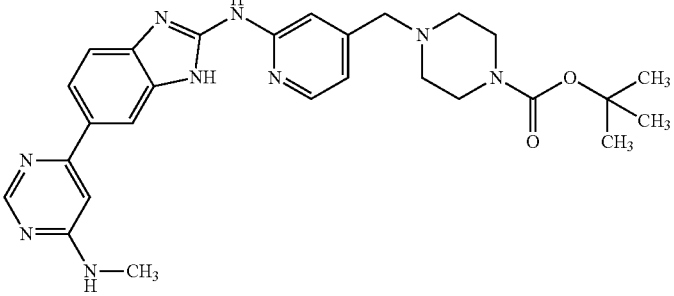<br>tert-butyl 4-{[2-({6-[6-(methylamino)pyrimidin-4-yl]-1H-benzimidazol-2-yl}amino)pyridin-4-yl]methyl}piperazine-1-carboxylate<br>LC-MS (Method 4): R$_t$ = 1.13 min; MS (ESIpos): m/z = 516 [M + H]⁺<br>¹H NMR (400 MHz, DMSO-d$_6$) δ ppm 1.40 (s, 9 H) 2.36 (br t, J = 4.82 Hz, 4 H) 2.86 (d, J = 4.82 Hz, 3 H) 3.34-3.38 (m, 4 H) 3.50 (s, 2 H) 6.86 (br s, 1 H) 6.93 (d, J = 5.32 Hz, 1 H) 7.14-7.21 (m, 1 H) 7.25 (br s, 1 H) 7.39 (br s, 0.5 H) 7.53 (br s, 0.5 H) 7.76 (br s, 1 H) 8.03 (br s, 0,5 H) 8.22 (br s, 0,5 H) 8.26 (d, J = 5.07 Hz, 1 H) 8.47 (s, 1 H) 10.71 (s, 1 H) 12.24 (br s, 1 H) |
| Example 151.01 | 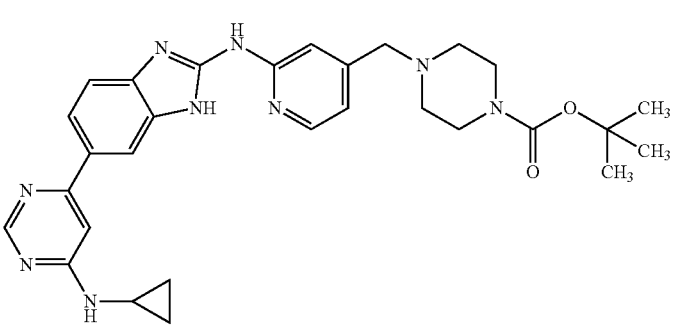 [SMILES: CC(C)(C)OC(=O)N1CCN(Cc2ccnc(Nc3nc4ccc(-c5cc(NC6CC6)ncn5)cc4[nH]3)c2)CC1] |

TABLE 15-continued

| Example | Structure<br>IUPAC-Name<br>LC-MS (method): Retention time; Mass found<br>¹H-NMR |
|---|---|
| Example 152.01 | tert-butyl 4-{[2-({6-[6-(cyclopropylamino)pyrimidin-4-yl]-1H-benzimidazol-2-yl}amino)pyridin-4-yl]methyl}piperazine-1-carboxylate<br>LC-MS (Method 2): $R_t$ = 1.19 min; MS (ESIpos): m/z = 542 [M + H]⁺<br>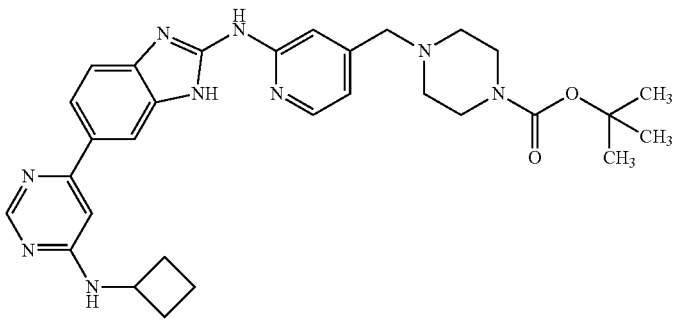 [SMILES: CC(C)(C)OC(=O)N1CCN(Cc2ccnc(Nc3nc4ccc(-c5cc(NC6CCC6)ncn5)cc4[nH]3)c2)CC1] |
| Example 153.01 | tert-butyl 4-{[2-({6-[6-(cyclobutylamino)pyrimidin-4-yl]-1H-benzimidazol-2-yl}amino)pyridin-4-yl]methyl}piperazine-1-carboxylate<br>LC-MS (Method 2): $R_t$ = 1.25 min; MS (ESIpos): m/z = 556 [M + H]⁺<br>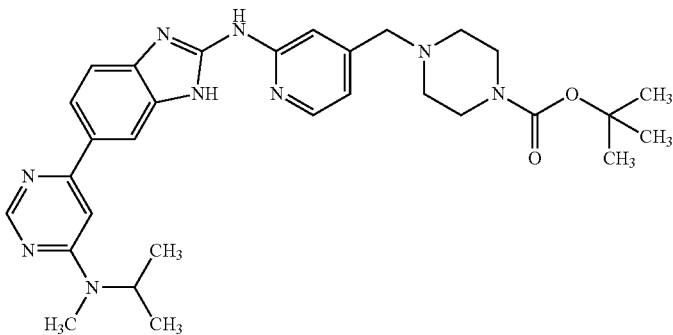 [SMILES: CC(C)N(C)c1cc(-c2ccc3nc(Nc4cc(CN5CCN(C(=O)OC(C)(C)C)CC5)ccn4)[nH]c3c2)ncn1]<br>tert-butyl 4-({2-[(6-{6-[methyl(propan-2-yl)amino]pyrimidin-4-yl}-1H-benzimidazol-2-yl)amino]pyridin-4-yl}methyl)piperazine-1-carboxylate<br>LC-MS (Method 4): $R_t$ = 1.32 min; MS (ESIpos): m/z = 558 [M + H]⁺<br>¹H-NMR (400 MHz, DMSO-$d_6$): δ [ppm] = 1.17 (d, 6H), 1.40 (s, 9H), 2.36 (br t, 4H), 2.94 (s, 3H), 3.34-3.39 (m, 4H), 3.50 (s, 2H), 6.93 (br d, 1H), 6.99-7.11 (m, 1H), 7.18 (s, 1H), 7.35-7.57 (m, 1H), 7.83-7.92 (m, 1H), 8.13-8.32 (m, 2H), 8.51 (d, 1H), 10.70 (br d, 1H), 12.21 (br d, 1H). |
| Example 154.01 | 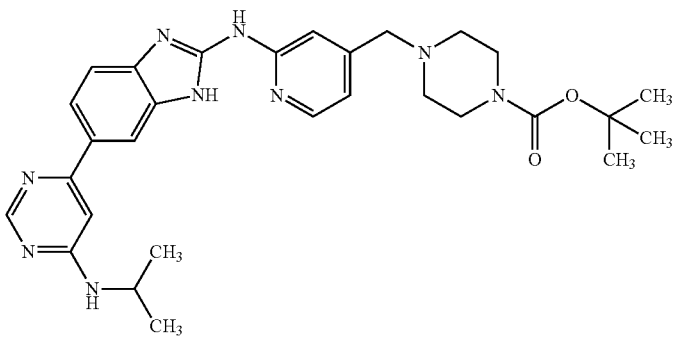<br>tert-butyl 4-{[2-({6-[6-(propan-2-ylamino)pyrimidin-4-yl]-1H-benzimidazol-2-yl}amino)pyridin-4-yl]methyl}piperazine-1-carboxylate<br>LC-MS (Method 4): $R_t$ = 1.23 min; MS (ESIpos): m/z = 544 [M + H]⁺<br>¹H-NMR (400 MHz, DMSO-$d_6$): δ [ppm] = 1.19 (d, 6H), 1.40 (s, 9H), 2.36 (br t, 4H), 3.34-3.37 (m, 4H), 3.50 (s, 2H), 4.12 (br s, 1H), 6.82-6.90 |

TABLE 15-continued

| Example | Structure<br>IUPAC-Name<br>LC-MS (method): Retention time; Mass found<br>¹H-NMR |
|---|---|
| | (m, 1H), 6.93 (d, 1H), 7.18 (br s, 2H), 7.35-7.57 (m, 1H), 7.72 (br s, 1H), 7.94-8.21 (m, 1H), 8.26 (d, 1H), 8.45 (s, 1H), 10.70 (s, 1H), 12.22 (br d, 1H). |
| Example 155.01 | 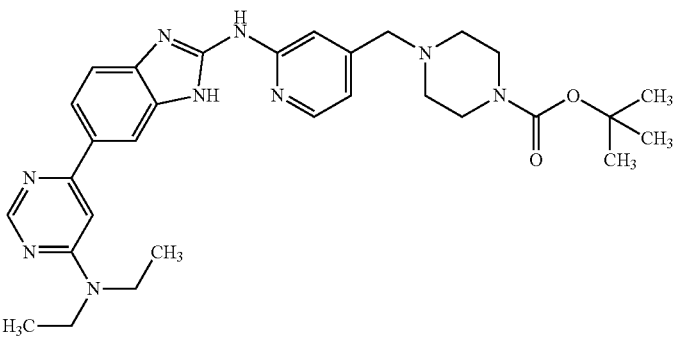 [SMILES: CCN(CC)c1cc(-c2ccc3nc(Nc4cc(CN5CCN(C(=O)OC(C)(C)C)CC5)ccn4)[nH]c3c2)ncn1]<br>tert-butyl 4-{[2-({6-[6-(diethylamino)pyrimidin-4-yl]-1H-benzimidazol-2-yl}amino)pyridin-4-yl]methyl}piperazine-1-carboxylate<br>LC-MS (Method 4): R$_t$ = 1.32 min; MS (ESIpos): m/z = 558 [M + H]⁺<br>¹H-NMR (400 MHz, DMSO-d$_6$): δ [ppm] = 1.16 (br t, 6H), 1.40 (s, 9H), 2.36 (br t, 4H), 3.35-3.39 (m, 4H), 3.50 (s, 2H), 3.60 (br d, 4H), 6.93 (br d, 1H), 6.96-7.08 (m, 1H), 7.18 (br s, 1H), 7.34-7.59 (m, 1H), 7.88 (br d, 1H), 8.26 (br d, 2H), 8.51 (s, 1H), 10.60-10.77 (m, 1H), 12.16-12.27 (m, 1H). |
| Example 156.01 | 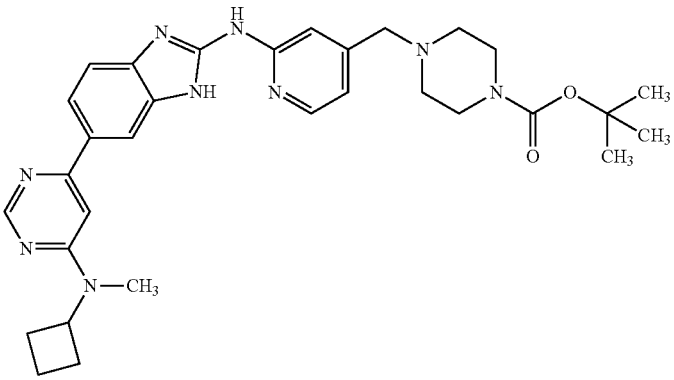 [SMILES: CN(c1cc(-c2ccc3nc(Nc4cc(CN5CCN(C(=O)OC(C)(C)C)CC5)ccn4)[nH]c3c2)ncn1)C1CCC1]<br>tert-butyl 4-({2-[(6-{6-[cyclobutyl(methyl)amino]pyrimidin-4-yl}-1H-benzimidazol-2-yl)amino]pyridin-4-yl}methyl)piperazine-1-carboxylate<br>LC-MS (Method 4): R$_t$ = 1.36 min; MS (ESIpos): m/z = 570 [M + H]⁺<br>¹H-NMR (400 MHz, DMSO-d$_6$): δ [ppm] = 1.40 (s, 9H), 1.65-1.75 (m, 2H), 2.13-2.29 (m, 4H), 2.36 (br t, 4H), 3.08 (s, 3H), 3.34-3.39 (m, 4H), 3.50 (s, 2H), 5.03 (br s, 1H), 6.93 (br d, 1H), 7.00-7.13 (m, 1H), 7.18 (s, 1H), 7.33-7.60 (m, 1H), 7.89 (br d, 1H), 8.11-8.33 (m, 2H), 8.53 (d, 1H), 10.70 (br d, 1H), 12.22 (br d, 1H). |
| Example 157.01 | 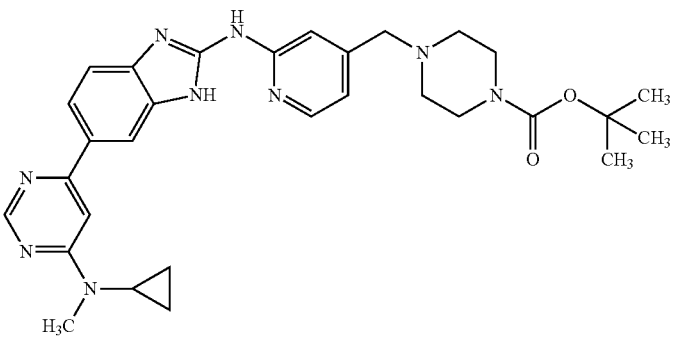 [SMILES: CN(c1cc(-c2ccc3nc(Nc4cc(CN5CCN(C(=O)OC(C)(C)C)CC5)ccn4)[nH]c3c2)ncn1)C1CC1] |

TABLE 15-continued

| Example | Structure<br>IUPAC-Name<br>LC-MS (method): Retention time; Mass found<br>$^1$H-NMR |
|---|---|
| | tert-butyl 4-({2-[(6-{6-[cyclopropyl(methyl)amino]pyrimidin-4-yl}-1H-benzimidazol-2-yl)amino]pyridin-4-yl}methyl)piperazine-1-carboxylate<br>LC-MS (Method 2): R$_t$ = 1.05 min; MS (ESIpos): m/z = 556 [M + H]$^+$<br>$^1$H NMR (400 MHz, DMSO-d$_6$) δ ppm 0.73 (br s, 2 H) 0.94-1.07 (m, 2 H) 1.17 (t, J = 7.10 Hz, 1 H) 1.40 (s, 9 H) 2.36 (br t, J = 4.82 Hz, 4 H) 3.13 (s, 3 H) 3.35 (br s, 4 H) 3.50 (s, 2 H) 6.93 (br d, J = 4.56 Hz, 1 H) 7.18 (s, 1 H) 7.30-7.37 (m, 1 H) 7.41 (br d, J = 8.36 Hz, 0,5 H) 7.57 (br d, J = 8.62 Hz, 0,5 H) 7.77-7.90 (m, 1 H) 8.08 (s, 0,5 H) 8.27 (d, J = 5.07 Hz, 0,5 H) 8.28 (br s, 1 H) 8.57 (d, J = 1.01 Hz, 1 H) 10.64-10.79 (m, 1 H) 12.18-12.31 (m, 1 H) |
| Example 158.01 | 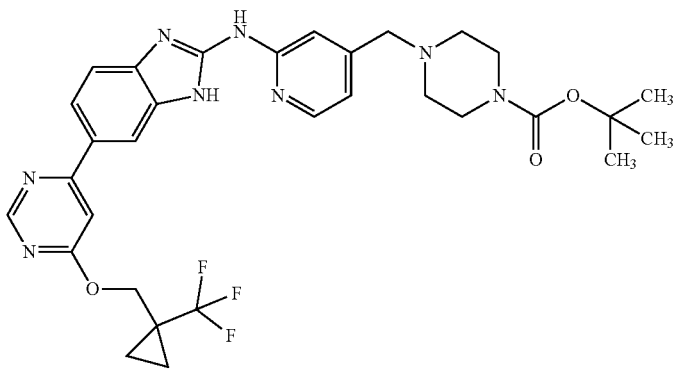 [SMILES: CC(C)(C)OC(=O)N1CCN(Cc2ccnc(Nc3nc4ccc(-c5cc(OCC6(C(F)(F)F)CC6)ncn5)cc4[nH]3)c2)CC1]<br>tert-butyl 4-[(2-{[6-(6-{[1-(trifluoromethyl)cyclopropyl]methoxy}pyrimidin-4-yl)-1H-benzimidazol-2-yl]amino}pyridin-4-yl)methyl]piperazine-1-carboxylate<br>LC-MS (Method 2): R$_t$ = 1.40 min; MS (ESIpos): m/z = 625 [M + H]$^+$<br>$^1$H-NMR (400 MHz, DMSO-d$_6$): δ [ppm] = 1.12 (br d, 4H), 1.40 (s, 9H), 2.34-2.38 (m, 4H), 3.35 (br s, 4H), 3.50 (s, 2H), 4.57 (s, 2H), 6.91-6.97 (m, 1H), 7.14-7.21 (m, 1H), 7.37 (s, 0,5H), 7.38-7.42 (m, 0,5H), 7.47-7.50 (m, 0,5H), 7.54-7.59 (m, 0,5H), 7.90-7.97 (m, 1H), 8.19-8.24 (m, 0,5H), 8.27 (d, 1H), 8.36-8.41 (m, 0,5H), 8.79 (d, 1H), 10.72-10.78 (m, 1H), 12.22-12.30 (m, 1H). |
| Example 159.01 | 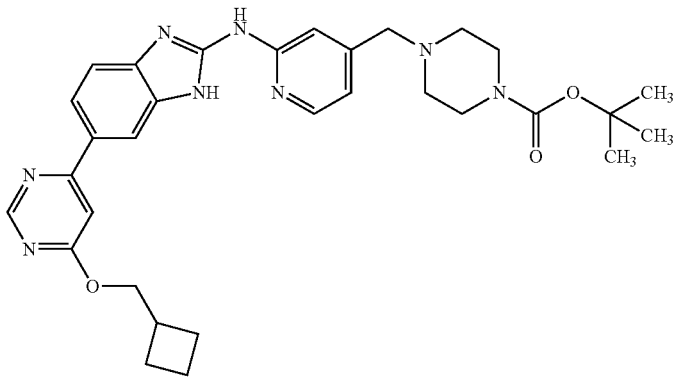 [SMILES: CC(C)(C)OC(=O)N1CCN(Cc2ccnc(Nc3nc4ccc(-c5cc(OCC6CCC6)ncn5)cc4[nH]3)c2)CC1]<br>tert-butyl 4-{[2-({6-[6-(cyclobutylmethoxy)pyrimidin-4-yl]-1H-benzimidazol-2-yl}amino)pyridin-4-yl]methyl}piperazine-1-carboxylate<br>LC-MS (Method 2): R$_t$ = 1.49 min; MS (ESIpos): m/z = 571 [M + H]$^+$<br>$^1$H-NMR (400 MHz, DMSO-d$_6$): δ [ppm] = 1.40 (s, 9H), 1.81-1.96 (m, 4H), 2.04-2.14 (m, 2H), 2.36 (br t, 4H), 2.77 (quin, 1H), 3.35 (br s, 4H), 3.50 (s, 2H), 4.37 (d, 2H), 6.94 (br s, 1H), 7.15-7.21 (m, 1H), 7.33 (s, 0,5H), 7.40 (br d, 0,5H), 7.44 (br s, 0,5H), 7.52-7.60 (m, 0,5H), 7.88-7.95 (m, 1H), 8.17-8.22 (m, 0,5H), 8.27 (d, 1H), 8.34-8.39 (m, 0,5H), 8.77 (s, 1H), 10.70-10.77 (m, 1H), 12.21-12.30 (m, 1H). |

TABLE 15-continued

| Example | Structure<br>IUPAC-Name<br>LC-MS (method): Retention time; Mass found<br>¹H-NMR |
|---|---|
| Example 160.01 | 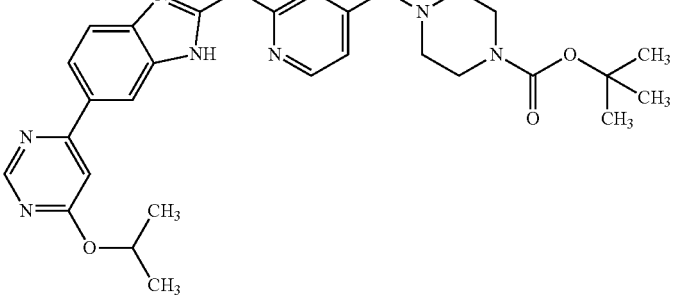<br>tert-butyl 4-{[2-({6-[6-(propan-2-yloxy)pyrimidin-4-yl]-1H-benzimidazol-2-yl}amino)pyridin-4-yl]methyl}piperazine-1-carboxylate<br>LC-MS (Method 2): R$_t$ = 1.40 min; MS (ESIpos): m/z = 545 [M + H]⁺<br>¹H-NMR (400 MHz, DMSO-d$_6$): δ [ppm] = 1.35 (d, 6H), 1.40 (s, 9H), 2.36 (br t, 4H), 3.35 (br s, 4H), 3.50 (s, 2H), 5.32-5.43 (m, 1H), 6.90-6.97 (m, 1H), 7.14-7.20 (m, 1H), 7.25-7.37 (m, 1H), 7.38-7.58 (m, 1H), 7.85-7.93 (m, 1H), 8.14-8.23 (m, 0,5H), 8.27 (d, 1H), 8.32-8.38 (m, 0,5H), 8.77 (d, 1H), 10.69-10.79 (m, 1H), 12.20-12.29 (m, 1H). |
| Example 161.01 | 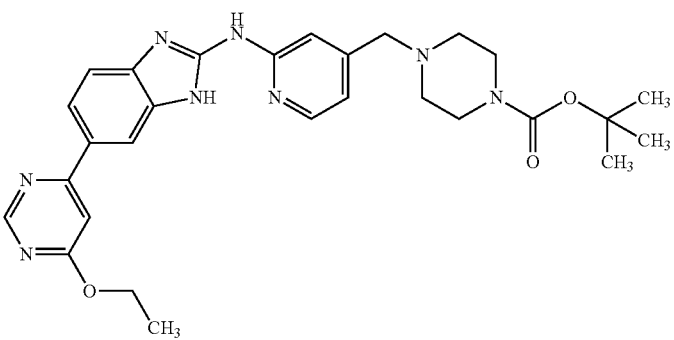 [SMILES: CCOc1cc(-c2ccc3nc(Nc4cc(CN5CCN(C(=O)OC(C)(C)C)CC5)ccn4)[nH]c3c2)ncn1]<br>tert-butyl 4-[(2-{[6-(6-ethoxypyrimidin-4-yl)-1H-benzimidazol-2-yl]amino}pyridin-4-yl)methyl]piperazine-1-carboxylate<br>LC-MS (Method 2): R$_t$ = 1.33 min; MS (ESIpos): m/z = 531 [M + H]⁺<br>¹H-NMR (400 MHz, DMSO-d$_6$): δ [ppm] = 1.35-1.39 (m, 3H), 1.40 (s, 9H), 2.36 (br t, 4H), 3.35 (br s, 4H), 3.50 (s, 2H), 4.43 (q, 2H), 6.94 (br s, 1H), 7.18 (br s, 1H), 7.29-7.60 (m, 2H), 7.91 (br t, 1H), 8.18 (s, 0,5H), 8.27 (d, 1H), 8.35 (s, 0,5H), 8.78 (d, 1H), 10.74 (br d, 1H), 12.28 (s, 1H). |
| Example 162.01 | 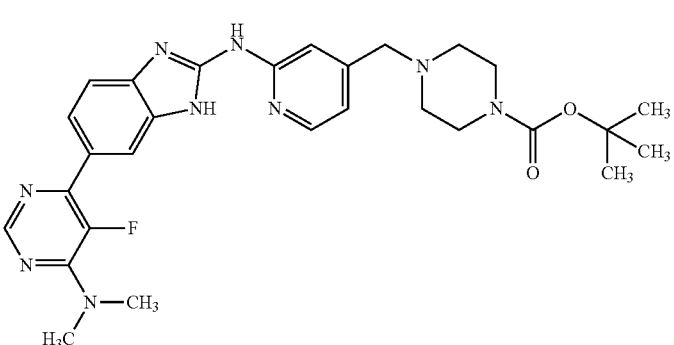<br>tert-butyl 4-{[2-({6-[6-(dimethylamino)-5-fluoropyrimidin-4-yl]-1H-benzimidazol-2-yl}amino)pyridin-4-yl]methyl}piperazine-1-carboxylate<br>LC-MS (Method 2): R$_t$ = 1.28 min; MS (ESIpos): m/z = 548 [M + H]⁺ |

The Example compounds shown below in table 16 were prepared according to the following general procedure:

The respective amine (1 eq.; see Compounds 130.01 to 163.01, respectively; Table 3), 3,3,3-trifluoropropionic acid (1.5 eq), NaHCO₃ (6 eq.) and HATU (1.5 eq.) were solubilised in DMF and the reaction mixture was stirred at rt between 2 and 48 hours. The crude mixture was directly purified by preparative HPLC without workup to give the respective title compound.

TABLE 16

| Example | Structure<br>IUPAC-Name<br>LC-MS (method): Retention time; Mass found<br>¹H-NMR |
|---|---|
| Example 130.02 | 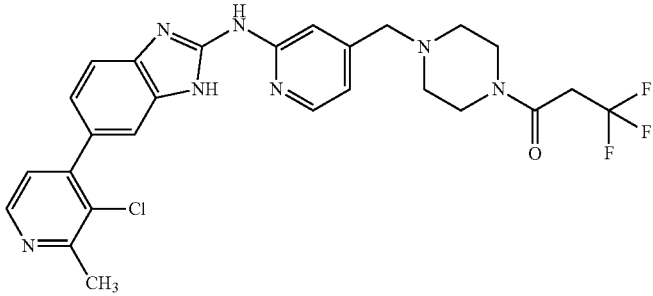 [SMILES: Cc1nccc(-c2ccc3nc(Nc4cc(CN5CCN(C(=O)CC(F)(F)F)CC5)ccn4)[nH]c3c2)c1Cl]<br>1-{4-[(2-{[6-(3-chloro-2-methylpyridin-4-yl)-1H-benzimidazol-2-yl]amino}pyridin-4-yl)methyl]piperazin-1-yl}-3,3,3-trifluoropropan-1-one<br>LC-MS (Method 2): $R_t$ = 1.15 min; MS (ESIpos): m/z = 544 [M + H]⁺<br>¹H-NMR (400 MHz, DMSO-d₆): δ [ppm] = 2.36-2.40 (m, 2H), 2.40-2.45 (m, 2H), 2.64 (s, 3H), 3.47 (br d, 2H), 3.48-3.52 (m, 2H), 3.52 (s, 2H), 3.65 (q, 2H), 6.94 (dd, 1H), 7.08-7.17 (m, 1H), 7.19 (s, 1H), 7.31 (d, 1H), 7.42 (br s, 1H), 7.53-7.69 (m, 1H), 8.27 (d, 1H), 8.41 (d, 1H), 10.70 (br s, 1H), 12.24 (br s, 1H). |
| Example 131.02 | 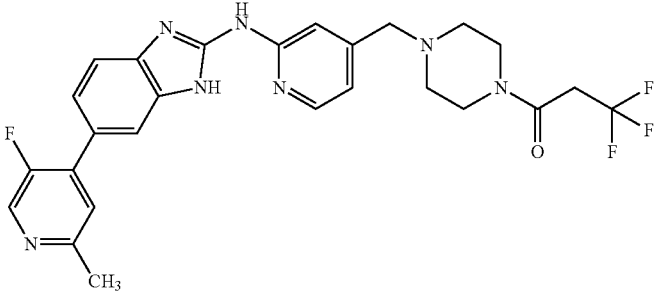 [SMILES: Cc1cc(-c2ccc3nc(Nc4cc(CN5CCN(C(=O)CC(F)(F)F)CC5)ccn4)[nH]c3c2)c(F)cn1]<br>3,3,3-trifluoro-1-{4-[(2-{[6-(5-fluoro-2-methylpyridin-4-yl)-1H-benzimidazol-2-yl]amino}pyridin-4-yl)methyl]piperazin-1-yl}propan-1-one<br>LC-MS (Method 2): $R_t$ = 1.1 min; MS (ESIpos): m/z = 528 [M + H]⁺<br>¹H-NMR (400 MHz, DMSO-d₆): δ [ppm] = 2.38 (br t, 2H), 2.40-2.45 (m, 2H), 3.48 (dt, 4H), 3.53 (s, 2H), 3.65 (q, 2H), 6.95 (dd, 1H), 7.19 (s, 1H), 7.28-7.41 (m, 1H), 7.43-7.54 (m, 2H), 7.62 (br s, 0,5H), 7.84 (br s, 0,5H), 8.27 (d, 1H), 8.45 (d, 1H), 10.74 (br s, 1H), 12.28 (br s, 1H). |
| Example 132.02 | 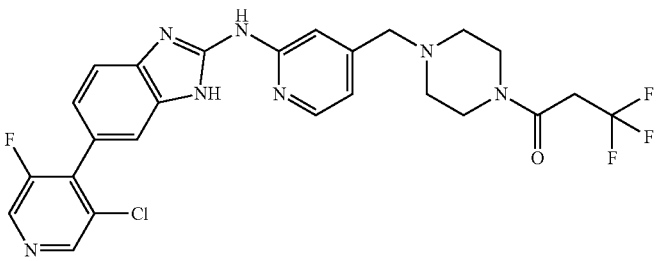 [SMILES: O=C(CC(F)(F)F)N1CCN(Cc2ccnc(Nc3nc4ccc(-c5c(F)cncc5Cl)cc4[nH]3)c2)CC1]<br>1-{4-[(2-{[6-(3-chloro-5-fluoropyridin-4-yl)-1H-benzimidazol-2-yl]amino}pyridin-4-yl)methyl]piperazin-1-yl}-3,3,3-trifluoropropan-1-one<br>LC-MS (Method 2): $R_t$ = 1.14 min; MS (ESIpos): m/z = 548 [M + H]⁺<br>¹H-NMR (400 MHz, DMSO-d₆): δ [ppm] = 2.38 (br t, 2H), 2.40-2.45 (m, 2H), 3.44-3.51 (m, 4H), 3.52 (s, 2H), 3.65 (q, 2H), 6.94 (d, 1H), 7.10 |

TABLE 16-continued

| | Structure<br>IUPAC-Name<br>LC-MS (method): Retention time; Mass found |
|---|---|
| Example | $^1$H-NMR |

(br s, 1H), 7.20 (s, 1H), 7.35-7.52 (m, 1H), 7.59 (br s, 1H), 8.28 (d, 1H), 8.67 (d, 2H), 10.74 (br s, 1H), 12.29 (br s, 1H).

Example 133.02

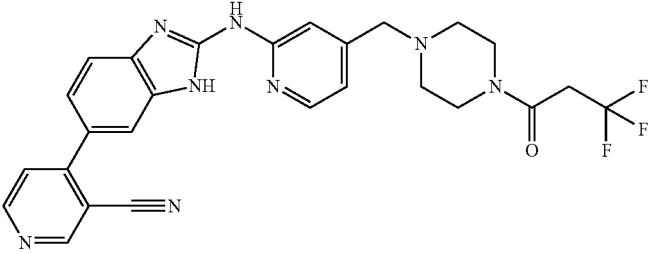 [SMILES: N#Cc1cnccc1-c1ccc2nc(Nc3cc(CN4CCN(C(=O)CC(F)(F)F)CC4)ccn3)[nH]c2c1]

4-{2-[(4-{[4-(3,3,3-trifluoropropanoyl)piperazin-1-yl]methyl}pyridin-2-yl)amino]-1H-benzimidazol-6-yl}pyridine-3-carbonitrile
LC-MS (Method 2): $R_t$ = 1.02 min; MS (ESIpos): m/z = 521 [M + H]$^+$
$^1$H-NMR (400 MHz, DMSO-d$_6$): δ [ppm] = 2.39 (br d, 2H), 2.43 (br s, 2H), 3.44-3.49 (m, 2H), 3.51 (br s, 2H), 3.54 (s, 2H), 3.65 (q, 2H), 6.96 (d, 1H), 7.20 (br s, 1H), 7.31-7.54 (m, 2H), 7.70 (br d, 2H), 8.29 (d, 1H), 8.84 (d, 1H), 9.06 (s, 1H), 10.72-10.84 (m, 1H), 12.32-12.42 (m, 1H).

Example 134.02

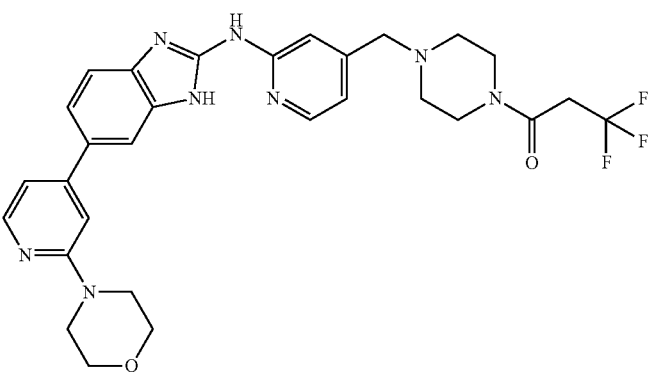 [SMILES: O=C(CC(F)(F)F)N1CCN(Cc2ccnc(Nc3nc4ccc(-c5ccnc(N6CCOCC6)c5)cc4[nH]3)c2)CC1]

3,3,3-trifluoro-1-(4-{[2-({6-[2-(morpholin-4-yl)pyridin-4-yl]-1H-benzimidazol-2-yl}amino)pyridin-4-yl]methyl}piperazin-1-yl)propan-1-one
LC-MS (Method 2): $R_t$ = 1.09 min; MS (ESIpos): m/z = 581 [M + H]$^+$
$^1$H-NMR (400 MHz, DMSO-d$_6$): δ [ppm] = 2.38 (br t, 2H), 2.40-2.45 (m, 2H), 3.44-3.49 (m, 2H), 3.49-3.55 (m, 8H), 3.65 (q, 2H), 3.70-3.75 (m, 4H), 6.94 (dd, 1H), 6.98-7.03 (m, 1H), 7.06 (br s, 1H), 7.20 (s, 1H), 7.39-7.93 (m, 3H), 8.15 (d, 1H), 8.27 (d, 1H), 10.72 (br s, 1H), 12.21 (br s, 1H).

Example 135.02

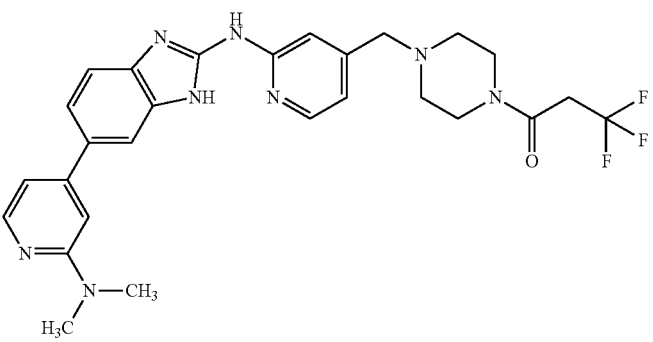 [SMILES: CN(C)c1cc(-c2ccc3nc(Nc4cc(CN5CCN(C(=O)CC(F)(F)F)CC5)ccn4)[nH]c3c2)ccn1]

1-(4-{[2-({6-[2-(dimethylamino)pyridin-4-yl]-1H-benzimidazol-2-yl}amino)pyridin-4-yl]methyl}piperazin-1-yl)-3,3,3-trifluoropropan-1-one
LC-MS (Method 2): $R_t$ = 1.14 min; MS (ESIpos): m/z = 539 [M + H]$^+$
$^1$H-NMR (400 MHz, DMSO-d$_6$): δ [ppm] = 2.36-2.40 (m, 2H), 2.41-2.45 (m, 2H), 3.09 (s, 6H), 3.44-3.49 (m, 2H), 3.50 (br d, 2H), 3.52 (s, 2H),

| Example | Structure<br>IUPAC-Name<br>LC-MS (method): Retention time; Mass found<br>¹H-NMR |
|---|---|
| | 3.65 (q, 2H), 6.80-6.91 (m, 2H), 6.94 (d, 1H), 7.19 (br s, 1H), 7.37-7.44 (m, 1H), 7.45-7.58 (m, 1H), 7.68-7.89 (m, 1H), 8.10 (br s, 1H), 8.27 (d, 1H), 10.68 (br d, 1H), 12.19 (br d, 1H). |
| Example 136.02 | 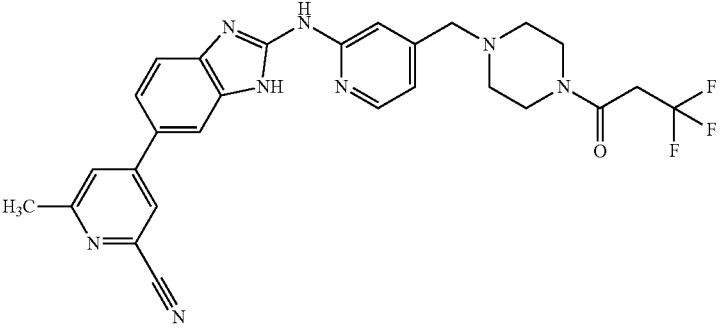 [SMILES: Cc1cc(-c2ccc3nc(Nc4cc(CN5CCN(C(=O)CC(F)(F)F)CC5)ccn4)[nH]c3c2)cc(C#N)n1]<br>6-methyl-4-{2-[(4-{[4-(3,3,3-trifluoropropanoyl)piperazin-1-yl]methyl}pyridin-2-yl)amino]-1H-benzimidazol-6-yl}pyridine-2-carbonitrile<br>LC-MS (Method 2): R$_t$ = 1.12 min; MS (ESIpos): m/z = 535 [M + H]⁺<br>¹H-NMR (400 MHz, DMSO-d₆): δ [ppm] = 2.38 (br t, 2H), 2.41-2.45 (m, 2H), 2.58 (s, 3H), 3.48 (dt, 4H), 3.53 (s, 2H), 3.65 (q, 2H), 6.95 (br d, 1H), 7.20 (s, 1H), 7.42-7.65 (m, 2H), 7.90 (br s, 1H), 8.00 (br s, 1H), 8.11-8.26 (m, 1H), 8.28 (d, 1H), 10.77 (br s, 1H), 12.28 (br s, 1H). |
| Example 137.02 | 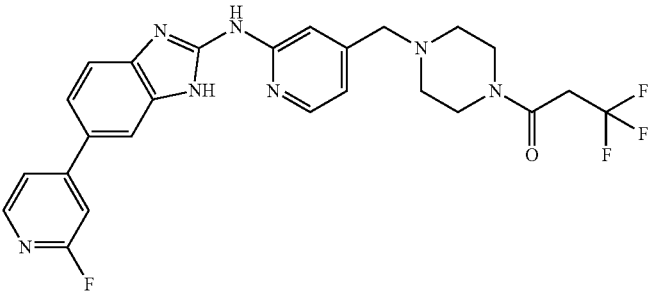 [SMILES: O=C(CC(F)(F)F)N1CCN(Cc2ccnc(Nc3nc4ccc(-c5ccnc(F)c5)cc4[nH]3)c2)CC1]<br>3,3,3-trifluoro-1-{4-[(2-{[6-(2-fluoropyridin-4-yl)-1H-benzimidazol-2-yl]amino}pyridin-4-yl)methyl]piperazin-1-yl}propan-1-one<br>LC-MS (Method 2): R$_t$ = 1.1 min; MS (ESIpos): m/z = 514 [M + H]⁺<br>¹H-NMR (400 MHz, DMSO-d₆): δ [ppm] = 2.41 (br d, 4H), 3.43-3.57 (m, 6H), 3.65 (q, 2H), 6.95 (d, 1H), 7.20 (s, 1H), 7.38-7.76 (m, 4H), 7.81-8.00 (m, 1H), 8.21-8.31 (m, 2H), 10.68-10.82 (m, 1H), 12.20-12.34 (m, 1H). |
| Example 138.02 | 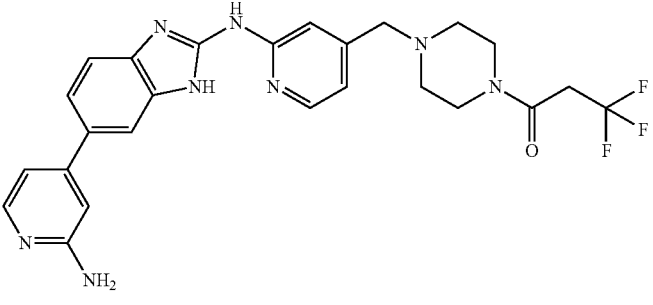 [SMILES: Nc1cc(-c2ccc3nc(Nc4cc(CN5CCN(C(=O)CC(F)(F)F)CC5)ccn4)[nH]c3c2)ccn1]<br>1-{4-[(2-{[6-(2-aminopyridin-4-yl)-1H-benzimidazol-2-yl]amino}pyridin-4-yl)methyl]piperazin-1-yl}-3,3,3-trifluoropropan-1-one<br>LC-MS (Method 2): R$_t$ = 0.95 min; MS (ESIpos): m/z = 511 [M + H]⁺<br>¹H-NMR (400 MHz, DMSO-d₆): δ [ppm] = 2.38 (br t, 2H), 2.40-2.46 (m, 2H), 3.45-3.49 (m, 2H), 3.50 (br d, 2H), 3.52 (s, 2H), 3.65 (q, 2H), 5.93 (br s, 2H), 6.73 (s, 1H), 6.80 (br d, 1H), 6.94 (dd, 1H), 7.18 (s, 1H), 7.34 |

| Example | Structure<br>IUPAC-Name<br>LC-MS (method): Retention time; Mass found<br>¹H-NMR |
|---|---|
| | (br d, 1H), 7.38-7.80 (m, 2H), 7.93 (d, 1H), 8.27 (d, 1H), 10.70 (br s, 1H), 12.20 (br s, 1H). |
| Example 139.02 | 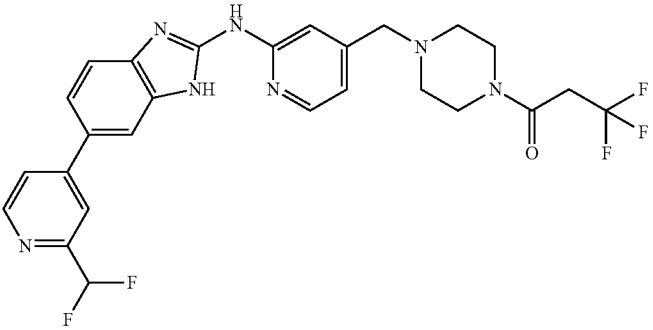 [SMILES: O=C(CC(F)(F)F)N1CCN(Cc2ccnc(Nc3nc4ccc(-c5ccnc(C(F)F)c5)cc4[nH]3)c2)CC1]<br>1-(4-{[2-({6-[2-(difluoromethyl)pyridin-4-yl]-1H-benzimidazol-2-yl}amino)pyridin-4-yl]methyl}piperazin-1-yl)-3,3,3-trifluoropropan-1-one<br>LC-MS (Method 2): R$_t$ = 1.11 min; MS (ESIpos): m/z = 546 [M + H]⁺<br>¹H-NMR (400 MHz, DMSO-d₆): δ [ppm] = 2.40 (dt, 4H), 3.43-3.56 (m, 6H), 3.65 (q, 2H), 6.84-7.23 (m, 3H), 7.39-7.67 (m, 2H), 7.80-8.04 (m, 3H), 8.28 (d, 1H), 8.69 (d, 1H), 10.76 (br s, 1H), 12.03-12.57 (m, 1H). |
| Example 140.02 | 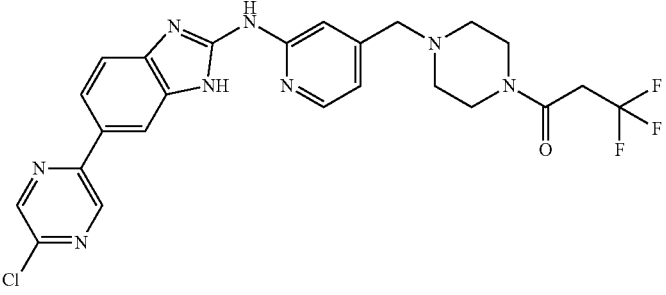 [SMILES: O=C(CC(F)(F)F)N1CCN(Cc2ccnc(Nc3nc4ccc(-c5cnc(Cl)cn5)cc4[nH]3)c2)CC1]<br>1-{4-[(2-{[6-(5-chloropyrazin-2-yl)-1H-benzimidazol-2-yl]amino}pyridin-4-yl)methyl]piperazin-1-yl}-3,3,3-trifluoropropan-1-one<br>LC-MS (Method 4): R$_t$ = 1.17 min; MS (ESIpos): m/z = 531 [M + H]⁺<br>¹H-NMR (400 MHz, DMSO-d₆): δ [ppm] = 2.39 (br d, 2H), 2.43 (br s, 2H), 3.44-3.49 (m, 2H), 3.51 (br s, 2H), 3.53 (s, 2H), 3.65 (q, 2H), 6.95 (d, 1H), 7.20 (s, 1H), 7.34-7.66 (m, 2H), 7.85 (br d, 1H), 8.28 (d, 1H), 8.79 (d, 1H), 9.07 (br s, 1H), 10.77 (br s, 1H), 12.30 (br s, 1H). |
| Example 141.02 | 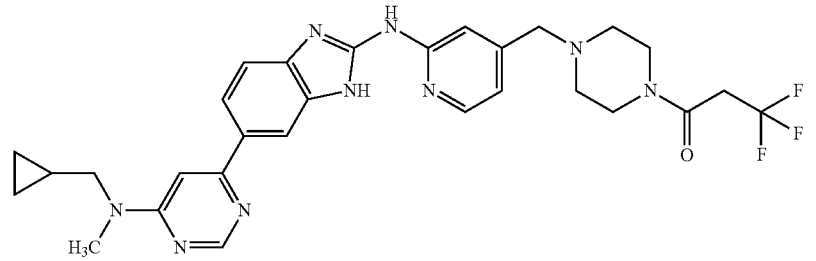 [SMILES: CN(CC1CC1)c1cc(-c2ccc3nc(Nc4cc(CN5CCN(C(=O)CC(F)(F)F)CC5)ccn4)[nH]c3c2)ncn1]<br>1-[4-({2-[(6-{6-[(cyclopropylmethyl)(methyl)amino]pyrimidin-4-yl}-1H-benzimidazol-2-yl)amino]pyridin-4-yl}methyl)piperazin-1-yl]-3,3,3-trifluoropropan-1-one<br>LC-MS (Method 2): R$_t$ = 1.17 min; MS (ESIpos): m/z = 580 [M + H]⁺<br>¹H NMR (400 MHz, DMSO-d₆) δ ppm 0.32 (q, J = 4.82 Hz, 2 H) 0.48 (br d, J = 7.86 Hz, 2 H) 1.04-1.13 (m, 1 H) 2.38 (br t, J = 4.69 Hz, 2 H) 2.41-2.45 (m, 2 H) 3.17 (s, 3 H) 3.45-3.49 (m, 2 H) 3.49-3.57 (m, 6 H) 3.65 (q, J = 10.90 Hz, 2 H) 6.95 (br s, 1 H) 7.02-7.13 (m, 1 H) 7.20 (s, 1 H) 7.36-7.57 (m, 1 H) 7.88 (br dd, J = 15.46, 8.87 Hz, 1 H) 8.15 (s, 0,5 H) |

8.27 (d, J = 5.32 Hz, 1 H) 8.30 (s, 0,5 H) 8.51 (d, J = 1.01 Hz, 1 H) 10.66-
10.76 (m, 1 H) 12.22 (br d, J = 17.74 Hz, 1 H)

Example
142.02

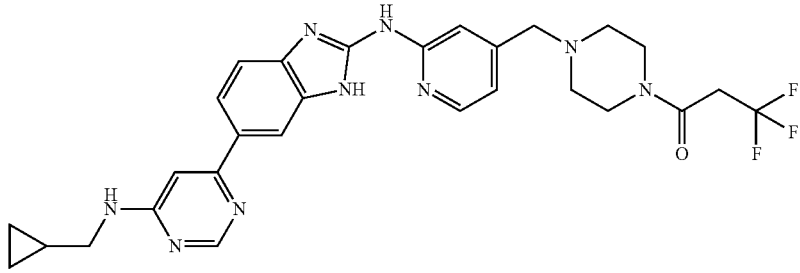 [SMILES: O=C(CC(F)(F)F)N1CCN(Cc2ccnc(Nc3nc4ccc(-c5cc(NCC6CC6)ncn5)cc4[nH]3)c2)CC1]

1-[4-({2-[(6-{6-[(cyclopropylmethyl)amino]pyrimidin-4-yl}-1H-
benzimidazol-2-yl)amino]pyridin-4-yl}methyl)piperazin-1-yl]-3,3,3-
trifluoropropan-1-one
LC-MS (Method 2): R$_t$ = 1.09 min; MS (ESIpos): m/z = 566 [M + H]$^+$
$^1$H-NMR (400 MHz, DMSO-d$_6$): δ [ppm] = 0.22-0.28 (m, 2H), 0.44-0.50
(m, 2H), 1.03-1.12 (m, 1H), 2.38 (br t, 2H), 2.40-2.44 (m, 2H), 3.23
(br t, 2H), 3.45-3.49 (m, 2H), 3.49-3.53 (m, 4H), 3.65 (q, 2H), 6.94 (br
d, 2H), 7.19 (s, 1H), 7.41 (br s, 2H), 7.74 (br s, 1H), 7.94-8.23 (m, 1H),
8.27 (d, 1H), 8.45 (s, 1H), 10.73 (br s, 1H), 12.24 (br s, 1H).

Example
143.02

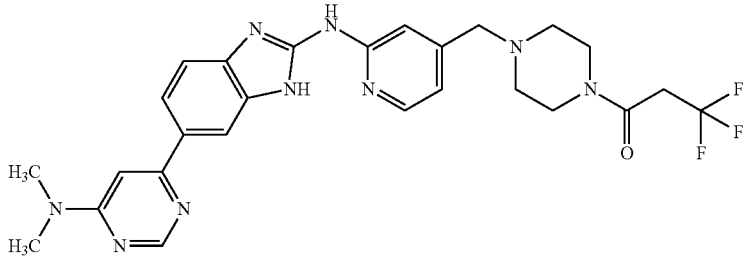 [SMILES: CN(C)c1cc(-c2ccc3nc(Nc4cc(CN5CCN(C(=O)CC(F)(F)F)CC5)ccn4)[nH]c3c2)ncn1]

1-(4-{[2-({6-[6-(dimethylamino)pyrimidin-4-yl]-1H-benzimidazol-2-
yl}amino)pyridin-4-yl]methyl}piperazin-1-yl)-3,3,3-trifluoropropan-
1-one
LC-MS (Method 2): R$_t$ = 1.03 min; MS (ESIpos): m/z = 540 [M + H]$^+$
$^1$H-NMR (400 MHz, DMSO-d$_6$): δ [ppm] = 2.35-2.40 (m, 2H), 2.41-2.45
(m, 2H), 3.15 (s, 6H), 3.43-3.49 (m, 2H), 3.51 (br s, 2H), 3.53 (s, 2H),
3.65 (q, 2H), 6.94 (d, 1H), 7.02-7.15 (m, 1H), 7.20 (s, 1H), 7.35-7.60
(m, 1H), 7.85-7.92 (m, 1H), 8.27 (d, 2H), 8.53 (d, 1H), 10.67-10.78
(m, 1H), 12.16-12.31 (m, 1H).

Example
144.02

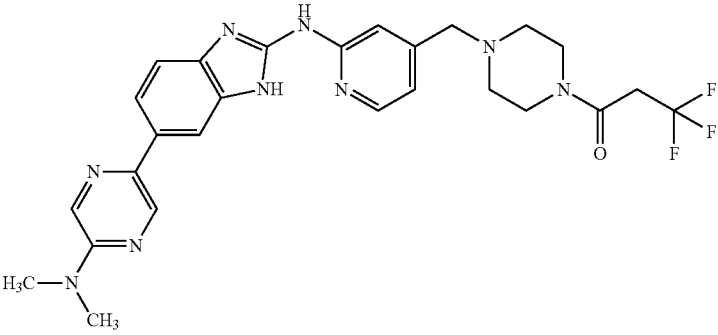 [SMILES: CN(C)c1cnc(-c2ccc3nc(Nc4cc(CN5CCN(C(=O)CC(F)(F)F)CC5)ccn4)[nH]c3c2)cn1]

1-(4-{[2-({6-[5-(dimethylamino)pyrazin-2-yl]-1H-benzimidazol-2-
yl}amino)pyridin-4-yl]methyl}piperazin-1-yl)-3,3,3-trifluoropropan-
1-one
LC-MS (Method 2): R$_t$ = 1.1 min; MS (ESIpos): m/z = 540 [M + H]$^+$
$^1$H NMR (400 MHz, DMSO-d$_6$) δ ppm 2.40 (dt, J = 16.29, 4.66 Hz, 4 H)
3.11 (s, 5 H) 3.44-3.49 (m, 2 H) 3.49-3.54 (m, 4 H) 3.65 (q, J = 11.07
Hz, 2 H) 6.93 (dd, J = 5.32, 1.01 Hz, 1 H) 7.19 (s, 1 H) 7.31-7.56 (m, 1

TABLE 16-continued

| Example | Structure<br>IUPAC-Name<br>LC-MS (method): Retention time; Mass found<br>¹H-NMR |
|---|---|

H) 7.65 (br s, 1 H) 8.07 (br d, J = 10.39 Hz, 1 H) 8.21 (s, 1 H) 8.26 (d, J = 5.30 Hz, 1 H) 8.61 (br s, 1 H) 10.63 (br s, 1 H) 12.12 (br s, 1 H)

Example 145.02

3,3,3-trifluoro-1-(4-{[2-({6-[6-(piperidin-1-yl)pyrimidin-4-yl]-1H-benzimidazol-2-yl}amino)pyridin-4-yl]methyl}piperazin-1-yl)propan-1-one
LC-MS (Method 2): R$_t$ = 1,21 min; MS (ESIpos): m/z = 580 [M + H]⁺
¹H NMR (400 MHz, DMSO-d₆) δ ppm 1.51-1.60 (m, 4 H) 1.60-1.71 (m, 2 H) 2.40 (dt, J = 16.22, 4.69 Hz, 4 H) 3.48 (dt, J = 9.70, 5.16 Hz, 4 H) 3.53 (s, 2 H) 3.65 (q, J = 10.90 Hz, 2 H) 3.69-3.78 (m, 4 H) 6.94 (d, J = 5.07 Hz, 1 H) 7.16-7.29 (m, 2 H) 7.46 (br s, 1 H) 7.90 (dd, J = 8.49, 1.39 Hz, 1 H) 8.15-8.37 (m, 2 H) 8.52 (d, J = 1.01 Hz, 1 H) 10.72 (br s, 1 H) 12.22 (br s, 1 H)

Example 146.02

3,3,3-trifluoro-1-[4-({2-[(6-{6-[methyl(2,2,2-trifluoroethyl)amino]pyrimidin-4-yl}-1H-benzimidazol-2-yl)amino]pyridin-4-yl}methyl)piperazin-1-yl]propan-1-one
LC-MS (Method 2): R$_t$ = 1.16 min; MS (ESIpos): m/z = 608 [M + H]⁺

Example 147.02

1-(4-{[2-({6-[6-(azetidin-1-yl)pyrimidin-4-yl]-1H-benzimidazol-2-yl}amino)pyridin-4-yl]methyl}piperazin-1-yl)-3,3,3-trifluoropropan-1-one
LC-MS (Method 2): R$_t$ = 1.02 min; MS (ESIpos): m/z = 552 [M + H]⁺
¹H NMR (400 MHz, DMSO-d₆) δ ppm 2.35-2.46 (m, 6 H) 3.43-3.49 (m, 2 H) 3.49-3.57 (m, 4 H) 3.65 (d, J = 10.90 Hz, 2 H) 4.10 (t, J = 7.48 Hz, 4 H) 6.76 (br s, 1 H) 6.94 (br d, J = 5.07 Hz, 1 H) 7.19 (s, 1 H) 7.38 (br d, J = 8.36 Hz, 1 H) 7.85 (br s, 1 H) 8.12 (br s, 0,5 H) 8.27 (d, J = 5.07 Hz, 1 H) 8.28 (br s, 0,5 H) 8.49 (d, J = 1.01 Hz, 1 H) 10.74 (br s, 1 H) 12.17-12.30 (m, 1 H)

TABLE 16-continued

| | Structure<br>IUPAC-Name<br>LC-MS (method): Retention time; Mass found |
|---|---|
| Example | $^1$H-NMR |

Example 148.02

1-[4({2-[(6-{6-[ethyl(methyl)amino]pyrimidin-4-yl}-1H-benzimidazol-2-yl)amino]pyridin-4-yl}methyl)piperazin-1-yl]-3,3,3-trifluoropropan-1-one LC-MS (Method 2): R$_t$ = 1.08 min; MS (ESIpos): m/z = 554 [M + H]$^+$ $^1$H NMR (400 MHz, DMSO-d$_6$) δ ppm 1.10-1.16 (m, 1 H) 1.13 (t, J = 6.97 Hz, 2 H) 2.36-2.45 (m, 4 H) 3.10 (s, 2 H) 3.45-3.51 (m, 4 H) 3.51-3.55 (m, 3 H) 3.60-3.70 (m, 4 H) 6.94 (d, J = 4.31 Hz, 1 H) 7.02 (br s, 1 H) 7.20 (s, 1 H) 7.35-7.59 (m, 1 H) 7.88 (br d, J = 8.36 Hz, 1 H) 8.14 (br s, 0,5 H) 8.27 (d, J = 5.07 Hz, 1 H) 8.28-8.34 (m, 0,5 H) 8.51 (d, J = 1.01 Hz, 1 H) 10.71 (br s, 1 H), 12.24 (br s, 1 H)

Example 149.02

1-(4-{[2-({6-[6-(ethylamino)pyrimidin-4-yl]-1H-benzimidazol-2-yl}amino)pyridin-4-yl]methyl}piperazin-1-yl)-3,3,3-trifluoropropan-1-one LC-MS (Method 2): R$_t$ = 0.99 min; MS (ESIpos): m/z = 540 [M + H]$^+$ $^1$H NMR (400 MHz, DMSO-d$_6$) δ ppm 1.17 (t, J = 7.22 Hz, 3 H) 2.40 (dt J = 16.22, 4.82 Hz, 4 H) 3.35-3.40 (m, 2 H) 3.45-3.54 (m, 6 H) 3.65 (d, J = 11.15 Hz, 2 H) 6.83-6.98 (m, 2 H) 7.19 (br s, 1 H) 7.31 (br s, 1 H) 7.35-7.57 (m, 1 H) 7.74 (br s, 1 H) 7.96-8.23 (m, 1 H) 8.27 (d, J = 5.07 Hz, 1 H) 8.45 (s, 1 H) 10.71 (br s, 1 H) 12.22 (br d, J = 9.13 Hz, 1 H)

Example 150.02

3,3,3-trifluoro-1-(4-{[2-({6-[6-(methylamino)pyrimidin-4-yl]-1H-benzimidazol-2-yl}amino)pyridin-4-yl]methyl}piperazin-1-yl)propan-1-one LC-MS (Method 2): R$_t$ = 0.93 min; MS (ESIpos): m/z = 526 [M + H]$^+$ $^1$H NMR (400 MHz, DMSO-d$_6$) δ ppm 2.40 (dt, J = 16.22, 4.69 Hz, 4 H) 2.86 (d, J = 4.56 Hz, 3 H) 3.44-3.49 (m, 2 H) 3.49-3.56 (m, 4 H) 3.65 (q, J = 10.90 Hz, 2 H) 6.84-6.92 (m, 1 H) 6.94 (d, J = 5.07 Hz, 1 H) 7.15-7.32 (m, 2 H) 7.34-7.58 (m, 1 H) 7.76 (br s, 0,5 H) 8.22 (br s, 0,5 H) 8.27 (d, J = 5.32 Hz, 1 H) 8.47 (br s, 1H) 10.71 (br s, 1 H) 12.23 (br d, J = 10.65 Hz, 1 H TABLE 16-continued Structure
IUPAC-Name
LC-MS (method): Retention time; Mass found
$^1$H-NMR Example 151.02

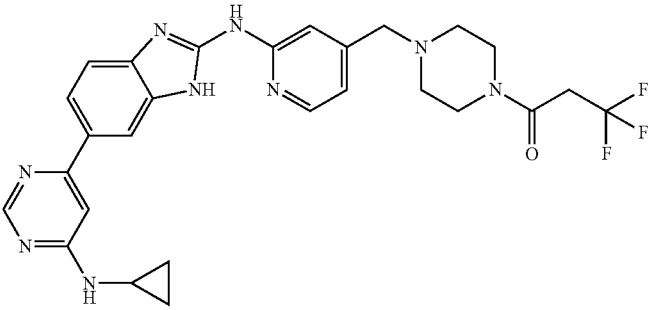 [SMILES: O=C(CC(F)(F)F)N1CCN(Cc2ccnc(Nc3nc4ccc(-c5cc(NC6CC6)ncn5)cc4[nH]3)c2)CC1]

1-(4-{[2-({6-[6-(cyclopropylamino)pyrimidin-4-yl]-1H-benzimidazol-2-yl}amino)pyridin-4-yl]methyl}piperazin-1-yl)-3,3,3-trifluoropropan-1-one
LC-MS (Method 2): R$_t$ = 1.03 min; MS (ESIpos): m/z = 552 [M + H]$^+$
$^1$H-NMR (400 MHz, DMSO-d$_6$): δ [ppm] = 0.52 (br s, 2H), 0.80 (br d, 2H), 2.40 (dt, 4H), 2.61-2.72 (m, 1H), 3.43-3.57 (m, 6H), 3.65 (q, 2H), 6.94 (d, 1H), 6.97-7.07 (m, 1H), 7.19 (s, 1H), 7.36-7.51 (m, 1H), 7.58 (br s, 1H), 7.74-7.84 (m, 1H), 8.27 (d, 1H), 8.47 (s, 1H), 10.73 (br s, 1H), 12.25 (br s, 1H).

Example 152.02

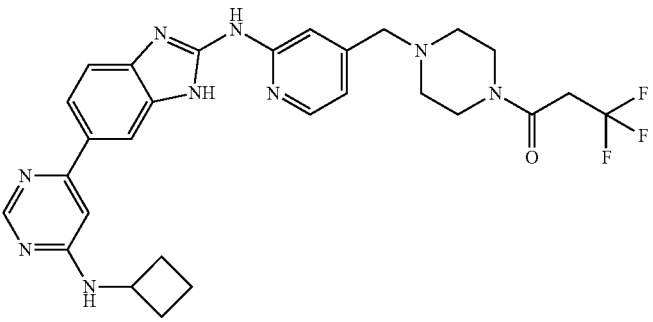 [SMILES: O=C(CC(F)(F)F)N1CCN(Cc2ccnc(Nc3nc4ccc(-c5cc(NC6CCC6)ncn5)cc4[nH]3)c2)CC1]

1-(4-{[2-({6-[6-(cyclobutylamino)pyrimidin-4-yl]-1H-benzimidazol-2-yl}amino)pyridin-4-yl]methyl}piperazin-1-yl)-3,3,3-trifluoropropan-1-one
LC-MS (Method 4): R$_t$ = 1.08 min; MS (ESIpos): m/z = 566 [M + H]$^+$
$^1$H-NMR (400 MHz, DMSO-d$_6$): δ [ppm] = 1.71 (br s, 2H), 1.94 (br d, 2H), 2.33 (br s, 2H), 2.38 (br s, 2H), 2.42 (br s, 2H), 3.45-3.54 (m, 6H), 3.65 (q, 2H), 4.24-4.59 (m, 1H), 6.83 (br d, 1H), 6.94 (br d, 1H), 7.19 (br s, 1H), 7.37-7.62 (m, 2H), 7.67-7.95 (m, 1H), 7.95-8.23 (m, 1H), 8.27 (br d, 1H), 8.44 (s, 1H), 10.72 (br s, 1H), 12.23 (br s, 1H).

Example 153.02

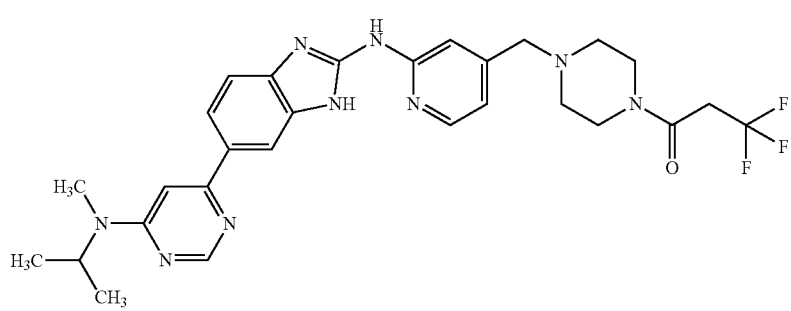 [SMILES: CC(C)N(C)c1cc(-c2ccc3nc(Nc4cc(CN5CCN(C(=O)CC(F)(F)F)CC5)ccn4)[nH]c3c2)ncn1]

3,3,3-trifluoro-1-[4-({2-[(6-{6-[methyl(propan-2-yl)amino]pyrimidin-4-yl}-1H-benzimidazol-2-yl)amino]pyridin-4-yl}methyl)piperazin-1-yl]propan-1-one
LC-MS (Method 2): R$_t$ = 1.16 min; MS (ESIpos): m/z = 568 [M + H]$^+$

| Example | Structure<br>IUPAC-Name<br>LC-MS (method): Retention time; Mass found<br>¹H-NMR |
|---|---|
| Example 154.02 | 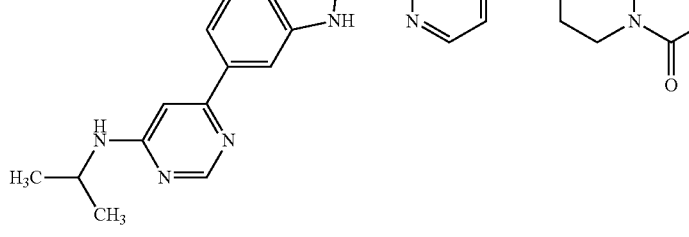<br>3,3,3-trifluoro-1-(4-{[2-({6-[6-(propan-2-ylamino)pyrimidin-4-yl]-1H-benzimidazol-2-yl}amino)pyridin-4-yl]methyl}piperazin-1-yl)propan-1-one<br>LC-MS (Method 2): $R_t$ = 1.05 min; MS (ESIpos): m/z = 554 [M + H]⁺<br>¹H NMR (400 MHz, DMSO-$d_6$) δ ppm 1.19 (d, J = 6.34 Hz, 6 H) 2.32-2.40 (m, 2 H) 2.40-2.46 (m, 2 H) 3.43-3.49 (m, 2 H) 3.49-3.57 (m, 4 H) 3.65 (d, J = 10.90 Hz, 2 H) 6.81-6.91 (m, 1 H) 6.94 (d J = 5.07 Hz, 1 H) 7.18 (br s, 2 H) 7.39 (br d, J = 6.84 Hz, 1 H) 7.71 (br s, 1 H) 8.19 (br s, 1 H) 8.27 (d, J = 5.32 Hz, 1 H) 8.45 (s, 1 H) 10.72 (br s, 1 H) 12.23 (br s, 1 H) |
| Example 155.02 | 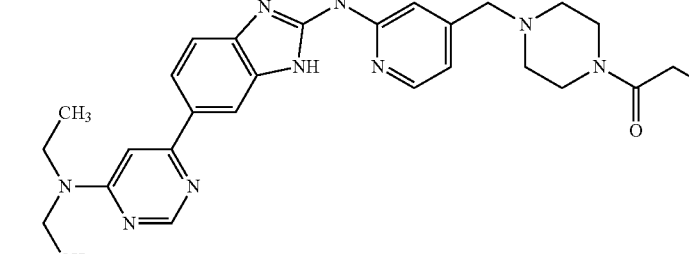<br>1-(4-{[2-({6-[6-(diethylamino)pyrimidin-4-yl]-1H-benzimidazol-2-yl}amino)pyridin-4-yl]methyl}piperazin-1-yl)-3,3,3-trifluoropropan-1-one<br>LC-MS (Method 2): $R_t$ = 1.18 min; MS (ESIneg): m/z = 566 [M − H]⁻<br>¹H-NMR (400 MHz, DMSO-$d_6$): δ [ppm] = 1.16 (t, 6H), 2.36-2.40 (m, 2H), 2.41-2.45 (m, 2H), 3.45-3.49 (m, 2H), 3.51 (br s, 2H), 3.53 (s, 2H), 3.57-3.70 (m, 6H), 6.94 (d, 1H), 6.99 (br s, 1H), 7.20 (s, 1H), 7.35-7.59 (m, 1H), 7.86 (br s, 1H), 8.09-8.32 (m, 2H), 8.51 (d, 1H), 10.72 (br s, 1H), 12.23 (br s, 1H). |
| Example 156.02 | 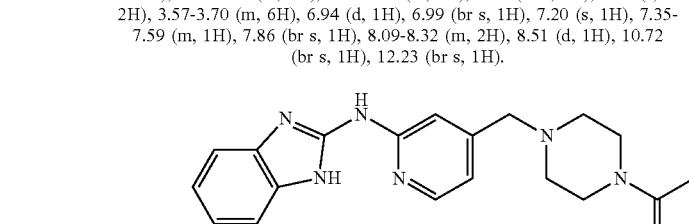<br>1-[4-({2-[(6-{6-[cyclobutyl(methyl)amino]pyrimidin-4-yl}-1H-benzimidazol-2-yl)amino]pyridin-4-yl}methyl)piperazin-1-yl]-3,3,3-trifluoropropan-1-one<br>LC-MS (Method 2): $R_t$ = 1.19 min; MS (ESIpos): m/z = 580 [M + H]⁺<br>¹H-NMR (400 MHz, DMSO-$d_6$): δ [ppm] = 1.64-1.75 (m, 2H), 2.15-2.28 (m, 4H), 2.38 (br t, 2H), 2.41-2.45 (m, 2H), 3.08 (s, 3H), 3.45-3.55 (m, 6H), 3.65 (q, 2H), 5.02 (br s, 1H), 6.94 (br d, 1H), 7.01-7.13 (m, 1H), 7.20 (s, 1H), 7.39 (br d, 1H), 7.83-7.93 (m, 1H), 8.27 (d, 2H), 8.53 (d, 1H), 10.71 (br d, 1H), 12.18-12.29 (m, 1H). |

| Example | Structure<br>IUPAC-Name<br>LC-MS (method): Retention time; Mass found<br>¹H-NMR |
|---|---|
| Example 157.02 | 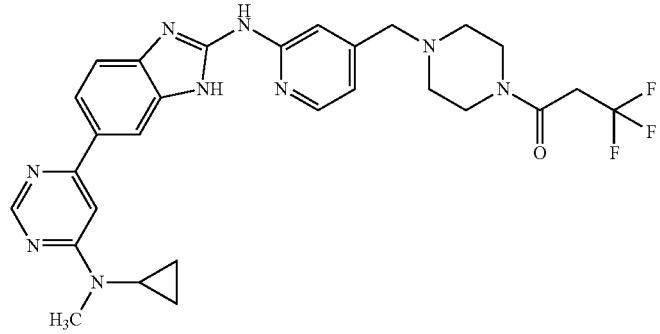 [SMILES: CN(c1cc(-c2ccc3nc(Nc4cc(CN5CCN(C(=O)CC(F)(F)F)CC5)ccn4)[nH]c3c2)ncn1)C1CC1]<br>1-[4-({2-[(6-{6-[cyclopropyl(methyl)amino]pyrimidin-4-yl}-1H-benzimidazol-2-yl)amino]pyridin-4-yl}methyl)piperazin-1-yl]-3,3,3-trifluoropropan-1-one<br>LC-MS (Method 2): R*t* = 1.14 min; MS (ESIpos): m/z = 566 [M + H]⁺<br>¹H NMR (400 MHz, DMSO-d₆) δ ppm 0.73 (br s, 2 H) 0.98-1.03 (m, 2 H) 2.38 (br t, J = 4.82 Hz, 2 H) 2.41-2.45 (m, 2 H) 2.73-2.80 (m, 1 H) 3.13 (s, 3 H) 3.42-3.52 (m, 4 H) 3.53 (s, 2 H) 3.65 (q, J = 10.90 Hz, 2 H) 6.94 (d, J = 4.82 Hz, 1 H) 7.20 (s, 1 H) 7.35 (br s, 0,5 H) 7.42 (br s, 1 H) 7.57 (br s, 0,5 H) 7.84 (br s, 1 H) 8.09 (br s, 0,5 H) 8.27 (d, J = 5.32 Hz, 1,5 H) 8.57 (d, J = 1.01 Hz, 1 H) 10.73 (br s, 1 H) 12.25 (br s, 1 H)) |
| Example 158.02 | 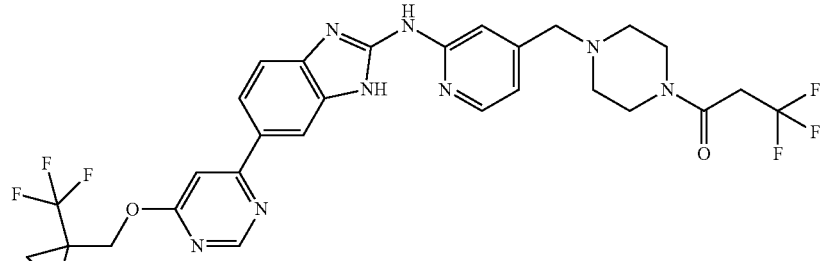<br>3,3,3-trifluoro-1-{4-[(2-{[6-(6-{[1-(trifluoromethyl)cyclopropyl]methoxy}pyrimidin-4-yl)-1H-benzimidazol-2-yl]amino}pyridin-4-yl)methyl]piperazin-1-yl}propan-1-one<br>LC-MS (Method 2): R*t* = 1.29 min; MS (ESIpos): m/z = 635 [M + H]⁺<br>¹H-NMR (400 MHz, DMSO-d₆): δ [ppm] = 1.12 (br d, 4H), 2.36-2.40 (m, 2H), 2.42 (m, 2H), 3.48 (m, 2H), 3.51 (m, 2H), 3.53 (s, 2H), 3.65 (q, 2H), 4.57 (s, 2H), 6.95 (br d, 1H), 7.20 (br s, 1H), 7.36-7.61 (m, 2H), 7.90-7.98 (m, 1H), 8.17-8.25 (m, 0,5H), 8.28 (d, 1H), 8.34-8.41 (m, 0,5H), 8.79 (s, 1H), 10.72-10.81 (m, 1H), 12.23-12.32 (m, 1H). |
| Example 159.02 | 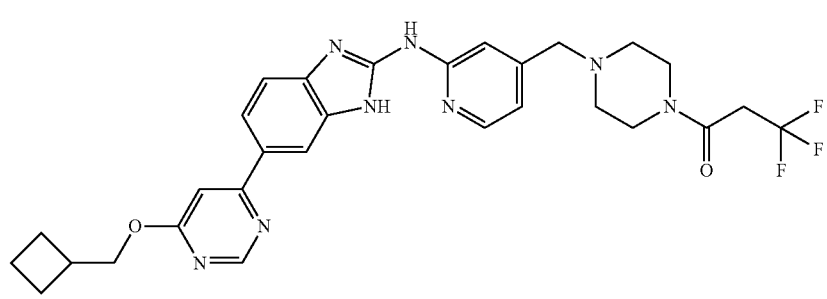 [SMILES: O=C(CC(F)(F)F)N1CCN(Cc2ccnc(Nc3nc4ccc(-c5cc(OCC6CCC6)ncn5)cc4[nH]3)c2)CC1]<br>1-(4-{[2-({6-[6-(cyclobutylmethoxy)pyrimidin-4-yl]-1H-benzimidazol-2-yl}amino)pyridin-4-yl]methyl}piperazin-1-yl)-3,3,3-trifluoropropan-1-one<br>LC-MS (Method 2): R*t* = 1.33 min; MS (ESIpos): m/z = 581 [M + H]⁺<br>¹H-NMR (400 MHz, DMSO-d₆): δ [ppm] = 1.79-1.99 (m, 4H), 2.08 (m, 2H), 2.40 (br d, 4H), 2.72-2.81 (m, 1H), 3.44-3.56 (m, 6H), 3.65 (q, |

| Example | Structure<br>IUPAC-Name<br>LC-MS (method): Retention time; Mass found<br>¹H-NMR |
|---|---|
| | 2H), 4.33-4.41 (br d, 2H), 6.95 (br s, 1H), 7.16-7.24 (m, 1H), 7.31-7.61 (m, 2H), 7.89-7.96 (m, 1H), 8.20 (br s, 0,5H), 8.28 (br d, 1H), 8.37 (br s, 0,5H), 8.77 (s, 1H), 10.71-10.79 (m, 1H), 12.21-12.34 (m, 1H). |
| Example 160.02 | 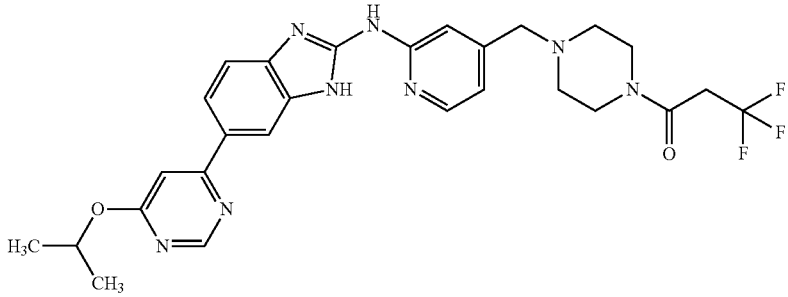<br>3,3,3-trifluoro-1-(4-{[2-({6-[6-(propan-2-yloxy)pyrimidin-4-yl]-1H-benzimidazol-2-yl}amino)pyridin-4-yl]methyl}piperazin-1-yl)propan-1-one<br>LC-MS (Method 2): R$_t$ = 1.22 min; MS (ESIpos): m/z = 555 [M + H]⁺<br>¹H-NMR (400 MHz, DMSO-d₆): δ [ppm] = 1.35 (d, 6H), 2.38 (br t, 2H), 2.41-2.44 (br t, 2H), 3.45-3.49 (br t, 2H), 3.50 (br t, 2H), 3.53 (s, 2H), 3.65 (q, 2H), 5.38 (quin, 1H), 6.94 (br s, 1H), 7.19 (br d, 1H), 7.25-7.37 (m, 1H), 7.38-7.58 (m, 1H), 7.89 (m, 1H), 8.13-8.20 (m, 0,5H), 8.28 (d, 1H), 8.32-8.38 (m, 0,5H), 8.77 (d, 1H), 10.69-10.80 (m, 1H), 12.21-12.30 (m, 1H). |
| Example 161.02 | 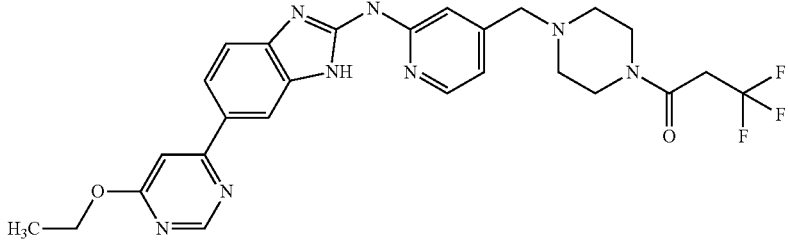<br>1-{4-[(2-{[6-(6-ethoxypyrimidin-4-yl)-1H-benzimidazol-2-yl]amino}pyridin-4-yl)methyl]piperazin-1-yl}-3,3,3-trifluoropropan-1-one<br>LC-MS (Method 2): R$_t$ = 1.15 min; MS (ESIpos): m/z = 541 [M + H]⁺<br>¹H-NMR (400 MHz, DMSO-d₆): δ [ppm] = 1.37 (br t, 3H), 2.41 (br d, 4H), 3.44-3.56 (m, 7H), 3.65 (q, 2H), 4.43 (br d, 2H), 6.95 (br s, 1H), 7.19 (br s, 1H), 7.30-7.59 (m, 2H), 7.90 (br s, 1H), 8.15-8.22 (m, 0,5H), 8.28 (br s, 1H), 8.35 (br s, 0,5H), 8.78 (s, 1H), 10.70-10.80 (m, 1H), 12.20-12.34 (m, 1H). |
| Example 162.02 | 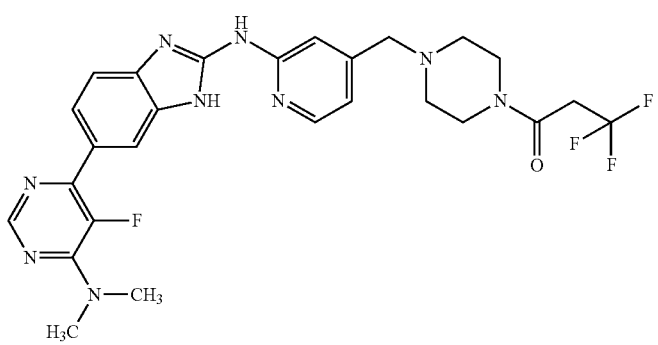 [SMILES: CN(C)c1ncnc(-c2ccc3nc(Nc4cc(CN5CCN(C(=O)CC(F)(F)F)CC5)ccn4)[nH]c3c2)c1F]<br>1-(4-{[2-({6-[6-(dimethylamino)-5-fluoropyrimidin-4-yl]-1H-benzimidazol-2-yl}amino)pyridin-4-yl]methyl}piperazin-1-yl)-3,3,3-trifluoropropan-1-one<br>LC-MS (Method 2): R$_t$ = 1.11 min; MS (ESIpos): m/z = 558 [M + H]⁺<br>¹H NMR (400 MHz, DMSO-d₆) δ ppm 2.35-2.45 (m, 4 H) 3.22 (d, |

TABLE 16-continued

Example | Structure<br>IUPAC-Name<br>LC-MS (method): Retention time; Mass found<br>¹H-NMR
--- | ---
 | J = 2.53 Hz, 6 H) 3.47 (br s, 2 H) 3.49-3.55 (m, 4 H) 3.65 (q, J = 11.07 Hz, 2 H) 6.94 (br d, J = 5.07 Hz, 1 H) 7.18 (s, 1 H) 7.37-7.59 (m, 1 H) 7.60-7.77 (m, 1 H) 7.87-8.17 (m, 1 H) 8.27 (d, J = 5.07 Hz, 1 H) 8.34 (d, J = 2.53 Hz, 1 H) 10.75 (br s, 1 H) 12.31 (br s, 1 H)
Example 163.02 | 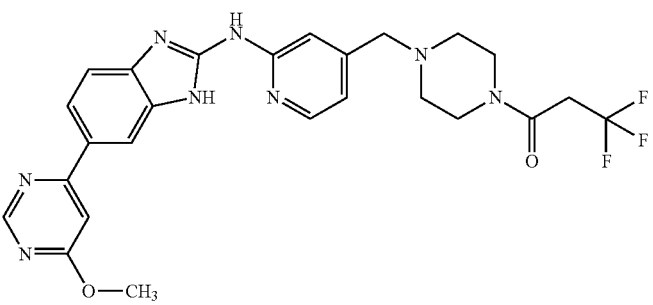 [SMILES: COc1cc(-c2ccc3nc(Nc4cc(CN5CCN(C(=O)CC(F)(F)F)CC5)ccn4)[nH]c3c2)ncn1]<br>3,3,3-trifluoro-1-{4-[(2-{[6-(6-methoxypyrimidin-4-yl)-1H-benzimidazol-2-yl]amino}pyridin-4-yl)methyl]piperazin-1-yl}propan-1-one<br>LC-MS (Method 4): R$_t$ = 1.07 min; MS (ESIpos): m/z = 527 [M + H]$^+$<br>¹H-NMR (400 MHz, DMSO-d$_6$): δ [ppm] = 2.40 (dt, 4H), 3.44-3.57 (m, 6H), 3.65 (q, 2H), 3.97 (s, 3H), 6.95 (br s, 1H), 7.19 (br s, 1H), 7.32-7.61 (m, 2H), 7.88-7.96 (m, 1H), 8.16-8.39 (m, 1H), 8.17-8.37 (m, 1H), 8.81 (d, 1H), 10.75 (br d, 1H), 12.27 (br d, 1H).

The Example compounds shown below in table 17 were prepared according to the following general procedure: The respective amine (1 eq.; see Compounds 130.01 to 163.01, respectively; Table 3), cyclopropanecarboxylic acid (1.5 eq), NaHCO$_3$ (6 eq.) and HATU (1.5 eq.) were solubilised in DMF and the reaction mixture was stirred at rt between 2 and 48 hours. The crude mixture was directly purified by preparative HPLC without workup to give the respective title compounds.

TABLE 17

Example | Structure<br>IUPAC-Name<br>LC-MS (method): Retention time; Mass found<br>¹H-NMR
--- | ---
Example 130.03 | 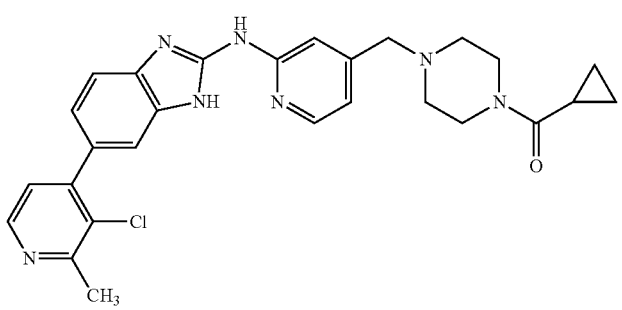 [SMILES: Cc1nccc(-c2ccc3nc(Nc4cc(CN5CCN(C(=O)C6CC6)CC5)ccn4)[nH]c3c2)c1Cl]<br>{4-[(2-{[6-(3-chloro-2-methylpyridin-4-yl)-1H-benzimidazol-2-yl]amino}pyridin-4-yl)methyl]piperazin-1-yl}(cyclopropyl)methanone<br>LC-MS (Method 2): R$_t$ = 1.11 min; MS (ESIpos): m/z = 502 [M + H]$^+$<br>¹H-NMR (400 MHz, DMSO-d$_6$): δ [ppm] = 0.68-0.74 (m, 4H), 1.93-2.01 (m, 1H), 2.36 (br s, 2H), 2.45 (br s, 2H), 2.64 (s, 3H), 3.50 (br s, 2H), 3.52 (s, 2H), 3.71 (br s, 2H), 6.95 (dd, 1H), 7.08-7.18 (m, 1H), 7.20 (s, 1H), 7.31 (d, 1H), 7.42 (br s, 1H), 7.55-7.66 (m, 1H), 8.28 (d, 1H), 8.41 (d, 1H), 10.71 (br s, 1H), 12.24 (br s, 1H).

TABLE 17-continued

| | Structure<br>IUPAC-Name<br>LC-MS (method): Retention time; Mass found |
|---|---|
| Example | ¹H-NMR |

Example 131.03 cyclopropyl{4-[(2-{[6-(5-fluoro-2-methylpyridin-4-yl)-1H-
benzimidazol-2-yl]amino}pyridin-4-yl)methyl]piperazin-1-
yl}methanone
LC-MS (Method 2): $R_t$ = 1.06 min; MS (ESIpos): m/z = 486 [M + H]⁺
¹H-NMR (400 MHz, DMSO-$d_6$): δ [ppm] = 0.67-0.74 (m, 4H), 1.93-2.00
(m, 1H), 2.36 (br s, 2H), 2.42-2.48 (m, 2H), 3.51 (br d, 2H), 3.52 (s,
2H), 3.71 (br s, 2H), 6.95 (dd, 1H), 7.20 (s, 1H), 7.30-7.41 (m, 1H),
7.43-7.54 (m, 2H), 7.62 (br s, 0, 5H), 7.84 (br s, 0, 5H), 8.28 (d, 1H),
8.45 (d, 1H), 10.74 (br s, 1H), 12.28 (br d, 1H).

Example 132.03

{4-[(2-{[6-(3-chloro-5-fluoropyridin-4-yl)-1H-benzimidazol-2-
yl]amino}pyridin-4-yl)methyl]piperazin-1-
yl}(cyclopropyl)methanone
LC-MS (Method 2): $R_t$ = 1.1 min; MS (ESIpos): m/z = 506 [M + H]⁺
¹H-NMR (400 MHz, DMSO-$d_6$): δ [ppm] = 0.66-0.74 (m, 4H), 1.96 (tt,
1H), 2.36 (br s, 2H), 2.45 (br s, 2H), 3.52 (s, 4H), 3.70 (br s, 2H), 6.95
(dd, 1H), 7.09 (br d, 1H), 7.20 (s, 1H), 7.37-7.52 (m, 1H), 7.59 (br s,
1H), 8.28 (d, 1H), 8.67 (d, 2H), 10.75 (br s, 1H), 12.29 (br s, 1H).

Example 134.03 cyclopropyl(4-{[2-({6-[2-(morpholin-4-yl)pyridin-4-yl]-1H-
benzimidazol-2-yl}amino)pyridin-4-yl]methyl}piperazin-1-
yl)methanone
LC-MS (Method 2): $R_t$ = 1.06 min; MS (ESIpos): m/z = 539 [M + H]⁺
¹H-NMR (400 MHz, DMSO-$d_6$): δ [ppm] = 0.67-0.74 (m, 4H), 1.92-2.00
(m, 1H), 2.36 (br s, 2H), 2.44 (br s, 2H), 3.49-3.55 (m, 8H), 3.67-3.75
(m, 6H), 6.94 (d, 1H), 7.01 (br d, 1H), 7.06 (br s, 1H), 7.21 (s, 1H), 7.46
(br s, 2H), 7.70-7.92 (m, 1H), 8.15 (d, 1H), 8.27 (d, 1H), 10.71 (br s,
1H), 12.21 (br s, 1H).

TABLE 17-continued

Structure
IUPAC-Name
LC-MS (method): Retention time; Mass found
Example ¹H-NMR

Example 135.03 cyclopropyl(4-{[2-({6-[2-(dimethylamino)pyridin-4-yl]-1H-benzimidazol-2-yl}amino)pyridin-4-yl]methyl}piperazin-1-yl)methanone
LC-MS (Method 2): $R_t$ = 1.09 min; MS (ESIpos): m/z = 497 [M + H]⁺
¹H-NMR (400 MHz, DMSO-$d_6$): δ [ppm] = 0.67-0.74 (m, 4H), 1.93-2.01 (m, 1H), 2.36 (br s, 2H), 2.45 (br s, 2H), 3.09 (s, 6H), 3.52 (s, 4H), 3.71 (br s, 2H), 6.83 (s, 1H), 6.87 (br d, 1H), 6.95 (dd, 1H), 7.20 (s, 1H), 7.38-7.55 (m, 2H), 7.67-7.91 (m, 1H), 8.10 (d, 1H), 8.27 (d, 1H), 10.69 (br s, 1H), 12.20 (br s, 1H).

Example 136.03

4-{2-[(4-{[4-(cyclopropylcarbonyl)piperazin-1-yl]methyl}pyridin-2-yl)amino]-1H-benzimidazol-6-yl}-6-methylpyridine-2-carbonitrile
LC-MS (Method 2): $R_t$ = 1.09 min; MS (ESIpos): m/z = 493 [M + H]⁺
¹H-NMR (400 MHz, DMSO-$d_6$): δ [ppm] = 0.66-0.75 (m, 4H), 1.92-2.01 (m, 1H), 2.34-2.47 (m, 4H), 2.59 (s, 3H), 3.45-3.56 (m, 4H), 3.64-3.75 (m, 2H), 6.93-6.99 (m, 1H), 7.17-7.23 (m, 1H), 7.43-7.67 (m, 2H), 7.88-8.02 (m, 2H), 8.12-8.26 (m, 1H), 8.28 (d, 1H), 10.72-10.82 (m, 1H), 12.24-12.32 (m, 1H).

Example 137.03 cyclopropyl{4-[(2-{[6-(2-fluoropyridin-4-yl)-1H-benzimidazol-2-yl]amino}pyridin-4-yl)methyl]piperazin-1-yl}methanone
LC-MS (Method 2): $R_t$ = 1.06 min; MS (ESIpos): m/z = 472 [M + H]⁺
¹H-NMR (400 MHz, DMSO-$d_6$): δ [ppm] = 0.65-0.75 (m, 4H), 1.93-2.01 (m, 1H), 2.33-2.47 (m, 4H), 3.45-3.58 (m, 4H), 3.71 (br s, 2H), 6.96 (br d, 1H), 7.21 (s, 1H), 7.40-7.76 (m, 4H), 7.83-8.00 (m, 1H), 8.20-8.32 (m, 2H), 10.75 (br d, 1H), 12.28 (br d, 1H).

TABLE 17-continued

Structure
IUPAC-Name
LC-MS (method): Retention time; Mass found
Example
¹H-NMR

Example 138.03

{4-[(2-{[6-(2-aminopyridin-4-yl)-1H-benzimidazol-2-
yl]amino}pyridin-4-yl)methyl]piperazin-1-
yl}(cyclopropyl)methanone
LC-MS (Method 2): $R_t$ = 0.92 min; MS (ESIpos): m/z = 469 [M + H]⁺
¹H-NMR (400 MHz, DMSO-d₆): δ [ppm] = 0.65-0.75 (m, 4H), 1.92-2.02
(m, 1H), 2.34-2.47 (m, 4H), 3.45-3.57 (m, 4H), 3.64-3.77 (m, 2H),
6.00-6.13 (m, 2H), 6.73-6.87 (m, 2H), 6.93-6.97 (m, 1H), 7.19 (s,
1H), 7.29-7.84 (m, 3H), 7.93 (d, 1H), 8.28 (d, 1H), 10.65-10.76 (m,
1H), 12.11-12.32 (m, 1H).

Example 139.03 cyclopropyl(4-{[2-({6-[2-(difluoromethyl)pyridin-4-yl]-1H-
benzimidazol-2-yl}amino)pyridin-4-yl]methyl}piperazin-1-
yl)methanone
LC-MS (Method 2): $R_t$ = 1.07 min; MS (ESIpos): m/z = 504 [M + H]⁺
¹H-NMR (400 MHz, DMSO-d₆): δ [ppm] = 0.65-0.75 (m, 4H), 1.97 (tt,
1H), 2.30-2.47 (m, 4H), 3.44-3.56 (m, 4H), 3.63-3.77 (m, 2H), 6.85-
7.22 (m, 3H), 7.40-7.65 (m, 2H), 7.81-8.05 (m, 3H), 8.28 (d, 1H), 8.69
(d, 1H), 10.77 (br s, 1H), 12.29 (br d, 1H).

Example 140.03

{4-[(2-{[6-(5-chloropyrazin-2-yl)-1H-benzimidazol-2-
yl]amino}pyridin-4-yl)methyl]piperazin-1-
yl}(cyclopropyl)methanone
LC-MS (Method 2): $R_t$ = 1.13 min; MS (ESIpos): m/z = 489 [M + H]⁺

TABLE 17-continued

| | Structure<br>IUPAC-Name<br>LC-MS (method): Retention time; Mass found |
|---|---|
| Example | ¹H-NMR |

Example 141.03

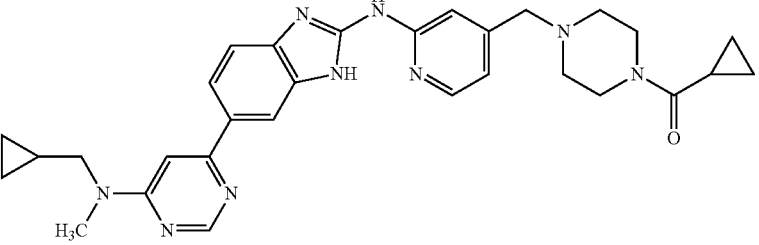

cyclopropyl[4-({2-[(6-{6-
[(cyclopropylmethyl)(methyl)amino]pyrimidin-4-yl}-1H-
benzimidazol-2-yl)amino]pyridin-4-yl}methyl)piperazin-1-
yl]methanone
LC-MS (Method 4): $R_t$ = 1.14 min; MS (ESIpos): m/z = 538 [M + H]⁺
¹H NMR (400 MHz, DMSO-d₆): δ ppm 0.27-0.38 (m, 2 H) 0.43-0.52
(m, 2 H) 0.66-0.69 (m, 1 H) 0.69-0.75 (m, 4 H) 1.04-1.15 (m, 1 H)
1.93-2.01 (m, 1 H) 2.36 (br s, 2 H) 2.44 (br s, 2 H) 3.17 (s, 3 H) 3.52
(s, 4 H) 3.55 (br s, 2 H) 3.71 (br s, 2 H) 6.95 (d, J = 5.32 Hz, 1 H) 7.07 (br
s, 1 H) 7.20 (s, 1 H) 7.37-7.57 (m, 1 H) 7.89 (br d, J = 7.10 Hz, 1 H)
8.15 (br s, 0, 5 H) 8.27 (d, J = 5.32 Hz, 1 H) 8.29-8.33 (m, 0, 5 H) 8.51
(d, J = 0.76 Hz, 1 H) 10.72 (br s, 1 H) 12.25 (br s, 1 H)

Example 142.03

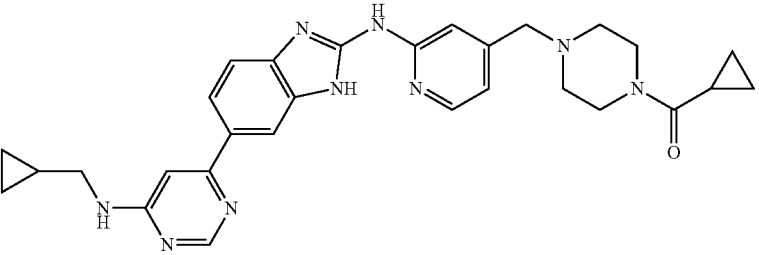 [SMILES: O=C(C1CC1)N1CCN(Cc2ccnc(Nc3nc4ccc(-c5cc(NCC6CC6)ncn5)cc4[nH]3)c2)CC1]

cyclopropyl[4-({2-[(6-{6-[(cyclopropylmethyl)amino]pyrimidin-4-yl}-
1H-benzimidazol-2-yl)amino]pyridin-4-yl}methyl)piperazin-1-
yl]methanone
LC-MS (Method 2): $R_t$ = 1.05 min; MS (ESIpos): m/z = 524 [M + H]⁺
¹H-NMR (400 MHz, DMSO-d₆): δ [ppm]: 0.229 (0.94), 0.240 (3.58), 0.244
(3.33), 0.252 (3.70), 0.266 (1.25), 0.447 (1.25), 0.457 (3.14), 0.462 (3.26),
0.468 (1.69), 0.473 (1.63), 0.478 (3.39), 0.482 (3.20), 0.492 (1.13), 0.666
(0.69), 0.678 (1.95), 0.685 (4.52), 0.691 (2.82), 0.698 (2.32), 0.705 (5.52),
0.709 (4.71), 0.713 (5.02), 0.721 (4.52), 0.726 (5.27), 0.733 (2.45), 0.745
(0.63), 1.066 (1.13), 1.074 (1.07), 1.231 (0.44), 1.936 (0.50), 1.948 (1.07),
1.955 (1.13), 1.967 (1.82), 1.979 (1.07), 1.986 (1.00), 1.999 (0.44), 2.084
(0.94), 2.318 (1.19), 2.322 (2.64), 2.326 (3.76), 2.332 (2.89), 2.336 (1.63),
2.364 (1.95), 2.445 (1.95), 2.518 (16.00), 2.522 (9.98), 2.660 (1.13), 2.664
(2.57), 2.669 (3.51), 2.673 (2.57), 2.678 (1.13), 3.211 (1.51), 3.226 (2.51),
3.241 (1.51), 3.523 (7.97), 3.710 (1.88), 6.903 (1.13), 6.942 (2.26), 6.955
(2.64), 7.187 (1.51), 7.378 (1.00), 7.399 (1.07), 7.551 (0.44), 7.736 (0.50),
8.205 (0.63), 8.245 (0.44), 8.260 (0.50), 8.268 (3.58), 8.281 (3.39), 8.445
(3.89), 10.712 (1.95), 12.211 (0.75), 12.236 (1.13).

Example 143.03

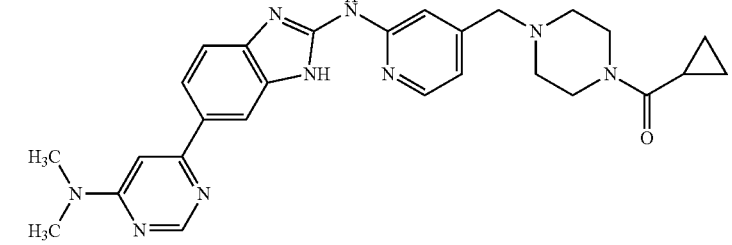

cyclopropyl(4-{[2-({6-[6-(dimethylamino)pyrimidin-4-yl]-1H-
benzimidazol-2-yl}amino)pyridin-4-yl]methyl}piperazin-1-
yl)methanone
LC-MS (Method 2): $R_t$ = 1.01 min; MS (ESIpos): m/z = 498 [M + H]⁺
¹H-NMR (400 MHz, DMSO-d₆) δ [ppm]: 0.654 (0.70), 0.662 (1.54), 0.667
(0.93), 0.674 (0.81), 0.681 (1.89), 0.686 (1.53), 0.691 (1.64), 0.698 (1.51), TABLE 17-continued

| Example | Structure<br>IUPAC-Name<br>LC-MS (method): Retention time; Mass found<br>¹H-NMR |
|---|---|
| | 0.703 (1.75), 0.710 (0.79), 1.043 (0.46), 1.941 (0.64), 2.347 (0.68), 3.126 (16.00), 3.478 (0.70), 3.506 (2.44), 3.686 (0.66), 6.921 (0.80), 6.924 (0.79), 6.934 (0.80), 6.937 (0.81), 7.053 (0.81), 7.182 (1.38), 7.853 (0.73), 7.857 (0.75), 7.874 (0.64), 7.878 (0.69), 8.241 (1.59), 8.255 (1.32), 8.503 (2.64), 8.506 (2.48). |
| Example 144.03 | cyclopropyl(4-{[2-({6-[5-(dimethylamino)pyrazin-2-yl]-1H-benzimidazol-2-yl}amino)pyridin-4-yl]methyl}piperazin-1-yl)methanone<br>LC-MS (Method 4): R$_t$ = 1.07 min; MS (ESIpos): m/z = 498 [M + H]⁺<br>¹H NMR (400 MHz, DMSO-d$_6$) δ ppm 0.66-0.75 (m, 4 H) 1.90-2.01 (m, 1 H) 2.34-2.47 (m, 4 H) 3.08-3.16 (m, 6 H) 3.43-3.59 (m, 4 H) 3.71 (br s, 2 H) 6.93 (dd, J = 5.32, 1.01 Hz, 1 H) 7.20 (s, 1 H) 7.33-7.54 (m, 1 H) 7.66 (br s, 1 H) 7.87-8.09 (m, 1 H) 8.21 (d, J = 1.27 Hz, 1 H) 8.26 (d, J = 5.32 Hz, 1 H) 8.57-8.68 (m, 1 H) 10.63 (br s, 1 H) 12.13 (br s, 1 H) |
| Example 145.03 | cyclopropyl(4-{[2-({6-[6-(piperidin-1-yl)pyrimidin-4-yl]-1H-benzimidazol-2-yl}amino)pyridin-4-yl]methyl}piperazin-1-yl)methanone<br>LC-MS (Method 4): R$_t$ = 1.15 min; MS (ESIpos): m/z = 538 [M + H]⁺<br>¹H NMR (400 MHz, DMSO-d$_6$) δ ppm 0.66-0.75 (m, 4 H) 1.51-1.60 (m, 4 H) 1.60-1.71 (m, 2 H) 1.93-2.01 (m, 1 H) 2.34-2.47 (m, 4 H) 3.52 (s, 4 H) 3.66-3.77 (m, 6 H) 6.95 (d, J = 5.07 Hz, 1 H) 7.15-7.32 (m, 2 H) 7.33-7.58 (m, 1 H) 7.90 (br d, J = 7.86 Hz, 1 H) 8.17 (br s, 1 H) 8.27 (d, J = 5.32 Hz, 1 H) 8.32 (br s, 1 H) 8.51 (d, J = 1.01 Hz, 1 H) 10.72 (br s, 1 H) 12.21 (br d, J = 14.45 Hz, 1 H) |
| Example 148.03 | |

TABLE 17-continued

| Example | Structure<br>IUPAC-Name<br>LC-MS (method): Retention time; Mass found<br>¹H-NMR |
|---|---|
| | cyclopropyl[4-({2-[(6-{6-[ethyl(methyl)amino]pyrimidin-4-yl}-1H-benzimidazol-2-yl)amino]pyridin-4-yl}methyl)piperazin-1-yl]methanone<br>LC-MS (Method 4): $R_t$ = 1.06 min; MS (ESIpos): m/z = 512 [M + H]⁺<br>¹H NMR (400 MHz, DMSO-$d_6$) δ ppm 0.66-0.75 (m, 4 H) 1.13 (t, J = 7.10 Hz, 3 H) 1.93-2.01 (m, 1 H) 2.34-2.47 (m, 4 H) 3.11 (s, 2 H) 3.50 (br s, 3 H) 3.54 (s, 2 H) 3.63-3.68 (m, 2 H) 3.70 (br d, J = 5.58 Hz, 2 H) 6.96 (dd, J = 5.32, 1.27 Hz, 1 H) 7.01-7.09 (m, 1 H) 7.21 (s, 1 H) 7.47 (br d, J = 5.58 Hz, 1 H) 7.88 (dd, J = 8.36, 1.77 Hz, 1 H) 8.23 (br s, 1 H) 8.28 (d, J = 5.07 Hz, 1 H) 8.52 (d, J = 1.01 Hz, 1 H) 10.74 (br s, 1 H) 12.27 (br s, 1 H) |
| Example 149.03 | cyclopropyl(4-{[2-({6-[6-(ethylamino)pyrimidin-4-yl]-1H-benzimidazol-2-yl}amino)pyridin-4-yl]methyl}piperazin-1-yl)methanone<br>LC-MS (Method 4): $R_t$ = 0.96 min; MS (ESIpos): m/z = 498 [M + H]⁺<br>¹H NMR (400 MHz, DMSO-$d_6$) δ ppm 0.66-0.74 (m, 4 H) 1.17 (t, J = 7.22 Hz, 3 H) 1.92-2.01 (m, 1 H) 2.32-2.47 (m, 4 H) 3.35-3.41 (m, 2 H) 3.45-3.58 (m, 4 H) 3.70 (br s, 2 H) 6.83-6.92 (m, 1 H) 6.95 (d, J = 5.07 Hz, 1 H) 7.19 (br s, 1 H) 7.29 (br s, 1 H) 7.36-7.56 (m, 1 H) 7.74 (br s, 1 H) 7.95-8.23 (m, 1 H) 8.27 (d, J = 5.32 Hz, 1 H) 8.45 (s, 1 H) 10.71 (br s, 1 H) 12.24 (br s, 1 H) |
| Example 150.03 | cyclopropyl(4-{[2-({6-[6-(methylamino)pyrimidin-4-yl]-1H-benzimidazol-2-yl}amino)pyridin-4-yl]methyl}piperazin-1-yl)methanone<br>LC-MS (Method 4): $R_t$ = 0.89 min; MS (ESIpos): m/z = 484 [M + H]⁺<br>¹H NMR (400 MHz, DMSO-$d_6$) δ ppm 0.66-0.75 (m, 4 H) 1.93-2.00 (m, 1 H) 2.34-2.47 (m, 4 H) 2.86 (d, J = 4.82 Hz, 3 H) 3.52 (s, 2 H) 3.71 (br s, 2 H) 6.81-6.92 (m, 1 H) 6.95 (d, J = 5.32 Hz, 1 H) 7.19 (br s, 1 H) 7.23 (br s, 1 H) 7.36-7.58 (m, 1 H) 7.76 (br s, 1 H) 7.95-8.24 (m, 1 H) 8.27 (d, J = 5.32 Hz, 1 H) 8.46 (s, 1 H) 10.71 (s, 1 H) 12.23 (br d, J = 11.91 Hz, 1 H) |
| Example 151.03 | |

TABLE 17-continued

| | Structure<br>IUPAC-Name<br>LC-MS (method): Retention time; Mass found |
|---|---|
| Example | ¹H-NMR | cyclopropyl(4-{[2-({6-[6-(cyclopropylamino)pyrimidin-4-yl]-1H-benzimidazol-2-yl}amino)pyridin-4-yl]methyl}piperazin-1-yl)methanone LC-MS (Method 4): $R_t$ = 0.97 min; MS (ESIpos): m/z = 510 [M + H]⁺

¹H-NMR (400 MHz, DMSO-$d_6$): δ [ppm] = 0.52 (br s, 2H), 0.67-0.74 (m, 4H), 0.80 (br d, 2H), 1.92-2.00 (m, 1H), 2.36 (br s, 2H), 2.45 (br s, 2H), 2.62-2.72 (m, 1H), 3.52 (s, 4H), 3.71 (br s, 2H), 6.95 (br d, 1H), 7.02 (br s, 1H), 7.19 (s, 1H), 7.36-7.50 (m, 1H), 7.58 (br s, 1H), 7.79 (br s, 1H), 8.02-8.24 (m, 1H), 8.27 (br d, 1H), 8.47 (s, 1H), 10.73 (br s, 1H), 12.25 (br s, 1H).

Example 152.03

(4-{[2-({6-[6-(cyclobutylamino)pyrimidin-4-yl]-1H-benzimidazol-2-yl}amino)pyridin-4-yl]methyl}piperazin-1-yl)(cyclopropyl)methanone LC-MS (Method 4): $R_t$ = 1.05 min; MS (ESIpos): m/z = 524 [M + H]⁺

¹H-NMR (400 MHz, DMSO-$d_6$): δ [ppm] = 0.66-0.75 (m, 4H), 1.63-1.77 (m, 2H), 1.89-2.00 (m, 3H), 2.26-2.33 (m, 2H), 2.36 (br s, 2H), 2.45 (br s, 2H), 3.52 (m, 4H), 3.70 (br s, 2H), 4.44 (br s, 1H), 6.83 (br d, 1H), 6.95 (br d, 1H), 7.19 (br s, 1H), 7.37-7.63 (m, 2H), 7.69-7.94 (m, 1H), 7.95-8.23 (m, 1H), 8.27 (d, 1H), 8.44 (s, 1H), 10.72 (br s, 1H), 12.24 (br s, 1H).

Example 153.03 cyclopropyl[4-({2-[(6-{6-[methyl(propan-2-yl)amino]pyrimidin-4-yl}-1H-benzimidazol-2-yl)amino]pyridin-4-yl}methyl)piperazin-1-yl]methanone LC-MS (Method 4): $R_t$ = 1.12 min; MS (ESIpos): m/z = 526 [M + H]⁺

¹H-NMR (400 MHz, DMSO-$d_6$): δ [ppm] = 0.68-0.74 (m, 4H), 1.17 (d, 6H), 1.93-2.01 (m, 1H), 2.37 (br s, 2H), 2.45 (br s, 2H), 2.94 (s, 3H), 3.47-3.54 (m, 4H), 3.71 (br s, 2H), 5.00 (br s, 1H), 6.95 (d, 1H), 7.05 (br s, 1H), 7.20 (s, 1H), 7.46 (br s, 1H), 7.88 (br d, 1H), 8.16-8.31 (m, 2H), 8.52 (s, 1H), 10.72 (br s, 1H), 12.24 (br s, 1H).

Example 154.03

TABLE 17-continued

Structure
IUPAC-Name
LC-MS (method): Retention time; Mass found
Example      ¹H-NMR Example 155.03 cyclopropyl(4-{[2-({6-[6-(propan-2-ylamino)pyrimidin-4-yl]-1H-
benzimidazol-2-yl}amino)pyridin-4-yl]methyl}piperazin-1-
yl)methanone
LC-MS (Method 4): R$_t$ = 1.02 min; MS (ESIpos): m/z = 512 [M + H]$^+$

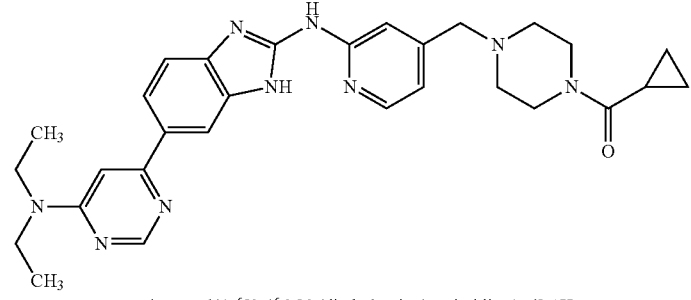

cyclopropyl(4-{[2-({6-[6-(diethylamino)pyrimidin-4-yl]-1H-
benzimidazol-2-yl}amino)pyridin-4-yl]methyl}piperazin-1-
yl)methanone
LC-MS (Method 4): R$_t$ = 1.12 min; MS (ESIpos): m/z = 526 [M + H]$^+$
¹H-NMR (400 MHz, DMSO-d$_6$): δ [ppm] = 0.66-0.75 (m, 4H), 1.16 (t,
6H), 1.91-2.03 (m, 1H), 2.38 (br s, 2H), 2.42-2.46 (m, 2H), 3.47-3.56
(m, 4H), 3.61 (q, 4H), 3.71 (br s, 2H), 6.96 (d, 1H), 7.01 (br s, 1H), 7.21
(s, 1H), 7.46 (br s, 1H), 7.86 (br d, 1H), 8.22 (br s, 1H), 8.27 (d, 1H),
8.52 (d, 1H), 10.73 (br s, 1H), 12.26 (br s, 1H).

Example 156.03

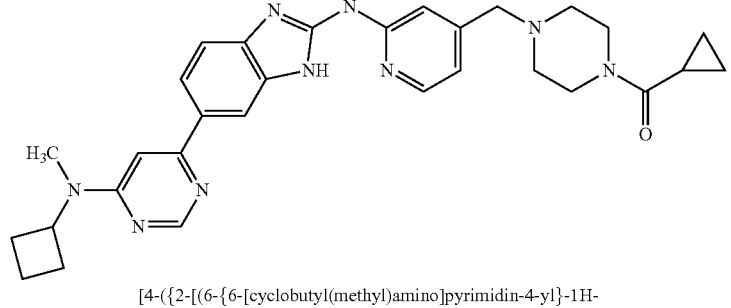

[4-({2-[(6-{6-[cyclobutyl(methyl)amino]pyrimidin-4-yl}-1H-
benzimidazol-2-yl)amino]pyridin-4-yl}methyl)piperazin-1-
yl](cyclopropyl)methanone
LC-MS (Method 2): R$_t$ = 1.16 min; MS (ESIpos): m/z = 538 [M + H]$^+$
¹H NMR (400 MHz, DMSO-d$_6$) δ ppm 0.67-0.75 (m, 4 H) 1.66-1.74
(m, 2 H) 1.92-2.01 (m, 1 H) 2.15-2.30 (m, 4 H) 2.33-2.46 (m, 4 H)
3.08 (s, 3 H) 3.45-3.45 (m, 1 H) 3.45-3.58 (m, 3 H) 3.71 (br s, 2 H)
5.03 (br s, 1 H) 6.95 (br d, J = 5.07 Hz, 1 H) 7.00-7.27 (m, 2 H) 7.36-
7.62 (m, 1 H) 7.90 (br d, J = 8.11 Hz, 1 H) 8.10-8.36 (m, 2 H) 8.53 (d,
J = 1.01 Hz, 1 H) 10.64-10.79 (m, 1 H) 12.22 (br d, J = 15.46 Hz, 1 H)

Example 157.03

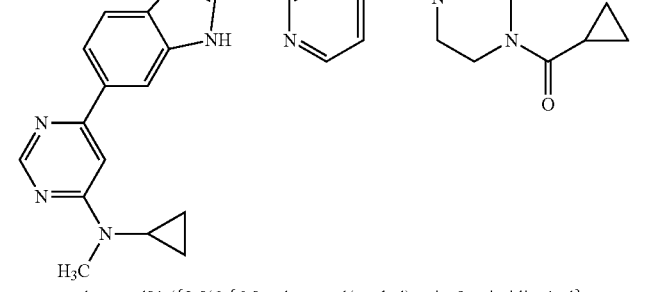

cyclopropyl[4-({2-[(6-{6-[cyclopropyl(methyl)amino]pyrimidin-4-yl}-
1H-benzimidazol-2-yl)amino]pyridin-4-yl}methyl)piperazin-1-
yl]methanone
LC-MS (Method 2): R$_t$ = 1.1 min; MS (ESIpos): m/z = 524 [M + H]$^+$
¹H NMR (400 MHz, DMSO-d$_6$) δ ppm 0.67-0.76 (m, 6 H) 0.98-1.04

| Example | Structure<br>IUPAC-Name<br>LC-MS (method): Retention time; Mass found<br>¹H-NMR |
|---|---|
| | (m, 2 H) 1.93-2.01 (m, 1 H) 2.34-2.47 (m, 4 H) 2.73-2.79 (m, 1 H) 3.13 (s, 3 H) 3.50 (br s, 2 H) 3.53 (s, 2 H) 3.71 (br s, 2 H) 6.95 (d, J = 5.32 Hz, 1 H) 7.20 (s, 1 H) 7.35 (s, 1 H) 7.39-7.62 (m, 1 H) 7.84 (br d, J = 7.60 Hz, 1 H) 8.28 (d, J = 5.32 Hz, 2 H) 8.57 (d, J = 1.01 Hz, 1 H) 10.73 (br s, 1 H) 12.25 (br s, 1 H) |
| Example 158.03 | 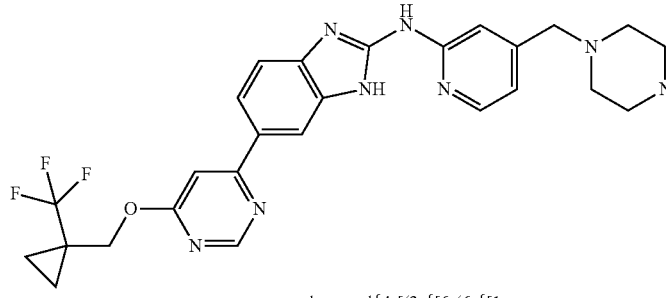<br>cyclopropyl{4-[(2-{[6-(6-{[1-(trifluoromethyl)cyclopropyl]methoxy}pyrimidin-4-yl)-1H-benzimidazol-2-yl]amino}pyridin-4-yl)methyl]piperazin-1-yl}methanone<br>LC-MS (Method 2): R$_t$ = 1.29 min; MS (ESIpos): m/z = 593 [M + H]$^+$<br>¹H-NMR (400 MHz, DMSO-d$_6$): δ [ppm] = 0.67-0.75 (m, 4H), 1.12 (br d, 4H), 1.93-2.00 (m, 1H), 2.37 (m, 2H), 2.45 (m, 2H), 3.46-3.56 (m, 4H), 3.71 (br s, 2H), 4.57 (s, 2H), 6.96 (br s, 1H), 7.20 (br d, 1H), 7.37 (s, 0, 5H), 7.40 (br d, 0, 5H), 7.48 (s, 0, 5H), 7.57 (br d, 0, 5H), 7.94 (br t, 1H), 8.22 (s, 0, 5H), 8.28 (d, 1H), 8.38 (s, 0, 5H), 8.79 (s, 1H), 10.77 (br s, 1H), 12.27 (br d, 1H). |
| Example 160.03 | 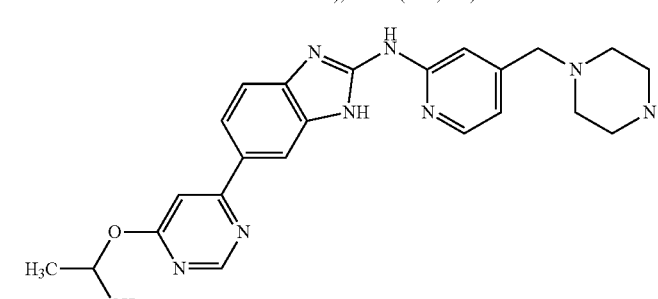<br>cyclopropyl(4-{[2-({6-[6-(propan-2-yloxy)pyrimidin-4-yl]-1H-benzimidazol-2-yl}amino)pyridin-4-yl]methyl}piperazin-1-yl)methanone<br>LC-MS (Method 2): R$_t$ = 1.19 min; MS (ESIpos): m/z = 513 [M + H]$^+$<br>¹H-NMR (400 MHz, DMSO-d$_6$): δ [ppm] = 0.68-0.73 (m, 4H), 1.35 (d, 6H), 1.93-2.01 (m, 1H), 2.34-2.42 (m, 4H), 3.47-3.51 (m, 2H), 3.53 (s, 2H), 3.67-3.74 (m, 2H), 5.38 (quin, 1H), 6.93-6.98 (m, 1H), 7.18-7.22 (m, 1H), 7.25-7.27 (m, 0, 5H), 7.35-7.38 (m, 0, 5H), 7.38-7.42 (m, 0, 5H), 7.53-7.58 (m, 0, 5H), 7.87-7.93 (m, 1H), 8.16-8.19 (m, 0, 5H), 8.27-8.30 (m, 1H), 8.34-8.37 (m, 0, 5H), 8.76-8.79 (m, 1H), 10.72-10.77 (m, 1H), 12.23-12.28 (m, 1H). |
| Example 161.03 | 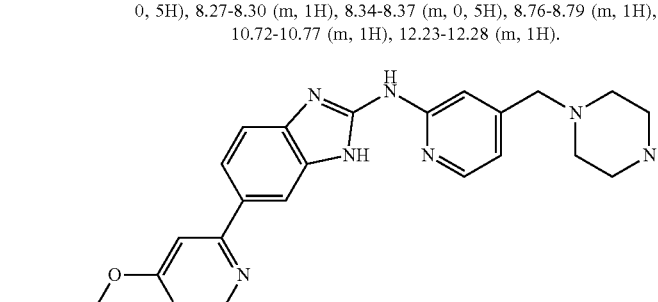<br>cyclopropyl{4-[(2-{[6-(6-ethoxypyrimidin-4-yl)-1H-benzimidazol-2-yl]amino}pyridin-4-yl)methyl]piperazin-1-yl}methanone<br>LC-MS (Method 2): R$_t$ = 1.14 min; MS (ESIneg): m/z = 497 [M − H]$^-$<br>¹H-NMR (400 MHz, DMSO-d$_6$): δ [ppm] = 0.66-0.76 (m, 4H), 1.37 (t, 3H), 1.92-2.00 (m, 1H), 2.36 (br s, 2H), 2.45 (br s, 2H), 3.44-3.57 (m, |

TABLE 17-continued

Example | Structure / IUPAC-Name / LC-MS (method): Retention time; Mass found / ¹H-NMR 4H), 3.71 (br s, 2H), 4.43 (q, 2H), 6.96 (br d, 1H), 7.20 (br s, 1H), 7.29-7.61 (m, 2H), 7.91 (br d, 1H), 8.19 (br s, 0, 5H), 8.28 (d, 1H), 8.35 (br s, 0, 5H), 8.78 (s, 1H), 10.75 (br s, 1H), 12.27 (br d, 1H).

Example 163.03

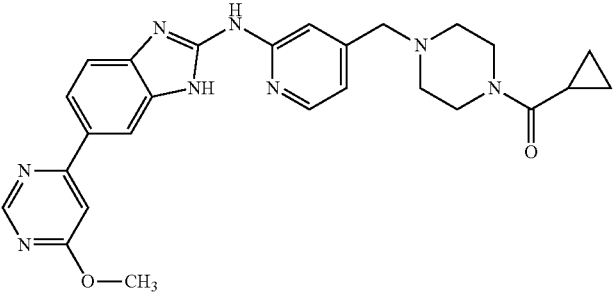 [SMILES: COc1cc(-c2ccc3nc(Nc4cc(CN5CCN(C(=O)C6CC6)CC5)ccn4)[nH]c3c2)ncn1]

cyclopropyl{4-[(2-{[6-(6-methoxypyrimidin-4-yl)-1H-benzimidazol-2-yl]amino}pyridin-4-yl)methyl]piperazin-1-yl}methanone
LC-MS (Method 4): $R_t$ = 1.03 min; MS (ESIpos): m/z = 485 [M + H]⁺
¹H-NMR (400 MHz, DMSO-$d_6$): δ [ppm] = 0.65-0.76 (m, 4H), 1.91-2.03 (m, 1H), 2.36 (br s, 2H), 2.44 (br s, 2H), 3.46-3.57 (m, 4H), 3.71 (br s, 2H), 3.97 (s, 3H), 6.96 (br d, 1H), 7.20 (s, 1H), 7.27-7.65 (m, 2H), 7.91 (br s, 1H), 8.18-8.38 (m, 2H), 8.80 (d, 1H), 10.77 (br s, 1H), 12.30 (br s, 1H).

The Example compounds in the following table 18 were synthesised according to the preparations, and from starting materials (SM), as specified for the respective Examples in their table entries below.

TABLE 18

Example | Structure / IUPAC-Name / LC-MS(method): Retention time; Mass found / ¹H-NMR / Starting material (SM): / Synthesis procedure in analogy to the preparation of:

Example 164.01

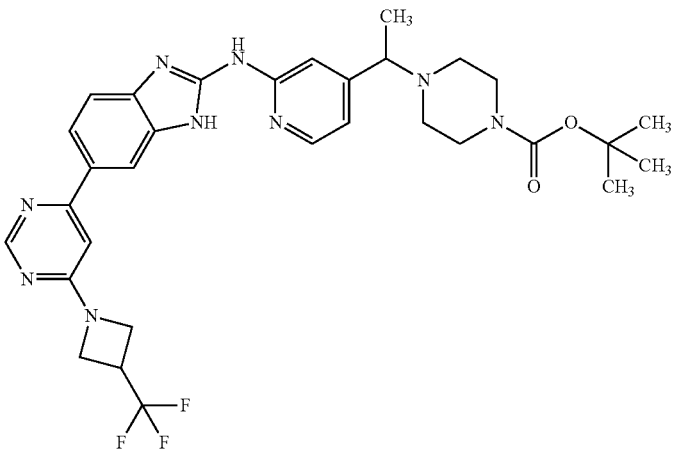 [SMILES: CC(c1ccnc(Nc2nc3ccc(-c4cc(N5CC(C(F)(F)F)C5)ncn4)cc3[nH]2)c1)N1CCN(C(=O)OC(C)(C)C)CC1]

tert-butyl 4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazine-1-carboxylate
LC-MS (Method 2): $R_t$ = 1.34 min; MS (ESIpos): m/z = 623.7 [M + H]⁺
¹H-NMR (400 MHz, DMSO-d6) δ [ppm]: 1.000 (1.18), 1.015 (1.18), 1.172 (0.46), 1.278 (1.65), 1.295 (1.66), 1.376 (16.00), 1.987 (0.85), 2.310 (0.43), 2.382 (0.44), 2.518 (0.59), 2.523 (0.42), 3.433 (0.48), 3.450 (0.46), 4.104 (0.44), 4.117 (0.45), 4.127 (0.57), 4.140 (0.47), 4.329 (0.64), 4.352 (1.14), 4.375 (0.49), 5.758 (5.12), 6.934 (0.54), 6.937 (0.55), 6.947 (0.56), 6.950

TABLE 18-continued

| | Structure<br>IUPAC-Name<br>LC-MS(method): Retention time; Mass found<br>¹H-NMR<br>Starting material (SM): |
|---|---|
| Example | Synthesis procedure in analogy to the preparation of: |

(0.57), 6.977 (0.51), 7.193 (0.70), 7.866 (0.61), 7.870 (0.60), 7.887 (0.52), 7.891 (0.54), 8.253 (1.05), 8.266 (0.91), 8.565 (1.58), 8.569 (1.59).
SM: Example 85.01
Synthesis in analogy to the preparation of Example 116.01

Example 165.01 tert-butyl 4-{(1R or 1S)-1-[2-({6-[6-(2,2-difluoropropoxy)pyrimidin-4-yl]-1H-benzimidazol-2-yl}amino)pyridin-4-yl]ethyl}piperazine-1-carboxylate
LC-MS (Method 2): $R_t$ = 1.42 min; MS (ESIneg): m/z = 593 [M − H]⁻
¹H-NMR (400 MHz, DMSO-d6) δ [ppm]: 1.172 (0.74), 1.278 (1.71), 1.295 (1.69), 1.370 (3.46), 1.376 (16.00), 1.385 (0.90), 1.720 (1.04), 1.769 (2.13), 1.817 (0.93), 1.987 (1.38), 2.295 (0.40), 2.310 (0.49), 2.383 (0.44), 2.518 (0.53), 3.322 (1.09), 3.332 (5.51), 4.678 (0.61), 4.711 (1.23), 4.744 (0.55), 7.167 (0.53), 8.268 (0.81), 8.282 (0.76), 8.828 (1.50), 8.830 (1.53).
SM: Example 85.01
Synthesis in analogy to the preparation of Example 119.01

Example 166.01 tert-butyl 4-{(1R or 1S)-1-[2-({6-[6-(2,2,3,3,3-pentafluoropropoxy)pyrimidin-4-yl]-1H-benzimidazol-2-yl}amino)pyridin-4-yl]ethyl}piperazine-1-carboxylate
LC-MS (Method 2): $R_t$ = 1.53 min; MS (ESIpos): m/z = 648.6 [M + H]⁺
¹H-NMR (400 MHz, DMSO-d6) δ [ppm]: 1.279 (1.64), 1.295 (1.66), 1.376 (16.00), 2.310 (0.42), 2.383 (0.42), 2.518 (0.63), 2.523 (0.45), 5.211 (0.48), 5.246 (0.89), 5.280 (0.43), 5.758 (0.77), 7.167 (0.60), 8.268 (0.82), 8.282 (0.76), 8.874 (1.48), 8.876 (1.49).
SM: Example 85.01
Synthesis in analogy to the preparation of Example 119.01

TABLE 18-continued

Structure
IUPAC-Name
LC-MS(method): Retention time; Mass found
¹H-NMR
Starting material (SM):
Synthesis procedure in analogy to the preparation of:

Example 167.01

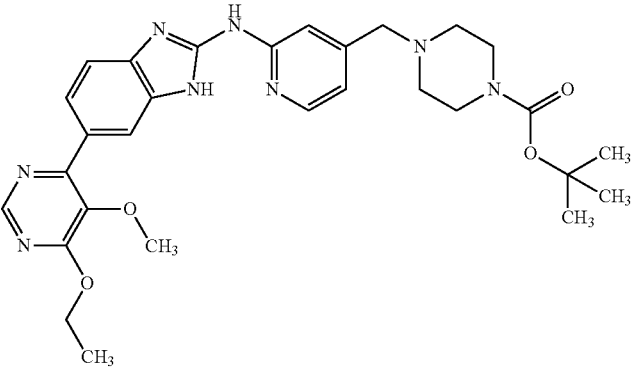 [SMILES: CCOc1ncnc(-c2ccc3nc(Nc4cc(CN5CCN(C(=O)OC(C)(C)C)CC5)ccn4)[nH]c3c2)c1OC]

tert-butyl 4-[(2-{[6-(6-ethoxy-5-methoxypyrimidin-4-yl)-1H-benzimidazol-2-yl]amino}pyridin-4-yl)methyl]piperazine-1-carboxylate
LC-MS (Method 2): R$_t$ = 1.33 min; MS (ESIpos): m/z = 561 [M + H]$^+$
¹H-NMR (400 MHz, DMSO-d6) δ [ppm]: 1.394 (16.00), 1.407 (3.67), 1.425 (1.63), 2.347 (0.98), 2.359 (1.40), 2.371 (0.96), 3.350 (1.13), 3.500 (1.76), 3.757 (1.08), 4.461 (0.43), 4.479 (1.37), 4.496 (1.32), 4.514 (0.40), 6.923 (0.49), 6.936 (0.49), 7.177 (0.42), 8.263 (0.73), 8.276 (0.69), 8.520 (1.75).
SM: Compound 60.01
Synthesis in analogy to the preparation of Example 119.01

Example 168.01

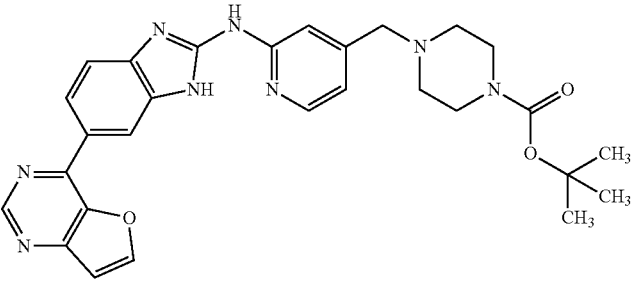 [SMILES: CC(C)(C)OC(=O)N1CCN(Cc2ccnc(Nc3nc4ccc(-c5ncnc6ccoc56)cc4[nH]3)c2)CC1]

tert-butyl 4-[(2-{[6-(furo[3,2-d]pyrimidin-4-yl)-1H-benzimidazol-2-yl]amino}pyridin-4-yl)methyl]piperazine-1-carboxylate
LC-MS (Method 2): R$_t$ = 1.2 min; MS (ESIpos): m/z = 526.6 [M + H]$^+$
¹H-NMR (400 MHz, DMSO-d6) δ [ppm]: 1.171 (0.65), 1.385 (1.04), 1.396 (16.00), 1.986 (1.10), 2.352 (0.82), 2.365 (1.14), 2.377 (0.79), 2.518 (0.65), 2.523 (0.51), 3.354 (1.16), 3.511 (1.43), 7.183 (0.44), 7.284 (1.84), 7.290 (1.84), 8.284 (0.49), 8.297 (0.49), 8.628 (1.81), 8.634 (1.75), 9.048 (0.57).
SM: Compound 01.04
Synthesis in analogy to the preparation of Compound 60.01

Example 169.01

TABLE 18-continued

| Example | Structure<br>IUPAC-Name<br>LC-MS(method): Retention time; Mass found<br>¹H-NMR<br>Starting material (SM):<br>Synthesis procedure in analogy to the preparation of: |
|---|---|
| | tert-butyl 4-[(1R or 1S)-1-{2-[(6-{1-[(3,3-difluorocyclobutyl)methyl]-1H-pyrazol-4-yl}-1H-benzimidazol-2-yl)amino]pyridin-4-yl}ethyl]piperazine-1-carboxylate<br>LC-MS (Method 2): R$_t$ = 1.34 min; MS (ESIpos): m/z = 593 [M + H]⁺<br>¹H-NMR (400 MHz, DMSO-d6) δ [ppm]: 1.066 (0.66), 1.265 (1.60), 1.274 (1.80), 1.282 (1.78), 1.291 (1.58), 1.371 (16.00), 1.376 (14.76), 2.278 (0.63), 2.290 (0.55), 2.305 (0.46), 2.322 (0.55), 2.326 (0.58), 2.331 (0.43), 2.382 (0.62), 2.518 (1.79), 2.522 (1.23), 2.649 (0.52), 2.664 (0.69), 2.669 (0.79), 2.673 (0.61), 3.329 (13.32), 3.422 (0.49), 3.439 (0.72), 3.455 (0.47), 4.250 (0.51), 5.759 (1.82), 6.910 (0.45), 6.925 (0.45), 6.999 (0.47), 7.012 (0.49), 7.155 (0.55), 8.211 (0.74), 8.224 (0.72), 8.237 (0.79), 8.251 (0.72).<br>SM: Compound 36.05 and Compound 169.04<br>Synthesis in analogy to the preparation of Example 59.01.01 |
| Example 170.01 | tert-butyl 4-[(1R or 1S)-1-(2-{[6-(1-{[(1RS)-2,2-dichlorocyclopropyl]methyl}-1H-pyrazol-4-yl)-1H-benzimidazol-2-yl]amino}pyridin-4-yl)ethyl]piperazine-1-carboxylate<br>LC-MS (Method 2): R$_t$ = 1.39 min; MS (ESIpos): m/z = 611 [M + H]⁺<br>¹H-NMR (400 MHz, DMSO-d6) δ [ppm]: 0.814 (0.62), 0.830 (1.39), 0.836 (0.98), 0.840 (0.70), 0.852 (1.22), 0.858 (1.84), 0.869 (0.49), 0.875 (0.54), 0.936 (0.88), 0.953 (0.94), 1.237 (0.99), 1.243 (0.93), 1.262 (0.43), 1.275 (1.91), 1.292 (1.83), 1.377 (16.00), 1.394 (1.49), 1.619 (0.46), 1.638 (0.90), 1.658 (0.57), 1.847 (0.45), 1.865 (0.50), 1.873 (0.59), 1.892 (0.48), 2.282 (0.41), 2.301 (0.65), 2.308 (0.58), 2.319 (0.69), 2.327 (0.67), 2.381 (0.47), 2.392 (0.41), 2.518 (0.76), 2.523 (0.52), 3.423 (0.42), 3.440 (0.42), 4.327 (0.69), 4.346 (0.62), 5.759 (1.02), 6.912 (0.53), 6.915 (0.53), 6.928 (0.58), 7.157 (0.83), 8.241 (0.89), 8.254 (0.90), 10.561 (0.47).<br>SM: Compound 36.05 and Compound 170.03<br>Synthesis in analogy to the preparation of Example 59.01.01 |
| Example 171.01 | tert-butyl 4-{(1R or 1S)-1-[2-({6-[1-(cyclobutylmethyl)-1H-pyrazol-4-yl]-7-fluoro-1H-benzimidazol-2-yl}amino)pyridin-4-yl]ethyl}piperazine-1-carboxylate<br>LC-MS (Method 2): R$_t$ = 1.44 min; MS (ESIneg): m/z = 573.4 [M − H]⁻<br>¹H-NMR (400 MHz, DMSO-d6) δ [ppm]: 1.154 (1.62), 1.172 (3.52), 1.190 (1.82), 1.273 (1.38), 1.290 (1.46), 1.309 (1.53), 1.325 (1.55), 1.369 (16.00), 1.376 (14.10), 1.810 (0.49), 1.822 (0.59), 1.827 (0.52), 1.832 (0.74), 1.987 (6.80), 1.995 (0.42), 2.304 (0.64), 2.317 (0.66), 2.322 (0.64), 2.327 (0.66), 2.332 (0.48), 2.391 (0.64), 2.518 (1.46), 2.523 (0.93), 3.999 (0.47), 4.017 (1.40), 4.034 (1.35), 4.052 (0.43), 4.161 (0.99), 4.178 (0.97), 6.948 (0.41), 7.028 (0.52), 7.032 (0.52), 7.044 (0.49), 7.048 (0.51), 7.101 (0.55), 7.297 (0.72), 7.328 (0.92), 7.822 (0.76), 8.062 (0.60), 8.252 (0.53), 8.266 (0.51), 8.552 (0.76), 8.568 (0.72), 10.774 (0.57).<br>SM: Compound 36.05 and Compound 171.03<br>Synthesis in analogy to the preparation of Example 59.01.01 |

TABLE 18-continued

Structure
IUPAC-Name
LC-MS(method): Retention time; Mass found
¹H-NMR
Starting material (SM):
Example | Synthesis procedure in analogy to the preparation of:

Example 172.01 tert-butyl 4-[(1R or 1S)-1-(2-{[7-fluoro-6-(6-methylpyrimidin-4-yl)-1H-benzimidazol-2-yl]amino}pyridin-4-yl)ethyl]piperazine-1-carboxylate
LC-MS (Method 2): $R_t$ = 1.26 min; MS (ESIpos): m/z = 533 [M + H]⁺
¹H-NMR (400 MHz, DMSO-d6) δ [ppm]: 1.277 (1.75), 1.293 (1.74), 1.375 (16.00), 2.308 (0.46), 2.384 (0.47), 2.518 (0.59), 2.523 (0.62), 2.531 (5.70), 3.444 (0.40), 6.960 (0.51), 6.973 (0.51), 7.127 (0.48), 7.814 (0.77), 8.277 (0.67), 8.290 (0.63), 9.093 (1.33), 9.096 (1.32), 10.901 (0.48).
SM: Compound 36.05 and Compound 172.02
Synthesis in analogy to the preparation of Example 59.01.01

Example 173.01 tert-butyl 4-{(1R or 1S)-1-[2-({7-fluoro-6-[6-(trifluoromethyl)pyrimidin-4-yl]-1H-benzimidazol-2-yl}amino)pyridin-4-yl]ethyl}piperazine-1-carboxylate
LC-MS (Method 2): $R_t$ = 1.45 min; MS (ESIpos): m/z = 587 [M + H]⁺
¹H-NMR (400 MHz, DMSO-d6) δ [ppm]: 1.152 (1.32), 1.170 (2.71), 1.187 (1.33), 1.277 (1.64), 1.293 (1.64), 1.374 (16.00), 1.985 (4.79), 2.309 (0.44), 2.384 (0.42), 4.015 (1.03), 4.033 (1.02), 6.971 (0.45), 6.984 (0.46), 7.137 (0.64), 7.502 (0.47), 7.523 (0.51), 8.283 (0.63), 8.296 (0.62), 8.314 (0.83), 9.486 (1.00), 10.971 (0.80), 12.594 (0.44).
SM: Compound 36.05 and Compound 173.01
Synthesis in analogy to the preparation of Example 59.01.01

The Example compounds in the following table 19 were synthesized in analogy to the preparation of Example 117.02, followed by purification by preparative reverse phase HPLC or silicagel chromatography.

TABLE 19

| Example | Structure<br>IUPAC-Name<br>LC-MS (method): Retention time; Mass found<br>¹H-NMR<br>Starting materials (SM): |
|---|---|
| Example 164.02 | 3,3,3-trifluoro-1-{4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}propan-1-one<br>LC-MS (Method 2): R$_t$ = 1.17 min; MS (ESIneg): m/z = 632 [M − H]⁻<br>¹H-NMR (400 MHz, DMSO-d6) δ [ppm]: 1.291 (15.79), 1.308 (16.00), 2.327 (4.14), 2.342 (3.57), 2.351 (3.32), 2.364 (2.91), 2.416 (3.86), 2.428 (4.31), 2.441 (3.24), 2.456 (2.58), 2.518 (5.50), 2.523 (3.69), 2.539 (1.15), 2.665 (0.98), 2.669 (1.39), 2.673 (0.98), 3.424 (4.18), 3.436 (7.38), 3.449 (5.46), 3.467 (8.12), 3.482 (9.85), 3.578 (2.83), 3.606 (8.08), 3.634 (7.63), 3.661 (2.42), 3.775 (1.11), 3.787 (1.56), 3.797 (1.48), 3.809 (1.56), 3.821 (1.19), 4.016 (1.39), 4.104 (4.18), 4.117 (4.39), 4.127 (5.42), 4.140 (4.55), 4.330 (6.28), 4.352 (11.32), 4.375 (4.84), 6.949 (4.84), 6.962 (4.43), 7.028 (1.35), 7.181 (7.43), 7.392 (1.07), 7.411 (1.19), 7.561 (0.86), 7.873 (3.65), 7.894 (3.24), 8.153 (1.31), 8.265 (8.82), 8.278 (8.29), 8.321 (1.81), 8.567 (14.11), 8.569 (14.56), 10.714 (1.19), 12.252 (0.45).<br>SM: Compound 164.01 and 3,3,3-trifluoropropanoic acid |
| Example 164.03 | cyclopropyl{4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}methanone<br>LC-MS (Method 2): R$_t$ = 1.14 min; MS (ESIpos): m/z = 591.6 [M + H]⁺<br>¹H-NMR (400 MHz, DMSO-d6) δ [ppm]: 0.643 (1.15), 0.655 (3.58), 0.663 (8.23), 0.668 (5.13), 0.675 (3.98), 0.682 (9.99), 0.686 (8.20), 0.691 (9.19), 0.698 (8.09), 0.703 (9.38), 0.710 (4.38), 0.723 (1.02), 1.147 (1.44), 1.163 (1.26), 1.228 (0.77), 1.293 (15.84), 1.310 (15.81), 1.752 (0.48), 1.893 (0.48), 1.902 (1.02), 1.915 (1.95), 1.921 (2.11), 1.934 (3.58), 1.946 (2.00), 1.953 (1.84), 1.965 (0.83), 2.322 (2.46), 2.326 (2.80), 2.331 (2.14), 2.395 (2.54), 2.518 (6.38), 2.522 (4.43), 2.539 (5.64), 2.664 (1.15), 2.668 (1.60), 2.673 (1.10), 2.685 (0.43), 3.432 (1.71), 3.449 (5.45), 3.466 (7.11), 3.672 (3.69), 3.764 (0.85), 3.775 (1.10), 3.786 (1.50), 3.798 (1.42), 3.809 (1.52), 3.822 |

TABLE 19-continued

| Example | Structure<br>IUPAC-Name<br>LC-MS (method): Retention time; Mass found<br>¹H-NMR<br>Starting materials (SM): |
|---|---|
| | (1.12), 4.104 (4.01), 4.117 (4.19), 4.127 (5.21), 4.140 (4.35), 4.330 (6.04), 4.352 (10.74), 4.374 (4.70), 6.937 (1.60), 6.956 (4.43), 6.970 (4.27), 7.027 (1.15), 7.193 (7.00), 7.411 (1.02), 7.544 (0.72), 7.872 (3.50), 7.893 (3.13), 8.154 (1.07), 8.265 (8.17), 8.278 (7.75), 8.321 (1.44), 8.567 (15.39), 8.570 (16.00), 8.585 (0.45), 8.588 (0.45), 10.732 (1.36), 12.247 (0.88), 12.299 (1.15).<br>SM: Compound 164.01 and cyclopropanecarboxylic acid |
| Example 164.04 | {4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}[1-(trifluoromethyl)cyclopropyl]methanone<br>LC-MS (Method 2): R_t = 1.23 min; MS (ESIneg): m/z = 658 [M − H]⁻<br>¹H-NMR (400 MHz, DMSO-d6) δ [ppm]: 1.036 (1.06), 1.053 (2.67), 1.071 (1.34), 1.159 (7.90), 1.213 (1.26), 1.252 (4.52), 1.264 (9.63), 1.284 (3.66), 1.297 (15.33), 1.314 (15.49), 1.678 (0.90), 1.753 (0.94), 2.323 (2.04), 2.327 (3.07), 2.332 (2.83), 2.347 (2.71), 2.361 (3.26), 2.375 (3.73), 2.461 (4.60), 2.518 (10.85), 2.523 (7.55), 2.540 (2.36), 2.665 (1.69), 2.669 (2.44), 2.673 (1.65), 2.679 (0.75), 3.431 (1.57), 3.448 (4.48), 3.465 (4.32), 3.482 (1.45), 3.572 (5.31), 3.761 (0.90), 3.772 (1.10), 3.784 (1.53), 3.795 (1.45), 3.806 (1.53), 3.818 (1.14), 4.102 (4.17), 4.114 (4.25), 4.125 (5.39), 4.138 (4.52), 4.326 (6.09), 4.349 (10.89), 4.372 (4.72), 6.930 (4.60), 6.943 (4.64), 6.968 (6.92), 7.457 (2.24), 7.478 (2.36), 7.842 (4.01), 7.846 (4.05), 7.863 (3.50), 7.867 (3.54), 8.233 (7.31), 8.245 (8.29), 8.557 (16.00), 8.560 (14.90).<br>SM: Compound 164.01 and 1-(trifluoromethyl)cyclopropanecarboxylic acid |
| Example 164.05 | ((1RS)-2,2-difluorocyclopropyl){4-[(1R or 1S)-1-[2-[(6-{6-[3-(trifluoromethyl)azetidin-1-yl]pyrimidin-4-yl}-1H-benzimidazol-2-yl)amino]pyridin-4-yl}ethyl]piperazin-1-yl}methanone<br>LC-MS (Method 2): R_t = 1.17 min; MS (ESIneg): m/z = 626 [M − H]⁻<br>¹H-NMR (400 MHz, DMSO-d6) δ [ppm]: 0.986 (1.42), 1.002 (1.42), 1.055 |

TABLE 19-continued

| Example | Structure<br>IUPAC-Name<br>LC-MS (method): Retention time; Mass found<br>¹H-NMR<br>Starting materials (SM): |
|---|---|
| | (1.91), 1.071 (2.04), 1.144 (0.53), 1.228 (0.76), 1.302 (14.95), 1.318 (15.08), 1.700 (0.72), 1.752 (1.28), 1.759 (0.49), 1.778 (1.02), 1.789 (1.42), 1.807 (1.68), 1.820 (1.68), 1.838 (1.51), 1.858 (1.71), 1.872 (2.17), 1.891 (1.94), 1.904 (1.28), 1.923 (0.49), 2.322 (3.16), 2.326 (3.75), 2.331 (3.16), 2.336 (2.34), 2.349 (1.94), 2.365 (2.11), 2.446 (3.75), 2.518 (8.33), 2.522 (5.73), 2.539 (5.60), 2.567 (1.02), 2.664 (1.45), 2.668 (1.98), 2.673 (1.38), 2.685 (0.43), 3.075 (1.42), 3.095 (1.55), 3.103 (1.81), 3.110 (1.78), 3.124 (1.61), 3.129 (1.88), 3.138 (1.55), 3.157 (1.35), 3.429 (0.72), 3.467 (3.16), 3.476 (3.23), 3.484 (3.65), 3.494 (4.02), 3.511 (4.41), 3.561 (2.57), 3.624 (2.07), 3.659 (1.19), 3.762 (0.92), 3.773 (1.09), 3.784 (1.65), 3.795 (1.48), 3.807 (1.61), 3.819 (1.22), 4.103 (4.35), 4.116 (4.44), 4.126 (5.50), 4.139 (4.48), 4.328 (6.12), 4.350 (10.80), 4.373 (4.64), 6.944 (4.91), 6.959 (5.40), 6.973 (5.79), 7.385 (0.66), 7.464 (1.81), 7.480 (1.84), 7.855 (5.00), 7.860 (4.97), 7.876 (4.41), 7.880 (4.51), 8.248 (9.02), 8.261 (7.37), 8.548 (0.56), 8.561 (15.37), 8.565 (16.00).<br>SM: Compound 164.01 and (1RS)-2,2-difluorocyclopropanecarboxylic acid |
| Example 165.02 | 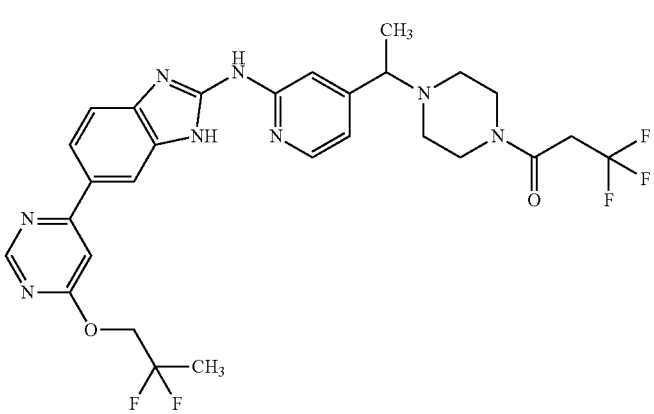 [SMILES: CC(c1ccnc(Nc2nc3ccc(-c4cc(OCC(C)(F)F)ncn4)cc3[nH]2)c1)N1CCN(C(=O)CC(F)(F)F)CC1]<br>1-(4-{(1R or 1S)-1-[2-({6-[6-(2,2-difluoropropoxy)pyrimidin-4-yl]-1H-benzimidazol-2-yl}amino)pyridin-4-yl]ethyl}piperazin-1-yl)-3,3,3-trifluoropropan-1-one<br>LC-MS (Method 2): R$_t$ = 1.25 min; MS (ESIneg): m/z = 603 [M − H]⁻<br>¹H-NMR (400 MHz, DMSO-d6) δ [ppm]: 1.035 (0.77), 1.053 (1.47), 1.070 (0.77), 1.143 (0.50), 1.229 (0.64), 1.293 (12.72), 1.310 (12.95), 1.721 (7.83), 1.769 (16.00), 1.817 (7.16), 2.323 (2.64), 2.327 (3.85), 2.331 (3.58), 2.337 (2.74), 2.345 (2.81), 2.367 (2.28), 2.419 (3.11), 2.430 (3.38), 2.442 (2.44), 2.457 (1.91), 2.518 (7.53), 2.523 (5.29), 2.537 (0.64), 2.665 (1.51), 2.669 (2.11), 2.673 (1.44), 3.425 (3.35), 3.438 (6.03), 3.450 (3.85), 3.473 (5.92), 3.482 (5.96), 3.580 (2.31), 3.608 (6.66), 3.635 (6.36), 3.662 (1.94), 4.017 (0.44), 4.355 (0.47), 4.679 (4.69), 4.712 (9.47), 4.745 (4.25), 6.965 (2.68), 7.174 (2.58), 7.404 (1.21), 7.425 (1.34), 7.482 (2.24), 7.568 (1.07), 7.599 (1.87), 7.944 (1.94), 8.228 (1.54), 8.278 (5.62), 8.291 (5.29), 8.397 (2.01), 8.828 (10.91), 8.831 (10.71), 10.764 (1.94), 12.276 (1.54), 12.299 (1.81).<br>SM: Compound 165.01 and 3,3,3-trifluoropropanoic acid |
| Example 165.03 | 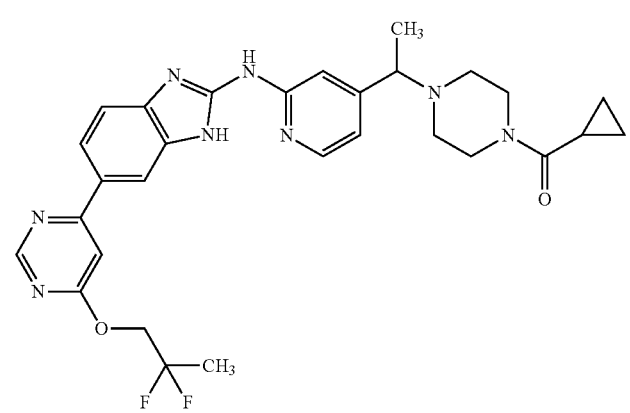 [SMILES: CC(c1ccnc(Nc2nc3ccc(-c4cc(OCC(C)(F)F)ncn4)cc3[nH]2)c1)N1CCN(C(=O)C2CC2)CC1] |

TABLE 19-continued

| Example | Structure<br>IUPAC-Name<br>LC-MS (method): Retention time; Mass found<br>$^1$H-NMR<br>Starting materials (SM): |
|---|---| cyclopropyl(4-{(1R or 1S)-1-[2-({6-[6-(2,2-difluoropropoxy)pyrimidin-4-yl]-1H-benzimidazol-2-yl}amino)pyridin-4-yl]ethyl}piperazin-1-yl)methanone
LC-MS (Method 2): $R_t$ = 1.22 min; MS (ESIneg): m/z = 561 [M − H]$^−$
$^1$H-NMR (400 MHz, DMSO-d6) δ [ppm]: 0.664 (7.23), 0.684 (8.95), 0.692 (9.59), 0.704 (8.98), 1.146 (0.51), 1.228 (0.67), 1.296 (13.28), 1.313 (13.70), 1.720 (7.92), 1.769 (16.00), 1.817 (7.35), 1.905 (0.79), 1.918 (1.66), 1.924 (2.06), 1.937 (3.12), 1.955 (1.75), 2.326 (3.24), 2.399 (2.81), 2.619 (0.42), 2.669 (1.78), 3.456 (5.57), 3.472 (7.02), 3.677 (3.99), 4.678 (4.84), 4.712 (9.71), 4.745 (4.51), 6.968 (3.45), 6.979 (3.66), 7.189 (5.53), 7.422 (1.09), 7.485 (1.60), 7.594 (1.51), 7.940 (3.05), 7.961 (2.78), 8.229 (1.09), 8.278 (6.29), 8.291 (6.02), 8.395 (1.39), 8.829 (11.74), 10.757 (2.15), 12.306 (1.63).
SM: Compound 165.01 and cyclopropanecarboxylic acid Example 166.02

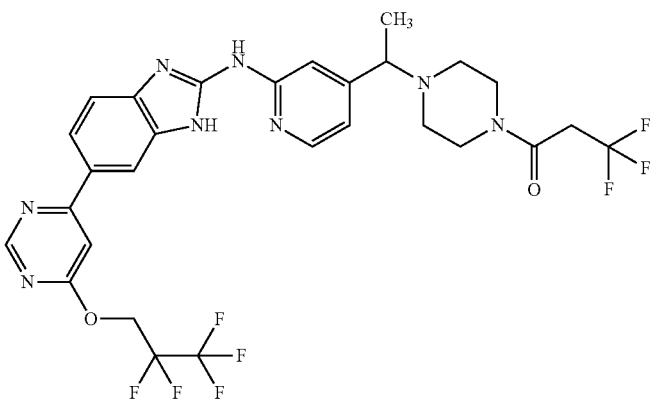 [SMILES: CC(c1ccnc(Nc2nc3ccc(-c4cc(OCC(F)(F)C(F)(F)F)ncn4)cc3[nH]2)c1)N1CCN(C(=O)CC(F)(F)F)CC1]

3,3,3-trifluoro-1-(4-{(1R or 1S)-1-[2-({6-[6-(2,2,3,3,3-pentafluoropropoxy)pyrimidin-4-yl]-1H-benzimidazol-2-yl}amino)pyridin-4-yl]ethyl}piperazin-1-yl)propan-1-one
LC-MS (Method 2): $R_t$ = 1.37 min; MS (ESIneg): m/z = 657 [M − H]$^−$
$^1$H-NMR (400 MHz, DMSO-d6) δ [ppm]: 1.035 (0.70), 1.052 (1.20), 1.070 (0.72), 1.144 (0.43), 1.228 (0.83), 1.293 (15.81), 1.310 (16.00), 2.318 (1.98), 2.323 (2.65), 2.327 (3.96), 2.331 (3.72), 2.344 (3.34), 2.353 (3.08), 2.366 (2.78), 2.418 (3.72), 2.429 (4.04), 2.443 (2.97), 2.458 (2.46), 2.518 (6.07), 2.523 (4.28), 2.539 (0.43), 2.665 (1.20), 2.669 (1.66), 2.673 (1.12), 3.425 (3.99), 3.437 (7.12), 3.450 (4.55), 3.472 (7.38), 3.481 (7.20), 3.488 (7.01), 3.579 (2.81), 3.607 (8.16), 3.634 (7.63), 3.662 (2.38), 4.017 (1.15), 5.212 (4.33), 5.246 (8.56), 5.280 (4.12), 6.963 (3.10), 6.971 (3.05), 7.179 (5.14), 7.408 (1.12), 7.429 (1.20), 7.539 (2.14), 7.573 (1.02), 7.592 (0.94), 7.664 (1.42), 7.964 (2.62), 7.985 (2.30), 8.253 (1.42), 8.278 (8.03), 8.291 (7.36), 8.415 (1.87), 8.875 (14.88), 8.877 (14.82), 10.761 (1.10).
SM: Compound 166.01 and 3,3,3-trifluoropropanoic acid Example 166.03

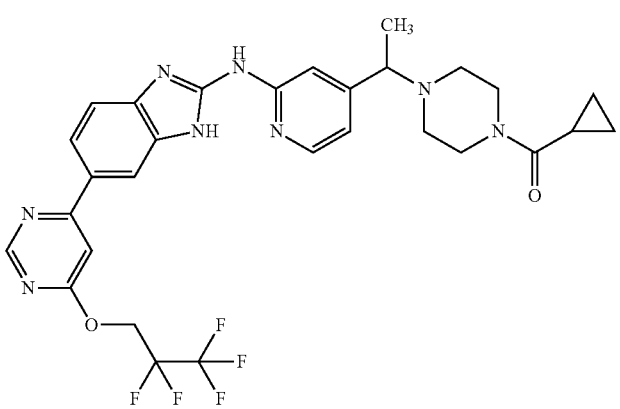 [SMILES: CC(c1ccnc(Nc2nc3ccc(-c4cc(OCC(F)(F)C(F)(F)F)ncn4)cc3[nH]2)c1)N1CCN(C(=O)C2CC2)CC1]

cyclopropyl(4-{(1R or 1S)-1-[2-({6-[6-(2,2,3,3,3-pentafluoropropoxy)pyrimidin-4-yl]-1H-benzimidazol-2-yl}amino)pyridin-4-yl]ethyl}piperazin-1-yl)methanone
LC-MS (Method 2): $R_t$ = 1.35 min; MS (ESIneg): m/z = 615 [M − H]$^−$ TABLE 19-continued

| Example | Structure<br>IUPAC-Name<br>LC-MS (method): Retention time; Mass found<br>¹H-NMR<br>Starting materials (SM): |
|---|---|
| | ¹H-NMR (400 MHz, DMSO-d6) δ [ppm]: 0.644 (1.13), 0.656 (3.58), 0.663 (8.25), 0.668 (5.01), 0.676 (4.03), 0.683 (9.99), 0.687 (8.36), 0.692 (9.15), 0.699 (8.14), 0.704 (9.46), 0.711 (4.40), 0.723 (1.00), 0.862 (0.63), 1.035 (1.08), 1.052 (1.98), 1.070 (1.11), 1.145 (0.45), 1.227 (0.79), 1.296 (15.97), 1.313 (16.00), 1.904 (1.05), 1.916 (2.00), 1.923 (2.16), 1.935 (3.58), 1.947 (2.00), 1.954 (1.85), 1.966 (0.84), 2.323 (2.56), 2.327 (2.87), 2.331 (2.21), 2.397 (2.58), 2.518 (6.41), 2.523 (4.59), 2.619 (0.98), 2.665 (1.19), 2.669 (1.63), 2.673 (1.13), 3.438 (2.00), 3.454 (6.25), 3.471 (7.57), 3.674 (3.77), 5.210 (4.53), 5.245 (8.94), 5.280 (4.38), 6.964 (4.80), 6.978 (4.85), 7.224 (4.85), 7.487 (1.05), 7.591 (1.79), 7.956 (4.82), 7.960 (4.88), 7.977 (4.43), 7.981 (4.48), 8.273 (8.62), 8.287 (8.22), 8.340 (1.13), 8.873 (15.29), 8.875 (15.08), 8.899 (0.63), 10.775 (0.61), 12.337 (0.45).<br>SM: Compound 166.01 and cyclopropanecarboxylic acid |
| Example 166.04 | 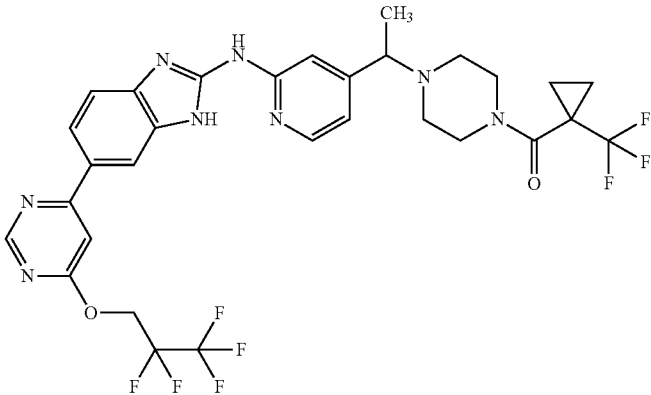 [SMILES: CC(c1ccnc(Nc2nc3ccc(-c4cc(OCC(F)(F)C(F)(F)F)ncn4)cc3[nH]2)c1)N1CCN(C(=O)C2(C(F)(F)F)CC2)CC1]<br>(4-{(1R or 1S)-1-[2-({6-[6-(2,2,3,3,3-pentafluoropropoxy)pyrimidin-4-yl]-1H-benzimidazol-2-yl}amino)pyridin-4-yl]ethyl}piperazin-1-yl)[1-(trifluoromethyl)cyclopropyl]methanone<br>LC-MS (Method 2): R$_t$ = 1.42 min; MS (ESIneg): m/z = 683 [M − H]⁻<br>¹H-NMR (400 MHz, DMSO-d6) δ [ppm]: 1.145 (1.85), 1.161 (6.49), 1.215 (0.99), 1.254 (3.75), 1.266 (8.13), 1.289 (14.31), 1.305 (13.68), 2.323 (1.67), 2.327 (2.55), 2.332 (2.32), 2.342 (2.24), 2.357 (2.66), 2.370 (3.15), 2.453 (3.31), 2.466 (3.13), 2.518 (6.49), 2.523 (4.51), 2.665 (1.15), 2.669 (1.62), 2.673 (1.09), 2.678 (0.50), 3.439 (1.04), 3.455 (3.44), 3.472 (3.47), 3.488 (1.15), 3.568 (4.38), 5.212 (3.57), 5.247 (7.06), 5.280 (3.41), 6.963 (3.52), 6.975 (3.57), 7.193 (5.47), 7.435 (0.55), 7.554 (0.91), 7.960 (3.28), 7.964 (3.28), 7.981 (2.92), 7.984 (2.97), 8.276 (7.48), 8.289 (7.01), 8.402 (0.50), 8.874 (16.00), 8.876 (15.79), 10.765 (1.15), 12.305 (1.17).<br>SM: Compound 166.01 and 1-(trifluoromethyl)cyclopropanecarboxylic acid |
| Example 166.05 | 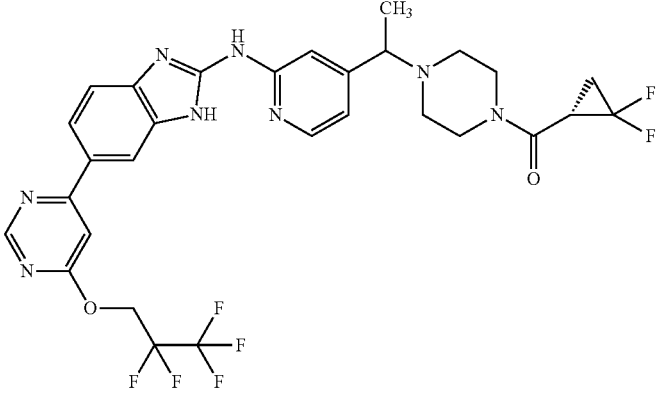 [SMILES: CC(c1ccnc(Nc2nc3ccc(-c4cc(OCC(F)(F)C(F)(F)F)ncn4)cc3[nH]2)c1)N1CCN(C(=O)[C@@H]2CC2(F)F)CC1]<br>((1RS)-2,2-difluorocyclopropyl)(4-{(1R or 1S)-1-[2-({6-[6-(2,2,3,3,3-pentafluoropropoxy)pyrimidin-4-yl]-1H-benzimidazol-2-yl}amino)pyridin-4-yl]ethyl}piperazin-1-yl)methanone<br>LC-MS (Method 2): R$_t$ = 1.37 min; MS (ESIpos): m/z = 653 [M + H]⁺<br>¹H-NMR (400 MHz, DMSO-d6) δ [ppm]: 1.297 (13.82), 1.314 (14.14), 1.782 (0.87), 1.792 (1.26), 1.810 (1.51), 1.822 (1.49), 1.841 (1.44), 1.854 (1.39), |

TABLE 19-continued

Structure
IUPAC-Name
LC-MS (method): Retention time; Mass found
¹H-NMR

| Example | Starting materials (SM): |
|---|---|

1.859 (1.56), 1.873 (1.86), 1.893 (1.71), 1.906 (1.14), 1.924 (0.40), 2.309
(1.29), 2.323 (2.50), 2.327 (2.95), 2.332 (2.50), 2.336 (2.18), 2.348 (1.66),
2.363 (2.38), 2.373 (1.93), 2.444 (2.95), 2.458 (2.23), 2.518 (7.18), 2.523
(4.98), 2.540 (0.77), 2.544 (0.74), 2.551 (0.84), 2.569 (0.87), 2.588 (0.59),
2.660 (0.47), 2.665 (1.07), 2.669 (1.51), 2.673 (1.07), 2.679 (0.50), 3.077
(1.21), 3.096 (1.36), 3.105 (1.54), 3.110 (1.61), 3.124 (1.39), 3.131 (1.63),
3.138 (1.39), 3.159 (1.16), 3.474 (2.75), 3.482 (3.15), 3.492 (3.72), 3.499
(3.86), 3.509 (3.34), 3.516 (3.37), 3.547 (1.93), 3.563 (2.28), 3.621 (1.73),
3.637 (1.54), 3.656 (0.92), 5.212 (3.94), 5.247 (7.75), 5.281 (3.74), 6.968
(3.64), 6.981 (3.72), 7.193 (5.52), 7.430 (0.57), 7.556 (0.99), 7.647 (0.72),
7.960 (3.39), 7.964 (3.44), 7.981 (3.02), 7.985 (3.12), 8.279 (7.73), 8.292
(7.23), 8.405 (0.59), 8.874 (15.98), 8.877 (16.00), 10.766 (1.21), 12.306
(0.94).
SM: Compound 166.01 and (1RS)-2,2-difluorocyclopropanecarboxylic acid Example 167.02

1-{4-[(2-{[6-(6-ethoxy-5-methoxypyrimidin-4-yl)-1H-benzimidazol-2-
yl]amino}pyridin-4-yl)methyl]piperazin-1-yl}-3,3,3-trifluoropropan-1-one
LC-MS (Method 2): $R_t$ = 1.16 min; MS (ESIpos): m/z = 571 [M + H]⁺
¹H-NMR (400 MHz, DMSO-d6) δ [ppm]: 1.391 (7.25), 1.408 (16.00), 1.426
(7.44), 2.372 (1.83), 2.384 (2.84), 2.397 (2.14), 2.413 (1.92), 2.426 (2.71),
2.437 (2.10), 2.518 (4.30), 2.523 (3.07), 3.461 (1.93), 3.473 (2.65), 3.485
(2.31), 3.497 (2.28), 3.510 (2.86), 3.526 (8.53), 3.610 (1.29), 3.637 (3.66),
3.665 (3.45), 3.692 (1.15), 3.759 (4.33), 4.047 (1.06), 4.462 (1.89), 4.480
(6.24), 4.498 (6.15), 4.515 (1.79), 6.935 (2.04), 6.948 (2.08), 7.192 (2.95),
7.415 (0.49), 7.875 (0.51), 8.272 (3.14), 8.285 (3.07), 8.311 (0.70), 8.521
(7.59).
SM: Compound 167.01 and 3,3,3-trifluoropropanoic acid Example 167.03 cyclopropyl{4-[(2-{[6-(6-ethoxy-5-methoxypyrimidin-4-yl)-1H-
benzimidazol-2-yl]amino}pyridin-4-yl)methyl]piperazin-1-yl}methanone
LC-MS (Method 2): $R_t$ = 1.12 min; MS (ESIpos): m/z = 529 [M + H]⁺
¹H-NMR (400 MHz, DMSO-d6) δ [ppm]: 0.662 (0.54), 0.673 (1.62), 0.681
(3.68), 0.686 (2.36), 0.693 (1.82), 0.700 (4.40), 0.706 (3.10), 0.712 (3.82),
0.719 (3.78), 0.724 (4.53), 0.731 (2.14), 0.743 (0.53), 1.389 (7.25), 1.406
(16.00), 1.424 (7.60), 1.927 (0.44), 1.939 (0.93), 1.946 (1.00), 1.959 (1.65),
1.970 (0.95), 1.978 (0.87), 2.327 (0.45), 2.331 (0.47), 2.363 (1.84), 2.442
(1.85), 2.518 (1.29), 2.523 (0.87), 3.519 (8.78), 3.703 (1.79), 3.757 (4.93),

TABLE 19-continued

| | Structure<br>IUPAC-Name<br>LC-MS (method): Retention time; Mass found<br>¹H-NMR |
|---|---|
| Example | Starting materials (SM): |

4.460 (1.92), 4.478 (6.23), 4.495 (6.15), 4.513 (1.88), 6.941 (2.21), 6.954 (2.25), 7.196 (2.83), 7.417 (0.44), 7.877 (0.47), 8.273 (3.45), 8.286 (3.35), 8.315 (0.61), 8.520 (8.23), 10.737 (0.74), 12.279 (0.74).

SM: Compound 167.01 and cyclopropanecarboxylic acid

Example 167.04

{4-[(2-{[6-(6-ethoxy-5-methoxypyrimidin-4-yl)-1H-benzimidazol-2-yl]amino}pyridin-4-yl)methyl]piperazin-1-yl}[1-(trifluoromethyl)cyclopropyl]methanone LC-MS (Method 2): $R_t$ = 1.22 min; MS (ESIpos): m/z = 597 [M + H]⁺

¹H-NMR (400 MHz, DMSO-d6) δ [ppm]: 1.182 (3.38), 1.236 (0.57), 1.275 (1.95), 1.287 (4.02), 1.307 (1.28), 1.390 (7.23), 1.408 (16.00), 1.425 (7.39), 2.423 (4.14), 2.518 (1.91), 2.523 (1.35), 3.525 (7.41), 3.596 (2.25), 3.760 (4.10), 4.462 (1.86), 4.479 (6.12), 4.497 (6.05), 4.515 (1.76), 6.936 (2.04), 6.949 (2.09), 7.190 (2.83), 7.416 (0.46), 7.875 (0.48), 8.273 (3.17), 8.285 (3.06), 8.315 (0.65), 8.520 (7.67), 10.733 (0.65), 12.238 (0.45), 12.273 (0.84).

SM: Compound 167.01 and 1-(trifluoromethyl)cyclopropanecarboxylic acid

Example 168.02

3,3,3-trifluoro-1-{4-[(2-{[6-(furo[3,2-d]pyrimidin-4-yl)-1H-benzimidazol-2-yl]amino}pyridin-4-yl)methyl]piperazin-1-yl}propan-1-one LC-MS (Method 2): $R_t$ = 1.02 min; MS (ESIpos): m/z = 537 [M + H]⁺

¹H-NMR (400 MHz, DMSO-d6) δ [ppm]: 2.377 (3.49), 2.389 (5.27), 2.401 (3.92), 2.418 (3.55), 2.430 (5.03), 2.441 (3.94), 2.518 (4.23), 2.523 (3.04), 2.539 (3.03), 3.375 (0.58), 3.388 (0.56), 3.464 (3.55), 3.476 (4.83), 3.488 (4.18), 3.501 (4.12), 3.514 (4.90), 3.535 (14.77), 3.613 (2.45), 3.640 (6.92), 3.668 (6.44), 3.695 (2.02), 4.050 (2.30), 6.961 (2.86), 6.973 (2.73), 7.199 (3.68), 7.285 (14.92), 7.291 (14.27), 7.523 (1.17), 7.544 (1.30), 7.691 (0.50), 8.291 (3.99), 8.304 (4.32), 8.328 (1.13), 8.504 (0.74), 8.629 (16.00), 8.635 (15.41), 8.740 (1.89), 9.047 (4.60), 10.862 (0.82).

SM: Compound 168.01 and 3,3,3-trifluoropropanoic acid

TABLE 19-continued

Example

Structure
IUPAC-Name
LC-MS (method): Retention time; Mass found
¹H-NMR
Starting materials (SM):

Example 168.03 cyclopropyl{4-[(2-{[6-(furo[3,2-d]pyrimidin-4-yl)-1H-benzimidazol-2-yl]amino}pyridin-4-yl)methyl]piperazin-1-yl}methanone
LC-MS (Method 2): R$_t$ = 0.97 min; MS (ESIpos): m/z = 495 [M + H]⁺
¹H-NMR (400 MHz, DMSO-d6) δ [ppm]: 0.655 (0.88), 0.667 (2.24), 0.674 (4.47), 0.680 (3.15), 0.687 (2.42), 0.694 (5.21), 0.699 (2.70), 0.705 (3.00), 0.710 (4.37), 0.717 (4.75), 0.722 (5.29), 0.729 (2.79), 0.741 (0.73), 1.916 (0.58), 1.928 (1.20), 1.936 (1.26), 1.948 (2.05), 1.960 (1.18), 1.967 (1.06), 1.979 (0.48), 2.327 (0.53), 2.360 (2.26), 2.436 (2.25), 2.518 (0.77), 2.523 (0.51), 2.539 (3.10), 3.496 (2.62), 3.520 (10.35), 3.694 (2.12), 6.953 (2.82), 6.956 (2.81), 6.966 (2.88), 6.969 (2.89), 7.228 (3.83), 7.278 (10.05), 7.284 (10.17), 7.587 (0.79), 7.603 (0.82), 8.286 (6.33), 8.299 (5.19), 8.621 (10.93), 8.627 (10.75), 8.636 (0.58), 8.659 (0.65), 9.047 (16.00).
SM: Compound 168.01 and cyclopropanecarboxylic acid Example 169.02

1-{4-[(1R or 1S)-1-{2-[(6-{1-[(3,3-difluorocyclobutyl)methyl]-1H-pyrazol-4-yl}-1H-benzimidazol-2-yl)amino]pyridin-4-yl}ethyl]piperazin-1-yl}-3,3,3-trifluoropropan-1-one
LC-MS (Method 2): R$_t$ = 1.17 min; MS (ESIpos): m/z = 603 [M + H]⁺
¹H-NMR (400 MHz, DMSO-d6) δ [ppm]: 1.071 (2.69), 1.088 (5.46), 1.106 (2.77), 1.138 (1.18), 1.230 (1.55), 1.289 (16.00), 1.306 (15.96), 2.084 (2.31), 2.327 (6.03), 2.649 (7.32), 2.668 (7.62), 3.372 (3.79), 3.389 (3.56), 3.436 (10.05), 3.477 (11.15), 3.578 (3.11), 3.606 (8.61), 3.633 (8.27), 3.661 (2.81), 4.245 (9.10), 4.259 (8.34), 5.759 (4.32), 6.926 (5.65), 6.939 (5.80), 7.169 (8.87), 7.235 (3.15), 7.255 (4.17), 7.369 (1.71), 7.577 (2.65), 7.825 (5.69), 8.123 (5.38), 8.250 (7.66), 8.263 (7.28), 10.586 (2.81), 12.055 (1.78).
SM: Compound 169.01 and 3,3,3-trifluoropropanoic acid TABLE 19-continued Example | Structure / IUPAC-Name / LC-MS (method): Retention time; Mass found / ¹H-NMR / Starting materials (SM):

Example 169.03 cyclopropyl{4-[(1R or 1S)-1-{2-[(6-{1-[(3,3-difluorocyclobutyl)methyl]-1H-pyrazol-4-yl}-1H-benzimidazol-2-yl)amino]pyridin-4-yl}ethyl]piperazin-1-yl}methanone
LC-MS (Method 2): R$_t$ = 1.13 min; MS (ESIpos): m/z = 561 [M + H]⁺
¹H-NMR (400 MHz, DMSO-d6) δ [ppm]: 0.642 (1.24), 0.654 (3.78), 0.661 (8.16), 0.666 (5.05), 0.674 (4.23), 0.680 (9.76), 0.685 (8.34), 0.690 (8.90), 0.697 (8.19), 0.702 (9.31), 0.709 (4.32), 0.721 (1.02), 1.227 (0.55), 1.288 (16.00), 1.304 (15.91), 1.898 (1.00), 1.911 (2.00), 1.918 (2.15), 1.930 (3.56), 1.942 (2.00), 1.949 (1.81), 1.961 (0.81), 2.307 (1.72), 2.318 (1.75), 2.322 (1.91), 2.326 (1.99), 2.331 (1.61), 2.390 (2.87), 2.425 (3.38), 2.444 (4.15), 2.458 (4.60), 2.465 (4.84), 2.518 (4.26), 2.522 (3.06), 2.539 (1.12), 2.608 (1.57), 2.628 (3.05), 2.636 (3.29), 2.647 (5.48), 2.664 (4.41), 2.668 (4.36), 2.673 (3.81), 2.702 (1.55), 2.723 (0.49), 3.417 (1.58), 3.433 (4.90), 3.450 (6.32), 3.466 (4.77), 3.666 (3.90), 4.243 (6.69), 4.257 (5.98), 6.926 (5.33), 6.929 (5.24), 6.939 (5.35), 6.942 (5.26), 7.174 (8.31), 7.248 (1.91), 7.311 (0.64), 7.419 (0.75), 7.544 (0.93), 7.618 (0.76), 7.833 (1.52), 8.127 (1.42), 8.247 (8.72), 8.260 (8.10), 10.573 (2.54), 12.034 (2.44).
SM: Compound 169.01 and cyclopropanecarboxylic acid Example 170.02

1-{4-[(1R or 1S)-1-(2-{[6-(1-{[(1RS)-2,2-dichlorocyclopropyl]methyl}-1H-pyrazol-4-yl)-1H-benzimidazol-2-yl]amino}pyridin-4-yl)ethyl]piperazin-1-yl}-3,3,3-trifluoropropan-1-one
LC-MS (Method 2): R$_t$ = 1.23 min; MS (ESIpos): m/z = 621 [M + H]⁺
¹H-NMR (400 MHz, DMSO-d6) δ [ppm]: 1.071 (2.54), 1.088 (5.35), 1.105 (2.36), 1.154 (5.03), 1.172 (10.36), 1.190 (4.99), 1.232 (0.65), 1.289 (7.05), 1.305 (7.18), 1.619 (2.05), 1.639 (4.11), 1.658 (2.54), 1.846 (2.22), 1.865 (2.34), 1.874 (2.81), 1.892 (2.25), 1.907 (1.61), 1.988 (16.00), 2.282 (0.67), 2.300 (1.76), 2.309 (1.16), 2.319 (2.26), 2.327 (3.38), 2.337 (2.15), 2.346 (2.41), 2.364 (1.70), 2.416 (1.58), 2.425 (1.70), 2.453 (1.19), 2.463 (0.78), 2.467 (0.74), 2.518 (3.18), 2.523 (2.32), 2.665 (0.64), 2.669 (0.88), 2.673 (0.64), 2.888 (0.42), 3.354 (0.90), 3.371 (2.55), 3.389 (2.61), 3.406 (0.99), 3.423 (1.80), 3.436 (3.45), 3.446 (2.18), 3.455 (2.58), 3.473 (3.51), 3.565 (0.78), 3.578 (1.32), 3.606 (3.80), 3.634 (3.55), 3.661 (1.13), 4.000 (1.22), 4.017 (3.76), 4.035 (3.74), 4.053 (1.23), 4.326 (2.89), 4.345 (2.31), 5.759 (0.52), 6.922 (2.23), 6.925 (2.25), 6.936 (2.25), 6.938 (2.29), 7.168 (3.54), 7.256 (0.73), 7.887 (0.61), 8.159 (0.54), 8.249 (3.84), 8.262 (3.68), 10.580 (0.71), 12.046 (0.78).
SM: Compound 170.01 and 3,3,3-trifluoropropanoic acid

TABLE 19-continued

| | Structure<br>IUPAC-Name<br>LC-MS (method): Retention time; Mass found<br>¹H-NMR |
|---|---|
| Example | Starting materials (SM): |

Example
171.02

1-(4-{(1R or 1S)-1-[2-({6-[1-(cyclobutylmethyl)-1H-pyrazol-4-yl]-7-fluoro-
1H-benzimidazol-2-yl}amino)pyridin-4-yl]ethyl}piperazin-1-yl)-3,3,3-
trifluoropropan-1-one LC-MS (Method 2): R$_t$ = 1.28 min; MS (ESIpos): m/z = 585 [M + H]⁺

¹H-NMR (400 MHz, DMSO-d6) δ [ppm]: 1.282 (15.89), 1.298 (16.00), 1.744
(0.44), 1.750 (0.54), 1.768 (2.52), 1.774 (1.39), 1.789 (3.94), 1.795 (2.47),
1.807 (5.88), 1.819 (7.01), 1.823 (5.97), 1.829 (8.55), 1.847 (2.97), 1.855
(3.45), 1.869 (1.68), 1.877 (2.39), 1.893 (0.93), 1.961 (2.16), 1.975 (3.23),
1.983 (4.45), 1.992 (4.04), 2.003 (4.30), 2.021 (1.88), 2.033 (0.47), 2.294
(0.88), 2.306 (1.68), 2.321 (3.05), 2.332 (3.84), 2.345 (3.32), 2.358 (2.82),
2.411 (3.87), 2.421 (4.25), 2.434 (3.08), 2.449 (2.40), 2.518 (1.79), 2.523
(1.24), 2.539 (0.87), 2.669 (0.44), 2.744 (0.97), 2.763 (2.31), 2.781 (3.05),
2.800 (2.57), 2.819 (1.15), 3.421 (4.30), 3.433 (7.79), 3.457 (5.93), 3.474
(9.37), 3.489 (4.98), 3.577 (2.96), 3.604 (8.55), 3.632 (8.02), 3.659 (2.50),
4.158 (13.39), 4.177 (13.20), 6.940 (5.18), 6.942 (5.23), 6.953 (5.23), 6.955
(5.27), 7.111 (4.90), 7.242 (1.40), 7.262 (3.00), 7.278 (2.80), 7.303 (5.13),
7.323 (2.27), 7.827 (10.80), 8.059 (8.48), 8.062 (8.19), 8.262 (6.76), 8.275
(6.36), 10.799 (1.32), 12.196 (0.41).

SM: Compound 171.01 and 3,3,3-trifluoropropanoic acid

Example
171.03

(4-{(1R or 1S)-1-[2-({6-[1-(cyclobutylmethyl)-1H-pyrazol-4-yl]-7-fluoro-1H-
benzimidazol-2-yl}amino)pyridin-4-yl]ethyl}piperazin-1-
yl)(cyclopropyl)methanone LC-MS (Method 2): R$_t$ = 1.25 min; MS (ESIpos): m/z = 543.3 [M + H]⁺

¹H-NMR (400 MHz, DMSO-d6) δ [ppm]: 0.639 (1.18), 0.651 (3.68), 0.659
(7.90), 0.671 (4.13), 0.678 (9.28), 0.684 (6.84), 0.690 (8.36), 0.697 (8.40),
0.702 (9.69), 0.709 (4.77), 0.721 (1.19), 1.282 (15.81), 1.299 (16.00), 1.743
(0.44), 1.749 (0.53), 1.767 (2.57), 1.788 (3.99), 1.795 (2.54), 1.807 (6.01),
1.819 (7.16), 1.823 (6.10), 1.828 (8.54), 1.847 (3.06), 1.854 (3.54), 1.869
(1.71), 1.876 (2.43), 1.892 (1.87), 1.904 (2.22), 1.911 (2.35), 1.923 (3.73),
1.935 (2.31), 1.942 (2.10), 1.955 (2.15), 1.960 (2.33), 1.974 (3.31), 1.982
(4.50), 1.992 (4.15), 2.003 (4.36), 2.021 (1.91), 2.033 (0.48), 2.302 (1.75),
2.322 (1.47), 2.327 (1.52), 2.331 (1.42), 2.384 (2.72), 2.437 (2.17), 2.518
(1.96), 2.523 (1.35), 2.539 (0.96), 2.609 (0.93), 2.669 (0.46), 2.744 (0.97),
2.762 (2.34), 2.780 (3.10), 2.799 (2.58), 2.818 (1.16), 3.421 (1.54), 3.437
(4.69), 3.454 (6.68), 3.468 (4.77), 3.661 (4.11), 4.158 (13.02), 4.176 (12.81),
6.947 (5.17), 6.959 (5.25), 7.112 (6.43), 7.241 (1.73), 7.260 (3.53), 7.277
(3.37), 7.303 (6.95), 7.324 (3.19), 7.826 (10.39), 8.059 (8.30), 8.262 (6.34),
8.275 (6.09), 10.800 (5.01), 12.278 (4.74).

SM: Compound 171.01 and cyclopropanecarboxylic acid

TABLE 19-continued

| | Structure<br>IUPAC-Name<br>LC-MS (method): Retention time; Mass found<br>$^1$H-NMR |
|---|---|
| Example | Starting materials (SM): |

Example 172.02

3,3,3-trifluoro-1-{4-[(1R or 1S)-1-(2-{[7-fluoro-6-(6-methylpyrimidin-4-yl)-1H-benzimidazol-2-yl]amino}pyridin-4-yl)ethyl]piperazin-1-yl}propan-1-one LC-MS (Method 2): $R_t$ = 1.08 min; MS (ESIpos): m/z = 543 [M + H]$^+$ $^1$H-NMR (400 MHz, DMSO-d6) δ [ppm]: 1.069 (3.62), 1.087 (7.43), 1.105 (3.67), 1.291 (5.27), 1.308 (5.29), 2.328 (1.44), 2.343 (1.39), 2.366 (1.12), 2.418 (1.49), 2.430 (1.77), 2.445 (1.37), 2.459 (1.14), 2.523 (2.62), 2.532 (16.00), 2.669 (0.45), 3.352 (1.36), 3.370 (3.73), 3.387 (3.68), 3.404 (1.34), 3.439 (2.85), 3.450 (1.85), 3.480 (3.19), 3.492 (2.72), 3.580 (1.00), 3.608 (2.85), 3.635 (2.70), 3.663 (0.88), 6.972 (1.61), 6.985 (1.66), 7.134 (2.53), 7.446 (1.88), 7.467 (2.09), 7.710 (0.96), 7.728 (1.31), 7.747 (0.85), 7.817 (2.58), 8.285 (2.01), 8.298 (1.96), 9.094 (3.76), 9.096 (3.73), 10.917 (2.79), 12.500 (1.71).

SM: Compound 172.01 and 3,3,3-trifluoropropanoic acid

Example 172.03 cyclopropyl{4-[(1R or 1S)-1-(2-{[7-fluoro-6-(6-methylpyrimidin-4-yl)-1H-benzimidazol-2-yl]amino}pyridin-4-yl)ethyl]piperazin-1-yl}methanone LC-MS (Method 2): $R_t$ = 1.05 min; MS (ESIpos): m/z = 501 [M + H]$^+$ $^1$H-NMR (400 MHz, DMSO-d6) δ [ppm]: 0.654 (1.11), 0.662 (2.46), 0.667 (1.55), 0.674 (1.25), 0.681 (2.92), 0.686 (2.44), 0.691 (2.63), 0.698 (2.45), 0.703 (2.84), 0.710 (1.32), 1.290 (4.81), 1.307 (4.86), 1.912 (0.61), 1.919 (0.66), 1.931 (1.06), 1.943 (0.59), 1.950 (0.54), 2.317 (0.51), 2.322 (0.54), 2.326 (0.54), 2.331 (0.45), 2.392 (0.80), 2.518 (0.96), 2.530 (16.00), 3.438 (0.59), 3.455 (1.87), 3.471 (2.20), 3.671 (1.17), 6.977 (1.47), 6.989 (1.47), 7.141 (1.11), 7.443 (0.76), 7.464 (0.82), 7.713 (0.46), 7.731 (0.71), 7.750 (0.43), 7.813 (2.20), 8.285 (2.07), 8.299 (1.95), 9.092 (3.64), 9.095 (3.71), 10.916 (1.11), 12.506 (0.71).

SM: Compound 172.01 and cyclopropanecarboxylic acid

TABLE 19-continued

Example | Structure / IUPAC-Name / LC-MS (method): Retention time; Mass found / ¹H-NMR / Starting materials (SM):

Example 172.04

{4-[(1R or 1S)-1-(2-{[7-fluoro-6-(6-methylpyrimidin-4-yl)-1H-benzimidazol-2-yl]amino}pyridin-4-yl)ethyl]piperazin-1-yl}[1-(trifluoromethyl)cyclopropyl]methanone LC-MS (Method 2): $R_t$ = 1.13 min; MS (ESIpos): m/z = 569 [M + H]⁺

¹H-NMR (400 MHz, DMSO-d6) δ[ppm]: 1.163 (9.51), 1.288 (16.00), 1.303 (13.93), 2.371 (6.84), 2.668 (2.55), 3.477 (4.12), 3.575 (8.74), 6.989 (4.50), 7.150 (5.99), 7.447 (3.61), 7.467 (4.00), 7.730 (3.61), 7.817 (6.49), 8.297 (4.53), 9.097 (7.11), 10.912 (5.96), 12.496 (4.89).

SM: Compound 172.01 and 1-(trifluoromethyl)cyclopropanecarboxylic acid

Example 173.02

3,3,3-trifluoro-1-(4-{(1R or 1S)-1-[2-({7-fluoro-6-[6-(trifluoromethyl)pyrimidin-4-yl]-1H-benzimidazol-2-yl}amino)pyridin-4-yl]ethyl}piperazin-1-yl)propan-1-one LC-MS (Method 2): $R_t$ = 1.28 min; MS (ESIpos): m/z = 597 [M + H]⁺

¹H-NMR (400 MHz, DMSO-d6) δ [ppm]: 0.811 (2.55), 0.828 (4.99), 0.833 (4.35), 0.855 (7.22), 0.934 (2.92), 0.950 (3.07), 1.031 (0.64), 1.049 (0.66), 1.069 (1.08), 1.086 (1.58), 1.104 (1.01), 1.133 (0.64), 1.240 (5.75), 1.293 (11.25), 1.309 (11.04), 1.393 (7.81), 1.483 (0.76), 1.515 (0.42), 1.580 (0.71), 1.705 (0.59), 2.331 (3.79), 2.344 (3.79), 2.432 (4.86), 2.446 (4.52), 2.618 (0.64), 2.669 (1.15), 3.330 (16.00), 3.370 (0.96), 3.387 (0.96), 3.483 (8.78), 3.580 (2.11), 3.608 (5.68), 3.635 (5.51), 3.662 (1.94), 5.758 (4.06), 6.985 (3.39), 6.997 (3.59), 7.147 (4.91), 7.506 (3.15), 7.527 (3.49), 7.834 (1.72), 7.852 (2.71), 7.870 (1.72), 8.293 (4.21), 8.307 (5.13), 8.317 (6.91), 9.490 (6.86), 10.986 (5.40), 12.599 (3.73).

SM: Compound 173.01 and 3,3,3-trifluoropropanoic acid

TABLE 19-continued

Structure
IUPAC-Name
LC-MS (method): Retention time; Mass found
¹H-NMR

Example | Starting materials (SM):

Example 173.03 cyclopropyl(4-{(1R or 1S)-1-[2-({7-fluoro-6-[6-(trifluoromethyl)pyrimidin-4-yl]-1H-benzimidazol-2-yl}amino)pyridin-4-yl]ethyl}piperazin-1-yl)methanone LC-MS (Method 2): $R_t$ = 1.23 min; MS (ESIpos): m/z = 555 [M + H]⁺

¹H-NMR (400 MHz, DMSO-d6) δ [ppm]: 0.666 (9.63), 0.692 (13.39), 0.704 (12.33), 0.826 (0.50), 0.859 (0.60), 1.144 (0.60), 1.225 (1.24), 1.296 (15.72), 1.312 (16.00), 1.925 (2.75), 1.937 (3.85), 2.323 (3.99), 2.327 (4.54), 2.331 (3.76), 2.398 (4.08), 2.523 (9.86), 2.540 (2.80), 2.620 (0.87), 2.665 (1.79), 2.669 (2.48), 2.673 (1.83), 3.466 (9.08), 3.481 (8.76), 3.503 (4.26), 3.676 (5.64), 6.992 (5.32), 7.004 (5.50), 7.177 (4.26), 7.494 (2.80), 7.513 (2.98), 7.859 (3.48), 8.294 (6.01), 8.314 (12.15), 9.487 (12.29), 10.966 (1.24), 12.561 (0.50).

SM: Compound 173.01 and cyclopropanecarboxylic acid

Example 173.04

(4-{(1R or 1S)-1-[2-({7-fluoro-6-[6-(trifluoromethyl)pyrimidin-4-yl]-1H-benzimidazol-2-yl}amino)pyridin-4-yl]ethyl}piperazin-1-yl)[1-(trifluoromethyl)cyclopropyl]methanone LC-MS (Method 2): $R_t$ = 1.33 min; MS (ESIpos): m/z = 623 [M + H]⁺

¹H-NMR (400 MHz, DMSO-d6) δ [ppm]: 1.161 (9.24), 1.218 (3.55), 1.285 (16.00), 1.300 (14.44), 2.368 (6.31), 2.668 (1.25), 3.332 (13.26), 3.481 (4.25), 6.994 (4.45), 7.169 (5.01), 7.503 (3.26), 7.523 (3.54), 7.851 (3.29), 8.311 (8.32), 9.486 (6.19), 10.977 (5.36), 12.585 (4.43).

SM: Compound 173.01 and 1-(trifluoromethyl)cyclopropanecarboxylic acid

Example 174.01 tert-butyl 4-{(1R or 1S)-1-[2-({6-[6-(difluoromethyl)pyrimidin-4-yl]-1H-benzimidazol-2-yl}amino)pyridin-4-yl]ethyl}piperazine-1-carboxylate

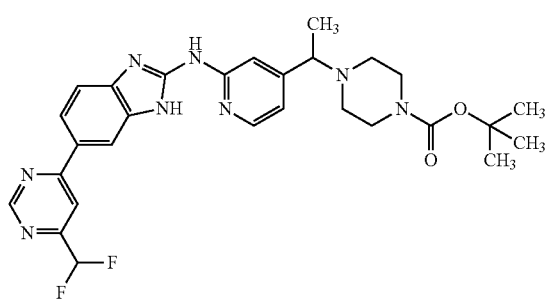 [SMILES: CC(c1ccnc(Nc2nc3ccc(-c4cc(C(F)F)ncn4)cc3[nH]2)c1)N1CCN(C(=O)OC(C)(C)C)CC1]

Tert-butyl 4-[(1R or 1S)-1-{2-[({2-amino-4-[6-(difluoromethyl)pyrimidin-4-yl]phenyl}carbamothioyl)amino]pyridin-4-yl}ethyl]piperazine-1-carboxylate (300 mg, see Compound 174.01.02) was solubilized in dichloromethane (6.6 ml) and DIC (240 µl, 1.5 mmol) was added. The reaction mixture was stirred overnight under inert atmosphere. The crude residue was purified, without further workup, by flash chromatography on silica gel to give 228 mg (90% purity) of the title compound.

LC-MS (Method 2): $R_t$=1.35 min; MS (ESIpos): m/z=551 [M+H]$^+$.

1H-NMR (400 MHz, DMSO-d6): δ [ppm]=1.29 (d, 3H), 1.34-1.42 (m, 9H), 2.23-2.34 (m, 2H), 2.35-2.44 (m, 2H), 3.33 (s, 4H), 3.45 (q, 1H), 6.86-7.21 (m, 3H), 7.38-7.69 (m, 1H), 7.98-8.23 (m, 2H), 8.26-8.53 (m, 2H), 9.29 (s, 1H), 10.83 (br s, 1H), 12.39 (br s, 1H).

Example 175.01 tert-butyl 4-[(2-{[6-(2-chlorothiophen-3-yl)-1H-benzimidazol-2-yl]amino}pyridin-4-yl)methyl]piperazine-1-carboxylate

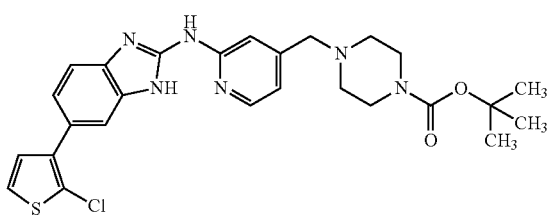 [SMILES: CC(C)(C)OC(=O)N1CCN(Cc2ccnc(Nc3nc4ccc(-c5ccsc5Cl)cc4[nH]3)c2)CC1]

tert-Butyl 4-{[2-({[4-amino-6-(2-chlorothiophen-3-yl)pyridin-3-yl]carbamothioyl}amino)pyridin-4-yl]methyl}piperazine-1-carboxylate (630 mg, see Compound 107.01.02) and EDCI (216 mg) were stirred in dichloromethane (15 ml) under inert atmosphere over the weekend at rt. The mixture was concentrated under reduced pressure. The crude residue was purified by flash chromatography on silica gel to give 160 mg of the title compound.

LC-MS (Method 2): $R_t$=1.44 min; MS (ESIpos): m/z=525 [M+H]$^+$.

$^1$H-NMR (400 MHz, DMSO-d6) δ[ppm]: 1.395 (16.00), 1.415 (1.94), 2.323 (0.56), 2.327 (0.68), 2.332 (0.68), 2.337 (0.69), 2.347 (1.16), 2.359 (1.40), 2.371 (1.01), 2.518 (1.71), 2.523 (1.21), 2.669 (0.44), 3.498 (1.76), 5.759 (5.93), 6.918 (0.50), 6.931 (0.50), 7.229 (0.42), 7.234 (0.54), 7.248 (0.61), 7.530 (0.56), 7.543 (0.47), 7.552 (0.41), 8.255 (0.67), 8.268 (0.63).

Example 176.01 tert-butyl 4-[(2-{[6-(morpholin-4-yl)-1H-benzimidazol-2-yl]amino}pyridin-4-yl)methyl]piperazine-1-carboxylate

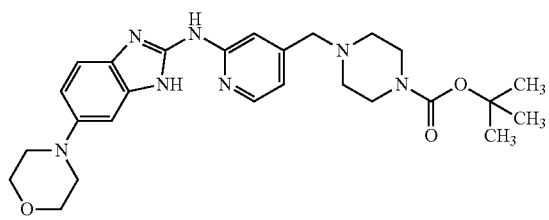 [SMILES: CC(C)(C)OC(=O)N1CCN(Cc2ccnc(Nc3nc4ccc(N5CCOCC5)cc4[nH]3)c2)CC1]

Tert-butyl 4-{[2-({[2-amino-4-(morpholin-4-yl)phenyl]carbamothioyl}amino)pyridin-4-yl]methyl}piperazine-1-carboxylate (380 mg, see Compound 176.01.03) and EDCI (138 mg) were stirred in dichloromethane (13 ml) under inert atmosphere overnight at rt. The mixture was concentrated under reduced pressure. The crude residue was purified by flash chromatography on silica gel to give 43.0 mg (95% purity) of the title compound.

LC-MS (Method 2): $R_t$=1.19 min; MS (ESIpos): m/z=494 [M+H]$^+$.

$^1$H-NMR (400 MHz, DMSO-d6): δ [ppm]=1.39 (s, 9H), 2.33-2.37 (m, 4H), 3.00-3.07 (m, 4H), 3.33-3.37 (m, 4H), 3.48 (s, 2H), 3.73-3.79 (m, 4H), 6.74 (br s, 1H), 6.85-7.10 (m, 2H), 7.14 (br s, 1H), 7.18-7.37 (m, 1H), 8.21 (d, 1H), 10.36-10.54 (m, 1H), 11.84 (br s, 1H).

The Example compounds shown in table 20 below were prepared according to the following general procedure:

Compound 01.04 (1 eq.) and the respective heteroaryl halide (1.3 eq) were solubilised in DME and an aqueous solution of Na$_2$CO$_3$ (2.5 eq, 2M) was added. The mixture was sparged with argon and 1,1'-bis(diphenylphosphino)ferrocene-palladium(II)dichloride dichloromethane complex (0.1 eq) was added. The reaction mixture was stirred at 150° C. for 2 hours (if the reaction was not complete, 1.3 eq. of heteroaryl halide as well as 0.1 eq. of catalyst were added and the reaction mixture was stirred between 2 and 20 additional hours at 150° C.). The reaction mixture was then filtered through silicone filter and concentrated under reduced pressure. The crude mixture was purified without work up by preparative HPLC to the desired compound.

TABLE 20

Structure
IUPAC-Name
LC-MS (method): Retention time; Mass found
Example     $^1$H-NMR Example 177.01 tert-butyl 4-{[2-({6-[2-(pyrrolidin-1-yl)pyrimidin-4-yl]-1H-benzimidazol-2-yl}amino)pyridin-4-yl]methyl}piperazine-1-carboxylate
LC-MS (Method 2): R$_t$ = 1.41 min; MS (ESIpos): m/z = 556.6 [M + H]$^+$
$^1$H-NMR (400 MHz, DMSO-d$_6$): δ [ppm] = 1.40 (s, 9H), 1.40-1.43 (m, 1H), 1.99 (m, 8H), 2.36 (br t, 4H), 3.35 (br s, 4H), 3.49-3.51 (m, 2H), 6.34 (d, 1H), 6.49 (d, 1H), 6.92 (d, 1H), 7.18 (s, 1H), 8.17 (br d, 1H), 8.20-8.24 (t, 2H), 8.26 (d, 1H), 10.68 (br s, 1H), 12.14-12.27 (m, 1H).

Example 178.01 tert-butyl 4-{[2-({6-[2-(dimethylamino)-6-methylpyrimidin-4-yl]-1H-benzimidazol-2-yl}amino)pyridin-4-yl]methyl}piperazine-1-carboxylate
LC-MS (Method 2): R$_t$ = 1.47 min; MS (ESIpos): m/z = 544.6 [M + H]$^+$ Example 179.01 tert-butyl 4-{[2-({6-[5-chloro-6-(dimethylamino)pyrimidin-4-yl]-1H-benzimidazol-2-yl}amino)pyridin-4-yl]methyl}piperazine-1-carboxylate
LC-MS (Method 2): R$_t$ = 1.3 min; MS (ESIpos): m/z = 564 [M + H]$^+$
$^1$H-NMR (400 MHz, DMSO-d$_6$): δ [ppm] = 1.39 (s, 9H), 2.36 (br t, 4H), 3.18 (s, 6H), 3.35 (br s, 4H), 3.50 (s, 2H), 6.93 (d, 1H), 7.17 (s, 1H), 7.40 (br s, 1H), 7.45-7.56 (m, 1H), 7.66-7.93 (m, 1H), 8.26 (d, 1H), 8.50 (s, 1H), 10.71 (br d, 1H), 12.25 (br d, 1H).

TABLE 20-continued

| Example | Structure<br>IUPAC-Name<br>LC-MS (method): Retention time; Mass found<br>¹H-NMR |
| --- | --- |

Example 180.01 tert-butyl 4-[(2-{[6-(pyrimidin-2-yl)-1H-benzimidazol-2-yl]amino}pyridin-4-yl)methyl]piperazine-1-carboxylate
LC-MS (Method 2): R$_t$ = 1.24 min; MS (ESIpos): m/z = 487 [M + H]$^+$
¹H-NMR (400 MHz, DMSO-d$_6$): δ ppm 1.40 (s, 9H) 2.33-2.41 (m, 4H) 3.35 (br s, 4H) 3.50 (s, 2H) 6.94 (d, 1H) 7.17 (br s, 1H) 7.30-7.37 (m, 1H) 7.37-7.61 (m, 1H) 8.19 (br s, 1H) 8.27 (d, 1H) 8.36-8.62 (m, 1H) 8.84 (d, 2H) 10.74 (s, 1H) 12.28 (b rs, 1H)

Example 181.01 tert-butyl 4-{[2-({6-[4-(dimethylamino)pyrimidin-2-yl]-1H-benzimidazol-2-yl}amino)pyridin-4-yl]methyl}piperazine-1-carboxylate
LC-MS (Method 2): R$_t$ = 2.32 min; MS (ESIpos): m/z = 530 [M + H]$^+$
¹H-NMR (400 MHz, CHLOROFORM-d): δ [ppm] = 1.43 (s, 9H), 2.33 (br s, 4H), 3.15-3.27 (m, 5H), 3.30-3.39 (m, 4H), 3.44 (br s, 2H), 6.25-6.38 (m, 1H), 6.86-6.99 (m, 1H), 7.19 (s, 1H), 7.46-7.73 (m, 1H), 8.23-8.77 (m, 4H), 12.40 (br s, 1H), 12.74 (br s, 1H).

Example 182.01 tert-butyl 4-[(2-{[6-(5,7-dihydrofuro[3,4-d]pyrimidin-4-yl)-1H-benzimidazol-2-yl]amino}pyridin-4-yl)methyl]piperazine-1-carboxylate
LC-MS (Method 2): R$_t$ = 1.2 min; MS (ESIpos): m/z = 529 [M + H]$^+$
¹H-NMR (400 MHz, DMSO-d$_6$): δ [ppm] = 1.35-1.43 (m, 9H), 2.36 (br t, 4H), 3.35 (br s, 4H), 3.51 (s, 2H), 4.99-5.04 (m, 2H), 5.49 (s, 2H), 6.96 (br d, 1H), 7.17 (s, 1H), 7.43-7.84 (m, 3H), 7.91-8.15 (m, 1H), 8.26-8.32 (m, 1H), 9.09 (s, 1H), 10.67-10.89 (m, 1H).

| Example | Structure<br>IUPAC-Name<br>LC-MS (method): Retention time; Mass found<br>¹H-NMR |
|---|---|
| Example 183.01 | tert-butyl 4-{[2-({6-[5-methyl-6-(trifluoromethyl)pyrimidin-4-yl]-1H-benzimidazol-2-yl}amino)pyridin-4-yl]methyl}piperazine-1-carboxylate<br>LC-MS (Method 2): $R_t$ = 1.39 min; MS (ESIpos): m/z = 569.5 [M + H]⁺<br>¹H-NMR (400 MHz, DMSO-d₆): δ [ppm] = 1.34-1.47 (m, 9H), 2.31-2.42 (m, 4H), 2.52 (br s, 3H), 3.35 (br s, 4H), 3.43-3.56 (m, 2H), 6.90-7.00 (m, 1H), 7.16-7.21 (m, 1H), 7.28-7.94 (m, 3H), 8.27 (d, 1H), 9.24 (s, 1H), 10.77 (br s, 1H), 12.31 (br s, 1H). |
| Example 184.01 | tert-butyl 4-[(2-{[6-(5-methylpyrimidin-4-yl)-1H-benzimidazol-2-yl]amino}pyridin-4-yl)methyl]piperazine-1-carboxylate<br>LC-MS (Method 2): $R_t$ = 1.2 min; MS (ESI pos): m/z = 501.5 [M + H]⁺<br>¹H-NMR (400 MHz, DMSO-d₆): δ [ppm] = 1.35-1.43 (m, 9H), 2.31-2.39 (m, 4H), 2.39-2.47 (m, 3H), 3.17-3.41 (m, 4H), 3.50 (s, 2H), 6.94 (d, 1H), 7.18 (s, 1H), 7.33-7.51 (m, 2H), 7.91 (br s, 1H), 8.27 (d, 1H), 8.68 (s, 1H), 9.04 (s, 1H), 10.74 (br s, 1H), 12.26 (br s, 1H). |
| Example 185.01 | tert-butyl 4-[(2-{[6-(6-chloro-2-methoxypyrimidin-4-yl)-1H-benzimidazol-2-yl]amino}pyridin-4-yl)methyl]piperazine-1-carboxylate<br>LC-MS (Method 4): $R_t$ = 1.37 min; MS (ESIpos): m/z = 551 [M + H]⁺<br>¹H-NMR (400 MHz, DMSO-d₆): δ ppm 1.40 (s, 9H) 2.33-2.41 (m, 4H) 3.34-3.39 (m, 3H) 3.51 (br s, 2H) 4.04 (s, 3H) 6.96 (br d, 1H) 7.19 (s, 1H) 7.36-7.66 (m, 1H) 7.72-7.94 (m, 1H) 7.99 (dd, 1H) 8.23-8.50 (m, 2H) 10.73-10.91 (m, 1H) 12.37 (br s, 1H) |

TABLE 20-continued

| Example | Structure<br>IUPAC-Name<br>LC-MS (method): Retention time; Mass found<br>¹H-NMR |
|---|---|
| Example 186.01 | tert-butyl 4-[(2-{[6-(6-chloro-2-methylpyrimidin-4-yl)-1H-benzimidazol-2-yl]amino}pyridin-4-yl)methyl]piperazine-1-carboxylate<br>LC-MS (Method 4): $R_t$ = 1.35 min; MS (ESIpos): m/z = 535 [M + H]⁺<br>¹H-NMR (400 MHz, DMSO-d₆): δ ppm 1.40 (s, 9H) 2.36 (br s, 4H) 2.64-2.68 (m, 3H) 3.35-3.35 (m, 4H) 3.51 (s, 2H) 6.95 (d, 1H) 7.18 (s, 1H) 7.35-7.72 (m, 1H) 7.98 (dd, 1.5H) 8.07 (br s, 0.5H) 8.27 (d, 1.5H) 8.45 (br s, 0.5H) 10.83 (br s, 1H) 12.22-12.47 (m, 1H) |
| Example 187.01 | tert-butyl 4-[(2-{[6-(6-chloro-5-fluoropyrimidin-4-yl)-1H-benzimidazol-2-yl]amino}pyridin-4-yl)methyl]piperazine-1-carboxylate<br>LC-MS (Method 2): $R_t$ = 1.37 min; MS (ESIpos): m/z = 539 [M + H]⁺<br>¹H-NMR (400 MHz, DMSO-d₆): δ [ppm]: 1.065 (0.73), 1.172 (0.67), 1.299 (8.15), 1.394 (15.51), 1.395 (16.00), 1.987 (1.24), 2.322 (0.56),, 2.326 (0.77), 2.332 (0.63), 2.352 (1.34), 2.363 (1.42), 2.518 (3.22), 2.522 (2.20), 2.664 (0.49), 2.668 (0.68), 2.673 (0.48), 3.492 (1.11), 3.510 (1.21), 5.758 (1.14), 7.173 (0.64), 8.084, (1.70), 8.238 (0.53), 8.252 (0.52), 8.276 (0.55), 8.289 (0.52), 8.884 (0.41). |
| Example 188.01 | tert-butyl 4-[(2-{[6-(3-chloropyrazin-2-yl)-1H-benzimidazol-2-yl]amino}pyridin-4-yl)methyl]piperazine-1-carboxylate<br>LC-MS (Method 2): $R_t$ = 1.25 min; MS (ESIpos): m/z = 521 [M + H]⁺<br>¹H-NMR (400 MHz, DMSO-d₆): δ ppm 1.07 (s, 9H) 2.36 (br t, 4H) 3.35 (br s, 4H) 3.50 (s, 2H) 6.94 (dd, 1H) 7.18 (s, 1H) 7.40-7.47 (m, 1H) 7.93-8.03 (m, 1H) 8.27 (d, 1H) 8.46 (br s, 1H) 8.74 (d, 1H) 10.75 (br s, 1H) 12.24-12.34 (m, 1H) |

The Example compounds shown in table 21 below were prepared as follows:

The respective chloride (example 145.01.01 or 145.01.02, if not specified otherwise in the table below) was solubilised in dioxane and the respective amine (4 to 6 eq) was added. In some cases K₂CO₃ or DIPEA (4 eq.) was used. The reaction mixture was stirred 16 hours at reflux. The reaction mixture was then filtered, concentrated under reduced pressure and purified by preparative HPLC. or The respective chloride (example 145.01.01 or 145.01.02, if not specified otherwise in the table below) was solubilised in dioxane and the respective alcohol (2 to 6 eq) and NaH (6 eq.) was added. The reaction mixture was stirred 1 to 3 hours at rt. The reaction was stopped by the addition of water and the aqueous phase was extracted three times with DCM. The organic phase was dried (silicone filter), concentrated under reduced pressure and purified by preparative HPLC.

TABLE 21

| Example | Structure<br>IUPAC-Name<br>LC-MS (method): Retention time; Mass found<br>¹H-NMR |
|---|---|
| Example 189.01 | 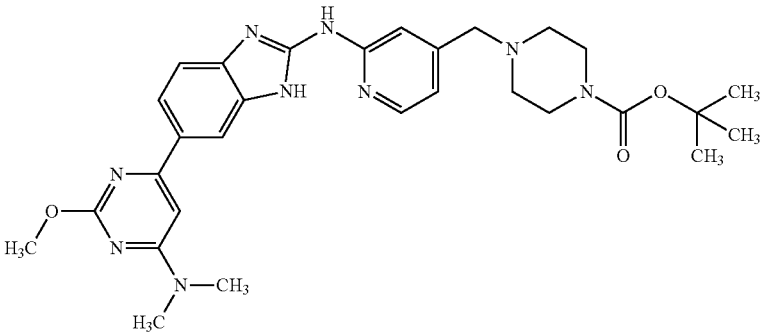 [SMILES: COc1nc(-c2ccc3nc(Nc4cc(CN5CCN(C(=O)OC(C)(C)C)CC5)ccn4)[nH]c3c2)cc(N(C)C)n1]<br>From example 185.01<br>tert-butyl 4-{[2-({6-[6-(dimethylamino)-2-methoxypyrimidin-4-yl]-1H-benzimidazol-2-yl}amino)pyridin-4-yl]methyl}piperazine-1-carboxylate<br>LC-MS (Method 2): Rt = 1.35 min; MS (ESIpos): m/z = 560 [M + H]⁺<br>¹H-NMR (400 MHz, DMSO-d₆): δ [ppm] = 1.40 (s, 9H), 2.33-2.39 (m, 4H), 3.13 (s, 6H), 3.35 (br s, 4H), 3.50 (s, 2H), 3.89-3.93 (m, 2H), 6.73-6.84 (m, 1H), 6.90-6.96 (m, 1H), 7.15-7.23 (m, 1H), 7.34-7.57 (m, 1H), 7.83-7.93 (m, 1H), 8.10-8.34 (m, 1H), 8.26 (d, 1H), 10.63-10.76 (m, 1H), 12.18-12.29 (m, 1H). |
| Example 190.01 | 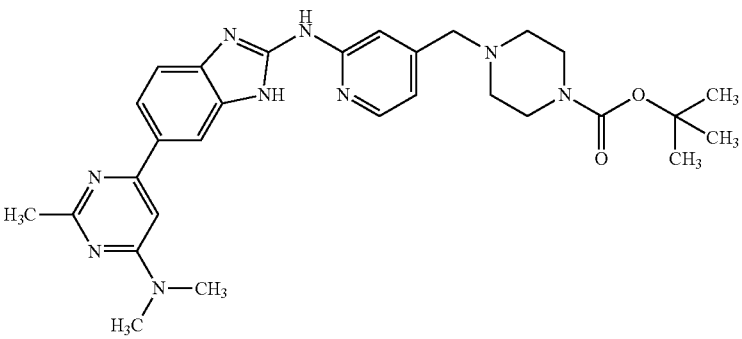 [SMILES: Cc1nc(-c2ccc3nc(Nc4cc(CN5CCN(C(=O)OC(C)(C)C)CC5)ccn4)[nH]c3c2)cc(N(C)C)n1]<br>From example 186.01<br>tert-butyl 4-{[2-({6-[6-(dimethylamino)-2-methylpyrimidin-4-yl]-1H-benzimidazol-2-yl}amino)pyridin-4-yl]methyl}piperazine-1-carboxylate<br>LC-MS (Method 2): Rt = 1.33 min; MS (ESIpos): m/z = 544 [M + H]⁺<br>¹H-NMR (400 MHz, DMSO-d₆): δ [ppm] = 1.36-1.42 (m, 9H), 2.33-2.39 (m, 4H), 2.45 (s, 3H), 3.13 (s, 5H), 3.34-3.37 (m, 1H), 3.35 (br s, 1H), 3.50 (s, 2H), 6.85-6.96 (m, 2H), 7.18 (br s, 1H), 7.52-7.66 (m, 1H), 7.86 (br s, 1H), 8.08-8.35 (m, 1H), 8.25 (d, 1H), 10.71 (br s, 1H), 12.16-12.31 (m, 1H). |

TABLE 21-continued

| Example | Structure<br>IUPAC-Name<br>LC-MS (method): Retention time; Mass found<br>$^1$H-NMR |
|---|---|
| Example 191.01 | 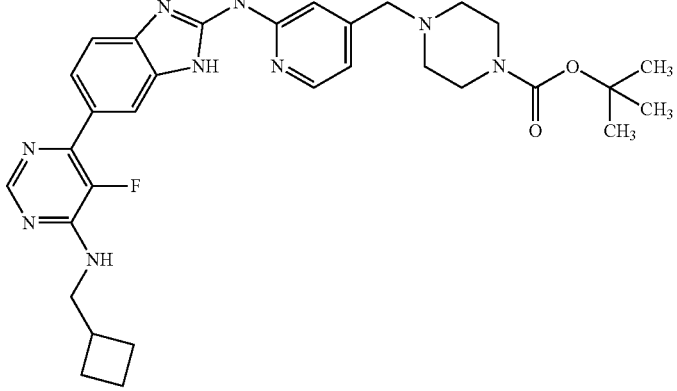<br>tert-butyl 4-({2-[(6-{6-[(cyclobutylmethyl)amino]-5-fluoropyrimidin-4-yl}-1H-benzimidazol-2-yl)amino]pyridin-4-yl}methyl)piperazine-1-carboxylate<br>LC-MS (Method 2): $R_t$ = 1.39 min; MS (ESIpos): m/z = 588 [M + H]$^+$<br>$^1$H NMR (400 MHz, DMSO-d$_6$) δ ppm 1.39 (s, 9H) 1.69-1.90 (m, 4H) 1.99-2.06 (m, 2H) 2.31-2.42 (m, 2H) 2.63-2.70 (m, 1H) 3.34-3.41 (m, 4H) 3.42-3.57 (m, 4H) 6.90-6.97 (m, 1H) 7.17 (s, 1H) 7.37-7.59 (m, 1H) 7.63-7.81 (m, 2H) 7.91-8.33 (m, 3H) 10.73 (br s, 1H) 12.28 (br s, 1H) |
| Example 192.01 | 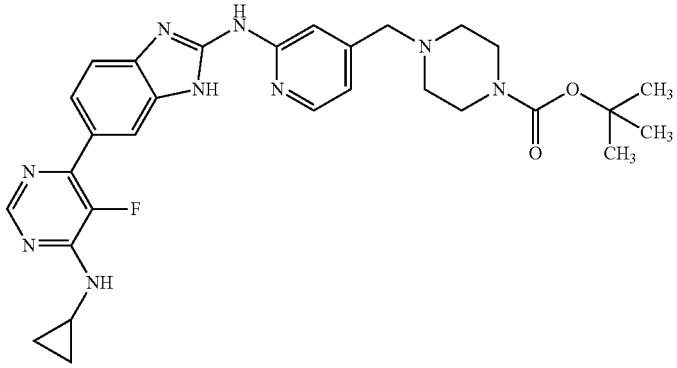 [SMILES: CC(C)(C)OC(=O)N1CCN(Cc2ccnc(Nc3nc4ccc(-c5ncnc(NC6CC6)c5F)cc4[nH]3)c2)CC1]<br>tert-butyl 4-{[2-({6-[6-(cyclopropylamino)-5-fluoropyrimidin-4-yl]-1H-benzimidazol-2-yl}amino)pyridin-4-yl]methyl}piperazine-1-carboxylate<br>LC-MS (Method 2): $R_t$ = 1.22 min; MS (ESIneg): m/z = 558 [M + H]$^-$<br>$^1$H NMR (400 MHz, DMSO-d$_6$) δ ppm 0.56-0.78 (m, 4H) 1.39 (s, 9H) 2.36 (br t, 4H) 2.86 (tq, 1H) 3.35 (br s, 4H) 3.50 (s, 2H) 6.93 (dd, 1H) 7.17 (s, 1H) 7.36-7.62 (m, 1H) 7.66-7.75 (m, 0.5H) 7.77 (br s, 1H) 8.21 (br d, 0.5H) 8.27 (d, 1H) 8.36 (d, 1H) 10.74 (br s, 1H) 12.29 (br s, 1H) |
| Example 193.01 | 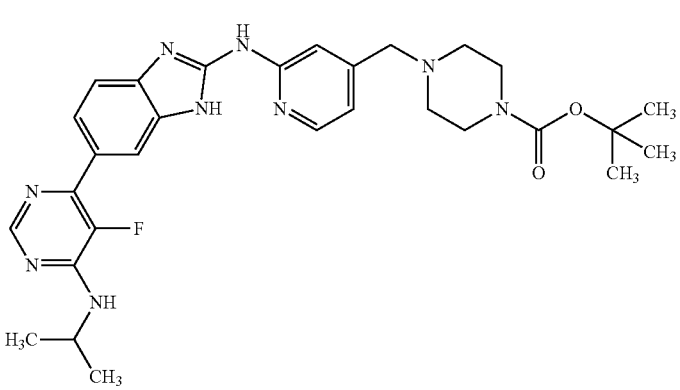 [SMILES: CC(C)Nc1ncnc(-c2ccc3nc(Nc4cc(CN5CCN(C(=O)OC(C)(C)C)CC5)ccn4)[nH]c3c2)c1F] |

| Example | Structure<br>IUPAC-Name<br>LC-MS (method): Retention time; Mass found<br>¹H-NMR |
|---|---|
| | tert-butyl 4-{[2-({6-[5-fluoro-6-(propan-2-ylamino)pyrimidin-4-yl]-1H-benzimidazol-2-yl}amino)pyridin-4-yl]methyl}piperazine-1-carboxylate<br>LC-MS (Method 2): $R_t$ = 1.31 min; MS (ESIpos): m/z = 562 [M + H]⁺<br>¹H NMR (400 MHz, DMSO-d₆) δ ppm 1.23 (d, 6H) 1.40 (s, 9H) 2.36 (br t, 4H) 3.34-3.40 (m, 4H) 3.50 (s, 2H) 4.23-4.35 (m, 1H) 6.93 (dd, 1H) 7.17 (s, 1H) 7.39 (br d, 1H) 7.55 (br s, 1H) 7.74 (br s, 1H) 8.17 (br s, 0.5H) 8.27 (d, 1H) 8.30 (d, 1H) 8.54 (br s, 0.5H) 10.74 (br s, 1H) 12.28 (br s, 1H) |
| Example 194.01 | 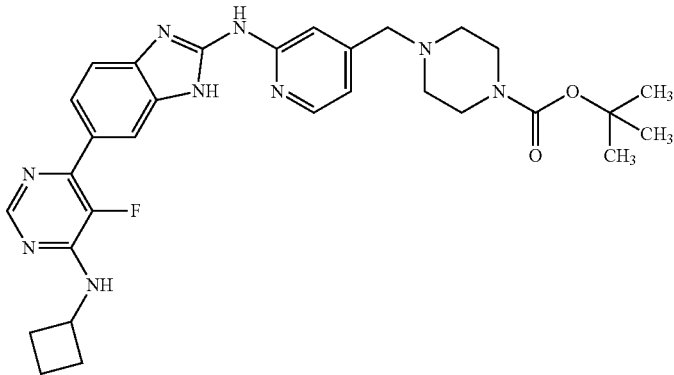 [SMILES: CC(C)(C)OC(=O)N1CCN(Cc2ccnc(Nc3nc4ccc(-c5ncnc(NC6CCC6)c5F)cc4[nH]3)c2)CC1]<br>tert-butyl 4-{[2-({6-[6-(cyclobutylamino)-5-fluoropyrimidin-4-yl]-1H-benzimidazol-2-yl}amino)pyridin-4-yl]methyl}piperazine-1-carboxylate<br>LC-MS (Method 2): $R_t$ = 1.33 min; MS (ESIpos): m/z = 574 [M + H]⁺<br>¹H NMR (400 MHz, DMSO-d₆) δ ppm 1.39 (s, 9H) 1.62-1.76 (m, 2H) 2.03-2.19 (m, 2H) 2.22-2.31 (m, 2H) 2.31-2.42 (m, 5H) 3.34-3.42 (m, 4H) 3.50 (s, 2H) 4.51-4.62 (m, 1H) 6.89-6.97 (m, 1H) 7.17 (s, 1H) 7.37-7.64 (m, 1H) 7.65-7.79 (m, 1H) 7.83 (br d, 1H) 7.95 (br s, 0.5H) 8.14-8.20 (m, 0.5H) 8.24-8.32 (m, 2H) 10.74 (br s, 1H) 12.28 (br s, 1H) |
| Example 195.01 | 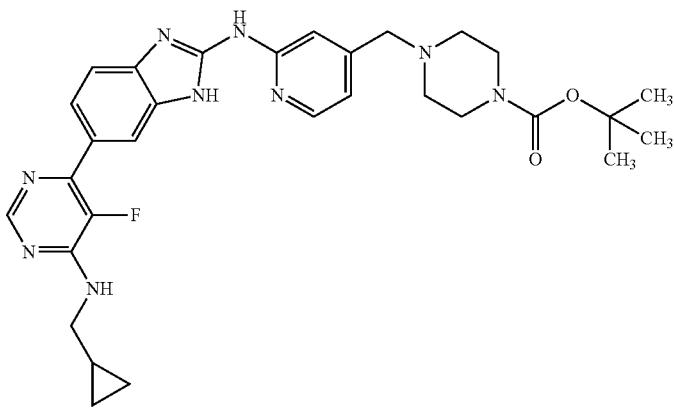 [SMILES: CC(C)(C)OC(=O)N1CCN(Cc2ccnc(Nc3nc4ccc(-c5ncnc(NCC6CC6)c5F)cc4[nH]3)c2)CC1]<br>tert-butyl 4-({2-[(6-{6-[(cyclopropylmethyl)amino]-5-fluoropyrimidin-4-yl}-1H-benzimidazol-2-yl)amino]pyridin-4-yl}methyl)piperazine-1-carboxylate<br>LC-MS (Method 2): $R_t$ = 1.32 min; MS (ESIpos): m/z = 574 [M + H]⁺<br>¹H NMR (400 MHz, DMSO-d₆) δ ppm 0.22-0.34 (m, 2H) 0.39-0.51 (m, 2H) 1.14-1.19 (m, 1H) 1.40 (s, 9H) 2.33-2.41 (m, 4H) 2.52 (d, 2H) 3.24-3.31 (m, 2H) 3.35-3.40 (m, 2H) 3.50 (s, 2H) 6.91-6.99 (m, 1H) 7.17 (s, 1H) 7.36-7.48 (m, 0.5H) 7.51-7.64 (m, 0.5H) 7.75 (br t, 2H) 7.92-8.00 (m, 0.5H) 8.21 (br d, 0.5H) 8.25-8.33 (m, 2H) 10.73 (br s, 1H) 12.29 (br s, 1H) |

TABLE 21-continued

| Example | Structure<br>IUPAC-Name<br>LC-MS (method): Retention time; Mass found<br>$^1$H-NMR |
|---|---|
| Example 196.01 | 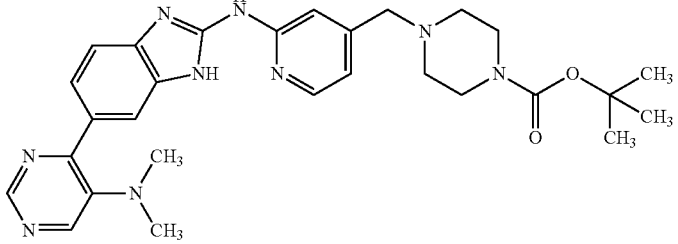<br><br>From example 188.01<br>tert-butyl 4-{[2-({6-[3-(dimethylamino)pyrazin-2-yl]-1H-benzimidazol-2-yl}amino)pyridin-4-yl]methyl}piperazine-1-carboxylate<br>LC-MS (Method 2): $R_t$ = 1.28 min; MS (ESIpos): m/z = 530 [M + H]$^+$<br>$^1$H NMR (400 MHz, DMSO-d$_6$) δ ppm 1.40 (s, 9H) 2.36 (br t, 4H) 2.73 (s, 6H) 3.35 (br s, 4H) 3.50 (s, 2H) 7.17 (s, 1H) 7.32-7.46 (m, 1H) 7.50 (br d, 1H) 7.65-7.93 (m, 1H) 8.04 (s, 1H) 8.07 (s, 1H) 8.26 (d, 1H) 10.67 (br s, 1H) 12.12-12.22 (m, 1H) |
| Example 197.01 | 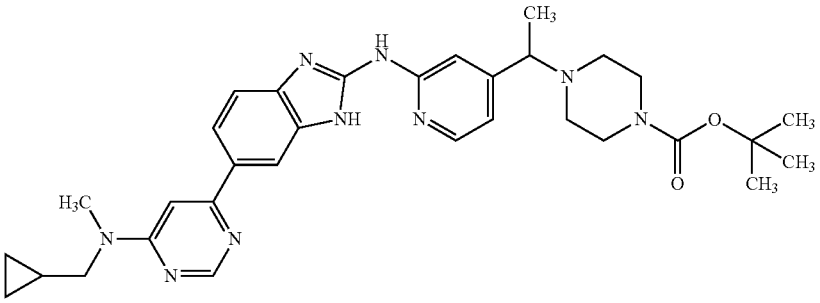 [SMILES: CC(c1ccnc(Nc2nc3ccc(-c4cc(N(C)CC5CC5)ncn4)cc3[nH]2)c1)N1CCN(C(=O)OC(C)(C)C)CC1]<br><br>tert-butyl 4-[(1R or 1S)-1-{2-[(6-{6-[(cyclopropylmethyl)(methyl)amino]pyrimidin-4-yl}-1H-benzimidazol-2-yl)amino]pyridin-4-yl}ethyl]piperazine-1-carboxylate<br>LC-MS (Method 2): $R_t$ = 1.38 min; MS (ESIpos): m/z = 584 [M + H]$^+$ |

Example 198.01 tert-butyl 4-{[2-({6-[6-(3,6-dihydro-2H-pyran-4-yl)pyrimidin-4-yl]-1H-benzimidazol-2-yl}amino)pyridin-4-yl]methyl}piperazine-1-carboxylate

50

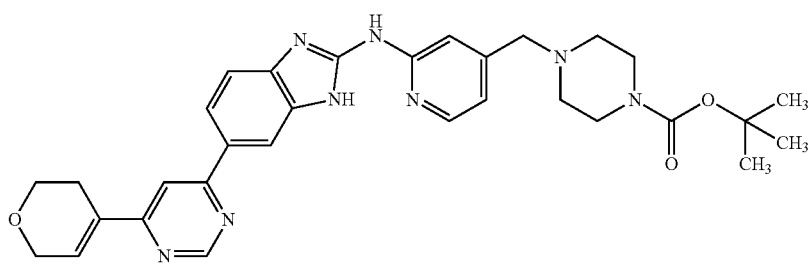 [SMILES: CC(C)(C)OC(=O)N1CCN(Cc2ccnc(Nc3nc4ccc(-c5cc(C6=CCOCC6)ncn5)cc4[nH]3)c2)CC1]

Tert-butyl 4-[(2-{[6-(6-chloropyrimidin-4-yl)-1H-benzimidazol-2-yl]amino}pyridin-4-yl)methyl]piperazine-1-carboxylate (150 mg see Example 145.01.01), 4-(4,4,5,5-tetramethyl-1,3,2-dioxaborolan-2-yl)-3,6-dihydro-2H-pyran (181 mg), an aqueous solution of Na$_2$CO$_3$ (430 μl, 2.0 M) and 1,1'-bis(diphenylphosphino)ferrocene-palladium(II)dichloride dichloromethane complex (23.5 mg, 28.8 μmol) were stirred in 1,4-dioxane (3.0 ml)/water (600 μl) for 3 h at 110° C. The mixture was then concentrated under reduced pressure. The crude residue was purified by flash chromatography on silica gel to give 30.1 mg (97% purity) of the title compound.

LC-MS (Method 2): R$_t$=1.24 min; MS (ESIpos): m/z=569 [M+H]$^+$.

$^1$H-NMR (400 MHz, DMSO-d$_6$): δ [ppm]=1.40 (s, 9H), 2.36 (br t, 4H), 2.62 (br s, 2H), 3.35-3.42 (m, 4H), 3.51 (s, 2H), 3.86 (t, 2H), 4.34 (br d, 2H), 6.95 (br s, 1H), 7.19 (s, 2H), 7.41-7.62 (m, 1H), 7.99-8.14 (m, 2H), 8.27 (d, 1H), 8.29-8.46 (m, 1H), 9.10 (d, 1H), 10.70-10.85 (m, 1H), 12.33 (br s, 1H).

Example 199.01 tert-butyl 4-{[2-({6-[6-(tetrahydro-2H-pyran-4-yl)pyrimidin-4-yl]-1H-benzimidazol-2-yl}amino)pyridin-4-yl]methyl}piperazine-1-carboxylate

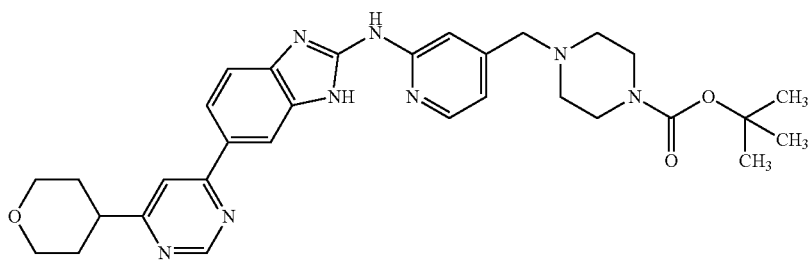 [SMILES: CC(C)(C)OC(=O)N1CCN(Cc2ccnc(Nc3nc4ccc(-c5cc(C6CCOCC6)ncn5)cc4[nH]3)c2)CC1]

Tert-butyl 4-{[2-({6-[6-(3,6-dihydro-2H-pyran-4-yl)pyrimidin-4-yl]-1H-benzimidazol-2-yl}amino)pyridin-4-yl]methyl}piperazine-1-carboxylate (30.1 mg) was solubilised in ethanol (2.0 ml), and the reaction vessel was purged three times with argon. Pd/C (1.68 g, 10% purity) was added to the mixture, and the vessel was purged three times with argon and three times with hydrogen gas. The reaction mixture was stirred under hydrogen atmosphere at rt overnight. The reaction mixture was filtered through Celite® and concentrated under reduced pressure. The crude title compound (27 mg) was used without further purification.

LC-MS (Method 2): R$_t$=1.20 min; MS (ESIpos): m/z=571 [M+H]$^+$.

$^1$H-NMR (400 MHz, DMSO-d6): δ [ppm]=1.40 (s, 9H), 1.85 (br d, 4H), 2.36 (br t, 4H), 2.94-3.05 (m, 1H), 3.34-3.40 (m, 4H), 3.40-3.55 (m, 4H), 3.95-4.04 (m, 2H), 6.94 (br d, 1H), 7.20 (s, 1H), 7.38-7.65 (m, 1H), 7.98 (br d, 2H), 8.21-8.45 (m, 2H), 9.08 (d, 1H), 10.78 (br d, 1H), 12.35 (d, 1H).

The Example compounds shown below in table 22 were prepared according to the following general procedure:

The respective amine (1 eq.; see Compounds 174.01 to 198.01, respectively; Table 6), 3,3,3-trifluoropropionic acid (1.5 eq), NaHCO$_3$ (6 eq.) and HATU (1.5 eq.) were solubilised in DMF and the reaction mixture was stirred at rt between 2 and 48 hours. The crude mixture was directly purified by preparative HPLC without workup to give the respective title compound.

TABLE 22

| Example | Structure<br>IUPAC-Name<br>LC-MS (method): Retention time; Mass found<br>¹H-NMR |
|---|---|
| Example 174.02 | 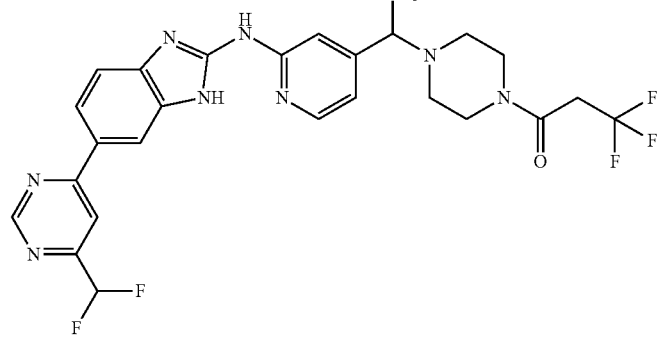<br>1-(4-{(1R or 1S)-1-[2-({6-[6-(difluoromethyl)pyrimidin-4-yl]-1H-benzimidazol-2-yl}amino)pyridin-4-yl]ethyl}piperazin-1-yl)-3,3,3-trifluoropropan-1-one<br>LC-MS (Method 4): $R_t$ = 1.13 min; MS (ESIpos): m/z = 561 [M + H]⁺<br>¹H-NMR (400 MHz, DMSO-$d_6$): δ [ppm] = 1.26-1.35 (m, 3H), 2.28-2.46 (m, 4H), 3.39-3.53 (m, 5H), 3.53-3.72 (m, 2H), 6.93-7.01 (m, 1H), 7.01-7.05 (m, 1H), 7.17-7.21 (m, 1H), 7.42-7.69 (m, 1H), 7.97-8.11 (m, 1H), 8.15-8.25 (m, 1H), 8.25-8.35 (m, 2H), 8.49 (br s, 1H), 9.25-9.34 (m, 1H), 10.70-11.08 (m, 1H), 12.26-12.57 (m, 1H). |
| Example 175.02 | 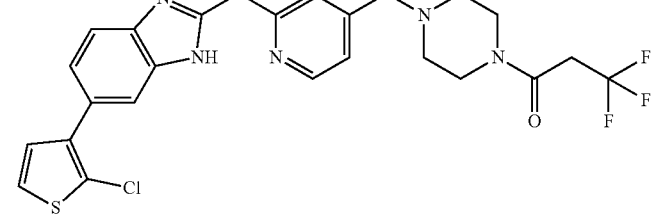<br>1-{4-[(2-{[6-(2-chlorothiophen-3-yl)-1H-benzimidazol-2-yl]amino}pyridin-4-yl)methyl]piperazin-1-yl}-3,3,3-trifluoropropan-1-one<br>LC-MS (Method 2): $R_t$ = 1.32 min; MS (ESIpos): m/z = 535 [M + H]⁺<br>¹H-NMR (400 MHz, DMSO-$d_6$): δ [ppm] = 2.38 (br t, 2H), 2.40-2.45 (m, 2H), 3.45-3.49 (m, 2H), 3.49-3.54 (m, 4H), 3.65 (q, 2H), 6.93 (dd, 1H), 7.19 (s, 1H), 7.24 (br s, 2H), 7.36-7.78 (m, 3H), 8.27 (d, 1H), 10.66 (br s, 1H), 12.18 (br d, 1H). |
| Example 176.02 | 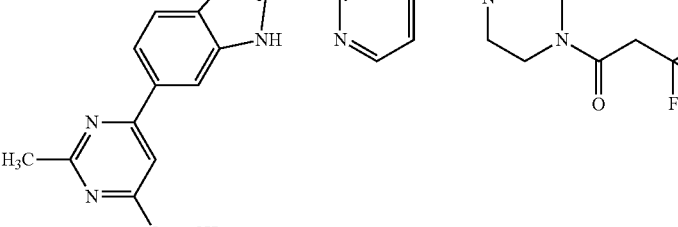<br>3,3,3-trifluoro-1-{4-[(2-{[6-(6-methoxy-2-methylpyrimidin-4-yl)-1H-benzimidazol-2-yl]amino}pyridin-4-yl)methyl]piperazin-1-yl}propan-1-one<br>LC-MS (HTpost2_basic): $R_t$ = 1.14 min; MS (ESIpos): m/z = 541.2 [M + H]⁺ |

TABLE 22-continued

| | Structure<br>IUPAC-Name<br>LC-MS (method): Retention time; Mass found |
|---|---|
| Example | $^1$H-NMR |

Example 177.02

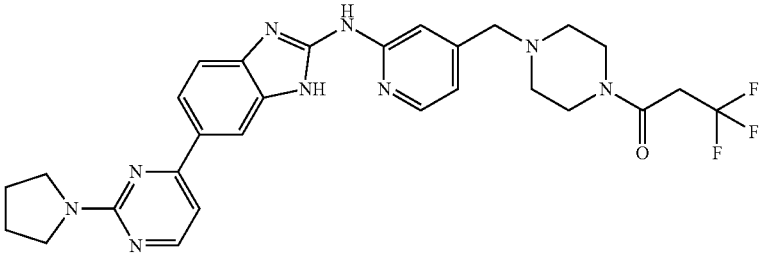 [SMILES: O=C(CC(F)(F)F)N1CCN(Cc2ccnc(Nc3nc4ccc(-c5ccnc(N6CCCC6)n5)cc4[nH]3)c2)CC1]

3,3,3-trifluoro-1-(4-{[2-({6-[2-(pyrrolidin-1-yl)pyrimidin-4-yl]-1H-benzimidazol-2-yl}amino)pyridin-4-yl]methyl}piperazin-1-yl)propan-1-one LC-MS (Method 2): $R_t$ = 1.21 min; MS (ESIpos): m/z = 566.7 [M + H]$^+$
$^1$H-NMR (400 MHz, DMSO-d$_6$): δ [ppm] = 1.99 (br s, 4H), 2.40 (dt, 4H), 3.43-3.54 (m, 7H), 3.65 (q, 3H), 6.34 (d, 1H), 6.93 (d, 1H), 7.19 (s, 1H), 7.29-7.55 (m, 1H), 8.17 (br d, 1H), 8.22 (d, 1H), 8.27 (d, 1H), 8.33-8.57 (m, 1H), 10.69 (br s, 1H), 12.20 (br s, 1H).

Example 178.02

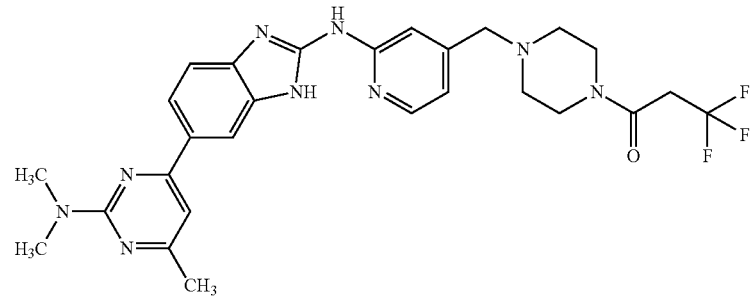 [SMILES: Cc1cc(-c2ccc3nc(Nc4cc(CN5CCN(C(=O)CC(F)(F)F)CC5)ccn4)[nH]c3c2)nc(N(C)C)n1]

1-(4-{[2-({6-[2-(dimethylamino)-6-methylpyrimidin-4-yl]-1H-benzimidazol-2-yl}amino)pyridin-4-yl]methyl}piperazin-1-yl)-3,3,3-trifluoropropan-1-one LC-MS (Method 2): $R_t$ = 1.29 min; MS (ESIpos): m/z = 554.7 [M + H]$^+$
$^1$H-NMR (400 MHz, DMSO-d$_6$): δ [ppm] = 2.34 (s, 3H), 2.40 (dt, 4H), 3.21 (s, 6H), 3.43-3.54 (m, 6H), 3.65 (q, 2H), 6.94 (br d, 1H), 6.98-7.12 (m, 1H), 7.20 (br s, 1H), 7.32-7.60 (m, 1H), 7.86 (dd, 1H), 8.08-8.39 (m, 1H), 8.27 (d, 1H), 10.75 (br s, 1H), 12.26 (br s, 1H).

Example 179.02

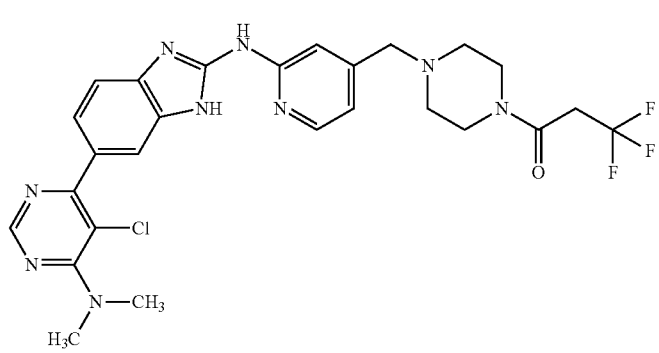 [SMILES: CN(C)c1ncnc(-c2ccc3nc(Nc4cc(CN5CCN(C(=O)CC(F)(F)F)CC5)ccn4)[nH]c3c2)c1Cl]

1-(4-{[2-({6-[5-chloro-6-(dimethylamino)pyrimidin-4-yl]-1H-benzimidazol-2-yl}amino)pyridin-4-yl]methyl}piperazin-1-yl)-3,3,3-trifluoropropan-1-one LC-MS (Method 4) $R_t$ = 1.14 min; MS (ESIpos): m/z = 574 [M + H]$^+$
$^1$H-NMR (400 MHz, DMSO-d$_6$): δ [ppm] = 2.38 (br t, 2H), 2.41-2.45 (m, 2H), 3.18 (s, 6H), 3.45-3.49 (m, 2H), 3.50 (br d, 2H), 3.52 (s, 2H), 3.65 (q, 2H), 6.94 (d, 1H), 7.19 (s, 1H), 7.40 (br s, 1H), 7.44-7.59 (m, 1H), 7.67-7.95 (m, 1H), 8.27 (d, 1H), 8.50 (s, 1H), 10.71 (br d, 1H), 12.20-12.30 (m, 1H).

TABLE 22-continued

Example | Structure / IUPAC-Name / LC-MS (method): Retention time; Mass found / ¹H-NMR Example 180.02

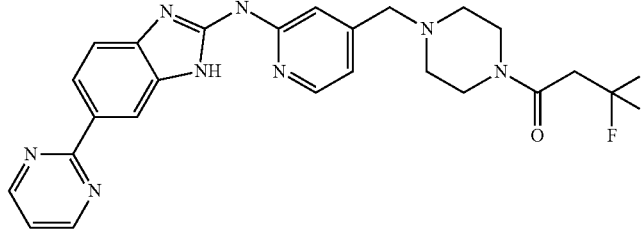

3,3,3-trifluoro-1-{4-[(2-{[6-(pyrimidin-2-yl)-1H-benzimidazol-2-yl]amino}pyridin-4-yl)methyl]piperazin-1-yl}propan-1-one
LC-MS (Method 4): $R_t$ = 1 min; MS (ESIpos): m/z = 497 [M + H]⁺
¹H NMR (400 MHz, DMSO-d₆) δ ppm 2.41 (dt, 4H) 3.41-3.49 (m, 2H) 3.49-3.57 (m, 4H) 3.65 (q, 2H) 6.95 (dd, 1H) 7.19 (s, 1H) 7.33 (t, 1H) 7.47 (br s, 0.5H) 8.19 (br d, 1H) 8.28 (d, 1H) 8.52 (br s, 0.5H) 8.84 (d, 2H) 10.76 (br s, 1H) 12.28 (br s, 1H)

Example 181.02

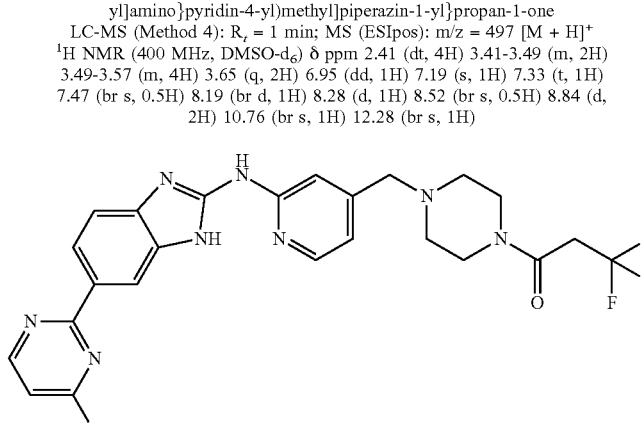

1-(4-{[2-({6-[4-(dimethylamino)pyrimidin-2-yl]-1H-benzimidazol-2-yl}amino)pyridin-4-yl]methyl}piperazin-1-yl)-3,3,3-trifluoropropan-1-one
LC-MS (Method 4): $R_t$ = 1.1 min; MS (ESIpos): m/z = 540.2 [M + H]⁺
¹H NMR (400 MHz, DMSO-d₆) δ ppm 2.40 (dt, 4H) 3.17 (br s, 6H) 3.42-3.49 (m, 2H) 3.49-3.56 (m, 4H) 3.65 (q, 2H) 6.53 (d, 1H) 6.93 (d, 1H) 7.19 (s, 1H) 7.30-7.57 (m, 1H) 8.10-8.23 (m, 1H) 8.25 (d, 1H) 8.27 (d, 1H) 8.29-8.57 (m, 1H) 10.69 (br s, 1H) 12.13-12.25 (m, 1H)

Example 182.02

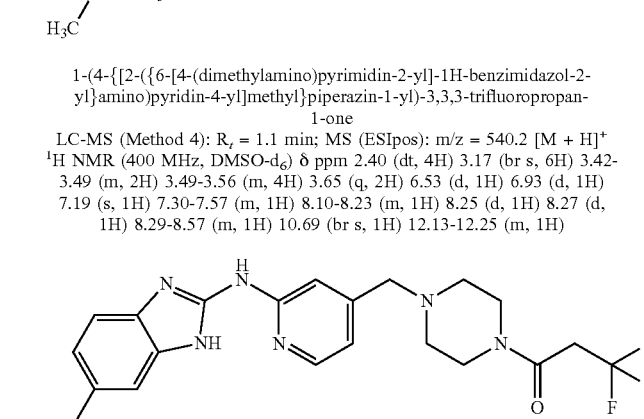

1-{4-[(2-{[6-(5,7-dihydrofuro[3,4-d]pyrimidin-4-yl)-1H-benzimidazol-2-yl]amino}pyridin-4-yl)methyl]piperazin-1-yl}-3,3,3-trifluoropropan-1-one
LC-MS (Method 4): $R_t$ = 0.97 min; MS (ESIpos): m/z = 539 [M + H]⁺
¹H-NMR (400 MHz, DMSO-d6) δ [ppm]: 2.323 (0.99), 2.327 (1.37), 2.331 (1.01), 2.373 (3.99), 2.385 (6.04), 2.397 (4.42), 2.415 (4.04), 2.427 (5.74), 2.438 (4.47), 2.518 (5.36), 2.523 (3.52), 2.665 (0.96), 2.669 (1.35), 2.673 (0.94), 3.372 (0.70), 3.462 (3.99), 3.474 (5.52), 3.485 (4.82), 3.498 (4.80), 3.510 (5.77), 3.532 (16.00), 3.611 (2.74), 3.638 (7.50), 3.666 (7.14), 3.693 (2.27), 4.049 (2.69), 4.976 (0.54), 5.014 (14.70), 5.488 (12.52), 5.758 (0.99), 6.961 (3.03), 7.189 (6.82), 7.456 (1.55), 7.476 (1.80), 7.595 (0.56), 7.630 (1.82), 7.782 (1.57), 7.802 (1.35), 7.940 (0.96), 8.116 (2.65), 8.290 (3.41), 8.302 (2.83), 9.095 (4.51), 10.770 (0.52), 10.851 (1.37), 12.343 (3.68).

TABLE 22-continued

| Example | Structure<br>IUPAC-Name<br>LC-MS (method): Retention time; Mass found<br>¹H-NMR |
|---|---|
| Example 183.02 | 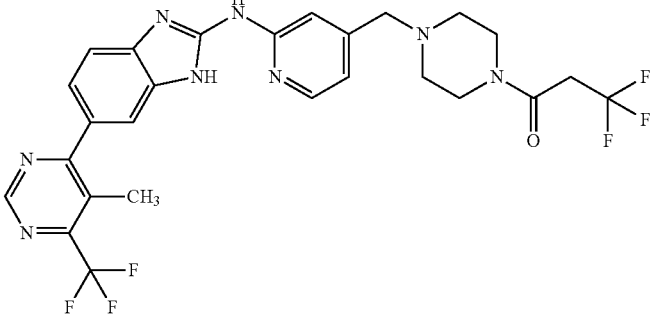<br>3,3,3-trifluoro-1-(4-{[2-({6-[5-methyl-6-(trifluoromethyl)pyrimidin-4-yl]-1H-benzimidazol-2-yl}amino)pyridin-4-yl]methyl}piperazin-1-yl)propan-1-one<br>LC-MS (Method 4): $R_t$ = 1.19 min; MS (ESIpos): m/z = 579 [M + H]⁺<br>¹H-NMR (400 MHz, DMSO-$d_6$): δ [ppm] = 2.35-2.39 (m, 1H), 2.38 (br t, 1H), 2.43 (br t, 2H), 2.52 (br d, 3H), 3.44-3.52 (m, 4H), 3.53 (s, 3H), 3.65 (q, 2H), 6.95 (d, 1H), 7.20 (s, 1H), 7.27-7.64 (m, 1H), 7.64-7.94 (m, 2H), 8.28 (d, 1H), 9.24 (s, 1H), 10.78 (br s, 1H), 12.25 (br s, 1H). |
| Example 184.02 | 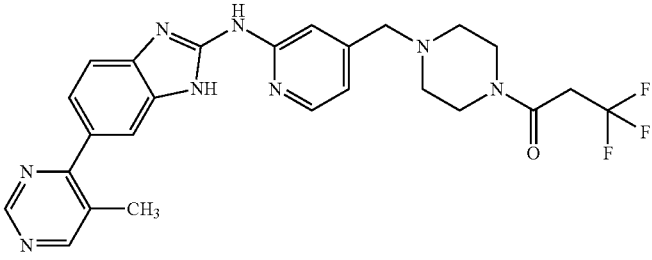 [SMILES: Cc1cncnc1-c1ccc2nc(Nc3cc(CN4CCN(C(=O)CC(F)(F)F)CC4)ccn3)[nH]c2c1]<br>3,3,3-trifluoro-1-{4-[(2-{[6-(5-methylpyrimidin-4-yl)-1H-benzimidazol-2-yl]amino}pyridin-4-yl)methyl]piperazin-1-yl}propan-1-one<br>LC-MS (Method 4): $R_t$ = 0.98 min; MS (ESIpos): m/z = 511 [M + H]⁺<br>¹H-NMR (400 MHz, DMSO-$d_6$): δ [ppm] = 2.34-2.46 (m, 7H), 3.42-3.57 (m, 6H), 3.65 (q, 2H), 6.94 (d, 1H), 7.19 (s, 1H), 7.31-8.02 (m, 3H), 8.28 (d, 1H), 8.68 (s, 1H), 9.04 (s, 1H), 10.74 (br s, 1H), 12.26 (br s, 1H). |
| Example 189.02 | 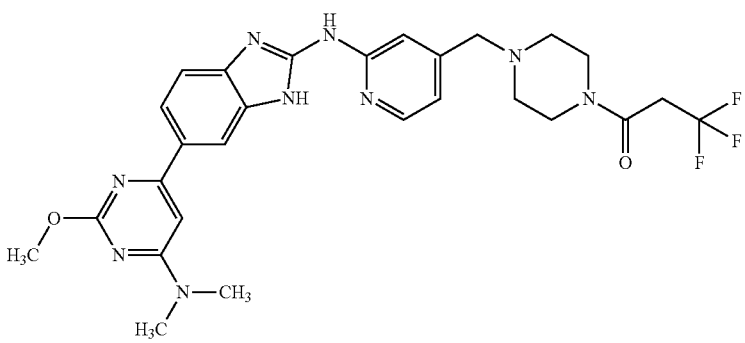 [SMILES: COc1nc(-c2ccc3nc(Nc4cc(CN5CCN(C(=O)CC(F)(F)F)CC5)ccn4)[nH]c3c2)cc(N(C)C)n1]<br>1-(4-{[2-({6-[6-(dimethylamino)-2-methoxypyrimidin-4-yl]-1H-benzimidazol-2-yl}amino)pyridin-4-yl]methyl}piperazin-1-yl)-3,3,3-trifluoropropan-1-one<br>LC-MS (Method 2): $R_t$ = 1.18 min; MS (ESIpos): m/z = 570 [M + H]⁺<br>¹H-NMR (400 MHz, DMSO-$d_6$): δ [ppm] = 2.38 (br t, 2H), 2.40-2.46 (m, 2H), 3.13 (s, 6H), 3.43-3.55 (m, 6H), 3.65 (q, 2H), 3.91 (s, 3H), 6.73-6.85 (m, 1H), 6.94 (br d, 1H), 7.20 (br s, 1H), 7.34-7.58 (m, 1H), 7.87 (br s, 1H), 8.11-8.35 (m, 1H), 8.27 (d, 1H), 10.63-10.78 (m, 1H), 12.22 (br d, 1H). |

TABLE 22-continued

Structure
IUPAC-Name
LC-MS (method): Retention time; Mass found
¹H-NMR

Example 190.02

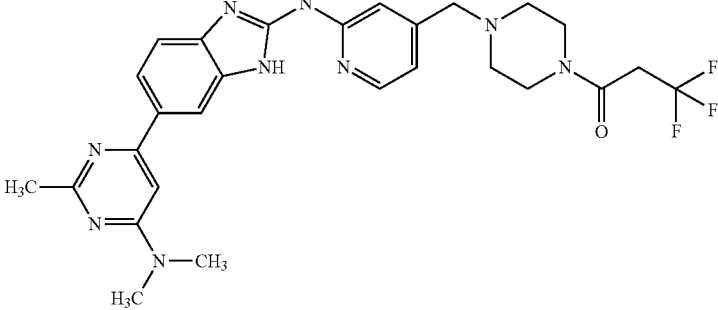

1-(4-{[2-({6-[6-(dimethylamino)-2-methylpyrimidin-4-yl]-1H-benzimidazol-2-yl}amino)pyridin-4-yl]methyl}piperazin-1-yl)-3,3,3-trifluoropropan-1-one
LC-MS (Method 2): R$_t$ = 1.15 min; MS (ESIpos): m/z = 554 [M + H]$^+$
¹H-NMR (400 MHz, DMSO-d$_6$): δ [ppm] = 2.38 (br s, 3H), 2.41-2.45 (m, 2H), 2.46 (s, 3H), 3.14 (s, 6H), 3.43-3.55 (m, 6H), 3.65 (q, 3H), 6.89-6.97 (m, 2H), 7.19 (s, 1H), 7.46 (br s, 1H), 7.53 (br s, 1H), 7.53-7.65 (m, 1H), 7.85 (br d, 1H), 8.26 (d, 1H), 10.73 (br s, 1H), 12.29 (br s, 1H).

Example 191.02

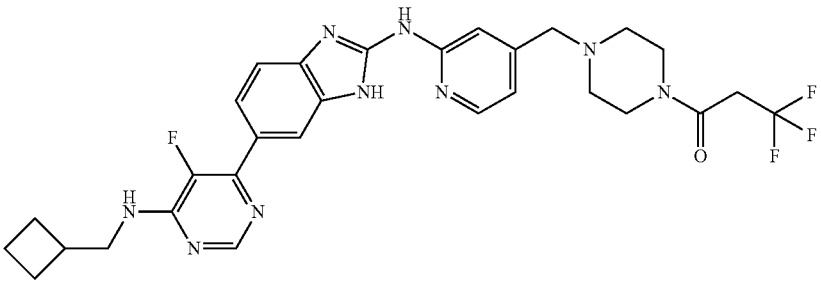 [SMILES: O=C(CC(F)(F)F)N1CCN(Cc2ccnc(Nc3nc4ccc(-c5ncnc(NCC6CCC6)c5F)cc4[nH]3)c2)CC1]

1-[4-({2-[(6-{6-[(cyclobutylmethyl)amino]-5-fluoropyrimidin-4-yl}-1H-benzimidazol-2-yl)amino]pyridin-4-yl}methyl)piperazin-1-yl]-3,3,3-trifluoropropan-1-one
LC-MS (Method 4): R$_t$ = 1.23 min; MS (ESIpos): m/z = 598 [M + H]$^+$
¹H NMR (400 MHz, DMSO-d$_6$) δ ppm 1.69-1.80 (m, 2H) 1.80-1.90 (m, 2H) 1.95-2.05 (m, 2H) 2.40 (dt, 4H) 2.58-2.66 (m, 1H) 3.42-3.49 (m, 4H) 3.49-3.56 (m, 4H) 3.65 (q, 2H) 6.94 (d, 1H) 7.18 (br s, 1H) 7.39-7.61 (m, 1H) 7.63-7.82 (m, 2H) 7.92-8.21 (m, 1H) 8.24-8.31 (m, 2H) 10.74 (br s, 1H) 12.22-12.31 (m, 1H)

Example 192.02

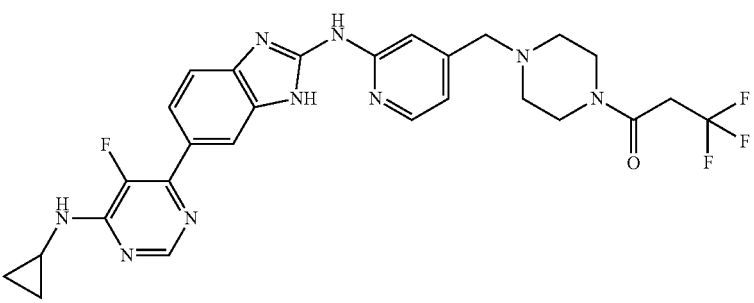 [SMILES: O=C(CC(F)(F)F)N1CCN(Cc2ccnc(Nc3nc4ccc(-c5ncnc(NC6CC6)c5F)cc4[nH]3)c2)CC1]

1-(4-{[2-({6-[6-(cyclopropylamino)-5-fluoropyrimidin-4-yl]-1H-benzimidazol-2-yl}amino)pyridin-4-yl]methyl}piperazin-1-yl)-3,3,3-trifluoropropan-1-one
LC-MS (Method 2): R$_t$ = 1.04 min; MS (ESIpos): m/z = 570 [M + H]$^+$
¹H NMR (400 MHz, DMSO-d$_6$) δ ppm 0.58-0.65 (m, 2H) 0.68-0.81 (m, 2H) 2.40 (dt, 4H) 2.86 (tq, 1H) 3.43-3.57 (m, 6H) 3.65 (q, 2H) 6.94 (d, 1H) 7.18 (br s, 1H) 7.42 (br d, 0.5H) 7.53-7.73 (m, 0.5H) 7.78 (br s, 0.5H) 7.89-8.22 (m, 1.5H) 8.27 (d, 1H) 8.36 (d, 1H) 10.69- 10.78 (m, 1H) 12.23-12.33 (m, 1H)

| Example | Structure<br>IUPAC-Name<br>LC-MS (method): Retention time; Mass found<br>¹H-NMR |
|---|---|
| Example 193.02 | 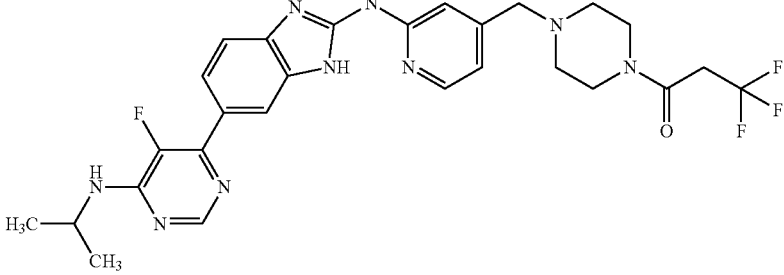<br>3,3,3-trifluoro-1-(4-{[2-({6-[5-fluoro-6-(propan-2-ylamino)pyrimidin-4-yl]-1H-benzimidazol-2-yl}amino)pyridin-4-yl]methyl}piperazin-1-yl)propan-1-one<br>LC-MS (Method 4): $R_t$ = 1.13 min; MS (ESIpos): m/z = 572 [M + H]⁺<br>¹H NMR (400 MHz, DMSO-d₆) δ ppm 1.23 (d, 6H) 2.40 (dt, 4H) 3.48 (dt, 4H) 3.53 (s, 2H) 3.65 (q, 2H) 4.24-4.36 (m, 1H) 6.94 (d, 1H) 7.19 (br s, 1H) 7.36-7.42 (m, 1H) 7.41-7.61 (m, 1H) 7.65-7.80 (m, 1H) 7.92-8.20 (m, 1H) 8.28 (d, 1H) 8.30 (d, 1H) 10.69-10.77 (m, 1H) 12.22-12.32 (m, 1H) |
| Example 194.02 | 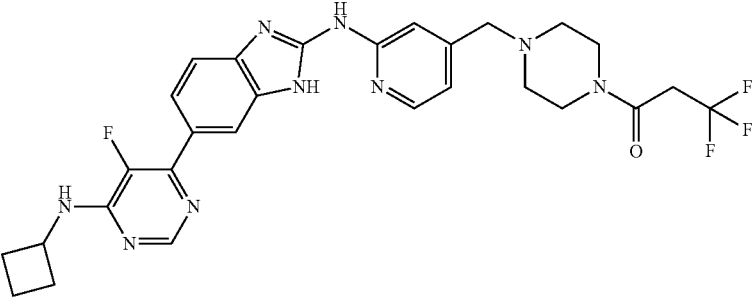 [SMILES: O=C(CC(F)(F)F)N1CCN(Cc2ccnc(Nc3nc4ccc(-c5ncnc(NC6CCC6)c5F)cc4[nH]3)c2)CC1]<br>1-(4-{[2-({6-[6-(cyclobutylamino)-5-fluoropyrimidin-4-yl]-1H-benzimidazol-2-yl}amino)pyridin-4-yl]methyl}piperazin-1-yl)-3,3,3-trifluoropropan-1-one<br>LC-MS(Method 4): $R_t$ = 1.16 min; MS (ESIpos): m/z = 584 [M + H]⁺<br>¹H NMR (400 MHz, DMSO-d₆) δ ppm 1.65-1.75 (m, 2H) 2.06-2.17 (m, 2H) 2.22-2.31 (m, 2H) 2.35-2.46 (m, 4H) 3.43-3.56 (m, 6H) 3.65 (q, 2H) 4.56 (sxt, 1H) 6.94 (d, 1H) 7.18 (br s, 1H) 7.39-7.61 (m, 1H) 7.66-7.80 (m, 1H) 7.83 (br d, 1H) 7.89-8.22 (m, 1H) 8.24-8.32 (m, 2H) 10.74 (br s, 1H) 12.20-12.34 (m, 1H) |
| Example 195.02 | 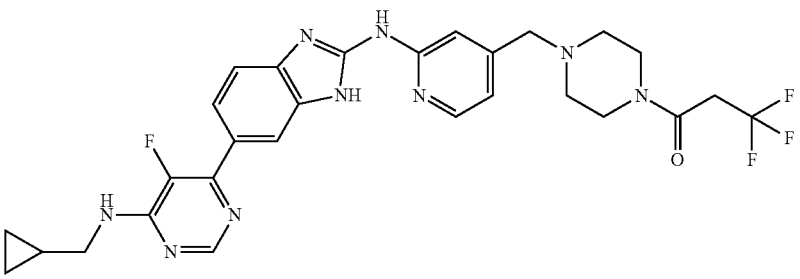 [SMILES: O=C(CC(F)(F)F)N1CCN(Cc2ccnc(Nc3nc4ccc(-c5ncnc(NCC6CC6)c5F)cc4[nH]3)c2)CC1]<br>1-[4-({2-[(6-{6-[(cyclopropylmethyl)amino]-5-fluoropyrimidin-4-yl}-1H-benzimidazol-2-yl)amino]pyridin-4-yl}methyl)piperazin-1-yl]-3,3,3-trifluoropropan-1-one<br>LC-MS (Method 4): $R_t$ = 1.15 min; MS (ESIpos): m/z = 584 [M + H]⁺<br>¹H NMR (400 MHz, DMSO-d₆) δ ppm 0.24-0.31 (m, 2H) 0.42-0.48 (m, 2H) 1.09-1.19 (m, 1H) 2.40 (dt, J = 16.22, 4.69 Hz, 4H) 3.27-3.32 (m, 2H) 3.48 (dt, J = 29.70, 4.91 Hz, 4H) 3.53 (s, 2H) 3.65 (d, J = 11.15 Hz, 2H) 6.95 (d, J = 5.32 Hz, 1H) 7.18 (br s, 1H) 7.39-7.61 (m, 1H) 7.66-7.81 (m, 2H) 7.95 (br s, 0.5H) 8.20 (s, 0.5H) 8.29 (d, J = 9.42 Hz, 1H) 10.69-10.78 (m, 1H) 12.24-12.32 (m, 1H) |

TABLE 22-continued

| Example | Structure<br>IUPAC-Name<br>LC-MS (method): Retention time; Mass found<br>¹H-NMR |
|---|---|
| Example 196.02 | 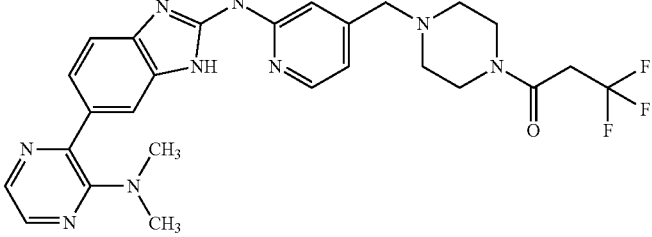<br>1-(4-{[2-({6-[3-(dimethylamino)pyrazin-2-yl]-1H-benzimidazol-2-yl}amino)pyridin-4-yl]methyl}piperazin-1-yl)-3,3,3-trifluoropropan-1-one<br>LC-MS (Method 2): R$_t$ = 1.1 min; MS (ESIpos): m/z = 540 [M + H]$^+$<br>¹H NMR (400 MHz, DMSO-d$_6$) δ ppm 2.40 (dt, 4H) 2.73 (s, 6H) 3.41-3.49 (m, 2H) 3.49-3.55 (m, 4H) 3.65 (q, 2H) 6.93 (d, 1H) 7.19 (s, 1H) 7.33-7.44 (m, 1H) 7.50 (br d, 1H) 7.65-7.93 (m, 1H) 8.04 (d, 1H) 8.05-8.08 (m, 1H) 8.27 (d, 1H) 10.68 (br s, 1H) 12.18 (br s, 1H) |
| Example 199.02 | 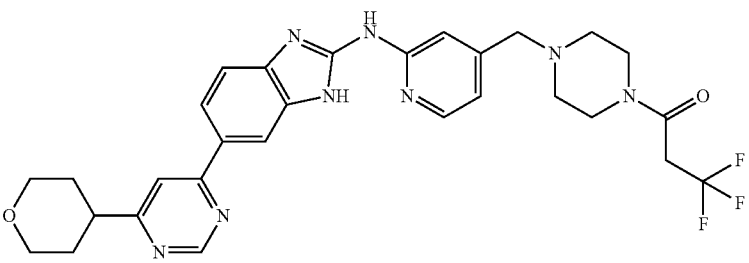 [SMILES: O=C(CC(F)(F)F)N1CCN(Cc2ccnc(Nc3nc4ccc(-c5cc(C6CCOCC6)ncn5)cc4[nH]3)c2)CC1]<br>3,3,3-trifluoro-1-(4-{[2-({6-[6-(tetrahydro-2H-pyran-4-yl)pyrimidin-4-yl]-1H-benzimidazol-2-yl}amino)pyridin-4-yl]methyl}piperazin-1-yl)propan-1-one<br>LC-MS (Method 2): R$_t$ = 1.03 min; MS (ESIpos): m/z = 581 [M + H]$^+$<br>¹H-NMR (400 MHz, DMSO-d$_6$): δ [ppm] = 1.78-1.92 (m, 4H), 2.35-2.46 (m, 4H), 2.94-3.05 (m, 1H), 3.42-3.56 (m, 8H), 3.65 (q, 2H), 3.94-4.04 (m, 2H), 6.95 (t, 1H), 7.20 (s, 1H), 7.39-7.63 (m, 1H), 7.86-8.02 (m, 2H), 8.21-8.46 (m, 2H), 9.08 (d, 1H), 10.78 (br d, 1H), 12.30 (br d, 1H). |

The Example compounds shown below in table 23 were prepared according to the following general procedure: The respective amine (1 eq.; see Compounds 174.01 to 198.01, respectively; Table 6), cyclopropanecarboxylic acid (1.5 eq), NaHCO$_3$ (6 eq.) and HATU (1.5 eq.) were solubilised in DMF and the reaction mixture was stirred at rt between 2 and 48 hours. The crude mixture was directly purified by preparative HPLC without workup to give the respective title compounds.

TABLE 23

| | Structure<br>IUPAC-Name<br>LC-MS (method): Retention time; Mass found |
|---|---|
| Example | ¹H-NMR |

Example 174.03 cyclopropyl(4-{(1R or 1S)-1-[2-({6-[6-(difluoromethyl)pyrimidin-4-yl]-1H-benzimidazol-2-yl}amino)pyridin-4-yl]ethyl}piperazin-1-yl)methanone LC-MS (Method 4): R$_t$ = 1.09 min; MS (ESIpos): m/z = 519 [M + H]⁺
¹H-NMR (400 MHz, DMSO-d$_6$): δ [ppm] = 0.61-0.77 (m, 4H), 1.30 (d, 3H), 1.86-1.98 (m, 1H), 2.24-2.48 (m, 4H), 3.39-3.55 (m, 3H), 3.67 (br s, 2H), 6.98 (dd, 1H), 7.00-7.16 (m, 1H), 7.22 (s, 1H), 7.53 (br s, 1H), 8.04 (dd, 1H), 8.25 (br s, 1H), 8.29 (d, 1H), 8.42 (br s, 1H), 9.29 (s, 1H), 10.82 (br s, 1H), 12.38 (br s, 1H).

Example 175.03

{4-[(2-{[6-(2-chlorothiophen-3-yl)-1H-benzimidazol-2-yl]amino}pyridin-4-yl)methyl]piperazin-1-yl}(cyclopropyl)methanone LC-MS (Method 4): R$_t$ = 1.27 min; MS (ESIpos): m/z = 493 [M + H]⁺
¹H-NMR (400 MHz, DMSO-d$_6$): δ [ppm] = 0.67-0.75 (m, 4H), 1.92-2.00 (m, 1H), 2.36 (br s, 2H), 2.45 (br s, 2H), 3.52 (s, 4H), 3.71 (br s, 2H), 6.94 (dd, 1H), 7.19 (br s, 1H), 7.24 (br s, 2H), 7.37-7.79 (m, 3H), 8.27 (d, 1H), 10.66 (br s, 1H), 12.19 (br d, 1H).

Example 179.03

(4-{[2-({6-[5-chloro-6-(dimethylamino)pyrimidin-4-yl]-1H-benzimidazol-2-yl}amino)pyridin-4-yl]methyl}piperazin-1-yl)(cyclopropyl)methanone LC-MS (Method 4): R$_t$ = 1.10 min; MS (ESIpos): m/z = 532 [M + H]⁺
¹H-NMR (400 MHz, DMSO-d$_6$): δ [ppm] = 0.66-0.74 (m, 4H), 1.91-2.01 (m, 1H), 2.36 (br s, 2H), 2.44 (br s, 2H), 3.18 (s, 6H), 3.46-3.54 (m, 4H), 3.71 (br s, 2H), 6.95 (dd, 1H), 7.19 (s, 1H), 7.40 (br s, 1H), 7.44-7.58 (m, 1H), 7.66-7.95 (m, 1H), 8.27 (d, 1H), 8.50 (s, 1H), 10.73 (br s, 1H), 12.25 (br d, 1H).

TABLE 23-continued

| Example | Structure<br>IUPAC-Name<br>LC-MS (method): Retention time; Mass found<br>¹H-NMR |
|---|---|
| Example 180.03 | 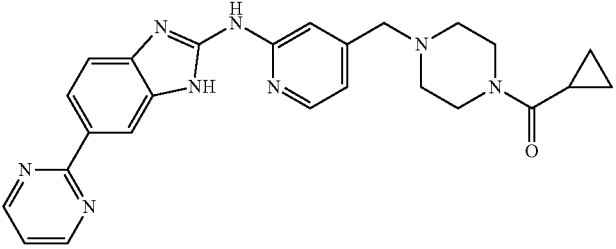 [SMILES: O=C(C1CC1)N1CCN(Cc2ccnc(Nc3nc4ccc(-c5ncccn5)cc4[nH]3)c2)CC1]<br>cyclopropyl{4-[(2-{[6-(pyrimidin-2-yl)-1H-benzimidazol-2-yl]amino}pyridin-4-yl)methyl]piperazin-1-yl}methanone<br>LC-MS (Method 4): $R_t$ = 0.96 min; MS (ESIpos): m/z = 455 [M + H]⁺<br>¹H NMR (400 MHz, DMSO-d₆) δ ppm 0.66-0.75 (m, 4H) 1.93-2.00 (m, 1H) 2.34-2.47 (m, 3H) 3.44-3.59 (m, 4H) 3.71 (br s, 2H) 6.95 (d, 1H) 7.19 (s, 1H) 7.33 (t, 1H) 7.38-7.62 (m, 1H) 8.19 (br d, 1H) 8.28 (d, 1H) 8.36-8.66 (m, 1H) 8.84 (d, 2H) 10.75 (br s, 1H) 12.28 (br s, 1H) |
| Example 181.03 | 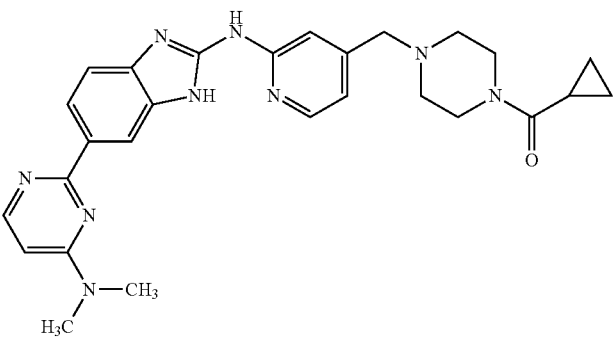 [SMILES: CN(C)c1ccnc(-c2ccc3nc(Nc4cc(CN5CCN(C(=O)C6CC6)CC5)ccn4)[nH]c3c2)n1]<br>cyclopropyl(4-{[2-({6-[4-(dimethylamino)pyrimidin-2-yl]-1H-benzimidazol-2-yl}amino)pyridin-4-yl]methyl}piperazin-1-yl)methanone<br>LC-MS (Method 4): $R_t$ = 1.06 min; MS (ESIpos): m/z = 498.3 [M + H]⁺<br>¹H NMR (400 MHz, DMSO-d₆) δ ppm 0.66-0.75 (m, 4H) 1.92-2.03 (m, 1H) 2.34-2.46 (m, 4H) 3.16 (br s, 5H) 3.53 (s, 4H) 3.71 (br s, 2H) 6.52 (d, 1H) 6.93 (d, 1H) 7.11-7.49 (m, 2H) 8.13 (br d, 1H) 8.20-8.30 (m, 2H) 8.48 (br s, 1H) 10.73 (s, 1H) 12.26 (s, 1H) |
| Example 182.03 | 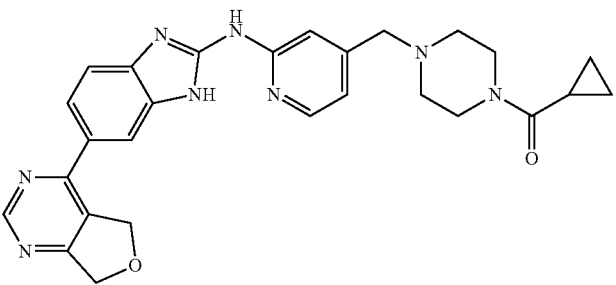 [SMILES: O=C(C1CC1)N1CCN(Cc2ccnc(Nc3nc4ccc(-c5ncnc6c5COC6)cc4[nH]3)c2)CC1]<br>cyclopropyl{4-[(2-{[6-(5,7-dihydrofuro[3,4-d]pyrimidin-4-yl)-1H-benzimidazol-2-yl]amino}pyridin-4-yl)methyl]piperazin-1-yl}methanone<br>LC-MS (Method 4): $R_t$ = 0.93 min; MS (ESIpos): m/z = 497 [M + H]⁺<br>¹H-NMR (400 MHz, DMSO-d₆): δ [ppm] = 0.66-0.75 (m, 4H), 1.91-2.02 (m, 1H), 2.36 (br s, 2H), 2.43 (br s, 2H), 3.50 (br s, 2H), 3.53 (s, 2H), 3.71 (br s, 2H), 5.01 (s, 2H), 5.49 (s, 2H), 6.96 (d, 1H), 7.29 (br s, 1H), 7.51 (br d, 1H), 7.72 (br d, 1H), 8.04 (br s, 1H), 8.25-8.31 (m, 1H), 9.09 (s, 1H), 10.79 (br s, 1H), 12.13-12.58 (m, 1H). |

TABLE 23-continued

| Example | Structure<br>IUPAC-Name<br>LC-MS (method): Retention time; Mass found<br>¹H-NMR |
|---|---|
| Example 183.03 | 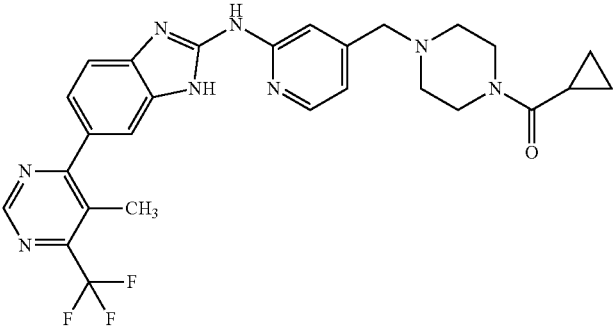 [SMILES: Cc1c(-c2ccc3nc(Nc4cc(CN5CCN(C(=O)C6CC6)CC5)ccn4)[nH]c3c2)ncnc1C(F)(F)F]<br>cyclopropyl(4-{[2-({6-[5-methyl-6-(trifluoromethyl)pyrimidin-4-yl]-1H-benzimidazol-2-yl}amino)pyridin-4-yl]methyl}piperazin-1-yl)methanone<br>LC-MS (Method 4): $R_t$ = 1.16 min; MS (ESIpos): m/z = 537 [M + H]⁺<br>¹H-NMR (400 MHz, DMSO-d₆): δ [ppm] = 0.63-0.77 (m, 4H), 1.91-2.03 (m, 1H), 2.30-2.40 (m, 2H), 2.41-2.47 (m, 2H), 2.51-2.54 (m, 2H), 3.50 (br s, 3H), 3.53 (s, 2H), 3.71 (br s, 2H), 6.96 (d, 1H), 7.21 (s, 1H), 7.26-7.64 (m, 2H), 7.64-7.92 (m, 1H), 8.28 (d, 1H), 9.24 (s, 1H), 10.78 (br d, 1H), 12.31 (s, 1H). |
| Example 184.03 | 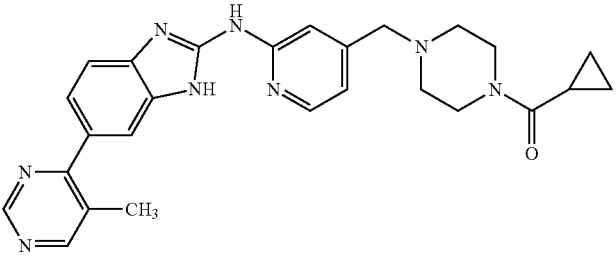 [SMILES: Cc1cncnc1-c1ccc2nc(Nc3cc(CN4CCN(C(=O)C5CC5)CC4)ccn3)[nH]c2c1]<br>cyclopropyl{4-[(2-{[6-(5-methylpyrimidin-4-yl)-1H-benzimidazol-2-yl]amino}pyridin-4-yl)methyl]piperazin-1-yl}methanone<br>LC-MS (Method 4): $R_t$ = 0.94 min; MS (ESIpos): m/z = 469 [M + H]⁺<br>¹H-NMR (400 MHz, DMSO-d₆): δ [ppm] = 0.60-0.78 (m, 4H), 1.90-2.02 (m, 1H), 2.31-2.47 (m, 7H), 3.43-3.59 (m, 4H), 3.71 (br s, 2H), 6.95 (d, 1H), 7.21 (s, 1H), 7.33-7.98 (m, 3H), 8.28 (d, 1H), 8.68 (s, 1H), 9.04 (s, 1H), 10.75 (br s, 1H), 12.28 (br s, 1H). |
| Example 191.03 | 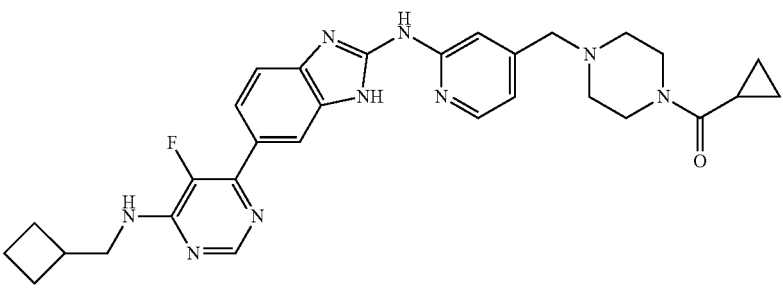 [SMILES: O=C(C1CC1)N1CCN(Cc2ccnc(Nc3nc4ccc(-c5ncnc(NCC6CCC6)c5F)cc4[nH]3)c2)CC1]<br>[4-({2-[(6-{6-[(cyclobutylmethyl)amino]-5-fluoropyrimidin-4-yl}-1H-benzimidazol-2-yl)amino]pyridin-4-yl}methyl)piperazin-1-yl]cyclopropyl)methanone<br>LC-MS (Method 2): $R_t$ = 1.22 min; MS (ESIpos): m/z = 556 [M + H]⁺<br>¹H NMR (400 MHz, DMSO-d₆) δ ppm 0.66-0.75 (m, 4H) 1.69-1.89 (m, 4H) 1.91-2.05 (m, 3H) 2.34-2.47 (m, 4H) 2.58-2.65 (m, 1H) 3.42-3.49 (m, 2H) 3.49-3.56 (m, 4H) 3.71 (br s, 2H) 6.95 (d, 1H) 7.19 (s, 1H) 7.37-7.62 (m, 1H) 7.63-7.81 (m, 2H) 7.91-8.23 (m, 1H) 8.24-8.33 (m, 2H) 10.69-10.78 (m, 1H) 12.23-12.31 (m, 1H) |

TABLE 23-continued

Example | Structure<br>IUPAC-Name<br>LC-MS (method): Retention time; Mass found<br>¹H-NMR Example 192.03

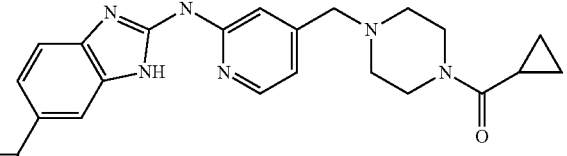

cyclopropyl(4-{[2-({6-[6-(cyclopropylamino)-5-fluoropyrimidin-4-yl]-
1H-benzimidazol-2-yl}amino)pyridin-4-yl]mnethyl}piperazin-1-
yl)methanone LC-MS (Method 4): $R_t$ = 1.01 min; MS (ESIpos): m/z = 528 [M + H]⁺
¹H NMR (400 MHz, DMSO-d₆) δ ppm 0.59-0.77 (m, 8H) 1.92-2.00
(m, 1H) 2.34-2.48 (m, 4H) 2.83-2.94 (m, 1H) 3.50 (br s, 2H) 3.52 (s,
2H) 3.70 (br s, 2H) 6.95 (d, 1H) 7.19 (s, 1H) 7.38-7.62 (m, 1H) 7.66-
7.81 (m, 2H) 7.91-8.22 (m, 1H) 8.27 (d, 1H) 8.36 (d, 1H) 10.74 (br s,
1H) 12.23-12.33 (m, 1H)

Example 193.03

cyclopropyl(4-{[2-({6-[5-fluoro-6-(propan-2-ylamino)pyrimidin-4-yl]-
1H-benzimidazol-2-yl}amino)pyridin-4-yl]methyl}piperazin-1-
yl)methanone LC-MS (Method 4): $R_t$ = 1.1 min; MS (ESIpos): m/z = 530 [M + H]⁺
¹H NMR (400 MHz, DMSO-d₆) δ ppm 0.66-0.76 (m, 4H) 1.23 (d, 6H)
1.96 (tt, 1H) 2.33-2.47 (m, 4H) 3.52 (s, 4H) 3.70 (br s, 2H) 4.25-4.37
(m, 1H) 6.95 (dd, 1H) 7.19 (s, 1H) 7.36-7.42 (m, 1H) 7.42-7.62 (m,
1H) 7.63-7.81 (m, 1H) 7.89-8.23 (m, 1H) 8.28 (d, 1H) 8.30 (d, 1H)
10.74 (br s, 1H) 12.24-12.32 (m, 1H)

Example 194.03

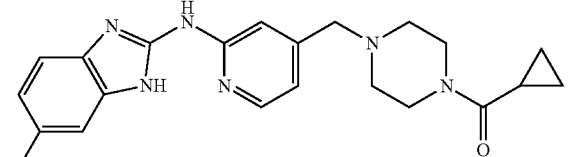

(4-{[2-({6-[6-(cyclobutylamino)-5-fluoropyrimidin-4-yl]-1H-
benzimidazol-2-yl}amino)pyridin-4-yl]methyl}piperazin-1-
yl)(cyclopropyl)methanone LC-MS (Method 4): $R_t$ = 1.13 min; MS (ESIpos): m/z = 542 [M + H]⁺
¹H NMR (400 MHz, DMSO-d₆) δ ppm 0.66-0.76 (m, 4H) 1.61-1.75
(m, 2H) 1.96 (tt, 1H) 2.06-2.18 (m, 2H) 2.22-2.32 (m, 2H) 2.33-2.47
(m, 4H) 3.43-3.60 (m, 4H) 3.70 (br s, 2H) 4.56 (sxt, 1H) 6.95 (dd, 1H)
7.22 (br s, 1H) 7.49 (br s, 1H) 7.73 (br d, 1H) 7.83 (br d, 1H) 7.96-8.21
(m, 1H) 8.23-8.36 (m, 2H) 10.75 (br s, 1H) 12.28 (br s, 1H)

TABLE 23-continued

| | Structure<br>IUPAC-Name<br>LC-MS (method): Retention time; Mass found |
|---|---|
| Example | $^1$H-NMR |

Example 195.03

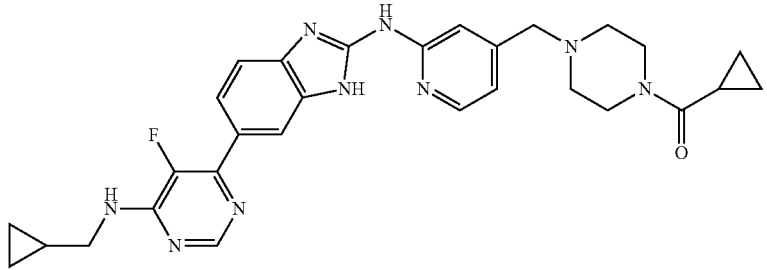 [SMILES: O=C(C1CC1)N1CCN(Cc2ccnc(Nc3nc4ccc(-c5ncnc(NCC6CC6)c5F)cc4[nH]3)c2)CC1]

cyclopropyl[4-({2-[(6-{6-[(cyclopropylmethyl)amino]-5-fluoropyrimidin-4-yl}-1H-benzimidazol-2-yl)amino]pyridin-4-yl}methyl)piperazin-1-yl]methanone
LC-MS (Method 4): R$_t$ = 1.12 min; MS (ESIpos): m/z = 542 [M + H]$^+$
$^1$H NMR (400 MHz, DMSO-d$_6$) δ ppm 0.25-0.31 (m, 2H) 0.39-0.48 (m, 2H) 0.66-0.75 (m, 4H) 1.09-1.19 (m, 1H) 1.93-2.00 (m, 1H) 2.33-2.47 (m, 4H) 3.30 (t, 2H) 3.46-3.54 (m, 4H) 3.70 (br s, 2H) 6.95 (dd, 1H) 7.20 (s, 1H) 7.45 (br s, 1H) 7.70-7.80 (m, 2H) 7.88-8.23 (m, 1H) 8.24-8.31 (m, 2H) 10.74 (br s, 1H) 12.28 (br s, 1H)

Example 196.03

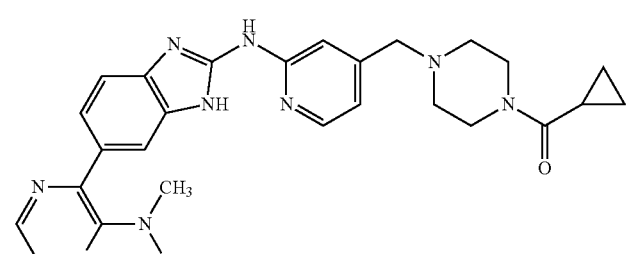

cyclopropyl(4-{[2-({6-[3-(dimethylamino)pyrazin-2-yl]-1H-benzimidazol-2-yl}amino)pyridin-4-yl]methyl}piperazin-1-yl)methanone
LC-MS (Method 2): R$_t$ = 1.06 min; MS (ESIpos): m/z = 498 [M + H]$^+$
$^1$H NMR (400 MHz, DMSO-d$_6$) δ ppm 0.66-0.77 (m, 4H) 1.91-2.00 (m, 1H) 2.34-2.47 (m, 4H) 2.73 (s, 6H) 3.52 (s, 4H) 3.71 (br s, 2H) 6.94 (d, 1H) 7.19 (s, 1H) 7.30-7.60 (m, 2H) 7.64-7.94 (m, 1H) 8.05 (d, 2H) 8.27 (d, 1H) 10.68 (br s, 1H) 12.19 (br s, 1H)

Example 197.04 45

{4-[(1R or 1S)-1-{2-[(6-{6-[(cyclopropylmethyl)(methyl)amino]pyrimidin-4-yl}-1H-benzimidazol-2-yl)amino]pyridin-4-yl}ethyl]piperazin-1-yl}[1-(trifluoromethyl)cyclopropyl]methanone

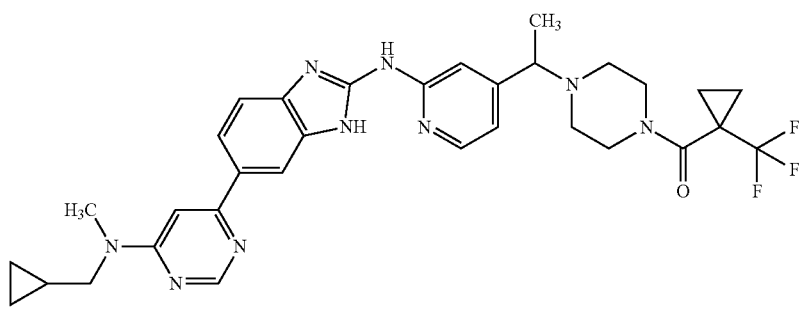 [SMILES: CC(c1ccnc(Nc2nc3ccc(-c4cc(N(C)CC5CC5)ncn4)cc3[nH]2)c1)N1CCN(C(=O)C2(C(F)(F)F)CC2)CC1]

A mixture of 6-{6-[(cyclopropylmethyl)(methyl)amino]pyrimidin-4-yl}-N-{4-[(1R or 1S)-1-(piperazin-1-yl)ethyl]pyridin-2-yl}-1H-benzimidazol-2-amine hydrochloride (115 mg), 1-(trifluoromethyl)cyclopropanecarboxylic acid (89.6 mg), solid NaHCO$_3$ (97.7 mg) and HATU (221 mg) was stirred in DMF (1.2 ml) overnight at rt. The crude mixture was purified without work up by preparative HPLC to give 35.3 mg (95% purity) of the title compound.

LC-MS (Method 2): R$_t$=1.29 min; MS (ESIpos): m/z=620 [M+H]$^+$.

$^1$H-NMR (400 MHz, DMSO-d6): δ [ppm]=0.26-0.54 (m, 4H), 1.01-1.20 (m, 3H), 1.22-1.35 (m, 5H), 2.29-2.47 (m, 4H), 3.17 (s, 3H), 3.42-3.50 (m, 1H), 3.51-3.66 (m, 6H), 6.96 (d, 1H), 7.08 (br s, 1H), 7.18 (s, 1H), 7.38-7.52 (m, 1H), 7.88 (dd, 1H), 8.14-8.34 (m, 2H), 8.52 (d, 1H), 10.72 (br s, 1H), 12.26 (br s, 1H).

Experimental Section—Biological Assays & Biological Data Part

Abbreviations

The following table 24 lists the abbreviations used herein, in particular in the Biological Assays & Biological Data part of the Experimental Section:

TABLE 24

| | |
|---|---|
| μg | microgram |
| μl | microliter |
| μM | micromolar |
| ALS | familial amyotrophic lateral sclerosis |
| ATP | Adenosine triphosphate |
| CCL5 | chemokine (C-C motif) ligand 5 |
| CDK9 | cyclin-dependent kinase 9 |
| CMV | Cytomegalovirus |
| CycT1 | cyclin T1 |
| DMEM | Dulbecco's Modified Eagle Medium |
| DMSO | dimethylsulphoxide |
| EDTA | ethylenediamine tetraacetic acid |
| ERalpha | estrogen receptor alpha |
| FCS | fetal calf serum |
| h | hours |
| HEPES | 4-(2-hydroxyethyl)-1-piperazineethanesulfonic acid |
| HTRF | Homogeneous Time Resolved Fluorescence |
| HUVEC | Human Umbilical Vein Endothelial Cells |
| IC$_{50}$ | half maximal inhibitory concentration |
| IFN | interferon |
| IFN-beta | interferon beta |
| IkBa | nuclear factor of kappa light polypeptide gene enhancer in B-cells inhibitor, alpha |
| IKK | I kappa B kinase |
| IKKα | inhibitor of kappa light polypeptide gene enhancer in B-cells, kinase alpha |
| IKKβ | inhibitor of kappa light polypeptide gene enhancer in B-cells, kinase beta |
| IKKε | inhibitor of kappa light polypeptide gene enhancer in B-cells, kinase epsilon |
| IL-6 | interleukin 6 (interferon, beta 2) |
| IRF | interferon regulatory factor |
| Kras | v-Ki-ras2 Kirsten rat sarcoma viral oncogene homolog |
| Luc2 | Firefly Luciferase 2 |
| MgCl$_2$ | Magnesiumchloride |
| μM | micromolar |
| mM | millimolar |
| NF-kB | nuclear factor of kappa light polypeptide gene enhancer in B-cells |
| Ni-NTA | Nitrilotriacetic acid |
| nM | nanomolar |
| nm | nanometer |
| ON | over night |
| Pca | prostate cancer |
| polyIC | Polyinosinic: polycytidylic acid |
| Poly (I: C)_HMW | Polyinosinic: polycytidylic acid, high molecular weight |

TABLE 24-continued

| | |
|---|---|
| pSer | phospho-serine |
| RalB | v-ral simian leukemia viral oncogene homolog B (ras related; GTP binding protein) |
| RANTES | chemokine (C-C motif) ligand 5 |
| TBK1 | TANK-binding kinase 1 |
| TR-FRET | Time-resolved-Fluorescence Resonance Energy Transfer |
| v/v | volume by volume |

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: TBK1 Low ATP Kinase Assay

TBK1-inhibitory activity of compounds of the present invention at a low ATP concentration after pre-incubation of enzyme and test compounds was quantified employing the TR-FRET-based TBK1 assay as described in the following paragraphs.

Recombinant full-length N-terminally His-tagged human TBK1, expressed in insect cells and purified by Ni-NTA affinity chromatography, was purchased from Life Technologies (Cat. No PR5618B) and used as enzyme. As substrate for the kinase reaction biotinylated peptide biotin-Ahx-GDEDFSSFAEPG (C-terminus in amide form) was used which can be purchased e.g. from the company Biosyntan (Berlin-Buch, Germany).

For the assay 50 nl of a 100-fold concentrated solution of the test compound in DMSO was pipetted into either a black low volume 384well microtiter plate or a black 1536well microtiter plate (Greiner Bio-One, Frickenhausen, Germany), 2 μl of a solution of TBK1 in aqueous assay buffer [50 mM HEPES pH 7.0, 10 mM MgCl$_2$, 1.0 mM dithiothreitol, 0.05% (w/v) bovine serum albumine, 0.01% (v/v) Nonidet-P40 (Sigma), protease inhibitor mixture ("Complete w/o EDTA" from Roche, 1 tablet per 5 ml)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.67 μM=>final conc. in the 5 μl assay volume is 1 μM) in assay buffer and the resulting mixture was incubated for a reaction time of 30 min at 22° C. The concentration of TBK1 was adjusted depending of the activity of the enzyme lot and was chosen appropriate to have the assay in the linear range, a typical concentration is 0.03 μg/ml. The reaction was stopped by the addition of 3 μl of a solution of TR-FRET detection reagents (0.33 μM streptavidine-XL665 [Cisbio Bioassays, Codolet, France], 2.5 nM anti-phospho-Serine anti-body [Merck Millipore, "STK antibody", cat. #35-C$_2$] and 1.25 nM LANCE EU-W1024 labeled anti-mouse IgG anti-body [Perkin-Elmer, product no. AD0077]) in an aqueous EDTA-solution (167 mM EDTA, 0.13% (w/v) bovine serum albumin in 100 mM HEPES/NaOH pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used)) in duplicate values for each concentration and $IC_{50}$ values were calculated using Genedata Screener™ software.

In Vitro Assay 2: TBK1 High ATP Kinase Assay

TBK1-inhibitory activity of compounds of the present invention at a high ATP concentration after pre-incubation of enzyme and test compounds was quantified employing the TR-FRET-based TBK1 assay as described in the following paragraphs.

Recombinant full-length N-terminally His-tagged human TBK1, expressed in insect cells and purified by Ni-NTA affinity chromatography, was purchased from Life Technologies (Cat. No PR5618B) and used as enzyme. As substrate for the kinase reaction biotinylated peptide biotin-Ahx-GDEDFSSFAEPG (C-terminus in amide form) was used which can be purchased e.g. from the company Biosyntan (Berlin-Buch, Germany).

For the assay 50 nl of a 100-fold concentrated solution of the test compound in DMSO was pipetted into either a black low volume 384well microtiter plate or a black 1536well microtiter plate (both Greiner Bio-One, Frickenhausen, Germany), 2 µl of a solution of TBK1 in aqueous assay buffer [50 mM HEPES pH 7.0, 10 mM $MgCl_2$, 1.0 mM dithiothreitol, 0.05% (w/v) bovine serum albumine, 0.01% (v/v) Nonidet-P40 (Sigma), protease inhibitor mixture ("Complete w/o EDTA" from Roche, 1 tablet per 5 ml)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 1.67 mM=>final conc. in the 5 µl assay volume is 1 mM) and substrate (1.67 µM=>final conc. in the 5 µl assay volume is 1 µM) in assay buffer and the resulting mixture was incubated for a reaction time of 30 min at 22° C. The concentration of TBK1 was adjusted depending of the activity of the enzyme lot and was chosen appropriate to have the assay in the linear range, typical concentrations were in the range of 0.002-0.004 µg/ml. The reaction was stopped by the addition of 3 µl of a solution of TR-FRET detection reagents (0.33 µM streptavidine-XL665 [Cisbio Bioassays, Codolet, France], 2.5 nM anti-phosho-Serine anti-body [Merck Millipore, "STK antibody", cat. #35-$C_2$] and 1.25 nM LANCE EU-W1024 labeled anti-mouse IgG anti-body [Perkin-Elmer, product no. AD0077]) in an aqueous EDTA-solution (100 mM EDTA, 0.13% (w/v) bovine serum albumin in 100 mM HEPES/NaOH pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalized (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

In Vitro Assay 3: CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchased from Life Technologies (Cat. No PV4131). As substrate for the kinase reaction biotinylated peptide biotin-Ttds-YISPLK-SPYKISEG (C-terminus in amide form) was used which can be purchased e.g. form the company JERINI peptide technologies (Berlin, Germany).

For the assay 50 nl of a 100 fold concentrated solution of the test compound in DMSO was pipetted into either a black low volume 384well microtiter plate or a black 1536well microtiter plate (both Greiner Bio-One, Frickenhausen, Germany), 2 µl of a solution of CDK9/CycT1 in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/ml. The reaction was stopped by the addition of 3 µl of a solution of TR-FRET detection reagents (0.33 µM streptavidine-XL665 [Cisbio Bioassays, Codolet, France] and 1.67 nM anti-RB(pSer807/pSer811)-anti-body from BD Pharmingen [#558389] and 2 nM LANCE EU-W1024 labeled anti-mouse IgG anti-body [Perkin-Elmer, product no. AD0077]) in an aqueous EDTA-solution (167 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

In Vitro Assay 4: IKKε Low ATP Kinase Assay

IKKε-inhibitory activity of compounds of the present invention at a low ATP concentration after preincubation of enzyme and test compounds was quantified employing the TR-FRET-based IKKε assay as described in the following paragraphs.

A recombinant fusion protein of GST (N-terminally) and full-length human IKKε, expressed in insect cells and purified by glutathione affinity chromatography, was purchased from Life Technologies (Cat. No PV4876) and used as enzyme. As substrate for the kinase reaction biotinylated peptide biotin-Ahx-GDEDFSSFAEPG (C-terminus in amide form) was used which can be purchased e.g. from the company Biosyntan (Berlin-Buch, Germany).

For the assay 50 nl of a 100 fold concentrated solution of the test compound in DMSO was pipetted into either a black low volume 384well microtiter plate or a black 1536well microtiter plate (both Greiner Bio-One, Frickenhausen, Germany), 2 µl of a solution of IKKε in aqueous assay buffer [50 mM HEPES pH 7.0, 10 mM $MgCl_2$, 1.0 mM dithiothreitol, 0.05% (w/v) bovine serum albumin, 0.01% (v/v) Nonidet-P40 (Sigma), protease inhibitor mixture ("Complete w/o EDTA" from Roche, 1 tablet per 5 ml)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 30 min at 22° C. The concentration of IKKε was adjusted depending of the activity of the enzyme lot and was chosen appropriate to have the assay in the linear range, a typical concentration is 0.01 µg/ml. The reaction was stopped by the addition of 3 µl of a solution of TR-FRET detection reagents (0.33 µM streptavidine-XL665 [Cisbio Bioassays, Codolet, France], 2.5 nM anti-phosho-Serine antibody [Merck Millipore, "STK antibody", cat. #35-$C_2$] and 1.25 nM LANCE EU-W1024 labeled anti-mouse IgG antibody [Perkin-Elmer, product no. AD0077]) in an aqueous EDTA-solution (167 mM EDTA, 0.13% (w/v) bovine serum albumin in 100 mM HEPES/NaOH pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.07 nM (20 µM, 5.7 µM, 1.6 µM, 0.47 µM, 0.13 µM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

In Vitro Assay 5: Assay for the Detection of Ikke/TBK1 Inhibition in MDA-MB231 Cells TBK1/IKKε kinases are involved in the regulation of the Toll-like receptor 3 dependent innate immune response pathway. Stimulation of TLR3 by poly-IC activates TBK1/IKKε which in turn phosphorylate the transcription factor IRF3. IRF3 translocates into the cell nucleus and activates the transcription of interferon regulated genes (e.g., IFN-beta, RANTES). The cellular assay for the determination of inhibition of IKKε and TBK1 was performed in MDA-MB231 cells (ATCC, Manassas, USA) that stably express an ISRE-Luciferase reporter responsive for IRF3. The promoter sequence was based on the pISRE-TA-Luc vector (available from Clontech) containing five copies of the ISRE enhancer element, located upstream of the minimal TA promoter. The coding sequence of optimized firefly luciferase luc2 (Promega) was placed downstream of the ISRE-TA element. The final reporter pISRE-TA-luc2 containing a Hygromycin resistance gene was integrated into a lentiviral expression system that was used to generate the stable reporter cells. The coding sequence of the ISRE promoter and luciferase gene is as follows:

```
ISRE-TA-luc2 sequence
                                                    (SEQ ID NO: 1)
1843 AATAGTAGACATAATAGCAACAGACATACAAACTAAAGAATTACAAAAACAAATTACAAA

1903 AATTCAAAATTTTATCGATACTAGTTCTTACGCGTGGTACCGAGCTCTTACGCGTGCTAG

1963 CGAAACTGAAACTGAAACTGAAACTGAAACTGAAACTGAAACTGAAACTGAAACTGAAAC

2023 TAGATCTGGGTATATAATGGAAGCTTGGCATTCCGGTACTGTTGGTAAAGCCACCATGGA
```

-continued

```
2083 AGATGCCAAAAACATTAAGAAGGGCCCAGCGCCATTCTACCCACTCGAAGACGGGACCGC

2143 CGGCGAGCAGCTGCACAAAGCCATGAAGCGCTACGCCCTGGTGCCCGGCACCATCGCCTT

2203 TACCGACGCACATATCGAGGTGGACATTACCTACGCCGAGTACTTCGAGATGAGCGTTCG

2263 GCTGGCAGAAGCTATGAAGCGCTATGGGCTGAATACAAACCATCGGATCGTGGTGTGCAG

2323 CGAGAATAGCTTGCAGTTCTTCATGCCCGTGTTGGGTGCCCTGTTCATCGGTGTGGCTGT

2383 GGCCCCAGCTAACGACATCTACAACGAGCGCGAGCTGCTGAACAGCATGGGCATCAGCCA

2443 GCCCACCGTCGTATTCGTGAGCAAGAAAGGGCTGCAAAAGATCCTCAACGTGCAAAAGAA

2503 GCTACCGATCATACAAAAGATCATCATCATGGATAGCAAGACCGACTACCAGGGCTTCCA

2563 AAGCATGTACACCTTCGTGACTTCCCATTTGCCACCCGGCTTCAACGAGTACGACTTCGT

2623 GCCCGAGAGCTTCGACCGGGACAAAACCATCGCCCTGATCATGAACAGTAGTGGCAGTAC

2683 CGGATTGCCCAAGGGCGTAGCCCTACCGCACCGCACCGCTTGTGTCCGATTCAGTCATGC

2743 CCGCGACCCCATCTTCGGCAACCAGATCATCCCCGACACCGCTATCCTCAGCGTGGTGCC

2803 ATTTCACCACGGCTTCGGCATGTTCACCACGCTGGGCTACTTGATCTGCGGCTTTCGGGT

2863 CGTGCTCATGTACCGCTTCGAGGAGGAGCTATTCTTGCGCAGCTTGCAAGACTATAAGAT

2923 TCAATCTGCCCTGCTGGTGCCCACACTATTTAGCTTCTTCGCTAAGAGCACTCTCATCGA

2983 CAAGTACGACCTAAGCAACTTGCACGAGATCGCCAGCGGCGGGGCGCCGCTCAGCAAGGA

3043 GGTAGGTGAGGCCGTGGCCAAACGCTTCCACCTACCAGGCATCCGCCAGGGCTACGGCCT

3103 GACAGAAACAACCAGCGCCATTCTGATCACCCCCGAAGGGGACGACAAGCCTGGCGCAGT

3163 AGGCAAGGTGGTGCCCTTCTTCGAGGCTAAGGTGGTGGACTTGGACACCGGTAAGACACT

3223 GGGTGTGAACCAGCGCGGCGAGCTGTGCGTCCGTGGCCCCATGATCATGAGCGGCTACGT

3283 TAACAACCCCGAGGCTACAAACGCTCTCATCGACAAGGACGGCTGGCTGCACAGCGGCGA

3343 CATCGCCTACTGGGACGAGGACGAGCACTTCTTCATCGTGGACCGGCTGAAGAGCCTGAT

3403 CAAATACAAGGGCTACCAGGTAGCCCCAGCCGAACTGGAGAGCATCCTGCTGCAACACCC

3463 CAACATCTTCGACGCCGGGGTCGCCGGCCTGCCCGACGACGATGCCGGCGAGCTGCCCGC

3523 CGCAGTCGTCGTGCTGGAACACGGTAAAACCATGACCGAGAAGGAGATCGTGGACTATGT

3583 GGCCAGCCAGGTTACAACCGCCAAGAAGCTGCGCGGTGGTGTTGTGTTCGTGGACGAGGT

3643 GCCTAAAGGACTGACCGGCAAGTTGGACGCCCGCAAGATCCGCGAGATTCTCATTAAGGC

3703 CAAGAAGGGCGGCAAGATCGCCGTGTAATAATTCTAGAACGAAGCGGCCGCAGGGTTTAA
```

ISRE-TA 1945-2040
Luc2 2078-3730 (1652 bp)

The ISRE-luc2-MDA-MB231 cells were cultured in DMEM/Ham's F12 (Gibco #21041) supplemented with 10% fetal calf serum (typically but not exclusively used: FCS Gold Gibco-No. 10500-064), 2 mM L-glutamine (Gibco-No. 35050-038), 150 µg/ml Hygromycin B, cryopreserved in 90% FCS+10% dimethylsulphoxide (DMSO) and stored as frozen aliquots of typically 5-10 million cells/vial at −150° C. or below until further use.

For the assay, sufficient cells were rapidly thawed in a 37° C. water bath and pipetted into pre-warmed assay medium (DMEM/Ham's F12, 10% FCS, 2 mM L-glutamine, 1% Penicillin/Streptomycin (Biochrom AG; #A2213)). The cells were centrifuged for 5 min at 180×g. The supernatant was removed and the cell pellet was resuspended in fresh medium to give a suspension of 2.4 million cells/ml. Poly (I:C) HMW (InvivoGen, #tlrl-pic) was diluted in assay medium to 0.2 mg/L and subsequently mixed with the cell suspension in 1:1 ratio.

Fifty nl of a 100-fold concentrated solution of the test compound in DMSO were transferred into a white microtiter test plate (384 or 1536, Greiner Bio-One, Frickenhausen, Germany). For this, either a Hummingbird liquid handler (Digilab, MA, USA) or an Echo acoustic system (Labcyte, CA, USA) was used. Five µl of a freshly prepared cell suspension was added to the wells of a test plate and incubated at 37° C. in a 5% $CO_2$ atmosphere. The inhibitor control cell suspension was added to empty wells at the side of the test plate. After completion of the incubation for 20-24 hours, 2.5 µl of Steady-Glo® Luciferase detection solution (Promega), prepared as recommended by the supplier, were added to all wells. The test plate was incubated at 20° C. for 30 min before measurement of the luminescence in a microplate reader (typically Pherastar by BMG, Germany, or ViewLux by Perkin-Elmer, USA). Data were normalized (cells without inhibitor=0% inhibition, cells with reference inhibitor=100% inhibition). Compounds were tested in duplicates at up to 11 concentrations (for example 20 µM, 5.7 µM, 1.6 µM, 0.47 µM, 0.13 µM, 38 nM, 11 nM, 3.1 nM, 0.89 nM, 0.25 nM and 0.073 nM). Dilution series were made prior to the assay in a 100 fold concentrated form by serial dilution. $IC_{50}$ values were calculated by 4-Parameter fitting using a commercial software package (Genedata Screener, Switzerland).

To prepare the inhibitor control cell suspension, a part of prepared the cell suspension mixture was supplemented with 10 µM of a reference inhibitor, for the generation of above mentioned 100% inhibition reference for data normalization.

In Vitro Assay 6: Counterassay for the Detection of Off-Target Inhibition in MDA-MB231 Cells The cellular assay for the determination of off-target inhibition for IKKε and TBK1 was performed in MDA-MB231 (ATCC, Manassas, USA) cells that stably express a constitutively active CMV-Luciferase reporter. Selective IKKε/TBK1 inhibitors are inactive, whereas inhibition of the firefly luciferase assay indicates off-target inhibition, e.g. transcriptional or translational inhibition, toxicity or inhibition of the luciferase activity. The coding sequence of the CMV promoter and luciferase gene is as follows:

```
                                                    (SEQ ID NO: 2)
   1 CTCGAGATCCGGCCATTAGCCATATTATTCATTGGTTATATAGCATAAATCAATATTGGC

61 TATTGGCCATTGCATACGTTGTATCCATATCATAATATGTACATTTATATTGGCTCATGT

121 CCAACATTACCGCCATGTTGACATTGATTATTGACTAGTTATTAATAGTAATCAATTACG

181 GGGTCATTAGTTCATAGCCCATATATGGAGTTCCGCGTTACATAACTTACGGTAAATGGC

241 CCGCCTGGCTGACCGCCCAACGACCCCCGCCCATTGACGTCAATAATGACGTATGTTCCC

301 ATAGTAACGCCAATAGGGACTTTCCATTGACGTCAATGGGTGGAGTATTTACGGTAAACT

361 GCCCACTTGGCAGTACATCAAGTGTATCATATGCCAAGTACGCCCCCTATTGACGTCAAT

421 GACGGTAAATGGCCCGCCTGGCATTATGCCCAGTACATGACCTTATGGGACTTTCCTACT

481 TGGCAGTACATCTACGTATTAGTCATCGCTATTACCATGGTGATGCGGTTTTGGCAGTAC

541 ATCAATGGGCGTGGATAGCGGTTTGACTCACGGGGATTTCCAAGTCTCCACCCCATTGAC

601 GTCAATGGGAGTTTGTTTTGGCACCAAAATCAACGGGACTTTCCAAAATGTCGTAACAAC

661 TCCGCCCCATTGACGCAAATGGGCGGTAGGCATGTACGGTGGGAGGTCTATATAAGCAGA

721 GCTCGTTTAGTGAACCGTCAGATCGCCTGGAGACGCCATCCACGCTGTTTTGACCTCCAT

781 AGAAGACACCGGGACCGATCCAGCCTCCGCGGCCCCAAGCTTGGCAATCCGGTACTGTTG

841 GTAAAGCCACCATGGAAGATGCCAAAAACATTAAGAAGGGCCCAGCGCCATTCTACCCAC

901 TCGAAGACGGGACCGCCGGCGAGCAGCTGCACAAAGCCATGAAGCGCTACGCCCTGGTGC

961 CCGGCACCATCGCCTTTACCGACGCACATATCGAGGTGGACATTACCTACGCCGAGTACT

1021 TCGAGATGAGCGTTCGGCTGGCAGAAGCTATGAAGCGCTATGGGCTGAATACAAACCATC

1081 GGATCGTGGTGTGCAGCGAGAATAGCTTGCAGTTCTTCATGCCCGTGTTGGGTGCCCTGT

1141 TCATCGGTGTGGCTGTGGCCCCAGCTAACGACATCTACAACGAGCGCGAGCTGCTGAACA

1201 GCATGGGCATCAGCCAGCCCACCGTCGTATTCGTGAGCAAGAAAGGGCTGCAAAAGATCC

1261 TCAACGTGCAAAAGAAGCTACCGATCATACAAAAGATCATCATCATGGATAGCAAGACCG

1321 ACTACCAGGGCTTCCAAAGCATGTACACCTTCGTGACTTCCCATTTGCCACCCGGCTTCA

1381 ACGAGTACGACTTCGTGCCCGAGAGCTTCGACCGGGACAAAACCATCGCCCTGATCATGA

1441 ACAGTAGTGGCAGTACCGGATTGCCCAAGGGCGTAGCCCTACCGCACCGCACCGCTTGTG

1501 TCCGATTCAGTCATGCCCGCGACCCCATCTTCGGCAACCAGATCATCCCCGACACCGCTA

1561 TCCTCAGCGTGGTGCCATTTCACCACGGCTTCGGCATGTTCACCACGCTGGGCTACTTGA

1621 TCTGCGGCTTTCGGGTCGTGCTCATGTACCGCTTCGAGGAGGAGCTATTCTTGCGCAGCT

1681 TGCAAGACTATAAGATTCAATCTGCCCTGCTGGTGCCCACACTATTTAGCTTCTTCGCTA

1741 AGAGCACTCTCATCGACAAGTACGACCTAAGCAACTTGCACGAGATCGCCAGCGGCGGGG

1801 CGCCGCTCAGCAAGGAGGTAGGTGAGGCCGTGGCCAAACGCTTCCACCTACCAGGCATCC

1861 GCCAGGGCTACGGCCTGACAGAAACAACCAGCGCCATTCTGATCACCCCCGAAGGGGACG
```

```
                                -continued
1921 ACAAGCCTGGCGCAGTAGGCAAGGTGGTGCCCTTCTTCGAGGCTAAGGTGGTGGACTTGG

1981 ACACCGGTAAGACACTGGGTGTGAACCAGCGCGGCGAGCTGTGCGTCCGTGGCCCCATGA

2041 TCATGAGCGGCTACGTTAACAACCCCGAGGCTACAAACGCTCTCATCGACAAGGACGGCT

2101 GGCTGCACAGCGGCGACATCGCCTACTGGGACGAGGACGAGCACTTCTTCATCGTGGACC

2161 GGCTGAAGAGCCTGATCAAATACAAGGGCTACCAGGTAGCCCCAGCCGAACTGGAGAGCA

2221 TCCTGCTGCAACACCCCAACATCTTCGACGCCGGGGTCGCCGGCCTGCCCGACGACGATG

2281 CCGGCGAGCTGCCCGCCGCAGTCGTCGTGCTGGAACACGGTAAAACCATGACCGAGAAGG

2341 AGATCGTGGACTATGTGGCCAGCCAGGTTACAACCGCCAAGAAGCTGCGCGGTGGTGTTG

2401 TGTTCGTGGACGAGGTGCCTAAAGGACTGACCGGCAAGTTGGACGCCCGCAAGATCCGCG

2461 AGATTCTCATTAAGGCCAAGAAGGGCGGCAAGATCGCCGTGTAATAATTCTAGAACGAAG

2521 CGGCCGCAGGGTTTAAACACGGTCGACGGTACCGCGGGCCCAACATCGATAAAATAAAAG

2581 ATTTTATTTAGTCTCCAGAAAAAGGGGGGAATGAAAGACCCCACCTGTAGGTTTGGCAAG

2641 CTAGCTTAAGTAACGCCATTTTGCAAGGCATGGAAAAATACATAACTGAGAATAGAGAAG

2701 TTCAGATCAAGGTCAGGAACAGATGGAACAGCTGAATATGGGCCAAACAGGATATCTGTG
```

CMV promoter 1-813
Luc2 852-2504 (1652 bp)

The CMV-luc2-MDA-MB231 cell were cultured in DMEM/Ham's F12 (Gibco #21041) supplemented with 10% fetal calf serum (typically but not exclusively used: FCS Gold Gibco-No. 10500-064), 150 µg/ml Hygromycin B, cryopreserved in 90% culture medium+10% dimethylsulfoxide (DMSO) and stored as frozen aliquots of typically 5-10 million cells/vial at −150° C. or below until further use.

For the assay, sufficient cells were rapidly thawed in a 37° C. water bath and pipetted into pre-warmed assay medium (DMEM/Ham's F12, 10% FCS, 2 mM L-glutamine, 1% Penicillin/Streptomycin (Biochrom AG; #A2213)). The cells were centrifuged for 5 min at 180×g. The supernatant was removed and the cell pellet was resuspended in fresh medium to give a suspension of 0.3 million cells/ml. Poly (I:C)_HMW (InvivoGen, #tlrl-pic) was diluted in assay medium to 0.2 mg/L and subsequently mixed with the cell suspension in 1:1 ratio.

To prepare the inhibitor control cell suspension, a part of prepared the cell suspension mixture was supplemented with 5 µM of Actinomycin D (Sigma A1410).

Fifty nl of a 100-fold concentrated solution of the test compound in DMSO were transferred into a white microtiter test plate (384 or 1536, Greiner Bio-One, Frickenhausen, Germany). For this, either a Hummingbird liquid handler (Digilab, MA, USA) or an Echo acoustic system (Labcyte, CA, USA) was used. Five µl of a freshly prepared cell suspension was added to the wells of a test plate and incubated at 37° C. in a 5% $CO_2$ atmosphere. The inhibitor control cell suspension was added to empty wells at the side of the test plate. After completion of the incubation for 20-24 hours, 2.5 µl of Steady-Glo® Luciferase detection solution (Promega), prepared as recommended by the supplier, were added to all wells. The test plate was incubated at 20° C. for 30 min before measurement of the luminescence in a microplate reader (typically Pherastar by BMG, Germany, or ViewLux by Perkin-Elmer, USA). Data were normalized (cells without inhibitor=0% inhibition, cells with reference inhibitor=100% inhibition). Compounds were tested in duplicates at up to 11 concentrations (for example 20 µM, 5.7 µM, 1.6 µM, 0.47 µM, 0.13 µM, 38 nM, 11 nM, 3.1 nM, 0.89 nM, 0.25 nM and 0.073 nM). Dilution series were made prior to the assay in a 100 fold concentrated form by serial dilution. $IC_{50}$ values were calculated by 4-Parameter fitting using a commercial software package (Genedata Screener, Switzerland).

In Vitro Assay 7: pIRF3 Cell Based Mechanistic Assay

IKKε and TBK1 are highly homologous serine/threonine kinases which are in involved in innate anti-viral immunity and which phosphorylates Interferon regulatory factor 3. pIRF3 (Ser 386) is measured in an HTRF assay (CisBio, Codolet, France). This assay is designed for the quantitative determination of phosphoSer(385/386) of human IRF3 protein. pSer(385/386) IRF3 is measured in a sandwich assay format using 2 different specific antibodies, one labelled with Cryptate (donor) and the second with d2 (acceptor). The two conjugates bind to the phosphorylated IRF3 present in the sample, thereby generating FRET. The intensity of the signal obtained is proportional to the number of antigen-antibody complexes formed and therefore the fluorescence is proportional to the concentration of the pSer(385/386) IRF3.

Protocol: The cellular assay for the determination of inhibition of IKKε and TBK1 was performed in MDA-MB231 cells (ATCC, Manassas, USA) that stably overexpress human IRF3 (human interferon regulatory factor 3 (IRF3; NM_001571)) under the control of the CMV promoter. The coding sequence for human IRF3 (from cDNA clone pCMV6-XL4-IRF3, Origene, Rockville, Md.; USA) was cloned into a lentiviral expression system containing a Hygromycin resistance gene. Derived lentiviral particles were used to generate the stable reporter cells. The clone MDA MB 231 mIRF3 #12 was selected for the assays.

The coding sequence of the CMV promoter and IRF3 gene is as follows:

```
                                                      (SEQ ID NO: 3)
ACTAGTATTATGCCCAGTACATGACCTTATGGGACTTTCCTACTTGGCAG

TACATCTACGTATTAGTCATCGCTATTACCATGGTGATGCGGTTTTGGCA
```

```
-continued
GTACATCAATGGGCGTGGATAGCGGTTTGACTCACGGGGATTTCCAAGTC

TCCACCCCATTGACGTCAATGGGAGTTTGTTTTGGCACCAAAATCAACGG

GACTTTCCAAAATGTCGTAACAACTCCGCCCCATTGACGCAAATGGGCGG

TAGGCGTGTACGGTGGGAGGTCTATATAAGCAGAGCTCGTTTAGTGAACC

GTCAGATCGCCTGGAGACGCCATCCACGCTGTTTTGACCTCCATAGAAGA

TTCTAGAGCTAGCGCTCAACTTTGTATAGAAAAGTTGACTAGTCCAGTGT

GGTGGAATTCTGCAGATATCAACAAGTTTGTACAAAAAAGCAGGCTGCCA

CCATGGGAACCCCAAAGCCACGGATCCTGCCCTGGCTGGTGTCGCAGCTG

GACCTGGGGCAACTGGAGGGCGTGGCCTGGGTGAACAAGAGCCGCACGCG

CTTCCGCATCCCTTGGAAGCACGGCCTACGGCAGGATGCACAGCAGGAGG

ATTTCGGAATCTTCCAGGCCTGGGCCGAGGCCACTGGTGCATATGTTCCC

GGGAGGGATAAGCCAGACCTGCCAACCTGGAAGAGGAATTTCCGCTCTGC

CCTCAACCGCAAAGAAGGGTTGCGTTTAGCAGAGGACCGGAGCAAGGACC

CTCACGACCCACATAAAATCTACGAGTTTGTGAACTCAGGAGTTGGGGAC

TTTTCCCAGCCAGACACCTCTCCGGACACCAATGGTGGAGGCAGTACTTC

TGATACCCAGGAAGACATTCTGGATGAGTTACTGGGTAACATGGTGTTGG

CCCCACTCCCAGATCCGGGACCCCCAAGCCTGGCTGTAGCCCCTGAGCCC

TGCCCTCAGCCCCTGCGGAGCCCCAGCTTGGACAATCCCACTCCCTTCCC

AAACCTGGGGCCCTCTGAGAACCCACTGAAGCGGCTGTTGGTGCCGGGGG

AAGAGTGGGAGTTCGAGGTGACAGCCTTCTACCGGGGCCGCCAAGTCTTC

CAGCAGACCATCTCCTGCCCGGAGGGCCTGCGGCTGGTGGGGTCCGAAGT

GGGAGACAGGACGCTGCCTGGATGGCCAGTCACACTGCCAGACCCTGGCA

TGTCCCTGACAGACAGGGGAGTGATGAGCTACGTGAGGCATGTGCTGAGC

TGCCTGGGTGGGGACTGGCTCTCTGGCGGGCCGGGCAGTGGCTCTGGGC

CCAGCGGCTGGGGCACTGCCACACATACTGGGCAGTGAGCGAGGAGCTGC

TCCCCAACAGCGGGCATGGGCCTGATGGCGAGGTCCCCAAGGACAAGGAA

GGAGGCGTGTTTGACCTGGGGCCCTTCATTGTAGATCTGATTACCTTCAC

GGAAGGAAGCGGACGCTCACCACGCTATGCCCTCTGGTTCTGTGTGGGGG

AGTCATGGCCCCAGGACCAGCCGTGGACCAAGAGGCTCGTGATGGTCAAG

GTTGTGCCCACGTGCCTCAGGGCCTTGGTAGAAATGGCCCGGGTAGGGGG

TGCCTCCTCCCTGGAGAATACTGTGGACCTGCACATTTCCAACAGCCACC

CACTCTCCCTCACCTCCGACCAGTACAAGGCCTACCTGCAGGACTTGGTG

GAGGGCATGGATTTCCAGGGCCCTGGGGAGAGCTGA
```

MDA MB 231 mIRF3 #12 cells were plated in 384well plates at 10.000 cells/well in 30 μl DMEM/Ham's F12+10% FCS per well. After ON incubation at 37° C./5% $CO_2$, the medium was exchanged for phenol red-free medium. Compounds were added by HP Dispenser with compounds diluted in DMSO, maximal compound concentration was 30 μM, then 1:3 dilution steps, i.e. 30 μM, 10 μM, 3.3, μM etc, were applied using a HP D300 digital dispenser (Tecan, Germany). Normalization was done with DMSO to a final concentration of 0.6% per well. The cells were incubated for 1 h in an incubator, then poly IC was added to stimulate the cells (100 μM poly IC were diluted in 1000 μl OptiMEM (Gibco); in parallel 300 μl Lipofectamine 2000 (Life Tech-nologies) were diluted in 1000 μl OptiMEM. Both solutions were mixed and incubated for 20 min at room temperature, then 3 μl per well (=0.15 μg/30 μl (5 μg/ml) PolyIC/Lipofectamine2000) were added. The cells were incubated for another hour in an incubator, then the plate was assayed according to the manufacturer (Cisbio Bioassays, Codolet, France, item #6FRF3PEH, IRF3 phospho-S385/386 kit): the medium was removed, then 18 μl of supplemented Lysis buffer #2 (1.9 ml Lysis buffer #2 (4×), +58 μl Blocking Reagent, included in Kit (100×), +3.84 ml ultrapure water) were added. 16 μl of the lysate were transferred into a 384well small volume white plate (Greiner Bio-One, Germany), the antibodies (included in the kit) were added and the plate was sealed with foil and incubated for 3 h at room temperature. Finally the measurement was done in a Pherastar (BMG, Germany) with 2 wavelengths (665 nm und 620 nm). $IC_{50}$ values were calculated by 4-Parameter fitting using a commercial software package (Genedata Screener, Switzerland).

In Vitro Assay 8: ACHN Antiproliferation Assay

Tissue cultured ACHN human kidney renal cell adenocarcinoma cells (ATCC, Manassas, USA) were plated at 300 cells/well in 50 μl Earle's MEM (Biochrom; #FG 0325, with stable glutamine and 10% FCS, typically but not exclusively used: FCS Gold Gibco-No. 10500-064) in 384well microtiter plates (Corning 3707 white/clear bottom, Corning, Germany). All plates were incubated ON in an incubator at 37° C., 5% $CO_2$. The next day one plate was measured for time zero determination (using CTG solution, see below). The rest of the plates were treated with test compounds by a HP D300 digital dispenser (Tecan, Germany) with a starting concentration of 30 μM and subsequent 1:3 dilution steps. The plates were incubated at 37° C. for 96 h. Thereafter the plates were measured by addition of 40 ul/well CTG solution (Promega Cell Titer Glo solution (catalog number G755B and G756B)), incubation for 30 min on a shaker (Heidolph Titramax 1000, Heidolph, Germany) in the dark and afterwards luminescence was measured in a VICTOR V (Perkin Elmer). $IC_{50}$ values were calculated by 4-Parameter fitting using a commercial software package (Genedata Screener, Switzerland).

In Vitro Assay 9: Calu-1 Antiproliferation Assay

Tissue cultured Calu-1 human lung epidermoid carcinoma cells (CLS Cell Lines Services, Eppelheim, Germany) were plated at 870 cells/well in 50 μl McCoy's 5A (Biochrom; #F 1015 and 10% FCS, typically but not exclusively used: FCS Gold Gibco-No. 10500-064) in 384well microtiter plates (Corning 3707 white/clear bottom, Corning, Germany). All plates were incubated ON in an incubator at 37° C., 5% $CO_2$. The next day one plate was measured for time zero determination (using CTG solution, see below). The rest of the plates were treated with test compounds by a HP D300 digital dispenser (Tecan, Germany) with a starting concentration of 30 μM and subsequent 1:3 dilution steps. The plates were incubated at 37° C. for 96 h. Thereafter the plates were measured by addition of 40 ul/well CTG solution (Promega Cell Titer Glo solution (catalog number G755B and G756B)), incubation for 30 min on a shaker (Heidolph Titramax 1000, Heidolph, Germany) in the dark and afterwards luminescence was measured in a VICTOR V (Perkin Elmer). $IC_{50}$ values were calculated by 4-Parameter fitting using a commercial software package (Genedata Screener, Switzerland).

TABLE 25

TBK1 low ATP kinase assay: IC$_{50}$ values of examples in in vitro assay 1

| Example | TBK1 low ATP kinase assay IC$_{50}$ [M] |
|---|---|
| Example 01.01 | 1.50E−7 |
| Example 01.02 | 4.20E−8 |
| Example 01.03 | 5.35E−8 |
| Example 01.04 | 5.55E−8 |
| Example 01.05 | 7.09E−8 |
| Example 02.01 | 1.31E−7 |
| Example 02.02 | 3.07E−8 |
| Example 02.03 | 3.68E−8 |
| Example 02.04 | 4.34E−8 |
| Example 02.05 | 4.98E−8 |
| Example 03.01 | 1.98E−7 |
| Example 03.02 | 2.32E−7 |
| Example 03.03 | 2.79E−7 |
| Example 03.04 | 2.88E−7 |
| Example 04.01 | 2.85E−8 |
| Example 04.02 | 1.64E−8 |
| Example 04.03 | 1.93E−8 |
| Example 04.04 | 2.24E−8 |
| Example 04.05 | 2.53E−8 |
| Example 04.06 | 3.02E−8 |
| Example 05.01 | 5.22E−8 |
| Example 06.01 | 4.31E−9 |
| Example 06.02 | 7.12E−9 |
| Example 06.03 | 8.26E−9 |
| Example 07.01 | 2.24E−7 |
| Example 07.02 | 2.77E−7 |
| Example 07.03 | 3.84E−7 |
| Example 07.04 | 4.44E−7 |
| Example 08.01 | 6.24E−7 |
| Example 09.01 | 2.51E−7 |
| Example 09.02 | 2.97E−7 |
| Example 09.03 | 3.24E−7 |
| Example 09.04 | 3.52E−7 |
| Example 10.01 | 2.26E−6 |
| Example 11.01 | 3.61E−6 |
| Example 12.01 | >2.00E−5 |
|  | >2.00E−5 |
|  | 1.00E−5 |
|  | 8.12E−6 |
| Example 12.02 | 9.24E−7 |
| Example 12.03 | 5.35E−7 |
| Example 13.01 | 1.25E−6 |
| Example 13.02 | 1.66E−7 |
| Example 13.03 | 1.90E−7 |
| Example 14.01 | 1.95E−7 |
| Example 14.02 | 2.83E−7 |
| Example 14.03 | 5.50E−7 |
| Example 15.01 | 3.39E−7 |
| Example 15.02 | 4.01E−7 |
| Example 15.03 | 3.81E−6 |
| Example 16.01.01 | 2.30E−7 |
| Example 16.01.02 | 1.09E−7 |
| Example 16.01.03 | 1.15E−7 |
| Example 16.01.04 | 6.70E−8 |
| Example 16.01.05 | 1.46E−7 |
| Example 16.01.06 | 2.08E−7 |
| Example 16.02.01 | 2.26E−6 |
| Example 16.02.02 | 3.35E−7 |
| Example 16.02.03 | 2.27E−7 |
| Example 16.02.04 | 2.68E−7 |
| Example 16.02.05 | 4.05E−7 |
| Example 16.03.01 | 1.25E−7 |
| Example 16.03.02 | 6.31E−8 |
| Example 16.03.03 | 6.70E−8 |
| Example 16.03.04 | 5.46E−8 |
| Example 16.03.05 | 8.47E−8 |
| Example 16.04.01 | >2.00E−5 |
|  | >2.00E−5 |
|  | 1.40E−6 |
|  | 2.61E−6 |
| Example 16.04.02 | 4.96E−7 |
| Example 16.04.03 | 3.78E−7 |
| Example 16.04.04 | 4.97E−7 |
| Example 16.04.05 | 4.91E−7 |
| Example 16.05.01 | 8.25E−8 |
| Example 16.05.02 | 3.30E−8 |
| Example 16.05.03 | 4.31E−8 |
| Example 16.06.01.A | Not determined |
| Example 16.06.02.A | 1.05E−7 |
| Example 16.06.02.B | 1.72E−8 |
| Example 16.06.03.A | 1.38E−8 |
| Example 17.01 | 9.78E−8 |
| Example 17.02 | 6.49E−8 |
| Example 17.03 | 5.65E−8 |
| Example 17.04 | 1.02E−7 |
| Example 17.05 | 3.82E−8 |
| Example 17.06 | 6.13E−8 |
| Example 17.07 | 1.02E−7 |
| Example 18.01 | 7.24E−8 |
| Example 18.02 | 1.54E−7 |
| Example 19.01 | 4.14E−7 |
| Example 20.01 | 6.85E−7 |
| Example 21.01 | 1.93E−7 |
| Example 22.01 | 4.81E−7 |
| Example 22.02 | 7.79E−7 |
| Example 23.01.01 | 3.34E−8 |
| Example 23.01.02 | 2.21E−8 |
| Example 23.02.01 | 2.04E−8 |
| Example 23.02.02 | 1.36E−8 |
| Example 23.03.01 | 1.61E−7 |
| Example 23.04.01 | 3.44E−9 |
| Example 23.04.02 | 2.42E−9 |
| Example 23.04.03 | 2.47E−9 |
| Example 23.05.01.A | 2.05E−9 |
| Example 23.05.01.B | 1.24E−8 |
| Example 23.05.02.A | 8.23E−9 |
| Example 23.05.02.B | 1.86E−9 |
| Example 23.05.03.A | 2.99E−9 |
| Example 23.05.03.B | 1.45E−8 |
| Example 24.01.01 | 3.54E−8 |
| Example 24.01.02 | 3.99E−8 |
| Example 24.01.03 | 4.32E−8 |
| Example 24.01.04 | 4.44E−8 |
| Example 24.02.01 | 4.58E−8 |
| Example 24.02.02 | 6.31E−8 |
| Example 24.03.01 | 4.78E−7 |
| Example 24.04.01 | 9.19E−9 |
| Example 24.04.02 | 1.61E−8 |
| Example 24.04.03 | 1.24E−8 |
| Example 24.04.04 | 1.44E−8 |
| Example 24.05.01.A | 4.54E−8 |
| Example 24.05.01.B | 6.62E−9 |
| Example 24.05.02.A | 1.10E−8 |
| Example 24.05.02.B | 5.51E−8 |
| Example 24.05.03.A | 4.54E−8 |
| Example 24.05.03.B | 1.38E−8 |
| Example 24.05.04.A | 6.67E−9 |
| Example 24.05.04.B | 3.39E−8 |
| Example 25.01.01 | 1.74E−7 |
| Example 25.01.02 | 2.18E−7 |
| Example 25.01.03 | 9.67E−8 |
| Example 25.01.04 | 7.90E−8 |
| Example 25.01.05 | 6.45E−8 |
| Example 25.02.01 | 3.46E−7 |
| Example 26.01.01 | 3.57E−8 |
| Example 26.01.02 | 8.58E−9 |
| Example 26.01.03 | 1.30E−8 |
| Example 26.01.04 | 1.16E−8 |
| Example 26.01.05 | 1.41E−8 |
| Example 26.02.01 | 4.68E−9 |
| Example 26.03.01.A | 2.98E−9 |
| Example 26.03.01.B | 1.95E−8 |
| Example 27.01 | 1.64E−7 |
| Example 27.02 | 2.20E−7 |
| Example 27.03 | 2.03E−7 |
| Example 27.04 | 1.97E−7 |
| Example 28.01 | 1.11E−7 |
| Example 29.01.01 | Not determined |

TABLE 25-continued

TBK1 low ATP kinase assay: IC$_{50}$ values
of examples in in vitro assay 1

| Example | TBK1 low ATP kinase assay IC$_{50}$ [M] |
|---|---|
| Example 29.01.02 | 3.47E−9 |
| Example 29.02.01.A | 9.23E−8 |
| Example 29.02.01.B | 8.64E−9 |
| Example 30.01.01 | 1.50E−8 |
| Example 30.01.02 | 1.85E−8 |
| Example 30.01.03 | 1.69E−8 |
| Example 30.01.04 | 1.23E−8 |
| Example 30.02.01 | 4.46E−9 |
| Example 30.02.02 | 7.86E−9 |
| Example 30.02.03 | 3.73E−9 |
| Example 30.02.04 | 9.35E−9 |
| Example 30.03.01.A | 1.80E−8 |
| Example 30.03.01.B | 2.15E−9 |
| Example 30.03.02.A | 4.15E−9 |
| Example 30.03.02.B | 2.75E−8 |
| Example 30.03.03.A | 3.06E−9 |
| Example 30.03.03.B | 1.40E−8 |
| Example 31.01 | 8.68E−8 |
| Example 31.02 | 7.70E−8 |
| Example 32.01 | 9.51E−7 |
| Example 32.02 | 1.17E−6 |
| Example 32.03 | 5.19E−6 |
| Example 33.01 | 3.54E−6 |
| Example 33.02 | 1.59E−6 |
| Example 33.03 | 1.50E−6 |
| Example 33.04 | 2.12E−6 |
| Example 34.01.01 | 5.06E−8 |
| Example 34.02.01 | 1.24E−8 |
| Example 34.02.02 | 9.10E−9 |
| Example 34.03.01.A | 1.21E−8 |
| Example 34.03.01.B | 5.01E−8 |
| Example 34.03.02.A | 4.64E−8 |
| Example 34.03.02.B | 7.22E−9 |
| Example 35.01.01 | 1.89E−8 |
| Example 35.01.02 | 1.80E−8 |
| Example 35.01.03 | 5.91E−8 |
| Example 35.01.04 | 2.69E−8 |
| Example 35.01.05 | 4.80E−8 |
| Example 35.01.06 | 4.79E−8 |
| Example 35.01.07 | 7.73E−8 |
| Example 35.01.08 | 2.43E−8 |
| Example 35.01.09 | 4.06E−8 |
| Example 35.01.10 | 3.50E−8 |
| Example 35.01.11 | 2.86E−8 |
| Example 35.01.12 | 3.24E−8 |
| Example 35.01.13 | 6.09E−8 |
| Example 35.01.14 | 2.28E−8 |
| Example 35.01.15 | 3.80E−8 |
| Example 35.01.16 | 4.59E−8 |
| Example 35.01.17 | 3.92E−8 |
| Example 35.01.18 | 4.18E−8 |
| Example 35.02.01 | 7.67E−9 |
| Example 35.02.02 | 1.15E−8 |
| Example 35.02.03 | 6.29E−9 |
| Example 35.02.04 | 1.04E−8 |
| Example 35.03.01.A | 3.85E−9 |
| Example 35.03.01.B | 3.00E−8 |
| Example 35.03.02.A | 8.33E−9 |
| Example 35.03.02.B | 3.28E−8 |
| Example 35.03.03.A | 5.62E−9 |
| Example 35.03.03.B | 3.17E−8 |
| Example 35.03.04.A | 8.38E−9 |
| Example 35.03.04.B | 3.45E−8 |
| Example 36.01 | Not determined |
| Example 36.02 | 1.96E−9 |
| Example 36.03 | 2.13E−9 |
| Example 36.04 | 2.50E−9 |
| Example 37.01 | 5.53E−8 |
| Example 37.02 | 6.25E−8 |
| Example 37.03 | 5.27E−8 |
| Example 37.04 | 7.39E−8 |
| Example 38.01 | Not determined |
| Example 38.02 | 5.04E−8 |
| Example 38.03 | 5.58E−8 |
| Example 39.01.01 | Not determined |
| Example 39.01.02 | 5.89E−9 |
| Example 39.01.03 | 5.35E−9 |
| Example 39.02.01 | 8.61E−9 |
| Example 39.02.02 | 1.80E−9 |
| Example 39.02.03 | 1.66E−9 |
| Example 40.01 | 1.13E−6 |
| Example 40.02 | 1.27E−6 |
| Example 40.03 | 9.88E−7 |
| Example 40.04 | 1.39E−6 |
| Example 41.01 | Not determined |
| Example 41.02 | 6.81E−7 |
| Example 41.03 | 7.70E−7 |
| Example 42.01 | 5.77E−7 |
| Example 42.02 | 3.97E−7 |
| Example 43.01 | 2.62E−7 |
| Example 43.02 | 1.84E−6 |
| Example 43.03 | 6.96E−7 |
| Example 44.01 | 9.40E−8 |
| Example 44.02 | 6.68E−8 |
| Example 44.03 | 8.58E−8 |
| Example 45.01.01 | 3.23E−7 |
| Example 45.01.02 | 3.97E−7 |
| Example 45.01.03 | 2.05E−7 |
| Example 45.02.01 | 1.24E−7 |
| Example 45.02.02 | 3.80E−7 |
| Example 45.03.01 | 3.79E−6 |
| Example 45.03.02 | 1.33E−6 |
| Example 45.04.01 | 2.24E−6 |
| Example 45.05.01 | 1.43E−6 |
| Example 45.05.02 | 1.02E−6 |
| Example 45.05.03 | 8.40E−7 |
| Example 46.01 | 3.25E−8 |
| Example 46.02 | 7.22E−8 |
| Example 47.01 | 3.94E−7 |
| Example 47.02 | 5.04E−7 |
| Example 48.01 | 1.93E−7 |
| Example 49.01 | 2.17E−7 |
| Example 50.01 | 4.99E−7 |
| Example 50.02 | 3.33E−7 |
| Example 50.03 | 6.45E−7 |
| Example 51.01 | 1.48E−7 |
| Example 51.02 | 2.70E−7 |
| Example 51.03 | 1.13E−7 |
| Example 51.04 | 2.03E−7 |
| Example 52.01 | 6.47E−8 |
| Example 52.02 | 3.69E−8 |
| Example 53.01 | 1.32E−7 |
| Example 53.02 | 1.21E−7 |
| Example 54.01 | 2.43E−7 |
| Example 54.02 | 2.29E−7 |
| Example 55.01 | 4.05E−9 |
| Example 55.02 | 1.06E−9 |
| Example 55.03 | 5.64E−10 |
| Example 56.01 | 1.65E−8 |
| Example 56.02 | 2.63E−9 |
| Example 57.01 | 7.83E−9 |
| Example 58.01.01 | 1.28E−8 |
| Example 58.01.02 | 9.81E−9 |
| Example 58.01.03 | 6.44E−9 |
| Example 59.01.01 | 1.42E−8 |
| Example 59.01.02 | 1.88E−9 |
| Example 59.01.03 | 2.59E−9 |
| Example 59.02.01 | 7.56E−9 |
| Example 59.02.02 | 6.71E−9 |
| Example 60.01 | 4.30E−8 |
| Example 61.01.01 | 1.97E−8 |
| Example 61.01.02 | 2.30E−8 |
| Example 62.01.01 | 5.73E−8 |
| Example 62.01.02 | 9.54E−9 |
| Example 62.01.03 | 3.38E−9 |
| Example 62.01.04 | 5.19E−9 |
| Example 63.01.01 | 3.64E−8 |
| Example 64.01.01 | 2.17E−7 |

TABLE 25-continued

TBK1 low ATP kinase assay: IC$_{50}$ values of examples in in vitro assay 1

| Example | TBK1 low ATP kinase assay IC$_{50}$ [M] |
|---|---|
| Example 64.01.02 | 3.37E−8 |
| Example 64.01.03 | 4.70E−8 |
| Example 65.01.01 | 2.55E−7 |
| Example 65.01.02 | 5.84E−8 |
| Example 66.01.01 | 3.33E−8 |
| Example 66.01.02 | 3.30E−8 |
| Example 55.01.01 | 5.5E−9 |
| Example 55.01.02 | 4.8E−9 |
| Example 55.02.01 | 7.2E−10 |
| Example 55.02.02 | 1.3E−9 |
| Example 55.03.01 | 6.1E−10 |
| Example 55.03.02 | 6.6E−10 |
| Example 67.01 | 4.6E−8 |
| Example 67.02 | 2.9E−9 |
| Example 67.03 | 2.0E−9 |
| Example 68.01 | 2.6E−8 |
| Example 68.02 | 1.5E−9 |
| Example 69.01 | 1.2E−8 |
| Example 69.02 | 6.4E−10 |
| Example 70.01 | 8.8E−10 |
| Example 70.02 | 7.3E−10 |
| Example 71.01 | 1.0E−7 |
| Example 71.02 | 7.1E−9 |
| Example 72.01 | 8.0E−7 |
| Example 72.02 | 2.5E−7 |
| Example 72.03 | 1.0E−7 |
| Example 73.01 | 6.7E−8 |
| Example 74.01 | 1.2E−7 |
| Example 74.02 | 1.9E−8 |
| Example 75.01 | 2.0E−8 |
| Example 75.02 | 1.4E−9 |
| Example 75.03 | 8.8E−10 |
| Example 76.01 | 3.2E−9 |
| Example 76.02 | 9.4E−9 |
| Example 77.01 | 9.2E−9 |
| Example 78.01 | 2.2E−8 |
| Example 78.02 | 1.5E−8 |
| Example 79.01 | 8.3E−9 |
| Example 79.02 | 4.8E−9 |
| Example 79.03 | 3.3E−9 |
| Example 80.01 | 3.3E−8 |
| Example 80.02 | 4.5E−9 |
| Example 80.03 | 2.9E−9 |
| Example 81.01 | 1.3E−8 |
| Example 82.01 | 3.6E−9 |
| Example 83.01 | 1.4E−8 |
| Example 83.02 | 1.0E−8 |
| Example 83.03 | 2.2E−9 |
| Example 83.04 | 1.5E−9 |
| Example 83.05 | 2.9E−9 |
| Example 84.01 | 1.1E−9 |
| Example 84.02 | 7.0E−10 |
| Example 84.03 | 1.7E−9 |
| Example 85.01 | 5.7E−9 |
| Example 85.02 | 1.4E−8 |
| Example 85.03 | 1.8E−9 |
| Example 86.01 | 1.1E−8 |
| Example 86.02 | 2.1E−9 |
| Example 86.03 | 1.5E−9 |
| Example 87.01 | 2.3E−9 |
| Example 87.02 | 2.0E−9 |
| Example 88.01 | 1.1E−5 |
| Example 88.02 | 8.6E−7 |
| Example 88.03 | 9.9E−7 |
| Example 89.01 | 6.1E−7 |
| Example 89.02 | 4.5E−7 |
| Example 89.03 | 3.2E−7 |
| Example 90.01 | 5.7E−9 |
| Example 90.02 | 1.1E−8 |
| Example 91.01 | 1.7E−8 |
| Example 91.02 | 1.2E−8 |
| Example 91.03 | 1.3E−8 |
| Example 92.01 | 8.8E−8 |
| Example 92.02 | 4.5E−7 |
| Example 93.01 | 2.3E−9 |
| Example 94.01 | 7.2E−9 |
| Example 95.01 | 6.6E−9 |
| Example 95.02 | 9.5E−9 |
| Example 96.01 | 4.6E−8 |
| Example 96.02 | 2.2E−8 |
| Example 97.01 | 2.1E−8 |
| Example 97.02 | 1.8E−8 |
| Example 97.03 | 2.9E−8 |
| Example 98.01 | 1.0E−7 |
| Example 98.02 | 4.4E−8 |
| Example 98.03 | 7.6E−8 |
| Example 99.01 | 3.3E−8 |
| Compound 95.01 | 3.9E−8 |
| Example 100.03 | 2.0E−9 |
| Example 100.01 | 1.5E−9 |
| Example 101.01 | 6.8E−7 |
| Example 101.02 | 6.8E−7 |
| Example 101.03 | 6.9E−7 |
| Example 101.04 | 3.0E−6 |
| Example 101.05 | 7.8E−7 |
| Example 101.06 | 9.9E−7 |
| Example 101.07 | 1.7E−7 |
| Example 101.08 | >2.0E−5 |
| Example 101.09 | 4.6E−7 |
| Example 101.10 | 1.8E−7 |
| Example 101.11 | >2.0E−5 |
| Example 101.12 | 4.5E−7 |
| Example 101.13 | 3.6E−7 |
| Example 101.14 | 4.3E−7 |
| Example 101.15 | 2.1E−7 |
| Example 101.16 | 1.9E−7 |
| Example 101.17 | 1.5E−7 |
| Example 101.18 | 1.5E−6 |
| Example 101.19 | 3.4E−7 |
| Example 101.20 | 5.6E−7 |
| Example 101.21 | >5.7E−5 |
| Example 101.22 | Not determined |
| Example 101.23 | 2.8E−7 |
| Example 101.24 | 1.6E−7 |
| Example 101.26 | 3.1E−7 |
| Example 101.27 | 3.5E−7 |
| Example 101.28 | 2.1E−7 |
| Example 101.29 | 4.5E−7 |
| Example 101.30 | 5.6E−7 |
| Example 101.31 | 5.1E−7 |
| Example 102.01 | 7.1E−7 |
| Example 103.01 | 3.6E−7 |
| Example 104.01 | 2.6E−6 |
| Example 105.01 | 2.7E−7 |
| Example 106.01 | 1.5E−6 |
| Compound 60.01 | 1.1E−7 |
| Example 107.01.01 | 5.2E−8 |
| Example 107.01.02 | 1.6E−8 |
| Example 107.01.03 | 1.3E−8 |
| Example 107.02.01 | 2.1E−8 |
| Example 107.02.02 | 5.9E−9 |
| Example 107.02.03 | 5.4E−9 |
| Example 107.02.04 | 5.2E−9 |
| Example 108.01 | 3.5E−8 |
| Example 108.02 | 8.2E−9 |
| Example 108.03 | 8.9E−9 |
| Example 109.01.01 | 9.2E−9 |
| Example 109.01.02 | 5.4E−9 |
| Example 109.01.03 | 8.7E−9 |
| Example 109.02.01 | 8.0E−9 |
| Example 109.02.02 | 2.0E−9 |
| Example 109.02.03 | 2.4E−9 |
| Example 110.01 | Not determined |
| Example 110.02 | 3.0E−8 |
| Example 110.03 | 5.2E−8 |
| Example 110.04 | 6.2E−8 |
| Example 111.01 | 2.6E−9 |
| Example 111.02 | 1.0E−9 |

TABLE 25-continued

TBK1 low ATP kinase assay: IC$_{50}$ values of examples in in vitro assay 1

| Example | TBK1 low ATP kinase assay IC$_{50}$ [M] |
|---|---|
| Example 111.03 | 1.4E−9 |
| Example 112.01 | 8.2E−9 |
| Example 112.02 | 1.3E−9 |
| Example 112.03 | 1.4E−9 |
| Example 113.01 | 6.1E−9 |
| Example 113.02 | 1.6E−9 |
| Example 113.03 | 1.1E−9 |
| Example 114.01 | 6.1E−8 |
| Example 115.01 | 1.4E−9 |
| Example 115.02 | 7.6E−10 |
| Example 115.03 | 6.2E−10 |
| Example 116.02 | 7.6E−10 |
| Example 116.03 | 1.3E−9 |
| Example 116.04 | 1.0E−9 |
| Example 117.01 | 2.0E−9 |
| Example 117.02 | 3.3E−10 |
| Example 117.03 | 4.9E−10 |
| Example 118.01 | 7.9E−9 |
| Example 118.02 | 3.3E−9 |
| Example 118.03 | 1.4E−9 |
| Example 118.04 | 2.6E−9 |
| Example 119.01 | Not determined |
| Example 120.02 | 1.7E−8 |
| Example 121.01 | 1.1E−8 |
| Example 121.02 | 2.5E−9 |
| Example 121.03 | 1.6E−9 |
| Example 122.01 | 9.3E−9 |
| Example 122.02 | 1.2E−9 |
| Example 122.03 | 1.1E−9 |
| Example 123.01 | 3.6E−8 |
| Example 123.02 | 3.5E−8 |
| Example 123.03 | 2.6E−8 |
| Example 124.02 | 1.0E−7 |
| Example 125.02 | 6.5E−7 |
| Example 126.02 | 3.9E−9 |
| Example 130.01 | 8.9E−7 |
| Example 130.02 | 1.9E−7 |
| Example 130.03 | 2.5E−7 |
| Example 131.01 | 1.4E−7 |
| Example 131.02 | 6.2E−8 |
| Example 131.03 | 3.2E−8 |
| Example 132.01 | 1.8E−7 |
| Example 132.02 | 1.9E−7 |
| Example 132.03 | 2.6E−7 |
| Example 133.01 | 2.8E−7 |
| Example 133.02 | 1.4E−7 |
| Example 134.01 | 5.7E−8 |
| Example 134.02 | 1.1E−8 |
| Example 134.03 | 1.9E−8 |
| Example 135.01 | 7.1E−8 |
| Example 135.02 | 2.3E−8 |
| Example 135.03 | 3.0E−8 |
| Example 136.01 | 5.3E−8 |
| Example 136.02 | 3.8E−8 |
| Example 136.03 | 2.1E−8 |
| Example 137.01 | 1.3E−8 |
| Example 137.02 | 5.8E−9 |
| Example 137.03 | 2.0E−8 |
| Example 138.01 | 5.8E−9 |
| Example 138.02 | 4.1E−9 |
| Example 138.03 | 4.3E−9 |
| Example 139.01 | 5.5E−8 |
| Example 139.02 | 1.5E−8 |
| Example 139.03 | 9.7E−9 |
| Example 140.01 | 1.3E−8 |
| Example 140.02 | 5.4E−7 |
| Example 140.03 | 2.9E−7 |
| Example 141.01 | 4.3E−8 |
| Example 141.02 | 1.9E−8 |
| Example 141.03 | 1.3E−8 |
| Example 142.01 | 7.5E−9 |
| Example 142.02 | 6.6E−9 |
| Example 142.03 | 3.0E−9 |
| Example 143.01 | 1.8E−8 |
| Example 143.02 | 8.2E−9 |
| Example 143.03 | 4.8E−9 |
| Example 144.01 | 5.1E−7 |
| Example 144.02 | 3.5E−7 |
| Example 144.03 | 4.4E−7 |
| Example 145.01 | 1.3E−8 |
| Example 145.02 | 2.9E−9 |
| Example 145.03 | 2.1E−9 |
| Example 146.01 | 1.4E−8 |
| Example 146.02 | 9.8E−9 |
| Example 147.01 | Not determined |
| Example 147.02 | 1.8E−9 |
| Example 148.01 | 2.5E−8 |
| Example 148.02 | 6.5E−9 |
| Example 148.03 | 4.8E−9 |
| Example 149.01 | 4.7E−9 |
| Example 149.02 | 2.0E−9 |
| Example 149.03 | 2.3E−9 |
| Example 150.01 | 1.5E−8 |
| Example 150.02 | 9.6E−9 |
| Example 150.03 | 5.4E−9 |
| Example 151.02 | 2.1E−9 |
| Example 151.03 | 1.0E−9 |
| Example 152.02 | 4.8E−10 |
| Example 152.03 | 9.6E−10 |
| Example 153.01 | 1.4E−8 |
| Example 153.02 | 5.9E−9 |
| Example 153.03 | 5.0E−9 |
| Example 154.01 | 4.2E−9 |
| Example 154.02 | 3.3E−9 |
| Example 154.03 | 1.4E−9 |
| Example 155.01 | 3.6E−8 |
| Example 155.02 | 1.5E−8 |
| Example 155.03 | 1.7E−8 |
| Example 156.01 | 3.8E−8 |
| Example 156.02 | 9.3E−9 |
| Example 156.03 | 1.9E−8 |
| Example 157.01 | 2.5E−8 |
| Example 157.02 | 8.9E−9 |
| Example 157.03 | 7.6E−9 |
| Example 158.01 | 1.6E−7 |
| Example 158.02 | 2.1E−8 |
| Example 158.03 | 1.3E−8 |
| Example 159.01 | 3.1E−7 |
| Example 159.02 | 1.5E−8 |
| Example 160.01 | 6.4E−8 |
| Example 160.02 | 1.3E−8 |
| Example 160.03 | 8.5E−9 |
| Example 161.01 | Not determined |
| Example 161.02 | 7.7E−9 |
| Example 161.03 | 6.7E−9 |
| Example 162.02 | 2.0E−8 |
| Example 163.02 | 1.9E−8 |
| Example 163.03 | 1.8E−8 |
| Example 04.07 | 1.00E−8 |
| Example 04.08 | 1.38E−8 |
| Example 04.09 | 2.85E−8 |
| Example 04.10 | 2.83E−8 |
| Example 16.06.04 | 2.17E−8 |
| Example 16.06.05 | 1.81E−8 |
| Example 16.06.06 | 7.30E−8 |
| Example 114.02 | 8.27E−9 |
| Example 114.03 | 8.07E−9 |
| Example 117.04 | 8.19E−10 |
| Example 117.05 | 4.73E−10 |
| Example 117.06 | 8.60E−10 |
| Example 117.07 | 2.70E−9 |
| Example 119.02 | 6.69E−9 |
| Example 119.03 | 5.93E−9 |
| Example 119.04 | 1.09E−8 |
| Example 119.05 | 6.35E−9 |
| Example 164.01 | 5.48E−9 |
| Example 164.02 | 9.43E−10 |
| Example 164.03 | 5.58E−10 |

TABLE 25-continued

TBK1 low ATP kinase assay: IC$_{50}$ values of examples in in vitro assay 1

| Example | TBK1 low ATP kinase assay IC$_{50}$ [M] |
|---|---|
| Example 164.04 | 8.32E−10 |
| Example 164.05 | 5.66E−10 |
| Example 165.01 | Not determined |
| Example 165.02 | 1.71E−9 |
| Example 165.03 | 1.79E−9 |
| Example 166.01 | 3.00E−7 |
| Example 166.02 | 2.05E−8 |
| Example 166.03 | 2.11E−8 |
| Example 166.04 | 5.42E−8 |
| Example 166.05 | 3.42E−8 |
| Example 167.01 | 2.22E−7 |
| Example 167.02 | 3.50E−8 |
| Example 167.03 | 4.13E−8 |
| Example 167.04 | 2.37E−8 |
| Example 168.01 | Not determined |
| Example 168.02 | 4.18E−9 |
| Example 168.03 | 7.12E−9 |
| Example 169.01 | Not determined |
| Example 169.02 | 1.16E−8 |
| Example 169.03 | 1.66E−8 |
| Example 170.01 | Not determined |
| Example 170.02 | 5.21E−9 |
| Example 171.01 | Not determined |
| Example 171.02 | 5.95E−9 |
| Example 171.03 | 2.85E−9 |
| Example 172.01 | 3.98E−8 |
| Example 172.02 | 1.21E−8 |
| Example 172.03 | 1.50E−8 |
| Example 172.04 | 2.09E−8 |
| Example 173.01 | 3.96E−7 |
| Example 173.02 | 7.71E−8 |
| Example 173.03 | 5.06E−8 |
| Example 173.04 | 1.49E−7 |
| Example 174.01 | 1.11E−8 |
| Example 174.02 | 3.63E−9 |
| Example 174.03 | 3.26E−9 |
| Example 175.01 | Not determined |
| Example 175.02 | 3.53E−7 |
| Example 175.03 | 2.23E−7 |
| Example 176.01 | Not determined |
| Example 176.02 | 3.58E−6 |
| Example 177.01 | 2.27E−7 |
| Example 177.02 | 7.45E−8 |
| Example 178.01 | 8.90E−7 |
| Example 178.02 | 4.02E−7 |
| Example 179.01 | 3.01E−6 |
| Example 179.02 | 1.14E−6 |
| Example 179.03 | 1.26E−6 |
| Example 180.01 | 5.76E−7 |
| Example 180.02 | 5.56E−7 |
| Example 180.03 | 3.64E−7 |
| Example 181.01 | 7.91E−7 |
| Example 181.02 | 1.52E−7 |
| Example 181.03 | 3.62E−7 |
| Example 182.01 | 2.75E−7 |
| Example 182.02 | 1.10E−7 |
| Example 182.03 | 1.36E−7 |
| Example 183.01 | 7.28E−6 |
| Example 183.02 | 2.10E−6 |
| Example 183.03 | 2.24E−6 |
| Example 184.01 | Not determined |
| Example 184.02 | 2.01E−7 |
| Example 184.03 | 2.16E−7 |
| Example 185.01 | 2.12E−7 |
| Example 186.01 | 5.91E−8 |
| Example 187.01 | Not determined |
| Example 188.01 | Not determined |
| Example 189.01 | Not determined |
| Example 189.02 | 2.86E−8 |
| Example 190.01 | Not determined |
| Example 190.02 | 8.68E−7 |
| Example 191.01 | Not determined |
| Example 191.02 | 9.53E−8 |
| Example 191.03 | 9.48E−8 |
| Example 192.01 | Not determined |
| Example 192.02 | 1.83E−8 |
| Example 192.03 | 8.30E−9 |
| Example 193.01 | 4.21E−8 |
| Example 193.02 | 3.46E−8 |
| Example 193.03 | 1.78E−8 |
| Example 194.01 | Not determined |
| Example 194.02 | 4.59E−8 |
| Example 194.03 | 4.94E−8 |
| Example 195.01 | 1.05E−7 |
| Example 195.02 | 3.37E−8 |
| Example 195.03 | 3.41E−8 |
| Example 196.01 | 1.53E−6 |
| Example 196.02 | 1.83E−6 |
| Example 196.03 | 1.42E−6 |
| Example 197.01 | Not determined |
| Example 198.01 | 4.38E−8 |
| Example 199.01 | Not determined |
| Example 199.02 | 4.19E−8 |
| Example 197.04 | 6.46E−9 |

The invention claimed is:
1. A compound of formula (I):

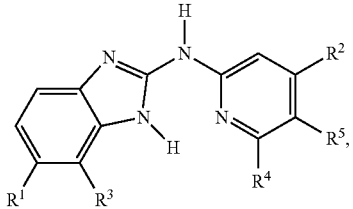

(I)

wherein
R¹ represents a group selected from

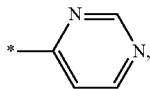

in which "*" represents the point of attachment to the rest of the molecule, said group being optionally substituted one or two times, differently or identically, with a $R^7$ group;
$R^2$ represents a group

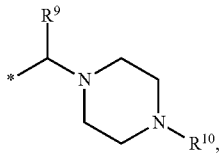

in which "*" represents the point of attachment to the rest of the molecule;
$R^3$ represents a hydrogen atom;
$R^4$ represents a hydrogen atom;
$R^5$ represents a hydrogen atom;
$R^7$ represents a group selected from the group consisting of methyl, (methoxy)-(methyl)-, ethylamino, isopropylamino, (cyclopropyl)-(methyl)-amino-, cyclopropylamino, cyclobutylamino, dimethylamino, azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-;
$R^9$ represents a methyl group;
$R^{10}$ represents a —C(=O)$R^{12}$ group;
$R^{12}$ represents a group selected from the group consisting of 2,2,2-trifluoroethyl, cyclopropyl, (1-trifluoromethyl)-(cyclopropyl)-, 2,2-difluorocyclopropyl and 2,2-difluoro-1-methylcyclopropyl,
or a stereoisomer, a tautomer, an N-oxide, a hydrate, a solvate, or a salt thereof, or a mixture of same.

2. The compound according to claim 1, which is selected from the group consisting of:
(rac)-cyclobutyl{4-[1-(2-{[6-(pyrimidin-4-yl)-1H-benzimidazol-2-yl]amino}pyridin-4-yl)ethyl]piperazin-1-yl}methanone;
(rac)-cyclopropyl{4-[1-(2-{[6-(pyrimidin-4-yl)-1H-benzimidazol-2-yl]amino}pyridin-4-yl)ethyl]piperazin-1-yl}methanone;
(rac)-3,3,3-trifluoro-1-{4-[1-(2-{[6-(pyrimidin-4-yl)-1H-benzimidazol-2-yl]amino}pyridin-4-yl)ethyl]piperazin-1-yl}propan-1-one;
cyclopropyl{4-[(1R)-1-(2-{[6-(pyrimidin-4-yl)-1H-benzimidazol-2-yl]amino}pyridin-4-yl)ethyl]piperazin-1-yl}methanone;
cyclopropyl{4-[(1S)-1-(2-{[6-(pyrimidin-4-yl)-1H-benzimidazol-2-yl]amino}pyridin-4-yl)ethyl]piperazin-1-yl}methanone;
3,3,3-trifluoro-1-{4-[(1R)-1-(2-{[6-(pyrimidin-4-yl)-1H-benzimidazol-2-yl]amino}pyridin-4-yl)ethyl]piperazin-1-yl}propan-1-one;
3,3,3-trifluoro-1-{4-[(1S)-1-(2-{[6-(pyrimidin-4-yl)-1H-benzimidazol-2-yl]amino}pyridin-4-yl)ethyl]piperazin-1-yl}propan-1-one;
cyclobutyl{4-[(1R)-1-(2-{[6-(pyrimidin-4-yl)-1H-benzimidazol-2-yl]amino}pyridin-4-yl)ethyl]piperazin-1-yl}methanone;
cyclobutyl{4-[(1S)-1-(2-{[6-(pyrimidin-4-yl)-1H-benzimidazol-2-yl]amino}pyridin-4-yl)ethyl]piperazin-1-yl}methanone;
(rac)-cyclopropyl{4-[1-(2-{[6-(2-methylpyrimidin-4-yl)-1H-benzimidazol-2-yl]amino}pyridin-4-yl)ethyl]piperazin-1-yl}methanone;
(rac)-cyclobutyl{4-[1-(2-{[6-(2-methylpyrimidin-4-yl)-1H-benzimidazol-2-yl]amino}pyridin-4-yl)ethyl]piperazin-1-yl}methanone;
(rac)-3,3,3-trifluoro-1-{4-[1-(2-{[6-(2-methylpyrimidin-4-yl)-1H-benzimidazol-2-yl]amino}pyridin-4-yl)ethyl]piperazin-1-yl}propan-1-one;
3,3,3-trifluoro-1-{4-[(1R)-1-(2-{[6-(2-methylpyrimidin-4-yl)-1H-benzimidazol-2-yl]amino}pyridin-4-yl)ethyl]piperazin-1-yl}propan-1-one;
3,3,3-trifluoro-1-{4-[(1S)-1-(2-{[6-(2-methylpyrimidin-4-yl)-1H-benzimidazol-2-yl]amino}pyridin-4-yl)ethyl]piperazin-1-yl}propan-1-one;
cyclobutyl{4-[(1R)-1-(2-{[6-(2-methylpyrimidin-4-yl)-1H-benzimidazol-2-yl]amino}pyridin-4-yl)ethyl]piperazin-1-yl}methanone;
cyclobutyl{4-[(1S)-1-(2-{[6-(2-methylpyrimidin-4-yl)-1H-benzimidazol-2-yl]amino}pyridin-4-yl)ethyl]piperazin-1-yl}methanone;
cyclopropyl{4-[(1R)-1-(2-{[6-(2-methylpyrimidin-4-yl)-1H-benzimidazol-2-yl]amino}pyridin-4-yl)ethyl]piperazin-1-yl}methanone;
cyclopropyl{4-[(1S)-1-(2-{[6-(2-methylpyrimidin-4-yl)-1H-benzimidazol-2-yl]amino}pyridin-4-yl)ethyl]piperazin-1-yl}methanone;
(rac)-1-{4-[1-(2-{[6-(2-ethoxypyrimidin-4-yl)-1H-benzimidazol-2-yl]amino}pyridin-4-yl)ethyl]piperazin-1-yl}-3,3,3-trifluoropropan-1-one;
1-{4-[(1R)-1-(2-{[6-(2-ethoxypyrimidin-4-yl)-1H-benzimidazol-2-yl]amino}pyridin-4-yl)ethyl]piperazin-1-yl}-3,3,3-trifluoropropan-1-one;
1-{4-[(1S)-1-(2-{[6-(2-ethoxypyrimidin-4-yl)-1H-benzimidazol-2-yl]amino}pyridin-4-yl)ethyl]piperazin-1-yl}-3,3,3-trifluoropropan-1-one;
(rac)-3,3,3-trifluoro-1-{4-[1-(2-{[6-(6-methylpyrimidin-4-yl)-1H-benzimidazol-2-yl]amino}pyridin-4-yl)ethyl]piperazin-1-yl}propan-1-one;
(rac)-cyclobutyl{4-[1-(2-{[6-(6-methylpyrimidin-4-yl)-1H-benzimidazol-2-yl]amino}pyridin-4-yl)ethyl]piperazin-1-yl}methanone;
(rac)-cyclopropyl{4-[1-(2-{[6-(6-methylpyrimidin-4-yl)-1H-benzimidazol-2-yl]amino}pyridin-4-yl)ethyl]piperazin-1-yl}methanone;

3,3,3-trifluoro-1-{4-[(1R)-1-(2-{[6-(6-methylpyrimidin-4-yl)-1H-benzimidazol-2-yl]amino}pyridin-4-yl)ethyl]piperazin-1-yl}propan-1-one;

3,3,3-trifluoro-1-{4-[(1S)-1-(2-{[6-(6-methylpyrimidin-4-yl)-1H-benzimidazol-2-yl]amino}pyridin-4-yl)ethyl]piperazin-1-yl}propan-1-one;

cyclobutyl{4-[(1R)-1-(2-{[6-(6-methylpyrimidin-4-yl)-1H-benzimidazol-2-yl]amino}pyridin-4-yl)ethyl]piperazin-1-yl}methanone;

cyclobutyl{4-[(1S)-1-(2-{[6-(6-methylpyrimidin-4-yl)-1H-benzimidazol-2-yl]amino}pyridin-4-yl)ethyl]piperazin-1-yl}methanone;

cyclopropyl{4-[(1R)-1-(2-{[6-(6-methylpyrimidin-4-yl)-1H-benzimidazol-2-yl]amino}pyridin-4-yl)ethyl]piperazin-1-yl}methanone;

cyclopropyl{4-[(1S)-1-(2-{[6-(6-methylpyrimidin-4-yl)-1H-benzimidazol-2-yl]amino}pyridin-4-yl)ethyl]piperazin-1-yl}methanone;

(rac)-3,3,3-trifluoro-1-{4-[1-(2-{[6-(6-methoxypyrimidin-4-yl)-1H-benzimidazol-2-yl]amino}pyridin-4-yl)ethyl]piperazin-1-yl}propan-1-one;

(rac)-cyclopropyl{4-[1-(2-{[6-(6-methoxypyrimidin-4-yl)-1H-benzimidazol-2-yl]amino}pyridin-4-yl)ethyl]piperazin-1-yl}methanone;

3,3,3-trifluoro-1-{4-[(1R)-1-(2-{[6-(6-methoxypyrimidin-4-yl)-1H-benzimidazol-2-yl]amino}pyridin-4-yl)ethyl]piperazin-1-yl}propan-1-one (single stereoisomer A);

3,3,3-trifluoro-1-{4-[(1S)-1-(2-{[6-(6-methoxypyrimidin-4-yl)-1H-benzimidazol-2-yl]amino}pyridin-4-yl)ethyl]piperazin-1-yl}propan-1-one;

cyclopropyl{4-[(1R)-1-(2-{[6-(6-methoxypyrimidin-4-yl)-1H-benzimidazol-2-yl]amino}pyridin-4-yl)ethyl]piperazin-1-yl}methanone;

cyclopropyl{4-[(1S)-1-(2-{[6-(6-methoxypyrimidin-4-yl)-1H-benzimidazol-2-yl]amino}pyridin-4-yl)ethyl]piperazin-1-yl}methanone;

(rac)-3,3,3-trifluoro-1-{4-[1-(2-{[6-(5-methoxypyrimidin-4-yl)-1H-benzimidazol-2-yl]amino}pyridin-4-yl)ethyl]piperazin-1-yl}propan-1-one;

(rac)-cyclopropyl{4-[1-(2-{[6-(5-methoxypyrimidin-4-yl)-1H-benzimidazol-2-yl]amino}pyridin-4-yl)ethyl]piperazin-1-yl}methanone;

(rac)-cyclobutyl{4-[1-(2-{[6-(5-methoxypyrimidin-4-yl)-1H-benzimidazol-2-yl]amino}pyridin-4-yl)ethyl]piperazin-1-yl}methanone;

3,3,3-trifluoro-1-{4-[(1R)-1-(2-{[6-(5-methoxypyrimidin-4-yl)-1H-benzimidazol-2-yl]amino}pyridin-4-yl)ethyl]piperazin-1-yl}propan-1-one;

3,3,3-trifluoro-1-{4-[(1S)-1-(2-{[6-(5-methoxypyrimidin-4-yl)-1H-benzimidazol-2-yl]amino}pyridin-4-yl)ethyl]piperazin-1-yl}propan-1-one;

cyclopropyl{4-[(1R)-1-(2-{[6-(5-methoxypyrimidin-4-yl)-1H-benzimidazol-2-yl]amino}pyridin-4-yl)ethyl]piperazin-1-yl}methanone;

cyclopropyl{4-[(1S)-1-(2-{[6-(5-methoxypyrimidin-4-yl)-1H-benzimidazol-2-yl]amino}pyridin-4-yl)ethyl]piperazin-1-yl}methanone;

cyclobutyl{4-[(1R)-1-(2-{[6-(5-methoxypyrimidin-4-yl)-1H-benzimidazol-2-yl]amino}pyridin-4-yl)ethyl]piperazin-1-yl}methanone);

cyclobutyl{4-[(1S)-1-(2-{[6-(5-methoxypyrimidin-4-yl)-1H-benzimidazol-2-yl]amino}pyridin-4-yl)ethyl]piperazin-1-yl}methanone (single stereoisomer B);

3,3,3-trifluoro-1-(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)propan-1-one (single stereoisomer A);

cyclopropyl(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)methanone (single stereoisomer A);

cyclobutyl(4-{(1R or 1S)-1-[2-({6-[5-(propan-2-yloxy)pyrimidin-4-yl]-1H-benzimidazol-2-yl}amino)pyridin-4-yl]ethyl}piperazin-1-yl)methanone (single stereoisomer A);

3,3,3-trifluoro-1-{4-[(1R or 1S)-1-(2-{[6-(5-methoxy-6-methylpyrimidin-4-yl)-1H-benzimidazol-2-yl]amino}pyridin-4-yl)ethyl]piperazin-1-yl}propan-1-one;

cyclopropyl{4-[(1R or 1S)-1-(2-{[6-(5-methoxy-6-methylpyrimidin-4-yl)-1H-benzimidazol-2-yl]amino}pyridin-4-yl)ethyl]piperazin-1-yl}methanone;

{4-[(1R or 1S)-1-(2-{[6-(5-methoxy-6-methylpyrimidin-4-yl)-1H-benzimidazol-2-yl]amino}pyridin-4-yl)ethyl]piperazin-1-yl}[1-(trifluoromethyl)cyclopropyl]methanone;

3,3,3-trifluoro-1-(4-{(1R or 1S)-1-[2-({6-[6-(methoxymethyl)pyrimidin-4-yl]-1H-benzimidazol-2-yl}amino)pyridin-4-yl]ethyl}piperazin-1-yl)propan-1-one;

cyclopropyl(4-{(1R or 1S)-1-[2-({6-[6-(methoxymethyl)pyrimidin-4-yl]-1H-benzimidazol-2-yl}amino)pyridin-4-yl]ethyl}piperazin-1-yl)methanone;

1-(4-{(1R or 1S)-1-[2-({6-[6-(cyclopropylmethoxy)pyrimidin-4-yl]-1H-benzimidazol-2-yl}amino)pyridin-4-yl]ethyl}piperazin-1-yl)-3,3,3-trifluoropropan-1-one;

1-(4-{(1R or 1S)-1-[2-({6-[6-(dimethylamino)pyrimidin-4-yl]-1H-benzimidazol-2-yl}amino)pyridin-4-yl]ethyl}piperazin-1-yl)-3,3,3-trifluoropropan-1-one;

cyclopropyl(4-{(1R or 1S)-1-[2-({6-[6-(dimethylamino)pyrimidin-4-yl]-1H-benzimidazol-2-yl}amino)pyridin-4-yl]ethyl}piperazin-1-yl)methanone;

cyclopropyl(4-{(1R or 1S)-1-[2-({6-[6-(dimethylamino)-5-methoxypyrimidin-4-yl]-1H-benzimidazol-2-yl}amino)pyridin-4-yl]ethyl}piperazin-1-yl)methanone;

1-(4-{(1R or 1S)-1-[2-({6-[6-(dimethylamino)-5-methoxypyrimidin-4-yl]-1H-benzimidazol-2-yl}amino)pyridin-4-yl]ethyl}piperazin-1-yl)-3,3,3-trifluoropropan-1-one;

(4-{(1R or 1S)-1-[2-({6-[6-(dimethylamino)-5-methoxypyrimidin-4-yl]-1H-benzimidazol-2-yl}amino)pyridin-4-yl]ethyl}piperazin-1-yl)[1-(trifluoromethyl)cyclopropyl]methanone;

cyclopropyl{4-[(1R or 1S)-1-{2-[(6-{6-[(cyclopropylmethyl)amino]-5-methoxypyrimidin-4-yl}-1H-benzimidazol-2-yl)amino]pyridin-4-yl}ethyl]piperazin-1-yl}methanone;

1-{4-[(1R or 1S)-1-{2-[(6-{6-[(cyclopropylmethyl)amino]-5-methoxypyrimidin-4-yl}-1H-benzimidazol-2-yl)amino]pyridin-4-yl}ethyl]piperazin-1-yl}-3,3,3-trifluoropropan-1-one;

(4-{(1R or 1S)-1-[2-({6-[6-(azetidin-1-yl)-5-methoxypyrimidin-4-yl]-1H-benzimidazol-2-yl}amino)pyridin-4-yl]ethyl}piperazin-1-yl)(cyclopropyl)methanone;

1-(4-{(1R or 1S)-1-[2-({6-[6-(azetidin-1-yl)-5-methoxypyrimidin-4-yl]-1H-benzimidazol-2-yl}amino)pyridin-4-yl]ethyl}piperazin-1-yl)-3,3,3-trifluoropropan-1-one;

cyclopropyl(4-{(1R or 1S)-1-[2-({6-[5-methoxy-6-(pyrrolidin-1-yl)pyrimidin-4-yl]-1H-benzimidazol-2-yl}amino)pyridin-4-yl]ethyl}piperazin-1-yl)methanone;

3,3,3-trifluoro-1-(4-{(1R or 1S)-1-[2-({6-[5-methoxy-6-(pyrrolidin-1-yl)pyrimidin-4-yl]-1H-benzimidazol-2-yl}amino)pyridin-4-yl]ethyl}piperazin-1-yl)propan-1-one;

1-(4-{(1R or 1S)-1-[2-({6-[6-(3,3-difluoroazetidin-1-yl)-5-methoxypyrimidin-4-yl]-1H-benzimidazol-2-yl}amino)pyridin-4-yl]ethyl}piperazin-1-yl)-3,3,3-trifluoropropan-1-one;

cyclopropyl(4-{(1R or 1S)-1-[2-({6-[6-(3,3-difluoroazetidin-1-yl)-5-methoxypyrimidin-4-yl]-1H-benzimidazol-2-yl}amino)pyridin-4-yl]ethyl}piperazin-1-yl)methanone;

1-(4-{(1R or 1S)-1-[2-({6-[6-(azetidin-1-yl)pyrimidin-4-yl]-1H-benzimidazol-2-yl}amino)pyridin-4-yl]ethyl}piperazin-1-yl)-3,3,3-trifluoropropan-1-one;

(4-{(1R or 1S)-1-[2-({6-[6-(azetidin-1-yl)pyrimidin-4-yl]-1H-benzimidazol-2-yl}amino)pyridin-4-yl]ethyl}piperazin-1-yl)(cyclopropyl)methanone;

cyclopropyl(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)methanone;

1-(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)-3,3,3-trifluoropropan-1-one;

(4-{(1R or 1S)-1-[2-({6-[6-(3,3-difluoroazetidin-1-yl)pyrimidin-4-yl]-1H-benzimidazol-2-yl}amino)pyridin-4-yl]ethyl}piperazin-1-yl)[1-(trifluoromethyl)cyclopropyl]methanone;

cyclopropyl(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)methanone;

3,3,3-trifluoro-1-(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)propan-1-one;

cyclopropyl(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)methanone;

3,3,3-trifluoro-1-(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)propan-1-one;

(4-{(1R or 1S)-1-[2-({6-[6-(morpholin-4-yl)pyrimidin-4-yl]-1H-benzimidazol-2-yl}amino)pyridin-4-yl]ethyl}piperazin-1-yl)[1-(trifluoromethyl)cyclopropyl]methanone;

(4-{(1R or 1S)-1-[2-({6-[6-(dimethylamino)pyrimidin-4-yl]-1H-benzimidazol-2-yl}amino)pyridin-4-yl]ethyl}piperazin-1-yl)[1-(trifluoromethyl)cyclopropyl]methanone;

1-(4-{(1R or 1S)-1-[2-({6-[6-(cyclobutylamino)-5-methoxypyrimidin-4-yl]-1H-benzimidazol-2-yl}amino)pyridin-4-yl]ethyl}piperazin-1-yl)-3,3,3-trifluoropropan-1-one;

(4-{(1R or 1S)-1-[2-({6-[6-(cyclobutylamino)-5-methoxypyrimidin-4-yl]-1H-benzimidazol-2-yl}amino)pyridin-4-yl]ethyl}piperazin-1-yl)(cyclopropyl)methanone;

(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)[1-(trifluoromethyl)cyclopropyl]methanone;

((1RS)-2,2-difluorocyclopropyl)(4-{(1R or 1S)-1-[2-({6-[6-(pyrrolidin-1-yl)pyrimidin-4-yl]-1H-benzimidazol-2-yl}amino)pyridin-4-yl]ethyl}piperazin-1-yl)methanone;

[(1RS)-2,2-difluoro-1-methylcyclopropyl](4-{(1R or S)-1-[2-({6-[6-(pyrrolidin-1-yl)pyrimidin-4-yl]-1H-benzimidazol-2-yl}amino)pyridin-4-yl]ethyl}piperazin-1-yl)methanone;

3,3,3-trifluoro-1-(4-{(1R)-1-[2-({6-[6-(2,2,2-trifluoroethoxy)pyrimidin-4-yl]-1H-benzimidazol-2-yl}amino)pyridin-4-yl]ethyl}piperazin-1-yl)propan-1-one;

cyclopropyl(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)methanone;

(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)[1-(trifluoromethyl)cyclopropyl]methanone;

((1RS)-2,2-difluorocyclopropyl)(4-{(1R or 1S)-1-[2-({6-[6-(2,2,2-trifluoroethoxy)pyrimidin-4-yl]-1H-benzimidazol-2-yl}amino)pyridin-4-yl]ethyl}piperazin-1-yl)methanone;

3,3,3-trifluoro-1-{4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}propan-1-one;

cyclopropyl{4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}methanone;

{4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}[1-(trifluoromethyl)cyclopropyl]methanone;

((1RS)-2,2-difluorocyclopropyl){4-[(1R or 1S)-1-{2-[(6-{6-[3-(trifluoromethyl)azetidin-1-yl]pyrimidin-4-yl}-1H-benzimidazol-2-yl)amino]pyridin-4-yl}ethyl]piperazin-1-yl}methanone;

1-(4-{(1R or 1S)-1-[2-({6-[6-(2,2-difluoropropoxy)pyrimidin-4-yl]-1H-benzimidazol-2-yl}amino)pyridin-4-yl]ethyl}piperazin-1-yl)-3,3,3-trifluoropropan-1-one;

cyclopropyl(4-{(1R or 1S)-1-[2-({6-[6-(2,2-difluoropropoxy)pyrimidin-4-yl]-1H-benzimidazol-2-yl}amino)pyridin-4-yl]ethyl}piperazin-1-yl)methanone;

or a stereoisomer, a tautomer, an N-oxide, a hydrate, a solvate, or a salt thereof, or a mixture of same.

3. A method of preparing a compound of formula (I) according to claim 1, said method comprising allowing an intermediate compound of formula (XL-A) or a salt thereof:

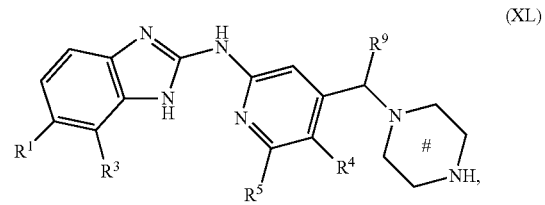

in which $R^1$, $R^3$, $R^4$, $R^5$ and $R^9$ are as defined for the compound of formula (I), to react with one reagent selected from the group (RG) consisting of $R^{12}$—C(=O)OH, and $R^{12}$—C(=O)-

LG⁷, in which R¹² is as defined for the compound of formula (I), and in which LG⁷ represents a leaving group, thereby giving a compound of formula (I)

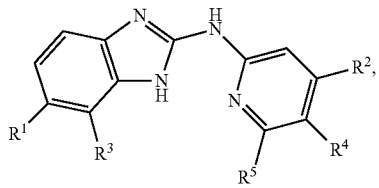
(I)

in which R¹, R², R³, R⁴ and R⁵ are as defined for the compound of formula (I).

4. A pharmaceutical composition comprising the compound of formula (I) according to claim 1 and one or more pharmaceutically acceptable excipients.

5. A pharmaceutical combination comprising:
one or more first active ingredients, wherein the one or more first active ingredients are compounds of formula (I) according to claim 1, and
one or more further active ingredients.

6. A medicament prepared from the compound of formula (I) according to claim 1 for treatment or prophylaxis of a disease.

7. A compound of formula (XL-A):

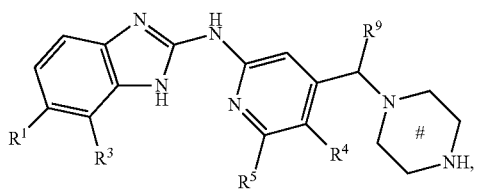
(XL)

wherein
R¹ represents a group

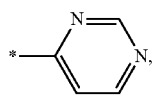

in which "*" represents the point of attachment to the rest of the molecule,
said group being optionally substituted one or two times, differently or identically, with a R⁷ group;
R³ represents a hydrogen atom;
R⁴ represents a hydrogen atom;
R⁵ represents a hydrogen atom;
R⁷ represents a group selected from methyl, (methoxy)-(methyl)-, ethylamino, isopropylamino, (cyclopropyl)-(methyl)-amino-, cyclopropylamino, cyclobutylamino, dimethylamino,azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-; and
R⁹ represents a methyl group.

8. The compound according to claim 1, wherein R¹ represents a group selected from

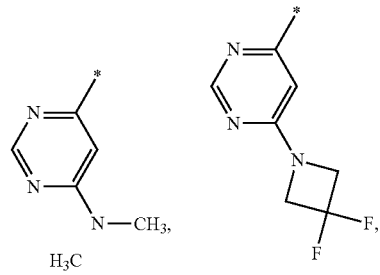

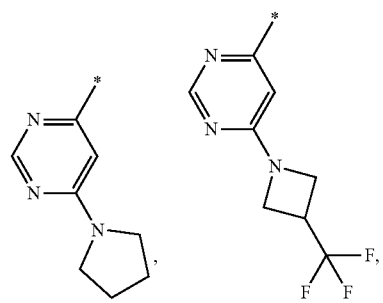

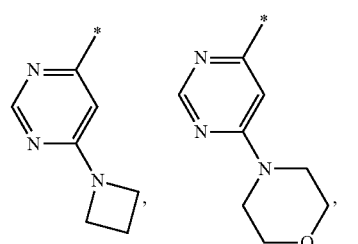

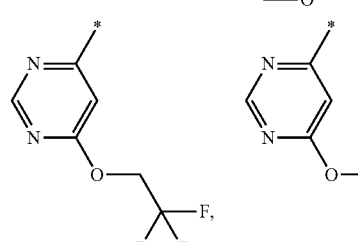

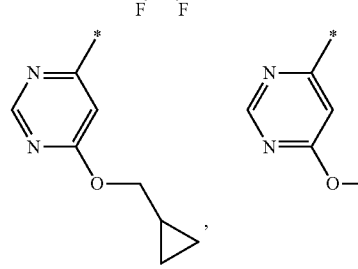

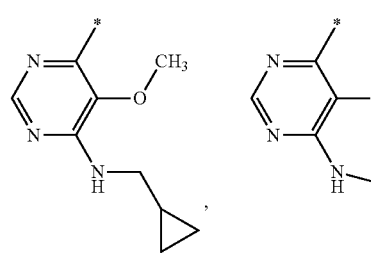

1019
-continued

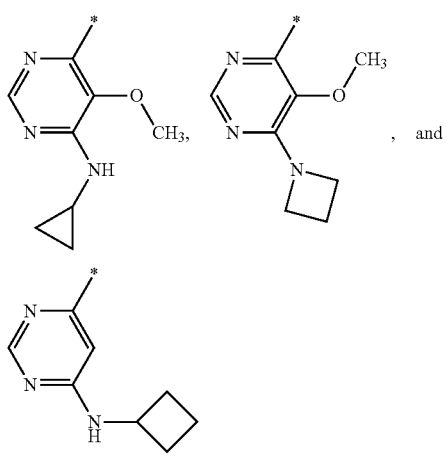

, and

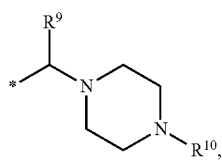

wherein "*" represents the point of attachment to the rest of the molecule,

R² represents a group

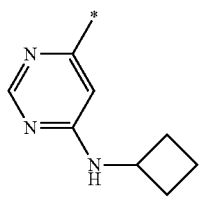

wherein "*" represents the point of attachment to the rest of the molecule,

R³ represents a hydrogen atom;
R⁴ represents a hydrogen atom;
R⁵ represents a hydrogen atom;
R⁹ represents a methyl group;
R¹⁰ represents a —C(=O)R¹² group;
R¹² represents a group selected from the group consisting of 2,2,2-trifluoroethyl, cyclopropyl, (1-trifluoromethyl)-(cyclopropyl)- 2,2-difluorocyclopropyl and 2,2-difluoro-1-methylcyclopropyl, or a stereoisomer, a tautomer, an N-oxide, a hydrate, a solvate, or a salt thereof, or a mixture of same.

9. The compound according to claim 1, wherein
R¹ represents a group selected from the group consisting of

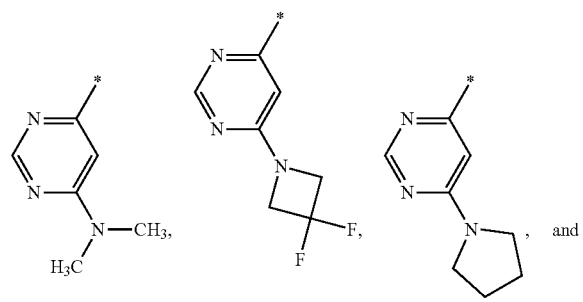

1020
-continued

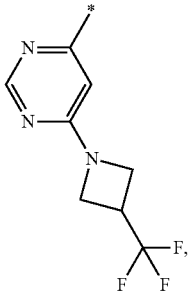

wherein "*" represents the point of attachment to the rest of the molecule,

R² represents a group

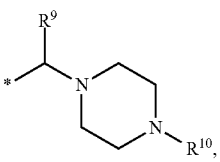

wherein "*" represents the point of attachment to the rest of the molecule;

R³ represents a hydrogen atom;
R⁴ represents a hydrogen atom;
R⁵ represents a hydrogen atom;
R⁹ represents a methyl group;
R¹⁰ represents a —C(=O)R¹² group;
R¹² represents a group selected from the group consisting of 2,2,2-trifluoroethyl, cyclopropyl, (1-trifluoromethyl)-(cyclopropyl)- 2,2-difluorocyclopropyl and 2,2-difluoro-1-methylcyclopropyl,
or a stereoisomer, a tautomer, an N-oxide, a hydrate, a solvate, or a salt thereof, or a mixture of same.

10. The compound according to claim 1, wherein
R¹ represents a group

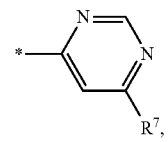

wherein "*" represents the point of attachment to the rest of the molecule, and wherein R⁷ represents a dimethylamino group, R² represents a group

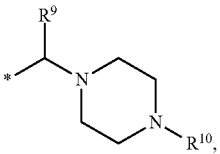

wherein "*" represents the point of attachment to the rest of the molecule;

R³ represents a hydrogen atom;
R⁴ represents a hydrogen atom;

$R^5$ represents a hydrogen atom;
$R^9$ represents a methyl group;
$R^{10}$ represents a —C(=O)$R^{12}$ group;
$R^{12}$ represents a group selected from the group consisting of 2,2,2-trifluoroethyl, cyclopropyl, (1-trifluoromethyl)-(cyclopropyl)- 2,2-difluorocyclopropyl and 2,2-difluoro-1-methylcyclopropyl, or a stereoisomer, a tautomer, an N-oxide, a hydrate, a solvate, or a salt thereof, or a mixture of same.

11. The compound according to claim 1, wherein $R^1$ represents a group

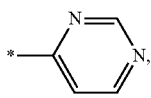

wherein "*" represents the point of attachment to the rest of the molecule, said group being optionally substituted one or two times, differently or identically, with a $R^7$ group, $R^2$ represents a group

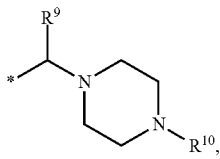

wherein "*" represents the point of attachment to the rest of the molecule;

$R^3$ represents a hydrogen atom;
$R^4$ represents a hydrogen atom;
$R^5$ represents a hydrogen atom;
$R^7$ represents a group selected from methyl, (methoxy)-(methyl)-, ethylamino, ispropylamino, (cyclopropyl)-(methyl)-amino-, cyclopropylamino, cyclobutylamino, dimethylamino,azetidin-1-yl, 3,3-difluoroazetidin-1-yl, 3-trifluoromethylazetidin-1-yl, pyrrolidin-1-yl, piperidin-1-yl, morpholinyl, methoxy, ethoxy, iso-propoxy, 2,2,2-trifluoroethoxy, 2,2-difluoropropoxy and (cyclopropyl)-(methoxy)-;
$R^9$ represents a methyl group;
$R^{10}$ represents a —C(=O)$R^{12}$ group, and in which $R^{12}$ represents a 2,2,2-trifluoroethyl group, or a stereoisomer, a tautomer, an N-oxide, a hydrate, a solvate, or a salt thereof, or a mixture of same.

12. The compound according to claim 1, which is 1-(4-{(1R or 1S)-1-[2-({6-[6-(dimethylamino)pyrimidin-4-yl]-1H-benzimidazol-2-yl}amino)pyridin-4-yl]ethyl}piperazin-1-yl)-3,3,3-trifluoropropan-1-one, or a stereoisomer, a tautomer, an N-oxide, a hydrate, a solvate, or a salt thereof, or a mixture of same.

13. The compound according to claim 1, which is 1-(4-{(1R or 1S)-1-[2-({6-[6-(dimethylamino)pyrimidin-4-yl]-1H-benzimidazol-2-yl}amino)pyridin-4-yl]ethyl}piperazin-1-yl)-3,3,3-trifluoropropan-1-one, or a pharmaceutically acceptable salt thereof.

14. The compound according to claim 1, which is 1-(4-{(1R or 1S)-1-[2-({6-[6-(dimethylamino)pyrimidin-4-yl]-1H-benzimidazol-2-yl}amino)pyridin-4-yl]ethyl}piperazin-1-yl)-3,3,3-trifluoropropan-1-one.

15. The pharmaceutical combination according to claim 5, wherein the one or more further active ingredients comprise anticancer agents.

* * * * *